US012686650B2

(12) United States Patent
Temme et al.

(10) Patent No.: US 12,686,650 B2
(45) Date of Patent: *Jul. 21, 2026

(54) METHODS AND COMPOSITIONS FOR IMPROVING PLANT TRAITS

(71) Applicant: Pivot Bio, Inc., Minnetonka, MN (US)

(72) Inventors: Karsten Temme, Oakland, CA (US); Alvin Tamsir, San Francisco, CA (US); Sarah Bloch, Emeryville, CA (US); Rosemary Clark, El Cerrito, CA (US); Emily Tung, Millbrae, CA (US); Kevin Hammill, Danville, CA (US); Douglas Higgins, Berkeley, CA (US); Austin Davis-Richardson, San Francisco, CA (US)

(73) Assignee: Pivot Bio, Inc., Minnetonka, MN (US)

( * ) Notice: Subject to any disclaimer, the term of this patent is extended or adjusted under 35 U.S.C. 154(b) by 791 days.

This patent is subject to a terminal disclaimer.

(21) Appl. No.: 17/027,030

(22) Filed: Sep. 21, 2020

(65) Prior Publication Data

US 2021/0009483 A1 Jan. 14, 2021

Related U.S. Application Data

(63) Continuation of application No. 16/159,542, filed on Oct. 12, 2018, now abandoned, which is a continuation of application No. PCT/US2018/013671, filed on Jan. 12, 2018.

(60) Provisional application No. 62/577,147, filed on Oct. 25, 2017, provisional application No. 62/566,199, filed on Sep. 29, 2017, provisional application No. 62/467,032, filed on Mar. 3, 2017, provisional application No. 62/447,889, filed on Jan. 18, 2017, provisional application No. 62/445,557, filed on Jan. 12, 2017, provisional application No. 62/445,570, filed on Jan. 12, 2017.

(51) Int. Cl.

| | |
|---|---|
| *C12N 1/20* | (2026.01) |
| *A01H 3/00* | (2006.01) |
| *A01H 6/46* | (2018.01) |
| *A01N 63/20* | (2020.01) |
| *C05F 11/08* | (2006.01) |
| *C12N 1/04* | (2006.01) |
| *C12N 1/205* | (2026.01) |
| *C12N 15/11* | (2006.01) |
| *C12N 15/52* | (2006.01) |
| *C12N 15/70* | (2006.01) |
| *C12N 15/74* | (2006.01) |
| *C12R 1/01* | (2006.01) |
| *C12R 1/025* | (2006.01) |
| *C12R 1/065* | (2006.01) |
| *C12R 1/07* | (2006.01) |
| *C12R 1/22* | (2006.01) |

(52) U.S. Cl.
CPC ................ *C05F 11/08* (2013.01); *A01H 3/00* (2013.01); *A01H 6/4684* (2018.05); *A01N 63/20* (2020.01); *C12N 1/04* (2013.01); *C12N 1/20* (2013.01); *C12N 1/205* (2021.05); *C12N 15/111* (2013.01); *C12N 15/52* (2013.01); *C12N 15/70* (2013.01); *C12N 15/743* (2013.01); *C12R 2001/01* (2021.05); *C12R 2001/025* (2021.05); *C12R 2001/065* (2021.05); *C12R 2001/07* (2021.05); *C12R 2001/22* (2021.05)

(58) Field of Classification Search
None
See application file for complete search history.

(56) References Cited

U.S. PATENT DOCUMENTS

| | | | |
|---|---|---|---|
| 1,520,545 | A | 12/1924 | Murphy |
| 4,782,022 | A | 11/1988 | Puhler et al. |
| 4,832,728 | A | 5/1989 | Allan et al. |
| 4,970,147 | A | 11/1990 | Huala et al. |
| 5,071,743 | A | 12/1991 | Slilaty et al. |
| 5,116,506 | A | 5/1992 | Williamson et al. |
| 5,188,960 | A | 2/1993 | Payne et al. |
| 5,229,291 | A | 7/1993 | Nielsen et al. |
| 5,354,670 | A | 10/1994 | Nickoloff et al. |
| 5,427,785 | A | 6/1995 | Ronson et al. |
| 5,610,044 | A | 3/1997 | Lam et al. |
| 5,780,270 | A | 7/1998 | Lesley |
| 5,789,166 | A | 8/1998 | Bauer et al. |
| 5,877,012 | A | 3/1999 | Estruch et al. |
| 5,880,275 | A | 3/1999 | Fischhoff et al. |
| 5,916,029 | A | 6/1999 | Smith et al. |
| 6,033,861 | A | 3/2000 | Schafer et al. |
| 6,033,874 | A | 3/2000 | Baum et al. |
| 6,083,499 | A | 7/2000 | Narva et al. |

(Continued)

FOREIGN PATENT DOCUMENTS

| | | |
|---|---|---|
| AU | 636565 | 5/1993 |
| CA | 2051071 | 3/1993 |

(Continued)

OTHER PUBLICATIONS

US 8,476,226 B2, 07/2013, Lira (withdrawn)

(Continued)

*Primary Examiner* — Charles Logsdon
(74) *Attorney, Agent, or Firm* — Fish & Richardson P.C.

(57) ABSTRACT

Methods and systems are provided for generating and utilizing a bacterial composition that comprises at least one genetically engineered bacterial strain that fixes atmospheric nitrogen in an agricultural system that has been fertilized with more than 20 lbs of Nitrogen per acre.

38 Claims, 44 Drawing Sheets

Specification includes a Sequence Listing.

(56) References Cited

U.S. PATENT DOCUMENTS

| | | |
|---|---|---|
| 6,107,279 A | 8/2000 | Estruch et al. |
| 6,114,148 A | 9/2000 | Seed et al. |
| 6,127,180 A | 10/2000 | Narva et al. |
| 6,137,033 A | 10/2000 | Estruch et al. |
| 6,218,188 B1 | 4/2001 | Cardineau et al. |
| 6,248,535 B1 | 6/2001 | Danenberg et al. |
| 6,326,351 B1 | 12/2001 | Donovan et al. |
| 6,340,593 B1 | 1/2002 | Cardineau et al. |
| 6,391,548 B1 | 5/2002 | Bauer et al. |
| 6,399,330 B1 | 6/2002 | Donovan et al. |
| 6,548,289 B1 | 4/2003 | Beynon et al. |
| 6,548,291 B1 | 4/2003 | Narva et al. |
| 6,596,509 B1 | 7/2003 | Bauer |
| 6,624,145 B1 | 9/2003 | Narva et al. |
| 6,673,610 B2 | 1/2004 | Miyawaki et al. |
| 6,713,063 B1 | 3/2004 | Malvar et al. |
| 6,713,285 B2 | 3/2004 | Bauer et al. |
| 6,773,900 B2 | 8/2004 | Short et al. |
| 6,841,358 B1 | 1/2005 | Locht et al. |
| 6,949,626 B2 | 9/2005 | Donovan et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,084,331 B2 | 8/2006 | Isawa et al. |
| 7,105,332 B2 | 9/2006 | Abad et al. |
| 7,132,265 B2 | 11/2006 | Bauer et al. |
| 7,244,820 B2 | 7/2007 | Miles et al. |
| 7,329,736 B2 | 2/2008 | Abad et al. |
| 7,378,499 B2 | 5/2008 | Abad et al. |
| 7,385,107 B2 | 6/2008 | Donovan et al. |
| 7,449,552 B2 | 11/2008 | Abad et al. |
| 7,462,760 B2 | 12/2008 | Abad et al. |
| 7,470,427 B2 | 12/2008 | Cocking |
| 7,476,781 B2 | 1/2009 | Abad et al. |
| 7,485,451 B2 | 2/2009 | Vandergheynst et al. |
| 7,491,698 B2 | 2/2009 | Hey et al. |
| 7,491,869 B2 | 2/2009 | Abad et al. |
| 7,504,229 B2 | 3/2009 | Donovan et al. |
| 7,615,686 B2 | 11/2009 | Miles et al. |
| 7,803,943 B2 | 9/2010 | Mao et al. |
| 7,858,849 B2 | 12/2010 | Cerf et al. |
| 7,888,552 B2 | 2/2011 | Ye et al. |
| 7,923,602 B2 | 4/2011 | Carozzi et al. |
| 8,076,142 B2 | 12/2011 | Huang et al. |
| 8,084,416 B2 | 12/2011 | Sampson et al. |
| 8,084,418 B2 | 12/2011 | Hey et al. |
| 8,137,665 B2 | 3/2012 | Cocking |
| 8,236,757 B2 | 8/2012 | Carozzi et al. |
| 8,237,020 B2 | 8/2012 | Miles et al. |
| 8,268,584 B1 | 9/2012 | Harwood et al. |
| 8,304,604 B2 | 11/2012 | Lira et al. |
| 8,304,605 B2 | 11/2012 | Lira et al. |
| 8,319,019 B2 | 11/2012 | Abad et al. |
| 8,334,366 B1 | 12/2012 | Hughes et al. |
| 8,334,431 B2 | 12/2012 | Sampson et al. |
| 8,377,671 B2 | 2/2013 | Cournac et al. |
| 8,481,026 B1 | 7/2013 | Woodruff et al. |
| 8,513,494 B2 | 8/2013 | Wu et al. |
| 8,530,411 B2 | 9/2013 | Cerf et al. |
| 8,575,433 B2 | 11/2013 | Cerf et al. |
| 8,686,233 B2 | 4/2014 | Cerf et al. |
| 8,759,619 B2 | 6/2014 | Sampson et al. |
| 8,795,965 B2 | 8/2014 | Zhang |
| 8,802,933 B2 | 8/2014 | Abad et al. |
| 8,802,934 B2 | 8/2014 | Abad et al. |
| 9,150,851 B2 | 10/2015 | Wigley et al. |
| 9,321,697 B2 | 4/2016 | Das et al. |
| 9,487,451 B2 | 11/2016 | Doty et al. |
| 9,512,431 B2 | 12/2016 | Mirsky et al. |
| 9,657,298 B2 | 5/2017 | Soto, Sr. et al. |
| 9,796,957 B2 | 10/2017 | Barney et al. |
| 9,957,509 B2 | 5/2018 | Mirsky et al. |
| 9,975,817 B2 | 5/2018 | Temme et al. |
| 9,994,557 B2 | 6/2018 | Davidson et al. |
| 10,384,983 B2 | 8/2019 | Temme et al. |
| 10,525,318 B2 | 1/2020 | Dougherty |
| 10,556,839 B2 | 2/2020 | Temme et al. |
| 10,662,432 B2 | 5/2020 | Mirsky et al. |
| 10,919,814 B2 | 2/2021 | Temme et al. |
| 10,934,226 B2 | 3/2021 | Temme et al. |
| 10,968,446 B2 | 4/2021 | Zhao et al. |
| 11,479,516 B2 | 10/2022 | Voigt et al. |
| 11,678,667 B2 | 6/2023 | Reisinger et al. |
| 11,678,668 B2 | 6/2023 | Reisinger et al. |
| 11,739,032 B2 | 8/2023 | Temme et al. |
| 11,946,162 B2 | 4/2024 | Zhao et al. |
| 11,963,530 B2 | 4/2024 | Reisinger et al. |
| 12,151,988 B2 | 11/2024 | Tamsir et al. |
| 2002/0061579 A1 | 5/2002 | Farrand et al. |
| 2004/0197916 A1 | 10/2004 | Carozzi et al. |
| 2004/0197917 A1 | 10/2004 | Carozzi et al. |
| 2004/0210964 A1 | 10/2004 | Carozzi et al. |
| 2004/0210965 A1 | 10/2004 | Carozzi et al. |
| 2004/0216186 A1 | 10/2004 | Carozzi et al. |
| 2004/0235663 A1 | 11/2004 | Cocking |
| 2004/0241847 A1 | 12/2004 | Okuyama et al. |
| 2004/0250311 A1 | 12/2004 | Carozzi et al. |
| 2005/0081262 A1 | 4/2005 | Cook et al. |
| 2005/0266541 A1 | 12/2005 | Dillon |
| 2006/0033867 A1 | 2/2006 | Krisko et al. |
| 2006/0096918 A1 | 5/2006 | Semmens |
| 2006/0112447 A1 | 5/2006 | Bogdanova et al. |
| 2006/0127988 A1 | 6/2006 | Wood et al. |
| 2006/0191034 A1 | 8/2006 | Baum |
| 2006/0243011 A1 | 11/2006 | Someus |
| 2007/0249018 A1 | 10/2007 | Vemuri et al. |
| 2008/0295207 A1 | 11/2008 | Baum et al. |
| 2008/0311632 A1 | 12/2008 | Figge et al. |
| 2009/0105076 A1 | 4/2009 | Stewart et al. |
| 2009/0137390 A1 | 5/2009 | Triplett |
| 2009/0144852 A1 | 6/2009 | Tomso et al. |
| 2009/0152195 A1 | 6/2009 | Rodgers et al. |
| 2009/0162477 A1 | 6/2009 | Nadel |
| 2009/0221049 A1 | 9/2009 | Shaw et al. |
| 2009/0258404 A1 | 10/2009 | Mikkelsen et al. |
| 2009/0308121 A1 | 12/2009 | Reddy et al. |
| 2010/0005543 A1 | 1/2010 | Sampson et al. |
| 2010/0017914 A1 | 1/2010 | Hart et al. |
| 2010/0028870 A1 | 2/2010 | Welch et al. |
| 2010/0184038 A1 | 7/2010 | Boddy et al. |
| 2010/0197592 A1 | 8/2010 | Heinrichs |
| 2010/0267147 A1 | 10/2010 | Qiao |
| 2010/0298211 A1 | 11/2010 | Carozzi et al. |
| 2011/0023184 A1 | 1/2011 | Desai et al. |
| 2011/0064710 A1 | 3/2011 | Benson et al. |
| 2011/0104690 A1 | 5/2011 | Yu et al. |
| 2011/0263488 A1 | 10/2011 | Carozzi et al. |
| 2012/0015409 A1 | 1/2012 | Tabata et al. |
| 2012/0015806 A1 | 1/2012 | Paikray et al. |
| 2012/0107889 A1 | 5/2012 | Doty et al. |
| 2012/0192605 A1 | 8/2012 | McSpadden Gardener |
| 2012/0220006 A1 | 8/2012 | Hardwood et al. |
| 2012/0266332 A1 | 10/2012 | Kuykendall |
| 2012/0278954 A1 | 11/2012 | Bowen et al. |
| 2012/0284813 A1 | 11/2012 | Olivier et al. |
| 2012/0311745 A1 | 12/2012 | Meade et al. |
| 2012/0311746 A1 | 12/2012 | Meade et al. |
| 2012/0317681 A1 | 12/2012 | Meade et al. |
| 2012/0317682 A1 | 12/2012 | Meade et al. |
| 2012/0324605 A1 | 12/2012 | Meade et al. |
| 2012/0324606 A1 | 12/2012 | Meade et al. |
| 2012/0331589 A1 | 12/2012 | Meade et al. |
| 2012/0331590 A1 | 12/2012 | Meade et al. |
| 2013/0116170 A1 | 5/2013 | Graser et al. |
| 2013/0126428 A1 | 5/2013 | Jones et al. |
| 2013/0167268 A1 | 6/2013 | Narva et al. |
| 2013/0167269 A1 | 6/2013 | Narva et al. |
| 2014/0011261 A1 | 1/2014 | Wang et al. |
| 2014/0155283 A1 | 6/2014 | Venkateswaran et al. |
| 2014/0182018 A1 | 6/2014 | Lang et al. |
| 2014/0196178 A1 | 7/2014 | Zaltsman |
| 2014/0223598 A1 | 8/2014 | Sampson et al. |
| 2014/0223599 A1 | 8/2014 | Sampson et al. |
| 2014/0230504 A1 | 8/2014 | Finlayson et al. |

(56)          References Cited

U.S. PATENT DOCUMENTS

| | | |
|---|---|---|
| 2014/0273226 A1 | 9/2014 | Wu |
| 2014/0283569 A1 | 9/2014 | Doty et al. |
| 2014/0301990 A1 | 10/2014 | Gregory et al. |
| 2014/0329326 A1 | 11/2014 | Mirsky et al. |
| 2014/0336050 A1 | 11/2014 | Soto, Sr. et al. |
| 2015/0080261 A1 | 3/2015 | Wigley et al. |
| 2015/0101373 A1 | 4/2015 | Munusamy et al. |
| 2015/0128670 A1 | 5/2015 | Das et al. |
| 2015/0237807 A1 | 8/2015 | Valiquette |
| 2015/0239789 A1 | 8/2015 | Kang et al. |
| 2015/0315570 A1 | 11/2015 | Zhao et al. |
| 2016/0174570 A1 | 6/2016 | Vujanovic et al. |
| 2016/0264929 A1 | 9/2016 | Barney et al. |
| 2016/0292355 A1 | 10/2016 | Lou et al. |
| 2016/0295868 A1 | 10/2016 | Jones et al. |
| 2016/0304842 A1 | 10/2016 | Donovan et al. |
| 2017/0035900 A1 | 2/2017 | Kowarik et al. |
| 2017/0086402 A1 | 3/2017 | Meadows-Smith et al. |
| 2017/0107160 A1 | 4/2017 | Newman et al. |
| 2017/0119690 A1 | 5/2017 | Hansen et al. |
| 2017/0152519 A1 | 6/2017 | Mirsky |
| 2017/0267997 A1 | 9/2017 | Nicol et al. |
| 2017/0367349 A1 | 12/2017 | Gruver et al. |
| 2018/0002243 A1 | 1/2018 | Temme et al. |
| 2018/0020671 A1 | 1/2018 | Bioconsortia |
| 2018/0065896 A1 | 3/2018 | Ibema et al. |
| 2018/0073028 A1 | 3/2018 | Mirsky |
| 2018/0273437 A1 | 9/2018 | Temme et al. |
| 2018/0290942 A1 | 10/2018 | Voigt et al. |
| 2018/0297905 A1 | 10/2018 | Temme et al. |
| 2018/0297906 A1 | 10/2018 | Temme et al. |
| 2019/0039964 A1 | 2/2019 | Temme et al. |
| 2019/0144352 A1 | 5/2019 | Temme et al. |
| 2020/0087221 A1 | 3/2020 | Temme et al. |
| 2020/0115715 A1 | 4/2020 | Mirsky et al. |
| 2020/0299637 A1 | 9/2020 | Voigt et al. |
| 2020/0308594 A1 | 10/2020 | Tamsir et al. |
| 2020/0331820 A1 | 10/2020 | Tamsir |
| 2021/0163374 A1 | 6/2021 | Bioch et al. |
| 2021/0214282 A1 | 7/2021 | Temme et al. |
| 2021/0284995 A1 | 9/2021 | Zhao et al. |
| 2021/0315212 A1 | 10/2021 | Rezaei et al. |
| 2022/0017911 A1 | 1/2022 | Temme et al. |
| 2022/0079163 A1 | 3/2022 | Reisinger et al. |
| 2022/0106238 A1 | 4/2022 | Rezaei et al. |
| 2022/0127627 A1 | 4/2022 | Bloch et al. |
| 2022/0211048 A1 | 7/2022 | Temme et al. |
| 2022/0282340 A1 | 9/2022 | Ryu et al. |
| 2022/0411344 A1 | 12/2022 | Voigt et al. |
| 2023/0257317 A1 | 8/2023 | Temme et al. |
| 2023/0295559 A1 | 9/2023 | Eskiyenenturk et al. |
| 2024/0010576 A1 | 1/2024 | Temme et al. |
| 2024/0294953 A1 | 9/2024 | Eskiyenenturk et al. |
| 2024/0327851 A1 | 10/2024 | Tamsir et al. |
| 2024/0360465 A1 | 10/2024 | Wood et al. |
| 2025/0115529 A1 | 4/2025 | Tamsir et al. |

FOREIGN PATENT DOCUMENTS

| | | |
|---|---|---|
| CA | 2991776 | 1/2017 |
| CA | 3072466 A1 | 2/2019 |
| CN | 1289852 A | 4/2001 |
| CN | 1355293 | 6/2002 |
| CN | 1355294 | 6/2002 |
| CN | 1421527 | 6/2003 |
| CN | 1500801 | 6/2004 |
| CN | 1552846 | 12/2004 |
| CN | 1746304 | 3/2006 |
| CN | 101328477 | 12/2008 |
| CN | 101880676 | 11/2010 |
| CN | 101899430 | 12/2010 |
| CN | 102041241 | 5/2011 |
| CN | 102417882 | 4/2012 |
| CN | 102690808 | 9/2012 |
| CN | 103451130 | 12/2013 |
| CN | 103917657 | 7/2014 |
| CN | 104136599 | 11/2014 |
| CN | 104204211 | 12/2014 |
| CN | 106086042 | 11/2016 |
| EA | 002757 | 8/2002 |
| EP | 0256889 | 2/1988 |
| EP | 0292984 | 11/1988 |
| EP | 0339830 | 11/1989 |
| EP | 1535913 | 6/2005 |
| EP | 2186890 | 5/2010 |
| EP | 3231874 | 10/2017 |
| EP | 3322679 | 5/2018 |
| FR | 2494297 A1 | 5/1982 |
| FR | 2910230 | 6/2008 |
| JP | H01-225483 | 9/1989 |
| JP | 2009-232721 | 10/2009 |
| JP | 2014096996 | 5/2014 |
| JP | 2015037385 | 2/2015 |
| JP | 2015042633 | 3/2015 |
| JP | 2015113274 | 6/2015 |
| JP | 2015518023 | 6/2015 |
| JP | 2015519352 | 7/2015 |
| JP | 2015-173652 | 10/2015 |
| JP | 2017-513480 | 6/2017 |
| RU | 94045882 | 9/1996 |
| WO | WO 1987/004182 | 7/1987 |
| WO | WO 1993/005154 | 3/1993 |
| WO | WO 1998/010088 | 3/1998 |
| WO | WO 1999/009834 | 3/1999 |
| WO | WO 2000/057183 | 9/2000 |
| WO | WO 2001/007567 | 2/2001 |
| WO | WO 2003/089640 A2 | 10/2003 |
| WO | WO 2004/074462 | 9/2004 |
| WO | WO 2005/021585 | 3/2005 |
| WO | WO 2005/038032 | 4/2005 |
| WO | WO 2006/005100 | 1/2006 |
| WO | WO 2006/083891 | 8/2006 |
| WO | WO 2006/098225 | 9/2006 |
| WO | WO 2006/119457 | 11/2006 |
| WO | WO 2007/027776 | 3/2007 |
| WO | WO 2009/060012 | 5/2009 |
| WO | WO 2009/091557 | 7/2009 |
| WO | WO 2010/080184 | 7/2010 |
| WO | WO 2010/105226 A2 | 9/2010 |
| WO | WO 2011/099019 | 8/2011 |
| WO | WO 2011/099024 | 8/2011 |
| WO | WO 2011/103247 | 8/2011 |
| WO | WO 2011/103248 | 8/2011 |
| WO | WO 2011/154960 | 12/2011 |
| WO | WO 2012/139004 | 10/2012 |
| WO | WO 2012/154651 | 11/2012 |
| WO | WO 2012/174271 | 12/2012 |
| WO | WO 2012/174646 | 12/2012 |
| WO | WO 2013/076687 | 5/2013 |
| WO | WO 2013/132518 | 9/2013 |
| WO | WO 2014/042517 | 3/2014 |
| WO | WO 2014/071182 | 5/2014 |
| WO | WO 2014/201044 | 12/2014 |
| WO | WO 2017/085235 | 11/2015 |
| WO | WO 2016/016629 | 2/2016 |
| WO | WO 2016/016630 | 2/2016 |
| WO | WO 2016/048587 | 3/2016 |
| WO | WO 2016/100727 | 6/2016 |
| WO | WO 2016/146955 | 9/2016 |
| WO | WO 2016/172655 | 10/2016 |
| WO | WO 2016/178580 | 11/2016 |
| WO | WO 2016/179046 | 11/2016 |
| WO | WO 2016/181228 | 11/2016 |
| WO | WO 2016/191828 | 12/2016 |
| WO | WO 2017/011602 | 1/2017 |
| WO | WO 2017/042833 | 3/2017 |
| WO | WO 2017/062412 | 4/2017 |
| WO | WO 2017/069717 | 4/2017 |
| WO | WO 2017/112827 | 6/2017 |
| WO | WO 2017/203440 | 11/2017 |
| WO | WO 2018/081543 | 5/2018 |
| WO | WO 2018/132774 | 7/2018 |
| WO | WO 2018/133774 | 7/2018 |
| WO | WO 2019/032926 | 2/2019 |

(56)　　References Cited

FOREIGN PATENT DOCUMENTS

| WO | WO 2019/084059 | 5/2019 |
| WO | WO 2019/084342 | 5/2019 |
| WO | WO 2019/140125 | 7/2019 |
| WO | WO 2020/006064 | 1/2020 |
| WO | WO 2020/006246 | 1/2020 |
| WO | WO 2020/014498 | 1/2020 |
| WO | WO 2020/023630 | 1/2020 |
| WO | WO 2020/061363 | 3/2020 |
| WO | WO 2020/092940 | 5/2020 |
| WO | WO 2020/118111 | 6/2020 |
| WO | WO 2020/146372 | 7/2020 |
| WO | WO 2020/163251 | 8/2020 |
| WO | WO 2020/190363 | 9/2020 |
| WO | WO 2020/191201 | 9/2020 |
| WO | WO 2020/219893 | 10/2020 |
| WO | WO 2020/219932 | 10/2020 |
| WO | WO 2021/113352 | 6/2021 |
| WO | WO 2021/146209 | 7/2021 |

OTHER PUBLICATIONS

Bhattacharjee, et al. "Use of nitrogen-fixing bacteria as biofertiliser for non-legumes: prospects and challenges." Applied microbiology and biotechnology 80 (2008): 199-209. (Year: 2008).*

Parsons "Physiological Regulation of Nitrogen Fixation in Soybean Root Nodules" The Australian National University (Australia), ProQuest Dissertations Publishing, 1989. 28831644. (Year: 1989).*

Mus et al. (Appl. Environ. Microbiol. 82.13 (2016): 3698-3710). (Year: 2016).*

Buddrus-Schiemann et al. (Microb Ecol (2010) 60:381-393). (Year: 2010).*

Okubo et al. (Microbes Environ. Vol. 29, No. 2, 184-190, 2014). (Year: 2014).*

Gibson (Australian Journal of Biological Sciences 16.1 (1963): 28-42) . (Year: 1963).*

Andersen et al. (Journal of General Microbiology (1977), 103, 107-122). (Year: 1977).*

Berge, et al. (Canadian Journal of Microbiology 37.3 (1991): 195-203). (Year: 1991).*

Muse et al., "The nac (Nitrogen Assimilation Control) Gene from Escherichia coli," Journal of Bacteriology, Mar. 1998, 180(5):1166-1173.

PCT International Preliminary Report on Patentability in International Appln. No. PCT/US2020/029894, dated Nov. 4, 2021, 13 pages.

PCT International Search Report and Written Opinion in International Appln. No. PCT/US2020/029894, mailed Aug. 31, 2020, 19 pages.

Robson et al., "Azotobacter Genomes: The Genome of Azotobacter chroococcum NCIMB 8003 (ATCC 4412)," PLOS ONE, Jun. 2015, 35 pages.

Saleh et al., "Involvement of gacS and rpoS in enhancement of the plant growth-promoting capabilities of Enterobacter cloacae CAL2 and UW4," Canadian Journal of Microbiology, Aug. 2001, 47(8):698-705.

Ausubel, et al. Glutamine Synthetase Mutations Which Affect Expression of Nitrogen Fixation Genes in Klebsiella pneumoniae. J Bacteriol 1979, 140(2):597.606.

Bender, et al. Regulatory mutations in the Klebsiella aerogenes structural gene for glutamine synthetase. J Bacteriol. Oct. 1977, vol. 132, No. 1, pp. 100-105.

PCT International Search Report and Written Opinion in International Appln. No. PCT/2020/29831, dated Nov. 16, 2020, 19 pages.

Aquino et al., "Effect of point mutations on Herbaspirillum seropedicae NifA activity," Brazilian Journal of Medical and Biological Research, Aug. 2015, 48(8):683-690.

Dunican et al., "Genetic transfer of nitrogen fixation from Rhizobium trifolii to Klebsiella aerogenes," Biochemical and Biophysical Research Communications, Mar. 1974, 57(1):62-72.

Invitation to Pay Additional Fees in International Appln. No. PCT/US2022/035873, mailed Sep. 30, 2022, 19 pages.

Paschen et al., "Rhodobacter capsulatus nifA mutants mediating nif gene expression in the presence of ammonium," FEMS Microbiology Letters, Jan. 2001, 207-213.

Rey et al., "Redirection of Metabolism for Biological Hydrogen Production," Applied and Environmental Microbiology, Mar. 2007, 73(5):1665-1671.

Zou et al., "Identification and functional characterization of NifA variants that are independent of GlnB activation in the photosynthetic bacterium Rhodospirillum rubrum," Microbiology, Sep. 2008, 154(9):2689-2699.

Lugtenberg et al., "Molecular Determinants of Rhizosphere Colonization by Pseudomonas," Annu. Rev. Phytopathol., Sep. 2001, 39(1):461-490, 31 pages.

Machado et al., "Excretion of ammonium by Azospirillum brasilense mutants resistant to ethylenediamine," Can. J. Microbiol., Jul. 1991, 37(7): 549-553, 2 pages (Abstract Only).

Pankievicz et al., "Robust biological nitrogen fixation in a model grass-bacterial association," The Plant Journal, 81(6), Mar. 2015, 907-919.

Amalraj et al., "Effect of Polymeric Additives, Adjuvants, Surfactants on Survival, Stability and Plant Growth Promoting Ability of Liquid Bioinoculants," J. Plant Physiol Pathol, 2013, 1:2, 6 pages.

Arriel-Elias et al., "Shelf life enhancement of plant growth promoting rhizobacteria using a simple formulation screening method," African Journal of Microbiology Research, Feb. 2018, 12(5):115-126.

Berninger et al., "Maintenance and assessment of cell viability in formulation of non-sporulating bacterial inoculants," Microb. Biotechnol., Mar. 2018, 11(2):277-301 (2018); doi: 10.1111/1751-7915.12880.

Bloch et al., "Biological nitrogen fixation in maize: optimizing nitrogenase expression in a root-associated diazotroph," Journal of Experimental Botany, Jul. 2020, 71(15):4591-4603.

cera-gmc.org [online], "GM Crop Database," Center for Environmental Risk Assessment (CERA), 2010, retrieved from URL <http://ucbiotech.org/biotech_info/PDFs/Center_for_Environmental_Risk_Assessment_CERA_2011_GM_Crop_Database.pdf>, 1 page.

Colby, "Calculating Synergistic and Antagonistic Responses of Herbicide Combinations," Weeds, Jan. 1967, 15(1):20-22, 4 pages.

Costerton et al., "Microbial Biofilms," Annu. Rev. Microbial., Oct. 1995, 49:711-745.

Da Silva et al., "Survival of endophytic bacteria in polymer-based inoculants and efficiency of their application to sugarcane," Plant Soil, May 2012, 356:231-243.

EP Partial Supplementary European Search Report Appln. No. 19826654.6 dated Mar. 17, 2022, 11 pages.

GenBank Accession No. CP016337.1 "Kosakonia sacchari strain BO-1 chromosome, complete genome," Jul. 11, 2016, 1119 pages.

Hoeschle-Zeledon et al., "Regulatory challenges for biological control," The CGIAR Systemwide Program on Integrated Pest Management, Jan. 2013, SP-IPM Secretariat, International Institute of Tropical Agriculture (IITA), Ibadan, Nigeria, 53 pages.

International Preliminary Report on Patentability in International Appln. No. PCT/US2019/039528, mailed Jan. 7, 2021, 15 pages.

International Preliminary Report on Patentability in International Appln. No. PCT/US2020/029831, mailed Nov. 4, 2021, 8 pages.

International Search Report and Written Opinion in International Appln. No. PCT/US2019/064782, mailed Apr. 16, 2020, 14 pages.

International Search Report and Written Opinion in International Appln. No. PCT/US2020/014083, mailed Jul. 20, 2020, 24 pages.

International Search Report and Written Opinion in International Appln. No. PCT/US2021/029993, mailed Sep. 15, 2021, 12 pages.

International Search Report and Written Opinion in International Appln. No. PCT/US2021/055858, dated Mar. 25, 2022, 12 pages.

Invitation to Pay Additional Fees in International Appln. No. PCT/US2020/014083, mailed May 28, 2020, 20 pages.

Jahn et al., "Extraction of Extracellular Polymeric Substances (EPS) from Biofilms Using a Cation Exchange Resin," Wat. Sci. Tech., 1995, 32(8):157-164.

Kabaluk et al., "The use and regulation of microbial pesticides in representative jurisdictions worldwide," IOBC Global, 2010, 99 pages.

(56)　　　　　References Cited

OTHER PUBLICATIONS

Lowman et al., "Strategies for enhancement of switchgrass (*Panicum virgatum* L.) performance under limited nitrogen supply based on utilization of N-fixing bacterial endophytes," Plant and Soil, Aug. 2016, 405(1):47-63, 17 pages.

Mao et al., "Silencing a cotton bollworm P450 monooxygenase gene by plant-mediated RNAi impairs larval tolerance of gossypol," Nature Biotechnology, Nov. 2007, 25(11): 1307-1313.

Nagy et al., "Nanofibrous solid dosage form of living bacteria prepared by electrospinning," eXPRESS Polymer Letters, 2014, 8(5):352-361.

Nielsen et al., "Conceptual model for production and composition of exopolymers in biofilms," Wat. Sci. Tech., 1997, 36(1): 11-19.

Nielsen et al., "Extraction of EPS," Wingender et al. (eds.), Microbial Extracellular Polymeric Substances, 1999, 24 pages.

Patil et al., "Liquid formulations of Acetobacter diazotrophicus L 1 and Herbaspirillum seropedicae J24 and their field trials on wheat," International Journal of Environmental Science, 2012, 3(3):1116-1129, 4 pages (Abstract Only).

Rakhee et al., "Extracellular polymeric substances of the marine fouling diatom amphora rostrata Wm.Sm," Biofouling, 2001, 17(2):117-127, 12 pages.

Rojas-Tapias et al., "Preservation of Azotobacter chroococcum vegetative cells in dry polymers," Univ. Sci., 2015, 20(2):201-207.

Ryu et al., "Control of nitrogen fixation in bacteria that associate with cereals," Nat. Microbiol., Feb. 2020, 5(2):314-330, 31 pages.

Schuler et al., "Potential side effects of insect-resistant transgenic plants on arthropod natural enemies," Trends Biotechnol., May 1999, 17(5):210-216.

Search Report in AP Appln. No. AP/P/2020/012401, dated Feb. 8, 2022, 4 pages.

Search Report in AP Appln. No. AP/P/2020/012402, dated Feb. 15, 2022, 5 pages.

Wang et al., "Biofilm formation enables free-living nitrogen-fixing rhizobacteria to fix nitrogen under aerobic conditions," The ISME Journal, Jul. 2017, 11:1602-1613.

Wimpenny et al., "Community structure and co-operation in biofilms," 59th Symposium of the Society for General Microbiology, Allison et al. (eds.), Sep. 2000, 23 pages.

Yu et al., "Recombineering Pseudomonas protegens CHA0: An innovative approach that improves nitrogen fixation with impressive bactericidal potency," Microbiological Research, Jan. 2019, 218:58-65.

EP Extended European Search Report in European Appln. No. 18843845.1, dated Jul. 22, 2021, 20 pages.

EP Extended European Search Report in European Appln. No. 18870346.6, dated Jul. 22, 2021, 5 pages.

Kim et al., "A 20 nucleotide upstream element is essential for the nopaline synthase (nos) promoter activity," Plant Mol Biol., Jan. 1994, 24(1):105-17.

Li et al., "Human Enhancers Are Fragile and Prone to Deactivating Mutations," Mol Biol Evol., Aug. 2015, 32(8):2161-80.

Pakula et al., "Genetic analysis of protein stability and function," Annu Rev Genet, 1989, 23:289-310.

PCT International Preliminary Report on Patentability in International Appln. No. PCT/US2019/068152, mailed Jul. 1, 2021, 12 pages.

Singer et al., "Genes and Genomes," Moscow: Mir, 1998, 1:33, 4 pages (with machine translation).

Wang et al., "Roles of poly-3-hydroxybutyrate (PHB) and glycogen in symbiosis of Sinorhizobium meliloti with *Medicago* sp.," Microbiology, Feb. 2007, 153(2):388-398.

Witkowski et al., "Conversion of a β-Ketoacyl synthase to a malonyl decarboxylase by replacement of the active-site cysteine with glutamine," Biochemistry, Sep. 1999, 38(36):11643-50.

Search Report in Russian Appln. No. 2020116764, dated Apr. 28, 2022, 15 pages (with English translation).

Adhikary et al., "Artificial citrate operon confers mineral phosphate solubilization ability to diverse fluorescent pseudomonads," PLoS One, Sep. 2014, 9(9):e107554, 12 pages.

Ambrosio et al., "Metabolic engineering of a diazotrophic bacterium improves ammonium release and biofertilization of plants and microalgae," Metab Eng., Mar. 2017, 40:59-68.

BLAST. Basic local alignment search tool. Available at http://blast.ncbi.nlm.nih.gov/Blast.cgi. Accessed on Oct. 10, 2016.

Dash et al., "Functionalities of Phosphate-Solubilizing Bacteria of Rice Rhizosphere: Techniques and Perspectives," Recent Advances in Applied Microbiology, 2017, 151-163.

EP Extended European Search Report in European Appln, No. 18739050.5, dated Feb. 1, 2021, 22 pages.

Intechopen.com, [online], "*Escherichia coli* as a Model Organism and Its Application in Biotechnology, IntechOpen," 2020, retrieved on Mar. 31, 2020, retrieved from URL<https://www.intechopen.com/books/-i-escherichia-coli-i-recent-advances-on-physiology-pathogenesis-and-biotechnological-applications/-i-escherichi%E2%80%A6>, 15 pages.

Jayaraman et al., "Strain Improvement of Phosphate Solubilizing Fungal Strains," Journal of Ecobiotechnology, Dec. 2010, 2(5):65-70.

Kumar et al., "Establishment of phosphate-solubilizing strains of *Azotobacter chroococcum* in the rhizosphere and their effect on wheat cultivars under green house conditions," Microbiol Res., 2001, 156(1):87-93.

Lenski et al., "Effects of Segregation and Selection on Instability of Plasmid pACYC184 in *Escherichia coli* B," Journal of Bacteriology, Nov. 1987, 169(11):5314-5316.

Liu et al., "Development of an engineered soil bacterium enabling to convert both insoluble inorganic and organic phosphate into plant available phosphate and its use as a biofertilizer," Mol Biotechnol., May 2015, 57(5):419-29.

Miller et al., "Biochemical and genomic comparison of inorganic phosphate solubilization in *Pseudomonas* species," Environ Microbiol Rep., Jun. 2010, 2(3):403-11.

Murphy et al., "A modified single solution method for the determination of phosphate in natural waters," Analytica Chimica Acta, 1962, 27:31-36.

Parts.igem.org, [online], "Registry of Standard Biological Parts," 2017, retrieved on Apr. 8, 2021, retrieved from URL<parts.igem.org/Catalog>, 4 pages.

PCT International Preliminary Report on Patentability in International Appln. No. PCT/US2019/052003, dated Mar. 23, 2021, 10 pages.

PCT International Search Report and Written Opinion in International Appln. No. PCT/US2019/052003, dated Dec. 19, 2019, 15 pages.

Poliner et al., "Nontransgenic Marker-Free Gene Disruption by an Episomal CRISPR System in the Oleaginous Microalga, Nannochloropsis oceanica CCMP1779," ACS Synth. Biol., 2018, 7(4):962-968.

Pyne et al., "Coupling the CRISPR/Cas9 System with Lambda Red Recombineering Enables Simplified Chromosomal Gene Replacement in *Escherichia coli*," Applied and Environmental Microbiology, Aug. 2015, 81(15):5103-5144.

Rajput et al., "Derepression of Mineral Phosphate Solubilization Phenotype by Insertional Inactivation of iclR in Klebsiella pneumoniae," PLoS One, Sep. 2015, 10(9):e0138235, 15 pages.

Ramirez et al., "Burkholderia and Paraburkholderia are Predominant Soybean Rhizobial Genera in Venezuelan Soils in Different Climatic and Topographical Regions," Microbes and Environments, Mar. 2019, 34(1):43-58.

Reyes et al., "Characteristics of phosphate solubilization by an isolate of a tropical Penicillium rugulosum and two UV-induced mutants," FEMS Microbiology Ecology, Mar. 1999, 28(3):291-295.

Rodriguez et al., "Genetics of phosphate solubilization and its potential applications for improving plant growth-promoting bacteria," Plant and Soil, Sep. 2006, 287(1-2):15-21.

Shulse et al., "Engineered Root Bacteria Release Plant-Available Phosphate from Phytate," Appl Environ Microbiol., Aug. 2019, 85(18):e01210-19.

Suzuki et al., "Immune-mediated motor polyneuropathy after hematopoietic stem cell transplantation," Bone Marrow Transplant., Aug. 2007, 40(3):289-91.

(56)                    References Cited

OTHER PUBLICATIONS

Vick et al., "Optimized compatible set of BioBrick™ vectors for metabolic pathway engineering," Appl Microbiol Biotechnol., Dec. 2011, 92(6):1275-86.

Wagh et al., "Heterologous expression of pyrroloquinoline quinone (pqq) gene cluster confers mineral phosphate solubilization ability to Herbaspirillum seropedicae Z67," Appl. Microbiol Biotechnol., Jun. 2014, 98(11):5117-29.

Werra et al., "Role of gluconic acid production in the regulation of biocontrol traits of Pseudomonas fluorescens CHAo," Appl Environ Microbiol., Jun. 2009, 75(12):4162-74.

Xie et al., "Interaction between NifL and NifA in the nitrogen-fixing Pseudomonas stutzeri A1501," Microbiology (Reading), Dec. 2006, 152(Pt 12):3535-3542.

EP Partial Supplementary European Search Report in European Appln. No. 18870036.3, dated Aug. 19, 2021, 19 pages.

Zhang et al., "Mutagenesis and functional characterization of the four domains of GlnD, a bifunctional nitrogen sensor protein," Journal of Bacteriology, Jun. 2010, 192(11):2711-2721.

Extended European Search Report in European Appln. No. 19833252.0, dated Mar. 14, 2022, 7 pages.

Abd-Elhafeez et al., "Isolation and characterization of Enterobacter strains causing potato soft rot disease in Egypt," Minia Science Bulletin, 2018, 29(1):1-13.

Becker et al., "Comparative Genomics Reveal a Flagellar System, a Type VI Secretion System and Plant Growth-Promoting Gene Clusters Unique to the Endophytic Bacterium Kosakonia radicincitans," Front Microbiol., Aug. 2018, 9(1997):1-22.

Berger et al., "Successful Formulation and Application of Plant Growth-Promoting Kosakonia radicincitans in Maize Cultivation," Biomed Res. Int., Mar. 2018, 8 pages.

Berger et al., "The plant growth-promoting bacterium Kosakonia radicincitans improves fruit yield and quality of Solanum lycopersicum," J. Sci. Food Agric., Apr. 2017, 97(14):4865-4871.

Brady et al., "Taxonomic evaluation of the genus Enterobacter based on multilocus sequence analysis (MLSA): Proposal to reclassify E. nimipressuralis and E. amnigenus into Lelliottia gen. nov. as Lelliottia nimipressuralis comb. nov. and Lelliottia amnigena comb. nov., respectively, E. gergovie and E. pyrinus into Pluralibacter gen. nov. as Pluralibacter gergoviae comb. nov. and Pluralibacter pyrinus comb. nov., respectively, E. cowanii, E. radicincitans, E. oryzae and E. arachidis into Kosakonia gen. nov. as Kosakonia cowanii comb. nov., Kosakonia radicincitans comb. nov., Kosakonia oryzae comb. nov. and Kosakonia arachidis comb. nov., respectively, and E. turicensis, E. helveticus and E. pulveris into Cronobacter as Cronobacter zurichensis nom. nov., Cronobacter helveticus comb. nov. and Cronobacter pulveris comb. nov., respectively, and emended description of the genera Enterobacter and Cronobacter," Syst. Appl. Microbiol., Jul. 2013, 36(5):309-319.

Flores-Núñez et al., "Functional Signatures of the Epiphytic Prokaryotic Microbiome of Agaves and Cacti," Front Microbiol., Jan. 2020, 10(3044):1-13.

Gao et al., "Groundwater nitrogen pollution and assessment of its health risks: a case study of a typical village in rural-urban continuum, China," PLoS One, Apr. 2012, 7(4):e33982, 8 pages.

Giri, "The First Report of Indigenous Free-Living Diazotroph Kosakonia sacchari Isolated from Himalayan Alder-Based Shifting Cultivation System in Nagaland, India," Journal of Soil Science and Plant Nutrition, Apr. 2019, 19:574-579.

Gu et al., "Enterobacter xiangfangensis sp. nov., isolated from Chinese traditional sourdough, and reclassification of Enterobacter sacchari Zhu et al. 2013 as Kosakonia sacchari comb. nov.," Int. J. Syst. Evo. Micro., Aug. 2014, 64(Pt8):2650-2656.

Hett, "Bacterial Growth and Cell Division: a Mycobacterial Perspective," Microbiology and Molecular Biology Reviews, Mar. 2008, 72(1):126-156.

Higdon et al., "Genomic characterization of a diazotrophic microbiota associated with maize aerial root mucilage," PLoS ONE, Sep. 2020, 26 pages.

Hosseini-Abari et al., "LC/MS detection of oligogalacturonic acids obtained from tragacanth degradation by pectinase producing bacteria," J Basic Microbiol., Dec. 2018, 59(3):249-255.

Hu et al., "Application of bryophyte rhizoid-associated bacteria increases silicon accumulation and growth in maize (Zea mays L.) seedlings," App. Ecol. Env. Res., Oct. 2019, 17(6):13423-13433.

Kou et al., "Identification of bacterial communities in sediments of Poyang Lake, the largest freshwater lake in China," Springerplus, Apr. 2016, 5(401):1-9.

Lauber et al., "Pyrosequencing-based assessment of soil pH as a predictor of soil bacterial community structure at the continental scale," Appl. Environ. Microbiol., Aug. 2009, 75(15):5111-5120.

Lindstrom et al., "Distribution of typical freshwater bacterial groups is associated with pH, temperature, and lake water retention time," Appl. Environ. Microbiol., Dec. 2005, 71(12):8201-8206.

Lindstrom, "Investigating Influential Factors on Bacterioplankton Community Composition: Results from a Field Study of Five Mesotrophic Lakes," Microbial Eco., Nov. 2001, 42(4):598-605.

Meng et al., "Draft Genome Sequence of Rice Endophyte-Associated Isolate Kosakonia oryzae KO348," Genome Announc., Jun. 2015, 3(3):e00594-15, 1 page.

Mosquito et al. "In Planta Colonization and Role of T6SS in Two Rice Kosakonia Endophytes," Molecular Plant-Microbe Interactions, Feb. 2020, 33(2):349-363.

Newton et al., "A Guide to the Natural History of Freshwater Lake Bacteria," Microbiol Mol. Biol. Rev., Mar. 2011, 75(1):14-49.

O'Brien et al., "Soil Salinity and pH Drive Soil Bacterial Community Composition and Diversity Along a Lateritic Slope in the Avon River Critical Zone Observatory, Western Australia," Front. Microbiol., Jul. 2019, 10(1486):1-20.

PreNewsWire.com [online], "Global Agricultural Inoculants Market Research Report—Industry Analysis, Size, Share, Growth, Trends and Forecast 2015-2022," Dec. 2016, retrieved on Mar. 24, 2023, retrieved from URL <https://www.prnewswire.com/news-releases/global-agricultural-inoculants-market-research-report---industry-analysis-size-share-growth-trends-and-forecast-2015---2022-300375864.html>, 4 pages.

Rivarez et al., "Defense Biopriming and Antimicrobial Activity of Endophytic Bacteria and Associated Bacillus Species Contribute to Bacterial Crown Rot Tolerance in Papaya," bioRxic, Dec. 2019, 24 pages.

Shahid et al., "Colonization of Vigna radiata by a halotolerant bacterium Kosakonia sacchari improves the ionic balance, stressor metabolites, antioxidant status and yield under NaCl stress," Appl. Soil Ecol., Feb. 2021, 158:1-14.

Shinjo et al., "Complete Genome Sequence of Kosakonia sacchari Strain BO-1, an Endophytic Diazotroph Isolated from a Sweet Potato," Genome Announcements, ASM., Sep. 2016, 4(5):e00868-16, 2 pages.

Tian et al., "Six New Families of Aerobic Arsenate Reducing Bacteria: Leclercia, Raoultella, Kosakonia, Lelliottia, Yokenella, and Kluyvera," Geomicrobiology Journal, Feb. 2019, 36(4):339-347.

Troisfontaines et al., "Type III Secretion: More Systems Than You Think," Physiology, Oct. 2005, 20:326-339.

Tyler et al., "Plants as a Habitat for Beneficial and/or Human Pathogenic Bacteria," Annu. Rev. Phytopathol., 2008, 46:53-73.

Wang et al., "Emergence of a novel mobile colistin resistance gene, mcr-8, in NDM-producing Klebsiella pneumoniae," Emerging Microbes & Infections, Jul. 2018, 7(1):1-9.

Wang et al., "High throughput sequencing analysis of bacterial communities in soils of a typical Poyang Lake wetland," Acta Ecologica Sinica, 2017, 37(5), 9 pages, English Abstract.

Wang et al., "Kosakonia quasisacchari sp. nov. recovered from human wound secretion in China," Int. J. Syst. Evol. Microbio., Oct. 2019, 69(10):3155-3160.

Wang et al., "Positive and negative regulation of transferred nif genes mediated by indigenous GlnR in Gram-positive Paenibacillus polymyxa," PLOS Genetics, Sep. 2018, 14(9):e1007629.

Wang et al., Screening, Identification and Growth Promotion Ability of Phosphate Solubilizing Bacteria from Soybean Rhizosphere under Maize-Soybean Intercropping Systems., bioRxiv, Dec. 2020, 25 pages.

(56) References Cited

OTHER PUBLICATIONS

Wu et al., "Effects of different amendments on contents of phenolic acids and specific microbes in rhizosphere of *Pseudostellaria heterophylla*," Ying Yong Sheng Tai Xue Bao, Nov. 2016, 18(27):3623-3630, English Abstract.

Wu et al., "Insights into the Mechanism of Proliferation on the Special Microbes Mediated by Phenolic Acids in the *Radix pseudostellariae* Rhizosphere under Continuous Monoculture Regimes," Front. Plant. Sci., May 2017, 8(659):1-15.

Wu et al., "Mixed Phenolic Acids Mediated Proliferation of Pathogens *Talaromyces helices* and Kosakonia sacchari in Continuously Monocultured *Radix pseudostellariae* Rhizosphere Soil," Frontiers in Microbiology, Mar. 2016, 7(335):1-14.

Wu et al., "The role of organic acids on microbial deterioration in the *Radix pseudostellariae* rhizosphere under continuous monoculture regimes," Sci. Rep., Jun. 2017, 7(1):1-13.

Yan et al., "Influence of salinity and water content on soil microorganisms," Int. Soil Water Conserv. Res., 2015, 3:316-323.

Zaller, "Editorial: Non-target Effects of Pesticides on Organisms Inhabiting Agroecosystems," Enviorn. Sci., May 2019, 7(75):1-3.

Zhao et al., "Soil bacterial community composition in rice-fish integrated farming systems with different planting years," Sci. Rep., 2021, 11(1):10855, 10 pages.

Zhu et al., "Genome sequence of *Enterobacter* sp. strain SP1, an endophytic nitrogen-fixing bacterium isolated from sugarcane," J. Bacteriol., Dec. 2012, 194(24):6963-6964.

Zhu et al., "*Enterobacter sacchari* sp. nov., a nitrogen-fixing bacterium associated with sugar cane (*Saccharum officinarum* L.)," International Journal of Systematic and Evolutionary Microbiology, 2013, 63(Pt7):2577-2582.

Baum et al., "Control of coleopteran insect pests through RNA interference," Nature Biotechnology, Nov. 2007, 25(11):1322-1326.

Bosmans et al., "Sea anemone venom as a source of insecticidal peptides acting on voltage-gated Na+ channels," Toxicon, Mar. 2007, 49(4):550-560.

Chakroun et al., "Bacterial Vegetative Insecticidal Proteins (Vip) from Entomopathogenic Bacteria," Microbiol Mol Biol Rev., Mar. 2016, 80(2):329-50.

Compant et al., "A review on the plant microbiome: Ecology, functions, and emerging trends in microbial application," Journal of Advanced Research, Sep. 2019, 19:29-37.

Crickmore et al., "Revision of the Nomenclature for the Bacillus thuringiensis Pesticidal Crystal Proteins," Microbiol Mol Biol Rev., Sep. 1998, 62(3):807-813.

EP Partial Supplementary European Search Report in European Appln. No. 18843845.1, dated Apr. 12, 2021, 17 pages.

Eyraud et al., "Expression and Biological Activity of the Cystine Knot Bioinsecticide PA1b (Pea Albumin 1 Subunit b)," PLOS One, Dec. 2013, 8(12):e81619, 9 pages.

Forner et al., "Treatment of hepatocellular carcinoma," Crit Rev Oncol Hematol., Nov. 2006, 60(2):89-98.

Janczarek et al., "Multiple copies of rosR and pssA genes enhance exopolysaccharide production, symbiotic competitiveness and clover nodulation in Rhizobium leguminosarum bv. *trifolii*," Antonie Van Leeuwenhoek, Nov. 2009, 96(4):471-86.

King et al., "Spider-Venom Peptides: Structure, Pharmacology, and Potential for Control of Insect Pests," Annu. Rev. Entomol., 2013, 58:475-96.

Lifesci.sussex.ac.uk, [online], "Bacillus thuringiensis Toxin Nomenclature," 2016, retrieved on Mar. 25, 2021, retrieved from URL<www.lifesci.sussex.ac.uk/home/Neil_Crickmore/Bt/> 1 page.

Lin et al., "PC, a Novel Oral Insecticidal Toxin from Bacillus bombysepticus Involved in Host Lethality via APN and BtR-175," Scientific Reports, Jun. 2015, 5:11101, 14 pages.

Martinelli et al., "Structure-function studies on jaburetox, a recombinant insecticidal peptide derived from jack bean (*Canavalia ensiformis*) urease," Biochimica et Biophysica Acta, Mar. 2014, 1840(3):935-44.

Naimov et al., "Solubilization, Activation, and Insecticidal Activity of Bacillus thuringiensis Serovar thompsoni HDS42 Crystal Proteins," Applied and Environmental Microbiology, Dec. 2008, 74(23):7145-7151.

Nature.com, [online], "Transcription Unit," 2005, retrieved on Apr. 15, 2021, retrieved from URL<https://www.nature.com/scitable/definition/transcription-unit-260>, 2 pages.

Parker et al., "Pore-forming protein toxins: from structure to function," Progress in Biophysics & Molecular Biology, 2005, 88:91-142.

PCT International Preliminary Report on Patentability in International Appln. No. PCT/US2019/041429, dated Jan. 12, 2021, 11 pages.

PCT International Search Report and Written Opinion in International Appl. No. PCT/US2019/039528, dated Nov. 6, 2019, 19 pages.

PCT International Search Report and Written Opinion in International Appln. No. PCT/US2018/057613, dated March 5. 2019, 11 pages.

PCT Written Opinion in International Appln. No. PCT/US2018/057174, dated Jan. 4, 2019, 3 pages.

Purcell et al., "Cholesterol oxidase: a potent insecticidal protein active against boll weevil larvae," Biochem Biophys Res Commun, Nov. 1993, 196(3):1406-13.

Qaim et al., "Yield Effects of Genetically Modified Crops in Developing Countries," Science, Feb. 2003, 299(5608):900-2.

Robledo et al., "Rhizobium cellulase CelC2 is essential for primary symbiotic infection of legume host roots," Proc Natl Acad Sci USA, May 2008, 105(19):7064-9.

Robledo et al., "Role of Rhizobium endoglucanase CelC2 in cellulose biosynthesis and biofilm formation on plant roots and abiotic surfaces," Microb Cell Fact., Sep. 2012, 11:125, 12 pages.

Sanahuja et al., "Bacillus thuringiensis: a century of research, development and commercial applications," Plant Biotechnology Journal, Apr. 2011, 9(3):283-300.

Sanyal et al., "The etiology of hepatocellular carcinoma and consequences for treatment," Oncologist, 2010, 15(Suppl 4):14-22.

Schuler et al., "Insect-resistant transgenic plants," Trends in Biotechnology, Apr. 1998, 16(4):168-175.

Tijssen, "Laboratory Techniques In Biochemistry And Molecular Biology," Elsevier, 1993, 24:65 pages.

Woolbright et al., "Novel insight into mechanisms of cholestatic liver injury," World J Gastroenterol., Sep. 2012, 18(36):4985-93.

Associative and Endophytic Nitrogen-fixing Bacteria and Cyanobacterial Association, C. Elmerich and W. E. Newton (eds.), 2007, Chapter 3, 31 pages.

Doroshchuk et al., "Regulation of nitrogen metabolism in grampositive bacteria," Molecular Biology, 2006, 40(5):829-836.

Leigh et al., "Nitrogen Regulation in Bacteria and Archaea," Annual Review of Microbiology, 2007, 61(10):349-377.

Terpolilli et al., "What Determines the Efficiency of $N_2$-Fixing Rhizobium-Legume Symbioses?," Advances in Microbial Physiology, 2012, 60:325-389.

Travis et al., "Molecular dissection of the glutamine synthetase-GlnR nitrogen regulatory circuitry in Gram-positive bacteria," Nature Communications, Jul. 2022, 13(3793), 15 pages.

Duca et al., "Indole-3-acetic acid in plant-microbe interactions," Antonie van Leeuwenhoek, Jan. 2014, 106(1):85-125, 41 pages.

Extended European Search Report in European Appln. No. 19826654.6, dated Jul. 4, 2022, 16 pages.

Schluter et al., "Global mapping of transcription start sites and promoter motifs in the symbiotic α-proteobacterium *Sinorhizobium meliloti*," BMC Genomics, Mar. 2013, 14(1):156, 21 pages.

Bittner et al., "RpoS and RpoN are involved in the growth-dependent regulation of rfaH transcription and O antigen expression in *Salmonella enterica* serovar typhi," Microbial Pathogenesis, Jan. 2004, 36(1):19-24.

Extended European Search Report in European Appln. No. 18870036.3, dated Dec. 14, 2021, 28 pages.

Katsnelson, "Engineered bacteria could boost corn yields: Gene-edited microbe offer continuous nitrogen fixation," Chemical &

(56)        References Cited

OTHER PUBLICATIONS

Engineering News, Dec. 28, 2021, retrieved from URL <https://cen.acs.org/food/agriculture/Engineered-bacteria-boost-corn-yields/99/web/2021/12>, 3 pages.

Kumar et al., "Metabolic regulation of *Escherichia coli* and its gdhA, glnL, gltB, D mutants under different carbon and nitrogen limitations in the continuous culture," Microbial Cell Factories, Jan. 2010, 9(8):1-17.

Liu et al., "Phenazine-1-carboxylic acid biosynthesis in Pseudomonas Chlororaphis GP72 is positively regulated by the sigma factor RpoN," World Journal of Microbiology and Biotechnology, Jan. 2008, 24(9):1961-1966.

Wen et al., "Enabling Biological Nitrogen Fixation for Cereal Crops in Fertilized Fields," ACS Synth. Biol., Dec. 2021, 10(12):3264-3277.

Wu et al., "Effects of biofertilizer containing N-fixer, P and K solubilizers and AM fungi on maize growth: a greenhouse trial," Geodernna, Mar. 2005, 125(1-2):155-166.

Yan et al., "Global transcriptional analysis of nitrogen fixation and ammonium repression in root-associated Pseudomonas stutzeri A1501," BMC Genomics, Jan. 2010, 11(11):1-13.

Yao et al., "Complementation analysis of heterologous nifA genes to nifA mutants of Sinorhizobium pallida," Chinese Science Bulletin, Oct. 2006, 51(19):2258-2264, 2 pages (English abstract only).

Zhang et al., "Mutagenesis and Functional Characterization of the glnB, glnA, and nifA Genes from the Photosynthetic Bacterium Rhodospirillum rubrum," Journal of Bacteriology, Feb. 2000, 182(4):983-992.

"New Plant Breeding Techniques," Science Council of Japan, retrieved from URL <http://www.scj.go.jp/ja/info/kohyo/pdf/kohyo-22-h140826.pdf>, Aug. 26, 2014, 82 pages (partial English translation).

"T7 RNA Polymerase Expression System for Bacillus megaterium"; T7 RNAP Expression System Handbook, Jan. 2010, © MoBiTec GmbH, 18 pages.

40 CFR 725.3 U.S. Government Publishing Office (Jul. 1, 2010) https://www.gpo.gov/fdsys/pkg/CFR-2010-title40-vol30/pdf/CFR-2010-title40-vol30-sec725-3.pdf (Year: 2010).

Aita, T., Husimi, Y. Adaptive walks by the fittest among finite random mutants on a Mt. Fugi-type fitness landscape. J. Theor. Biol. 193:383-405 (1998).

Alper et al., "Tuning genetic control through promoter engineering," Proc Natl Acad Sci U SA, 2005, 102(36):12678-12683.

Altschul et al. "Basic local alignment search tool," J Mol Biol., 1990, 215(3):403-441.

Altschul et al., "Gapped BLAST and PSI-BLAST: a new generation of protein database search programs," Nucleic Acids Res., 1997, 25:3389-3402.

An et al., "Constitutive expression of the nifA gene activates associative nitrogen fixation of Enterobacter gergoviae 57-7, an opportunistic endophytic diazotroph," Journal of Applied Microbiology, 2007, 103(3):613-620.

Andersen et al. "Herpesvirus-mediated gene delivery into the rat brain: specificity and efficiency of the neuron-specific enolase promoter," Cell. Mol. Neurobiol., 1993, 13:503-515.

Anderson, J.C., et al. "BglBricks: A flexible standard for biological part assembly," Journal of Biological Engineering, 2010, 4:1, 12 pages.

Andrews et al. Use of Nitrogen Fixing Bacteria Inoculants as a Substitute for Nitrogen Fertiliser for Dryland Graminaceous Crops: Progress Made, Mechanisms of Action and Future Potential. Symbiosis 34 (2003). 21 pages.

Andrianantoandro E, et al., "Synthetic biology: new engineering rules for an emerging discipline," Mol Syst Biol 2:2006.0028 (2006).

Arbuthnot et al. "In vitro and in vivo hepatoma cell-specific expression of a gene transferred with an adenoviral vector," Hum Gene Ther., 1996, 7(13):1503-1514.

Arnold et al., (1988) Nucleotide sequence of a 24,206-base-pair DNA fragment carrying the entire nitrogen fixation gene cluster of Klebsiella pneumoniae. J Mol Biol 203(3):715-738.

Arsene et al., "Modulation of NifA activity by PII in Azospirillum brasilense: Evidence for a Regulatory role of the NifA N-Terminal Domain," Journal of Bacteriology, Aug. 1996, 178(16):4830-4838.

Austin et al. "Characterisation of the Klebsiella pneumoniae nitrogen-fixation regulatory proteins NIFA and NIFL in vitro," Eur J Biochem., 1990, 187(2):353-360.

Bageshwar, et al. An Environmentally Friendly Engineered Azotobacter Strain That Replaces a Substantial Amount of Urea Fertilizer while Sustaining the Same Wheat Yield. Appl Environ Microbial. Aug. 1, 2017; 83(15): e00590-17.

Bali et al., "Excretion of Ammonium by a nifL Mutant of Azotobacter vinelandii fixing Nitrogen." Applied and Environmental Microbiology, May 1992, 58(5):1711-1718.

Barney et al., "Gene deletions resulting in increased nitrogen release by azotobacter vinelandii: application of a novel nitrogen biosensor." Appl. Environ. Microbial. Jul. 2015, 81(13):4316-4328.

Barney et al., "Transcriptional analysis of an Ammonium-excreting stain of azotobacter vinelandii deregulated for nitrogen fixation." Appl. Environ. Microbial. Jul. 2017, 83(20):1-22.

Barrangou et al., "Exploiting CRISPR-Cas immune systems for genome editing in bacteria." Curr. Opin. Biotechnol. Nov. 2016, 37:61-68.

Batista et al. "Manipulating nitrogen regulation in diazotrophic bacteria for agronomic benefit." Biochem Soc Trans., 2019, 47(2):603-614.

Batzer et al., "Enhanced evolutionary PCR using oligonucleotides with inosine at the 3'-termins," Nucleic Acid Res. 19: 5081 (1991).

Bayer TS, et al. (2009) Synthesis of Methyl Halides from Biomass Using Engineered Microbes. J Am Chem Soc 131 (18):6508-6515.

Beringer et al., "Genetic engineering and nitrogen fixation." Biotech. Gen. Eng. Rev. Feb. 1984, 1(1):65-88.

Beynon J, Cannon M, Buchanan-Wollaston V, & Cannon F (1983) The nifpromoters of Klebsiella pneumoniae have a characteristic primary structure. Cell 34(2):665-671.

Biggins JB, Liu, X., Feng, Z., Brady, S.F. (2011) Metabolites from the induced expression of crypic single operons found in the genome of Burkolderia pseudomallei. JACS 133:1638-1641.

Bikard et al., "The synthetic integron: an in vivo genetic shuffling device," Nucleic Acids Res., 2010, 38(15):e153.

Bilitchenko et al., Eugene—a domain specific language for specifying and constraining synthetic biological parts, devices, and systems. PLoS One. Apr. 29, 2011;6(4):e18882.

Blanco et al., "Sequence and molecular analysis of the nifL gene of Azotobacter vine landii." Mol Microbial. Aug. 1993, 9(4):869-79.

BLAST. Basic local alignment search tool. Available at http://blast.nebi.nlm.nih.gov/Blast.cgi. Accessed on Oct. 10, 2016.

Bonde et al., "MODEST: a web-based design tool for oligonucleotide-mediated genome engineering and recombineering," Nucleic Acids Res., 2014, 42(W1):W408-W415.

Boshart et al. "A very strong enhancer is located upstream of an immediate early gene of human cytomegalovirus," Cell, 1985, 41(2):521-30.

Bosworth, et al. "Alfalfa yield response to inoculation with recombinant strains of Rhizobium meliloti with an extra copy of detABD and/or modified nifA expression." Appl Environ Microbial. Oct. 1994, 60(10):3815-32.

Boyle et al. "Tools for genome-wide strain design and construction," Curr Opin Biotechnol., 2012, 23(5):666-671. doi: 10.1016/j.copbio.2012.01.012.

Brandl et al., "*Salmonella* interactions with plants and their associated microbiota," Phytopathology, 2013, 103:316-325.

Brewin et al., "The Basis of Ammonium release in nifL Mutants of Azotobacter vinelandii." Journal of Bacteriology, Dec. 1999, 181(23):7356-7362.

Buchanan-Wollaston, et al. Role of the nifA gene product in the regulation of nif expression in Klebsiella pneumoniae. Nature. Dec. 24, 1981;294(5843):776-8.

Buck M & Cannon W (1987) Frameshifts close to the Klebsiella pneumoniae nifH promoter prevent multicopy inhibition by hybrid nifH plasmids. Mal Gen Genet 207(2-3):492-498.

(56) References Cited

OTHER PUBLICATIONS

Buckley Lab NifH database, retrieved via WayBack Machine from URL <http://www.css.cornell.edu/faculty/buckley/nifh.htm>, available on or before Jan. 10, 2018, 2 pages.

Buddrus-Schiemann et al., "Root colonization by *Pseudomonas* sp. DSMZ 13134 and impact on the indigenous rhizosphere bacterial community of barley." Microb Ecol. Aug. 2010, 60(2):381-393.

Burris et al., "Nitrogenases," J Biol Chem., 266(15):9339-9342.

Cardinale, S., & Arkin, A.P. Contextualizing context for synthetic biology identifying causes of failure of synthetic biological systems. Biotechnol. J. 7:856-866 (2012).

Carr et al., "Enhanced multiplex genome engineering through co-operative oligonucleotide coselection," Nucleic Acids Res., 2012, 40(17):e132.

cerestrust.org [online]. "Year-end Final Report" Young et al., Ceres Trust, retreieved from URL <https://cerestrust.org/wpcontent/uploads/NitrogenFixingBacteriaCorn.pdf>. 2012, 9 pages.

Chan et al., "Refactoring bacteriophage T7," Molecular Systems Biology, 2005, 1(1):E1-E10.

Chen et al., "Complete genome sequence of Kosakonia sacchari type strain SPIT." Stand Genomic Sci., Jun. 15, 2014, 9(3):1311-1318.

Chen, et al. "Expression of rat bone sialoprotein promoter in transgenic mice." J Bone Miner Res., May 1996, 11(5):654-64.

Chen, Y.J., et al. Characterization of 582 natural and synthetic terminators and quantification of their design constraints. Nat. Methods, 2013, 10:659-664.

Chiang et al., "Mutagenic Oligonucleotide-directed PCR Amplification (Mod-PCR): An Efficient Method for Generating Random Base Substitution Mutations in a DNA sequence element." PCR methods and applications. 1993, 2:210-217.

Chin JW "Programming and engineering biological networks," Curr Opin Struct Biol 16: 551-556 (2006).

Choi, et al. A Th7-based broad-range bacterial cloning and expression system. Nat Methods. Jun. 2005;2(6):443-8.

Choudhary, et al. Interactions of *Bacillus* spp. and Plants—With Special Reference to Induced Systemic Resistance (ISR). Microbiological Research. 2009, vol. 164, No. 5; pp. 493-513.

Clancy et al., "The domains carrying the opposing activities in adenylyltransferase are separated by a central regulatory domain." FEBS Journal, 2007, 274(11):2865-2877.

Cobb et al., Directed evolution: an evolving and enabling synthetic biology tool. Curr Opin Chem Biol. Aug. 2012:16(3-4):285-91.

Cohen, "In vitro Tomato Fruit Cultures Demonstrate a Role for Indole-3-acetic Acid in Regulating Fruit Ripening." J. Amer. Soc. Hort. Sci. 1996 121 (3):520-524.

Colebatch et al. "Symbiotic nitrogen fixation research in the postgenomics era," New Phytologist., 2002, 153(1):37-42 doi:10.1046/j.0028-646X.2001.00304.x.

Colnaghi et al., "Strategies for increased ammonium production in free-living or plant associated nitrogen fixing bacteria." Plant and Soil, Nov. 1997, 194:145-154.

Colnaghi, et al. Lethality of glnD null mutations in Azotobacter vinelandii is suppressible by prevention of glutamine synthetase adenylylation. Microbiology. May 2001;147(Pt 5):1267-76.

Conniff, "Microbes Help Grow Better Crops." (Sep. 1, 2013) Scientific American. Reteived from URL <https://www.scientificamerican.com/article/microbes-helpgrow-better-crops/>. (Year: 2013).

Contreras et al., "The product of the nitrogen fixation regulatory gene nfrX of Azotobacter vinelandii is functionally and structurally homologous to the uridylyltransferase encoded by glnD in enteric bacteria." J Bacterial. Dec. 1991, 173(24):7741-7749.

Cornelis et al., "The type III secretion injectisome," Nature Reviews Mocrobilogy, 2006, 4(11):811-825.

Crameri, A., Dawes, G., Rodriguez Jr., E., Silver, S., & Stemmer, W.P.C. Molecular evolution of an arsenate detoxification pathway by DNA shuffling. Nat. Biotechnol. 15:436-438 (1997).

Crook, N.C., Freeman, E.S., & Alper, H.S. Re-engineering multicloning sites for function and convenience. Nucl. Acids Res. 39:e92, 2011.

Curatti et al., "Genes required for rapid expression of nitrogenase activity in Azotobacter vinelandii." PNAS May 2005; 102(18):6291-6296.

Czar MJ, Anderson JC, Bader JS, & Peccoud J (2009) Gene synthesis demystified. Trends Biotechnol 27(2):63-72.

Dandekar, T., Snel, B., Huynen, M., & Bork, P. Conservation of gene order: a fingerprint of proteins that physically interact. Trends Biochem. Sci. 23:324-328 (1998).

Datsenko et al., "One-step inactivation of chromosomal genes in *Escherichia coli* K-12 using PCR products." PNAS, Jun. 2000, 97(12):6640-6645.

De Raad, M., Kooijmans, S.A.A., Teunissen, E.A., & Mastrobattista, E. A solid-phase platform for combinatorial and scarless multipart gene assembly. ACS Synth. Biol. 2:316-326 (2013).

DeBruijn et al., "The Cloning and characterization of the glnF (ntrA) Gene of Klebsiella pneumoniae: Role of glnF (ntrA) in the Regulation of Nitrogen Fixation (nif) and other Nitrogen assimilation genes." Mol. Genet. Aug. 1983; 192:342-353.

Delaux et al., "Tracing the evolutionary path to nitrogen-fixing crops." Curr. Opin. Plant Biol. Jun. 2015, 26:95-99.

Dent et al., "Establishing symbiotic nitrogen fixation in cereals and other non-legume crops: The greener nitrogen revolution." Agric & Food Secur, Dec. 2017, 6(7):1-9.

Desnoues et al., "Nitrogen fixation genetics and regulation in a Pseudomonas stutzeri strain associated with rice." Microbiology, May 2003; 149:2251-2262.

Dixon et al., Genetic regulation of biological nitrogen fixation. Nature Reviews, Aug. 2004, 2:621-631.

Dixon RA & Postgate JR (1972) Genetic transfer of nitrogen fixation from Klebsiella pneumoniae to *Escherichia coli*. Nature 237(5350):102-103.

Dong, et al. Kinetics and Strain Specificity of Rhizosphere and Endophytic Colonization by Enteric Bacteria on Seedlings of *Medicago sativa* and *Medicago truncatula*. Appl Environ Microbial. Mar. 2003; 69(3): 1783-1790.

Dos Santos, et al., "Distribution of nitrogen fixation and nitrogenase-like sequences amongst microbial genomes." BMC Genomics, Dec. 2012, 13(1):162, 12 pages.

Du et al., Customized optimization of metabolic pathways by combinatorial transcriptional engineering. Nucleic Acids Res. Oct. 2012:40(18):e142.

Dykxhoorn et al., (1996) A set of compatible tac promoter expression vectors. Gene 177(1-2):133-136.

Easter, et al., "Role of the parCBA Operon of the Broad-Host-Range Plasmid RK2 in Stable Plasmid Maintenance," Journal Of Bacteriology, 1998, 180(22):6023-6030.

Egener et al., "Identification of NifL-like protein in a diazotroph of the b-subgroup of the proteobacteria, *azoarcus* sp. strain BH72," Microbiology, Oct. 2002, 148(10):3203-3212.

Emboss. Emboss Needle: Pairwise Sequence Alignment (Nucleotide). Available at http://www.ebi.ac.uk/Tools/psa/emboss_needle/nucleotide.html. Accessed on Oct. 10, 2016.

Emboss. Emboss Water: Pairwise Sequence Alignment (Nucleotide). Available at http://www.ebi.ac.uk/Tools/psa/emboss_water/nucleotide.html. Accessed on Oct. 10, 2016.

Endy et al., "Foundations for engineering biology," Nature, 2005, 438:449-453.

Engler, et al. "A one pot, one step, precision cloning method with high throughput capability," PLoS One, 2008;3(11):e3647.

Engler, et al. "Golden gate shuffling: a one-pot DNA shuffling method based on type lls restriction enzymes," PLoS One. 2009;4(5):e5553.

Enkh-Amgalan, et al., "Molecular evolution of the nif gene cluster carrying nifl1 and nifl2 genes in the Gram-positive phototrophic bacterium Heliobacterium chlorum," International Journal of Systematic and Evolutionary Microbiology, 2006, 56:65-74.

EP Extended European Search Report in European Appln. No. 12800054.4, mailed Dec. 19, 2014, 8 pages.

EP Extended European Search Report in European Appln. No. 16825147.8, dated Jun. 6, 2019, 19 pages.

(56)                References Cited

OTHER PUBLICATIONS

EP Extended European Search Report in European Appln. No. 16854192.8, dated Feb. 20, 2019, 11 pages.
EP Extended European Search Report in European Appln. No. 19186353.9, dated Nov. 13, 2019. 9 pages.
EP Partial Supplementary European Search Report Appln. No. 16825147.8 dated Mar. 4, 2019, 21 pages.
Estrem, et al., "Identification of an UP element consensus sequence for bacterial promoters," PNAS, 95 (11):9761-9766 (1998).
Fani et al., "Molecular evolution of nitrogen fixation: the evolutionary history of the niID, nifK, nifE, and nifN gene," J Mo/ Evol., 2000, 51 ( 1 ): 1-11.
Feher, et al. In the fast lane: large-scale bacterial genome engineering. J Biotechnol. Jul. 31, 2012 :160(1-2):72-9.
Ferrieres, et al. The yjbEFGH locus in *Escherichia coli* K-12 is an operon encoding proteins involved in exopolysaccharide production. Microbiology. Apr. 2007;153(Pt 4):1070-80.
Fischbach et al., "Prokaryotic gene clusters: A rich toolbox for synthetic biology," Biotechnology Journal, 2010, 15(12): 1277-1296.
Fischbach, et al., The evolution of gene collectives: how natural selection drives chemical innovation. Proc. Natl. Acad. Sci. USA 105:4601-4608 (2008).
Fontana, et al., RNA folding and combinatory landscapes. Phys. Rev. E. 47:2083-2099 (1993).
Fox et al., "Major cereal crops benefit from biological nitrogen fixation when inoculated with the nitrogen-fixing bacterium Pseudomonas protegens Pf-5 X940." Environmental Microbiology, 2016, 18(10):3522-3534.
Frasch et al., Design-based re-engineering of biosynthetic gene clusters: plug-and-play in practice. Curr Opin Biotechnol. Dec. 2013:24(6):1144-50.
Gaby and Buckley, "A comprehensive aligned nifH gene database: a multipurpose tool for studies of nitrogen-fixing bacteria." Database 2014 (2014): bau001.
Gamer, et al. A T7 RNA polymerase-dependent gene expression system for Bacillus megaterium. Appl Micro biol Biotechnol. Apr. 2009;82(6) :1195-203.
Gebeyehu, G., et al., "Novel biotinylated nucleotide-analogs for labeling and colorimetric detection of DNA," Nucl. Acids Res. 15:4513 (1987).
Geddes et al., "Use of plant colonizing bacteria as chassis for transfer of N2-fixation to cereals." Curr. Opin. Biotechnol. 2015, 32:216-222.
Georg J & Hess WR (2011) cis-antisense RNA, another level of gene regulation in bacteria. Microbiol Mol Biol Rev 75(2):286-300.
Gibson DG, et al. (2009) Enzymatic assembly of DNA molecules up to several hundred kilobases. Nat Methods 6(5):343-345.
Gibson, "Physical Environment and Symbiotic Nitrogen Fixation." Australian Journal of Biological Sciences. 1963, 16(1):28-42.
Gibson, et al., Chemical synthesis of the mouse mitochondrial genome. Nat. Methods 7, 901-903 (2010).
Gosink, Franklin and Roberts, The product of the Klebsiella pneumoniae nifX gene is a negative regulator of the nitrogen fixation (nit) regulon, J Bacteriology, 1990, 172(3):1441-1447.
Gossen et al. Tight control of gene expression in mammalian cells by tetracycline-responsive promoters. PNAS USA89.12 (1992): 5547-5551.
Gossen et al. Transcriptional activation by tetracyclines in mammalian cells. Science 268(5218):1766-1769 (1995).
Gottelt et al., (2010) Deletion of a regulatory gene within the cpk gene cluster reveals novel antibacterial activity in *Streptomyces coelicolor* A3(2). Microbiology 156:2343-2353.
Govantes et al., "Mechanism of coordinated synthesis of the antagonistic regulatory proteins NifL and NifA of Klebsiella pneumoniae." J Bacterial. Dec. 1996, 178(23):6817-6823.
Guell et al., (2011) Bacterial transcriptomics: what is beyond the RNA horiz-ome? Nature reviews. Microbiology 9(9):658-669.
Guell, M., et al. Transcriptome complexity in a genome-reduced bacterium. Science 326: 1268-1271 (2009).

Guo et al., Discovery of Reactive Microbiota-Derived Metabolites that Inhibit Host Proteases. Cell. Jan. 26, 2017;168(3):517-526.e18.
Haapalainen, et al., Soluble plant cell signals induce the expression of the type Ill secretion system of Pseudomonas syringae and upregulate the production of pilus protein Hrp.A. Mol. Plant Microbe Interact. 22, 282-290 (2009).
Hale et al., "An efficient stress-free strategy to displace stable bacterial plasmids." BioTechniques, Mar. 2010, 48:223-228.
Hansal, et al. Cutting Edge: Induction of antigen-specific hyporesponsiveness by transplantation of hemopoietic cells containing an MHC class I transgene regulated by a lymphocyte-specific promoter. J Immunol. Aug. 1, 1998 ;161(3):1063-8.
Harvey, et al. Inducible control of gene expression: prospects for gene therapy. Curr Opin Chem Biol. Aug. 1998:2(4):512-8.
Herlache, et al. Characterization of the Agrobacterium vitis pehA gene and comparison of the encoded polygalacturonase with the homologous enzymes from Erwinia carotovora and Ralstonia solanacearum. Appl Environ Microbial. Jan. 1997; 63(1): 338-346.
Hernandez, J.A., et al. "Biochemical analysis of the recombinant Fur (ferric uptake regulator) protein from Anabaena PCC 7119: factors affecting its oligomerization state," Biochem J., 2002, 366:315-322.
Hidaka, et al. Promotion of the Growth of Rice by Inoculation of Nitrogen-Fixing-Activity-Enhanced Bacteria to the Rhizosphere. In Nitrogen Fixation: From Molecules to Crop Productivity (Part of the Current Plant Science and Biotechnology in Agriculture book series (PSBA, vol. 38)), pp. 445; 2002.
Holden, et al. Colonization outwith the colon: plants as an alternative environmental reservoir for human pathogenic enterobacteria. FEMS Microbiol. Rev. 33, 689-703 (2009).
Hu et al., (2008) Assembly of nitrogenase MoFe protein. Biochemistry 47(13):3973-3981.
Hunter, "'Genetically Modified Lite' placates public but not activists." EMBO Reports, Jan. 2014, 15(2):138-141.
Huynen,et al., Smoothness within ruggedness: the role of neutrality in adaptation. Proc. Natl. Acad. Sci. USA 93:397-401 (1996).
Iber, D. A quantitative study of the benefits of co-regulation using the spoIIA operon as an example. Mol. Sys. Biol. 2, 1-6 (2006).
Idalia and Bernardo, "*Escherichia coli* as a model organism and its application in biotechnology," Recent Advances on Physiology, Pathogenesis, and Biotechnological Applications, Chapter 13, 2017, pp. 253-274.
Iniguez et al., "Nitrogen Fixation in Wheat Provided by Klebsiella pneumoniae 342." MPMI, 2004, 17(10):1078-1085.
International Preliminary Report on Patentability dated Jul. 16, 2019 in connection with Application No. PCT/US2018/013671, 6 pages.
International Preliminary Report on Patentability dated May 14, 2015 in connection with Application No. PCT/US2013/068055.
International Preliminary Report on Patentability in International Appln. No. PCT/US2018/046148, dated Feb. 11, 2020, 12 pages.
International Preliminary Report on Patentability in International Appln. No. PCT/US2018/057174, dated Apr. 28, 2020, 5 pages.
International Preliminary Report on Patentability in International Appln. No. PCT/US2018/057613, dated Apr. 28, 2020, 8 pages.
International Preliminary Report on Patentability in PCT Appln. No. PCT/US2012/042502, dated Dec. 17, 2013, 8 pages.
International Preliminary Report on Patentability in PCT Appln. No. PCT/US2016/042170, dated Jan. 16, 2018, 19 pages.
International Preliminary Report on Patentability mailed Apr. 19, 2018 for Application No. PCT/US2016/055429.
International Search Report and Written Opinion in International Appln. No. PCT/US2012/042502, dated Jan. 31, 2013, 11 pages.
International Search Report and Written Opinion in International Appln. No. PCT/US2013/068055, dated Feb. 18, 2014, 15 pages.
International Search Report and Written Opinion in International Appln. No. PCT/US2016/042170, dated Dec. 2, 2016, 26 pages.
International Search Report and Written Opinion in International Appln. No. PCT/US2016/055429. dated Dec. 30, 2016, 16 pages.
International Search Report and Written Opinion in International Appln. No. PCT/US2018/0013671, dated Mar. 22, 2018, 8 pages.
International Search Report and Written Opinion in International Appln. No. PCT/US2018/046148, dated Dec. 3, 2018, 6 pages.

(56)  References Cited

OTHER PUBLICATIONS

International Search Report and Written Opinion in International Appln. No. PCT/US2018/057613, dated Mar. 5, 2019.

International Search Report and Written Opinion in International Appln. No. PCT/US2019/068152, dated Jun. 25, 2020.

Ishihama A (2010) Prokaryotic genome regulation: multifactor promoters, multitarget regulators and hierarchic networks. FEMS Microbial Rev 34(5):628-645.

Ivanova et al. "Artificial Regulation of Genes, Of the coding proteins of the nitrogenase complex Rhizobial bacteria," Natural Sciences, 2014, 13(174):36-39 (Machine Translation).

Izquierdo et al., "Distribution of Extensive nifH Gene Diversity Across Physical Soil Microenvironments," Microbial Ecology, 2006, 51(4):441-452.

Jacob et al., (1987) Solid-state NMR studies of Klebsiella pneumoniae grown under nitrogen-fixing conditions. J Biol Chem 262(1):254-259.

Jacoby et al., "The Role of Soil Microorganisms in Plant Mineral Nutrition-Current Knowledge and Future Directions," Frontiers in Plant Scients, 2017, 8(19):1-19.

Jaschke, et al. A fully decompressed synthetic bacteriophage 0X174 genome assembled and archived in yeast. Virology 434, 278-284 (2012).

Jensen, K.F. The *Escherichia coli* K-12 "wild types" W3110 and MG1655 have an rph frameshift mutation that leads to pyrimidine starvation due to low pyre expression levels. J. Bacteriol. 175:3401-3407 (1993).

Johnson ZI & Chisholm SW (2004) Properties of overlapping genes are conserved across microbial genomes. Genome Res 14(11):2268-2272.

Kalir S, et al. (2001) Ordering genes in a flagella pathway by analysis of expression kinetics from living bacteria. Science 292(5524):2080-2083.

Kaneko, T., et al. Complete genomic structure of the cultivated rice endophyte *Azospirillum* sp. B510. DNA Res. 17:37-50 (2010).

Kant et al., "Understanding plant response to nitrogen limitation for the improvement of crop nitrogen use efficiency." Journal of Experimental Botany, 2011, 62(4):1499-1509.

Karlin, et al. Applications and statistics for multiple high-scoring segments in molecular sequences. Proc Natl Acad Sci USA. Jun. 15, 1993;90(12):5873-7.

Karlin, et al. Methods for assessing the statistical significance of molecular sequence features by using general scoring schemes. Proc Natl Acad Sci USA. Mar. 1990;87(6):2264-8.

Kececiglu, J., et al. "Of mice and men: Algorithms for evolutionary distances between genomes with translocation," SODA: Proceedings of the sixth annual ACM-SIA< symposium on Discrete algorithms, 1995, 10 pages.

Kelly JR, et al. (2009) Measuring the activity of BioBrick promoters using an in vivo reference standard. J Biol Eng 3 :4.

Kent et al., "A Transposable Partitioning Locus Used To Stabilize Plasmid-Borne Hydrogen Oxidation and Trifolitoxin Production Genes in a Sinorhizobium Strain," Appl. Environ. Microbiol., 1998, 64(5):1657-1662.

Kerby et al., "Photoproduction of ammonium by immobilized mutant strains of Anabaena variabilis." Applied Microbiology and Biotechnology. Apr. 1986, 24(1):42-46.

Kim et al., "Constitutive expression of nitrogenase system in Klebsiella oxytoca by gene targeting mutation to the chromosomal nifLA operon." Journal of Biotechnology. Jun. 1989, 10(3-4):293-301.

Kingsford et al., "Rapid, accurate, computational discovery of Rho-independent transcription terminators illuminates their relationship to DNA uptake," Genome Bio. 2007, 8(2):R22.

Kitano H (2002) Systems biology: a brief overview. Science 295(5560):1662-1664.

Knight, T., "Idempotent Vector Design for Standard Assembly of Biobricks," MIT Artificial Intelligence Laboratory, The TTL Data Book for Design Engineers, 2003, 11 pages.

Kovacs et al., (2009) Stochasticity in protein levels drives colinearity of gene order in metabolic operons of *Escherichia coli*. PLoS Biol 7(5):e1000115.

Kurzweil, "Plant Bacteria breakthrough enables crops worldwide to take nitrogen from the air." Plant Bacteria Breakthrough Enables Crops Worldwide Take Nitrogen From Air. Aug. 1, 2013. http://www.kurzweilai.neUplant-bacteria-breakthrough-enables-cropsworldwide-to-take-nitrogen-from- the-air. 4 pages.

Kutter, et al. Colonization of barley (*Hordeum vulgare*) with *Salmonella enterica* and *Listeria* spp. FEMS Microbial. Ecol. 56, 262-271 (2006).

Lauritsen et al., "A versatile one-step CRISPR-Cas9 based approach to plasmid-curing." Microb Cell Fact, 2017, 16(135):1-10.

Leang, et al. Genome-wide analysis of the RpoN regulon in Geobacter sulfurreducens. BMC Genomics. Jul. 22, 2009:10:331.

Lee et al., "The class IId bacteriocin thuricin-17 increases plant growth," Planta, 2009, 229:747-755.

Levin-Karp, A., et al. Quantifying translational coupling in *E. coli* synthetic operons using RBS modulation and fluorescent reporters. ACS Synth. Biol. 2:327-336 (2013).

Liang et al., Minimal effect of gene clustering on expression in *Escherichia coli*. Genetics. Feb. 2013;193(2):453-65.

Lim, et al. Fundamental relationship between operon organization and gene expression. Proc Natl Acad Sci US =A. Jun. 28, 2011;108(26):10626-31.

Liu, et al. Whole genome analysis of halotolerant and alkalotolerant plant growth-promoting rhizobacterium *Klebsiella* sp. D5A. Sci Rep. May 24, 2016; 6: 1-10.

Lombo et al., (1999) The mithramycin gene cluster of *Streptomyces argillaceus* contains a positive regulatory gene and two repeated DNA sequences that are located at both ends of the cluster. J. Bacterial. 181:642-647.

Lucks et al., Toward scalable parts families for predictable design of biological circuits. Curr. Opin. Microbiol. 11, 567-573 (2008).

Ma et al., "Effect of nicotine from tobacco root exudates on chemotaxis, growth, biocontrol efficiency, and colonization byPseudomonas aeruginosaNXHG29," Antonie van Leeuwenhoek, 2018, 111(7):1237-1257.

MacNeil et al., "Fine-structure mapping and complementation analysis of nif (nitrogen fixation) genes in Klebsiella pneumoniae." J Bacterial. Oct. 1978, 136(1):253-266.

MacNeil et al., "Mutations in nif genes that cause Klebsiella pneumoniae to be derepressed for nitrogenase synthesis in the presence of ammonium." J Bacterial. Nov. 1980, 144(2):744-751.

Maduro M (2011) Random DNA Generator, retrieved from URL <http://www.faculty.ucr.edu/~mmaduro/random.htm>, 1 page.

Magari, et al. Pharmacologic control of a humanized gene therapy system implanted into nude mice. J Clin Invest. Dec. 1, 1997; 100(11): 2865-2872.

Mandal M & Breaker RR (2004) Gene regulation by riboswitches. Nat Rev Mol Cell Biol 5(6):451-463.

Marroqui et al. "Enhanced Symbiotic Performance by Rhizobium tropici Glycogen Synthase 17, 18 Mutants," Journal of Bacteriology, Feb. 1, 2001, vol. 183, No. 3, pp. 854-864.

Martinez-Noel et al., NifB and NifEN protein levels are regulated by ClpX2 under nitrogen fixation conditions in Azotobacter vinelandii. Mol Microbiol. Mar. 2011;79(5):1182-93.

Marx, et al. Broad-host-range ere-lox system for antibiotic marker recycling in gram-negative bacteria. Biotechniques. Nov. 2002;33(5):1062-7.

Masepohl et al., "Organization and regulation of genes encoding the molybdenum nitrogenase and the alternative nitrogenase in Rhodobacter capsulatus." Arch. Microbial. Sep. 1996;165:80-90.

Mason CA & Hamer G (1987) Cryptic Growth in Klebsiella-Pneumoniae. Appl Microbiol Biot 25(6):577-584.

Matsubayashi, et al. Peptide hormones in plants. Annu Rev Plant Biol. 2006:57:649-74.

Medema et al., (2011) Synthetic biology in *Streptomyces* bacteria. Methods Enzymol 497:485-502.

Medema et al., Computational tools for the synthetic design of biochemical pathways. Nat Rev Microbiol. Jan. 23, 2012;10(3):191-202.

(56)     References Cited

OTHER PUBLICATIONS

Medema, et al., Exploiting plug-and-play synthetic biology for drug discovery and production in microorganisms. Nat. Rev. Microbiol. 9:131-137 (2011).

Mengel, "Roots, growth and nutrient uptake." Dept. of Agronomy publication #AGRY-95-08 (Rev. May 1995), 8 pages.

Merriam-Webster "originate" accessed Jul. 7, 2020 (Year: 2020).

Mirsky, Ethan M., Refactoring the *Salmonella* Type Ill Secretion System. (Doctoral Dissertation) Apr. 12, 2012, 60 pages.

Mirzahoseini, et al., "Heterologous Proteins Production in *Escherichia coli*: An Investigation on the Effect of Codon Usage and Expression Host Optimization," Cell Journal (Yakhteh) 12(4):453 Winter 2011.

Mitra, Ranjana. Regulation of nifLA operon in Azotobacter vinelandii. Thesis submitted to the Jawaharlal Nebru University, New Delhi, for the degree of doctor of philosophy. 2000.

Miyazaki K (2003) Creating random mutagenesis libraries by megaprimer PCR of whole plasmid (MEGA WHOP). Methods Mol Biol 231 :23-28.

Moon et al., Genetic programs constructedfrom layered logic gates in single cells. Nature. Nov. 8, 2012;491(7423):249-53.

Mueller, et al. Closing yield gaps through nutrient and water management. Nature 490, 254-257 (2012).

Mus et al., "Symbiotic Nitrogen Fixation and the Challenges to Its Extension to Nonlegumes." Appl Environ Microbial. Jul. 2016, 82(13):3698-3710.

Mutalik, V.K., et al. Quantitative estimation of activity and quality for collections of functional genetic elements. Nat. Methods 10:347-353 (2013).

Nassar et al.. "Promotion of plant growth by an auxin-producing isolate of the yeast Williopsis saturnus endophytic in maize (*Zea mays* L.) roots." Biology and Fertility of Soils, 2005, 42:97-108.

Nelissen et al., Translational research:from pot to plot. Plant Biotechnology Journal, Jan. 2014 12:277-285.

Nestmann, "Mutagenesis by nitrosoguanidine, ethyl methanesulfonate, and mutator gene mutH in continuous cultures of *Escherichia coli*." Science Direct. Jun. 1975, 28(3):323-330.

Nichkawade, Anuradha. Studies on upstream regulatory sequence of the nifLA promoter of Klebsiella pnuemoniae. Thesis submitted to the Jawaharlal Nehru University, New Delhi, for the degree of doctor of philosophy. 1996.

Nielsen, "Transgenic organisms—time for conceptual diversification?" Nature Biotechnology 2003; 21:227-228.

No, et al., "Ecdysone-inducible gene expression in mammalian cells and transgenic mice" Proc. Natl. Acad. Sci. USA vol. 93, Issue 8, pp. 3346-3351, Apr. 1996.

Noskov, V.N., et al. Assembly of large, high G+C bacterial DNA fragments in yeast. ACS Synth. Biol. 1:267-273 (2012).

Oh, et al., "Organization of nif gene cluster in *Frankia* sp. EuIK1 strain, a symbiont of Elaeagnus umbellata," Arch. Microbiol., 2012, 194:29-34.

Ohta et al., "Associative N2-fixation of Rice with Soil and Microorganisms", 1985, 27:17-27 (Abstract Only).

Ohtsuka et al., "An alternative approach to deoxyoligonucleotides as hybridization probes by insertion of deoxyinosine at ambiguous codon positions," J. Biol. Chem. 260:2605-2608 (1985).

Okubo et al., "Effects of Elevated Carbon Dioxide, Elevated Temperature, and Rice Growth Stage on the Community Structure of Rice Root-Associated Bacteria." Microbes Environ. Jun. 2014, 29(2):184-190 Published online May 31, 2014.doi: 10.1264/jsme2. ME14011.

Orme-Johnson WH (1985) Molecular basis of biological nitrogen fixation. Annu Rev Biophys Biophys Chem 14:419-459.

Ortiz-Marquez et al., "Association with an Ammonium-excreting bacterium allows diazotrophic culture of oil-rich Eukaryotic microalagae." Appl. Microbial. 2012; 78(7):2345-2352.

Pfleger et al., "Combinatorial engineering of intergenic regions in operons tunes expression of multiple genes"; Nature Biotechnology; 24(8):1027-1031 (2006).

Philippe et al., (2004) Improvement of pCVD442, a suicide plasmid for gene allele exchange in bacteria. Plasmid 51(3):246-255.

Piccioli, et al. Neuroantibodies: ectopic expression of a recombinant anti-substance P antibody in the central nervous system of transgenic mice. Neuron. Aug. 1995;15(2):373-84.

Piccioli, et al. Neuroantibodies: molecular cloning of a monoclonal antibody against substance P for expression in the central nervous system. Proc Natl Acad Sci U SA. Jul. 1, 1991; 88(13): 5611-5615.

Pickens LB, Tang, Y., Chooi, Y-H. (2011) Metabolic engineering for the production of natural products. Annu. Rev. Chem. Biomol. Eng. 2:211-236.

Plotnikova, et a. Pathogenesis of the human opportunistic pathogen Pseudomonas aeruginosa PA14 in *Arabidopsis*. Plant Physiol. 124, 1766-1774 (2000).

Price, M.N., Arkin, A.P., & Alm, E.J. The life-cycle of operons. PLoS Genet. 2, e96. (2006).

Price, M.N., Huang, K.H., Arkin, A.P., & Alm, E.J. Operon formation is driven by coregulation and not by horizontal gene transfer. Genome Res. 15, 809-819 (2005).

Purnick PE & Weiss R (2009) The second wave of synthetic biology: from modules to systems. Nat Rev Mol Cell Biol 10(6):410-422.

Q. An et al: "Constitutive expression of the nifA gene activates associative nitrogen fixation of Enterobacter gergoviae 57-7, an opportunistic endophytic diazotroph", Journal of Applied Microbiology., vol. 103, No. 3, Sep. 1, 2007, h-613-620.

Qiu, et al. Construction of genetically engineered strains of Enterobacter cloacae (nifl~(-)A~(c)). Acta Phytophysiologica Sinica. [Jan. 1, 1999, 25(3):269-273].

Ramon, A., & Smith, H.O. Single-step linker-based combinatorial assembly of promoter and gene cassettes for pathway engineering. Biotechnol. Lett. 33:549-555 (2011).

Ran et al., Genome erosion in a nitrogen-fixing vertically transmitted endosymbiotic multicellular cyanobacterium. PLoS One. Jul. 8, 2010;5(7):e11486.

Resendis-Antonio, et al. Systems biology of bacterial nitrogen fixation: High-throughput technology and its integrative description with constraint-based modeling. BMC Syst Biol. 2011: 5: 120.

Riedel et al., (1983) Nitrogen fixation by Klebsiella pneumoniae is inhibited by certain multicopy hybrid nif plasmids. J Bacterial 153(1):45-56.

Roberts, et al. Regulation and characterization of protein products coded by the nif (nitrogen fixation) genes of Klebsiella pneumoniae. J Bacterial. Oct. 1978; 136(1): 267-279.

Rogers, et al., Synthetic biology approaches to engineering the nitrogen symbiosis in cereals. Journal of Experimental Botany, 2014; 65(8):1939-1946.

Rommens, et al. Intergeneric transfer and functional expression of the tomato disease resistance gene pto. Plant Cell. Oct. 1995; 7(10): 1537-1544.

Roncato-Maccari, et al., Endophytic Herbaspirillum seropedicae expresses nif genes in gramineous plants. FEMS Microbiology Ecology. 2003; 45: 39-47.

Rong et al., "Promoter specificity determinants of T7 RNA polymerase," Proc. Natl. Acad. Sci. USA, 95(2):515-519 (1998).

Rosenblueth et al. Nitrogen Fixation in Cereals. Frontiers in Microbiology, vol. 9, Article 1794. (Aug. 9, 2018). 13 pages.

Rosenblueth, et al. Bacterial endophytes and their interactions with hosts. Mol Plant Microbe Interact. Aug. 2006 ;19(8):827-37.

Rossolini et al., "Use of Deoxyinosine-Containing Primers vs Degenerate Primers for Polymerase Chain Reaction Based on Ambiguous Sequence Information" Mol. Cell. Probes 8:91-98 (1994).

Rubio and Ludden, Maturation of Nitrogenase: a Biochemical Puzzle, J. Bacteriology, 2005, 187(2):405-414.

Saikia et al., "Biological nitrogen fixation with non-legumes: An achievable target or a dogma?" Curr. Sci. Feb. 2007, 92(3): 317-322.

Salis et al., (2009) Automated design of synthetic ribosome binding sites to control protein expression. Nat Biotechnol 27(10):946-950.

Sandoval, et al. Strategy for directing combinatorial genome engineering in *Escherichia coli*. Proc Natl Acad Sci USA. Jun. 26, 2012;109(26):10540-5.

Sanjuan and Olivares, "Multicopy plasmids carrying the Klebsiella pneumoniae nifA gene enhance Rhizobium meliloti nodulation competitiveness on alfalfa," Molecular Plant-Microbe Interactions, 1991, 4(4):365-369.

(56) References Cited

OTHER PUBLICATIONS

Santi et al., Biological nitrogen fixation in non-legume plants. Annals of Botany, Jan. 2013, 111:743-767.

Schmidt-Dannert, et al., Molecular breeding of carotenoid biosynthetic pathways. Nat. Biotechnol. 18:750-753 (2000).

Schmitz, et al. "Iron is required to relieve inhibitory effects on NifI on transcriptional activation by NifA in Klebsiella pneumoniae." J Bacterial. Aug. 1996, 178(15):4679-4687.

Schouten et al., "Do cisgenic plants warrant less stringent oversight?" Nature Biotechnology, Jul. 2006, 24(7):753.

Service, R. Genetically engineered microbes make their own fertilizer, could feed the world's poorest. Science Apr. 2017: doi:I0.1126/science.aal1000.

Setten, et al., Engineering Pseudomonas protegens Pf-5 for Nitrogen Fixation and its application to improve plant growth under nitrogen-deficient conditions, PLOS One 2013; 8(5):1-14.

Shamseldin, "The role of different genes involoved in symbiotic nitrogen fixation—review." Global Journal of Biotechnology & Biochemistry, 2013, 8(4):84-94.

Shetty et al., (2008) Engineering BioBrick vectors from BioBrick parts. J Biol Eng 2:5.

Sibold et al., "A nif mutant of Klebsiella pneumoniae fixing nitrogen in the presence of ammonia." FEMS Microbiology Letters 10(1):37-41 (Jan. 1, 1981).

Sibold et al., "Constitutive expression of nitrogen fixation (nif) genes of Klebsiella pneumoniae due to a DNA duplication." EMBO J. 1982, 1(12):1551-8.

Siddavattam et al., "Regulation of nif Gene expression in Enterobacter agglomerans: Nucleotide sequence of the nifLA operon and influence of temperature and ammonium on its transcription." Molecular and general genetics. Dec. 1995, 249(6):629-636.

Simon et al., (1996) Perturbation of nifF expression in Klebsiella pneumoniae has limited effect on nitrogen fixation. J Bacteriol 178(10):2975-2977.

Singh et al., "An L-methionine-D,L-sulfoximine-resistant mutant of the cyanobacterium Nostoc muscorum showing inhibitor-resistant y-glutamyl-transferase, defective glutamine synthetase and producing extracellular ammonia during N2 fixation." FESS Letters. Apr. 5, 1983, 154(1):10-14.

Sivaraman et al., "Codon choice in genes depends on flanking sequence information—implications for theoretical reverse translation," Nucleic Acids Res. 36:e16 (2008).

Sleight et al., Designing and engineering evolutionary robust genetic circuits. J Biol Engin. 2010;4(12):1-20.

Sleight, S.C., & Sauro, H.M. Randomized BioBrick assembly: a novel DNA assembly method for randomizing and optimizing genetic circuits and metabolic pathways. ACS Synth. Biol., 2013, 2(9):506-518.

Smanski et al., "Engineered *Streptomyces platensis* strains that overproduce antibiotics platensimycin and platencin," Antimicrob. Agents Chemother., 2009, 53:1299-12304.

Smanski et al., Synthetic biology to access and expand nature's chemical diversity. Nat Rev Microbial. Mar. 2016;14(3):135-49.

Smanski, et al. "Functional optimization of gene clusters by combinatorial design and assembly," Nat Biotechnol., 2014, 32(12):1241-1249.

Sorek and Cossart, Prokaryotic transcriptomics: a new view on regulation, physiology, and pathogenicity. Nat. Rev. Genet. 11:9-16 (2010).

Souza et al., "The N-Terminus of the NIFA protein of herbaspirillum seropedicae is probably involved in sensing of ammonia." In Tikhonovich et al. (Eds.) Proceedings of the 10th International Congress on Nitrogen Fixation, St. Petersburg, Russia, May 28-Jun. 3, 1995 (p. 260) Dordrecht: Kluwer.

Spiller, et al. Isolation and characterization of nitrogenase-derepressed mutant strains of cyanobacterium Anabaena variabilis. J Bacterial. Feb. 1986, 165(2):412-419.

Staron et al., "The Third Pillar of Bacterial Signal Transduction: Classification of the Extracytoplasmic Function (ECF) Sigma Factor Protein Family," Mol Microbiol 14(3): 557-81 (2009).

Steenhoudt et al., "Azospirillum, a free-living nitrogen-fixing bacterium closely associated with grasses: genetic, biochemical and ecological aspects." FEMS Microbial. Rev. 2000; 24:487-506.

Stein, et al. The osteocalcin gene: a model for multiple parameters of skeletal-specific transcriptional control. Mol Biol Rep. Aug. 1997:24(3):185-96.

Stemmer, "DNA shuffling by random fragmentation and reassembly: In vitro recombination for molecular evolution" Oct. 1994, Proc. Natl. Acad. Sci. USA 91:10747-10751.

Stemple, "Tilling—a high-throughput harvest for functional genomics." Nature Reviews Genetics 5, 1-7 (Feb. 2004), doi: 10.1038/nrg1273.

Stephanopoulos. Challenges in engineering microbes for biofuels production. Science. Feb. 9, 2007;315(5813):801-4.

Stewart et al., (1967) In situ studies on nitrogen fixation with the acetylene reduction technique. Science 158(3800):536.

Stucken, K., et al. The smallest known genomes of multicellular and toxic cyanobacteria: comparison, minimal gene sets for linked traits and the evolutionary implications. PLoS ONE 5:e9235 (2010).

Subtil, et al. Secretion of Predicted Inc Proteins of Chlamydia pneumoniae by a Heterologous Type Ill Machinery. Molecular Microbiology. Feb. 2001, vol. 39, No. 3; pp. 792-800.

Suh,et al., Functional expression of the FeMo-cofactor-specific biosynthetic genes nifEN as a NifE-N fusion protein synthesizing unit in Azotobacter vinelandii. Biochem. Biophys. Res. Comm. 299:233-240 (2002).

Swain et al., "Nitrogen fixation and its improvement through genetic engineering." J. Global Biosciences, 2013, 2(5): 98-112.

Tamsir et al., (2011) Robust multicellular computing using genetically encoded NOR gates and chemical 'wires'. Nature 469(7329):212-215.

Tan C, "A synthetic biology challenge: making cells compute," Mol Biosyst 3: 343-353 (2007).

Temme et al., "Designing and Engineering Complex Behavior in Living Machines." (Doctoral Dissertation) Oct. 1, 2011. Retrieved from URL <escholarship.org/uc/item/lr41x99s>, 75 pages.

Temme et al., "Refactoring the nitrogen fixation gene cluster from Klebsiella oxytoca," Proc. Natl. Acad. Sci. USA, 2012, 109(18):7085-7090.

Temme et al., Modular control of multiple pathways using engineered orthogonal T7 polymerases. Nucleic Acids Res. Sep. 1, 2012;40(17):8773-81.

Temme K, et al. (2008) Induction and relaxation dynamics of the regulatory network controlling the type III secretion system encoded within *Salmonella* pathogenicity island 1. J Mol Biol 377(1):47-61.

Thiel, T., Lyons, E.M., & Erker, J.C., Characterization of genes for a second Modependent nitrogenase in the cyanobacterium Anabaena variabilis. J. Bact. 179:5222-5225 (1997).

Thomas et al., "Ammonium Excretion by an I-Methionine-dl-Sulfoximine-Resistant Mutant of the Rice Field Cyanobacterium Anabaena siamensis." Appl Environ Microbial. Nov. 1990, 56(11):3499-3504.

Tilman et al. "Global food demand and the sustainable intensification of agriculture." PNAS 108:20260-20264 (2011).

Triplett, "Diazotrophic endophytes: progress and prospects for nitrogen fixation in monocots." Plant and Soil 1996; 186:29-38.

Tritt et al., "An Integrated Pipeline for de Novo Assembly of Microbial Genomes." Sep. 13, 2012. PLOS one. https://doi.org/10.1371 /journal.pone.0042304, 9 pages.

Ueda, et al., Remarkable N2-Fixing Bacterial Diversity Detected in Rice Roots by Molecular Evolutionary Analysis of nifH Gene Sequences. Journal of Bacteriology, Mar. 1995, p. 177:1414-1417.

Van Dongen, S.A., "Performance criteria for graph clustering and Markov cluster experiments," CWI, 2000, 36 pages.

Vernon et al., Analysis of 16S rRNA gene sequences and circulating cell-free DNA from plasma of chronic fatigue syndrome and non-fatigued subjects. BMC Microbiology 2002; 2:39.

Villa et al., "Azotobacter vinelandii siderophore can provide nitrogen to support the culture of the green algae neochloris oleoabundans and scenedesmus." FEMS Microbial. Lett. 2014, 351(1):70-77.

Villalobos et al., (2006) Gene Designer: a synthetic biology tool for constructing artificial ONA segments. BMC Bioinformatics 7:285.

(56) References Cited

OTHER PUBLICATIONS

Voigt, "Genetic parts to program bacteria," Current Opinion in Biotechnology, 2006, 17(5):548-557.

Voigt, C., "Gaining Access: Rebuilding Genetics from the Ground Up". Institute of Medicine Board on Global Health Forum on Microbial Threats. Mar. 14, 2011. Retrieved from the web at iom.edu//media/Files/ActivityFiles/PublicHealth/MicrobialThreats/2011-MAR- 14Noigt.pdf.

Wang et al., Positive and negative regulation of gene expression in eukaryotic cells with an inducible transcriptional regulator. Gene Ther., 4.5 (May 1997): 432-441.

Wang et al., Using Synthetic biology to distinguish and overcome regulatory and functional barriers related to nitrogen fixation. PLoS One. 2013;8(7):e68677. 11 pages.

Wang, et al. Ligand-inducible and liver-specific target gene expression in transgenic mice. Nat Biotechnol. Mar. 1997;15(3):239-43.

Wang, et al. Programming cells by multiplex genome engineering and accelerated evolution. Nature. Aug. 13, 2009;460(7257):894-8.

Wang, et al., "A minimal nitrogen fixation gene cluster from *paenibacillus* sp. WLY78 enables expression of active nitrogenase in *Escheichia coli*. Plos Genetics," 2013, 9(10):1-11.

Watanabe et al., (2006) Total biosynthesis of antitumor nonribosomal peptides in *Escherichia coli*. Nature Chemical Biology, 2:423-428.

Watanabe et al., Chapter 15. Plasmid-borne gene cluster assemblage and heterologous biosynthesis of nonribosomal peptides in *Escherichia coli*. Methods Enzymol. 2009; 458:379-99.

Weber, et al. A modular cloning system for standardized assembly of multigene constructs. PLoS One. Feb. 18, 2011;6(2):e16765.

Wei et al. (Biology and fertility of soils 50.4 (2014): 657-666). (Year: 2014).

Welch et al. (2009) "Design Parameters to Control Synthetic Gene Expression in *Escherichia coli*" PLoS One 4(9):e7002.

Wells, J.A. Additivity of mutational effects in proteins. Biochemistry 29:8509-8517 (1990).

Wenzel SC & Muller R (2005) Recent developments towards the heterologous expression of complex bacterial natural product biosynthetic pathways. Curr Opin Biotechnol 16(6):594-606.

Werner et al., Fast track assembly of multigene constructs using Golden Gate cloning and the MoClo system. Bioeng Bugs. 2012, ;3(1):38-43.

Widmaier, et al. Engineering the *Salmonella* type Ill secretion system to export spider silk monomers. Mol. Syst. Biol. 5, 309 (2009).

Wootton, et al. Statistics of local complexity in amino acid sequences and sequence databases. Computers & Chemistry. vol. 17, Issue 2, Jun. 1993, pp. 149-163.

Wu et al., "Root exudates from two tobacco cultivars affect colonization of Ralstonia solanacearum and the disease index," European Journal of Plant Pathology, 2014, 141(4):667-677.

Wu, J., et al. Multivariate modular metabolic engineering of *Escherichia coli* to produce resveratrol from L-tyrosine. J. Biotechnol. (2013), 167:404-411.

Xu, et al., ePathBrick: a synthetic biology platform for engineering metabolic pathways in *E. coli*. ACS Synth. Biol., 1:256-266 (2012).

Yarza, et al., "Uniting the classification of cultured and uncultured bacteria and archaea using 16S rRNA gene sequences," Nature Rev. Micro., 2014 12:635-345.

Ye et al., "Primer-BLAST: a tool to design target-specific primers for polymerase chain reaction," BMC Bioinformatics., Jun. 2012, 13(134), 1-11.

Yokobayashi et al, (2002) Directed evolution of a genetic circuit. Proc Natl Acad Sci USA 99(26):16587-16591.

Yoshida et al., Atmospheric dinitrogen fixation in the flooded rice rhizosphere as determined by the N-15 isotope technique. Soil Science and Plant Nutrition, Dec. 1980, 26(4):551-559.

Zaslaver et al.,(2006) Optimal gene partition into operons correlates with gene functional order. Phys Biol 3(3): 183-189.

Zazopoulos E, et al. (2003) A genomics-guided approach for discovering and expressing cryptic metabolic pathways. Nat Biotechnol 21 (2): 187-190.

Zehr et al., New Nitrogen-Fixing Microorganisms Detected in Oligotrophic Oceans by Amplification of Nitrogenase (nifH) Genes. Appl Environ Microbial. Sep. 1998, 64(9):3444-3450.

Zehr lab NifH database, retrieved from URL <https://wwwzehr. pmc.ucsc.edu/nifH_Database_Public/>, Apr. 4, 2014, 1 page.

Zhang et al., "Influence of different factors on the nitrogenase activity of the engineered *Escherichia coli* 78-7," World J Microbiol Biotechnol. Jun. 2015, 31(6):921-7.

Zhang et al., "Involvement of the ammonium transporter AmtB in nitrogenase regulation and ammonium excretion in Pseudomonas stutzeri A 1501." Res. Microbial, Jun. 2012, 163(5):332-339.

Zhang, et al. "GlnD Is Essential for NifA Activation, NtrB/NtrC-Regulated Gene Expression, and Posttranslational Regulation of Nitrogenase Activity in the Photosynthetic, Nitrogen-Fixing Bacterium Rhodospirillum rubrum," J. Bacteriol., Feb. 2005, 187(4): 1254-1265.

Zhao et al., "Evidence for nifU and nifS participation in the biosynthesis of the iron-molybdenum cofactor of nitrogenase," J. Biol. Chem., 2007, 282(51):37016-37025.

Zomer AL (2011) PPP: Perform Promoter Prediction, retrieved from URL <http://bioinformatics.biol.rug.nl/websoftware/ppp/ppp_start.php>, 2 pages.

Bashor, "Understanding biological regulation through synthetic biology," Annu. Rev. Biophys., May 2018, 47:399-423, 52 pages.

Dessaux et al., "Engineering the Rhizosphere," Trends in Plant Science, Mar. 2016, 21(3):266-278.

Drummond et al., "Expression from the nifB promoter of *Azotobacter vinelandii* Can Be Activated by NifA, VnfA, or AnfA Transcriptional Activators," Journal of Bacteriology, Feb. 1996, 178(3):788-792.

Fernandes et al., "Glutamine synthetase stabilizes the binding of GlnR to nitrogen fixation gene operators," The FEBS Journal, Feb. 2017, 284(6):903-918.

Fisher et al., "Mutations in the *Bacillus subtilis* glnRA Operon that Cause Nitrogen Source-Dependent Defects in Regulation of TnrA Activity," Journal of Bacteriology, Aug. 2002, 184(16):4636-4639.

Fisher et al., "Novel trans-Acting *Bacillus subtilis* glnA Mutations that Derepress glnRA Expression," Journal of Bacteriology, Apr. 2009, 191(8):2485-2492.

International Preliminary Report on Patentability in International Application No. PCT/US2020/031201, mailed on Nov. 10, 2022, 17 pages.

International Preliminary Report on Patentability in International Application No. PCT/US2021/029895, mailed on Nov. 10, 2022, 14 pages.

International Preliminary Report on Patentability in International Application No. PCT/US2021/031808, mailed on Nov. 24, 2022, 17 pages.

International Search Report and Written Opinion in International Application No. PCT/US2021/031808, mailed on Mar. 9, 2022 , 29 pages.

International Search Report and Written Opinion in International Application No. PCT/US2022/035873, mailed on Dec. 21, 2022, 31 pages.

Noindorf et al., "Role of Pll proteins in nitrogen fixation control of *Herbaspirillum seropedicae* strain SmR1," BMC Microbiology, Jan. 2011, 11(1), 8 pages.

Schreier et al., "*Bacillus subtilis* glnR mutants defective in regulation," Gene., Aug. 1995, 161(1):51-56.

Venkateshwaran, "Exploring the Feasibility of Transferring Nitrogen Fixation to Cereal Crops," Principles of Plant-microbe Interactions, 2015, 403-410.

Yurgel et al., "A Mutant GlnD Nitrogen Sensor Protein Leads to a Nitrogen-fixing but Ineffective *Sinorhizobium meliloti* Symbiosis with Alfalfa," PNAS, Dec. 2008, 105(48):18958-18963.

Klose et al., "Glutamate at the site of phosphorylation of nitrogen-regulatory protein NTRC mimics aspartyl-phosphate and activates the protein," J Mol Biol., Jul. 1993, 232(1):67-78.

Kranz et al., "Ammonia-constitutive nitrogen fixation mutants of Rhodobacter capsulatus," Gene, Nov. 1988, 71(1):65-74.

Mus et al., "Diazotrophic Growth Allows Azotobacter vinelandii To Overcome the Deleterious Effects of a glnE Deletion," Appl Environ Microbiol., Jun. 2017, 83(13):e00808-17.

(56) References Cited

OTHER PUBLICATIONS

PCT International Search Report and Written Opinion in International Appln. No. PCT/US2020/031201, dated Mar. 9, 2021, 28 pages.

Das et al. "Microbial assay of N2 fixation rate, a simple alternate for acetylene reduction assay" MethodsX, 2018, 5: 909-914.

Davin-Regli et al. "Enterobacter aerogenes and Enterobacter cloacae; versatile bacterial 1-3, 7, 12, 17-24, 26-32, pathogens confronting antibiotic treatment," Front Microbiol, 2015, 6, 35, 41-45, 49, 54, 56-66, 392:1-10.

De Freitas J R ED—Eisenhauer Nico et al: "Yield and N assimilation of winter wheat (*Triticum aestivum* L., var. Norstar) inoculated with rhizobacteria", Pedobiologia, Elsevier, Amsterdam, NL, vol. 44, No. 2, Jan. 1, 2000 (Jan. 1, 2000), pp. 97-104, XP004633526, ISSN: 0031-4056, DOI: 10.1078/S0031-4056(04)70031-1.

GenBank CP007215 "Kosakonia sacchari SPI chromosome, complete genome" Sep. 4, 193-46 2017 (online]. [Retrieved Oct. 28, 2019]. Retrieved from the internet (URL:https://www.ncbi.nlm.nih.gov/nuccore/CP007215).

Joseph et al., "Recent developments of the synthetic biology toolkit for Clostridum." Frontiers in microbiology, 2018, 9(154):1-13.

Levican et al. "Comparative genomie analysis of carbon and nitrogen assimilation mechanisms in three indigenous bioleaching bacteria: predictions and validations" BMC Genomics 2008, 9:581, 19 pages.

Mabrouk et al. "Chapter 6: Potential of Rhizobia in Improving Nitrogen Fixation and Yields of Legumes," Symbiosis, May 30, 2018 (May 30, 2018), IntechOpen, pp. 1-16. Retrieved from the Internet:<https://www.intechopen.com/books/symbiosis/potential-of-rhizobia-in-improving-B351nitrogen-fixation-and-yields-of-legumes> on Nov. 18, 2019 (Nov. 18, 2019).

Magasanik "Genetic Control of Nitrogen Assimilation in Bacteria" Ann. Rev. Genet 1982. 16:135-68 (Year: 1982).

PCT International Search Report in International Appl. No. PCT/US2019/041429, Dec. 3, 2019, 18 pages.

PCT International Search Report in International Appl. No. PCT/US2019/059450, Mar. 10, 2020, 6 pages.

PCT International Search Report in International Appl. No. PCT/US2019/39217, Nov. 19, 2019. 5 pages.

PCT International Search Report in International Appl. No. PCT/US2019/39528, Nov. 6, 2019, 6 pages.

PCT Supplementary Partial European Search Report in International Appln. No. PCT/US2018013671, dated Oct. 27, 2020, 18 pages.

Takeshi Uozumi et al: "Cloning and Expression of the nit A Gene of Klebsiella oxytoca in K. pneumoniae and Azospirillum lipoferum", Agricultural and Biological Chemistry, 1986, 50(6):1539-1544.

Van Heeswijk et al. "Nitrogen Assimilation in *Escherichia coli*: Putting Molecular Data into a Systems Perspective" Microbiology and Molecular Biology Reviews p. 628-695 Dec. 2013 vol. 77 No. 4 (Year: 2013).

Biswas et al., "Rhizobia Inoculation Improves Nutrient Uptake and Growth of Lowland Rice," Soil Science Society of America Journal, Sep. 2000, 64(5):1644-1650.

Biswas et al., "Rhizobial Inoculation Influences Seedling Vigor and Yield of Rice," Agronomy Journal, Sep. 2000, 92(5):880-886.

Cannon et al., "Chromosomal Integration of *Klebsiella* Nitrogen Fixation Genes in *Escherichia coli*," Journal of General Microbiology, Jan. 1974, 80(1):227-239.

Cannon et al., "Plasmids Formed in Nitrogen-fixing *Escherichia coli-Klebsiella pneumoniae* Hybrids," Journal of General Microbiology, Jan. 1974, 80(1):241-251.

Edgar, "Muscle: multiple sequence alignment with high accuracy and high throughput," Nucleic Acids Res., Mar. 19, 2004, 32(5):1792-1797.

Ferri et al., "Plasmid electroporation of *Sinorhizobium* strains: The role of the restriction gene hsdR in type strain Rm1021," Plasmid, May 2010, 63(3):128-135.

Galvão et al., "Adaptation of the Yeast URA3 Selection System to Gram-Negative Bacteria and Generation of a AbetCDE *Pseudomonas putida* Strain," Applied and Environmental Microbiology, Feb. 2005, 71(2):883-892.

Gorochowski et al., "Genetic circuit characterization and debugging using RNA-seq," Mol Syst Biol., Nov. 9, 2017, 13(11):952, 16 pages.

Gutiérrez-Zamora et al., "Natural endophytic association between *Rhizobium etli* and maize (*Zea mays* L.)," J Biotechnol., Oct. 4, 2001, 91(2-3):117-126.

Igiehon et al., "Rhizosphere Microbiome Modulators: Contributions of Nitrogen Fixing Bacteria towards Sustainable Agriculture," Int J Environ Res Public Health, Mar. 23, 2018, 15(4):574, 25 pages.

Jones et al., "Soil microbial community analysis using two-dimensional polyacrylamide gel electrophoresis of the bacterial ribosomal internal transcribed spacer regions," J Microbiol Methods, May 2007, 69(2):256-267.

Kechris et al., "Quantitative exploration of the occurrence of lateral gene transfer by using nitrogen fixation genes as a case study," Proc Natl Acad Sci U S A., Jun. 20, 2006, 103(25):9584-9589.

Li et al., "The anti-Shine-Dalgarno sequence drives translational pausing and codon choice in bacteria," Nature, Mar. 28, 2012, 484(7395):538-541.

Li et al., "Using synthetic biology to increase nitrogenase activity," Microb Cell Fact., 2016, 15(43):1-11.

Mahmood et al., "Seed biopriming with plant growth promoting rhizobacteria: a review," FEMS Microbiol Ecol., Aug. 2016, 92(8): fiw112, 14 pages.

Malik et al., "Association of nitrogen-fixing, plant-growth-promoting rhizobacteria (PGPR) with kallar grass and rice," Plant and Soil, Oct. 1997, 194:37-44.

Martinez-Argudo et al., "The NifL-NifA System: a Multidomain Transcriptional Regulatory Complex That Integrates Environmental Signals," Journal of Bacteriology, Feb. 9, 2004, 186(3):601-10.

Pascuan et al., "Exploring the Ancestral Mechanisms of Regulation of Horizontally Acquired Nitrogenases," J Mol Evol., Oct. 2015, 81(3-4):84-89.

Perrine-Walker et al., "Infection process and the interaction of rice roots with rhizobia," Journal of Experimental Botany, Sep. 2007, 58(12):3343-3350.

Shanks et al., "*Saccharomyces cerevisiae*-based molecular tool kit for manipulation of genes from gram-negative bacteria," Applied and Environmental Microbiology, Jul. 2006, 72(7):5027-5036.

Tang et al., "Biology of Nitrogen Fixers" (Chinese), Northeast Forestry University Press, First Edition, Jun. 30, 2009, pp. 172-183 (with English Translation).

Thony, et al., "Dual Control of the *Bradyrhizobium japonicum* Symbiotic Nitrogen Fixation Regulatory Operon fixR nifA: Analysis of cis- and trans-Acting Elements," J Bacteriol., Aug. 1989, 171(8):4162-4169.

Tsukada et al., "Comparative Genome-Wide Transcriptional Profiling of *Azorhizobium caulinodans* ORS571 Grown under Free-Living and Symbiotic Conditions," Appl Environ Microbiol., Aug. 2009, 75(15):5037-5046.

Xu et al., "Advance of Study on Nitrogenase" (Chinese), Journal of Biology, Aug. 31, 2011, 8(4):61-64 (English Abstract).

Yan et al., "Nitrogen fixation island and rhizosphere competence traits in the genome of root-associated *Pseudomonas stutzeri* A1501," Proc Natl Acad Sci U S A, May 27, 2008, 105(21):7564-7569.

European Search Report in European Application No. EP 20795673. 1, dated May 22, 2023, 9 pages.

Iniguez et al., "Regulation of Enteric Endophytic Bacterial Colonization by Plant Defense, " MPMI, 2005, 18(2):169-178.

Merrick et al., "Nitrogen control of the nif regulon in *Klebsiella pneumoniae*: involvement of the ntrA gene and analogies between ntrC and nifA," The EMBO Journal, Jan. 1, 1983, 2:39-44.

Schreier et al., "Altered Regulation of the glnA Gene in Glutamine Synthetase Mutants of *Bacillus subtilis*," Jul. 1, 1986, 167(1):35-43.

Streicher et al., "Genetic Control of Glutamine Synthetase in *Klebsiella aerogens*," Journal of Bacteriology, Jan. 1, 1975, 121(1):320-331.

(56) References Cited

OTHER PUBLICATIONS

Willardson et al., "Development and Testing of a Bacterial Biosensor for Toluene-Based Environmental Contaminants," Applied and Environmental Microbiology, Mar. 1, 1998, 64(3):1006-1012.

Xiao et al., "Developing a Genetically Encoded, Cross-Species Biosensor for Detecting Ammonium and Regulating Biosynthesis of Cyanophycin," ACS Synthetic Biology, Jul. 13, 2017, 6(10):1807-1815.

Zhang et al., "Expression of the $N_2$ fixation gene operon of *Paenibacillus* sp. WLY78 under the control of the T7 promoter in *Escherichia coli* BL21," Biotechnol. Lett., Oct. 2015, 37(10):1999-2004.

AddGene.org [online], "Plasmids 101: Inducible Promoters," Jan. 2018, retrieved on Oct. 23, 2023, retrieved from URL<https://blog.addgene.org/plasmids-101-inducible-promoters>, 8 pages.

Genbank Accession No. AGN85586.1, "cellulose synthase [*Enterobacter* sp. R4-368]," Jun. 29, 2015, 2 pages.

GenBank Accession No. AHJ75701.1, "hypothetical protein C813_13915 [*Kosakonia sacchari* SP1]," Sep. 19, 2017, 2 pages.

GenBank Accession No. AHJ76132.1, "hypothetical protein C813_16530 [*Kosakonia sacchari* SP1]," Sep. 19, 2017, 2 pages.

Steyert et al., "Development of a Novel Genetic System To Create Markerless Deletion Mutants of *Bdellovibrio bacteriovorus*," Appl. Environ. Microbiol., Aug. 2007, 73(15):4717-4724.

Bennett, "Engineering Nitrogenases for Synthetic Nitrogen Fixation: From Pathway Engineering to Directed Evolution," BioDesign Research, Feb. 7, 2023, 5(0005):1-12.

Bush et al., "The role of bacterial enhancer binding proteins as specialized activators of σ54-dependent transcription," Microbiology and Molecular Biology Reviews, Sep. 2012, 76(3):497-529.

Chen et al., "Engagement of Arginine Finger to ATP Triggers Large Conformational Changes in NtrC1 AAA+ ATPase for Remodeling Bacterial RNA Polymerase," Structure, Nov. 10, 2010, 18(11):1420-1430.

Chen et al., "Functional analysis of the GAF domain of NifA in *Azospirillum brasilense*: effects of Tyr→Phe mutations on NifA and its interaction with GlnB," Mol Genet Genomics, Jun. 2005, 5:415-422.

Chen et al., "Plant Physiology and Molecular Biology," Editor-in-Chief, Higher Education Publishing House, Jun. 30, 2007, 3rd edition, pp. 261-269, 18 pages (with Machine Translation).

De Castro et al., "ScanProsite: detection of PROSITE signature matches and ProRule-associated functional and structural residues in proteins," Nucleic Acids Res., Jul. 2006, 34:W362-365.

Iltis et al., "*Zea diploperennis* (Gramineae): A New Teosinte from Mexico," Science, Jan. 1979, 203(4376):186-188.

Inaba et al., "Mutational analysis of GlnB residues critical for NifA activation in *Azospirillum brasilense*," Microbiological Research, Feb. 2015, 171:65-72.

Jumper et al., " Highly accurate protein structure prediction with AlphaFold," Nature, Aug. 2021, 596(7873):583-589.

Letunic et al., "20 years of the SMART protein domain annotation resource," Nucleic Acids Res., Jan. 4, 2018, 46(D1):D493-496.

Lim et al., "Methionine in Proteins: It's Not Just for Protein Initiation Anymore," Neurochemical Research, Jan. 15, 2019, 44(1):247-257.

McKinlay et al., "Carbon dioxide fixation as a central redox cofactor recycling mechanism in bacteria," Proceedings of the National Academy of Sciences, Jun. 29, 2010, 107(26):11669-11675.

Monteiro et al., "In-trans regulation of the N-truncated-NIFA protein of *Herbaspirillum seropedicae* by the N-terminal domain," FEMS Microbiol Lett., 1999, 180(2):157-161.

Monteiro et al., "Expression and functional analysis of an N-truncated NifA protein of *Herbaspirillum seropedicae*," FEBS Lett., 1999, 447(2-3):283-286.

Nagy et al., "Structural Characterization of Arginine Fingers: Identification of an Arginine Finger for the Pyrophosphatase dUTPases," J Am Chem Soc., Nov. 16, 2016, 138(45):15035-15045.

Oliveira et al., "Interaction of GlnK with the GAF domain of *Herbaspirillum seropedicae* NifA mediates $NH_4^+$-regulation," Biochimie, 2012, 94(4):1041-1047.

Oliveira et al., "Role of conserved cysteine residues in *Herbaspirillum seropedicae* NifA activity," Res Microbiol., Jul. 2009, 160:389-395.

Sotomaior et al., "Effect of ATP and 2-oxoglutarate on the in vitro interaction between the NifA GAF domain and the GlnB protein of *Azospirillum brasilense*," Braz J Med Biol Res., Dec. 2012, 45(12):1135-40.

Souza et al., "Expression of the nifA gene of *Herbaspirillum seropedicae*: role of the NtrC and NifA binding sites and of the—24/-12 promoter element," Microbiology, 2000, 146:1407-1418.

Yousuf et al., "The AAA+ superfamily: a review of the structural and mechanistic principles of these molecular machines," Crit. Rev. Biochem. Mol. Biol., Apr. 2022, 57(2):156-187.

Berrada et al., "Taxonomy of the Rhizobia: Current Perspectives," British Microbiology Research Journal, Jan. 2014, 4(6):616-639.

Merrick et al., "Repressor properties of the nifL gene product in *Klebsiella pneumoniae*," Mol. Gen. Genet., Mar. 1982, 185:75-81.

Bürgmann et al., "Effects of model root exudates on structure and activity of a soil diazotroph community," Environmental Microbiology, Nov. 2005, 7(11):1711-1124.

Eberhart et al., "A methodology for markerless genetic modifications in *Azotobacter vinelandii*," Journal of Applied Microbiology, Jun. 2016, 120(6):1595-1604.

Priyanka et al., "Diversity Study of Nitrate Reducing Bacteria from Soil Samples—A Metagenomics Approach," Journal of Computer Science and Systems Biology, Jul. 2015, 8(4): 191-198.

Brophy et al., "Engineered integrative and conjugative elements for efficient and inducible DNA transfer to undomesticated bacteria.," Nat. Microbio., Sep. 2018, 3(9):1043-1053.

Burén et al., "Formation of Nitrogenase NifDK Tetramers in the Mitochondria of *Saccharomyces cerevisiae*," ACS Synthetic Biology, Jun. 16, 2017, 6(6):1043-1055.

Delmotte et al., "An integrated proteomics and transcriptomics reference data set provides new insights into the *Bradyrhizobium japonicum* bacteroid metabolism in soybean root nodules," Proteomics, Apr. 8, 2010, 10(7):1391-1400.

Haskett et al., "Engineered plant control of associative nitrogen fixation," PNAS, Apr. 19, 2022, 119(16):e2117465119, 9 pages.

Hoover et al., "Homocitrate is a Component of the Iron-Molybdenum Cofactor of Nitrogenase," Biochemistry, Apr. 4, 1989, 28(7):2768-2771.

International Preliminary Report on Patentability in International Application No. PCT/US2022/035873, mailed on Jan. 11, 2024, 18 pages.

Kornberg, "DNA Replication," W. H. Freeman & Co., San Francisco, 1980, Section 2-12:75-77.

Sandig et al., "HBV-derived promoters direct liver-specific expression of an adenovirally transduced LDL receptor gene," Gene Therapy, Nov. 1996, 3(11):1002-1009.

Woodruff et al., "Registry in a tube: multiplexed pools of retrievable parts for genetic design space exploration," Nucleic Acids Research, Feb. 17, 2017, 45(3):1553-1565.

Martinez et al., "Symbiotic autoregulation of nifA expression in *Rhizobium leguminosarum* bv. viciae," J. Bacteriol., Oct. 2004, 186(19):6586-6594.

Gruber et al., "Versatile plasmid-based expression systems for Gram-negative bacteria—General essentials exemplified with the bacterium *Ralstonia eutropha* H16," New Biotechnology, Dec. 25, 2015, 32(6):552-558.

Montañez et al., "Biological nitrogen fixation in maize (*Zea mays* L.) by 15N isotope-dilution and identification of associated culturable diazotrophs," Biology and Fertility of Soils, Feb. 2009, 45:253-263.

Riggs et al., "Enhanced maize productivity by inoculation with diazotrophic bacteria," Australian Journal of Plant Physiology, Sep. 3, 2001, 28(9):829-836 (Abstract only).

Bageshwar et al., "Studies on Some Nitrogen Fixing Genes of *Azotobacter vinelandii*," Thesis for the degree of Doctor of Philosophy, Jamia Millia Islamia, Department of Biosciences, Aug. 1994, 255 pages.

(56) References Cited

OTHER PUBLICATIONS

Bender et al., "A NAC for regulating metabolism: the nitrogen assimilation control protein (NAC) from *Klebsiella pneumoniae*," Journal of Bacteriology, Jul. 30, 2010, 192(19):4801-11.

Chaurasia et al., "Improved eco-friendly recombinant *Anabaena* sp. strain PCC7120 with enhanced nitrogen biofertilizer potential," Applied and Environmental Microbiology, Jan. 15, 2011, 77(2):395-9.

Espin et al., "Complementation analysis of gln A-linked mutations which affect nitrogen fixation in *Klebsiella pneumoniae*," Molecular and General Genetics, Dec. 1981, 184:213-7.

Hesketh et al., "The GlnD and GlnK homologues of *Streptomyces coelicolor* A3 (2) are functionally dissimilar to their nitrogen regulatory system counterparts from enteric bacteria," Molecular microbiology, Oct. 2002, 46(2):319-30.

Kim et al., "Cloning and expression of pyrroloquinoline quinone (PQQ) genes from a phosphate-solubilizing bacterium *Enterobacter intermedium*," Current Microbiology, Dec. 2003, 47:457-461.

Krishnan et al., "Citrate synthase mutants of *Sinorhizobium fredii* USDA257 form ineffective nodules with aberrant ultrastructure," Applied and environmental microbiology, Jun. 2003, 69(6):3561-8.

Lee et al., "The class IId bacteriocin thuricin-17 increases plant growth," Planta, Mar. 2009, 229:747-55.

Pan et al., "Phosphate-solubilizing bacteria: advances in their physiology, molecular mechanisms and microbial community effects," Microorganisms, Dec. 2023, 11(12):2904, 22 pages.

Peralta et al., "Engineering the nifH promoter region and abolishing poly-β-hydroxybutyrate accumulation in *Rhizobium etli* enhance nitrogen fixation in symbiosis with *Phaseolus vulgaris*," Applied and Environmental Microbiology, Jun. 2004, 70(6):3272-81.

Sia et al., "Different relative importances of the par operons and the effect of conjugal transfer on the maintenance of intact promiscuous plasmid RK2," Journal of bacteriology, May 1995, 177(10):2789-97.

Simon et al., "Importance of cis determinants and nitrogenase activity in regulated stability of the *Klebsiella pneumoniae* nitrogenase structural gene mRNA," Journal of Bacteriology, Jun. 15, 1999, 181(12):3751-60.

* cited by examiner

| | no glutamine | 1mM glutamine | 10 mM glutamine | |
|------|----------|----------|----------|--------|
| amtB | 716462 | 175150 | 1045 | |
| galK | 15 | 405 | 814 | |
| glnB | 8025 | 10275 | 7493 | |
| glnK | 752360 | 183994 | 320 | |
| nifA | 306663 | 92963 | 194 | 0% air |
| nifH | 12387186 | 3599183 | 161 | |
| nifL | 226368 | 42825 | 123 | |
| ntrB | 50439 | 25236 | 1081 | |
| ntrC | 78056 | 35760 | 1216 | |
| amtB | 241247 | 139599 | 1207 | |
| galK | 404 | 770 | 1012 | |
| glnB | 8296 | 6899 | 9376 | |
| glnK | 241645 | 158973 | 288 | |
| nifA | 237483 | 115545 | 197 | 10% air |
| nifH | 4702957 | 2448758 | 108 | |
| nifL | 173765 | 66818 | 75 | |
| ntrB | 25676 | 19630 | 1118 | |
| ntrC | 40312 | 30703 | 1295 | |
| amtB | 160293 | 167736 | 1353 | |
| galK | 1311 | 976 | 1200 | |
| glnB | 8522 | 8185 | 9445 | |
| glnK | 166653 | 191992 | 366 | |
| nifA | 200774 | 164973 | 198 | 20% air |
| nifH | 862984 | 2337297 | 80 | |
| nifL | 129054 | 99096 | 80 | |
| ntrB | 17326 | 21370 | 1146 | |
| ntrC | 24115 | 31446 | 1370 | |

FIG. 5

In planta nifH mRNA
quantification (au)

Microbe Breeding

Map Metabolism and Link to Genetics

Measure Microbiome Composition

Identify Species of Interest

Introduce Targeted Genetic Variation (Example Methods Listed Below)
1. Conjugation and Recombination
2. Chemical Mutagenesis
3. Adaptive Evolution
4. Gene Editing Inoculate Crops With Derivative Microbes And Select Best Crop Phenotypes

Colonization Sampling

For older roots, the entire root is not necessary as long as it fits the requirements listed below.

Sample size: 5 grams of tissue with roughly the same number and size (smaller ok) of lateral roots. The samples do not have to be cleaned of soil.

For transcriptomics, sample size is required to be packed in a solution and shipped on dry ice

| Strain Name | Activity (mmol N / Microbe hr) | Peak Colonization (CFU / g fw) |
|---|---|---|
| CI006 | 4.45E-16 | 2.55E+05 |
| CM038 | 3.26E-13 | 7.39E+05 |
| CM014 | 2.72E-13 | 7.39E+05 |
| CM093 | 4.27E-13 | 7.39E+05 |
| CM094 | 5.49E-13 | 7.39E+05 |
| CM029 | 2.95E-13 | 7.39E+05 |
| CI019 | 4.32E-17 | 2.89E+07 |
| CM011 | 2.95E-15 | 3.49E+07 |
| CM067 | 2.30E-17 | 3.49E+07 |
| CM069 | 3.10E-17 | 3.49E+07 |
| CM081 | 8.63E-16 | 3.49E+07 |
| 19-715 | 1.28E-15 | 3.49E+07 |
| 19-714 | 1.57E-15 | 3.49E+07 |
| 19-594 | 3.31E-15 | 3.49E+07 |
| 19-590 | 1.14E-14 | 3.49E+07 |
| 19-713 | 1.96E-14 | 3.49E+07 |
| 19-724 | 2.41E-14 | 3.49E+07 |
| CI911 | 3.48E-17 | 1.24E+07 |
| CI730 | 5.64E-17 | 2.89E+07 |

FIG. 29A
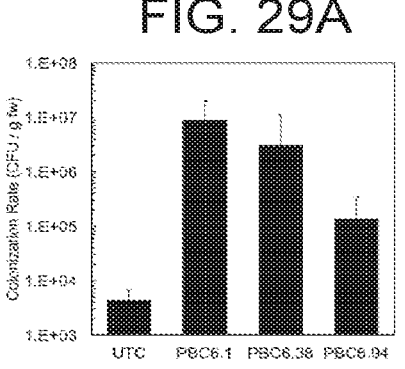
FIG. 29B
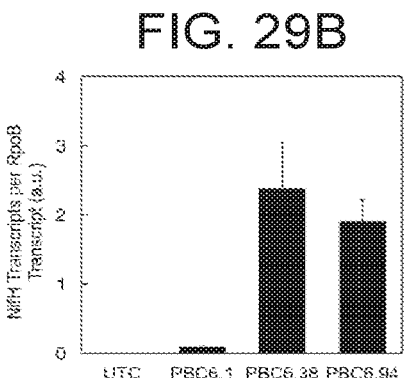
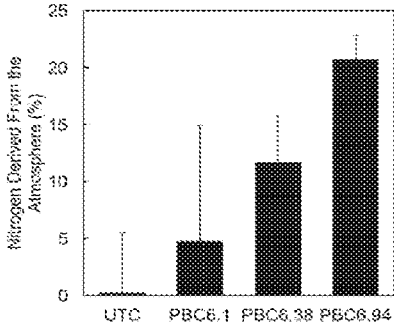
FIG. 29C

Nutrient Stress

Sufficient Fertilizer 910 1246

SEQUENCE LISTING

<160> NUMBER OF SEQ ID NOS: 424

<210> SEQ ID NO 1
<211> LENGTH: 9
<212> TYPE: PRT
<213> ORGANISM: Unknown
<220> FEATURE:
<223> OTHER INFORMATION: Description of Unknown:
      "LAGLIDADG" family peptide motif sequence

<400> SEQUENCE: 1

Leu Ala Gly Leu Ile Asp Ala Asp Gly
1               5

<210> SEQ ID NO 2
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gttgatcaga ccgatgttcg gaccttccaa ggtttcgatc ggacatacgc gaccgtagtg       60
ggtcgggtgt acgtctcgaa cttcaaagcc                                        90

<210> SEQ ID NO 3
<211> LENGTH: 257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gcctctcggg gcgctttttt ttattccggc actagccgct attaataaaa atgcaaatcg       60
gaatttacta tttaacgcga gattatctaa gatgaatccg atggaagcgc gctgttttca      120
ctcgcctttt taaagttacg tgatgatttc gatgcttctt tgagcgaacg atcaaaaata      180
agcgtattca ggtaaaaaaa tattctcatc acaaaaaagt ttgtgtaata cttgtaacgc      240
tacatggaga ttaactc                                                     257

<210> SEQ ID NO 4
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ggttcacata aacataatta tcgccacggc gatagccgta cgcttttttgc gtcacaacat      60 ccatggtgaa gccggctttt tcaagaacac gcgccacctc atcgggtctt aaatacatac     120
tcattcctca ttatctttta ccgcacgtta accttacctt attcattaaa ggcaacgctt     180
tcggaatatt ccataaaggg ctatttacag cataattcaa aatcttgtcc tacacttata     240
gactcaatgg aattaaggga                                                  260

<210> SEQ ID NO 5
<211> LENGTH: 260
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 5
gcgcggaaaa tcgacgcata gcgcattctc agaagccggc ctggtctcgg tggaaaagcg      60
aatctttccc acgaccgccg ggcctttaac aaaagaatca atgacctgat taatgtcgct     120
atccattctc tctccgcgta atgcgatctt ttttcatcat acctaacaaa ctggcagagg     180
gaaaagccgc gcggtttttc tgcgaagtgt attgtaagat ttgtttgata tgttatatcg     240
taacatatta ttgcaaacat                                                 260

<210> SEQ ID NO 6
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ctgacgaagc gagttacatc accggtgaaa ctctgcacgt caacggcgga atgtatatgg      60
tctgaccgag atttgcgcaa aacgctcagg aaccgcgcag tctgtgcggt tcactgtaat     120
gttttgtaca aaatgatttg cgttatgagg gcaaacagcc gcaaaatagc gtaaaatcgt     180
ggtaagacct gccgggattt agttgcaaat ttttcaacat tttatacact acgaaaacca     240
tcgcgaaagc gagttttga                                                  259

<210> SEQ ID NO 7
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
acgcctgggg cgccgaccag cgggaagagt gatttggcca acgaggcgcc gctctgaatg      60
gaaatcatgg cgattaaaat aaccagtatc ggcaaccatg ccggtacctt acgagacgag     120
ccgggcatcc tttctcctgt caattttgtc aaatgcggta aaggttccag tgtaattgaa     180
ttaccccgcg ccggttgagc taatgttgaa aaaaagggtc ttaaaagcag tacaataggg     240
cgggtctgaa gataatttca                                                 260

<210> SEQ ID NO 8
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
tctgattcct gatgaaaata aacgcgacct tgaagaaatt ccggataacg ttatcgccga      60
tttagatatc catccggtga aacgaatcga ggaagttctg gcacttgcgc tacagaacga     120
accgtttgga atggaagtcg tcacggcaaa atagtgattt cgcgcaaata gcgctaagaa     180
aaatagggct ggtaagtaaa ttcgtacttg ccagcctttt tttgtgtagc taacttagat     240
cgctggcagg ggggtcaatt                                                 260

```
<210> SEQ ID NO 9
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gtaagaaagt cggcctgcgt aaagcacgtc gtcgtcctca gttctccaaa cgttaattgt      60
tttctgctca cgcagaacaa tttgcgaaaa aacccgcttc ggcgggtttt tttatggata     120
aatttgccat tttccctcta caaacgcccc attgttacca ctttttcagc atttccagaa     180
tcccctcacc acaacgtctt caaaatctgg taaactatca tccaattttc tgcccaaatg     240
caggtgattg ttcattttt                                                  259

<210> SEQ ID NO 10
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gtcaaagccg tattatcgac cccttaggga caacgcttgc cggggcggga gagcggccgc      60
agttgatttt tgccgaactt tcagctgatt atattcagca ggtacgcgag cgcctgccgg     120
tgttgcgcaa tcgccgcttt gcgccaccgc aattattatg acgttttttt aaacaaggct     180
tgattcacct tgttacagat tgctattgtg tccgcgcgtc aaatagccgt taattgtatg     240
cgtgtatgat ggcgtattcg                                                 260

<210> SEQ ID NO 11
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggcggtgg ttgaccgtat cggtcccgag catcatgagc tttcggggcg agcgaaagat      60
atgggatcgg cggcggtact gctggcgatt atcatcgcgc tgatcgcgtg gggaacgctg     120
ctgtgggcga actaccgcta agtcttgtcg tagctgctcg caaaacggaa agaaactcct     180
gatttttgtg tgaaatgtgg ttccaaaatc accgttagct gtatatactc acagcataac     240
tgtatataca cccagggggc                                                 260

<210> SEQ ID NO 12
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
taagaaaagc ggcctgtacg aagacggcgt acgtaaagac aggctggata acgacgatat      60
gatcgatcag ctggaagcgc gtattcgcgc taaagcatcg atgctggatg aggcgcgtcg     120
tatcgatatc cagcaggttg aagcgaaata acgtgttggg aagcgatacg cttcccgtgt     180
```
atgattgaac ctgcgggcgc gaggcgccgg ggttcatttt tgtatatata aagagaataa      240
acgtggcaaa gaacattcaa                                                 260

<210> SEQ ID NO 13
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgaatcgta ctaaactggt actgggcgcg gtaatcctgg gttctactct gctggctggt       60
tgctccagca atgctaaaat cgatcagctg tcttctgacg ttcagactct gaacgctaaa      120
gttgaccagc tgagcaacga cgtgaacgca atgcgttccg acgttcaggc tgctaaagat      180
gacgcagctc gcgctaacca gcgtctggac aacgcagcta ctaaataccg taagtaa        237

<210> SEQ ID NO 14
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atggccaacc gagcaaaccg caacaacgta gaagagagcg ctgaagatat ccataacgat       60
gtcagccaat tagcggatac gctggaagag gtgctgaaat cgtggggcag cgacgccaaa      120
gacgaagcgg aggccgcgcg caaaaaagcg caggcgctgc tgaaagagac ccgcgcccgg      180
cttaacggca acaaccgcgt ccagcaggcg gcgtgcgacg ccatgggctg cgctgacagc      240
tacgtgcgcg acaaaccgtg gcaaagcgtc ggcgccgcag cagccgttgg ggtatttatt      300
ggcgtattac tgaatttacg tcgataa                                         327

<210> SEQ ID NO 15
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgaccaaaa agatttccgc cctagcgttt ggcattggca tggtaatggc gagcagccag       60
gcttttgccc acggtcacca tagtcatggc ccggcgctga ccgaagcgga acaaaaggcg      120
agtgaaggca tttttgctga ccaggacgta aaggacaggg cgctgagcga ctgggagggg      180
atctggcagt cggttaaccc ctatctgctg aacggggatt tagatccggt tctggagcag      240
aaggccaaaa aggccggtaa aagcgtggcg gaatatcggg aatattataa gaagggctac      300
gctaccgatg tcgaccagat tggtatcgag gataacgtca tggagtttca cgtcgggaaa      360
accgtcaacg cctgtaagta cagctattcc ggttacaaaa ttctgaccta cgcatccggt      420
aaaaaaggcg tgcgctacct gttcgaatgc agcaggcgg attcaaaagc gccgaagttt       480
gttcagttta gcgatcacac catcgcgcca cgcaagtccc agcatttcca catctttatg      540
ggcaatgagt cccaggaagc gctgctgaaa gagatggata actggccaac ctactatcct      600
tatgcgctgc ataaagagca gattgtcgac gaaatgctgc accactaa                  648

-continued

```
<210> SEQ ID NO 16
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgagcacta tcgaagaacg cgttaagaaa attatcggcg aacagctggg cgttaagcag      60
gaagaagtta ccaacaatgc ttccttcgtt gaagacctgg gcgctgattc tcttgacacc     120
gttgagctgg taatggctct ggaagaagag tttgatactg agattccgga cgaagaagct     180
gagaaaatca ctactgttca ggctgccatt gattacatca acggccacca ggcgtaa        237

<210> SEQ ID NO 17
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgaataaaa ttgcacgttt ttcagcactg gccgttgttc tggctgcatc cgtaggtacc      60
actgctttcg ctgcgacttc taccgttacc ggtggctacg cgcagagcga catgcagggt     120
gaagcgaaca aagctggcgg tttcaacctg aagtaccgct acgagcaaga caacaacccg     180
ctgggtgtta tcggttcttt cacctacacc gaaaaagatc gttctgaatc tggcgtttac     240
aaaaaaggcc agtactacgg catcaccgca ggtccggctt accgtctgaa cgactgggct     300
agcatctacg gcgtagtggg tgttggttac ggtaaattcc aggacaacag ctacccgaac     360
aaatctgata tgagcgacta cggtttctct tacggcgctg gtctgcagtt caacccgatc     420
gaaaacgttg ccctggactt ctcctacgag cagtctcgca ttcgtaacgt tgacgttggc     480
acctggattg ctggcgtagg ttaccgcttc taa                                  513

<210> SEQ ID NO 18
<211> LENGTH: 273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gtgaataaat ctcaactgat tgacaaaatt gctgccggtg cggacatttc taaagccgca      60
gctggacgtg cgttagatgc tttaatcgct tctgttactg aatctctgca ggctggagat     120
gacgttgcgc tggtagggtt tggtactttt gctgttaaag agcgcgctgc ccgtactggt     180
cgcaatccgc aaacaggcaa agaaatcacc attgctgctg ctaaagttcc gggtttccgc     240
gcaggtaaag cgctgaaaga cgcggtaaac tga                                  273

<210> SEQ ID NO 19
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
```

```
atggctgtcg ctgccaacaa acgttcggta atgacgctgt tttctggtcc tactgacatc      60
tatagccatc aggtccgcat cgtgctggcc gaaaaaggtg ttagtttga datagagcac      120 gtggagaagg acaacccgcc tcaggatctg attgacctca acccgaatca aagcgtaccg      180
acgcttgtgg atcgtgagct cactctgtgg gaatctcgca tcattatgga atatctggat      240
gagcgtttcc cgcatccgcc gctcatgccg gtttacccgg tggcgcgtgg ggaaagccgt      300
ctgtatatgc agcgtatcga aaaggactgg tattcgttga tgaataccat tcagaccggt      360
accgctgcgc aggctgatac tgcgcgtaag cagctgcgtg aagaactaca ggcgattgcg      420 ccagtttca cccagaagcc ctacttcctg agcgatgagt tcagcctggt ggactgctac      480
ctggcaccac tgctgtggcg tctgccggtt ctcggcgtag agctggtcgg cgctggcgcg      540
aaagagctta aaggctatat gactcgcgta tttgagcgcg actctttcct cgcttcttta      600
actgaagccg aacgtgaaat gcgtctcggt cggggctaa                           639
```

```
<210> SEQ ID NO 20
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atgggtgaga ttagtattac caaactgctg gtagtcgcag cgctgattat cctggtgttt      60
ggtaccaaaa agttacgcac gctgggtgga gacctgggct cggctatcaa aggctttaaa      120
aaagccatga gcgatgacga tgacagtgcg aagaagacca gtgctgaaga agcgccggca      180
cagaagctct ctcataaaga gtaa                                            204
```

```
<210> SEQ ID NO 21
<211> LENGTH: 609
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgaaagcgt taacgaccag gcagcaagag gtgtttgatc tcattcggga tcatatcagc      60
cagacgggca tgccgccgac gcgtgcggag attgctcagc gcttggggtt tcgctcccca      120 aacgcggcg aagagcatct gaaagcgctg gcgcgtaaag cgcaatcga gatcgtttcc       180 ggcgcctccc gcggtattcg tctgctgacg gaagaagaaa ccggtctgcc gcttattggc      240
cgcgtcgcgg caggtgagcc gctgctagcg cagcagcaca ttgaaggcca ctaccaggtg      300
gacccggcca tgtttaagcc gaacgccgat tttctgctgc gtgttagcgg tatgtcgatg      360
aaggatatcg gtattctcga tggcgacctg ctggctgtcc ataaaacgca ggatgtgcgc      420
aatggtcagg tggttgtggc gcgtatcgac gaagaagtga ccgtgaagcg tctgaaaaaa      480
cagggtaacg tcgtggaatt gctgccggaa aacagcgaat ctcgccgat cgtggtcgac       540 cttcgcgaac aaagctttac tattgaaggc ctggccgtcg cgttatccg caacggcaac       600 tggcaataa                                                            609
```

```
<210> SEQ ID NO 22
<211> LENGTH: 1245
<212> TYPE: DNA
```

-continued

```
<213> ORGANISM: Artificial Sequence
<220> FEATURE:
<223> OTHER INFORMATION: Description of Artificial Sequence: Synthetic
      polynucleotide

<400> SEQUENCE: 22
atgaacgatt atctgccggg cgaaaccgct ctctggcagc gcattgaagg ctcactgaag      60
caggtgcttg gtagctacgg ttacagcgaa atccgtttgc cgattgtaga gcagaccccg     120
ttattcaaac gcgctatcgg cgaagtgacc gacgtggttg aaaaagagat gtacaccttt     180
gaggaccgta acggcgatag cctgactcta cgtccggaag gcacggctgg ctgcgtacgc     240
gccggtatcg aacatggtct cctgtacaat caagaacagc gcctgtggta cattgggccg     300
atgttccgcc acgaacgtcc gcaaaaaggc cgctaccgtc agttccacca gattggcgcc     360
gaagcgtttg gcctgcaggg gccggatatc gatgccgagc tgattatgct gaccgcccgc     420
tggtggcgcg agctgggcat ctccggccac gttgcgctgg agctgaactc tatcggttcg     480
ctggaggctc gcgctaacta tcgcgacgcg ctggtggcct atcttgagca gtttaaagat     540
aagctggacg aagactgcaa acgccgcatg tacaccaacc cgctgcgcgt gctggattct     600
aaaaacccgg acgtccaggc gctgctgaac gacgccccga cgctgggcga ctatcttgat     660
gaagagtcca aaacgcattt tgccgggctg tgcgcgctgc tggatgatgc cggtattcgc     720
tataccgtga atcagcgtct ggtacgcggt ctcgactact acaaccgcac cgtgtttgag     780
tgggtcacca ccagcctcgg ttcccagggc accgtctgcg ccggaggccg ttacgatggt     840
ctggttgagc agcttggcgg tcgcgctacc cctggcgtcg gctttgcgat ggggctggaa     900
cgtcttgttt tactggttca ggcagtgaat ccggaattta agccgatcc tgttgtcgat     960 atatacctgg tagcctccgg aactgacacc cagtccgcag caatgcgtct ggctgaacag    1020
gtacgcgatg cgttacccgg cgttaagctg atgaccaacc atggcggcgg caactttaag    1080
aagcagtttg cgcgcgctga taaatggggc gctcgcgttg cgctggtgct gggcgaatca    1140
gaaatcgccg acggaaacgt ggtagtgaaa gatttacgct caggtgagca aactaccgta    1200
acgcaggata gcgttgctgc gcatttgcgc acacttctgg gttaa                    1245
```

```
<210> SEQ ID NO 23
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atgaaaaaga ccaaaattgt ttgcaccatc ggtccgaaaa ccgaatccga agagatgttg      60
accaaaatgc tggacgcggg catgaacgtt atgcgtctga acttctctca cggtgactat     120
gcggaacacg tcagcgcat ccagaatctg cgcaatgtga tgagtaaaac cggtaagaaa      180
gcggcaatcc tgctggacac caaaggtccg gaaatccgta ccattaagct ggaaggcggc     240
aacgacgtct ccctgaaagc gggccagacc ttcaccttca ccaccgataa atccgttgtc     300
ggtaataacg aaatcgttgc ggtgacctat gaaggcttca ccagcgacct gagcgttggc     360
aacacggtac tggttgacga tggtctgatc ggtatggaag tgaccgctat cgaaggcaac     420
aaagttgttt gtaaagtgct gaacaacggc gacctcggcg agaacaaagg cgttaacctg     480
ccgggcgtat ctatcgcgct gccggcgctg gctgaaaaag acaaacagga tctgatcttc     540
ggttgcgaac agggcgttga ctttgttgcg gcatcctta tccgtaagcg ttctgacgtt     600
```

-continued

```
gttgaaatcc gtgagcacct gaaagcccac ggcggcgaga agatccagat catctccaaa        660
atcgaaaacc aggaaggcct gaacaacttc gacgaaatcc tcgaagcctc tgacggcatc        720
atggtagccc gtggcgacct gggcgttgaa atcccggttg aagaagttat cttcgcgcag        780
aagatgatga tcgagaaatg tatccgcgcg cgtaaagtcg ttatcaccgc gacccagatg        840
ctggattcca tgatcaaaaa cccgcgtccg acccgtgcgg aagcaggcga cgtggccaac        900
gccatcctcg acggcaccga cgcagttatg ctgtccggcg aatccgcgaa aggtaaatac        960
ccgctggaag cggtcaccat catggcgacc atctgcgaac gtaccgaccg cgtcatgacc       1020
agccgtcttg agtacaacaa cgacaaccgt aagctgcgca tcaccgaagc ggtgtgccgc       1080
ggtgcggtag aaacggctga aaaactggaa gcgccgctga tcgttgtggc aacccagggc       1140
ggtaaatccg cgcgcgccgt acgtaaatac ttcccggatg ccactatcct ggcgctgacc       1200
accaacgaaa ccaccgcgcg tcagctggtg ctgagcaaag gcgttgtggc acagctggtt       1260
gaagatatct cctctaccga tgcgttctac atccagggta agaactggc gctgcagagc        1320 ggtctggcgc gtaaaggcga cgtggttgtt atggtttccg gcgcgttagt cccgagcgga       1380
accaccaata ccgcttccgt gcacgtgctg taa                                    1413
```

```
<210> SEQ ID NO 24
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atgtatttaa gacccgatga ggtggcgcgt gttcttgaaa aagccggctt caccatggat        60
gttgtgacgc aaaaagcgta cggctatcgc cgtggcgata attatgttta tgtgaaccgt       120
gaagctcgta tggggcgtac cgcgttaatt attcatccgg ctttaaaaga gcgcagcaca       180
acgcttgcgg agcccgcgtc ggatatcaaa acctgcgatc attatgagca gttcccgctc       240
tatttagcgg gggatgctca acagcattat ggtattccac acgggttcag ttcgcgaatg       300
gcgcttgagc gttttctgag tggcctgttt ggcgaaacgc agtatagctg a                351
```

```
<210> SEQ ID NO 25
<211> LENGTH: 864
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggatagcg acattaatca ggtcattgat tcttttgtta aaggcccggc ggtcgtggga        60
aagattcgct tttccaccga gaccaggccg gcttctgaga atgcgctatg cgtcgatttt       120
ccgcgcctcg aaatcatgct tgcgggtcag cttcacgatc cggcgattaa agccgatcgc       180
gcccagctca tgccgcacga tgtgctgtat attcccgctg gcggatggaa tgacccgcaa       240
tggctggcgc cctccactct gctcactatc ttatttggta aacagcagct ggaattcgtc       300
ctgcgccact gggacggcag cgcgcttaac gtgctggata aacagcaggt tccgcgccgc       360
ggtccccggg tcggctcttt tctgctgcag gcgctgaatg aaatgcagat gcagccgcgg       420
gagcagcaca cggcccgctt tattgtcacc agcctgctca gccactgtgc cgatctgctg       480
```

-continued

```
ggcagccagg tacaaacctc atcgcgcagc caggcgcttt ttgaagcgat tcgtaagcat      540
attgacgccc actttgccga cccgttaacc cgggagtcgg tggcgcaggc gttttacctc      600
tcgccaaact atctatccca cctgttccag aaatgcgggc caatgggctt taacgagtat      660
ctgaatcaca tccgcctgga gcaggccaga atgctgttaa aaggccacga tatgaaagtg      720
aaagatatcg cccacgcctg cggtttcgcc gacagcaact acttctgccg cctgtttcgc      780
aaaaacaccg aacgctcgcc gtcggagtat cgccgtcaat atcacagcca gctgacggaa      840
aaaacagccc cggcaaaaaa ctag                                            864
```

```
<210> SEQ ID NO 26
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atgagttttg aaggaaaaat cgcgctggtt accggtgcaa gtcgcgggat tggccgcgca       60
atcgctgaaa cgctcgttgc ccgtggcgcg aaagttatcg ggactgcgac cagcgaaagc      120
ggcgcgcagg cgatcagcga ttatttaggt gctaacggta aaggtctgct gctgaatgtg      180
accgatcctg catctattga atctgttctg ggaaatattc gcgcagaatt tggtgaagtt      240
gatatcctgg tgaacaatgc cgggatcact cgtgataacc tgttaatgcg catgaaagat      300
gatgagtgga acgatattat cgaaaccaac ctgtcatctg ttttccgtct gtcaaaagcg      360
gtaatgcgcg ctatgatgaa aaagcgtcat ggacgtatta tcactatcgg ttctgtggtt      420
ggtaccatgg gaaatgcggg tcaggccaac tacgctgcgg cgaaagcggg tctgattggc      480
ttcagtaaat cactggctcg cgaagttgcg tcccgcggta ttactgtaaa cgttgttgct      540
ccgggcttta ttgaaacgga catgacgcgt gcgctgaccg atgagcagcg tgcggggtacg      600 ctggcggcag ttcctgcggg gcgcctcggc tctccaaatg aaatcgccag tgcggtggca      660
tttttagcct ctgacgaagc gagttacatc accggtgaaa ctctgcacgt caacggcgga      720
atgtatatgg tctga                                                      735
```

```
<210> SEQ ID NO 27
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
atgcccggct cgtctcgtaa ggtaccggca tggttgccga tactggttat tttaatcgcc       60
atgatttcca t                                                           71
```

```
<210> SEQ ID NO 28
<211> LENGTH: 2355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
atgaatcctg agcgttctga acgcattgaa atccccgtat tgccgttgcg cgatgtggtg       60
```

-continued

```
gtttatccgc acatggtcat acccctgttt gtagggcggg aaaaatctat ccgttgtctc       120
gaagcagcca tggaccatga taaaaaaatc atgctggttg cgcagaaaga agcctcgacg       180
gatgagccgg gtgtaaacga tcttttcacc gtcgggaccg tggcgtctat tttgcaaatg       240
ctgaagctac cggacggtac tgttaaagtg ctggtcgaag gtttgcagcg cgcgcgcatc       300
tctgcgctgt ctgataatgg cgaacatttt tcggcgaagg cggaatacct tgaatcgccg       360
gcgattgacg aacgcgagca ggaagtgctg gttcgtaccg ctatcagcca gtttgaaggc       420
tacatcaagc tgaacaaaaa aatccctccg gaagtgctga cgtcgctgaa tagcatcgac       480
gatccggcgc gtctggcgga taccatcgct gcgcatatgc cgctgaagct ggcggacaaa       540
cagtccgtgc tggagatgtc cgacgttaac gagcgtctgg aatatctgat ggcgatgatg       600
gagtcggaaa tcgatctgct gcaggtggag aagcgtattc gcaaccgcgt gaaaaagcag       660
atggagaaat ctcagcgcga gtactatctg aatgagcaaa tgaaagccat tcaaaaagag       720
ctcggcgaga tggacgacgc cccggacgag aacgaagcgc tgaagcgtaa gatcgacgcg       780
gcgaaaatgc cgaaagaggc aaaagagaaa accgaagcgg aactgcaaaa actgaaaatg       840
atgtccccga tgtcggcgga agcgaccgtc gttcgcggct acatcgactg gatggtgcag       900
gtaccgtgga acgctcgcag caaggttaaa aaagacctgc gtcaggctca ggagatcctc       960
gataccgatc actacggcct tgagcgcgtg aaggatcgca ttcttgagta cctcgcggtg      1020
cagagccgtg ttaacaagct caaagggccg atcctgtgcc tggttgggcc tccgggggta      1080
ggtaaaacct ctctcggcca atccatcgcc aaagcaactg acgcaaata tgtgcgtatg       1140 gcgctgggcg gcgtgcgtga tgaagcggaa atccgcggtc accgccgtac ctatattggc      1200
tcaatgccgg gcaaactgat ccagaaaatg gctaaagtgg gcgttaaaaa cccgctgttc      1260
ttgctggatg agatcgacaa gatgtcttct gacatgcgcg gcgatccggc ctcggcgctg      1320
ctggaggtgt tggatccgga acagaacgtg gcctttaacg accactatct ggaagtggat      1380
tacgatctca gcgacgtgat gttcgttgcg acctctaact ccatgaacat cccggcgccg      1440
ctgctggatc gtatggaagt gatccgcctc tccggctata ccgaagatga gaagctaaac      1500
atcgccaaac gccatctgct gtcaaaacag attgagcgta acgcgctcaa gaaaggcgag      1560
ctgacggtgg atgacagcgc gattatcggc atcattcgct actacacccg tgaagcaggc      1620
gtgcgtggtc tggagcgtga aatctcgaaa ctgtgccgca aagcggtgaa acagctgctg      1680
ctggataagt cgctgaaaca catcgagatt aacggcgaca acctgcacga tttccttggc      1740
gtgcagcgct acgactatgg tcgtgcggat agcgaaaacc gcgtaggtca ggtgaccgga      1800
ctggcgtgga cggaagtggg cggcgatctg ctgaccattg aaaccgcctg cgttccgggt      1860
aaaggcaaac tgacctacac cggttcactg ggtgaagtca tgcaggaatc catccaggcg      1920
gcgctgacgg tggttcgttc acgtgcggat aagctgggta ttaactcaga cttttacgaa      1980
aaacgtgata ttcacgttca cgtgccggaa ggcgcgacgc cgaaggatgg tccaagcgcc      2040
ggtatcgcga tgtgcaccgc gctggtttcc tgtctgacgg gtaatccggt acgcgccgac      2100
gtggcgatga ccggtgagat taccctccgt ggccaggtat tgccgattgg tggtctgaag      2160
gaaaaactgt ggccgcgca tcgcggcggc attaagactg ttctgattcc tgatgaaaat      2220
aaacgcgacc ttgaagaaat tccggataac gttatcgccg atttagatat ccatccggtg      2280
aaacgaatcg aggaagttct ggcacttgcg ctacagaacg aaccgtttgg aatggaagtc      2340
gtcacggcaa aatag                                                       2355
```

-continued

```
<210> SEQ ID NO 29
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atggctgaaa atcaatacta cggcaccggt cgccgcaaaa gttccgcagc tcgcgttttc      60
atcaaaccgg gcaacggtaa aatcgttatc aaccagcgtt ctctggaaca gtacttcggt     120
cgtgaaactg cccgcatggt agttcgtcag ccgctggaac tggtcgacat ggttgagaaa     180
ttagatctgt acatcaccgt taaaggtggt ggtatctctg tcaggctgg tgcgatccgt      240 cacggtatca cccgcgctct gatggagtac gacgagtccc tgcgtggcga actgcgtaaa     300
gctggtttcg ttactcgtga tgctcgtcag gttgaacgta agaaagtcgg cctgcgtaaa     360
gcacgtcgtc gtcctcagtt ctccaaacgt taa                                  393

<210> SEQ ID NO 30
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atgtttgttg ctgccggaca atttgccgta acgccggact ggacgggaaa cgcgcagacc      60
tgcgtcagca tgatgcgcca ggccgcggag cggggggcgt cgcttctggt tctgcctgag     120
gcgttgctgg cgcgagacga taacgatgcg gatttatcgg ttaaatccgc ccagcagctg     180
gatggcggct tcttacagct cttgctggcg gagagcgaaa acagcgcttt gacgacggtg     240 ctgacccctgc atatcccttc cggcgaaggt cgagcgacga atacgctggt ggccctgcgt     300
caggggaaga ttgtggcgca atatcagaaa ctgcatctct atgatgcgtt caatatccag     360
gaatccaggc tggtcgatgc cgggcggcaa attccgccgc tgatcgaagt cgacgggatg     420
cgcgtcgggc tgatgacctg ctacgattta cgtttccctg agctggcgct gtcgttagcg     480
ctcagcggcg cgcagctcat agtgttgcct gccgcgtggg taaaagggcc gctgaaggaa     540
catcactggg cgacgctgct ggcggcgcgg gcgctggata caacctgcta tattgtcgcc     600
gcaggagagt gcgggacgcg taatatcggt caaagccgta ttatcgaccc cttagggaca     660
acgcttgccg gggcgggaga gcggccgcag ttgattttg ccgaactttc agctgattat      720
attcagcagg tacgcgagcg cctgccggtg ttgcgcaatc gccgctttgc gccaccgcaa     780
ttattatga                                                            789

<210> SEQ ID NO 31
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
atggccaata ataccactgg gttaacccga attattaaag cggccgggta ttcctggaaa      60
ggattccgtg cggcgtgggt caatgaggcc gcatttcgtc aggaaggcat cgcggccgtt     120
attgccgtgg cgatcgcctg ctggttggac gtcgatgcca tcacgcgggt gctgctcatt     180
```

-continued

```
agctcggtcc tgttagtgat gatagttgaa attatcaata gcgcgattga ggcggtggtt        240
gaccgtatcg gtcccgagca tcatgagctt tcggggcgag cgaaagatat gggatcggcg        300
gcggtactgc tggcgattat catcgcgctg atcgcgtggg gaacgctgct gtgggcgaac        360
taccgctaa                                                                 369

<210> SEQ ID NO 32
<211> LENGTH: 1122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atgcataacc aggctccgat tcaacgtaga aaatcaaaac gaatttacgt tgggaatgtg         60
ccgattggcg atggcgcccc catcgccgta cagtcgatga caaacacgcg caccaccgat        120
gtggcggcga cggtaaatca aattaaagcc ctcgagcgcg ttggcgcgga tatcgtgcgc        180
gtttcggtgc cgacgatgga tgcggcggaa gcgttcaaac ttatcaaaca gcaggttaac        240
gtcccgctgg ttgccgatat ccacttcgat taccgcattg cgctgaaggt agcggaatac        300
ggcgttgatt gcctgcgtat taacccgggc aatatcggca acgaagagcg tatccgcatg        360
gtggtggact cgcgctcgcga taaaaatatt cctatccgta tcggggtaaa cgccggttct        420
ctggaaaaag atctccagga aaaatacggc gaaccgactc cgcaggcgct gctggaatcg        480
gcaatgcgcc atgttgatca tctcgatcgt ctcaacttcg atcagtttaa agtcagcgta        540
aaagcctccg atgtgttcct cgcggttgaa tcctatcgcc tgttggcgaa acagatcgat        600
cagcctctgc acctcgggat caccgaagcg ggcggcgcgc gcagcggcgc ggtgaagtcc        660
gcgatcggcc tcggcctgct gctgtctgaa gggattggcg atacgctgcg cgtctctctg        720
gcggcggatc ccgttgaaga gatcaaagtg ggcttcgata ttctcaagtc gctgcgtatt        780
cgctctcgcg ggatcaactt tattgcctgc ccgacctgtt cacgtcagga gtttgacgtt        840
atcggtaccg ttaacgcgct ggagcagcgc ctggaagata tcattacgcc gatggatatt        900
tcgatcattg gctgcgtggt aaacggtccc ggcgaggcgc tggtttccac cctcggcgta        960
accggcggca ataagaaaag cggcctgtac gaagacggcg tacgtaaaga caggctggat       1020
aacgacgata tgatcgatca gctggaagcg cgtattcgcg ctaaagcatc gatgctggat       1080
gaggcgcgtc gtatcgatat ccagcaggtt gaagcgaaat aa                          1122

<210> SEQ ID NO 33
<211> LENGTH: 876
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atgagccata ttcaacggga aacgtcttgc tccaggccgc gattaaattc caacatggat         60
gctgatttat atgggtataa atgggctcgc gataatgtcg ggcaatcagg tgcgacaatc        120
tatcgattgt atgggaagcc cgatgcgcca gagttgtttc tgaaacatgg caaaggtagc        180
gttgccaatg atgttacaga tgagatggtc agactaaact ggctgacgga atttatgcct        240
cttccgacca tcaagcattt tatccgtact cctgatgatg catggttact caccactgcg        300
```

```
atccccggga aaacagcatt ccaggtatta gaagaatatc ctgattcagg tgaaaatatt      360
gttgatgcgc tggcagtgtt cctgcgccgg ttgcattcga ttcctgtttg taattgtcct      420
tttaacagcg atcgcgtatt tcgtctcgct caggcgcaat cacgaatgaa taacggtttg      480
gttgatgcga gtgattttga tgacgagcgt aatggctggc ctgttgaaca agtctggaaa      540
gaaatgcata agcttttgcc attctcaccg gattcagtcg tcactcatgg tgatttctca      600
cttgataacc ttattttga cgaggggaaa ttaataggtt gtattgatgt tggacgagtc       660
ggaatcgcag accgatacca ggatcttgcc atcctatgga actgcctcgg tgagttttct      720
ccttcattac agaaacggct tttttcaaaaa tatggtattg ataatcctga tatgaataaa     780
ttgcagtttc atttgatgct cgatgagttt ttctaataag cctgcctggt tctgcgtttc      840
ccgctcttta ataccctgac cggaggtgag caatga                                876
```

<210> SEQ ID NO 34
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
atgagcatca cggcgttatc agcatcattt cctgagggga atatcgccag ccgcttgtcg       60
ctgcaacatc cttcactgtt ttataccgtg gttgaacaat cttcggtggc gagcgtgttg      120
agtcatcctg actagctgag atgagggctc gcccccctcgt cccgacactt ccagatcgcc      180
atagcgcaca gcgcctcgag cggtggtaac ggcgcagtgg cggttttcat ggcttgttat      240
gactgttttt ttggggtaca gtctatgcct cgggcatcca agcagcaagc gcgttacgcc      300
gtgggtcgat gtttgatgtt atggagcagc aacgatgtta cgcagcaggg cagtcgccct      360
aaaacaaagt aaacatcat gagggaagcg gtgatcgccg aagtatcgac tcaactatca      420
gaggtagttg gcgtcatcga gcgccatctc gaaccgacgt tgctggccgt acatttgtac      480
ggctccgcag tggatggcgg cctgaagcca cacagtgata ttgatttgct ggttacggtg      540
accgtaaggc ttgatgaaac aacgcggcga gctttgatca cgaccttttt ggaaacttcg      600
gcttcccctg gagagagcga gattctccgc gctgtagaag tcaccattgt tgtgcacgac      660
gacatcattc cgtggcgtta tccagctaag cgcgaactgc aatttggaga atggcagcgc      720
aatgacattc ttgcaggtat cttcgagcca gccacgatcg acattgatct ggctatcttg      780
ctgacaaaag caagagaaca tagccgttgcc ttggtaggtc cagcggcgga ggaactcttt     840
gatccggttc ctgaacagga tctatttgag gcgctaaatg aaaccttaac gctatggaac      900
tcgccgcccg actgggctgg cgatgagcga aatgtagtgc ttacgttgtc ccgcatttgg      960
tacagcgcag taaccggcaa aatcgcgccg aaggatgtcg ctgccgactg gcaatggag     1020 cgcctgccgg cccagtatca gcccgtcata cttgaagcta gacaggctta tcttggacaa     1080
gaagaagatc gcttggcctc gcgcgcagat cagttggaag aatttgtcca ctacgtgaaa     1140
ggcgagatca ccaaggtagt cggcaaataa tgtctaacaa ttcgttcaag ccgacgccgc     1200
ttcgcggcgc ggcttaactc aagcgttaga tgcactaagc acataattgc tcacagccaa     1260
actatcaggt caagtctgct tttattattt ttaagcgtgc ataataagcc ctacacaaat    1320
ggtacccgac cggtggtgaa tttaatctcg ctgacgtgta gacattccct tatccagacg     1380
ctgatcgccc atcatcgcgg ttctttagat ctctcggtcc gccctgatgg cggcaccttg    1440
```

-continued

```
ctgacgttac gcctgccggt acagcaggtt atcaccggag gcttaaaatg a        1491

<210> SEQ ID NO 35
<211> LENGTH: 1021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
ctgatccttc aactcagcaa aagttcgatt tattcaacaa agccacgttg tgtctcaaaa        60
tctctgatgt tacattgcac aagataaaaa tatatcatca tgaacaataa aactgtctgc       120
ttacataaac agtaatacaa ggggtgttat gagccatatt caacgggaaa cgtcttgctc       180
caggccgcga ttaaattcca acatggatgc tgatttatat gggtataaat gggctcgcga       240
taatgtcggg caatcaggtg cgacaatcta tcgattgtat gggaagcccg atgcgccaga       300
gttgtttctg aaacatggca aaggtagcgt tgccaatgat gttacagatg agatggtcag       360
actaaactgg ctgacggaat ttatgcctct tccgaccatc aagcatttta tccgtactcc       420
tgatgatgca tggttactca ccactgcgat ccccgggaaa acagcattcc aggtattaga       480
agaatatcct gattcaggtg aaaatattgt tgatgcgctg gcagtgttcc tgcgccggtt       540
gcattcgatt cctgtttgta attgtccttt aacagcgat cgcgtatttc gtctcgctca       600
ggcgcaatca cgaatgaata acggtttggt tgatgcgagt gattttgatg acgagcgtaa       660
tggctggcct gttgaacaag tctggaaaga aatgcataag cttttgccat tctcaccgga       720
ttcagtcgtc actcatggtg atttctcact tgataacctt attttttgacg aggggaaatt       780 aataggttgt attgatgttg gacgagtcgg aatcgcagac cgataccagg atcttgccat       840
cctatggaac tgcctcggtg agtttttctcc ttcattacag aaacggcttt ttcaaaaata       900
tggtattgat aatcctgata tgaataaatt gcagtttcat ttgatgctcg atgagttttt       960
ctaataagcc ttgacccta c gattcccgct atttcattca ctgaccggag gttcaaaatg      1020
a                                                                        1021

<210> SEQ ID NO 36
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
atgaagatag caacaatgaa aacaggtctg ggagcgttgg ctcttcttcc ctgatccttc        60
aactcagcaa aagttcgatt tattcaacaa agccacgttg tgtctcaaaa tctctgatgt       120
tacattgcac aagataaaaa tatatcatca tgaacaataa aactgtctgc ttacataaac       180
agtaatacaa ggggtgttat gagccatatt caacgggaaa cgtcttgctc ccgtccgcgc       240
ttaaactcca acatggacgc tgatttatat gggtataaat gggctcgcga taatgtcggg       300
caatcaggtg cgacaatcta tcgcttgtat gggaagcccg atgcgccaga gttgtttctg       360
aaacatggca aaggtagcgt tgccaatgat gttacagatg agatggtccg tctcaactgg       420
ctgacggagt ttatgcctct cccgaccatc aagcatttta tccgtactcc tgatgatgcg       480
tggttactca ccaccgcgat tcctgggaaa acagccttcc aggtattaga agaatatcct       540
gattcaggtg aaaatattgt tgatgcgctg gccgtgttcc tgcgccggtt acattcgatt       600
```

```
cctgtttgta attgtccttt taacagcgat cgtgtatttc gtcttgctca ggcgcaatca      660
cgcatgaata acggtttggt tgatgcgagt gattttgatg acgagcgtaa tggctggcct      720
gttgaacaag tctggaaaga aatgcacaag ctcttgccat tctcaccgga ttcagtcgtc      780
actcatggtg atttctcact tgataacctt attttttgacg aggggaaatt aataggttgt      840
attgatgttg acgggtcgg  aatcgcagac cgttaccagg accttgccat tctttggaac      900
tgcctcggtg agtttctcc  ttcattacag aaacggcttt ttcaaaaata tggtattgat      960
aatcctgata tgaataaatt gcagtttcat ttgatgctcg atgagttttt ctaataagcc     1020
tgtgaagggc tggacgtaaa cagccacggc gaaaacgcct acaacgcctg a              1071
```

```
<210> SEQ ID NO 37
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
```

```
atgaccctga atatgatgct cgataacgcc gtacccgagg cgattgccgg ctgatccttc       60
aactcagcaa aagttcgatt tattcaacaa agccacgttg tgtctcaaaa tctctgatgt      120
tacattgcac aagataaaaa tatatcatca tgaacaataa aactgtctgc ttacataaac      180
agtaatacaa ggggtgttat gagccatatt caacgggaaa cgtcttgctc cgtccgcgc       240 ttaaactcca acatggacgc tgatttatat gggtataaat gggctcgcga taatgtcggg      300
caatcaggtg cgacaatcta tcgcttgtat gggaagcccg atgcgccaga gttgtttctg      360
aaacatggca aaggtagcgt tgccaatgat gttacagatg agatggtccg tctcaactgg      420
ctgacggagt ttatgcctct cccgaccatc aagcatttta tccgtactcc tgatgatgcg      480
tggttactca ccaccgcgat tcctgggaaa acagccttcc aggtattaga agaatatcct      540
gattcaggtg aaaatattgt tgatgcgctg gccgtgttcc tgcgccggtt acattcgatt      600
cctgtttgta attgtccttt taacagcgat cgtgtatttc gtcttgctca ggcgcaatca      660
cgcatgaata acggtttggt tgatgcgagt gattttgatg acgagcgtaa tggctggcct      720
gttgaacaag tctggaaaga aatgcacaag ctcttgccat tctcaccgga ttcagtcgtc      780
actcatggtg atttctcact tgataacctt attttttgacg aggggaaatt aataggttgt      840
attgatgttg acgggtcgg  aatcgcagac cgttaccagg accttgccat tctttggaac      900
tgcctcggtg agtttctcc  ttcattacag aaacggcttt ttcaaaaata tggtattgat      960
aatcctgata tgaataaatt gcagtttcat ttgatgctcg atgagttttt ctaataagcc     1020
ttggttctgc gtttcccgct ctttaatacc ctgaccggag gtgagcaatg a              1071
```

```
<210> SEQ ID NO 38
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
```

```
atgaccctga atatgatgat ggatgccggc ggacatcatc gcgacaaaca atattaatac       60
cggcaaccac accggcaatt tacgagactg cgcaggcatc ctttctcccg tcaatttctg      120
```

-continued

```
tcaaataaag taaaagaggc agtctacttg aattacccc ggctggttga gcgtttgttg      180
aaaaaaagta actgaaaaat ccgtagaata gcgccactct gatggttaat taacctattc      240
aattaagaat tatctggatg aatgtgccat taaatgcgca gcataatggt gcgttgtgcg      300
ggaaaactgc ttttttttga aagggttggt cagtagcgga aacaactcac ttcacacccc      360
gaagggggaa gttgcctgac cctacgattc ccgctatttc attcactgac cggaggttca      420
aaatga                                                                  426
```

```
<210> SEQ ID NO 39
<211> LENGTH: 446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atgaccctga atatgatgat ggatgccggc tcaccacggc gataaccata ggttttcggc       60
gtggccacat ccatggtgaa tcccactttt tccagcacgc gcgccacttc atcgggtctt      120
aaatacatag attttcctcg tcatctttcc aaagcctcgc caccttacat gactgagcat      180
ggaccgtgac tcagaaaatt ccacaaacga acctgaaagg cgtgattgcc gtctggcctt      240
aaaaattatg gtctaaacta aaatttacat cgaaaacgag ggaggatcct atgtttaaca      300
aaccgaatcg ccgtgacgta gatgaaggtg ttgaggatat taaccacgat gttaaccagc      360
tcgaactcac ttcacacccc gaagggggaa gttgcctgac cctacgattc ccgctatttc      420
attcactgac cggaggttca aaatga                                           446
```

```
<210> SEQ ID NO 40
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atgaccctga atatgatgat ggatgccggc tgacgaggca ggttacatca ctggtgaaac       60
cctgcacgtc aatggcggaa tgtatatggt ttaaccacga tgaaaattat ttgcgttatt      120
agggcgaaag gcctcaaaat agcgtaaaat cgtggtaaga actgccggga tttagttgca      180 aattttcaa cattttatac actacgaaaa ccatcgcgaa agcgagtttt gataggaaat       240
ttaagagtat gagcactatc gaagaacgcg ttaagaaaat tatcggcgaa cagctgggcg      300
ttaagcagga agaagttacc aacaatgctt ccttcgttga agacctgggc gctgattctc      360
ttgacaccga actcacttca cacccgaag ggggaagttg cctgacccta cgattcccgc       420
tatttcattc actgaccgga ggttcaaaat ga                                    452
```

```
<210> SEQ ID NO 41
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atgaccctga atatgatgat ggatgccggc cgtcctgtaa taataaccgg acaattcgga       60
```

```
ctgattaaaa aagcgccctt gtggcgcttt ttttatattc ccgcctccat ttaaaataaa      120
aaatccaatc ggatttcact atttaaactg gccattatct aagatgaatc cgatggaagc      180
tcgctgtttt aacacgcgtt ttttaacctt ttattgaaag tcggtgcttc tttgagcgaa      240
cgatcaaatt taagtggatt cccatcaaaa aaatattctc aacctaaaaa agtttgtgta      300
atacttgtaa cgctacatgg agattaactc aatctagagg gtattaataa tgaatcgtac      360
taaactggta ctgggcgcaa ctcacttcac accccgaagg gggaagttgc ctgaccctac      420
gattcccgct atttcattca ctgaccggag gttcaaaatg a                         461
```

<210> SEQ ID NO 42
<211> LENGTH: 463
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
atgaccctga atatgatgat ggatgccggc atattgacac catgacgcgc gtaatgctga       60
ttggttctgt gacgctggta atgattgtcg aaattctgaa cagtgccatc gaagccgtag      120
tagaccgtat tggtgcagaa ttccatgaac tttccgggcg ggcgaaggat atggggtcgg      180
cggcggtgct gatgtccatc ctgctggcga tgtttacctg gatcgcatta ctctggtcac      240
attttcgata acgcttccag aattcgataa cgccctggtt ttttgcttaa atttggttcc      300
aaaatcgcct ttagctgtat atactcacag cataactgta tatacaccca gggggcggga      360
tgaaagcatt aacggccagg aactcacttc acaccccgaa gggggaagtt gcctgaccct      420
acgattcccg ctatttcatt cactgaccgg aggttcaaaa tga                       463
```

<210> SEQ ID NO 43
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
atgaccctga atatgatgat ggatgccggc atcatattgc gctccctggt tatcatttgt       60
tactaaatga aatgttataa tataacaatt ataaatacca catcgctttc aattcaccag      120
ccaaatgaga ggagcgccgt ctgacatagc cagcgctata aaacatagca ttatctatat      180
gtttatgatt aataactgat ttttgcgttt tggatttggc tgtggcatcc ttgccgctct      240
tttcgcagcg tctgcgtttt tgccctccgg tcagggcatt taagggtcag caatgagttt      300
ttacgcaatt acgattcttg ccttcggcat gtcgatggat gctttaactc acttcacacc      360
ccgaaggggg aagttgcctg accctacgat tcccgctatt tcattcactg accggaggtt      420
caaaatga                                                              428
```

<210> SEQ ID NO 44
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

-continued

```
atgaccctga atatgatgat ggatgccggc cgcgtcaggt tgaacgtaaa aaagtcggtc       60
tgcgcaaagc acgtcgtcgt ccgcagttct ccaaacgtta attggtttct gcttcggcag      120
aacgattggc gaaaaaaccc ggtgcgaacc gggtttttttt atggataaag atcgtgttat     180
ccacagcaat ccattgatta tctcttcttt ttcagcattt ccagaatccc ctcaccacaa      240
agcccgcaaa atctggtaaa ctatcatcca attttctgcc caaatggctg ggattgttca      300 tttttttgttt gccttacaac gagagtgaca gtacgcgcgg gtagttaact caacatctga     360
ccggtcgata actcacttca caccccgaag ggggaagttg cctgacccta cgattcccgc      420
tatttcattc actgaccgga ggttcaaaat ga                                    452
```

```
<210> SEQ ID NO 45
<211> LENGTH: 410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atgaccctga atatgatgat ggatgccggc cctgtatgaa gatggcgtgc gcaaagatcg       60
cctggataac agcgatatga ttagccagct tgaagcccgc attcgcgcga aagcgtcaat      120
gctggacgaa gcgcgtcgta tcgatgtgca acaggtagaa aaataaggtt gctgggaagc      180
ggcaggcttc ccgtgtatga tgaacccgcc cggcgcgacc cgttgttcgt cgcggccccg      240
agggttcatt ttttgtatta ataaagagaa taaacgtggc aaaaaatatt caagccattc      300
gcggcatgaa cgattatctg cctggcgaac tcacttcaca ccccgaaggg ggaagttgcc      360
tgaccctacg attcccgcta tttcattcac tgaccggagg ttcaaaatga                 410
```

```
<210> SEQ ID NO 46
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atgaaaaaga ttgatgcgat tattaaacct ttcaaactgg atgacgtgcg ctgatccttc       60
aactcagcaa aagttcgatt tattcaacaa agccacgttg tgtctcaaaa tctctgatgt      120
tacattgcac aagataaaaa tatatcatca tgaacaataa aactgtctgc ttacataaac      180
agtaatacaa ggggtgttat gagccatatt caacgggaaa cgtcttgctc ccgtccgcgc      240
ttaaactcca acatggacgc tgatttatat gggtataaat gggctcgcga taatgtcggg      300
caatcaggtg cgacaatcta tcgcttgtat gggaagcccg atgcgccaga gttgtttctg      360
aaacatggca aaggtagcgt tgccaatgat gttacagatg agatggtccg tctcaactgg      420
ctgacggagt ttatgcctct cccgaccatc aagcatttta tccgtactcc tgatgatgcg      480
tggttactca ccaccgcgat tcctgggaaa acagccttcc aggtattaga agaatatcct      540
gattcaggtg aaaatattgt tgatgcgctg gccgtgttcc tgcgccggtt acattcgatt      600
cctgtttgta attgtccttt aacagcgat cgtgtatttc gtcttgctca ggcgcaatca      660
cgcatgaata acggtttggt tgatgcgagt gattttgatg acgagcgtaa tggctggcct      720
gttgaacaag tctggaaaga aatgcacaag ctccttgccat tctcaccgga ttcagtcgtc      780
actcatggtg atttctcact tgataacctt attttttgacg aggggaaatt aataggttgt      840
```

```
attgatgttg gacgggtcgg aatcgcagac cgttaccagg accttgccat tctttggaac        900
tgcctcggtg agttttctcc ttcattacag aaacggcttt ttcaaaaata tggtattgat        960
aatcctgata tgaataaatt gcagtttcat ttgatgctcg atgagttttt ctaataagcc       1020
tcgcgcgtga ttcgtatccg caccggcgaa gaagacgacg cggcgattta a               1071
```

```
<210> SEQ ID NO 47
<211> LENGTH: 1295
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atgaccatga acctgatgac ggatgtcgtc tcagccaccg ggatcgccgg gttgctttca         60
cgacaacacc cgacgctgtt ttttacacta attgaacagg cccccgtggc gatcacgctg        120
acggataccg ctgcccgcat tgtctatgcc aacccgggcg tgttgagtca tcctgactag        180
ctgagatgag ggctcgcctg atccttcaac tcagcaaaag ttcgatttat tcaacaaagc        240
cacgttgtgt ctcaaaatct ctgatgttac attgcacaag ataaaaatat atcatcatga        300
acaataaaac tgtctgctta cataaacagt aatacaaggg gtgttatgag ccatattcaa        360
cgggaaacgt cttgctccag gccgcgatta aattccaaca tggatgctga tttatatggg        420
tataaatggg ctcgcgataa tgtcgggcaa tcaggtgcga caatctatcg attgtatggg        480
aagcccgatg cgccagagtt gtttctgaaa catggcaaag gtagcgttgc caatgatgtt        540
acagatgaga tggtcagact aaactggctg acggaattta tgcctcttcc gaccatcaag        600
cattttatcc gtactcctga tgatgcatgg ttactcacca ctgcgatccc cgggaaaaca        660
gcattccagg tattagaaga atatcctgat tcaggtgaaa atattgttga tgcgctggca        720
gtgttcctgc gccggttgca ttcgattcct gtttgtaatt gtccttttaa cagcgatcgc        780
gtatttcgtc tcgctcaggc gcaatcacga atgaataacg gtttggttga tgcgagtgat        840
tttgatgacg agcgtaatgg ctggcctgtt gaacaagtct ggaaagaaat gcataagctt        900
ttgccattct caccggattc agtcgtcact catggtgatt tctcacttga taaccttatt        960
tttgacgagg gaaattaat aggttgtatt gatgttggac gagtcggaat cgcagaccga       1020
taccaggatc ttgccatcct atggaactgc ctcggtgagt tttctccttc attacagaaa       1080 cggcttttc aaaaatatgg tattgataat cctgatatga ataaattgca gtttcatttg       1140
atgctcgatg agttttctta ataagcctga ccggtggtga atttaatctc gctgacgtgt       1200
agacattcat cgatctgcat ccacggtccg gcggcggtac ctgcctgacg ctacgtttac       1260
cgctctttta tgaactgacc ggaggcccaa gatga                                  1295
```

```
<210> SEQ ID NO 48
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
atgagcatca cggcgttatc agcatcattt cctgagggga atatcgccag ccgcttgtcg         60
ctgcaacatc cttcactgtt ttataccgtg gttgaacaat cttcggtggc gagcgtgttg        120
```

```
agtcatcctg actagctgag atgagggctc gcccctcgt cccgacactt ccagatcgcc       180
atagcgcaca gcgcctcgag cggtggtaac ggcgcagtgg cggttttcat ggcttgttat       240
gactgttttt ttggggtaca gtctatgcct cgggcatcca agcagcaagc gcgttacgcc       300
gtgggtcgat gtttgatgtt atggagcagc aacgatgtta cgcagcaggg cagtcgccct       360
aaaacaaagt taaacatcat gagggaagcg gtgatcgccg aagtatcgac tcaactatca       420
gaggtagttg gcgtcatcga gcgccatctc gaaccgacgt tgctggccgt acatttgtac       480
ggctccgcag tggatggcgg cctgaagcca cacagtgata ttgatttgct ggttacggtg       540
accgtaaggc ttgatgaaac aacgcggcga gctttgatca acgacctttt ggaaacttcg       600 gcttccctg gagagagcga gattctccgc gctgtagaag tcaccattgt tgtgcacgac       660
gacatcattc cgtggcgtta tccagctaag cgcgaactgc aatttggaga atggcagcgc       720
aatgacattc ttgcaggtat cttcgagcca gccacgatcg acattgatct ggctatcttg       780
ctgacaaaag caagagaaca tagcgttgcc ttggtaggtc cagcggcgga ggaactcttt       840
gatccggttc ctgaacagga tctatttgag gcgctaaatg aaaccttaac gctatggaac       900
tcgccgcccg actgggctgg cgatgagcga aatgtagtgc ttacgttgtc ccgcatttgg       960
tacagcgcag taaccggcaa aatcgcgccg aaggatgtcg ctgccgactg ggcaatggag      1020
cgcctgccgg cccagtatca gcccgtcata cttgaagcta gacaggctta tcttggacaa      1080
gaagaagatc gcttggcctc gcgcgcagat cagttggaag aatttgtcca ctacgtgaaa      1140
ggcgagatca ccaaggtagt cggcaaataa tgtctaacaa ttcgttcaag ccgacgccgc      1200
ttcgcggcgc ggcttaactc aagcgttaga tgcactaagc acataattgc tcacagccaa      1260
actatcaggt caagtctgct tttattattt ttaagcgtgc ataataagcc ctacacaaat      1320
ggtacccgac cggtggtgaa tttaatctcg ctgacgtgta gacattccct tatccagacg      1380
ctgatcgccc atcatcgcgg ttctttagat ctctcggtcc gccctgatgg cggcaccttg      1440
ctgacgttac gcctgccggt acagcaggtt atcaccggag gcttaaaatg a              1491
```

<210> SEQ ID NO 49
<211> LENGTH: 1021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
ctgatccttc aactcagcaa aagttcgatt tattcaacaa agccacgttg tgtctcaaaa        60
tctctgatgt tacattgcac aagataaaaa tatatcatca tgaacaataa aactgtctgc       120
ttacataaac agtaatacaa ggggtgttat gagccatatt caacgggaaa cgtcttgctc       180
caggccgcga ttaaattcca acatggatgc tgatttatat gggtataaat gggctcgcga       240
taatgtcggg caatcaggtg cgacaatcta tcgattgtat gggaagcccg atgcgccaga       300
gttgtttctg aaacatggca aaggtagcgt tgccaatgat gttacagatg agatggtcag       360
actaaactgg ctgacggaat ttatgcctct tccgaccatc aagcatttta tccgtactcc       420
tgatgatgca tggttactca ccactgcgat ccccgggaaa acagcattcc aggtattaga       480
agaatatcct gattcaggtg aaaatattgt tgatgcgctg gcagtgttcc tgcgccggtt       540
gcattcgatt cctgtttgta attgtccttt aacagcgat cgcgtatttc gtctcgctca        600
ggcgcaatca cgaatgaata acggtttggt tgatgcgagt gattttgatg acgagcgtaa       660
```

```
tggctggcct gttgaacaag tctggaaaga aatgcataag cttttgccat tctcaccgga     720
ttcagtcgtc actcatggtg atttctcact tgataacctt attttgacg aggggaaatt     780 aataggttgt attgatgttg gacgagtcgg aatcgcagac cgataccagg atcttgccat     840
cctatggaac tgcctcggtg agttttctcc ttcattacag aaacggcttt ttcaaaaata     900
tggtattgat aatcctgata tgaataaatt gcagtttcat ttgatgctcg atgagttttt     960
ctaataagcc ttgaccctac gattcccgct atttcattca ctgaccggag gttcaaaatg     1020
a                                                                     1021

<210> SEQ ID NO 50
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
atgaccctga atatgatgct cgataacgcc gtacccgagg cgattgccgg ctgatccttc      60
aactcagcaa aagttcgatt tattcaacaa agccacgttg tgtctcaaaa tctctgatgt     120
tacattgcac aagataaaaa tatatcatca tgaacaataa aactgtctgc ttacataaac     180
agtaatacaa ggggtgttat gagccatatt caacgggaaa cgtcttgctc ccgtccgcgc     240
ttaaactcca acatggacgc tgatttatat gggtataaat gggctcgcga taatgtcggg     300
caatcaggtg cgacaatcta tcgcttgtat gggaagcccg atgcgccaga gttgtttctg     360
aaacatggca aaggtagcgt tgccaatgat gttacagatg agatggtccg tctcaactgg     420
ctgacggagt ttatgcctct cccgaccatc aagcatttta tccgtactcc tgatgatgcg     480
tggttactca ccaccgcgat tcctgggaaa acagccttcc aggtattaga agaatatcct     540
gattcaggtg aaaatattgt tgatgcgctg gccgtgttcc tgcgccggtt acattcgatt     600
cctgtttgta attgtccttt aacagcgat cgtgtatttc gtcttgctca ggcgcaatca     660
cgcatgaata acggtttggt tgatgcgagt gattttgatg acgagcgtaa tggctggcct     720
gttgaacaag tctggaaaga aatgcacaag ctcttgccat tctcaccgga ttcagtcgtc     780
actcatggtg atttctcact tgataacctt attttgacg aggggaaatt aataggttgt     840
attgatgttg gacgggtcgg aatcgcagac cgttaccagg accttgccat tctttggaac     900
tgcctcggtg agttttctcc ttcattacag aaacggcttt ttcaaaaata tggtattgat     960
aatcctgata tgaataaatt gcagtttcat ttgatgctcg atgagttttt ctaataagcc     1020
ttggttctgc gtttcccgct ctttaatacc ctgaccggag gtgagcaatg a             1071

<210> SEQ ID NO 51
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
atgaccctga atatgatgat ggatgccggc cgtcctgtaa taataaccgg acaattcgga      60
ctgattaaaa aagcgccctt gtggcgcttt ttttatattc ccgcctccat ttaaaataaa     120
aaatccaatc ggatttcact atttaaactg gccattattc aagatgaatc cgatggaagc     180
tcgctgtttt aacacgcgtt ttttaacctt ttattgaaag tcggtgcttc tttgagcgaa     240
```

```
cgatcaaatt taagtggatt cccatcaaaa aaatattctc aacctaaaaa agtttgtgta      300
atacttgtaa cgctacatgg agattaactc aatctagagg gtattaataa tgaatcgtac      360
taaactggta ctgggcgcaa ctcacttcac accccgaagg gggaagttgc ctgaccctac      420
gattcccgct atttcattca ctgaccggag gttcaaaatg a                          461
```

```
<210> SEQ ID NO 52
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
atgaccctga atatgatgat ggatgccggc ggacatcatc gcgacaaaca atattaatac       60
cggcaaccac accggcaatt tacgagactg cgcaggcatc ctttctcccg tcaatttctg      120
tcaaataaag taaaagaggc agtctacttg aattacccccc ggctggttga gcgtttgttg     180
aaaaaaagta actgaaaaat ccgtagaata gcgccactct gatggttaat taacctattc      240
aattaagaat tatctggatg aatgtgccat taaatgcgca gcataatggt gcgttgtgcg      300
ggaaaactgc ttttttttga aagggttggt cagtagcgga aacaactcac ttcacacccc      360 gaaggggggaa gttgcctgac cctacgattc ccgctatttc attcactgac cggaggttca      420
aaatga                                                                 426
```

```
<210> SEQ ID NO 53
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atgaccctga atatgatgat ggatgccggc tgacgaggca ggttacatca ctggtgaaac       60
cctgcacgtc aatggcggaa tgtatatggt ttaaccacga tgaaaattat ttgcgttatt      120
agggcgaaag gcctcaaaat agcgtaaaat cgtggtaaga actgccggga tttagttgca      180 aattttcaa cattttatac actacgaaaa ccatcgcgaa agcgagtttt gataggaaat        240
ttaagagtat gagcactatc gaagaacgcg ttaagaaaat tatcggcgaa cagctgggcg      300
ttaagcagga agaagttacc aacaatgctt ccttcgttga agacctgggc gctgattctc      360
ttgacaccga actcacttca caccccgaag ggggaagttg cctgacccta cgattcccgc      420
tatttcattc actgaccgga ggttcaaaat ga                                    452
```

```
<210> SEQ ID NO 54
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atgaccctga atatgatgat ggatgccggc ggacatcatc gcgacaaaca atattaatac       60
cggcaaccac accggcaatt tacgagactg cgcaggcatc ctttctcccg tcaatttctg      120
tcaaataaag taaaagaggc agtctacttg aattacccccc ggctggttga gcgtttgttg     180
```

```
aaaaaaagta actgaaaaat ccgtagaata gcgccactct gatggttaat taacctattc      240
aattaagaat tatctggatg aatgtgccat taaatgcgca gcataatggt gcgttgtgcg      300
ggaaaactgc tttttttttga aagggttggt cagtagcgga aacaactcac ttcacacccc     360 gaaggggggaa gttgcctgac cctacgattc ccgctatttc attcactgac cggaggttca     420
aaatga                                                                  426
```

```
<210> SEQ ID NO 55
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atgaccctga atatgatgat ggatgccggc cgtcctgtaa taataaccgg acaattcgga       60
ctgattaaaa aagcgccctt gtggcgcttt ttttatattc ccgcctccat ttaaaataaa      120
aaatccaatc ggatttcact atttaaactg gccattatct aagatgaatc cgatggaagc      180
tcgctgtttt aacacgcgtt ttttaacctt ttattgaaag tcggtgcttc tttgagcgaa      240
cgatcaaatt taagtggatt cccatcaaaa aaatattctc aacctaaaaa agtttgtgta      300
atacttgtaa cgctacatgg agattaactc aatctagagg gtattaataa tgaatcgtac      360
taaactggta ctgggcgcaa ctcacttcac accccgaagg gggaagttgc ctgaccctac      420
gattcccgct atttcattca ctgaccggag gttcaaaatg a                          461
```

```
<210> SEQ ID NO 56
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atgagcatca cggcgttatc agcatcattt cctgagggga atatcgccag ccgcttgtcg       60
ctgcaacatc cttcactgtt ttataccgtg gttgaacaat cttcggtggc gagcgtgttg      120
agtcatcctg actagctgag atgagggctc gccccctcgt cccgacactt ccagatcgcc      180
atagcgcaca gcgcctcgag cggtggtaac ggcgcagtgg cggttttcat ggcttgttat      240
gactgttttt ttggggtaca gtctatgcct cgggcatcca agcagcaagc gcgttacgcc      300
gtgggtcgat gtttgatgtt atggagcagc aacgatgtta cgcagcaggg cagtcgccct      360
aaaacaaagt taaacatcat gagggaagcg gtgatcgccg aagtatcgac tcaactatca      420
gaggtagttg gcgtcatcga gcgccatctc gaaccgacgt tgctggccgt acatttgtac      480
ggctccgcag tggatggcgg cctgaagcca cacagtgata ttgatttgct ggttacggtg      540
accgtaaggc ttgatgaaac aacgcggcga gctttgatca acgacctttt ggaaacttcg      600
gcttcccctg gagagagcga gattctccgc gctgtagaag tcaccattgt tgtgcacgac      660
gacatcattc cgtggcgtta tccagctaag cgcgaactgc aatttggaga atggcagcgc      720
aatgacattc ttgcaggtat cttcgagcca gccacgatcg acattgatct ggctatcttg      780
ctgacaaaag caagagaaca tagcgttgcc ttggtaggtc cagcggcgga ggaactcttt      840
gatccggttc ctgaacagga tctatttgag gcgctaaatg aaaccttaac gctatggaac      900
```

```
tcgccgcccg actgggctgg cgatgagcga aatgtagtgc ttacgttgtc ccgcatttgg    960
tacagcgcag taaccggcaa aatcgcgccg aaggatgtcg ctgccgactg ggcaatggag    1020
cgcctgccgg cccagtatca gcccgtcata cttgaagcta gacaggctta tcttggacaa    1080
gaagaagatc gcttggcctc gcgcgcagat cagttggaag aatttgtcca ctacgtgaaa    1140
ggcgagatca ccaaggtagt cggcaaataa tgtctaacaa ttcgttcaag ccgacgccgc    1200
ttcgcggcgc ggcttaactc aagcgttaga tgcactaagc acataattgc tcacagccaa    1260
actatcaggt caagtctgct tttattattt ttaagcgtgc ataataagcc ctacacaaat    1320
ggtacccgac cggtggtgaa tttaatctcg ctgacgtgta gacattccct tatccagacg    1380
ctgatcgccc atcatcgcgg ttctttagat ctctcggtcc gccctgatgg cggcaccttg    1440
ctgacgttac gcctgccggt acagcaggtt atcaccggag gcttaaaatg a             1491
```

```
<210> SEQ ID NO 57
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
```

```
atgagcatca cggcgttatc agcatcattt cctgagggga atatcgccag ccgcttgtcg    60
ctgcaacatc cttcactgtt ttataccgtg gttgaacaat cttcggtggc gagcgtgttg    120
agtcatcctg actagctgag atgagggctc gcccctcgt cccgacactt ccagatcgcc     180
atagcgcaca gcgcctcgag cggtggtaac ggcgcagtgg cggtttttcat ggcttgttat    240 gactgttttt ttggggtaca gtctatgcct cgggcatcca agcagcaagc gcgttacgcc    300
gtgggtcgat gtttgatgtt atggagcagc aacgatgtta cgcagcaggg cagtcgccct    360
aaaacaaagt taaacatcat gagggaagcg gtgatcgccg aagtatcgac tcaactatca    420
gaggtagttg gcgtcatcga gcgccatctc gaaccgacgt tgctggccgt acatttgtac    480
ggctccgcag tggatggcgg cctgaagcca cacagtgata ttgatttgct ggttacggtg    540
accgtaaggc ttgatgaaac aacgcggcga gctttgatca cgacctttt ggaaacttcg     600 gcttcccctg agagagcga gattctccgc gctgtagaag tcaccattgt tgtgcacgac     660
gacatcattc cgtggcgtta tccagctaag cgcgaactgc aatttggaga atggcagcgc    720
aatgacattc ttgcaggtat cttcgagcca gccacgatcg acattgatct ggctatcttg    780
ctgacaaaag caagagaaca tagcgttgcc ttggtaggtc cagcggcgga ggaactcttt    840
gatccggttc ctgaacagga tctatttgag gcgctaaatg aaaccttaac gctatggaac    900
tcgccgcccg actgggctgg cgatgagcga aatgtagtgc ttacgttgtc ccgcatttgg    960
tacagcgcag taaccggcaa aatcgcgccg aaggatgtcg ctgccgactg ggcaatggag    1020
cgcctgccgg cccagtatca gcccgtcata cttgaagcta gacaggctta tcttggacaa    1080
gaagaagatc gcttggcctc gcgcgcagat cagttggaag aatttgtcca ctacgtgaaa    1140
ggcgagatca ccaaggtagt cggcaaataa tgtctaacaa ttcgttcaag ccgacgccgc    1200
ttcgcggcgc ggcttaactc aagcgttaga tgcactaagc acataattgc tcacagccaa    1260
actatcaggt caagtctgct tttattattt ttaagcgtgc ataataagcc ctacacaaat    1320
ggtacccgac cggtggtgaa tttaatctcg ctgacgtgta gacattccct tatccagacg    1380
ctgatcgccc atcatcgcgg ttctttagat ctctcggtcc gccctgatgg cggcaccttg    1440
```

```
ctgacgttac gcctgccggt acagcaggtt atcaccggag gcttaaaatg a          1491
```

```
<210> SEQ ID NO 58
<211> LENGTH: 1021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ctgatccttc aactcagcaa aagttcgatt tattcaacaa agccacgttg tgtctcaaaa       60
tctctgatgt tacattgcac aagataaaaa tatatcatca tgaacaataa aactgtctgc      120
ttacataaac agtaatacaa ggggtgttat gagccatatt caacgggaaa cgtcttgctc      180
caggccgcga ttaaattcca acatggatgc tgatttatat gggtataaat gggctcgcga      240
taatgtcggg caatcaggtg cgacaatcta tcgattgtat gggaagcccg atgcgccaga      300
gttgtttctg aaacatggca aaggtagcgt tgccaatgat gttacagatg agatggtcag      360
actaaactgg ctgacggaat ttatgcctct tccgaccatc aagcatttta tccgtactcc      420
tgatgatgca tggttactca ccactgcgat ccccgggaaa acagcattcc aggtattaga      480
agaatatcct gattcaggtg aaaatattgt tgatgcgctg gcagtgttcc tgcgccggtt      540
gcattcgatt cctgtttgta attgtccttt aacagcgat cgcgtatttc gtctcgctca       600
ggcgcaatca cgaatgaata cggtttggt tgatgcgagt gattttgatg acgagcgtaa       660
tggctggcct gttgaacaag tctggaaaga aatgcataag cttttgccat tctcaccgga      720
ttcagtcgtc actcatggtg atttctcact tgataacctt attttgacg aggggaaatt       780 aataggttgt attgatgttg gacgagtcgg aatcgcagac cgataccagg atcttgccat      840
cctatggaac tgcctcggtg agttttctcc ttcattacag aaacggcttt ttcaaaaata      900
tggtattgat aatcctgata tgaataaatt gcagtttcat ttgatgctcg atgagttttt      960
ctaataagcc ttgaccctac gattcccgct atttcattca ctgaccggag gttcaaaatg     1020
a                                                                    1021
```

```
<210> SEQ ID NO 59
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
atgagcatca cggcgttatc agcatcattt cctgagggga atatcgccag ccgcttgtcg       60
ctgcaacatc cttcactgtt ttataccgtg gttgaacaat cttcggtggc gagcgtgttg      120
agtcatcctg actagctgag atgagggctc gccccctcgt cccgacactt ccagatcgcc      180
atagcgcaca gcgcctcgag cggtggtaac ggcgcagtgg cggttttcat ggcttgttat      240
gactgttttt ttggggtaca gtctatgcct cgggcatcca agcagcaagc gcgttacgcc      300
gtgggtcgat gtttgatgtt atggagcagc aacgatgtta cgcagcaggg cagtcgccct      360
aaaacaaagt taaacatcat gagggaagcg gtgatcgccg aagtatcgac tcaactatca      420
gaggtagttg gcgtcatcga cgccatctc gaaccgacgt tgctggccgt acatttgtac       480
ggctccgcag tggatggcgg cctgaagcca cacagtgata ttgatttgct ggttacggtg      540
accgtaaggc ttgatgaaac aacgcggcga gctttgatca cgacctttt ggaaacttcg       600
```

```
gcttcccctg gagagagcga gattctccgc gctgtagaag tcaccattgt tgtgcacgac        660
gacatcattc cgtggcgtta tccagctaag cgcgaactgc aatttggaga atggcagcgc        720
aatgacattc ttgcaggtat cttcgagcca gccacgatcg acattgatct ggctatcttg        780
ctgacaaaag caagagaaca tagcgttgcc ttggtaggtc cagcggcgga ggaactcttt        840
gatccggttc ctgaacagga tctatttgag gcgctaaatg aaaccttaac gctatggaac        900
tcgccgcccg actgggctgg cgatgagcga aatgtagtgc ttacgttgtc ccgcatttgg        960
tacagcgcag taaccggcaa aatcgcgccg aaggatgtcg ctgccgactg ggcaatggag       1020
cgcctgccgg cccagtatca gcccgtcata cttgaagcta gacaggctta tcttggacaa       1080
gaagaagatc gcttggcctc gcgcgcagat cagttggaag aatttgtcca ctacgtgaaa       1140
ggcgagatca ccaaggtagt cggcaaataa tgtctaacaa ttcgttcaag ccgacgccgc       1200
ttcgcggcgc ggcttaactc aagcgttaga tgcactaagc acataattgc tcacagccaa       1260
actatcaggt caagtctgct tttattattt ttaagcgtgc ataataagcc ctacacaaat       1320
ggtacccgac cggtggtgaa tttaatctcg ctgacgtgta gacattccct tatccagacg       1380
ctgatcgccc atcatcgcgg ttctttagat ctctcggtcc gccctgatgg cggcaccttg       1440
ctgacgttac gcctgccggt acagcaggtt atcaccggag gcttaaaatg a               1491
```

```
<210> SEQ ID NO 60
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
```

```
atgagcatca cggcgttatc agcatcattt cctgagggga atatcgccag ccgcttgtcg         60
ctgcaacatc cttcactgtt ttataccgtg gttgaacaat cttcggtggc gagcgtgttg        120
agtcatcctg actagctgag atgagggctc gcccctcgt cccgacactt ccagatcgcc        180
atagcgcaca gcgcctcgag cggtggtaac ggcgcagtgg cggttttcat ggcttgttat        240
gactgttttt ttggggtaca gtctatgcct cgggcatcca agcagcaagc gcgttacgcc        300
gtgggtcgat gtttgatgtt atggagcagc aacgatgtta cgcagcaggg cagtcgccct        360
aaaacaaagt taaacatcat gagggaagcg gtgatcgccg aagtatcgac tcaactatca        420
gaggtagttg gcgtcatcga gcgccatctc gaaccgacgt tgctggccgt acatttgtac        480
ggctccgcag tggatggcgg cctgaagcca cacagtgata ttgatttgct ggttacggtg        540
accgtaaggc ttgatgaaac aacgcggcga gctttgatca cgacctttt ggaaacttcg        600 gcttcccctg gagagagcga gattctccgc gctgtagaag tcaccattgt tgtgcacgac        660
gacatcattc cgtggcgtta tccagctaag cgcgaactgc aatttggaga atggcagcgc        720
aatgacattc ttgcaggtat cttcgagcca gccacgatcg acattgatct ggctatcttg        780
ctgacaaaag caagagaaca tagcgttgcc ttggtaggtc cagcggcgga ggaactcttt        840
gatccggttc ctgaacagga tctatttgag gcgctaaatg aaaccttaac gctatggaac        900
tcgccgcccg actgggctgg cgatgagcga aatgtagtgc ttacgttgtc ccgcatttgg        960
tacagcgcag taaccggcaa aatcgcgccg aaggatgtcg ctgccgactg ggcaatggag       1020
cgcctgccgg cccagtatca gcccgtcata cttgaagcta gacaggctta tcttggacaa       1080
gaagaagatc gcttggcctc gcgcgcagat cagttggaag aatttgtcca ctacgtgaaa       1140
```

```
ggcgagatca ccaaggtagt cggcaaataa tgtctaacaa ttcgttcaag ccgacgccgc   1200
ttcgcggcgc ggcttaactc aagcgttaga tgcactaagc acataattgc tcacagccaa   1260
actatcaggt caagtctgct tttattattt ttaagcgtgc ataataagcc ctacacaaat   1320
ggtacccgac cggtggtgaa tttaatctcg ctgacgtgta gacattccct tatccagacg   1380
ctgatcgccc atcatcgcgg ttctttagat ctctcggtcc gccctgatgg cggcaccttg   1440
ctgacgttac gcctgccggt acagcaggtt atcaccggag gcttaaaatg a             1491
```

```
<210> SEQ ID NO 61
<211> LENGTH: 1563
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
```

```
atgtttaacg atctgattgg cgatgatgaa acggattcgc cggaagatgc gctttctgag     60
agctggcgcg aattgtggca ggatgcgttg caggaggagg attccacgcc cgtgctggcg    120
catctctcag aggacgatcg ccgccgcgtg gtggcgctga ttgccgattt tcgcaaagag    180
ttggataaac gcaccattgg cccgcgaggg cggcaggtac tcgatcactt aatgccgcat    240
ctgctcagcg atgtatgctc gcgcgacgat gcgccagtac cgctgtcacg cctgacgccg    300
ctgctcaccg gaattattac ccgcaccact taccttgagc tgctaagtga atttcccggc    360
gcactgaaac acctcatttc cctgtgtgcc gcgtcgccga tggttgccag tcagctggcg    420
cgctacccga tcctgcttga tgaattgctc gacccgaata cgctctatca accgacggcg    480
atgaatgcct atcgcgatga gctgcgccaa tacctgctgc gcgtgccgga agatgatgaa    540
gagcaacagc ttgaggcgct gcggcagttt aagcaggcgc agttgctgcg cgtggcggcg    600
gcggatattg ccggtacgtt gccagtaatg aaagtgagcg atcacttaac ctggctggcg    660
gaagcgatta ttgatgcggt ggtgcagcaa gcctggggg agatggtggc gcgttatggc    720
cagccaacgc atctgcacga tcgcgaaggg cgcggttttg cggtggtcgg ttatggcaag    780
ctgggcggct gggagctggg ttacagctcc gatctggatc tggtattcct gcacgactgc    840
ccgatggatg tgatgaccga tggcgagcgt gaaatcgatg tcgccagtt ctatttgcgt     900 ctcgcgcagc gcgtgatgca cctgtttagc acgcgcacgt cgtccggcat cctttatgaa    960
gttgatgcgc gtctgcgtcc atctggcgct gcggggatgc tggtcactac tacggaatcg   1020
ttcgccgatt accagcaaaa cgaagcctgg acgtgggaac atcaggcgct ggcccgtgcg   1080
cgcgtggtgt acggcgatcc gcaactgacc gccgaatttg acgccattcg ccgcgatatt   1140
ctgatgacgc ctcgcgacgg cgcaacgctg caaaccgacg tgcgagaaat gcgcgagaaa   1200
atgcgtgccc atcttggcaa caagcataaa gaccgcttcg atctgaaagc cgatgaaggc   1260
ggtatcaccg acatcgagtt tatcgcccaa tatctggtgc tgcgctttgc ccatgacaag   1320
ccgaaactga cgcgctggtc ggataatgtg cgcattctcg aagggctggc gcaaaacggc   1380
atcatggagg agcaggaagc gcaggcattg acgctggcgt acaccacatt gcgtgatgag   1440
ctgcaccacc tggcgctgca agagttgccg ggacatgtgg cgctctcctg ttttgtcgcc   1500
gagcgtgcgc ttattaaaac cagctgggac aagtggctgg tggaaccgtg cgccccggcg   1560
taa                                                                  1563
```

```
<210> SEQ ID NO 62
<211> LENGTH: 1536
<212> TYPE: DNA
<213> ORGANISM: Kosakonia sacchari
<220> FEATURE:
<223> OTHER INFORMATION: 16S rDNA - contig 5, strain CI006

<400> SEQUENCE: 62
ttgaagagtt tgatcatggc tcagattgaa cgctggcggc aggcctaaca catgcaagtc      60
gaacggtagc acagagagct tgctctcggg tgacgagtgg cggacgggtg agtaatgtct     120
gggaaactgc ctgatggagg gggataacta ctggaaacgg tagctaatac cgcataacgt     180
cgcaagacca aagaggggga ccttcgggcc tcttgccatc agatgtgccc agatgggatt     240
agctagtagg tggggtaacg gctcacctag gcgacgatcc ctagctggtc tgagaggatg     300
accagccaca ctggaactga gacacggtcc agactcctac gggaggcagc agtggggaat     360
attgcacaat gggcgcaagc ctgatgcagc catgccgcgt gtgtgaagaa ggccttcggg     420
ttgtaaagca ctttcagcgg ggaggaaggg agtaaggtta ataaccttat tcattgacgt     480
tacccgcaga agaagcaccg gctaactccg tgccagcagc cgcggtaata cggagggtgc     540
aagcgttaat cggaattact gggcgtaaag cgcacgcagg cggtctgtca gtcggatgt     600 gaaatccccg ggctcaacct gggaactgca tccgaaactg gcaggcttga gtctcgtaga     660
gggaggtaga attccaggtg tagcggtgaa atgcgtagag atctggagga ataccggtgg     720
cgaaggcggc ctcctggacg aagactgacg ctcaggtgcg aaagcgtggg gagcaaacag     780
gattagatac cctggtagtc cacgccgtaa acgatgtcta tttggaggtt gtgcccttga     840
ggcgtggctt ccggagctaa cgcgttaaat agaccgcctg gggagtacgg ccgcaaggtt     900
aaaactcaaa tgaattgacg gggcccgca caagcggtgg agcatgtggt ttaattcgat     960
gcaacgcgaa gaaccttacc tggtcttgac atccacagaa ctttccagag atggattggt    1020
gccttcggga actgtgagac aggtgctgca tggctgtcgt cagctcgtgt tgtgaaatgt    1080
tgggttaagt cccgcaacga gcgcaaccct tatcctttgt tgccagcggt ccggccggga    1140
actcaaagga gactgccagt gataaactgg aggaaggtgg ggatgacgtc aagtcatcat    1200
ggcccttacg accagggcta cacacgtgct acaatggcgc atacaaagag aagcgacctc    1260
gcgagagtaa gcggacctca taaagtgcgt cgtagtccgg attggagtct gcaactcgac    1320
tccatgaagt cggaatcgct agtaatcgtg gatcagaatg ccacggtgaa tacgttcccg    1380
ggccttgtac acaccgcccg tcacaccatg ggagtgggtt gcaaaagaag taggtagctt    1440
aaccttcggg agggcgctta ccactttgtg attcatgact ggggtgaagt cgtaacaagg    1500
taaccgtagg ggaacctgcg gttggatcac ctcctt                             1536

<210> SEQ ID NO 63
<211> LENGTH: 1537
<212> TYPE: DNA
<213> ORGANISM: Kosakonia sacchari
<220> FEATURE:
<223> OTHER INFORMATION: 16S rDNA - contig 8, strain CI006
<220> FEATURE:
<221> NAME/KEY: modified_base
<222> LOCATION: (450)..(450)
<223> OTHER INFORMATION: a, c, g, or t
<220> FEATURE:
<221> NAME/KEY: modified_base
<222> LOCATION: (452)..(452)
<223> OTHER INFORMATION: a, c, g, or t
<220> FEATURE:
<221> NAME/KEY: modified_base
<222> LOCATION: (455)..(455)
```

<223> OTHER INFORMATION: a, c, g, or t
<220> FEATURE:
<221> NAME/KEY: modified_base
<222> LOCATION: (473)..(473)
<223> OTHER INFORMATION: a, c, g, or t

<400> SEQUENCE: 63

```
ttgaagagtt tgatcatggc tcagattgaa cgctggcggc aggcctaaca catgcaagtc      60
gaacggtagc acagagagct tgctctcggg tgacgagtgg cggacgggtg agtaatgtct     120
gggaaactgc ctgatggagg gggataacta ctggaaacgg tagctaatac cgcataacgt     180
cgcaagacca aagagggGga ccttcgggcc tcttgccatc agatgtgccc agatgggatt     240
agctagtagg tggggtaacg gctcacctag gcgacgatcc ctagctggtc tgagaggatg     300
accagccaca ctggaactga gacacggtcc agactcctac gggaggcagc agtgggGaat     360
attgcacaat gggcgcaagc ctgatgcagc catgccgcgt gtgtgaagaa ggccttcggg     420
ttgtaaagca ctttcagcgg ggaggaaggn antanggtta ataacctgtg ttnattgacg     480
ttacccgcag aagaagcacc ggctaactcc gtgccagcag ccgcggtaat acggagggtg     540
caagcgttaa tcggaattac tgggcgtaaa gcgcacgcag gcggtctgtc aagtcggatg     600
tgaaatcccc gggctcaacc tgggaactgc atccgaaact ggcaggcttg agtctcgtag     660
agggaggtag aattccaggt gtagcggtga aatgcgtaga gatctggagg aataccggtg     720
gcgaaggcgg cctcctggac gaagactgac gctcaggtgc gaaagcgtgg ggagcaaaca     780
ggattagata ccctggtagt ccacgccgta aacgatgtct atttggaggt tgtgcccttg     840
aggcgtggct tccggagcta acgcgttaaa tagaccgcct ggGgagtacg gccgcaaggt     900
taaaactcaa atgaattgac ggggGcccgc acaagcggtg gagcatgtgg tttaattcga     960
tgcaacgcga agaaccttac ctggtcttga catccacaga acttagcaga gatgctttgg    1020
tgccttcggg aactgtgaga caggtgctgc atggctgtcg tcagctcgtg ttgtgaaatg    1080
ttgggttaag tcccgcaacg agcgcaaccc ttatcctttg ttgccagcgg ttaggccggg    1140
aactcaaagg agactgccag tgataaactg gaggaaggtg gggatgacgt caagtcatca    1200
tggcccttac gaccagggct acacacgtgc tacaatggcg catacaaaga gaagcgacct    1260
cgcgagagta agcggacctc ataaagtgcg tcgtagtccg gattggagtc tgcaactcga    1320
ctccatgaag tcggaatcgc tagtaatcgt ggatcagaat gccacggtga atacgttccc    1380
gggccttgta cacaccgccc gtcacaccat gggagtgggt tgcaaaagaa gtaggtagct    1440
taaccttcgg gagggcgctt accactttgt gattcatgac tggggtgaag tcgtaacaag    1500
gtaaccgtag gggaacctgc ggttggatca cctcctt                             1537
```

<210> SEQ ID NO 64
<211> LENGTH: 1540
<212> TYPE: DNA
<213> ORGANISM: Rahnella sp.
<220> FEATURE:
<223> OTHER INFORMATION: 16S rDNA, strain CI019
<220> FEATURE:
<221> NAME/KEY: modified_base
<222> LOCATION: (70)..(70)
<223> OTHER INFORMATION: a, c, g, or t
<220> FEATURE:
<221> NAME/KEY: modified_base
<222> LOCATION: (267)..(267)
<223> OTHER INFORMATION: a, c, g, or t
<220> FEATURE:
<221> NAME/KEY: modified_base
<222> LOCATION: (455)..(455)
<223> OTHER INFORMATION: a, c, g, or t

```
<220> FEATURE:
<221> NAME/KEY: modified_base
<222> LOCATION: (458)..(458)
<223> OTHER INFORMATION: a, c, g, or t
<220> FEATURE:
<221> NAME/KEY: modified_base
<222> LOCATION: (473)..(473)
<223> OTHER INFORMATION: a, c, g, or t
<220> FEATURE:
<221> NAME/KEY: modified_base
<222> LOCATION: (1135)..(1135)
<223> OTHER INFORMATION: a, c, g, or t

<400> SEQUENCE: 64
attgaagagt ttgatcatgg ctcagattga acgctggcgg caggcctaac acatgcaagt      60
cgagcggcan cgggaagtag cttgctactt tgccggcgag cggcggacgg gtgagtaatg     120
tctgggaaac tgcctgatgg aggggggataa ctactggaaa cggtagctaa taccgcatga     180
cctcgaaaga gcaaagtggg ggatcttcgg acctcacgcc atcggatgtg cccagatggg     240
attagctagt aggtgaggta atggctacc taggcgacga tccctagctg gtctgagagg     300
atgaccagcc acactggaac tgagacacgg tccagactcc tacgggaggc agcagtgggg     360
aatattgcac aatgggcgca agcctgatgc agccatgccg cgtgtgtgaa gaaggcctta     420
gggttgtaaa gcactttcag cgaggaggaa ggcancanac ttaatacgtg tgntgattga     480
cgttactcgc agaagaagca ccggctaact ccgtgccagc agccgcggta atacggaggg     540
tgcaagcgtt aatcggaatt actgggcgta aagcgcacgc aggcggtttg ttaagtcaga     600
tgtgaaatcc ccgagcttaa cttgggaact gcatttgaaa ctggcaagct agagtcttgt     660 agagggggggt agaattccag gtgtagcggt gaaatgcgta gagatctgga ggaataccgg     720
tggcgaaggc ggcccccctgg acaaagactg acgctcaggt gcgaaagcgt ggggagcaaa     780
caggattaga taccctggta gtccacgctg taaacgatgt cgacttggag gttgtgccct     840
tgaggcgtgg cttccggagc taacgcgtta agtcgaccgc ctggggagta cggccgcaag     900
gttaaaactc aaatgaattg acggggggccc gcacaagcgg tggagcatgt ggtttaattc     960
gatgcaacgc gaagaacctt acctactctt gacatccaga gaatttgcca gagatggcga    1020
agtgccttcg ggaactctga gacaggtgct gcatggctgt cgtcagctcg tgttgtgaaa    1080
tgttgggtta agtcccgcaa cgagcgcaac ccttatcctt tgttgccagc acgtnatggt    1140
gggaactcaa aggagactgc cggtgataaa ccggaggaag gtggggatga cgtcaagtca    1200
tcatggccct tacgagtagg gctacacacg tgctacaatg gcatatacaa agagaagcga    1260
actcgcgaga gcaagcggac ctcataaagt atgtcgtagt ccggattgga gtctgcaact    1320
cgactccatg aagtcggaat cgctagtaat cgtagatcag aatgctacgg tgaatacgtt    1380
cccgggcctt gtacacaccg cccgtcacac catgggagtg ggttgcaaaa gaagtaggta    1440
gcttaacctt cgggagggcg cttaccactt tgtgattcat gactggggtg aagtcgtaac    1500
aaggtaaccg tagggaacc tgcggttgga tcacctcctt                           1540

<210> SEQ ID NO 65
<211> LENGTH: 882
<212> TYPE: DNA
<213> ORGANISM: Kosakonia sacchari
<220> FEATURE:
<223> OTHER INFORMATION: nifH, strain CI006

<400> SEQUENCE: 65
atgaccatgc gtcaatgcgc catttacggc aaaggtggga tcggcaaatc gaccaccaca      60
```

-continued

```
cagaacctgg tcgccgcgct ggcggagatg ggtaaaaaag tcatgattgt cggctgtgac      120
ccgaaagccg attccacgcg tttgatcctg catgcgaaag cgcagaacac cattatggag      180
atggctgctg aagtcggctc cgtggaagac ctggagttag aagacgtgct gcaaatcggt      240
tacggcggcg tgcgctgcgc agagtccggc ggcccggagc caggcgtggg ctgtgccggt      300 cgcgggggtga tcaccgcgat taacttcctc gaagaagaag gcgcttacgt gccggatctc      360
gattttgttt tctacgacgt gctgggcgac gtggtatgcg gtggtttcgc catgccgatt      420
cgtgaaaaca aagcgcagga gatctacatc gtttgctctg gcgaaatgat ggcgatgtac      480
gccgccaaca acatctccaa aggcatcgtg aaatacgcca aatccggtaa agtgcgcctc      540
ggcgggctga tttgtaactc cgcgccagacc gaccgtgaag atgaactgat cattgcgctg      600
gcagaaaaac tcggcacgca gatgatccac tttgttcccc gcgacaacat tgtgcagcgt      660
gcggaaatcc gccgtatgac ggttatcgaa atgacccga cctgcaatca ggcgaacgaa      720
tatcgcagcc ttgccagcaa aatcgtcaac aacaccaaaa tggtggtgcc caccccctgc      780
accatggatg aactggaaga actgctgatg gagttcggca ttatggatgt ggaagacacc      840
agcatcattg gtaaaaccgc cgccgaagaa aacgccgtct ga                        882
```

<210> SEQ ID NO 66
<211> LENGTH: 1449
<212> TYPE: DNA
<213> ORGANISM: Kosakonia sacchari
<220> FEATURE:
<223> OTHER INFORMATION: NifD, strain CI006

<400> SEQUENCE: 66

```
atgagcaatg caacaggcga acgcaacctg gagataatcg agcaggtgct cgaggttttc       60
ccggagaaga cgcgcaaaga cgcagaaaa cacatgatgg tgacggaccc ggagcaggaa       120
agcgtcggta agtgcatcat ctctaaccgc aaatcgcagc caggcgtgat gaccgtgcgc       180
ggctgctcgt atgccggttc gaaaggggtg gtatttgggc aatcaagga tatggcgcat       240 atctcgcatg gcccaatcgg ctgcggccaa tactcccgcg ccgggcggcg gaactactac       300 accgcgtca gcggcgtgga cagcttcggc acgctcaact tcacctccga ttttcaggag       360
cgcgacatcg tgtttggcgg cgataaaaag ctcgccaaac tgattgaaga gctggaagag       420
ctgttcccgc tgaccaaagg catttcgatt cagtcggaat gcccggtcgg cctgattggc       480
gatgacattg aggccgtcgc gaacgccagc cgcaaagcca tcaacaaacc ggttattccg       540
gtgcgttgcg aaggctttcg cggcgtgtcg caatccctcg gtcaccatat tgccaacgat       600
gtgatccgcg actgggtgct ggataaccgc gaaggcaaac cgttcgaatc caccccttac       660
gatgtggcga tcatcggcga ttacaacatc ggcggcgatg cctgggcttc cgcgattttg       720
ctcgaagaga tgggcttgcg ggtggtggca cagtggtctg cgacggtac gctggtggag       780 atggaaaaca cgccgttcgt caaactgaac ctggtgcatt gttaccgctc aatgaactac       840
atctcgcgcc atatggagga gaagcacggt attccgtgga tggaatacaa cttctttggt       900
ccgacgaaaa tcgcggaatc gctgcgcaaa atcgccgacc agtttgacga caccattcgc       960
gccaacgccg aagcggtgat cgccagatac caggcgcaaa cgacgccat tatcgccaaa       1020 tatcgcccgc gtctggaggg cgcgcaaagtg ctgctttata tgggcgggct cgcgtccgcgc      1080 catgtgattg cgcctatga agacctggga atggagatca tcgctgccgg ttatgagttc       1140
ggtcataacg atgattacga ccgcaccttg ccggatctga agaggggcac gctgctgttt       1200
gatgatgcca gcagttatga gctggaggcg ttcgtcaacg cgctgaaacc ggatctcatc       1260
```

```
ggttccggca tcaaagagaa gtacatcttt cagaaaatgg gcgtgccgtt tcgccagatg      1320
cactcctggg attactccgg cccgtaccac ggctatgacg gcttcgccat cttcgcccgc      1380
gatatggata tgacgctcaa caaccccgcg tggggccagt tgaccgcgcc gtggctgaaa      1440
tccgcctga                                                              1449
```

<210> SEQ ID NO 67
<211> LENGTH: 1563
<212> TYPE: DNA
<213> ORGANISM: Kosakonia sacchari
<220> FEATURE:
<223> OTHER INFORMATION: nifK, strain CI006

<400> SEQUENCE: 67

```
atgagccaga ctgctgagaa aatacagaat tgccatcccc tgtttgaaca ggatgcttac        60
cagacgctgt ttgccggtaa acgggcactc gaagaggcgc actcgccgga gcgggtgcag       120
gaagtgtttc aatggaccac taccccggaa tatgaagcgc tgaactttaa acgcgaagcg       180
ctgactatcg acccggcaaa agcctgccag ccgctgggcg cggtgctctg ttcgctgggg       240
tttgccaata ccctaccgta tgtgcacggt tcacagggtt gcgtggccta tttccgcacg       300
tactttaacc gccactttaa agaaccggtg gcctgcgtgt cggattcaat gacggaagac       360
gcggcggtgt tcggcgggaa taacaacctc aacaccggct acaaaacgc cagcgcgctg       420 tataaaccgg agattatcgc cgtctctacc acctgtatgg cggaagtgat cggtgatgat       480
ttgcaggcct ttatcgccaa cgccaaaaaa gatggttttc tcgatgccgc catccccgtg       540
ccctacgcgc acacccccag ttttatcggc agccatatca ccggctggga taacatgttt       600
gaaggttttg cccggacctt tacggcagac catgaagctc agcccggcaa actttcacgc       660
atcaacctgg tgaccgggtt tgaaacctat ctcggcaatt tccgcgtgct gaaacgcatg       720
atggaacaaa tggaggtgcc ggcgagtgtg ctctccgatc cgtcggaagt gctggatact       780
cccgccaacg ggcattacca gatgtacgcg ggcgggacga cgcagcaaga gatgcgcgag       840
gcgccggatg ctatcgacac cctgttgctg cagccctggc aactggtgaa aagcaaaaaa       900
gtggtgcagg agatgtggaa tcagcccgcc accgaggttt ctgttcccgt tgggctggca       960
ggaacagacg aactgttgat ggcgattagc cagttaaccg gcaaggccat tcccgattca      1020
ctggcgctga gcgcgggcg gctggtcgat atgatgctcg attcccacac ctggttgcac       1080
ggtaaaaaat tcggcctgtt tggcgatccg gattttgtca tgggattgac ccgtttcctg      1140
ctggagctgg ctgcgaacc gaccgttatc ctctgccaca cggtaacaa acgctggcag       1200 aaagcaatga gaaaatgct tgacgcctcg ccgtacggcc aggagagcga agtgtttatc      1260
aactgcgatt tgtggcattt ccgctcgctg atgtttaccc gccagccgga ttttatgatt      1320
ggcaactcgt acggcaagtt cattcagcgc gacaccttag ccaaaggcga gcagtttgaa      1380
gttccgctga tccgcctcgg ttttcccctg ttcgaccgcc accatctgca ccgccagacc      1440 acctgggggct acgagggcgc catgagcatt ctcactaccc ttgtgaatgc ggtactggag      1500
aaagtggaca aagagaccat caagctcggc aaaaccgact acagcttcga tcttatccgt      1560
taa                                                                    1563
```

<210> SEQ ID NO 68
<211> LENGTH: 1488
<212> TYPE: DNA
<213> ORGANISM: Kosakonia sacchari
<220> FEATURE:

-continued

<223> OTHER INFORMATION: nifL, strain CI006

<400> SEQUENCE: 68

```
atgaccctga atatgatgat ggatgccggc gcgcccgagg caatcgccgg tgcgctttcg      60
cgacaccatc ctgggctgtt ttttaccatc gttgaagaag cgcccgtcgc catttcgctg     120
actgatgccg acgcacgcat tgtctatgcc aacccggctt tctgccgcca gaccggctat     180
gaactagaag cgttgttgca gcaaaatccc cgcctgcttg caagtcgcca accccacgg     240 gaaatctatc aggatatgtg gcacaccttg ttacaacgcc gaccgtggcg cgggcaattg     300
attaaccgcc accgcgacgg cagcctgtat ctggtcgaga tcgatatcac cccggtgatt     360
aacccgtttg gcgaactgga acactacctg gcaatgcagc gcgatatcag cgccagttat     420
gcgctggagc agcggttgcg caatcacatg acgctgaccg aagcggtgct gaataacatt     480
ccggcggcgg tggttgtagt ggatgaacgc gatcatgtgg ttatggataa ccttgcctac     540
aaaacgttct gtgccgactg cggcggaaaa gagctcctga gcgaactcaa tttttcagcc     600
cgaaaagcgg agctggcaaa cggccaggtc ttaccggtgg tgctgcgcgg tgaggtgcgc     660
tggttgtcgg tgacctgctg ggcgctgccg ggcgtcagcg aagaagccag tcgctacttt     720
attgataaca ggctgacgcg cacgctggtg gtgatcaccg acgacaccca acaacgccag     780
cagcaggaac agggccgact tgaccgcctt aaacagcaga tgaccaacgg caaactactg     840
gcagcgatcc gcgaagcgct tgacgccgcg ctgatccagc ttaactgccc catcaatatg     900
ctggcggcgg cgcgacgttt aaacggcagt gataacaaca atgtggcgct cgacgccgcg     960
tggcgcgaag gtgaagaggc gatggcgcgg ctgaaacgtt gccgcccgtc gctggaactg    1020
gaaagtgcgg ccgtctggcc gctgcaaccc tttttttgacg atctgcgcgc gctttatcac    1080
acccgctacg agcaggggaa aaatttgcag gtcacgctgg attcccatca tctggtggga    1140
tttggtcagc gtacgcaact gttagcctgc ctgagtctgt ggctcgatcg cacgctggat    1200
attgccgccg ggctgggtga tttcaccgcg caaacgcaga tttacgcccg cgaagaagag    1260
ggctggctct ctttgtatat cactgacaat gtgccgctga tcccgctgcg ccacacccac    1320
tcgccggatg cgcttaacgc tccgggaaaa ggcatggagc tgcgcctgat ccagacgctg    1380
gtggcacacc accacggcgc aatagaactc acttcacacc ccgaaggggg aagttgcctg    1440
accctacgat tcccgctatt tcattcactg accggaggtt caaaatga               1488
```

<210> SEQ ID NO 69
<211> LENGTH: 1575
<212> TYPE: DNA
<213> ORGANISM: Kosakonia sacchari
<220> FEATURE:
<223> OTHER INFORMATION: nifA, strain CI006

<400> SEQUENCE: 69

```
atgacccagc gaaccgagtc gggtaatacc gtctggcgct cgatttgtc ccagcagttc      60 actgcgatgc agcgcataag cgtggtactc agccgggcga ccgaggtcga tcagacgctc     120
cagcaagtgc tgtgcgtatt gcacaatgac gcctttttgc agcacggcat gatctgtctg     180
tacgacagcc agcaggcgat tttgaatatt gaagcgttgc aggaagccga tcagcagtta     240
atccccggca gctcgcaaat ccgctatcgt ccgggcgaag ggctggtcgg gacggtgctt     300
tcgcagggcc aatcattagt gctggcgcgc gttgctgacg atcagcgctt tcttgaccgg     360
ctcgggttgt atgattacaa cctgccgttt atcgccgtgc cgctgatagg ccagatgcg     420 cagactttcg gtgtgctgac ggcacaaccc atggcgcgtt acgaagagcg attacccgcc     480
```

-continued

```
tgcacccgct ttctggaaac ggtcgctaac ctggtcgcgc aaaccgtgcg tttgatggca    540
ccaccggcag tgcgcccttc cccgcgcgcc gccataacac aggccgccag cccgaaatcc    600
tgcacggcct cacgcgcatt tggttttgaa aatatggtcg gtaacagtcc ggcgatgcgc    660
cagaccatgg agattatccg tcaggtttcg cgctgggaca ccaccgttct ggtacgcggc    720
gagagtggca ccggcaagga gctgattgcc aacgccatcc accaccattc gccgcgtgcc    780
ggtgcgccat ttgtgaaatt caactgtgcg gcgctgccgg acacactgct ggaaagcgaa    840
ttgttcggtc acgagaaagg ggcatttacc ggcgcggtac gccagcgtaa aggccgtttt    900
gagctggccg atggcggcac gctgtttctt gacgagatcg gcgagagtag cgcctcgttt    960
caggctaagc tgctgcgcat tttgcaggaa ggcgaaatgg aacgcgtcgg cggcgacgag   1020
acattgcaag tgaatgtgcg cattattgcc gcgacgaacc gcaatcttga agatgaagtc   1080
cggctggggc actttcgcga agatctctat tatcgcctga atgtgatgcc catcgccctg   1140
ccgccactac gcgaacgcca ggaggacatt gccgagctgg cgcactttct ggtgcgtaaa   1200
atcgcccata accagagccg tacgctgcgc attagcgagg cgcgctatccg cctgctgatg   1260 agctacaact ggcccggtaa tgtgcgcgaa ctggaaaact gccttgagcg ctcagcggtg   1320
atgtcggaga acggtctgat cgatcgggat gtgattttgt ttaatcatcg cgaccagcca   1380
gccaaaccgc cagttatcag cgtctcgcat gatgataact ggctcgataa caaccttgac   1440
gagcgccagc ggctgattgc ggcgctggaa aaagcgggat gggtacaagc caaagccgcg   1500
cgcttgctgg ggatgacgcc gcgccaggtc gcctatcgta ttcagacgat ggatataacc   1560
ctgccaaggc tataa                                                   1575
```

<210> SEQ ID NO 70
<211> LENGTH: 876
<212> TYPE: DNA
<213> ORGANISM: Rahnella sp.
<220> FEATURE:
<223> OTHER INFORMATION: nifH, strain CI019

<400> SEQUENCE: 70

```
atggcaatgc gtcaatgtgc aatctacggg aaaggggta ttggtaaatc caccactacc     60
caaaaccttg tagcggctct ggccgaaatg aataagaagg tcatgatcgt cggctgtgac   120
cctaaggctg attcaacccg cctcattctg catgcgaaag cacagaacac catcatggaa   180
atggccgctg aagtgggctc cgtggaagat ctggagctgg aagatgtgat gcaaatcggc   240
tatggcggcg tgcgctgtgc ggaatcaggc ggccctgagc ctggtgtggg ttgtgccgga   300 cgcgggtga tcaccgccat caacttcctc gaagaagaag cgcgtatgt gccggatctg     360 gatttcgtgt tttacgacgt attgggcgat gtggtctgtg cggtttcgc gatgccaatt    420 cgcgaaaaca aagcgcagga atctacatc gtatgctccg gtgaaatgat ggcgatgtat     480
gccgccaaca catttccaa aggcatcgtg aaatacgcga atcgggcaa agttcgcctg      540 gccgggctga tctgtaactc ccgccagacg atcgcgaag atgaactgat catcgcgctg     600
gctgaaaaac ttggcacgca aatgatccac ttcgtgccgc gtgacaacat tgtgcaacgc   660
gctgaaatcc gccgcatgac ggtcatcgaa tacgacccga cttgtgcgca ggcagatcag   720
tatcgtgcac tggcgaacaa aatcgtcaac aacaccaaaa tggtggtgcc gacaccggtc   780
accatggatg agctggaagc cctgttaatg gaatttggca ttatggaaga agaagacctg   840
accatcgtcg gtcgtaccgc cgccgaagag gcgtga                             876
```

<210> SEQ ID NO 71
<211> LENGTH: 1449
<212> TYPE: DNA
<213> ORGANISM: Rahnella sp.
<220> FEATURE:
<223> OTHER INFORMATION: nifD, strain CI019

<400> SEQUENCE: 71
atgaccagtg aaacacgcga acgtaacgag gcattgatcc aggaagtgct ggagatcttc      60
cccgagaagg cgcttaaaga tcgtaagaaa cacatgatga ccaccgaccc ggcgatggaa     120
tctgtcggca agtgtattgt ctcaaaccgc aaatcacagc cgggcgtgat gaccgtgcga     180
ggctgcgctt acgccggttc caaaggcgtg gtctttggcc cgatcaaaga catggcgcat     240
atctcccacg gcccggttgg ttgcggccag tattctcgtg ccggacgccg taactattac     300
accggctgga gcggcgtgaa cagctttggc accctcaact tcaccagtga ttttcaggaa     360
cgggacatcg tatttggcgg cgataaaaag ctcgacaaac tgatcgacga actggagatg     420
ttgttcccgc tgaccaaagg catttcggta cagtcggaat gtccggtcgg tctgatcggc     480
gatgacattt ctgccgtcgc caaagccagc agcgccaaaa tcggtaagcc ggtcgtgccg     540
gtacgctgcg aggggttccg cggtgtgtcg caatcgctcg ccatcacat tgctaacgat     600 gtcatccgcg actgggtgct ggataaccgc gaaggcaatg aatttgaaac cacgccttac     660
gacgtggcga ttatcggcga ctacaacatc ggcggtgacg cctgggcctc acgtattctg     720
ctcgaagaaa tggggctgcg tgtggtggcg cagtggtccg gcgacggcac gctggtggag     780
atggaaaaca ccccgaaagt cgcactcaat ctggtgcact gctaccgctc gatgaactac     840
atctcccgtc atatggaaga aaaacacggc attccgtgga tggaatacaa cttcctttggc    900 ccgaccaaaa ttgcggaatc tctgcgcgaa atcgcggcgc gttttgacga taccatccgg     960
aaaaacgccg aagcggtgat tgaaaaatat caggcgcaaa cgcaggcggt gatcgacaaa    1020
taccgtccgc gtctggaagg caaaaaggtg ctgttgtatc tcggcggttt acgtccgcgc    1080
cacatcatcg gggcgtatga agatctggga atggaaatca tcggtaccgg ctatgaattc    1140
ggtcataacg atgattacga ccgcacctta ccgatgctca agaaggcac gttgctgttc     1200 gatgacctga gcagttatga gctggaagcg ttcgttaaag cgctgaaacc ggatcttgtc    1260
gggtcaggca tcaaagaaaa atacatttttc cagaaaatgg gcgtgccgtt ccgccagatg    1320
cactcctggg attattccgg cccttatcac ggctacgacg gtttcggcat ttttgcccgt    1380
gacatggaca tgacgctgaa caatccgggc tggagtcagc tgaccgcccc ctggttgaaa    1440
tcggcctga                                                            1449

<210> SEQ ID NO 72
<211> LENGTH: 1569
<212> TYPE: DNA
<213> ORGANISM: Rahnella sp.
<220> FEATURE:
<223> OTHER INFORMATION: nifK, strain CI019

<400> SEQUENCE: 72
atgagtcaag atcttggcac cccaaaatcc tgtttcccgc tgttcgagca ggatgaatac      60
cagagtatgt ttacccacaa acgcgcgctg aagaagcac acggcgaggc gaaagtgcgg     120
gaagtgtttg aatggaccac cacgcaggaa tatcaggatc tgaacttctc gcgtgaagcg     180
ctgaccgtcg accccgcgaa agcctgccag ccgttaggcg cggtactttg cgcgctgggt     240
tttgccaaca cgttgccgta tgtccacggt tcacaaggct gtgtggcgta tttccgtacc     300

-continued

```
tattttaatc gtcatttcaa agagccggtg gcctgtgttt ccgactcaat gaccgaagat      360
gccgccgttt ttggcggaaa taacaacatg aatgtcggtc tggaaaacgc cagcgcgctg      420
tacaagccgg aaattattgc tgtctccacc acctgtatgg cggaagtgat cggtgatgac      480
ctgcaggctt ttatcgccaa cgccaaaaaa gacggatttg tggatgccgg tatgccaatc      540
ccgtatgccc atacaccgag ttttctgggc agtcatgtca ccggctggga caacatgttt      600
gaaggcttcg cccgtacctt taccaccgac gccacgcggg aatatcagcc gggcaaactt      660
gccaaactga acgtggtgac cggttttgaa acttatctcg gcaactaccg ggttattcac      720
cgcatgatga gccagatggg ggtcgaatgc agcgtcttgt ccgatccgtc tgaagtgctc      780
gacacccggg ctgacggcca ataccgcatg tatgccggcg gcaccacgca aaccgaaatg      840
cgtgatgcac cggatgccat cgacaccttg ctgctgcaac cgtggcaatt gcagaaaacc      900
aaaaaagtgg tgcagggcga ctggaatcag ccgggcaccg aagtcagtgt accgattggc      960
ctggcggcga ccgatgcctt gctgatgacg gtaagcgaac tgaccggcaa accgatagct     1020
gacacgctgg cgactgaacg tggccgtctg gtggacatga tgctcgattc ccacacctgg     1080
ctgcatggca agcgtttcgg tctctacggt gacccggatt ttgtgatggg catgaccgca     1140
ttcctgctgg aactgggctg tgaaccgacc accattctca gccataacgg caacaaacgc     1200
tggcagaaag ccatgaagaa aatgctggct gattcgcctt acgggcagga cagcgaagtg     1260
tatgtgaact gcgatctgtg gcatttccgc tcgctgatgt ttacccgtaa accggacttt     1320
atgatcggca actcttacgg aaaattcatt cagcgtgaca cgctggccaa aggcgaacag     1380
ttcgaagtgc cgctgatccg catcggtttt ccgatttttg accggcacca tttgcaccgt     1440
cagaccacct ggggatacga aggggcgatg agcatactga cgcaactggt gaatgcggta     1500
cttgaacaac tggatcgcga aaccatgaag ctcggcaaaa ccgactacaa cttcgacctg     1560
atccgctaa                                                            1569
```

<210> SEQ ID NO 73
<211> LENGTH: 1488
<212> TYPE: DNA
<213> ORGANISM: Rahnella sp.
<220> FEATURE:
<223> OTHER INFORMATION: nifL, strain CI019

<400> SEQUENCE: 73

```
atgagcatca cggcgttatc agcatcattt cctgagggga atatcgccag ccgcttgtcg       60
ctgcaacatc cttcactgtt ttataccgtg gttgaacaat cttcggtggc gatttcgctg      120
accgatccgc aggcgcgcat ttgttatgcc aatccggcat tctgccgcca gacgggtttt      180
gcacttgaga cacttttggg cgagaaccac cgtctgctgg ccagccagca gacgccgaaa      240
catatctatg acgaaatgtg gcgcactttg ttgcagggca aatcctggaa cggccaactg      300
atcaaccggc gtaataaccg ttcgctttat ctggcggatg tcactatcac gcctgtttta      360
ggcgcggacg ggcaggtgga gcattacctc ggcatgcaca aagatatcag cgagaaatac      420
gcgctggaac agcggttgcg caaccacatc accttgttca cggaggtgct gaacaatatt      480
cccgccgccg tggtggtggt ggatgagcag gacaatgtgg tgatggacaa tctggcctac      540
aaaacccttt gcgcggactg cggcggcaaa gagctgctgg ctgaaatggg ctatccgcaa      600
ctcaaagaga tgctcaacag tggcgaaccg gtgccggttt ccatgcgcgg caacgtacgc      660 tggtttttctt tcggtcaatg gttattgcag ggcgttaatg aagaggccag ccgcttttttt      720
```

-continued

```
accggcatta ccgcgccggg aaaactgatt gttctgaccg actgcaccga tcagcatcac      780
cggcagcagc aggggttatct tgaccggctt aagcaaaaac tcaccaacgg caaattattg     840
gcggccatcc gtgagtcgct cgatgccgcg cttatccagc tcaacgggcc aatcaatatg      900
ctggcggctg cgcgtcgtct taacggcgaa gaaggcaaca acatggcgct ggaattcgcc      960
tggcgcgaag gcgagcaggc ggtgagtcgc ttacaggcct gccgtccgtc gctggatttt     1020
gagccgcagg cagaatggcc ggtcagtgaa ttctttgacg atctgagcgc gctgtacgac     1080 agccatttttc tcagtgacgg tgaattgcgt tacgtggtca tgccatctga tctgcacgct     1140
gtcgggcaac gaacgcaaat ccttaccgcg ctgagcttat ggattgatca cacgctgtca     1200
caggcgcagg ccatgccgtc tctgaagctc tcggtgaaca ttgttgcgag gcaggatgcg     1260
agctggttgt gttttgacat taccgataat gtgccgcgtg aacgggtgcg ttatgcccgc     1320
ccggaagcgg cgtttttcccg tccggggaat ggcatggagc tgcgccttat ccagacgctg    1380
atcgcccatc atcgcggttc tttagatctc tcggtccgcc ctgatggcgg caccttgctg     1440
acgttacgcc tgccggtaca gcaggttatc accggaggct taaaatga                  1488
```

<210> SEQ ID NO 74
<211> LENGTH: 1557
<212> TYPE: DNA
<213> ORGANISM: Rahnella sp.
<220> FEATURE:
<223> OTHER INFORMATION: nifA, strain CI019

<400> SEQUENCE: 74

```
atgacccagt tacctaccgc gggccggtt atccggcgct ttgatatgtc tgcccagttt        60
acggcgcttt atcgcatcag cgtggcgctg agtcaggaaa gcaacaccgg cgcgcactg       120 gcggcgatcc tcgaagtgct tcacgatcat gcatttatgc aatacggcat ggtgtgtctg      180
tttgataaag aacgcaatgc actctttgtg gaatccctgc atggcatcga cggcgaaagg      240
aaaaaagaga cccgccatgt ccgttaccgc atgggggaag gcgtgatcgg cgcggtgatg      300
agccagcgtc aggcgctggt gttaccgcgc atttcagacg atcagcgttt tctcgaccgc      360
ctgaatattt acgattacag cctgccgttg attggcgtgc cgatccccgg tgcggataat      420
cagccatcgg gcgtgctggt ggcacagccg atggcgttgc acgaagaccg gctgactgcc      480
agtacgcggt ttttagaaat ggtcgccaat ctcatcagcc agccactgcg ttctgccacg      540
cccccggaat cattgcctgc tcaaacgccg gtccggtgca gtgttccgcg ccagtttggt      600
ttcgagcaga tggtcgggaa aagtcaggcg atgcgccaga cgatggacat tttacggcag      660
gtttccaaat gggataccac ggttctggtg cgtggtgaaa gcggcaccgg caaggaactt      720
atcgccaatg ccattcatta caactcaccc cgtgcggccg cgccatttgt gaaattcaac      780
tgcgccgcgc tgccggataa cctgctggaa agcgaactgt tcggtcatga aaaagggggcc     840 ttcaccggcg ctatccgtac ccgtaaaggc cgctttgaac tggcggacgg gggcacgtta     900
ttcctcgatg aaatcggcga atcgagcgcg tcgtttcagg ccaaattgct gcgcattttg      960
caggaaggtg aaatggaacg ggtcggcggc gataccacgc tgaaagttga tgtgcgcatt     1020
attgctgcca ccaaccgtaa tcttgaagag gaagtgcgtg ccgggaattt cgcgaagac     1080 ctgtattatc gcctgaacgt gatgccggtt tcgctgcctg cactgcgtga aaggctggat     1140
gatatcgccg atctggcgcc gtttctggtc aaaaagattg cgctgcgtca ggggcgggaa     1200
ctgcgcatca cgacggtgc ggtgcgtctg ctgatgacct acagctggcc aggcaacgtg      1260
cgtgaactgg aaaactgtct cgaacgggcg tcggtaatga ccgatgaagg gctgatcgac     1320
```

```
cgcgacgtga tcctgttcaa tcaccatgaa tccccggcgc tgtccgtcaa acccggcctg    1380
ccgctcgcga cagatgaaag ctggctggat caggaactcg acgaacgcca gcgggtgatt    1440
gccgcactgg agaaaaccgg ctgggtgcag gccaaagcgg cccgactgct gggcatgaca    1500
ccgcgccaga ttgcctaccg tatccagatt atggacatca acatgcaccg tatctga       1557
```

```
<210> SEQ ID NO 75
<211> LENGTH: 1314
<212> TYPE: DNA
<213> ORGANISM: Kosakonia sacchari
<220> FEATURE:
<223> OTHER INFORMATION: Prm5 with 500bp flanking regions, strain CI006

<400> SEQUENCE: 75
aaaactaccg ccgcaattaa tgaacccaac gctactgttg ccgggccatg ctcttccccg      60
gcgcgctgcc cggaaaggat atagattgcc cagcacgcgc cagcaccaag cgcgaacgcc     120
gcgccagtga gatcaacatg tgaaacattt tcgcccagcg gcagcagata caagaggcca     180
agtaccgcca ggatcaccca gatgaaatcc accgggcggc gtgaggcaaa aagcgccacc     240
gccagcgggc cggtaaattc cagcgccacc gcaacgccga gcggtatcgt ctggatcgat     300
aaatagaaca tatagttcat ggcgccgagc gacaggccat aaaacagcag tggcaggcgt     360
tgttcacggg taaaatgtaa acgccagggc ttgaacacta cgaccaaaat aagggtgcca     420
agtgcgagac gcagcgcggt gacgccgggt gcgccaacaa tcggaaacag tgatttcgcc     480
agcgacgcgc ctccctgaat ggacatcatc gcgacaaaca atattaatac cggcaaccac     540
accggcaatt tacgagactg cgcaggcatc ctttctcccg tcaatttctg tcaaataaag     600
taaaagaggc agtctacttg aattacccccc ggctggttga gcgtttgttg aaaaaaagta     660
actgaaaaat ccgtagaata gcgccactct gatggttaat taacctattc aattaagaat     720
tatctggatg aatgtgccat taaatgcgca gcataatggt gcgttgtgcg ggaaaactgc     780
ttttttttga aagggttggt cagtagcgga aactttctgt tacatcaaat ggcgctttag     840
accccaattc ccgcaaagag tttcttaact aattttgata tatttaaacg cgtaggacgt     900
aggatttact tgaagcacat ttgaggtgga ttatgaaaaa aattgcatgt ctttcagcac     960
tggccgcact tctggcggtt tctgcaggtt ccgcagtagc agcaacttca accgtaactg    1020
gcggctacgc tcagagcgac gctcagggta ttgctaacaa aactaacggt ttcaacctga    1080
aatatcgcta cgagcaggac aacaacccgc tgggtgttat cggttccttt acttacactg    1140
aaaaagatcg caccgaaagc agcgtttata acaaagcgca gtactacggc atcaccgcag    1200
gcccggctta ccgcatcaac gactgggcga gcatctacgg tgttgtgggt gtaggttacg    1260
gtaaattcca gcagactgta gacaccgcta aagtgtctga caccagcgac tacg          1314
```

```
<210> SEQ ID NO 76
<211> LENGTH: 3413
<212> TYPE: DNA
<213> ORGANISM: Kosakonia sacchari
<220> FEATURE:
<223> OTHER INFORMATION: nifLA operon - upstream intergenic region plus
      nifL and nifA CDSs, strain CI006

<400> SEQUENCE: 76
aacacacgct cctgttgaaa aagagatccc gccgggaaat gcggtgaacg tgtctgatat      60
tgcgaagagt gtgccagttt tggtcgcggg caaaacctgc accagtttgg ttattaatgc     120
accagtctgg cgcttttttt cgccgagttt ctcctcgcta atgcccgcca ggcgcggctt     180
```

-continued

```
tggcgctgat agcgcgctga ataccgatct ggatcaaggt tttgtcgggt tatcagccaa      240
aaggtgcact ctttgcatgg ttatacgtgc ctgacatgtt gtccgggcga caaacggcct      300
ggtggcacaa attgtcagaa ctacgacacg actaactgac cgcaggagtg tgcgatgacc      360
ctgaatatga tgatggatgc cggcgcgccc gaggcaatcg ccggtgcgct ttcgcgacac      420
catcctgggc tgttttttac catcgttgaa gaagcgcccg tcgccatttc gctgactgat      480
gccgacgcac gcattgtcta tgccaacccg gctttctgcc gccagaccgg ctatgaacta      540
gaagcgttgt tgcagcaaaa tccccgcctg cttgcaagtc gccaaacccc acgggaaatc      600
tatcaggata tgtggcacac cttgttacaa cgccgaccgt ggcgcgggca attgattaac      660
cgccaccgcg acggcagcct gtatctggtc gagatcgata tcaccccggt gattaacccg      720
tttggcgaac tggaacacta cctggcaatg cagcgcgata tcagcgccag ttatgcgctg      780
gagcagcggt tgcgcaatca catgacgctg accgaagcgg tgctgaataa cattccggcg      840
gcggtggttg tagtggatga acgcgatcat gtggttatgg ataaccttgc ctacaaaacg      900
ttctgtgccg actgcggcgg aaaagagctc ctgagcgaac tcaatttttc agcccgaaaa      960
gcggagctgg caaacggcca ggtcttaccg gtggtgctgc gcggtgaggt gcgctggttg     1020
tcggtgacct gctgggcgct gccgggcgtc agcgaagaag ccagtcgcta ctttattgat     1080
aacaggctga cgcgcacgct ggtggtgatc accgacgaca cccaacaacg ccagcagcag     1140
gaacagggcc gacttgaccg ccttaaacag cagatgacca acggcaaact actggcagcg     1200
atccgcgaag cgcttgacgc cgcgctgatc cagcttaact gccccatcaa tatgctggcg     1260
gcggcgcgac gtttaaacgg cagtgataac aacaatgtgg cgctcgacgc cgcgtggcgc     1320
gaaggtgaag aggcgatggc gcggctgaaa cgttgccgcc cgtcgctgga actggaaagt     1380
gcggccgtct ggccgctgca accctttttt gacgatctgc gcgcgcttta tcacacccgc     1440
tacgagcagg ggaaaaattt gcaggtcacg ctggattccc atcatctggt gggatttggt     1500
cagcgtacgc aactgttagc ctgcctgagt ctgtggctcg atcgcacgct ggatattgcc     1560
gccgggctgg gtgatttcac cgcgcaaacg cagatttacg cccgcgaaga agagggctgg     1620
ctctctttgt atatcactga caatgtgccg ctgatcccgc tgcgccacac ccactcgccg     1680
gatgcgctta acgctccggg aaaaggcatg gagctgcgcc tgatccagac gctggtggca     1740
caccaccacg gcgcaataga actcacttca caccccgaag ggggaagttg cctgacccta     1800
cgattcccgc tatttcattc actgaccgga ggttcaaaat gacccagcga accgagtcgg     1860
gtaataccgt ctggcgcttc gatttgtccc agcagttcac tgcgatgcag cgcataagcg     1920
tggtactcag ccgggcgacc gaggtcgatc agacgctcca gcaagtgctg tgcgtattgc     1980
acaatgacgc cttttttgcag cacggcatga tctgtctgta cgacagccag caggcgattt     2040
tgaatattga agcgttgcag gaagccgatc agcagttaat ccccggcagc tcgcaaatcc     2100
gctatcgtcc gggcgaaggg ctggtcggga cggtgctttc gcaggccaa tcattagtgc      2160 tggcgcgcgt tgctgacgat cagcgctttc ttgaccggct cgggttgtat gattacaacc     2220
tgccgtttat cgccgtgccg ctgatagggc cagatgcgca gactttcggt gtgctgacgg     2280
cacaacccat ggcgcgttac gaagagcgat taccgcctg cacccgcttt ctggaaacgg      2340
tcgctaacct ggtcgcgcaa accgtgcgtt tgatggcacc accggcagtg cgcccttccc     2400
cgcgcgccgc cataacacag gccgccagcc cgaaatcctg cacggcctca cgcgcatttg     2460
gttttgaaaa tatggtcggt aacagtccgg cgatgcgcca gaccatggag attatccgtc     2520
```

-continued

```
aggtttcgcg ctgggacacc accgttctgg tacgcggcga gagtggcacc ggcaaggagc    2580
tgattgccaa cgccatccac caccattcgc cgcgtgccgg tgcgccattt gtgaaattca    2640
actgtgcggc gctgccggac acactgctgg aaagcgaatt gttcggtcac gagaaagggg    2700
catttaccgg cgcggtacgc cagcgtaaag gccgtttttga gctggccgat ggcggcacgc    2760
tgtttcttga cgagatcggc gagagtagcg cctcgtttca ggctaagctg ctgcgcattt    2820
tgcaggaagg cgaaatggaa cgcgtcggcg gcgacgagac attgcaagtg aatgtgcgca    2880
ttattgccgc gacgaaccgc aatcttgaag atgaagtccg gctggggcac tttcgcgaag    2940
atctctatta tcgcctgaat gtgatgccca tcgccctgcc gccactacgc gaacgccagg    3000
aggacattgc cgagctggcg cactttctgg tgcgtaaaat cgcccataac cagagccgta    3060
cgctgcgcat tagcgagggc gctatccgcc tgctgatgag ctacaactgg cccggtaatg    3120
tgcgcgaact ggaaaactgc cttgagcgct cagcggtgat gtcggagaac ggtctgatcg    3180
atcgggatgt gattttgttt aatcatcgcg accagccagc caaaccgcca gttatcagcg    3240
tctcgcatga tgataactgg ctcgataaca accttgacga gcgccagcgg ctgattgcgg    3300
cgctggaaaa agcgggatgg gtacaagcca agccgcgcg cttgctgggg atgacgccgc    3360
gccaggtcgc ctatcgtatt cagacgatgg atataaccct gccaaggcta taa          3413
```

<210> SEQ ID NO 77
<211> LENGTH: 495
<212> TYPE: PRT
<213> ORGANISM: Kosakonia sacchari
<220> FEATURE:
<223> OTHER INFORMATION: NifL, strain CI006

<400> SEQUENCE: 77

```
Met Thr Leu Asn Met Met Met Asp Ala Gly Ala Pro Glu Ala Ile Ala
1               5                   10                  15

Gly Ala Leu Ser Arg His His Pro Gly Leu Phe Phe Thr Ile Val Glu
            20                  25                  30

Glu Ala Pro Val Ala Ile Ser Leu Thr Asp Ala Asp Ala Arg Ile Val
        35                  40                  45

Tyr Ala Asn Pro Ala Phe Cys Arg Gln Thr Gly Tyr Glu Leu Glu Ala
    50                  55                  60

Leu Leu Gln Gln Asn Pro Arg Leu Leu Ala Ser Arg Gln Thr Pro Arg
65                  70                  75                  80

Glu Ile Tyr Gln Asp Met Trp His Thr Leu Leu Gln Arg Arg Pro Trp
                85                  90                  95

Arg Gly Gln Leu Ile Asn Arg His Arg Asp Gly Ser Leu Tyr Leu Val
            100                 105                 110

Glu Ile Asp Ile Thr Pro Val Ile Asn Pro Phe Gly Glu Leu Glu His
        115                 120                 125

Tyr Leu Ala Met Gln Arg Asp Ile Ser Ala Ser Tyr Ala Leu Glu Gln
    130                 135                 140

Arg Leu Arg Asn His Met Thr Leu Thr Glu Ala Val Leu Asn Asn Ile
145                 150                 155                 160

Pro Ala Ala Val Val Val Val Asp Glu Arg Asp His Val Val Met Asp
                165                 170                 175

Asn Leu Ala Tyr Lys Thr Phe Cys Ala Asp Cys Gly Gly Lys Glu Leu
            180                 185                 190

Leu Ser Glu Leu Asn Phe Ser Ala Arg Lys Ala Glu Leu Ala Asn Gly
        195                 200                 205
```

-continued

```
Gln Val Leu Pro Val Val Leu Arg Gly Glu Val Arg Trp Leu Ser Val
    210             215             220

Thr Cys Trp Ala Leu Pro Gly Val Ser Glu Glu Ala Ser Arg Tyr Phe
225             230             235             240

Ile Asp Asn Arg Leu Thr Arg Thr Leu Val Val Ile Thr Asp Asp Thr
                245             250             255

Gln Gln Arg Gln Gln Gln Glu Gln Gly Arg Leu Asp Arg Leu Lys Gln
                260             265             270

Gln Met Thr Asn Gly Lys Leu Leu Ala Ala Ile Arg Glu Ala Leu Asp
                275             280             285

Ala Ala Leu Ile Gln Leu Asn Cys Pro Ile Asn Met Leu Ala Ala Ala
    290             295             300

Arg Arg Leu Asn Gly Ser Asp Asn Asn Asn Val Ala Leu Asp Ala Ala
305             310             315             320

Trp Arg Glu Gly Glu Glu Ala Met Ala Arg Leu Lys Arg Cys Arg Pro
                325             330             335

Ser Leu Glu Leu Glu Ser Ala Ala Val Trp Pro Leu Gln Pro Phe Phe
                340             345             350

Asp Asp Leu Arg Ala Leu Tyr His Thr Arg Tyr Glu Gln Gly Lys Asn
                355             360             365

Leu Gln Val Thr Leu Asp Ser His His Leu Val Gly Phe Gly Gln Arg
    370             375             380

Thr Gln Leu Leu Ala Cys Leu Ser Leu Trp Leu Asp Arg Thr Leu Asp
385             390             395             400

Ile Ala Ala Gly Leu Gly Asp Phe Thr Ala Gln Thr Gln Ile Tyr Ala
                405             410             415

Arg Glu Glu Glu Gly Trp Leu Ser Leu Tyr Ile Thr Asp Asn Val Pro
                420             425             430

Leu Ile Pro Leu Arg His Thr His Ser Pro Asp Ala Leu Asn Ala Pro
    435             440             445

Gly Lys Gly Met Glu Leu Arg Leu Ile Gln Thr Leu Val Ala His His
    450             455             460

His Gly Ala Ile Glu Leu Thr Ser His Pro Glu Gly Gly Ser Cys Leu
465             470             475             480

Thr Leu Arg Phe Pro Leu Phe His Ser Leu Thr Gly Gly Ser Lys
                485             490             495
```

```
<210> SEQ ID NO 78
<211> LENGTH: 524
<212> TYPE: PRT
<213> ORGANISM: Kosakonia sacchari
<220> FEATURE:
<223> OTHER INFORMATION: NifA, strain CI006

<400> SEQUENCE: 78
```

```
Met Thr Gln Arg Thr Glu Ser Gly Asn Thr Val Trp Arg Phe Asp Leu
1               5               10              15

Ser Gln Gln Phe Thr Ala Met Gln Arg Ile Ser Val Val Leu Ser Arg
                20              25              30

Ala Thr Glu Val Asp Gln Thr Leu Gln Gln Val Leu Cys Val Leu His
        35              40              45

Asn Asp Ala Phe Leu Gln His Gly Met Ile Cys Leu Tyr Asp Ser Gln
    50              55              60

Gln Ala Ile Leu Asn Ile Glu Ala Leu Gln Glu Ala Asp Gln Gln Leu
65              70              75              80
```

---

```
Ile Pro Gly Ser Ser Gln Ile Arg Tyr Arg Pro Gly Glu Gly Leu Val
                85                  90                  95

Gly Thr Val Leu Ser Gln Gly Gln Ser Leu Val Leu Ala Arg Val Ala
            100                 105                 110

Asp Asp Gln Arg Phe Leu Asp Arg Leu Gly Leu Tyr Asp Tyr Asn Leu
            115                 120                 125

Pro Phe Ile Ala Val Pro Leu Ile Gly Pro Asp Ala Gln Thr Phe Gly
    130                 135                 140

Val Leu Thr Ala Gln Pro Met Ala Arg Tyr Glu Glu Arg Leu Pro Ala
145                 150                 155                 160

Cys Thr Arg Phe Leu Glu Thr Val Ala Asn Leu Val Ala Gln Thr Val
                165                 170                 175

Arg Leu Met Ala Pro Pro Ala Val Arg Pro Ser Pro Arg Ala Ala Ile
            180                 185                 190

Thr Gln Ala Ala Ser Pro Lys Ser Cys Thr Ala Ser Arg Ala Phe Gly
            195                 200                 205

Phe Glu Asn Met Val Gly Asn Ser Pro Ala Met Arg Gln Thr Met Glu
    210                 215                 220

Ile Ile Arg Gln Val Ser Arg Trp Asp Thr Thr Val Leu Val Arg Gly
225                 230                 235                 240

Glu Ser Gly Thr Gly Lys Glu Leu Ile Ala Asn Ala Ile His His His
                245                 250                 255

Ser Pro Arg Ala Gly Ala Pro Phe Val Lys Phe Asn Cys Ala Ala Leu
            260                 265                 270

Pro Asp Thr Leu Leu Glu Ser Glu Leu Phe Gly His Glu Lys Gly Ala
            275                 280                 285

Phe Thr Gly Ala Val Arg Gln Arg Lys Gly Arg Phe Glu Leu Ala Asp
    290                 295                 300

Gly Gly Thr Leu Phe Leu Asp Glu Ile Gly Glu Ser Ser Ala Ser Phe
305                 310                 315                 320

Gln Ala Lys Leu Leu Arg Ile Leu Gln Glu Gly Glu Met Glu Arg Val
                325                 330                 335

Gly Gly Asp Glu Thr Leu Gln Val Asn Val Arg Ile Ile Ala Ala Thr
            340                 345                 350

Asn Arg Asn Leu Glu Asp Glu Val Arg Leu Gly His Phe Arg Glu Asp
            355                 360                 365

Leu Tyr Tyr Arg Leu Asn Val Met Pro Ile Ala Leu Pro Pro Leu Arg
    370                 375                 380

Glu Arg Gln Glu Asp Ile Ala Glu Leu Ala His Phe Leu Val Arg Lys
385                 390                 395                 400

Ile Ala His Asn Gln Ser Arg Thr Leu Arg Ile Ser Glu Gly Ala Ile
                405                 410                 415

Arg Leu Leu Met Ser Tyr Asn Trp Pro Gly Asn Val Arg Glu Leu Glu
            420                 425                 430

Asn Cys Leu Glu Arg Ser Ala Val Met Ser Glu Asn Gly Leu Ile Asp
            435                 440                 445

Arg Asp Val Ile Leu Phe Asn His Arg Asp Gln Pro Ala Lys Pro Pro
    450                 455                 460

Val Ile Ser Val Ser His Asp Asp Asn Trp Leu Asp Asn Asn Leu Asp
465                 470                 475                 480

Glu Arg Gln Arg Leu Ile Ala Ala Leu Glu Lys Ala Gly Trp Val Gln
                485                 490                 495

Ala Lys Ala Ala Arg Leu Leu Gly Met Thr Pro Arg Gln Val Ala Tyr
```

-continued

```
                500              505              510
Arg Ile Gln Thr Met Asp Ile Thr Leu Pro Arg Leu
          515              520

<210> SEQ ID NO 79
<211> LENGTH: 2850
<212> TYPE: DNA
<213> ORGANISM: Kosakonia sacchari
<220> FEATURE:
<223> OTHER INFORMATION: glnE, strain CI006

<400> SEQUENCE: 79
atgccgcacc acgcaggatt gtcgcagcac tggcaaacgg tattttctcg tctgccggaa      60
tcgctcaccg cgcagccatt gagcgcgcag gcgcagtcag tgctcacttt tagtgatttt     120
gttcaggaca gcatcatcgc gcatcctgag tggctggcag agcttgaaag cgcgccgccg     180
cctgcgaacg aatggcaaca ctatgcgcaa tggctgcaag cggcgctgga tggcgtcacc     240
gatgaagcct cgctgatgcg cgcgctgcgg ctgtttcgcc gtcgcatcat ggtgcgcatc     300
gcctggagcc aggcgttaca gttggtggcg aagaagata tcctgcaaca gcttagcgtg     360
ctggcggaaa ccctgatcgt cgccgcgcgc gactggcttt atgaggcctg ctgccgtgag     420
tggggaacgc cgagcaatcc acaaggcgtg gcgcagccga tgctggtact cggcatgggc     480
aaactgggtg gcggcgaact caatttctca tccgatatcg atttgatttt cgcctggccg     540
gaaaatggcg caacgcgcgg tggacgccgt gagctggata cgcgcaatt tttcactcgc     600 cttggtcaac ggctgattaa agtcctcgac cagccaacgc aggatggctt tgtctaccgc     660
gtcgatatgc gcttgcgccc gtttggcgac agcggcccgc tggtgctgag ctttgccgcg     720
ctggaagatt actaccagga gcaggggcgc gattgggaac gctacgcgat ggtgaaagcg     780
cgcattatgg gcgataacga cggcgaccat gcgcgggagt tgcgcgcaat gctgcgcccg     840 tttgtttttcc gccgttatat cgacttcagc gtgattcagt ccctgcgtaa catgaaaggc     900
atgattgccc gcgaagtgcg tcgccgtggc ctgaaggaca acattaagct cggcgcgggc     960
gggatccgcg aaatagaatt tatcgtccag gttttccagc tgattcgcgg cggtcgcgag    1020
cctgcactgc aatcgcgttc actgttgccg acgcttgctg ccatagatca actgcatctg    1080
ctgccggatg gcgacgcaac ccggctgcgc gaggcgtatt tgtggctgcg acggctggag    1140
aacctgctgc aaagcatcaa tgacgaacag acacagacgc tgccgggcga tgaactgaat    1200
cgcgcgcgcc tcgcctgggg aatgggcaaa gatagctggg aagcgctctg cgaaacgctg    1260
gaagcgcata tgtcggcggt gcgtcagata tttaacgatc tgattggcga tgatgaaacg    1320
gattcgccgg aagatgcgct ttctgagagc tggcgcgaat gtggcaggat gcgttgcag    1380 gaggaggatt ccacgcccgt gctggcgcat ctctcagagg acgatcgccg ccgcgtggtg    1440
gcgctgattg ccgattttcg caaagagttg ataaacgca ccattggccc gcgagggcgg    1500
caggtactcg atcacttaat gccgcatctg ctcagcgatg tatgctcgcg cgacgatgcg    1560
ccagtaccgc tgtcacgcct gacgccgctg ctcaccggaa ttattacccg caccacttac    1620
cttgagctgc taagtgaatt ccccggcgca ctgaaacacc tcatttccct gtgtgccgcg    1680
tcgccgatgg ttgccagtca gctggcgcgc tacccgatcc tgcttgatga attgctcgac    1740
ccgaatacgc tctatcaacc gacggcgatg aatgcctatc gcgatgagct gcgccaatac    1800
ctgctgcgcg tgccggaaga tgatgaagag caacagcttg aggcgctgcg gcagtttaag    1860
caggcgcagt tgctgcgcgt ggcggcggcg gatattgccg gtacgttgcc agtaatgaaa    1920
```

-continued

```
gtgagcgatc acttaacctg gctggcggaa gcgattattg atgcggtggt gcagcaagcc      1980
tgggggcaga tggtggcgcg ttatggccag ccaacgcatc tgcacgatcg cgaagggcgc      2040
ggttttgcgg tggtcggtta tggcaagctg ggcggctggg agctgggtta cagctccgat      2100
ctggatctgg tattcctgca cgactgcccg atggatgtga tgaccgatgg cgagcgtgaa      2160
atcgatggtc gccagttcta tttgcgtctc gcgcagcgcg tgatgcacct gtttagcacg      2220
cgcacgtcgt ccggcatcct ttatgaagtt gatgcgcgtc tgcgtccatc tggcgctgcg      2280
gggatgctgg tcactactac ggaatcgttc gccgattacc agcaaaacga agcctggacg      2340
tgggaacatc aggcgctggc ccgtgcgcgc gtggtgtacg gcgatccgca actgaccgcc      2400
gaatttgacg ccattcgccg cgatattctg atgacgcctc gcgacggcgc aacgctgcaa      2460
accgacgtgc gagaaatgcg cgagaaaatg cgtgcccatc ttggcaacaa gcataaagac      2520
cgcttcgatc tgaaagccga tgaaggcggt atcaccgaca tcgagtttat cgcccaatat      2580
ctggtgctgc gctttgccca tgacaagccg aaactgacgc gctggtcgga taatgtgcgc      2640
attctcgaag ggctggcgca aaacggcatc atggaggagc aggaagcgca ggcattgacg      2700
ctggcgtaca ccacattgcg tgatgagctg caccacctgg cgctgcaaga gttgccggga      2760
catgtggcgc tctcctgttt tgtcgccgag cgtgcgctta ttaaaaccag ctgggacaag      2820
tggctggtgg aaccgtgcgc cccggcgtaa                                       2850
```

```
<210> SEQ ID NO 80
<211> LENGTH: 1563
<212> TYPE: DNA
<213> ORGANISM: Kosakonia sacchari
<220> FEATURE:
<223> OTHER INFORMATION: glnE_KO1, strain CI006

<400> SEQUENCE: 80
atgtttaacg atctgattgg cgatgatgaa acggattcgc cggaagatgc gctttctgag        60
agctggcgcg aattgtggca ggatgcgttg caggaggagg attccacgcc cgtgctggcg       120
catctctcag aggacgatcg ccgccgcgtg gtggcgctga ttgccgattt tcgcaaagag       180
ttggataaac gcaccattgg cccgcgaggg cggcaggtac tcgatcactt aatgccgcat       240
ctgctcagcg atgtatgctc gcgcgacgat cgcccagtac cgctgtcacg cctgacgccg       300
ctgctcaccg gaattattac ccgcaccact taccttgagc tgctaagtga atttcccggc       360
gcactgaaac acctcatttc cctgtgtgcc gcgtcgccga tggttgccag tcagctggcg       420
cgctacccga tcctgcttga tgaattgctc gacccgaata cgctctatca accgacggcg       480
atgaatgcct atcgcgatga gctgcgccaa tacctgctgc gcgtgccgga agatgatgaa       540
gagcaacagc ttgaggcgct gcggcagttt aagcaggcgc agttgctgcg cgtggcggcg       600
gcggatattg ccggtacgtt gccagtaatg aaagtgagcg atcacttaac ctggctggcg       660
gaagcgatta ttgatgcggt ggtgcagcaa gcctgggggc agatggtggc gcgttatggc       720
cagccaacgc atctgcacga tcgcgaaggg cgcggttttg cggtggtcgg ttatggcaag       780
ctgggcggct gggagctggg ttacagctcc gatctggatc tggtattcct gcacgactgc       840
ccgatggatg tgatgaccga tggcgagcgt gaaatcgatg gtcgccagtt ctatttgcgt       900
ctcgcgcagc gcgtgatgca cctgtttagc acgcgcacgt cgtccggcat cctttatgaa       960
gttgatgcgc gtctgcgtcc atctggcgct gcggggatgc tggtcactac tacggaatcg      1020
ttcgccgatt accagcaaaa cgaagcctgg acgtgggaac atcaggcgct ggcccgtgcg      1080
cgcgtggtgt acggcgatcc gcaactgacc gccgaatttg acgccattcg ccgcgatatt      1140
```

-continued

```
ctgatgacgc ctcgcgacgg cgcaacgctg caaaccgacg tgcgagaaat gcgcgagaaa      1200
atgcgtgccc atcttggcaa caagcataaa gaccgcttcg atctgaaagc cgatgaaggc      1260
ggtatcaccg acatcgagtt tatcgcccaa tatctggtgc tgcgctttgc ccatgacaag      1320
ccgaaactga cgcgctggtc ggataatgtg cgcattctcg aagggctggc gcaaaacggc      1380
atcatggagg agcaggaagc gcaggcattg acgctggcgt acaccacatt gcgtgatgag      1440
ctgcaccacc tggcgctgca agagttgccg ggacatgtgg cgctctcctg ttttgtcgcc      1500
gagcgtgcgc ttattaaaac cagctgggac aagtggctgg tggaaccgtg cgccccggcg      1560
taa                                                                    1563
```

<210> SEQ ID NO 81
<211> LENGTH: 949
<212> TYPE: PRT
<213> ORGANISM: Kosakonia sacchari
<220> FEATURE:
<223> OTHER INFORMATION: glnE, strain CI006

<400> SEQUENCE: 81

```
Met Pro His His Ala Gly Leu Ser Gln His Trp Gln Thr Val Phe Ser
1               5                   10                  15

Arg Leu Pro Glu Ser Leu Thr Ala Gln Pro Leu Ser Ala Gln Ala Gln
            20                  25                  30

Ser Val Leu Thr Phe Ser Asp Phe Val Gln Asp Ser Ile Ile Ala His
        35                  40                  45

Pro Glu Trp Leu Ala Glu Leu Glu Ser Ala Pro Pro Pro Ala Asn Glu
    50                  55                  60

Trp Gln His Tyr Ala Gln Trp Leu Gln Ala Ala Leu Asp Gly Val Thr
65                  70                  75                  80

Asp Glu Ala Ser Leu Met Arg Ala Leu Arg Leu Phe Arg Arg Arg Ile
                85                  90                  95

Met Val Arg Ile Ala Trp Ser Gln Ala Leu Gln Leu Val Ala Glu Glu
            100                 105                 110

Asp Ile Leu Gln Gln Leu Ser Val Leu Ala Glu Thr Leu Ile Val Ala
            115                 120                 125

Ala Arg Asp Trp Leu Tyr Glu Ala Cys Cys Arg Glu Trp Gly Thr Pro
        130                 135                 140

Ser Asn Pro Gln Gly Val Ala Gln Pro Met Leu Val Leu Gly Met Gly
145                 150                 155                 160

Lys Leu Gly Gly Gly Glu Leu Asn Phe Ser Ser Asp Ile Asp Leu Ile
                165                 170                 175

Phe Ala Trp Pro Glu Asn Gly Ala Thr Arg Gly Gly Arg Arg Glu Leu
            180                 185                 190

Asp Asn Ala Gln Phe Phe Thr Arg Leu Gly Gln Arg Leu Ile Lys Val
            195                 200                 205

Leu Asp Gln Pro Thr Gln Asp Gly Phe Val Tyr Arg Val Asp Met Arg
        210                 215                 220

Leu Arg Pro Phe Gly Asp Ser Gly Pro Leu Val Leu Ser Phe Ala Ala
225                 230                 235                 240

Leu Glu Asp Tyr Tyr Gln Glu Gln Gly Arg Asp Trp Glu Arg Tyr Ala
                245                 250                 255

Met Val Lys Ala Arg Ile Met Gly Asp Asn Asp Gly Asp His Ala Arg
            260                 265                 270

Glu Leu Arg Ala Met Leu Arg Pro Phe Val Phe Arg Arg Tyr Ile Asp
```

-continued

```
              275                   280                   285

Phe Ser Val Ile Gln Ser Leu Arg Asn Met Lys Gly Met Ile Ala Arg
    290                   295                   300

Glu Val Arg Arg Arg Gly Leu Lys Asp Asn Ile Lys Leu Gly Ala Gly
305                   310                   315                   320

Gly Ile Arg Glu Ile Glu Phe Ile Val Gln Val Phe Gln Leu Ile Arg
                  325                   330                   335

Gly Gly Arg Glu Pro Ala Leu Gln Ser Arg Ser Leu Leu Pro Thr Leu
                  340                   345                   350

Ala Ala Ile Asp Gln Leu His Leu Leu Pro Asp Gly Asp Ala Thr Arg
                  355                   360                   365

Leu Arg Glu Ala Tyr Leu Trp Leu Arg Arg Leu Glu Asn Leu Leu Gln
    370                   375                   380

Ser Ile Asn Asp Glu Gln Thr Gln Thr Leu Pro Gly Asp Glu Leu Asn
385                   390                   395                   400

Arg Ala Arg Leu Ala Trp Gly Met Gly Lys Asp Ser Trp Glu Ala Leu
                  405                   410                   415

Cys Glu Thr Leu Glu Ala His Met Ser Ala Val Arg Gln Ile Phe Asn
                  420                   425                   430

Asp Leu Ile Gly Asp Asp Glu Thr Asp Ser Pro Glu Asp Ala Leu Ser
                  435                   440                   445

Glu Ser Trp Arg Glu Leu Trp Gln Asp Ala Leu Gln Glu Glu Asp Ser
    450                   455                   460

Thr Pro Val Leu Ala His Leu Ser Glu Asp Asp Arg Arg Arg Val Val
465                   470                   475                   480

Ala Leu Ile Ala Asp Phe Arg Lys Glu Leu Asp Lys Arg Thr Ile Gly
                  485                   490                   495

Pro Arg Gly Arg Gln Val Leu Asp His Leu Met Pro His Leu Leu Ser
                  500                   505                   510

Asp Val Cys Ser Arg Asp Asp Ala Pro Val Pro Leu Ser Arg Leu Thr
                  515                   520                   525

Pro Leu Leu Thr Gly Ile Ile Thr Arg Thr Thr Tyr Leu Glu Leu Leu
    530                   535                   540

Ser Glu Phe Pro Gly Ala Leu Lys His Leu Ile Ser Leu Cys Ala Ala
545                   550                   555                   560

Ser Pro Met Val Ala Ser Gln Leu Ala Arg Tyr Pro Ile Leu Leu Asp
                  565                   570                   575

Glu Leu Leu Asp Pro Asn Thr Leu Tyr Gln Pro Thr Ala Met Asn Ala
                  580                   585                   590

Tyr Arg Asp Glu Leu Arg Gln Tyr Leu Leu Arg Val Pro Glu Asp Asp
                  595                   600                   605

Glu Glu Gln Gln Leu Glu Ala Leu Arg Gln Phe Lys Gln Ala Gln Leu
    610                   615                   620

Leu Arg Val Ala Ala Ala Asp Ile Ala Gly Thr Leu Pro Val Met Lys
625                   630                   635                   640

Val Ser Asp His Leu Thr Trp Leu Ala Glu Ala Ile Ile Asp Ala Val
                  645                   650                   655

Val Gln Gln Ala Trp Gly Gln Met Val Ala Arg Tyr Gly Gln Pro Thr
                  660                   665                   670

His Leu His Asp Arg Glu Gly Arg Gly Phe Ala Val Val Gly Tyr Gly
                  675                   680                   685

Lys Leu Gly Gly Trp Glu Leu Gly Tyr Ser Ser Asp Leu Asp Leu Val
    690                   695                   700
```

-continued

```
Phe Leu His Asp Cys Pro Met Asp Val Met Thr Asp Gly Glu Arg Glu
705                 710             715                 720

Ile Asp Gly Arg Gln Phe Tyr Leu Arg Leu Ala Gln Arg Val Met His
                    725             730                 735

Leu Phe Ser Thr Arg Thr Ser Ser Gly Ile Leu Tyr Glu Val Asp Ala
            740             745             750

Arg Leu Arg Pro Ser Gly Ala Ala Gly Met Leu Val Thr Thr Thr Glu
            755             760             765

Ser Phe Ala Asp Tyr Gln Gln Asn Glu Ala Trp Thr Trp Glu His Gln
        770             775             780

Ala Leu Ala Arg Ala Arg Val Val Tyr Gly Asp Pro Gln Leu Thr Ala
785                 790             795                 800

Glu Phe Asp Ala Ile Arg Arg Asp Ile Leu Met Thr Pro Arg Asp Gly
                805             810             815

Ala Thr Leu Gln Thr Asp Val Arg Glu Met Arg Glu Lys Met Arg Ala
            820             825             830

His Leu Gly Asn Lys His Lys Asp Arg Phe Asp Leu Lys Ala Asp Glu
            835             840             845

Gly Gly Ile Thr Asp Ile Glu Phe Ile Ala Gln Tyr Leu Val Leu Arg
        850             855             860

Phe Ala His Asp Lys Pro Lys Leu Thr Arg Trp Ser Asp Asn Val Arg
865                 870             875                 880

Ile Leu Glu Gly Leu Ala Gln Asn Gly Ile Met Glu Glu Gln Glu Ala
                885             890             895

Gln Ala Leu Thr Leu Ala Tyr Thr Thr Leu Arg Asp Glu Leu His His
            900             905             910

Leu Ala Leu Gln Glu Leu Pro Gly His Val Ala Leu Ser Cys Phe Val
            915             920             925

Ala Glu Arg Ala Leu Ile Lys Thr Ser Trp Asp Lys Trp Leu Val Glu
        930             935             940

Pro Cys Ala Pro Ala
945
```

```
<210> SEQ ID NO 82
<211> LENGTH: 520
<212> TYPE: PRT
<213> ORGANISM: Kosakonia sacchari
<220> FEATURE:
<223> OTHER INFORMATION: GlnE_KO1, strain CI006

<400> SEQUENCE: 82

Met Phe Asn Asp Leu Ile Gly Asp Asp Glu Thr Asp Ser Pro Glu Asp
1               5               10              15

Ala Leu Ser Glu Ser Trp Arg Glu Leu Trp Gln Asp Ala Leu Gln Glu
            20              25              30

Glu Asp Ser Thr Pro Val Leu Ala His Leu Ser Glu Asp Asp Arg Arg
        35              40              45

Arg Val Val Ala Leu Ile Ala Asp Phe Arg Lys Glu Leu Asp Lys Arg
    50              55              60

Thr Ile Gly Pro Arg Gly Arg Gln Val Leu Asp His Leu Met Pro His
65              70              75              80

Leu Leu Ser Asp Val Cys Ser Arg Asp Asp Ala Pro Val Pro Leu Ser
                85              90              95

Arg Leu Thr Pro Leu Leu Thr Gly Ile Ile Thr Arg Thr Thr Tyr Leu
            100             105             110
```

-continued

```
Glu Leu Leu Ser Glu Phe Pro Gly Ala Leu Lys His Leu Ile Ser Leu
        115                 120                 125

Cys Ala Ala Ser Pro Met Val Ala Ser Gln Leu Ala Arg Tyr Pro Ile
        130                 135                 140

Leu Leu Asp Glu Leu Leu Asp Pro Asn Thr Leu Tyr Gln Pro Thr Ala
145                 150                 155                 160

Met Asn Ala Tyr Arg Asp Glu Leu Arg Gln Tyr Leu Leu Arg Val Pro
                165                 170                 175

Glu Asp Asp Glu Glu Gln Gln Leu Glu Ala Leu Arg Gln Phe Lys Gln
                180                 185                 190

Ala Gln Leu Leu Arg Val Ala Ala Ala Asp Ile Ala Gly Thr Leu Pro
        195                 200                 205

Val Met Lys Val Ser Asp His Leu Thr Trp Leu Ala Glu Ala Ile Ile
        210                 215                 220

Asp Ala Val Val Gln Gln Ala Trp Gly Gln Met Val Ala Arg Tyr Gly
225                 230                 235                 240

Gln Pro Thr His Leu His Asp Arg Glu Gly Arg Gly Phe Ala Val Val
                245                 250                 255

Gly Tyr Gly Lys Leu Gly Gly Trp Glu Leu Gly Tyr Ser Ser Asp Leu
        260                 265                 270

Asp Leu Val Phe Leu His Asp Cys Pro Met Asp Val Met Thr Asp Gly
        275                 280                 285

Glu Arg Glu Ile Asp Gly Arg Gln Phe Tyr Leu Arg Leu Ala Gln Arg
        290                 295                 300

Val Met His Leu Phe Ser Thr Arg Thr Ser Ser Gly Ile Leu Tyr Glu
305                 310                 315                 320

Val Asp Ala Arg Leu Arg Pro Ser Gly Ala Ala Gly Met Leu Val Thr
                325                 330                 335

Thr Thr Glu Ser Phe Ala Asp Tyr Gln Gln Asn Glu Ala Trp Thr Trp
                340                 345                 350

Glu His Gln Ala Leu Ala Arg Ala Arg Val Val Tyr Gly Asp Pro Gln
        355                 360                 365

Leu Thr Ala Glu Phe Asp Ala Ile Arg Arg Asp Ile Leu Met Thr Pro
        370                 375                 380

Arg Asp Gly Ala Thr Leu Gln Thr Asp Val Arg Glu Met Arg Glu Lys
385                 390                 395                 400

Met Arg Ala His Leu Gly Asn Lys His Lys Asp Arg Phe Asp Leu Lys
                405                 410                 415

Ala Asp Glu Gly Gly Ile Thr Asp Ile Glu Phe Ile Ala Gln Tyr Leu
                420                 425                 430

Val Leu Arg Phe Ala His Asp Lys Pro Lys Leu Thr Arg Trp Ser Asp
        435                 440                 445

Asn Val Arg Ile Leu Glu Gly Leu Ala Gln Asn Gly Ile Met Glu Glu
        450                 455                 460

Gln Glu Ala Gln Ala Leu Thr Leu Ala Tyr Thr Thr Leu Arg Asp Glu
465                 470                 475                 480

Leu His His Leu Ala Leu Gln Glu Leu Pro Gly His Val Ala Leu Ser
                485                 490                 495

Cys Phe Val Ala Glu Arg Ala Leu Ile Lys Thr Ser Trp Asp Lys Trp
                500                 505                 510

Leu Val Glu Pro Cys Ala Pro Ala
        515                 520
```

```
<210> SEQ ID NO 83
<211> LENGTH: 341
<212> TYPE: PRT
<213> ORGANISM: Kosakonia sacchari
<220> FEATURE:
<223> OTHER INFORMATION: GlnE ATase domain, strain CI006

<400> SEQUENCE: 83

Glu Glu Gln Gln Leu Glu Ala Leu Arg Gln Phe Lys Gln Ala Gln Leu
1               5                   10                  15

Leu Arg Val Ala Ala Ala Asp Ile Ala Gly Thr Leu Pro Val Met Lys
                20                  25                  30

Val Ser Asp His Leu Thr Trp Leu Ala Glu Ala Ile Ile Asp Ala Val
            35                  40                  45

Val Gln Gln Ala Trp Gly Gln Met Val Ala Arg Tyr Gly Gln Pro Thr
        50                  55                  60

His Leu His Asp Arg Glu Gly Arg Gly Phe Ala Val Val Gly Tyr Gly
65                  70                  75                  80

Lys Leu Gly Gly Trp Glu Leu Gly Tyr Ser Ser Asp Leu Asp Leu Val
                85                  90                  95

Phe Leu His Asp Cys Pro Met Asp Val Met Thr Asp Gly Glu Arg Glu
            100                 105                 110

Ile Asp Gly Arg Gln Phe Tyr Leu Arg Leu Ala Gln Arg Val Met His
            115                 120                 125

Leu Phe Ser Thr Arg Thr Ser Ser Gly Ile Leu Tyr Glu Val Asp Ala
        130                 135                 140

Arg Leu Arg Pro Ser Gly Ala Ala Gly Met Leu Val Thr Thr Thr Glu
145                 150                 155                 160

Ser Phe Ala Asp Tyr Gln Gln Asn Glu Ala Trp Thr Trp Glu His Gln
                165                 170                 175

Ala Leu Ala Arg Ala Arg Val Val Tyr Gly Asp Pro Gln Leu Thr Ala
            180                 185                 190

Glu Phe Asp Ala Ile Arg Arg Asp Ile Leu Met Thr Pro Arg Asp Gly
            195                 200                 205

Ala Thr Leu Gln Thr Asp Val Arg Glu Met Arg Glu Lys Met Arg Ala
        210                 215                 220

His Leu Gly Asn Lys His Lys Asp Arg Phe Asp Leu Lys Ala Asp Glu
225                 230                 235                 240

Gly Gly Ile Thr Asp Ile Glu Phe Ile Ala Gln Tyr Leu Val Leu Arg
                245                 250                 255

Phe Ala His Asp Lys Pro Lys Leu Thr Arg Trp Ser Asp Asn Val Arg
            260                 265                 270

Ile Leu Glu Gly Leu Ala Gln Asn Gly Ile Met Glu Glu Gln Glu Ala
            275                 280                 285

Gln Ala Leu Thr Leu Ala Tyr Thr Thr Leu Arg Asp Glu Leu His His
        290                 295                 300

Leu Ala Leu Gln Glu Leu Pro Gly His Val Ala Leu Ser Cys Phe Val
305                 310                 315                 320

Ala Glu Arg Ala Leu Ile Lys Thr Ser Trp Asp Lys Trp Leu Val Glu
                325                 330                 335

Pro Cys Ala Pro Ala
            340

<210> SEQ ID NO 84
<211> LENGTH: 1342
```

<212> TYPE: DNA
<213> ORGANISM: Kosakonia sacchari
<220> FEATURE:
<223> OTHER INFORMATION: Prm5 inserted into nifL region, strain CI006,
      now strain CM029

<400> SEQUENCE: 84
ccgagcgtcg gggtgcctaa tatcagcacc ggatacgaga gaaaagtgtc tacatcggtt      60
cggttgatat tgaccggcgc atccgccagc ccgcccagtt tctggtggat ctgtttggcg     120
attttgcggg tcttgccggt gtcggtgccg aaaaaaatac caatatttgc cataacacac     180
gctcctgttg aaaaagagat cccgccggga aatgcggtga acgtgtctga tattgcgaag     240
agtgtgccag ttttggtcgc gggcaaaacc tgcaccagtt tggttattaa tgcaccagtc     300
tggcgctttt tttcgccgag tttctcctcg ctaatgcccg ccaggcgcgg ctttggcgct     360
gatagcgcgc tgaataccga tctggatcaa ggttttgtcg ggttatcagc caaaggtgc     420 actctttgca tggttatacg tgcctgacat gttgtccggg cgacaaacgg cctggtggca     480
caaattgtca gaactacgac acgactaact gaccgcagga gtgtgcgatg accctgaata     540
tgatgatgga tgccggcgga catcatcgcg acaaacaata ttaataccgg caaccacacc     600
ggcaatttac gagactgcgc aggcatcctt tctcccgtca atttctgtca aataaagtaa     660
aagaggcagt ctacttgaat tacccccggc tggttgagcg tttgttgaaa aaaagtaact     720
gaaaaatccg tagaatagcg ccactctgat ggttaattaa cctattcaat taagaattat     780
ctggatgaat gtgccattaa atgcgcagca taatggtgcg ttgtgcggga aaactgcttt     840
tttttgaaag ggttggtcag tagcggaaac aactcacttc acaccccgaa gggggaagtt     900
gcctgaccct acgattcccg ctatttcatt cactgaccgg aggttcaaaa tgacccagcg     960
aaccgagtcg ggtaataccg tctggcgctt cgatttgtcc cagcagttca ctgcgatgca    1020
gcgcataagc gtggtactca gccgggcgac cgaggtcgat cagacgctcc agcaagtgct    1080
gtgcgtattg cacaatgacg ccttttttgca gcacggcatg atctgtctgt acgacagcca    1140
gcaggcgatt ttgaatattg aagcgttgca ggaagccgat cagcagttaa tccccggcag    1200
ctcgcaaatc cgctatcgtc cgggcgaagg gctggtcggg acggtgcttt cgcagggcca    1260
atcattagtg ctggcgcgcg ttgctgacga tcagcgcttt cttgaccggc tcgggttgta    1320
tgattacaac ctgccgttta tc                                             1342

<210> SEQ ID NO 85
<211> LENGTH: 1270
<212> TYPE: DNA
<213> ORGANISM: Rahnella aquatilis
<220> FEATURE:
<223> OTHER INFORMATION: 16S
<220> FEATURE:
<221> NAME/KEY: modified_base
<222> LOCATION: (186)..(186)
<223> OTHER INFORMATION: a, c, t, g, unknown or other
<220> FEATURE:
<221> NAME/KEY: modified_base
<222> LOCATION: (458)..(458)
<223> OTHER INFORMATION: a, c, t, g, unknown or other
<220> FEATURE:
<221> NAME/KEY: modified_base
<222> LOCATION: (1041)..(1041)
<223> OTHER INFORMATION: a, c, t, g, unknown or other
<220> FEATURE:
<221> NAME/KEY: modified_base
<222> LOCATION: (1131)..(1132)
<223> OTHER INFORMATION: a, c, t, g, unknown or other
<220> FEATURE:
<221> NAME/KEY: modified_base

```
<222> LOCATION: (1135)..(1135)
<223> OTHER INFORMATION: a, c, t, g, unknown or other
<220> FEATURE:
<221> NAME/KEY: modified_base
<222> LOCATION: (1139)..(1140)
<223> OTHER INFORMATION: a, c, t, g, unknown or other

<400> SEQUENCE: 85
attgaagagt ttgatcatgg ctcagattga acgctggcgg caggcctaac acatgcaagt      60
cgagcggcag cgggaagtag cttgctactt tgccggcgag cggcggacgg gtgagtaatg     120
tctgggaaac tgcctgatgg aggggggataa ctactggaaa cggtagctaa taccgcatga    180
cctcgnaaga gcaaagtggg ggatcttcgg acctcacgcc atcggatgtg cccagatggg     240
attagctagt aggtgaggta atggctcacc taggcgacga tccctagctg gtctgagagg     300
atgaccagcc acactggaac tgagacacgg tccagactcc tacgggaggc agcagtgggg     360
aatattgcac aatgggcgca agcctgatgc agccatgccg cgtgtgtgaa gaaggcctta     420
gggttgtaaa gcactttcag cgaggaggaa ggcatcanac ttaatacgtg tggtgattga     480
cgttactcgc agaagaagca ccggctaact ccgtgccagc agccgcggta atacggaggg     540
tgcaagcgtt aatcggaatt actgggcgta aagcgcacgc aggcggtttg ttaagtcaga     600
tgtgaaatcc ccgcgcttaa cgtgggaact gcatttgaaa ctggcaagct agagtcttgt     660
agaggggggg agaattccag gtgtagcggt gaaatgcgta gagatctgga ggaataccgg     720
tggcgaaggc ggccccctgg acaaagactg acgctcaggt gcgaaagcgt ggggagcaaa     780
caggattaga taccctggta gtccacgctg taaacgatgt cgacttggag gttgtgccct     840
tgaggcgtgg cttccggagc taacgcgtta agtcgaccgc ctggggagta cggccgcaag     900
gttaaaactc aaatgaattg acgggggccc gcacaagcgg tggagcatgt ggtttaattc     960
gatgcaacgc gaagaacctt acctactctt gacatccacg gaattcgcca gagatggctt    1020
agtgccttcg ggaaccgtga nacaggtgct gcatggctgt cgtcagctcg tgttgtgaaa    1080
tgttgggtta agtcccgcaa cgagcgcaac ccttatcctt tgttgccagc nngtnatgnn    1140
gggaactcaa aggagactgc cggtgataaa ccggaggaag gtggggatga cgtcaagtca    1200
tcatggccct tacgagtagg gctacacacg tgctacaatg gcatatacaa agagaagcga    1260
actcgcgagg                                                           1270

<210> SEQ ID NO 86
<211> LENGTH: 876
<212> TYPE: DNA
<213> ORGANISM: Rahnella aquatilis
<220> FEATURE:
<223> OTHER INFORMATION: nifH

<400> SEQUENCE: 86
atggcaatgc gtcaatgcgc aatctacggg aaaggggggta ttgggaaatc caccactacc      60
caaaaccttg tagcggctct ggccgaaatg aataagaagg tcatgatcgt cggctgtgac     120
cctaaggctg attcaacccg cctcattctg catgcgaaag cacagaacac catcatggaa     180
atggccgctg aagtgggctc cgtggaagat ctggagctgg aagatgtgat gcaaatcggc     240
tatgccggcg tgcgctgtgc ggaatcaggc ggccctgagc ctggtgtggg ttgtgccgga     300
cgcggggtga tcaccgccat caacttcctc gaagaagaag gcgcgtatgt gccggatctg     360
gattttgtgt tttacgacgt attgggcgat gtggtctgtg gcggtttcgc gatgccaatt     420
cgcgaaaaca aagcgcagga aatctacatc gtgtgctccg gtgaaatgat ggcgatgtat     480
```

-continued

```
gccgccaaca acatttccaa aggcatcgtg aaatacgcga aatcgggcaa agttcgcctg        540
gccgggctga tctgtaactc ccgccagacg gatcgcgaag atgaactgat catcgcgctg        600
gctgaaaaac ttggcacgca aatgatccac ttcgtgccgc gtgacaacat tgtgcaacgc        660
gctgaaatcc gccgcatgac ggtcatcgaa tacgacccga cttgtgcgca ggcagatcag        720
tatcgtgcac tggcgaacaa aatcgtcaac aacaccaaaa tggtggtgcc gacaccggtc        780
accatggatg agctggaagc cctgttaatg gaatttggca ttatggaaga agaagacctg        840
gccatcgtcg gtcgtaccgc cgccgaagag gcgtga                                 876
```

```
<210> SEQ ID NO 87
<211> LENGTH: 1374
<212> TYPE: DNA
<213> ORGANISM: Rahnella aquatilis
<220> FEATURE:
<223> OTHER INFORMATION: nifD1

<400> SEQUENCE: 87
```

```
atgaaggcaa aagagattct ggcgctgatt gatgagccag cctgtgagca taaccacaag         60
cagaagtcgg gttgcagcct gccgaaaccg ggcgcgacgg caggcggttg tgcgtttgat        120
ggcgcgcaga ttgcgctgct gccggtcgcg gacgtcgcgc atctggtgca cggcccgatt        180
ggctgtaccg gcagttcatg ggacaaccgt ggcagccgca gttccgggcc ttccatcaac        240
cgcatgggct tcaccaccga catgagcgag caggatgtga ttatgggcg cggcgagcga         300 cgcttatttc acgccgtgca gcacatcgtc agccattacc atccggtggc ggtctttatt        360
tacaacacct gcgtacccgc gatggaaggg gatgacgttg aagccgtgtg tcgcgccgca        420
tcggccgctg ccggtgtgcc ggttatttca gtcgatgccg ccggtttcta cggcagcaaa        480
aatctcggta accgcattgc cggggacgtg atggtcaaaa aggtgatcgg ccagcgcgaa        540
cccgcgccgt ggccggaaaa ctcaccgatc cccgccggac accgccacag catcagcctg        600
attggcgaat tcaatattgc cggcgagttc tggcacgttc tgccgctgct cgatgagctc        660
gggatccgcg tgctgtgcag cctttccggg gattcccgtt ttgctgaaat ccagactatg        720
caccgtggcg aagccaacat gctggtgtgc tcgcgggcgc tgatcaacgt cgcccgaaaa        780
atggaagagc gttaccagat cccatggttt gaaggcagtt tttatggcct gcgttccatg        840
gctgattccc tgcgcacgat cgccgtgctg ctcaaagacc cggatttaca ggcgcgcaca        900
gaacgtctga ttgagcgcga ggaggcggcg acacatcttg cgcttgcgcc ttaccgtgcg        960
cggctcagcg ggcgcaaggc gctgctgtat accggtggcg tgaaatcctg gtcggtggtc       1020
tcggcgttac aggatttagg catcacggtg gtggcgaccg gcacccgaaa atcaaccgaa       1080
gaagacaagc agcgtattcg cgaactgatg ggtgaagacg tgctgatgct cgacgaaggc       1140
aatgccagaa ccttgctcga caccctctat cgtttcggcg gcgacatcat gatcgccggg       1200
ggccgcaaca tgtataccgc gtacaaagcc cgcctgccgt tcctggatat caatcaggag       1260
cgcgagcatg cgtttgccgg atatcacggg ctggtaaatc tggccgaaca gttgtgtatc       1320
accctggaaa gcccggtctg ggcgcaggtc aaccgtctgg cgccgtggcg ctaa            1374
```

```
<210> SEQ ID NO 88
<211> LENGTH: 1449
<212> TYPE: DNA
<213> ORGANISM: Rahnella aquatilis
<220> FEATURE:
<223> OTHER INFORMATION: nifD2

<400> SEQUENCE: 88
```

```
atgaccagtg aaacacgcga acgtaacgag gcattgatcc aggaagtgct ggagatcttc    60
cccgagaagg cgcttaaaga tcgtaagaaa cacatgatga ccaccgaccc ggcgatggaa   120
tctgtcggca agtgtattgt ctcaaaccgc aaatcacagc cgggcgtgat gaccgtgcga   180
ggctgcgctt acgccggttc caaaggcgtg gtctttggcc cgatcaaaga catggcgcat   240
atctcccacg gcccggttgg ttgcggccag tattcccgtg ccggacgccg taactattac   300
accggctgga gcgcgtgaa cagctttggc accctcaact tcaccagtga ttttcaggaa    360
cgggacatcg tatttggcgg cgataaaaag ctcgacaaat tgatcgatga actggagatg   420
ttgttcccgc tgagcaaagg catttcggtg cagtcggaat gtccggtcgg tctgatcggc   480
gatgacattt ctgccgtcgc caaagccagc agcgccaaaa tcggtaagcc ggtcgtgccg   540
gtacgctgcg aggggttccg cggtgtgtcg caatcgctcg gccatcacat tgctaacgat   600
gtcatccgcg actgggtgct ggataaccgc gaaggcaatg aatttgaaac cacgccttac   660
gacgtggcga ttatcggcga ctacaacatc ggcggtgacg cctgggcctc acgtattctg   720
ctcgaagaaa tggggctgcg cgtggtggcg cagtggtccg gcgacggcac gctggtggag   780
atggaaaaca ccccgaaagt cgcgctcaat ctggtgcact gctaccgctc gatgaactac   840
atctcccgtc atatggaaga aaaacacggc attccgtgga tggaatacaa cttctttggc   900
ccgaccaaaa ttgcggaatc tctgcgcgaa atcgcggcgc gttttgacga taccatccgg   960
aaaaacgccg aagcggtgat tgaaaaatat caggcgcaaa cgcaggcggt gatcgacaaa  1020
taccgtccgc gtctggaagg caaaaaggtg ctgttgtatc tcggcggttt acgtccgcgc  1080
cacatcatcg gggcgtatga agatctggga atggaaatca tcggtaccgg ctatgaattc  1140
ggtcataacg atgattacga ccgcacctta ccgatgctca agaaggcac gttgctgttc   1200 gatgacctga gcagttatga gctggaagcg ttcgttaaag cgctgaaacc ggatcttgtc  1260
gggtcaggta tcaaagaaaa atacattttc cagaaaatgg gcgtgccgtt ccgccagatg  1320
cactcctggg attattccgg cccttatcac ggctacgacg gtttcggcat ttttgcccgt  1380
gacatggaca tgacgctgaa caatccgggc tggagtcagc tgaccgcccc ctggttgaaa  1440
acggcctga                                                          1449
```

```
<210> SEQ ID NO 89
<211> LENGTH: 1386
<212> TYPE: DNA
<213> ORGANISM: Rahnella aquatilis
<220> FEATURE:
<223> OTHER INFORMATION: nifK1

<400> SEQUENCE: 89
```

```
atggctcaaa ttctgcgtaa tgccaagccg cttgccacca cgcctgtcaa aagcgggcaa    60
ccgctcgggg cgatcctggc cagtcagggg ctggaaaatt gcatcccgct ggttcacggc   120
gcgcaaggtt gtagcgcgtt cgccaaagtt ttcttcatcc agcattttca cgatccgatc   180
ccgttgcagt ccacggcgat ggaatcgacc acgactatca tgggctcgga tggcaacgtc   240
agtactgcgt tgaccacgtt gtgtcagcgc agtaatccaa aagccattgt gattttgagc   300
accggactgt cagaagcgca gggcagtgat ttgtcgatgg cgctgcgtga gtttcgcgac   360
aaagaaccgc gctttaatgc catcgctatt ctgaccgtta acacgccgga ttttttacggc   420 tcgctggaaa acggctacag cgcgctgatg gaaagcgtga tcactcagtg ggtgccggaa   480
aagccgccga ccggcatgcg taacaagcgc gtgaacctgc tggtgagcca tctgctgacg   540
```

```
ccgggggatc tggaattact gcgcagctat gtcgaagcct ttggcctgca accggtgatc      600
ctgccggatt tatcacagtc gctggacgga catctggcga atggcgattt caatccggtc      660
acgcagggcg gcacgtcgca acgccagatt gaacaaatgg ggcagagcct gaccaccatt      720
accattggca gttcgctcaa ctgcgccgcc agtctgatgg cgatgcgcag ccgtggcatg      780
gcgctgaacc tgccgcacct gatgacgctg gaaaacatgg acagtctgat ccgccatctg      840
catcaggtgt caggccgcga ggtaccggca tggattgagc gccagcgcgg gcaactgctg      900
gacgccatga tcgactgcca tacctggctg cagtcacagc gtattgcgct ggcggcagaa      960
gcggatttgc tggtggcgtg gtgcgatttc gctcagagcc agggaatgcg cgtcgggccg     1020
gtgattgcgc cggttaatca gcagtcactg gccgggctgc cggtcgaaca ggtggtgatc     1080
ggcgatctgg aagatttaca aacccggctc gacagctacc cggtttcact gctggtggcg     1140
aactcccacg ctgcaccact ggcggaaaaa aacggtatcg cgctggtacg tgccggtttc     1200
ccgctttacg accgtctcgg ggaatttcgc cgcgtgcggc agggctatgc gggtattcgc     1260
gacaccttgt tcgaactcgc gaacctgatg caggcgcgcc atcacatgct gacggcgtat     1320
cactcaccgc ttaggcaggt gttcggcctg agcccggtac cggaggccag tcatgaggcg     1380
cgctaa                                                                 1386

<210> SEQ ID NO 90
<211> LENGTH: 1569
<212> TYPE: DNA
<213> ORGANISM: Rahnella aquatilis
<220> FEATURE:
<223> OTHER INFORMATION: nifK2

<400> SEQUENCE: 90
atgagtcaag atcttggcac cccaaaatcc tgtttcccgc tgttcgagca ggatgaatac       60
cagaatatgt ttacccacaa acgcgcgctg aagaagcac acggcgaggc gaaagtgcgg       120
gaagtgtttg aatggaccac cacgcaggaa tatcaggatc tgaacttctc gcgtgaagcg       180
ctgaccgtcg acccggcgaa agcctgccag ccgttaggcg cggtactttg cgcgctgggt       240
tttaccaaca cgttgccgta tgtccatggt tcacaaggct gtgtggcgta tttccgtacc       300
tattttaatc gtcatttcaa agagccggtg gcctgtgttt ccgactcaat gaccgaagat       360
gccgccgttt ttggcggaaa taacaacatg aatgtcggtc tggaaaacgc cagcgcgctg       420
tacaagccgg aaattattgc ggtctccacc acctgtatgg cggaagtgat cggtgatgac       480
ctgcaggctt ttatcgccaa cgccaaaaaa gacggatttg tggatgccgg tatgccaatc       540
ccgtatgccc atacaccgag ttttctgggc agtcatgtca ccggctggga caacatgttt       600
gaaggcttcg cccgtacctt taccaccgac gccacgcggg aatatcagcc gggcaaactt       660
gccaaactga acgtggtgac cggttttgaa acttatctcg gcaactaccg ggttattcac       720
cgcatgatga ccagatgggg ggtcgaatgc agcgtcttgt ccgatccgtc tgaagtgctc       780
gacacccggg ctgacggcca ataccgcatg tatgccggcg gcaccacgca aaccgaaatg       840
cgtgatgcac cggatgccat cgacaccttg ctgctgcaac cgtggcaatt acagaaaacc       900
aaaaaggtgg tgcagggcga ctggaatcag ccgggcaccg aagtcagtgt accgattggc       960
ctggcggcga ccgatgcctt gctgatgacg gtaagcgaac tgaccggcaa accgatagct     1020
gacgcgctgc cgactgaacg tggccgtctg gtggacatga tgctcgattc tcacacctgg     1080
ctgcacggca agcgtttcgg tctctacggt gacccggatt ttgtgatggg catgaccgca     1140
ttcctgctgg aactgggctg tgaaccgacc accattctca gccataacgg caacaaacgc     1200
```

-continued

```
tggcagaaag ccatgaagaa aatgctggct gattcgcctt acggacagga cagcgaagtg      1260
tatgtgaact gcgatctgtg gcatttccgc tcgctgatgt ttacccgtaa accggacttt      1320
atgatcggca actcttacgg aaaattcatt cagcgtgaca cgctggccaa aggcgaacag      1380
ttcgaagtgc cgctgatccg tatcggattc ccgatttttg accggcacca tttgcaccgt      1440
cagaccacct ggggatacga gggcgcgatg agcatcctga cgcaactggt gaatgcggtg      1500
ctcgaacagc tggatcgcga aaccatgaag ctcggcaaaa ccgactacaa cttcgatctg      1560
atccgctaa                                                             1569
```

```
<210> SEQ ID NO 91
<211> LENGTH: 1488
<212> TYPE: DNA
<213> ORGANISM: Rahnella aquatilis
<220> FEATURE:
<223> OTHER INFORMATION: nifL

<400> SEQUENCE: 91
atgagcatca cggcgttatc agcatcattt cctgagggga atatcgccag ccgcttgtcg       60
ctgcaacatc cttcactgtt ttataccgtg gttgaacaat catcggtggc gatttcgctg      120
accgatccgc aggcgcgcat ttgttatgcc aatccggcat tctgccgcca gacgggtttt      180
gcacttgaga cacttttggg cgagaaccac cgtctgctgg ccagccagca gacgccgaaa      240
catatctatg acgaaatgtg gcgcactttg ttgcagggca atcctggaa cggccaactg       300 atcaaccggc gtaataaccg ttcgctttat ctggcggatg tcactatcac gcctgtttta      360
ggcgcggacg ggcaggtgga gcattacctc ggcatgcaca aagatatcag cgagaaatac      420
gcgctggagc agcggttgcg caaccacatc accttgttca cggaggtgct gaacaatatt      480
cccgccgccg tggtggtggt ggatgagcag gacaatgtgg tgatggacaa tctggcctac      540
aaaaccctgt gcgctgactg cggcggaaaa gagctgttgg ccgaaatggg ctatccgcaa      600
ctcaaagaga tgctcaacag tggcgaaccg gtgccggttt ccatgcgcgg caacgtacgc      660 tggtttctt tcggtcagtg gtcattgcag ggcgttaatg aagaggccag ccgctttttt       720
accggcatta ccgcgccggg aaaactgatt gttctcaccg actgcaccga tcagcatcac      780
cggcagcagc agggttatct tgaccggctc aagcaaaaac ttaccaacgg caaattgctg      840
gcagccatcc gcgagtcgct tgatgccgcg ctgattcagc tcaacgggcc aattaatatg      900
ctggcggctg cgcgtcgtct taacggcgaa gaaggcaaca acatggcgct ggaattcgcc      960
tggcgcgaag gcgagcaggc ggtgagtcgc ttacaggcct gccgtccgtc gctggatttt     1020
gagccgcagg cagaatggcc ggtcagtgaa ttcttcgacg atctgagcgc gctgtacgac     1080
agccattttc tcagtgacgg tgaattgcgt tacgtggtca tgccatctga tctgcacgct     1140
gtcgggcaac gaacgcaaat ccttaccgcg ctgagcttat ggattgatca cacgctgtca     1200
caggcgcagg ccatgccgtc tctgaagctc tcggtgaaca ttgttgcgaa gcaggatgcg     1260
agctggttgt gttttgacat taccgataat gtgccgcgtg aacgggtgcg ttatgcccgc     1320
ccggaagcgg cgttttcccg tccggggaat ggcatggagc tgcgccttat ccagacgctg     1380
atcgcccatc atcgcggttc tttagatctc tcggtccgcc ctgatggcgg caccttgctg     1440
acgttacgcc tgccggtaca gcaggttatc accggaggct taaaatga               1488
```

```
<210> SEQ ID NO 92
<211> LENGTH: 1557
<212> TYPE: DNA
```

-continued

```
<213> ORGANISM: Rahnella aquatilis
<220> FEATURE:
<223> OTHER INFORMATION: nifA

<400> SEQUENCE: 92
atgacccagt tacctaccgc gggcccggtt atccggcgct ttgatatgtc tgcccagttt      60
acggcgcttt atcgcatcag cgtggcgctg agtcaggaaa gcaataccgc gcgcgcactg     120
gcggcgatcc tcgaagtgct tcacgatcat gcatttatgc aatacggcat ggtgtgtctg     180
ttcgataaag aacgcaatgc actgtttgtg gaatccctgc atggcatcga cggcgaaagg     240
aaaaaagaga cccgccatgt ccgttaccgc atggggaag gcgtgatcgg cgcggtgatg      300
agccagcgtc aggcgctggt gttaccgcgc atttcagacg atcagcgttt tctcgaccgc     360
ctgaatattt acgattacag cctgccgctg attggtgtgc cgatccccgg tgcggataat     420
cagcctgcgg gtgtgctggt ggcacagccg atggcgttgc acgaagaccg gctggctgcc     480
agtacgcggt ttttagaaat ggtcgccaat ctcatcagcc agccactgcg ttctgccacg     540
cccccggaat cattgcctgc tcaaacgccg gtccggtgca gtgttccgcg ccagtttggt     600
tttgagcaga tggtcgggaa aagtcaggcg atgcgccaga cgatggacat tttacggcag     660
gtttccaaat gggataccac ggttctggtg cgtggtgaaa gcggcaccgg caaggaactt     720
atcgccaatg ccattcatta caactcaccc cgtgcggccg cgccatttgt gaaattcaac     780
tgcgccgcgc tgccggataa cctgctggaa agcgaactgt tcggtcatga aaaagggggcc    840 ttcaccggcg ctatacgcac ccgaaaaggc cgctttgaac tggcggacgg gggcacgtta    900
ttcctcgatg aaatcggcga atcgagcgcg tcgtttcagg ccaaattgct gcgcattttg    960
caggaaggtg aaatggaacg ggtcggcggc gataccacgc tgaaagttga tgtgcgcatt   1020
attgctgcca ccaaccgtaa tcttgaggag gaagtgcgtg ccgggaattt cgcgaagac    1080 ctgtattatc gcctgaacgt gatgccggtt tcgctgcctg cactgcgtga aaggctggat   1140
gatatcgccg atctggcgcc gtttctggtc aaaaagattg cgctgcgtca ggggcgggaa   1200
ctgcgcatca gtgatggtgc ggtgcgtctg ctgatgacct acagctggcc aggcaacgtg   1260
cgtgaactgg aaaactgcct cgaacgggcg tcggtaatga ccgatgaagg gctgatcgac   1320
cgcgacgtga tcctgttcaa tcaccatgag tccccggcgc tgtccgtcaa acccggtctg   1380
ccgctggcga cagatgaaag ctggctggat caggaactcg acgaacgcca gcgggtgatt   1440
gctgcactgg agaaaaccgg ctgggtgcag gccaaagcgg cccgactgct gggcatgaca   1500
ccgcgccaga ttgcctaccg tatccagatt atggacatca acatgcaccg tatctga      1557
```

```
<210> SEQ ID NO 93
<211> LENGTH: 2838
<212> TYPE: DNA
<213> ORGANISM: Rahnella aquatilis
<220> FEATURE:
<223> OTHER INFORMATION: glnE

<400> SEQUENCE: 93
atgttgccac tttcttctgt tttgcaaagc cacgcgcaga gtttgcctga acgctggcat      60
gaacatcctg aaaacctgcc cctccccgat gatgaacagc tggctgtgct gagcagcagt     120
gaattcatga cggacagttt gctggctttt ccgcagtggt ggcatgaaat tgtccaaaat     180 cccccctcagg cgcaggagtg gcaacttttac cgtcagtggc tggatgaatc gctgacgcag    240
gtgactgacg aagccgggtt aatgaaagct ttgcgtctgt tccgccgccg tattctgacc     300
cgcattgcgt ggtcacagtc cgcgcaaacc agcgaagcaa aagatacgct tcaccagctg     360
```

```
agtgaactgg cggaattatt gattgtcagc gcccgtgact ggctgtatgc cgcttgctgt    420
cgcgagttcg gtacgccggt caatgccgca ggggaaccgc agagaatgct gatcctcggg    480
atgggcaaac tcggcggtgg cgagctgaat ttctcatcgg acatcgacct gattttgct    540 tatccggaaa atggccagac acgcggcggt cggcgtgaac tggataacgc acaattttc    600 acccggctcg gccagcgtct gatcaaagcg ctggatcagc ccactatcga cggttttgtc    660 tatcgcgtg acatgcgttt gcgtccgttc ggcgacagtg gcccgctggt gatgagcttc    720
ccggcactgg aagattatta tcaggaacag gggcgcgact gggaacgcta cgcaatggtg    780
aaagcgcgtc tgatgggcgg cgcggaggac atcagcagtc aggaattgcg taaaatgctg    840
atgccttttg tcttccgccg ttatatcgat ttcagtgtga tccagtccct gcgtaacatg    900
aaaggcatga tcgcccgcga agtacgccgc cgtggtctga aagacaacat caaactcggc    960
gcaggcggta ttcgtgaaat tgaatttatc gtgcaggtat ttcagctgat ccgtggcggt   1020
cgtgaaccgg cattgcagca gcgtgcgttg ttgccaacgc ttcaggcgct ggaaaatctg   1080
gggctgctgc cggtagagca ggtgttgcag ttgcgtaaca gctatctgtt cctgcgacgt   1140
ctggaaaacc tgttgcaggc cattgctgac gagcaaacgc aaaccttacc gtccgatgag   1200
ctgaatcagg cgcgtctggc gtgggggatg aattacgctg gctggccgca gcttctggat   1260
gcagtgaatg ctcacatgca ggccgtacgc gcggtattta acgatctgat tggcgatgac   1320
acgccagatg ccgaagatga cgtgcaactc tcccggttca gcagtttatg gattgatacg   1380
cttgagcctg acgagctggc tccgctggtg ccgcaacttg acgaaaatgc gcaacggcat   1440
gttttacatc agattgctga ttttcgccgt gacgtggata aacgcacgat agggccacgt   1500
gggcgtgatc agttggattt gctgatgccg cgtttactgg cccaggtctg cacctataaa   1560
aatgcggatg tgacgttaca gcgcctgatg cagttgctgc tcaatatcgt cacgcgcacg   1620
acgtatatcg agctgctggt ggaatatccc ggtgcgctca aacagttaat acgtctgtgc   1680
gctgcctcgc cgatggtggc gacgcaactt gcgcgtcatc ctttattgct cgacgaactg   1740
ctcgacccgc gcacgcttta ccagccgatt gagccgggcg cgtaccgtga tgaactgcgg   1800
caatatctga tgcgggtgcc aaccgaagac gaagaacaac agcttgaagc cgtgcgccag   1860
ttcaaacagg cacagcattt acgtattgcg gccggggata tttccggtgc gttgccggtg   1920
atgaaagtca gtgaccattt aacctacctt gcggaggcca ttctcgacgt tgtggtgcaa   1980
caggcgtggg aacaaatggt cgtaaaatac ggtcagccaa cccatcttca gcaccgtaaa   2040
gggcgcggtt ttgccgtggt gggttacgga aaactcggtg gctgggagct gggttacagc   2100
tcggatctgg atctggtctt cctgctcgat tgcgcgccgg aagtcatgac cgacggcgaa   2160
cgcagcattg acgggcgtca gttttatctg cggctggcgc agcgcatcat gcatttattc   2220
agcacccgta cgtcgtcagg cattctttat gaggttgacc cgcgtctgcg gccttccggt   2280
gcttccggca tgctggtcag caccatcgaa gcttttgcgg attatcaggc caacgaagcc   2340
tggacatggg agcatcaggc gctggttcgc gcgcgtgtgg tttatggtga tccgcaactg   2400
acgcagcaat ttaatgccac gcgtcgcgac attctttgcc gccagcgcga tgccgacggc   2460
ttgcgtaagg aagtccgtga aatgcgcgag aaaatgtatg cccatctggg cagcaaaaga   2520
gccgacgagt ttgatctgaa agccgatccg ggtggcataa cggatattga attcatcgca   2580
caatatctgg ttctgcgttt cgcgcatgat gagccgaagc tgacccgctg gtctgataac   2640
gtgcggattt tcgaactgat ggcgcgacat gacatcatgc cggaagagga agcacgccat   2700
```

-continued

```
ctgacgcagg cttacgtgac attgcgcgat gaaattcatc atctggcgtt gcaggaacac      2760
agcgggaaag tggccgcaga cagctttgcc actgagcgcg cgcaaatccg cgccagctgg      2820
gcaaactggc ttggctga                                                    2838

<210> SEQ ID NO 94
<211> LENGTH: 1290
<212> TYPE: DNA
<213> ORGANISM: Rahnella aquatilis
<220> FEATURE:
<223> OTHER INFORMATION: amtB

<400> SEQUENCE: 94
atgaaaaaac ttttatccat gatggggctt ggtgcagtgg ctttgctacc ttcgcttgcc        60
atggcagcag caccagcagc ggcaaacggt gctgataacg cctttatgat gatttgtacc       120
gcgctggtat tgttcatgac cgtacccggt gtggcgttgt tctacggcgg cttactgcgt       180
tctaaaaacg ttttgtccat gctgactcag gttattgtta cctttgctct ggtctgcgtc       240
ctgtggatcc tctacggtta cagccttgcc ttcagtgaag gtaacgcgtt cttcggtggt       300
ttcagcaacg taatgatgaa aggcattggc ctggattctg tgactggcac cttctcgcag       360
atgatccacg ttgcattcca gtgttcattt gcctgcatca ctgtagcgct gatcgtaggt       420
ggtattgctg aacgtgtgcg tttctcagca gttctgattt tcactgtgat ctggctgact       480
ttctcttata ttccgatggc tcacatggta tgggcaggcg gtttcctggc tgctgacggt       540
gcgctggact ttgccggtgg taccgttgtt catatcaatg ccgcaattgc tggcctggta       600
ggggcttatc tgctgggtaa acgcgccggt tttggcaaag aagctttcaa accacacaac       660
ctgccaatgg tcttcactgg cgcctcaatc ctgtatgtgg gctggttcgg cttcaatgcg       720
ggttcagcaa gtgccgcaag ctctgttgcc gcgctggctt tcctgaacac tgtcattgct       780
actgctggcg caatcctgtc ctggacgctg gttgagtgga tggtgcgcgg taagccctca       840
ctgctgggcg caagctccgg tgctatcgca ggtctggtgg ctatcacgcc tgcatgtggt       900
acggtcggcg taggtggtgc tctgattatc ggtctggtag gcggtatcac tggtctgtgg       960
ggggttgtta ccctgaaaaa atggctgcgt gttgatgaca cctgtgatgt gttcggtgtt      1020
catggcgtgt gcggtatcgt aggttgtctg ctgacgggtg tattcacgtc cagttcactt      1080
ggcggcgtgg gctacgcaga aggcgtgacc atgggccatc aggtttgggt gcagttcttc      1140
agcgtgtgcg taacattggt ctggtcaggc gttgttgcct tcatcggtta caaagtggct      1200
gacatgatcg taggtctgcg tgttcctgaa gaacaagaac gcgaaggtct ggacgttaac      1260
agccacggcg aaaacgctta caaccaataa                                      1290

<210> SEQ ID NO 95
<211> LENGTH: 500
<212> TYPE: DNA
<213> ORGANISM: Rahnella aquatilis
<220> FEATURE:
<223> OTHER INFORMATION: PinfC

<400> SEQUENCE: 95
tgaatatcac tgactcacaa gctacctatg tcgaagaatt aactaaaaaa ctgcaagatg        60
caggcattcg cgttaaagcc gacttgagaa atgagaagat tggctttaaa attcgcgaac       120
acacgctacg ccgtgttcct tatatgttag tttgtggcga taaagaggtc gaagcaggca       180
aagttgctgt tcgtactcgt cgcggcaaag acttaggaag catggatgtt agcgaagtcg       240
ttgacaaact gctggcggaa atccgcagca gaagtcatca tcaactggag gaataaagta       300
```

-continued

```
ttaaaggcgg aaaacgagtt caaccggcgc gtcctaatcg cattaacaaa gagattcgcg      360
cgcaagaagt tcgcctcacc ggcgtcgatg gcgagcagat tggtattgtc agtctgaatg      420
aagctcttga aaaagctgag gaagcgggcg tcgatttagt agaaatcagt ccgaatgccg      480
agccgccagt ttgtcgaatc                                                 500

<210> SEQ ID NO 96
<211> LENGTH: 1085
<212> TYPE: DNA
<213> ORGANISM: Klebsiella variicola
<220> FEATURE:
<223> OTHER INFORMATION: 16S

<400> SEQUENCE: 96
attgaagagt ttgatcatgg ctcagattga acgctggcgg caggcctaac acatgcaagt       60
cgagcggtag cacagagagc ttgctctcgg gtgacgagcg gcggacgggt gagtaatgtc      120
tgggaaactg cctgatggag ggggataact actggaaacg gtagctaata ccgcataacg      180
tcgcaagacc aaagtggggg accttcgggc ctcatgccat cagatgtgcc cagatgggat      240
tagctagtag gtggggtaac ggctcaccta ggcgacgatc cctagctggt ctgagaggat      300
gaccagccac actggaactg agacacggtc cagactccta cgggaggcag cagtggggaa      360
tattgcacaa tgggcgcaag cctgatgcag ccatgccgcg tgtgtgaaga aggccttcgg      420
gttgtaaagc actttcagcg gggaggaagg cggtgaggtt aataacctca ccgattgacg      480
ttacccgcag aagaagcacc ggctaactcc gtgccagcag ccgcggtaat acggagggtg      540
caagcgttaa tcggaattac tgggcgtaaa gcgcacgcag gcggtctgtc aagtcggatg      600
tgaaatcccc gggctcaacc tgggaactgc attcgaaact ggcaggctag agtcttgtag      660 agggggtag aattccaggt gtagcggtga atgcgtaga gatctggagg aataccggtg        720
gcgaaggcgg cccctggac aaagactgac gctcaggtgc gaaagcgtgg ggagcaaaca       780
ggattagata ccctggtagt ccacgctgta aacgatgtcg atttggaggt tgtgcccttg      840
aggcgtggct tccggagcta acgcgttaaa tcgaccgcct ggggagtacg gccgcaaggt      900
taaaactcaa atgaattgac ggggggcccgc acaagcggtg gagcatgtgg tttaattcga     960
tgcaacgcga agaaccttac ctggtcttga catccacaga actttccaga gatggattgg     1020
tgccttcggg aactgtgaga caggtgctgc atggctgtcg tcagctcgtg ttgtgaaatg     1080
ttggg                                                               1085

<210> SEQ ID NO 97
<211> LENGTH: 882
<212> TYPE: DNA
<213> ORGANISM: Klebsiella variicola
<220> FEATURE:
<223> OTHER INFORMATION: nifH1

<400> SEQUENCE: 97
atgaccatgc gtcaatgcgc tatctacggt aaaggcggta tcggtaaatc caccaccacc       60
cagaatctcg tcgcggccct cgccgagatg ggtaagaaag tgatgatcgt cggctgcgat      120
ccgaaagcgg attccacccg tctgatcctc cacgctaaag cccagaacac catcatggag      180
atggcggcgg aagtgggctc ggtcgaggat ctggagctcg aagacgttct gcaaatcggc      240
tatggcgatg tccgttgcgc cgaatccggc ggcccggagc aggcgtcgg ctgcgccgga        300 cgcgggtga tcaccgccat caacttcctc gaggaagaag gcgcctatga agaagatttg       360
```

```
gatttcgtct tctatgacgt cctcggcgac gtggtctgcg gcggcttcgc tatgccgatc        420
cgcgaaaaca aagcccagga gatctacatc gtctgctccg gcgagatgat ggcgatgtat        480
gccgccaaca atatctccaa agggatcgtg aagtacgcca aatccggcaa ggtgcgcctc        540
ggcggcctga tctgtaactc gcgcaaaacc gaccgggaag acgaactgat catcgccctg        600
gcggagaagc ttggcacgca gatgatccac ttcgttcccc gcgacaacat tgtgcagcgc        660
gcggagatcc gccggatgac ggtgatcgag tacgacccga cctgtcagca ggcgaatgaa        720
tatcgtcaac tggcgcagaa gatcgtcaat aacaccaaaa aagtggtgcc gacgccgtgc        780
accatggacg agctggaatc gctgctgatg gagttcggca tcatggaaga agaagacacc        840
agcatcattg gtaaaaccgc cgctgaagaa aacgcggcct ga                          882
```

```
<210> SEQ ID NO 98
<211> LENGTH: 1113
<212> TYPE: DNA
<213> ORGANISM: Klebsiella variicola
<220> FEATURE:
<223> OTHER INFORMATION: nifH2

<400> SEQUENCE: 98
atggttagga aaagtagaag taaaaataca aatatagaac taactgaaca tgaccattta         60
ttaataagtc aaataaaaaa gcttaaaaca caaaccactt gctttttaa taataaagga        120 ggggttggga agactacatt agtagcaaat ttaggagcag agctatcaat aaactttagt        180
gcaaaagttc ttattgtgga tgccgaccct caatgtaatc tcacgcagta tgtattaagt        240
gatgaagaaa ctcaggactt atatgggcaa gaaaatccag atagtattta tacagtaata        300
agaccactat cctttggtaa aggatatgaa agtgacctcc ctataaggca tgtagagaat        360
ttcggttttg acataattgt cggtgaccct agacttgctt tacaggaaga ccttttagct        420
ggagactggc gagatgccaa aggcggtggg atgcgaggaa ttaggacaac ttttgtattt        480
gcagagttaa ttaagaaagc tcgtgagcta aattatgatt ttgttttctt tgacatggga        540
ccatcattag gcgcaatcaa cagggcagta ttactggcaa tggaattctt tgtcgtccca        600
atgtcaatcg atgtattttc actatgggct attaaaaata ttggctccac ggtttcaata        660
tggaaaaaag aattagacac agggattcgg ctctcagagg aacctagcga attatcacaa        720
ttatcacctc aaggaaaact aaagtttctc ggttacgtca cccaacaaca taagaacgc         780 tctggatacg atacaattca gcttgagaat actgaggaag aaataaaatc gaaacgtcgg        840
gtaaaggcgt atgaagacat tggagaggtg tttccttcta aaattactga gcatctttct        900
aaactttatg catcaaaaga tatgaaccca caccttggag atatacgtca tttaggtagt        960
ttagctccga aatcacaatc acaacacgtt ccgatgatat cagtgtctgg tacaggaaat       1020
tacaccagac ttagaaaaag cgcgcgtgaa ctttatcgag atattgcaag aagatactta       1080
gagaacattc agactgctaa tggcgagaaa tag                                    1113
```

```
<210> SEQ ID NO 99
<211> LENGTH: 1374
<212> TYPE: DNA
<213> ORGANISM: Klebsiella variicola
<220> FEATURE:
<223> OTHER INFORMATION: nifD1

<400> SEQUENCE: 99
atgaagggaa aggaaattct ggcgctgctg gacgaacccg cctgcgagca caaccagaag         60
caaaaatccg gctgcagcgc ccctaagccc ggcgctaccg ccggcggttg cgccttcgac        120
```

-continued

```
ggcgcgcaga taacgctcct gcccatcgcc gacgtcgcgc acctggtgca cggccccatc    180
ggctgcgcgg gcagctcgtg ggataaccgc ggcagcgtca gcgccggccc ggccctcaac    240
cggctcggct ttaccaccga tcttaacgaa caggatgtga ttatgggccg cggcgaacgc    300
cgcctgttcc acgccgtgcg tcacatcgtc gaccgctatc atccggcggc ggtctttatc    360
tacaacacct gcgtaccggc gatggagggc gatgacatcg aggcggtctg ccaggccgca    420
cagaccgcca ccggcgtccc ggtcatcgct attgacgccg ccggtttcta cggcagtaaa    480
aatcttggca accgaatggc gggcgacgtg atgctcaggc aggtgattgg ccagcgcgaa    540
ccggccccgt ggccagacaa cacgcccttt gccccggccc agcgccacga tatcggcctg    600
attggcgaat tcaatatcgc cggcgagttc tggcaggtcc agccgctgct cgacgagctg    660
gggatccgcg tcctcggcag cctctccggc gacggccgct ttgccgagat ccagaccctg    720
caccgggcgc aggccaatat gctggtgtgc tcgcgcgcgc tgatcaacgt cgcccggggg    780
ctggagctgc gctacggcac gccgtggttt gaaggcagct tctacgggat ccgcgccacc    840
tccgacgcct tgcgccagct ggcgacgctg ctgggggatg acgacctgcg ccgccgcacc    900
gaggcgctga tcgcccgcga agagcaggcg gcggagcagg ctcttgcgcc gtggcgtgag    960
cagctccgcg ggcgcaaagt gctgctctat accggcggcg tgaaatcctg gtcggtggta   1020
tcggccctgc aggatctcgg catgaccgtg gtggccaccg gcacgcgcaa atccaccgag   1080
gaggacaaac agcggatccg tgagctgatg ggcgacgagg cggtgatgct tgaggagggc   1140
aatgcccgca ccctgctcga cgtggtgtac cgctatcagg ccgacctgat gatcgccggc   1200
ggacgcaata tgtacaccgc ctggaaagcc cggctgccgt ttctcgatat caatcaggag   1260
cgcgagcacg cctacgccgg ctatcagggc atcatcaccc tcgcccgcca gctctgtctg   1320
accctcgcca gccccgtctg gccgcaaacg catacccgcg ccccgtggcg ctag          1374
```

```
<210> SEQ ID NO 100
<211> LENGTH: 1449
<212> TYPE: DNA
<213> ORGANISM: Klebsiella variicola
<220> FEATURE:
<223> OTHER INFORMATION: nifD2

<400> SEQUENCE: 100
```

```
atgaccaacg caacaggcga acgtaacctt gcgctcatcc aggaagtcct ggaggtgttt     60
cccgaaaccg cgcgcaaaga gcgcagaaag cacatgatga tcagcgatcc gcagatggag    120
agcgtcggca agtgcattat ctcgaaccgt aaatcgcagc ccggggtgat gaccgtgcgc    180
ggctgcgcct atgcgggctc gaaaggggtg gtgtttgggc caatcaaaga catggcccat    240
atctcgcacg gccccatcgg ctgcggccag tattcccgcg ccggacggcg caactactat    300
accggcgtca gcggtgtcga cagcttcggc accctgaact tcacctctga ttttcaggag    360
cgcgatattg ttttcggcgg cgataaaaag ctgaccaaac tgatcgaaga gatggagctg    420
ctgttcccgc tgaccaaagg gatcaccatc cagtcggagt gcccggtggg cctgatcggc    480
gatgacatca cgccgtagc caacgccagc agcaaggcgc tggataaacc ggtgatcccg    540
gtgcgctgcg aaggctttcg cggcgtatcg caatcgctgg ccaccatat cgccaacgac    600 gtggtgcgcg actgggtgct gaacaatcgc gaagggcagc cgtttgccag caccccgtac    660
gatgttgcca tcattggcga ttacaacatc ggcggcgacg cctgggcctc gcgcattctg    720
ctggaagaga tggggctgcg cgtagtggcg cagtggtccg gcgacggcac cctggtggag    780
```

-continued

```
atggagaaca ccccattcgt taagcttaac ctcgtccact gctaccgttc gatgaactat      840
atcgcccgcc atatggagga gaaacatcag atcccatgga tggaatataa cttcttcggc      900
ccgaccaaaa tcgccgaatc gctgcgcaag atcgccgatc aatttgatga caccattcgc      960
gccaatgcgg aagcggtgat cgccaaatat gaggggcaga tggcggccat catcgccaaa     1020
tatcgcccgc ggctggaggg gcgcaaagtg ctgctgtaca tggggggggct gcggccgcgc     1080 cacgtcatcg gcgcctatga ggatctcggg atggagatca tcgccgccgg ctacgagttt     1140
gcccataacg atgattacga ccgcaccctg ccggacctga aagagggcac cctgctgtt t     1200 gacgatgcca gcagctatga gctggaggcc ttcgtcaaag cgctgaaacc tgacctcatc     1260
ggctccggga tcaaagagaa atatatcttc cagaaaatgg gggtgccgtt ccgccagatg     1320
cactcctggg actattccgg cccctatcac ggctatgacg gcttcgccat ctttgcccgc     1380
gatatggata tgaccctgaa caatccggcg tggaacgaac tgactgcccc gtggctgaag     1440
tctgcgtga                                                           1449
```

```
<210> SEQ ID NO 101
<211> LENGTH: 1386
<212> TYPE: DNA
<213> ORGANISM: Klebsiella variicola
<220> FEATURE:
<223> OTHER INFORMATION: nifK1

<400> SEQUENCE: 101
```

```
atggcagata ttatccgcag tgaaaaaccg ctggcggtga gcccgattaa aaccgggcaa       60
ccgctcgggg cgatcctcgc cagcctcggg ctggcccagg ccatccccgct ggtccacggc      120 gcccagggct gcagcgcctt cgccaaagtt ttctttattc agcatttcca tgacccggtg       180
ccgctgcagt cgacggccat ggatccgacc gccacgatca tggggggccga cggcaatatc      240 ttcaccgcgc tcgacaccct ctgccagcgc cacagcccgc aggccatcgt gctgctcagc       300
accggtctgg cggaagcgca gggcagcgat atcgcccggg tggtcgcgcca gtttcgcgag      360 gcgcatccgc gccataacgg cgtggcgatc ctcaccgtca ataccccgga ttttttttggc      420 tctatggaaa acggctacag cgcggtgatc gagagcgtga tcgagcagtg ggtcgcgccg       480
acgccgcgtc cggggcagcg gccccggcgg gtcaacctgc tggtcagcca cctctgttcg      540
ccaggggata tcgaatggct gggccgctgc gtggaggcct ttggcctgca gccggtgatc       600
ctgccggacc tctcgcagtc aatggatggc cacctcggtg aaggggattt tacgcccctg       660
acccagggcg gcgcctcgct gcgccagatt gcccagatgg gccagagtct gggcagcttc       720
gccattggcg tgtcgctcca gcgggcggca tcgctcctga cccaacgcag ccgcggcgac       780
gtgatcgccc tgccgcatct gatgaccctc gaccattgcg ataccttttat ccatcagctg      840 gcgaagatgt ccggacgccg cgtaccggcc tggattgagc gccagcgtgg ccagctgcag       900
gatgcgatga tcgactgcca tatgtggctt cagggccagc gcatggcgat ggcggcggag       960
ggcgacctgc tggcggcgtg gtgtgatttc gcccgcagcc aggggatgca gcccggcccg      1020
ctggtcgccc ccaccagcca ccccagcctg cgccagctgc cggtcgagca agtcgtgccg      1080
ggggatcttg aggatctgca gcagctgctg agccaccaac ccgccgatct gctggtggct      1140
aactctcacg cccgcgatct ggcggagcag tttgccctgc cgctgatccg cgtcggtttt      1200
cccctcttcg accggctcgg tgagtttcgt cgcgtccgcc aggggtacgc cggtatgcga      1260
gatacgctgt ttgaactggc caatctgctg cgcgaccgcc atcaccacac cgccctctac      1320
cgctcgccgc ttcgccaggg cgccgacccc cagccggctt caggagacgc ttatgccgcc      1380
```

-continued

```
cattaa                                                              1386

<210> SEQ ID NO 102
<211> LENGTH: 1563
<212> TYPE: DNA
<213> ORGANISM: Klebsiella variicola
<220> FEATURE:
<223> OTHER INFORMATION: nifK2

<400> SEQUENCE: 102
atgagccaaa cgatcgataa aattcacagc tgttatccgc tgtttgaaca ggatgaatac     60
cagaccctgt tccagaataa aaagaccctt gaagaggcgc acgacgcgca gcgtgtgcag    120
gaggtttttg cctggaccac caccgccgag tatgaagcgc tgaacttcca gcgcgaggcg    180
ctgaccgtcg acccgccaa  agcctgccag ccgctcggcg ccgtactctg cgcgctgggg    240
ttcgccggca ccctgcccta cgtgcacggc tcccagggct gcgtcgccta ttttcgcacc    300
tactttaacc gccattttaa agagccggtc gcctgcgtct ccgactccat gaccgaggac    360
gcggcggtgt tcggcggcaa caacaacatg aatctgggcc tgcagaatgc cagcgcgctg    420
tataaacccg agattatcgc cgtctccacc acctgtatgg ccgaggtgat cggcgacgat    480
ctgcaggcgt ttatcgccaa cgccaaaaaa gagggatttg ttgacgaccg catcgccatt    540
ccttacgccc ataccccag  ctttatcggc agccatgtca ccggctggga caatatgttc    600
gaagggttcg cgaagacctt taccgctgac tacgccgggc agccgggcaa acagcaaaag    660
ctcaatctgg tgaccggatt tgagacctat ctcggcaact tccgcgtgct gaagcggatg    720
atggcgcaga tggatgtccc gtgcagcctg ctctccgacc catcagaggt gctcgacacc    780
cccgccgacg gccattaccg gatgtacgcc ggcggcacca gccagcagga gatcaaaacc    840
gcgccggacg ccattgacac cctgctgctg cagccgtggc agctggtgaa aagcaaaaag    900
gtggttcagg agatgtggaa ccagcccgcc accgaggtgg ccgttccgct gggcctggcc    960
gccaccgacg cgctgctgat gaccgtcagt cagctgaccg gcaaaccgat cgccgacgct   1020
ctgaccctgg agcgcggccg gctggtcgac atgatgctgg attcccacac ctggctgcat   1080
ggcaaaaaat tcggcctcta cggcgatccg gatttcgtga tggggctgac gcgcttcctg   1140
ctggagctgg gctgcgagcc gacggtgatc ctcagtcata cgccaataa  acgctggcaa   1200 aaagcgatga agaaaatgct cgatgcctcg ccgtacggtc aggaaagcga gtgttcatc   1260 aactgcgacc tgtggcactt ccggtcgctg atgttcaccc gtcagccgga ctttatgatc   1320
ggtaactcct acggcaagtt tatccagcgc gataccctgg caaagggcaa agccttcgaa   1380
gtgccgctga tccgtctggg ctttccgctg ttcgaccgcc atcatctgca ccgccagacc   1440
acctggggct atgaaggcgc aatgaacatc gtcacgacgc tggtgaacgc cgtgctggaa   1500
aaactggacc acgacaccag ccagttgggc aaaaccgatt acagcttcga cctcgttcgt   1560
taa                                                               1563

<210> SEQ ID NO 103
<211> LENGTH: 1485
<212> TYPE: DNA
<213> ORGANISM: Klebsiella variicola
<220> FEATURE:
<223> OTHER INFORMATION: nifL

<400> SEQUENCE: 103
atgaccctga atatgatgct cgataacgcc gcgccggagg ccatcgccgg cgcgctgact     60
```

-continued

```
caacaacatc cggggctgtt ttttaccatg gtggaacagg cctcggtggc catctccctc      120
accgatgcca gcgccaggat catttacgcc aacccggcgt tttgccgcca gaccggctat      180
tcgctggcgc aattgttaaa ccagaacccg cgcctgctgg ccagcagcca gacgccgcgc      240
gagatctatc aggagatgtg gcataccctg ctccagcgtc agccctggcg cggtcagctg      300
attaatcagc gtcgggacgg cggcctgtac ctggtggaga ttgacatcac cccggtgctt      360
agcccgcaag gggaactgga gcattatctg gcgatgcagc gggatatcag cgtcagctac      420
accctcgaac agcggctgcg caaccatatg accctgatgg aggcggtgct gaataatatc      480
cccgccgccg tggtagtggt ggacgagcag gatcgggtgg tgatggacaa cctcgcctac      540
aaaaccttct gcgctgactg cggcggccgg gagctgctca ccgagctgca ggtctcccct      600
ggccggatga cgcccggcgt ggaggcgatc ctgccggtgg cgctgcgcgg ggccgcgcgc      660
tggctgtcgg taacctgctg gccgttgccc ggcgtcagtg aagaggccag ccgctacttt      720
atcgacagcg cgctggcgcg gaccctggtg gtgatcgccg actgtaccca gcagcgtcag      780
cagcaggagc aagggcgcct tgaccggctg aagcagcaaa tgaccgccgg caagctgctg      840
gcggcgatcc gcgagtcgct ggacgccgcg ctgatccagc tgaactgccc gattaatatg      900
ctggcggcag cccgtcggct gaacggcgag ggaagcggga atgtggcgct ggaggccgcc      960
tggcgtgaag gggaagaggc gatggcgcgg ctccagcgct gtcgcccatc gctggaactc     1020
gaaaaccccg ccgtctggcc gctgcagccc tttttcgacg atctgtgcgc cctctaccgt     1080
acacgcttcg atcccgacgg gctgcaggtc gacatggcct caccgcatct gatcggcttt     1140
ggccagcgca ccccactgct ggcgtgctta agcctgtggc tcgatcgcac cctggccctc     1200
gccgccgaac tcccctccgt gccgctggcg atgcagctct acgccgagga gaacgacggc     1260
tggctgtcgc tgtatctgac tgacaacgta ccgctgctgc aggtgcgcta cgctcactcc     1320
cccgacgcgc tgaactcgcc gggcaaaggc atggagctgc ggctgatcca gaccctggtg     1380
gcgcaccatc gcggggccat tgagctggct tcccgaccgc agggcggcac ctgcctgacc     1440
ctgcgtttcc cgctgtttaa caccctgacc ggaggtgaag catga                    1485
```

<210> SEQ ID NO 104
<211> LENGTH: 1575
<212> TYPE: DNA
<213> ORGANISM: Klebsiella variicola
<220> FEATURE:
<223> OTHER INFORMATION: nifA

<400> SEQUENCE: 104

```
atgatccctg aatccgaccc ggacaccacc gtcagacgct tcgacctctc tcagcagttc       60
accgccatgc agcggataag cgtggtgctg agccgggcca ccgaggccag caaaacgctg      120
caggaggtgc tcagcgtatt acacaacgat gcctttatgc agcacgggat gatctgcctg      180
tacgacagcg agcaggagat cctcagtatc gaagcgctgc agcaaaccgg ccagcagccc      240
ctccccggca gcacgcagat ccgctatcgc cccggcgagg gactggtggg gaccgtgctg      300
gcccaggggc agtcgctggt gctgccccgg gtcgccgacg atcagcgttt tctcgaccgc      360
ctgagcctct acgattacga tctgccgttt atcgccgtac cgttgatggg gcccaacgcc      420
cggccaatag gggtgctggc ggcccagccg atggcgcgcc aggaagagcg gctgccggcc      480
tgcacccgtt ttctcgaaac cgtcgccaac ctcgtcgccc agaccatccg gctgatgatc      540
cttccggcct cacccgccct gtcgagccgc cagccgccga aggtggaacg gccgccggcc      600
tgctcgtcgt cgcgcggcgt gggcccttgac aatatggtcg gcaagagccc ggcgatgcgc      660
```

```
cagatcgtgg aggtgatccg tcaggtttcg cgctgggaca ccaccgtgct ggtacgcggc        720
gaaagcggca ccgggaaaga gctgatcgcc aacgccatcc atcaccattc gccacgggct        780
ggcgccgcct tcgtcaaatt taactgcgcg gcgctgccgg acaccctgct ggaaagcgaa        840
ctgttcggcc atgagaaagg cgcctttacc ggggcggtgc gtcagcgtaa aggacgtttt        900
gagctggcgg atggcggcac cctgttcctc gatgagattg gtgaaagcag cgcctcgttc        960
caggccaagc tgctgcgtat cctccaggag ggggagatgg agcgggtcgg cggcgatgag       1020
accctgcggg tgaatgtccg catcatcgcc gccaccaacc gtcacctgga ggaggaggtc       1080
cggctggggc atttccgcga ggatctctac tatcgtctga acgtgatgcc catcgccctg       1140
cccccgctgc gcgagcgtca ggaggacatc gccgagctgg cgcacttcct ggtgcgcaaa       1200
atcggccagc atcaggggcg cacgctgcgg atcagcgagg cgcgatccg cctgctgatg       1260 gagtacagct ggccgggtaa cgttcgcgaa ctggagaact gcctcgaacg atcggcggtg       1320
atgtcggaga gtggcctgat cgatcgcgac gtgatcctct tcactcacca ggatcgtccc       1380
gccaaagccc tgcctgccag cgggccagcg gaagacagct ggctggacaa cagcctggac       1440
gaacgtcagc gactgatcgc cgcgctggaa aaagccggct gggtgcaggc caaggcggca       1500
cggctgctgg ggatgacgcc gcgccaggtc gcttatcgga tccagatcat ggatatcacc       1560
ctgccgcgtc tgtag                                                        1575

<210> SEQ ID NO 105
<211> LENGTH: 2838
<212> TYPE: DNA
<213> ORGANISM: Klebsiella variicola
<220> FEATURE:
<223> OTHER INFORMATION: glnE

<400> SEQUENCE: 105
atgatgccgc tttctccgca attacagcag cactggcaga cggtcgctga ccgtctgcca         60
gcggattttc ccattgccga actgagccca caggccaggt cggtcatggc gttcagcgat        120
tttgtcgaac agagtgtgat cgcccagccg ggctggctga atgagcttgc ggactcctcg        180
ccggaggcgg aagagtggcg gcattacgag gcctggctgc aggatcgcct gcaggccgtc        240
actgacgaag cggggttgat gcgagagctg cgtctcttcc gccgccagat gatggtccgc        300
atcgcctggg cgcaggcgct gtcgctggtg agcgaagaag agactctgca gcagctgagc        360
gtcctggcgg agaccctgat tgtcgccgcc cgcgactggc tgtacgccgc ctgctgtaag        420
gagtggggaa cgccatgcaa tgccgagggc cagccgcagc cgctgctgat cctcgggatg        480
ggaaagctgg cggcggcga gctgaacttc tcttccgata tcgatctgat ctttgcctgg        540
cctgagcatg cgccacccg cggcggccgc gcgagctgg ataacgccca gttctttacc        600
cgtctggggc agcggctgat caaggccctt gaccagccga cgcaggacgg ctttgtctat        660
cgggttgaca tgcgcctgcg gccgtttggc gacagtgggc cgctggtact cagttttgcg        720
gcgctggaag attattacca ggagcagggt cgggactggg aacgctatgc gatggtgaaa        780
gcgcggatca tgggcgataa cgacggcgtg tacgccagcg agttgcgcgc gatgctccgt        840
cctttcgtct ccgccgtta tatcgacttc agcgtgatcc agtcgctgcg taacatgaaa        900
ggcatgatcg cccgcgaagt gcggcgtcgc gggctgaaag acaacatcaa gctcggcgcc        960
ggcgggatcc gtgaaattga gtttatcgtt caggtctttc aactgatccg cggtggtcgc       1020
gaacctgcac tgcagcagcg cgccctgctg ccgacgctgg cggcgattga tgagctacat       1080
```

```
ctgctgccgg aaggcgacgc ggcgctgctg cgcgaggcct atctgttcct gcgccggctg      1140
gaaaacctgc tgcaaagcat caacgatgag cagacccaga ccctgccgca ggatgaactt      1200
aaccgcgcca ggctggcgtg ggggatgcat accgaagact gggagacgct gagcgcgcag      1260
ctggcgagcc agatggccaa cgtgcggcga gtgtttaatg aactgatcgg cgatgatgag      1320
gatcagtccc cggatgagca actggccgag tactggcgcg agctgtggca ggatgcgctg      1380
gaagaagatg acgccagccc ggcgctggcg catttaaacg ataccgaccg ccgtagcgtg      1440
ctggcgctga ttgccgattt tcgtaaagag ctggatcggc gcaccatcgg cccgcgcggc      1500
cgccaggtgc tggatcagct gatgccgcat ctgctgagcg aaatctgctc gcgcgccgat      1560
gcgccgctgc tctggcgcg gatcacgccg ctgttgaccg ggatcgtcac ccgtaccacc      1620
tatcttgagc tgctgagcga attccccggc gcgctgaagc acctgatcac gctctgcgcg      1680
gcgtcgccga tggtcgccag ccagctggcg cgccacccgc tgctgctgga tgagctgctg      1740
gatcccaaca ccctctatca gccgacggcg accgatgcct atcgcgacga gctgcgccag      1800
tacctgctgc gcgtgccgga agaggatgaa gagcagcagc tggaggcgtt gcgccagttt      1860
aagcaggcgc agcagctgca tatcgcggcg gcggatatcg ctggtaccct gccggtgatg      1920
aaggtcagcg atcacttaac ctggcttgcc gaagcgatcc tcgacgcggt ggtgcagcag      1980 gcatggggggc agatggtcgc tcgctacggc cagccgaccc acctgacga tcgccagggt      2040 cgcggcttcg ccgtcgtcgg ctacggtaag cttggcggct gggagctggg ctacagctcc      2100
gatctcgatc tggtgttcct ccatgactgc ccggcggagg tgatgaccga cggcgagcgg      2160
gagattgacg gccgtcagtt ctacctgcgg ctggcccagc ggatcatgca cctgttcagc      2220
acccgcacct cgtccggtat tctctacgaa gtggacgccc ggctgcgtcc ttctggcgcg      2280
gcggggatgc tggtcaccac cgccgacgcg tttgctgact atcagcagaa cgaagcctgg      2340
acgtgggaac atcaggcgct ggtgcgcgcc cgcgtggtct atggcgaccc ggcgctgcag      2400
gcgcgctttg acgccattcg tcgcgatatc ctgaccaccc cgcgggaggg gatgaccctg      2460
cagaccgagg ttcgcgagat gcgcgagaag atgcgcgccc accttggcaa caaacatccc      2520
gatcgttttg atatcaaagc cgatgccggc gggatcaccg atattgaatt tattactcag      2580
tatctggtcc tacgctatgc cagtgacaag ccgaagctga cccgctggtc tgacaacgtg      2640
cgtattcttg agctgctggc gcagaacgac atcatggacg aggaggaggc gcgcgcctta      2700
acgcatgcgt acaccacctt gcgtgatgcg ctccatcacc tggccctgca ggagcagccg      2760
ggacacgtgg cgccagaggc cttcagccgg gagcgtcagc aggtcagcgc cagctggcag      2820
aagtggctga tggcttaa                                                     2838
```

<210> SEQ ID NO 106
<211> LENGTH: 500
<212> TYPE: DNA
<213> ORGANISM: Klebsiella variicola
<220> FEATURE:
<223> OTHER INFORMATION: PinfC
<400> SEQUENCE: 106

```
agcgtcaggt accggtcatg attcaccgtg cgattctcgg ttccctggag cgcttcattg       60
gcatcctgac cgaagagttc gctggcttct tcccaacctg gattgcacca gtgcaggtag      120
tggtcatgaa tattaccgat tctcaggctg aatacgttaa cgaattgacg cgtaaactac      180
aaaatgcggg cattcgtgta aaagcagact tgagaaatga gaagattggc tttaaaatcc      240
gcgagcacac tttacgtcgt gtcccgtata tgttggtctg tggcgacaaa gaagtcgaag      300
```

-continued

```
ccggcaaagt ggccgtgcgc acccgtcgcg ggaaagacct cggcagcatg gacgtaagtg      360
aagtgattga gaagctgcaa caagagattc gcagccgcag tcttcaacaa ctggaggaat      420
aaggtattaa aggcggaaaa cgagttcaaa cggcacgtcc gaatcgtatc aatggcgaga      480
ttcgcgccct ggaagttcgc                                                  500

<210> SEQ ID NO 107
<211> LENGTH: 1287
<212> TYPE: DNA
<213> ORGANISM: Klebsiella variicola
<220> FEATURE:
<223> OTHER INFORMATION: amtB

<400> SEQUENCE: 107
atgaaaatgg caacaatgaa atcgggtctg ggggcattag cccttcttcc gggactggca       60
atggccgcgc ccgcagtggc ggacaaagcc gataacgcgt ttatgatgat ttgcaccgcg      120
ctggttctgt ttatgaccat cccgggggatc gcgctgtttt acggcggcct gatccgcggc      180
aaaaacgtcc tttccatgct gactcaggtg attgtgacct ttggcctggt ctgcgtactg      240
tgggtgattt atggctatac cctggccttc ggcaccggcg gcagcttctt cggtagtttt      300
gactgggtga tgctgaaaaa tattgaactg aaagcgctga tgggcacctt ctatcagtac      360
atccacgtgg ccttccaggg ctcgttcgcc tgtatcaccg tcgggctgat cgtggggcg       420 ctggctgagc gtattcgttt ctccgccgtg ctgatttttg tggtggtgtg gatgacgctc      480
tcttatgttc cgattgcgca catggtctgg ggcggcggtc tgctggcgac ccacggcgcg      540
ctggacttcg cgggcggcac cgttgtacac atcaacgccg cggttgccgg gctggtgggt      600
gcgtacatga tgggcaaacg tgtgggcttc ggcaaagaag cgttcaaacc gcacaatctg      660
ccgatggtgt tcaccggaac cgccatcctc tacgtgggct ggttcggctt caacgccggc      720
tccgccagcg cagcgaacga aattgccgca ttggctttcg tcaacaccgt cgtcgccaca      780
gcggctgcca tcctggcgtg gacctttggc gaatgggccc tgcgcggtaa accttcactg      840 ctggcgcct gctccggggc gattgccggt ctggttggcg tcacaccagc ctgtgggtat      900
atcggtgtcg gtggggcgtt gattgtgggt atcgcatctg gtctggcggg catctggggc      960
gtaacggcgc tgaaacgctg gctgcggggtt gatgacccctt gcgacgtctt cggcgtccac     1020
ggcgtctgcg gcatcgtcgg ctgtatcctg accggtatct tcgcggccac ctctctgggc     1080
ggcgtgggtt atgcagaagg cgtcaccatg ggccatcagc tgctggtgca actcgagagt     1140
atcgcgatta ccatcgtctg gtcgggcgtt gtcgctttca ttggctacaa agtggcggac     1200
atgaccgtgg ggctgcgcgt accagaagag caggagcgcg aaggactgga cgtcaacagc     1260
catggcgaaa acgcctacaa cgcctga                                        1287

<210> SEQ ID NO 108
<211> LENGTH: 299
<212> TYPE: DNA
<213> ORGANISM: Klebsiella variicola
<220> FEATURE:
<223> OTHER INFORMATION: Prm8.2

<400> SEQUENCE: 108
cgccgtcctc gcagtaccat tgcaaccgac tttacagcaa gaagtgattc tggcacgcat       60
ggaacaaatt cttgccagtc gggctttatc cgatgacgaa cgcgcacagc tttttatatga      120 gcgcggagtg ttgtatgata gtctcggtct gagggcatta gcgcgaaatg atttttcaca      180
```

-continued

```
agcgctggca atccgacccg atatgcctga agtattcaat tacttaggca tttacttaac      240
gcaggcaggc aattttgatg ctgcctatga agcgtttgat tctgtacttg agcttgatc       299

<210> SEQ ID NO 109
<211> LENGTH: 300
<212> TYPE: DNA
<213> ORGANISM: Klebsiella variicola
<220> FEATURE:
<223> OTHER INFORMATION: Prm6.2

<400> SEQUENCE: 109
gctaaagttc tcggctaatc gctgataaca tttgacgcaa tgcgcaataa aagggcatca       60
tttgatgccc tttttgcacg ctttcatacc agaacctggc tcatcagtga ttttttttgt      120
cataatcatt gctgagacag gctctgaaga gggcgtttat acaccaaacc attcgagcgg      180
tagcgcgacg gcaagtcagc gttctccttt gcaatagcag ggaagaggcg ccagaaccgc      240
cagcgttgaa gcagtttgaa cgcgttcagt gtataatccg aaacttaatt tcggtttgga      300

<210> SEQ ID NO 110
<211> LENGTH: 400
<212> TYPE: DNA
<213> ORGANISM: Klebsiella variicola
<220> FEATURE:
<223> OTHER INFORMATION: Prm1.2

<400> SEQUENCE: 110
gcccgctgac cgaccagaac ttccaccttg gactcggcta tacccttggc gtgacggcgc       60
gcgataactg ggactacatc cccattccgg tgatcttacc attggcgtca ataggttacg      120
gtccggcgac tttccagatg acctatattc ccggcaccta caataacggt aacgtttact      180
tcgcctgggc tcgtatacag ttttaattcg ctaagtctta gcaataaatg agataagcgg      240
tgtgtcttgt ggaaaaacaa ggactaaagc gttacccact aaaaaagata gcgactttta      300
tcacttttta gcaaagttgc actggacaaa aggtaccaca attggtgtac tgatactcga      360
cacagcatta gtgtcgattt ttcatataaa ggtaattttg                            400

<210> SEQ ID NO 111
<211> LENGTH: 1536
<212> TYPE: DNA
<213> ORGANISM: Klebsiella variicola
<220> FEATURE:
<223> OTHER INFORMATION: 16S
<220> FEATURE:
<221> NAME/KEY: modified_base
<222> LOCATION: (245)..(245)
<223> OTHER INFORMATION: a, c, t, g, unknown or other
<220> FEATURE:
<221> NAME/KEY: modified_base
<222> LOCATION: (452)..(452)
<223> OTHER INFORMATION: a, c, t, g, unknown or other
<220> FEATURE:
<221> NAME/KEY: modified_base
<222> LOCATION: (454)..(454)
<223> OTHER INFORMATION: a, c, t, g, unknown or other
<220> FEATURE:
<221> NAME/KEY: modified_base
<222> LOCATION: (1131)..(1132)
<223> OTHER INFORMATION: a, c, t, g, unknown or other

<400> SEQUENCE: 111
ttgaagagtt tgatcatggc tcagattgaa cgctggcggc aggcctaaca catgcaagtc       60
gagcggtagc acagagagct tgctctcggg tgacgagcgg cggacgggtg agtaatgtct      120
gggaaactgc ctgatggagg gggataacta ctggaaacgg tagctaatac cgcataacgt      180
```

-continued

```
cgcaagacca aagtgggga ccttcgggcc tcatgccatc agatgtgccc agatgggatt      240
agctngtagg tggggtaacg gctcacctag gcgacgatcc ctagctggtc tgagaggatg      300
accagccaca ctggaactga gacacggtcc agactcctac gggaggcagc agtgggaat      360 attgcacaat gggcgcaagc ctgatgcagc catgccgcgt gtgtgaagaa ggccttcggg      420
ttgtaaagca ctttcagcgg ggaggaaggc gntnaggtta ataaccttgt cgattgacgt      480
tacccgcaga agaagcaccg gctaactccg tgccagcagc cgcggtaata cggagggtgc      540
aagcgttaat cggaattact gggcgtaaag cgcacgcagg cggtctgtca agtcggatgt      600
gaaatccccg ggctcaacct gggaactgca ttcgaaactg gcaggctaga gtcttgtaga      660
ggggggtaga attccaggtg tagcggtgaa atgcgtagag atctggagga ataccggtgg      720
cgaaggcggc cccctggaca aagactgacg ctcaggtgcg aaagcgtggg gagcaaacag      780
gattagatac cctggtagtc cacgctgtaa acgatgtcga tttggaggtt gtgcccttga      840
ggcgtggctt ccggagctaa cgcgttaaat cgaccgcctg gggagtacgg ccgcaaggtt      900
aaaactcaaa tgaattgacg ggggcccgca caagcggtgg agcatgtggt ttaattcgat      960
gcaacgcgaa gaaccttacc tggtcttgac atccacagaa ctttccagag atggattggt     1020
gccttcggga actgtgagac aggtgctgca tggctgtcgt cagctcgtgt tgtgaaatgt     1080
tgggttaagt cccgcaacga gcgcaaccct tatcctttgt tgccagcggt nnggccggga     1140
actcaaagga gactgccagt gataaactgg aggaaggtgg ggatgacgtc aagtcatcat     1200
ggcccttacg accagggcta cacacgtgct acaatggcat atacaaagag aagcgacctc     1260
gcgagagcaa gcggacctca taaagtatgt cgtagtccgg attggagtct gcaactcgac     1320
tccatgaagt cggaatcgct agtaatcgta gatcagaatg ctacggtgaa tacgttcccg     1380
ggccttgtac acaccgcccg tcacaccatg ggagtgggtt gcaaaagaag taggtagctt     1440
aaccttcggg agggcgctta ccactttgtg attcatgact ggggtgaagt cgtaacaagg     1500
taaccgtagg ggaacctgcg gttggatcac ctcctt                               1536
```

```
<210> SEQ ID NO 112
<211> LENGTH: 882
<212> TYPE: DNA
<213> ORGANISM: Klebsiella variicola
<220> FEATURE:
<223> OTHER INFORMATION: nifH

<400> SEQUENCE: 112
atgaccatgc gtcaatgcgc tatctacggt aaaggcggta tcggtaaatc caccaccacc       60
cagaatctcg tcgcggccct cgccgagatg ggtaagaaag tgatgatcgt cggctgcgat      120
ccgaaagcgg actccacccg tctgatcctt cacgctaaag cccagaacac catcatggag      180
atggcggcgg aagtgggctc ggtcgaggat ctggagctcg aagacgttct gcaaatcggc      240 tatgcgatg tccgttgcgc cgaatccggc ggccggagc caggcgtcgg ctgcgccgga      300
cgcggggtga tcaccgccat caacttcctc gaggaagaag cgcctatga ggaagatttg      360 gatttcgtct tctatgacgt cctcggcgac gtagtctgcg gcggcttcgc catgccgatc      420
cgcgaaaaca aagcccagga gatctacatc gtctgctccg gcgagatgat ggcgatgtat      480
gccgccaaca atatctccaa ggggatcgtg aagtacgcga aatctggcaa ggtgcgcctc      540
ggcggcctga tctgtaactc gcgcaaaacc gaccgggag acgaactgat catcgccctg      600
gcggagaagc ttggcacgca gatgatccac ttcgttcccc gcgacaacat tgtgcagcgc      660
```

-continued

```
gcggagatcc gccggatgac ggtgatcgag tacgacccga cctgtcagca ggcgaatgaa    720
tatcgtcaac tggcgcagaa gatcgtcaat aacaccaaaa aagtggtgcc aacgccgtgc    780
accatggacg agctggaatc gctgctgatg gagttcggca tcatggaaga agaagacacc    840
agcatcattg gtaaaaccgc cgctgaagaa aacgcggcct ga                       882
```

```
<210> SEQ ID NO 113
<211> LENGTH: 1449
<212> TYPE: DNA
<213> ORGANISM: Klebsiella variicola
<220> FEATURE:
<223> OTHER INFORMATION: nifD1

<400> SEQUENCE: 113
atgaccaacg caacaggcga acgtaacctt gcgctcatcc aggaagtcct ggaggtgttt     60
cccgaaaccg cgcgcaaaga gcgcagaaag cacatgatga tcagcgatcc gcagatggag    120
agcgtcggca agtgcattat ctcgaaccgt aaatcgcagc ccgggggtgat gaccgtgcgt    180 ggctgcgcct atgcgggctc gaaaggggtg gtgtttgggc caatcaaaga catggcccat    240
atctcgcacg gccccatcgg ctgcggccag tactcgcgcg ccggacggcg caactactat    300
accggcgtca gcggtgtcga cagcttcggc accctgaact tcacctctga ttttcaggag    360
cgcgatattg ttttcggcgg cgataaaaag ctgaccaaac tgatcgaaga gatggagctg    420
ctgttcccgc tgaccaaagg gatcaccatc cagtcggagt gcccggtggg cctgatcggc    480
gatgacatca gcgccgtggc caacgccagc agcaaggcgc tggataaacc ggtgatcccg    540
gtgcgctgcg aaggctttcg cggcgtatcg caatcgctgg ccaccatat cgccaacgac    600 gtggtgcgcg actgggtgct gaacaatcgc gaagggcagc cgtttgccag caccccgtat    660
gatgttgcca tcattggcga ttacaacatc ggcggcgacg cctgggcctc gcgcattctg    720
ctggaagaga tggggctgcg cgtagtggcg cagtggtccg gcgacggcac cctggtggag    780
atggagaaca ccccattcgt taagcttaac ctcgtccact gctaccgttc gatgaactat    840
atcgcccgcc atatggagga gaaacatcag atcccgtgga tggaatataa cttcttcggc    900
ccgaccaaaa tcgccgaatc gctgcgcaag atcgccgatc aatttgatga caccattcgc    960
gccaatgcgg aagcggtgat cgccaaatat gaggggcaga tggcggccat catcgccaaa   1020
tatcgcccgc ggctggaggg cgcgcaaagtg ctgctgtaca tggggggggct gcggccgcgc   1080 cacgtcatcg gcgcctatga ggatctcggg atggagatca tcgccgccgg ctacgagttt   1140
gcccataacg atgattacga ccgcacccctg ccggacctga agagggcac cctgctgttt   1200 gacgatgcca gcagctatga gctggaggcc ttcgtcaaag cgctgaaacc tgacctcatc   1260
ggctccggga tcaaagagaa atatatcttc cagaaaatgg gggtgccgtt ccgccagatg   1320
cactcctggg actattccgg cccctatcac ggctatgacg gcttcgccat ctttgcccgc   1380
gatatggata tgaccctgaa caatccggcg tggaacgaac tgactgcccc gtggctgaag   1440
tctgcgtga                                                           1449
```

```
<210> SEQ ID NO 114
<211> LENGTH: 1374
<212> TYPE: DNA
<213> ORGANISM: Klebsiella variicola
<220> FEATURE:
<223> OTHER INFORMATION: nifD2

<400> SEQUENCE: 114
atgaagggaa aggaaattct ggcgctgctg gacgaacccg cctgcgagca caaccagaag     60
```

-continued

```
caaaaatccg gctgcagcgc tcctaagccc ggcgcaaccg ccggcggctg cgccttcgac    120
ggcgcgcaga taacgctcct gcccatcgcc gacgtcgcgc acctggtgca cggccccatc    180
ggctgcgcgg gcagctcgtg ggataaccgc ggcagcgtca gcgccggccc ggccctcaac    240
cggctcggct ttaccaccga tcttaacgaa caggatgtga ttatgggccg cggcgaacgc    300
cgcctgttcc acgccgtccg tcacatcgtc gaccgctatc atccggcggc ggtctttatc    360
tacaacacct gcgtaccggc gatggagggg gatgacctgg aggccgtctg ccaggccgca    420
cagaccgcca ccggcgtccc ggtcatcgcc attgacgccg ccggtttcta cggcagtaaa    480
aatcttggca accgaatggc gggcgacgtg atgctcaggc aggtgattgg ccagcgcgaa    540
ccggccccgt ggccagacaa cacgcccttt gccccggccc agcgccacga tatcggcctg    600
attggcgaat tcaatatcgc cggcgagttc tggcaggtcc agccgctgct cgacgagctg    660
gggatccgcg tcctcggcag cctctccggc gacggccgct ttgccgagat ccagaccctg    720
caccgggcgc aggccaatat gctggtgtgc tcgcgcgcgc tgatcaacgt cgcccggggg    780
ctggagctgc gctacggcac gccgtggttt gaaggcagct tctacgggat ccgcgccacc    840
tccgacgcct tgcgccagct ggcggcgctg ctggggatg acgacctgtg ccgccgcacc    900
gaggcgctga tcgcccgcga agagcaggcg gcggagcagg cgctggcgcc gtggcgcgag    960
cagctccgtg ggcgcaaagt gttgctctac accggcggcg tgaaatcctg gtcggtggta   1020
tcagccctgc aggatctcgg catgaccgtg gtggccaccg gcacgcggaa atccaccgag   1080
gaggacaaac agcggatccg tgagctgatg ggcgacgagg cggtgatgct tgaggagggc   1140
aatgcccgca ccctgctcga cgtggtgtac cgctatcagg ccgacctgat gatcgccggc   1200
ggacgcaata tgtacaccgc ctggaaagcc cggctgccgt ttctcgatat caatcaggag   1260
cgcgagcacg cctacgccgg ctatcagggc atcatcaccc tcgcccgcca gctctgtctg   1320
accctcgcca gtcccgtctg gccgcaaacg cataccgcg ccccgtggcg ctag           1374
```

<210> SEQ ID NO 115
<211> LENGTH: 1386
<212> TYPE: DNA
<213> ORGANISM: Klebsiella variicola
<220> FEATURE:
<223> OTHER INFORMATION: nifK1

<400> SEQUENCE: 115

```
atggcagaca ttatccgcag tgaaaaaccg ctggcggtga gcccgattaa aaccgggcaa     60
ccgctcgggg cgatcctcgc cagcctcggg ctggcccagg ccatcccgct ggtccacggc    120
gcccagggct gcagcgcctt cgccaaagtt ttctttattc agcatttcca tgacccggtg    180
ccgctgcagt cgacggccat ggatccgacc gccacgatca tggggggccga cggcaatatc    240 ttcaccgcgc tcgacaccct ctgccagcgc cacagcccgc aggccatcgt gctgctcagc    300
accggtctgg cggaagcgca gggcagcgat atcgcccggg tggtcgcgcca gtttcgtgag    360 gcgcatccgc gccataacgg cgtggcgatc ctcaccgtca ataccccgga ttttttttggc    420 tcgatggaaa acggctacag cgcggtgatc gagagcgtga tcgagcagtg ggtcgcgccg    480
acgccgcgtc cggggcagcg gccccggcgg gtcaacctgc tggtcagcca cctctgttcg    540 ccagggggata tcgaatggct gggccgctgc gtggaggcct ttggcctgca gccggtgatc    600
ctgccggacc tctcgcagtc aatggatggc cacctcggtg aagggggattt tacgcccctg    660 acccagggcg cgcctcgct cgcgccagatt gcccagatgg gccagagtct gggcagcttc    720
```

-continued

```
gccattggcg tgtcgctcca gcgggcggca tcgctcctga cccaacgcag ccgcggcgac      780
gtgatcgccc tgccgcatct gatgaccctc gaccattgcg ataccttat ccatcagctg      840 gcgaagatgt ccggacgccg cgtaccggcc tggattgagc gccagcgcgg ccagctgcag      900
gatgcgatga tcgactgcca tatgtggctt cagggccagc gcatgcgat ggcggcggag      960 ggcgacctgc tggcggcgtg gtgtgatttc gcccgcagcc aggggatgca gcccggcccg     1020
ctggtcgccc ccaccagcca ccccagcctg cgccagctgc cggtcgatca ggtcgtgccg     1080
ggggatcttg aggatctgca gcagctgctg agccaccaac ccgccgatct gctggtggct     1140
aactctcacg cccgcgatct ggcggagcag tttgccctgc cgctgatccg cgtcggtttt     1200
cccctcttcg accggctcgg tgagtttcgt cgcgtccgcc aggggtacgc cggtatgcga     1260
gatacgctgt ttgagctggc caatctgctg cgcgaccgcc atcaccacac cgccctctac     1320
cgctcgccgc ttcgccaggg cgccgacccc ctgccggctt caggagacgc ttatgccgcc     1380
cattaa                                                                1386
```

<210> SEQ ID NO 116
<211> LENGTH: 183
<212> TYPE: DNA
<213> ORGANISM: Klebsiella variicola
<220> FEATURE:
<223> OTHER INFORMATION: nifK2

<400> SEQUENCE: 116

```
gtgccgctga tccgtctggg ctttccgctg ttcgaccgcc atcatctgca ccgccagacc       60
acctggggct atgaaggcgc aatgaacatc gtcacgacgc tggtgaacgc cgtgctggaa      120
aaactggacc acgacaccag ccagttgggc aaaaccgatt acagcttcga cctcgttcgt      180
taa                                                                    183
```

<210> SEQ ID NO 117
<211> LENGTH: 1485
<212> TYPE: DNA
<213> ORGANISM: Klebsiella variicola
<220> FEATURE:
<223> OTHER INFORMATION: nifL

<400> SEQUENCE: 117

```
atgaccctga atatgatgct cgataacgcc gcaccggagg ccatcgccgg cgcgctgact       60
caacaacatc cggggctgtt ttttaccatg gtggaacagg cctcggtggc catatccctc      120
accgatgcca cgccaggat catttacgcc aacccagcgt tttgccgcca gaccggctat       180
tcgctggcgc aattgttaaa ccagaacccg cgcctgctgg ccagcagcca gacgccgcgc      240
gcgatctatc aggagatgtg gcataccctg ctccagcgtc agcccggcg cggtcagctg       300 attaatcagc gtcgggacgg cggcctgtgc ctggtggaga ttgacatcac cccggtgctt      360
agcccgcaag gggaactgga gcattatctg gcgatgcagc gggatatcag cgtcagctac      420
accctcgaac aacggctgcg caaccatatg accctgatgg aggcggtgct gaataatatc      480
cccgccgccg tggtggtggt ggacgagcag gatcgggtgg tgatggacaa cctcgcctac      540
aaaaccttct cgctgactg cggcggccgg gagctgctca ccgagctgca ggtctcccct       600
ggccggatga cgcccggcgt ggaggcgatc ctgccggtag cgctgcgcgg ggccgcgcgc      660
tggctgtcgg taacctgctg gccgttgccc ggcgtcagtg aagaggccag ccgctacttt      720
atcgacagcg cgctggcgcg gaccctggtg gtgatcgccg actgtaccca gcagcgtcag      780
cagcaggagc aaggacgcct tgaccggctg aagcagcaaa tgaccgccgg caagctgctg      840
```
gcggcgatcc gcgagtcgct ggacgccgcg ctgatccagc tgaactgccc gattaatatg        900
ctggcggcag cccgtcggct gaacggcgag ggaagcggga atgtggcgct ggaggccgcc        960
tggcgtgaag gggaagaggc gatggcgcgg ctccagcgct gtcgcccatc gctggaactc       1020
gaaaaccccg ccgtctggcc gctgcagccc tttttcgacg atctgtgcgc cctctaccgt       1080
acccgcttcg atcccgacgg gctgcaggtc gacatggcct caccgcatct gatcggcttt       1140
ggccagcgca ccccgctgct ggcgtgctta agcctgtggc tcgaccgcac cctgccctc        1200 gccgccgaat tgccctccgt gccgctggcg atgcagctct atgccgagga gaacgacggc       1260
tggctgtcgc tgtacctgac tgataacgta ccgctgttgc aggtgcgcta cgcccactcc       1320
cccgacgcgc tgaactcgcc gggtaaaggc atggagctgc ggctgatcca gaccctggtg       1380
gcgcaccatc gcggggccat tgagctggct tcccgaccgc agggcggcac ctgcctgacc       1440
ctgcgtttcc cgctgtttaa caccctgacc ggaggtgaag catga                        1485

<210> SEQ ID NO 118
<211> LENGTH: 1575
<212> TYPE: DNA
<213> ORGANISM: Klebsiella variicola
<220> FEATURE:
<223> OTHER INFORMATION: nifA

<400> SEQUENCE: 118
atgatccctg aatccgaccc ggacaccacc gtcagacgct tcgacctctc tcagcagttc          60
accgccatgc agcggataag cgtggtgctg agccgggcca ccgaggccag caaaacgctg         120
caggaggtac tcactgtatt gcacaacgat gcctttatgc agcacgggat gatctgcctg         180
tacgacagcg agcaggagat cctcagtatc gaagcgctgc agcaaaccgg ccagcagccc         240
ctccccggca gcacgcagat ccgctatcgc cccggcgagg gactggtggg gaccgtgctg         300
gcccagggcc agtcgctggt gctgcccgg gtcgccgacg atcagcgttt tctcgaccgc          360
ctgagcctct acgattacga tctgccgttt atcgccgtac cgttgatggg gcccaacgcc         420
cggccaatag gggtgctggc ggcccagccg atggcgcgcc aggaagagcg gctgccggcc         480
tgcacccgtt ttctcgaaac cgtcgccaac ctcgtcgccc agaccatccg gctgatgatc         540
cttccggcct cacccgccct gtcgagccgc cagccgccga aggtggaacg gccgccggcc         600
tgctcgtcgt cgcgcggcgt gggccttgac aatatggtcg gcaagagccc ggcgatgcgc         660
cagatcgtgg aggtgatccg tcaggtttcg cgctgggaca ccaccgtgct ggtgcgcggt         720
gaaagcggca ccgggaaaga gctgatcgcc aacgccatcc atcaccattc gccacgggct         780
ggcgccgcct cgtcaaatt taactgcgcg gcgctgccgg acaccctgct ggaaagcgaa          840
ctgttcggcc atgagaaagg cgcctttacc ggggcggtgc gtcagcgtaa aggacgtttt         900
gagctggcgg atggcggcac cctgttcctc gatgagattg gtgaaagcag cgcctcgttc         960
caggccaagc tgctgcgtat cctccaggag ggggagatgg agcgggtcgg cggcgatgag        1020
accctgcggg tgaatgtccg catcatcgcc gccaccaacc gtcacctgga ggaggaggtc        1080
cggctgggcc atttccgcga ggatctctat tatcgtctga acgtgatgcc catcgccctg        1140
cccccgctgc gcgagcgtca ggaggacatc gccgagctgg cgcacttcct ggtgcgcaaa        1200
atcggccagc atcaggggcg cacgctgcgg atcagcgagg gcgcgatccg cctgctgatg        1260
gagtacagct ggccgggtaa cgttcgcgaa ctggagaact gcctcgaacg atcgcggtg         1320 atgtcggaga gtggcctgat cgatcgcgac gtgatcctct tcactcacca ggatcgtccc        1380

-continued

```
gccaaagccc tgcctgccag cgggccagcg gaagacagct ggctggacaa cagcctggac    1440
gaacgtcagc gactgatcgc cgcgctggaa aaagccggct gggtgcaggc caaggcggca    1500
cggctgctgg ggatgacgcc gcgccaggtc gcttaccgga tccagatcat ggatatcacc    1560
ctgccgcgtc tgtag                                                     1575

<210> SEQ ID NO 119
<211> LENGTH: 2838
<212> TYPE: DNA
<213> ORGANISM: Klebsiella variicola
<220> FEATURE:
<223> OTHER INFORMATION: glnE

<400> SEQUENCE: 119
atgatgccgc tttctccgca attacagcag cactggcaga cggtcgctga ccgtctgcca     60
gcggattttc ccattgcaga actgagccca caggccaggt cggtcatggc gttcagcgat    120
tttgtcgaac agagtgtgat cgcccagccg ggctggctga atgagcttgc ggactcctcg    180
ccggaggcgg aagagtggcg gcattacgag gcctggctgc aggatcgcct gcaggccgtc    240
actgacgaag cggggttgat gcgagagctg cgtctcttcc gccgccagat gatggtccgc    300
atcgcctggg cgcaggcgct gtcgctggtg agcgaagaag agaccctgca gcagctgagc    360
gccctggcgg agaccctgat tgtcgccgcc cgcgactggc tctacgccgc ctgctgtaag    420
gagtggggaa cgccatgcaa tgccgagggc cagccgcagc cgctgctgat cctcgggatg    480
ggaaagctgg cggcggcga gctgaacttc tcttccgata tcgatctgat ctttgcctgg    540
cctgagcatg cgccacccg cggcggccgc cgcgagctgg ataacgccca gttctttacc    600
cgtctggggc agcggctgat caaggccctt gaccagccga cgcaggacgg ctttgtctat    660
cgggttgaca tgcgcctgcg gccgtttggc gacagtgggc cgctggtact cagctttgcg    720
gcactggaag attattacca ggagcagggt cgggactggg aacgctatgc gatggtgaaa    780
gcgcggatca tgggcgataa cgacggcgtg tacgccagcg agttgcgcgc gatgctccgt    840
cctttcgtct ccgccgtta tatcgacttc agcgtgatcc agtcgctgcg taacatgaaa    900
ggcatgatcg cccgcgaagt gcggcgtcgc gggctgaaag acaacatcaa gctcggcgcc    960
ggcgggatcc gtgaaattga gtttatcgtt caggtctttc agctgatccg cggtggtcgc   1020
gaacctgcac tgcagcagcg cgccctgctg ccgacgctgg cggcgattga tgagctacat   1080
ctgctgccgg aaggcgacgc ggcgctgctg cgcgaggcct atctgttcct cgcgccggctg  1140 gaaaacctgc tgcaaagcat caacgatgaa cagacccaga ccctgccgca ggatgaactt   1200
aaccgcgcca ggctggcgtg ggggatgcat accgaagact gggagacgct gagcgcgcag   1260
ctggcgagcc agatggccaa cgtgcggcga gtgtttaatg aactgatcgg cgatgatgag   1320
gatcagtccc cggatgagca actggccgag tactggcgcg agctgtggca ggatgcgctg   1380
gaagaagatg acgccagccc ggcgctggcg catttaaacg ataccgaccg ccgtagcgtg   1440
ctggcgctga ttgccgattt tcgtaaagag ctggatcggc gcaccatcgg cccgcgcggc   1500
cgccaggtgc tggatcagct gatgccgcat ctgctgagcg aaatctgctc gcgtgccgat   1560
gcgccgctgc ctctggcgcg gatcacgccg ctgttgaccg ggatcgtcac ccgtaccacc   1620
tatcttgagc tgctgagcga attccccggc gcgctgaagc acctgatcac gctctgcgcg   1680
gcgtcgccga tggtcgccag ccagctggcg cgccacccgc tgctgctgga tgagctgctg   1740
gatcccaaca ccctctatca gccgacggcg accgatgcct atcgcgacga gctgcgccag   1800
tacctgctgc gcgtgccgga agaggatgaa gagcagcagc tggaggcgtt gcgccagttt   1860
```

-continued

```
aagcaggcgc agcagctgca tatcgcggcg gcggatatcg ctggtaccct gccggtgatg    1920
aaggtcagcg atcacttaac ctggcttgcc gaagcgatcc tcgacgcggt ggtgcagcag    1980
gcatgggggc agatggtcgc tcgctacggt cagccgaccc acctgcacga tcgccagggt    2040
cgcggcttcg ccgttgtcgg ctacggtaag ctcggcggct gggagctggg ctacagctcc    2100
gatctcgatc tggtgttcct ccatgactgc ccggcggagg tgatgaccga cggcgagcgg    2160
gagattgacg gccgtcagtt ctacctgcgg ctggcccagc ggatcatgca cctgttcagc    2220
acccgcacct cgtccggtat tctctacgaa gtggacgccc ggctgcgtcc ttctggcgcg    2280
gcggggatgc tggtcaccac cgccgacgcg tttgctgact atcagcagaa cgaagcctgg    2340
acgtgggaac atcaggcgct ggtgcgcgcc cgcgtggtct atggcgaccc ggcgctgcag    2400
gcgcgctttg acgccattcg tcgcgatatc ctgaccaccc cgcgggaggg gacgaccctg    2460
cagaccgagg ttcgcgagat gcgcgagaag atgcgcgccc accttggcaa caaacatccc    2520
gatcgttttg atatcaaagc cgatgccggc gggatcaccg atattgaatt tattactcag    2580
tatctggtcc tacgctatgc cagtgacaag ccgaagctga cccgctggtc tgacaacgtg    2640
cgtattcttg agctgctggc gcagaacgac atcatggacg aggaggaggc gcgcgcctta    2700
acgcatgcat acaccacctt gcgtgatgcg ctccatcacc tggccctgca ggagcagccg    2760
ggacacgtgg cgccagaggc cttcagccgg gagcgtcagc aggtcagcgc cagctggcag    2820
aagtggctga tggcttaa                                                   2838
```

<210> SEQ ID NO 120
<211> LENGTH: 1287
<212> TYPE: DNA
<213> ORGANISM: Klebsiella variicola
<220> FEATURE:
<223> OTHER INFORMATION: amtB

<400> SEQUENCE: 120

```
atgaaaatgg caacaatgaa atcgggtctg ggggcattag cccttcttcc gggactggca     60
atggccgcgc ccgcagtggc ggacaaagcc gataacgcgt ttatgatgat ttgcaccgcg    120
ctggttctgt ttatgaccat cccggggatc gcgctgtttt acggcggcct gatccgcggc    180
aaaaacgtcc tttccatgct gactcaggtg attgtgacct ttggcctggt ctgcgtactg    240
tgggtgattt atggctatac cctggccttc ggcaccggcg gcagcttctt cggtagcttt    300
gactgggtga tgctgaaaaa tattgaactg aaagcgctga tgggcacctt ctatcagtac    360
atccacgtgg ccttccaggg ctcgttcgcc tgtatcaccg tcgggctgat cgtggggcg     420 ctggctgagc gtattcgttt ctccgccgtg ctgattttcg tggtggtgtg gatgacgctc    480
tcttatgttc cgattgcgca catggtctgg ggcggcggtc tgctggcgac ccacggcgcg    540
ctggacttcg cgggcggcac cgttgtacac atcaacgccg cggttgccgg gctggtgggt    600
gcgtatatga tgggcaaacg tgtgggcttc ggcaaagaag cgttcaaacc gcacaatctg    660
ccgatggtgt tcaccggaac cgccatcctc tacgtgggct ggttcggctt caacgccggc    720
tccgccagcg cagcgaacga aattgccgca ctggctttcg tcaacaccgt cgtcgccaca    780
gcggcagcca tcctggcctg gacctttggc gaatgggctc tgcgcggcaa accttcactg    840
ctgggcgcct gctccggggc gattgccggt ctggttggcg tcacaccagc ctgtgggtat    900
atcggtgtcg gtggggcgtt gattgtgggt atcgcatctg gtctggcggg catctggggc    960
gtaacggcgc tgaaacgctg gctgcgggtt gatgaccctt gcgacgtctt cggcgtccac   1020
```

-continued

```
ggcgtctgcg gcatcgtcgg ctgtatcctg accggtatct tcgcggccac ctctctgggc    1080
ggcgtgggtt atgcagaagg cgtcaccatg ggccatcagc tgctggtgca actcgagagt    1140
atcgcgatta ccatcgtctg gtcgggcgtt gtcgctttca ttggctacaa agtggcggac    1200
atgaccgtgg ggctgcgcgt accagaagag caggagcgcg aaggactgga cgtcaacagc    1260
catggcgaaa acgcctacaa cgcctga                                        1287
```

<210> SEQ ID NO 121
<211> LENGTH: 1435
<212> TYPE: DNA
<213> ORGANISM: Achromobacter spiritinus
<220> FEATURE:
<223> OTHER INFORMATION: 16S
<220> FEATURE:
<221> NAME/KEY: modified_base
<222> LOCATION: (255)..(255)
<223> OTHER INFORMATION: a, c, t, g, unknown or other
<220> FEATURE:
<221> NAME/KEY: modified_base
<222> LOCATION: (454)..(454)
<223> OTHER INFORMATION: a, c, t, g, unknown or other

<400> SEQUENCE: 121

```
ctgaagagtt tgatcctggc tcagattgaa cgctagcggg atgccttaca catgcaagtc      60
gaacggcagc acggacttcg gtctggtggc gagtggcgaa cgggtgagta atgtatcgga     120
acgtgcctag tagcggggga taactacgcg aaagcgtagc taataccgca tacgccctac     180
gggggaaagc aggggatcgc aagaccttgc actattagag cggccgatat cggattagct     240
agttggtggg gtaanggctc accaaggcga cgatccgtag ctggtttgag aggacgacca     300
gccacactgg gactgagaca cggcccagac tcctacggga ggcagcagtg gggaattttg     360
gacaatgggg gaaaccctga tccagccatc ccgcgtgtgc gatgaaggcc ttcgggttgt     420
aaagcacttt tggcaggaaa gaaacgtcat gggntaatac cccgtgaaac tgacggtacc     480
tgcagaataa gcaccggcta actacgtgcc agcagccgcg gtaatacgta gggtgcaagc     540
gttaatcgga attactgggc gtaaagcgtg cgcaggcggt tcggaagaa agatgtgaaa      600 tcccagagct taactttgga actgcatttt taactaccgg ctagagtgt gtcagaggga      660 ggtggaattc cgcgtgtagc agtgaaatgc gtagatatgc ggaggaacac cgatggcgaa     720
ggcagcctcc tgggataaca ctgacgctca tgcacgaaag cgtggggagc aaacaggatt     780
agataccctg gtagtccacg ccctaaacga tgtcaactag ctgttggggc cttcgggcct     840
tagtagcgca gctaacgcgt gaagttgacc gcctggggag tacggtcgca agattaaaac     900
tcaaaggaat tgacggggac ccgcacaagc ggtggatgat gtggattaat tcgatgcaac     960
gcgaaaaacc ttacctaccc ttgacatgtc tggaattctg aagagattcg gaagtgctcg    1020
caagagaacc ggaacacagg tgctgcatgg ctgtcgtcag ctcgtgtcgt gagatgttgg    1080
gttaagtccc gcaacgagcg caacccttgt cattagttgc tacgaaaggg cactctaatg    1140
agactgccgg tgacaaaccg gaggaaggtg gggatgacgt caagtcctca tggcccttat    1200
gggtagggct tcacacgtca tacaatggtc gggacagagg gtcgccaacc cgcgagggggg    1260 agccaatccc agaaacccga tcgtagtccg gatcgcagtc tgcaactcga ctgcgtgaag    1320
tcggaatcgc tagtaatcgc ggatcagcat gtcgcggtga atacgttccc gggtcttgta    1380
cacaccgccc gtcacaccat gggagtgggt tttaccagaa gtagttagcc taacc          1435
```

<210> SEQ ID NO 122
<211> LENGTH: 1528

```
<212> TYPE: DNA
<213> ORGANISM: Achromobacter marplatensis
<220> FEATURE:
<223> OTHER INFORMATION: 16S
<220> FEATURE:
<221> NAME/KEY: modified_base
<222> LOCATION: (255)..(255)
<223> OTHER INFORMATION: a, c, t, g, unknown or other
<220> FEATURE:
<221> NAME/KEY: modified_base
<222> LOCATION: (999)..(999)
<223> OTHER INFORMATION: a, c, t, g, unknown or other
<220> FEATURE:
<221> NAME/KEY: modified_base
<222> LOCATION: (1009)..(1009)
<223> OTHER INFORMATION: a, c, t, g, unknown or other
<220> FEATURE:
<221> NAME/KEY: modified_base
<222> LOCATION: (1437)..(1437)
<223> OTHER INFORMATION: a, c, t, g, unknown or other

<400> SEQUENCE: 122
ctgaagagtt tgatcctggc tcagattgaa cgctagcggg atgccttaca catgcaagtc        60
gaacggcagc acggacttcg gtctggtggc gagtggcgaa cgggtgagta atgtatcgga       120
acgtgcctag tagcggggga taactacgcg aaagcgtagc taataccgca tacgccctac       180
gggggaaagc aggggatcgc aagaccttgc actattagag cggccgatat cggattagct       240
agttggtggg gtaanggctc accaaggcga cgatccgtag ctggtttgag aggacgacca       300
gccacactgg gactgagaca cggcccagac tcctacggga ggcagcagtg gggaattttg       360
gacaatgggg gaaaccctga tccagccatc ccgcgtgtgc gatgaaggcc ttcgggttgt       420
aaagcacttt tggcaggaaa gaaacgtcat gggttaatac cccgtgaaac tgacggtacc       480
tgcagaataa gcaccggcta actacgtgcc agcagccgcg gtaatacgta gggtgcaagc       540
gttaatcgga attactgggc gtaaagcgtg cgcaggcggt tcggaagaa  agatgtgaaa       600 tcccagagct taactttgga actgcatttt taactaccgg ctagagtgt  gtcagaggga       660 ggtggaattc cgcgtgtagc agtgaaatgc gtagatatgc ggaggaacac cgatggcgaa       720
ggcagcctcc tgggataaca ctgacgctca tgcacgaaag cgtggggagc aaacaggatt       780
agataccctg gtagtccacg ccctaaacga tgtcaactag ctgttggggc cttcgggcct       840
tagtagcgca gctaacgcgt gaagttgacc gcctggggag tacggtcgca agattaaaac       900
tcaaaggaat tgacggggac ccgcacaagc ggtggatgat gtggattaat tcgatgcaac       960
gcgaaaaacc ttacctaccc ttgacatgtc tggaattcng aagagattng gaagtgctcg      1020
caagagaacc ggaacacagg tgctgcatgg ctgtcgtcag ctcgtgtcgt gagatgttgg      1080
gttaagtccc gcaacgagcg caacccttgt cattagttgc tacgaaaggg cactctaatg      1140
agactgccgg tgacaaaccg gaggaaggtg gggatgacgt caagtcctca tggcccttat      1200
gggtagggct tcacacgtca tacaatggtc gggacagagg gtcgccaacc cgcgaggggg      1260
agccaatccc agaaacccga tcgtagtccg gatcgcagtc tgcaactcga ctgcgtgaag      1320
tcggaatcgc tagtaatcgc ggatcagcat gtcgcggtga atacgttccc gggtcttgta      1380
cacaccgccc gtcacaccat gggagtgggt tttaccagaa gtagttagcc taaccgnaag      1440
gggggcgatt accacggtag gattcatgac tggggtgaag tcgtaacaag gtagccgtat      1500
cggaaggtgc ggctggatca cctcctttt                                       1528

<210> SEQ ID NO 123
<211> LENGTH: 1522
<212> TYPE: DNA
```

<213> ORGANISM: Microbacterium murale
<220> FEATURE:
<223> OTHER INFORMATION: 16S

<400> SEQUENCE: 123

```
tacggagagt ttgatcctgg ctcaggatga acgctggcgg cgtgcttaac acatgcaagt      60
cgaacggtga acacggagct tgctctgtgg gatcagtggc gaacgggtga gtaacacgtg     120
agcaacctgc ccctgactct gggataagcg ctggaaacgg cgtctaatac tggatatgtg     180
acgtggccgc atggtctgcg tctggaaaga atttcggttg gggatgggct cgcggcctat     240
cagcttgttg gtgaggtaat ggctcaccaa ggcgtcgacg ggtagccggc ctgagagggt     300
gaccggccac actgggactg agacacggcc cagactccta cgggaggcag cagtggggaa     360
tattgcacaa tgggcgcaag cctgatgcag caacgccgcg tgagggatga cggccttcgg     420
gttgtaaacc tcttttagca gggaagaagc gaaagtgacg gtacctgcag aaaaagcgcc     480
ggctaactac gtgccagcag ccgcggtaat acgtagggcg caagcgttat ccggaattat     540
tgggcgtaaa gagctcgtag gcggtttgtc gcgtctgctg tgaaatccgg aggctcaacc     600
tccggcctgc agtgggtacg ggcagactag agtgcggtag gggagattgg aattcctggt     660
gtagcggtgg aatgcgcaga tatcaggagg aacaccgatg gcgaaggcag atctctgggc     720
cgtaactgac gctgaggagc gaaagggtgg ggagcaaaca ggcttagata ccctggtagt     780
ccaccccgta aacgttggga actagttgtg gggtccattc cacggattcc gtgacgcagc     840
taacgcatta gttccccgc ctggggagta cggccgcaag gctaaaactc aaaggaattg     900
acggggaccc gcacaagcgg cggagcatgc ggattaattc gatgcaacgc gaagaacctt     960
accaaggctt gacatatacg agaacgggcc agaaatggtc aactctttgg acactcgtaa    1020
acaggtggtg catggttgtc gtcagctcgt gtcgtgagat gttgggttaa gtcccgcaac    1080
gagcgcaacc ctcgttctat gttgccagca cgtaatggtg ggaactcatg ggatactgcc    1140
ggggtcaact cggaggaagg tggggatgac gtcaaatcat catgcccctt atgtcttggg    1200
cttcacgcat gctacaatgg ccggtacaaa gggctgcaat accgcgaggt ggagcgaatc    1260
ccaaaaagcc ggtcccagtt cggattgagg tctgcaactc gacctcatga agtcggagtc    1320
gctagtaatc gcagatcagc aacgctgcgg tgaatacgtt cccgggtctt gtacacaccg    1380
cccgtcaagt catgaaagtc ggtaacacct gaagccggtg gcctaaccct tgtggaggga    1440
gccgtcgaag gtgggatcgg taattaggac taagtcgtaa caaggtagcc gtaccggaag    1500
gtgcggctgg atcacctcct tt                                            1522
```

<210> SEQ ID NO 124
<211> LENGTH: 1537
<212> TYPE: DNA
<213> ORGANISM: Kluyvera intermedia
<220> FEATURE:
<223> OTHER INFORMATION: 16S
<220> FEATURE:
<221> NAME/KEY: modified_base
<222> LOCATION: (455)..(455)
<223> OTHER INFORMATION: a, c, t, g, unknown or other
<220> FEATURE:
<221> NAME/KEY: modified_base
<222> LOCATION: (1004)..(1004)
<223> OTHER INFORMATION: a, c, t, g, unknown or other

<400> SEQUENCE: 124

```
attgaagagt ttgatcatgg ctcagattga acgctggcgg caggcctaac acatgcaagt      60
cgaacggtag cacagagagc ttgctctcgg gtgacgagtg gcggacgggt gagtaatgtc     120
```

-continued

```
tgggaaactg cccgatggag ggggataact actggaaacg gtagctaata ccgcataatg      180
tcgcaagacc aaagagggg accttcgggc ctcttgccat cggatgtgcc cagatgggat       240
tagcttgttg gtgaggtaat ggctcaccaa ggcgacgatc cctagctggt ctgagaggat      300
gaccagccac actggaactg agacacggtc cagactccta cgggaggcag cagtggggaa      360
tattgcacaa tgggcgcaag cctgatgcag ccatgccgcg tgtgtgaaga aggccttcgg      420
gttgtaaagc actttcagcg gggaggaagg cgatncggtt aataaccgtg ttgattgacg      480
ttacccgcag aagaagcacc ggctaactcc gtgccagcag ccgcggtaat acggagggtg      540
caagcgttaa tcggaattac tgggcgtaaa gcgcacgcag gcggtctgtc aagtcggatg      600
tgaaatcccc gggctcaacc tgggaactgc attcgaaact ggcaggcttg agtcttgtag      660
aggggggtag aattccaggt gtagcggtga aatgcgtaga gatctggagg aataccggtg      720
gcgaaggcgg cccctggac aaagactgac gctcaggtgc gaaagcgtgg ggagcaaaca      780
ggattagata ccctggtagt ccacgccgta aacgatgtcg acttggaggt tgtgcccttg      840
aggcgtggct tccggagcta acgcgttaag tcgaccgcct ggggagtacg gccgcaaggt      900
taaaactcaa atgaattgac gggggcccgc acaagcggtg gagcatgtgg tttaattcga      960
tgcaacgcga agaaccttac ctggtcttga catccacgga attnggcaga gatgccttag     1020
tgccttcggg aaccgtgaga caggtgctgc atggctgtcg tcagctcgtg ttgtgaaatg     1080
ttgggttaag tcccgcaacg agcgcaaccc ttatcctttg ttgccagcgg tccggccggg     1140
aactcaaagg agactgccag tgataaactg gaggaaggtg gggatgacgt caagtcatca     1200
tggcccttac gaccagggct acacacgtgc tacaatggca tatacaaaga gaagcgacct     1260
cgcgagagca agcggacctc ataaagtatg tcgtagtccg gattggagtc tgcaactcga     1320
ctccatgaag tcggaatcgc tagtaatcgt ggatcagaat gccacggtga atacgttccc     1380
gggccttgta cacaccgccc gtcacaccat gggagtgggt tgcaaaagaa gtaggtagct     1440
taaccttcgg gagggcgctt accactttgt gattcatgac tggggtgaag tcgtaacaag     1500
gtaaccgtag gggaacctgc ggttggatca cctcctt                            1537
```

<210> SEQ ID NO 125
<211> LENGTH: 882
<212> TYPE: DNA
<213> ORGANISM: Kluyvera intermedia
<220> FEATURE:
<223> OTHER INFORMATION: nifH

<400> SEQUENCE: 125

```
atgaccatgc gtcaatgcgc catttatggc aaaggtggga tcggcaaatc caccaccacg       60
caaaacctcg tcgccgctct cgcggaaatg ggtaaaaaag tgatgatcgt cggctgcgac      120
ccgaaagcgg actccacccg tctgatcctg catgcgaaag cacagaacac cattatggag      180
atggccgccg aagtgggttc agtggaagac cttgaactgg aagatgtgct gcaaatcggt      240
tacggcggcg tgcgttgtgc agaatccggc ggcccggagc aggcgtggg ttgtgcaggc       300 cgcggcgtta ttaccgccat taacttcctt gaagaagaag cgcctatgt cagcgacctc        360 gactttgtct ctatgacgt cctcggtgac gtggtctgcg gcgggttcgc catgccgatt       420
cgtgaaaaca aagcgcaaga gatctatatc gtctgctccg gggaaatgat ggcgatgtat      480
gccgctaaca catctccaa aggcatcgtg aaatacgcta atccggcaa ggtgcgcctg         540 ggcgggctga tttgtaactc ccgtcagacc gaccgcgaag atgaactgat catcgcgctg      600
```

-continued

```
gcagaaaaac tgggcaccca gatgattcac tttgtgccac gcgacaacat cgtccagcgc    660
gcggaaattc gccgtatgac ggttatcgaa tatgacccga aatgcaacca ggccgacgaa    720
taccgcgcgc tggcgaacaa gatcgtcaac aacaccctga tggtcgtccc gacccccttgc   780 accatggatg aactggaaga gctgctgatg gaattcggca ttatggatgt ggaagacgcc    840
agcatcatcg gtaaaaccgc cgccgaagaa aacgcggcct ga                       882
```

<210> SEQ ID NO 126
<211> LENGTH: 660
<212> TYPE: DNA
<213> ORGANISM: Kluyvera intermedia
<220> FEATURE:
<223> OTHER INFORMATION: Dinitrogenase iron-molybdenum cofactor CDS

<400> SEQUENCE: 126

```
atgaacgata acgatgtcct tttctggcgc atgctggcgc tatttcagtg tctgccggaa     60
ctgcaacccg cgcagatcct ggcctggctg acaggagaac gcgacgacgc cttaaccccg    120
gcgtacctcg ataagcttaa cgtccgcgaa ctggaagcga ccttcccgtc tgaaacggcg    180
atgatgtcgc ccgcacgctg gagccgcgtt aacgcgtgcc ttcacggtac gctgcccgca    240
cacctgcagg taaaaagcac cactcgtcag gggcaattac gggtagcctt ttgttcacag    300
gatggattgc tgatcaatgg tcattttggt cagggggggc tgtttttttat ctacgccttt   360 gatgaacagg gcggatggct acacgcgtta cgccgtcttc cctcggcccc gcaaacccag    420
gagccgaatg aagttcgcgc gcagctcctg agtgattgcc acctgctgtt ttgtgaagcc    480
attggcggcc ctgcggcggc ccggctgatt cgtcacaata tccacccgat gaaagtgtcg    540
ccagggatgt ccattgccgc ccagtgtgat gccattaccg cactgctgag cggacgtctg    600
ccaccgtggc tggcaaaacg tcttgagaaa gccaacccgc tggaagagcg ggtgttttaa    660
```

<210> SEQ ID NO 127
<211> LENGTH: 1374
<212> TYPE: DNA
<213> ORGANISM: Kluyvera intermedia
<220> FEATURE:
<223> OTHER INFORMATION: nifD1

<400> SEQUENCE: 127

```
atgaagggaa atgacattct cgcgctgctg gatgaacccg cctgcgaaca caatcacaaa     60
cagaaatccg gctgtagcgc ccctaaaccc ggtgccacgg cgggcggttg cgcgttcgac    120
ggcgcgcaaa tcaccctgtt gccgctgtcg gatgtggcgc acctggtcca cggaccgatt    180
ggctgcacgg gaagctcctg ggataaccgg ggcagtatga gctccggccc cagtctcaac    240 cggctcgggct ttaccaccga cctgaacgag caggatgtca ttatggggcg cggcgaacgg    300
cggcttttcc acgcggtgcg tcatatcgtc aaccgttatc accctgccgc cgtgtttatc    360
tataacacct gcgttccggc gatggagggt gatgatattg acgccgtctg tcaggcggcg    420
gaaaccgcca ccggcgtgcc agtgattgcc gttgatgccg ccgggttcta tggcagcaaa    480
aaccttggca accgtctcgc gggtgaagtg atggttaaca aggtcattgg acggcgcccg    540 cccgcccct ggccggacga tacccccttc gcgccggaac accgccacga tatcggcctg     600
attggcgaat ttaatatcgc cggggagttc tggcacgttc agccgctgct cgatgagctg    660
ggtattcgcg tgctggggcag cctttccggg gatggccgtt ttagtgaaat ccagaccctg    720
caccacgcgc aggtcaatat gctggtctgc tcaagagcgc tgatcaatgt gccccgcacc    780
ctggaacagc gctatggcac ccccctggttt gagggcagtt tttacggcgt gcgcgctacc    840
```

-continued

```
tccgatgccc tgcgtcaact ggcatccctg cttggcgaca gcgatctgat tgcccgcacc     900
gaagccgtta ttgcccgcga agaagccacg gcaaatcagg cgctcgcccc gtggcgcgaa     960
cggctacagg gtcgcaaagt gctgctctat accggtgggg tgaaatcctg gtcggtggtc    1020
tccgcattgc aggatttagg gatgaccgtc gtggcgactg gcacccgcaa atctaccgaa    1080
gaagataagc agcgtattcg cgaattaatg ggcgatgacg cgctaatgct ggaagaaggc    1140
aacgcccgca ccctgctgga tgtggtgtac cgctatcagg cggatttgat gatcgctggg    1200
gggcgtaaca tgtataccgc gtacaaagcg cggctgccgt ttctggatat caaccaggag    1260
cgtgaacacg cctttgcggg ttatcgcggc atcgtcaccc tcgcccaaca gctttgccag    1320
actattgaaa gccccgtctg gccgcaaaca cacgcccgcg cgccgtggca ataa          1374
```

```
<210> SEQ ID NO 128
<211> LENGTH: 1449
<212> TYPE: DNA
<213> ORGANISM: Kluyvera intermedia
<220> FEATURE:
<223> OTHER INFORMATION: nifD2

<400> SEQUENCE: 128
```

```
atgagcaatg caacaggcga acgtaatctg gaaattatcc aggaagtgct ggagatcttt      60
cccgaaaaaa cgcgcaaaga acgcagaaag cacatgatgg tgaccgaccc ggagatggaa     120
agcgtcggga aatgcatcat ctctaaccgc aaatcgcagc cgggtgtgat gactgtccgc     180
ggctgctcct acgccgggtc gaaaggcgtg gtttttgggc cgattaaaga tatggcccac     240
atctcccacg gcccgatcgg ctgtgggcag tactcccgtg ccgggcggcg caactactac     300
accggggtca gcgcgcgttga ttccttcggg acgctgaact ttacctctga ttttcaggag     360
cgcgatatcg tcttcggcgg cgataaaaag ctcaccaaac tgattgagga gatggaggaa     420
ctgttcccgc tgaccaaagg catctccatt cagtcggagt gcccggtagg tttaatcggt     480
gacgatatcg aagcggtggc gaatgccagt aaaaaagcgc tcaacaagcc ggtgatcccg     540
gtgcgttgcg aaggctttcg cggcgtgtcg cagtcgctcg gtcaccatat cgccaacgac     600
gttatccgcg actgggtgct ggataaccgc gaagggaagc ccttcgaatc taccccctat     660
gacgtggcca tcatcggcga ttacaacatc gggggggatg cctgggcgtc gcgcattctg     720
cttgaagaga tggggttacg cgtggtggcg cagtggtccg gtgacggcac gctggtagag     780
atggaaaaca ccccgttcgt caagctgaac ctggtgcact gctaccgctc tatgaactac     840
atctctcgcc atatggaaga aaacacggt atcccgtgga tggagtacaa cttcttcggc      900
ccgaccaaaa tcgccgaatc gctgcgtaag atcgccgatc aatttgacga caccatccgc     960
gccaatgcgg aagcggtgat cgccaaatat caggcgcaaa acgatgcgat tatcgccaaa    1020
taccgcccgc gtctcgaagg ccgcaaggtg ctgctctata tgggtggcct gcgtcctcgc    1080
cacgtgattg gcgcgtatga ggatttgggc atggagattg tcgccgccgg gtatgaattt    1140
gcccataacg acgattacga ccgcaccctg ccggacctca agagggcac gctgttgttc     1200 gacgatgcca gcagttatga actggaagcc ttcgtgaagg cgattaagcc ggacctcatt    1260
ggctcaggca tcaaggaaaa atacattttc cagaaatgg gggtaccgtt tcgccagatg     1320
cactcctggg attactccgg cccgtatcac ggctatgacg gctttgccat ctttgcccgc    1380
gatatggaca tgacgctcaa caatcccgcc tgggcgagt tgaccgcacc ctggctgaaa     1440
tcagcctga                                                            1449
```

-continued

```
<210> SEQ ID NO 129
<211> LENGTH: 1383
<212> TYPE: DNA
<213> ORGANISM: Kluyvera intermedia
<220> FEATURE:
<223> OTHER INFORMATION: nifK1

<400> SEQUENCE: 129
atggcagata tcatccgtaa tcagaaaccg ctggcggtaa gcccggtaaa aagcggccag      60
ccgttaggcg ccattctggc gagcctcggc tttgagcaca gtattccact ggtgcacggt     120
gcgcagggat gcagcgcgtt cgccaaagtg ttttttatcc aacattttca tgaccctatt     180
ccgctgcaat ccacggcgat ggaccccacc tcaacggtca tggggcgga cggcaatatc      240 cttgccgcgc tcaatacgct gtgccagcgc aacaccccga aagctatcgt cctgttgagt     300
accggcctgt ctgaggcgca gggcagcgat atcagccgcg tggtacgtca gtttcgtgag     360
gattttcccc gccacaaaaa tatcgccctc ctgacggtca acaccccgga tttttacggc     420
acgctggaga acggctttag tgcggtggtg gaaagcgtca tcgaacagtg ggtgccggaa     480
aagcctcagc atggcctgcg taaccggcgg gtcaacttgt tgttaagtca cctgctgacg     540
cccggtgatg ttgagttgct gcgcagctac gtggaggctt ttggcctgca accggtgatc     600
gtgccggatc tttcacagtc gctggatggt cacctggcaa gcggtgattt ttcgccggtc     660 actcagggg gaacgcccct gcgcattatc gaacagatgg acagagcct gtgcacgttt       720 gctattggcg tgtcgctgtc ccgtgcggca tcgctgctgg cacagcgtag ccgtggcgag     780
gtgatcgtgc ttccccatct gatgaccatg gaacattgcg accgttttat tcatcaactg     840
aagatcattt ccgggcgcga ggttcccgcc tggattgagc gccagcgcgg acaattgcag     900
gatgcgatga tcgattgtca tatgtggttg caggataccc ggctcgcgct ggccgccgag     960
ggcgatctgc tggcgggctg gtgtgatttc gcccgtagcc agggcatgct ccccggcccc    1020
gttgtggcgc cggtcagcca gccgggcctg caacagcttc ccgtggagaa agtggtcatt    1080
ggcgatctgg aagatatgca ggatttactc tgcgctatgc ctgctgacct gctggtcgcc    1140
aactcccatg ccgcagacct ggccgaacaa ttctccatcc cgctgatccg cgccgggttc    1200
cctatcttcg acaggcttgg cgaatttcgt cgcgtgcgtc agggataccc cggcattcgc    1260
gacacgctgt ttgagctggc gaacctgatg cgcgaacgtc atcaccacct gcccgtctac    1320
cgctcccccc tgcgccagca atttgcccag gacgctgacg gaggccgcta tgcaacatgt    1380
taa                                                                  1383

<210> SEQ ID NO 130
<211> LENGTH: 1563
<212> TYPE: DNA
<213> ORGANISM: Kluyvera intermedia
<220> FEATURE:
<223> OTHER INFORMATION: nifK2

<400> SEQUENCE: 130
atgagccaaa ctgctgagaa aattgtcacc tgtcatccgc tgtttgaaca ggacgaatac      60
cagacgctgt ttcgcaataa gcgcggtctg gaagaggcgc acgacccgca gcgcgtgcaa     120 gaggttttg aatggaccac cacggcggag tatgaagcgc tgaactttaa gcgtgaagcg      180
ttaaccgtcg atccggcaaa ggcctgccag cctttaggat cggtactctg ctcgctgggt     240
tttgccaata cgctgcctta tgtgcacggt tcccaggggc tgtgtggcta tttccgcacc     300
tattttaacc gtcatttcaa agagccgatc gcttgcgttt ccgactctat gacagaggat     360
```

-continued

```
gcggcggtct tcggcggcaa caacaacctt aacaccgggt tgcaaaatgc cagcgccctg      420
tacaaaccgg aaattgtcgc tgtctccact acctgtatgg cggaggtcat cggcgatgac      480
ctgcaggcct ttatcgccaa cgccaaaaag gacgggttta ttgatgccgc cattccggtg      540
ccctacgccc atacgccaag ttttatcggt agccacatca ccggctggga caacatgttt      600
gaaggtttcg cccgggcatt taccgccgat cacgtggcgc aaccgggcaa actggcgaag      660
ctaaacctgg tgaccggttt tgaaacctat cttggcaatt accgcgtgct caaacgcatg      720
atggcccaga tggaggtgcc ctgtagcctg ctgtctgacc cgtctgaggt gttagatacg      780
ccagccgacg gccactatcg catgtatgcg ggcggcacaa cgcaacaaga gatgcgcgac      840
gcccccgatg ctatcgacac cctgctgctg caaccctggc atctggtgaa gagtaaaaaa      900
gtggtgcagg agtcctgggg ccagcccgcc acagaagtgt ccatcccaat gggactgacc      960
gggaccgacg aactgctgat ggcagtcagt cagttaaccg gcaaaccggt ggccgatgaa     1020
ctgacgctgg agcgtgggcg cctggtggat atgattctcg attcacacac ctggctgcac     1080
ggtaagaaat tcggtctcta cggcgatccg gattttgtga tggggctgac gcgtttcctg     1140
ctggaactgg gctgcgagcc gacggttatc ctctgtcata acggtagcaa gcgctggcag     1200
aaagcgatga agaaaatgct tgaggcatcg ccctacggtc aggagagcga agtgttcatc     1260
aactgcgatc tgtggcattt ccgctcgctg atgtttaccc gcaaaccgga ctttatgatc     1320
ggcaactcgt acgccaaatt catccagcgt gacacgctgg cgaaaggcga acagtttgaa     1380
gttccgctga tccgtcttgg cttcccgttg ttcgaccgcc accacctgca tcgccagacc     1440
acatggggtt atgaaggggc gatgaatatc gtcaccaccc tggtcaacgc cgtgctggaa     1500
aaagtcgacc gcgataccat caaactgggc aaaacggact acagcttcga ccttgtccgc     1560
taa                                                                   1563
```

<210> SEQ ID NO 131
<211> LENGTH: 1488
<212> TYPE: DNA
<213> ORGANISM: Kluyvera intermedia
<220> FEATURE:
<223> OTHER INFORMATION: nifL

<400> SEQUENCE: 131

```
atgaccttta atatgatgct ggagaccagc gcaccgcagc acattgcggg caacctctca       60
cttcaacatc ccggactgtt ttccacgatg gttgaacagg ctccgatcgc gatttcgctg      120
accgacccgg acgcgaggat tctgtacgct aatccggcct tttgtcgcca gaccggttat      180
agcctggaag agctgctcaa ccagaaccat cgcatactgg caagccaaca gacgccgcgc      240
agcatttatc aggaactgtg gcaaacgctg ctgcaacaga tgccctggcg cggtcagctc      300
atcaatcgcc gtcgggatgg cagcctttat ctggctgagg tcgatatcac cccggtcgtc      360
aacaaacagg cgaactgga acactacctc gccatgcaac gtgatatcag cgccagctat      420
gcgctcgaac agcgattgcg caatcacacc accatgagcg aggcggtgct gaacaacatt      480
cctgccgccg tggtggtggt caacgagcag gaccaggtag tcatggacaa cctcgcctac      540
aaaaccttct gtgccgactg cggtggcaag gagctgctca ccgaactgga tttctcccgg      600
cgcaaaagcg atctctatgc cgggcaaata ctgcctgtgg tgctgcgcgg cgccgtgcgc      660
tggctctctg tcacctgctg gaccttgccg ggggtgagcg aagaagccag ccgctacttt      720
attgataccg cgctgccccg caccctggtg gtgatcaccg actgcacccca gcaacaacaa      780
```

-continued

```
caggccgaac agggccgtct cgatcgtctc aaacaggaga tgaccaccgg gaagctgctg      840
gccgcgatcc gtgaatcgtt ggatgccgcg ctggttcagc taaactgccc catcaatatg      900
ctggcggcgg cgcgacgtct caacggtgaa gataaccata acgtggcgct ggatgccgcg      960
tggcgcgagg gggaagaggc gctggcccgc ctgcaacgct gccgcccttc tctcgatctg     1020
gaagagagcg cgctgtggcc tctgcaaccg ctgtttgacg acctgcgcgc cctttaccat     1080
acccgctata acaatggcga aaatctgcac gttgaaatgg cctctccgca tctggcgggg     1140
tttggtcagc gcacgcagat ccttgcctgt ctcagtttgt ggctcgaccg tacgctggcc     1200
ctcgccgccg cgctaccgga cagaacgctg catacccagc tttacgcccg tgaagaagat     1260
ggctggctgt ccatttggct gacagataat gtgccgctca tccatgtgcg atacgcccac     1320
tcccccgatg ccctgaacgc ccccggcaaa gggatggagc tgcgattgat tcaaaccctg     1380
gttgcccatc atcgcggcgc aatagaacta actacccgcc ctgaaggcgg tacctgcctg     1440
accctgcgat tcccgttatt tcattcactg accggaggcc cacgatga               1488
```

```
<210> SEQ ID NO 132
<211> LENGTH: 1572
<212> TYPE: DNA
<213> ORGANISM: Kluyvera intermedia
<220> FEATURE:
<223> OTHER INFORMATION: nifA

<400> SEQUENCE: 132
```

```
atgacccagc gacccgagtc gggcaccacc gtctggcgtt ttgatctctc acagcaattt       60
accgccatgc agcgcatcag cgtggtgttg agtcgcgcaa ccgagataag ccagacgctg      120
caggaggtgc tgtgtgttct gcataatgac gcatttatgc aacacggcat gctgtgtctg      180
tatgacaacc agcaggaaat tctgagtatt gaagccttgc aggaggcaga ccaacatctg      240
atccccggca gctcgcaaat tcgctatcgc cctggcgaag ggctggtagg agccgtactg      300
tcccagggac aatctcttgt gctgccgcgt gtcgccgacg atcaacgctt tctcgacagg      360
cttggcatct atgattacaa cctgccgttt atcgccgtcc ccttaatggg gccaggcgcg      420
cagacgattg gcgtgctcgc cgcgcagccg atggcgcgtc tggaggagcg gcttccttcc      480
tgtacgcgct ttctggaaac cgtcgccaat ctggtcgcac agacagtccg gctgatgacc      540
ccgcctgccg ccgccacacc gcgcgccgcg attgcccaga ccgaacgcca cgcgcaactgt      600 ggcactcctc gccccttcgg ctttgagaat atggtgggca aaagcccggc catgcagcag      660
acaatggaca ttatccgcca ggtttcgcgc tgggatacca cggtactggt gcgcggcgaa      720
agcggcaccg gtaaagaact tatcgccaat gctattcatc acaactcccc tcgcgccgcc      780
gcgccctttg tgaaatttaa ctgcgcgcg ctaccggata cgctactgga gagcgaattg      840
ttcggccatg aaaaaggggc gttcaccggc gcggttcgcc agcgtaaagg acgtttttgaa      900 ctggccgatg cggcacact gtttcttgat gaaattggcg aaagcagcgc ctcgttccag      960
gccaaactgc tgcgtatttt gcaggaggt gaaatggagc gcgttggcgg cgacgaaacc     1020
ctgcgcgtca atgtgcgtat catcgccgcc accaaccgga atctggaaga agaggtgcgg     1080
atgggcaatt ccgcgagga tctctattat cgcctcaacg taatgcccat ctccctgccc     1140
ccgctgcgtg aacgtcagga ggacattgcc gagctggcgc actttctggt gcgcaaaatc     1200
gcccataacc aggggcgtac gctcgcatc agtgatggcg ccatccgtct gctgatgggt     1260
tacaactggc ccggtaacgt gcgtgagctg aaaattgcc tggaacgttc ggcagtgatg     1320
tcagaaaacg gcctgatcga ccgcgatgtg gtgctctta accaccgtga gaacacgcca     1380
```

-continued

```
aaactcgcta tcgccgccgc gccaaaagag gatagctggc ttgatcaaac gctggatgaa      1440
cgtcaacggc tgattgccgc gctggaaaaa gccgggtggg tgcaggccaa agcggcgcgt      1500
ctgctgggta tgacgccccg tcaggtcgcc tatcggatac aaattatgga tatcagcatg      1560
cccaggatgt ga                                                        1572

<210> SEQ ID NO 133
<211> LENGTH: 2853
<212> TYPE: DNA
<213> ORGANISM: Kluyvera intermedia
<220> FEATURE:
<223> OTHER INFORMATION: glnE

<400> SEQUENCE: 133
atgatgccgc actctccaca gctacagcag cactggcaaa ctgtactggc ccgcttgcct        60
gagtcattca gtgaaacacc gcttagtgaa caagcgcagt tagtgcttac tttcagtgat       120
tttgtgcagg atagccttgc cgcgcatcct gactggctgg ctgagctgga aagcgcaccg       180
ccacaggcgg acgagtggaa gcagtatgcg caaacccttc gcgaatcgct ggaaggtgtg       240
ggagatgagg catcattaat gcgtgcgctg cgcctgttcc gtcgccatat gatggtgcgc       300
attgcctggg cgcagtcgct ggcgctggtg gcagaagatg agacgttgca gcagttgagc       360
gtactggcgg agaccctgat cgtcgctgca cgcgactggc tttacgatgc ctgctgtcgc       420
gagtggggaa cgccgtgcaa tcagcagggg gaaccgcagc cgttgctgat cctgggcatg       480
ggcaagctgg gtggcgggga gcttaacttt tcgtccgata tcgatctgat ttttgcctgg       540
ccggaaaacg gttcaacgcg cggtgggcga cgcgaacttg ataacgccca gtttttttact       600 cgcttgggac agcgcctgat caaagtgctc gaccagccga cgcaggatgg ctttgtctat       660
cgcgtggata tgcggctgcg cccgtttggc gacagcggtc cgctggtgct gagttttgcc       720
gcgctggaag attattatca ggagcagggg cgcgactggg aacgttatgc gatggtgaaa       780
gcccgcatta tgggcgataa ggacgatgtt tacgctggcg aattacgggc catgctgcgg       840
ccgttcgtct tccgtcgcta tatcgatttc agcgttattc agtctctgcg taacatgaaa       900
gggatgattg cccgcgaagt gcgccgccgt ggtctgaaag ataacattaa gctgggcgcg       960
ggcggcatcc gtgagattga gtttatcgtt caggtgttcc agttgatacg cggtgggcgc      1020
gagccgtcgt tgcagtcccg ttcactgtta ccgacgctgg acgctatcga taagctgggt      1080
ttgctgccgc ctggcgatgc accggcgtta cgccaggcct atttgtatct gcgccgtctg      1140
gaaaacctgc tgcaaagcat taacgacgaa caaacgcaga cgctgccgac agatgaactc      1200
aatcgcgcgc gtctggcctg ggggatgcgg gtcgcagact gggaaaccct gaccgctgag      1260
cttgaaaagc agatgtctgc cgtacgaggg atattcaaca ccctgattgg cgatgacgaa      1320
gccgaagagc aggggggatgc gctctgcggg caatggagtg agttgtggca ggatgcgttt      1380
caggaagatg acagcacgcc tgtgctggcg caccttttctg acgatgatcg ccgccgcgtg      1440
gtcgcgatga ttgctgattt cgcaaagag ctggataaac gcaccattgg cccacgcggc      1500
cgccaggtgc tcgaccatct gatgccgcat ctgttgagtg atgtctgctc ccgtgaggat      1560
gcccctgtac cgttgtctcg cgtgacgccg ctgttaacgg gaattgtcac gcgtacgacg      1620
tatcttgagc tgctcagcga gtttcctggt gcgcgtaagc atctgatttc actctgtgcc      1680
gcctcgccga tggtggccag taagctggcg cgctatccgt tattgctgga tgagttgctc      1740
gatccgaata cccctttatca gcccacggcg atgaatgcct accgggatga gctacgtcag      1800
```

-continued

```
tatctgctgc gtgtgccgga tgacgatgaa gagcagcaac tggaggcgtt acgccagttt    1860
aaacaggctc aattgttgcg tgtggcggca gcagatctgg caggcacact ccccgtgatg    1920
aaagtgagcg atcacttaac atggcttgcc gaagccatca ttgaagccgt ggtacaacag    1980
gcgtggagcc tgatggtatc gcgttatggg cagccgaaac acttacgcga ccgtgaaggc    2040
cgtgggtttg cagtggtcgg ttacggcaaa ctgggcggtt gggagctggg ctatagttcc    2100
gatctggatt tgattttcct tcatgactgt ccggtggacg tgatgactga cggcgagcgg    2160
gaaatcgatg ccgccaatt ttatctgcgc cttgcccagc gcgtgatgca cctgttcagt    2220
acgcgcacct catccgggat cctgtatgag gtagacgcgc gcttgcgccc gtccggtgcg    2280
gcgggaatgc tggtgacctc aaccgaatcc tttgccgact accagcgcac cgaagcctgg    2340
acctgggaac atcaggcgct ggttcgcgcc cgcgttgtct atggcgatcc acaattaaac    2400
gcgcaatttg atgccatccg ccgcgatatc accatgaccg tgcgtaatgg tgcaacgtta    2460
caaaccgagg tgcgcgagat gcgcgaaaaa atgcgcgccc acttgagcaa taagcacaag    2520
gatcgctttg atattaaagc cgatgagggt ggaattaccg atatcgaatt tatcacccag    2580
tatctggtgc tgcgttatgc ccatgccaaa ccgaaactga cgcgctggtc ggacaatgtc    2640
cgcattctgg aagggctggc gcaaaacggc attatggaag agcaggaagc gcaggcactt    2700
accaccgcct atacaacgtt gcgtgatgag ctgcatcacc tggcgctaca ggagctgcca    2760
ggacatgttc cggaggcatg tttttgtcgct gaacgcgcga tggtgcgagc ctgctggaac    2820
aagtggttgg tggagccgtg cgaggacgcg taa                                 2853
```

<210> SEQ ID NO 134
<211> LENGTH: 1290
<212> TYPE: DNA
<213> ORGANISM: Kluyvera intermedia
<220> FEATURE:
<223> OTHER INFORMATION: amtB

<400> SEQUENCE: 134

```
atgaagaaag cactattaaa agcgggtctg gcctcgctgg cattactgcc gtgtctggct     60
atggcagccg atccggttgt cgtcgataaa gccgacaatg cctttatgat gatttgcacc    120
gcgctggtgc tgtttatgtc aattccgggc atcgccctgt tctatggtgg tttaatccgc    180
ggtaaaaacg tcctttctat gctgacacag gttgcggtta cgttcgcact ggtgtgcgtg    240
ctgtgggtgg tttacggcta ctctctggcc tttggcactg gcggcagctt cttcggtagc    300
ttcgactggg tgatgctgaa aaatattgag ctgaaagcgc tgatgggcac catctatcag    360
tacattcacg ttgcgttcca gggctcgttt gcctgtatta ccgtcggcct gattgtcggt    420
gcgctggcag aacgtatccg tttctccgca gtactgattt cgtcgtggt atggctgacg    480 ctgtcctacg tgccgatcgc acacatggtc tggggcggcg gtctgctggc aacccatggc    540
gccatggatt ttgcgggcgg tacagtcgtt cacatcaacg cagccgttgc aggcctggtg    600
ggtgcttacc tgattggcaa acgtgtcggt ttcggtaaag aagcgtttaa accgcacaac    660
ctgccgatgg tgtttaccgg tacggcaatc ctctactttg ctggttcgg attcaacgcg    720 ggttctgcaa gcgcggcgaa cgaaattgcg ggtctggctt ttgttaacac cgtcgtggca    780
acagcgggtg caatcctctc ctgggtcttc ggtgagtggg cgctgcgcgg caaaccgtct    840
ctgttgggtg cctgttctgg tgcgattgct ggcctcgtgg gtatcacccc ggcgtgtggt    900
tacgttggtg tgggtggcgc gctgatcgtg ggcatcgttg caggcctggc gggtctgtgg    960
ggcgttaccg cgctgaaacg ctggctgcgt gttgacgacc cgtgtgatgt cttcggtgtt    1020
```

```
cacggcgtgt gcggtatcgt aggttgtatc atgacaggta tcttcgcagc cacttcactg      1080
ggcggcgtgg gttatgccga aggcgtgacc atgggccatc aggttctggt acaactggaa      1140
agtatcgcca ttactatcgt atggtctggt atcgtcgcct ttatcggtta caaactggct      1200
gatatgacag tgggtctgcg tgttccggaa gatcaggaac gcgaagggct ggacgtcaac      1260
agccacggcg agaacgccta caacgcctga      1290

<210> SEQ ID NO 135
<211> LENGTH: 498
<212> TYPE: DNA
<213> ORGANISM: Kluyvera intermedia
<220> FEATURE:
<223> OTHER INFORMATION: PinfC

<400> SEQUENCE: 135
ctggggtcac tggagcgctt tatcggcatc ctgaccgaag aatttgccgg tttcttcccg       60
acctggctgg cccctgttca ggttgtggtg atgaatatca ctgattctca agctgaatat      120
gtcaacgaat tgacccgtaa attgcaaaat gcgggcattc gtgtaaaagc ggacttgaga      180
aacgagaaga ttggctttaa aatccgcgag cacactttac gtcgtgtccc ttatatgttg      240
gtctgtggtg ataaagaggt ggaagcaggc aaagtggccg ttcgcacccg ccgcggtaaa      300
gacctgggca gcctggacgt aagtgaagtg attgagaagc tgcaacaaga gattcgcagc      360
cgcagtcttc aacaactgga ggaataaggt attaaaggcg gaaaacgagt tcaaacggca      420
cgtccgaatc gtatcaatgg cgagattcgc gcccaggaag ttcgcttaac tggtctggaa      480
ggtgagcagc tgggtatt      498

<210> SEQ ID NO 136
<211> LENGTH: 1537
<212> TYPE: DNA
<213> ORGANISM: Kosakonia pseudosacchari
<220> FEATURE:
<223> OTHER INFORMATION: 16S
<220> FEATURE:
<221> NAME/KEY: modified_base
<222> LOCATION: (454)..(454)
<223> OTHER INFORMATION: a, c, t, g, unknown or other

<400> SEQUENCE: 136
attgaagagt ttgatcatgg ctcagattga acgctggcgg caggcctaac acatgcaagt       60
cgaacggtag cacagagagc ttgctctcgg gtgacgagtg cggacgggt gagtaatgtc       120 tgggaaactg cctgatggag ggggataact actggaaacg gtagctaata ccgcataacg      180
tcgcaagacc aaagaggggg accttcgggc ctcttgccat cagatgtgcc cagatgggat      240
tagctagtag gtggggtaac ggctcaccta ggcgacgatc cctagctggt ctgagaggat      300
gaccagccac actggaactg agacacggtc cagactccta cgggaggcag cagtgggaa      360 tattgcacaa tgggcgcaag cctgatgcag ccatgccgcg tgtatgaaga aggccttcgg      420
gttgtaaagt actttcagcg gggaggaagg cganacggtt aataaccgtg ttgattgacg      480
ttacccgcag aagaagcacc ggctaactcc gtgccagcag ccgcggtaat acggagggtg      540
caagcgttaa tcggaattac tgggcgtaaa gcgcacgcag gcggtctgtc aagtcggatg      600
tgaaatcccc gggctcaacc tgggaactgc atccgaaact ggcaggcttg agtctcgtag      660
agggaggtag aattccaggt gtagcggtga aatgcgtaga gatctggagg aataccggtg      720
gcgaaggcgg cctcctggac gaagactgac gctcaggtgc gaaagcgtgg ggagcaaaca      780
```

-continued

```
ggattagata ccctggtagt ccacgccgta aacgatgtct atttggaggt tgtgcccttg      840
aggcgtggct tccggagcta acgcgttaaa tagaccgcct ggggagtacg gccgcaaggt      900
taaaactcaa atgaattgac gggggcccgc acaagcggtg gagcatgtgg tttaattcga      960
tgcaacgcga agaaccttac ctggtcttga catccacaga acttgccaga gatggcttgg     1020
tgccttcggg aactgtgaga caggtgctgc atggctgtcg tcagctcgtg ttgtgaaatg     1080
ttgggttaag tcccgcaacg agcgcaaccc ttatcctttg ttgccagcgg tccgccgggg     1140
aactcaaagg agactgccag tgataaactg gaggaaggtg gggatgacgt caagtcatca     1200
tggcccttac gaccagggct acacgtgc tacaatggcg catacaaaga gaagcgacct     1260
cgcgagagca agcggacctc ataaagtgcg tcgtagtccg gattggagtc tgcaactcga     1320
ctccatgaag tcggaatcgc tagtaatcgt ggatcagaat gccacggtga atacgttccc     1380
gggccttgta cacaccgccc gtcacaccat gggagtgggt tgcaaaagaa gtaggtagct     1440
taaccttcgg gagggcgctt accactttgt gattcatgac tggggtgaag tcgtaacaag     1500
gtaaccgtag gggaacctgc ggttggatca cctcctt                              1537

<210> SEQ ID NO 137
<211> LENGTH: 882
<212> TYPE: DNA
<213> ORGANISM: Kosakonia pseudosacchari
<220> FEATURE:
<223> OTHER INFORMATION: nifH

<400> SEQUENCE: 137
atgaccatgc gtcaatgcgc catttacggc aaaggtggga tcggtaaatc gaccaccaca       60
cagaacctgg tcgccgcgct ggcggagatg ggtaagaaag tcatgatcgt cggctgcgat      120
ccgaaagccg actccacgcg tttgatcctg catgcgaaag cgcagaacac cattatggag      180
atggccgccg aagtcggctc cgtcgaagac ctggaattag aagacgtgct gcaaatcggt      240
tacgccggcg tgcgctgcgc ggaatccggt ggcccggagc caggtgtggg ttgtgccggt      300
cgtggcgtga tcaccgcgat taacttcctc gaagaagaag cgcttacgt gccggatctg      360 gattttgttt tctacgacgt gctgggcgac gtggtatgcg gtggtttcgc catgccgatt      420
cgtgaaaaca aagcgcagga gatctacatc gtttgctctg gcgaaatgat ggcgatgtac      480
gccgccaata acatctccaa aggcatcgtg aaatatgcca aatccggtaa agtgcgcctc      540
ggcgggctga tttgtaactc gcgccagacc gaccgcgaag atgaactcat cattgcgctg      600
gcggaaaaac tcggcacgca aatgatccac tttgttcccc gcgacaacat tgtgcagcgt      660
gcggaaatcc gccgtatgac ggttatcgaa tatgacccga cctgcaatca ggccaacgaa      720
tatcgcagcc ttgccagcaa aatcgtcaac aacaccaaaa tggtggtacc aacccctgc       780 accatggatg aactggaaga actgctgatg gagttcggca ttatggatgt ggaagacgcc      840
agcatcattg gtaaaaccgc cgccgaagaa aacgccgtct ga                         882

<210> SEQ ID NO 138
<211> LENGTH: 1449
<212> TYPE: DNA
<213> ORGANISM: Kosakonia pseudosacchari
<220> FEATURE:
<223> OTHER INFORMATION: nifD1

<400> SEQUENCE: 138
atgagcaatg caacaggcga acgtaacctg gaaatcatcg agcaggtgct ggaggttttc       60
ccggaaaaga cgcgcaaaga gcgcagaaaa cacatgatgg tgacggaccc ggagcaggag      120
```

-continued

```
agcgtcggca agtgcatcat ctctaaccgc aaatcgcagc cgggcgtgat gaccgtgcgt      180
ggctgctcgt atgccggatc aaaaggggtg gtatttgggc caatcaaaga tatggcgcat      240
atctcccacg gcccgatcgg ctgcgggcag tactcccgcg ccgggcggcg taactactat      300
accggcgtca gcggcgtgga cagtttcggc acgctcaact tcacctccga tttccaggag      360
cgcgacatcg tgtttggcgg cgacaaaaag ctcgccaaac tgattgaaga gctggaagaa      420
ctgtttccgc tgaccaaagg catttcgatt cagtcggaat gcccggtcgg cctgattggc      480
gatgatattg aagccgtggc gaacgccagc cgcaaagcga tcaacaaacc ggttattccg      540
gtgcgttgcg aaggctttcg cggcgtgtcg caatccctcg gtcaccatat tgccaacgat      600
gtgatccgcg actgggtact ggataaccgc gaaggcaaac cgtttgaatc caccccttac      660
gatgtggcga tcatcggcga ttacaacatc ggtggcgacg cctgggcctc gcgcattttg      720
ctcgaagaga tggggttgcg ggtggtcgcg cagtggtccg gcgacggtac gctggtggag      780
atggaaaaca cgccgttcgt caaactgaac ctggtgcact gctaccgctc gatgaactac      840
atctcgcgcc atatggagga gaagcacggt attccgtgga tggaatacaa cttctttggc      900
ccgacgaaaa tcgcggaatc gctgcgcaaa atcgccgacc tgttcgacga caccattcgc      960
gccaacgccg aagcggtgat cgcccgatac caggcgcaga acgacgccat tatcgccaaa     1020
tatcgcccac gtctggaggg tcgcaaagtg ttgctctata tgggcgggct gcgtccgcgc     1080
catgtgattg gcgcctatga agatctggga atggagatca tcgccgccgg ttatgagttt     1140
ggtcataacg acgattacga ccgcaccctg ccggatctga agagggcac gctgctgttt      1200 gatgacgcca gcagctatga gctggaggcg tttgtcaacg cgctgaaacc ggatctcatc     1260
ggttccggca tcaaagagaa gtacatcttt cagaaaatgg gcgtgccgtt tcgccagatg     1320
cactcctggg attactccgg cccgtaccac ggctatgacg gcttcgccat cttcgcccgc     1380
gatatggata tgacgctcaa caaccccgcc tggggtcagt tgaccgcgcc gtggcttaaa     1440
tccgcctga                                                             1449
```

```
<210> SEQ ID NO 139
<211> LENGTH: 1374
<212> TYPE: DNA
<213> ORGANISM: Kosakonia pseudosacchari
<220> FEATURE:
<223> OTHER INFORMATION: nifD2

<400> SEQUENCE: 139
```

```
atgaagggga acgacatcct ggctctgctc gatgaaccag cctgcgagca taaccataaa       60
cagaaaaccg gctgtagcgc gccaaaaccc ggcgccaccg ccggaggctg cgccttcgac      120
ggcgcacaga tcaccctgct gccactttcc gatgtggcgc atctggtaca tggcccgatt      180
ggctgcgccg gcagctcatg ggataaccgt ggcagcctga gttctggccc gctgattaac      240
cgactcggat tcaccactga tttgaacgaa caggatgtca tcatggggcg cggcgagcgg      300
cggttgtttc acgcggtgcg ccatattgtc gagcgctatc acccggcggc ggtatttatt      360
tacaacacct gcgttccggc tatggaaggc gatgacattg acgcggtctg ccaggccgcc      420
gcgaccgcca ccggtgtgcc cgtgattgcc gtagatgtgg ccggttttta cggtagcaaa      480
aacctgggta accgcctcgc gggcgaggtg atggtgaaaa agttatcgg cgggcgcgaa      540 cccgcgccgt ggccggacaa tacacctttt gccccggcgc accgccatga cataggcctg      600
attggcgaat ttaacatcgc cggcgagttc tggcatatcc agccgctgct tgatgagctg      660
```

```
ggtattcgcg tccttggctc cctttccggc gacgggcgct ttgccgagat ccagacgttg      720
caccgcgcgc aggtcaatat gctggtgtgc tccaggcgc tgattaatgt cgccagatcg      780
cttgaacaac gttatggcac accctggttt gaaggcagtt tttatggcgt tcgcgccacc      840
tccgatgccc tgcgccagct ggcaacactc accggcgata cgcgatttaat ggcgcgaacc      900 gaacggctga tcgcacgtga agagcaagcc acagaacagg cgctagcacc gctgcgtgaa      960
cggttacacg gccggaaagt gctgctctat accggtggcg tgaaatcctg gtcggtggtt     1020
tcggcgctgc aggatctcgg catgacggtc gttgctaccg gaacgcgcaa atccaccgaa     1080
gaggataaac aacgcatccg tgaactgatg ggcgatgacg ccatcatgct ggatgaaggc     1140
aatgcccgcg ccttgctgga tgtggtctat cgctacaaag ccgacatgat gatcgcgggc     1200
gggcgcaaca tgtacaccgc ctataaagcg cgtctgccct ttctggatat caaccaggag     1260
cgtgaacacg cgtttgccgg ttatcgcggc atcatcacgc ttgccgaaca actttgtcag     1320
acgctggaaa gcccggtctg gccgcaaaca catgcccgcg ccccgtggca ataa          1374
```

```
<210> SEQ ID NO 140
<211> LENGTH: 1563
<212> TYPE: DNA
<213> ORGANISM: Kosakonia pseudosacchari
<220> FEATURE:
<223> OTHER INFORMATION: nifK1

<400> SEQUENCE: 140
atgagccaga ctgctgagaa aatacagaat tgccatcccc tgtttgaaca ggacgcctac       60
cagacactat ttgccggtaa acgggcactc gaagaggctc actcgccgga gcgggtgcag      120
gaagtgtttc aatggaccac caccccggaa tacgaagcgc tgaacttcaa acgcgaagcg      180
ctgactatcg accccggcaaa agcctgccag ccgctggggg cggtgctctg ttcgctgggg      240
tttgccaaca ccctgccgta tgtgcacggt tcacagggtt gtgtggccta tttccgtacg      300
tactttaacc gccacttcaa agaaccggtg gcctgcgtgt cggattcgat gacggaagac      360
gcggccgtgt cggcgggaa taacaacctc aacaccgggt tacaaaacgc cagcgcactg      420
tataaaccgg agattatcgc cgtctctacc acctgtatgg cggaagtgat cggtgatgat      480
ttacaggcgt ttatcgccaa cgccaaaaaa gatggttttc tcgatgccgc catccccgtg      540
ccctacgccc acacccccag tttttatcggt agccatatca ccggctggga caacatgttt      600
gaaggttttg cccgtacctt taccgcaaac catcagccac agcccggtaa actttcacgc      660
ctgaacctgg tgaccgggtt tgaaacctat ctcggcaatt tccgcgtgct gaaacgcatg      720
atggaacaaa tggaggtgca ggcgagtgtg ctctccgatc cgtcggaggt gctggacacc      780
cccgccaatg gccattacca gatgtacgcg ggcggtacga cgcagcaaga gatgcgcgag      840
gcaccggatg ccatcgacac cctgctgctg caaccgtggc agctggtgaa aagcaaaaaa      900
gtggtgcagg agatgtggaa tcagcccgcc accgaggttg ccattcccgt cgggctggca      960
ggcacagacg aactgttgat ggcgattagc cagttaaccg gcaaagccat tcccgattcg     1020
ctggcgctgg agcgcgggcg gctggtcgat atgatgctcg actcccacac ctggttacac     1080
ggtaaaaaat tcggtctgtt tggcgatccg gattttgtca tgggattgac ccgcttcctg     1140
ctggaactgg gctgtgaacc tgccgtcatc ctctgccata acggtaacaa acgctggcaa     1200
aaagcgatga gaaaaatgct cgatgcttca ccgtacggcc aggagagcga agtgtttatc     1260
aactgcgact gtggcatttt ccgctcgctg atgttcaccc gccagccgga ttttatgatt     1320
ggcaactcgt acgccaagtt tattcagcgc gacaccttag ccaagggcga acagtttgaa     1380
```

-continued

```
gtcccgctga tccgcctcgg ttttccgctg ttcgaccgtc accatctgca ccgccagacc    1440
acctggggct acgagggcgc gatgagcatt ctcacgacgc tggtgaatgc ggtactggag    1500
aaagtggaca aagagaccat caagctcggc aaaaccgact acagcttcga tcttatccgt    1560
taa                                                                  1563

<210> SEQ ID NO 141
<211> LENGTH: 1386
<212> TYPE: DNA
<213> ORGANISM: Kosakonia pseudosacchari
<220> FEATURE:
<223> OTHER INFORMATION: nifK2

<400> SEQUENCE: 141
atggctgata ttgttcgtag taaaaaaccg ctggcggtga gcccgataaa aagcggccag      60
ccgctggggg cgatcctggc aagcctgggt ttcgaacagt gcataccgct ggtacacggc     120
gctcaggggt gcagcgcgtt cgcgaaagtg ttctttattc aacattttca cgacccgatc     180
ccgctgcaat cgacggcgat ggacccgact tccaccatta tgggcgccga tgaaaacatt     240
tttaccgcgc tcaatgttct ctgccagcgc aacgccgcga aagccatcgt gctgctcagc     300
accgggctgt cagaagccca gggcagcgat atttcacgag tggtgcgcca gtttcgtgat     360
gactttccgc ggcataaaaa cgtggcgctg ctcaccgtca acacccccgga tttctacggc    420 tcgctggaaa acggctacag cgccgtgctg gaaagcatga ttgaacagtg ggtgcccgcg     480
cagcccgccg ccagcctgcg caaccgtcgc gtcaacctgc tggtcagcca tttactgacg     540
ccgggcgata tcgaactgtt acgcagttat gtggaagcat tcggtctgca accggtgatt     600
gtgccggatc tatcgcagtc gctggacgga catctggcca acggtgattt ttcgcccgtc     660 acccagggggg gaacaccgct gcgcatgatt gaacagatgg ggcaaaacct ggccactttt    720
gtgattggcc actcgctggg gcgggcggcg gcgttactgg cgcagcgcag ccgtggcgag     780
gtgatcgccc tgccgcatct gatgacgctt gatgcgtgcg acacctttat ccatcgcctg     840
aaaaccctct ccgggcgcga cgtgcccgcg tggattgagc gccagcgcgg gcaagtgcag     900
gatgcgatga tcgattgcca tatgtggttg cagggcgcgg ctatcgccat ggccgcagaa     960
ggcgatcacc tggcggcatg gtgcgatttc gcccgcagcc agggcatgat ccccggcccg    1020
gttgtcgcgc cggtcagcca gccggggttg caaaatctgc cggttgaaat ggtggtcatc    1080
ggcgatctgg aagatatgca ggatcggctt tgcgcgacgc ccgccgcgtt actggtggcc    1140
aattctcatg ccgccgatct cgccacgcag tttgatatgt cgcttatccg cgccgggttt    1200
ccggtgtatg accggctggg ggaatttcgt cggctgcgcc aggggtatag cggcattcgt    1260
gacacgctgt ttgagctggc gaatgtgatg cgcgaacgcc attgcccgct gcaacctac     1320 cgctcgccgc tgcgtcagcg cttcggcgac aacgttacgc caggagatcg gtatgccgca    1380
tgttaa                                                              1386

<210> SEQ ID NO 142
<211> LENGTH: 1488
<212> TYPE: DNA
<213> ORGANISM: Kosakonia pseudosacchari
<220> FEATURE:
<223> OTHER INFORMATION: nifL

<400> SEQUENCE: 142
atgaccctga atatgatgat ggatgccagc gcgcccgagg ccatcgccgg tgcgctttcg      60
```

-continued

```
caacaacatc ctgggctgtt ttttaccatc gttgaagaag cccccgtcgc tatttcacta     120
accgatgccg aggcacgtat tgtctatgcc aacccggcat tctgccgcca gaccggctat     180
gagcttgagg agttgttgca gcaaaatccc cgcctgcttg ccagtcagca gaccccacgg     240
gaaatctacc aggatatgtg gcacaccctg ttacaacgtc gaccatggcg cgggcaattg     300
atcaaccgcc accgtgacgg cagccttttt ctggttgaga tcgatatcac cccggtgatt     360
aacccgtttg gcgaactgga acactacctg gccatgcagc gcgatatcag cgccggttat     420
gcgctggagc agcggttgcg taatcacatg gcgctgaccg aagcggtgct gaataacatt     480 ccggcggcg tggtcgtggt cgatgaacgc gatcgtgtgg ttatggataa cctcgcctat     540
aaaactttct gtgctgattg cggcggaaaa gagctactga gcgaactcca ttttttcagcc     600 cgtaaagcgg agctggcaaa cggccaggtc ttaccggtgg tgctgcgcgg cgcggtgcgc     660
tggttgtcgg tcacctgctg ggcgctgcca ggcgtcagcg aagaagccag tcgctacttt     720
attgataata ccttgacgcg cacgctggtg gtcatcaccg acgaccccca gcagcgccag     780
cagcaagagc aaggacggct tgaccgcctt aaacagcaga tgaccagcgg caaactgctg     840
gcggcgatcc gcgaagcgct tgacgccgcg ctgatccagc ttaactgccc catcaatatg     900
ctggcggcgg cgcggcgttt aaacggcagt gataacagca cgtagcgct ggacgccgcg     960 tggcgcgaag gtgaagaagc gatggcgcgg ctgaaacggt gccgcccgtc gctggagctg    1020
gaaagtgccg ccgtctggcc gctgcaaccc ttttttgacg acttgcgcgc gctttatcac    1080
acccgctacg agcagggtaa aaatttgcag gtcacgctgg attcgacgca tctggtggga    1140
tttggtcagc gaacccaact gctggcctgc ctgagtctgt ggctcgatcg cacgctggat    1200
attgccgtcg ggctgcgtga tttcaccgcc caaacgcaga tttacgcccg ggaagaagcg    1260
ggctggctct cgttgtatat cactgacaat gtgccgttga ttccgctgcg ccatacccat    1320
tcgccggatg cgcttaacgc accgggaaaa ggtatggagt tgcggctgat ccagacgctg    1380
gtagcgcatc acaacggcgc gatagaactc acttcacgcc ccgaagggg aagctgcctg    1440 accctacgat tcccgctatt tcattcactg accggaggtt caaaatga               1488
```

<210> SEQ ID NO 143
<211> LENGTH: 1575
<212> TYPE: DNA
<213> ORGANISM: Kosakonia pseudosacchari
<220> FEATURE:
<223> OTHER INFORMATION: nifA

<400> SEQUENCE: 143

```
atgacccagc gaaccgagtc gggtaatacc gtctggcgct tcgatttatc ccagcagttc      60
accgcgatgc agcggataag cgtggttctc agccgggcga ccgaggttga acagacactc     120
cagcaggtgc tgtgcgtatt gcacaatgac gccttttttgc agcacggcat gatctgtctg     180
tacgacagcc agcaggcgat tttgactatt gaagcgttgc aggaagccga tcagcagttg     240
atccccggca gctcgcaaat tcgctaccgt ccgggtgaag ggctggtcgg acggtgctt     300 tcgcaggggc aatcgttagt gctggcgcgt gtggctgacg atcagcgctt tcttgaccgc     360
ctgggactgt atgattacaa cctgccgttt atcgccgtgc cgctgatagg ccggatgcg     420 cagacttttg gcgtgctgac ggcgcaaccg atggcgcgtt acgaagagcg gttacccgcc     480
tgcacccgct ttctggaaac ggtcgcgaat ctggtggcgc agaccgtgcg tttgatgacg     540
ccgcggctac acgccccttc cccacgcgct gccatcacgc caaccgccag cccgaaatcg     600
tgcagtactt cacgcgcgtt cggcttcgaa aatatggtcg gcaacagccc ggcaatgcgc     660
```

-continued

```
cagaccatgg agattatccg tcaggtttcg cgctgggata ccaccgttct ggtgcgcggc      720
gagagcggca ccggcaagga actgattgcc aacgccatcc atcacaattc gccgcgcgcc      780
agtgcgccat ttgtgaaatt caactgtgcg gcgctgccgg acacattgct tgaaagcgaa      840
ttatttggtc atgaaaaagg cgcctttacc ggcgcggtac gccagcgtaa aggccgtttt      900
gagctggccg atggcggcac gctgtttctt gacgaaattg gggaaagcag cgcctcgttt      960
caggctaagc tgctgcgtat tttgcaggag ggcgaaatgg aacgcgtcgg tggtgacgag     1020
acattgcaag tgaatgtgcg catcattgcc gcgacgaacc gcaaccttga agatgaagta     1080
cgcctgggac attttcgcga agatctctat taccgcctga atgtgatgcc catcgccctg     1140
ccgccgctgc gcgaacgcca ggacgacatc gccgaactgg cacattttct ggtgcgtaaa     1200
atcgcccaca accagaaccg cacgctgcgc attagcgagg cgctatccg cctgctgatg     1260 agctacagct ggcccggcaa tgtgcgcgaa ctggaaaact gccttgagcg ctctgcggtg     1320
atgtcggaaa acggtctgat cgatcgggac gtgattttat ttaatcatcg cgaccagcca     1380
gccaaaccgc cggttatcag cgtcacgccc gacgataact ggctcgataa cacccttgac     1440
gagcgccagc ggctgattgc cgcgctggaa aaagcgggat gggtacaagc caaagccgcc     1500
cgcttgctgg ggatgacgcc gcgccaggtc gcttatcgta ttcagaccat ggatatcacc     1560
ctgccaaggc tataa                                                     1575
```

```
<210> SEQ ID NO 144
<211> LENGTH: 2850
<212> TYPE: DNA
<213> ORGANISM: Kosakonia pseudosacchari
<220> FEATURE:
<223> OTHER INFORMATION: glnE

<400> SEQUENCE: 144
```

```
atgccgcacc acgcaggatt gtcgcagcac tggcaaacgg tttttttctcg tctgccggaa       60 gcgctcaccg cgcaaccatt gagcgcgcag cgcagtcag tgctcacttt tagtgatttt      120
gttcaggaca gcatcatcgt gcatcctgag tggctggcag agcttgaaag cgcaccgccg      180
ccagcgaacg agtggcaaca ctacgcgcaa tggctgcaag cggcgctgga gggcgtcacc      240
gatgaaacct cgctgatgcg cacgctgcgg ctgtttcgcc gtcgcattat ggtgcgcatc      300
gcctggagtc aggcgctaca gttggtggcg gaagaggata tcctgcaaca gctcagcgtg      360
ctggcggaaa ctctgatcgt cgccgcgcgc gactggctct atgacgcctg ctgccgtgag      420
tggggaacgc cgtgcaatcc gcaaggcgtc gcgcagccga tgctggtgct cggcatgggc      480
aaacttggcg gcggcgaact caatttctca tccgatatcg atttgatttt tgcctggccg      540
gaaaatggcc ccacgcgcgg cggacgccgt gaactggata cgcgcagtt ttttacccgc      600 cttggtcaac ggctaattaa agtcctcgac cagcccacgc aggatggctt tgtctaccgc      660
gtcgatatgc gcttgcgtcc ctttggcgac agcggcccgc tggtgctgag ttttgccgcg      720
ctggaagatt actaccagga gcaggggcgc gactgggaac gatacgcgat ggtgaaagcg      780
cgcattatgg gggacaacga cggcgaccat gcgcgagagt gcgcgcgcat gctgcgcccg      840 ttcgtttttcc gccgctatat cgacttcagc gtgatccagt ctctgcgcaa catgaaaggc      900
atgattgccc gcgaagtgcg gcgtcgcggc ctgaaggaca acataaaact cggcgcgggc      960
ggtattcgcg aaatagagtt tatcgtgcag gttttccagt tgattcgcgg cggtcgcgag     1020
cctgcgctgc aatcgcgttc gctgttgccg acgcttgctg ccattgatca actacatctg     1080
```

-continued

```
ctgccggatg gtgatgcacc ccggctgcgc gaggcgtatt tgtggctgcg acggctggaa    1140
aacttgctgc aaagcattaa tgacgaacag acacagacgc tgccggccga tgatttgaat    1200
cgcgcgcgcc tcgcctgggg aatgggcaaa gagagctggg aagcgctctg cgaaacgctg    1260
gaagcgcata tgtcggcggt gcggcagatt ttcaacgatc tgattggcga tgatgaaacg    1320
gattcgccgg aagatgcgct ttctgagggc tggcgcgaat tgtggcagga tgcgttgcag    1380
gaagaggact ctacgcccgt gctggcgcat ctttccgagg acgatcgccg ccgcgtggtg    1440
gcgctgattg ctgattttcg caaagagctg gataaacgca ccattggccc gcgcgggcga    1500
caggtactcg atcacttaat gccgcatctg ctcagcgatg tatgctcgcg tgacgatgcg    1560
ccagtgccgc tgtcgcgtct gacgccgctg ctcaccggta ttattacgcg caccacttac    1620
cttgagctgc tgagtgaatt ccccggtgcg ctgaaacacc tcatttccct gtgcgccgcg    1680
tcgccgatgg tggccagcca actggcgcgc tacccgatcc tgctcgatga actgctcgac    1740
ccgaacacgc tctatcaacc gacggcgatg aacgcctatc gcgatgaact gcgacaatac    1800
ctgttgcgcg tgccggaaga ggatgaagag cagcaactgg aggcgctacg gcagtttaag    1860
caggcgcagt tgttgcgcgt agcggcggcg gatatcgccg gtacgttacc cgtcatgaaa    1920
gtgagcgatc acttaacctg gctggcggaa gcgattatcg atgcggtggt gcagcaagcc    1980
tggaaccaga tggtggcgcg ttacggccag ccgacgcatc tgcacgatcg cgaagggcgc    2040
ggtttcgccg tggtcggtta cggcaaactt ggcggctggg aattaggtta cagctccgat    2100
ctggatctgg tgttcctgca cgactgcccc atggatgtga tgaccgatgg cgagcgtgaa    2160
atcgatggcc gccagttcta tttgcgcctc gcgcagcgcg tgatgcacct gttcagcacg    2220
cgcacgtcgt ccggcattct ttatgaagtc gatgcgcgtt tgcgcccgtc cggcgcggcc    2280
ggaatgctgg tgaccactgc ggaagcgttc gccgattatc aaaaaaatga agcctggaca    2340
tgggagcatc aggcgctggc gcgtgcgcgc gtggtgtacg gcgatccgca actgaccgcc    2400
gaatttgacg ccattcgccg cgatatcctg atgacctccc gcgatgccgc taccctgcaa    2460
accgaagtgc gggaaatgcg tgagaaatg cgcgcccatc ttggtaacaa gcacaaagac    2520
cgtttcgatc tgaaagccga tgaaggcggt atcaccgata ttgagtttat cgctcagtat    2580
ctggtgctgc gctttgccca tgagaagccg aaactgacgc gctggtcgga taatgtgcgc    2640
atcctcgaag ggctggcgca aaacggcatc atggatgagc aggaagcgca ggcattgacg    2700
ctggcgtaca ccacgttgcg tgatgagctg caccacctgg cgctgcaaga gctgccagga    2760
catgtggcgc tctcctgttt tgtcgccgag cgtgcgctta tcaaaaccag ctgggacaag    2820
tggctggtgg aaccgtgcgc cccggcgtaa                                     2850
```

```
<210> SEQ ID NO 145
<211> LENGTH: 1287
<212> TYPE: DNA
<213> ORGANISM: Kosakonia pseudosacchari
<220> FEATURE:
<223> OTHER INFORMATION: amtB

<400> SEQUENCE: 145
```

```
atgaaaaaca caacattaaa aacggctctt gcttcgctgg cgttgctgcc aggcctggcg     60
atggcggctc ccgctgtggc ggataaagcc gacaacggct ttatgatgat ttgcaccgcg    120
ctggtgctgt ttatgaccat tccgggcatt gcgctgttct acggcggttt gatccgcggt    180
aaaaacgtgc tgtcgatgct gacgcaggtt gccgtcacct tcgctctggt gtgcatcctg    240
tgggtggttt acggctactc tctggcattt ggcgagggca acagcttctt cggcagtttc    300
```

```
aactgggcga tgttgaaaaa catcgaattg aaagccgtga tgggcagcat ttatcagtac    360
atccacgtgg cgttccaggg ctcctttgct tgtatcaccg ttggcctgat tgtcggtgcg    420
ctggctgagc gtattcgctt ctctgcggtg ctgattttg tggtggtatg gctgacgctt     480
tcttatgtgc cgattgcgca catggtctgg ggtggcggtc tgctggcaac ccacggcgcg    540
ctggatttcg cgggcggtac ggttgttcac atcaacgccg cgatcgcagg tctggtgggg    600
gcttacctga ttggcaaacg cgtgggcttt ggcaaagaag cgttcaaacc gcataacctg    660
ccgatggtct tcaccggcac cgcgatcctc tatgttggct ggtttggctt caacgccggc    720
tctgcaagct cggcgaacga aatcgctgcg ctggctttcg tgaacacggt tgttgccact    780
gcggccgcta ttctggcgtg ggtatttggc gagtgggcaa tgcgcggtaa gccgtctctg    840
ctcggtgcct gttctggtgc catcgcgggt ctggttggta tcaccccggc gtgcggttat    900
gtgggtgtcg gcggcgcgct gattgtgggt ctgattgccg gtctggcagg gctgtggggc    960
gttactgcac tgaaacgtat gttgcgtgtt gatgacccat gcgatgtctt cggtgtgcac    1020
ggcgtgtgcg gcatcgtggg ttgtatcctg accggtatct tcgcgtctac gtcgctgggc    1080
ggtgtcggtt tcgctgaagg ggtgaccatg ggccatcagg tactggtaca gctggaaagc    1140
gttgccatca ctatcgtgtg gtctggcgtg gtggcctta tcggttacaa actggcggat     1200
atgacggtag gcctgcgcgt accggaagag caagagcgtg aagggctgga tgtgaacagc     1260
cacggcgaaa atgcgtataa cgcctga                                        1287
```

```
<210> SEQ ID NO 146
<211> LENGTH: 500
<212> TYPE: DNA
<213> ORGANISM: Kosakonia pseudosacchari
<220> FEATURE:
<223> OTHER INFORMATION: PinfC

<400> SEQUENCE: 146
ttcttggttc tctggagcgc tttatcggca tcctgactga agaatttgca ggcttcttcc     60
caacctggct tgcacccgtg caggtagttg tgatgaacat cactgattcg caggctgaat    120
acgttaacga attgacccgt aaactgcaaa atgcgggcat tcgtgtaaaa gcagacttga    180
gaaacgagaa gattggcttt aaaatccgcg agcacacttt acgtcgtgtc ccttatatgc    240
tggtttgtgg tgacaaagag gtcgaagccg gcaaagttgc tgtgcgtacc cgtcgcggta    300
aagacctggg tagcctggac gtaaatgatg ttatcgagaa gctgcaacaa gagattcgca    360
gccgcagtct tcaacaactg gaggaataag gtattaaagg cggaaaacga gttcaaacgg    420
cgcgtcccaa tcgtattaat ggcgagattc gcgccacgga agttcgctta acaggtctgg    480
aaggcgagca gcttggtatt                                                500
```

```
<210> SEQ ID NO 147
<211> LENGTH: 348
<212> TYPE: DNA
<213> ORGANISM: Kosakonia pseudosacchari
<220> FEATURE:
<223> OTHER INFORMATION: Prm1

<400> SEQUENCE: 147
cgttctgtaa taataaccgg acaattcgga ctgattaaaa aagcgccctc gcggcgcttt     60
ttttatattc tcgactccat ttaaaataaa aaatccaatc ggatttcact atttaaactg    120
gccattatct aagatgaatc cgatggaagc tcgctgtttt aacacgcgtt ttttaacctt    180
```

-continued ttattgaaag tcggtgcttc tttgagcgaa cgatcaaatt taagtggatt cccatcaaaa      240
aaatattctc aacctaaaaa agtttgtgta atacttgtaa cgctacatgg agattaactc      300
aatctagagg gtattaataa tgaatcgtac taaactggta ctgggcgc                   348

<210> SEQ ID NO 148
<211> LENGTH: 339
<212> TYPE: DNA
<213> ORGANISM: Kosakonia pseudosacchari
<220> FEATURE:
<223> OTHER INFORMATION: Prm7

<400> SEQUENCE: 148
cgcgtcaggt tgaacgtaaa aaagtcggtc tgcgcaaagc acgtcgtcgt ccgcagttct       60
ccaaacgtta attggtttct gcttcggcag aacgattggc gaaaaaaccc ggtgcgaacc      120
gggttttttt atggataaag atcgtgttat ccacagcaat ccattgatta tctcttcttt      180
ttcagcattt ccagaatccc ctcaccacaa agcccgcaaa atctggtaaa ctatcatcca      240
attttctgcc caaatggctg ggattgttca tttttgttt gccttacaac gagagtgaca       300
gtacgcgcgg gtagttaact caacatctga ccggtcgat                             339

<210> SEQ ID NO 149
<211> LENGTH: 1538
<212> TYPE: DNA
<213> ORGANISM: Enterobacter sp.
<220> FEATURE:
<223> OTHER INFORMATION: 16S
<220> FEATURE:
<221> NAME/KEY: modified_base
<222> LOCATION: (62)..(62)
<223> OTHER INFORMATION: a, c, t, g, unknown or other
<220> FEATURE:
<221> NAME/KEY: modified_base
<222> LOCATION: (265)..(265)
<223> OTHER INFORMATION: a, c, t, g, unknown or other
<220> FEATURE:
<221> NAME/KEY: modified_base
<222> LOCATION: (457)..(457)
<223> OTHER INFORMATION: a, c, t, g, unknown or other
<220> FEATURE:
<221> NAME/KEY: modified_base
<222> LOCATION: (469)..(469)
<223> OTHER INFORMATION: a, c, t, g, unknown or other
<220> FEATURE:
<221> NAME/KEY: modified_base
<222> LOCATION: (539)..(539)
<223> OTHER INFORMATION: a, c, t, g, unknown or other
<220> FEATURE:
<221> NAME/KEY: modified_base
<222> LOCATION: (551)..(552)
<223> OTHER INFORMATION: a, c, t, g, unknown or other
<220> FEATURE:
<221> NAME/KEY: modified_base
<222> LOCATION: (559)..(559)
<223> OTHER INFORMATION: a, c, t, g, unknown or other
<220> FEATURE:
<221> NAME/KEY: modified_base
<222> LOCATION: (561)..(561)
<223> OTHER INFORMATION: a, c, t, g, unknown or other
<220> FEATURE:
<221> NAME/KEY: modified_base
<222> LOCATION: (576)..(576)
<223> OTHER INFORMATION: a, c, t, g, unknown or other
<220> FEATURE:
<221> NAME/KEY: modified_base
<222> LOCATION: (587)..(587)
<223> OTHER INFORMATION: a, c, t, g, unknown or other
<220> FEATURE:
<221> NAME/KEY: modified_base
<222> LOCATION: (591)..(591)
<223> OTHER INFORMATION: a, c, t, g, unknown or other

```
<220> FEATURE:
<221> NAME/KEY: modified_base
<222> LOCATION: (655)..(657)
<223> OTHER INFORMATION: a, c, t, g, unknown or other
<220> FEATURE:
<221> NAME/KEY: modified_base
<222> LOCATION: (665)..(665)
<223> OTHER INFORMATION: a, c, t, g, unknown or other
<220> FEATURE:
<221> NAME/KEY: modified_base
<222> LOCATION: (678)..(678)
<223> OTHER INFORMATION: a, c, t, g, unknown or other
<220> FEATURE:
<221> NAME/KEY: modified_base
<222> LOCATION: (706)..(706)
<223> OTHER INFORMATION: a, c, t, g, unknown or other
<220> FEATURE:
<221> NAME/KEY: modified_base
<222> LOCATION: (710)..(710)
<223> OTHER INFORMATION: a, c, t, g, unknown or other
<220> FEATURE:
<221> NAME/KEY: modified_base
<222> LOCATION: (714)..(714)
<223> OTHER INFORMATION: a, c, t, g, unknown or other
<220> FEATURE:
<221> NAME/KEY: modified_base
<222> LOCATION: (718)..(718)
<223> OTHER INFORMATION: a, c, t, g, unknown or other
<220> FEATURE:
<221> NAME/KEY: modified_base
<222> LOCATION: (735)..(735)
<223> OTHER INFORMATION: a, c, t, g, unknown or other
<220> FEATURE:
<221> NAME/KEY: modified_base
<222> LOCATION: (755)..(755)
<223> OTHER INFORMATION: a, c, t, g, unknown or other
<220> FEATURE:
<221> NAME/KEY: modified_base
<222> LOCATION: (759)..(759)
<223> OTHER INFORMATION: a, c, t, g, unknown or other
<220> FEATURE:
<221> NAME/KEY: modified_base
<222> LOCATION: (796)..(796)
<223> OTHER INFORMATION: a, c, t, g, unknown or other
<220> FEATURE:
<221> NAME/KEY: modified_base
<222> LOCATION: (1006)..(1007)
<223> OTHER INFORMATION: a, c, t, g, unknown or other
<220> FEATURE:
<221> NAME/KEY: modified_base
<222> LOCATION: (1016)..(1017)
<223> OTHER INFORMATION: a, c, t, g, unknown or other
<220> FEATURE:
<221> NAME/KEY: modified_base
<222> LOCATION: (1133)..(1133)
<223> OTHER INFORMATION: a, c, t, g, unknown or other

<400> SEQUENCE: 149
ttgaagagtt tgatcatggc tcagattgaa cgctggcggc aggcctaaca catgcaagtc     60
gngcggaagc acaggagagc ttgctctctg ggtgacgagc ggcggacggg tgagtaatgt    120
ctgggaaact gcctgatgga gggggataac tactggaaac ggtagctaat accgcataac    180
gtcgcaagac caaagagggg gaccttcggg cctcttgcca tcagatgtgc ccagatggga    240
ttagctagta ggtggggtaa cggcncacct aggcgacgat ccctagctgg tctgagagga    300
tgaccagcca cactggaact gagacacggt ccagactcct acgggaggca gcagtgggga    360
atattgcaca atgggcgcaa gcctgatgca gccatgccgc gtgtatgaag aaggccttcg    420
ggttgtaaag tactttcagc ggggaggaag gtgttgnggt taataaccnc agcaattgac    480
gttacccgca gaagaagcac cggctaactc cgtgccagca gccgcggtaa tacggaggnt    540
gcaagcgtta nncggaatna ntgggcgtaa agcgtncgca ggcggtntgt naagtcggat    600
```

-continued

```
gtgaaatccc cgggctcaac ctgggaactg cattcgaaac tggcaggcta gagtnnngta       660
gaggngggta gaattccngg tgtagcggtg aaatgcgtag agatcnggan gaanaccngt       720
ggcgaaggcg gcccnctgga caaagactga cgctnaggng cgaaagcgtg gggagcaaac       780
aggattagat accctngtag tccacgccgt aaacgatgtc gacttggagg ttgtgccctt       840
gaggcgtggc ttccggagct aacgcgttaa gtcgaccgcc tggggagtac ggccgcaagg       900
ttaaaactca aatgaattga cgggggcccg cacaagcggt ggagcatgtg gtttaattcg       960
atgcaacgcg aagaacctta cctactcttg acatccagag aacttnncag agatgnnttg      1020
gtgccttcgg gaactctgag acaggtgctg catggctgtc gtcagctcgt gttgtgaaat      1080
gttgggttaa gtcccgcaac gagcgcaacc cttatccttt gttgccagcg gtncggccgg      1140
gaactcaaag gagactgcca gtgataaact ggaggaaggt ggggatgacg tcaagtcatc      1200
atggccctta cgagtagggc tacacacgtg ctacaatggc gcatacaaag agaagcgacc      1260
tcgcgagagc aagcggacct cataaagtgc gtcgtagtcc ggattggagt ctgcaactcg      1320
actccatgaa gtcggaatcg ctagtaatcg tagatcagaa tgctacggtg aatacgttcc      1380
cgggccttgt acacaccgcc cgtcacacca tgggagtggg ttgcaaaaga agtaggtagc      1440
ttaaccttcg ggagggcgct taccactttg tgattcatga ctggggtgaa gtcgtaacaa      1500
ggtaaccgta ggggaacctg cggttggatc acctcctt                            1538
```

```
<210> SEQ ID NO 150
<211> LENGTH: 882
<212> TYPE: DNA
<213> ORGANISM: Enterobacter sp.
<220> FEATURE:
<223> OTHER INFORMATION: nifH

<400> SEQUENCE: 150
atgaccatgc gtcaatgtgc catttacggc aaaggtggta tcggtaaatc cactaccacg        60
caaaacctgg tcgccgcgct ggcggagatg ggcaagaaag taatgatcgt cggctgcgac       120
ccgaaagcag actccactcg tctgatcctg catgcgaaag cgcagaacac cattatggag       180
atggcggctg aagtcggctc cgtggaagac cttgaactgg aagatgtgct gcaaatcggt       240
tacggcgacg tacgctgcgc agaatccggc ggcccggaac caggcgttgg ctgtgctggt       300
cgcggggtaa ttaccgccat caacttcctg gaagaagaag cgcctatgt tcccgacctc       360 gatttcgtct tttacgacgt gttgggcgac gtggtgtgcg gggggttcgc catgccgatt       420
cgcgaaaaca aagcgcagga gatctacatc gtctgctccg gcgaaatgat ggcgatgtac       480
gccgccaaca acatctctaa aggcatcgtg aaatacgcca aatccggcaa agtgcgcctt       540
ggcgggctga tctgtaactc ccgtcagacc gaccgcgaag atgagctgat catagcgctg       600
gcggaaaaac tcggcaccca gatgatccac ttcgtgccgc gcgacaacat cgtgcaacgc       660
gctgaaatcc gccgtatgac ggtgattgag tacgatccga atgcaaccca ggccaatgaa       720
taccgcacgc tggcgaacaa gatcgtcaac aacaccaaaa tggtcgtgcc aacgcccatc       780
accatggacg aactggaaga gctgttgatg gaattcggca ttatggatgt ggaagacacc       840
agcattatcg gtaaaaccgc cgcagaagaa aacgcggttt ga                         882
```

```
<210> SEQ ID NO 151
<211> LENGTH: 1449
<212> TYPE: DNA
<213> ORGANISM: Enterobacter sp.
<220> FEATURE:
<223> OTHER INFORMATION: nifD1
```

<400> SEQUENCE: 151

```
atgagcaatg caacaggcga acgtaatctg gagatcatcc aggaagtgct ggagatcttt      60
ccggaaaaaa cgcgcaaaga acgcagaaag cacatgatgg tgagcgaccc ggagatggaa     120
agcgtcggga aatgcatcat ctccaaccgt aagtcgcagc ccggcgtaat gaccgtcgcc     180
ggttgctctt acgccggttc taaaggggtg gtattcgggc cgatcaaaga tatggcccat     240
atttcccacg gcccggtcgg ctgcggtcag tactcccgcg ccgggcggcg taactactac     300
accggcgtca gcggtgtgga tagcttcggt acgctcaact ttacctccga ttttcaggag     360
cgcgatatcg tgtttggcgg cgataaaaag ctgaccaaac tgattgaaga gatggagacg     420
ctgttcccgc tgaccaaagg gatctccatt cagtccgaat gcccggtcgg cctgattggc     480
gacgacattg aagccgttgc caacgccagc cgcaaagcca tcaataaacc ggtcattccg     540
gtgcgctgcg aaggttttcg cggcgtttcc cagtcactcg gtcaccacat tgccaacgac     600
gtgatccgcg actgggtact ggataaccgc gaaggcaagc cgtttgaggc cggtccttat     660
gacgtggcga tcatcggcga ttacaacatc ggcggcgatg cctgggcgtc gcgcattttg     720
ctcgaagaga tgggcctgcg cgtggtggcg cagtggtccg cgacggcac gctggttgag      780 atggagaaca cgccgttcgt caaactcaac cttgtgcact gctaccgctc aatgaactat     840
atctcccgcc atatggagga gaaacacggt attccgtgga tggagtacaa cttcttcggt     900
ccgaccaaag tcgccgaatc gttgcgcaaa atcgccgata tgtttgatga caccattcgc     960
gccaacgccg aagcggtgat cgccaaatat caggcgcaga acgacgccat catcgccaaa    1020
taccgtccgc gtctggaagg ccgcaaagtg ctgctgtata tgggcggttt acgtcctcgc    1080
catgtgattg cgcttatga agatctgggg atggaaatta tcgctgcggg ttatgaattc     1140
gcccacaacg atgactacga ccgcaccctg ccggatctga agaaggcac cttgctgttc      1200 gacgatgcca gcagttatga actggaagcc tttgtcaaag cgctgaagcc ggatctgatc    1260
ggctccggca ttaaagagaa gtacatcttc cagaaaatgg gcgtgccgtt cgccagatg     1320 cactcctggg attactccgg cccctatcac ggttatgacg gctttgccat cttcgcccgc    1380
gatatggata tgacgatcaa caaccccgcg tggggccagt tgaccgcgcc gtggctgaaa    1440
tccgcctga                                                           1449
```

<210> SEQ ID NO 152
<211> LENGTH: 1092
<212> TYPE: DNA
<213> ORGANISM: Enterobacter sp.
<220> FEATURE:
<223> OTHER INFORMATION: nifD2
<220> FEATURE:
<221> NAME/KEY: modified_base
<222> LOCATION: (709)..(709)
<223> OTHER INFORMATION: a, c, t, g, unknown or other

<400> SEQUENCE: 152

```
atgggacgcg gcgagcgccg cctgttccat gccgtgcgcc acatcgtcaa ccgctaccac      60
ccggccgccg tctttatcta taacacctgc gttcccgcga tggagggcga cgatatcgaa     120
gccgtctgcc aggcggcaga aaccgccatc ggcgtaccgg tgattgccgt tgatgtcgcc     180 gggtttacg gcagcaaaaa tctcggcaac cggttggccg gtgaagtgat ggtgaaaaag      240
gtgattggcg ggcgtgaacc cgcgccgtgg ccggaagata cccctttttgc cccgcgcac     300 cgccacgata tcgggctgat tggcgaattc aatattgccg gagagttctg gcatattcag     360
```

```
ccgctgctcg atgagctggg tattcgcgtg ctcggcagcc tctccggcga cgggcgcttc      420
agtgaaatcc agacgctgca ccgggcgcag gtcaatatgc tggtctgctc cagggcgctg      480
atcaacgtcg cccgctcgct ggagcagcgc tacggcacgc cgtggtttga aggcagtttt      540
tatggtgttc gcgccacctc tgacgccctg cgccaactgg cggcgctgac cggagaccgc      600
gatctgatgc agcgcaccga acagctcatt gcccgcgaag agcagcaaac agagcaggcg      660
ctggccccgc tgcgcgagcg cctgcgcggg cgcaaagcgc tgctctatnc cggcggcgtg      720
aaatcctggt cggtggtttc ggcgcttcag gatctgggca tggaagtggt ggcgaccggc      780
acgcgcaaat ccaccgaaga ggataaacag cgcatccgcg aactgatggg cgccgacgcg      840
ctgatgcttg atgaaggtaa cgcccgctcg ctgctggacg tggtttaccg ctacaaggcg      900
gacatgatga tcgccggggg acgcaatatg tacaccgcct acaaagcgcg gctgccgttc      960
ctcgatatca atcaggagcg cgagcacgcc tttgccggct accgcggcat tgtcaccctg     1020
gccgaacagc tctgcctgac catggaaagc ccggtctggc cgcaaaccca ttcccgcgca     1080
ccgtggcaat aa                                                         1092
```

<210> SEQ ID NO 153
<211> LENGTH: 846
<212> TYPE: DNA
<213> ORGANISM: Enterobacter sp.
<220> FEATURE:
<223> OTHER INFORMATION: nifK

<400> SEQUENCE: 153

```
atgatggagc aaatggacgt gccgtgcagc ctgctttccg atccctccga agtgctggat       60
accccggctg acgggcatta ccacatgtat gcgggcggta cgacccagca ggagatgcgc      120
gaagcgcctg acgctatcga caccctgctg ctgcaaccct ggcaactggt gaaaaccaaa      180
aaagtggtgc aggaaagctg gaaccagccc gctaccgagg tgcaaatccc aatggggctg      240
gccggaaccg acgagctgct gatgacggta agccagttaa ccggcaaagc cattccggat      300
agcttagcgc tggaacgcgg tcggctggtg gatatgatgc tcgactccca cacctggctg      360
cacggcaaga aattcggcct gttcggtgac ccggattttg tcatggggct gacccgcttc      420
ctgctggaac tgggctgcga accgacggtg attctgtgcc ataacggcag caagcgctgg      480
cagaaagcga tgaagaaaat gcttgaagcc tcgccgtacg ggaaagagag cgaagtcttt      540
atcaactgcg atttgtggca tttccgctcg ctgatgttta cccgtcagcc ggactttatg      600
atcggcaact cctacgccaa gtttatccag cgcgatacgc tggcgaaggg tgagcagttt      660
gaagtgccgc tgatccgcct ggggttcccg ctgttcgatc gccaccatct gcaccgccag      720
accacctggg gttacgaagg ggccatgagt atcctcacca cgctggttaa tgcggtgctg      780
gagaaagtcg acagagagac catcaagctc ggcaaaaccg actacagctt cgatcttatc      840
cgttaa                                                                846
```

<210> SEQ ID NO 154
<211> LENGTH: 1095
<212> TYPE: DNA
<213> ORGANISM: Enterobacter sp.
<220> FEATURE:
<223> OTHER INFORMATION: nifL
<220> FEATURE:
<221> NAME/KEY: modified_base
<222> LOCATION: (942)..(942)
<223> OTHER INFORMATION: a, c, t, g, unknown or other

<400> SEQUENCE: 154

```
atgcagcgcg acatcagcac cagctacgcg ctggaacaac ggctgcgcaa tcatatgacg      60
ctgaccgaag ccgtcttgaa taacattccg gcggcggttg tagtggtgga tgaacgcgat     120
cgggtggtga tggataacct cgcctacaaa acctttttgcg ccgattgcgg cggtaaagaa    180
ctactcaccg aaatcaactt ttccgcccat aaggcggagc tggcgcaggg cctggtactg     240
ccggtagtgc tgcgcggcac cgtgcgctgg ttgtccgtta cctgttgggc gctgccgggc     300
gtcagcgaag aagcaggccg ctactttatt gatagcgccg tgccgcgcac gctggtggtg     360
atcaccgata atactcagca gcagcaacaa caggagcagg ggcgtcttga tcgtctgaag     420
cagcagataa ccagcggtaa attgctggcg gcgatccgcg aatcgctgga cgccgcgctg     480
gtacaactca attgcccaat taatatgctg gccgccgcac gccgcttaaa tggcgacgag     540
catagcaatc tggcgctgga tgccgcatgg cgtgaaggcg aagaagcgat ggcgcggttg     600
cagcgctgcc gcccgtcgct ggaactggaa agcccggcag tctggccgct ccagccgttc     660
cttgacgatc tgcgtgccct gtatcacacc cgatataacc agggcgaaaa cctgcaaatt     720
gagctggaat cccccgacct ggtgggcttt ggccagcgaa cacaactgct tgcctgcctg     780
agcctgtggc tcgacagaac cctggatatt gccgcggagc tacgtgattt cacggtacag     840
actcaacttt acgcccgcga agagagcggc tggctgtcgt tctatttaaa cgacaatgtg     900
ccgctgattc aggtgcgcta cacccattca cccgatgcac tnaatgcgcc cggtaaaggc     960
atggagctgc ggctgatcca gacgctggtc gcccaccatc gaggcgcaat agaactgacc    1020
tcacgccctc agggaggcac ctgtctgatc ctgcgtttcc cattattttta ctcgctgaca    1080 ggaggctcac tatga                                                     1095
```

```
<210> SEQ ID NO 155
<211> LENGTH: 219
<212> TYPE: DNA
<213> ORGANISM: Enterobacter sp.
<220> FEATURE:
<223> OTHER INFORMATION: nifA partial gene

<400> SEQUENCE: 155
atgactcagc gaaccgagtc gggtacaacc gtctggcgct ttgacctctc ccaacagttt      60
acagccatgc agcgtatcag tgtggtgtta agccgcgcga cggagatcgg gcagacgcta     120
caggaagtgc tgtgcgtgct gcacaacgat gcctttatgc agcacgggat gatctgtccg     180
tacgcgcggg tgcgcgtctt cgcgagcgta tggctttga                           219
```

```
<210> SEQ ID NO 156
<211> LENGTH: 1635
<212> TYPE: DNA
<213> ORGANISM: Enterobacter sp.
<220> FEATURE:
<223> OTHER INFORMATION: glnE
<220> FEATURE:
<221> NAME/KEY: modified_base
<222> LOCATION: (234)..(234)
<223> OTHER INFORMATION: a, c, t, g, unknown or other
<220> FEATURE:
<221> NAME/KEY: modified_base
<222> LOCATION: (274)..(274)
<223> OTHER INFORMATION: a, c, t, g, unknown or other
<220> FEATURE:
<221> NAME/KEY: modified_base
<222> LOCATION: (1535)..(1535)
<223> OTHER INFORMATION: a, c, t, g, unknown or other

<400> SEQUENCE: 156
```

```
atgcgcgtgg aagactggtc aacgctgacc gaacggctcg atgcccatat ggcaggcgtg    60
cgccgaatct ttaacgaact gatcggtgat gacgaaagtg agtcgcagga cgatgcgctc    120
tccgagcact ggcgcgagct gtggcaggac gcgcttcagg aagatgacac cacgccggtg    180
ctgacgcact taaccgacga cgcgcgccat cgcgtggtgg cgctgatcgc tganttccgt    240
cttgagctga acaaacgcgc catcggcccg cgtngtcgcc aggtgctgga tcacctgatg    300
ccgcacctgc tgagcgaagt ctgctcgcgt gccgatgcgc cggtgccgct gtcgcggatg    360
atgcccctgc tgagcgggat tatcacccgt actacctacc ttgaactcct gagcgagttc    420
cctggcgcgc ttaagcacct gatttcactc tgcgccgcgt cgccgatggt ggccaacaag    480
ctggcgcgtt acccgctgct gctggatgag ctgctcgatc cgaataccct ttatcaaccg    540
acggcgaccg acgcctaccg ggacgaactg cgtcagtatc tgctgcgcgt gccggaagaa    600
gacgaagagc aacagctgga ggcgctgcgt cagtttaagc aggcccagat gctgcgcgtg    660
gcggccgcag atattgccgg aacgctgccg gtgatgaaag tgagcgatca cttaacctgg    720
cttgcggaag cgattatcga cgcggtggtg catcaggcct gggtgcagat ggtggcgcgc    780
tatggccagc cgaaacatct ggctgaccgt gatggtcgcg gcttcgcggt ggtgggttac    840
ggtaagctcg gcggttggga gctgggctat agctccgatc tggatttaat cttcctccac    900
gactgcccgg ttgatgtgat gaccgacggc gagcgcgaga ttgacgggcg tcagttctac    960
ctgcgcctgc cgcagcgcat catgcacctg ttcagcaccc gcacctcgtc gggcattttg    1020
tatgaagtgg atgcccgtct gcgcccgtcc ggcgcggcgg gcatgctggt cacctcgacg    1080
gagtccttcg ctgattacca gaagaatgaa gcctggacgt gggagcatca ggcgctggtg    1140
cgcgcccgtg tggtgtatgg cgatccgctg ctgaaaacgc agtttgacgt gattcgtaag    1200
gaagtcatga ccaccgtgcg cgatggcagc acgctgcaaa cggaagtgcg cgaaatcgcg    1260
gagaaaatgc gcgcgcactt aggcaataaa catcgcgatc gctttgatat taaagccgat    1320
gagggcggta ttaccgatat tgagtttatt acccagtatc tggtgttgct gcacgcgcat    1380
gacaagccga agctgacgcg ctggtcggat aacgtgcgca ttctggaact gctggcgcaa    1440
aacgacatta tggacgagca ggaggcgcag gccttaaccc gtgcctatac aacgcttcgc    1500
gatgagctcc atcatctggc gttgcaggag cagcnggac acgtggcgct ggactgtttc     1560
accgctgaac gcgctcaggt aacggccagc tggcagaagt ggctggtgga accgtgcgta    1620
acaaatcaag tgtga                                                     1635
```

```
<210> SEQ ID NO 157
<211> LENGTH: 1316
<212> TYPE: DNA
<213> ORGANISM: Enterobacter sp.
<220> FEATURE:
<223> OTHER INFORMATION: 16S
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (247)..(247)
<223> OTHER INFORMATION: a, c, t, g, unknown or other
<220> FEATURE:
<221> NAME/KEY: modified_base
<222> LOCATION: (784)..(785)
<223> OTHER INFORMATION: a, c, t, g, unknown or other
<220> FEATURE:
<221> NAME/KEY: modified_base
<222> LOCATION: (794)..(795)
<223> OTHER INFORMATION: a, c, t, g, unknown or other
```

-continued

```
<400> SEQUENCE: 157
agatgtgccc agatgggatt agctagtagg tggggtaacg gcncacctag gcgacgatcc      60
ctagctggtc tgagaggatg accagccaca ctggaactga gacacggtcc agactcctac     120
gggaggcagc agtgggggaat attgcacaat gggcgcaagc ctgatgcagc catgccgcgt     180
gtatgaagaa ggccttcggg ttgtaaagta ctttcagcgg ggaggaaggt gttgtggtta     240
ataaccncag caattgacgt tacccgcaga agaagcaccg gctaactccg tgccagcagc     300
cgcggtaata cggagggtgc aagcgttaat cggaattact gggcgtaaag cgcacgcagg     360
cggtctgtca agtcggatgt gaaatccccg ggctcaacct gggaactgca ttcgaaactg     420
gcaggctaga gtcttgtaga ggggggtaga attccaggtg tagcggtgaa atgcgtagag     480
atctggagga ataccggtgg cgaaggcggc ccctggaca aagactgacg ctcaggtgcg     540
aaagcgtggg gagcaaacag gattagatac cctggtagtc cacgccgtaa acgatgtcga     600
cttggaggtt gtgcccttga ggcgtggctt ccggagctaa cgcgttaagt cgaccgcctg     660
gggagtacgg ccgcaaggtt aaaactcaaa tgaattgacg ggggcccgca caagcggtgg     720
agcatgtggt ttaattcgat gcaacgcgaa gaaccttacc tactcttgac atccagagaa     780
cttnncagag atgnnttggt gccttcggga actctgagac aggtgctgca tggctgtcgt     840
cagctcgtgt tgtgaaatgt tgggttaagt cccgcaacga gcgcaaccct tatcctttgt     900
tgccagcggt ccggccggga actcaaagga gactgccagt gataaactgg aggaaggtgg     960
ggatgacgtc aagtcatcat ggcccttacg agtagggcta cacacgtgct acaatggcgc    1020
atacaaagag aagcgacctc gcgagagcaa gcggacctca taaagtgcgt cgtagtccgg    1080
attggagtct gcaactcgac tccatgaagt cggaatcgct agtaatcgta gatcagaatg    1140
ctacggtgaa tacgttcccg ggccttgtac acaccgcccg tcacaccatg ggagtgggtt    1200
gcaaaagaag taggtagctt aaccttcggg agggcgctta ccactttgtg attcatgact    1260
ggggtgaagt cgtaacaagg taaccgtagg ggaacctgcg gttggatcac ctcctt        1316

<210> SEQ ID NO 158
<211> LENGTH: 882
<212> TYPE: DNA
<213> ORGANISM: Enterobacter sp.
<220> FEATURE:
<223> OTHER INFORMATION: nifH

<400> SEQUENCE: 158
atgaccatgc gtcaatgtgc catttacggc aaaggtggta tcggtaaatc cactaccacg      60
caaaacctgg tcgccgcgct ggcggagatg ggcaagaaag taatgatcgt cggctgcgac     120
ccgaaagcag actccactcg tctgatcctg catgcgaaag cgcagaacac cattatggag     180
atggcggctg aagtcggctc cgtggaagac cttgaactgg aagatgtgct gcaaatcggt     240
tacggcgacg tacgctgcgc agaatccggc ggcccggaac caggcgttgg ctgtgctggt     300
cgcggggtaa ttaccgccat caacttcctg gaagaagaag cgcctatgt tcccgacctc     360 gatttcgtct tttacgacgt gttgggcgac gtggtgtgcg gggggttcgc catgccgatt     420
cgcgaaaaca aagcgcagga gatctacatc gtctgctccg cgaaatgat ggcgatgtac     480 gccgccaaca acatctctaa aggcatcgtg aaatacgcca atccggcaa agtgcgcctt     540 ggcgggctga tctgtaactc ccgtcagacc gaccgcgaag atgagctgat catagcgctg     600
gcggaaaaac tcggcaccca gatgatccac ttcgtgccgc gcgacaacat cgtgcaacgc     660
```

```
gctgaaatcc gccgtatgac ggtgattgag tacgatccga aatgcaacca ggccaatgaa      720
taccgcacgc tggcgaacaa gatcgtcaac aacaccaaaa tggtcgtgcc aacgcccatc      780
accatggacg aactggaaga gctgttgatg gaattcggca ttatggatgt ggaagacacc      840
agcattatcg gtaaaaccgc cgcagaagaa aacgcggttt ga                        882

<210> SEQ ID NO 159
<211> LENGTH: 1449
<212> TYPE: DNA
<213> ORGANISM: Enterobacter sp.
<220> FEATURE:
<223> OTHER INFORMATION: nifD1

<400> SEQUENCE: 159
atgagcaatg caacaggcga acgtaatctg gagatcatcc aggaagtgct ggagatcttt       60
ccggaaaaaa cgcgcaaaga acgcagaaag cacatgatgg tgagcgaccc ggagatggaa      120
agcgtcggga aatgcatcat ctccaaccgt aagtcgcagc ccggcgtaat gaccgtgcgc      180
ggttgctctt acgccggttc taaaggggtg gtattcgggc cgatcaaaga tatggcccat      240
atttcccacg gccggtcgg ctgcggtcag tactcccgcg ccgggcggcg taactactac       300
accggcgtca gcggtgtgga tagcttcggt acgctcaact ttacctccga ttttcaggag      360
cgcgatatcg tgtttggcgg cgataaaaag ctgaccaaac tgattgaaga gatggagacg      420
ctgttcccgc tgaccaaagg gatctccatt cagtccgaat gcccggtcgg cctgattggc      480
gacgacattg aagccgttgc caacgccagc cgcaaagcca tcaataaacc ggtcattccg      540
gtgcgctgcg aaggttttcg cggcgtttcc cagtcactcg gtcaccacat gccaacgac       600 gtgatccgcg actgggtact ggataaccgc gaaggcaagc cgtttgaggc cggtccttat      660
gacgtggcga tcatcggcga ttacaacatc ggcggcgatg cctgggcgtc gcgcattttg      720
ctcgaagaga tgggcctgcg cgtggtggcg cagtggtccg gcgacggcac gctggttgag      780
atggagaaca cgccgttcgt caaactcaac cttgtgcact gctaccgctc aatgaactat      840
atctcccgcc atatggagga gaaacacggt attccgtgga tggagtacaa cttcttcggt      900
ccgaccaaag tcgccgaatc gttgcgcaaa atcgccgata tgtttgatga caccattcgc      960
gccaacgccg aagcggtgat cgccaaatat caggcgcaga cgacgccat catcgccaaa      1020 taccgtccgc gtctggaagg ccgcaaagtg ctgctgtata tgggcggttt acgtcctcgc     1080
catgtgattg gcgcttatga agatctgggg atggaaatta tcgctgcggg ttatgaattc     1140
gcccacaacg atgactacga ccgcacctg ccggatctga agaaggcac cttgctgttc      1200 gacgatgcca gcagttatga actggaagcc tttgtcaaag cgctgaagcc ggatctgatc     1260
ggctccggca ttaaagagaa gtacatcttc cagaaaatgg gcgtgccgtt tcgccagatg     1320
cactcctggg attactccgg ccctatcac ggttatgacg gctttgccat cttcgcccgc      1380
gatatggata tgacgatcaa caaccccgcg tggggccagt tgaccgcgcc gtggctgaaa     1440
tccgcctga                                                            1449

<210> SEQ ID NO 160
<211> LENGTH: 1374
<212> TYPE: DNA
<213> ORGANISM: Enterobacter sp.
<220> FEATURE:
<223> OTHER INFORMATION: nifD2

<400> SEQUENCE: 160
atgaagggga acgagatcct ggctttgctc gatgaacctg cctgcgagca caaccataaa       60
```

-continued

```
cagaaatccg gctgcagcgc gccgaaaccc ggcgcgacag cgggcggctg cgcctttgac      120
ggtgcgcaga tcaccctgct gccactctcc gatgttgccc acctggtaca cggccccatt      180
ggttgtaccg gtagctcatg ggataaccgt ggcagcttca gttccggccc gacgatcaac      240
cggctgggtt ttaccaccga tctgagcgaa caggatgtga tcatgggacg cggcgagcgc      300
cgcctgttcc atgccgtgcg ccacatcgtc aaccgctacc acccggccgc cgtctttatc      360
tataacacct gcgttcccgc gatggagggc gacgatatcg aagccgtctg ccaggcggca      420
gaaaccgcca tcggcgtacc ggtgattgcc gttgatgtcg ccgggtttta cggcagcaaa      480
aatctcggca accggttggc cggtgaagtg atggtgaaaa aggtgattgg cgggcgtgaa      540
cccgcgccgt ggccggaaga taccccattt gccccggcgc accgccacga tatcgggctg      600
attggcgaat tcaatattgc cggagagttc tggcatattc agccgctgct cgatgagctg      660
ggtattcgcg tgctcggcag cctctccggc gacgggcgct tcagtgaaat ccagacgctg      720
caccgggcgc aggtcaatat gctggtctgc tccaggcgc tgatcaacgt cgcccgctcg       780
ctggagcagc gctacggcac gccgtggttt gaaggcagtt tttatggtgt tcgcgccacc      840
tctgacgccc tgcgccaact ggcggcgctg accggagacc gcgatctgat gcagcgcacc      900
gaacagctca ttgcccgcga agagcagcaa acagagcagg cgctggcccc gctgcgcgag      960
cgcctgcgcg ggcgcaaagc gctgctctat accggcggcg tgaaatcctg gtcggtggtt     1020
tcggcgcttc aggatctggg catggaagtg gtggcgaccg gcacgcgcaa atccaccgaa     1080
gaggataaac agcgcatccg cgaactgatg ggcgccgacg cgctgatgct tgatgaaggt     1140
aacgcccgct cgctgctgga cgtggtttac cgctacaagg cggacatgat gatcgccggg     1200
ggacgcaata tgtacaccgc ctacaaagcg cggctgccgt tcctcgatat caatcaggag     1260
cgcgagcacg cctttgccgg ctaccgcggc attgtcaccc tggccgaaca gctctgcctg     1320
accatggaaa gcccggtctg gccgcaaacc cattcccgcg caccgtggca ataa           1374
```

```
<210> SEQ ID NO 161
<211> LENGTH: 1563
<212> TYPE: DNA
<213> ORGANISM: Enterobacter sp.
<220> FEATURE:
<223> OTHER INFORMATION: nifK1

<400> SEQUENCE: 161
```

```
atgagccaaa gtgctgagaa aattcaaaac tgtcatccgc tgtttgaaca ggatgcgtac       60
cagatgctgt ttaaagataa acggcaactg gaagaggccc acgatccggc gcgcgtgcag      120
gaggtctttc aatggaccac caccgccgag tatgaagcgc ttaactttca acgcgaagcg      180
ctgactatcg atccggccaa agcctgccag ccgctgggtg cggtactgtg ctcgctgggc      240
tttgccaata ccctgcccta tgttcacggc tcccaggggt gcgtggccta tttccgcacc      300
tattttaacc gtcactttaa agagccgatt gcctgtgttt ctgactcgat gacggaagat      360
gcggcagtat tcggcggcaa caacaacctg aacaccgggt tgcagaacgc cagcgccctc      420
tacaagccgg aaatcattgc cgtctccacc acctgtatgg cggaggtcat cggcgacgac      480
ctgcaggcgt ttattgctaa cgccaaaaaa gacggcttta tcgacgcggc gatcccggtg      540
ccttacgcgc acacgccaag ctttatcggc agccatatca ccggctggga caatatgttt      600
gagggcttcg cccgtacctt taccgccgat tacagcggac aaccgggcaa attaccgcgt      660
atcaatctgg tcagcggatt tgaaacctat ctcggtaatt tccgcgtgct gaaacgcatg      720
```

```
atggagcaaa tggacgtgcc gtgcagcctg ctttccgatc cctccgaagt gctggatacc    780
ccggctgacg ggcattacca catgtatgcg ggcggtacga cccagcagga gatgcgcgaa    840
gcgcctgacg ctatcgacac cctgctgctg caaccctggc aactggtgaa aaccaaaaaa    900
gtggtgcagg aaagctggaa ccagcccgct accgaggtgc aaatcccaat ggggctggcc    960
ggaaccgacg agctgctgat gacggtaagc cagttaaccg gcaaagccat tccggatagc   1020
ttagcgctgg aacgcggtcg gctggtggat atgatgctcg actcccacac ctggctgcac   1080
ggcaagaaat tcggcctgtt cggtgacccg gattttgtca tggggctgac ccgcttcctg   1140
ctggaactgg gctgcgaacc gacggtgatt ctgtgccata acggcagcaa gcgctggcag   1200
aaagcgatga agaaaatgct tgaagcctcg ccgtacggga aagagagcga agtctttatc   1260
aactgcgatt tgtggcattt ccgctcgctg atgtttaccc gtcagccgga ctttatgatc   1320
ggcaactcct acgccaagtt tatccagcgc gatacgctgg cgaagggtga gcagtttgaa   1380
gtgccgctga tccgcctggg gttcccgctg ttcgatcgcc accatctgca ccgccagacc   1440 acctgggggtt acgaaggggc catgagtatc ctcaccacgc tggttaatgc ggtgctggag   1500
aaagtcgaca gagagaccat caagctcggc aaaaccgact acagcttcga tcttatccgt   1560
taa                                                                 1563
```

```
<210> SEQ ID NO 162
<211> LENGTH: 1386
<212> TYPE: DNA
<213> ORGANISM: Enterobacter sp.
<220> FEATURE:
<223> OTHER INFORMATION: nifK2

<400> SEQUENCE: 162
```

```
atggcagaaa ttatccgtag taaaaagccg ctggccgtca gcccggtaaa aagtggccag     60
ccgctgggcg cgattctggc gagcatgggc tttgaacaga gcattccgct ggttcatggc    120
gctcaggggt gcagcgcctt cgcgaaggtc tttttttatcc agcattttca cgatccgatc    180
ccgctgcaat cgacggcaat ggacccgaca tcgaccatta tgggtgccga tgagaacatc    240
tttaccgcgc tgaatgtgct gtgttcacgc aacaacccga aagcgattgt tctgctgagc    300
actggccttt ccgaggcgca gggcagcgat atttcgcgcg tggtgcgcca gttccgcgat    360
gaatatccgc gccataaagg ggtggcgctg ctgaccgtca cacgccgga ttttttacggc    420 agcctggaaa acggctacag cgcggtgctg gagagcatgg ttgaacagtg ggtgccggaa    480
aaaccgcagc cgggcgtgcg caatcgccgc gtgaacctgc tgctcagcca tttgcttacg    540
ccgggcgaca ttgagctgct gcgaagttat gtcgaggcat ttggcctgca gccggtgatg    600
gtgccggatc tttcccagtc gctggatggc atctcgcca gcggggattt ctcgccaatt    660
acccagggcg gcagcagcct gcggctgatt aacagatgg gacagagtct tggcacgttc    720
gccattggcg tatccctctc ccgcgccgcg caattgctgg cgcagcgcag ccatgcggaa    780
gtggtcaccc tgccgcatct gatgaccatg agccagtgcg atacgtttat tcatcaactg    840
aagcgcctct ccgggcgcga tgttccggcg tggatcgaac cagcgcgg gcaactgcag    900 gatgcgatga tcgattgtca tatgtggttg caggcgcgc ctgtcgcgct ggcgccgag    960 ggcgatctgc tcgccgcctg gtgcgatttc gcctgcgata tgggcatggt gcccggcccg   1020
gtggtggcgc cggtgagcca gaaagggttg caggatctgc cggtcgaaaa agtcattatc   1080
ggcgatctga aggatatgca ggatctgttg tgtgaaacgc ctgcatcgct gctcgtctct   1140
aattctcacg ccgctgattt ggccgggcag ttcgacattc cgctggtgcg cgccggtttc   1200
```

-continued

```
cccctgttcg accgtctggg cgagtttcgc cgcgtgcgcc agggttacgc cgggatgcgc    1260
gacaccttgt ttgagctggc gaatgcgctg cgcgatcgcc atcatcatct tgccgcttat    1320
cactcgccgc tgcgccagcg tttttacgaa cccgcatctt cgggaggtga ctatgcaaca    1380
tgttaa                                                              1386
```

<210> SEQ ID NO 163
<211> LENGTH: 1488
<212> TYPE: DNA
<213> ORGANISM: Enterobacter sp.
<220> FEATURE:
<223> OTHER INFORMATION: nifL

<400> SEQUENCE: 163

```
atgaccctga atatgatgat ggacgccacc gcgcccgccg agatcgccgg agcgctctca     60
caacagcatc ccgggttgtt tttcaccatg gttgaacagg cgcccgtcgc gatttcactg    120
accgatgccg atgcccacat tctctacgcc aacccgcgt tttgtcgcca gtcggggtat     180
gaactggaag agttgttgca gcaaaacccg cgcctgcttg ccagtaagca gacgccgcgt    240
gaaatctacc aggaaatgtg gcacaccctg ctgcaacacc gtccgtggcg cggacaactg    300
atcaaccgtc gccgcgacgg cagcctgttt ctggtggaaa tcgacatcac cccactgttt    360
gatgcgttcg gcaaactcga acattacctg gccatgcagc gcgacatcag caccagctac    420
gcgctggaac aacggctgcg caatcatatg acgctgaccg aagccgtctt gaataacatt    480 ccggcggcg ttgtagtggt ggatgaacgc gatcgggtgg tgatggataa cctcgcctac    540
aaaacctttt gcgccgattg cggcggtaaa gaactactca ccgaaatcaa cttttccgcc    600
cataaggcgg agctggcgca gggcctggta ctgccggtag tgctgcgcgg caccgtgcgc    660
tggttgtccg ttacctgttg ggcgctgccg ggcgtcagcg aagaagcagg ccgctacttt    720
attgatagcg ccgtgccgcg cacgctggtg gtgatcaccg ataatactca gcagcagcaa    780
caacaggagc aggggcgtct tgatcgtctg aagcagcaga taaccagcgg taaattgctg    840
gcggcgatcc gcgaatcgct ggacgccgcg ctggtacaac tcaattgccc aattaatatg    900
ctggccgccg cacgccgctt aaatggcgac gagcatagca atctggcgct ggatgccgca    960
tggcgtgaag gcgaagaagc gatggcgcgg ttgcagcgct gccgcccgtc gctggaactg   1020
gaaagcccgg cagtctggcc gctccagccg ttccttgacg atctgcgtgc cctgtatcac   1080
acccgatata accagggcga aaacctgcaa attgagctgg aatcccccga cctggtgggc   1140
tttggccagc gaacacaact gcttgcctgc ctgagcctgt ggctcgacag aaccctggat   1200
attgccgcgg agctacgtga tttcacggta cagactcaac tttacgcccg cgaagagagc   1260
ggctggctgt cgttctattt aaacgacaat gtgccgctga ttcaggtgcg ctacaccccat   1320 tcacccgatg cactcaatgc gcccggtaaa ggcatggagc tgcggctgat ccagacgctg   1380
gtcgcccacc atcgaggcgc aatagaactg acctcacgcc ctcagggagg cacctgtctg   1440
atcctgcgtt tccattatt ttactcgctg acaggaggct cactatga                1488
```

<210> SEQ ID NO 164
<211> LENGTH: 1575
<212> TYPE: DNA
<213> ORGANISM: Enterobacter sp.
<220> FEATURE:
<223> OTHER INFORMATION: nifA

<400> SEQUENCE: 164

-continued

```
atgactcagc gaaccgagtc gggtacaacc gtctggcgct ttgacctctc ccaacagttt      60
acagccatgc agcgtatcag tgtggtgtta agccgcgcga cggagatcgg gcagacgcta     120
caggaagtgc tgtgcgtgct gcacaacgat gcctttatgc agcacgggat gatctgtctg     180
tacgacagta agcaagcgat cctttccatt gaagccttgc atgaggccga tcagcagtta     240
attcccggca gttcacagat tcgctaccgt ccgggcgaag ggctggtagg cacggtgctt     300
tcacagggac agtcgctggt actgccctgt gtctccgacg atcggcgttt tctcgatcgc     360
ctgggattgt atgattacag cttgccgttt atcgccgtgc cgctgatggg gccaaactcg     420
cagcctatcg gcgtgctggc cgcccagcct atggcgcgtt acgaggagcg gctgcccgcc     480
tgcacgcgtt ttcttgaaac cgtcgccaat ctggtggcgc aaaccgttcg cctgatgaca     540
ccgcccagcg tcgcgtctcc accccgtgct gctgccgcgc agattgccag ccagcgcggg     600
tgcgcgtctt cgcgagcgta tggctttgaa aacatggtcg gtaaaagcgc ggctatgcgt     660
cagacgctgg aaattattcg ccaggtatca cgctgggaca ccaccgtgct ggtgcgtggc     720
gaaagcggaa ccggtaaaga gttgatagcc aacgctatcc accacaattc accgcgcgcc     780
gccgcgccgt ttgtcaaatt caactgcgcg gcgctgcccg atacgctgct ggagagtgaa     840
ctcttcggtc atgaaaaagg cgcgtttacc ggcgcggtgc gccagcgcaa aggccgtttc     900
gaactggcgg atggcggtac gctgtttctt gatgagatcg gcgaaagtag cgcctcgttt     960
caggcgaaat tgctgcgtat cttgcaggaa ggcgaaatga aacgcgtcgg cggcgacgaa    1020
acgctgcggg tgaatgtacg gatcattgcc gccaccaacc gcaatctgga agaggaagtg    1080
cggctgggta atttttcgcga agatctctac tatcgcctta atgtgatgcc gatctccctg    1140
cccccgctcc gcgagcgtca ggaggacatc gtcgagctgg cgcattttct ggtgcgcaaa    1200
atcgcgcaaa accagaaccg cacgctgcgc atcagcgatg gcgcgatccg tttgttgatg    1260
agctatagct ggcctggaaa cgtgcgtgag ctggaaaact gccttgagcg atcggcggtg    1320
atgtcggaaa acgggctgat cgatcgcgac gtgattttgt ttcaccacag gaaaatctg    1380 ccaaaaacgc cacagaccag tgcgccgcgc gaagagagct ggctcgatca gaacctcgat    1440
gagcgacaaa gattgatcgc cgcgctggag aaagccggtt gggtacaggc aaaagccgcg    1500
cgcctgctgg gaatgacccc gcgccaggtg gcctatcgta ttcagacgat ggacattgcc    1560
atgccgagat tgtag                                                      1575
```

```
<210> SEQ ID NO 165
<211> LENGTH: 2856
<212> TYPE: DNA
<213> ORGANISM: Enterobacter sp.
<220> FEATURE:
<223> OTHER INFORMATION: glnE

<400> SEQUENCE: 165
```

```
atgccgcttt cttcgcagtt acagcagcag tggcagaccg tttgcgaacg tctgcctgag     60
tcattaccgg cgtcatcgtt aagcgagcag gcaaagagcg tgctcgtctt cagtgatttt    120
gtgcaggaaa gtatcaccgc caacccgaac tggctggcgg aacttgagaa cgcaccaccg    180
caggcagaag agtggcggca ctatgctggc tggctgcaaa ctgtactcga agacgttacg    240
gatgaggcca cgctgatgcg cgtcctgcgc cagttccgtc gtcgggtgat ggtgcgcatt    300
gcctgggctc aggcgctgga actggtgagc gaagagagta cgctgcagca gttaagcgag    360
ctggcgcaaa cgttgattgt cgccgcgcga gactggctct atgccgcctg ctgtaaagag    420
tggggcacgc cgtgcagcga ggaagggggt cctcagccgc tgttgattct ggggatggga    480
```

-continued

```
aagctgggcg gctgcgagct gaacttctcc tctgatatcg acctgatttt tgcctggccg      540
gagaacggct ccacgcgcgg aggccgccgc gagctggaca acgcgcagtt ctttacccgt      600
ctcggccagc gcctgattaa agcgctggat cagcccacgc aggacggttt tgtttaccgc      660
gtggacatgc gcctgcgtcc gtttggcgac agcgggccgc tggtgctgag ctttgcggcg      720
ctggaagatt attaccagga gcaaggtcgc gactgggagc gttacgcgat ggtcaaagcg      780
cggatcatgg gcgacagcga cgacgcttat gccaacgagc tgcgcgccat gctgcgtccg      840
ttcgtgttcc gtcgctatat cgacttcagc gtcatccagt ccctgcgaaa tatgaaaggg      900
atgattgccc gcgaggtgcg ccgccgtggg ctgaaagaca atatcaagct cggtgcgggc      960
ggcatccgcg aaatcgaatt tatcgtccag gtcttccagc ttattcgcgg cggacgcgag     1020
ccgtcgctgc agtcccgttc cttattaccg acgctgagcg ccattgcgca gctgcatctc     1080
ctgccggacg gcgacgcgca aaccctgcgc gaggcctatc ttttcctgcg tcgtctggaa     1140
aacctgctgc aaagcattaa tgacgaacag acccaaaccc tgccgggcga cgaccttaac     1200
cgggcgcgtc tggcctgggg aatgcgcgtg gaagactggt caacgctgac cgaacggctc     1260
gatgcccata tggcaggcgt gcgccgaatc tttaacgaac tgatcggtga tgacgaaagt     1320
gagtcgcagg acgatgcgct ctccgagcac tggcgcgagc tgtggcagga cgcgcttcag     1380
gaagatgaca ccacgccggt gctgacgcac ttaaccgacg acgcgcgcca tcgcgtggtg     1440
gcgctgatcg ctgatttccg tcttgagctg aacaaacgcg ccatcggccc gcgtggtcgc     1500
caggtgctgg atcacctgat gccgcacctg ctgagcgaag tctgctcgcg tgccgatgcg     1560
ccggtgccgc tgtcgcggat gatgcccctg ctgagcggga ttatcacccg tactacctac     1620
cttgaactcc tgagcgagtt ccctggcgcg cttaagcacc tgatttcact ctgcgccgcg     1680
tcgccgatgg tggccaacaa gctggcgcgt tacccgctgc tgctggatga gctgctcgat     1740
ccgaataccc tttatcaacc gacggcgacc gacgcctacc gggacgaact gcgtcagtat     1800
ctgctgcgcg tgccggaaga agacgaagag caacagctgg aggcgctgcg tcagtttaag     1860
caggcccaga tgctgcgcgt ggcggccgca gatattgccg gaacgctgcc ggtgatgaaa     1920
gtgagcgatc acttaacctg gcttgcggaa gcgattatcg acgcggtggt gcatcaggcc     1980
tgggtgcaga tggtggcgcg ctatggccag ccgaaacatc tggctgaccg tgatggtcgc     2040
ggcttcgcgg tggtgggtta cggtaagctc ggcggttggg agctgggcta tagctccgat     2100
ctggatttaa tcttcctcca cgactgcccg gttgatgtga tgaccgacgg cgagcgcgag     2160
attgacgggc gtcagttcta cctgcgcctg gcgcagcgca tcatgcacct gttcagcacc     2220
cgcacctcgt cgggcatttt gtatgaagtg gatgcccgtc tgcgcccgtc cggcgcggcg     2280
ggcatgctgg tcacctcgac ggagtccttc gctgattacc agaagaatga agcctggacg     2340
tgggagcatc aggcgctggt gcgcgcccgt gtggtgtatg gcgatccgct gctgaaaacg     2400
cagtttgacg tgattcgtaa ggaagtcatg accaccgtgc gcgatggcag cacgctgcaa     2460
acggaagtgc gcgaaatgcg cgagaaaatg cgcgcgcact taggcaataa acatcgcgat     2520
cgctttgata ttaaagccga tgagggcggt attaccgata ttgagtttat tacccagtat     2580
ctggtgttgc tgcacgcgca tgacaagccg aagctgacgc gctggtcgga taacgtgcgc     2640
attctggaac tgctggcgca aaacgacatt atggacgagc aggaggcgca ggccttaacc     2700
cgtgcctata caacgcttcg cgatgagctc catcatctgg cgttgcagga gcagccggga     2760
cacgtggcgc tggactgttt caccgctgaa cgcgctcagg taacggccag ctggcagaag     2820
```

```
tggctggtgg aaccgtgcgt aacaaatcaa gtgtga                              2856

<210> SEQ ID NO 166
<211> LENGTH: 1290
<212> TYPE: DNA
<213> ORGANISM: Enterobacter sp.
<220> FEATURE:
<223> OTHER INFORMATION: amtB

<400> SEQUENCE: 166
atgaagatag caacacttaa aacgggtctg ggttcgctgg cactgctgcc gggcctggcg        60
ctggctgctg cacctgcggt ggcagacaaa gccgataacg cctttatgat gatcagcacc       120
gcgctggtgc tgttcatgtc cattccgggc attgcgctgt tctatggcgg cctgatccgt       180
ggcaaaaacg ttctctccat gctgacgcag gttgccgtaa cgttcgcgct ggtctgcgta       240
ctgtgggtgg tttacggtta ctcgctggct ttcggcacgg caacgcgtt ctttggtaac        300 ttcgactggg tgatgctgaa aaatattgaa ctgaccgcgc tgatgggcag tttctaccag       360
tatattcacg ttgctttcca gggctcgttc gcctgcatta ccgtcgggct gattgtaggc       420
gcgcttgccg agcgtattcg tttctctgcg gtcctgatct tcgtggtggt ctggctgacg       480
ctctcctatg tgccgattgc gcacatggtc tggggtggcg gtctgctggc gacgcatggc       540
gcgctggact cgcgggcgg taccgttgtg cacattaacg ccgcggtagc gggtctggtt        600
ggcgcatacc tgattggcaa acgcgtgggc ttcggtaaag aagcgttcaa accgcacaac       660
ctgccgatgg tcttcaccgg taccgcgatc ctctactttg ctggtttggg tttcaacgcc       720
ggctcagcaa gtgccgcgaa cgaaatcgcc gcgctggcct tcgtgaatac cgttgtggcc       780
acggcaggtg caatcctctc ctgggtctttt ggcgagtggg ctgtgcgcgg taaaccttct      840
ctgctgggtg cctgttcggg ggcgattgct ggtctggtcg gtatcaccccc agcatgtggt      900 tatgtcggtg tgggtggcgc gctgctggtc ggcctggtgt caggtctggc gggtctgtgg       960 ggcgtgacg cgctgaaacg tattctgcgc gttgatgacc cttgcgatgt gtttggcgtg       1020
cacggcgtgt gcggcatcgt cggctgtatc atgaccggta tctttgcagc gaaatcgctg      1080
ggtggcgtgg ctacgcagaa aggcgtcacc atggcccatc aggtgctggt gcagctggaa      1140
agtattgctg tcaccgtggt gtggtctgcc gttgtcgctt tcattggcta caaactggcg      1200
gacatgacgg ttggtctgcg cgtgccggaa gagcaggaac gcgaaggtct ggacgtcaac      1260
agccacggcg agaatgcgta taacgcatga                                      1290

<210> SEQ ID NO 167
<211> LENGTH: 1299
<212> TYPE: DNA
<213> ORGANISM: Azospirillum lipoferum
<220> FEATURE:
<223> OTHER INFORMATION: 16S
<220> FEATURE:
<221> NAME/KEY: modified_base
<222> LOCATION: (294)..(294)
<223> OTHER INFORMATION: a, c, t, g, unknown or other
<220> FEATURE:
<221> NAME/KEY: modified_base
<222> LOCATION: (299)..(299)
<223> OTHER INFORMATION: a, c, t, g, unknown or other
<220> FEATURE:
<221> NAME/KEY: modified_base
<222> LOCATION: (302)..(302)
<223> OTHER INFORMATION: a, c, t, g, unknown or other
<220> FEATURE:
<221> NAME/KEY: modified_base
<222> LOCATION: (309)..(310)
<223> OTHER INFORMATION: a, c, t, g, unknown or other
```

```
<220> FEATURE:
<221> NAME/KEY: modified_base
<222> LOCATION: (332)..(332)
<223> OTHER INFORMATION: a, c, t, g, unknown or other
<220> FEATURE:
<221> NAME/KEY: modified_base
<222> LOCATION: (346)..(346)
<223> OTHER INFORMATION: a, c, t, g, unknown or other
<220> FEATURE:
<221> NAME/KEY: modified_base
<222> LOCATION: (351)..(351)
<223> OTHER INFORMATION: a, c, t, g, unknown or other
<220> FEATURE:
<221> NAME/KEY: modified_base
<222> LOCATION: (438)..(438)
<223> OTHER INFORMATION: a, c, t, g, unknown or other
<220> FEATURE:
<221> NAME/KEY: modified_base
<222> LOCATION: (445)..(445)
<223> OTHER INFORMATION: a, c, t, g, unknown or other
<220> FEATURE:
<221> NAME/KEY: modified_base
<222> LOCATION: (454)..(454)
<223> OTHER INFORMATION: a, c, t, g, unknown or other
<220> FEATURE:
<221> NAME/KEY: modified_base
<222> LOCATION: (469)..(469)
<223> OTHER INFORMATION: a, c, t, g, unknown or other
<220> FEATURE:
<221> NAME/KEY: modified_base
<222> LOCATION: (477)..(477)
<223> OTHER INFORMATION: a, c, t, g, unknown or other
<220> FEATURE:
<221> NAME/KEY: modified_base
<222> LOCATION: (492)..(492)
<223> OTHER INFORMATION: a, c, t, g, unknown or other
<220> FEATURE:
<221> NAME/KEY: modified_base
<222> LOCATION: (504)..(504)
<223> OTHER INFORMATION: a, c, t, g, unknown or other
<220> FEATURE:
<221> NAME/KEY: modified_base
<222> LOCATION: (555)..(555)
<223> OTHER INFORMATION: a, c, t, g, unknown or other
<220> FEATURE:
<221> NAME/KEY: modified_base
<222> LOCATION: (775)..(775)
<223> OTHER INFORMATION: a, c, t, g, unknown or other

<400> SEQUENCE: 167
gccgagagag gggcccgcgt cggattaggt agttggtgag gtaatggctc accaagcctt      60
cgatccgtag ctggtctgag aggatgatca gccacactgg gactgagaca cggcccagac     120
tcctacggga ggcagcagtg gggaatattg dacaatgggc gcaagcctga tccagcaatg     180
ccgcgtgagt gatgaaggcc ttagggttgt aaagctcttt cgcacgcgac gatgatgacg     240
gtagcgtgag aagaagcccc ggctaacttc gtgccagcag ccgcggtaat acgnagggng     300
cnagcgttnn tcggaattac tgggcgtaaa gngcgcgtag gcggcntgtt nagtcagaag     360
tgaaagcccc gggctcaacc tgggaatagc ttttgatact ggcaggcttg agttccggag     420
aggatggtgg aattcccngt gtagnggtga aatncgtaga tattgggang aacaccngtg     480
gcgaaggcgg cnatctggac gganactgac gctgaggcgc gaaagcgtgg ggagcaaaca     540
ggattagata ccctngtagt ccacgccgta aacgatgaat gctagacgtc ggggtgcatg     600
cacttcggtg tcgccgctaa cgcattaagc attccgcctg gggagtacgg ccgcaaggtt     660
aaaactcaaa ggaattgacg ggggcccgca caagcggtgg agcatgtggt ttaattcgaa     720
gcaacgcgca gaaccttacc aaccccttgac atgtccactt tgggctcgag agatngggtc     780
cttcagttcg gctgggtgga acacaggtgc tgcatggctg tcgtcagctc gtgtcgtgag     840
```

-continued

```
atgttgggtt aagtcccgca acgagcgcaa cccctaccgt cagttgccat cattcagttg      900
ggcactctgg tggaaccgcc ggtgacaagc cggaggaagg cggggatgac gtcaagtcct      960
catggccctt atgggttggg ctacacacgt gctacaatgg cggtgacagt gggaagcgaa     1020
gtcgcgagat ggagcaaatc cccaaaagcc gtctcagttc ggatcgcact ctgcaactcg     1080
agtgcgtgaa gttggaatcg ctagtaatcg cggatcagca cgccgcggtg aatacgttcc     1140
cgggccttgt acacaccgcc cgtcacacca tgggagttgg ttttacccga aggtggtgcg     1200
ctaaccgcaa ggaggcagcc aaccacggta aggtcagcga ctggggtgaa gtcgtaacaa     1260
ggtagccgta ggggaacctg cggctggatc acctccttt                           1299
```

```
<210> SEQ ID NO 168
<211> LENGTH: 897
<212> TYPE: DNA
<213> ORGANISM: Azospirillum lipoferum
<220> FEATURE:
<223> OTHER INFORMATION: nifH

<400> SEQUENCE: 168
atggccaaag cgcctctgcg tcagatcgcc ttttacggca agggcggtat cggcaagtcc       60
accacctctc agaacacgct ggccgcgctg gtcgagctgg atcagaggat cctgatcgtc      120
ggctgcgacc cgaaggccga ctcgacccgc ctgatcctgc acgcaaaggc ccaggacacc      180
gtcctgcatc tggccgccga ggccggctcg gtcgaggatc tggagctcga ggacgttctc      240
aagatcggct acaagaacat caagtgcgtc gagtccggcg gtccggagcc gggggtcggc      300
tgcgccggcc gcgcgtcat cacctcgatc aacttcctgg aagagaacgg cgcctacgac      360
gacgtggact atgtgtccta cgacgtgctg ggcgacgtgg tctgcggcgg cttcgccatg      420
ccgatccgcg agaacaaggc ccaggaaatc tacatcgtca tgtccggcga gatgatggcg      480
ctgtacgccg ccaacaacat cgccaagggc atcctgaagt acgcgcacag cggcggcgtc      540
cgtctcggcg gcctgatctg caacgagcgc cagaccgaca aggaatggga tctgccgac       600 gcgctggcca agcgcctggg ctccaagctg atccacttcg tgccgcgcga caacatcgtc      660
cagcacgccg agctgcgccg catgacggtc atcgagtacg ccccggacag caagcaggcc      720
ggcgaatacc gcgcgctcgc caacaagatc catgcgaact ccggccaggg ttgcatcccg      780
accccgatca ccatggaaga gctggaagag atgctgatgg acttcggcat catgaagacc      840
gaggagcagc agctcgccga gctcgccgcc aaggaagcgg cgaaggccgg cgcctga        897
```

```
<210> SEQ ID NO 169
<211> LENGTH: 1440
<212> TYPE: DNA
<213> ORGANISM: Azospirillum lipoferum
<220> FEATURE:
<223> OTHER INFORMATION: nifD1

<400> SEQUENCE: 169
atgagcctgt ccgagaacac cacggtcgac gtcaagaacc tcgtcaacga agtcctcgaa       60
gcctatcccg aaaaatcccg caagcgccgc gccaagcacc tgaacgtgct ggaggccgag      120
gccaaggact cggcgtcaa gtcgaacgtc aagtccatcc ccggcgtcat gaccatccgc      180
ggctgcgcct atgccggctc caagggcgtg gtgtggggtc cgatcaagga catgatccac      240
atctcccacg gtccggtcgg ctgcggctac tactcctggt ccggccgcgc caactactac      300 atcgcgaca ccggtgtgga cagctggggc acgatgcact tcacctccga cttccaggag      360
aaggacatcg tcttcggcgg cgacaagaag ctgcacaagg tcatcgagga aatcaacgag      420
```

-continued

```
ctgttcccgc tggtgaacgg catctcgatc cagtcggaat gcccgatcgg cctgatcggc    480
gacgacatcg aggctgtcgc ccgcgccaag tcggcggaaa tcggcaagcc ggtcatcccc    540
gtgcgctgcg aaggcttccg cggcgtgtcc cagtcgctgg gccaccacat cgccaacgac    600
gccatccgag actgggtgtt cgagaagacg gaacccaagg ccggcttcgt ctccacccccc   660 tatgacgtca ccatcatcgg cgactacaac atcggcggcg acgcctggtc gtcccgcatc    720
ctgctggagg agatcggcct gcgcgtgatc gcccagtggt cgggcgacgg cacgctcgcc    780
gaactggaga acacgccgaa ggccaaggtc aacctgatcc actgctaccg ctcgatgaac    840
tacatcgcgc gccacatgga agagaagttc aacattcctt ggatggaata caacttcttc    900
ggcccgagcc agatcgccga atccctgcgc aagatcgccg ctctcttcga cgacaagatc    960
aaggagaacg ccgagaaggt catcgcccgc taccagccga tggtcgatgc ggtcatcgcc   1020
aagtacaagc cgcggctcga aggcaagaag gtcatgatct acgtcggcgg cctgcgtccc   1080
cgccacgtcg tcgatgccta ccatgacctc ggcatggaga tcaccggcac cggctacgag   1140
ttcgcccaca cgacgacta tcagcgcacg cagcactacg tgaaggaagg cacgctgatc    1200
tacgacgacg tcaccgcgtt cgaactggag aagttcgtcg aggcgatgcg tcccgacctc   1260
gtcgcgtcgg gcatcaagga aaagtacgtg ttccagaaga tgggcctgcc gttccgccag   1320
atgcacagct gggactactc cggcccgtac cacggctatg acggcttcgc gatcttcgcc   1380
cgcgacatgg acctggccat caacaacccc gtctggggcg tgatgaaggc cccgttctga   1440
```

```
<210> SEQ ID NO 170
<211> LENGTH: 1419
<212> TYPE: DNA
<213> ORGANISM: Azospirillum lipoferum
<220> FEATURE:
<223> OTHER INFORMATION: nifD2

<400> SEQUENCE: 170
```

```
atgctccagg acaagatcca ggatgtcttc aacgaaccgg gctgcgcgac caaccaagcc     60
aaatcggcca aggagaagaa gaagggctgc accaagtcgc tgaaaccggg ggcggcagcc    120
ggcggctgcg cctatgacgg ggcgatgatc gtgctccagc cgatcgccga cgccgcccat    180
ctggtccatg gccccatcgc ctgcctcgga aacagttggg acaaccgcgg ctccaaatcc    240
tccggctcgc agctctaccg caccggcttc accaccgatc tgtcggaact ggacgtcatc    300
ggcggcggcg agaagaagct ctaccgcgcc atcaaggaga tcgttcagca atacgacccg    360
ccggccgtct tcgtctatca gacctgcgtg cccgccatga ccggcgacga catcgccgcg    420
gtctgcaagt cgccacgca gaagctgggc aagccggtga tcccggtgga ctcgccgggc    480
ttcgtcgggt cgaagaatct cggcaacaag ctggccggcg aagccctgct ggagcatgtc    540
atcggcacgg tcgaaccgga ctacaccacc ccgaccgacg tctgcatcat cggcgaatac    600
aaccttgccg gcgagctgtg gctggtcaag ccgctgctgg acgagatcgg catccgcctc    660
ctgtcctgca tttccggcga cggccgctac cgggaggtgg cgcaggccca ccgcgcccgc    720
gtcaccatga tggtgtgcag ccaggcgctg gtgaatgtcg ggcgcaagat ggaggagcgc    780
tacggcatcc cctatttcga ggggtccttc tacggcgtgt ccgacatgtc ggacaccctg    840
cgcaccatga cccgcatgct ggtggagcgc ggcgccgaca agggcctgat cgaccgggcg    900
gagggcgtga tcgcgcggga ggaaagccgg gtctggcgcc ggctggaacc ctacaagccg    960
cgcttcgacg gcaagcgcgt ccttctcttc accggcggcg tcaagagctg gtcgatggtc   1020
```

-continued

```
agcgcgctgg agggtgcggg gctgaccatc ctcggcacct ccaccaagaa atcgaccagg      1080
gaggacaagg agcgcatcaa gaagatgaag ggcgaagagt tccaccagtg ggacgatttg      1140
aagccgcgcg acatctacag gatgctggcc gacgatcagg ccgacatcat gatgtccggc      1200
ggccgctcgc agttcatctc gctgaaggcc aaggttccct ggctcgacat caaccaggag      1260
cgccaccacg cctatgccgg ctatgacggc atcgtcaatc tctgcgagga gatcgacaaa      1320
acgctgtcga atccgatctg gcgtcaggtg cgtcagccgg caccgtggga gtccggcgcg      1380
tcctccaccc ttctggcttc ctcgatggcg gcggagtga                             1419
```

```
<210> SEQ ID NO 171
<211> LENGTH: 1383
<212> TYPE: DNA
<213> ORGANISM: Azospirillum lipoferum
<220> FEATURE:
<223> OTHER INFORMATION: nifK

<400> SEQUENCE: 171
```

```
atgtcccaca tccagcgctt cccctccgcc gccaaggccg cctccaccaa cccgctgaag       60
atgagccagc cgctgggtgc ggctctggcc tatctcggcg tcgaccgctg cctgccgctg      120
ttccatggct cgcagggctg caccgccttc gggctggtcc tgctggtgcg ccatttccgc      180
gaggcgatcc cgctccagac cacggcgatg gatcaggtcg ccaccatcct cggcggctac      240
gacaatctgg agcaggcgat ccgcaccatc gtcgagcgca accagcccgc catgatcggc      300
gtcgccacca ccggcgtcac cgagaccaag ggcgaggata tggccggaca gtacacgctg      360 ttcgccagc gcaaccccga cttggccgac acggccctgg tcttcgccaa cacccccgac      420
ttcgccggcg gcttcgagga cggcttcgcc gccgcggtca ccgcgatggt cgagcggttg      480
gtcgaaccgt cgccggtgcg catcccgacc caggtcaacg tgctggccgg ctgccatctg      540
tcccccggcg acgtggagga actgcgcgac atcatcgaag gcttcggcct gtcgccgatc      600
ttcctgcccg acctgtcgct gtcgatggcg gccgccagc cggccgactt caccgccacc      660
tcgctgggcg gcgtgaccgt cgatcagatc cgcgccatgg gcgcttcggc cctcaccatc      720
gtggtcggtg agcatatgcg ggtggccggt aacgcgctgg agctgaagac cgacgtgccc      780
agccatttct tcaaccgcct gaccgggctg gaggcgacgg acaagctggt ccggctgctg      840
atggagttgt cgggcaagcc ggcgcccgcc cggctgcggc gccagcgcga aagcctggtc      900
gatgccatgc tcgacgggca tttcttctac agccgcaagc gcatcgccgt cgcgctggag      960
cccgacctgc tctatgccgt caccggcttc ctcgccgaca tggggggccga ggtgatcgcc     1020 gcggtgtccc cgacgcagag cccggtgctg gagcggttga aggccgccac catcatggtc     1080
ggcgatcatt ccgacgtgga gacgctggcc cgcgacgccg acctgatcgt ctccaactcg     1140
cacgggcggc agggagccgc gcggatcggc gtggctctgc accgcatggg cctgccgctg     1200
ttcgaccggc tggggggccgg cctgcgcgtc caggtcggct accgcggcac gcgggaactg     1260
ctgtgcgaca tcggcaacct gttcctcgcc cgcgagatgg accacgagca cgggcacgag     1320
agccacgacc acggggaatc ccacggctgc ggaggcggat catgcggatg caacgccgtc     1380
tga                                                                    1383
```

```
<210> SEQ ID NO 172
<211> LENGTH: 1560
<212> TYPE: DNA
<213> ORGANISM: Azospirillum lipoferum
<220> FEATURE:
<223> OTHER INFORMATION: nifK1
```

<400> SEQUENCE: 172

```
atgaccgaca agctttcgca gagcgccgac aaggtcctcg accactacac cctcttccgg     60
cagcccgaat acgcggcgat gttcgagaag aagaagaccg agttcgagta cggccattcg    120
gacgaggaag tcgcccgcgt gtccgaatgg accaagtccg aggactacaa ggcgaagaac    180
ttcgcccgtg aagcggtcgt catcaacccg accaaggcct gccagccgat cggcgcaatg    240
ttcgccgccc agggcttcga aggcaccctg cccttcgtcc acggctccca gggctgcgtc    300
gcctattacc gcacccacct gacccgtcac ttcaaggagc cgaacagcgc ggtctcctcg    360
tcgatgacgg aggacgcggc ggtgttcggc ggcctgaaca acatgatcga cggcctggcg    420
aacgcctatg cgctctacaa gccgaagatg atcgcggtga tgaccacctg catggccgaa    480
gtcatcggcg acgatttgca gggcttcatc gccaatgcga agaccaagga cagcgtcccg    540
gccgacttcc cggtcccccta cgcccacacc ccggccttcg tcggcagcca tcgtcggc     600 tacgacaaca tgatcaaggg gatcctgacc aacttctggg gtacgtcgga gaatttcgac    660
acacccaaga ccgagcagat caacctgatc ccgggcttcg acggcttcgc cgtcggcaac    720
aaccgcgaac tgaagcgcat cgccggcgaa ttcggcgtga agctgcaaat cctgtccgac    780
gtgtccgaca atttcgacac gccgatggat ggcgagtacc gcatgtatga cggcggcacc    840
accatcgagg agaccaagga ggccctgcac gccaaggcca ccatctccat gcaggagtac    900
aacacgaccc agaccctgca attctgcaag gagaagggtc aggaagtcgc caagttcaac    960
tacccgatgg gcgtcaccgg caccgacgag ctgctgctga agctcgccga actgtcgggc   1020
aagccggtcc cggccagcct gaagctggag cgcggccgtc tggtcgacgc catcgccgac   1080
agccacaccc acatgcacgg caagcgcttc gccgtctatg cgacccgga cttctgcctg    1140 ggcatgtcca agttcctgct ggagctgggt gcggagccgg tgcacatcct gtcgacgtcg   1200
ggctccaaga gtgggagaa gcaggtccag aaggtgctgg acggctcgcc cttcggcgcc   1260
tcgggcaagg cccatggcgg caaggatctg tggcacctgc gttcgctgat cttcaccgac   1320
aaggtggact acatcatcgg caacagctac ggcaagtatc tggagcgcga caccaaggtt   1380
ccgctgatcc gcctgaccta cccgatcttc gaccgccacc accaccaccg ctacccgacc   1440
tggggctacc agggcgcgct gaacgtgctg gtacggatcc tggaccggat cttcgaggac   1500
atcgacgcca acaccaacat cgtcggccag accgactact cgttcgacct gatccgctga   1560
```

```
<210> SEQ ID NO 173
<211> LENGTH: 1530
<212> TYPE: DNA
<213> ORGANISM: Azospirillum lipoferum
<220> FEATURE:
<223> OTHER INFORMATION: nifA
```

<400> SEQUENCE: 173

```
atgttgacct ctgatattgt tggcaaattg cgctgcatcg cagcagaccc caaagcgggc     60
atcgcaaggg gcctcgacac cgggacgacg aagatcggtc ccgtttggga gggtgacgtg    120
ggcgacaccg tggatttcga agcgctgcgc cagcgggcgg tccactccct gttcgaacat    180
ctggaatcca tgtgcgtcgg cgccgtcgcc gtcgaccaca ccggccgcat cgcctggatg    240
gacgagaagt acaaggctct gctgggcgtt cccgacgacc cgcgcggccg gcaggtggag    300
gacgtcatcc ccaacagcca gctgcgccgg gtgatcgaca cgggccagcc gcagccgctg    360
gacatcatgg agttcgacga ccggtccttc gtggtgacgc ggatgccgct gttcggcacc    420
```

-continued

```
gacggttcga tcatcggcgc catcggcttc gtgctgttcg accgcgccga atatctccgc      480
ccgctggtcc gcaaatacga gaagatgcag gaggagctgg cccgcaccca gcaggagctg      540
gcgcatgagc gccgcgccaa atactccttc tcgcagttcc tgggcgccag cgaatcgatc      600
cgcgagatca agcggctggg gcgccgcgcc gcccagatgg attcgaccgt cctgctgctg      660
ggcgaaaccg ggaccggcaa ggagctgctg gcccaggcca tccattccgc cagcccgcgg      720
gcgtccaagc ccttcgtcgg cgtcaatgtc gccgccattc cggaaaccct gctggaggcg      780
gagttcttcg gcgtcgcccc cggcgccttc accggcgccg accgccgcca ccgcgacggc      840
aagttccagc tcgccaacgg cggcaccctg ttcctcgacg agatcggcga catgccgctg      900
ccggtgcagg ccaagcttct gcgcgtgctg caggagcggg agatcgagcc gctcggctcc      960
aacaaggtgg tgcgggtcga tgtccgcatc atcgccgcca ccagccgtga cctgcacgcc     1020
ctggtgcgtg agaagcagtt ccgcgccgac ctctattacc ggctgaatgt ggtgccgatc     1080
accctgccgc cgctgcgcga ccggccggag gacatcgaga gcatcgccga ccgcatcctg     1140
gaacagctgg cgatccagca gggcacgccg ccgcgcgagc tgctggaatc ggcggtgcag     1200
gtgctgcgcg actatgactg gcccggcaat gtgcgcgagc tttacaacac gctggaacgg     1260
gtggtggcgc tgaccgatgc gccgatcctg accgcgccgc acatccgcag cgtgctgccc     1320
ggccagcatc cggccggcgc gtcggccctg ccgctggcgg ccggcgcgcg gccgttgcag     1380
gaggtgctgc acgccgccga gcgccacgcc atcgccgcgg cgcttgagga ggcgaacggc     1440
gtcaaggcgc gggcggcgaa gctgctgggc atttcgcgcg cgtcgctgta cgaacgcatg     1500
gtgacgctgg ggttggggc gacgcagtag                                       1530
```

```
<210> SEQ ID NO 174
<211> LENGTH: 3030
<212> TYPE: DNA
<213> ORGANISM: Azospirillum lipoferum
<220> FEATURE:
<223> OTHER INFORMATION: glnE

<400> SEQUENCE: 174
```

```
atgccgagtc ccatcgcgtt ctcaagcccc ttgccgaagc ctttcgacag cgcgcaggcg       60
gcgctgggga tggagcgctg gcgccagcag gccgccgcgg cggagccgga gaccccgcgcc      120 tgggcggaag ccttcgccga ttcggagacc ggccggcgc tgatcggggc ggtgtgcggc       180
aacagcccgt atctcggcca cagcctgacg cgggagttgc ccttcgtcgc ccgtacagtg      240
caggacggct cgacgacac cttcgccgcg ctgatcgccg ctctccatgc cgagcatggc       300
gaggagaaat cgatggaccg gctgatggcc ggcctgcggg tggcgaagcg gcgggcggcg      360
ctgctgatcg cgctggccga catcgccggc gcgtggccgc tgttccgcgt caccggcgcc      420
ctgtcggagc tggcggagac gggggtgcag ctggccgcga atttcctgct gcgccgcgcc      480
agggaggcgg ggacgctgac gctgccggat ccgcagcgac cgtgggtcgg ttcgggcctg      540
atcgttttgg gcatgggtaa gcttggcggg cgcgaactca actattccag cgacatcgac      600
ctgatcgtcc tgtatgacga cgctgttgtg cagacgcccc agccggacaa cctcgcgcga      660
accttcatca ggctcgcacg cgatcttgtc cgcattatgg atgaacggac caaggacggc      720
tacgtcttcc gcaccgacct tcggcttagg cccgatcccg gcgccacgcc gctggcggtt      780
tccgtctccg cagccgaaat ttattacggc agcgtcggtc agaactggga acgcgcggcg      840
atgatcaagg cccgtcccat cgccggcgat ctggaggcgg gcgcctcctt gtccgcttc       900 ctggagcccct tcgtctggcg ccgcaacctg gatttcgccg ccatccagga catccattcg      960
```

-continued

```
atcaaacgcc agatcaacgc ccacaagggc caccgcgagg tgacggtcaa cggccacgac     1020
atcaaggtcg gccgcggcgg catccgcgag atcgagttct tcgcccagac ccagcagctg     1080
atcttcggcg ggcgcgaccc gcgcgtgcga atcgctccga ccctgatggc gaacgaggcg     1140
ctgcgcgacg tcggccgcgt gccgccgcag acggtggaag agcttgccgg ggcctatcat     1200
ttcctgcgcc gtgtcgaaca tcgcatccag atgatcgacg accagcagac ccatcgtatt     1260
cccgccgacg atgccggggt ggcgcatttg gccaccttcc tcggctatga cgaccccgcc     1320
gccttccggg cggaactgct ggcgacgctg gggcaggtgg aggaccgcta tgccgagctg     1380
ttcgaggagg cgccgtcgct ttccggcccc ggcaatctgg tcttcaccgg caccgacccc     1440
gatccgggca cgatggagac gctgaagggc atgggcttcg ccgatccggc ccgcgtcatc     1500
agcgtggtgt cggcctggca tcgcggccgc taccgcgcca cccggtcggg ccgggcgcgg     1560
gagctgctga cggagctgac gccggccctg ctgagtgcgc tgaccaagac cccggccccc     1620
gattcggcgc tgatgaactt cgacgatttc ctcggcaagc tgccggccgg cgtcggtctg     1680
ttctcgctgt tcgtcgccaa tccctggctc ctggagctgg tggcggagat catgggcatc     1740
gcgccgcaga tggcgcagac gctgtcgcgc aacccgtcgc tgctcgacgc cgtgctgtcg     1800
ccggacttct tcgacccgct gccgggcaag gaggacgggc tggccgacga ccacgcccgc     1860
gtgatggcgc cggcccgcga tttcgaggat gcgctgaccc tgtcgcggcg ctggaccaac     1920
gaccagcgct tccgcgccgg ggtgcatatc ctgcgcggca tcaccgatgg cgaccgctgc     1980
ggcgccttcc tggccgatct ggccgacatc gtcgtccccg accttgcccg ccgggtggag     2040
gaggagttcg cccagcgcca cggccatatt cccgcggcg cctgggtggt ggtggcgatg     2100
ggcaagctcg gcagccggca gctgaccatc acgtccgaca tcgacctgat cgtcatctac     2160
gatgtggcgc cgggccaagg gggcggggc ggtccccgct tgtcggatgg tgccaagccg     2220
ctgtcgccca acgagtatta catcaagctg actcagcgtc tgaccaacgc cattaccgcg     2280
ccgatgggcg acggccggct ctacgaggtc gacatgcggc tgcgcccgtc gggcaacgcc     2340
gggccgctcg ccacctcgct ggacgctttc ctgaaatatc aggcgaccga tgcctggacc     2400
tgggagcata tggccctgac ccgcgcccgg gtgatcggcg gtgatgcgga gctggccggg     2460
cgggtgtcgg cagcgatccg ctcggtgctg acggcgccgc gcgatgccga ccggctgctg     2520
tgggacgtgg ccgacatgcg gcggcggatc gagaaggagt tcgggacgac caatgtctgg     2580
aacgtcaaat acgcccgcgg cggcctgatc gacatcgagt tcatcgccca gtacctgcaa     2640
ctgcgccatg tcacgagcg gccggacatc ctgcacatcg gcaccgccaa ggcgctgggc     2700
tgcgccgccc ggacgggcgc gctggcgccg gaggtggcgg aggatctgga gacgacgctg     2760
cggctgtggc ggcgggtgca gggctttctg cggttgacca ccgccggggt gctcgatccc     2820
aatcaggtgt cgcccagcct gctggccggg ctggtccgcg ccgcctttcc tgctgacttt     2880
cagggcgagc gtgagcctgg cactgttgac ttccccgaac tggaccacaa aatccgtgcc     2940
gtcgccgccc gcgcccatgg tcatttcaag accctggtcg aggaaccggc gggccgtctg     3000
gccccacccg ccaccacgcc tccagcctga                                     3030
```

<210> SEQ ID NO 175
<211> LENGTH: 1440
<212> TYPE: DNA
<213> ORGANISM: Azospirillum lipoferum
<220> FEATURE:
<223> OTHER INFORMATION: amtB1

-continued

<400> SEQUENCE: 175

```
atgaaccgtc tgttccttat ggccgcaccg atgatggcgg ttgctctggg cgcggtcggc      60
atgccggccg cagcccttgc ccaggatccg gcggctgccg ccgctgccgc ggctgcggct     120
gcggctgccg ccgctgctgc cgcaccggcg gctccggcgc tgaatggcgg cgacaccgcc     180
tggatgctca tctccaccgc gctggtgctg atgatgacca tccccggcct ggcgctgttc     240
tacggcggca tggtccgcaa gatgaacgtg ctgtcgacgg tgatgcagag cttcgccatc     300
acctgcctga tcagcgtcct gtggtacgtc atcggctaca gcctggcctt caccggcacc     360
ggtgcctatg tcggcggtct cgaccggctg ttcctcaacg ggctcgactt cacgaaggcc     420
ttcgtgctgg gcgaggcgac cgggtcgggc gtcccgacga ccatccccga gccggtcttc     480
atgatgttcc agatgacctt tgcgatcatc accccggccc tgatcaccgg cgccttcgcc     540
gaccgcatga agttctcctc cctgctggtc ttcaccgcgc tgtggtcgat cgtggtctat     600
gcgccgatcg cccactgggt ctggtacccg tcgggcttcc tgttcggcct gggcgtgctg     660
gacttcgccg gcggcacggt cgtgcacatc aacgccggcg tcgccggcct ggtcgccgcg     720
ctggtgatcg gcaagcgcaa gggctacccg aaggaagcct tcatgccgca caacctggtg     780
ctgtcgctga tcggcgcctc gctgctgtgg gtcggctggt tcggcttcaa cgccggttcg     840
gccctgaccg ccggtccgcg tgccggcatg gcgctggccg ccacgcacat cgccaccgcc     900
ggtgccgcca tgggctggct gttcgcggag tggatcgtca aggggcaagcc gtcgatcctc     960 ggcatcatct ccggcgccgt cgccggcctg gtcgcggtga ccccggccgc cggcttcgtc    1020
gacccgacgg gcgccatcgt catcggcatc gtcgccggcc tggtctgctt ctggtcggcc    1080
accagcctca agcacatgct gggctatgac gacagcctgg acgccttcgg cgtgcacggc    1140
gtcggcggcc tgatcggcgc catcctgacc ggcgtcttcg ccaagatgtc ggtgtccaac    1200
agcgaaggcg gcttcgcctc cgtcctgcag gccgacccga aggccacgct gggcctgctg    1260
gaaggcaacg ccgccgccgt ctggatccag gtccagggcg tcctctacac catggtctgg    1320
tgcgccatcg ccaccttcgt cctgctgaag atcgtcgatg tggtcatggg cctgcgcgtc    1380
gaagaggatg tggagcgcga cggtctcgac ctcgccctgc atggcgagag catccactaa    1440
```

```
<210> SEQ ID NO 176
<211> LENGTH: 1227
<212> TYPE: DNA
<213> ORGANISM: Azospirillum lipoferum
<220> FEATURE:
<223> OTHER INFORMATION: amtB2
```

<400> SEQUENCE: 176

```
atggatgcgg caaagacggg tggcgacgtc cttttcgtgc tgatgggcgc ggtgatggtg      60
ctggcgatgc attgcggctt cgccctgctg gaggtcggga cggtccggcg caagaatcag     120
gtcaacgcgc tggtgaagat cctgtcggac ttcgccatgt cgaccatcgc ctattttttc     180
gtcggttatg ccgtggccta cggcatcgac ttcttcgccg acgcccacac gctggtcggc     240
aagggaagcg gcgggttcgc ggcctatggc tacgatctgg tgaagttctt cttcctggcg     300
accttcgccg ccgcggtgcc ggccatcgtc tcgggcggca tcgccgagcg tgctaggttc     360
tggccgcagg ccgccgccac gctggcgctg atcgcgctgt tctatccatt gctggaaggc     420
acggtctggg gcacccgctt cggcctgcaa agctggatgg ccgcgacctt cggccagcct     480
ttccacgact cgccggatc tgtggtggtg catgccttcg cgggctgggt ggcgctgggt     540
gccgtgctga acctcggcaa ccgccgcggc cgctaccgtc cgaacggctc gctgatcgcc     600
```

-continued

___ attccgccgt cgaacatccc cttcctggcg ctgggcgcct gggtgctgtg cgtggggtgg        660
ttcggcttca acgtgatgag cgcccaggtg ctggatggcg tgacgggtct ggtggcgctg        720
aactcgctga tggcgatggt cggcggcatc gtcacctcgc tggtgatcag ccgcaccgat        780
cccggcttcg tccacaacgg cgcgctggcc ggtctggtgg cggtctgcgc cgggtccgac        840
gtgatgcacc cgctgggcgc gctggtcacc ggcggcatcg ccgggctgct gttcgtctgg        900
gccttcaaca aatgccagat cgactggaag atcgacgacg tgctgggcgt ctggccgctg        960
cacggtctgt gcggcctgac cggcggcctg ctggccggcg tcttcgggca ggaggcactg       1020
ggcggccttg cgcgcgtgtc gatcctcagc cagatcgtcg gcacggcaag cggcgccagc       1080
ttcggattcg tctcgggtct ggcggtctac ggcctgctgc gcgtcaccgt cggcatccgc       1140
ctcgatcccg agcaggagta caagggcgcc gacttgtcgt tgcaccatat caccgcgtac       1200
ccggaagagg acgcgccgac cctgtaa       1227

<210> SEQ ID NO 177
<211> LENGTH: 613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC

<400> SEQUENCE: 177
atgaccctga atatgatgat ggattcttgg ttctctggag cgctttatcg gcatcctgac         60
tgaagaattt gcaggcttct tcccaacctg gcttgcaccc gtgcaggtag ttgtgatgaa        120
catcactgat tcgcaggctg aatacgttaa cgaattgacc cgtaaactgc aaaatgcggg        180
cattcgtgta aaagcagact tgagaaacga gaagattggc tttaaaatcc gcgagcacac        240
tttacgtcgt gtcccttata tgctggtttg tggtgacaaa gaggtcgaag ccggcaaagt        300
tgctgtgcgt acccgtcgcg gtaaagacct gggtagcctg gacgtaaatg atgttatcga        360
gaagctgcaa caagagattc gcagccgcag tcttcaacaa ctggaggaat aaggtattaa        420
aggcggaaaa cgagttcaaa cggcgcgtcc caatcgtatt aatggcgaga ttcgcgccac        480
ggaagttcgc ttaacaggtc tggaaggcga gcagcttggt attgcgatag aactcacttc        540
acgccccgaa gggggaagct gcctgaccct acgattcccg ctatttcatt cactgaccgg        600
aggttcaaaa tga       613

<210> SEQ ID NO 178
<211> LENGTH: 1613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC with 500bp flank

<400> SEQUENCE: 178
accggataag agagaaaagt gtcgacgtcg gtccggttga tattgaccgg cgcatccgcc         60
agctcgccca gttttttggtg gatctgtttg gcgattttgc gggtcttgcc ggtgtcggtg       120
ccgaaaaaaa taccaatatt tgccataaca cacgctcctg ttgaaaaaga gatcccgcgg        180
ggaaaatgcg gtgaacatgt cagctattgc gaagagtgtg ccagtttttgc tcacgggcaa       240

```
aagctgcacc agaatgggta ttaatgcacc agcctggcgc ttttttttcgc ggcacgtccc      300 ctcgctaatg cccgtctggc gcggctttga cgctgataag gcgctgaata ccgatctgga      360
tcaaggtttt gtcgggttat cgtccaaaag gtgcactctt tgcatggtta taagtgcctg      420
acatggtgtc cggcgaacg tcgccaggtg gcacaaattg tcagaactac gacacgacta       480
accgaccgca ggagtgtgcg atgaccctga atatgatgat ggattcttgg ttctctggag      540
cgctttatcg gcatcctgac tgaagaattt gcaggcttct tcccaacctg gcttgcaccc      600
gtgcaggtag ttgtgatgaa catcactgat tcgcaggctg aatacgttaa cgaattgacc      660
cgtaaactgc aaaatgcggg cattcgtgta aaagcagact tgagaaacga gaagattggc      720
tttaaaatcc gcgagcacac tttacgtcgt gtcccttata tgctggtttg tggtgacaaa      780
gaggtcgaag ccggcaaagt tgctgtgcgt acccgtcgcg gtaaagacct gggtagcctg      840
gacgtaaatg atgttatcga gaagctgcaa caagagattc gcagccgcag tcttcaacaa      900
ctggaggaat aaggtattaa aggcggaaaa cgagttcaaa cggcgcgtcc caatcgtatt      960
aatggcgaga ttcgcgccac ggaagttcgc ttaacaggtc tggaaggcga gcagcttggt      1020
attgcgatag aactcacttc acgccccgaa gggggaagct gcctgaccct acgattcccg      1080
ctatttcatt cactgaccgg aggttcaaaa tgacccagcg aaccgagtcg ggtaataccg      1140
tctggcgctt cgatttatcc cagcagttca ccgcgatgca gcggataagc gtggttctca      1200
gccgggcgac cgaggttgaa cagacactcc agcaggtgct gtgcgtattg cacaatgacg      1260
cctttttgca gcacggcatg atctgtctgt acgacagcca gcaggcgatt ttgactattg      1320
aagcgttgca ggaagccgat cagcagttga tccccggcag ctcgcaaatt cgctaccgtc      1380
cgggtgaagg gctggtcggg acggtgcttt cgcaggggca atcgttagtg ctggcgcgtg      1440
tggctgacga tcagcgcttt cttgaccgcc tgggactgta tgattacaac ctgccgttta      1500
tcgccgtgcc gctgataggg ccggatgcgc agacttttgg cgtgctgacg gcgcaaccga      1560
tggcgcgtta cgaagagcgg ttacccgcct gcacccgctt tctggaaacg gtc            1613
```

```
<210> SEQ ID NO 179
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 179
```

```
tccctgtgcg ccgcgtcgcc gatggtggcc agccaactgg cgcgctaccc gatcctgctc      60
gatgaactgc tcgacccgaa cacgctctat caaccgacgg cgatgaacgc ctatcgcgat      120
gaactgcgac aatacctgtt gcgcgtgccg gaagaggatg aagagcagca actggaggcg      180
ctacggcagt ttaagcaggc gcagttgttg cgcgtagcgg cggcggatat cgccggtacg      240
ttacccgtca tgaaagtgag cgatcactta acctggctgg cggaagcgat tatcgatgcg      300
gtggtgcagc aagcctggaa ccagatggtg gcgcgttacg ccagccgac gcatctgcac      360 gatcgcgaag ggcgcggttt cgccgtggtc ggttacggca aacttggcgg ctgggaatta      420
ggttacagct ccgatctgga tctggtgttc ctgcacgact gccccatgga tgtgatgacc      480
gatggcgagc gtgaaatcga tggccgccag ttctatttgc gcctcgcgca gcgcgtgatg      540
cacctgttca gcacgcgcac gtcgtccggc attctttatg aagtcgatgc gcgtttgcgc      600
```

-continued

```
ccgtccggcg cggccggaat gctggtgacc actgcggaag cgttcgccga ttatcaaaaa      660
aatgaagcct ggacatggga gcatcaggcg ctggcgcgtg cgcgcgtggt gtacggcgat      720
ccgcaactga ccgccgaatt tgacgccatt cgccgcgata tcctgatgac ctcccgcgat      780
gccgctaccc tgcaaaccga agtgcgggaa atgcgtgaga aaatgcgcgc ccatcttggt      840
aacaagcaca aagaccgttt cgatctgaaa gccgatgaag gcggtatcac cgatattgag      900
tttatcgctc agtatctggt gctgcgcttt gcccatgaga agccgaaact gacgcgctgg      960
tcggataatg tgcgcatcct cgaagggctg gcgcaaaacg gcatcatgga tgagcaggaa      1020
gcgcaggcat tgacgctggc gtacaccacg ttgcgtgatg agctgcacca cctggcgctg      1080
caagagctgc caggacatgt ggcgctctcc tgttttgtcg ccgagcgtgc gcttatcaaa      1140
accagctggg acaagtggct ggtggaaccg tgcgccccgg cgtaa                       1185
```

<210> SEQ ID NO 180
<211> LENGTH: 2085
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 180

```
taaagcgagc gctcacttac gtgatctgtt gacgcagtcc gaagcgacca ttacttcagc      60
cgtttcagca gatacggcgg tgtggagtgc gcaatcagcc ctggcgaaac tggtgctcac      120
cgagtggtta gtgacgcagg gctggcgaac cttccttgat gaaaaagcgc aggctaagtt      180
tgccgactcc tttaaacgct ttgctgacgt tcatctgtca cgcagcgccc ccgagctgaa      240
aaaagccttt gcccagccgc tgggcgacag ctatcgcgac cagttaccgc ggctggcgcg      300
tgatatcgac agcgcgttat tgctggccgg acattacgat cgcgcgcgcg ccgtggagtg      360
gctggaaaac tggcaggggc ttcagcacgc tattgaaacg cgccagagag ttgaaatcga      420
acatttccgt aataccgcca ttacccagga gccgttctgg ttgcacagcg gaaaacgtta      480
acgaaaggat atttcgcatg tccctgtgcg ccgcgtcgcc gatggtggcc agccaactgg      540
cgcgctaccc gatcctgctc gatgaactgc tcgacccgaa cacgctctat caaccgacgg      600
cgatgaacgc ctatcgcgat gaactgcgac aatacctgtt gcgcgtgccg gaagaggatg      660
aagagcagca actggaggcg ctacggcagt ttaagcaggc gcagttgttg cgcgtagcgg      720
cggcggatat cgccggtacg ttacccgtca tgaaagtgag cgatcactta acctggctgg      780
cggaagcgat tatcgatgcg gtggtgcagc aagcctggaa ccagatggtg gcgcgttacg      840
gccagccgac gcatcgcac gatcgcgaag ggcgcgtttc gccgtggtc ggttacggca      900 aacttggcgg ctgggaatta ggttacagct ccgatctgga tctggtgttc ctgcacgact      960
gccccatgga tgtgatgacc gatggcgagc gtgaaatcga tggccgccag ttctatttgc      1020
gcctcgcgca gcgcgtgatg cacctgttca gcacgcgcac gtcgtccggc attctttatg      1080
aagtcgatgc gcgtttgcgc ccgtccggcg cggccggaat gctggtgacc actgcggaag      1140
cgttcgccga ttatcaaaaa aatgaagcct ggacatggga gcatcaggcg ctggcgcgtg      1200
cgcgcgtggt gtacggcgat ccgcaactga ccgccgaatt tgacgccatt cgccgcgata      1260
tcctgatgac ctcccgcgat gccgctaccc tgcaaaccga agtgcgggaa atgcgtgaga      1320
aaatgcgcgc ccatcttggt aacaagcaca aagaccgttt cgatctgaaa gccgatgaag      1380
```

```
gcggtatcac cgatattgag tttatcgctc agtatctggt gctgcgcttt gcccatgaga    1440
agccgaaact gacgcgctgg tcggataatg tgcgcatcct cgaagggctg cgcgcaaaacg    1500 gcatcatgga tgagcaggaa gcgcaggcat tgacgctggc gtacaccacg ttgcgtgatg    1560
agctgcacca cctggcgctg caagagctgc caggacatgt ggcgctctcc tgttttgtcg    1620
ccgagcgtgc gcttatcaaa accagctggg acaagtggct ggtggaaccg tgcgccccgg    1680
cgtaagtgtg gtatcatcgc gcgcaaattt tgtatctctc aggagacagg aatgaaagtt    1740
acgctgccag agttcaatca agccggtgtc atggtggtgg gtgatgtgat gctggatcgc    1800
tactggtacg gcccaaccag ccgcatttct ccggaagcgc cagttccggt tgttaaagtc    1860
gatactattg aagagcgacc gggcggtgcg gcaaacgtgg cgatgaacat tgcctcgctg    1920
ggcgcaacgg cgcgtctggt tggcctgact ggcattgatg atgcggcgcg cgcgctgagc    1980
aaagcgctgg cggatgttaa tgttaaatgt gacttcgttt ctgttccgac tcaccccacc    2040
atcactaagc tgcgcgtgct gtcgcgtaac cagcaactga ttcgc                   2085
```

```
<210> SEQ ID NO 181
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 181
atgaccctga atatgatgat ggatgccagc cgttctgtaa taataaccgg acaattcgga     60
ctgattaaaa aagcgccctc gcggcgcttt ttttatattc tcgactccat ttaaaataaa    120
aaatccaatc ggatttcact atttaaactg gccattatct aagatgaatc cgatggaagc    180
tcgctgtttt aacacgcgtt ttttaacctt ttattgaaag tcggtgcttc tttgagcgaa    240
cgatcaaatt taagtggatt cccatcaaaa aaatattctc aacctaaaaa agtttgtgta    300
atacttgtaa cgctacatgg agattaactc aatctagagg gtattaataa tgaatcgtac    360
taaactggta ctgggcgcaa ctcacttcac gccccgaagg gggaagctgc ctgaccctac    420
gattcccgct atttcattca ctgaccggag gttcaaaatg a                       461
```

```
<210> SEQ ID NO 182
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 182
accggataag agagaaaagt gtcgacgtcg gtccggttga tattgaccgg cgcatccgcc     60
agctcgccca gttttttggtg gatctgtttg gcgattttgc gggtcttgcc ggtgtcggtg    120
ccgaaaaaaa taccaatatt tgccataaca cacgctcctg ttgaaaaaga gatcccgcgg    180
ggaaaatgcg gtgaacatgt cagctattgc gaagagtgtg ccagtttttgc tcacgggcaa    240 aagctgcacc agaatgggta ttaatgcacc agcctggcgc tttttttcgc ggcacgtccc    300
ctcgctaatg cccgtctggc gcggctttga cgctgataag gcgctgaata ccgatctgga    360
tcaaggtttt gtcgggttat cgtccaaaag gtgcactctt tgcatggtta taagtgcctg    420
```

```
acatggtgtc cgggcgaacg tcgccaggtg gcacaaattg tcagaactac gacacgacta        480
accgaccgca ggagtgtgcg atgaccctga atatgatgat ggatgccagc cgttctgtaa        540
taataaccgg acaattcgga ctgattaaaa aagcgccctc gcggcgcttt ttttatattc        600
tcgactccat ttaaaataaa aaatccaatc ggatttcact atttaaactg gccattatct        660
aagatgaatc cgatggaagc tcgctgtttt aacacgcgtt ttttaacctt ttattgaaag        720
tcggtgcttc tttgagcgaa cgatcaaatt taagtggatt cccatcaaaa aaatattctc        780
aacctaaaaa agtttgtgta atacttgtaa cgctacatgg agattaactc aatctagagg        840
gtattaataa tgaatcgtac taaactggta ctgggcgcaa ctcacttcac gccccgaagg        900
gggaagctgc ctgaccctac gattcccgct atttcattca ctgaccggag gttcaaaatg        960
acccagcgaa ccgagtcggg taataccgtc tggcgcttcg atttatccca gcagttcacc       1020
gcgatgcagc ggataagcgt ggttctcagc cgggcgaccg aggttgaaca gacactccag       1080
caggtgctgt gcgtattgca caatgacgcc tttttgcagc acggcatgat ctgtctgtac       1140
gacagccagc aggcgatttt gactattgaa gcgttgcagg aagccgatca gcagttgatc       1200
cccggcagct cgcaaattcg ctaccgtccg ggtgaagggc tggtcgggac ggtgctttcg       1260
caggggcaat cgttagtgct ggcgcgtgtg gctgacgatc agcgctttct tgaccgcctg       1320
ggactgtatg attacaacct gccgtttatc gccgtgccgc tgatagggcc ggatgcgcag       1380
acttttggcg tgctgacggc gcaaccgatg gcgcgttacg aagagcggtt acccgcctgc       1440
acccgctttc tggaaacggt c                                              1461
```

```
<210> SEQ ID NO 183
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 183
```

```
tccctgtgcg ccgcgtcgcc gatggtggcc agccaactgg cgcgctaccc gatcctgctc         60
gatgaactgc tcgacccgaa cacgctctat caaccgacgg cgatgaacgc ctatcgcgat        120
gaactgcgac aatacctgtt gcgcgtgccg gaagaggatg aagagcagca actggaggcg        180
ctacggcagt ttaagcaggc gcagttgttg cgcgtagcgg cggcggatat cgccggtacg        240
ttacccgtca tgaaagtgag cgatcactta acctggctgg cggaagcgat tatcgatgcg        300
gtggtgcagc aagcctggaa ccagatggtg gcgcgttacg ccagccgac gcatctgcac        360 gatcgcgaag ggcgcggttt cgccgtggtc ggttacggca aacttggcgg ctgggaatta        420
ggttacagct ccgatctgga tctggtgttc ctgcacgact gccccatgga tgtgatgacc        480
gatggcgagc gtgaaatcga tggccgccag ttctatttgc gcctcgcgca gcgcgtgatg        540
cacctgttca gcacgcgcac gtcgtccggc attctttatg aagtcgatgc gcgtttgcgc        600
ccgtccggcg cggccggaat gctggtgacc actgcggaag cgttcgccga ttatcaaaaa        660
aatgaagcct ggacatggga gcatcaggcg ctggcgcgtg cgcgcgtggt gtacggcgat        720
ccgcaactga ccgccgaatt tgacgccatt cgccgcgata tcctgatgac ctcccgcgat        780
gccgctaccc tgcaaaccga agtgcgggaa atgcgtgaga aaatgcgcgc ccatcttggt        840
aacaagcaca aagaccgttt cgatctgaaa gccgatgaag gcggtatcac cgatattgag        900
```

```
tttatcgctc agtatctggt gctgcgcttt gcccatgaga agccgaaact gacgcgctgg      960
tcggataatg tgcgcatcct cgaagggctg gcgcaaaacg gcatcatgga tgagcaggaa     1020
gcgcaggcat tgacgctggc gtacaccacg ttgcgtgatg agctgcacca cctggcgctg     1080
caagagctgc caggacatgt ggcgctctcc tgttttgtcg ccgagcgtgc gcttatcaaa     1140
accagctggg acaagtggct ggtggaaccg tgcgccccgg cgtaa                     1185
```

```
<210> SEQ ID NO 184
<211> LENGTH: 2085
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 184
```

```
taaagcgagc gctcacttac gtgatctgtt gacgcagtcc gaagcgacca ttacttcagc       60
cgtttcagca gatacggcgg tgtggagtgc gcaatcagcc ctggcgaaac tggtgctcac      120
cgagtggtta gtgacgcagg gctggcgaac cttccttgat gaaaaagcgc aggctaagtt      180
tgccgactcc tttaaacgct ttgctgacgt tcatctgtca cgcagcgccg ccgagctgaa      240
aaaagccttt gcccagccgc tgggcgacag ctatcgcgac cagttaccgc ggctggcgcg      300
tgatatcgac agcgcgttat tgctggccgg acattacgat cgcgcgcgcg ccgtggagtg      360
gctggaaaac tggcaggggc ttcagcacgc tattgaaacg cgccagagag ttgaaatcga      420
acatttccgt aataccgcca ttacccagga gccgttctgg ttgcacagcg aaaacgtta      480 acgaaaggat atttcgcatg tccctgtgcg ccgcgtcgcc gatggtggcc agccaactgg      540
cgcgctaccc gatcctgctc gatgaactgc tcgacccgaa cacgctctat caaccgacgg      600
cgatgaacgc ctatcgcgat gaactgcgac aatacctgtt gcgcgtgccg gaagaggatg      660
aagagcagca actggaggcg ctacggcagt ttaagcaggc gcagttgttg cgcgtagcgg      720
cggcggatat cgccggtacg ttacccgtca tgaaagtgag cgatcactta acctggctgg      780
cggaagcgat tatcgatgcg gtggtgcagc aagcctggaa ccagatggtg gcgcgttacg      840
gccagccgac gcatctgcac gatcgcgaag ggcgcggttt cgccgtggtc ggttacggca      900
aacttggcgg ctgggaatta ggttacagct ccgatctgga tctggtgttc ctgcacgact      960
gccccatgga tgtgatgacc gatggcgagc gtgaaatcga tggccgccag ttctatttgc     1020
gcctcgcgca gcgcgtgatg cacctgttca gcacgcgcac gtcgtccggc attctttatg     1080
aagtcgatgc gcgtttgcgc ccgtccggcg cggccggaat gctggtgacc actgcggaag     1140
cgttcgccga ttatcaaaaa aatgaagcct ggacatggga gcatcaggcg ctggcgcgtg     1200
cgcgcgtggt gtacgcgat ccgcaactga ccgccgaatt tgacgccatt cgccgcgata     1260
tcctgatgac ctcccgcgat gccgctaccc tgcaaaccga agtgcgggaa atgcgtgaga     1320
aaatgcgcgc ccatcttggt aacaagcaca agaccgtttt cgatctgaaa gccgatgaag     1380
gcggtatcac cgatattgag tttatcgctc agtatctggt gctgcgcttt gcccatgaga     1440
agccgaaact gacgcgctgg tcggataatg tgcgcatcct cgaagggctg gcgcaaaacg     1500
gcatcatgga tgagcaggaa gcgcaggcat tgacgctggc gtacaccacg ttgcgtgatg     1560
agctgcacca cctggcgctg caagagctgc caggacatgt ggcgctctcc tgttttgtcg     1620
ccgagcgtgc gcttatcaaa accagctggg acaagtggct ggtggaaccg tgcgccccgg     1680
```

-continued

```
cgtaagtgtg gtatcatcgc gcgcaaattt tgtatctctc aggagacagg aatgaaagtt    1740
acgctgccag agttcaatca agccggtgtc atggtggtgg gtgatgtgat gctggatcgc    1800
tactggtacg gcccaaccag ccgcatttct ccggaagcgc cagttccggt tgttaaagtc    1860
gatactattg aagagcgacc gggcggtgcg gcaaacgtgg cgatgaacat tgcctcgctg    1920
ggcgcaacgg cgcgtctggt tggcctgact ggcattgatg atgcggcgcg cgcgctgagc    1980
aaagcgctgg cggatgttaa tgttaaatgt gacttcgttt ctgttccgac tcaccccacc    2040
atcactaagc tgcgcgtgct gtcgcgtaac cagcaactga ttcgc                    2085
```

```
<210> SEQ ID NO 185
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 185
```

```
atgaccctga atatgatgat ggatgccagc cgttctgtaa taataaccgg acaattcgga      60
ctgattaaaa aagcgccctc gcggcgcttt ttttatattc tcgactccat ttaaaataaa     120
aaatccaatc ggatttcact atttaaactg gccattatct aagatgaatc cgatggaagc     180
tcgctgtttt aacacgcgtt ttttaacctt ttattgaaag tcggtgcttc tttgagcgaa     240
cgatcaaatt taagtggatt cccatcaaaa aaatattctc aacctaaaaa agtttgtgta     300
atacttgtaa cgctacatgg agattaactc aatctagagg gtattaataa tgaatcgtac     360
taaactggta ctgggcgcaa ctcacttcac gccccgaagg gggaagctgc ctgaccctac     420
gattcccgct atttcattca ctgaccggag gttcaaaatg a                         461
```

```
<210> SEQ ID NO 186
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 186
```

```
accggataag agagaaaagt gtcgacgtcg gtccggttga tattgaccgg cgcatccgcc      60
agctcgccca gttttttggtg gatctgtttg gcgattttgc gggtcttgcc ggtgtcggtg     120
ccgaaaaaaa taccaatatt tgccataaca cacgctcctg ttgaaaaaga gatcccgcgg     180
ggaaaatgcg gtgaacatgt cagctattgc gaagagtgtg ccagtttttgc tcacgggcaa     240 aagctgcacc agaatgggta ttaatgcacc agcctggcgc tttttttttcgc ggcacgtccc     300 ctcgctaatg cccgtctggc gcggctttga cgctgataag gcgctgaata ccgatctgga     360
tcaaggtttt gtcgggttat cgtccaaaag gtgcactctt tgcatggtta taagtgcctg     420
acatggtgtc cggcgaacg tcgccaggtg gcacaaattg tcagaactac gacacgacta     480
accgaccgca ggagtgtgcg atgaccctga atatgatgat ggatgccagc cgttctgtaa     540
taataaccgg acaattcgga ctgattaaaa aagcgccctc gcggcgcttt ttttatattc     600
tcgactccat ttaaaataaa aaatccaatc ggatttcact atttaaactg gccattatct     660
```

-continued

```
aagatgaatc cgatggaagc tcgctgtttt aacacgcgtt ttttaacctt ttattgaaag      720
tcggtgcttc tttgagcgaa cgatcaaatt taagtggatt cccatcaaaa aaatattctc      780
aacctaaaaa agtttgtgta atacttgtaa cgctacatgg agattaactc aatctagagg      840
gtattaataa tgaatcgtac taaactggta ctgggcgcaa ctcacttcac gccccgaagg      900
gggaagctgc ctgaccctac gattcccgct atttcattca ctgaccggag gttcaaaatg      960
acccagcgaa ccgagtcggg taataccgtc tggcgcttcg atttatccca gcagttcacc     1020
gcgatgcagc ggataagcgt ggttctcagc cgggcgaccg aggttgaaca gacactccag     1080
caggtgctgt gcgtattgca caatgacgcc tttttgcagc acggcatgat ctgtctgtac     1140
gacagccagc aggcgatttt gactattgaa gcgttgcagg aagccgatca gcagttgatc     1200
cccggcagct cgcaaattcg ctaccgtccg ggtgaagggc tggtcgggac ggtgctttcg     1260
caggggcaat cgttagtgct ggcgcgtgtg gctgacgatc agcgctttct tgaccgcctg     1320
ggactgtatg attacaacct gccgtttatc gccgtgccgc tgatagggcc ggatgcgcag     1380
acttttggcg tgctgacggc gcaaccgatg gcgcgttacg aagagcggtt acccgcctgc     1440
acccgctttc tggaaacggt c                                                1461
```

<210> SEQ ID NO 187
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 187

```
tccctgtgcg ccgcgtcgcc gatggtggcc agccaactgg cgcgctaccc gatcctgctc       60
gatgaactgc tcgacccgaa cacgctctat caaccgacgg cgatgaacgc ctatcgcgat      120
gaactgcgac aatacctgtt gcgcgtgccg gaagaggatg aagagcagca actggaggcg      180
ctacggcagt ttaagcaggc gcagttgttg cgcgtagcgg cggcggatat cgccggtacg      240
ttacccgtca tgaaagtgag cgatcactta acctggctgg cggaagcgat tatcgatgcg      300
gtggtgcagc aagcctggaa ccagatggtg gcgcgttacg gccagccgac gcatctgcac      360
gatcgcgaag ggcgcggttt cgccgtggtc ggttacggca aacttggcgg ctgggaatta      420
ggttacagct ccgatctgga tctggtgttc ctgcacgact gccccatgga tgtgatgacc      480
gatggcgagc gtgaaatcga tggccgccag ttctatttgc gcctcgcgca gcgcgtgatg      540
cacctgttca gcacgcgcac gtcgtccggc attctttatg aagtcgatgc gcgtttgcgc      600
ccgtccggcg cggccggaat gctggtgacc actgcgcgaag cgttcgccga ttatcaaaaa      660
aatgaagcct ggacatggga gcatcaggcg ctggcgcgtg cgcgcgtggt gtacggcgat      720
ccgcaactga ccgccgaatt tgacgccatt cgccgcgata tcctgatgac ctcccgcgat      780
gccgctaccc tgcaaaccga agtgcgggaa atgcgtgaga aaatgcgcgc ccatcttggt      840
aacaagcaca aagaccgttt cgatctgaaa gccgatgaag cggtatcac cgatattgag      900 tttatcgctc agtatctggt gctgcgcttt gcccatgaga agccgaaact gacgcgctgg      960
tcggataatg tgcgcatcct cgaagggctg gcgcaaaacg gcatcatgga tgagcaggaa     1020
gcgcaggcat tgacgctggc gtacaccacg ttgcgtgatg agctgcacca cctggcgctg     1080
caagagctgc aggacatgt ggcgctctcc tgttttgtcg ccgagcgtgc gcttatcaaa      1140
```

-continued accagctggg acaagtggct ggtggaaccg tgcgcccggg cgtaa                    1185

<210> SEQ ID NO 188
<211> LENGTH: 2085
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 188
taaagcgagc gctcacttac gtgatctgtt gacgcagtcc gaagcgacca ttacttcagc      60
cgtttcagca gatacggcgg tgtggagtgc gcaatcagcc ctggcgaaac tggtgctcac     120
cgagtggtta gtgacgcagg gctggcgaac cttccttgat gaaaaagcgc aggctaagtt     180
tgccgactcc tttaaacgct ttgctgacgt tcatctgtca cgcagcgccg ccgagctgaa     240
aaagcctttt gcccagccgc tgggcgacag ctatcgcgac cagttaccgc ggctggcgcg     300
tgatatcgac agcgcgttat tgctggccgg acattacgat cgcgcgcgcg ccgtggagtg     360
gctggaaaac tggcaggggc ttcagcacgc tattgaaacg cgccagagag ttgaaatcga     420
acatttccgt aataccgcca ttacccagga gccgttctgg ttgcacagcg aaaacgtta     480 acgaaaggat atttcgcatg tccctgtgcg ccgcgtcgcc gatggtggcc agccaactgg     540
cgcgctaccc gatcctgctc gatgaactgc tcgacccgaa cacgctctat caaccgacgg     600
cgatgaacgc ctatcgcgat gaactgcgac aataccgtt gcgcgtgccg gaagaggatg     660
aagagcagca actggaggcg ctacggcagt ttaagcaggc gcagttgttg cgcgtagcgg     720
cggcggatat cgccggtacg ttacccgtca tgaaagtgag cgatcactta acctggctgg     780
cggaagcgat tatcgatgcg gtggtgcagc aagcctggaa ccagatggtg gcgcgttacg     840
gccagccgac gcatctgcac gatcgcgaag ggcgcggttt cgccgtggtc ggttacggca     900
aacttggcgg ctgggaatta ggttacagct ccgatctgga tctggtgttc ctgcacgact     960
gccccatgga tgtgatgacc gatggcgagc gtgaaatcga tggccgccag ttctatttgc    1020
gcctcgcgca gcgcgtgatg cacctgttca gcacgcgcac gtcgtccggc attctttatg    1080
aagtcgatgc gcgtttgcgc ccgtccggcg cggccggaat gctggtgacc actgcggaag    1140
cgttcgccga ttatcaaaaa aatgaagcct ggacatggga gcatcaggcg ctggcgcgtg    1200
cgcgcgtggt gtacggcgat ccgcaactga ccgccgaatt tgacgccatt cgccgcgata    1260
tcctgatgac ctcccgcgat gccgctaccc tgcaaaccga agtgcgggaa atgcgtgaga    1320
aaatgcgcgc ccatcttggt aacaagcaca agaccgtttt cgatctgaaa gccgatgaag    1380
gcggtatcac cgatattgag tttatcgctc agtatctggt gctgcgcttt gcccatgaga    1440
agccgaaact gacgcgctgg tcggataatg tgcgcatcct cgaagggctg gcgcaaaacg    1500
gcatcatgga tgagcaggaa gcgcaggcat tgacgctggc gtacaccacg ttgcgtgatg    1560
agctgcacca cctggcgctg caagagctgc caggacatgt ggcgctctcc tgttttgtcg    1620
ccgagcgtgc gcttatcaaa accagctggg acaagtggct ggtggaaccg tgcgcccggg    1680
cgtaagtgtg gtatcatcgc gcgcaaattt tgtatctctc aggagacagg aatgaaagtt    1740
acgctgccag agttcaatca agccggtgtc atggtggtgg gtgatgtgat gctggatcgc    1800
tactggtacg gccaaccag ccgcatttct ccggaagcgc cagttccggt tgttaaagtc    1860
gatactattg aagagcgacc gggcggtgcg gcaaacgtgg cgatgaacat tgcctcgctg    1920

-continued

```
ggcgcaacgg cgcgtctggt tggcctgact ggcattgatg atgcggcgcg cgcgctgagc   1980
aaagcgctgg cggatgttaa tgttaaatgt gacttcgttt ctgttccgac tcaccccacc   2040
atcactaagc tgcgcgtgct gtcgcgtaac cagcaactga ttcgc               2085
```

```
<210> SEQ ID NO 189
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm7

<400> SEQUENCE: 189
atgaccctga atatgatgat ggatgccagc cgcgtcaggt tgaacgtaaa aaagtcggtc    60
tgcgcaaagc acgtcgtcgt ccgcagttct ccaaacgtta attggtttct gcttcggcag   120
aacgattggc gaaaaaaccc ggtgcgaacc gggttttttt atggataaag atcgtgttat   180
ccacagcaat ccattgatta tctcttcttt ttcagcattt ccagaatccc ctcaccacaa   240
agcccgcaaa atctggtaaa ctatcatcca attttctgcc caaatggctg ggattgttca   300 tttttttgttt gccttacaac gagagtgaca gtacgcgcgg gtagttaact caacatctga   360
ccggtcgata actcacttca cgccccgaag ggggaagctg cctgacccta cgattcccgc   420
tatttcattc actgaccgga ggttcaaaat ga                              452
```

```
<210> SEQ ID NO 190
<211> LENGTH: 1451
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm7 with 500bp flank

<400> SEQUENCE: 190
accggataag agagaaaagt gtcgacgtcg gtccggttga tattgaccgg cgcatccgcc    60
agctcgccca gttttttggtg gatctgtttg gcgattttgc gggtcttgcc ggtgtcggtg   120
ccgaaaaaaa taccaatatt tgccataaca cacgctcctg ttgaaaaaga gatcccgcgg   180
ggaaaatgcg gtgaacatgt cagctattgc gaagagtgtg ccagtttttgc tcacgggcaa   240 aagctgcacc agaatgggta ttaatgcacc agcctggcgc tttttttcgc ggcacgtccc   300
ctcgctaatg cccgtctggc gcggctttga cgctgataag gcgctgaata ccgatctgga   360
tcaaggtttt gtcgggttat cgtccaaaag gtgcactctt tgcatggtta taagtgcctg   420
acatggtgtc cgggcgaacg tcgccaggtg gcacaaattg tcagaactac gacacgacta   480
accgaccgca ggagtgtgcg atgaccctga atatgatgat ggatgccagc cgcgtcaggt   540
tgaacgtaaa aaagtcggtc tgcgcaaagc acgtcgtcgt ccgcagttct ccaaacgtta   600
attggtttct gcttcggcag aacgattggc gaaaaaaccc ggtgcgaacc gggttttttt   660
atggataaag atcgtgttat ccacagcaat ccattgatta tctcttcttt ttcagcattt   720
ccagaatccc ctcaccacaa agcccgcaaa atctggtaaa ctatcatcca attttctgcc   780
caaatggctg ggattgttca tttttttgttt gccttacaac gagagtgaca gtacgcgcgg   840
gtagttaact caacatctga ccggtcgata actcacttca cgccccgaag ggggaagctg   900
cctgacccta cgattcccgc tatttcattc actgaccgga ggttcaaaat gacccagcga   960
```

-continued accgagtcgg gtaataccgt ctggcgcttc gatttatccc agcagttcac cgcgatgcag        1020
cggataagcg tggttctcag ccgggcgacc gaggttgaac agacactcca gcaggtgctg        1080
tgcgtattgc acaatgacgc cttttttgcag cacggcatga tctgtctgta cgacagccag       1140
caggcgattt tgactattga agcgttgcag gaagccgatc agcagttgat ccccggcagc        1200
tcgcaaattc gctaccgtcc gggtgaaggg ctggtcggga cggtgctttc gcaggggcaa        1260
tcgttagtgc tggcgcgtgt ggctgacgat cagcgctttc ttgaccgcct gggactgtat        1320
gattacaacc tgccgtttat cgccgtgccg ctgatagggc cggatgcgca gacttttggc        1380
gtgctgacgg cgcaaccgat ggcgcgttac gaagagcggt tacccgcctg cacccgcttt        1440
ctggaaacgg t                                                            1451

<210> SEQ ID NO 191
<211> LENGTH: 1191
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 191
atggcgctga agcacctgat cacgctctgc gcggcgtcgc cgatggtcgc cagccagctg          60
gcgcgccacc cgctgctgct ggatgagctg ctggatccca acaccctcta tcagccgacg         120
gcgaccgatg cctatcgcga cgagctgcgc cagtacctgc tgcgcgtgcc ggaagaggat         180
gaagagcagc agctggaggc gttgcgccag tttaagcagg cgcagcagct gcatatcgcg         240
gcggcggata tcgctggtac cctgccggtg atgaaggtca gcgatcactt aacctggctt         300
gccgaagcga tcctcgacgc ggtggtgcag caggcatggg ggcagatggt cgctcgctac         360
ggccagccga cccacctgca cgatcgccag ggtcgcggct tcgccgtcgt cggctacggt         420
aagcttggcg gctgggagct gggctacagc tccgatctcg atctggtgtt cctccatgac        480
tgccccggcg aggtgatgac cgacggcgag cgggagattg acggccgtca gttctacctg        540
cggctggccc agcggatcat gcacctgttc agcacccgca cctcgtccgg tattctctac        600
gaagtggacg cccggctgcg tccttctggc gcggcgggga tgctggtcac caccgccgac        660
gcgtttgctg actatcagca gaacgaagcc tggacgtggg aacatcaggc gctggtgcgc        720
gcccgcgtgg tctatggcga cccggcgctg caggcgcgct ttgacgccat tcgtcgcgat        780
atcctgacca ccccgcggga ggggatgacc ctgcagaccg aggttcgcga gatgcgcgag        840
aagatgcgcg cccaccttgg caacaaacat cccgatcgtt ttgatatcaa agccgatgcc        900
ggcgggatca ccgatattga atttattact cagtatctgg tcctacgcta tgccagtgac        960
aagccgaagc tgacccgctg gtctgacaac gtgcgtattc ttgagctgct ggcgcagaac       1020
gacatcatgg acgaggagga ggcgcgcgcc ttaacgcatg cgtacaccac cttgcgtgat       1080
gcgctccatc acctggccct gcaggagcag ccgggacacg tggcgccaga ggccttcagc       1140
cgggagcgtc agcaggtcag cgccagctgg cagaagtggc tgatggctta a                1191

<210> SEQ ID NO 192
<211> LENGTH: 2191
<212> TYPE: DNA
<213> ORGANISM: Artificial Sequence
<220> FEATURE:
<223> OTHER INFORMATION: Description of Artificial Sequence: Synthetic

```
      polynucleotide
<220> FEATURE:
<223> OTHER INFORMATION: glnE-delta-AR-2 with 500bp flank

<400> SEQUENCE: 192
cgtaaggcga ccacccagct ccgcgcgttg ctgaacgacg ctgaagccgt tctgctggcc      60
gcggacaccg ccgacgaggc gttattccgc accgaggtcg tcggcgccaa actggccctg     120
actgaatggc tggtccagcg cggctggcgt ccgttcctca acgaggcagg agagaaaaaa     180
atagccggat cgttcaaacg gtttgccgat attaacctct cgcgggtggc ggccgagctg     240
cgcagcgccg tgcagcatct ggcggttgaa gatgccgccg accagttgcc gaagctgtcc     300
cgcgacatcg acagcgtcca gctgctggcg ggcgcctatg gcgacgccgt cgcgccgtgg     360
ctggagaact ggcaggagct tcaccgtgca atagcacatg acgatcgcag cgtctttgaa     420
tatttccgtc gccaggcgct ggctgccgag ccgttctggc tgcatagtgg aaaacgataa     480
tttcaggcca gggagcccct atggcgctga agcacctgat cacgctctgc gcggcgtcgc     540
cgatggtcgc cagccagctg gcgcgccacc cgctgctgct ggatgagctg ctggatccca     600
acaccctcta tcagccgacg cgaccgatg cctatcgcga cgagctgcgc cagtacctgc      660
tgcgcgtgcc ggaagaggat gaagagcagc agctggaggc gttgcgccag tttaagcagg     720
cgcagcagct gcatatcgcg gcggcggata tcgctggtac cctgccggtg atgaaggtca     780
gcgatcactt aacctggctt gccgaagcga tcctcgacgc ggtggtgcag caggcatggg     840
ggcagatggt cgctcgctac ggccagccga cccacctgca cgatcgccag ggtcgcggct     900
tcgccgtcgt cggctacggt aagcttggcg gctgggagct gggctacagc tccgatctcg     960
atctggtgtt cctccatgac tgcccggcgg aggtgatgac cgacggcgag cgggagattg    1020
acggccgtca gttctacctg cggctggccc agcggatcat gcacctgttc agcacccgca    1080
cctcgtccgg tattctctac gaagtggacg cccggctgcg tccttctggc gcggcgggga    1140
tgctggtcac caccgccgac gcgtttgctg actatcagca gaacgaagcc tggacgtggg    1200
aacatcaggc gctggtgcgc gcccgcgtgg tctatggcga cccggcgctg caggcgcgct    1260
ttgacgccat tcgtcgcgat atcctgacca ccccgcggga ggggatgacc ctgcagaccg    1320
aggttcgcga gatgcgcgag aagatgcgcg cccaccttgg caacaaacat cccgatcgtt    1380
ttgatatcaa agccgatgcc ggcgggatca ccgatattga atttattact cagtatctgg    1440
tcctacgcta tgccagtgac aagccgaagc tgacccgctg gtctgacaac gtgcgtattc    1500
ttgagctgct ggcgcagaac gacatcatgg acgaggagga ggcgcgcgcc ttaacgcatg    1560
cgtacaccac cttgcgtgat gcgctccatc acctggccct gcaggagcag ccgggacacg    1620
tggcgccaga ggccttcagc cgggagcgtc agcaggtcag cgccagctgg cagaagtggc    1680
tgatggctta actataaaat cgggtgtgct attatcgcgc gcaaagtttg cgtctcgcag    1740
gagagagtca tgaaagtaac gctgccggag tttgaacgtg caggagtgtt ggtggtgggt    1800
gatgtgatgc tggaccgcta ctggtacggc cccaccagtc gtatttcccc ggaagccccg    1860
gtgccggtgg tgaaggtgga aaatatcgaa gaacgtcctg cggcgcgcggc aaacgtagcg    1920 atgaacatcg cctccctggg ggcaacgtcg cgcctggtgg gattgaccgg gattgatgac    1980 gctgccgcg cgctgagcca ggcgctggcc aatgtgaatg tgaagtgcga cttcgtctcc    2040
gtcccgactc acccgaccat caccaagctg cgggtgctgt cgcgcaatca gcagctgatc    2100
cgcctcgact ttgaagaggg cttctccggc gtggatccgc agccgatgca tgagcgcatt    2160
cagcaggcgc tgggagccat tggcgcactg g                                    2191
```

```
<210> SEQ ID NO 193
<211> LENGTH: 613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC

<400> SEQUENCE: 193
atgaccctga atatgatgct agaagcgtca ggtaccggtc atgattcacc gtgcgattct      60
cggttccctg gagcgcttca ttggcatcct gaccgaagag ttcgctggct tcttcccaac     120
ctggattgca ccagtgcagg tagtggtcat gaatattacc gattctcagg ctgaatacgt     180
taacgaattg acgcgtaaac tacaaaatgc gggcattcgt gtaaaagcag acttgagaaa     240
tgagaagatt ggctttaaaa tccgcgagca cactttacgt cgtgtcccgt atatgttggt     300
ctgtggcgac aaagaagtcg aagccggcaa agtggccgtg cgcacccgtc gcgggaaaga     360
cctcggcagc atggacgtaa gtgaagtgat tgagaagctg caacaagaga ttcgcagccg     420
cagtcttcaa caactggagg aataaggtat taaaggcgga aaacgagttc aaacggcacg     480
tccgaatcgt atcaatggcg agattcgcgc cctggaagtt cgcgccattg agctggcttc     540
ccgaccgcag ggcggcacct gcctgaccct gcgtttcccg ctgtttaaca ccctgaccgg     600
aggtgaagca tga                                                        613

<210> SEQ ID NO 194
<211> LENGTH: 1613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC with 500bp flank

<400> SEQUENCE: 194
ggccgtcgcc cagcgtcggc gtccccaaca gcagggccgg gtaggccagc aggtccgcca      60
gcgtggcgcg gttaatattg accggggcgg cggcggcctc ccccagctgc ttgtggatca     120
ttttcgcgat cttgcgggtt ttaccggtat cggtaccaaa gaaaatgcca atgttcgcca     180
tagtacgctc ctgtcggaat ggtgttgaaa aaaggaatga cgacagaggt attgcgaagg     240
ctgtgccagg ttgccctgca ccgcgacggc ccatccctgc cccatcagga tcgcttcgca     300
tcacgatgcc gcgcgccaaa ggcgcacccg gcggggcgaa aggtaaaaat ccgtgaattt     360
tccccctgtc ggatcaatgt ttcgcgtggt cgttccgata agggcgcaca ctttgcatgg     420
ttatccgggt tcggcttacc ccgccgcgtt ttgcgcacgg tgtcggacaa tttgtcataa     480
ctgcgacaca ggagtttgcg atgaccctga atatgatgct agaagcgtca ggtaccggtc     540
atgattcacc gtgcgattct cggttccctg gagcgcttca ttggcatcct gaccgaagag     600
ttcgctggct tcttcccaac ctggattgca ccagtgcagg tagtggtcat gaatattacc     660
gattctcagg ctgaatacgt taacgaattg acgcgtaaac tacaaaatgc gggcattcgt     720
gtaaaagcag acttgagaaa tgagaagatt ggctttaaaa tccgcgagca cactttacgt     780
cgtgtcccgt atatgttggt ctgtggcgac aaagaagtcg aagccggcaa agtggccgtg     840
cgcacccgtc gcgggaaaga cctcggcagc atggacgtaa gtgaagtgat tgagaagctg     900
```

-continued

```
caacaagaga ttcgcagccg cagtcttcaa caactggagg aataaggtat taaaggcgga    960
aaacgagttc aaacggcacg tccgaatcgt atcaatggcg agattcgcgc cctggaagtt   1020
cgcgccattg agctggcttc ccgaccgcag ggcggcacct gcctgaccct gcgtttcccg   1080
ctgtttaaca ccctgaccgg aggtgaagca tgatccctga atccgacccg gacaccaccg   1140
tcagacgctt cgacctctct cagcagttca ccgccatgca gcggataagc gtggtgctga   1200
gccgggccac cgaggccagc aaaacgctgc aggaggtgct cagcgtatta cacaacgatg   1260
cctttatgca gcacgggatg atctgcctgt acgacagcga gcaggagatc ctcagtatcg   1320
aagcgctgca gcaaaccggc cagcagcccc tccccggcag cacgcagatc cgctatcgcc   1380
ccggcgaggg actggtgggg accgtgctgg cccaggggca gtcgctggtg ctgccccggg   1440
tcgccgacga tcagcgtttt ctcgaccgcc tgagcctcta cgattacgat ctgccgttta   1500
tcgccgtacc gttgatgggg cccaacgccc ggccaatagg ggtgctggcg gcccagccga   1560
tggcgcgcca ggaagagcgg ctgccggcct gcacccgttt tctcgaaacc gtc           1613
```

<210> SEQ ID NO 195
<211> LENGTH: 1155
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 36bp deletion

<400> SEQUENCE: 195

```
atggcgctga agcacctgat cacgctctgc gcggcgtcgc cgatggtcgc cagccagctg     60
gcgcgccacc cgctgctgct ggatgagctg ctggatccca acaccctcta tcagccgacg    120
gcgaccgatg cctatcgcga cgagctgcgc cagtacctgc tgcgcgtgcc ggaagaggat    180
gaagagcagc agctgcatat cgcggcggcg gatatcgctg gtaccctgcc ggtgatgaag    240
gtcagcgatc acttaacctg gcttgccgaa gcgatcctcg acgcggtggt gcagcaggca    300
tgggggcaga tggtcgctcg ctacggccag ccgacccacc tgcacgatcg ccagggtcgc    360
ggcttcgccg tcgtcggcta cggtaagctt ggcggctggg agctgggcta cagctccgat    420
ctcgatctgg tgttcctcca tgactgcccg gcggaggtga tgaccgacgg cgagcgggag    480
attgacggcc gtcagttcta cctgcggctg gcccagcgga tcatgcacct gttcagcacc    540
cgcacctcgt ccggtattct ctacgaagtg gacgcccggc tgcgtccttc tggcgcggcg    600
gggatgctgg tcaccaccgc cgacgcgttt gctgactatc agcagaacga gcctggacg     660 tgggaacatc aggcgctggt gcgcgcccgc gtggtctatg cgacccggc gctgcaggcg     720 cgctttgacg ccattcgtcg cgatatcctg accacccgc gggaggggat gaccctgcag     780
accgaggttc gcgagatgcg cgagaagatg cgcgcccacc ttggcaacaa acatcccgat    840 cgtttttgata tcaaagccga tgccggcggg atcaccgata ttgaatttat tactcagtat   900
ctggtcctac gctatgccag tgacaagccg aagctgaccc gctggtctga caacgtgcgt    960
attcttgagc tgctggcgca gaacgacatc atggacgagg aggaggcgcg cgccttaacg   1020
catgcgtaca ccaccttgcg tgatgcgctc catcacctgg ccctgcagga gcagccggga   1080
cacgtggcgc cagaggcctt cagccgggag cgtcagcagg tcagcgccag ctggcagaag   1140
tggctgatgg cttaa                                                    1155
```

<210> SEQ ID NO 196

<211> LENGTH: 2155
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 36bp deletion

<400> SEQUENCE: 196

```
cgtaaggcga ccacccagct ccgcgcgttg ctgaacgacg ctgaagccgt tctgctggcc       60
gcggacaccg ccgacgaggc gttattccgc accgaggtcg tcggcgccaa actggccctg      120
actgaatggc tggtccagcg cggctggcgt ccgttcctca acgaggcagg agagaaaaaa      180
atagccggat cgttcaaacg gtttgccgat attaacctct cgcgggtggc ggccgagctg      240
cgcagcgccg tgcagcatct ggcggttgaa gatgccgccg accagttgcc gaagctgtcc      300
cgcgacatcg acagcgtcca gctgctggcg ggcgcctatg cgacgccgt cgcgccgtgg      360 ctggagaact ggcaggagct tcaccgtgca atagcacatg acgatcgcag cgtctttgaa      420
tatttccgtc gccaggcgct ggctgccgag ccgttctggc tgcatagtgg aaaacgataa      480
tttcaggcca gggagccctt atggcgctga agcacctgat cacgctctgc gcggcgtcgc      540
cgatggtcgc cagccagctg gcgcgccacc cgctgctgct ggatgagctg ctggatccca      600
acaccctcta tcagccgacg gcgaccgatg cctatcgcga cgagctgcgc cagtacctgc      660
tgcgcgtgcc ggaagaggat gaagagcagc agctgcatat cgcggcggcg gatatcgctg      720
gtaccctgcc ggtgatgaag gtcagcgatc acttaacctg gcttgccgaa gcgatcctcg      780
acgcggtggt gcagcaggca tggggcagat ggtcgctcg ctacggccag ccgacccacc      840
tgcacgatcg ccagggtcgc ggcttcgccg tcgtcggcta cggtaagctt ggcggctggg      900
agctgggcta cagctccgat ctcgatctgg tgttcctcca tgactgcccg gcggaggtga      960
tgaccgacgg cgagcgggag attgacggcc gtcagttcta cctgcggctg gcccagcgga     1020
tcatgcacct gttcagcacc cgcacctcgt ccggtattct ctacgaagtg gacgcccggc     1080
tgcgtccttc tggcgcggcg gggatgctgg tcaccaccgc cgacgcgttt gctgactatc     1140
agcagaacga agcctggacg tgggaacatc aggcgctggt gcgcgccgc gtggtctatg     1200 gcgacccggc gctgcaggcg cgctttgacg ccattcgtcg cgatatcctg accaccccgc     1260
gggaggggat gaccctgcag accgaggttc gcgagatgcg cgagaagatg cgcgcccacc     1320
ttggcaacaa acatcccgat cgttttgata tcaaagccga tgccggcggg atcaccgata     1380
ttgaatttat tactcagtat ctggtcctac gctatgccag tgcacaagccg aagctgaccc     1440 gctggtctga caacgtgcgt attcttgagc tgctggcgca gaacgacatc atggacgagg     1500
aggaggcgcg cgccttaacg catgcgtaca ccaccttgcg tgatgcgctc catcacctgg     1560
ccctgcagga gcagccggga cacgtggcgc cagaggcctt cagccgggag cgtcagcagg     1620
tcagcgccag ctggcagaag tggctgatgg cttaactata aaatcgggtg tgctattatc     1680
gcgcgcaaag tttgcgtctc gcaggagaga gtcatgaaag taacgctgcc ggagtttgaa     1740
cgtgcaggag tgttggtggt gggtgatgtg atgctggacc gctactggta cggccccacc     1800
agtcgtattt ccccggaagc cccggtgccg gtggtgaagg tggaaaatat cgaagaacgt     1860
cctggcggcg cggcaaacgt agcgatgaac atcgcctccc tggggggcaac gtcgcgcctg     1920 gtgggattga ccgggattga tgacgctgcc cgcgcgctga gccaggcgct ggccaatgtg     1980
aatgtgaagt gcgacttcgt ctccgtcccg actcacccga ccatcaccaa gctgcgggtg     2040
```

```
ctgtcgcgca atcagcagct gatccgcctc gactttgaag agggcttctc cggcgtggat      2100
ccgcagccga tgcatgagcg cattcagcag gcgctgggag ccattggcgc actgg          2155
```

```
<210> SEQ ID NO 197
<211> LENGTH: 412
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm8.2

<400> SEQUENCE: 197
atgaccctga atatgatgct cgacgccgtc ctcgcagtac cattgcaacc gactttacag        60
caagaagtga ttctggcacg catggaacaa attcttgcca gtcgggcttt atccgatgac       120
gaacgcgcac agctttttata tgagcgcgga gtgttgtatg atagtctcgg tctgagggca       180
ttagcgcgaa atgattttttc acaagcgctg gcaatccgac ccgatatgcc tgaagtattc       240
aattacttag gcatttactt aacgcaggca ggcaattttg atgctgccta tgaagcgttt       300
gattctgtac ttgagcttga tcgccattga gctggcttcc cgaccgcagg gcggcacctg       360
cctgaccctg cgtttcccgc tgtttaacac cctgaccgga ggtgaagcat ga              412
```

```
<210> SEQ ID NO 198
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm8.2 with 500bp flank

<400> SEQUENCE: 198
cccaacagca gggccgggta ggccagcagg tccgccagcg tggcgcggtt aatattgacc        60
ggggcggcgg cggcctcccc cagctgcttg tggatcattt tcgcgatctt gcgggttttta      120 ccggtatcgg taccaaagaa aatgccaatg ttcgccatag tacgctcctg tcggaatggt       180
gttgaaaaaa ggaatgacga cagaggtatt gcgaaggctg tgccaggttg ccctgcaccg       240
cgacggccca tccctgcccc atcaggatcg cttcgcatca cgatgccgcg cgccaaaggc       300
gcacccggcg gggcgaaagg taaaaatccg tgaattttcc ccctgtcgga tcaatgtttc       360
gcgtggtcgt tccgataagg cgcgcacactt tgcatggtta tccgggttcg gcttaccccg      420
ccgcgttttg cgcacggtgt cggacaattt gtcataactg cgacacagga gtttgcgatg       480
accctgaata tgatgctcga cgccgtcctc gcagtaccat tgcaaccgac tttacagcaa       540
gaagtgattc tggcacgcat ggaacaaatt cttgccagtc gggctttatc cgatgacgaa       600
cgcgcacagc tttttatatga gcgcggagtt ttgtatgata gtctcggtct gagggcatta      660
gcgcgaaatg attttttcaca agcgctggca atccgacccg atatgcctga gtattcaat       720 tacttaggca tttacttaac gcaggcaggc aattttgatg ctgcctatga agcgtttgat       780
tctgtacttg agcttgatcg ccattgagct ggcttcccga ccgcagggcg cacctgcct       840 gaccctgcgt ttcccgctgt ttaacaccct gaccggaggt gaagcatgat ccctgaatcc       900
gacccggaca ccaccgtcag acgcttcgac ctctctcagc agttcaccgc catgcagcgg       960
ataagcgtgg tgctgagccg ggccaccgag gccagcaaaa cgctgcagga ggtgctcagc      1020
gtattacaca acgatgcctt tatgcagcac gggatgatct gcctgtacga cagcgagcag      1080
```
gagatcctca gtatcgaagc gctgcagcaa accggccagc agcccctccc cgggcagcacg      1140 cagatccgct atcgccccgg cgagggactg gtggggaccg tgctggccca ggggcagtcg      1200
ctggtgctgc cccgggtcgc cgacgatcag cgttttctcg accgcctgag cctctacgat      1260
tacgatctgc cgtttatcgc cgtaccgttg atggggccca acgcccggcc aataggggtg      1320
ctggcggccc agccgatggc gcgccaggaa gagcggctgc cggcctgcac ccgttttctc      1380
gaaaccgtc                                                              1389

<210> SEQ ID NO 199
<211> LENGTH: 1155
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 36bp deletion

<400> SEQUENCE: 199
atggcgctga agcacctgat cacgctctgc gcggcgtcgc cgatggtcgc cagccagctg        60
gcgcgccacc cgctgctgct ggatgagctg ctggatccca acaccctcta tcagccgacg       120
gcgaccgatg cctatcgcga cgagctgcgc cagtacctgc tgcgcgtgcc ggaagaggat       180
gaagagcagc agctgcatat cgcggcggcg gatatcgctg gtaccctgcc ggtgatgaag       240
gtcagcgatc acttaacctg gcttgccgaa gcgatcctcg acgcggtggt gcagcaggca       300
tgggggcaga tggtcgctcg ctacggccag ccgacccacc tgcacgatcg ccagggtcgc       360
ggcttcgccg tcgtcggcta cggtaagctt ggcggctggg agctgggcta cagctccgat       420
ctcgatctgg tgttcctcca tgactgcccg gcggaggtga tgaccgacgg cgagcgggag       480
attgacggcc gtcagttcta cctgcggctg gcccagcgga tcatgcacct gttcagcacc       540
cgcacctcgt ccggtattct ctacgaagtg gacgcccggc tgcgtccttc tggcgcggcg       600
gggatgctgg tcaccaccgc cgacgcgttt gctgactatc agcagaacga agcctggacg       660
tgggaacatc aggcgctggt gcgcgcccgc gtggtctatg cgacccggc gctgcaggcg        720 cgctttgacg ccattcgtcg cgatatcctg accaccccgc gggaggggat gaccctgcag       780
accgaggttc gcgagatgcg cgagaagatg cgcgcccacc ttggcaacaa acatcccgat       840
cgttttgata tcaaagccga tgccggcggg atcaccgata ttgaatttat tactcagtat       900
ctggtcctac gctatgccag tgacaagccg aagctgaccc gctggtctga caacgtgcgt       960
attcttgagc tgctggcgca gaacgacatc atggacgagg aggaggcgcg cgccttaacg      1020
catgcgtaca ccaccttgcg tgatgcgctc catcacctgg ccctgcagga gcagccggga      1080
cacgtggcgc cagaggcctt cagccgggag cgtcagcagg tcagcgccag ctggcagaag      1140
tggctgatgg cttaa                                                      1155

<210> SEQ ID NO 200
<211> LENGTH: 2155
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 36bp deletion

<400> SEQUENCE: 200

```
cgtaaggcga  ccacccagct  ccgcgcgttg  ctgaacgacg  ctgaagccgt  tctgctggcc        60
gcggacaccg  ccgacgaggc  gttattccgc  accgaggtcg  tcggcgccaa  actggccctg       120
actgaatggc  tggtccagcg  cggctggcgt  ccgttcctca  acgaggcagg  agagaaaaaa       180
atagccggat  cgttcaaacg  gtttgccgat  attaacctct  cgcgggtggc  ggccgagctg       240
cgcagcgccg  tgcagcatct  ggcggttgaa  gatgccgccg  accagttgcc  gaagctgtcc       300
cgcgacatcg  acagcgtcca  gctgctggcg  ggcgcctatg  cgacgccgt   cgcgccgtgg       360 ctggagaact  ggcaggagct  tcaccgtgca  atagcacatg  acgatcgcag  cgtctttgaa       420
tatttccgtc  gccaggcgct  ggctgccgag  ccgttctggc  tgcatagtgg  aaaacgataa       480
tttcaggcca  gggagccctt  atggcgctga  agcacctgat  cacgctctgc  gcggcgtcgc       540
cgatggtcgc  cagccagctg  gcgcgccacc  cgctgctgct  ggatgagctg  ctggatccca       600
acaccctcta  tcagccgacg  gcgaccgatg  cctatcgcga  cgagctgcgc  cagtacctgc       660
tgcgcgtgcc  ggaagaggat  gaagagcagc  agctgcatat  cgcggcggcg  gatatcgctg       720
gtaccctgcc  ggtgatgaag  gtcagcgatc  acttaacctg  gcttgccgaa  gcgatcctcg       780
acgcggtggt  gcagcaggca  tgggggcaga  tggtcgctcg  ctacggccag  ccgacccacc       840
tgcacgatcg  ccagggtcgc  ggcttcgccg  tcgtcggcta  cggtaagctt  ggcggctggg       900
agctgggcta  cagctccgat  ctcgatctgg  tgttcctcca  tgactgcccg  gcggaggtga       960 tgaccgacg   cgagcgggag  attgacggcc  gtcagttcta  cctgcggctg  gcccagcgga      1020
tcatgcacct  gttcagcacc  cgcacctcgt  ccggtattct  ctacgaagtg  gacgcccggc      1080
tgcgtccttc  tggcgcggcg  gggatgctgg  tcaccaccgc  cgacgcgttt  gctgactatc      1140
agcagaacga  agcctggacg  tgggaacatc  aggcgctggt  gcgcgcccgc  gtggtctatg      1200 gcgaccggc   gctgcaggcg  cgctttgacg  ccattcgtcg  cgatatcctg  accaccccgc      1260
gggaggggat  gaccctgcag  accgaggttc  gcgagatgcg  cgagaagatg  cgcgcccacc      1320
ttggcaacaa  acatcccgat  cgttttgata  tcaaagccga  tgccggcggg  atcaccgata      1380
ttgaatttat  tactcagtat  ctggtcctac  gctatgccag  tgacaagccg  aagctgaccc      1440
gctggtctga  caacgtgcgt  attcttgagc  tgctggcgca  gaacgacatc  atggacgagg      1500
aggaggcgcg  cgccttaacg  catgcgtaca  ccaccttgcg  tgatgcgctc  catcacctgg      1560
ccctgcagga  gcagccggga  cacgtggcgc  cagaggcctt  cagccgggag  cgtcagcagg      1620
tcagcgccag  ctggcagaag  tggctgatgg  cttaactata  aaatcgggtg  tgctattatc      1680
gcgcgcaaag  tttgcgtctc  gcaggagaga  gtcatgaaag  taacgctgcc  ggagtttgaa      1740
cgtgcaggag  tgttggtggt  gggtgatgtg  atgctggacc  gctactggta  cggccccacc      1800
agtcgtattt  ccccggaagc  cccggtgccg  gtggtgaagg  tggaaaatat  cgaagaacgt      1860
cctggcggcg  cggcaaacgt  agcgatgaac  atcgcctccc  tggggggcaac  gtcgcgcctg      1920 gtgggattga  ccgggattga  tgacgctgcc  cgcgcgctga  gccaggcgct  ggccaatgtg      1980
aatgtgaagt  gcgacttcgt  ctccgtcccg  actcacccga  ccatcaccaa  gctgcgggtg      2040
ctgtcgcgca  atcagcagct  gatccgcctc  gactttgaag  agggcttctc  cggcgtggat      2100
ccgcagccga  tgcatgagcg  cattcagcag  gcgctgggag  ccattggcgc  actgg          2155
```

<210> SEQ ID NO 201
<211> LENGTH: 413
<212> TYPE: DNA
<213> ORGANISM: Artificial Sequence
<220> FEATURE:
<223> OTHER INFORMATION: Description of Artificial Sequence: Synthetic

```
        polynucleotide
<220> FEATURE:
<223> OTHER INFORMATION: delta-nifL::Prm6.2

<400> SEQUENCE: 201
atgaccctga atatgatgct cgagctaaag ttctcggcta atcgctgata acatttgacg      60
caatgcgcaa taaaagggca tcatttgatg cccttttttgc acgctttcat accagaacct     120
ggctcatcag tgattttttt tgtcataatc attgctgaga caggctctga agagggcgtt     180
tatacaccaa accattcgag cggtagcgcg acggcaagtc agcgttctcc tttgcaatag     240
cagggaagag cgccagaac cgccagcgtt gaagcagttt gaacgcgttc agtgtataat     300
ccgaaactta atttcggttt ggagccattg agctggcttc ccgaccgcag ggcggcacct     360
gcctgaccct gcgtttcccg ctgtttaaca ccctgaccgg aggtgaagca tga          413

<210> SEQ ID NO 202
<211> LENGTH: 1413
<212> TYPE: DNA
<213> ORGANISM: Artificial Sequence
<220> FEATURE:
<223> OTHER INFORMATION: Description of Artificial Sequence: Synthetic
        polynucleotide
<220> FEATURE:
<223> OTHER INFORMATION: delta-nifL::Prm6.2 with 500bp flank

<400> SEQUENCE: 202
ggccgtcgcc cagcgtcggc gtccccaaca gcagggccgg gtaggccagc aggtccgcca      60
gcgtggcgcg gttaatattg accggggcgg cggcggcctc ccccagctgc ttgtggatca     120
ttttcgcgat cttgcgggtt ttaccggtat cggtaccaaa gaaaatgcca atgttcgcca     180
tagtacgctc ctgtcggaat ggtgttgaaa aaaggaatga cgacagaggt attgcgaagg     240
ctgtgccagg ttgccctgca ccgcgacggc ccatccctgc cccatcagga tcgcttcgca     300
tcacgatgcc gcgcgccaaa ggcgcacccg gcggggcgaa aggtaaaaat ccgtgaattt     360
tccccctgtc ggatcaatgt ttcgcgtggt cgttccgata agggcgcaca ctttgcatgg     420
ttatccgggt tcggcttacc ccgccgcgtt ttgcgcacgg tgtcggacaa tttgtcataa     480
ctgcgacaca ggagtttgcg atgaccctga atatgatgct cgagctaaag ttctcggcta     540
atcgctgata acatttgacg caatgcgcaa taaaagggca tcatttgatg cccttttttgc     600 acgctttcat accagaacct ggctcatcag tgattttttt tgtcataatc attgctgaga     660
caggctctga agagggcgtt tatacaccaa accattcgag cggtagcgcg acggcaagtc     720
agcgttctcc tttgcaatag cagggaagag cgccagaac cgccagcgtt gaagcagttt     780
gaacgcgttc agtgtataat ccgaaactta atttcggttt ggagccattg agctggcttc     840
ccgaccgcag ggcggcacct gcctgaccct gcgtttcccg ctgtttaaca ccctgaccgg     900
aggtgaagca tgatccctga atccgacccg gacaccaccg tcagacgctt cgacctctct     960
cagcagttca ccgccatgca gcggataagc gtggtgctga gccgggccac cgaggccagc    1020
aaaacgctgc aggaggtgct cagcgtatta cacaacgatg cctttatgca gcacgggatg    1080
atctgcctgt acgacagcga gcaggagatc ctcagtatcg aagcgctgca gcaaaccggc    1140
cagcagcccc tccccggcag cacgcagatc cgctatcgcc ccggcgaggg actggtgggg    1200
accgtgctgg cccaggggca gtcgctggtg ctgccccggg tcgccgacga tcagcgtttt    1260
ctcgaccgcc tgagcctcta cgattacgat ctgccgttta tcgccgtacc gttgatgggg    1320
cccaacgccc ggccaatagg ggtgctggcg gcccagccga tggcgcgcca ggaagagcgg    1380
```

-continued

```
ctgccggcct gcacccgttt tctcgaaacc gtc                              1413
```

```
<210> SEQ ID NO 203
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1.2

<400> SEQUENCE: 203
atgaccctga atatgatgct cgagcccgct gaccgaccag aacttccacc ttggactcgg      60
ctataccctt ggcgtgacgg cgcgcgataa ctgggactac atccccattc cggtgatctt     120
accattggcg tcaataggtt acggtccggc gactttccag atgacctata ttcccggcac     180
ctacaataac ggtaacgttt acttcgcctg ggctcgtata cagtttaat tcgctaagtc      240 ttagcaataa atgagataag cggtgtgtct tgtggaaaaa caaggactaa agcgttaccc     300
actaaaaaag atagcgactt ttatcacttt ttagcaaagt tgcactggac aaaaggtacc     360
acaattggtg tactgatact cgacacagca ttagtgtcga tttttcatat aaaggtaatt     420
ttggccattg agctggcttc ccgaccgcag ggcggcacct gcctgaccct gcgtttcccg     480
ctgtttaaca ccctgaccgg aggtgaagca tga                                  513
```

```
<210> SEQ ID NO 204
<211> LENGTH: 1513
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1.2 with 500bp flank

<400> SEQUENCE: 204
ggccgtcgcc cagcgtcggc gtccccaaca gcagggccgg gtaggccagc aggtccgcca      60
gcgtggcgcg gttaatattg accggggcgg cggcggcctc ccccagctgc ttgtggatca     120
ttttcgcgat cttgcgggtt ttaccggtat cggtaccaaa gaaaatgcca atgttcgcca     180
tagtacgctc ctgtcggaat ggtgttgaaa aaaggaatga cgacagaggt attgcgaagg     240
ctgtgccagg ttgccctgca ccgcgacggc ccatccctgc cccatcagga tcgcttcgca     300
tcacgatgcc gcgcgccaaa ggcgcacccg gcggggcgaa aggtaaaaat ccgtgaattt     360 tcccctgtc ggatcaatgt ttcgcgtggt cgttccgata agggcgcaca ctttgcatgg      420
ttatccgggt tcggcttacc ccgccgcgtt ttgcgcacgg tgtcggacaa tttgtcataa     480
ctgcgacaca ggagtttgcg atgaccctga atatgatgct cgagcccgct gaccgaccag     540
aacttccacc ttggactcgg ctataccctt ggcgtgacgg cgcgcgataa ctgggactac     600
atccccattc cggtgatctt accattggcg tcaataggtt acggtccggc gactttccag     660
atgacctata ttcccggcac ctacaataac ggtaacgttt acttcgcctg ggctcgtata     720
cagttttaat tcgctaagtc ttagcaataa atgagataag cggtgtgtct tgtggaaaaa     780
caaggactaa agcgttaccc actaaaaaag atagcgactt ttatcacttt ttagcaaagt     840
tgcactggac aaaaggtacc acaattggtg tactgatact cgacacagca ttagtgtcga     900 ttttcatat aaaggtaatt ttggccattg agctggcttc ccgaccgcag ggcggcacct      960
gcctgaccct gcgtttcccg ctgtttaaca ccctgaccgg aggtgaagca tgatccctga    1020
```

```
atccgacccg gacaccaccg tcagacgctt cgacctctct cagcagttca ccgccatgca    1080
gcggataagc gtggtgctga gccgggccac cgaggccagc aaaacgctgc aggaggtgct    1140
cagcgtatta cacaacgatg cctttatgca gcacgggatg atctgcctgt acgacagcga    1200
gcaggagatc ctcagtatcg aagcgctgca gcaaaccggc cagcagcccc tccccggcag    1260
cacgcagatc cgctatcgcc ccggcgaggg actggtgggg accgtgctgg cccaggggca    1320
gtcgctggtg ctgccccggg tcgccgacga tcagcgtttt ctcgaccgcc tgagcctcta    1380
cgattacgat ctgccgttta tcgccgtacc gttgatgggg cccaacgccc ggccaatagg    1440
ggtgctggcg gcccagccga tggcgcgcca ggaagagcgg ctgccggcct gcacccgttt    1500
tctcgaaacc gtc                                                        1513
```

<210> SEQ ID NO 205
<211> LENGTH: 1155
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 36bp deletion

<400> SEQUENCE: 205

```
atggcgctga agcacctgat cacgctctgc gcggcgtcgc cgatggtcgc cagccagctg      60
gcgcgccacc cgctgctgct ggatgagctg ctggatccca acaccctcta tcagccgacg     120
gcgaccgatg cctatcgcga cgagctgcgc cagtacctgc tgcgcgtgcc ggaagaggat     180
gaagagcagc agctgcatat cgcggcggcg gatatcgctg gtaccctgcc ggtgatgaag     240
gtcagcgatc acttaacctg gcttgccgaa gcgatcctcg acgcggtggt gcagcaggca     300
tgggggcaga tggtcgctcg ctacggccag ccgacccacc tgcacgatcg ccagggtcgc     360
ggcttcgccg tcgtcggcta cggtaagctt ggcggctggg agctgggcta cagctccgat     420
ctcgatctgg tgttcctcca tgactgcccg gcggaggtga tgaccgacgg cgagcgggag     480
attgacggcc gtcagttcta cctgcggctg gcccagcgga tcatgcacct gttcagcacc     540
cgcacctcgt ccggtattct ctacgaagtg gacgcccggc tgcgtccttc tggcgcggcg     600
gggatgctgg tcaccaccgc cgacgcgttt gctgactatc agcagaacga gcctggacg      660 tgggaacatc aggcgctggt gcgcgcccgc gtggtctatg gcgacccggc gctgcaggcg     720
cgctttgacg ccattcgtcg cgatatcctg accacccgc gggaggggat gaccctgcag      780
accgaggttc gcgagatgcg cgagaagatg cgcgcccacc ttggcaacaa acatcccgat     840
cgttttgata tcaaagccga tgccggcggg atcaccgata ttgaatttat tactcagtat     900
ctggtcctac gctatgccag tgacaagccg aagctgaccc gctggtctga caacgtgcgt     960
attcttgagc tgctggcgca gaacgacatc atggacgagg aggaggcgcg cgccttaacg    1020
catgcgtaca ccaccttgcg tgatgcgctc catcacctgg ccctgcagga gcagccggga    1080
cacgtggcgc cagaggcctt cagccgggag cgtcagcagg tcagcgccag ctggcagaag    1140
tggctgatgg cttaa                                                     1155
```

<210> SEQ ID NO 206
<211> LENGTH: 2155
<212> TYPE: DNA
<213> ORGANISM: Artificial Sequence
<220> FEATURE:
<223> OTHER INFORMATION: Description of Artificial Sequence: Synthetic -continued

```
        polynucleotide
<220> FEATURE:
<223> OTHER INFORMATION: glnE-delta-AR-2 36bp deletion

<400> SEQUENCE: 206
cgtaaggcga ccacccagct ccgcgcgttg ctgaacgacg ctgaagccgt tctgctggcc      60
gcggacaccg ccgacgaggc gttattccgc accgaggtcg tcggcgccaa actggccctg     120
actgaatggc tggtccagcg cggctggcgt ccgttcctca acgaggcagg agagaaaaaa     180
atagccggat cgttcaaacg gtttgccgat attaacctct cgcgggtggc ggccgagctg     240
cgcagcgccg tgcagcatct ggcggttgaa gatgccgccg accagttgcc gaagctgtcc     300
cgcgacatcg acagcgtcca gctgctggcg ggcgcctatg gcgacgccgt cgcgccgtgg     360
ctggagaact ggcaggagct tcaccgtgca atagcacatg acgatcgcag cgtctttgaa     420
tatttccgtc gccaggcgct ggctgccgag ccgttctggc tgcatagtgg aaaacgataa     480
tttcaggcca gggagccctt atggcgctga agcacctgat cacgctctgc gcggcgtcgc     540
cgatggtcgc cagccagctg gcgcgccacc cgctgctgct ggatgagctg ctggatccca     600
acaccctcta tcagccgacg gcgaccgatg cctatcgcga cgagctgcgc cagtacctgc     660
tgcgcgtgcc ggaagaggat gaagagcagc agctgcatat cgcggcggcg gatatcgctg     720
gtaccctgcc ggtgatgaag gtcagcgatc acttaacctg gcttgccgaa gcgatcctcg     780
acgcggtggt gcagcaggca tggggggcaga tggtcgctcg ctacggccag ccgacccacc     840
tgcacgatcg ccagggtcgc ggcttcgccg tcgtcggcta cggtaagctt ggcggctggg     900
agctgggcta cagctccgat ctcgatctgg tgttcctcca tgactgcccg gcggaggtga     960
tgaccgacgg cgagcgggag attgacggcc gtcagttcta cctgcggctg gcccagcgga    1020
tcatgcacct gttcagcacc cgcacctcgt ccggtattct ctacgaagtg gacgcccggc    1080
tgcgtccttc tggcgcggcg gggatgctgg tcaccaccgc cgacgcgttt gctgactatc    1140
agcagaacga agcctggacg tgggaacatc aggcgctggt gcgcgcccgc gtggtctatg    1200
gcgacccggc gctgcaggcg cgctttgacg ccattcgtcg cgatatcctg accaccccgc    1260
gggaggggat gaccctgcag accgaggttc gcgagatgcg cgagaagatg cgcgcccacc    1320
ttggcaacaa acatcccgat cgttttgata tcaaagccga tgccggcggg atcaccgata    1380
ttgaatttat tactcagtat ctggtcctac gctatgccag tgacaagccg aagctgaccc    1440
gctggtctga caacgtgcgt attcttgagc tgctggcgca gaacgacatc atggacgagg    1500
aggaggcgcg cgccttaacg catgcgtaca ccaccttgcg tgatgcgctc catcacctgg    1560
ccctgcagga gcagccggga cacgtggcgc cagaggcctt cagccgggag cgtcagcagg    1620
tcagcgccag ctggcagaag tggctgatgg cttaactata aaatcgggtg tgctattatc    1680
gcgcgcaaag tttgcgtctc gcaggagaga gtcatgaaag taacgctgcc ggagtttgaa    1740
cgtgcaggag tgttggtggt gggtgatgtg atgctggacc gctactggta cggccccacc    1800
agtcgtattt ccccggaagc cccggtgccg gtggtgaagg tggaaaatat cgaagaacgt    1860
cctggcggcg cggcaaacgt agcgatgaac atcgcctccc tggggcaac gtcgcgcctg    1920 gtgggattga ccgggattga tgacgctgcc cgcgcgctga gccaggcgct ggccaatgtg    1980
aatgtgaagt gcgacttcgt ctccgtcccg actcacccga ccatcaccaa gctgcgggtg    2040
ctgtcgcgca atcagcagct gatccgcctc gactttgaag agggcttctc cggcgtggat    2100
ccgcagccga tgcatgagcg cattcagcag gcgctgggag ccattggcgc actgg         2155
```

```
<210> SEQ ID NO 207
<211> LENGTH: 613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC

<400> SEQUENCE: 207
atgaccctga atatgatgct agaagcgtca ggtaccggtc atgattcacc gtgcgattct        60
cggttccctg gagcgcttca ttggcatcct gaccgaagag ttcgctggct tcttcccaac       120
ctggattgca ccagtgcagg tagtggtcat gaatattacc gattctcagg ctgaatacgt       180
taacgaattg acgcgtaaac tacaaaatgc gggcattcgt gtaaaagcag acttgagaaa       240
tgagaagatt ggctttaaaa tccgcgagca cactttacgt cgtgtcccgt atatgttggt       300
ctgtggcgac aaagaagtcg aagccggcaa agtggccgtg cgcacccgtc gcgggaaaga       360
cctcggcagc atggacgtaa gtgaagtgat tgagaagctg caacaagaga ttcgcagccg       420
cagtcttcaa caactggagg aataaggtat taaaggcgga aaacgagttc aaacggcacg       480
tccgaatcgt atcaatggcg agattcgcgc cctggaagtt cgcgccattg agctggcttc       540
ccgaccgcag ggcggcacct gcctgaccct gcgtttcccg ctgtttaaca ccctgaccgg       600
aggtgaagca tga                                                          613

<210> SEQ ID NO 208
<211> LENGTH: 1613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC with 500bp flank

<400> SEQUENCE: 208
ggccgtcgcc cagcgtcggc gtccccaaca gcagggccgg gtaggccagc aggtccgcca        60
gcgtggcgcg gttaatattg accggggcgg cggcggcctc ccccagctgc ttgtggatca       120
ttttcgcgat cttgcgggtt ttaccggtat cggtaccaaa gaaaatgcca atgttcgcca       180
tagtacgctc ctgtcggaat ggtgttgaaa aaaggaatga cgacagaggt attgcgaagg       240
ctgtgccagg ttgccctgca ccgcgacggc ccatccctgc cccatcagga tcgcttcgca       300
tcacgatgcc gcgcgccaaa ggcgcacccg gcggggcgaa aggtaaaaat ccgtgaattt       360
tccccctgtc ggatcaatgt ttcgcgtggt cgttccgata agggcgcaca ctttgcatgg       420
ttatccgggt cggcttacc ccgccgcgtt ttgcgcacgg tgtcggacaa tttgtcataa       480
ctgcgacaca ggagtttgcg atgaccctga atatgatgct agaagcgtca ggtaccggtc       540
atgattcacc gtgcgattct cggttccctg gagcgcttca ttggcatcct gaccgaagag       600
ttcgctggct tcttcccaac ctggattgca ccagtgcagg tagtggtcat gaatattacc       660
gattctcagg ctgaatacgt taacgaattg acgcgtaaac tacaaaatgc gggcattcgt       720
gtaaaagcag acttgagaaa tgagaagatt ggctttaaaa tccgcgagca cactttacgt       780
cgtgtcccgt atatgttggt ctgtggcgac aaagaagtcg aagccggcaa agtggccgtg       840
cgcacccgtc gcgggaaaga cctcggcagc atggacgtaa gtgaagtgat tgagaagctg       900
caacaagaga ttcgcagccg cagtcttcaa caactggagg aataaggtat taaaggcgga       960
```

-continued

```
aaacgagttc aaacggcacg tccgaatcgt atcaatggcg agattcgcgc cctggaagtt    1020
cgcgccattg agctggcttc ccgaccgcag ggcggcacct gcctgaccct gcgtttcccg    1080
ctgtttaaca ccctgaccgg aggtgaagca tgatccctga atccgacccg gacaccaccg    1140
tcagacgctt cgacctctct cagcagttca ccgccatgca gcggataagc gtggtgctga    1200
gccgggccac cgaggccagc aaaacgctgc aggaggtgct cagcgtatta cacaacgatg    1260
cctttatgca gcacgggatg atctgcctgt acgacagcga gcaggagatc ctcagtatcg    1320
aagcgctgca gcaaaccggc cagcagcccc tccccggcag cacgcagatc cgctatcgcc    1380
ccggcgaggg actggtgggg accgtgctgg cccaggggca gtcgctggtg ctgccccggg    1440
tcgccgacga tcagcgtttt ctcgaccgcc tgagcctcta cgattacgat ctgccgttta    1500
tcgccgtacc gttgatgggg cccaacgccc ggccaatagg ggtgctggcg cccagccga     1560 tggcgcgcca ggaagagcgg ctgccggcct gcacccgttt tctcgaaacc gtc            1613
```

```
<210> SEQ ID NO 209
<211> LENGTH: 1191
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 209
```

```
atggcgctga agcacctgat cacgctctgc gcggcgtcgc cgatggtcgc cagccagctg     60
gcgcgccacc cgctgctgct ggatgagctg ctggatccca acaccctcta tcagccgacg    120
gcgaccgatg cctatcgcga cgagctgcgc cagtacctgc tgcgcgtgcc ggaagaggat    180
gaagagcagc agctggaggc gttgcgccag tttaagcagg cgcagcagct gcatatcgcg    240
gcggcggata tcgctggtac cctgccggtg atgaaggtca gcgatcactt aacctggctt    300
gccgaagcga tcctcgacgc ggtggtgcag caggcatggg ggcagatggt cgctcgctac    360
ggccagccga cccacctgca cgatcgccag ggtcgcggct cgccgtcgt cggctacggt     420 aagcttggcg gctgggagct gggctacagc tccgatctcg atctggtgtt cctccatgac    480
tgcccggcgg aggtgatgac cgacggcgag cgggagattg acggccgtca gttctacctg    540
cggctggccc agcggatcat gcacctgttc agcacccgca cctcgtccgg tattctctac    600
gaagtggacg cccggctgcg tccttctggc gcggcgggga tgctggtcac caccgccgac    660
gcgtttgctg actatcagca gaacgaagcc tggacgtggg aacatcaggc gctggtgcgc    720
gcccgcgtgg tctatggcga cccggcgctg caggcgcgct ttgacgccat tcgtcgcgat    780
atcctgacca ccccgcggga ggggatgacc ctgcagaccg aggttcgcga gatgcgcgag    840
aagatgcgcg cccaccttgg caacaaacat cccgatcgtt ttgatatcaa agccgatgcc    900
ggcgggatca ccgatattga atttattact cagtatctgg tcctacgcta tgccagtgac    960
aagccgaagc tgaccgctg gtctgacaac gtgcgtattc ttgagctgct ggcgcagaac    1020
gacatcatgg acgaggagga ggcgcgcgcc ttaacgcatg cgtacaccac cttgcgtgat    1080
gcgctccatc acctggccct gcaggagcag ccggacacg tggcgccaga ggccttcagc    1140
cgggagcgtc agcaggtcag cgccagctgg cagaagtggc tgatggctta a             1191
```

```
<210> SEQ ID NO 210
<211> LENGTH: 2191
<212> TYPE: DNA
```

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 210
cgtaaggcga ccacccagct ccgcgcgttg ctgaacgacg ctgaagccgt tctgctggcc        60
gcggacaccg ccgacgaggc gttattccgc accgaggtcg tcggcgccaa actggccctg       120
actgaatggc tggtccagcg cggctggcgt ccgttcctca acgaggcagg agagaaaaaa       180
atagccggat cgttcaaacg gtttgccgat attaacctct cgcgggtggc ggccgagctg       240
cgcagcgccg tgcagcatct ggcggttgaa gatgccgccg accagttgcc gaagctgtcc       300
cgcgacatcg acagcgtcca gctgctggcg ggcgcctatg cgacgccgt cgcgccgtgg       360 ctggagaact ggcaggagct tcaccgtgca atagcacatg acgatcgcag cgtctttgaa       420
tatttccgtc gccaggcgct ggctgccgag ccgttctggc tgcatagtgg aaaacgataa       480
tttcaggcca gggagccctt atggcgctga agcacctgat cacgctctgc gcggcgtcgc       540
cgatggtcgc cagccagctg gcgcgccacc cgctgctgct ggatgagctg ctggatccca       600
acaccctcta tcagccgacg gcgaccgatg cctatcgcga cgagctgcgc cagtacctgc       660
tgcgcgtgcc ggaagaggat gaagagcagc agctggaggc gttgcgccag tttaagcagg       720
cgcagcagct gcatatcgcg gcggcggata tcgctggtac cctgccggtg atgaaggtca       780
gcgatcactt aacctggctt gccgaagcga tcctcgacgc ggtggtgcag caggcatggg       840
ggcagatggt cgctcgctac ggccagccga cccacctgca cgatcgccag ggtcgcggct       900
tcgccgtcgt cggctacggt aagcttggcg gctgggagct gggctacagc tccgatctcg       960
atctggtgtt cctccatgac tgcccggcgg aggtgatgac cgacggcgag cgggagattg      1020
acggccgtca gttctacctg cggctggccc agcggatcat gcacctgttc agcacccgca      1080
cctcgtccgg tattctctac gaagtggacg cccggctgcg tccttctggc gcggcgggga      1140
tgctggtcac caccgccgac gcgtttgctg actatcagca gaacgaagcc tggacgtggg      1200
aacatcaggc gctggtgcgc gcccgcgtgg tctatggcga cccggcgctg caggcgcgct      1260
ttgacgccat tcgtcgcgat atcctgacca ccccgcggga ggggatgacc ctgcagaccg      1320
aggttcgcga gatgcgcgag aagatgcgcg cccaccttgg caacaaacat cccgatcgtt      1380
ttgatatcaa agccgatgcc ggcgggatca ccgatattga atttattact cagtatctgg      1440
tcctacgcta tgccagtgac aagccgaagc tgacccgctg gtctgacaac gtgcgtattc      1500
ttgagctgct ggcgcagaac gacatcatgg acgaggagga ggcgcgcgcc ttaacgcatg      1560
cgtacaccac cttgcgtgat gcgctccatc acctggccct gcaggagcag ccgggacacg      1620
tggcgccaga ggccttcagc cgggagcgtc agcaggtcag cgccagctgg cagaagtggc      1680
tgatggctta actataaaat cgggtgtgct attatcgcgc gcaaagtttg cgtctcgcag      1740
gagagagtca tgaaagtaac gctgccggag tttgaacgtg caggagtgtt ggtggtgggt      1800
gatgtgatgc tggaccgcta ctggtacggc cccaccagtc gtatttcccc ggaagccccg      1860
gtgccggtgg tgaaggtgga aaatatcgaa gaacgtcctg cggcgcggc aaacgtagcg      1920 atgaacatcg cctccctggg ggcaacgtcg cgcctggtgg gattgaccgg gattgatgac      1980 gctgccgcg cgctgagcca ggcgctggcc aatgtgaatg tgaagtgcga cttcgtctcc      2040
gtcccgactc acccgaccat caccaagctg cgggtgctgt cgcgcaatca gcagctgatc      2100

-continued

```
cgcctcgact ttgaagaggg cttctccggc gtggatccgc agccgatgca tgagcgcatt   2160
cagcaggcgc tgggagccat tggcgcactg g                                    2191

<210> SEQ ID NO 211
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 211
atggcgctca aacagttaat ccgtctgtgt gccgcctcgc cgatggtcgc gacacaactt     60
gcacgtcatc ctttattgct cgatgaactg ctcgacccgc gcacgcttta ccagccgatt    120
gagccgggcg cttaccgcga cgaactgcgt cagtatctga tgcgggtgcc aacagaagac    180
gaagaacagc agcttgaagc cgtgcgccag ttcaaacagg cccagcattt gcgtatcgca    240
gccggggata tttccggggc attgccggtg atgaaagtca gtgaccattt aacctacctt    300
gccgaggcca ttctcgatgt cgtggtgcag catgcgtggg aacaaatggt cgtaaaatac    360
gggcagcccg cgcatcttca gcaccgtgag gggcgcggtt ttgccgtggt cggttacggg    420
aaactcggtg gctgggagct gggttatagc tcagatctgg atctggtctt cctgctcgat    480
tgcgcgccgg aggtgatgac ggacggcgaa cgcagcatcg acggacgtca gttttatctt    540
cggctggcgc agcgcattat gcacttattc agcacccgga catcgtcagg cattctttac    600
gaggttgatc cgcgtctgcg accttccggc gcatccggca tgctggtcag taccattgaa    660
gcgtttgcag attatcaggc caatgaagcc tggacgtggg agcatcaggc gctggttcgc    720
gcgcgcgtgg tttacgggga tccgcaactg acacagcaat ttaacgccac gcgtcgcgac    780
attctttgcc gccagcgcga tggcgacggc ctgcgtaagg aggtccgtga aatgcgcgag    840
aaaatgtatg cccatctggg gagtaaaaaa gcccacgagt ttgatctgaa agccgatccg    900
ggtggcatca cggatattga attcattgca caatacctgg ttctgcgttt cgcgcatgat    960
gagccgaagc tgacgcgctg gtctgataac gtgcggattt ttgaactgat ggcacgatat   1020
gacatcatgc cggaagagga agcgcgccat ctgacgcagg cttatgtgac gctgcgcgat   1080
gaaattcatc atctggcgtt gcaggaacac agcgggaaag tggccgcgga cagctttgct   1140
actgagcgcg cgcagatccg tgccagctgg gcaaagtggc tcggctga                1188

<210> SEQ ID NO 212
<211> LENGTH: 2188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 212
cggtactgga acagaaatcg gcggatgcgc aggaaatttg ttatgacacg gcctgtctga     60
agtgcaagtt agtgcttact tcctggctgg caacctcagg ctggacgccg tttattgatg    120
ataaatctgc gaagaaactg gacgcttcct tcaaacgttt tgctgacatc atgctcggtc    180
gtaccgcagc ggatctgaaa gaagcctttg cgcagccact gacggaagaa ggttatcgcg    240
atcagctggc gcgcctgaaa cgccagatca ttaccttcca tttgcttgcc ggtgcttacc    300
```

-continued

```
ctgaaaaaga cgtcgatgcg tatattgccg gctgggtgga cctgcaacag gccatcgttc      360
agcagcaaca cgcctgggag gattcggccc gttctcacgc ggtgatgatg gatgctttct      420
ggttaaacgg gcaacctcgt taactgactg actagcctgg gcaaactgcc cgggcttttt      480
tttgcaagga atctgatttc atggcgctca aacagttaat ccgtctgtgt gccgcctcgc      540
cgatggtcgc gacacaactt gcacgtcatc ctttattgct cgatgaactg ctcgacccgc      600
gcacgcttta ccagccgatt gagccgggcg cttaccgcga cgaactgcgt cagtatctga      660
tgcgggtgcc aacagaagac gaagaacagc agcttgaagc cgtgcgccag ttcaaacagg      720
cccagcattt gcgtatcgca gccggggata tttccggggc attgccggtg atgaaagtca      780
gtgaccattt aacctacctt gccgaggcca ttctcgatgt cgtggtgcag catgcgtggg      840
aacaaatggt cgtaaaatac gggcagcccg cgcatcttca gcaccgtgag gggcgcggtt      900
ttgccgtggt cggttacggg aaactcggtg gctgggagct gggttatagc tcagatctgg      960
atctggtctt cctgctcgat tgcgcgccgg aggtgatgac ggacggcgaa cgcagcatcg     1020
acggacgtca gttttatctt cggctggcgc agcgcattat gcacttattc agcacccgga     1080
catcgtcagg cattctttac gaggttgatc cgcgtctgcg accttccggc gcatccggca     1140
tgctggtcag taccattgaa gcgtttgcag attatcaggc caatgaagcc tggacgtggg     1200
agcatcaggc gctggttcgc gcgcgcgtgg tttacgggga tccgcaactg acacagcaat     1260
ttaacgccac gcgtcgcgac attctttgcc gccagcgcga tggcgacggc ctgcgtaagg     1320
aggtccgtga aatgcgcgag aaaatgtatg cccatctggg gagtaaaaaa gcccacgagt     1380
ttgatctgaa agccgatccg ggtggcatca cggatattga attcattgca caatacctgg     1440
ttctgcgttt cgcgcatgat gagccgaagc tgacgcgctg gtctgataac gtgcggattt     1500
ttgaactgat ggcacgatat gacatcatgc cggaagagga agcgcgccat ctgacgcagg     1560
cttatgtgac gctgcgcgat gaaattcatc atctggcgtt gcaggaacac agcgggaaag     1620
tggccgcgga cagctttgct actgagcgcg cgcagatccg tgccagctgg gcaaagtggc     1680
tcggctgagg gttttttattc ggctaacagg cgcttgtgat attatccggc gcattgtatt     1740
tacccgattt gatttatctg ttttggagtc ttgggatgaa agtgactttg cctgattttc     1800
accgcgcagg tgtgctggtt gtcggtgacg taatgttaga ccgttactgg tatggcccga     1860
ccaatcgtat ttctccggaa gctccggtgc cggtggtgaa ggtcagtacc attgaagagc     1920
ggcctggcgg tgcagctaac gtggcgatga acatttcatc tctgggcgcc tcttcctgtc     1980
tgatcggcct gaccggcgta gacgacgctg cgcgtgccct cagtgagcgt ctggcagaag     2040
tgaaagttaa ctgcgatttc gtcgcactat ccacacatcc taccatcacc aaactgcgaa     2100
ttttgtcccg taaccagcaa ctgatccgcc tcgactttga ggaaggtttt gaaggcgttg     2160
atctcgagcc gatgctgacc aaaataga                                         2188
```

```
<210> SEQ ID NO 213
<211> LENGTH: 635
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm6.1

<400> SEQUENCE: 213
atgagcatca cggcgttatc agcatcattt cctgagggga atatcgccag ccgcttgtcg       60
```

-continued

```
ctgcaacatc cttcactgtt ttataccgtg gttgaacaat cttcggtggc gatttcgctg      120
accgatccgc aggcgcgcat ttgttatgcc aatccggca tctgccgcca gacgggtttt       180
gcacttgaga cactttggg cgagaaccac cgtctgctgg aattttttt cacaaagcgt        240 agcgttattg aatcgcacat tttaaactgt tggccgctgt ggaagcgaat attggtgaaa      300
ggtgcggttt taaggccttt ttctttgact ctctgtcgtt acaaagttaa tatgcgcgcc      360
ctccgtctct gaagctctcg gtgaacattg ttgcgaggca ggatgcgagc tggttgtgtt      420
ttgacattac cgataatgtg ccgcgtgaac gggtgcgtta tgcccgcccg gaagcggcgt      480
tttcccgtcc ggggaatggc atggagctgc gccttatcca gacgctgatc gcccatcatc      540
gcggttcttt agatctctcg gtccgccctg atggcggcac cttgctgacg ttacgcctgc      600
cggtacagca ggttatcacc ggaggcttaa aatga                                 635
```

```
<210> SEQ ID NO 214
<211> LENGTH: 1635
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm6.1 with 500bp flank

<400> SEQUENCE: 214
tgtttcgtct cgaggccggg caactgagcg gccccgttga aaccgacctg ggctggcatc       60
tgttgttgtg cgaacaaatt cgcctgccgc aacccttgcc gaaagccgaa gccttaacgc      120
gggtgcgtca gcaactgatt gcccggcaac agaaacatta tcagcgccag tggctgcaac      180
aactgatcaa cgcctgagcc tgttctcctt cttgttgatg cagacgggtt aatgcccgtt      240
ttgcacgaaa aatgcacata aattgcctgc gttgccttat aacagcgcag ggaaatcctg      300
cctccggcct tgtgccacac cgcgctttgc ctggtttgtg gtaaaaactg gcccgctttg      360
catcctgatg cttaaaacac cccgttcaga tcaacctttg ggcagataag cccgcgaaag      420
gcctgcaaat tgcacggtta ttccgggtga gtatatgtgt gatttgggtt ccggcattgc      480
gcaataaagg ggagaaagac atgagcatca cggcgttatc agcatcattt cctgaggga       540 atatcgccag ccgcttgtcg ctgcaacatc cttcactgtt ttataccgtg gttgaacaat      600
cttcggtggc gatttcgctg accgatccgc aggcgcgcat ttgttatgcc aatccggcat      660
tctgccgcca gacgggtttt gcacttgaga cactttggg cgagaaccac cgtctgctgg       720 aattttttt cacaaagcgt agcgttattg aatcgcacat tttaaactgt tggccgctgt       780
ggaagcgaat attggtgaaa ggtgcggttt taaggccttt ttctttgact ctctgtcgtt      840
acaaagttaa tatgcgcgcc ctccgtctct gaagctctcg gtgaacattg ttgcgaggca      900
ggatgcgagc tggttgtgtt ttgacattac cgataatgtg ccgcgtgaac gggtgcgtta      960
tgcccgcccg gaagcggcgt tttcccgtcc ggggaatggc atggagctgc gccttatcca     1020
gacgctgatc gcccatcatc gcggttcttt agatctctcg gtccgccctg atggcggcac     1080
cttgctgacg ttacgcctgc cggtacagca ggttatcacc ggaggcttaa aatgacccag     1140
ttacctaccg cgggcccggt tatccggcgc tttgatatgt ctgcccagtt tacggcgctt     1200
tatcgcatca gcgtggcgct gagtcaggaa agcaacaccg ggcgcgcact ggcggcgatc     1260
ctcgaagtgc ttcacgatca tgcatttatg caatacggca tggtgtgtct gtttgataaa     1320
gaacgcaatg cactctttgt ggaatccctg catggcatcg acggcgaaag gaaaaaagag     1380
```

```
acccgccatg tccgttaccg catgggggaa ggcgtgatcg gcgcggtgat gagccagcgt      1440
caggcgctgg tgttaccgcg catttcagac gatcagcgtt ttctcgaccg cctgaatatt      1500
tacgattaca gcctgccgtt gattggcgtg ccgatccccg gtgcggataa tcagccatcg      1560
ggcgtgctgg tggcacagcc gatggcgttg cacgaagacc ggctgactgc cagtacgcgg      1620
tttttagaaa tggtc                                                      1635
```

```
<210> SEQ ID NO 215
<211> LENGTH: 635
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm6.1

<400> SEQUENCE: 215
```

```
atgagcatca cggcgttatc agcatcattt cctgagggga atatcgccag ccgcttgtcg        60
ctgcaacatc cttcactgtt ttataccgtg gttgaacaat cttcggtggc gatttcgctg       120
accgatccgc aggcgcgcat ttgttatgcc aatccggcat tctgccgcca gacgggtttt       180
gcacttgaga cactttttggg cgagaaccac cgtctgctgg aatttttttt cacaaagcgt      240
agcgttattg aatcgcacat tttaaactgt tggccgctgt ggaagcgaat attggtgaaa       300
ggtgcggttt taaggccttt ttctttgact ctctgtcgtt acaaagttaa tatgcgcgcc       360
ctccgtctct gaagctctcg gtgaacattg ttgcgaggca ggatgcgagc tggttgtgtt       420
ttgacattac cgataatgtg ccgcgtgaac gggtgcgtta tgcccgcccg gaagcggcgt       480
tttcccgtcc ggggaatggc atggagctgc gccttatcca gacgctgatc gcccatcatc       540
gcggttcttt agatctctcg gtccgccctg atggcggcac cttgctgacg ttacgcctgc       600
cggtacagca ggttatcacc ggaggcttaa aatga                                 635
```

```
<210> SEQ ID NO 216
<211> LENGTH: 1635
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm6.1 with 500bp flank

<400> SEQUENCE: 216
```

```
tgtttcgtct cgaggccggg caactgagcg ccccgttga aaccgacctg ggctggcatc        60
tgttgttgtg cgaacaaatt cgcctgccgc aacccttgcc gaaagccgaa gccttaacgc      120
gggtgcgtca gcaactgatt gcccggcaac agaaacatta tcagcgccag tggctgcaac      180
aactgatcaa cgcctgagcc tgttctcctt cttgttgatg cagacgggtt aatgcccgtt      240
ttgcacgaaa aatgcacata aattgcctgc gttgccttat aacagcgcag ggaaatcctg      300
cctccggcct tgtgccacac cgcgctttgc ctggtttgtg gtaaaaactg gcccgctttg      360
catcctgatg cttaaaacac cccgttcaga tcaacctttg ggcagataag cccgcgaaag      420
gcctgcaaat tgcacggtta ttccgggtga gtatatgtgt gatttgggtt ccggcattgc      480
gcaataaagg ggagaaagac atgagcatca cggcgttatc agcatcattt cctgagggga      540
atatcgccag ccgcttgtcg ctgcaacatc cttcactgtt ttataccgtg gttgaacaat      600
```

-continued

```
cttcggtggc gatttcgctg accgatccgc aggcgcgcat ttgttatgcc aatccggcat      660
tctgccgcca gacgggtttt gcacttgaga cacttttggg cgagaaccac cgtctgctgg      720 aattttttt cacaaagcgt agcgttattg aatcgcacat tttaaactgt tggccgctgt      780
ggaagcgaat attggtgaaa ggtgcggttt taaggccttt ttctttgact ctctgtcgtt      840
acaaagttaa tatgcgcgcc ctccgtctct gaagctctcg gtgaacattg ttgcgaggca      900
ggatgcgagc tggttgtgtt ttgacattac cgataatgtg ccgcgtgaac gggtgcgtta      960
tgcccgcccg gaagcggcgt tttcccgtcc ggggaatggc atggagctgc gccttatcca     1020
gacgctgatc gcccatcatc gcggttcttt agatctctcg gtccgccctg atggcggcac     1080
cttgctgacg ttacgcctgc cggtacagca ggttatcacc ggaggcttaa aatgacccag     1140
ttacctaccg cgggcccggt tatccggcgc tttgatatgt ctgcccagtt tacgcgcctt     1200
tatcgcatca gcgtggcgct gagtcaggaa agcaacaccg ggcgcgcact ggcggcgatc     1260
ctcgaagtgc ttcacgatca tgcatttatg caatacggca tggtgtgtct gtttgataaa     1320
gaacgcaatg cactctttgt ggaatccctg catggcatcg acggcgaaag gaaaaaagag     1380
acccgccatg tccgttaccg catgggggaa ggcgtgatcg gcgcggtgat gagccagcgt     1440
caggcgctgg tgttaccgcg catttcagac gatcagcgtt ttctcgaccg cctgaatatt     1500
tacgattaca gcctgccgtt gattggcgtg ccgatccccg gtgcggataa tcagccatcg     1560
ggcgtgctgg tggcacagcc gatggcgttg cacgaagacc ggctgactgc cagtacgcgg     1620
tttttagaaa tggtc                                                     1635
```

```
<210> SEQ ID NO 217
<211> LENGTH: 786
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm7.1

<400> SEQUENCE: 217
atgagcatca cggcgttatc agcatcattt cctgagggga atatcgccag ccgcttgtcg       60
ctgcaacatc cttcactgtt ttataccgtg gttgaacaat cttcggtggc gatttcgctg      120
accgatccgc aggcgcgcat ttgttatgcc aatccggcat tctgccgcca gacgggtttt      180
gcacttgaga cacttttggg cgagaaccac cgtctgctgg ttaaaaacgt gaccacgagc      240
attaataaac gccacgaaat gtggcgttta tttattcaaa aagtatcttc tttcataaaa      300
agtgctaaat gcagtagcag caaaattggg ataagtccca tggaatacgg ctgttttcgc      360
tgcaattttt aacttttcg taaaaaaaga tgtttcttg agcgaacgat caaaatatag      420
cgttaaccgg caaaaaatta ttctcattag aaaatagttt gtgtaatact tgtaacgcta      480
catggagatt aacttaatct agagggtttt ataccgtctc tgaagctctc ggtgaacatt      540
gttgcgaggc aggatgcgag ctggttgtgt tttgacatta ccgataatgt gccgcgtgaa      600
cgggtgcgtt atgcccgccc ggaagcggcg ttttcccgtc cggggaatgg catggagctg      660
cgccttatcc agacgctgat cgcccatcat cgcggttctt tagatctctc ggtccgccct      720
gatggcggca ccttgctgac gttacgcctg ccggtacagc aggttatcac cggaggctta      780
aaatga                                                               786
```

```
<210> SEQ ID NO 218
```

<211> LENGTH: 1786
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm7.1 with 500bp flank

<400> SEQUENCE: 218

```
gtttcgtctc gaggccgggc aactgagcgg ccccgttgaa accgacctgg gctggcatct     60
gttgttgtgc gaacaaattc gcctgccgca acccttgccg aaagccgaag ccttaacgcg    120
ggtgcgtcag caactgattg cccggcaaca gaaacattat cagcgccagt ggctgcaaca    180
actgatcaac gcctgagcct gttctccttc ttgttgatgc agacgggtta atgcccgttt    240
tgcacgaaaa atgcacataa attgcctgcg ttgcccttata acagcgcagg gaaatcctgc    300
ctccggcctt gtgccacacc gcgctttgcc tggtttgtgg taaaaactgg cccgctttgc    360
atcctgatgc ttaaaacacc ccgttcagat caacctttgg gcagataagc ccgcgaaagg    420
cctgcaaatt gcacggttat tccgggtgag tatatgtgtg atttgggttc cggcattgcg    480
caataaaggg gagaaagaca tgagcatcac ggcgttatca gcatcatttc ctgaggggaa    540
tatcgccagc cgcttgtcgc tgcaacatcc ttcactgttt tataccgtgg ttgaacaatc    600
ttcggtggcg atttcgctga ccgatccgca ggcgcgcatt tgttatgcca atccggcatt    660
ctgccgccag acgggttttg cacttgagac acttttgggc gagaaccacc gtctgctggt    720
taaaaacgtg accacgagca ttaataaacg ccacgaaatg tggcgtttat ttattcaaaa    780
agtatcttct ttcataaaaa gtgctaaatg cagtagcagc aaaattggga taagtcccat    840
ggaatacggc tgttttcgct gcaattttta actttttcgt aaaaaaagat gtttctttga    900
gcgaacgatc aaaatatagc gttaaccggc aaaaaattat tctcattaga aaatagtttg    960
tgtaatactt gtaacgctac atggagatta acttaatcta gagggtttta taccgtctct   1020
gaagctctcg gtgaacattg ttgcgaggca ggatgcgagc tggttgtgtt ttgacattac   1080
cgataatgtg ccgcgtgaac gggtgcgtta tgcccgcccg gaagcggcgt tttcccgtcc   1140
ggggaatggc atggagctgc gccttatcca gacgctgatc gcccatcatc gcggttcttt   1200
agatctctcg gtccgccctg atggcggcac cttgctgacg ttacgcctgc cggtacagca   1260
ggttatcacc ggaggcttaa aatgacccag ttacctaccg cgggcccggt tatccggcgc   1320
tttgatatgt ctgcccagtt tacggcgctt tatcgcatca gcgtggcgct gagtcaggaa   1380
agcaacaccg ggcgcgcact ggcggcgatc ctcgaagtgc ttcacgatca tgcatttatg   1440
caatacggca tggtgtgtct gtttgataaa gaacgcaatg cactctttgt ggaatccctg   1500
catggcatcg acggcgaaag gaaaaaagag acccgccatg tccgttaccg catgggggaa   1560
ggcgtgatcg gcgcggtgat gagccagcgt caggcgctgg tgttaccgcg catttcagac   1620
gatcagcgtt ttctcgaccg cctgaatatt tacgattaca gcctgccgtt gattggcgtg   1680
ccgatccccg gtgcggataa tcagccatcg ggcgtgctgg tggcacagcc gatggcgttg   1740
cacgaagacc ggctgactgc cagtacgcgg tttttagaaa tggtcg                  1786
```

<210> SEQ ID NO 219
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide <220> FEATURE:
<223> OTHER INFORMATION: delta-nifL::Prm1.2

<400> SEQUENCE: 219

```
atgagcatca cggcgttatc agcatcattt cctgagggga atatcgccag ccgcttgtcg      60
ctgcaacatc cttcactgtt ttataccgtg gttgaacaat cttcggtggc gatttcgctg     120
accgatccgc aggcgcgcat ttgttatgcc aatccggcat tctgccgcca gacgggtttt     180
gcacttgaga cacttttggg cgagaaccac cgtctgctgg tgaacatcac tgatgcacaa     240
gctacctatg tcgaagaatt aactaaaaaa ctgcaagatg caggcattcg cgttaaagcc     300
gacttgagaa atgagaagat tggctttaaa attcgcgaac acacgctacg ccgtgttcct     360
tatatgttag tttgtggcga taaagaggtc gaagcaggca agttgctgt tcgtacccgc      420 cgcggcaaag acttaggaag catggatgtt agcgaagtcg ttgacaaact gctggcggaa     480
atccgcagca gaagtcttca tcaactggag gaataaagta ttaaaggcgg aaaacgagtt     540
caaccggcgc gtcctaatcg cattaacaaa gagattcgcg cgcaagagt tcgcctcaca      600 ggcgtcgatg gcgagcagat tggtattgtc agtctgaatg aagctcttga aaaagctgag     660
gaagcgggcg tcgatttagt agaaatcagt ccgaatgccg agccgccagt ttgtcgaatc     720
ccgtctctga agctctcggt gaacattgtt gcgaggcagg atgcgagctg gttgtgtttt     780
gacattaccg ataatgtgcc gcgtgaacgg gtgcgttatg cccgcccgga agcggcgttt     840
tcccgtccgg ggaatggcat ggagctgcgc cttatccaga cgctgatcgc ccatcatcgc     900
ggttctttag atctctcggt ccgccctgat ggcggcacct tgctgacgtt acgcctgccg     960
gtacagcagg ttatcaccgg aggcttaaaa tga                                  993
```

<210> SEQ ID NO 220
<211> LENGTH: 1993
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1.2 with 500bp flank

<400> SEQUENCE: 220

```
tgtttcgtct cgaggccggg caactgagcg gccccgttga aaccgacctg ggctggcatc      60
tgttgttgtg cgaacaaatt cgcctgccgc aacccttgcc gaaagccgaa gccttaacgc     120
gggtgcgtca gcaactgatt gcccggcaac agaaacatta tcagcgccag tggctgcaac     180
aactgatcaa cgcctgagcc tgttctcctt cttgttgatg cagacgggtt aatgcccgtt     240
ttgcacgaaa aatgcacata aattgcctgc gttgccttat aacagcgcag ggaaatcctg     300
cctccggcct tgtgccacac cgcgctttgc ctggtttgtg gtaaaaactg gcccgctttg     360
catcctgatg cttaaaacac cccgttcaga tcaacctttg ggcagataag cccgcgaaag     420
gcctgcaaat tgcacggtta ttccgggtga gtatatgtgt gatttgggtt ccggcattgc     480
gcaataaagg ggagaaagac atgagcatca cggcgttatc agcatcattt cctgagggga     540
atatcgccag ccgcttgtcg ctgcaacatc cttcactgtt ttataccgtg gttgaacaat     600
cttcggtggc gatttcgctg accgatccgc aggcgcgcat ttgttatgcc aatccggcat     660
tctgccgcca gacgggtttt gcacttgaga cacttttggg cgagaaccac cgtctgctgg     720
tgaacatcac tgatgcacaa gctacctatg tcgaagaatt aactaaaaaa ctgcaagatg     780
caggcattcg cgttaaagcc gacttgagaa atgagaagat tggctttaaa attcgcgaac     840
```

```
acacgctacg ccgtgttcct tatatgttag tttgtggcga taaagaggtc gaagcaggca      900
aagttgctgt tcgtacccgc cgcggcaaag acttaggaag catggatgtt agcgaagtcg      960
ttgacaaact gctggcggaa atccgcagca gaagtcttca tcaactggag gaataaagta     1020
ttaaaggcgg aaaacgagtt caaccggcgc gtcctaatcg cattaacaaa gagattcgcg     1080
cgcaagaagt tcgcctcaca ggcgtcgatg gcgagcagat tggtattgtc agtctgaatg     1140
aagctcttga aaaagctgag gaagcgggcg tcgatttagt agaaatcagt ccgaatgccg     1200
agccgccagt ttgtcgaatc ccgtctctga agctctcggt gaacattgtt gcgaggcagg     1260
atgcgagctg gttgtgtttt gacattaccg ataatgtgcc gcgtgaacgg gtgcgttatg     1320
cccgcccgga agcggcgttt tcccgtccgg ggaatggcat ggagctgcgc cttatccaga     1380
cgctgatcgc ccatcatcgc ggttctttag atctctcggt ccgccctgat ggcggcacct     1440
tgctgacgtt acgcctgccg gtacagcagg ttatcaccgg aggcttaaaa tgacccagtt     1500
acctaccgcg ggcccggtta tccggcgctt tgatatgtct gcccagttta cggcgcttta     1560
tcgcatcagc gtggcgctga gtcaggaaag caacaccggg cgcgcactgg cggcgatcct     1620
cgaagtgctt cacgatcatg catttatgca atacggcatg gtgtgtctgt ttgataaaga     1680
acgcaatgca ctctttgtgg aatccctgca tggcatcgac ggcgaaagga aaaaagagac     1740
ccgccatgtc cgttaccgca tgggggaagg cgtgatcggc gcggtgatga gccagcgtca     1800
ggcgctggtg ttaccgcgca tttcagacga tcagcgtttt ctcgaccgcc tgaatattta     1860
cgattacagc ctgccgttga ttggcgtgcc gatccccggt gcggataatc agccatcggg     1920
cgtgctggtg gcacagccga tggcgttgca cgaagaccgg ctgactgcca gtacgcggtt     1980
tttagaaatg gtc                                                        1993
```

```
<210> SEQ ID NO 221
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1.2

<400> SEQUENCE: 221
atgagcatca cggcgttatc agcatcattt cctgagggga atatcgccag ccgcttgtcg       60
ctgcaacatc cttcactgtt ttataccgtg gttgaacaat cttcggtggc gatttcgctg      120
accgatccgc aggcgcgcat ttgttatgcc aatccggcat tctgccgcca gacgggtttt      180
gcacttgaga cactttttggg cgagaaccac cgtctgctgg tgaacatcac tgatgcacaa      240
gctacctatg tcgaagaatt aactaaaaaa ctgcaagatg caggcattcg cgttaaagcc      300
gacttgagaa atgagaagat tggctttaaa attcgcgaac acacgctacg ccgtgttcct      360
tatatgttag tttgtggcga taaagaggtc gaagcaggca aagttgctgt tcgtacccgc      420
cgcggcaaag acttaggaag catggatgtt agcgaagtcg ttgacaaact gctggcggaa      480
atccgcagca gaagtcttca tcaactggag gaataaagta ttaaaggcgg aaaacgagtt      540
caaccggcgc gtcctaatcg cattaacaaa gagattcgcg cgcaagaagt tcgcctcaca      600
ggcgtcgatg gcgagcagat tggtattgtc agtctgaatg aagctcttga aaaagctgag      660
gaagcgggcg tcgatttagt agaaatcagt ccgaatgccg agccgccagt ttgtcgaatc      720
ccgtctctga agctctcggt gaacattgtt gcgaggcagg atgcgagctg gttgtgtttt      780
```

-continued

```
gacattaccg ataatgtgcc gcgtgaacgg gtgcgttatg cccgcccgga agcggcgttt      840
tcccgtccgg ggaatggcat ggagctgcgc cttatccaga cgctgatcgc ccatcatcgc      900
ggttctttag atctctcggt ccgccctgat ggcggcacct tgctgacgtt acgcctgccg      960
gtacagcagg ttatcaccgg aggcttaaaa tga                                   993
```

```
<210> SEQ ID NO 222
<211> LENGTH: 1993
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1.2 with 500bp flank

<400> SEQUENCE: 222
```

```
tgtttcgtct cgaggccggg caactgagcg gccccgttga aaccgacctg ggctggcatc       60
tgttgttgtg cgaacaaatt cgcctgccgc aacccttgcc gaaagccgaa gccttaacgc      120
gggtgcgtca gcaactgatt gcccggcaac agaaacatta tcagcgccag tggctgcaac      180
aactgatcaa cgcctgagcc tgttctcctt cttgttgatg cagacgggtt aatgcccgtt      240
ttgcacgaaa aatgcacata aattgcctgc gttgccttat aacagcgcag ggaaatcctg      300
cctccggcct tgtgccacac cgcgctttgc ctggtttgtg gtaaaaactg gcccgctttg      360
catcctgatg cttaaaacac cccgttcaga tcaacctttg ggcagataag cccgcgaaag      420
gcctgcaaat tgcacggtta ttccgggtga gtatatgtgt gatttgggtt ccggcattgc      480
gcaataaagg ggagaaagac atgagcatca cggcgttatc agcatcattt cctgagggga      540
atatcgccag ccgcttgtcg ctgcaacatc cttcactgtt ttataccgtg gttgaacaat      600
cttcggtggc gatttcgctg accgatccgc aggcgcgcat ttgttatgcc aatccggcat      660
tctgccgcca gacgggtttt gcacttgaga cacttttggg cgagaaccac cgtctgctgg      720
tgaacatcac tgatgcacaa gctacctatg tcgaagaatt aactaaaaaa ctgcaagatg      780
caggcattcg cgttaaagcc gacttgagaa atgagaagat tggctttaaa attcgcgaac      840
acacgctacg ccgtgttcct tatatgttag tttgtggcga taaagaggtc gaagcaggca      900
aagttgctgt tcgtacccgc cgcggcaaag acttaggaag catggatgtt agcgaagtcg      960
ttgacaaact gctggcggaa atccgcagca gaagtcttca tcaactggag gaataaagta     1020
ttaaaggcgg aaaacgagtt caaccggcgc gtcctaatcg cattaacaaa gagattcgcg     1080
cgcaagaagt tcgcctcaca ggcgtcgatg gcgagcagat tggtattgtc agtctgaatg     1140
aagctcttga aaaagctgag gaagcgggcg tcgatttagt agaaatcagt ccgaatgccg     1200
agccgccagt ttgtcgaatc ccgtctctga gctctcggt gaacattgtt gcgaggcagg      1260
atgcgagctg gttgtgtttt gacattaccg ataatgtgcc gcgtgaacgg gtgcgttatg     1320
cccgcccgga agcggcgttt tcccgtccgg ggaatggcat ggagctgcgc cttatccaga     1380
cgctgatcgc ccatcatcgc ggttctttag atctctcggt ccgccctgat ggcggcacct     1440
tgctgacgtt acgcctgccg gtacagcagg ttatcaccgg aggcttaaaa tgacccagtt     1500
acctaccgcg ggcccggtta tccggcgctt tgatatgtct gcccagtttta cggcgcttta     1560 tcgcatcagc gtggcgctga gtcaggaaag caacaccggg cgcgcactgg cggcgatcct     1620
cgaagtgctt cacgatcatg catttatgca atacggcatg gtgtgtctgt ttgataaaga     1680
acgcaatgca ctctttgtgg aatccctgca tggcatcgac ggcgaaagga aaaaagagac     1740
```

-continued

```
ccgccatgtc cgttaccgca tgggggaagg cgtgatcggc gcggtgatga gccagcgtca    1800
ggcgctggtg ttaccgcgca tttcagacga tcagcgtttt ctcgaccgcc tgaatattta    1860
cgattacagc ctgccgttga ttggcgtgcc gatccccggt gcggataatc agccatcggg    1920
cgtgctggtg gcacagccga tggcgttgca cgaagaccgg ctgactgcca gtacgcggtt    1980
tttagaaatg gtc                                                       1993
```

```
<210> SEQ ID NO 223
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 223
```

```
atggcgctca aacagttaat ccgtctgtgt gccgcctcgc cgatggtcgc gacacaactt     60
gcacgtcatc ctttattgct cgatgaactg ctcgacccgc gcacgcttta ccagccgatt    120
gagccgggcg cttaccgcga cgaactgcgt cagtatctga tgcgggtgcc aacagaagac    180
gaagaacagc agcttgaagc cgtgcgccag ttcaaacagg cccagcattt gcgtatcgca    240 gccgggggata tttccggggc attgccggtg atgaaagtca gtgaccattt aacctacctt    300
gccgaggcca ttctcgatgt cgtggtgcag catgcgtggg aacaaatggt cgtaaaatac    360
gggcagcccg cgcatcttca gcaccgtgag gggcgcggtt ttgccgtggt cggttacggg    420
aaactcggtg gctgggagct gggttatagc tcagatctgg atctggtctt cctgctcgat    480
tgcgcgccgg aggtgatgac ggacggcgaa cgcagcatcg acggacgtca gttttatctt    540
cggctggcgc agcgcattat gcacttattc agcacccgga catcgtcagg cattctttac    600
gaggttgatc cgcgtctgcg accttccggc gcatccggca tgctggtcag taccattgaa    660
gcgtttgcag attatcaggc caatgaagcc tggacgtggg agcatcaggc gctggttcgc    720
gcgcgcgtgg tttacgggga tccgcaactg acacagcaat ttaacgccac gcgtcgcgac    780
attctttgcc gccagcgcga tggcgacggc ctgcgtaagg aggtccgtga aatgcgcgag    840
aaaatgtatg cccatctggg gagtaaaaaa gcccacgagt ttgatctgaa agccgatccg    900
ggtggcatca cggatattga attcattgca caatacctgg ttctgcgttt cgcgcatgat    960
gagccgaagc tgacgcgctg gtctgataac gtgcggattt ttgaactgat ggcacgatat   1020
gacatcatgc cggaagagga agcgcgccat ctgacgcagg cttatgtgac gctgcgcgat   1080
gaaattcatc atctggcgtt gcaggaacac agcgggaaag tggccgcgga cagctttgct   1140
actgagcgcg cgcagatccg tgccagctgg gcaaagtggc tcggctga                1188
```

```
<210> SEQ ID NO 224
<211> LENGTH: 2188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 224
```

```
cggtactgga acagaaatcg gcggatgcgc aggaaatttg ttatgacacg gcctgtctga     60
```

```
agtgcaagtt agtgcttact tcctggctgg caacctcagg ctggacgccg tttattgatg    120
ataaatctgc gaagaaactg gacgcttcct tcaaacgttt tgctgacatc atgctcggtc    180
gtaccgcagc ggatctgaaa gaagcctttg cgcagccact gacggaagaa ggttatcgcg    240
atcagctggc gcgcctgaaa cgccagatca ttaccttcca tttgcttgcc ggtgcttacc    300
ctgaaaaaga cgtcgatgcg tatattgccg gctgggtgga cctgcaacag gccatcgttc    360
agcagcaaca cgcctgggag gattcggccc gttctcacgc ggtgatgatg gatgctttct    420
ggttaaacgg gcaacctcgt taactgactg actagcctgg gcaaactgcc cgggcttttt    480
tttgcaagga atctgatttc atggcgctca aacagttaat ccgtctgtgt gccgcctcgc    540
cgatggtcgc gacacaactt gcacgtcatc ctttattgct cgatgaactg ctcgacccgc    600
gcacgcttta ccagccgatt gagccgggcg cttaccgcga cgaactgcgt cagtatctga    660
tgcgggtgcc aacagaagac gaagaacagc agcttgaagc cgtgcgccag ttcaaacagg    720
cccagcattt gcgtatcgca gccggggata tttccggggc attgccggtg atgaaagtca    780
gtgaccattt aacctacctt gccgaggcca ttctcgatgt cgtggtgcag catgcgtggg    840
aacaaatggt cgtaaaatac gggcagcccg cgcatcttca gcaccgtgag gggcgcggtt    900
ttgccgtggt cggttacggg aaactcggtg gctgggagct gggttatagc tcagatctgg    960
atctggtctt cctgctcgat tgcgcgccgg aggtgatgac ggacggcgaa cgcagcatcg   1020
acggacgtca gttttatctt cggctggcgc agcgcattat gcacttattc agcacccgga   1080
catcgtcagg cattctttac gaggttgatc cgcgtctgcg accttccggc gcatccggca   1140
tgctggtcag taccattgaa gcgtttgcag attatcaggc caatgaagcc tggacgtggg   1200
agcatcaggc gctggttcgc gcgcgcgtgg tttacgggga tccgcaactg acacagcaat   1260
ttaacgccac gcgtcgcgac attctttgcc gccagcgcga tggcgacggc ctgcgtaagg   1320
aggtccgtga aatgcgcgag aaaatgtatg cccatctggg gagtaaaaaa gcccacgagt   1380
ttgatctgaa agccgatccg ggtggcatca cggatattga attcattgca caatacctgg   1440
ttctgcgttt cgcgcatgat gagccgaagc tgacgcgctg gtctgataac gtgcggattt   1500
ttgaactgat ggcacgatat gacatcatgc cggaagagga agcgcgccat ctgacgcagg   1560
cttatgtgac gctgcgcgat gaaattcatc atctggcgtt gcaggaacac agcgggaaag   1620
tggccgcgga cagctttgct actgagcgcg cgcagatccg tgccagctgg gcaaagtggc   1680
tcggctgagg gttttattc ggctaacagg cgcttgtgat attatccggc gcattgtatt   1740
tacccgattt gatttatctg ttttggagtc ttgggatgaa agtgactttg cctgattttc   1800
accgcgcagg tgtgctggtt gtcggtgacg taatgttaga ccgttactgg tatggcccga   1860
ccaatcgtat ttctccggaa gctccggtgc cggtggtgaa ggtcagtacc attgaagagc   1920
ggcctggcgg tgcagctaac gtggcgatga acatttcatc tctgggcgcc tcttcctgtc   1980
tgatcggcct gaccggcgta gacgacgctg cgcgtgccct cagtgagcgt ctggcagaag   2040
tgaaagttaa ctgcgatttc gtcgcactat ccacacatcc taccatcacc aaactgcgaa   2100
ttttgtcccg taaccagcaa ctgatccgcc tcgactttga ggaaggtttt gaaggcgttg   2160
atctcgagcc gatgctgacc aaaatagga                                     2188
```

<210> SEQ ID NO 225
<211> LENGTH: 663
<212> TYPE: DNA
<213> ORGANISM: Artificial Sequence
<220> FEATURE:
<223> OTHER INFORMATION: Description of Artificial Sequence: Synthetic

```
        polynucleotide
<220> FEATURE:
<223> OTHER INFORMATION: delta-nifL::Prm3.1

<400> SEQUENCE: 225
atgagcatca cggcgttatc agcatcattt cctgagggga atatcgccag ccgcttgtcg      60
ctgcaacatc cttcactgtt ttataccgtg gttgaacaat cttcggtggc gatttcgctg     120
accgatccgc aggcgcgcat ttgttatgcc aatccggcat tctgccgcca gacgggtttt     180
gcacttgaga cacttttggg cgagaaccac cgtctgctgg tacagtagcg cctctcaaaa     240
atagataaac ggctcatgta cgtgggccgt ttatttttc tacccataat cgggaaccgg      300
tgttataatg ccgcgccctc atattgtggg gatttcttaa tgacctatcc tgggtcctaa     360
agttgtagtt gacattagcg gagcactaac ccgtctctga agctctcggt gaacattgtt     420
gcgaggcagg atgcgagctg gttgtgtttt gacattaccg ataatgtgcc gcgtgaacgg     480
gtgcgttatg cccgcccgga agcggcgttt tcccgtccgg ggaatggcat ggagctgcgc     540
cttatccaga cgctgatcgc ccatcatcgc ggttctttag atctctcggt ccgccctgat     600
ggcggcacct tgctgacgtt acgcctgccg gtacagcagg ttatcaccgg aggcttaaaa     660
tga                                                                    663

<210> SEQ ID NO 226
<211> LENGTH: 1663
<212> TYPE: DNA
<213> ORGANISM: Artificial Sequence
<220> FEATURE:
<223> OTHER INFORMATION: Description of Artificial Sequence: Synthetic
        polynucleotide
<220> FEATURE:
<223> OTHER INFORMATION: delta-nifL::Prm3.1 with 500bp flank

<400> SEQUENCE: 226
tgtttcgtct cgaggccggg caactgagcg gccccgttga aaccgacctg ggctggcatc      60
tgttgttgtg cgaacaaatt cgcctgccgc aacccttgcc gaaagccgaa gccttaacgc     120
gggtgcgtca gcaactgatt gcccggcaac agaaacatta tcagcgccag tggctgcaac     180
aactgatcaa cgcctgagcc tgttctcctt cttgttgatg cagacgggtt aatgcccgtt     240
ttgcacgaaa aatgcacata aattgcctgc gttgccttat aacagcgcag ggaaatcctg     300
cctccggcct tgtgccacac cgcgctttgc ctggtttgtg gtaaaaactg gcccgctttg     360
catcctgatg cttaaaacac cccgttcaga tcaacctttg ggcagataag cccgcgaaag     420
gcctgcaaat tgcacggtta ttccgggtga gtatatgtgt gatttgggtt ccggcattgc     480
gcaataaagg ggagaaagac atgagcatca cggcgttatc agcatcattt cctgagggga     540
atatcgccag ccgcttgtcg ctgcaacatc cttcactgtt ttataccgtg gttgaacaat     600
cttcggtggc gatttcgctg accgatccgc aggcgcgcat ttgttatgcc aatccggcat     660
tctgccgcca gacgggtttt gcacttgaga cacttttggg cgagaaccac cgtctgctgg     720
tacagtagcg cctctcaaaa atagataaac ggctcatgta cgtgggccgt ttatttttc     780 tacccataat cgggaaccgg tgttataatg ccgcgccctc atattgtggg gatttcttaa     840
tgacctatcc tgggtcctaa agttgtagtt gacattagcg gagcactaac ccgtctctga     900
agctctcggt gaacattgtt gcgaggcagg atgcgagctg gttgtgtttt gacattaccg     960
ataatgtgcc gcgtgaacgg gtgcgttatg cccgcccgga agcggcgttt tcccgtccgg    1020
ggaatggcat ggagctgcgc cttatccaga cgctgatcgc ccatcatcgc ggttctttag    1080
```

-continued

```
atctctcggt ccgccctgat ggcggcacct tgctgacgtt acgcctgccg gtacagcagg      1140
ttatcaccgg aggcttaaaa tgacccagtt acctaccgcg ggcccggtta tccggcgctt      1200
tgatatgtct gcccagttta cggcgcttta tcgcatcagc gtggcgctga gtcaggaaag      1260
caacaccggg cgcgcactgg cggcgatcct cgaagtgctt cacgatcatg catttatgca      1320
atacggcatg gtgtgtctgt ttgataaaga acgcaatgca ctctttgtgg aatccctgca      1380
tggcatcgac ggcgaaagga aaaaagagac ccgccatgtc cgttaccgca tgggggaagg      1440
cgtgatcggc gcggtgatga ccagcgtca ggcgctggtg ttaccgcgca tttcagacga      1500
tcagcgtttt ctcgaccgcc tgaatattta cgattacagc ctgccgttga ttggcgtgcc      1560
gatccccggt gcggataatc agccatcggg cgtgctggtg gcacagccga tggcgttgca      1620
cgaagaccgg ctgactgcca gtacgcggtt tttagaaatg gtc                        1663
```

```
<210> SEQ ID NO 227
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 227
```

```
atggcgctca aacagttaat ccgtctgtgt gccgcctcgc cgatggtcgc gacacaactt       60
gcacgtcatc ctttattgct cgatgaactg ctcgacccgc gcacgcttta ccagccgatt      120
gagccgggcg cttaccgcga cgaactgcgt cagtatctga tgcgggtgcc aacagaagac      180
gaagaacagc agcttgaagc cgtgcgccag ttcaaacagg cccagcattt gcgtatcgca      240
gccggggata tttccggggc attgccggtg atgaaagtca gtgaccattt aacctacctt      300
gccgaggcca ttctcgatgt cgtggtgcag catgcgtggg aacaaatggt cgtaaaatac      360
gggcagcccg cgcatcttca gcaccgtgag gggcgcggtt ttgccgtggt cggttacggg      420
aaactcggtg gctgggagct gggttatagc tcagatctgg atctggtctt cctgctcgat      480
tgcgcgccgg aggtgatgac ggacggcgaa cgcagcatcg acggacgtca gtttttatctt      540 cggctggcgc agcgcattat gcacttattc agcacccgga catcgtcagg cattctttac      600
gaggttgatc cgcgtctgcg accttccggc gcatccggca tgctggtcag taccattgaa      660
gcgtttgcag attatcaggc caatgaagcc tggacgtggg agcatcaggc gctggttcgc      720
gcgcgcgtgg tttacgggga tccgcaactg acacagcaat ttaacgccac gcgtcgcgac      780
attctttgcc gccagcgcga tggcgacggc ctgcgtaagg aggtccgtga aatgcgcgag      840
aaaatgtatg cccatctggg gagtaaaaaa gcccacgagt ttgatctgaa agccgatccg      900
ggtggcatca cggatattga attcattgca caatacctgg ttctgcgttt cgcgcatgat      960
gagccgaagc tgacgcgctg gtctgataac gtgcggattg ttgaactgat ggcacgatat     1020
gacatcatgc cggaagagga agcgcgccat ctgacgcagg cttatgtgac gctgcgcgat     1080
gaaattcatc atctggcgtt gcaggaacac agcgggaaag tggccgcgga cagctttgct     1140
actgagcgcg cgcagatccg tgccagctgg gcaaagtggc tcggctga                 1188
```

```
<210> SEQ ID NO 228
<211> LENGTH: 2188
<212> TYPE: DNA
<213> ORGANISM: Artificial Sequence
<220> FEATURE:
```

<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 228
cggtactgga acagaaatcg gcggatgcgc aggaaatttg ttatgacacg gcctgtctga        60
agtgcaagtt agtgcttact tcctggctgg caacctcagg ctggacgccg tttattgatg       120
ataaatctgc gaagaaactg gacgcttcct tcaaacgttt tgctgacatc atgctcggtc       180
gtaccgcagc ggatctgaaa gaagcctttg cgcagccact gacggaagaa ggttatcgcg       240
atcagctggc gcgcctgaaa cgccagatca ttaccttcca tttgcttgcc ggtgcttacc       300
ctgaaaaaga cgtcgatgcg tatattgccg gctgggtgga cctgcaacag gccatcgttc       360
agcagcaaca cgcctgggag gattcggccc gttctcacgc ggtgatgatg gatgctttct       420
ggttaaacgg gcaacctcgt taactgactg actagcctgg gcaaactgcc cgggcttttt       480
tttgcaagga atctgatttc atggcgctca aacagttaat ccgtctgtgt gccgcctcgc       540
cgatggtcgc gacacaactt gcacgtcatc ctttattgct cgatgaactg ctcgacccgc       600
gcacgcttta ccagccgatt gagccgggcg cttaccgcga cgaactgcgt cagtatctga       660
tgcgggtgcc aacagaagac gaagaacagc agcttgaagc cgtgcgccag ttcaaacagg       720
cccagcattt gcgtatcgca gccggggata tttccggggc attgccggtg atgaaagtca       780
gtgaccattt aacctacctt gccgaggcca ttctcgatgt cgtggtgcag catgcgtggg       840
aacaaatggt cgtaaaatac gggcagcccg cgcatcttca gcaccgtgag gggcgcggtt       900
ttgccgtggt cggttacggg aaactcggtg gctgggagct gggttatagc tcagatctgg       960
atctggtctt cctgctcgat tgcgcgccgg aggtgatgac ggacggcgaa cgcagcatcg      1020
acggacgtca gttttatctt cggctggcgc agcgcattat gcacttattc agcacccgga      1080
catcgtcagg cattctttac gaggttgatc cgcgtctgcg accttccggc gcatccggca      1140
tgctggtcag taccattgaa gcgtttgcag attatcaggc caatgaagcc tggacgtggg      1200
agcatcaggc gctggttcgc gcgcgcgtgg tttacgggga tccgcaactg acacagcaat      1260
ttaacgccac gcgtcgcgac attctttgcc gccagcgcga tggcgacggc ctgcgtaagg      1320
aggtccgtga aatgcgcgag aaaatgtatg cccatctggg gagtaaaaaa gcccacgagt      1380
ttgatctgaa agccgatccg ggtggcatca cggatattga attcattgca caatacctgg      1440
ttctgcgttt cgcgcatgat gagccgaagc tgacgcgctg gtctgataac gtgcggattt      1500
ttgaactgat ggcacgatat gacatcatgc cggaagagga agcgcgccat ctgacgcagg      1560
cttatgtgac gctgcgcgat gaaattcatc atctggcgtt gcaggaacac agcgggaaag      1620
tggccgcgga cagctttgct actgagcgcg cgcagatccg tgccagctgg gcaaagtggc      1680
tcggctgagg gtttttattc ggctaacagg cgcttgtgat attatccggc gcattgtatt      1740
tacccgattt gatttatctg ttttggagtc ttgggatgaa agtgactttg cctgatttc      1800 accgcgcagg tgtgctggtt gtcggtgacg taatgttaga ccgttactgg tatggcccga      1860
ccaatcgtat ttctccggaa gctccggtgc cggtggtgaa ggtcagtacc attgaagagc      1920
ggcctggcgg tgcagctaac gtggcgatga acatttcatc tctgggcgcc tcttcctgtc      1980
tgatcggcct gaccggcgta gacgacgctg cgcgtgccct cagtgagcgt ctggcagaag      2040
tgaaagttaa ctgcgatttc gtcgcactat ccacacatcc taccatcacc aaactgcgaa      2100
ttttgtcccg taaccagcaa ctgatccgcc tcgactttga ggaaggtttt gaaggcgttg      2160

-continued

```
atctcgagcc gatgctgacc aaaataga                                       2188

<210> SEQ ID NO 229
<211> LENGTH: 613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC

<400> SEQUENCE: 229
atgagcatca cggcgttatc agctgaatat cactgactca caagctacct atgtcgaaga        60
attaactaaa aaactgcaag atgcaggcat tcgcgttaaa gccgacttga gaaatgagaa       120
gattggcttt aaaattcgcg aacacacgct acgccgtgtt ccttatatgt tagtttgtgg       180
cgataaagag gtcgaagcag gcaaagttgc tgttcgtact cgtcgcggca aagacttagg       240
aagcatggat gttagcgaag tcgttgacaa actgctggcg gaaatccgca gcagaagtca       300
tcatcaactg gaggaataaa gtattaaagg cggaaaacga gttcaaccgg cgcgtcctaa       360
tcgcattaac aaagagattc gcgcgcaaga agttcgcctc accggcgtcg atggcgagca       420
gattggtatt gtcagtctga atgaagctct tgaaaaagct gaggaagcgg gcgtcgattt       480
agtagaaatc agtccgaatg ccgagccgcc agtttgtcga atctctttag atctctcggt       540
ccgccctgat ggcggcacct tgctgacgtt acgcctgccg gtacagcagg ttatcaccgg       600
aggcttaaaa tga                                                        613

<210> SEQ ID NO 230
<211> LENGTH: 1613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC with 500bp flank

<400> SEQUENCE: 230
tgtttcgtct cgaagccggg caactgagca gccccgttga aaccgaactg ggctggcatc        60
tgttgttgtg cgaacaaatt cgcctgccgc aaccccttgcc gaaagccgag gccttaacgc      120
gggtgcgtca gcaactgatt gcccggcaac agaatcatta tcagcgccag tggctgcaac       180
aactgatcaa cgcctgagcc tgttctcctt cttgttggtg cagacgggtt aatgcccgtt       240
ttgcacgaaa aatgcacata aactgccttc gctgccttat aacagcgcat ggaaatcctg       300
cctcctgcct tgtgccacgc cgcgctttgc ctggtttgtg gtaaaaactg cccgcctttg       360
catcctgatg tttaaaacac cccgttcaga tcaacctttg ggcagataag cccgcgaaag       420
gcctgcaaat tgcacggtta ttccgggtga gtatatgtgt gatttgggtt ccggcattgc       480
gcaataaagg ggagaaagac atgagcatca cggcgttatc agctgaatat cactgactca       540
caagctacct atgtcgaaga attaactaaa aaactgcaag atgcaggcat tcgcgttaaa       600
gccgacttga gaaatgagaa gattggcttt aaaattcgcg aacacacgct acgccgtgtt       660
ccttatatgt tagtttgtgg cgataaagag gtcgaagcag gcaaagttgc tgttcgtact       720
cgtcgcggca aagacttagg aagcatggat gttagcgaag tcgttgacaa actgctggcg       780
gaaatccgca gcagaagtca tcatcaactg gaggaataaa gtattaaagg cggaaaacga       840
gttcaaccgg cgcgtcctaa tcgcattaac aaagagattc gcgcgcaaga agttcgcctc       900
```

```
accggcgtcg atggcgagca gattggtatt gtcagtctga atgaagctct tgaaaaagct    960
gaggaagcgg gcgtcgattt agtagaaatc agtccgaatg ccgagccgcc agtttgtcga   1020
atctctttag atctctcggt ccgccctgat ggcggcacct tgctgacgtt acgcctgccg   1080
gtacagcagg ttatcaccgg aggcttaaaa tgacccagtt acctaccgcg ggcccggtta   1140
tccggcgctt tgatatgtct gcccagttta cggcgcttta tcgcatcagc gtggcgctga   1200
gtcaggaaag caataccgcg cgcgcactgg cggcgatcct cgaagtgctt cacgatcatg   1260
catttatgca atacggcatg gtgtgtctgt tcgataaaga acgcaatgca ctgtttgtgg   1320
aatccctgca tggcatcgac ggcgaaagga aaaaagaaac ccgccatgtc cgttaccgca   1380 tggggggaagg cgtgatcggc gcggtgatga gccagcgtca ggcgctggtg ttaccgcgca   1440
tttcagacga tcagcgtttt ctcgaccgcc tgaatattta cgattacagc ctgccgctga   1500
ttggtgtgcc gatccccggt gcggataatc agcctgcggg tgtgctggtg gcacagccga   1560
tggcgttgca cgaagaccgg ctggctgcca gtacgcggtt tttagaaatg gtc          1613

<210> SEQ ID NO 231
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm5

<400> SEQUENCE: 231
atgaccctga atatgatgat ggatgccggc ggacatcatc gcgacaaaca atattaatac     60
cggcaaccac accggcaatt tacgagactg cgcaggcatc ctttctcccg tcaatttctg    120
tcaaataaag taaaagaggc agtctacttg aattacccc ggctggttga gcgtttgttg    180
aaaaaaagta actgaaaaat ccgtagaata gcgccactct gatggttaat taacctattc    240
aattaagaat tatctggatg aatgtgccat taaatgcgca gcataatggt gcgttgtgcg    300
ggaaaactgc ttttttttga aagggttggt cagtagcgga aacaactcac ttcacacccc    360
gaagggggaa gttgcctgac cctacgattc ccgctatttc attcactgac cggaggttca    420
aaatga                                                              426

<210> SEQ ID NO 232
<211> LENGTH: 1426
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm5 with 500bp flank

<400> SEQUENCE: 232
accggatacg agagaaaagt gtctacatcg gttcggttga tattgaccgg cgcatccgcc     60
agcccgccca gtttctggtg gatctgtttg gcgattttgc gggtcttgcc ggtgtcggtg    120
ccgaaaaaaa taccaatatt tgccataaca cacgctcctg ttgaaaaaga gatcccgccg    180
ggaaatgcgg tgaacgtgtc tgatattgcg aagagtgtgc cagttttggt cgcgggcaaa    240
acctgcacca gtttggttat taatgcacca gtctggcgct ttttttcgcc gagtttctcc    300
tcgctaatgc ccgccaggcg cggctttggc gctgatagcg cgctgaatac cgatctggat    360
```

```
caaggttttg tcgggttatc agccaaaagg tgcactcttt gcatggttat acgtgcctga     420
catgttgtcc gggcgacaaa cggcctggtg gcacaaattg tcagaactac gacacgacta     480
actgaccgca ggagtgtgcg atgaccctga atatgatgat ggatgccggc ggacatcatc     540
gcgacaaaca atattaatac cggcaaccac accggcaatt tacgagactg cgcaggcatc     600
ctttctcccg tcaatttctg tcaaataaag taaagaggc agtctacttg aattaccccc      660
ggctggttga gcgtttgttg aaaaaaagta actgaaaaat ccgtagaata gcgccactct     720
gatggttaat taacctattc aattaagaat tatctggatg aatgtgccat taaatgcgca     780
gcataatggt gcgttgtgcg ggaaaactgc ttttttttga aagggttggt cagtagcgga     840
aacaactcac ttcacacccc gaagggggaa gttgcctgac cctacgattc ccgctatttc     900
attcactgac cggaggttca aaatgaccca gcgaaccgag tcgggtaata ccgtctggcg     960
cttcgatttg tcccagcagt tcactgcgat gcagcgcata agcgtggtac tcagccgggc    1020
gaccgaggtc gatcagacgc tccagcaagt gctgtgcgta ttgcacaatg acgccttttt    1080
gcagcacggc atgatctgtc tgtacgacag ccagcaggcg attttgaata ttgaagcgtt    1140
gcaggaagcc gatcagcagt taatccccgg cagctcgcaa atccgctatc gtccgggcga    1200
agggctggtc gggacggtgc tttcgcaggg ccaatcatta gtgctggcgc gcgttgctga    1260
cgatcagcgc tttcttgacc ggctcgggtt gtatgattac aacctgccgt ttatcgccgt    1320
gccgctgata gggccagatg cgcagacttt cggtgtgctg acggcacaac ccatggcgcg    1380
ttacgaagag cgattacccg cctgcacccg ctttctggaa acggtc               1426
```

```
<210> SEQ ID NO 233
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 233
atgaccctga atatgatgat ggatgccggc cgtcctgtaa taataaccgg acaattcgga      60
ctgattaaaa aagcgccctt gtggcgcttt ttttatattc ccgcctccat ttaaaataaa     120
aaatccaatc ggatttcact atttaaactg gccattatct aagatgaatc cgatggaagc     180
tcgctgtttt aacacgcgtt ttttaacctt ttattgaaag tcggtgcttc tttgagcgaa     240
cgatcaaatt taagtggatt cccatcaaaa aaatattctc aacctaaaaa agtttgtgta     300
atacttgtaa cgctacatgg agattaactc aatctagagg gtattaataa tgaatcgtac     360
taaactggta ctgggcgcaa ctcacttcac accccgaagg gggaagttgc ctgaccctac     420
gattcccgct atttcattca ctgaccggag gttcaaaatg a                        461
```

```
<210> SEQ ID NO 234
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 234
accggatacg agagaaaagt gtctacatcg gttcggttga tattgaccgg cgcatccgcc      60
```

-continued

```
agcccgccca gtttctggtg gatctgtttg gcgattttgc gggtcttgcc ggtgtcggtg      120
ccgaaaaaaa taccaatatt tgccataaca cacgctcctg ttgaaaaaga gatcccgccg      180
ggaaatgcgg tgaacgtgtc tgatattgcg aagagtgtgc cagttttggt cgcgggcaaa      240
acctgcacca gtttggttat taatgcacca gtctggcgct ttttttcgcc gagtttctcc      300
tcgctaatgc ccgccaggcg cggctttggc gctgatagcg cgctgaatac cgatctggat      360
caaggttttg tcgggttatc agccaaaagg tgcactcttt gcatggttat acgtgcctga      420
catgttgtcc gggcgacaaa cggcctggtg gcacaaattg tcagaactac gacacgacta      480
actgaccgca ggagtgtgcg atgaccctga atatgatgat ggatgccggc cgtcctgtaa      540
taataaccgg acaattcgga ctgattaaaa aagcgccctt gtggcgcttt ttttatattc      600
ccgcctccat ttaaaataaa aaatccaatc ggatttcact atttaaactg gccattatct      660
aagatgaatc cgatggaagc tcgctgtttt aacacgcgtt ttttaacctt ttattgaaag      720
tcggtgcttc tttgagcgaa cgatcaaatt taagtggatt cccatcaaaa aaatattctc      780
aacctaaaaa agtttgtgta atacttgtaa cgctacatgg agattaactc aatctagagg      840
gtattaataa tgaatcgtac taaactggta ctgggcgcaa ctcacttcac accccgaagg      900
gggaagttgc ctgaccctac gattcccgct atttcattca ctgaccggag gttcaaaatg      960
acccagcgaa ccgagtcggg taataccgtc tggcgcttcg atttgtccca gcagttcact     1020
gcgatgcagc gcataagcgt ggtactcagc cgggcgaccg aggtcgatca gacgctccag     1080
caagtgctgt gcgtattgca caatgacgcc tttttgcagc acggcatgat ctgtctgtac     1140
gacagccagc aggcgatttt gaatattgaa gcgttgcagg aagccgatca gcagttaatc     1200
cccggcagct cgcaaatccg ctatcgtccg ggcgaagggc tggtcgggac ggtgctttcg     1260
cagggccaat cattagtgct ggcgcgcgtt gctgacgatc agcgctttct tgaccggctc     1320
gggttgtatg attacaacct gccgtttatc gccgtgccgc tgatagggcc agatgcgcag     1380
actttcggtg tgctgacggc acaacccatg gcgcgttacg aagagcgatt acccgcctgc     1440
acccgctttc tggaaacggt c                                              1461
```

<210> SEQ ID NO 235
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 235

```
atgaccctga atatgatgat ggatgccggc cgtcctgtaa taataaccgg acaattcgga       60
ctgattaaaa aagcgccctt gtggcgcttt ttttatattc ccgcctccat ttaaaataaa      120
aaatccaatc ggatttcact atttaaactg gccattatct aagatgaatc cgatggaagc      180
tcgctgtttt aacacgcgtt ttttaacctt ttattgaaag tcggtgcttc tttgagcgaa      240
cgatcaaatt taagtggatt cccatcaaaa aaatattctc aacctaaaaa agtttgtgta      300
atacttgtaa cgctacatgg agattaactc aatctagagg gtattaataa tgaatcgtac      360
taaactggta ctgggcgcaa ctcacttcac accccgaagg gggaagttgc ctgaccctac      420
gattcccgct atttcattca ctgaccggag gttcaaaatg a                          461
```

```
<210> SEQ ID NO 236
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 236
accggatacg agagaaaagt gtctacatcg gttcggttga tattgaccgg cgcatccgcc       60
agcccgccca gtttctggtg gatctgtttg gcgattttgc gggtcttgcc ggtgtcggtg      120
ccgaaaaaaa taccaatatt tgccataaca cacgctcctg ttgaaaaaga gatcccgccg      180
ggaaatgcgg tgaacgtgtc tgatattgcg aagagtgtgc cagttttggt cgcgggcaaa      240
acctgcacca gtttggttat taatgcacca gtctggcgct ttttttcgcc gagtttctcc      300
tcgctaatgc ccgccaggcg cggctttggc gctgatagcg cgctgaatac cgatctggat      360
caaggttttg tcgggttatc agccaaaagg tgcactcttt gcatggttat acgtgcctga      420
catgttgtcc gggcgacaaa cggcctggtg gcacaaattg tcagaactac gacacgacta      480
actgaccgca ggagtgtgcg atgaccctga atatgatgat ggatgccggc cgtcctgtaa      540
taataaccgg acaattcgga ctgattaaaa aagcgccctt gtggcgcttt ttttatattc      600
ccgcctccat ttaaaataaa aaatccaatc ggatttcact atttaaactg gccattatct      660
aagatgaatc cgatggaagc tcgctgtttt aacacgcgtt ttttaacctt ttattgaaag      720
tcggtgcttc tttgagcgaa cgatcaaatt taagtggatt cccatcaaaa aaatattctc      780
aacctaaaaa agtttgtgta atacttgtaa cgctacatgg agattaactc aatctagagg      840
gtattaataa tgaatcgtac taaactggta ctgggcgcaa ctcacttcac accccgaagg      900
gggaagttgc ctgaccctac gattcccgct atttcattca ctgaccggag gttcaaaatg      960
acccagcgaa ccgagtcggg taataccgtc tggcgcttcg atttgtccca gcagttcact     1020
gcgatgcagc gcataagcgt ggtactcagc cgggcgaccg aggtcgatca gacgctccag     1080
caagtgctgt gcgtattgca caatgacgcc tttttgcagc acggcatgat ctgtctgtac     1140
gacagccagc aggcgatttt gaatattgaa gcgttgcagg aagccgatca gcagttaatc     1200
cccggcagct cgcaaatccg ctatcgtccg ggcgaagggc tggtcgggac ggtgctttcg     1260
cagggccaat cattagtgct ggcgcgcgtt gctgacgatc agcgctttct tgaccggctc     1320
gggttgtatg attacaacct gccgtttatc gccgtgccgc tgatagggcc agatgcgcag     1380
actttcggtg tgctgacggc acaacccatg gcgcgttacg aagagcgatt acccgcctgc     1440
acccgctttc tggaaacggt c                                             1461

<210> SEQ ID NO 237
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 237
atggcactga aacacctcat ttccctgtgt gccgcgtcgc cgatggttgc cagtcagctg       60
gcgcgctacc cgatcctgct tgatgaattg ctcgacccga atacgctcta tcaaccgacg      120
```

```
gcgatgaatg cctatcgcga tgagctgcgc caatacctgc tgcgcgtgcc ggaagatgat    180
gaagagcaac agcttgaggc gctgcggcag tttaagcagg cgcagttgct gcgcgtggcg    240
gcggcggata ttgccggtac gttgccagta atgaaagtga gcgatcactt aacctggctg    300
gcggaagcga ttattgatgc ggtggtgcag caagcctggg ggcagatggt ggcgcgttat    360
ggccagccaa cgcatctgca cgatcgcgaa gggcgcggtt ttgcggtggt cggttatggc    420
aagctgggcg gctgggagct gggttacagc tccgatctgg atctggtatt cctgcacgac    480
tgcccgatgg atgtgatgac cgatggcgag cgtgaaatcg atggtcgcca gttctatttg    540
cgtctcgcgc agcgcgtgat gcacctgttt agcacgcgca cgtcgtccgg catcctttat    600
gaagttgatg cgcgtctgcg tccatctggc gctgcgggga tgctggtcac tactacggaa    660
tcgttcgccg attaccagca aaacgaagcc tggacgtggg aacatcaggc gctggcccgt    720
gcgcgcgtgg tgtacggcga tccgcaactg accgccgaat ttgacgccat tcgccgcgat    780
attctgatga cgcctcgcga cggcgcaacg ctgcaaaccg acgtgcgaga aatgcgcgag    840
aaaatgcgtg cccatcttgg caacaagcat aaagaccgct tcgatctgaa agccgatgaa    900
ggcggtatca ccgacatcga gtttatcgcc caatatctgg tgctgcgctt tgcccatgac    960
aagccgaaac tgacgcgctg gtcggataat gtgcgcattc tcgaagggct ggcgcaaaac   1020
ggcatcatgg aggagcagga agcgcaggca ttgacgctgg cgtacaccac attgcgtgat   1080
gagctgcacc acctggcgct gcaagagttg ccgggacatg tggcgctctc ctgtttttgtc   1140 gccgagcgtg cgcttattaa aaccagctgg gacaagtggc tggtggaa                 1188
```

```
<210> SEQ ID NO 238
<211> LENGTH: 2206
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 238
```

```
gcgcaaagcg agtgctcact tacgtgatct gttgacacaa tctgaagcga ccataacttc     60
tgccgtttca gcgaatacgg cggtgtggag cgcacaatca gccctggcga agctggtgct    120
caccgagtgg ctagtgacgc agggctggcg aaccttcctt gatgaaaaag cgcaggccaa    180
attcgccgac tcctttaaac gctttgctga catccatctg tcacgcagcg ccgccgagct    240
gaaaaaagcc tttgcccaac cgctgggcga cagctatcgc gaccagttgc cgcgcctggc    300
gcgtgatatc gactcgcgcgt tactgctggc cgggcattac gatcgcgcgc gcgccgtgga    360
atggctggaa aactggcagg ggcttcagca cgccattgaa acgcgccaga gagtcgaaat    420
cgaacatttc cgtaataccg cgattaccca ggagccgttc tggttgcaca gcggaaaacg    480
ttaacgaaag gatatttcgc atggcactga aacacctcat ttccctgtgt gccgcgtcgc    540
cgatggttgc cagtcagctg gcgcgctacc cgatcctgct tgatgaattg ctcgacccga    600
atacgctcta tcaaccgacg gcgatgaatg cctatcgcga tgagctgcgc caatacctgc    660
tgcgcgtgcc ggaagatgat gaagagcaac agcttgaggc gctgcggcag tttaagcagg    720
cgcagttgct gcgcgtggcg gcggcggata ttgccggtac gttgccagta atgaaagtga    780
gcgatcactt aacctggctg gcggaagcga ttattgatgc ggtggtgcag caagcctggg    840
ggcagatggt ggcgcgttat ggccagccaa cgcatctgca cgatcgcgaa gggcgcggtt    900
```

-continued

```
ttgcggtggt cggttatggc aagctgggcg gctgggagct gggttacagc tccgatctgg     960
atctggtatt cctgcacgac tgcccgatgg atgtgatgac cgatggcgag cgtgaaatcg    1020
atggtcgcca gttctatttg cgtctcgcgc agcgcgtgat gcacctgttt agcacgcgca    1080
cgtcgtccgg catcctttat gaagttgatg cgcgtctgcg tccatctggc gctgcgggga    1140
tgctggtcac tactacggaa tcgttcgccg attaccagca aaacgaagcc tggacgtggg    1200
aacatcaggc gctggcccgt gcgcgcgtgg tgtacggcga tccgcaactg accgccgaat    1260
ttgacgccat tcgccgcgat attctgatga cgcctcgcga cggcgcaacg ctgcaaaccg    1320
acgtgcgaga aatgcgcgag aaaatgcgtg cccatcttgg caacaagcat aaagaccgct    1380
tcgatctgaa agccgatgaa ggcggtatca ccgacatcga gtttatcgcc caatatctgg    1440
tgctgcgctt tgcccatgac aagccgaaac tgacgcgctg gtcggataat gtgcgcattc    1500
tcgaagggct ggcgcaaaac ggcatcatgg aggagcagga agcgcaggca ttgacgctgg    1560
cgtacaccac attgcgtgat gagctgcacc acctggcgct gcaagagttg ccgggacatg    1620
tggcgctctc ctgttttgtc gccgagcgtg cgcttattaa aaccagctgg gacaagtggc    1680
tggtggaacc gtgcgccccg gcgtaagtgt ggtatcatcg cgcgcaaatt ttgtatctct    1740
caggagacag gaatgaaagt gacgctgcca gagtttaagc aagccggtgt aatggtggtg    1800
ggtgatgtga tgctggatcg ttactggtat ggcccaacca gccgtatctc tccggaagcg    1860
ccagtcccgg ttgttaaagt cgataccatt gaagagcgtc ctggcggcgc ggcaaacgtg    1920
gcgatgaata tcgcctcact gggcgccacg gcgcgtctgg ttggcctgac tggcattgac    1980
gatgcggcgc gcgcgctgag caaagcgctg gccgatgtta acgttaaatg tgacttcgtt    2040
tctgttccga cgcatcccac catcactaag ctgcgcgtgc tgtcgcgtaa ccagcagctg    2100
attcgcctgg actttgaaga gggttttgaa ggagtcgatc cgcaaccgat gcatgaacgc    2160
atcagccagg cgcttggtaa tattggcgcg ctggtgctgt cggatt              2206
```

```
<210> SEQ ID NO 239
<211> LENGTH: 1563
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-1

<400> SEQUENCE: 239
atgtttaacg atctgattgg cgatgatgaa acggattcgc cggaagatgc gctttctgag      60
agctggcgcg aattgtggca ggatgcgttg caggaggagg attccacgcc cgtgctggcg     120
catctctcag aggacgatcg ccgccgcgtg gtggcgctga ttgccgattt tcgcaaagag     180
ttggataaac gcaccattgg cccgcgaggg cggcaggtac tcgatcactt aatgccgcat     240
ctgctcagca tgtatgctc gcgcgacgat gcgccagtac cgctgtcacg cctgacgccg     300
ctgctcaccg gaattattac ccgcaccact taccttgagc tgctaagtga atttcccggc     360
gcactgaaac acctcatttc cctgtgtgcc gcgtcgccga tggttgccag tcagctggcg     420
cgctacccga tcctgcttga tgaattgctc gacccgaata cgctctatca accgacggcg     480
atgaatgcct atcgcgatga gctgcgccaa tacctgctgc gcgtgccgga agatgatgaa     540
gagcaacagc ttgaggcgct gcggcagttt aagcaggcgc agttgctgcg cgtgcggcg     600 gcggatattg ccggtacgtt gccagtaatg aaagtgagcg atcacttaac ctggctggcg     660
```

-continued

```
gaagcgatta ttgatgcggt ggtgcagcaa gcctgggggc agatggtggc gcgttatggc    720
cagccaacgc atctgcacga tcgcgaaggg cgcggttttg cggtggtcgg ttatggcaag    780
ctgggcggct gggagctggg ttacagctcc gatctggatc tggtattcct gcacgactgc    840
ccgatggatg tgatgaccga tggcgagcgt gaaatcgatg tcgccagtt ctatttgcgt     900 ctcgcgcagc gcgtgatgca cctgtttagc acgcgcacgt cgtccggcat cctttatgaa    960
gttgatgcgc gtctgcgtcc atctggcgct gcggggatgc tggtcactac tacggaatcg   1020
ttcgccgatt accagcaaaa cgaagcctgg acgtgggaac atcaggcgct ggcccgtgcg   1080
cgcgtggtgt acggcgatcc gcaactgacc gccgaatttg acgccattcg ccgcgatatt   1140
ctgatgacgc ctcgcgacgg cgcaacgctg caaaccgacg tgcgagaaat gcgcgagaaa   1200
atgcgtgccc atcttggcaa caagcataaa gaccgcttcg atctgaaagc cgatgaaggc   1260
ggtatcaccg acatcgagtt tatcgcccaa tatctggtgc tgcgctttgc ccatgacaag   1320
ccgaaactga cgcgctggtc ggataatgtg cgcattctcg aagggctggc gcaaaacggc   1380
atcatggagg agcaggaagc gcaggcattg acgctggcgt acaccacatt gcgtgatgag   1440
ctgcaccacc tggcgctgca agagttgccg ggacatgtgg cgctctcctg ttttgtcgcc   1500
gagcgtgcgc ttattaaaac cagctgggac aagtggctgg tggaaccgtg cgccccggcg   1560
taa                                                                 1563
```

<210> SEQ ID NO 240
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 240

```
atgaccctga atatgatgat ggatgccggc cgtcctgtaa taataaccgg acaattcgga     60
ctgattaaaa aagcgccctt gtggcgcttt ttttatattc ccgcctccat ttaaaataaa    120
aaatccaatc ggatttcact atttaaactg gccattatct aagatgaatc cgatggaagc    180
tcgctgtttt aacacgcgtt ttttaacctt ttattgaaag tcggtgcttc tttgagcgaa    240
cgatcaaatt taagtggatt cccatcaaaa aaatattctc aacctaaaaa agtttgtgta    300
atacttgtaa cgctacatgg agattaactc aatctagagg gtattaataa tgaatcgtac    360
taaactggta ctgggcgcaa ctcacttcac accccgaagg gggaagttgc ctgaccctac    420
gattcccgct atttcattca ctgaccggag gttcaaaatg a                        461
```

<210> SEQ ID NO 241
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 241

```
accggatacg agagaaaagt gtctacatcg gttcggttga tattgaccgg cgcatccgcc     60
agcccgccca gtttctggtg gatctgtttg gcgattttgc gggtcttgcc ggtgtcggtg    120
ccgaaaaaaa taccaatatt tgccataaca cacgctcctg ttgaaaaaga gatcccgccg    180
```

-continued

```
ggaaatgcgg tgaacgtgtc tgatattgcg aagagtgtgc cagttttggt cgcgggcaaa      240
acctgcacca gtttggttat taatgcacca gtctggcgct tttttcgcc gagtttctcc        300 tcgctaatgc ccgccaggcg cggctttggc gctgatagcg cgctgaatac cgatctggat      360
caaggttttg tcgggttatc agccaaaagg tgcactcttt gcatggttat acgtgcctga      420
catgttgtcc gggcgacaaa cggcctggtg gcacaaattg tcagaactac gacacgacta      480
actgaccgca ggagtgtgcg atgaccctga atatgatgat ggatgccggc cgtcctgtaa      540
taataaccgg acaattcgga ctgattaaaa aagcgccctt gtggcgcttt ttttatattc      600
ccgcctccat ttaaaataaa aaatccaatc ggatttcact atttaaactg gccattatct      660
aagatgaatc cgatggaagc tcgctgtttt aacacgcgtt ttttaacctt ttattgaaag      720
tcggtgcttc tttgagcgaa cgatcaaatt taagtggatt cccatcaaaa aaatattctc      780
aacctaaaaa agtttgtgta atacttgtaa cgctacatgg agattaactc aatctagagg      840
gtattaataa tgaatcgtac taaactggta ctgggcgcaa ctcacttcac accccgaagg      900
gggaagttgc ctgaccctac gattcccgct atttcattca ctgaccggag gttcaaaatg      960
acccagcgaa ccgagtcggg taataccgtc tggcgcttcg atttgtccca gcagttcact     1020
gcgatgcagc gcataagcgt ggtactcagc cgggcgaccg aggtcgatca gacgctccag     1080
caagtgctgt gcgtattgca caatgacgcc tttttgcagc acggcatgat ctgtctgtac     1140
gacagccagc aggcgatttt gaatattgaa gcgttgcagg aagccgatca gcagttaatc     1200
cccggcagct cgcaaatccg ctatcgtccg ggcgaagggc tggtcgggac ggtgctttcg     1260
cagggccaat cattagtgct ggcgcgcgtt gctgacgatc agcgctttct tgaccggctc     1320
gggttgtatg attacaacct gccgtttatc gccgtgccgc tgatagggcc agatgcgcag     1380
actttcggtg tgctgacggc acaacccatg gcgcgttacg aagagcgatt acccgcctgc     1440
acccgctttc tggaaacggt c                                               1461
```

<210> SEQ ID NO 242
<211> LENGTH: 2563
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-1 with 500bp flank

<400> SEQUENCE: 242

```
gcgcaaagcg agtgctcact tacgtgatct gttgacacaa tctgaagcga ccataacttc       60
tgccgtttca gcgaatacgg cggtgtggag cgcacaatca gccctggcga agctggtgct      120
caccgagtgg ctagtgacgc agggctggcg aaccttcctt gatgaaaaag cgcaggccaa      180
attcgccgac tcctttaaac gctttgctga catccatctg tcacgcagcg ccgccgagct      240
gaaaaaagcc tttgcccaac cgctgggcga cagctatcgc gaccagttgc cgcgcctggc      300
gcgtgatatc gactgcgcgt tactgctggc cgggcattac gatcgcgcgc gcgccgtgga      360
atggctggaa aactggcagg ggcttcagca cgccattgaa acgcgccaga gagtcgaaat      420
cgaacatttc cgtaataccg cgattaccca ggagccgttc tggttgcaca gcggaaaacg      480
ttaacgaaag gatatttcgc atgtttaacg atctgattgg cgatgatgaa acggattcgc      540
cggaagatgc gctttctgag agctggcgcg aattgtggca ggatgcgttg caggaggagg      600
attccacgcc cgtgctggcg catctctcag aggacgatcg ccgccgcgtg gtggcgctga      660
```

```
ttgccgattt tcgcaaagag ttggataaac gcaccattgg cccgcgaggg cggcaggtac      720
tcgatcactt aatgccgcat ctgctcagcg atgtatgctc gcgcgacgat gcgccagtac      780
cgctgtcacg cctgacgccg ctgctcaccg gaattattac ccgcaccact taccttgagc      840
tgctaagtga atttcccggc gcactgaaac acctcatttc cctgtgtgcc gcgtcgccga      900
tggttgccag tcagctggcg cgctacccga tcctgcttga tgaattgctc gacccgaata      960
cgctctatca accgacggcg atgaatgcct atcgcgatga gctgcgccaa tacctgctgc     1020
gcgtgccgga agatgatgaa gagcaacagc ttgaggcgct gcggcagttt aagcaggcgc     1080
agttgctgcg cgtggcggcg gcggatattg ccggtacgtt gccagtaatg aaagtgagcg     1140
atcacttaac ctggctggcg gaagcgatta ttgatgcggt ggtgcagcaa gcctgggggc     1200
agatggtggc gcgttatggc cagccaacgc atctgcacga tcgcgaaggg cgcggttttg     1260
cggtggtcgg ttatggcaag ctgggcggct gggagctggg ttacagctcc gatctggatc     1320
tggtattcct gcacgactgc ccgatggatg tgatgaccga tggcgagcgt gaaatcgatg     1380
gtcgccagtt ctatttgcgt ctcgcgcagc gcgtgatgca cctgtttagc acgcgcacgt     1440
cgtccggcat cctttatgaa gttgatgcgc gtctgcgtcc atctggcgct gcggggatgc     1500
tggtcactac tacggaatcg ttcgccgatt accagcaaaa cgaagcctgg acgtgggaac     1560
atcaggcgct ggcccgtgcg cgcgtggtgt acggcgatcc gcaactgacc gccgaatttg     1620
acgccattcg ccgcgatatt ctgatgacgc ctcgcgacgg cgcaacgctg caaaccgacg     1680
tgcgagaaat gcgcgagaaa atgcgtgccc atcttggcaa caagcataaa gaccgcttcg     1740
atctgaaagc cgatgaaggc ggtatcaccg acatcgagtt tatcgcccaa tatctggtgc     1800
tgcgctttgc ccatgacaag ccgaaactga cgcgctggtc ggataatgtg cgcattctcg     1860
aagggctggc gcaaaacggc atcatggagg agcaggaagc gcaggcattg acgctggcgt     1920
acaccacatt gcgtgatgag ctgcaccacc tggcgctgca agagttgccg ggacatgtgg     1980
cgctctcctg ttttgtcgcc gagcgtgcgc ttattaaaac cagctgggac aagtggctgg     2040
tggaaccgtg cgccccggcg taagtgtggt atcatcgcgc gcaaattttg tatctctcag     2100
gagacaggaa tgaaagtgac gctgccagag tttaagcaag ccggtgtaat ggtggtgggt     2160
gatgtgatgc tggatcgtta ctggtatggc ccaaccagcc gtatctctcc ggaagcgcca     2220
gtcccggttg ttaaagtcga taccattgaa gagcgtcctg gcggcgcggc aaacgtggcg     2280
atgaatatcg cctcactggg cgccacggcg cgtctggttg gcctgactgg cattgacgat     2340
gcggcgcgcg cgctgagcaa agcgctggcc gatgttaacg ttaaatgtga cttcgtttct     2400
gttccgacgc atcccaccat cactaagctg cgcgtgctgt cgcgtaacca gcagctgatt     2460
cgcctggact ttgaagaggg ttttgaagga gtcgatccgc aaccgatgca tgaacgcatc     2520
agccaggcgc ttggtaatat tggcgcgctg gtgctgtcgg att                       2563
```

<210> SEQ ID NO 243
<211> LENGTH: 1563
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: glnE-delta-AR-1

<400> SEQUENCE: 243

```
atgtttaacg atctgattgg cgatgatgaa acggattcgc cggaagatgc gctttctgag       60
```

```
agctggcgcg aattgtggca ggatgcgttg caggaggagg attccacgcc cgtgctggcg      120
catctctcag aggacgatcg ccgccgcgtg gtggcgctga ttgccgattt tcgcaaagag      180
ttggataaac gcaccattgg cccgcgaggg cggcaggtac tcgatcactt aatgccgcat      240
ctgctcagcg atgtatgctc gcgcgacgat gcgccagtac cgctgtcacg cctgacgccg      300
ctgctcaccg gaattattac ccgcaccact taccttgagc tgctaagtga atttcccggc      360
gcactgaaac acctcatttc cctgtgtgcc gcgtcgccga tggttgccag tcagctggcg      420
cgctacccga tcctgcttga tgaattgctc gacccgaata cgctctatca accgacggcg      480
atgaatgcct atcgcgatga gctgcgccaa tacctgctgc gcgtgccgga agatgatgaa      540
gagcaacagc ttgaggcgct gcggcagttt aagcaggcgc agttgctgcg cgtggcggcg      600
gcggatattg ccggtacgtt gccagtaatg aaagtgagcg atcacttaac ctggctggcg      660
gaagcgatta ttgatgcggt ggtgcagcaa gcctgggggc agatggtggc gcgttatggc      720
cagccaacgc atctgcacga tcgcgaaggg cgcggttttg cggtggtcgg ttatggcaag      780
ctgggcggct gggagctggg ttacagctcc gatctggatc tggtattcct gcacgactgc      840
ccgatggatg tgatgaccga tggcgagcgt gaaatcgatg tcgccagtt ctatttgcgt      900 ctcgcgcagc gcgtgatgca cctgtttagc acgcgcacgt cgtccggcat cctttatgaa      960
gttgatcgcg tctgcgtcc atctggcgct gcggggatgc tggtcactac tacggaatcg     1020
ttcgccgatt accagcaaaa cgaagcctgg acgtgggaac atcaggcgct ggcccgtgcg     1080
cgcgtggtgt acggcgatcc gcaactgacc gccgaatttg acgccattcg ccgcgatatt     1140
ctgatgacgc ctcgcgacgg cgcaacgctg caaaccgacg tgcgagaaat gcgcgagaaa     1200
atgcgtgccc atcttggcaa caagcataaa gaccgcttcg atctgaaagc cgatgaaggc     1260
ggtatcaccg acatcgagtt tatcgcccaa tatctggtgc tgcgctttgc ccatgacaag     1320
ccgaaactga cgcgctggtc ggataatgtg cgcattctcg aagggctggc gcaaaacggc     1380
atcatggagg agcaggaagc gcaggcattg acgctggcgt acaccacatt gcgtgatgag     1440
ctgcaccacc tggcgctgca agagttgccg ggacatgtgg cgctctcctg ttttgtcgcc     1500
gagcgtgcgc ttattaaaac cagctgggac aagtggctgg tggaaccgtg cgccccggcg     1560
taa                                                                    1563
```

<210> SEQ ID NO 244
<211> LENGTH: 2563
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-1 with 500bp flank

<400> SEQUENCE: 244

```
gcgcaaagcg agtgctcact tacgtgatct gttgacacaa tctgaagcga ccataacttc       60
tgccgtttca gcgaatacgg cggtgtggag cgcacaatca gccctggcga agctggtgct      120
caccgagtgg ctagtgacgc agggctggcg aaccttcctt gatgaaaaag cgcaggccaa      180
attcgccgac tcctttaaac gctttgctga catccatctg tcacgcagcg ccgccgagct      240
gaaaaaagcc tttgcccaac cgctgggcga cagctatcgc gaccagttgc cgcgcctggc      300
gcgtgatatc gactgcgcgt tactgctggc cgggcattac gatcgcgcgc gcgccgtgga      360
atggctggaa aactggcagg ggcttcagca cgccattgaa acgcgccaga gagtcgaaat      420
```

-continued

```
cgaacatttc cgtaataccg cgattaccca ggagccgttc tggttgcaca gcggaaaacg      480
ttaacgaaag gatatttcgc atgtttaacg atctgattgg cgatgatgaa acggattcgc      540
cggaagatgc gctttctgag agctggcgcg aattgtggca ggatgcgttg caggaggagg      600
attccacgcc cgtgctggcg catctctcag aggacgatcg ccgccgcgtg gtggcgctga      660
ttgccgattt tcgcaaagag ttggataaac gcaccattgg cccgcgaggg cggcaggtac      720
tcgatcactt aatgccgcat ctgctcagcg atgtatgctc gcgcgacgat gcgccagtac      780
cgctgtcacg cctgacgccg ctgctcaccg gaattattac ccgcaccact taccttgagc      840
tgctaagtga atttcccggc gcactgaaac acctcatttc cctgtgtgcc gcgtcgccga      900
tggttgccag tcagctggcg cgctacccga tcctgcttga tgaattgctc gacccgaata      960
cgctctatca accgacggcg atgaatgcct atcgcgatga gctgcgccaa tacctgctgc     1020
gcgtgccgga agatgatgaa gagcaacagc ttgaggcgct gcggcagttt aagcaggcgc     1080
agttgctgcg cgtggcggcg gcggatattg ccggtacgtt gccagtaatg aaagtgagcg     1140
atcacttaac ctggctggcg gaagcgatta ttgatgcggt ggtgcagcaa gcctgggggc     1200
agatggtggc gcgttatggc cagccaacgc atctgcacga tcgcgaaggg cgcggttttg     1260
cggtggtcgg ttatggcaag ctgggcggct gggagctggg ttacagctcc gatctggatc     1320
tggtattcct gcacgactgc ccgatggatg tgatgaccga tggcgagcgt gaaatcgatg     1380
gtcgccagtt ctatttgcgt ctcgcgcagc gcgtgatgca cctgtttagc acgcgcacgt     1440
cgtccggcat cctttatgaa gttgatgcgc gtctgcgtcc atctggcgct gcggggatgc     1500
tggtcactac tacggaatcg ttcgccgatt accagcaaaa cgaagcctgg acgtgggaac     1560
atcaggcgct ggcccgtgcg cgcgtggtgt acggcgatcc gcaactgacc gccgaatttg     1620
acgccattcg ccgcgatatt ctgatgacgc ctcgcgacgg cgcaacgctg caaaccgacg     1680
tgcgagaaat gcgcgagaaa atgcgtgccc atcttggcaa caagcataaa gaccgcttcg     1740
atctgaaagc cgatgaaggc ggtatcaccg acatcgagtt tatcgcccaa tatctggtgc     1800
tgcgctttgc ccatgacaag ccgaaactga cgcgctggtc ggataatgtg cgcattctcg     1860
aagggctggc gcaaaacggc atcatggagg agcaggaagc gcaggcattg acgctggcgt     1920
acaccacatt gcgtgatgag ctgcaccacc tggcgctgca agagttgccg ggacatgtgg     1980
cgctctcctg ttttgtcgcc gagcgtgcgc ttattaaaac cagctgggac aagtggctgg     2040
tggaaccgtg cgccccggcg taagtgtggt atcatcgcgc gcaaattttg tatctctcag     2100
gagacaggaa tgaaagtgac gctgccagag tttaagcaag ccggtgtaat ggtggtgggt     2160
gatgtgatgc tggatcgtta ctggtatggc ccaaccagcc gtatctctcc ggaagcgcca     2220
gtcccggttg ttaaagtcga taccattgaa gagcgtcctg cgggcgcggc aaacgtggcg     2280
atgaatatcg cctcactggg cgccacggcg cgtctggttg gcctgactgg cattgacgat     2340
gcggcgcgcg cgctgagcaa agcgctggcc gatgttaacg ttaaatgtga cttcgtttct     2400
gttccgacgc atcccaccat cactaagctg cgcgtgctgt cgcgtaacca gcagctgatt     2460
cgcctggact ttgaagaggg ttttgaagga gtcgatccgc aaccgatgca tgaacgcatc     2520
agccaggcgc ttggtaatat tggcgcgctg gtgctgtcgg att                      2563
```

<210> SEQ ID NO 245
<211> LENGTH: 426
<212> TYPE: DNA
<213> ORGANISM: Artificial Sequence
<220> FEATURE:

-continued

```
<223> OTHER INFORMATION: Description of Artificial Sequence: Synthetic
      polynucleotide
<220> FEATURE:
<223> OTHER INFORMATION: delta-nifL::Prm5

<400> SEQUENCE: 245
atgaccctga atatgatgat ggatgccggc ggacatcatc gcgacaaaca atattaatac       60
cggcaaccac accggcaatt tacgagactg cgcaggcatc ctttctcccg tcaatttctg      120
tcaaataaag taaaagaggc agtctacttg aattaccccc ggctggttga gcgtttgttg      180
aaaaaaagta actgaaaaat ccgtagaata gcgccactct gatggttaat taacctattc      240
aattaagaat tatctggatg aatgtgccat taaatgcgca gcataatggt gcgttgtgcg      300
ggaaaactgc ttttttttga aagggttggt cagtagcgga aacaactcac ttcacacccc      360 gaaggggggaa gttgcctgac cctacgattc ccgctatttc attcactgac cggaggttca      420
aaatga                                                                  426

<210> SEQ ID NO 246
<211> LENGTH: 1426
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm5 with 500bp flank

<400> SEQUENCE: 246
accggatacg agagaaaagt gtctacatcg gttcggttga tattgaccgg cgcatccgcc       60
agcccgccca gtttctggtg gatctgtttg gcgattttgc gggtcttgcc ggtgtcggtg      120
ccgaaaaaaa taccaatatt tgccataaca cacgctcctg ttgaaaaaga gatcccgccg      180
ggaaatgcgg tgaacgtgtc tgatattgcg aagagtgtgc cagttttggt cgcgggcaaa      240
acctgcacca gtttggttat taatgcacca gtctggcgct ttttttcgcc gagtttctcc      300
tcgctaatgc ccgccaggcg cggctttggc gctgatagcg cgctgaatac cgatctggat      360
caaggttttg tcgggttatc agccaaaagg tgcactcttt gcatggttat acgtgcctga      420
catgttgtcc gggcgacaaa cggcctggtg gcacaaattg tcagaactac gacacgacta      480
actgaccgca ggagtgtgcg atgaccctga atatgatgat ggatgccggc ggacatcatc      540
gcgacaaaca atattaatac cggcaaccac accggcaatt tacgagactg cgcaggcatc      600
ctttctcccg tcaatttctg tcaaataaag taaaagaggc agtctacttg aattaccccc      660
ggctggttga gcgtttgttg aaaaaaagta actgaaaaat ccgtagaata gcgccactct      720
gatggttaat taacctattc aattaagaat tatctggatg aatgtgccat taaatgcgca      780
gcataatggt gcgttgtgcg ggaaaactgc ttttttttga aagggttggt cagtagcgga      840
aacaactcac ttcacacccc gaaggggggaa gttgcctgac cctacgattc ccgctatttc      900
attcactgac cggaggttca aaatgaccca gcgaaccgag tcgggtaata ccgtctggcg      960
cttcgatttg tcccagcagt tcactgcgat gcagcgcata agcgtggtac tcagccgggc     1020
gaccgaggtc gatcagacgc tccagcaagt gctgtgcgta ttgcacaatg acgccttttt     1080
gcagcacggc atgatctgtc tgtacgacag ccagcaggcg attttgaata ttgaagcgtt     1140
gcaggaagcc gatcagcagt taatccccgg cagctcgcaa atccgctatc gtccgggcga     1200
agggctggtc gggacggtgc tttcgcaggg ccaatcatta gtgctggcgc gcgttgctga     1260
cgatcagcgc tttcttgacc ggctcgggtt gtatgattac aacctgccgt ttatcgccgt     1320
```

-continued

```
gccgctgata gggccagatg cgcagacttt cggtgtgctg acggcacaac ccatggcgcg    1380
ttacgaagag cgattacccg cctgcacccg ctttctggaa acggtc                   1426

<210> SEQ ID NO 247
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 247
atgaccctga atatgatgat ggatgccggc cgtcctgtaa taataaccgg acaattcgga      60
ctgattaaaa aagcgccctt gtggcgcttt ttttatattc ccgcctccat ttaaaataaa     120
aaatccaatc ggatttcact atttaaactg gccattatct aagatgaatc cgatggaagc     180
tcgctgtttt aacacgcgtt ttttaacctt ttattgaaag tcggtgcttc tttgagcgaa     240
cgatcaaatt taagtggatt cccatcaaaa aaatattctc aacctaaaaa agtttgtgta     300
atacttgtaa cgctacatgg agattaactc aatctagagg gtattaataa tgaatcgtac     360
taaactggta ctgggcgcaa ctcacttcac accccgaagg gggaagttgc ctgaccctac     420
gattcccgct atttcattca ctgaccggag gttcaaaatg a                         461

<210> SEQ ID NO 248
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 248
accggatacg agagaaaagt gtctacatcg gttcggttga tattgaccgg cgcatccgcc      60
agcccgccca gtttctggtg gatctgtttg gcgattttgc gggtcttgcc ggtgtcggtg     120
ccgaaaaaaa taccaatatt tgccataaca cacgctcctg ttgaaaaaga gatcccgccg     180
ggaaatgcgg tgaacgtgtc tgatattgcg aagagtgtgc cagttttggt cgcgggcaaa     240
acctgcacca gtttggttat taatgcacca gtctggcgct ttttttcgcc gagtttctcc     300
tcgctaatgc ccgccaggcg cggctttggc gctgatagcg cgctgaatac cgatctggat     360
caaggttttg tcgggttatc agccaaaagg tgcactcttt gcatggttat acgtgcctga     420
catgttgtcc gggcgacaaa cggcctggtg cacaaattg tcagaactac gacacgacta     480
actgaccgca ggagtgtgcg atgaccctga atatgatgat ggatgccggc cgtcctgtaa     540
taataaccgg acaattcgga ctgattaaaa aagcgccctt gtggcgcttt ttttatattc     600
ccgcctccat ttaaaataaa aaatccaatc ggatttcact atttaaactg gccattatct     660
aagatgaatc cgatggaagc tcgctgtttt aacacgcgtt ttttaacctt ttattgaaag     720
tcggtgcttc tttgagcgaa cgatcaaatt taagtggatt cccatcaaaa aaatattctc     780
aacctaaaaa agtttgtgta atacttgtaa cgctacatgg agattaactc aatctagagg     840
gtattaataa tgaatcgtac taaactggta ctgggcgcaa ctcacttcac accccgaagg     900
gggaagttgc ctgaccctac gattcccgct atttcattca ctgaccggag gttcaaaatg     960
```

-continued

```
acccagcgaa ccgagtcggg taataccgtc tggcgcttcg atttgtccca gcagttcact      1020
gcgatgcagc gcataagcgt ggtactcagc cgggcgaccg aggtcgatca gacgctccag      1080
caagtgctgt gcgtattgca caatgacgcc tttttgcagc acggcatgat ctgtctgtac      1140
gacagccagc aggcgatttt gaatattgaa gcgttgcagg aagccgatca gcagttaatc      1200
cccggcagct cgcaaatccg ctatcgtccg ggcgaagggc tggtcgggac ggtgctttcg      1260
cagggccaat cattagtgct ggcgcgcgtt gctgacgatc agcgctttct tgaccggctc      1320
gggttgtatg attacaacct gccgtttatc gccgtgccgc tgatagggcc agatgcgcag      1380
actttcggtg tgctgacggc acaacccatg gcgcgttacg aagagcgatt acccgcctgc      1440
acccgctttc tggaaacggt c                                                1461
```

<210> SEQ ID NO 249
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 249

```
atggcactga aacacctcat ttccctgtgt gccgcgtcgc cgatggttgc cagtcagctg       60
gcgcgctacc cgatcctgct tgatgaattg ctcgacccga atacgctcta tcaaccgacg      120
gcgatgaatg cctatcgcga tgagctgcgc caatacctgc tgcgcgtgcc ggaagatgat      180
gaagagcaac agcttgaggc gctgcggcag tttaagcagg cgcagttgct gcgcgtggcg      240
gcggcggata ttgccggtac gttgccagta atgaaagtga gcgatcactt aacctggctg      300
gcggaagcga ttattgatgc ggtggtgcag caagcctggg ggcagatggt ggcgcgttat      360
ggccagccaa cgcatctgca cgatcgcgaa gggcgcggtt ttgcggtggt cggttatggc      420
aagctgggcg gctgggagct gggttacagc tccgatctgg atctggtatt cctgcacgac      480
tgcccgatgg atgtgatgac cgatggcgag cgtgaaatcg atggtcgcca gttctatttg      540
cgtctcgcgc agcgcgtgat gcacctgttt agcacgcgca cgtcgtccgg catcctttat      600
gaagttgatg cgcgtctgcg tccatctggc gctgcgggga tgctggtcac tactacggaa      660
tcgttcgccg attaccagca aaacgaagcc tggacgtggg aacatcaggc gctggcccgt      720
gcgcgcgtgg tgtacggcga tccgcaactg accgccgaat ttgacgccat tcgccgcgat      780
attctgatga cgcctcgcga cggcgcaacg ctgcaaaccg acgtgcgaga aatgcgcgag      840
aaaatgcgtg cccatcttgg caacaagcat aaagaccgct tcgatctgaa agccgatgaa      900
ggcggtatca ccgacatcga gtttatcgcc caatatctgg tgctgcgctt tgcccatgac      960
aagccgaaac tgacgcgctg gtcggataat gtgcgcattc tcgaagggct ggcgcaaaac     1020
ggcatcatgg aggagcagga agcgcaggca ttgacgctgg cgtacaccac attgcgtgat     1080
gagctgcacc acctggcgct gcaagagttg ccgggacatg tggcgctctc ctgttttgtc     1140
gccgagcgtg cgcttattaa aaccagctgg gacaagtggc tggtggaa                  1188
```

<210> SEQ ID NO 250
<211> LENGTH: 2206
<212> TYPE: DNA
<213> ORGANISM: Artificial Sequence
<220> FEATURE:
<223> OTHER INFORMATION: Description of Artificial Sequence: Synthetic
      polynucleotide -continued <220> FEATURE:
<223> OTHER INFORMATION: glnE-delta-AR-2 with 500bp flank

<400> SEQUENCE: 250

```
gcgcaaagcg agtgctcact tacgtgatct gttgacacaa tctgaagcga ccataacttc      60
tgccgtttca gcgaatacgg cggtgtggag cgcacaatca gccctggcga agctggtgct     120
caccgagtgg ctagtgacgc agggctggcg aaccttcctt gatgaaaaag cgcaggccaa     180
attcgccgac tcctttaaac gctttgctga catccatctg tcacgcagcg ccgccgagct     240
gaaaaaagcc tttgcccaac cgctgggcga cagctatcgc gaccagttgc cgcgcctggc     300
gcgtgatatc gactgcgcgt tactgctggc cgggcattac gatcgcgcgc gcgccgtgga     360
atggctggaa aactggcagg ggcttcagca cgccattgaa acgcgccaga gagtcgaaat     420
cgaacatttc cgtaataccg cgattaccca ggagccgttc tggttgcaca gcggaaaacg     480
ttaacgaaag gatatttcgc atggcactga aacacctcat ttccctgtgt gccgcgtcgc     540
cgatggttgc cagtcagctg gcgcgctacc cgatcctgct tgatgaattg ctcgacccga     600
atacgctcta tcaaccgacg gcgatgaatg cctatcgcga tgagctgcgc caatacctgc     660
tgcgcgtgcc ggaagatgat gaagagcaac agcttgaggc gctgcggcag tttaagcagg     720
cgcagttgct gcgcgtggcg gcggcggata ttgccggtac gttgccagta atgaaagtga     780
gcgatcactt aacctggctg gcgggaagcga ttattgatgc ggtggtgcag caagcctggg     840
ggcagatggt ggcgcgttat ggccagccaa cgcatctgca cgatcgcgaa gggcgcggtt     900
ttgcggtggt cggttatggc aagctgggcg gctgggagct gggttacagc tccgatctgg     960
atctggtatt cctgcacgac tgcccgatgg atgtgatgac cgatggcgag cgtgaaatcg    1020
atggtcgcca gttctatttg cgtctcgcgc agcgcgtgat gcacctgttt agcacgcgca    1080
cgtcgtccgg catcctttat gaagttgatg cgcgtctgcg tccatctggc gctgcgggga    1140
tgctggtcac tactacggaa tcgttcgccg attaccagca aaacgaagcc tggacgtggg    1200
aacatcaggc gctggcccgt gcgcgcgtgg tgtacggcga tccgcaactg accgccgaat    1260
ttgacgccat tcgccgcgat attctgatga cgcctcgcga cggcgcaacg ctgcaaaccg    1320
acgtgcgaga aatgcgcgag aaaatgcgtg cccatcttgg caacaagcat aaagaccgct    1380
tcgatctgaa agccgatgaa ggcggtatca ccgacatcga gtttatcgcc caatatctgg    1440
tgctgcgctt tgcccatgac aagccgaaac tgacgcgctg gtcggataat gtgcgcattc    1500
tcgaagggct ggcgcaaaac ggcatcatgg aggagcagga agcgcaggca ttgacgctgg    1560
cgtacaccac attgcgtgat gagctgcacc acctggcgct gcaagagttg ccgggacatg    1620
tggcgctctc ctgttttgtc gccgagcgtg cgcttattaa aaccagctgg gacaagtggc    1680
tggtggaacc gtgcgccccg gcgtaagtgt ggtatcatcg cgcgcaaatt ttgtatctct    1740
caggagacag gaatgaaagt gacgctgcca gagtttaagc aagccggtgt aatggtggtg    1800
ggtgatgtga tgctggatcg ttactggtat ggcccaacca gccgtatctc tccggaagcg    1860
ccagtcccgg ttgttaaagt cgataccatt gaagagcgtc ctggcggcgc ggcaaacgtg    1920
gcgatgaata tcgcctcact gggcgccacg gcgcgtctgg ttggcctgac tggcattgac    1980
gatgcggcgc gcgcgctgag caaagcgctg gccgatgtta acgttaaatg tgacttcgtt    2040
tctgttccga cgcatcccac catcactaag ctgcgcgtgc tgtcgcgtaa ccagcagctg    2100
attcgcctgg actttgaaga gggttttgaa ggagtcgatc cgcaaccgat gcatgaacgc    2160
atcagccagg cgcttggtaa tattggcgcg ctggtgctgt cggatt          2206
```

-continued

```
<210> SEQ ID NO 251
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-amtB

<400> SEQUENCE: 251
tttcgctgaa ggtgtgacca tgggccatca ggtgctggtg cagctggaaa gtgttgccat      60
cactatcgtg tggtctggcg tggtggcctt tattggttac aaactggcgg acatgacggt     120
aggcctgcgc gtaccggaag aacaagaacg tgaagggctg gatgtaaaca gccacggcga     180
aaacgcctat aacgcctga                                                   199

<210> SEQ ID NO 252
<211> LENGTH: 1199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-amtB with 500bp flank

<400> SEQUENCE: 252
tttcctttct gactctgccc gtccgggcgc actaacggcc tgaaatactc cctcttttca      60
ttcctggcac aacgattgca atgtctgttg cgtgttagct gcggccatta tcgaattcga     120
ctggaggggg atctatgaag ctggttaccg tggtgattaa gccattcaaa cttgaagacg     180
tgcgtgaagc gctttcttct attggtattc aagggttgac cgtaactgaa gtgaaaggct     240
ttggccgtca gaagggtcac gctgagctgt accgcggtgc ggaatatagc gttaatttcc     300
tgccgaaagt gaaaattgat gtggcgatcg ctgacgatca actcgatgaa gtaatcgatg     360
tgatcagcaa agcggcctac accggaaaaa ttggcgacgg caaaattttc gttgctgagc     420
tgcaacgcgt cattcgtatt cgtaccggcg aagccgacga agcggcactg taatacaaga     480
cacacagtga tggggatcgg tttcgctgaa ggtgtgacca tgggccatca ggtgctggtg     540
cagctggaaa gtgttgccat cactatcgtg tggtctggcg tggtggcctt tattggttac     600
aaactggcgg acatgacggt aggcctgcgc gtaccggaag aacaagaacg tgaagggctg     660
gatgtaaaca gccacggcga aaacgcctat aacgcctgat tgcgttgagt tatctcctga     720
gcataaaaaa gcctccattc ggaggctttt ctttttttaa gtttaaagcg cggttagttg     780
cgattgcgca tgacgccttc ctgcacgctg gacgcgacca gcacccctc ttgcgtatag      840 aactcgccgc gcacaaaacc gcgagcgctg gaggctgacg tgctttccac actgtagagc     900
agccattcgt tcatattaaa cgggcgatgg aaccacatgg agtggtcaat ggtggcaacc     960
tgcataccgc gctcaaggaa gcccacgccg tgcggctgaa gtgcaaccgg caggaagtta    1020
aagtctgagg catatccaag cagatattga tgtacgcgaa aatcgtccgg caccgtgccg    1080
tttgcgcgga tccatacctg gcgggtggga tcggcaacgt ggcctttcag cgggttatga    1140
aactcaaccg ggcggatctc cagtggttta tcactaagaa acttctcttt ggcctgcgg     1199

<210> SEQ ID NO 253
<211> LENGTH: 1563
<212> TYPE: DNA
<213> ORGANISM: Artificial Sequence
```

-continued

```
<220> FEATURE:
<223> OTHER INFORMATION: Description of Artificial Sequence: Synthetic
      polynucleotide
<220> FEATURE:
<223> OTHER INFORMATION: glnE-delta-AR-1

<400> SEQUENCE: 253
atgtttaacg atctgattgg cgatgatgaa acggattcgc cggaagatgc gctttctgag      60
agctggcgcg aattgtggca ggatgcgttg caggaggagg attccacgcc cgtgctggcg     120
catctctcag aggacgatcg ccgccgcgtg gtggcgctga ttgccgattt tcgcaaagag     180
ttggataaac gcaccattgg cccgcgaggg cggcaggtac tcgatcactt aatgccgcat     240
ctgctcagcg atgtatgctc gcgcgacgat gcgccagtac cgctgtcacg cctgacgccg     300
ctgctcaccg gaattattac ccgcaccact taccttgagc tgctaagtga atttcccggc     360
gcactgaaac acctcatttc cctgtgtgcc gcgtcgccga tggttgccag tcagctggcg     420
cgctacccga tcctgcttga tgaattgctc gacccgaata cgctctatca accgacggcg     480
atgaatgcct atcgcgatga gctgcgccaa tacctgctgc gcgtgccgga agatgatgaa     540
gagcaacagc ttgaggcgct gcggcagttt aagcaggcgc agttgctgcg cgtggcggcg     600
gcggatattg ccggtacgtt gccagtaatg aaagtgagcg atcacttaac ctggctggcg     660
gaagcgatta ttgatgcggt ggtgcagcaa gcctggggc agatggtggc gcgttatggc      720
cagccaacgc atctgcacga tcgcgaaggg cgcggttttg cggtggtcgg ttatggcaag     780
ctgggcggct gggagctggg ttacagctcc gatctggatc tggtattcct gcacgactgc     840
ccgatggatg tgatgaccga tggcgagcgt gaaatcgatg tcgccagtt ctatttgcgt       900 ctcgcgcagc gcgtgatgca cctgtttagc acgcgcacgt cgtccggcat cctttatgaa     960
gttgatgcgc gtctgcgtcc atctggcgct gcggggatgc tggtcactac tacggaatcg    1020
ttcgccgatt accagcaaaa cgaagcctgg acgtgggaac atcaggcgct ggcccgtgcg    1080
cgcgtggtgt acggcgatcc gcaactgacc gccgaatttg acgccattcg ccgcgatatt    1140
ctgatgacgc ctcgcgacgg cgcaacgctg caaaccgacg tgcgagaaat gcgcgagaaa    1200
atgcgtgccc atcttggcaa caagcataaa gaccgcttcg atctgaaagc cgatgaaggc    1260
ggtatcaccg acatcgagtt tatcgcccaa tatctggtgc tgcgctttgc ccatgacaag    1320
ccgaaactga cgcgctggtc ggataatgtg cgcattctcg aagggctggc gcaaaacggc    1380
atcatggagg agcaggaagc gcaggcattg acgctggcgt acaccacatt gcgtgatgag    1440
ctgcaccacc tggcgctgca agagttgccg ggacatgtgg cgctctcctg ttttgtcgcc    1500
gagcgtgcgc ttattaaaac cagctgggac aagtggctgg tggaaccgtg cgccccggcg    1560
taa                                                                   1563

<210> SEQ ID NO 254
<211> LENGTH: 2563
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-1 with 500bp flank

<400> SEQUENCE: 254
gcgcaaagcg agtgctcact tacgtgatct gttgacacaa tctgaagcga ccataacttc       60
tgccgtttca gcgaatacgg cggtgtggag cgcacaatca gccctggcga agctggtgct      120
```

-continued

```
caccgagtgg ctagtgacgc agggctggcg aaccttcctt gatgaaaaag cgcaggccaa    180
attcgccgac tcctttaaac gctttgctga catccatctg tcacgcagcg ccgccgagct    240
gaaaaaagcc tttgcccaac cgctgggcga cagctatcgc gaccagttgc cgcgcctggc    300
gcgtgatatc gactgcgcgt tactgctggc cgggcattac gatcgcgcgc gcgccgtgga    360
atggctggaa aactggcagg ggcttcagca cgccattgaa acgcgccaga gagtcgaaat    420
cgaacatttc cgtaataccg cgattaccca ggagccgttc tggttgcaca gcggaaaacg    480
ttaacgaaag gatatttcgc atgtttaacg atctgattgg cgatgatgaa acggattcgc    540
cggaagatgc gctttctgag agctggcgcg aattgtggca ggatgcgttg caggaggagg    600
attccacgcc cgtgctggcg catctctcag aggacgatcg ccgccgcgtg gtggcgctga    660
ttgccgattt tcgcaaagag ttggataaac gcaccattgg cccgcgaggg cggcaggtac    720
tcgatcactt aatgccgcat ctgctcagcg atgtatgctc gcgcgacgat cgcgccagtac   780 cgctgtcacg cctgacgccg ctgctcaccg gaattattac ccgcaccact taccttgagc    840
tgctaagtga atttcccggc gcactgaaac acctcatttc cctgtgtgcc gcgtcgccga    900
tggttgccag tcagctggcg cgctacccga tcctgcttga tgaattgctc gacccgaata    960
cgctctatca accgacggcg atgaatgcct atcgcgatga gctgcgccaa tacctgctgc   1020
gcgtgccgga agatgatgaa gagcaacagc ttgaggcgct gcggcagttt aagcaggcgc   1080
agttgctgcg cgtggcggcg gcggatattg ccggtacgtt gccagtaatg aaagtgagcg   1140
atcacttaac ctggctggcg gaagcgatta ttgatgcggt ggtgcagcaa gcctgggggc   1200
agatggtggc gcgttatggc cagccaacgc atctgcacga tcgcgaaggg cgcggttttg   1260
cggtggtcgg ttatggcaag ctgggcggct gggagctggg ttacagctcc gatctggatc   1320
tggtattcct gcacgactgc ccgatggatg tgatgaccga tggcgagcgt gaaatcgatg   1380
gtcgccagtt ctatttgcgt ctcgcgcagc gcgtgatgca cctgtttagc acgcgcacgt   1440
cgtccggcat cctttatgaa gttgatgcgc gtctgcgtcc atctggcgct gcggggatgc   1500
tggtcactac tacggaatcg ttcgccgatt accagcaaaa cgaagcctgg acgtgggaac   1560
atcaggcgct ggcccgtgcg cgcgtggtgt acggcgatcc gcaactgacc gccgaatttg   1620
acgccattcg ccgcgatatt ctgatgacgc ctcgcgacgg cgcaacgctg caaaccgacg   1680
tgcgagaaat gcgcgagaaa atgcgtgccc atcttggcaa caagcataaa gaccgcttcg   1740
atctgaaagc cgatgaaggc ggtatcaccg acatcgagtt tatcgcccaa tatctggtgc   1800
tgcgctttgc ccatgacaag ccgaaactga cgcgctggtc ggataatgtg cgcattctcg   1860
aagggctggc gcaaaacggc atcatggagg agcaggaagc gcaggcattg acgctggcgt   1920
acaccacatt gcgtgatgag ctgcaccacc tggcgctgca agagttgccg ggacatgtgg   1980
cgctctcctg ttttgtcgcc gagcgtgcgc ttattaaaac cagctgggac aagtggctgg   2040
tggaaccgtg cgcccggcg taagtgtggt atcatcgcgc gcaaattttg tatctctcag   2100
gagacaggaa tgaaagtgac gctgccagag tttaagcaag ccggtgtaat ggtggtgggt   2160
gatgtgatgc tggatcgtta ctggtatggc ccaaccagcc gtatctctcc ggaagcgcca   2220
gtcccggttg ttaaagtcga taccattgaa gagcgtcctg gcggcgcggc aaacgtggcg   2280
atgaatatcg cctcactggg cgccacggcg cgtctggttg gcctgactgg cattgacgat   2340
gcggcgcgcg cgctgagcaa agcgctggcc gatgttaacg ttaaatgtga cttcgtttct   2400
gttccgacgc atcccaccat cactaagctg cgcgtgctgt cgcgtaacca gcagctgatt   2460
cgcctggact ttgaagaggg ttttgaagga gtcgatccgc aaccgatgca tgaacgcatc   2520
```

```
agccaggcgc ttggtaatat tggcgcgctg gtgctgtcgg att                    2563
```

<210> SEQ ID NO 255
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 255

```
atgaccctga atatgatgat ggatgccggc cgtcctgtaa taataaccgg acaattcgga     60
ctgattaaaa aagcgccctt gtggcgcttt ttttatattc ccgcctccat ttaaaataaa    120
aaatccaatc ggatttcact atttaaactg gccattatct aagatgaatc cgatggaagc    180
tcgctgtttt aacacgcgtt ttttaacctt ttattgaaag tcggtgcttc tttgagcgaa    240
cgatcaaatt taagtggatt cccatcaaaa aaatattctc aacctaaaaa agtttgtgta    300
atacttgtaa cgctacatgg agattaactc aatctagagg gtattaataa tgaatcgtac    360
taaactggta ctgggcgcaa ctcacttcac accccgaagg gggaagttgc ctgaccctac    420
gattcccgct atttcattca ctgaccggag gttcaaaatg a                        461
```

<210> SEQ ID NO 256
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 256

```
accggatacg agagaaaagt gtctacatcg gttcggttga tattgaccgg cgcatccgcc     60
agcccgccca gtttctggtg gatctgtttg gcgattttgc gggtcttgcc ggtgtcggtg    120
ccgaaaaaaa taccaatatt tgccataaca cacgctcctg ttgaaaaaga gatcccgccg    180
ggaaatgcgg tgaacgtgtc tgatattgcg aagagtgtgc cagttttggt cgcgggcaaa    240
acctgcacca gtttggttat taatgcacca gtctggcgct ttttttcgcc gagtttctcc    300
tcgctaatgc ccgccaggcg cggctttggc gctgatagcg cgctgaatac cgatctggat    360
caaggttttg tcgggttatc agccaaaagg tgcactcttt gcatggttat acgtgcctga    420
catgttgtcc gggcgacaaa cggcctggtg gcacaaattg tcagaactac gacacgacta    480
actgaccgca ggagtgtgcg atgaccctga atatgatgat ggatgccggc cgtcctgtaa    540
taataaccgg acaattcgga ctgattaaaa aagcgccctt gtggcgcttt ttttatattc    600
ccgcctccat ttaaaataaa aaatccaatc ggatttcact atttaaactg gccattatct    660
aagatgaatc cgatggaagc tcgctgtttt aacacgcgtt ttttaacctt ttattgaaag    720
tcggtgcttc tttgagcgaa cgatcaaatt taagtggatt cccatcaaaa aaatattctc    780
aacctaaaaa agtttgtgta atacttgtaa cgctacatgg agattaactc aatctagagg    840
gtattaataa tgaatcgtac taaactggta ctgggcgcaa ctcacttcac accccgaagg    900
gggaagttgc ctgaccctac gattcccgct atttcattca ctgaccggag gttcaaaatg    960
acccagcgaa ccgagtcggg taataccgtc tggcgcttcg atttgtccca gcagttcact   1020
```

-continued

```
gcgatgcagc gcataagcgt ggtactcagc cgggcgaccg aggtcgatca gacgctccag    1080
caagtgctgt gcgtattgca caatgacgcc tttttgcagc acggcatgat ctgtctgtac    1140
gacagccagc aggcgatttt gaatattgaa gcgttgcagg aagccgatca gcagttaatc    1200
cccggcagct cgcaaatccg ctatcgtccg ggcgaagggc tggtcgggac ggtgctttcg    1260
cagggccaat cattagtgct ggcgcgcgtt gctgacgatc agcgctttct tgaccggctc    1320
gggttgtatg attacaacct gccgtttatc gccgtgccgc tgatagggcc agatgcgcag    1380
actttcggtg tgctgacggc acaacccatg gcgcgttacg aagagcgatt acccgcctgc    1440
acccgctttc tggaaacggt c                                             1461
```

<210> SEQ ID NO 257
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-amtB

<400> SEQUENCE: 257

```
tttcgctgaa ggtgtgacca tgggccatca ggtgctggtg cagctggaaa gtgttgccat      60
cactatcgtg tggtctggcg tggtggcctt tattggttac aaactggcgg acatgacggt     120
aggcctgcgc gtaccggaag aacaagaacg tgaagggctg gatgtaaaca gccacggcga     180
aaacgcctat aacgcctga                                                 199
```

<210> SEQ ID NO 258
<211> LENGTH: 1199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-amtB with 500bp flank

<400> SEQUENCE: 258

```
tttcctttct gactctgccc gtccgggcgc actaacggcc tgaaatactc cctcttttca      60
ttcctggcac aacgattgca atgtctgttg cgtgttagct gcggccatta tcgaattcga     120
ctggaggggg atctatgaag ctggttaccg tggtgattaa gccattcaaa cttgaagacg     180
tgcgtgaagc gctttcttct attggtattc aaggggttgac cgtaactgaa gtgaaaggct     240
ttggccgtca gaagggtcac gctgagctgt accgcggtgc ggaatatagc gttaatttcc     300
tgccgaaagt gaaaattgat gtggcgatcg ctgacgatca actcgatgaa gtaatcgatg     360
tgatcagcaa agcggcctac accggaaaaa ttggcgacgg caaaattttc gttgctgagc     420
tgcaacgcgt cattcgtatt cgtaccggcg aagccgacga agcggcactg taatacaaga     480
cacacagtga tggggatcgg tttcgctgaa ggtgtgacca tgggccatca ggtgctggtg     540
cagctggaaa gtgttgccat cactatcgtg tggtctggcg tggtggcctt tattggttac     600
aaactggcgg acatgacggt aggcctgcgc gtaccggaag aacaagaacg tgaagggctg     660
gatgtaaaca gccacggcga aaacgcctat aacgcctgat tgcgttgagt tatctcctga     720
gcataaaaaa gcctccattc ggaggctttt cttttttaa gtttaaagcg cggttagttg     780
cgattgcgca tgacgccttc ctgcacgctg gacgcgacca gcacaccctc ttgcgtatag     840
aactcgccgc gcacaaaacc gcgagcgctg gaggctgacg tgctttccac actgtagagc     900
```

```
agccattcgt tcatattaaa cgggcgatgg aaccacatgg agtggtcaat ggtggcaacc      960
tgcataccgc gctcaaggaa gcccacgccg tgcggctgaa gtgcaaccgg caggaagtta     1020
aagtctgagg catatccaag cagatattga tgtacgcgaa aatcgtccgg caccgtgccg     1080
tttgcgcgga tccatacctg gcgggtggga tcggcaacgt ggcctttcag cgggttatga     1140
aactcaaccg ggcggatctc cagtggttta tcactaagaa acttctcttt ggcctgcgg      1199
```

<210> SEQ ID NO 259
<211> LENGTH: 607
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC

<400> SEQUENCE: 259

```
atgaccttta atatgatgcc tggggtcact ggagcgcttt atcggcatcc tgaccgaaga       60
atttgccggt ttcttcccga cctggctggc ccctgttcag gttgtggtga tgaatatcac      120
tgattctcaa gctgaatatg tcaacgaatt gacccgtaaa ttgcaaaatg cgggcattcg      180
tgtaaaagcg gacttgagaa acgagaagat tggctttaaa atccgcgagc acactttacg      240
tcgtgtccct tatatgttgg tctgtggtga taaagaggtg gaagcaggca aagtggccgt      300
tcgcacccgc cgcggtaaag acctgggcag cctggacgta agtgaagtga ttgagaagct      360
gcaacaagag attcgcagcc gcagtcttca acaactggag gaataaggta ttaaaggcgg      420
aaaacgagtt caaacggcac gtccgaatcg tatcaatggc gagattcgcg cccaggaagt      480
tcgcttaact ggtctggaag gtgagcagct gggtattgca atagaactaa ctacccgccc      540
tgaaggcggt acctgcctga ccctgcgatt cccgttattt cattcactga ccggaggccc      600
acgatga                                                                607
```

<210> SEQ ID NO 260
<211> LENGTH: 1607
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC with 500bp flank

<400> SEQUENCE: 260

```
ggtacgacaa aaacgtctcc agcgacgtgc ggttaatatt gactggcgca tccgccacat       60
cccccagttt ttgctggatc agtttggcga ttttgcgggt ttttcccgtg tcactgccaa      120
aaaaaatacc aatgttagcc atgtcgcgct cctgttgaga aagaataagg ccgcctgcaa      180
acggcggata tccttctcc tgttgcgaag gctgtgccag gttttttaa ggccttctgt        240 gcactgaaat gggtgaaaaa atgactcttt tttgtgcagg caccgtcctc tctccgctat       300
ccagacctgc tttgaaggcc tctgagggcc aaatcagggc caaaacacga atcaggatca      360
atgtttcggc gcgttacctg ttcgaaaggt gcactctttg catggttaat cacacccaat      420
cagggctgcg gatgtcgggc gtttcacaac acaaaatgtt gtaaatgcga cacagccggg      480
cctgaaacca ggagcgtgtg atgacctta atatgatgcc tggggtcact ggagcgcttt      540
atcggcatcc tgaccgaaga atttgccggt ttcttcccga cctggctggc ccctgttcag      600
```

-continued

```
gttgtggtga tgaatatcac tgattctcaa gctgaatatg tcaacgaatt gacccgtaaa      660
ttgcaaaatg cgggcattcg tgtaaaagcg gacttgagaa acgagaagat tggctttaaa      720
atccgcgagc acactttacg tcgtgtccct tatatgttgg tctgtggtga taaagaggtg      780
gaagcaggca aagtggccgt tcgcacccgc cgcggtaaag acctgggcag cctggacgta      840
agtgaagtga ttgagaagct gcaacaagag attcgcagcc gcagtcttca acaactggag      900
gaataaggta ttaaaggcgg aaaacgagtt caaacggcac gtccgaatcg tatcaatggc      960
gagattcgcg cccaggaagt tcgcttaact ggtctggaag gtgagcagct gggtattgca     1020
atagaactaa ctacccgccc tgaaggcggt acctgcctga ccctgcgatt cccgttattt     1080
cattcactga ccggaggccc acgatgaccc agcgacccga gtcgggcacc accgtctggc     1140
gttttgatct ctcacagcaa tttaccgcca tgcagcgcat cagcgtggtg ttgagtcgcg     1200
caaccgagat aagccagacg ctgcaggagg tgctgtgtgt tctgcataat gacgcattta     1260
tgcaacacgg catgctgtgt ctgtatgaca accagcagga aattctgagt attgaagcct     1320
tgcaggaggc agaccaacat ctgatccccg gcagctcgca aattcgctat cgccctggcg     1380
aagggctggt aggagccgta ctgtcccagg acaatctct tgtgctgccg cgtgtcgccg     1440
acgatcaacg ctttctcgac aggcttggca tctatgatta caacctgccg tttatcgccg     1500
tccccttaat ggggccaggc gcgcagacga ttggcgtgct cgccgcgcag ccgatggcgc     1560
gtctggagga gcggcttcct tcctgtacgc gctttctgga aaccgtc                   1607
```

<210> SEQ ID NO 261
<211> LENGTH: 1536
<212> TYPE: DNA
<213> ORGANISM: Kosakonia sacchari
<220> FEATURE:
<223> OTHER INFORMATION: 16S-1

<400> SEQUENCE: 261

```
ttgaagagtt tgatcatggc tcagattgaa cgctggcggc aggcctaaca catgcaagtc       60
gaacggtagc acagagagct tgctctcggg tgacgagtgg cggacgggtg agtaatgtct      120
gggaaactgc ctgatggagg gggataacta ctggaaacgg tagctaatac cgcataacgt      180
cgcaagacca aagagggggga ccttcgggcc tcttgccatc agatgtgccc agatgggatt      240
agctagtagg tggggtaacg gctcacctag gcgacgatcc ctagctggtc tgagaggatg      300
accagccaca ctggaactga gacacggtcc agactcctac gggaggcagc agtggggaat      360
attgcacaat gggcgcaagc ctgatgcagc catgccgcgt gtgtgaagaa ggccttcggg      420
ttgtaaagca ctttcagcgg ggaggaaggg agtaaggtta ataaccttat tcattgacgt      480
tacccgcaga agaagcaccg gctaactccg tgccagcagc cgcggtaata cggagggtgc      540
aagcgttaat cggaattact gggcgtaaag cgcacgcagg cggtctgtca agtcggatgt      600
gaaatccccg ggctcaacct gggaactgca tccgaaactg gcaggcttga gtctcgtaga      660
gggaggtaga attccaggtg tagcggtgaa atgcgtagag atctggagga ataccggtgg      720
cgaaggcggc ctcctggacg aagactgacg ctcaggtgcg aaagcgtggg agcaaacag       780 gattagatac cctggtagtc cacgccgtaa acgatgtcta tttggaggtt gtgcccttga      840
ggcgtggctt ccggagctaa cgcgttaaat agaccgcctg gggagtacgg ccgcaaggtt      900
aaaactcaaa tgaattgacg ggggcccgca caagcggtgg agcatgtggt ttaattcgat      960
gcaacgcgaa gaaccttacc tggtcttgac atccacagaa ctttccagag atggattggt     1020
gccttcggga actgtgagac aggtgctgca tggctgtcgt cagctcgtgt tgtgaaatgt     1080
```

-continued

```
tgggttaagt cccgcaacga gcgcaaccct tatcctttgt tgccagcggt ccggccggga    1140
actcaaagga gactgccagt gataaactgg aggaaggtgg ggatgacgtc aagtcatcat    1200
ggcccttacg accagggcta cacacgtgct acaatggcgc atacaaagag aagcgacctc    1260
gcgagagtaa gcggacctca taaagtgcgt cgtagtccgg attggagtct gcaactcgac    1320
tccatgaagt cggaatcgct agtaatcgtg gatcagaatg ccacggtgaa tacgttcccg    1380
ggccttgtac acaccgcccg tcacaccatg ggagtgggtt gcaaaagaag taggtagctt    1440
aaccttcggg agggcgctta ccactttgtg attcatgact ggggtgaagt cgtaacaagg    1500
taaccgtagg ggaacctgcg gttggatcac ctcctt    1536
```

```
<210> SEQ ID NO 262
<211> LENGTH: 1537
<212> TYPE: DNA
<213> ORGANISM: Kosakonia sacchari
<220> FEATURE:
<223> OTHER INFORMATION: 16S-2
<220> FEATURE:
<221> NAME/KEY: modified_base
<222> LOCATION: (450)..(450)
<223> OTHER INFORMATION: a, c, t, g, unknown or other
<220> FEATURE:
<221> NAME/KEY: modified_base
<222> LOCATION: (452)..(452)
<223> OTHER INFORMATION: a, c, t, g, unknown or other
<220> FEATURE:
<221> NAME/KEY: modified_base
<222> LOCATION: (455)..(455)
<223> OTHER INFORMATION: a, c, t, g, unknown or other
<220> FEATURE:
<221> NAME/KEY: modified_base
<222> LOCATION: (473)..(473)
<223> OTHER INFORMATION: a, c, t, g, unknown or other

<400> SEQUENCE: 262
```

```
ttgaagagtt tgatcatggc tcagattgaa cgctggcggc aggcctaaca catgcaagtc    60
gaacggtagc acagagagct tgctctcggg tgacgagtgg cggacgggtg agtaatgtct    120
gggaaactgc ctgatggagg gggataacta ctggaaacgg tagctaatac cgcataacgt    180
cgcaagacca aagaggggga ccttcgggcc tcttgccatc agatgtgccc agatgggatt    240
agctagtagg tggggtaacg gctcacctag gcgacgatcc ctagctggtc tgagaggatg    300
accagccaca ctggaactga gacacggtcc agactcctac gggaggcagc agtggggaat    360
attgcacaat gggcgcaagc ctgatgcagc catgccgcgt gtgtgaagaa ggccttcggg    420
ttgtaaagca ctttcagcgg ggaggaaggn antanggtta ataacctgtg ttnattgacg    480
ttacccgcag aagaagcacc ggctaactcc gtgccagcag ccgcggtaat acggagggtg    540
caagcgttaa tcggaattac tgggcgtaaa gcgcacgcag gcggtctgtc aagtcggatg    600
tgaaatcccc gggctcaacc tgggaactgc atccgaaact ggcaggcttg agtctcgtag    660
agggaggtag aattccaggt gtagcggtga atgcgtaga gatctggagg aataccggtg    720
gcgaaggcgg cctcctggac gaagactgac gctcaggtgc gaaagcgtgg ggagcaaaca    780
ggattagata ccctggtagt ccacgccgta aacgatgtct atttggaggt tgtgcccttg    840
aggcgtggct tccggagcta acgcgttaaa tagaccgcct ggggagtacg gccgcaaggt    900
taaaactcaa atgaattgac ggggggccgc acaagcggtg gagcatgtgg tttaattcga    960
tgcaacgcga agaaccttac ctggtcttga catccacaga acttagcaga gatgctttgg    1020
tgccttcggg aactgtgaga caggtgctgc atggctgtcg tcagctcgtg ttgtgaaatg    1080
```

```
ttgggttaag tcccgcaacg agcgcaaccc ttatcctttg ttgccagcgg ttaggccggg    1140
aactcaaagg agactgccag tgataaactg gaggaaggtg gggatgacgt caagtcatca    1200
tggcccttac gaccagggct acacacgtgc tacaatggcg catacaaaga gaagcgacct    1260
cgcgagagta agcggacctc ataaagtgcg tcgtagtccg gattggagtc tgcaactcga    1320
ctccatgaag tcggaatcgc tagtaatcgt ggatcagaat gccacggtga atacgttccc    1380
gggccttgta cacaccgccc gtcacaccat gggagtgggt tgcaaaagaa gtaggtagct    1440
taaccttcgg gagggcgctt accactttgt gattcatgac tggggtgaag tcgtaacaag    1500
gtaaccgtag gggaacctgc ggttggatca cctcctt                            1537
```

<210> SEQ ID NO 263
<211> LENGTH: 882
<212> TYPE: DNA
<213> ORGANISM: Kosakonia sacchari
<220> FEATURE:
<223> OTHER INFORMATION: nifH

<400> SEQUENCE: 263

```
atgaccatgc gtcaatgcgc catttacggc aaaggtggga tcggcaaatc gaccaccaca     60
cagaacctgg tcgccgcgct ggcggagatg ggtaaaaaag tcatgattgt cggctgtgac    120
ccgaaagccg attccacgcg tttgatcctg catgcgaaag cgcagaacac cattatggag    180
atggctgctg aagtcggctc cgtggaagac ctggagttag aagacgtgct gcaaatcggt    240
tacggcggcg tgcgctgcgc agagtccggc ggcccggagc caggcgtggg ctgtgccggt    300
cgcggggtga tcaccgcgat taacttcctc gaagaagaag cgcttacgt gccggatctc    360 gattttgttt tctacgacgt gctgggcgac gtggtatgcg gtggtttcgc catgccgatt    420
cgtgaaaaca aagcgcagga gatctacatc gtttgctctg gcgaaatgat ggcgatgtac    480
gccgccaaca acatctccaa aggcatcgtg aaatacgcca aatccggtaa agtgcgcctc    540
ggcgggctga tttgtaactc gcgccagacc gaccgtgaag atgaactgat cattgcgctg    600
gcagaaaaac tcggcacgca gatgatccac tttgttcccc gcgacaacat tgtgcagcgt    660
gcggaaatcc gccgtatgac ggttatcgaa atgaccccga cctgcaatca ggcgaacgaa    720
tatcgcagcc ttgccagcaa aatcgtcaac aacaccaaaa tggtggtgcc cacccctgc    780 accatggatg aactggaaga actgctgatg gagttcggca ttatggatgt ggaagacacc    840
agcatcattg gtaaaaccgc cgccgaagaa aacgccgtct ga                      882
```

<210> SEQ ID NO 264
<211> LENGTH: 1449
<212> TYPE: DNA
<213> ORGANISM: Kosakonia sacchari
<220> FEATURE:
<223> OTHER INFORMATION: nifD2

<400> SEQUENCE: 264

```
atgagcaatg caacaggcga acgcaacctg gagataatcg agcaggtgct cgaggttttc     60
ccggagaaga cgcgcaaaga acgcagaaaa cacatgatgg tgacggaccc ggagcaggaa    120
agcgtcggta agtgcatcat ctctaaccgc aaatcgcagc caggcgtgat gaccgtgcgc    180
ggctgctcgt atgccggttc gaaaggggtg gtatttgggc caatcaagga tatggcgcat    240
atctcgcatg gcccaatcgg ctgcggccaa tactcccgcg ccgggcggcg gaactactac    300
accggcgtca gcggcgtgga cagcttcggc acgctcaact tcacctccga ttttcaggag    360
cgcgacatcg tgtttggcgg cgataaaaag ctcgccaaac tgattgaaga gctggaagag    420
```

```
ctgttcccgc tgaccaaagg catttcgatt cagtcggaat gcccggtcgg cctgattggc        480
gatgacattg aggccgtcgc gaacgccagc cgcaaagcca tcaacaaacc ggttattccg        540
gtgcgttgcg aaggctttcg cggcgtgtcg caatccctcg gtcaccatat tgccaacgat        600
gtgatccgcg actgggtgct ggataaccgc gaaggcaaac cgttcgaatc cacccccttac      660 gatgtggcga tcatcggcga ttacaacatc ggcggcgatg cctgggcttc gcgcattttg        720
ctcgaagaga tgggcttgcg ggtggtggca cagtggtctg cgacggtac gctggtggag         780 atggaaaaca cgccgttcgt caaactgaac ctggtgcatt gttaccgctc aatgaactac        840
atctcgcgcc atatggagga gaagcacggt attccgtgga tggaatacaa cttctttggt        900
ccgacgaaaa tcgcggaatc gctgcgcaaa atcgccgacc agtttgacga caccattcgc        960
gccaacgccg aagcggtgat cgccagatac caggcgcaaa acgacgccat tatcgccaaa       1020
tatcgcccgc gtctggaggg gcgcaaagtg ctgctttata tgggcgggct gcgtccgcgc       1080
catgtgattg gcgcctatga agacctggga atggagatca tcgctgccgg ttatgagttc       1140
ggtcataacg atgattacga ccgcaccttg ccggatctga agagggcac gctgctgttt        1200 gatgatgcca gcagttatga gctggaggcg ttcgtcaacg cgctgaaacc ggatctcatc       1260
ggttccggca tcaaagagaa gtacatcttt cagaaaatgg gcgtgccgtt tcgccagatg       1320
cactcctggg attactccgg cccgtaccac ggctatgacg gcttcgccat cttcgcccgc       1380
gatatggata tgacgctcaa caaccccgcg tggggccagt tgaccgcgcc gtggctgaaa       1440
tccgcctga                                                              1449
```

```
<210> SEQ ID NO 265
<211> LENGTH: 1563
<212> TYPE: DNA
<213> ORGANISM: Kosakonia sacchari
<220> FEATURE:
<223> OTHER INFORMATION: nifK2

<400> SEQUENCE: 265
```

```
atgagccaga ctgctgagaa aatacagaat tgccatcccc tgtttgaaca ggatgcttac         60
cagacgctgt ttgccggtaa acgggcactc gaagaggcgc actcgccgga gcgggtgcag        120
gaagtgtttc aatggaccac tacccccggaa tatgaagcgc tgaactttaa acgcgaagcg       180
ctgactatcg acccggcaaa agcctgccag ccgctgggcg cggtgctctg ttcgctgggg        240
tttgccaata ccctaccgta tgtgcacggt tcacagggtt gcgtggccta tttccgcacg        300
tactttaacc gccactttaa agaaccggtg gcctgcgtgt cggattcaat gacggaagac        360
gcggcggtgt cggcgggaa taacaacctc aacaccggct acaaaacgc cagcgcgctg          420 tataaaccgg agattatcgc cgtctctacc acctgtatgg cggaagtgat cggtgatgat        480
ttgcaggcct ttatcgccaa cgccaaaaaa gatggttttc tcgatgccgc catccccgtg        540
ccctacgcgc acaccccag tttatcggc agccatatca ccggctggga taacatgttt         600
gaaggttttg cccggacctt tacggcagac catgaagctc agcccggcaa actttcacgc        660
atcaacctgg tgaccgggt tgaaacctat ctcggcaatt tccgcgtgct gaaacgcatg         720
atggaacaaa tggaggtgcc ggcgagtgtg ctctccgatc cgtcggaagt gctggatact       780
cccgccaacg ggcattacca gatgtacgcg ggcgggacga cgcagcaaga gatgcgcgag       840
gcgccggatg ctatcgacac cctgttgctg cagccctggc aactggtgaa aagcaaaaaa       900
gtggtgcagg agatgtggaa tcagcccgcc accgaggttt ctgttcccgt tgggctggca       960
```

-continued

```
ggaacagacg aactgttgat ggcgattagc cagttaaccg gcaaggccat tcccgattca    1020
ctggcgctgg agcgcgggcg gctggtcgat atgatgctcg attcccacac ctggttgcac    1080
ggtaaaaaat tcggcctgtt tggcgatccg gattttgtca tgggattgac ccgtttcctg    1140
ctggagctgg gctgcgaacc gaccgttatc ctctgccaca acggtaacaa acgctggcag    1200
aaagcaatga agaaaatgct tgacgcctcg ccgtacggcc aggagagcga agtgtttatc    1260
aactgcgatt tgtggcattt ccgctcgctg atgtttaccc gccagccgga ttttatgatt    1320
ggcaactcgt acggcaagtt cattcagcgc gacaccttag ccaaaggcga gcagtttgaa    1380
gttccgctga tccgcctcgg ttttcccctg ttcgaccgcc accatctgca ccgccagacc    1440
acctggggct acgagggcgc catgagcatt ctcactaccc ttgtgaatgc ggtactggag    1500
aaagtggaca agagaccat caagctcggc aaaaccgact acagcttcga tcttatccgt    1560
taa                                                                   1563
```

<210> SEQ ID NO 266
<211> LENGTH: 1488
<212> TYPE: DNA
<213> ORGANISM: Kosakonia sacchari
<220> FEATURE:
<223> OTHER INFORMATION: nifL

<400> SEQUENCE: 266

```
atgaccctga atatgatgat ggatgccggc gcgcccgagg caatcgccgg tgcgctttcg      60
cgacaccatc ctgggctgtt ttttaccatc gttgaagaag cgcccgtcgc catttcgctg     120
actgatgccg acgcacgcat tgtctatgcc aacccggctt tctgccgcca gaccggctat     180
gaactagaag cgttgttgca gcaaaatccc cgcctgcttg caagtcgcca aaccccacgg     240
gaaatctatc aggatatgtg gcacaccttg ttacaacgcc gaccgtggcg cgggcaattg     300
attaaccgcc accgcgacgg cagcctgtat ctggtcgaga tcgatatcac cccggtgatt     360
aacccgtttg gcgaactgga acactacctg gcaatgcagc gcgatatcag cgccagttat     420
gcgctggagc agcggttgcg caatcacatg acgctgaccg aagcggtgct gaataacatt     480
ccggcggcgg tggttgtagt ggatgaacgc gatcatgtgg ttatggataa ccttgcctac     540
aaaacgttct gtgccgactg cggcggaaaa gagctcctga gcgaactcaa ttttttcagcc    600 cgaaaagcgg agctggcaaa cggccaggtc ttaccggtgg tgctgcgcgg tgaggtgcgc     660
tggttgtcgg tgacctgctg ggcgctgccg ggcgtcagcg aagaagccag tcgctacttt     720
attgataaca ggctgacgcg cacgctggtg gtgatcaccg acgacaccca acaacgccag     780
cagcaggaac agggccgact tgaccgcctt aaacagcaga tgaccaacgg caaactactg     840
gcagcgatcc gcgaagcgct tgacgccgcg ctgatccagc ttaactgccc catcaatatg     900
ctggcggcgg cgcgacgttt aaacggcagt gataacaaca atgtggcgct cgacgccgcg     960
tggcgcgaag gtgaagaggc gatggcgcgg ctgaaacgtt gccgcccgtc gctggaactg    1020
gaaagtgcgg ccgtctggcc gctgcaaccc tttttttgacg atctgcgcgc gctttatcac    1080
acccgctacg agcagggaa aaatttgcag gtcacgctgg attcccatca tctggtggga    1140
tttggtcagc gtacgcaact gttagcctgc ctgagtctgt ggctcgatcg cacgctggat    1200
attgccgccg ggctgggtga tttcaccgcg caaacgcaga tttacgcccg cgaagaagag    1260
ggctggctct ctttgtatat cactgacaat gtgccgctga tccgctgcg ccacacccac    1320 tcgccggatg cgcttaacgc tccgggaaaa ggcatggagc tgcgcctgat ccagacgctg    1380
gtggcacacc accacggcgc aatagaactc acttcacacc ccgaaggggg aagttgcctg    1440
```

```
accctacgat tcccgctatt tcattcactg accggaggtt caaaatga                1488

<210> SEQ ID NO 267
<211> LENGTH: 1575
<212> TYPE: DNA
<213> ORGANISM: Kosakonia sacchari
<220> FEATURE:
<223> OTHER INFORMATION: nifA

<400> SEQUENCE: 267
atgacccagc gaaccgagtc gggtaatacc gtctggcgct tcgatttgtc ccagcagttc     60
actgcgatgc agcgcataag cgtggtactc agccgggcga ccgaggtcga tcagacgctc    120
cagcaagtgc tgtgcgtatt gcacaatgac gccttttttgc agcacggcat gatctgtctg   180
tacgacagcc agcaggcgat tttgaatatt gaagcgttgc aggaagccga tcagcagtta   240
atccccggca gctcgcaaat ccgctatcgt ccgggcgaag ggctggtcgg gacggtgctt    300
tcgcagggcc aatcattagt gctggcgcgc gttgctgacg atcagcgctt tcttgaccgg    360
ctcgggttgt atgattacaa cctgccgttt atcgccgtgc cgctgatagg gccagatgcg    420
cagactttcg gtgtgctgac ggcacaaccc atggcgcgtt acgaagagcg attacccgcc    480
tgcacccgct ttctggaaac ggtcgctaac ctggtcgcgc aaaccgtgcg tttgatggca    540
ccaccggcag tgcgcccttc cccgcgcgcc gccataacac aggccgccag cccgaaatcc     600
tgcacggcct cacgcgcatt tggttttgaa aatatggtcg gtaacagtcc ggcgatgcgc    660
cagaccatgg agattatccg tcaggtttcg cgctgggaca ccaccgttct ggtacgcggc    720
gagagtggca ccggcaagga gctgattgcc aacgccatcc accaccattc gccgcgtgcc    780
ggtgcgccat ttgtgaaatt caactgtgcg gcgctgccgg acacactgct ggaaagcgaa    840
ttgttcggtc acgagaaagg ggcatttacc ggcgcggtac gccagcgtaa aggccgtttt    900
gagctggccg atggcggcac gctgtttctt gacgagatcg gcgagagtag cgcctcgttt    960
caggctaagc tgctgcgcat tttgcaggaa ggcgaaatgg aacgcgtcgg cggcgacgag   1020
acattgcaag tgaatgtgcg cattattgcc gcgacgaacc gcaatcttga agatgaagtc   1080
cggctggggc actttcgcga agatctctat tatcgcctga atgtgatgcc catcgccctg   1140
ccgccactac gcgaacgcca ggaggacatt gccgagctgg cgcactttct ggtgcgtaaa   1200
atcgcccata accagagccg tacgctgcgc attagcgagg cgctatccg cctgctgatg    1260 agctacaact ggcccggtaa tgtgcgcgaa ctggaaaact gccttgagcg ctcagcggtg   1320
atgtcggaga acggtctgat cgatcgggat gtgattttgt ttaatcatcg cgaccagcca   1380
gccaaaccgc cagttatcag cgtctcgcat gatgataact ggctcgataa caaccttgac   1440
gagcgccagc ggctgattgc ggcgctgaa aaagcgggat gggtacaagc caaagccgcg    1500
cgcttgctgg ggatgacgcc gcgccaggtc gcctatcgta ttcagacgat ggatataacc   1560
ctgccaaggc tataa                                                    1575

<210> SEQ ID NO 268
<211> LENGTH: 2850
<212> TYPE: DNA
<213> ORGANISM: Kosakonia sacchari
<220> FEATURE:
<223> OTHER INFORMATION: glnE

<400> SEQUENCE: 268
atgccgcacc acgcaggatt gtcgcagcac tggcaaacgg tattttctcg tctgccggaa     60
```

```
tcgctcaccg cgcagccatt gagcgcgcag gcgcagtcag tgctcacttt tagtgatttt      120
gttcaggaca gcatcatcgc gcatcctgag tggctggcag agcttgaaag cgcgccgccg      180
cctgcgaacg aatggcaaca ctatgcgcaa tggctgcaag cggcgctgga tggcgtcacc      240
gatgaagcct cgctgatgcg cgcgctgcgg ctgtttcgcc gtcgcatcat ggtgcgcatc      300
gcctggagcc aggcgttaca gttggtggcg gaagaagata tcctgcaaca gcttagcgtg      360
ctggcggaaa ccctgatcgt cgccgcgcgc gactggcttt atgaggcctg ctgccgtgag      420
tggggaacgc cgagcaatcc acaaggcgtg gcgcagccga tgctggtact cggcatgggc      480
aaactgggtg gcggcgaact caatttctca tccgatatcg atttgatttt cgcctggccg      540
gaaaatggcg caacgcgcgg tggacgccgt gagctggata acgcgcaatt tttcactcgc      600
cttggtcaac ggctgattaa agtcctcgac cagccaacgc aggatggctt tgtctaccgc      660
gtcgatatgc gcttgcgccc gtttggcgac agcggcccgc tggtgctgag ctttgccgcg      720
ctggaagatt actaccagga gcaggggcgc gattgggaac gctacgcgat ggtgaaagcg      780
cgcattatgg gcgataacga cggcgaccat gcgcgggagt tgcgcgcaat gctgcgcccg      840 tttgtttttcc gccgttatat cgacttcagc gtgattcagt ccctgcgtaa catgaaaggc      900
atgattgccc gcgaagtgcg tcgccgtggc ctgaaggaca acattaagct cggcgcgggc      960
gggatccgcg aaatagaatt tatcgtccag gttttccagc tgattcgcgg cggtcgcgag     1020
cctgcactgc aatcgcgttc actgttgccg acgcttgctg ccatagatca actgcatctg     1080
ctgccggatg gcgacgcaac ccggctgcgc gaggcgtatt tgtggctgcg acggctggag     1140
aacctgctgc aaagcatcaa tgacgaacag acacagacgc tgccgggcga tgaactgaat     1200
cgcgcgcgcc tcgcctgggg aatgggcaaa gatagctggg aagcgctctg cgaaacgctg     1260
gaagcgcata tgtcggcggt gcgtcagata tttaacgatc tgattggcga tgatgaaacg     1320
gattcgccgg aagatgcgct ttctgagagc tggcgcgaat tgtggcagga tgcgttgcag     1380
gaggaggatt ccacgcccgt gctggcgcat ctctcagagg acgatcgccg ccgcgtggtg     1440
gcgctgattg ccgatttttcg caaagagttg gataaacgca ccattggccc gcgagggcgg     1500
caggtactcg atcacttaat gccgcatctg ctcagcgatg tatgctcgcg cgacgatgcg     1560
ccagtaccgc tgtcacgcct gacgccgctg ctcaccggaa ttattacccg caccacttac     1620
cttgagctgc taagtgaatt tcccggcgca ctgaaacacc tcatttccct gtgtgccgcg     1680
tcgccgatgg ttgccagtca gctggcgcgc tacccgatcc tgcttgatga attgctcgac     1740
ccgaatacgc tctatcaacc gacggcgatg aatgcctatc gcgatgagct cgcgccaatac     1800 ctgctgcgcg tgccggaaga tgatgaagag caacagcttg aggcgctgcg gcagtttaag     1860
caggcgcagt tgctgcgcgt ggcggcggcg gatattgccg gtacgttgcc agtaatgaaa     1920
gtgagcgatc acttaacctg gctggcggaa gcgattattg atgcggtggt gcagcaagcc     1980
tgggggcaga tggtggcgcg ttatggccag ccaacgcatc tgcacgatcg cgaagggcgc     2040
ggttttgcgg tggtcggtta tggcaagctg ggcggctggg agctgggtta cagctccgat     2100
ctggatctgg tattcctgca cgactgcccg atggatgtga tgaccgatgg cgagcgtgaa     2160
atcgatggtc gccagttcta tttgcgtctc gcgcagcgcg tgatgcacct gtttagcacg     2220
cgcacgtcgt ccggcatcct ttatgaagtt gatgcgcgtc tgcgtccatc tggcgctgcg     2280
gggatgctgg tcactactac ggaatcgttc gccgattacc agcaaaacga agcctggacg     2340
tgggaacatc aggcgctggc ccgtgcgcgc gtggtgtacg gcgatccgca actgaccgcc     2400
gaatttgacg ccattcgccg cgatattctg atgacgcctc gcgacggcgc aacgctgcaa     2460
```

```
accgacgtgc gagaaatgcg cgagaaaatg cgtgcccatc ttggcaacaa gcataaagac      2520
cgcttcgatc tgaaagccga tgaaggcggt atcaccgaca tcgagtttat cgcccaatat      2580
ctggtgctgc gctttgccca tgacaagccg aaactgacgc gctggtcgga taatgtgcgc      2640
attctcgaag ggctggcgca aaacggcatc atggaggagc aggaagcgca ggcattgacg      2700
ctggcgtaca ccacattgcg tgatgagctg caccacctgg cgctgcaaga gttgccggga      2760
catgtggcgc tctcctgttt tgtcgccgag cgtgcgctta ttaaaaccag ctgggacaag      2820
tggctggtgg aaccgtgcgc cccggcgtaa                                       2850

<210> SEQ ID NO 269
<211> LENGTH: 1536
<212> TYPE: DNA
<213> ORGANISM: Kosakonia sacchari
<220> FEATURE:
<223> OTHER INFORMATION: 16S-3
<220> FEATURE:
<221> NAME/KEY: modified_base
<222> LOCATION: (766)..(776)
<223> OTHER INFORMATION: a, c, t, g, unknown or other
<220> FEATURE:
<221> NAME/KEY: modified_base
<222> LOCATION: (905)..(905)
<223> OTHER INFORMATION: a, c, t, g, unknown or other

<400> SEQUENCE: 269
attgaagagt ttgatcatgg ctcagattga acgctggcgg caggcctaac acatgcaagt        60
cgaacggtag cacagagagc ttgctctcgg gtgacgagtg cggacgggt gagtaatgtc        120 tgggaaactg cctgatggag ggggataact actggaaacg gtagctaata ccgcataacg       180
tcgcaagacc aaagagggggg accttcgggc ctcttgccat cagatgtgcc cagatgggat      240
tagctagtag gtgggggtaac ggctcaccta ggcgacgatc cctagctggt ctgagaggat      300
gaccagccac actggaactg agacacggtc cagactccta cgggaggcag cagtggggaa       360
tattgcacaa tgggcgcaag cctgatgcag ccatgccgcg tgtgtgaaga aggccttcgg       420
gttgtaaagc actttcagcg gggaggaagg gagtaaggtt aataaccttg ctcattgacg       480
ttacccgcag aagaagcacc ggctaactcc gtgccagcag ccgcggtaat acggagggtg       540
caagcgttaa tcggaattac tgggcgtaaa gcgcacgcag gcggtctgtc aagtcggatg       600
tgaaatcccc gggctcaacc tgggaactgc atccgaaact ggcaggcttg agtctcgtag       660
agggaggtag aattccaggt gtagcggtga aatgcgtaga gatctggagg aataccggtg       720
gcgaaggcgg cctcctggac gaagactgac gctcaggtgc gaaagnnnnn nnnnnnaaca       780
ggattagata ccctggtagt ccatgccgta aacgatgtct actagccgtt ggggcctttg       840
aggctttagt ggcgcagcta acgcgataag tagaccgcct ggggagtacg tcgcaagac        900 taaanctcaa atgaattgac ggggggcccgc acaagcggtg gagcatgtgg tttaattcga      960
tgcaacgcga agaaccttac ctggccttga catagtaaga atttccagag atggattgg        1020 tgccttcggg aacttacata caggtgctgc atggctgtcg tcagctcgtg tcgtgagatg      1080
ttgggttaag tcccgcaacg agcgcaaccc ttgtcattag ttgctacatt tagttgggca      1140
ctctaatgag actgccggtg acaaaccgga ggaaggtggg gatgacgtca agtcctcatg      1200
gcccttatag gtggggctac acacgtcata caatggctgg tacaaagggt tgccaacccg      1260 cgaggggggag ctaatcccat aaaaccagtc gtagtccgga tcgcagtctg caactcgact      1320
gcgtgaagtc ggaatcgcta gtaatcgtgg atcagaatgt cacggtgaat acgttcccgg      1380
```

```
gtcttgtaca caccgcccgt cacaccatgg gagcgggttc tgccagaagt agttagctta    1440
accgcaagga gggcgattac cacggcaggg ttcgtgactg gggtgaagtc gtaacaaggt    1500
agccgtatcg gaaggtgcgg ctggatcacc tccttt                              1536
```

```
<210> SEQ ID NO 270
<211> LENGTH: 882
<212> TYPE: DNA
<213> ORGANISM: Kosakonia sacchari
<220> FEATURE:
<223> OTHER INFORMATION: nifD1

<400> SEQUENCE: 270
atgaccatgc gtcaatgcgc catttacggc aaaggtggga tcggcaaatc gaccaccaca      60
cagaacctgg tcgccgcgct ggcggagatg ggtaaaaaag tcatgattgt cggctgtgac     120
ccgaaagccg attccacgcg tttgatcctg catgcgaaag cgcagaacac cattatggag     180
atggctgctg aagtcggctc cgtggaagac ctggagttag aagacgtgct gcaaatcggt     240
tacggcggcg tgcgctgcgc agagtccggc ggcccggagc aggcgtggg ctgtgccggt      300 cgcggggtga tcaccgcgat taacttcctc gaagaagaag gcgcttacgt gccggatctc     360
gattttgttt tctacgacgt gctgggcgac gtggtatgcg gtggtttcgc catgccgatt     420
cgtgaaaaca agcgcagga gatctacatc gtttgctctg gcgaaatgat ggcgatgtac      480
gccgccaaca acatctccaa aggcatcgtg aaatacgcca atccggtaa agtgcgcctc      540 ggcgggctga tttgtaactc gcgccagacc gaccgtgaag atgaactgat cattgcgctg     600
gcagaaaaac tcggcacgca gatgatccac tttgttcccc gcgacaacat tgtgcagcgt     660
gcggaaatcc gccgtatgac ggttatcgaa tatgacccga cctgcaatca ggcgaacgaa     720
tatcgcagcc ttgccagcaa aatcgtcaac aacaccaaaa tggtggtgcc cacccctgc     780 accatggatg aactggaaga actgctgatg gagttcggca ttatggatgt ggaagacacc     840
agcatcattg gtaaaaccgc cgccgaagaa aacgccgtct ga                       882
```

```
<210> SEQ ID NO 271
<211> LENGTH: 1386
<212> TYPE: DNA
<213> ORGANISM: Kosakonia sacchari
<220> FEATURE:
<223> OTHER INFORMATION: nifK1

<400> SEQUENCE: 271
atggccgaaa ttctgcgcag taaaaaaccg ctggcggtca gcccgataaa aagcggccag      60
ccgctggggg cgatcctcgc aagcctgggt gtcgaacagt gcataccgct ggtacacggc     120
gcacagggat gtagcgcgtt cgcgaaggtg ttctttattc aacattttca cgatccgatc     180
ccgctgcaat cgacggcgat ggatccgact tccaccatta tgggcgccga tgaaaacatt     240
tttaccgcgc tcaatgtgct ctgccagcgc aacgccgcga aagccattgt gctgctcagc     300
accgggcttt cagaagccca gggcagcgac atttcgcggg tggtgcgcca gtttcgtgat     360
gattttcccc ggcataaagg cgttgcgctg ctcaccgtca acacacccga tttctacggc     420
tcgctggaaa acggctacag cgccgtgctg aaaagcatga ttgaacagtg ggtacccgca     480
cagcccgccg ccagcctgcg caaccgccgt gtcaacctgc tggtcagcca tttactgaca     540
ccaggcgata tcgaactgtt gcgcagttat gttgaagcct tcggcctgca accggtgatt     600
gtgccggatc tgtcgctgtc gctggacggg catctggcag acggtgattt ttcgcctgtt     660
acccaagggg gaacatcgct gcgcatgatt gaacagatgg ggcaaaacct ggccaccttt     720
```
gtgattggcg cctcgctggg ccgtgcggcg gcgttactgg cgcagcgcag ccgtggcgag        780
gtgatcgccc tgccgcatct gatgacgctt gcagcctgcg acacgtttat tcatcgactg        840
aaaaccctct ccgggcgcga tgtccccgcg tggattgagc gccagcgcgg ccaagttcag        900
gatgcgatga tcgattgcca tatgtggctg cagggtgcgg ctatcgccat ggcagcagaa        960
ggcgatcacc tggcggcatg gtgcgatttc gcccgcagcc agggcatgat ccccggcccg       1020
attgtcgcac cggtcagcca gccggggttg caaaatctgc cggttgaaac cgtggttatc       1080
ggcgatctgg aagatatgca ggatcggctt tgcgcgacgc ccgccgcgtt actggtggcc       1140
aattctcatg ccgccgatct cgccacgcag tttgatttgt cacttatccg cgccgggttc       1200
ccggtgtatg accggctggg ggaatttcgt cgcctgcgcc aggggtacag cggcattcgt       1260
gacacgctgt ttgagctggc gaatgtgatg cgcgagcgcc atcacccgct tgcaacctac       1320
cgctcgccgc tgcgccagca cgccgacgac aacgttacgc ctggagatct gtatgccgca       1380
tgttaa                                                                    1386

<210> SEQ ID NO 272
<211> LENGTH: 1287
<212> TYPE: DNA
<213> ORGANISM: Kosakonia sacchari
<220> FEATURE:
<223> OTHER INFORMATION: amtB

<400> SEQUENCE: 272
atgaaaaaca caacattaaa aacagcgctt gcttcgctgg cgttactgcc tggcctggcg         60
atggcggctc ccgctgtggc ggataaagcc gacaacggct ttatgatgat ttgcaccgcg        120
ctggtgctgt ttatgaccat tccgggcatt gcgctgttct acggcggttt gatccgcggt        180
aaaaacgtgc tgtcgatgct gacgcaggtt gccgtcacct tcgcactggt gtgcattctg        240
tgggtggtgt atggctactc gctggcattt ggcgagggca cagcttctt cgggagtttt        300 aactgggcga tgttgaaaaa catcgaactg aaagccgtga tgggcagcat ttatcagtat        360
atccacgtgg cgttccaggg ttccttcgcc tgtatcaccg ttggcctgat tgtcggtgca        420
ctggctgagc gtattcgctt ctctgcggtg ctgatttttg tggtgtatg gctgacgctt        480 tcttacgtgc cgattgcaca catggtgtgg ggcggcggtc tgctggcaac ccacggtgcg        540
ctggatttcg caggcggtac ggttgttcac atcaacgctg cgattgcagg tctggtgggg        600
gcttacctga ttggcaaacg cgtgggcttt ggcaaagaag cattcaaacc gcataacctg        660
ccgatggtct tcactggcac cgctatcctg tatgttggct ggtttggttt caacgccggc        720
tccgcaagct cggcgaacga aattgctgcg ctggccttcg tgaacactgt cgttgccact        780
gctgccgcta ttctggcgtg ggtatttggc gaatgggcaa tgcgcggcaa gccgtctctg        840
ctcggtgcct gttctggtgc catcgcgggt ctggttggta tcacccccgc ctgtggttat        900
gtgggtgtcg gcggtcgcgct gattgtgggt ctgattgccg tctggctgg ctgtgggggc        960 gttactgcgc tgaaacgtat gttgcgtgtc gatgacccgt gtgacgtatt cggtgtgcac       1020
ggcgtgtgcg gcatcgtggg ctgtatcctg acgggtatct cgcctctac gtcgctgggt       1080 ggtgtcggtt tcgctgaagg tgtgaccatg ggccatcagg tgctggtgca gctggaaagt       1140
gttgccatca ctatcgtgtg gtctggcgtg gtggccttta ttggttacaa actggcggac       1200
atgacggtag gcctgcgcgt accggaagaa caagaacgtg aagggctgga tgtaaacagc       1260
cacggcgaaa acgcctataa cgcctga                                            1287

-continued

```
<210> SEQ ID NO 273
<211> LENGTH: 348
<212> TYPE: DNA
<213> ORGANISM: Kosakonia sacchari
<220> FEATURE:
<223> OTHER INFORMATION: Prm1

<400> SEQUENCE: 273
cgtcctgtaa taataaccgg acaattcgga ctgattaaaa aagcgccctt gtggcgcttt      60
ttttatattc ccgcctccat ttaaaataaa aaatccaatc ggatttcact atttaaactg     120
gccattatct aagatgaatc cgatggaagc tcgctgtttt aacacgcgtt ttttaacctt     180
ttattgaaag tcggtgcttc tttgagcgaa cgatcaaatt taagtggatt cccatcaaaa     240
aaatattctc aacctaaaaa agtttgtgta atacttgtaa cgctacatgg agattaactc     300
aatctagagg gtattaataa tgaatcgtac taaactggta ctgggcgc                  348

<210> SEQ ID NO 274
<211> LENGTH: 313
<212> TYPE: DNA
<213> ORGANISM: Kosakonia sacchari
<220> FEATURE:
<223> OTHER INFORMATION: Prm5

<400> SEQUENCE: 274
ggacatcatc gcgacaaaca atattaatac cggcaaccac accggcaatt tacgagactg      60
cgcaggcatc ctttctcccg tcaatttctg tcaaataaag taaagaggc agtctacttg      120 aattaccccc ggctggttga gcgtttgttg aaaaaaagta actgaaaaat ccgtagaata     180
gcgccactct gatggttaat taacctattc aattaagaat tatctggatg aatgtgccat     240
taaatgcgca gcataatggt gcgttgtgcg ggaaaactgc ttttttttga aagggttggt     300
cagtagcgga aac                                                        313

<210> SEQ ID NO 275
<211> LENGTH: 1485
<212> TYPE: DNA
<213> ORGANISM: Rahnella aquatilis
<220> FEATURE:
<223> OTHER INFORMATION: nifL

<400> SEQUENCE: 275
atgaccctga atatgatgct cgataacgcc gcgccggagg ccatcgccgg cgcgctgact      60
caacaacatc cggggctgtt ttttaccatg gtggaacagg cctcggtggc catctccctc     120
accgatgcca gcgccaggat catttacgcc aacccggcgt tttgccgcca gaccggctat     180
tcgctggcgc aattgttaaa ccagaacccg cgcctgctgg ccagcagcca gacgccgcgc     240
gagatctatc aggagatgtg gcataccctg ctccagcgtc agccctggcg cggtcagctg     300
attaatcagc gtcgggacgg cggcctgtac ctggtggaga ttgacatcac cccggtgctt     360
agcccgcaag gggaactgga gcattatctg gcgatgcagc gggatatcag cgtcagctac     420
accctcgaac agcggctgcg caaccatatg accctgatgg aggcggtgct gaataatatc     480
cccgccgccg tggtagtggt ggacgagcag gatcgggtgg tgatggacaa cctcgcctac     540
aaaaccttct gcgctgactg cggcggccgg gagctgctca ccgagctgca ggtctcccct     600
ggccggatga cgcccggcgt ggaggcgatc ctgccggtgg cgctgcgcgg ggccgcgcgc     660
tggctgtcgg taacctgctg gccgttgccc ggcgtcagtg aagaggccag ccgctacttt     720
atcgacagcg cgctggcgcg gaccctggtg gtgatcgccg actgtaccca gcagcgtcag     780
```

-continued

```
cagcaggagc aagggcgcct tgaccggctg aagcagcaaa tgaccgccgg caagctgctg      840
gcggcgatcc gcgagtcgct ggacgccgcg ctgatccagc tgaactgccc gattaatatg      900
ctggcggcag cccgtcggct gaacggcgag ggaagcggga atgtggcgct ggaggccgcc      960
tggcgtgaag gggaagaggc gatggcgcgg ctccagcgct gtcgcccatc gctggaactc     1020
gaaaaccccg ccgtctggcc gctgcagccc tttttcgacg atctgtgcgc cctctaccgt     1080
acacgcttcg atcccgacgg gctgcaggtc gacatggcct caccgcatct gatcggcttt     1140
ggccagcgca ccccactgct ggcgtgctta agcctgtggc tcgatcgcac cctggccctc     1200
gccgccgaac tcccctccgt gccgctggcg atgcagctct acgccgagga gaacgacggc     1260
tggctgtcgc tgtatctgac tgacaacgta ccgctgctgc aggtgcgcta cgctcactcc     1320
cccgacgcgc tgaactcgcc gggcaaaggc atggagctgc ggctgatcca gaccctggtg     1380
gcgcaccatc gcggggccat tgagctggct tcccgaccgc agggcggcac ctgcctgacc     1440
ctgcgtttcc cgctgtttaa caccctgacc ggaggtgaag catga                      1485
```

```
<210> SEQ ID NO 276
<211> LENGTH: 1575
<212> TYPE: DNA
<213> ORGANISM: Rahnella aquatilis
<220> FEATURE:
<223> OTHER INFORMATION: nifA

<400> SEQUENCE: 276
```

```
atgatccctg aatccgaccc ggacaccacc gtcagacgct tcgacctctc tcagcagttc       60
accgccatgc agcggataag cgtggtgctg agccgggcca ccgaggccag caaaacgctg      120
caggaggtgc tcagcgtatt acacaacgat gcctttatgc agcacgggat gatctgcctg      180
tacgacagcg agcaggagat cctcagtatc gaagcgctgc agcaaaccgg ccagcagccc      240
ctccccggca gcacgcagat ccgctatcgc cccggcgagg gactggtggg gaccgtgctg      300
gcccaggggc agtcgctggt gctgccccgg gtcgccgacg atcagcgttt tctcgaccgc      360
ctgagcctct acgattacga tctgccgttt atcgccgtac cgttgatggg gcccaacgcc      420
cggccaatag gggtgctggc ggcccagccg atggcgcgcc aggaagagcg gctgccggcc      480
tgcacccgtt ttctcgaaac cgtcgccaac ctcgtcgccc agaccatccg gctgatgatc      540
cttccggcct cacccgccct gtcgagccgc cagccgccga aggtggaacg gccgccggcc      600
tgctcgtcgt cgcgcggcgt gggccttgac aatatggtcg gcaagagccc ggcgatgcgc      660
cagatcgtgg aggtgatccg tcaggtttcg cgctgggaca ccaccgtgct ggtacgcggc      720
gaaagcggca ccgggaaaga gctgatcgcc aacgccatcc atcaccattc gccacgggct      780
ggcgccgcct tcgtcaaatt taactgcgcg cgcgctgccgg acaccctgct ggaaagcgaa      840
ctgttcggcc atgagaaagg cgcctttacc ggggcggtgc gtcagcgtaa aggacgtttt      900
gagctggcga tggcggcac cctgttcctc gatgagattg tgaaagcag cgcctcgttc       960 caggccaagc tgctgcgtat cctccaggag ggggagatgg agcgggtcgg cggcgatgag     1020
accctgcggg tgaatgtccg catcatcgcc gccaccaacc gtcacctgga ggaggaggtc     1080
cggctgggcc atttccgcga ggatctctac tatcgtctga acgtgatgcc catcgccctg     1140 ccccgctgc gcgagcgtca ggaggacatc gccgagctgg cgcacttcct ggtgcgcaaa     1200
atcggccagc atcaggggcg cacgctgcgg atcagcgagg gcgcgatccg cctgctgatg     1260
gagtacagct ggccgggtaa cgttcgcgaa ctggagaact gcctcgaacg atcggcggtg     1320
```

-continued

```
atgtcggaga gtggcctgat cgatcgcgac gtgatcctct tcactcacca ggatcgtccc    1380
gccaaagccc tgcctgccag cgggccagcg gaagacagct ggctggacaa cagcctggac    1440
gaacgtcagc gactgatcgc cgcgctggaa aaagccggct gggtgcaggc caaggcggca    1500
cggctgctgg ggatgacgcc gcgccaggtc gcttatcgga tccagatcat ggatatcacc    1560
ctgccgcgtc tgtag                                                     1575
```

<210> SEQ ID NO 277
<211> LENGTH: 1540
<212> TYPE: DNA
<213> ORGANISM: Rahnella aquatilis
<220> FEATURE:
<223> OTHER INFORMATION: 16S-1

<400> SEQUENCE: 277

```
attgaagagt ttgatcatgg ctcagattga acgctggcgg caggcctaac acatgcaagt      60
cgagcggcag cgggaagtag cttgctactt tgccggcgag cggcggacgg gtgagtaatg     120
tctgggaaac tgcctgatgg aggggataa ctactggaaa cggtagctaa taccgcatga     180
cctcgaaaga gcaaagtggg ggatcttcgg acctcacgcc atcggatgtg cccagatggg     240
attagctagt aggtgaggta atggctcacc taggcgacga tccctagctg gtctgagagg     300
atgaccagcc acactggaac tgagacacgg tccagactcc tacgggaggc agcagtgggg     360
aatattgcac aatgggcgca agcctgatgc agccatgccg cgtgtgtgaa gaaggcctta     420
gggttgtaaa gcactttcag cgaggaggaa ggcatcatac ttaatacgtg tggtgattga     480
cgttactcgc agaagaagca ccggctaact ccgtgccagc agccgcggta atacggaggg     540
tgcaagcgtt aatcggaatt actgggcgta aagcgcacgc aggcggtttg ttaagtcaga     600
tgtgaaatcc ccgagcttaa cttgggaact gcatttgaaa ctggcaagct agagtcttgt     660
agaggggggt agaattccag gtgtagcggt gaaatgcgta gagatctgga ggaataccgg     720
tggcgaaggc ggccccctgg acaaagactg acgctcaggt gcgaaagcgt ggggagcaaa     780
caggattaga taccctggta gtccacgctg taaacgatgt cgacttggag gttgtgccct     840
tgaggcgtgg cttccggagc taacgcgtta agtcgaccgc ctggggagta cggccgcaag     900
gttaaaactc aaatgaattg acggggcccc gcacaagcgg tggagcatgt ggtttaattc     960
gatgcaacgc gaagaacctt acctactctt gacatccaga gaatttgcca gagatggcga    1020
agtgccttcg ggaactctga dacaggtgct gcatggctgt cgtcagctcg tgttgtgaaa    1080
tgttgggtta agtcccgcaa cgagcgcaac ccttatcctt tgttgccagc acgtaatggt    1140
gggaactcaa aggagactgc cggtgataaa ccggaggaag gtgggatga cgtcaagtca    1200 tcatggccct tacgagtagg gctacacacg tgctacaatg gcatatacaa agagaagcga    1260
actcgcgaga gcaagcggac ctcataaagt atgtcgtagt ccggattgga gtctgcaact    1320
cgactccatg aagtcggaat cgctagtaat cgtagatcag aatgctacgg tgaatacgtt    1380
cccgggcctt gtacacaccg cccgtcacac catgggagtg ggttgcaaaa gaagtaggta    1440
gcttaacctt cgggagggcg cttaccactt tgtgattcat gactggggtg aagtcgtaac    1500
aaggtaaccg tagggggaacc tgcggttgga tcacctcctt                        1540
```

<210> SEQ ID NO 278
<211> LENGTH: 1540
<212> TYPE: DNA
<213> ORGANISM: Rahnella aquatilis
<220> FEATURE:
<223> OTHER INFORMATION: 16S-2

```
<220> FEATURE:
<221> NAME/KEY: modified_base
<222> LOCATION: (267)..(267)
<223> OTHER INFORMATION: a, c, t, g, unknown or other

<400> SEQUENCE: 278
attgaagagt ttgatcatgg ctcagattga acgctggcgg caggcctaac acatgcaagt        60
cgagcggcat cgggaagtag cttgctactt tgccggcgag cggcggacgg gtgagtaatg       120
tctgggaaac tgcctgatgg aggggggataa ctactggaaa cggtagctaa taccgcatga      180
cctcgaaaga gcaaagtggg ggatcttcgg acctcacgcc atcggatgtg cccagatggg       240
attagctagt aggtgaggta atggctnacc taggcgacga tccctagctg gtctgagagg       300
atgaccagcc acactggaac tgagacacgg tccagactcc tacgggaggc agcagtgggg       360
aatattgcac aatgggcgca agcctgatgc agccatgccg cgtgtgtgaa gaaggcctta       420
gggttgtaaa gcactttcag cgaggaggaa ggcatcatac ttaatacgtg tggtgattga       480
cgttactcgc agaagaagca ccggctaact ccgtgccagc agccgcggta atacggaggg       540
tgcaagcgtt aatcggaatt actgggcgta aagcgcacgc aggcggtttg ttaagtcaga       600
tgtgaaatcc ccgagcttaa cttgggaact gcatttgaaa ctggcaagct agagtcttgt       660
agaggggggt agaattccag gtgtagcggt gaaatgcgta gagatctgga ggaataccgg       720
tggcgaaggc ggccccctgg acaaagactg acgctcaggt gcgaaagcgt ggggagcaaa       780
caggattaga taccctggta gtccacgctg taaacgatgt cgacttggag gttgtgccct       840
tgaggcgtgg cttccggagc taacgcgtta agtcgaccgc ctggggagta cggccgcaag       900
gttaaaactc aaatgaattg acggggggccc gcacaagcgg tggagcatgt ggtttaattc       960
gatgcaacgc gaagaacctt acctactctt gacatccaga gaatttgcca gagatggcga      1020
agtgccttcg ggaactctga dacaggtgct gcatggctgt cgtcagctcg tgttgtgaaa      1080
tgttgggtta agtcccgcaa cgagcgcaac ccttatcctt tgttgccagc acgtgatggt      1140
gggaactcaa aggagactgc cggtgataaa ccggaggaag gtggggatga cgtcaagtca      1200
tcatggccct tacgagtagg gctacacacg tgctacaatg gcatatacaa agagaagcga      1260
actcgcgaga gcaagcggac ctcataaagt atgtcgtagt ccggattgga gtctgcaact      1320
cgactccatg aagtcggaat cgctagtaat cgtagatcag aatgctacgg tgaatacgtt      1380
cccgggcctt gtacacaccg cccgtcacac catgggagtg ggttgcaaaa gaagtaggta      1440
gcttaacctt cgggagggcg cttaccactt tgtgattcat gactggggtg aagtcgtaac      1500
aaggtaaccg taggggaacc tgcggttgga tcacctcctt                            1540

<210> SEQ ID NO 279
<211> LENGTH: 1540
<212> TYPE: DNA
<213> ORGANISM: Rahnella aquatilis
<220> FEATURE:
<223> OTHER INFORMATION: 16S-3
<220> FEATURE:
<221> NAME/KEY: modified_base
<222> LOCATION: (455)..(455)
<223> OTHER INFORMATION: a, c, t, g, unknown or other

<400> SEQUENCE: 279
attgaagagt ttgatcatgg ctcagattga acgctggcgg caggcctaac acatgcaagt        60
cgagcggcag cgggaagtag cttgctactt tgccggcgag cggcggacgg gtgagtaatg       120
tctgggaaac tgcctgatgg aggggggataa ctactggaaa cggtagctaa taccgcatga      180
```

-continued

```
cctcgaaaga gcaaagtggg ggatcttcgg acctcacgcc atcggatgtg cccagatggg      240
attagctagt aggtgaggta atggctcacc taggcgacga tccctagctg gtctgagagg      300
atgaccagcc acactggaac tgagacacgg tccagactcc tacgggaggc agcagtgggg      360
aatattgcac aatgggcgca agcctgatgc agccatgccg cgtgtgtgaa gaaggcctta      420
gggttgtaaa gcactttcag cgaggaggaa ggcancatac ttaatacgtg tggtgattga      480
cgttactcgc agaagaagca ccggctaact ccgtgccagc agccgcggta atacggaggg      540
tgcaagcgtt aatcggaatt actgggcgta aagcgcacgc aggcggtttg ttaagtcaga      600
tgtgaaatcc ccgagcttaa cttgggaact gcatttgaaa ctggcaagct agagtcttgt      660 agagggggt agaattccag gtgtagcggt gaaatgcgta gagatctgga ggaataccgg      720
tggcgaaggc ggccccctgg acaaagactg acgctcaggt gcgaaagcgt ggggagcaaa      780
caggattaga taccctggta gtccacgctg taaacgatgt cgacttggag gttgtgccct      840
tgaggcgtgg cttccggagc taacgcgtta agtcgaccgc ctggggagta cggccgcaag      900
gttaaaactc aaatgaattg acgggggccc gcacaagcgg tggagcatgt ggtttaattc      960
gatgcaacgc gaagaacctt acctactctt gacatccaga gaatttgcca gagatggcga     1020
agtgccttcg ggaactctga dacaggtgct gcatggctgt cgtcagctcg tgttgtgaaa     1080
tgttgggtta agtcccgcaa cgagcgcaac ccttatcctt tgttgccagc acgtgatggt     1140
gggaactcaa aggagactgc cggtgataaa ccggaggaag gtggggatga cgtcaagtca     1200
tcatggccct tacgagtagg gctacacacg tgctacaatg gcatatacaa agagaagcga     1260
actcgcgaga gcaagcggac ctcataaagt atgtcgtagt ccggattgga gtctgcaact     1320
cgactccatg aagtcggaat cgctagtaat cgtagatcag aatgctacgg tgaatacgtt     1380
cccgggcctt gtacacaccg cccgtcacac catgggagtg ggttgcaaaa gaagtaggta     1440
gcttaacctt cgggagggcg cttaccactt tgtgattcat gactggggtg aagtcgtaac     1500
aaggtaaccg tagggggaacc tgcggttgga tcacctcctt                          1540
```

```
<210> SEQ ID NO 280
<211> LENGTH: 1540
<212> TYPE: DNA
<213> ORGANISM: Rahnella aquatilis
<220> FEATURE:
<223> OTHER INFORMATION: 16S-4
<220> FEATURE:
<221> NAME/KEY: modified_base
<222> LOCATION: (70)..(70)
<223> OTHER INFORMATION: a, c, t, g, unknown or other

<400> SEQUENCE: 280
```

```
attgaagagt ttgatcatgg ctcagattga acgctggcgg caggcctaac acatgcaagt       60
cgagcggcan cgggaagtag cttgctactt tgccggcgag cggcggacgg gtgagtaatg      120
tctgggaaac tgcctgatgg aggggggataa ctactggaaa cggtagctaa taccgcatga      180
cctcgaaaga gcaaagtggg ggatcttcgg acctcacgcc atcggatgtg cccagatggg      240
attagctagt aggtgaggta atggcttacc taggcgacga tccctagctg gtctgagagg      300
atgaccagcc acactggaac tgagacacgg tccagactcc tacgggaggc agcagtgggg      360
aatattgcac aatgggcgca agcctgatgc agccatgccg cgtgtgtgaa gaaggcctta      420
gggttgtaaa gcactttcag cgaggaggaa ggcatcacac ttaatacgtg tggtgattga      480
cgttactcgc agaagaagca ccggctaact ccgtgccagc agccgcggta atacggaggg      540
tgcaagcgtt aatcggaatt actgggcgta aagcgcacgc aggcggtttg ttaagtcaga      600
```

```
tgtgaaatcc ccgagcttaa cttgggaact gcatttgaaa ctggcaagct agagtcttgt       660 agagggggt agaattccag gtgtagcggt gaaatgcgta gagatctgga ggaataccgg        720
tggcgaaggc ggccccctgg acaaagactg acgctcaggt gcgaaagcgt ggggagcaaa       780
caggattaga taccctggta gtccacgctg taaacgatgt cgacttggag gttgtgccct       840
tgaggcgtgg cttccggagc taacgcgtta agtcgaccgc ctggggagta cggccgcaag       900
gttaaaactc aaatgaattg acgggggccc gcacaagcgg tggagcatgt ggtttaattc       960
gatgcaacgc gaagaacctt acctactctt gacatccaga gaatttgcca gagatggcga      1020
agtgccttcg ggaactctga dacaggtgct gcatggctgt cgtcagctcg tgttgtgaaa      1080
tgttgggtta agtcccgcaa cgagcgcaac ccttatcctt tgttgccagc acgtgatggt      1140
gggaactcaa aggagactgc cggtgataaa ccggaggaag gtggggatga cgtcaagtca      1200
tcatggccct tacgagtagg gctacacacg tgctacaatg gcatatacaa agagaagcga      1260
actcgcgaga gcaagcggac ctcataaagt atgtcgtagt ccggattgga gtctgcaact      1320
cgactccatg aagtcggaat cgctagtaat cgtagatcag aatgctacgg tgaatacgtt      1380
cccgggcctt gtacacaccg cccgtcacac catgggagtg ggttgcaaaa gaagtaggta      1440
gcttaacctt cgggagggcg cttaccactt tgtgattcat gactggggtg aagtcgtaac      1500
aaggtaaccg tagggggaacc tgcggttgga tcacctcctt                            1540
```

```
<210> SEQ ID NO 281
<211> LENGTH: 1540
<212> TYPE: DNA
<213> ORGANISM: Rahnella aquatilis
<220> FEATURE:
<223> OTHER INFORMATION: 16S-5

<400> SEQUENCE: 281
attgaagagt ttgatcatgg ctcagattga acgctggcgg caggcctaac acatgcaagt        60
cgagcggcag cgggaagtag cttgctactt tgccggcgag cggcggacgg gtgagtaatg       120
tctgggaaac tgcctgatgg aggggggataa ctactggaaa cggtagctaa taccgcatga      180
cctcgaaaga gcaaagtggg ggatcttcgg acctcacgcc atcggatgtg cccagatggg       240
attagctagt aggtgaggta atggctcacc taggcgacga tccctagctg gtctgagagg       300
atgaccagcc acactggaac tgagacacgg tccagactcc tacgggaggc agcagtgggg       360
aatattgcac aatgggcgca agcctgatgc agccatgccg cgtgtgtgaa gaaggcctta       420
gggttgtaaa gcactttcag cgaggaggaa ggcatcacac ttaatacgtg tgttgattga       480
cgttactcgc agaagaagca ccggctaact ccgtgccagc agccgcggta atacggaggg       540
tgcaagcgtt aatcggaatt actgggcgta aagcgcacgc aggcggtttg ttaagtcaga       600
tgtgaaatcc ccgagcttaa cttgggaact gcatttgaaa ctggcaagct agagtcttgt       660 agagggggt agaattccag gtgtagcggt gaaatgcgta gagatctgga ggaataccgg        720
tggcgaaggc ggccccctgg acaaagactg acgctcaggt gcgaaagcgt ggggagcaaa       780
caggattaga taccctggta gtccacgctg taaacgatgt cgacttggag gttgtgccct       840
tgaggcgtgg cttccggagc taacgcgtta agtcgaccgc ctggggagta cggccgcaag       900
gttaaaactc aaatgaattg acgggggccc gcacaagcgg tggagcatgt ggtttaattc       960
gatgcaacgc gaagaacctt acctactctt gacatccaga gaatttgcca gagatggcga      1020
agtgccttcg ggaactctga dacaggtgct gcatggctgt cgtcagctcg tgttgtgaaa      1080
```

```
tgttgggtta agtcccgcaa cgagcgcaac ccttatcctt tgttgccagc acgtgatggt    1140
gggaactcaa aggagactgc cggtgataaa ccggaggaag gtggggatga cgtcaagtca    1200
tcatggccct tacgagtagg gctacacacg tgctacaatg gcatatacaa agagaagcga    1260
actcgcgaga gcaagcggac ctcataaagt atgtcgtagt ccggattgga gtctgcaact    1320
cgactccatg aagtcggaat cgctagtaat cgtagatcag aatgctacgg tgaatacgtt    1380
cccgggcctt gtacacaccg cccgtcacac catgggagtg ggttgcaaaa gaagtaggta    1440
gcttaacctt cgggagggcg cttaccactt tgtgattcat gactggggtg aagtcgtaac    1500
aaggtaaccg taggggaacc tgcggttgga tcacctcctt                          1540
```

```
<210> SEQ ID NO 282
<211> LENGTH: 1009
<212> TYPE: DNA
<213> ORGANISM: Rahnella aquatilis
<220> FEATURE:
<223> OTHER INFORMATION: 16S-6
<220> FEATURE:
<221> NAME/KEY: modified_base
<222> LOCATION: (296)..(296)
<223> OTHER INFORMATION: a, c, t, g, unknown or other
<220> FEATURE:
<221> NAME/KEY: modified_base
<222> LOCATION: (311)..(311)
<223> OTHER INFORMATION: a, c, t, g, unknown or other
<220> FEATURE:
<221> NAME/KEY: modified_base
<222> LOCATION: (973)..(973)
<223> OTHER INFORMATION: a, c, t, g, unknown or other

<400> SEQUENCE: 282
```

```
gtagctaata ccgcatgacc tcgaaagagc aaagtggggg atcttcggac ctcacgccat      60
cggatgtgcc cagatgggat tagctagtag gtgaggtaat ggctcaccta ggcgacgatc     120
cctagctggt ctgagaggat gaccagccac actggaactg agacacggtc cagactccta     180
cgggaggcag cagtggggaa tattgcacaa tgggcgcaag cctgatgcag ccatgccgcg     240
tgtgtgaaga aggccttagg gttgtaaagc actttcagcg aggaggaagg catcanactt     300
aatacgtgtg ntgattgacg ttactcgcag aagaagcacc ggctaactcc gtgccagcag     360
ccgcggtaat acgaggggtg caagcgttaa tcggaattac tgggcgtaaa gcgcacgcag     420
gcggtttgtt aagtcagatg tgaaatcccc gagcttaact tgggaactgc atttgaaact     480
ggcaagctag agtcttgtag agggggtag aattccaggt gtagcggtga atgcgtaga     540 gatctggagg aataccggtg gcgaaggcgg cccctggac aaagactgac gctcaggtgc     600
gaaagcgtgg ggagcaaaca ggattagata ccctggtagt ccacgctgta aacgatgtcg     660
acttggaggt tgtgcccttg aggcgtggct ccggagcta acgcgttaag tcgaccgcct     720
ggggagtacg gccgcaaggt taaaactcaa atgaattgac ggggccccgc acaagcggtg     780
gagcatgtgg tttaattcga tgcaacgcga agaaccttac ctactcttga catccagaga     840
atttgccaga gatggcgaag tgccttcggg aactctgaga caggtgctgc atggctgtcg     900
tcagctcgtg ttgtgaaatg ttgggttaag tcccgcaacg agcgcaaccc ttatcctttg     960
ttgccagcac gtnatggtgg gaactcaaag gagactgccg gtgataaac                1009
```

```
<210> SEQ ID NO 283
<211> LENGTH: 1519
<212> TYPE: DNA
<213> ORGANISM: Rahnella aquatilis
<220> FEATURE:
<223> OTHER INFORMATION: 16S-7
```

-continued

<400> SEQUENCE: 283

```
attgaagagt ttgatcatgg ctcagattga acgctggcgg caggcctaac acatgcaagt     60
cgagcggcag cgggaagtag cttgctactt tgccggcgag cggcggacgg gtgagtaatg    120
tcctgatgga ggggataact actggaacgg tagctaatac cgcacctcga aagagcaaag    180
tgggggatct tcggacctca cgccatcgga tgtgcccaga tgggattagc tagtaggtga    240
ggtaatggct cacctaggcg acgatcccta gctggtctga gaggatgacc agccacactg    300
gaactgagac acggtccaga ctcctacggg aggcagcagt ggggaatatt gcacaatggg    360
cgcaagcctg atgcagccat gccgcgtgtg tgaagaaggc cttagggttg taaagcactt    420
tcagcgagga ggaaggcatc atacttaata cgtgtggtga ttgacgttac tcgcagaaga    480
agcaccggct aactccgtgc cagcagccgc ggtaatacgg agggtgcaag cttaatcgga    540
attactgggc gtaaagcgca cgcaggcggt tgttaagtca gatgtgaaat ccccgagctt    600
aacttgggaa ctgcatttga aactggcaag ctagagtctt gtagagggggg gtagaattcc    660 aggtgtagcg gtgaaatgcg tagagatctg gaggaatacc ggtggcgaag gcggcccccct    720 ggacaaagac tgacgctcag gtgcgaaagc gtggggagca aacaggatta ataccctggt    780
agtccacgct gtaacgatgt cgacttggag gttgtgccct gaggcgtggc ttccggagct    840
aacgcgttaa gtcgaccgcc tggggagtac ggccgcaagg ttaaaactca aatgaattga    900 cggggggcccg cacaagcggt ggagcatgtg gtttaattcg atgcaacgcg aagaacctta    960
cctactcttg acatccagag aatttgccag agatggcgaa gtgccttcgg gaactctgag   1020
acaggtgctg catggctgtc gtcagctcgt gttgtgaaat gttgggttaa gtcccgcaac   1080
gagcgcaacc cttatccttt gttgccagca cgtaatggtg ggaactcaaa ggagactgcc   1140
ggtgataaac cggaggaagg tggggatgac gtcaagtcat catggccctt acgagtaggg   1200
ctacacacgt gctacaatgg catatacaaa gagaagcgaa ctcgcgagag caagcggacc   1260
tcataaagta tgtcgtagtc cggattggag tctgcaactc gactccatga agtcggaatc   1320
gctagtaatc gtagatcaga atgctacggt gaatacgttc ccgggccttg tacacaccgc   1380
ccgtcacacc atgggagtgg gttgcaaaag aagtaggtag cttaaccttc gggagggcgc   1440
ttaccacttt gtgattcatg actggggtga agtcgtaaca aggtaaccgt aggggaacct   1500
gcggttggat cacctcctt                                               1519
```

<210> SEQ ID NO 284
<211> LENGTH: 882
<212> TYPE: DNA
<213> ORGANISM: Rahnella aquatilis
<220> FEATURE:
<223> OTHER INFORMATION: nifH1

<400> SEQUENCE: 284

```
atgaccatgc gtcaatgcgc tatctacggt aaaggcggta tcggtaaatc caccaccacc     60
cagaatctcg tcgcggccct cgccgagatg ggtaagaaag tgatgatcgt cggctgcgat    120
ccgaaagcgg attccacccg tctgatcctc cacgctaaag cccagaacac catcatggag    180 atggcggcg aagtgggctc ggtcgaggat ctggagctcg aagacgttct gcaaatcggc    240
tatggcgatg tccgttgcgc cgaatccggc ggcccggagc caggcgtcgg ctgcgccgga    300
cgcggggtga tcaccgccat caacttcctc gaggaagaag cgccctatga agaagatttg    360
gatttcgtct tctatgacgt cctcggcgac gtggtctgcg gcggcttcgc tatgccgatc    420
```
cgcgaaaaca aagcccagga gatctacatc gtctgctccg gcgagatgat ggcgatgtat          480
gccgccaaca atatctccaa agggatcgtg aagtacgcca aatccggcaa ggtgcgcctc          540
ggcggcctga tctgtaactc gcgcaaaacc gaccgggaag acgaactgat catcgccctg          600
gcggagaagc ttggcacgca gatgatccac ttcgttcccc gcgacaacat tgtgcagcgc          660
gcggagatcc gccggatgac ggtgatcgag tacgacccga cctgtcagca ggcgaatgaa          720
tatcgtcaac tggcgcagaa gatcgtcaat aacaccaaaa aagtggtgcc gacgccgtgc          780
accatggacg agctggaatc gctgctgatg gagttcggca tcatggaaga agaagacacc          840
agcatcattg gtaaaaccgc cgctgaagaa aacgcggcct ga                            882

<210> SEQ ID NO 285
<211> LENGTH: 1113
<212> TYPE: DNA
<213> ORGANISM: Rahnella aquatilis
<220> FEATURE:
<223> OTHER INFORMATION: nifH2

<400> SEQUENCE: 285
atggttagga aaagtagaag taaaaataca aatatagaac taactgaaca tgaccattta           60
ttaataagtc aaataaaaaa gcttaaaaca caaaccactt gctttttttaa taataaagga          120 ggggttggga agactacatt agtagcaaat ttaggagcag agctatcaat aaactttagt          180
gcaaaagttc ttattgtgga tgccgaccct caatgtaatc tcacgcagta tgtattaagt          240
gatgaagaaa ctcaggactt atatgggcaa gaaaatccag atagtattta tacagtaata          300
agaccactat cctttggtaa aggatatgaa agtgacctcc ctataaggca tgtagagaat          360
ttcggttttg acataattgt cggtgaccct agacttgctt tacaggaaga cctttttagct          420 ggagactggc gagatgccaa aggcggtggg atgcgaggaa ttaggacaac ttttgtattt          480
gcagagttaa ttaagaaagc tcgtgagcta aattatgatt ttgtttttctt tgacatggga          540 ccatcattag gcgcaatcaa cagggcagta ttactggcaa tggaattctt tgtcgtccca          600
atgtcaatcg atgtattttc actatgggct attaaaaata ttggctccac ggtttcaata          660
tggaaaaaag aattagacac agggattcgg ctctcagagg aacctagcga attatcacaa          720
ttatcacctc aaggaaaact aaagtttctc ggttacgtca cccaacaaca taaagaacgc          780
tctggatacg atacaattca gcttgagaat actgaggaag aaataaaatc gaaacgtcgg          840
gtaaaggcgt atgaagacat tggagaggtg tttccttcta aaattactga gcatctttct          900
aaactttatg catcaaaaga tatgaaccca caccttggag atatacgtca tttaggtagt          960
ttagctccga aatcacaatc acaacacgtt ccgatgatat cagtgtctgg tacaggaaat          1020
tacaccagac ttagaaaaag cgcgcgtgaa ctttatcgag atattgcaag aagatactta          1080
gagaacattc agactgctaa tggcgagaaa tag                                       1113

<210> SEQ ID NO 286
<211> LENGTH: 1374
<212> TYPE: DNA
<213> ORGANISM: Rahnella aquatilis
<220> FEATURE:
<223> OTHER INFORMATION: nifD1

<400> SEQUENCE: 286
atgaagggaa aggaaattct ggcgctgctg gacgaacccg cctgcgagca caaccagaag           60
caaaaatccg gctgcagcgc ccctaagccc ggcgctaccg ccggcggttg cgccttcgac          120
ggcgcgcaga taacgctcct gcccatcgcc gacgtcgcgc acctggtgca cggccccatc          180

```
ggctgcgcgg gcagctcgtg ggataaccgc ggcagcgtca gcgccggccc ggccctcaac      240
cggctcggct ttaccaccga tcttaacgaa caggatgtga ttatgggccg cggcgaacgc      300
cgcctgttcc acgccgtgcg tcacatcgtc gaccgctatc atccggcggc ggtctttatc      360
tacaacacct gcgtaccggc gatggagggc gatgacatcg aggcggtctg ccaggccgca      420
cagaccgcca ccggcgtccc ggtcatcgct attgacgccg ccggtttcta cggcagtaaa      480
aatcttggca accgaatggc gggcgacgtg atgctcaggc aggtgattgg ccagcgcgaa      540
ccggccccgt ggccagacaa cacgcccttt gccccggccc agcgccacga tatcggcctg      600
attggcgaat tcaatatcgc cggcgagttc tggcaggtcc agccgctgct cgacgagctg      660
gggatccgcg tcctcggcag cctctccggc gacggccgct ttgccgagat ccagaccctg      720
caccgggcgc aggccaatat gctggtgtgc tcgcgcgcgc tgatcaacgt cgcccggggg      780
ctggagctgc gctacggcac gccgtggttt gaaggcagct tctacgggat ccgcgccacc      840
tccgacgcct tgcgccagct ggcgacgctg ctggggatg acgacctgcg ccgccgcacc      900
gaggcgctga tcgcccgcga agagcaggcg gcggagcagg ctcttgcgcc gtggcgtgag      960
cagctccgcg ggcgcaaagt gctgctctat accggcggcg tgaaatcctg gtcggtggta     1020
tcggccctgc aggatctcgg catgaccgtg gtggccaccg gcacgcgcaa atccaccgag     1080
gaggacaaac agcggatccg tgagctgatg ggcgacgagg cggtgatgct tgaggagggc     1140
aatgcccgca ccctgctcga cgtggtgtac cgctatcagg ccgacctgat gatcgccggc     1200
ggacgcaata tgtacaccgc ctggaaagcc cggctgccgt ttctcgatat caatcaggag     1260
cgcgagcacg cctacgccgg ctatcagggc atcatcaccc tcgcccgcca gctctgtctg     1320
accctcgcca gccccgtctg gccgcaaacg cataccccgcg ccccgtggcg ctag         1374
```

```
<210> SEQ ID NO 287
<211> LENGTH: 1449
<212> TYPE: DNA
<213> ORGANISM: Rahnella aquatilis
<220> FEATURE:
<223> OTHER INFORMATION: nifD2

<400> SEQUENCE: 287
atgaccaacg caacaggcga acgtaacctt gcgctcatcc aggaagtcct ggaggtgttt       60
cccgaaaccg cgcgcaaaga gcgcagaaag cacatgatga tcagcgatcc gcagatggag      120
agcgtcggca agtgcattat ctcgaaccgt aaatcgcagc ccggggtgat gaccgtgcgc      180
ggctgcgcct atgcgggctc gaaaggggtg gtgtttgggc caatcaaaga catggcccat      240
atctcgcacg gccccatcgg ctgcggccag tattcccgcg ccggacggcg caactactat      300
accgccgtca gcggtgtcga cagcttcggc accctgaact tcacctctga ttttcaggag      360 gcgatattg ttttcggcgg cgataaaaag ctgaccaaac tgatcgaaga gatggagctg      420
ctgttcccgc tgaccaaagg gatcaccatc agtcggagt gcccggtggg cctgatcggc      480
gatgacatca gcgccgtagc caacgccagc agcaaggcgc tggataaacc ggtgatcccg      540
gtgcgctgcg aaggctttcg cggcgtatcg caatcgctgg ccaccatat cgccaacgac      600 gtggtgcgca ctgggtgct gaacaatcgc gaagggcagc cgtttgccag cacccccgtac      660 gatgttgcca tcattggcga ttacaacatc ggcggcgacg cctgggcctc gcgcattctg      720
ctggaagaga tggggctgcg cgtagtggcg cagtggtccg gcgacggcac cctggtggag      780
atggagaaca ccccattcgt taagcttaac ctcgtccact gctaccgttc gatgaactat      840
```

-continued

_____

```
atcgcccgcc atatggagga gaaacatcag atcccatgga tggaatataa cttcttcggc      900
ccgaccaaaa tcgccgaatc gctgcgcaag atcgccgatc aatttgatga caccattcgc      960
gccaatgcgg aagcggtgat cgccaaatat gaggggcaga tggcggccat catcgccaaa     1020
tatcgcccgc ggctggaggg cgcgcaaagtg ctgctgtaca tggggggggct gcggccgcgc     1080 cacgtcatcg gcgcctatga ggatctcggg atggagatca tcgccgccgg ctacgagttt     1140
gcccataacg atgattacga ccgcaccctg ccggacctga agagggcac cctgctgttt     1200 gacgatgcca gcagctatga gctggaggcc ttcgtcaaag cgctgaaacc tgacctcatc     1260
ggctccggga tcaaagagaa atatatcttc cagaaaatgg gggtgccgtt ccgccagatg     1320
cactcctggg actattccgg cccctatcac ggctatgacg gcttcgccat cttttgcccgc     1380 gatatggata tgaccctgaa caatccggcg tggaacgaac tgactgcccc gtggctgaag     1440
tctgcgtga                                                            1449
```

<210> SEQ ID NO 288
<211> LENGTH: 1386
<212> TYPE: DNA
<213> ORGANISM: Rahnella aquatilis
<220> FEATURE:
<223> OTHER INFORMATION: nifK1

<400> SEQUENCE: 288

```
atggcagata ttatccgcag tgaaaaaccg ctggcggtga gcccgattaa aaccgggcaa       60
ccgctcgggg cgatcctcgc cagcctcggg ctggcccagg ccatcccgct ggtccacggc      120
gcccagggct gcagcgcctt cgccaaagtt ttctttattc agcatttcca tgacccggtg      180
ccgctgcagt cgacggccat ggatccgacc gccacgatca tggggggccga cggcaatatc      240 ttcaccgcgc tcgacaccct ctgccagcgc cacagcccgc aggccatcgt gctgctcagc      300
accggtctgg cggaagcgca gggcagcgat atcgcccggg tggtgcgcca gtttcgcgag      360
gcgcatccgc gccataacgg cgtggcgatc ctcaccgtca ataccccgga ttttttttggc      420 tctatggaaa acggctacag cgcggtgatc gagagcgtga tcgagcagtg ggtcgcgccg      480
acgccgcgtc cggggcagcg gccccggcgg gtcaacctgc tggtcagcca cctctgttcg      540 ccagggggata tcgaatggct gggccgctgc gtggaggcct ttggcctgca gccggtgatc      600
ctgccggacc tctcgcagtc aatggatggc cacctcggtg aagggggattt tacgcccctg      660 acccagggcg gcgcctcgct cgcgccagatt gcccagatgg gccagagtct gggcagcttc      720
gccattggcg tgtcgctcca gcgggcggca tcgctcctga cccaacgcag ccgcggcgac      780
gtgatcgccc tgccgcatct gatgaccctc gaccattgcg ataccttttat ccatcagctg      840 gcgaagatgt ccggacgccg cgtaccggcc tggattgagc gccagcgtgg ccagctgcag      900
gatgcgatga tcgactgcca tatgtggctt cagggccagc gcatggcgat ggcggcggag      960
ggcgacctgc tggcggcgtg gtgtgatttc gcccgcagcc aggggatgca gcccggcccg     1020
ctggtcgccc ccaccagcca ccccagcctg cgccagctgc cggtcgagca agtcgtgccg     1080
ggggatcttg aggatctgca gcagctgctg agccaccaac ccgccgatct gctggtggct     1140
aactctcacg cccgcgatct ggcggagcag tttgccctgc cgctgatccg cgtcggtttt     1200
cccctcttcg accggctcgg tgagtttcgt cgcgtccgcc aggggtacgc cggtatgcga     1260
gatacgctgt ttgaactggc caatctgctg cgcgaccgcc atcaccacac cgccctctac     1320
cgctcgccgc ttcgccaggg cgccgacccc cagccggctt caggagacgc ttatgccgcc     1380
cattaa                                                               1386
```

-continued

```
<210> SEQ ID NO 289
<211> LENGTH: 1563
<212> TYPE: DNA
<213> ORGANISM: Rahnella aquatilis
<220> FEATURE:
<223> OTHER INFORMATION: nifK2

<400> SEQUENCE: 289
atgagccaaa cgatcgataa aattcacagc tgttatccgc tgtttgaaca ggatgaatac      60
cagaccctgt tccagaataa aaagaccctt gaagaggcgc acgacgcgca gcgtgtgcag     120
gaggtttttg cctggaccac caccgccgag tatgaagcgc tgaacttcca gcgcgaggcg     180
ctgaccgtcg acccggccaa agcctgccag ccgctcggcg ccgtactctg cgcgctgggg     240
ttcgccggca ccctgcccta cgtgcacggc tcccagggct cgtcgcccta ttttcgcacc     300
tactttaacc gccatttta agagccggtc gcctgcgtct ccgactccat gaccgaggac     360
gcggcggtgt tcggcggcaa caacaacatg aatctgggcc tgcagaatgc cagcgcgctg     420
tataaacccg agattatcgc cgtctccacc acctgtatgg ccgaggtgat cggcgacgat     480
ctgcaggcgt ttatcgccaa cgccaaaaaa gagggatttg ttgacgaccg catcgccatt     540
ccttacgccc atacccccag ctttatcggc agccatgtca ccggctggga caatatgttc     600
gaagggttcg cgaagacctt taccgctgac tacgccgggc agccgggcaa acagcaaaag     660
ctcaatctgg tgaccggatt tgagacctat ctcggcaact tccgcgtgct gaagcggatg     720
atggcgcaga tggatgtccc gtgcagcctg ctctccgacc catcagaggt gctcgacacc     780
cccgccgacg gccattaccg gatgtacgcc ggcggcacca gccagcagga gatcaaaacc     840
gcgccggacg ccattgacac cctgctgctg cagccgtggc agctggtgaa aagcaaaaag     900
gtggttcagg agatgtggaa ccagcccgcc accgaggtgg ccgttccgct gggcctggcc     960
gccaccgacg cgctgctgat gaccgtcagt cagctgaccg gcaaaccgat cgccgacgct    1020
ctgaccctgg agcgcggccg gctggtcgac atgatgctgg attcccacac ctggctgcat    1080
ggcaaaaaat tcggcctcta cggcgatccg gatttcgtga tggggctgac gcgcttcctg    1140
ctggagctgg gctgcgagcc gacggtgatc ctcagtcata cgccaataa acgctggcaa    1200 aaagcgatga agaaaatgct cgatgcctcg ccgtacggtc aggaaagcga agtgttcatc    1260
aactgcgacc tgtggcactt ccggtcgctg atgttcaccc gtcagccgga ctttatgatc    1320
ggtaactcct acggcaagtt tatccagcgc gataccctgg caaagggcaa agccttcgaa    1380
gtgccgctga tccgtctggg cttttccgctg ttcgaccgcc atcatctgca ccgccagacc    1440
acctggggct atgaaggcgc aatgaacatc gtcacgacgc tggtgaacgc cgtgctggaa    1500
aaactggacc acgacaccag ccagttgggc aaaaccgatt acagcttcga cctcgttcgt    1560
taa                                                                  1563

<210> SEQ ID NO 290
<211> LENGTH: 2838
<212> TYPE: DNA
<213> ORGANISM: Rahnella aquatilis
<220> FEATURE:
<223> OTHER INFORMATION: glnE

<400> SEQUENCE: 290
atgatgccgc tttctccgca attacagcag cactggcaga cggtcgctga ccgtctgcca      60
gcggattttc ccattgccga actgagccca caggccaggt cggtcatggc gttcagcgat     120
```

-continued

```
tttgtcgaac agagtgtgat cgcccagccg ggctggctga atgagcttgc ggactcctcg     180
ccggaggcgg aagagtggcg gcattacgag gcctggctgc aggatcgcct gcaggccgtc     240
actgacgaag cggggttgat gcgagagctg cgtctcttcc gccgccagat gatggtccgc     300
atcgcctggg cgcaggcgct gtcgctggtg agcgaagaag agactctgca gcagctgagc     360
gtcctggcgg agaccctgat tgtcgccgcc cgcgactggc tgtacgccgc ctgctgtaag     420 gagtgggggaa cgccatgcaa tgccgagggc cagccgcagc cgctgctgat cctcgggatg     480
ggaaagctgg gcggcggcga gctgaacttc tcttccgata tcgatctgat ctttgcctgg     540
cctgagcatg gcgccacccg cggcggccgc cgcgagctgg ataacgccca gttctttacc     600
cgtctggggc agcggctgat caaggccctt gaccagccga cgcaggacgg ctttgtctat     660
cgggttgaca tgcgcctgcg gccgtttggc gacagtgggc cgctggtact cagtttttgcg     720 gcgctggaag attattacca ggagcagggt cgggactggg aacgctatgc gatggtgaaa     780
gcgcggatca tgggcgataa cgacggcgtg tacgccagcg agttgcgcgc gatgctccgt     840
cctttcgtct tccgccgtta tatcgacttc agcgtgatcc agtcgctgcg taacatgaaa     900
ggcatgatcg cccgcgaagt gcggcgtcgc gggctgaaag acaacatcaa gctcggcgcc     960
ggcgggatcc gtgaaattga gtttatcgtt caggtctttc aactgatccg cggtggtcgc    1020
gaacctgcac tgcagcagcg cgccctgctg ccgacgctgg cggcgattga tgagctacat    1080
ctgctgccga aaggcgacgc ggcgctgctg cgcgaggcct atctgttcct gcgccggctg    1140
gaaaacctgc tgcaaagcat caacgatgag cagacccaga ccctgccgca ggatgaactt    1200
aaccgcgcca ggctggcgtg ggggatgcat accgaagact gggagacgct gagcgcgcag    1260
ctggcgagcc agatggccaa cgtgcggcga gtgtttaatg aactgatcgg cgatgatgag    1320
gatcagtccc cggatgagca actggccgag tactggcgcg agctgtggca ggatgcgctg    1380
gaagaagatg acgccagccc ggcgctggcg catttaaacg ataccgaccg ccgtagcgtg    1440
ctggcgctga ttgccgattt tcgtaaagag ctggatcggc gcaccatcgg cccgcgcggc    1500
cgccaggtgc tggatcagct gatgccgcat ctgctgagcg aaatctgctc gcgcgccgat    1560
gcgccgctgc ctctggcgcg gatcacgccg ctgttgaccg ggatcgtcac ccgtaccacc    1620
tatcttgagc tgctgagcga attccccggc gcgctgaagc acctgatcac gctctgcgcg    1680
gcgtcgccga tggtcgccag ccagctggcg cgccacccgc tgctgctgga tgagctgctg    1740
gatcccaaca ccctctatca gccgacggcg accgatgcct atcgcgacga gctgcgccag    1800
tacctgctgc gcgtgccgga agaggatgaa gagcagcagc tggaggcgtt gcgccagttt    1860
aagcaggcgc agcagctgca tatcgcggcg gcggatatcg ctggtaccct gccggtgatg    1920
aaggtcagcg atcacttaac ctggcttgcc gaagcgatcc tcgacgcggt ggtgcagcag    1980 gcatggggc agatggtcgc tcgctacggc cagccgaccc acctgcacga tcgccagggt    2040
cgcggcttcg ccgtcgtcgg ctacggtaag cttggcggct gggagctggg ctacagctcc    2100
gatctcgatc tggtgttcct ccatgactgc ccggcggagg tgatgaccga cggcgagcgg    2160
gagattgacg gccgtcagtt ctacctgcgg ctggcccagc ggatcatgca cctgttcagc    2220
acccgcacct cgtccggtat tctctacgaa gtggacgccc ggctgcgtcc ttctggcgcg    2280
gcggggatgc tggtcaccac cgccgacgcg tttgctgact atcagcagaa cgaagcctgg    2340
acgtgggaac atcaggcgct ggtgcgcgcc cgcgtggtct atggcgaccc ggcgctgcag    2400
gcgcgctttg acgccattcg tcgcgatatc ctgaccaccc cgcgggaggg gatgaccctg    2460
cagaccgagg ttcgcgagat gcgcgagaag atgcgcgcgc ccaccttggcaa caaacatccc    2520
```

-continued

```
gatcgttttg atatcaaagc cgatgccggc gggatcaccg atattgaatt tattactcag      2580
tatctggtcc tacgctatgc cagtgacaag ccgaagctga cccgctggtc tgacaacgtg      2640
cgtattcttg agctgctggc gcagaacgac atcatggacg aggaggaggc gcgcgcctta      2700
acgcatgcgt acaccacctt gcgtgatgcg ctccatcacc tggccctgca ggagcagccg      2760
ggacacgtgg cgccagaggc cttcagccgg gagcgtcagc aggtcagcgc cagctggcag      2820
aagtggctga tggcttaa                                                   2838

<210> SEQ ID NO 291
<211> LENGTH: 449
<212> TYPE: DNA
<213> ORGANISM: Rahnella aquatilis
<220> FEATURE:
<223> OTHER INFORMATION: Prm4

<400> SEQUENCE: 291
agtctgaact catcctgcgg cagtcggtga gacgtatttt tgaccaaaga gtgatctaca        60
tcacggaatt ttgtggttgt tgctgcttaa aagggcaaat ctacccttag aatcaactgt       120
tatatcaggg ggattcagag agatattagg aatttgcaca agcgcacaat ttaaccacat       180
catgataacg ccatgtaaaa caaagataaa aaaacaaat gcagtgactt acatcgcaag        240
caaggcattt tcttatccaa ttgctcaaag tttggccttt catatcgcaa cgaaaatgcg       300
taatatacgc gcccttgcgg acatcagtat ggtcattcct agttcatgcg catcggacac       360
caccagctta caaattgcct gattgcggcc ccgatggccg gtatcactga ccgaccattt       420
cgtgccttat gtcatgcgat gggggctgg                                         449

<210> SEQ ID NO 292
<211> LENGTH: 500
<212> TYPE: DNA
<213> ORGANISM: Rahnella aquatilis
<220> FEATURE:
<223> OTHER INFORMATION: Prm1.2

<400> SEQUENCE: 292
tgaacatcac tgatgcacaa gctacctatg tcgaagaatt aactaaaaaa ctgcaagatg        60
caggcattcg cgttaaagcc gacttgagaa atgagaagat tggctttaaa attcgcgaac       120
acacgctacg ccgtgttcct tatatgttag tttgtggcga taaagaggtc gaagcaggca       180
aagttgctgt tcgtacccgc cgcggcaaag acttaggaag catggatgtt agcgaagtcg       240
ttgacaaact gctggcggaa atccgcagca gaagtcttca tcaactggag gaataaagta       300
ttaaaggcgg aaaacgagtt caaccggcgc gtcctaatcg cattaacaaa gagattcgcg       360
cgcaagaagt tcgcctcaca ggcgtcgatg gcgagcagat tggtattgtc agtctgaatg       420
aagctcttga aaaagctgag gaagcgggcg tcgatttagt agaaatcagt ccgaatgccg       480
agccgccagt ttgtcgaatc                                                   500

<210> SEQ ID NO 293
<211> LENGTH: 170
<212> TYPE: DNA
<213> ORGANISM: Rahnella aquatilis
<220> FEATURE:
<223> OTHER INFORMATION: Prm3.1

<400> SEQUENCE: 293
tacagtagcg cctctcaaaa atagataaac ggctcatgta cgtgggccgt ttattttttc        60
```

```
tacccataat cgggaaccgg tgttataatg ccgcgccctc atattgtggg gatttcttaa      120
tgacctatcc tgggtcctaa agttgtagtt gacattagcg gagcactaac                170

<210> SEQ ID NO 294
<211> LENGTH: 142
<212> TYPE: DNA
<213> ORGANISM: Rahnella aquatilis
<220> FEATURE:
<223> OTHER INFORMATION: Prm6.1

<400> SEQUENCE: 294
aatttttttt cacaaagcgt agcgttattg aatcgcacat tttaaactgt tggccgctgt       60
ggaagcgaat attggtgaaa ggtgcggttt taaggccttt ttctttgact ctctgtcgtt      120
acaaagttaa tatgcgcgcc ct                                              142

<210> SEQ ID NO 295
<211> LENGTH: 293
<212> TYPE: DNA
<213> ORGANISM: Rahnella aquatilis
<220> FEATURE:
<223> OTHER INFORMATION: Prm7.1

<400> SEQUENCE: 295
ttaaaaacgt gaccacgagc attaataaac gccacgaaat gtggcgttta tttattcaaa       60
aagtatcttc tttcataaaa agtgctaaat gcagtagcag caaaattggg ataagtccca      120
tggaatacgg ctgttttcgc tgcaattttt aactttttcg taaaaaaaga tgtttctttg      180
agcgaacgat caaaatatag cgttaaccgg caaaaaatta ttctcattag aaaatagttt      240
gtgtaatact tgtaacgcta catggagatt aacttaatct agagggtttt ata             293

<210> SEQ ID NO 296
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 296
atggcgctca aacagttaat ccgtctgtgt gccgcctcgc cgatggtcgc gacacaactt       60
gcacgtcatc ctttattgct cgatgaactg ctcgacccgc gcacgcttta ccagccgatt      120
gagccgggcg cttaccgcga cgaactgcgt cagtatctga tgcgggtgcc aacagaagac      180
gaagaacagc agcttgaagc cgtgcgccag ttcaaacagg cccagcattt gcgtatcgca      240 gccgggggata tttccggggc attgccggtg atgaaagtca gtgaccattt aacctacctt      300
gccgaggcca ttctcgatgt cgtggtgcag catgcgtggg aacaaatggt cgtaaaatac      360
gggcagcccg cgcatcttca gcaccgtgag gggcgcggtt ttgccgtggt cggttacggg      420
aaactcggtg gctgggagct gggttatagc tcagatctgg atctggtctt cctgctcgat      480
tgcgcgccgg aggtgatgac ggacggcgaa cgcagcatcg acggacgtca gttttatctt      540
cggctggcgc agcgcattat gcacttattc agcacccgga catcgtcagg cattctttac      600
gaggttgatc cgcgtctgcg accttccggc gcatccggca tgctggtcag taccattgaa      660
gcgtttgcag attatcaggc caatgaagcc tggacgtggg agcatcaggc gctggttcgc      720
gcgcgcgtgg tttacgggga tccgcaactg acacagcaat ttaacgccac gcgtcgcgac      780
```

-continued

```
attctttgcc gccagcgcga tggcgacggc ctgcgtaagg aggtccgtga aatgcgcgag      840
aaaatgtatg cccatctggg gagtaaaaaa gcccacgagt ttgatctgaa agccgatccg      900
ggtggcatca cggatattga attcattgca caatacctgg ttctgcgttt cgcgcatgat      960
gagccgaagc tgacgcgctg gtctgataac gtgcggattt ttgaactgat ggcacgatat     1020
gacatcatgc cggaagagga agcgcgccat ctgacgcagg cttatgtgac gctgcgcgat     1080
gaaattcatc atctggcgtt gcaggaacac agcgggaaag tggccgcgga cagctttgct     1140
actgagcgcg cgcagatccg tgccagctgg gcaaagtggc tcggctga                  1188
```

```
<210> SEQ ID NO 297
<211> LENGTH: 2188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 297
```

```
cggtactgga acagaaatcg gcggatgcgc aggaaatttg ttatgacacg gcctgtctga       60
agtgcaagtt agtgcttact tcctggctgg caacctcagg ctggacgccg tttattgatg      120
ataaatctgc gaagaaactg gacgcttcct tcaaacgttt tgctgacatc atgctcggtc      180
gtaccgcagc ggatctgaaa gaagcctttg cgcagccact gacggaagaa ggttatcgcg      240
atcagctggc gcgcctgaaa cgccagatca ttaccttcca tttgcttgcc ggtgcttacc      300
ctgaaaaaga cgtcgatgcg tatattgccg gctgggtgga cctgcaacag gccatcgttc      360
agcagcaaca cgcctgggag gattcggccc gttctcacgc ggtgatgatg gatgctttct      420
ggttaaacgg gcaacctcgt taactgactg actagcctgg gcaaactgcc cgggcttttt      480
tttgcaagga atctgatttc atggcgctca aacagttaat ccgtctgtgt gccgcctcgc      540
cgatggtcgc gacacaactt gcacgtcatc ctttattgct cgatgaactg ctcgacccgc      600
gcacgcttta ccagccgatt gagccgggcg cttaccgcga cgaactgcgt cagtatctga      660
tgcgggtgcc aacagaagac gaagaacagc agcttgaagc cgtgcgccag ttcaaacagg      720
cccagcattt gcgtatcgca gccgggggata tttccggggc attgccggtg atgaaagtca      780
gtgaccattt aacctacctt gccgaggcca ttctcgatgt cgtggtgcag catgcgtggg      840
aacaaatggt cgtaaaatac gggcagcccg cgcatcttca gcaccgtgag gggcgcggtt      900
ttgccgtggt cggttacggg aaactcggtg gctgggagct gggttatagc tcagatctgg      960
atctggtctt cctgctcgat tgcgcgccgg aggtgatgac ggacggcgaa cgcagcatcg     1020
acggacgtca gttttatctt cggctggcgc agcgcattat gcacttattc agcacccgga     1080
catcgtcagg cattctttac gaggttgatc cgcgtctgcg accttccggc gcatccggca     1140
tgctggtcag taccattgaa gcgtttgcag attatcaggc caatgaagcc tggacgtggg     1200
agcatcaggc gctggttcgc gcgcgcgtgg tttacgggga tccgcaactg acacagcaat     1260
ttaacgccac gcgtcgcgac attctttgcc gccagcgcga tggcgacggc ctgcgtaagg     1320
aggtccgtga aatgcgcgag aaaatgtatg cccatctggg gagtaaaaaa gcccacgagt     1380
ttgatctgaa agccgatccg ggtggcatca cggatattga attcattgca caatacctgg     1440
ttctgcgttt cgcgcatgat gagccgaagc tgacgcgctg gtctgataac gtgcggattt     1500
ttgaactgat ggcacgatat gacatcatgc cggaagagga agcgcgccat ctgacgcagg     1560
```

```
cttatgtgac gctgcgcgat gaaattcatc atctggcgtt gcaggaacac agcgggaaag    1620
tggccgcgga cagctttgct actgagcgcg cgcagatccg tgccagctgg gcaaagtggc    1680
tcggctgagg gttttattc ggctaacagg cgcttgtgat attatccggc gcattgtatt      1740
tacccgattt gatttatctg ttttggagtc ttgggatgaa agtgactttg cctgattttc     1800
accgcgcagg tgtgctggtt gtcggtgacg taatgttaga ccgttactgg tatggcccga     1860
ccaatcgtat ttctccggaa gctccggtgc cggtggtgaa ggtcagtacc attgaagagc     1920
ggcctggcgg tgcagctaac gtggcgatga acatttcatc tctgggcgcc tcttcctgtc     1980
tgatcggcct gaccggcgta gacgacgctg cgcgtgccct cagtgagcgt ctggcagaag     2040
tgaaagttaa ctgcgatttc gtcgcactat ccacacatcc taccatcacc aaactgcgaa     2100
ttttgtcccg taaccagcaa ctgatccgcc tcgactttga ggaaggtttt gaaggcgttg     2160
atctcgagcc gatgctgacc aaaatagaa                                        2188
```

<210> SEQ ID NO 298
<211> LENGTH: 524
<212> TYPE: DNA
<213> ORGANISM: Artificial Sequence
<220> FEATURE:
<223> OTHER INFORMATION: Description of Artificial Sequence: Synthetic
       polynucleotide
<220> FEATURE:
<223> OTHER INFORMATION: delta-nifL::null-v1

<400> SEQUENCE: 298

```
atgagcatca cggcgttatc agcatcattt cctgaggrga atatcgccag ccgcttgtcg      60
ctgcaacatc cttcactgtt ttataccgtg gttgaacaat cttcggtggc gatttcgctg     120
accgatccgc aggcgcgcat ttgttatgcc aatccggcat tctgccgcca gacgggtttt     180
gcacttgaga cacttttggg cgagaaccac cgtctgctgg agtctgaact catcctgcga     240
tgggggctgg gccgtctctg aagctctcgg tgaacattgt tgcgaggcag gatgcgagct     300
ggttgtgttt tgacattacc gataatgtgc cgcgtgaacg ggtgcgttat gcccgcccgg     360
aagcggcgtt ttcccgtccg gggaatggca tggagctgcg ccttatccag acgctgatcg     420
cccatcatcg cggttcttta gatctctcgg tccgccctga tggcggcacc ttgctgacgt     480
tacgcctgcc ggtacagcag gttatcaccg gaggcttaaa atga                       524
```

<210> SEQ ID NO 299
<211> LENGTH: 1524
<212> TYPE: DNA
<213> ORGANISM: Artificial Sequence
<220> FEATURE:
<223> OTHER INFORMATION: Description of Artificial Sequence: Synthetic
       polynucleotide
<220> FEATURE:
<223> OTHER INFORMATION: delta-nifL::null-v1 with 500bp flank

<400> SEQUENCE: 299

```
tgtttcgtct cgaggccggg caactgagcg gccccgttga aaccgacctg ggctggcatc      60
tgttgttgtg cgaacaaatt cgcctgccgc aacccttgcc gaaagccgaa gccttaacgc     120
gggtgcgtca gcaactgatt gcccggcaac agaaacatta tcagcgccag tggctgcaac     180
aactgatcaa cgcctgagcc tgttctcctt cttgttgatg cagacgggtt aatgcccgtt     240
ttgcacgaaa aatgcacata aattgcctgc gttgccttat aacagcgcag ggaaatcctg     300
cctccggcct tgtgccacac cgcgctttgc ctggtttgtg gtaaaaactg gcccgctttg     360
catcctgatg cttaaaacac cccgttcaga tcaacctttg ggcagataag cccgcgaaag     420
```

```
gcctgcaaat tgcacggtta ttccgggtga gtatatgtgt gatttgggtt ccggcattgc      480
gcaataaagg ggagaaagac atgagcatca cggcgttatc agcatcattt cctgagggga      540
atatcgccag ccgcttgtcg ctgcaacatc cttcactgtt ttataccgtg gttgaacaat      600
cttcggtggc gatttcgctg accgatccgc aggcgcgcat ttgttatgcc aatccggcat      660
tctgccgcca gacgggtttt gcacttgaga cacttttggg cgagaaccac cgtctgctgg      720
agtctgaact catcctgcga tgggggctgg gccgtctctg aagctctcgg tgaacattgt      780
tgcgaggcag gatgcgagct ggttgtgttt tgacattacc gataatgtgc cgcgtgaacg      840
ggtgcgttat gcccgcccgg aagcggcgtt ttcccgtccg gggaatggca tggagctgcg      900
ccttatccag acgctgatcg cccatcatcg cggttcttta gatctctcgg tccgccctga      960
tggcggcacc ttgctgacgt tacgcctgcc ggtacagcag gttatcaccg gaggcttaaa     1020
atgacccagt tacctaccgc gggcccggtt atccggcgct ttgatatgtc tgcccagttt     1080
acggcgcttt atcgcatcag cgtggcgctg agtcaggaaa gcaacaccgg gcgcgcactg     1140
gcggcgatcc tcgaagtgct tcacgatcat gcatttatgc aatacggcat ggtgtgtctg     1200
tttgataaag aacgcaatgc actctttgtg gaatccctgc atggcatcga cggcgaaagg     1260
aaaaaagaga cccgccatgt ccgttaccgc atgggggaag gcgtgatcgg cgcggtgatg     1320
agccagcgtc aggcgctggt gttaccgcgc atttcagacg atcagcgttt tctcgaccgc     1380
ctgaatattt acgattacag cctgccgttg attggcgtgc cgatccccgg tgcggataat     1440
cagccatcgg gcgtgctggt ggcacagccg atggcgttgc acgaagaccg gctgactgcc     1500
agtacgcggt ttttagaaat ggtc                                            1524

<210> SEQ ID NO 300
<211> LENGTH: 266
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::null-v2

<400> SEQUENCE: 300
atgagcatca cggcgttatc agcatcattt cctgagggga atatcgccag ccgcttgtcg       60
ctgcaacatc cttcactgtt ttataccgtg gttgaacaat cttcggtggc gatttcgctg      120
accgatccgc aggcgcgcat ttgttatgcc aatccggcat tctgccgcca gacgggtttt      180
gcacttgaga cacttttggg cgagaaccac cgtctgctgg ttaaagcctg ccggtacagc      240
aggttatcac cggaggctta aaatga                                           266

<210> SEQ ID NO 301
<211> LENGTH: 1266
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::null-v2 with 500bp flank

<400> SEQUENCE: 301
tgtttcgtct cgaggccggg caactgagcg gccccgttga aaccgacctg ggctggcatc       60
tgttgttgtg cgaacaaatt cgcctgccgc aaccccttgcc gaaagccgaa gccttaacgc      120
```

-continued

```
gggtgcgtca gcaactgatt gcccggcaac agaaacatta tcagcgccag tggctgcaac        180
aactgatcaa cgcctgagcc tgttctcctt cttgttgatg cagacggggt aatgcccgtt        240
ttgcacgaaa aatgcacata aattgcctgc gttgccttat aacagcgcag ggaaatcctg        300
cctccggcct tgtgccacac cgcgctttgc ctggtttgtg gtaaaaactg cccgctttg         360 catcctgatg cttaaaacac cccgttcaga tcaacctttg ggcagataag cccgcgaaag        420
gcctgcaaat tgcacggtta ttccgggtga gtatatgtgt gatttgggtt ccggcattgc        480
gcaataaagg ggagaaagac atgagcatca cggcgttatc agcatcattt cctgagggga        540
atatcgccag ccgcttgtcg ctgcaacatc cttcactgtt ttataccgtg gttgaacaat        600
cttcggtggc gatttcgctg accgatccgc aggcgcgcat ttgttatgcc aatccggcat        660
tctgccgcca gacgggtttt gcacttgaga cacttttggg cgagaaccac cgtctgctgg        720
ttaaagcctg ccggtacagc aggttatcac cggaggctta aaatgaccca gttacctacc        780
gcgggcccgg ttatccggcg ctttgatatg tctgcccagt ttacggcgct ttatcgcatc        840
agcgtggcgc tgagtcagga aagcaacacc gggcgcgcac tggcggcgat cctcgaagtg        900
cttcacgatc atgcatttat gcaatacggc atggtgtgtc tgtttgataa agaacgcaat        960
gcactctttg tggaatccct gcatggcatc gacggcgaaa ggaaaaaaga gacccgccat      1020
gtccgttacc gcatggggga aggcgtgatc ggcgcggtga tgagccagcg tcaggcgctg      1080
gtgttaccgc gcatttcaga cgatcagcgt tttctcgacc gcctgaatat ttacgattac      1140
agcctgccgt tgattggcgt gccgatcccc ggtgcggata tcagccatc gggcgtgctg       1200 gtggcacagc cgatggcgtt gcacgaagac cggctgactg ccagtacgcg gttttttagaa     1260 atggtc                                                                  1266
```

```
<210> SEQ ID NO 302
<211> LENGTH: 943
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm4

<400> SEQUENCE: 302
atgagcatca cggcgttatc agcatcattt cctgagggga atatcgccag ccgcttgtcg         60
ctgcaacatc cttcactgtt ttataccgtg gttgaacaat cttcggtggc gatttcgctg        120
accgatccgc aggcgcgcat ttgttatgcc aatccggcat tctgccgcca gacgggtttt        180
gcacttgaga cacttttggg cgagaaccac cgtctgctgg agtctgaact catcctgcgg        240
cagtcggtga gacgtatttt tgaccaaaga gtgatctaca tcacggaatt ttgtggttgt        300
tgctgcttaa aagggcaaat ctacccttag aatcaactgt tatatcaggg ggattcagag        360
agatattagg aatttgcaca agcgcacaat ttaaccacat catgataacg ccatgtaaaa        420
caaagataaa aaaacaaaat gcagtgactt acatcgcaag caaggcattt tcttatccaa        480
ttgctcaaag tttggccttt catatcgcaa cgaaaatgcg taatatacgc gcccttgcgg        540
acatcagtat ggtcattcct agttcatgcg catcggcac caccagctta caaattgcct         600
gattgcggcc ccgatggccg gtatcactga ccgaccattt cgtgccttat gtcatgcgat        660
gggggctggg ccgtctctga agctctcggt gaacattgtt gcgaggcagg atgcgagctg        720
gttgtgtttt gacattaccg ataatgtgcc gcgtgaacgg gtgcgttatg cccgcccgga        780
```
agcggcgttt tcccgtccgg ggaatggcat ggagctgcgc cttatccaga cgctgatcgc      840
ccatcatcgc ggttctttag atctctcggt ccgccctgat ggcggcacct tgctgacgtt      900
acgcctgccg gtacagcagg ttatcaccgg aggcttaaaa tga      943

<210> SEQ ID NO 303
<211> LENGTH: 1943
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm4 with 500bp flank

<400> SEQUENCE: 303
tgtttcgtct cgaggccggg caactgagcg gccccgttga aaccgacctg ggctggcatc       60
tgttgttgtg cgaacaaatt cgcctgccgc aaccccttgcc gaaagccgaa gccttaacgc      120
gggtgcgtca gcaactgatt gcccggcaac agaaacatta tcagcgccag tggctgcaac      180
aactgatcaa cgcctgagcc tgttctcctt cttgttgatg cagacgggtt aatgcccgtt      240
ttgcacgaaa aatgcacata aattgcctgc gttgccttat aacagcgcag ggaaatcctg      300
cctccggcct tgtgccacac cgcgctttgc ctggtttgtg gtaaaaactg gcccgctttg      360
catcctgatg cttaaaacac cccgttcaga tcaacctttg ggcagataag cccgcgaaag      420
gcctgcaaat tgcacggtta ttccgggtga gtatatgtgt gatttgggtt ccggcattgc      480
gcaataaagg ggagaaagac atgagcatca cggcgttatc agcatcattt cctgagggga      540
atatcgccag ccgcttgtcg ctgcaacatc cttcactgtt ttataccgtg gttgaacaat      600
cttcggtggc gatttcgctg accgatccgc aggcgcgcat ttgttatgcc aatccggcat      660
tctgccgcca gacgggtttt gcacttgaga cacttttggg cgagaaccac cgtctgctgg      720
agtctgaact catcctgcgg cagtcggtga gacgtatttt tgaccaaaga gtgatctaca      780
tcacggaatt ttgtggttgt tgctgcttaa aagggcaaat ctacccttag aatcaactgt      840
tatatcaggg ggattcagag agatattagg aatttgcaca agcgcacaat ttaaccacat      900
catgataacg ccatgtaaaa caaagataaa aaaacaaaat gcagtgactt acatcgcaag      960
caaggcattt tcttatccaa ttgctcaaag tttggccttt catatcgcaa cgaaaatgcg     1020
taatatacgc gcccttgcgg acatcagtat ggtcattcct agttcatgcg catcggacac     1080
caccagctta caaattgcct gattgcggcc ccgatggccg gtatcactga ccgaccattt     1140
cgtgccttat gtcatgcgat gggggctggg ccgtctctga agctctcggt gaacattgtt     1200
gcgaggcagg atgcgagctg gttgtgtttt gacattaccg ataatgtgcc gcgtgaacgg     1260
gtgcgttatg cccgcccgga agcggcgttt tcccgtccgg ggaatggcat ggagctgcgc     1320
cttatccaga cgctgatcgc ccatcatcgc ggttctttag atctctcggt ccgccctgat     1380
ggcggcacct tgctgacgtt acgcctgccg gtacagcagg ttatcaccgg aggcttaaaa     1440
tgacccagtt acctaccgcg ggcccggtta tccggcgctt tgatatgtct gcccagttta     1500
cggcgcttta tcgcatcagc gtggcgctga gtcaggaaag caacaccggg cgcgcactgg     1560
cggcgatcct cgaagtgctt cacgatcatg catttatgca atacggcatg gtgtgtctgt     1620
ttgataaaga acgcaatgca ctctttgtgg aatccctgca tggcatcgac ggcgaaagga     1680
aaaaagagac ccgccatgtc cgttaccgca tgggggaagg cgtgatcggc gcggtgatga     1740
gccagcgtca ggcgctggtg ttaccgcgca tttcagacga tcagcgtttt ctcgaccgcc     1800
tgaatattta cgattacagc ctgccgttga ttggcgtgcc gatccccggt gcggataatc    1860
agccatcggg cgtgctggtg gcacagccga tggcgttgca cgaagaccgg ctgactgcca    1920
gtacgcggtt tttagaaatg gtc                                             1943

<210> SEQ ID NO 304
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 304
tggtgtccgg gcgaacgtcg ccaggtggca caaattgtca gaactacgac acgactaacc      60
gaccgcagga gtgtgcgatg accctgaata tgatgatgga                            100

<210> SEQ ID NO 305
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 305
cggaaaacga gttcaaacgg cgcgtcccaa tcgtattaat ggcgagattc gcgccacgga      60
agttcgctta acaggtctgg aaggcgagca gcttggtatt                            100

<210> SEQ ID NO 306
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 306
cgccagagag ttgaaatcga acatttccgt aataccgcca ttacccagga gccgttctgg      60
ttgcacagcg gaaaacgtta acgaaaggat atttcgcatg                            100

<210> SEQ ID NO 307
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 307
cgggcgaacg tcgccaggtg gcacaaattg tcagaactac gacacgacta accgaccgca      60
ggagtgtgcg atgaccctga atatgatgat ggatgccagc                            100

<210> SEQ ID NO 308
<211> LENGTH: 100
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 308
tcaacctaaa aaagtttgtg taatacttgt aacgctacat ggagattaac tcaatctaga      60
gggtattaat aatgaatcgt actaaactgg tactgggcgc                           100

<210> SEQ ID NO 309
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 309
cgggcgaacg tcgccaggtg gcacaaattg tcagaactac gacacgacta accgaccgca      60
ggagtgtgcg atgaccctga atatgatgat ggatgccagc                           100

<210> SEQ ID NO 310
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 310
aattttctgc ccaaatggct gggattgttc attttttgtt tgccttacaa cgagagtgac      60
agtacgcgcg ggtagttaac tcaacatctg accggtcgat                           100

<210> SEQ ID NO 311
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 311
gtaaccaata aaggccacca cgccagacca cacgatagtg atggcaacac tttccagctg      60
caccagcacc tgatggccca tggtcacacc ttcagcgaaa                           100

<210> SEQ ID NO 312
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 312
tggtattgtc agtctgaatg aagctcttga aaaagctgag gaagcgggcg tcgatttagt      60
agaaatcagt ccgaatgccg agccgccagt ttgtcgaatc                           100
```

-continued

```
<210> SEQ ID NO 313
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 313
accgatccgc aggcgcgcat ttgttatgcc aatccggcat tctgccgcca gacgggtttt      60
gcacttgaga cactttttggg cgagaaccac cgtctgctgg                           100

<210> SEQ ID NO 314
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 314
cgggaaccgg tgttataatg ccgcgccctc atattgtggg gatttcttaa tgacctatcc      60
tgggtcctaa agttgtagtt gacattagcg gagcactaac                           100

<210> SEQ ID NO 315
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 315
accgatccgc aggcgcgcat ttgttatgcc aatccggcat tctgccgcca gacgggtttt      60
gcacttgaga cactttttggg cgagaaccac cgtctgctgg                           100

<210> SEQ ID NO 316
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 316
tcaacctaaa aaagtttgtg taatacttgt aacgctacat ggagattaac tcaatctaga      60
gggtattaat aatgaatcgt actaaactgg tactgggcgc                           100

<210> SEQ ID NO 317
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction
```

-continued

```
<400> SEQUENCE: 317
gggcgacaaa cggcctggtg gcacaaattg tcagaactac gacacgacta actgaccgca       60
ggagtgtgcg atgaccctga atatgatgat ggatgccggc                            100

<210> SEQ ID NO 318
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 318
gggcgacaaa cggcctggtg gcacaaattg tcagaactac gacacgacta actgaccgca       60
ggagtgtgcg atgaccctga atatgatgat ggatgccggc                            100

<210> SEQ ID NO 319
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 319
taagaattat ctggatgaat gtgccattaa atgcgcagca taatggtgcg ttgtgcggga       60
aaactgcttt tttttgaaag ggttggtcag tagcggaaac                            100

<210> SEQ ID NO 320
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 320
cgccagagag tcgaaatcga acatttccgt aataccgcga ttacccagga gccgttctgg       60
ttgcacagcg gaaaacgtta acgaaaggat atttcgcatg                            100

<210> SEQ ID NO 321
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 321
cgccagagag tcgaaatcga acatttccgt aataccgcga ttacccagga gccgttctgg       60
ttgcacagcg gaaaacgtta acgaaaggat atttcgcatg                            100

<210> SEQ ID NO 322
<211> LENGTH: 100
<212> TYPE: DNA
```

-continued

```
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 322
gatgatggat gctttctggt taaacgggca acctcgttaa ctgactgact agcctgggca      60
aactgcccgg gctttttttt gcaaggaatc tgatttcatg                          100

<210> SEQ ID NO 323
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 323
accgatccgc aggcgcgcat ttgttatgcc aatccggcat tctgccgcca gacgggtttt      60
gcacttgaga cacttttggg cgagaaccac cgtctgctgg                          100

<210> SEQ ID NO 324
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 324
catcggacac caccagctta caaattgcct gattgcggcc ccgatggccg gtatcactga      60
ccgaccattt cgtgccttat gtcatgcgat gggggctggg                          100

<210> SEQ ID NO 325
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 325
tcttcaacaa ctggaggaat aaggtattaa aggcggaaaa cgagttcaaa cggcacgtcc      60
gaatcgtatc aatggcgaga ttcgcgccct ggaagttcgc                          100

<210> SEQ ID NO 326
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 326
tccgggttcg gcttaccccg ccgcgttttg cgcacggtgt cggacaattt gtcataactg      60
```

```
cgacacagga gtttgcgatg accctgaata tgatgctcga                                100

<210> SEQ ID NO 327
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 327
atcgcagcgt ctttgaatat ttccgtcgcc aggcgctggc tgccgagccg ttctggctgc         60
atagtggaaa acgataattt caggccaggg agcccttatg                                100

<210> SEQ ID NO 328
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 328
tccgggttcg gcttaccccg ccgcgttttg cgcacggtgt cggacaattt gtcataactg         60
cgacacagga gtttgcgatg accctgaata tgatgctcga                                100

<210> SEQ ID NO 329
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 329 tcactttta gcaaagttgc actggacaaa aggtaccaca attggtgtac tgatactcga          60
cacagcatta gtgtcgattt ttcatataaa ggtaattttg                                100

<210> SEQ ID NO 330
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 330
tccgggttcg gcttaccccg ccgcgttttg cgcacggtgt cggacaattt gtcataactg         60
cgacacagga gtttgcgatg accctgaata tgatgctcga                                100

<210> SEQ ID NO 331
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

-continued

```
<223> OTHER INFORMATION: 100 bp upstream of junction

<400> SEQUENCE: 331
gttctccttt gcaatagcag ggaagaggcg ccagaaccgc cagcgttgaa gcagtttgaa      60
cgcgttcagt gtataatccg aaacttaatt tcggtttgga                          100

<210> SEQ ID NO 332
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 332
tccgggttcg gcttaccccg ccgcgttttg cgcacggtgt cggacaattt gtcataactg      60
cgacacagga gtttgcgatg accctgaata tgatgctcga                          100

<210> SEQ ID NO 333
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 333
gatatgcctg aagtattcaa ttacttaggc atttacttaa cgcaggcagg caattttgat      60
gctgcctatg aagcgtttga ttctgtactt gagcttgatc                          100

<210> SEQ ID NO 334
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 334
tggtattgtc agtctgaatg aagctcttga aaaagctgag gaagcgggcg tcgatttagt      60
agaaatcagt ccgaatgccg agccgccagt ttgtcgaatc                          100

<210> SEQ ID NO 335
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 335
tgcaaattgc acggttattc cgggtgagta tatgtgtgat ttgggttccg gcattgcgca      60
ataaagggga gaaagacatg agcatcacgg cgttatcagc                          100

<210> SEQ ID NO 336
<211> LENGTH: 100
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 336
tcagggctgc ggatgtcggg cgtttcacaa cacaaaatgt tgtaaatgcg acacagccgg      60
gcctgaaacc aggagcgtgt gatgaccttt aatatgatgc                          100

<210> SEQ ID NO 337
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 337
cggaaaacga gttcaaacgg cacgtccgaa tcgtatcaat ggcgagattc gcgcccagga      60
agttcgctta actggtctgg aaggtgagca gctgggtatt                          100

<210> SEQ ID NO 338
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 338
ttcttggttc tctggagcgc tttatcggca tcctgactga agaatttgca ggcttcttcc      60
caacctggct tgcacccgtg caggtagttg tgatgaacat                          100

<210> SEQ ID NO 339
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 339
gcgatagaac tcacttcacg ccccgaaggg ggaagctgcc tgaccctacg attcccgcta      60
tttcattcac tgaccggagg ttcaaaatga cccagcgaac                          100

<210> SEQ ID NO 340
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 340
tccctgtgcg ccgcgtcgcc gatggtggcc agccaactgg cgcgctaccc gatcctgctc      60
```
gatgaactgc tcgacccgaa cacgctctat caaccgacgg                          100

<210> SEQ ID NO 341
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 341
cgttctgtaa taataaccgg acaattcgga ctgattaaaa aagcgccctc gcggcgcttt       60
ttttatattc tcgactccat ttaaaataaa aaatccaatc                           100

<210> SEQ ID NO 342
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 342
aactcacttc acgccccgaa gggggaagct gcctgaccct acgattcccg ctatttcatt       60
cactgaccgg aggttcaaaa tgacccagcg aaccgagtcg                           100

<210> SEQ ID NO 343
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 343
cgcgtcaggt tgaacgtaaa aaagtcggtc tgcgcaaagc acgtcgtcgt ccgcagttct       60
ccaaacgtta attggtttct gcttcggcag aacgattggc                           100

<210> SEQ ID NO 344
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 344
aactcacttc acgccccgaa gggggaagct gcctgaccct acgattcccg ctatttcatt       60
cactgaccgg aggttcaaaa tgacccagcg aaccgagtcg                           100

<210> SEQ ID NO 345
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide -continued

```
<220> FEATURE:
<223> OTHER INFORMATION: 100 bp downstream of junction

<400> SEQUENCE: 345
ccgatcccca tcactgtgtg tcttgtatta cagtgccgct tcgtcggctt cgccggtacg      60
aatacgaatg acgcgttgca gctcagcaac gaaaattttg                           100

<210> SEQ ID NO 346
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 346
ccgtctctga agctctcggt gaacattgtt gcgaggcagg atgcgagctg gttgtgtttt      60
gacattaccg ataatgtgcc gcgtgaacgg gtgcgttatg                           100

<210> SEQ ID NO 347
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 347
tgaacatcac tgatgcacaa gctacctatg tcgaagaatt aactaaaaaa ctgcaagatg      60
caggcattcg cgttaaagcc gacttgagaa atgagaagat                           100

<210> SEQ ID NO 348
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 348
ccgtctctga agctctcggt gaacattgtt gcgaggcagg atgcgagctg gttgtgtttt      60
gacattaccg ataatgtgcc gcgtgaacgg gtgcgttatg                           100

<210> SEQ ID NO 349
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 349
tacagtagcg cctctcaaaa atagataaac ggctcatgta cgtgggccgt ttatttttc      60 tacccataat cgggaaccgg tgttataatg ccgcgccctc                           100

<210> SEQ ID NO 350
```

-continued

```
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 350
aactcacttc acaccccgaa gggggaagtt gcctgaccct acgattcccg ctatttcatt       60
cactgaccgg aggttcaaaa tgacccagcg aaccgagtcg                            100

<210> SEQ ID NO 351
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 351
cgtcctgtaa taataaccgg acaattcgga ctgattaaaa aagcgccctt gtggcgcttt       60
ttttatattc ccgcctccat ttaaaataaa aaatccaatc                            100

<210> SEQ ID NO 352
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 352
ggacatcatc gcgacaaaca atattaatac cggcaaccac accggcaatt tacgagactg       60
cgcaggcatc ctttctcccg tcaatttctg tcaaataaag                            100

<210> SEQ ID NO 353
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 353
aactcacttc acaccccgaa gggggaagtt gcctgaccct acgattcccg ctatttcatt       60
cactgaccgg aggttcaaaa tgacccagcg aaccgagtcg                            100

<210> SEQ ID NO 354
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 354
```

-continued tttaacgatc tgattggcga tgatgaaacg gattcgccgg aagatgcgct ttctgagagc        60
tggcgcgaat tgtggcagga tgcgttgcag gaggaggatt                             100

<210> SEQ ID NO 355
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 355
gcactgaaac acctcatttc cctgtgtgcc gcgtcgccga tggttgccag tcagctggcg        60
cgctacccga tcctgcttga tgaattgctc gacccgaata                             100

<210> SEQ ID NO 356
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 356
gcgctcaaac agttaatccg tctgtgtgcc gcctcgccga tggtcgcgac acaacttgca        60
cgtcatcctt tattgctcga tgaactgctc gacccgcgca                             100

<210> SEQ ID NO 357
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 357
agtctgaact catcctgcgg cagtcggtga gacgtatttt tgaccaaaga gtgatctaca        60
tcacggaatt ttgtggttgt tgctgcttaa aagggcaaat                             100

<210> SEQ ID NO 358
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 358
ccgtctctga agctctcggt gaacattgtt gcgaggcagg atgcgagctg gttgtgtttt        60
gacattaccg ataatgtgcc gcgtgaacgg gtgcgttatg                             100

<210> SEQ ID NO 359
<211> LENGTH: 100
<212> TYPE: DNA
<213> ORGANISM: Artificial Sequence
<220> FEATURE:
<223> OTHER INFORMATION: Description of Artificial Sequence: Synthetic -continued

```
            polynucleotide
<220> FEATURE:
<223> OTHER INFORMATION: 100 bp downstream of junction

<400> SEQUENCE: 359
gccattgagc tggcttcccg accgcagggc ggcacctgcc tgaccctgcg tttcccgctg       60
tttaacaccc tgaccggagg tgaagcatga tccctgaatc                             100

<210> SEQ ID NO 360
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 360
agcgtcaggt accggtcatg attcaccgtg cgattctcgg ttccctggag cgcttcattg       60
gcatcctgac cgaagagttc gctggcttct tcccaacctg                             100

<210> SEQ ID NO 361
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 361
gcgctgaagc acctgatcac gctctgcgcg gcgtcgccga tggtcgccag ccagctggcg       60
cgccacccgc tgctgctgga tgagctgctg gatcccaaca                             100

<210> SEQ ID NO 362
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 362
gcccgctgac cgaccagaac ttccaccttg gactcggcta tacccttggc gtgacggcgc       60
gcgataactg ggactacatc cccattccgg tgatcttacc                             100

<210> SEQ ID NO 363
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 363
gccattgagc tggcttcccg accgcagggc ggcacctgcc tgaccctgcg tttcccgctg       60
tttaacaccc tgaccggagg tgaagcatga tccctgaatc                             100
```

```
<210> SEQ ID NO 364
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 364
gctaaagttc tcggctaatc gctgataaca tttgacgcaa tgcgcaataa aagggcatca        60
tttgatgccc tttttgcacg ctttcatacc agaacctggc                             100

<210> SEQ ID NO 365
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 365
gccattgagc tggcttcccg accgcagggc ggcacctgcc tgaccctgcg tttcccgctg        60 tttaacacccc tgaccggagg tgaagcatga tccctgaatc                            100

<210> SEQ ID NO 366
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 366
cgccgtcctc gcagtaccat tgcaaccgac tttacagcaa gaagtgattc tggcacgcat        60
ggaacaaatt cttgccagtc gggctttatc cgatgacgaa                             100

<210> SEQ ID NO 367
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 367
gccattgagc tggcttcccg accgcagggc ggcacctgcc tgaccctgcg tttcccgctg        60 tttaacacccc tgaccggagg tgaagcatga tccctgaatc                            100

<210> SEQ ID NO 368
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 368
```

-continued tctttagatc tctcggtccg ccctgatggc ggcaccttgc tgacgttacg cctgccggta      60
cagcaggtta tcaccggagg cttaaaatga cccagttacc                           100

<210> SEQ ID NO 369
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 369
tgaatatcac tgactcacaa gctacctatg tcgaagaatt aactaaaaaa ctgcaagatg      60
caggcattcg cgttaaagcc gacttgagaa atgagaagat                           100

<210> SEQ ID NO 370
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 370
ctggggtcac tggagcgctt tatcggcatc ctgaccgaag aatttgccgg tttcttcccg      60
acctggctgg cccctgttca ggttgtggtg atgaatatca                           100

<210> SEQ ID NO 371
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 371
gcaatagaac taactacccg ccctgaaggc ggtacctgcc tgaccctgcg attcccgtta      60
tttcattcac tgaccggagg cccacgatga cccagcgacc                           100

<210> SEQ ID NO 372
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / PinfC

<400> SEQUENCE: 372
tggtgtccgg gcgaacgtcg ccaggtggca caaattgtca gaactacgac acgactaacc      60
gaccgcagga gtgtgcgatg accctgaata tgatgatgga ttcttggttc tctggagcgc     120
tttatcggca tcctgactga agaatttgca ggcttcttcc caacctggct tgcacccgtg     180
caggtagttg tgatgaacat                                                 200

<210> SEQ ID NO 373

```
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PinfC / disrupted nifL gene

<400> SEQUENCE: 373
cggaaaacga gttcaaacgg cgcgtcccaa tcgtattaat ggcgagattc gcgccacgga      60
agttcgctta acaggtctgg aaggcgagca gcttggtatt gcgatagaac tcacttcacg     120
ccccgaaggg ggaagctgcc tgaccctacg attcccgcta tttcattcac tgaccggagg     180
ttcaaaatga cccagcgaac                                                 200

<210> SEQ ID NO 374
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' UTR and ATG / truncated glnE gene

<400> SEQUENCE: 374
cgccagagag ttgaaatcga acatttccgt aataccgcca ttacccagga gccgttctgg      60
ttgcacagcg gaaaacgtta acgaaaggat atttcgcatg tccctgtgcg ccgcgtcgcc     120
gatggtggcc agccaactgg cgcgctaccc gatcctgctc gatgaactgc tcgacccgaa     180
cacgctctat caaccgacgg                                                 200

<210> SEQ ID NO 375
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm1

<400> SEQUENCE: 375
cgggcgaacg tcgccaggtg gcacaaattg tcagaactac gacacgacta accgaccgca      60
ggagtgtgcg atgaccctga atatgatgat ggatgccagc cgttctgtaa taataaccgg     120
acaattcgga ctgattaaaa aagcgccctc gcggcgcttt ttttatattc tcgactccat     180
ttaaaataaa aaatccaatc                                                 200

<210> SEQ ID NO 376
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm1 / disrupted nifL gene

<400> SEQUENCE: 376
tcaacctaaa aaagtttgtg taatacttgt aacgctacat ggagattaac tcaatctaga      60
gggtattaat aatgaatcgt actaaactgg tactgggcgc aactcacttc acgccccgaa     120
gggggaagct gcctgaccct acgattcccg ctatttcatt cactgaccgg aggttcaaaa     180
```

```
tgacccagcg aaccgagtcg                                              200

<210> SEQ ID NO 377
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm7

<400> SEQUENCE: 377
cgggcgaacg tcgccaggtg gcacaaattg tcagaactac gacacgacta accgaccgca      60
ggagtgtgcg atgaccctga atatgatgat ggatgccagc cgcgtcaggt tgaacgtaaa     120
aaagtcggtc tgcgcaaagc acgtcgtcgt ccgcagttct ccaaacgtta attggtttct     180
gcttcggcag aacgattggc                                              200

<210> SEQ ID NO 378
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm4 / disrupted nifL gene

<400> SEQUENCE: 378
aattttctgc ccaaatggct gggattgttc attttttgtt tgccttacaa cgagagtgac      60
agtacgcgcg ggtagttaac tcaacatctg accggtcgat aactcacttc acgccccgaa     120
gggggaagct gcctgaccct acgattcccg ctatttcatt cactgaccgg aggttcaaaa     180
tgacccagcg aaccgagtcg                                              200

<210> SEQ ID NO 379
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' UTR up to ATG-4bp of amtB gene / disrupted
      amtB gene

<400> SEQUENCE: 379
gtaaccaata aaggccacca cgccagacca cacgatagtg atggcaacac tttccagctg      60
caccagcacc tgatggccca tggtcacacc ttcagcgaaa ccgatcccca tcactgtgtg     120
tcttgtatta cagtgccgct tcgtcggctt cgccggtacg aatacgaatg acgcgttgca     180
gctcagcaac gaaaattttg                                              200

<210> SEQ ID NO 380
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm1.2 / disrupted nifL gene

<400> SEQUENCE: 380
```

-continued

```
tggtattgtc agtctgaatg aagctcttga aaaagctgag gaagcgggcg tcgatttagt      60
agaaatcagt ccgaatgccg agccgccagt ttgtcgaatc ccgtctctga agctctcggt     120
gaacattgtt gcgaggcagg atgcgagctg gttgtgtttt gacattaccg ataatgtgcc     180
gcgtgaacgg gtgcgttatg                                                 200

<210> SEQ ID NO 381
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm1.2

<400> SEQUENCE: 381
accgatccgc aggcgcgcat ttgttatgcc aatccggcat tctgccgcca gacgggtttt      60
gcacttgaga cacttttggg cgagaaccac cgtctgctgg tgaacatcac tgatgcacaa     120
gctacctatg tcgaagaatt aactaaaaaa ctgcaagatg caggcattcg cgttaaagcc     180
gacttgagaa atgagaagat                                                 200

<210> SEQ ID NO 382
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm3.1 / disrupted nifL gene

<400> SEQUENCE: 382
cgggaaccgg tgttataatg ccgcgccctc atattgtggg gatttcttaa tgacctatcc      60
tgggtcctaa agttgtagtt gacattagcg gagcactaac ccgtctctga agctctcggt     120
gaacattgtt gcgaggcagg atgcgagctg gttgtgtttt gacattaccg ataatgtgcc     180
gcgtgaacgg gtgcgttatg                                                 200

<210> SEQ ID NO 383
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm3.1

<400> SEQUENCE: 383
accgatccgc aggcgcgcat ttgttatgcc aatccggcat tctgccgcca gacgggtttt      60
gcacttgaga cacttttggg cgagaaccac cgtctgctgg tacagtagcg cctctcaaaa     120
atagataaac ggctcatgta cgtgggccgt ttattttttc tacccataat cgggaaccgg     180
tgttataatg ccgcgccctc                                                 200

<210> SEQ ID NO 384
<211> LENGTH: 200
<212> TYPE: DNA
<213> ORGANISM: Artificial Sequence
<220> FEATURE:
<223> OTHER INFORMATION: Description of Artificial Sequence: Synthetic
```

-continued

```
          polynucleotide
<220> FEATURE:
<223> OTHER INFORMATION: Prm1 / disrupted nifL gene

<400> SEQUENCE: 384
tcaacctaaa aaagtttgtg taatacttgt aacgctacat ggagattaac tcaatctaga      60
gggtattaat aatgaatcgt actaaactgg tactgggcgc aactcacttc acaccccgaa     120
gggggaagtt gcctgaccct acgattcccg ctatttcatt cactgaccgg aggttcaaaa     180
tgacccagcg aaccgagtcg                                                  200

<210> SEQ ID NO 385
<211> LENGTH: 200
<212> TYPE: DNA
<213> ORGANISM: Artificial Sequence
<220> FEATURE:
<223> OTHER INFORMATION: Description of Artificial Sequence: Synthetic
          polynucleotide
<220> FEATURE:
<223> OTHER INFORMATION: disrupted nifL gene / Prm1

<400> SEQUENCE: 385
gggcgacaaa cggcctggtg gcacaaattg tcagaactac gacacgacta actgaccgca      60
ggagtgtgcg atgaccctga atatgatgat ggatgccggc cgtcctgtaa taataaccgg     120
acaattcgga ctgattaaaa aagcgccctt gtggcgcttt ttttatattc ccgcctccat     180
ttaaaataaa aaatccaatc                                                  200

<210> SEQ ID NO 386
<211> LENGTH: 200
<212> TYPE: DNA
<213> ORGANISM: Artificial Sequence
<220> FEATURE:
<223> OTHER INFORMATION: Description of Artificial Sequence: Synthetic
          polynucleotide
<220> FEATURE:
<223> OTHER INFORMATION: disrupted nifL gene / Prm5

<400> SEQUENCE: 386
gggcgacaaa cggcctggtg gcacaaattg tcagaactac gacacgacta actgaccgca      60
ggagtgtgcg atgaccctga atatgatgat ggatgccggc ggacatcatc gcgacaaaca     120
atattaatac cggcaaccac accggcaatt tacgagactg cgcaggcatc ctttctcccg     180
tcaatttctg tcaaataaag                                                  200

<210> SEQ ID NO 387
<211> LENGTH: 200
<212> TYPE: DNA
<213> ORGANISM: Artificial Sequence
<220> FEATURE:
<223> OTHER INFORMATION: Description of Artificial Sequence: Synthetic
          polynucleotide
<220> FEATURE:
<223> OTHER INFORMATION: Prm5 / disrupted nifL gene

<400> SEQUENCE: 387
taagaattat ctggatgaat gtgccattaa atgcgcagca taatggtgcg ttgtgcggga      60
aaactgcttt tttttgaaag ggttggtcag tagcggaaac aactcacttc acaccccgaa     120
gggggaagtt gcctgaccct acgattcccg ctatttcatt cactgaccgg aggttcaaaa     180
tgacccagcg aaccgagtcg                                                  200

<210> SEQ ID NO 388
```

<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' UTR and ATG / truncated glnE gene

<400> SEQUENCE: 388
cgccagagag tcgaaatcga acatttccgt aataccgcga ttacccagga gccgttctgg        60
ttgcacagcg gaaaacgtta acgaaaggat atttcgcatg tttaacgatc tgattggcga       120
tgatgaaacg gattcgccgg aagatgcgct ttctgagagc tggcgcgaat gtggcagga       180 tgcgttgcag gaggaggatt                                                   200

<210> SEQ ID NO 389
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' UTR and ATG / truncated glnE gene

<400> SEQUENCE: 389
cgccagagag tcgaaatcga acatttccgt aataccgcga ttacccagga gccgttctgg        60
ttgcacagcg gaaaacgtta acgaaaggat atttcgcatg gcactgaaac acctcatttc       120
cctgtgtgcc gcgtcgccga tggttgccag tcagctggcg cgctacccga tcctgcttga       180
tgaattgctc gacccgaata                                                   200

<210> SEQ ID NO 390
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' UTR and ATG / truncated glnE gene

<400> SEQUENCE: 390
gatgatggat gctttctggt taaacgggca acctcgttaa ctgactgact agcctgggca        60
aactgcccgg gctttttttt gcaaggaatc tgatttcatg gcgctcaaac agttaatccg       120
tctgtgtgcc gcctcgccga tggtcgcgac acaacttgca cgtcatcctt tattgctcga       180
tgaactgctc gacccgcgca                                                   200

<210> SEQ ID NO 391
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm4

<400> SEQUENCE: 391
accgatccgc aggcgcgcat ttgttatgcc aatccggcat tctgccgcca gacgggtttt        60
gcacttgaga cacttttggg cgagaaccac cgtctgctgg agtctgaact catcctgcgg       120
cagtcggtga gacgtatttt tgaccaaaga gtgatctaca tcacggaatt ttgtggttgt       180

-continued

```
tgctgcttaa aagggcaaat                                              200

<210> SEQ ID NO 392
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm4 / disrupted nifL gene

<400> SEQUENCE: 392
catcggacac caccagctta caaattgcct gattgcggcc ccgatggccg gtatcactga      60
ccgaccattt cgtgccttat gtcatgcgat gggggctggg ccgtctctga agctctcggt     120
gaacattgtt gcgaggcagg atgcgagctg gttgtgtttt gacattaccg ataatgtgcc     180
gcgtgaacgg gtgcgttatg                                                  200

<210> SEQ ID NO 393
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PinfC / disrupted nifL gene

<400> SEQUENCE: 393
tcttcaacaa ctggaggaat aaggtattaa aggcggaaaa cgagttcaaa cggcacgtcc      60
gaatcgtatc aatggcgaga ttcgcgccct ggaagttcgc gccattgagc tggcttcccg     120
accgcagggc ggcacctgcc tgaccctgcg tttcccgctg tttaacaccc tgaccggagg     180
tgaagcatga tccctgaatc                                                  200

<210> SEQ ID NO 394
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / PinfC

<400> SEQUENCE: 394
tccgggttcg gcttaccccg ccgcgttttg cgcacggtgt cggacaattt gtcataactg      60
cgacacagga gtttgcgatg accctgaata tgatgctcga agcgtcaggt accggtcatg     120
attcaccgtg cgattctcgg ttccctggag cgcttcattg gcatcctgac cgaagagttc     180
gctggcttct ccccaacctg                                                  200

<210> SEQ ID NO 395
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' UTR and ATG / truncated glnE gene

<400> SEQUENCE: 395
```

-continued

```
atcgcagcgt ctttgaatat ttccgtcgcc aggcgctggc tgccgagccg ttctggctgc      60
atagtggaaa acgataattt caggccaggg agcccttatg gcgctgaagc acctgatcac     120
gctctgcgcg gcgtcgccga tggtcgccag ccagctggcg cgccacccgc tgctgctgga     180
tgagctgctg gatcccaaca                                                 200
```

```
<210> SEQ ID NO 396
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm1.2

<400> SEQUENCE: 396
tccgggttcg gcttaccccg ccgcgttttg cgcacggtgt cggacaattt gtcataactg      60
cgacacagga gtttgcgatg accctgaata tgatgctcga gcccgctgac cgaccagaac     120
ttccaccttg gactcggcta tacccttggc gtgacggcgc gcgataactg ggactacatc     180
cccattccgg tgatcttacc                                                 200
```

```
<210> SEQ ID NO 397
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm1.2 / disrupted nifL gene

<400> SEQUENCE: 397 tcactttta gcaaagttgc actggacaaa aggtaccaca attggtgtac tgatactcga      60
cacagcatta gtgtcgattt ttcatataaa ggtaattttg gccattgagc tggcttcccg     120
accgcagggc ggcacctgcc tgaccctgcg tttcccgctg tttaacaccc tgaccggagg     180
tgaagcatga tccctgaatc                                                 200
```

```
<210> SEQ ID NO 398
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm6.2

<400> SEQUENCE: 398
tccgggttcg gcttaccccg ccgcgttttg cgcacggtgt cggacaattt gtcataactg      60
cgacacagga gtttgcgatg accctgaata tgatgctcga gctaaagttc tcggctaatc     120
gctgataaca tttgacgcaa tgcgcaataa aagggcatca tttgatgccc tttttgcacg     180
ctttcatacc agaacctggc                                                 200
```

```
<210> SEQ ID NO 399
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<223> OTHER INFORMATION: Prm6.2 / disrupted nifL gene

<400> SEQUENCE: 399
gttctccttt gcaatagcag ggaagaggcg ccagaaccgc cagcgttgaa gcagtttgaa      60
cgcgttcagt gtataatccg aaacttaatt tcggtttgga gccattgagc tggcttcccg     120
accgcagggc ggcacctgcc tgaccctgcg tttcccgctg tttaacaccc tgaccggagg     180
tgaagcatga tccctgaatc                                                  200

<210> SEQ ID NO 400
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm8.2

<400> SEQUENCE: 400
tccgggttcg gcttaccccg ccgcgttttg cgcacggtgt cggacaattt gtcataactg      60
cgacacagga gtttgcgatg accctgaata tgatgctcga cgccgtcctc gcagtaccat     120
tgcaaccgac tttacagcaa gaagtgattc tggcacgcat ggaacaaatt cttgccagtc     180
gggctttatc cgatgacgaa                                                  200

<210> SEQ ID NO 401
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm8.2 / disrupted nifL gene

<400> SEQUENCE: 401
gatatgcctg aagtattcaa ttacttaggc atttacttaa cgcaggcagg caattttgat      60
gctgcctatg aagcgtttga ttctgtactt gagcttgatc gccattgagc tggcttcccg     120
accgcagggc ggcacctgcc tgaccctgcg tttcccgctg tttaacaccc tgaccggagg     180
tgaagcatga tccctgaatc                                                  200

<210> SEQ ID NO 402
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PinfC / disrupted nifL gene

<400> SEQUENCE: 402
tggtattgtc agtctgaatg aagctcttga aaaagctgag gaagcgggcg tcgatttagt      60
agaaatcagt ccgaatgccg agccgccagt ttgtcgaatc tctttagatc tctcggtccg     120
ccctgatggc ggcaccttgc tgacgttacg cctgccggta cagcaggtta tcaccggagg     180
cttaaaatga cccagttacc                                                  200

<210> SEQ ID NO 403
<211> LENGTH: 200
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / PinfC

<400> SEQUENCE: 403
tgcaaattgc acggttattc cgggtgagta tatgtgtgat ttgggttccg gcattgcgca      60
ataaagggga gaaagacatg agcatcacgg cgttatcagc tgaatatcac tgactcacaa     120
gctacctatg tcgaagaatt aactaaaaaa ctgcaagatg caggcattcg cgttaaagcc     180
gacttgagaa atgagaagat                                                 200

<210> SEQ ID NO 404
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / PinfC

<400> SEQUENCE: 404
tcagggctgc ggatgtcggg cgtttcacaa cacaaaatgt tgtaaatgcg acacagccgg      60
gcctgaaacc aggagcgtgt gatgaccttt aatatgatgc ctggggtcac tggagcgctt     120
tatcggcatc ctgaccgaag aatttgccgg tttcttcccg acctggctgg cccctgttca     180
ggttgtggtg atgaatatca                                                 200

<210> SEQ ID NO 405
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PinfC / disrupted nifL gene

<400> SEQUENCE: 405
cggaaaacga gttcaaacgg cacgtccgaa tcgtatcaat ggcgagattc gcgcccagga      60
agttcgctta actggtctgg aaggtgagca gctgggtatt gcaatagaac taactacccg     120
ccctgaaggc ggtacctgcc tgaccctgcg attcccgtta tttcattcac tgaccggagg     180
cccacgatga cccagcgacc                                                 200

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
caagaagttc gcctcacagg                                                  20

<210> SEQ ID NO 407
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 407
tgcctcgcaa caatgttcac                                                        20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
cgccctcata ttgtggggat                                                        20

<210> SEQ ID NO 409
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
ggcataacgc acccgttca                                                         19

<210> SEQ ID NO 410
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 410
tctgaagctc tcggt                                                             15

<210> SEQ ID NO 411
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
taaactggta ctgggcgcaa ct                                                     22

<210> SEQ ID NO 412
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
caaatcgaag cgccagacgg tat                                                    23

<210> SEQ ID NO 413
<211> LENGTH: 15
<212> TYPE: DNA
<213> ORGANISM: Artificial Sequence
<220> FEATURE:
<223> OTHER INFORMATION: Description of Artificial Sequence: Synthetic probe

<400> SEQUENCE: 413
gaccctacga ttccc                                                          15

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
ggtgcactct ttgcatggtt                                                     20

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
gcgcagtctc gtaaattgcc                                                     20

<210> SEQ ID NO 416
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 416
gcgatgaccc tgaat                                                          15

<210> SEQ ID NO 417
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
ctcggcagca tggacgtaa                                                      19

<210> SEQ ID NO 418
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
agggtgttaa acagcgggaa a                                                   21

<210> SEQ ID NO 419
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 419
tccgaatcgt atcaa                                                    15

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
gagccgttct ggctgcatag                                               20

<210> SEQ ID NO 421
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
gccgtcggct gatagagg                                                 18

<210> SEQ ID NO 422
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 422
tgaagcacct gatca                                                    15

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
ggaaaacgag ttcaaccggc                                               20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
gggcggaccg agagatctaa                                               20
```

METHODS AND COMPOSITIONS FOR IMPROVING PLANT TRAITS

CROSS-REFERENCE

This application is a continuation of U.S. application Ser. No. 16/159,542, filed on Oct. 12, 2018, which is a continuation application of PCT/US2018/13671, filed on Jan. 12, 2018, which claims the benefit of U.S. Provisional Application No. 62/445,570, filed Jan. 12, 2017; U.S. Provisional Application No. 62/445,557, filed Jan. 12, 2017; U.S. Provisional Application No. 62/447,889, filed Jan. 18, 2017; U.S. Provisional Application No. 62/467,032, filed Mar. 3, 2017; U.S. Provisional Application No. 62/566,199, filed Sep. 29, 2017; and U.S. Provisional Application No. 62/577, 147, filed Oct. 25, 2017, which applications are incorporated herein by reference.

STATEMENT AS TO FEDERALLY SPONSORED RESEARCH

This invention was made with the support of the United States government under SBIR grant 1520545 awarded by the National Science Foundation. The government has certain rights in the disclosed subject matter.

STATEMENT REGARDING SEQUENCE LISTING

The instant application contains a Sequence Listing which has been submitted electronically in ASCII format and is hereby incorporated by reference in its entirety. Said ASCII copy, created on Sep. 21, 2020, is named 0009003SEQ.txt and is ≈585 kb in size.

BACKGROUND OF THE INVENTION

Plants are linked to the microbiome via a shared metabolome. A multidimensional relationship between a particular crop trait and the underlying metabolome is characterized by a landscape with numerous local maxima. Optimizing from an inferior local maximum to another representing a better trait by altering the influence of the microbiome on the metabolome may be desirable for a variety of reasons, such as for crop optimization. Economically-, environmentally-, and socially-sustainable approaches to agriculture and food production are required to meet the needs of a growing global population. By 2050 the United Nations' Food and Agriculture Organization projects that total food production must increase by 70% to meet the needs of the growing population, a challenge that is exacerbated by numerous factors, including diminishing freshwater resources, increasing competition for arable land, rising energy prices, increasing input costs, and the likely need for crops to adapt to the pressures of a drier, hotter, and more extreme global climate.

One area of interest is in the improvement of nitrogen fixation. Nitrogen gas ($N_2$) is a major component of the atmosphere of Earth. In addition, elemental nitrogen (N) is an important component of many chemical compounds which make up living organisms. However, many organisms cannot use $N_2$ directly to synthesize the chemicals used in physiological processes, such as growth and reproduction. In order to utilize the $N_2$, the $N_2$ must be combined with hydrogen. The combining of hydrogen with $N_2$ is referred to as nitrogen fixation. Nitrogen fixation, whether accomplished chemically or biologically, requires an investment of large amounts of energy. In biological systems, an enzyme known as nitrogenase catalyzes the reaction which results in nitrogen fixation. An important goal of nitrogen fixation research is the extension of this phenotype to non-leguminous plants, particularly to important agronomic grasses such as wheat, rice, and maize. Despite enormous progress in understanding the development of the nitrogen-fixing symbiosis between *rhizobia* and legumes, the path to use that knowledge to induce nitrogen-fixing nodules on non-leguminous crops is still not clear. Meanwhile, the challenge of providing sufficient supplemental sources of nitrogen, such as in fertilizer, will continue to increase with the growing need for increased food production.

SUMMARY OF THE INVENTION

An aspect of the invention provides a bacterial composition that comprises at least one genetically engineered bacterial strain that fixes atmospheric nitrogen in an agricultural system that has been fertilized with more than 20 lbs of Nitrogen per acre.

Another aspect of the invention provides a bacterial composition that comprises at least one bacterial strain that has been bred to fix atmospheric nitrogen in an agricultural system that has been fertilized with more than 20 lbs of Nitrogen per acre.

An additional aspect of the invention provides a bacterial composition that comprises at least one genetically engineered bacterial strain that fixes atmospheric nitrogen, the at least one genetically engineered bacterial strain comprising exogenously added DNA wherein said exogenously added DNA shares at least 80% identity to a corresponding native bacterial strain.

A further aspect of the invention provides a seed composition comprising a seed of a plant that is inoculated with a bacterial composition.

Another aspect of the invention provides a method of growing a crop using a plurality of seeds having a seed composition that is inoculated with a bacterial composition.

An additional aspect of the invention provides a method of applying a bacterial composition to a field.

A further aspect of the invention provides a fertilizer composition comprising a bacterial composition.

Another aspect of the invention provides a method of maintaining soil nitrogen levels. The method comprises planting, in soil of a field, a crop inoculated by a genetically engineered bacterium that fixes atmospheric nitrogen. The method also comprises harvesting said crop, wherein no more than 90% of a nitrogen dose required for producing said crop is administered to said soil of said field between planting and harvesting.

An additional aspect of the invention provides a method of delivering a probiotic supplement to a crop plant. The method comprises coating a crop seed with a seed coating, seed treatment, or seed dressing. Said seed coating, seed dressing, or seed treatment comprises living representatives of said probiotic. Additionally, the method comprises applying, in soil of a field, said crop seeds.

In a further aspect of the invention, the genetically engineered bacterial strain is a genetically engineered Gram-positive bacterial strain. In some cases, the genetically engineered Gram-positive bacterial strain has an altered expression level of a regulator of a Nif cluster. In some cases, the genetically engineered Gram-positive bacterial strain expresses a decreased amount of a negative regulator of a Nif cluster. In some cases, the genetically engineered bacterial strain expresses a decreased amount of GlnR. In some cases, the genome of the genetically engineered bacterial strain encodes a polypeptide with at least 75% identity to a sequence from the Zehr lab NifH database. In some cases, the genome of the genetically engineered bacterial strain encodes a polypeptide with at least 85% identity to a sequence from the Zehr lab NifH database. In some cases, the genome of the genetically engineered bacterial strain encodes a polypeptide with at least 75% identity to a sequence from the Buckley lab NifH database. In some cases, the genome of the genetically engineered bacterial strain encodes a polypeptide with at least 85% identity to a sequence from the Buckley lab NifH database.

Another aspect of the invention provides a method of increasing nitrogen fixation in a non-leguminous plant. The method comprises applying to the plant a plurality of non-intergeneric bacteria, said plurality comprising non-intergeneric bacteria that (i) have an average colonization ability per unit of plant root tissue of at least about $1.0 \times 10^4$ bacterial cells per gram of fresh weight of plant root tissue and (ii) produce fixed N of at least about $1 \times 10^{-17}$ mmol N per bacterial cell per hour. Additionally, the plurality of non-intergeneric bacteria, in planta, produce 1% or more of the fixed nitrogen in the plant. Further, each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

An additional aspect of the invention provides a method of increasing nitrogen fixation in a non-leguminous plant. The method comprises applying to the plant a plurality of non-intergeneric bacteria, said plurality comprising non-intergeneric bacteria that (i) have an average colonization ability per unit of plant root tissue of at least about $1.0 \times 10^4$ bacterial cells per gram of fresh weight of plant root tissue and/or (ii) produce fixed N of at least about $1 \times 10^{-17}$ mmol N per bacterial cell per hour. Additionally, the plurality of non-intergeneric bacteria, in planta, produce 1% or more of the fixed nitrogen in the plant. Further, each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

A further aspect of the invention provides a method of breeding microbial strains to improve specific traits of agronomic relevance. The method comprises providing a plurality of microbial strains that have the ability to colonize a desired crop. The method also comprises improving regulatory networks influencing the trait through intragenomic rearrangement. Further, the method comprises assessing microbial strains within the plurality of microbial strains to determine a measure of the trait. Additionally, the method comprises selecting one or more microbial strains of the plurality of microbial strains that generate an improvement in the trait in the presence of the desired crop.

Another aspect of the invention provides a method of breeding microbial strains to improve specific traits of agronomic relevance. The method comprises providing a plurality of microbial strains that have the ability to colonize a desired crop. The method also comprises introducing genetic diversity into the plurality of microbial strains. Additionally, the method comprises assessing microbial strains within the plurality of microbial strains to determine a measure of the trait. Further, the method comprises selecting one or more microbial strains of the plurality of microbial strains that generate an improvement in the trait in the presence of the desired crop.

Another aspect of the invention provides a method of increasing the amount of atmospheric derived nitrogen in a non-leguminous plant. The method comprises exposing said non-leguminous plant to engineered non-intergeneric microbes, said engineered non-intergeneric microbes comprising at least one genetic variation introduced into a nitrogen fixation genetic regulatory network or at least one genetic variation introduced into a nitrogen assimilation genetic regulatory network.

A further aspect of the invention provides a method of increasing an amount of atmospheric derived nitrogen in a corn plant. The method comprises exposing said corn plant to engineered non-intergeneric microbes comprising engineered genetic variations within at least two genes selected from the group consisting of nifL, glnB, glnE, and amtB.

Another aspect of the invention provides a method of increasing an amount of atmospheric derived nitrogen in a corn plant. The method comprises exposing said corn plant to engineered non-intergeneric microbes comprising at least one genetic variation introduced into a nitrogen fixation genetic regulatory network and at least one genetic variation introduced into a nitrogen assimilation genetic regulatory network, wherein said engineered non-intergeneric microbes, in planta, produce at least 5% of fixed nitrogen in said corn plant as measured by dilution of 15N in crops grown in fields treated with fertilizer containing 1.2% 15N.

An additional aspect of the invention provides a method of increasing nitrogen fixation in a non-leguminous plant. The method comprises applying to the plant a plurality of non-intergeneric bacteria, said plurality comprising non-intergeneric bacteria that (i) have an average colonization ability per unit of plant root tissue of at least about $1.0 \times 10^4$ bacterial cells per gram of fresh weight of plant root tissue and (ii) produce fixed N of at least about $1 \times 10^{-17}$ mmol N per bacterial cell per hour. Additionally, the product of (i) the average colonization ability per unit of plant root tissue and (ii) produced fixed N per bacterial cell per hour, is at least about $2.5 \times 10^{-8}$ mmol N per gram of fresh weight of plant root tissue per hour. Further, the plurality of non-intergeneric bacteria, in planta, produce 1% or more of the fixed nitrogen in the plant. Additionally, each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

Another aspect of the invention provides a method of increasing nitrogen fixation in a non-leguminous plant. The method comprises applying to the plant a plurality of bacteria, said plurality comprising bacteria that (i) have an average colonization ability per unit of plant root tissue of at least about $1.0 \times 10^4$ bacterial cells per gram of fresh weight of plant root tissue and/or (ii) produce fixed N of at least about $1 \times 10^{-17}$ mmol N per bacterial cell per hour. Additionally, the plurality of bacteria, in planta, produce 1% or more of the fixed nitrogen in the plant.

An additional aspect of the invention provides a non-intergeneric bacterial population capable of increasing nitrogen fixation in a non-leguminous plant, comprising a plurality of non-intergeneric bacteria that (i) have an average colonization ability per unit of plant root tissue of at least about $1.0 \times 10^4$ bacterial cells per gram of fresh weight of plant root tissue and/or (ii) produce fixed N of at least about $1\times10^{-17}$ mmol N per bacterial cell per hour. Additionally, the plurality of non-intergeneric bacteria, in planta, produce 1% or more of the fixed nitrogen in a plant grown in the presence of the plurality of non-intergeneric bacteria. Further, each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

A further aspect of the invention provides a bacterial population capable of increasing nitrogen fixation in a non-leguminous plant, the bacterial population comprising a plurality of bacteria that (i) have an average colonization ability per unit of plant root tissue of at least about $1.0\times10^{4}$ bacterial cells per gram of fresh weight of plant root tissue; and/or (ii) produce fixed N of at least about $1\times10^{-17}$ mmol N per bacterial cell per hour. Additionally, the plurality of bacteria, in planta, produce 1% or more of the fixed nitrogen in the plant.

In another aspect of the invention, a bacterium is provided that (i) has an average colonization ability per unit of plant root tissue of at least about $1.0\times10^{4}$ bacterial cells per gram of fresh weight of plant root tissue and/or (ii) produces fixed N of at least about $1\times10^{-17}$ mmol N per bacterial cell per hour.

In a further aspect of the invention, a non-intergeneric bacterium is provided that comprises at least one genetic variation introduced into at least one gene, or non-coding polynucleotide, of the nitrogen fixation or assimilation genetic regulatory network, such that the non-intergeneric bacterium is capable of fixing atmospheric nitrogen in the presence of exogenous nitrogen, and wherein said bacterium (i) has an average colonization ability per unit of plant root tissue of at least about $1.0\times10^{4}$ bacterial cells per gram of fresh weight of plant root tissue and/or (ii) produces fixed N of at least about $1\times10^{-17}$ mmol N per bacterial cell per hour.

In an additional aspect of the invention provides a method for increasing nitrogen fixation in a plant, comprising administering to the plant an effective amount of a composition that comprises a purified population of bacteria that comprises bacteria with a 16S nucleic acid sequence that is at least about 97% identical to a nucleic acid sequence selected from SEQ ID NOs: 85, 96, 111, 121, 122, 123, 124, 136, 149, 157, 167, 261, 262, 269, 277-283; a purified population of bacteria that comprises bacteria with a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, 284-295; and/or a purified population of bacteria that comprises bacteria with a nucleic acid sequence that is at least about 90% identical to a nucleic acid sequence selected from SEQ ID NOs: 177-260, 296-303; and wherein the plant administered the effective amount of the composition exhibits an increase in nitrogen fixation, as compared to a plant not having been administered the composition.

A further aspect of the invention provides an isolated bacteria comprising a 16S nucleic acid sequence that is at least about 97% identical to a nucleic acid sequence selected from SEQ ID NOs: 85, 96, 111, 121, 122, 123, 124, 136, 149, 157, 167, 261, 262, 269, 277-283; a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, 284-295; and/or a nucleic acid sequence that is at least about 90% identical to a nucleic acid sequence selected from SEQ ID NOs: 177-260, 296-303.

Another aspect of the invention provides a method of detecting a non-native junction sequence, comprising: amplifying a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 372-405.

An additional aspect of the invention provides a method of detecting a non-native junction sequence, comprising: amplifying a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least a 10 contiguous base pair fragment contained in SEQ ID NOs: 372-405, said contiguous base pair fragment being comprised of nucleotides at the intersection of: an upstream sequence comprising SEQ ID NOs: 304-337 and downstream sequence comprising SEQ ID NOs: 338-371.

A further aspect of the invention provides a non-native junction sequence comprising a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 372-405.

An additional aspect of the invention provides a non-native junction sequence comprising a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least a 10 contiguous base pair fragment contained in SEQ ID NOs: 372-405, said contiguous base pair fragment being comprised of nucleotides at the intersection of: an upstream sequence comprising SEQ ID NOs: 304-337 and downstream sequence comprising SEQ ID NOs: 338-371.

A further aspect of the invention provides a bacterial composition comprising at least one remodeled bacterial strain that fixes atmospheric nitrogen, the at least one remodeled bacterial strain comprising exogenously added DNA wherein said exogenously added DNA shares at least 80% identity to a corresponding native bacterial strain.

An additional aspect of the invention provides a method of maintaining soil nitrogen levels. The method comprises planting, in soil of a field, a crop inoculated by a remodeled bacterium that fixes atmospheric nitrogen. The method also comprises harvesting said crop, wherein no more than 90% of a nitrogen dose required for producing said crop is administered to said soil of said field between planting and harvesting.

Another aspect of the invention provides a method of delivering a probiotic supplement to a crop plant. The method comprises coating a crop seed with a seed coating, seed treatment, or seed dressing, wherein said seed coating, seed dressing, or seed treatment comprise living representatives of said probiotic. The method also comprises applying said crop seeds in soil of a field.

An additional aspect of the invention provides a method of increasing the amount of atmospheric derived nitrogen in a non-leguminous plant. The method comprises exposing said non-leguminous plant to remodeled non-intergeneric microbes, said remodeled non-intergeneric microbes comprising at least one genetic variation introduced into a nitrogen fixation genetic regulatory network or at least one genetic variation introduced into a nitrogen assimilation genetic regulatory network.

A further aspect of the invention provides a method of increasing an amount of atmospheric derived nitrogen in a corn plant. The method comprises exposing said corn plant to remodeled non-intergeneric microbes comprising remodeled genetic variations within at least two genes selected from the group consisting of nifL, glnB, glnE, and amtB.

Another aspect of the invention provides a method of increasing an amount of atmospheric derived nitrogen in a corn plant. The method comprises exposing said corn plant to remodeled non-intergeneric microbes comprising at least one genetic variation introduced into a nitrogen fixation genetic regulatory network and at least one genetic variation introduced into a nitrogen assimilation genetic regulatory network, wherein said remodeled non-intergeneric microbes, in planta, produce at least 5% of fixed nitrogen in said corn plant as measured by dilution of 15N in crops grown in fields treated with fertilizer containing 1.2% 15N.

Additional aspects of the invention provide genus of microbes that are evolved and optimized for in planta nitrogen fixation in non-leguminous crops. In particular, methods of increasing nitrogen fixation in a non-leguminous plant are disclosed. The methods can comprise exposing the plant to a plurality of bacteria. Each member of the plurality comprises one or more genetic variations introduced into one or more genes of non-coding polynucleotides of the bacteria's nitrogen fixation or assimilation genetic regulatory network, such that the bacteria are capable of fixing atmospheric nitrogen in the presence of exogenous nitrogen. The bacteria are not intergeneric microorganisms. Additionally, the bacteria, in planta, produce 1% or more of the fixed nitrogen in the plant.

Further aspects of the invention provide beneficial isolated microbes and microbial compositions. In particular, isolated and biologically pure microorganisms that have applications, inter alia, in increasing nitrogen fixation in a crop are provided. The disclosed microorganism can be utilized in their isolated and biologically pure states, as well as being formulated into compositions. Furthermore, the disclosure provides microbial compositions containing at least two members of the disclosed microorganisms, as well as methods of utilizing said microbial compositions.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 depicts in culture expression profile of 9 different genes in strains CI006 involved in diazotrophic nitrogen fixation. Numbers represent counts of each transcript. Various conditions (0, 1, 10 mM Glutamine and 0%, 10%, 20% atmospheric air in N2) are indicated.

FIGS. 28A-28E illustrate derivative microbes that fix and excrete nitrogen in vitro under conditions similar to high nitrate agricultural soils. FIG. 28A illustrates the regulatory network controlling nitrogen fixation and assimilation in PBC6.1 is shown, including the key nodes NifL, NifA, GS, GlnE depicted as the two-domain ATase-AR enzyme, and AmtB.

FIG. 28B illustrates the genome of *Kosakonia sacchari* isolate PBC6.1 is shown. The three tracks circumscribing the genome convey transcription data from PBC6.1, PBC6.38, and the differential expression between the strains respectively. FIG. 28C illustrates the nitrogen fixation gene cluster and transcription data is expanded for finer detail. FIG. 28D illustrates nitrogenase activity under varying concentrations of exogenous nitrogen is measured with the acetylene reduction assay. The wild type strain exhibits repression of nitrogenase activity as glutamine concentrations increase, while derivative strains show varying degrees of robustness. Error bars represent standard error of the mean of at least three biological replicates. FIG. 28E illustrates temporal excretion of ammonia by derivative strains is observed at mM concentrations. Wild type strains are not observed to excrete fixed nitrogen, and negligible ammonia accumulates in the media. Error bars represent standard error of the mean.

FIGS. 29A-29C illustrate greenhouse experiments demonstrate microbial nitrogen fixation in corn. FIG. 29A illustrates microbe colonization six weeks after inoculation of corn plants by PBC6.1 derivative strains. Error bars show standard error of the mean of at least eight biological replicates. FIG. 29B illustrates in planta transcription of nifH measured by extraction of total RNA from roots and subsequent Nanostring analysis. Only derivative strains show nifH transcription in the root environment. Error bars show standard error of the mean of at least 3 biological replicates. FIG. 29C illustrates microbial nitrogen fixation measured by the dilution of isotopic tracer in plant tissues. Derivative microbes exhibit substantial transfer of fixed nitrogen to the plant. Error bars show standard error of the mean of at least ten biological replicates.

DETAILED DESCRIPTION OF THE INVENTION

Figure 1A:
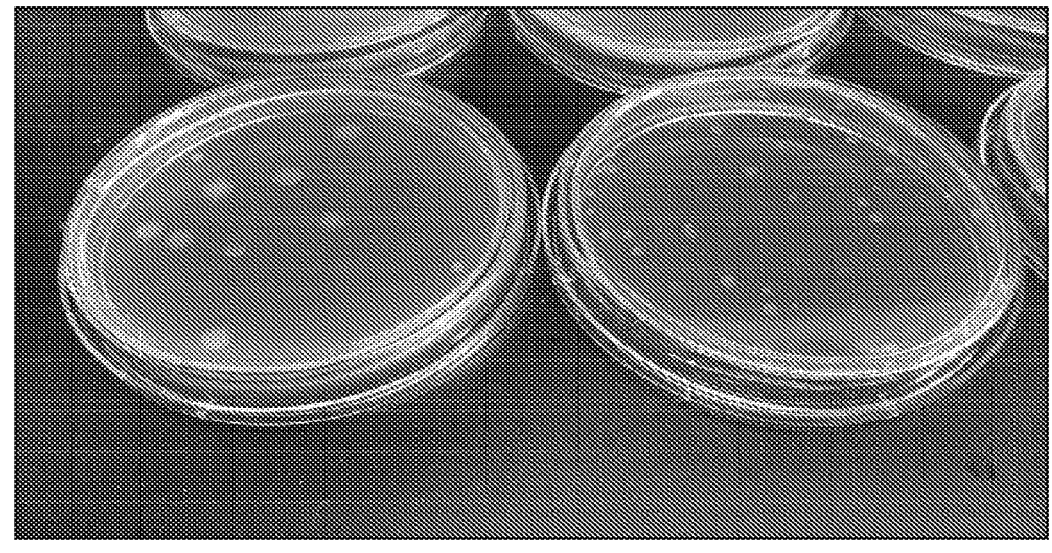
FIGS. 1A-B depict enrichment and isolation of nitrogen fixing bacteria. (A) Nfb agar plate was used to isolate single colonies of nitrogen fixing bacteria. (B) Semi-solid Nfb agar casted in Balch tube. The arrow points to pellicle of enriched nitrogen fixing bacteria.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Increased fertilizer utilization brings with it environmental concerns and is also likely not possible for many economically stressed regions of the globe. Furthermore, many industry players in the microbial arena are focused on creating intergeneric microbes. However, there is a heavy regulatory burden placed on engineered microbes that are characterized/classified as intergeneric. These intergeneric microbes face not only a higher regulatory burden, which makes widespread adoption and implementation difficult, but they also face a great deal of public perception scrutiny.

Currently, there are no engineered microbes on the market that are non-intergeneric and that are capable of increasing nitrogen fixation in non-leguminous crops. This dearth of such a microbe is a missing element in helping to usher in a truly environmentally friendly and more sustainable 21$^{st}$ century agricultural system.

The present disclosure solves the aforementioned problems and provides a non-intergeneric microbe that has been engineered to readily fix nitrogen in crops. These microbes are not characterized/classified as intergeneric microbes and thus will not face the steep regulatory burdens of such. Further, the taught non-intergeneric microbes will serve to help 21$^{st}$ century farmers become less dependent upon utilizing ever increasing amounts of exogenous nitrogen fertilizer.

Definitions

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is complementary to a first sequence is referred to as the "complement" of the first sequence. The term "hybridizable" as applied to a polynucleotide refers to the ability of the polynucleotide to form a complex that is stabilized via hydrogen bonding between the bases of the nucleotide residues in a hybridization reaction.

"Complementarity" refers to the ability of a nucleic acid to form hydrogen bond(s) with another nucleic acid sequence by either traditional Watson-Crick or other nontraditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/embossneedle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

In general, "stringent conditions" for hybridization refer to conditions under which a nucleic acid having complementarity to a target sequence predominantly hybridizes with a target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "about" is used synonymously with the term "approximately." Illustratively, the use of the term "about" with regard to an amount indicates that values slightly outside the cited values, e.g., plus or minus 0.1% to 10%.

The term "biologically pure culture" or "substantially pure culture" refers to a culture of a bacterial species described herein containing no other bacterial species in quantities sufficient to interfere with the replication of the culture or be detected by normal bacteriological techniques.

"Plant productivity" refers generally to any aspect of growth or development of a plant that is a reason for which the plant is grown. For food crops, such as grains or vegetables, "plant productivity" can refer to the yield of grain or fruit harvested from a particular crop. As used herein, improved plant productivity refers broadly to improvements in yield of grain, fruit, flowers, or other plant parts harvested for various purposes, improvements in growth of plant parts, including stems, leaves and roots, promotion of plant growth, maintenance of high chlorophyll content in leaves, increasing fruit or seed numbers, increasing fruit or seed unit weight, reducing $NO_2$ emission due to reduced nitrogen fertilizer usage and similar improvements of the growth and development of plants.

Microbes in and around food crops can influence the traits of those crops. Plant traits that may be influenced by microbes include: yield (e.g., grain production, biomass generation, fruit development, flower set); nutrition (e.g., nitrogen, phosphorus, potassium, iron, micronutrient acquisition); abiotic stress management (e.g., drought tolerance, salt tolerance, heat tolerance); and biotic stress management (e.g., pest, weeds, insects, fungi, and bacteria). Strategies for altering crop traits include: increasing key metabolite concentrations; changing temporal dynamics of microbe influence on key metabolites; linking microbial metabolite production/degradation to new environmental cues; reducing negative metabolites; and improving the balance of metabolites or underlying proteins.

As used herein, a "control sequence" refers to an operator, promoter, silencer, or terminator.

As used herein, "in planta" refers to in the plant, and wherein the plant further comprises plant parts, tissue, leaves, roots, stems, seed, ovules, pollen, flowers, fruit, etc.

In some embodiments, native or endogenous control sequences of genes of the present disclosure are replaced with one or more intrageneric control sequences.

As used herein, "introduced" refers to the introduction by means of modern biotechnology, and not a naturally occurring introduction.

In some embodiments, the bacteria of the present disclosure have been modified such that they are not naturally occurring bacteria.

In some embodiments, the bacteria of the present disclosure are present in the plant in an amount of at least $10^3$ cfu, $10^4$ cfu, $10^5$ cfu, $10^6$ cfu, $10^7$ cfu, $10^8$ cfu, $10^9$ cfu, $10^{10}$ cfu, $10^{11}$ cfu, or $10^{12}$ cfu per gram of fresh or dry weight of the plant. In some embodiments, the bacteria of the present disclosure are present in the plant in an amount of at least about $10^3$ cfu, about $10^4$ cfu, about $10^5$ cfu, about $10^6$ cfu, about $10^7$ cfu, about $10^8$ cfu, about $10^9$ cfu, about $10^{10}$ cfu, about $10^{11}$ cfu, or about $10^{12}$ cfu per gram of fresh or dry weight of the plant. In some embodiments, the bacteria of the present disclosure are present in the plant in an amount of at least $10^3$ to $10^9$, $10^3$ to $10^7$, $10^3$ to $10^5$, $10^5$ to $10^9$, $10^5$ to $10^7$, $10^6$ to $10^{10}$, $10^6$ to $10^7$ cfu per gram of fresh or dry weight of the plant.

Fertilizers and exogenous nitrogen of the present disclosure may comprise the following nitrogen-containing molecules: ammonium, nitrate, nitrite, ammonia, glutamine, etc. Nitrogen sources of the present disclosure may include anhydrous ammonia, ammonia sulfate, urea, diammonium phosphate, urea-form, monoammonium phosphate, ammonium nitrate, nitrogen solutions, calcium nitrate, potassium nitrate, sodium nitrate, etc.

As used herein, "exogenous nitrogen" refers to non-atmospheric nitrogen readily available in the soil, field, or growth medium that is present under non-nitrogen limiting conditions, including ammonia, ammonium, nitrate, nitrite, urea, uric acid, ammonium acids, etc.

As used herein, "non-nitrogen limiting conditions" refers to non-atmospheric nitrogen available in the soil, field, media at concentrations greater than about 4 mM nitrogen, as disclosed by Kant et al. (2010. J. Exp. Biol. 62(4):1499-1509), which is incorporated herein by reference.

As used herein, an "intergeneric microorganism" is a microorganism that is formed by the deliberate combination of genetic material originally isolated from organisms of different taxonomic genera. An "intergeneric mutant" can be used interchangeably with "intergeneric microorganism". An exemplary "intergeneric microorganism" includes a microorganism containing a mobile genetic element which was first identified in a microorganism in a genus different from the recipient microorganism. Further explanation can be found, inter alia, in 40 C.F.R. § 725.3.

In aspects, microbes taught herein are "non-intergeneric," which means that the microbes are not intergeneric.

As used herein, an "intrageneric microorganism" is a microorganism that is formed by the deliberate combination of genetic material originally isolated from organisms of the same taxonomic genera. An "intrageneric mutant" can be used interchangeably with "intrageneric microorganism".

As used herein, "introduced genetic material" means genetic material that is added to, and remains as a component of, the genome of the recipient.

In some embodiments, the nitrogen fixation and assimilation genetic regulatory network comprises polynucleotides encoding genes and non-coding sequences that direct, modulate, and/or regulate microbial nitrogen fixation and/or assimilation and can comprise polynucleotide sequences of the nif cluster (e.g., nifA, nifB, nifC, . . . , nifZ), polynucleotides encoding nitrogen regulatory protein C, polynucleotides encoding nitrogen regulatory protein B, polynucleotide sequences of the gln cluster (e.g. glnA and glnD), draT, and ammonia transporters/permeases. In some cases, the Nif cluster may comprise NifB, NifH, NifD, NifK, NifE, NifN, NifX, hesa, and NifV. In some cases, the Nif cluster may comprise a subset of NifB, NifH, NifD, NifK, NifE, NifN, NifX, hesa, and NifV.

In some embodiments, fertilizer of the present disclosure comprises at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% nitrogen by weight.

In some embodiments, fertilizer of the present disclosure comprises at least about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% nitrogen by weight.

In some embodiments, fertilizer of the present disclosure comprises about 5% to 50%, about 5% to 75%, about 10% to 50%, about 10% to 75%, about 15% to 50%, about 15% to 75%, about 20% to 50%, about 20% to 75%, about 25% to 50%, about 25% to 75%, about 30% to 50%, about 30% to 75%, about 35% to 50%, about 35% to 75%, about 40% to 50%, about 40% to 75%, about 45% to 50%, about 45% to 75%, or about 50% to 75% nitrogen by weight.

In some embodiments, the increase of nitrogen fixation and/or the production of 1% or more of the nitrogen in the plant are measured relative to control plants, which have not been exposed to the bacteria of the present disclosure. All increases or decreases in bacteria are measured relative to control bacteria. All increases or decreases in plants are measured relative to control plants.

As used herein, a "constitutive promoter" is a promoter, which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related species to achieve efficient and reliable expression of transgenes in particular tissues. This is one of the main reasons for the large amount of tissue-specific promoters isolated from particular tissues found in both scientific and patent literature.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

In aspects, "applying to the plant a plurality of non-intergeneric bacteria," includes any means by which the plant (including plant parts such as a seed, root, stem, tissue, etc.) is made to come into contact (i.e. exposed) with said bacteria at any stage of the plant's life cycle. Consequently, "applying to the plant a plurality of non-intergeneric bacteria," includes any of the following means of exposing the plant (including plant parts such as a seed, root, stem, tissue, etc.) to said bacteria: spraying onto plant, dripping onto plant, applying as a seed coat, applying to a field that will then be planted with seed, applying to a field already planted with seed, applying to a field with adult plants, etc.

As used herein "MRTN" is an acronym for maximum return to nitrogen and is utilized as an experimental treatment in the Examples. MRTN was developed by Iowa State University and information can be found at: http://cnrc.agron.iastate.edu/The MRTN is the nitrogen rate where the economic net return to nitrogen application is maximized.

The approach to calculating the MRTN is a regional approach for developing corn nitrogen rate guidelines in individual states. The nitrogen rate trial data was evaluated for Illinois, Iowa, Michigan, Minnesota, Ohio, and Wisconsin where an adequate number of research trials were available for corn plantings following soybean and corn plantings following corn. The trials were conducted with spring, sidedress, or split preplant/sidedress applied nitrogen, and sites were not irrigated except for those that were indicated for irrigated sands in Wisconsin. MRTN was developed by Iowa State University due to apparent differences in methods for determining suggested nitrogen rates required for corn production, misperceptions pertaining to nitrogen rate guidelines, and concerns about application rates. By calculating the MRTN, practitioners can determine the following: (1) the nitrogen rate where the economic net return to nitrogen application is maximized, (2) the economic optimum nitrogen rate, which is the point where the last increment of nitrogen returns a yield increase large enough to pay for the additional nitrogen, (3) the value of corn grain increase attributed to nitrogen application, and the maximum yield, which is the yield where application of more nitrogen does not result in a corn yield increase. Thus the MRTN calculations provide practitioners with the means to maximize corn crops in different regions while maximizing financial gains from nitrogen applications.

The term mmol is an abbreviation for millimole, which is a thousandth $(10^{-3})$ of a mole, abbreviated herein as mol.

As used herein the terms "microorganism" or "microbe" should be taken broadly. These terms, used interchangeably, include but are not limited to, the two prokaryotic domains, Bacteria and Archaea. The term may also encompass eukaryotic fungi and protists.

The term "microbial consortia" or "microbial consortium" refers to a subset of a microbial community of individual microbial species, or strains of a species, which can be described as carrying out a common function, or can be described as participating in, or leading to, or correlating with, a recognizable parameter, such as a phenotypic trait of interest.

The term "microbial community" means a group of microbes comprising two or more species or strains. Unlike microbial consortia, a microbial community does not have to be carrying out a common function, or does not have to be participating in, or leading to, or correlating with, a recognizable parameter, such as a phenotypic trait of interest.

As used herein, "isolate," "isolated," "isolated microbe," and like terms, are intended to mean that the one or more microorganisms has been separated from at least one of the materials with which it is associated in a particular environment (for example soil, water, plant tissue, etc.). Thus, an "isolated microbe" does not exist in its naturally occurring environment; rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain). In aspects, the isolated microbe may be in association with an acceptable carrier, which may be an agriculturally acceptable carrier.

In certain aspects of the disclosure, the isolated microbes exist as "isolated and biologically pure cultures." It will be appreciated by one of skill in the art, that an isolated and biologically pure culture of a particular microbe, denotes that said culture is substantially free of other living organisms and contains only the individual microbe in question.

The culture can contain varying concentrations of said microbe. The present disclosure notes that isolated and biologically pure microbes often "necessarily differ from less pure or impure materials." See, e.g. In re *Bergstrom,* 427 F.2d 1394, (CCPA 1970) (discussing purified prostaglandins), see also, In re *Bergy,* 596 F.2d 952 (CCPA 1979) (discussing purified microbes), see also, *Parke-Davis & Co.* v. *H.K. Mulford & Co.,* 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., *Merck & Co.* v. *Olin Mathieson Chemical Corp.,* 253 F.2d 156 (4th Cir. 1958) (discussing purity limitations for vitamin B12 produced by microbes), incorporated herein by reference.

As used herein, "individual isolates" should be taken to mean a composition, or culture, comprising a predominance of a single genera, species, or strain, of microorganism, following separation from one or more other microorganisms.

Microbes of the present disclosure may include spores and/or vegetative cells. In some embodiments, microbes of the present disclosure include microbes in a viable but non-culturable (VBNC) state. As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be nonconducive to the survival or growth of vegetative cells.

As used herein, "microbial composition" refers to a composition comprising one or more microbes of the present disclosure. In some embodiments, a microbial composition is administered to plants (including various plant parts) and/or in agricultural fields.

As used herein, "carrier," "acceptable carrier," or "agriculturally acceptable carrier" refers to a diluent, adjuvant, excipient, or vehicle with which the microbe can be administered, which does not detrimentally effect the microbe.

Regulation of Nitrogen Fixation

In some cases, nitrogen fixation pathway may act as a target for genetic engineering and optimization. One trait that may be targeted for regulation by the methods described herein is nitrogen fixation. Nitrogen fertilizer is the largest operational expense on a farm and the biggest driver of higher yields in row crops like corn and wheat. Described herein are microbial products that can deliver renewable forms of nitrogen in non-leguminous crops. While some endophytes have the genetics necessary for fixing nitrogen in pure culture, the fundamental technical challenge is that wild-type endophytes of cereals and grasses stop fixing nitrogen in fertilized fields. The application of chemical fertilizers and residual nitrogen levels in field soils signal the microbe to shut down the biochemical pathway for nitrogen fixation.

Changes to the transcriptional and post-translational levels of components of the nitrogen fixation regulatory network may be beneficial to the development of a microbe capable of fixing and transferring nitrogen to corn in the presence of fertilizer. To that end, described herein is Host-Microbe Evolution (HoME) technology to precisely evolve regulatory networks and elicit novel phenotypes. Also described herein are unique, proprietary libraries of nitrogen-fixing endophytes isolated from corn, paired with extensive omics data surrounding the interaction of microbes and host plant under different environmental conditions like nitrogen stress and excess. In some embodiments, this technology enables precision evolution of the genetic regulatory network of endophytes to produce microbes that actively fix nitrogen even in the presence of fertilizer in the field. Also described herein are evaluations of the technical potential of evolving microbes that colonize corn root tissues and produce nitrogen for fertilized plants and evaluations of the compatibility of endophytes with standard formulation practices and diverse soils to determine feasibility of integrating the microbes into modern nitrogen management strategies.

In order to utilize elemental nitrogen (N) for chemical synthesis, life forms combine nitrogen gas (N$_2$) available in the atmosphere with hydrogen in a process known as nitrogen fixation. Because of the energy-intensive nature of biological nitrogen fixation, diazotrophs (bacteria and archaea that fix atmospheric nitrogen gas) have evolved sophisticated and tight regulation of the nif gene cluster in response to environmental oxygen and available nitrogen. Nif genes encode enzymes involved in nitrogen fixation (such as the nitrogenase complex) and proteins that regulate nitrogen fixation. Shamseldin (2013. Global J. Biotechnol. Biochem. 8(4):84-94) discloses detailed descriptions of nif genes and their products, and is incorporated herein by reference. Described herein are methods of producing a plant with an improved trait comprising isolating bacteria from a first plant, introducing a genetic variation into a gene of the isolated bacteria to increase nitrogen fixation, exposing a second plant to the variant bacteria, isolating bacteria from the second plant having an improved trait relative to the first plant, and repeating the steps with bacteria isolated from the second plant.

In Proteobacteria, regulation of nitrogen fixation centers around the $\sigma_{54}$-dependent enhancer-binding protein NifA, the positive transcriptional regulator of the nif cluster. Intracellular levels of active NifA are controlled by two key factors: transcription of the nifLA operon, and inhibition of NifA activity by protein-protein interaction with NifL. Both of these processes are responsive to intracelluar glutamine levels via the PII protein signaling cascade. This cascade is mediated by GlnD, which directly senses glutamine and catalyzes the uridylylation or deuridylylation of two PII regulatory proteins—GlnB and GlnK—in response the absence or presence, respectively, of bound glutamine. Under conditions of nitrogen excess, unmodified GlnB signals the deactivation of the nifLA promoter. However, under conditions of nitrogen limitation, GlnB is post-translationally modified, which inhibits its activity and leads to transcription of the nifLA operon. In this way, nifLA transcription is tightly controlled in response to environmental nitrogen via the PII protein signaling cascade. On the post-translational level of NifA regulation, GlnK inhibits the NifL/NifA interaction in a matter dependent on the overall level of free GlnK within the cell.

NifA is transcribed from the nifLA operon, whose promoter is activated by phosphorylated NtrC, another $\sigma_{54}$-dependent regulator. The phosphorylation state of NtrC is mediated by the histidine kinase NtrB, which interacts with deuridylylated GlnB but not uridylylated GlnB. Under conditions of nitrogen excess, a high intracellular level of glutamine leads to deuridylylation of GlnB, which then interacts with NtrB to deactivate its phosphorylation activity and activate its phosphatase activity, resulting in dephosphorylation of NtrC and the deactivation of the nifLA promoter. However, under conditions of nitrogen limitation, a low level of intracellular glutamine results in uridylylation of GlnB, which inhibits its interaction with NtrB and allows the phosphorylation of NtrC and transcription of the nifLA operon. In this way, nifLA expression is tightly controlled in response to environmental nitrogen via the PII protein signaling cascade. nifA, ntrB, ntrC, and glnB, are all genes that can be mutated in the methods described herein. These processes may also be responsive to intracellular or extracellular levels of ammonia, urea or nitrates.

The activity of NifA is also regulated post-translationally in response to environmental nitrogen, most typically through NifL-mediated inhibition of NifA activity. In general, the interaction of NifL and NifA is influenced by the PII protein signaling cascade via GlnK, although the nature of the interactions between GlnK and NifL/NifA varies significantly between diazotrophs. In *Klebsiella pneumoniae*, both forms of GlnK inhibit the NifL/NifA interaction, and the interaction between GlnK and NifL/NifA is determined by the overall level of free GlnK within the cell. Under nitrogen-excess conditions, deuridylylated GlnK interacts with the ammonium transporter AmtB, which serves to both block ammonium uptake by AmtB and sequester GlnK to the membrane, allowing inhibition of NifA by NifL. On the other hand, in *Azotobacter vinelandii*, interaction with deuridylylated GlnK is required for the NifL/NifA interaction and NifA inhibition, while uridylylation of GlnK inhibits its interaction with NifL. In diazotrophs lacking the nifL gene, there is evidence that NifA activity is inhibited directly by interaction with the deuridylylated forms of both GlnK and GlnB under nitrogen-excess conditions. In some bacteria the Nif cluster may be regulated by glnR, and further in some cases this may comprise negative regulation. Regardless of the mechanism, post-translational inhibition of NifA is an important regulator of the nif cluster in most known diazotrophs. Additionally, nifL, amtB, glnK, and glnR are genes that can be mutated in the methods described herein.

In addition to regulating the transcription of the nif gene cluster, many diazotrophs have evolved a mechanism for the direct post-translational modification and inhibition of the nitrogenase enzyme itself, known as nitrogenase shutoff. This is mediated by ADP-ribosylation of the Fe protein (NifH) under nitrogen-excess conditions, which disrupts its interaction with the MoFe protein complex (NifDK) and abolishes nitrogenase activity. DraT catalyzes the ADP-ribosylation of the Fe protein and shutoff of nitrogenase, while DraG catalyzes the removal of ADP-ribose and reactivation of nitrogenase. As with nifLA transcription and NifA inhibition, nitrogenase shutoff is also regulated via the PII protein signaling cascade. Under nitrogen-excess conditions, deuridylylated GlnB interacts with and activates DraT, while deuridylylated GlnK interacts with both DraG and AmtB to form a complex, sequestering DraG to the membrane. Under nitrogen-limiting conditions, the uridylylated forms of GlnB and GlnK do not interact with DraT and DraG, respectively, leading to the inactivation of DraT and the diffusion of DraG to the Fe protein, where it removes the ADP-ribose and activates nitrogenase. The methods described herein also contemplate introducing genetic variation into the nifH, nifD, nifK, and draT genes.

Although some endophytes have the ability to fix nitrogen in vitro, often the genetics are silenced in the field by high levels of exogenous chemical fertilizers. One can decouple the sensing of exogenous nitrogen from expression of the nitrogenase enzyme to facilitate field-based nitrogen fixation. Improving the integral of nitrogenase activity across time further serves to augment the production of nitrogen for utilization by the crop. Specific targets for genetic variation to facilitate field-based nitrogen fixation using the methods described herein include one or more genes selected from the group consisting of nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

An additional target for genetic variation to facilitate field-based nitrogen fixation using the methods described herein is the NifA protein. The NifA protein is typically the activator for expression of nitrogen fixation genes. Increasing the production of NifA (either constitutively or during high ammonia condition) circumvents the native ammonia-sensing pathway. In addition, reducing the production of NifL proteins, a known inhibitor of NifA, also leads to an increased level of freely active NifA. In addition, increasing the transcription level of the nifAL operon (either constitutively or during high ammonia condition) also leads to an overall higher level of NifA proteins. Elevated level of nifAL expression is achieved by altering the promoter itself or by reducing the expression of NtrB (part of ntrB and ntrC signaling cascade that originally would result in the shutoff of nifAL operon during high nitrogen condition). High level of NifA achieved by these or any other methods described herein increases the nitrogen fixation activity of the endophytes.

Another target for genetic variation to facilitate field-based nitrogen fixation using the methods described herein is the GlnD/GlnB/GlnK PII signaling cascade. The intracellular glutamine level is sensed through the GlnD/GlnB/GlnK PII signaling cascade. Active site mutations in GlnD that abolish the uridylyl-removing activity of GlnD disrupt the nitrogen-sensing cascade. In addition, reduction of the GlnB concentration short circuits the glutamine-sensing cascade. These mutations "trick" the cells into perceiving a nitrogen-limited state, thereby increasing the nitrogen fixation level activity. These processes may also be responsive to intracellular or extracellular levels of ammonia, urea or nitrates.

The amtB protein is also a target for genetic variation to facilitate field-based nitrogen fixation using the methods described herein. Ammonia uptake from the environment can be reduced by decreasing the expression level of amtB protein. Without intracellular ammonia, the endophyte is not able to sense the high level of ammonia, preventing the down-regulation of nitrogen fixation genes. Any ammonia that manages to get into the intracellular compartment is converted into glutamine. Intracellular glutamine level is the major currency of nitrogen sensing. Decreasing the intracellular glutamine level prevents the cells from sensing high ammonium levels in the environment. This effect can be achieved by increasing the expression level of glutaminase, an enzyme that converts glutamine into glutamate. In addition, intracellular glutamine can also be reduced by decreasing glutamine synthase (an enzyme that converts ammonia into glutamine). In diazotrophs, fixed ammonia is quickly assimilated into glutamine and glutamate to be used for cellular processes. Disruptions to ammonia assimilation may enable diversion of fixed nitrogen to be exported from the cell as ammonia. The fixed ammonia is predominantly assimilated into glutamine by glutamine synthetase (GS), encoded by glnA, and subsequently into glutamine by glutamine oxoglutarate aminotransferase (GOGAT). In some examples, glnS encodes a glutamine synthetase. GS is regulated post-translationally by GS adenylyl transferase (GlnE), a bi-functional enzyme encoded by glnE that catalyzes both the adenylylation and de-adenylylation of GS through activity of its adenylyl-transferase (AT) and adenylyl-removing (AR) domains, respectively. Under nitrogen limiting conditions, glnA is expressed, and GlnE's AR domain de-adynylylates GS, allowing it to be active. Under conditions of nitrogen excess, glnA expression is turned off, and GlnE's AT domain is activated allosterically by glutamine, causing the adenylylation and deactivation of GS.

Furthermore, the draT gene may also be a target for genetic variation to facilitate field-based nitrogen fixation using the methods described herein. Once nitrogen fixing enzymes are produced by the cell, nitrogenase shut-off represents another level in which cell downregulates fixation activity in high nitrogen condition. This shut-off could be removed by decreasing the expression level of DraT.

Methods for imparting new microbial phenotypes can be performed at the transcriptional, translational, and post-translational levels. The transcriptional level includes changes at the promoter (such as changing sigma factor affinity or binding sites for transcription factors, including deletion of all or a portion of the promoter) or changing transcription terminators and attenuators. The translational level includes changes at the ribosome binding sites and changing mRNA degradation signals. The post-translational level includes mutating an enzyme's active site and changing protein-protein interactions. These changes can be achieved in a multitude of ways. Reduction of expression level (or complete abolishment) can be achieved by swapping the native ribosome binding site (RBS) or promoter with another with lower strength/efficiency. ATG start sites can be swapped to a GTG, TTG, or CTG start codon, which results in reduction in translational activity of the coding region. Complete abolishment of expression can be done by knocking out (deleting) the coding region of a gene. Frameshifting the open reading frame (ORF) likely will result in a premature stop codon along the ORF, thereby creating a non-functional truncated product. Insertion of in-frame stop codons will also similarly create a non-functional truncated product. Addition of a degradation tag at the N or C terminal can also be done to reduce the effective concentration of a particular gene.

Conversely, expression level of the genes described herein can be achieved by using a stronger promoter. To ensure high promoter activity during high nitrogen level condition (or any other condition), a transcription profile of the whole genome in a high nitrogen level condition could be obtained and active promoters with a desired transcription level can be chosen from that dataset to replace the weak promoter. Weak start codons can be swapped out with an ATG start codon for better translation initiation efficiency. Weak ribosomal binding sites (RBS) can also be swapped out with a different RBS with higher translation initiation efficiency. In addition, site specific mutagenesis can also be performed to alter the activity of an enzyme.

Increasing the level of nitrogen fixation that occurs in a plant can lead to a reduction in the amount of chemical fertilizer needed for crop production and reduce greenhouse gas emissions (e.g., nitrous oxide).

Generation of Bacterial Populations

Isolation of Bacteria

Microbes useful in methods and compositions disclosed herein can be obtained by extracting microbes from surfaces or tissues of native plants. Microbes can be obtained by grinding seeds to isolate microbes. Microbes can be obtained by planting seeds in diverse soil samples and recovering microbes from tissues. Additionally, microbes can be obtained by inoculating plants with exogenous microbes and determining which microbes appear in plant tissues. Non-limiting examples of plant tissues may include a seed, seedling, leaf, cutting, plant, bulb, or tuber.

A method of obtaining microbes may be through the isolation of bacteria from soils. Bacteria may be collected from various soil types. In some example, the soil can be characterized by traits such as high or low fertility, levels of moisture, levels of minerals, and various cropping practices. For example, the soil may be involved in a crop rotation where different crops are planted in the same soil in successive planting seasons. The sequential growth of different crops on the same soil may prevent disproportionate depletion of certain minerals. The bacteria can be isolated from the plants growing in the selected soils. The seedling plants can be harvested at 2-6 weeks of growth. For example, at least 400 isolates can be collected in a round of harvest. Soil and plant types reveal the plant phenotype as well as the conditions, which allow for the downstream enrichment of certain phenotypes.

Microbes can be isolated from plant tissues to assess microbial traits. The parameters for processing tissue samples may be varied to isolate different types of associative microbes, such as rhizospheric bacteria, epiphytes, or endophytes. The isolates can be cultured in nitrogen-free media to enrich for bacteria that perform nitrogen fixation. Alternatively, microbes can be obtained from global strain banks.

In planta analytics are performed to assess microbial traits. In some embodiments, the plant tissue can be processed for screening by high throughput processing for DNA and RNA. Additionally, non-invasive measurements can be used to assess plant characteristics, such as colonization. Measurements on wild microbes can be obtained on a plant-by-plant basis. Measurements on wild microbes can also be obtained in the field using medium throughput methods. Measurements can be done successively over time. Model plant system can be used including, but not limited to, *Setaria*.

Microbes in a plant system can be screened via transcriptional profiling of a microbe in a plant system. Examples of screening through transcriptional profiling are using methods of quantitative polymerase chain reaction (qPCR), molecular barcodes for transcript detection, Next Generation Sequencing, and microbe tagging with fluorescent markers. Impact factors can be measured to assess colonization in the greenhouse including, but not limited to, microbiome, abiotic factors, soil conditions, oxygen, moisture, temperature, inoculum conditions, and root localization. Nitrogen fixation can be assessed in bacteria by measuring 15N gas/fertilizer (dilution) with IRMS or NanoSIMS as described herein NanoSIMS is high-resolution secondary ion mass spectrometry. The NanoSIMS technique is a way to investigate chemical activity from biological samples. The catalysis of reduction of oxidation reactions that drive the metabolism of microorganisms can be investigated at the cellular, subcellular, molecular and elemental level. NanoSIMS can provide high spatial resolution of greater than 0.1 μm. NanoSIMS can detect the use of isotope tracers such as $^{13}$C, $^{15}$N, and $^{18}$O. Therefore, NanoSIMS can be used to the chemical activity nitrogen in the cell.

Automated greenhouses can be used for planta analytics. Plant metrics in response to microbial exposure include, but are not limited to, biomass, chloroplast analysis, CCD camera, volumetric tomography measurements.

One way of enriching a microbe population is according to genotype. For example, a polymerase chain reaction (PCR) assay with a targeted primer or specific primer. Primers designed for the nifH gene can be used to identity diazotrophs because diazotrophs express the nifH gene in the process of nitrogen fixation. A microbial population can also be enriched via single-cell culture-independent approaches and chemotaxis-guided isolation approaches. Alternatively, targeted isolation of microbes can be performed by culturing the microbes on selection media. Premeditated approaches to enriching microbial populations for desired traits can be guided by bioinformatics data and are described herein.

Enriching for Microbes with Nitrogen Fixation Capabilities Using Bioinformatics

Bioinformatic tools can be used to identify and isolate plant growth promoting rhizobacteria (PGPRs), which are selected based on their ability to perform nitrogen fixation. Microbes with high nitrogen fixing ability can promote favorable traits in plants. Bioinformatic modes of analysis for the identification of PGPRs include, but are not limited to, genomics, metagenomics, targeted isolation, gene sequencing, transcriptome sequencing, and modeling.

Genomics analysis can be used to identify PGPRs and confirm the presence of mutations with methods of Next Generation Sequencing as described herein and microbe version control.

Metagenomics can be used to identify and isolate PGPR using a prediction algorithm for colonization. Metadata can also be used to identify the presence of an engineered strain in environmental and greenhouse samples.

Transcriptomic sequencing can be used to predict genotypes leading to PGPR phenotypes. Additionally, transcriptomic data is used to identify promoters for altering gene expression. Transcriptomic data can be analyzed in conjunction with the Whole Genome Sequence (WGS) to generate models of metabolism and gene regulatory networks.

Domestication of Microbes

Microbes isolated from nature can undergo a domestication process wherein the microbes are converted to a form that is genetically trackable and identifiable. One way to domesticate a microbe is to engineer it with antibiotic resistance. The process of engineering antibiotic resistance can begin by determining the antibiotic sensitivity in the wild type microbial strain. If the bacteria are sensitive to the antibiotic, then the antibiotic can be a good candidate for antibiotic resistance engineering. Subsequently, an antibiotic resistant gene or a counterselectable suicide vector can be incorporated into the genome of a microbe using recombineering methods. A counterselectable suicide vector may consist of a deletion of the gene of interest, a selectable marker, and the counterselectable marker sacB. Counterselection can be used to exchange native microbial DNA sequences with antibiotic resistant genes. A medium throughput method can be used to evaluate multiple microbes simultaneously allowing for parallel domestication. Alternative methods of domestication include the use of homing nucleases to prevent the suicide vector sequences from looping out or from obtaining intervening vector sequences.

DNA vectors can be introduced into bacteria via several methods including electroporation and chemical transformations. A standard library of vectors can be used for transformations. An example of a method of gene editing is CRISPR preceded by Cas9 testing to ensure activity of Cas9 in the microbes.

Non-Transgenic Engineering of Microbes

A microbial population with favorable traits can be obtained via directed evolution. Direct evolution is an approach wherein the process of natural selection is mimicked to evolve proteins or nucleic acids towards a user-defined goal. An example of direct evolution is when random mutations are introduced into a microbial population, the microbes with the most favorable traits are selected, and the growth of the selected microbes is continued. The most favorable traits in growth promoting rhizobacteria (PGPRs) may be in nitrogen fixation. The method of directed evolution may be iterative and adaptive based on the selection process after each iteration.

Plant growth promoting rhizobacteria (PGPRs) with high capability of nitrogen fixation can be generated. The evolution of PGPRs can be carried out via the introduction of genetic variation. Genetic variation can be introduced via polymerase chain reaction mutagenesis, oligonucleotide-directed mutagenesis, saturation mutagenesis, fragment shuffling mutagenesis, homologous recombination, CRISPR/Cas9 systems, chemical mutagenesis, and combinations thereof. These approaches can introduce random mutations into the microbial population. For example, mutants can be generated using synthetic DNA or RNA via oligonucleotide-directed mutagenesis. Mutants can be generated using tools contained on plasmids, which are later cured. Genes of interest can be identified using libraries from other species with improved traits including, but not limited to, improved PGPR properties, improved colonization of cereals, increased oxygen sensitivity, increased nitrogen fixation, and increased ammonia excretion. Intrageneric genes can be designed based on these libraries using software such as Geneious or Platypus design software. Mutations can be designed with the aid of machine learning. Mutations can be designed with the aid of a metabolic model. Automated design of the mutation can be done using a la Platypus and will guide RNAs for Cas-directed mutagenesis.

The intra-generic genes can be transferred into the host microbe. Additionally, reporter systems can also be transferred to the microbe. The reporter systems characterize promoters, determine the transformation success, screen mutants, and act as negative screening tools.

The microbes carrying the mutation can be cultured via serial passaging. A microbial colony contains a single variant of the microbe. Microbial colonies are screened with the aid of an automated colony picker and liquid handler. Mutants with gene duplication and increased copy number express a higher genotype of the desired trait.

Selection of Plant Growth Promoting Microbes Based on Nitrogen Fixation

The microbial colonies can be screened using various assays to assess nitrogen fixation. One way to measure nitrogen fixation is via a single fermentative assay, which measures nitrogen excretion. An alternative method is the acetylene reduction assay (ARA) with in-line sampling over time. ARA can be performed in high throughput plates of microtube arrays. ARA can be performed with live plants and plant tissues. The media formulation and media oxygen concentration can be varied in ARA assays. Another method of screening microbial variants is by using biosensors. The use of NanoSIMS and Raman microspectroscopy can be used to investigate the activity of the microbes. In some cases, bacteria can also be cultured and expanded using methods of fermentation in bioreactors. The bioreactors are designed to improve robustness of bacteria growth and to decrease the sensitivity of bacteria to oxygen. Medium to high TP plate-based microfermentors are used to evaluate oxygen sensitivity, nutritional needs, nitrogen fixation, and nitrogen excretion. The bacteria can also be co-cultured with competitive or beneficial microbes to elucidate cryptic pathways. Flow cytometry can be used to screen for bacteria that produce high levels of nitrogen using chemical, colorimetric, or fluorescent indicators. The bacteria may be cultured in the presence or absence of a nitrogen source. For example, the bacteria may be cultured with glutamine, ammonia, urea or nitrates.

Microbe Breeding

Figure 17A:
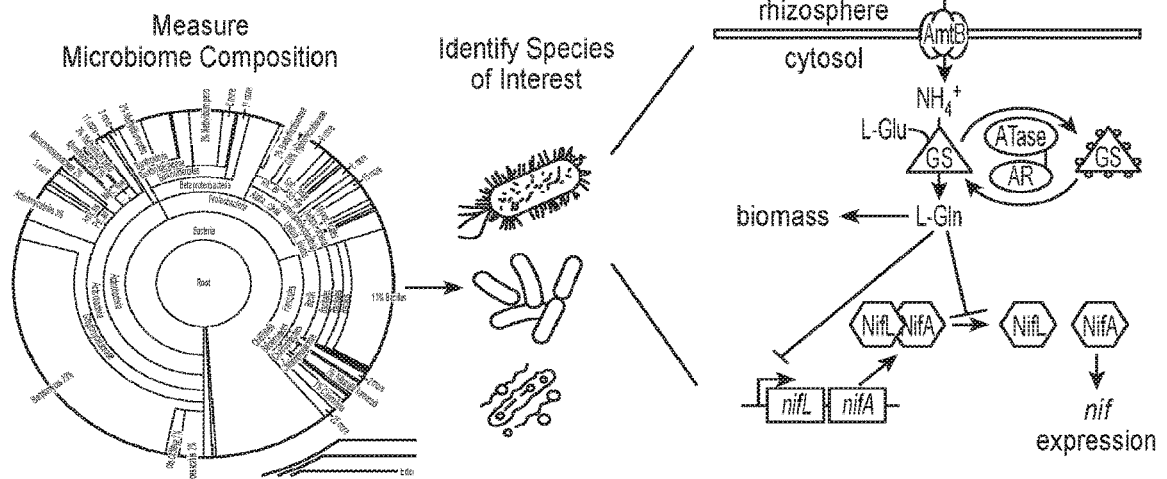
FIG. 17A depicts a schematic of microbe breeding, in accordance with embodiments.
Figure 17A:
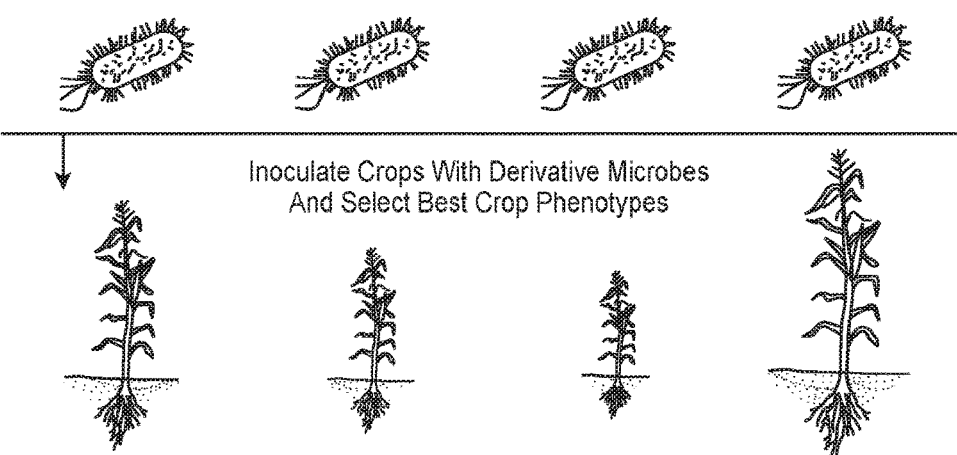

Microbe breeding is a method to systematically identify and improve the role of species within the crop microbiome. The method comprises three steps: 1) selection of candidate species by mapping plant-microbe interactions and predicting regulatory networks linked to a particular phenotype, 2) pragmatic and predictable improvement of microbial phenotypes through intra-species crossing of regulatory networks and gene clusters, and 3) screening and selection of new microbial genotypes that produce desired crop phenotypes. To systematically assess the improvement of strains, a model is created that links colonization dynamics of the microbial community to genetic activity by key species. The model is used to predict genetic targets breeding and improve the frequency of selecting improvements in microbiome-encoded traits of agronomic relevance. See, FIG. 17A for a graphical representation of an embodiment of the process. In particular, FIG. 17A depicts a schematic of microbe breeding, in accordance with embodiments. As illustrated in FIG. 17A, rational improvement of the crop microbiome may be used to increase soil biodiversity, tune impact of keystone species, and/or alter timing and expression of important metabolic pathways. To this end, the inventors have developed a microbe breeding pipeline to identify and improve the role of strains within the crop microbiome. The method comprises three steps: 1) selection of candidate species by mapping plant-microbe interactions and predicting regulatory networks linked to a particular phenotype, 2) pragmatic and predictable improvement of microbial phenotypes through intragenomic crossing of gene regulatory networks and gene clusters, and 3) screening and selection of new microbial genotypes that produce desired crop phenotypes. To systematically assess the improvement of strains, the inventors employ a model that links colonization dynamics of the microbial community to genetic activity by key species. This process represents a methodology for breeding and selecting improvements in microbiome-encoded traits of agronomic relevance.

Production of bacteria to improve plant traits (e.g., nitrogen fixation) can be achieved through serial passage. The production of this bacteria can be done by selecting plants, which have a particular improved trait that is influenced by the microbial flora, in addition to identifying bacteria and/or compositions that are capable of imparting one or more improved traits to one or more plants. One method of producing a bacteria to improve a plant trait includes the steps of: (a) isolating bacteria from tissue or soil of a first plant; (b) introducing a genetic variation into one or more of the bacteria to produce one or more variant bacteria; (c) exposing a plurality of plants to the variant bacteria; (d) isolating bacteria from tissue or soil of one of the plurality of plants, wherein the plant from which the bacteria is isolated has an improved trait relative to other plants in the plurality of plants; and (e) repeating steps (b) to (d) with bacteria isolated from the plant with an improved trait (step (d)). Steps (b) to (d) can be repeated any number of times (e.g., once, twice, three times, four times, five times, ten times, or more) until the improved trait in a plant reaches a desired level. Further, the plurality of plants can be more than two plants, such as 10 to 20 plants, or 20 or more, 50 or more, 100 or more, 300 or more, 500 or more, or 1000 or more plants.

In addition to obtaining a plant with an improved trait, a bacterial population comprising bacteria comprising one or more genetic variations introduced into one or more genes (e.g., genes regulating nitrogen fixation) is obtained. By repeating the steps described above, a population of bacteria can be obtained that include the most appropriate members of the population that correlate with a plant trait of interest. The bacteria in this population can be identified and their beneficial properties determined, such as by genetic and/or phenotypic analysis. Genetic analysis may occur of isolated bacteria in step (a). Phenotypic and/or genotypic information may be obtained using techniques including: high through-put screening of chemical components of plant origin, sequencing techniques including high throughput sequencing of genetic material, differential display techniques (including DDRT-PCR, and DD-PCR), nucleic acid microarray techniques, RNA-sequencing (Whole Transcriptome Shotgun Sequencing), and qRT-PCR (quantitative real time PCR). Information gained can be used to obtain community profiling information on the identity and activity of bacteria present, such as phylogenetic analysis or microarray-based screening of nucleic acids coding for components of rRNA operons or other taxonomically informative loci. Examples of taxonomically informative loci include 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, coxl gene, nifD gene. Example processes of taxonomic profiling to determine taxa present in a population are described in US20140155283. Bacterial identification may comprise characterizing activity of one or more genes or one or more signaling pathways, such as genes associated with the nitrogen fixation pathway. Synergistic interactions (where two components, by virtue of their combination, increase a desired effect by more than an additive amount) between different bacterial species may also be present in the bacterial populations.

Genetic Variation—Locations and Sources of Genomic Alteration

The genetic variation may be a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ. The genetic variation may be a variation in a gene encoding a protein with functionality selected from the group consisting of: glutamine synthetase, glutaminase, glutamine synthetase adenylyltransferase, transcriptional activator, anti-transcriptional activator, pyruvate flavodoxin oxidoreductase, flavodoxin, or NAD+-dinitrogen-reductase aDP-D-ribosyltransferase. The genetic variation may be a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD. Introducing a genetic variation may comprise insertion and/or deletion of one or more nucleotides at a target site, such as 1, 2, 3, 4, 5, 10, 25, 50, 100, 250, 500, or more nucleotides. The genetic variation introduced into one or more bacteria of the methods disclosed herein may be a knock-out mutation (e.g. deletion of a promoter, insertion or deletion to produce a premature stop codon, deletion of an entire gene), or it may be elimination or abolishment of activity of a protein domain (e.g. point mutation affecting an active site, or deletion of a portion of a gene encoding the relevant portion of the protein product), or it may alter or abolish a regulatory sequence of a target gene. One or more regulatory sequences may also be inserted, including heterologous regulatory sequences and regulatory sequences found within a genome of a bacterial species or genus corresponding to the bacteria into which the genetic variation is introduced. Moreover, regulatory sequences may be selected based on the expression level of a gene in a bacterial culture or within a plant tissue. The genetic variation may be a pre-determined genetic variation that is specifically introduced to a target site. The genetic variation may be a random mutation within the target site. The genetic variation may be an insertion or deletion of one or more nucleotides. In some cases, a plurality of different genetic variations (e.g. 2, 3, 4, 5, 10, or more) are introduced into one or more of the isolated bacteria before exposing the bacteria to plants for assessing trait improvement. The plurality of genetic variations can be any of the above types, the same or different types, and in any combination. In some cases, a plurality of different genetic variations are introduced serially, introducing a first genetic variation after a first isolation step, a second genetic variation after a second isolation step, and so forth so as to accumulate a plurality of genetic variations in bacteria imparting progressively improved traits on the associated plants.

Genetic Variation—Methods of Introducing Genomic Alteration

In general, the term "genetic variation" refers to any change introduced into a polynucleotide sequence relative to a reference polynucleotide, such as a reference genome or portion thereof, or reference gene or portion thereof. A genetic variation may be referred to as a "mutation," and a sequence or organism comprising a genetic variation may be referred to as a "genetic variant" or "mutant". Genetic variations can have any number of effects, such as the increase or decrease of some biological activity, including gene expression, metabolism, and cell signaling. Genetic variations can be specifically introduced to a target site, or introduced randomly. A variety of molecular tools and methods are available for introducing genetic variation. For example, genetic variation can be introduced via polymerase chain reaction mutagenesis, oligonucleotide-directed mutagenesis, saturation mutagenesis, fragment shuffling mutagenesis, homologous recombination, recombineering, lambda red mediated recombination, CRISPR/Cas9 systems, chemical mutagenesis, and combinations thereof. Chemical methods of introducing genetic variation include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, diethyl sulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Genetic variation can also be introduced into a nucleic acid using, e.g., trimethylpsoralen with ultraviolet light. Random or targeted insertion of a mobile DNA element, e.g., a transposable element, is another suitable method for generating genetic variation. Genetic variations can be introduced into a nucleic acid during amplification in a cell-free in vitro system, e.g., using a polymerase chain reaction (PCR) technique such as error-prone PCR. Genetic variations can be introduced into a nucleic acid in vitro using DNA shuffling techniques (e.g., exon shuffling, domain swapping, and the like). Genetic variations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Example descriptions of various methods for introducing genetic variations are provided in e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

Genetic variations introduced into microbes may be classified as transgenic, cisgenic, intragenomic, intrageneric, intergeneric, synthetic, evolved, rearranged, or SNPs.

Genetic variation may be introduced into numerous metabolic pathways within microbes to elicit improvements in the traits described above. Representative pathways include sulfur uptake pathways, glycogen biosynthesis, the glutamine regulation pathway, the molybdenum uptake pathway, the nitrogen fixation pathway, ammonia assimilation, ammonia excretion or secretion, nitrogen uptake, glutamine biosynthesis, annamox, phosphate solubilization, organic acid transport, organic acid production, agglutinins production, reactive oxygen radical scavenging genes, Indole Acetic Acid biosynthesis, trehalose biosynthesis, plant cell wall degrading enzymes or pathways, root attachment genes, exopolysaccharide secretion, glutamate synthase pathway, iron uptake pathways, siderophore pathway, chitinase pathway, ACC deaminase, glutathione biosynthesis, phosphorous signaling genes, quorum quenching pathway, cytochrome pathways, hemoglobin pathway, bacterial hemoglobin-like pathway, small RNA rsmZ, rhizobitoxine biosynthesis, lapA adhesion protein, AHL quorum sensing pathway, phenazine biosynthesis, cyclic lipopeptide biosynthesis, and antibiotic production.

CRISPR/Cas9 (Clustered regularly interspaced short palindromic repeats)/CRISPR-associated (Cas) systems can be used to introduce desired mutations. CRISPR/Cas9 provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on the association of the protein with two naturally occurring or synthetic RNA molecules called crRNA and tracrRNA (also called guide RNAs). In some cases, the two molecules are covalently link to form a single molecule (also called a single guide RNA ("sgRNA")). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-stranded break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Further exemplary descriptions of CRISPR systems for introducing genetic variation can be found in, e.g. U.S. Pat. No. 8,795,965.

As a cyclic amplification technique, polymerase chain reaction (PCR) mutagenesis uses mutagenic primers to introduce desired mutations. PCR is performed by cycles of denaturation, annealing, and extension. After amplification by PCR, selection of mutated DNA and removal of parental plasmid DNA can be accomplished by: 1) replacement of dCTP by hydroxymethylated-dCTP during PCR, followed by digestion with restriction enzymes to remove non-hydroxymethylated parent DNA only; 2) simultaneous mutagenesis of both an antibiotic resistance gene and the studied gene changing the plasmid to a different antibiotic resistance, the new antibiotic resistance facilitating the selection of the desired mutation thereafter; 3) after introducing a desired mutation, digestion of the parent methylated template DNA by restriction enzyme Dpnl which cleaves only methylated DNA, by which the mutagenized unmethylated chains are recovered; or 4) circularization of the mutated PCR products in an additional ligation reaction to increase the transformation efficiency of mutated DNA. Further description of exemplary methods can be found in e.g. U.S. Pat. Nos. 7,132,265, 6,713,285, 6,673,610, 6,391,548, 5,789,166, 5,780,270, 5,354,670, 5,071,743, and US20100267147.

Oligonucleotide-directed mutagenesis, also called site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, or insertion, or a combination of these. The single-strand primer is then extended using a DNA polymerase, which copies the rest of the gene. The gene thus copied contains the mutated site, and may then be introduced into a host cell as a vector and cloned. Finally, mutants can be selected by DNA sequencing to check that they contain the desired mutation.

Genetic variations can be introduced using error-prone PCR. In this technique the gene of interest is amplified using a DNA polymerase under conditions that are deficient in the fidelity of replication of sequence. The result is that the amplification products contain at least one error in the sequence. When a gene is amplified and the resulting product(s) of the reaction contain one or more alterations in sequence when compared to the template molecule, the resulting products are mutagenized as compared to the template. Another means of introducing random mutations is exposing cells to a chemical mutagen, such as nitrosoguanidine or ethyl methanesulfonate (Nestmann, Mutat Res 1975 June; 28(3):323-30), and the vector containing the gene is then isolated from the host.

Saturation mutagenesis is another form of random mutagenesis, in which one tries to generate all or nearly all possible mutations at a specific site, or narrow region of a gene. In a general sense, saturation mutagenesis is comprised of mutagenizing a complete set of mutagenic cassettes (wherein each cassette is, for example, 1-500 bases in length) in defined polynucleotide sequence to be mutagenized (wherein the sequence to be mutagenized is, for example, from 15 to 100,000 bases in length). Therefore, a group of mutations (e.g. ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Fragment shuffling mutagenesis, also called DNA shuffling, is a way to rapidly propagate beneficial mutations. In an example of a shuffling process, DNAse is used to fragment a set of parent genes into pieces of e.g. about 50-100 bp in length. This is then followed by a polymerase chain reaction (PCR) without primers—DNA fragments with sufficient overlapping homologous sequence will anneal to each other and are then be extended by DNA polymerase. Several rounds of this PCR extension are allowed to occur, after some of the DNA molecules reach the size of the parental genes. These genes can then be amplified with another PCR, this time with the addition of primers that are designed to complement the ends of the strands. The primers may have additional sequences added to their 5' ends, such as sequences for restriction enzyme recognition sites needed for ligation into a cloning vector. Further examples of shuffling techniques are provided in US20050266541.

Homologous recombination mutagenesis involves recombination between an exogenous DNA fragment and the targeted polynucleotide sequence. After a double-stranded break occurs, sections of DNA around the 5' ends of the break are cut away in a process called resection. In the strand invasion step that follows, an overhanging 3' end of the broken DNA molecule then "invades" a similar or identical DNA molecule that is not broken. The method can be used to delete a gene, remove exons, add a gene, and introduce point mutations. Homologous recombination mutagenesis can be permanent or conditional. Typically, a recombination template is also provided. A recombination template may be a component of another vector, contained in a separate vector, or provided as a separate polynucleotide. In some embodiments, a recombination template is designed to serve as a template in homologous recombination, such as within or near a target sequence nicked or cleaved by a site-specific nuclease. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Non-limiting examples of site-directed nucleases useful in methods of homologous recombination include zinc finger nucleases, CRISPR nucleases, TALE nucleases, and meganuclease. For a further description of the use of such nucleases, see e.g. U.S. Pat. No. 8,795,965 and US20140301990.

Mutagens that create primarily point mutations and short deletions, insertions, transversions, and/or transitions, including chemical mutagens or radiation, may be used to create genetic variations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitro-samine, N-methyl-N'-nitro-Nitrosoguanidine, nitrosoguani-dine, 2-aminopurine, 7,12 dimethyl-benz(a)anthracene, eth-ylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)amino-propylamino]acridine dihydrochloride and formaldehyde.

Introducing genetic variation may be an incomplete process, such that some bacteria in a treated population of bacteria carry a desired mutation while others do not. In some cases, it is desirable to apply a selection pressure so as to enrich for bacteria carrying a desired genetic variation. Traditionally, selection for successful genetic variants involved selection for or against some functionality imparted or abolished by the genetic variation, such as in the case of inserting antibiotic resistance gene or abolishing a metabolic activity capable of converting a non-lethal compound into a lethal metabolite. It is also possible to apply a selection pressure based on a polynucleotide sequence itself, such that only a desired genetic variation need be introduced (e.g. without also requiring a selectable marker). In this case, the selection pressure can comprise cleaving genomes lacking the genetic variation introduced to a target site, such that selection is effectively directed against the reference sequence into which the genetic variation is sought to be introduced. Typically, cleavage occurs within 100 nucleotides of the target site (e.g. within 75, 50, 25, 10, or fewer nucleotides from the target site, including cleavage at or within the target site). Cleaving may be directed by a site-specific nuclease selected from the group consisting of a Zinc Finger nuclease, a CRISPR nuclease, a TALE nuclease (TALEN), or a meganuclease. Such a process is similar to processes for enhancing homologous recombination at a target site, except that no template for homologous recombination is provided. As a result, bacteria lacking the desired genetic variation are more likely to undergo cleavage that, left unrepaired, results in cell death. Bacteria surviving selection may then be isolated for use in exposing to plants for assessing conferral of an improved trait.

A CRISPR nuclease may be used as the site-specific nuclease to direct cleavage to a target site. An improved selection of mutated microbes can be obtained by using Cas9 to kill non-mutated cells. Plants are then inoculated with the mutated microbes to re-confirm symbiosis and create evolutionary pressure to select for efficient symbionts. Microbes can then be re-isolated from plant tissues. CRISPR nuclease systems employed for selection against non-vari-ants can employ similar elements to those described above with respect to introducing genetic variation, except that no template for homologous recombination is provided. Cleav-age directed to the target site thus enhances death of affected cells.

Other options for specifically inducing cleavage at a target site are available, such as zinc finger nucleases, TALE nuclease (TALEN) systems, and meganuclease. Zinc-finger nucleases (ZFNs) are artificial DNA endonucleases gener-ated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double stranded breaks. Tran-scription activator-like effector nucleases (TALENs) are artificial DNA endonucleases generated by fusing a TAL (Transcription activator-like) effector DNA binding domain to a DNA cleavage domain. TALENS can be quickly engi-neered to bind practically any desired DNA sequence and when introduced into a cell, TALENs can be used to edit target DNA in the cell (e.g., the cell's genome) by inducing double strand breaks. Meganucleases (homing endonu-clease) are endodeoxyribonucleases characterized by a large recognition site (double-stranded DNA sequences of 12 to 40 base pairs. Meganucleases can be used to replace, elimi-nate or modify sequences in a highly targeted way. By modifying their recognition sequence through protein engi-neering, the targeted sequence can be changed. Meganucle-ases can be used to modify all genome types, whether bacterial, plant or animal and are commonly grouped into four families: the LAGLIDADG family (SEQ ID NO: 1), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

Genetic Variation—Methods of Identification

The microbes of the present disclosure may be identified by one or more genetic modifications or alterations, which have been introduced into said microbe. One method by which said genetic modification or alteration can be identi-fied is via reference to a SEQ ID NO that contains a portion of the microbe's genomic sequence that is sufficient to identify the genetic modification or alteration.

Further, in the case of microbes that have not had a genetic modification or alteration (e.g. a wild type, WT) introduced into their genomes, the disclosure can utilize 16S nucleic acid sequences to identify said microbes. A 16S nucleic acid sequence is an example of a "molecular marker" or "genetic marker," which refers to an indicator that is used in methods for visualizing differences in char-acteristics of nucleic acid sequences. Examples of other such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Markers further include polynucleotide sequences encoding 16S or 18S rRNA, and internal transcribed spacer (ITS) sequences, which are sequences found between small-subunit and large-subunit rRNA genes that have proven to be especially useful in elucidating relationships or distinctions when compared against one another. Furthermore, the dis-closure utilizes unique sequences found in genes of interest (e.g. nifH, D, K, L, A, glnE, amtB, etc.) to identify microbes disclosed herein.

The primary structure of major rRNA subunit 16S com-prise a particular combination of conserved, variable, and hypervariable regions that evolve at different rates and enable the resolution of both very ancient lineages such as domains, and more modern lineages such as genera. The secondary structure of the 16S subunit include approximately 50 helices which result in base pairing of about 67% of the residues. These highly conserved secondary structural features are of great functional importance and can be used to ensure positional homology in multiple sequence alignments and phylogenetic analysis. Over the previous few decades, the 16S rRNA gene has become the most sequenced taxonomic marker and is the cornerstone for the current systematic classification of bacteria and archaea (Yarza et al. 2014. Nature Rev. Micro. 12:635-45).

Thus, in certain aspects, the disclosure provides for a sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any sequence in Tables E, F, G, or H.

Thus, in certain aspects, the disclosure provides for a microbe that comprises a sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 62-303. These sequences and their associated descriptions can be found in Tables F, G, and H.

In some aspects, the disclosure provides for a microbe that comprises a 16S nucleic acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 85, 96, 111, 121, 122, 123, 124, 136, 149, 157, 167, 261, 262, 269, 277-283. These sequences and their associated descriptions can be found in Tables G and H.

In some aspects, the disclosure provides for a microbe that comprises a nucleic acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 86-95, 97-110, 112-120, 125-135, 137-148, 150-156, 158-166, 168-176, 263-268, 270-274, 275, 276, 284-295. These sequences and their associated descriptions can be found in Tables G and H.

In some aspects, the disclosure provides for a microbe that comprises a nucleic acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 177-260, 296-303. These sequences and their associated descriptions can be found in Tables G and H.

In some aspects, the disclosure provides for a microbe that comprises, or primer that comprises, or probe that comprises, or non-native junction sequence that comprises, a nucleic acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 304-424. These sequences and their associated descriptions can be found in Table E.

In some aspects, the disclosure provides for a microbe that comprises a non-native junction sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 372-405. These sequences and their associated descriptions can be found in Table E.

In some aspects, the disclosure provides for a microbe that comprises an amino acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 77, 78, 81, 82, or 83. These sequences and their associated descriptions can be found in Tables F and H.

Genetic Variation—Methods of Detection: Primers, Probes, and Assays

The present disclosure teaches primers, probes, and assays that are useful for detecting the microbes taught herein. In some aspects, the disclosure provides for methods of detecting the WT parental strains. In other aspects, the disclosure provides for methods of detecting the non-intergeneric engineered microbes derived from the WT strains. In aspects, the present disclosure provides methods of identifying non-intergeneric genetic alterations in a microbe.

In aspects, the genomic engineering methods of the present disclosure lead to the creation of non-natural nucleotide "junction" sequences in the derived non-intergeneric microbes. These non-naturally occurring nucleotide junctions can be used as a type of diagnostic that is indicative of the presence of a particular genetic alteration in a microbe taught herein.

The present techniques are able to detect these non-naturally occurring nucleotide junctions via the utilization of specialized quantitative PCR methods, including uniquely designed primers and probes. In some aspects, the probes of the disclosure bind to the non-naturally occurring nucleotide junction sequences. In some aspects, traditional PCR is utilized. In other aspects, real-time PCR is utilized. In some aspects, quantitative PCR (qPCR) is utilized.

Thus, the disclosure can cover the utilization of two common methods for the detection of PCR products in real-time: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence. In some aspects, only the non-naturally occurring nucleotide junction will be amplified via the taught primers, and consequently can be detected via either a non-specific dye, or via the utilization of a specific hybridization probe. In other aspects, the primers of the disclosure are chosen such that the primers flank either side of a junction sequence, such that if an amplification reaction occurs, then said junction sequence is present.

Aspects of the disclosure involve non-naturally occurring nucleotide junction sequence molecules per se, along with other nucleotide molecules that are capable of binding to said non-naturally occurring nucleotide junction sequences under mild to stringent hybridization conditions. In some aspects, the nucleotide molecules that are capable of binding to said non-naturally occurring nucleotide junction sequences under mild to stringent hybridization conditions are termed "nucleotide probes."

In aspects, genomic DNA can be extracted from samples and used to quantify the presence of microbes of the disclosure by using qPCR. The primers utilized in the qPCR reaction can be primers designed by Primer Blast (https://www.ncbi.nlm.nih.gov/tools/primer-blast/) to amplify unique regions of the wild-type genome or unique regions of the engineered non-intergeneric mutant strains. The qPCR reaction can be carried out using the SYBR GreenER qPCR SuperMix Universal (Thermo Fisher P/N 11762100) kit, using only forward and reverse amplification primers; alternatively, the Kapa Probe Force kit (Kapa Biosystems P/N KK4301) can be used with amplification primers and a TaqMan probe containing a FAM dye label at the 5' end, an internal ZEN quencher, and a minor groove binder and fluorescent quencher at the 3' end (Integrated DNA Technologies).

Certain primer, probe, and non-native junction sequences are listed in Table E. qPCR reaction efficiency can be measured using a standard curve generated from a known quantity of gDNA from the target genome. Data can be normalized to genome copies per g fresh weight using the tissue weight and extraction volume.

Quantitative polymerase chain reaction (qPCR) is a method of quantifying, in real time, the amplification of one or more nucleic acid sequences. The real time quantification of the PCR assay permits determination of the quantity of nucleic acids being generated by the PCR amplification steps by comparing the amplifying nucleic acids of interest and an appropriate control nucleic acid sequence, which may act as a calibration standard.

TaqMan probes are often utilized in qPCR assays that require an increased specificity for quantifying target nucleic acid sequences. TaqMan probes comprise a oligonucleotide probe with a fluorophore attached to the 5' end and a quencher attached to the 3' end of the probe. When the TaqMan probes remain as is with the 5' and 3' ends of the probe in close contact with each other, the quencher prevents fluorescent signal transmission from the fluorophore. TaqMan probes are designed to anneal within a nucleic acid region amplified by a specific set of primers. As the Taq polymerase extends the primer and synthesizes the nascent strand, the 5' to 3' exonuclease activity of the Taq polymerase degrades the probe that annealed to the template. This probe degradation releases the fluorophore, thus breaking the close proximity to the quencher and allowing fluorescence of the fluorophore. Fluorescence detected in the qPCR assay is directly proportional to the fluorophore released and the amount of DNA template present in the reaction.

The features of qPCR allow the practitioner to eliminate the labor-intensive post-amplification step of gel electrophoresis preparation, which is generally required for observation of the amplified products of traditional PCR assays. The benefits of qPCR over conventional PCR are considerable, and include increased speed, ease of use, reproducibility, and quantitative ability Improvement of Traits Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, resistance to nematode stress, resistance to a fungal pathogen, resistance to a bacterial pathogen, resistance to a viral pathogen, level of a metabolite, and proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the improved traits) grown under identical conditions.

A preferred trait to be introduced or improved is nitrogen fixation, as described herein. In some cases, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under the same conditions in the soil. In additional examples, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under similar conditions in the soil.

The trait to be improved may be assessed under conditions including the application of one or more biotic or abiotic stressors. Examples of stressors include abiotic stresses (such as heat stress, salt stress, drought stress, cold stress, and low nutrient stress) and biotic stresses (such as nematode stress, insect herbivory stress, fungal pathogen stress, bacterial pathogen stress, and viral pathogen stress).

The trait improved by methods and compositions of the present disclosure may be nitrogen fixation, including in a plant not previously capable of nitrogen fixation. In some cases, bacteria isolated according to a method described herein produce 1% or more (e.g. 2%, 3%, 4%, 5%, 6%, 7%, 8%, 9%, 10%, 15%, 20%, or more) of a plant's nitrogen, which may represent an increase in nitrogen fixation capability of at least 2-fold (e.g. 3-fold, 4-fold, 5-fold, 6-fold, 7-fold, 8-fold, 9-fold, 10-fold, 20-fold, 50-fold, 100-fold, 1000-fold, or more) as compared to bacteria isolated from the first plant before introducing any genetic variation. In some cases, the bacteria produce 5% or more of a plant's nitrogen. The desired level of nitrogen fixation may be achieved after repeating the steps of introducing genetic variation, exposure to a plurality of plants, and isolating bacteria from plants with an improved trait one or more times (e.g. 1, 2, 3, 4, 5, 10, 15, 25, or more times). In some cases, enhanced levels of nitrogen fixation are achieved in the presence of fertilizer supplemented with glutamine, ammonia, or other chemical source of nitrogen. Methods for assessing degree of nitrogen fixation are known, examples of which are described herein.

Microbe breeding is a method to systematically identify and improve the role of species within the crop microbiome. The method comprises three steps: 1) selection of candidate species by mapping plant-microbe interactions and predicting regulatory networks linked to a particular phenotype, 2) pragmatic and predictable improvement of microbial phenotypes through intra-species crossing of regulatory networks and gene clusters, and 3) screening and selection of new microbial genotypes that produce desired crop phenotypes. To systematically assess the improvement of strains, a model is created that links colonization dynamics of the microbial community to genetic activity by key species. The model is used to predict genetic targets breeding and improve the frequency of selecting improvements in micro-biome-encoded traits of agronomic relevance.

Measuring Nitrogen Delivered in an Agriculturally Relevant Field Context

In the field, the amount of nitrogen delivered can be determined by the function of colonization multiplied by the activity.

$$\text{Nitrogen delivered} = \int\limits_{\text{Time \& Space}} \text{Colonization} \times \text{Activity}$$

The above equation requires (1) the average colonization per unit of plant tissue, and (2) the activity as either the amount of nitrogen fixed or the amount of ammonia excreted by each microbial cell. To convert to pounds of nitrogen per acre, corn growth physiology is tracked over time, e.g., size of the plant and associated root system throughout the maturity stages.

The pounds of nitrogen delivered to a crop per acre-season can be calculated by the following equation:

$$\text{Nitrogen delivered} = \int \text{Plant Tissue}(t) \times \text{Colonization}(t) \times \text{Activity}(t) dt$$

The Plant Tissue(t) is the fresh weight of corn plant tissue over the growing time (t). Values for reasonably making the calculation are described in detail in the publication entitled Roots, Growth and Nutrient Uptake (Mengel. Dept. of Agronomy Pub. #AGRY-95-08 (Rev. May 1995. p. 1-8).

The Colonization (t) is the amount of the microbes of interest found within the plant tissue, per gram fresh weight of plant tissue, at any particular time, t, during the growing season. In the instance of only a single timepoint available, the single timepoint is normalized as the peak colonization rate over the season, and the colonization rate of the remaining timepoints are adjusted accordingly.

Activity(t) is the rate of which N is fixed by the microbes of interest per unit time, at any particular time, t, during the growing season. In the embodiments disclosed herein, this activity rate is approximated by in vitro acetylene reduction assay (ARA) in ARA media in the presence of 5 mM glutamine or Ammonium excretion assay in ARA media in the presence of 5 mM ammonium ions.

The Nitrogen delivered amount is then calculated by numerically integrating the above function. In cases where the values of the variables described above are discretely measured at set timepoints, the values in between those timepoints are approximated by performing linear interpolation.

Nitrogen Fixation

Described herein are methods of increasing nitrogen fixation in a plant, comprising exposing the plant to bacteria comprising one or more genetic variations introduced into one or more genes regulating nitrogen fixation, wherein the bacteria produce 1% or more of nitrogen in the plant (e.g. 2%, 5%, 10%, or more), which may represent a nitrogen-fixation capability of at least 2-fold as compared to the plant in the absence of the bacteria. The bacteria may produce the nitrogen in the presence of fertilizer supplemented with glutamine, urea, nitrates or ammonia. Genetic variations can be any genetic variation described herein, including examples provided above, in any number and any combination. The genetic variation may be introduced into a gene selected from the group consisting of nifA, nifL, ntrB, ntrC, glutamine synthetase, glnA, glnB, glnK, draT, amtB, gluta-minase, glnD, glnE, nifJ, nifH, nifD, nifK, nifY, nifE, nifN, nifU, nifS, nifV, nifW, nifZ, nifM, nifF, nifB, and nifQ. The genetic variation may be a mutation that results in one or more of: increased expression or activity of nifA or gluta-minase; decreased expression or activity of nifL, ntrB, glutamine synthetase, glnB, glnK, draT, amtB; decreased adenylyl-removing activity of GlnE; or decreased uridylyl-removing activity of GlnD. The genetic variation introduced into one or more bacteria of the methods disclosed herein may be a knock-out mutation or it may abolish a regulatory sequence of a target gene, or it may comprise insertion of a heterologous regulatory sequence, for example, insertion of a regulatory sequence found within the genome of the same bacterial species or genus. The regulatory sequence can be chosen based on the expression level of a gene in a bacterial culture or within plant tissue. The genetic variation may be produced by chemical mutagenesis. The plants grown in step (c) may be exposed to biotic or abiotic stressors.

The amount of nitrogen fixation that occurs in the plants described herein may be measured in several ways, for example by an acetylene-reduction (AR) assay. An acety-lene-reduction assay can be performed in vitro or in vivo. Evidence that a particular bacterium is providing fixed nitrogen to a plant can include: 1) total plant N significantly increases upon inoculation, preferably with a concomitant increase in N concentration in the plant; 2) nitrogen defi-ciency symptoms are relieved under N-limiting conditions upon inoculation (which should include an increase in dry matter); 3) $N_2$ fixation is documented through the use of an $^{15}N$ approach (which can be isotope dilution experiments, $^{15}N_2$ reduction assays, or $^{15}N$ natural abundance assays); 4) fixed N is incorporated into a plant protein or metabolite; and 5) all of these effects are not be seen in non-inoculated plants or in plants inoculated with a mutant of the inoculum strain.

The wild-type nitrogen fixation regulatory cascade can be represented as a digital logic circuit where the inputs $O_2$ and $NH_4^+$ pass through a NOR gate, the output of which enters an AND gate in addition to ATP. In some embodiments, the methods disclosed herein disrupt the influence of $NH_4^+$ on this circuit, at multiple points in the regulatory cascade, so that microbes can produce nitrogen even in fertilized fields. However, the methods disclosed herein also envision alter-ing the impact of ATP or $O_2$ on the circuitry, or replacing the circuitry with other regulatory cascades in the cell, or altering genetic circuits other than nitrogen fixation. Gene clusters can be re-engineered to generate functional products under the control of a heterologous regulatory system. By eliminating native regulatory elements outside of, and within, coding sequences of gene clusters, and replacing them with alternative regulatory systems, the functional products of complex genetic operons and other gene clusters can be controlled and/or moved to heterologous cells, including cells of different species other than the species from which the native genes were derived. Once re-engi-neered, the synthetic gene clusters can be controlled by genetic circuits or other inducible regulatory systems, thereby controlling the products' expression as desired. The expression cassettes can be designed to act as logic gates, pulse generators, oscillators, switches, or memory devices. The controlling expression cassette can be linked to a promoter such that the expression cassette functions as an environmental sensor, such as an oxygen, temperature, touch, osmotic stress, membrane stress, or redox sensor.

As an example, the nifL, nifA, nifT, and nifX genes can be eliminated from the nif gene cluster. Synthetic genes can be designed by codon randomizing the DNA encoding each amino acid sequence. Codon selection is performed, specifying that codon usage be as divergent as possible from the codon usage in the native gene. Proposed sequences are scanned for any undesired features, such as restriction enzyme recognition sites, transposon recognition sites, repetitive sequences, sigma 54 and sigma 70 promoters, cryptic ribosome binding sites, and rho independent terminators. Synthetic ribosome binding sites are chosen to match the strength of each corresponding native ribosome binding site, such as by constructing a fluorescent reporter plasmid in which the 150 bp surrounding a gene's start codon (from −60 to +90) is fused to a fluorescent gene. This chimera can be expressed under control of the Ptac promoter, and fluorescence measured via flow cytometry. To generate synthetic ribosome binding sites, a library of reporter plasmids using 150 bp (−60 to +90) of a synthetic expression cassette is generated. Briefly, a synthetic expression cassette can consist of a random DNA spacer, a degenerate sequence encoding an RBS library, and the coding sequence for each synthetic gene. Multiple clones are screened to identify the synthetic ribosome binding site that best matched the native ribosome binding site. Synthetic operons that consist of the same genes as the native operons are thus constructed and tested for functional complementation. A further exemplary description of synthetic operons is provided in US20140329326.

Bacterial Species

Microbes useful in the methods and compositions disclosed herein may be obtained from any source. In some cases, microbes may be bacteria, archaea, protozoa or fungi. The microbes of this disclosure may be nitrogen fixing microbes, for example a nitrogen fixing bacteria, nitrogen fixing archaea, nitrogen fixing fungi, nitrogen fixing yeast, or nitrogen fixing protozoa. Microbes useful in the methods and compositions disclosed herein may be spore forming microbes, for example spore forming bacteria. In some cases, bacteria useful in the methods and compositions disclosed herein may be Gram positive bacteria or Gram negative bacteria. In some cases, the bacteria may be an endospore forming bacteria of the Firmicute phylum. In some cases, the bacteria may be a diazotroph. In some cases, the bacteria may not be a diazotroph.

The methods and compositions of this disclosure may be used with an archaea, such as, for example, *Methanothermobacter thermoautotrophicus*.

In some cases, bacteria which may be useful include, but are not limited to, *Agrobacterium radiobacter, Bacillus acidocalciarius, Bacillus acidoterrestris, Bacillus agri, Bacillus aizawai, Bacillus albolactis, Bacillus alcalophilus, Bacillus alvei, Bacillus aminoglucosidicus, Bacillus aminovorans, Bacillus amylolyticus* (also known as *Paenibacillus amylolyticus*) *Bacillus amyloliquefaciens, Bacillus aneurinolyticus, Bacillus atrophaens, Bacillus azoiatarmans, Bacillus badius, Bacillus cereus* (synonyms: *Bacillus endorhythmos, Bacillus medusa*), *Bacillus chitinosporus, Bacillus circulans, Bacillus coagulans, Bacillus endoparasiticus Bacillus fastidiosus, Bacillus firmus, Bacillus kurstaki, Bacillus lacticola, Bacillus lactimorbus, Bacillus lactis, Bacillus laterosporus* (also known as *Brevibacillus laterosporus*), *Bacillus lautus, Bacillus lentimorbus, Bacillus lentils, Bacillus lichenformis, Bacillus maroccanus, Bacillus megaterium, Bacillus metiens, Bacillus mycoides, Bacillus natto, Bacillus nematocida, Bacillus nigrificans, Bacillus nigrum, Bacillus pantothenticus, Bacillus popillae, Bacillus pychrosaccharolyticus, Bacillus pumilus, Bacillus siamensis, Bacillus smithii, Bacillus sphaericus, Bacillus thuringiensis, Bacillus uniflagellants, Bradyrhizobium japonicum, Brevibacillus brevis Brevibacillus laterosporus* (formerly *Bacillus laterosporus*), *Chromobacterium subtsugae, Delftia acidovorans, Lactobacillus acidophilus, Lysobacter antibioticus, Lysobacter enzymogenes, Paenibacillus alvei, Paenibacillus polymyxa, Paenibacillus popilliae* (formerly *Bacillus popilliae*), *Pantoea agglomerans, Pasteuria penetrans* (formerly *Bacillus penetrans*), *Pasteuria usgae, Pecobacterium carotovorum* (formerly *Erwinia carotovora*), *Pseudomonas aeruginosa, Pseudomonas aureofaciens, Pseudomonas cepacia* (formerly known as *Burkholderia cepacia*), *Pseudomonas chlororaphis, Pseudomonas fluorescens, Pseudomonas proradix, Pseudomonas putida, Pseudomonas syringae, Serratia entomophila, Serratia marcescens, Streptomyces colombiensis, Strepomyces galbus, Streptomyces goshikiensis, Streptomyces griseoviridis, Streptomyces lavendulae, Streptomyces prasinus, Streptomyces saraceticus, Streptomyces venezuelae, Xanthomonas campestris, Xenorhabdus luminescens, Xenorhabdus neinatophila, Rhodococcus globerulus* AQ719 (NRRL Accession No. B-21663), *Bacillus* sp. AQ175 (ATCC Accession No. 55608), *Bacillus* sp. AQ 177 (ATCC Accession No. 55609), *Bacillus* sp. AQ178 (ATCC Accession No. 53522), and *Streptomyces* sp. strain NRRL Accession No. B-30145. In some cases the bacterium may be *Azotobacter chroococcum, Methanosarcina barkeri, Klesiella pneumoniae, Azotobacter vinelandii, Rhodobacter spharoides, Rhodobacter capsulatus, Rhodobcter palustris, Rhodosporillum rubrum, Rhizobium leguminosarum* or *Rhizobium etli*.

In some cases the bacterium may be a species of *Clostridium*, for example *Clostridium pasteurianum, Clostridium beijerinckii, Clostridium perfringens, Clostridium tetani, Clostridium acetobutylicum*.

In some cases, bacteria used with the methods and compositions of the present disclosure may be cyanobacteria. Examples of cyanobacterial genuses include *Anabaena* (for example *Anagaena* sp. PCC7120), *Nostoc* (for example *Nostoc punctiforme*), or *Synechocystis* (for example *Synechocystis* sp. PCC6803).

In some cases, bacteria used with the methods and compositions of the present disclosure may belong to the phylum Chlorobi, for example *Chlorobium tepidum*.

In some cases, microbes used with the methods and compositions of the present disclosure may comprise a gene homologous to a known NifH gene. Sequences of known NifH genes may be found in, for example, the Zehr lab NifH database, (https://www.zehr.pmc.ucsc.edu/nifH_Database_Public/, Apr. 4, 2014), or the Buckley lab NifH database (http://www.css.cornell.edu/faculty/buckley/nifh.htm, and Gaby, John Christian, and Daniel H. Buckley. "A comprehensive aligned nifH gene database: a multipurpose tool for studies of nitrogen-fixing bacteria," *Database* 2014 (2014): bau001). In some cases, microbes used with the methods and compositions of the present disclosure may comprise a sequence which encodes a polypeptide with at least 60%, 70%, 80%, 85%, 90%, 95%, 96%, 96%, 98%, 99% or more than 99% sequence identity to a sequence from the Zehr lab NifH database, (https://wwwzehr.pmc.ucsc.edu/nifH_Database_Public/Apr. 4, 2014). In some cases, microbes used with the methods and compositions of the present disclosure may comprise a sequence which encodes a polypeptide with at least 60%, 70%, 80%, 85%, 90%, 95%, 96%, 96%, 98%, 99% or more than 99% sequence identity to a sequence from the Buckley lab NifH database, (Gaby, John Christian, and Daniel H. Buckley. "A comprehensive aligned nifH gene database: a multipurpose tool for studies of nitrogen-fixing bacteria." *Database* 2014 (2014): bau0011).

Microbes useful in the methods and compositions disclosed herein can be obtained by extracting microbes from surfaces or tissues of native plants; grinding seeds to isolate microbes; planting seeds in diverse soil samples and recovering microbes from tissues; or inoculating plants with exogenous microbes and determining which microbes appear in plant tissues. Non-limiting examples of plant tissues include a seed, seedling, leaf, cutting, plant, bulb or tuber. In some cases, bacteria are isolated from a seed. The parameters for processing samples may be varied to isolate different types of associative microbes, such as rhizospheric, epiphytes, or endophytes. Bacteria may also be sourced from a repository, such as environmental strain collections, instead of initially isolating from a first plant. The microbes can be genotyped and phenotyped, via sequencing the genomes of isolated microbes; profiling the composition of communities in planta; characterizing the transcriptomic functionality of communities or isolated microbes; or screening microbial features using selective or phenotypic media (e.g., nitrogen fixation or phosphate solubilization phenotypes). Selected candidate strains or populations can be obtained via sequence data; phenotype data; plant data (e.g., genome, phenotype, and/or yield data); soil data (e.g., pH, N/P/K content, and/or bulk soil biotic communities); or any combination of these.

The bacteria and methods of producing bacteria described herein may apply to bacteria able to self-propagate efficiently on the leaf surface, root surface, or inside plant tissues without inducing a damaging plant defense reaction, or bacteria that are resistant to plant defense responses. The bacteria described herein may be isolated by culturing a plant tissue extract or leaf surface wash in a medium with no added nitrogen. However, the bacteria may be unculturable, that is, not known to be culturable or difficult to culture using standard methods known in the art. The bacteria described herein may be an endophyte or an epiphyte or a bacterium inhabiting the plant rhizosphere (rhizospheric bacteria). The bacteria obtained after repeating the steps of introducing genetic variation, exposure to a plurality of plants, and isolating bacteria from plants with an improved trait one or more times (e.g. 1, 2, 3, 4, 5, 10, 15, 25, or more times) may be endophytic, epiphytic, or rhizospheric. Endophytes are organisms that enter the interior of plants without causing disease symptoms or eliciting the formation of symbiotic structures, and are of agronomic interest because they can enhance plant growth and improve the nutrition of plants (e.g., through nitrogen fixation). The bacteria can be a seed-borne endophyte. Seed-borne endophytes include bacteria associated with or derived from the seed of a grass or plant, such as a seed-borne bacterial endophyte found in mature, dry, undamaged (e.g., no cracks, visible fungal infection, or prematurely germinated) seeds. The seed-borne bacterial endophyte can be associated with or derived from the surface of the seed; alternatively, or in addition, it can be associated with or derived from the interior seed compartment (e.g., of a surface-sterilized seed). In some cases, a seed-borne bacterial endophyte is capable of replicating within the plant tissue, for example, the interior of the seed. Also, in some cases, the seed-borne bacterial endophyte is capable of surviving desiccation.

The bacterial isolated according to methods of the disclosure, or used in methods or compositions of the disclosure, can comprise a plurality of different bacterial taxa in combination. By way of example, the bacteria may include Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas*), Firmicutes (such as *Bacillus, Pae-*

*nibacillus, Lactobacillus, Mycoplasma*, and *Acetabacterium*), and Actinobacteria (such as *Streptomyces, Rhodacoccus, Microbacterium*, and *Curtobacterium*). The bacteria used in methods and compositions of this disclosure may include nitrogen fixing bacterial consortia of two or more species. In some cases, one or more bacterial species of the bacterial consortia may be capable of fixing nitrogen. In some cases, one or more species of the bacterial consortia may facilitate or enhance the ability of other bacteria to fix nitrogen. The bacteria which fix nitrogen and the bacteria which enhance the ability of other bacteria to fix nitrogen may be the same or different. In some examples, a bacterial strain may be able to fix nitrogen when in combination with a different bacterial strain, or in a certain bacterial consortia, but may be unable to fix nitrogen in a monoculture. Examples of bacterial genuses which may be found in a nitrogen fixing bacterial consortia include, but are not limited to, *Herbaspirillum, Azospirillum, Enterobacter*, and *Bacillus*.

Bacteria that can be produced by the methods disclosed herein include *Azotobacter* sp., *Bradyrhizobium* sp., *Klebsiella* sp., and *Sinorhizobium* sp. In some cases, the bacteria may be selected from the group consisting of: *Azotobacter vinelandii, Bradyrhizobium japonicum, Klebsiella pneumoniae*, and *Sinorhizobium meliloti*. In some cases, the bacteria may be of the genus *Enterobacter* or *Rahnella*. In some cases, the bacteria may be of the genus *Frankia*, or *Clostridium*. Examples of bacteria of the genus *Clostridium* include, but are not limited to, *Clostridium acetobutilicum, Clostridium pasteurianum, Clostridium beijerinckii, Clostridium perfringens*, and *Clostridium tetani*. In some cases, the bacteria may be of the genus *Paenibacillus*, for example *Paenibacillus azotofixans, Paenibacillus borealis, Paenibacillus durus, Paenibacillus macerans, Paenibacillus polymyxa, Paenibacillus alvei, Paenibacillus amylolyticus, Paenibacillus campinasensis, Paenibacillus chibensis, Paenibacillus glucanolyticus, Paenibacillus illinoisensis, Paenibacillus larvae* sub sp. *Larvae, Paenibacillus larvae* sub sp. *Pulvifaciens, Paenibacillus lautus, Paenibacillus macerans, Paenibacillus macquariensis, Paenibacillus macquariensis, Paenibacillus pabuli, Paenibacillus peoriae*, or *Paenibacillus polymyxa*.

In some examples, bacteria isolated according to methods of the disclosure can be a member of one or more of the following taxa: *Achromobacter, Acidithiobacillus, Acidovorax, Acidovoraz, Acinetobacter, Actinoplanes, Adlercreutzia, Aerococcus, Aeromonas, Afipia, Agromyces, Ancylobacter, Arthrobacter, Atopostipes, Azospirillum, Bacillus, Bdellovibrio, Beijerinckia, Bosea, Bradyrhizobium, Brevibacillus, Brevundimonas, Burkholderia, Candidatus Haloredivivus, Caulobacter, Cellulomonas, Cellvibrio, Chryseobacterium, Citrobacter, Clostridium, Coraliomargarita, Corynebacterium, Cupriavidus, Curtobacterium, Curvibacter, Deinococcus, Delftia, Desemzia, Devosia, Dokdonella, Dyella, Enhydrobacter, Enterobacter, Enterococcus, Envinia, Escherichia, Escherichia/Shigella, Exiguobacterium, Ferroglobus, Filimonas, Finegoldia, Flavisolibacter, Flavobacterium, Frigoribacterium, Gluconacetobacter, Hafnia, Halobaculum, Halomonas, Halosimplex, Herbaspirillum, Hymenobacter, Klebsiella, Kocuria, Kosakonia, Lactobacillus, Leclercia, Lentzea, Luteibacter, Luteimonas, Massilia, Mesorhizobium, Methylobacterium, Microbacterium, Micrococcus, Microvirga, Mycobacterium, Neisseria, Nocardia, Oceanibaculum, Ochrobactrum, Okibacterium, Oligotropha, Oryzihumus, Oxalophagus, Paenibacillus, Panteoa, Pantoea, Pelomonas, Perlucidibaca, Plantibacter, Polynucleobacter, Propionibacterium, Propioniciclava,*

*Pseudoclavibacter, Pseudomonas, Pseudonocardia, Pseudoxanthomonas, Psychrobacter, Rahnella, Ralstonia, Rheinheimera, Rhizobium, Rhodococcus, Rhodopseudomonas, Roseateles, Ruminococcus, Sebaldella, Sediminibacillus, Sediminibacterium, Serratia, Shigella, Shinella, Sinorhizobium, Sinosporangium, Sphingobacterium, Sphingomonas, Sphingopyxis, Sphingosinicella, Staphylococcus,* 25 *Stenotrophomonas, Strenotrophomonas, Streptococcus, Streptomyces, Stygiolobus, Sulfurisphaera, Tatumella, Tepidimonas, Thermomonas, Thiobacillus, Variovorax,* WPS-2 genera *incertae sedis, Xanthomonas,* and *Zimmermannella.*

In some cases, a bacterial species selected from at least one of the following genera are utilized: *Enterobacter, Klebsiella, Kosakonia,* and *Rahnella.* In some cases, a combination of bacterial species from the following genera are utilized: *Enterobacter, Klebsiella, Kosakonia,* and *Rahnella.* In some cases, the species utilized can be one or more of: *Enterobacter sacchari, Klebsiella variicola, Kosakonia sacchari,* and *Rahnella aquatilis.*

In some cases, a Gram positive microbe may have a Molybdenum-Iron nitrogenase system comprising: nifH, nifD, nifK, nifB, nifE, nifN, nifX, hesA, nifV, nifW, nifU, nifS, nifI1, and nifI2. In some cases, a Gram positive microbe may have a vanadium nitrogenase system comprising: vnfDG, vnfK, vnfE, vnfN, vupC, vupB, vupA, vnfV, vnfR1, vnfH, vnfR2, vnfA (transcriptional regulator). In some cases, a Gram positive microbe may have an iron-only nitrogenase system comprising: anfK, anfG, anfD, anfH, anfA (transcriptional regulator). In some cases a Gram positive microbe may have a nitrogenase system comprising glnB, and glnK (nitrogen signaling proteins). Some examples of enzymes involved in nitrogen metabolism in Gram positive microbes include glnA (glutamine synthetase), gdh (glutamate dehydrogenase), bdh (3-hydroxy-butyrate dehydrogenase), glutaminase, gltAB/gltB/gltS (glutamate synthase), asnA/asnB (aspartate-ammonia ligase/asparagine synthetase), and ansA/ansZ (asparaginase). Some examples of proteins involved in nitrogen transport in Gram positive microbes include amtB (ammonium transporter), glnK (regulator of ammonium transport), glnPHQ/glnQHMP (ATP-dependent glutamine/glutamate transporters), glnT/alsT/yrbD/yflA (glutamine-like proton symport transporters), and gltP/gltT/yhcl/nqt (glutamate-like proton symport transporters).

Examples of Gram positive microbes which may be of particular interest include *Paenibacillus polymixa, Paenibacillus riograndensis, Paenibacillus* sp., *Frankia* sp., *Heliobacterium* sp., *Heliobacterium chlorum, Heliobacillus* sp., *Heliophilum* sp., *Heliorestis* sp., *Clostridium acetobutylicum, Clostridium* sp., *Mycobacterium flaum, Mycobacterium* sp., *Arthrobacter* sp., *Agromyces* sp., *Corynebacterium autitrophicum, Corynebacterium* sp., *Micromonspora* sp., *Propionibacteria* sp., *Streptomyces* sp., and *Microbacterium* sp.

Some examples of genetic alterations which may be make in Gram positive microbes include: deleting glnR to remove negative regulation of BNF in the presence of environmental nitrogen, inserting different promoters directly upstream of the nif cluster to eliminate regulation by GlnR in response to environmental nitrogen, mutating glnA to reduce the rate of ammonium assimilation by the GS-GOGAT pathway, deleting amtB to reduce uptake of ammonium from the media, mutating glnA so it is constitutively in the feedback-inhibited (FBI-GS) state, to reduce ammonium assimilation by the GS-GOGAT pathway.

In some cases, glnR is the main regulator of N metabolism and fixation in *Paenibacillus* species. In some cases, the genome of a *Paenibacillus* species may not contain a gene to produce glnR. In some cases, the genome of a *Paenibacillus* species may not contain a gene to produce glnE or glnD. In some cases, the genome of a *Paenibacillus* species may contain a gene to produce glnB or glnK. For example *Paenibacillus* sp. WLY78 doesn't contain a gene for glnB, or its homologs found in the archaeon *Methanococcus maripaludis*, nifI1 and nifI2. In some cases, the genomes of *Paenibacillus* species may be variable. For example, *Paenibacillus polymixa* E681 lacks glnK and gdh, has several nitrogen compound transporters, but only amtB appears to be controlled by GlnR. In another example, *Paenibacillus* sp. JDR2 has glnK, gdh and most other central nitrogen metabolism genes, has many fewer nitrogen compound transporters, but does have glnPHQ controlled by GlnR. *Paenibacillus riograndensis* SBR5 contains a standard glnRA operon, an fdx gene, a main nif operon, a secondary nif operon, and an anf operon (encoding iron-only nitrogenase). Putative glnR/tnrA sites were found upstream of each of these operons. GlnR may regulate all of the above operons, except the anf operon. GlnR may bind to each of these regulatory sequences as a dimer.

*Paenibacillus* N-fixing strains may fall into two subgroups: Subgroup I, which contains only a minimal nif gene cluster and subgroup II, which contains a minimal cluster, plus an uncharacterized gene between nifX and hesA, and often other clusters duplicating some of the nif genes, such as nifH, nifHDK, nifBEN, or clusters encoding vanadium nitrogenase (vnf) or iron-only nitrogenase (anf) genes.

In some cases, the genome of a *Paenibacillus* species may not contain a gene to produce glnB or glnK. In some cases, the genome of a *Paenibacillus* species may contain a minimal nif cluster with 9 genes transcribed from a sigma-70 promoter. In some cases a *Paenibacillus* nif cluster may be negatively regulated by nitrogen or oxygen. In some cases, the genome of a *Paenibacillus* species may not contain a gene to produce sigma-54. For example, *Paenibacillus* sp. WLY78 does not contain a gene for sigma-54. In some cases, a nif cluster may be regulated by glnR, and/or TnrA. In some cases, activity of a nif cluster may be altered by altering activity of glnR, and/or TnrA.

In Bacilli, glutamine synthetase (GS) is feedback-inhibited by high concentrations of intracellular glutamine, causing a shift in confirmation (referred to as FBI-GS). Nif clusters contain distinct binding sites for the regulators GlnR and TnrA in several Bacilli species. GlnR binds and represses gene expression in the presence of excess intracellular glutamine and AMP. A role of GlnR may be to prevent the influx and intracellular production of glutamine and ammonium under conditions of high nitrogen availability. TnrA may bind and/or activate (or repress) gene expression in the presence of limiting intracellular glutamine, and/or in the presence of FBI-GS. In some cases the activity of a Bacilli nif cluster may be altered by altering the activity of GlnR.

Feedback-inhibited glutamine synthetase (FBI-GS) may bind GlnR and stabilize binding of GlnR to recognition sequences. Several bacterial species have a GlnR/TnrA binding site upstream of the nif cluster. Altering the binding of FBI-GS and GlnR may alter the activity of the nif pathway.

Sources of Microbes

The bacteria (or any microbe according to the disclosure) may be obtained from any general terrestrial environment, including its soils, plants, fungi, animals (including invertebrates) and other biota, including the sediments, water and biota of lakes and rivers; from the marine environment, its biota and sediments (for example, sea water, marine muds, marine plants, marine invertebrates (for example, sponges), marine vertebrates (for example, fish)); the terrestrial and marine geosphere (regolith and rock, for example, crushed subterranean rocks, sand and clays); the cryosphere and its meltwater; the atmosphere (for example, filtered aerial dusts, cloud and rain droplets); urban, industrial and other man-made environments (for example, accumulated organic and mineral matter on concrete, roadside gutters, roof surfaces, and road surfaces).

The plants from which the bacteria (or any microbe according to the disclosure) are obtained may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the bacteria may be collected from commercial crops grown in such environments, or more specifically from individual crop plants best displaying a trait of interest amongst a crop grown in any specific environment: for example the fastest-growing plants amongst a crop grown in saline-limiting soils, or the least damaged plants in crops exposed to severe insect damage or disease epidemic, or plants having desired quantities of certain metabolites and other compounds, including fiber content, oil content, and the like, or plants displaying desirable colors, taste or smell. The bacteria may be collected from a plant of interest or any material occurring in the environment of interest, including fungi and other animal and plant biota, soil, water, sediments, and other elements of the environment as referred to previously.

The bacteria (or any microbe according to the disclosure) may be isolated from plant tissue. This isolation can occur from any appropriate tissue in the plant, including for example root, stem and leaves, and plant reproductive tissues. By way of example, conventional methods for isolation from plants typically include the sterile excision of the plant material of interest (e.g. root or stem lengths, leaves), surface sterilization with an appropriate solution (e.g. 2% sodium hypochlorite), after which the plant material is placed on nutrient medium for microbial growth. Alternatively, the surface-sterilized plant material can be crushed in a sterile liquid (usually water) and the liquid suspension, including small pieces of the crushed plant material spread over the surface of a suitable solid agar medium, or media, which may or may not be selective (e.g. contain only phytic acid as a source of phosphorus). This approach is especially useful for bacteria which form isolated colonies and can be picked off individually to separate plates of nutrient medium, and further purified to a single species by well-known methods. Alternatively, the plant root or foliage samples may not be surface sterilized but only washed gently thus including surface-dwelling epiphytic microorganisms in the isolation process, or the epiphytic microbes can be isolated separately, by imprinting and lifting off pieces of plant roots, stem or leaves onto the surface of an agar medium and then isolating individual colonies as above. This approach is especially useful for bacteria, for example. Alternatively, the roots may be processed without washing off small quantities of soil attached to the roots, thus including microbes that colonize the plant rhizosphere. Otherwise, soil adhering to the roots can be removed, diluted and spread out onto agar of suitable selective and non-selective media to isolate individual colonies of rhizospheric bacteria.

Budapest Treaty on the International Recognition of the Deposit of Microorganisms for the Purpose of Patent Procedures The microbial deposits of the present disclosure were made under the provisions of the Budapest Treaty on the International Recognition of the Deposit of Microorganisms for the Purpose of Patent Procedure (Budapest Treaty).

Applicants state that pursuant to 37 C.F.R. § 1.808(a)(2) "all restrictions imposed by the depositor on the availability to the public of the deposited material will be irrevocably removed upon the granting of the patent." This statement is subject to paragraph (b) of this section (i.e. 37 C.F.R. § 1.808(b)).

Biologically pure cultures of *Rahnella aquatilis* and *Enterobacter sacchari* were deposited on Jul. 14, 2015 with the American Type Culture Collection (ATCC; an International Depositary Authority), 10801 University Blvd., Manassas, VA 20110, USA, and assigned ATTC Patent Deposit Designation numbers PTA-122293 and PTA-122294, respectively. The applicable deposit information is found below in Table A.

The *Enterobacter sacchari* has now been reclassified as *Kosakonia sacchari*, the name for the organism may be used interchangeably throughout the manuscript.

Figure 18:
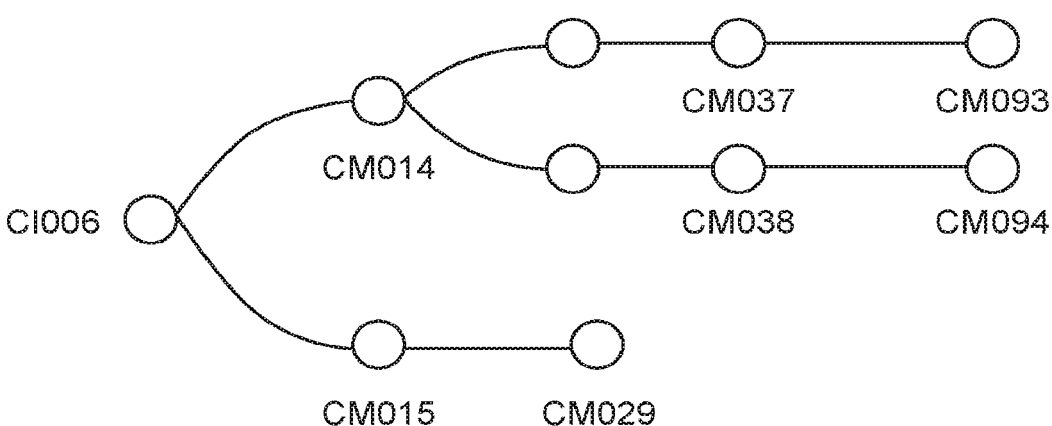
FIG. 18 depicts the lineage of modified strains that were derived from strain CI006.
Figure 19:
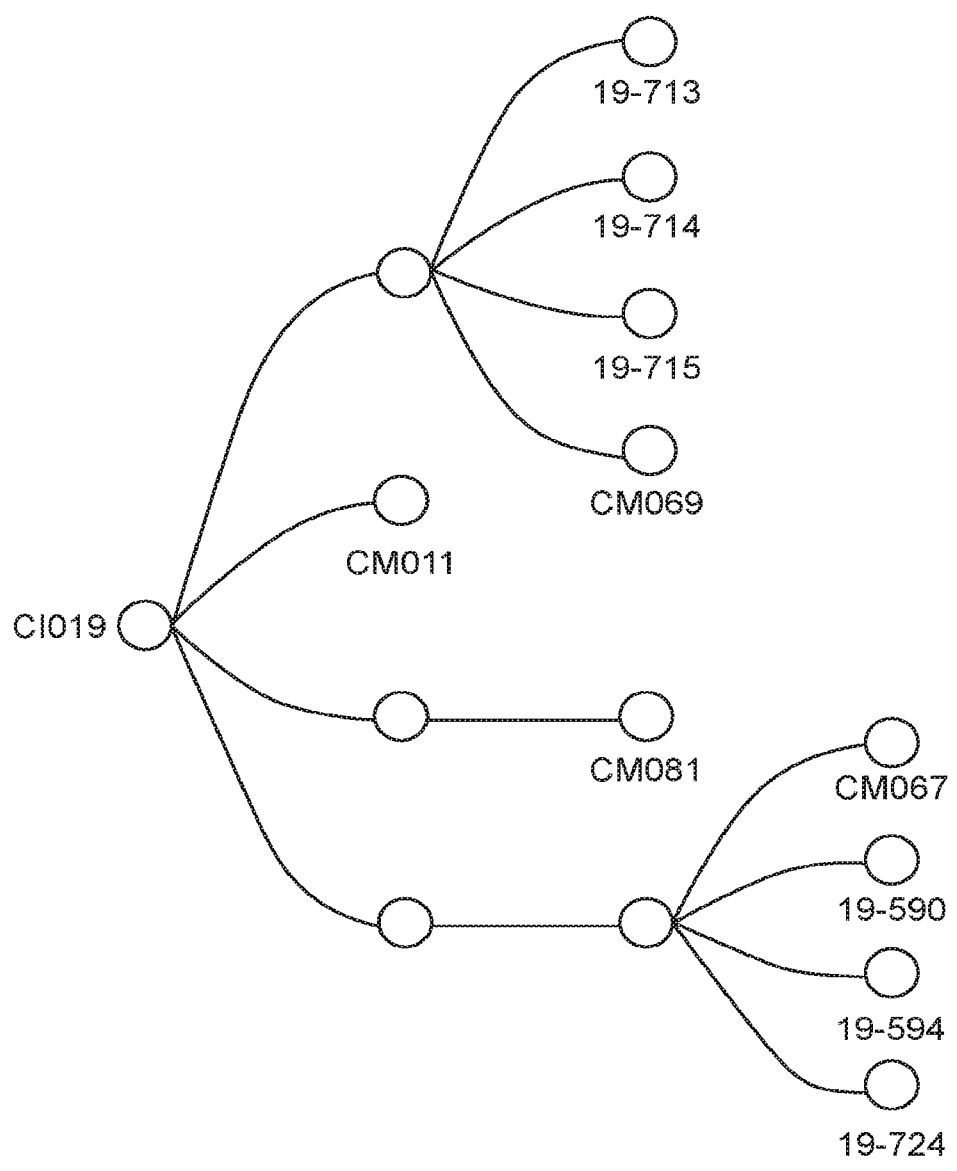
FIG. 19 depicts the lineage of modified strains that were derived from strain CI019.

Many microbes of the present disclosure are derived from two wild-type strains, as depicted in FIG. 18 and FIG. 19. Strain CI006 is a bacterial species previously classified in the genus *Enterobacter* (see aforementioned reclassification into *Kosakonia*), and FIG. 19 identifies the lineage of the mutants that have been derived from CI006. Strain CI019 is a bacterial species classified in the genus *Rahnella*, and FIG. 19 identifies the lineage of the mutants that have been derived from CI019. With regard to FIG. 18 and FIG. 19, it is noted that strains comprising CM in the name are mutants of the strains depicted immediately to the left of said CM strain. The deposit information for the CI006 *Kosakonia* wild type (WT) and CI019 *Rahnella* WT are found in the below Table A.

Some microorganisms described in this application were deposited on Jan. 6, 2017 or Aug. 11, 2017 with the Bigelow National Center for Marine Algae and Microbiota (NCMA), located at 60 Bigelow Drive, East Boothbay, Maine 04544, USA. As aforementioned, all deposits were made under the terms of the Budapest Treaty on the International Recognition of the Deposit of Microorganisms for the Purposes of Patent Procedure. The Bigelow National Center for Marine Algae and Microbiota accession numbers and dates of deposit for the aforementioned Budapest Treaty deposits are provided in Table A.

Biologically pure cultures of *Kosakonia sacchari* (WT), *Rahnella aquatilis* (WT), and a variant *Kosakonia sacchari* strain were deposited on Jan. 6, 2017 with the Bigelow National Center for Marine Algae and Microbiota (NCMA), located at 60 Bigelow Drive, East Boothbay, Maine 04544, USA, and assigned NCMA Patent Deposit Designation numbers 201701001, 201701003, and 201701002, respectively. The applicable deposit information is found below in Table A.

Biologically pure cultures of variant *Kosakonia sacchari* strains were deposited on Aug. 11, 2017 with the Bigelow National Center for Marine Algae and Microbiota (NCMA), located at 60 Bigelow Drive, East Boothbay, Maine 04544, USA, and assigned NCMA Patent Deposit Designation numbers 201708004, 201708003, and 201708002, respectively. The applicable deposit information is found below in Table A.

A biologically pure culture of *Klebsiella variicola* (WT) was deposited on Aug. 11, 2017 with the Bigelow National Center for Marine Algae and Microbiota (NCMA), located at 60 Bigelow Drive, East Boothbay, Maine 04544, USA, and assigned NCMA Patent Deposit Designation number 201708001. Biologically pure cultures of two *Klebsiella variicola* variants were deposited on Dec. 20, 2017 with the Bigelow National Center for Marine Algae and Microbiota (NCMA), located at 60 Bigelow Drive, East Boothbay, Maine 04544, USA, and assigned NCMA Patent Deposit Designation numbers 201712001 and 201712002, respectively. The applicable deposit information is found below in Table A.

Compositions

Compositions comprising bacteria or bacterial populations produced according to methods described herein and/or having characteristics as described herein can be in the form of a liquid, a foam, or a dry product. Compositions comprising bacteria or bacterial populations produced according to methods described herein and/or having characteristics as described herein may also be used to improve plant traits. In some examples, a composition comprising bacterial populations may be in the form of a dry powder, a slurry of powder and water, or a flowable seed treatment. The compositions comprising bacterial populations may be coated on a surface of a seed, and may be in liquid form.

The composition can be fabricated in bioreactors such as continuous stirred tank reactors, batch reactors, and on the farm. In some examples, compositions can be stored in a

TABLE A

| | | Microorganisms Deposited under the Budapest Treaty | | |
|---|---|---|---|---|
| Depository | Pivot Strain Designation (some strains have multiple designations) | Taxonomy | Accession Number | Date of Deposit |
| ATCC | | *Rahnella aquatilis* | PTA-122293 | Jul. 14, 2015 |
| ATCC | | *Enterobacter sacchari* (taxonomically reclassified after deposit as *Kosakonia sacchari*) | PTA-122294 | Jul. 14, 2015 |
| NCMA | CI006, PBC6.1, 6 | *Kosakonia sacchari* (WT) | 201701001 | Jan. 6, 2017 |
| NCMA | CI019, 19 | *Rahnella aquatilis* (WT) | 201701003 | Jan. 6, 2017 |
| NCMA | CM029, 6-412 | *Kosakonia sacchari* | 201701002 | Jan. 6, 2017 |
| NCMA | 6-403 CM037 | *Kosakonia sacchari* | 201708004 | Aug. 11, 2017 |
| NCMA | 6-404, CM38, PBC6.38 | *Kosakonia sacchari* | 201708003 | Aug. 11, 2017 |
| NCMA | CM094, 6-881, PBC6.94 | *Kosakonia sacchari* | 201708002 | Aug. 11, 2017 |
| NCMA | CI137, 137, PB137 | *Klebsiella variicola* (WT) | 201708001 | Aug. 11, 2017 |
| NCMA | 137-1034 | *Klebsiella variicola* | 201712001 | Dec. 20, 2017 |
| NCMA | 137-1036 | *Klebsiella variicola* | 201712002 | Dec. 20, 2017 |

Isolated and Biologically Pure Microorganisms

The present disclosure, in certain embodiments, provides isolated and biologically pure microorganisms that have applications, inter alia, in agriculture. The disclosed microorganisms can be utilized in their isolated and biologically pure states, as well as being formulated into compositions (see below section for exemplary composition descriptions). Furthermore, the disclosure provides microbial compositions containing at least two members of the disclosed isolated and biologically pure microorganisms, as well as methods of utilizing said microbial compositions. Furthermore, the disclosure provides for methods of modulating nitrogen fixation in plants via the utilization of the disclosed isolated and biologically pure microbes.

In some aspects, the isolated and biologically pure microorganisms of the disclosure are those from Table A. In other aspects, the isolated and biologically pure microorganisms of the disclosure are derived from a microorganism of Table A. For example, a strain, child, mutant, or derivative, of a microorganism from Table A are provided herein. The disclosure contemplates all possible combinations of microbes listed in Table A, said combinations sometimes forming a microbial consortia. The microbes from Table A, either individually or in any combination, can be combined with any plant, active (synthetic, organic, etc.), adjuvant, carrier, supplement, or biological, mentioned in the disclosure.

container, such as a jug or in mini bulk. In some examples, compositions may be stored within an object selected from the group consisting of a bottle, jar, ampule, package, vessel, bag, box, bin, envelope, carton, container, silo, shipping container, truck bed, and/or case.

Compositions may also be used to improve plant traits. In some examples, one or more compositions may be coated onto a seed. In some examples, one or more compositions may be coated onto a seedling. In some examples, one or more compositions may be coated onto a surface of a seed. In some examples, one or more compositions may be coated as a layer above a surface of a seed. In some examples, a composition that is coated onto a seed may be in liquid form, in dry product form, in foam form, in a form of a slurry of powder and water, or in a flowable seed treatment. In some examples, one or more compositions may be applied to a seed and/or seedling by spraying, immersing, coating, encapsulating, and/or dusting the seed and/or seedling with the one or more compositions. In some examples, multiple bacteria or bacterial populations can be coated onto a seed and/or a seedling of the plant. In some examples, at least two, at least three, at least four, at least five, at least six, at least seven, at least eight, at least nine, at least ten, or more than ten bacteria of a bacterial combination can be selected from one of the following genera: Acidovorax, *Agrobacterium, Bacillus, Burkholderia, Chryseobacterium, Curtobac-*

*terium, Enterobacter, Escherichia, Methylobacterium, Paenibacillus, Pantoea, Pseudomonas, Ralstonia, Saccharibacillus, Sphingomonas,* and *Stenotrophomonas.*

In some examples, at least two, at least three, at least four, at least five, at least six, at least seven, at least eight, at least nine, at least ten, or more than ten bacteria and bacterial populations of an endophytic combination are selected from one of the following families: Bacillaceae, Burkholderiaceae, Comamonadaceae, Enterobacteriaceae, Flavobacteriaceae, Methylobacteriaceae, Microbacteriaceae, Paenibacillileae, Pseudomonnaceae, Rhizobiaceae, Sphingomonadaceae, Xanthomonadaceae, Cladosporiaceae, Gnomoniaceae, *Incertae sedis*, Lasiosphaeriaceae, Netriaceae, and Pleosporaceae.

In some examples, at least two, at least three, at least four, at least five, at least six, at least seven, at least eight, at least night, at least ten, or more than ten bacteria and bacterial populations of an endophytic combination are selected from one of the following families: Bacillaceae, Burkholderiaceae, Comamonadaceae, Enterobacteriaceae, Flavobacteriaceae, Methylobacteriaceae, Microbacteriaceae, Paenibacillileae, Pseudomonnaceae, Rhizobiaceae, Sphingomonadaceae, Xanthomonadaceae, Cladosporiaceae, Gnomoniaceae, *Incertae sedis*, Lasiosphaeriaceae, Netriaceae, Pleosporaceae.

Examples of compositions may include seed coatings for commercially important agricultural crops, for example, sorghum, canola, tomato, strawberry, barley, rice, maize, and wheat. Examples of compositions can also include seed coatings for corn, soybean, canola, sorghum, potato, rice, vegetables, cereals, and oilseeds. Seeds as provided herein can be genetically modified organisms (GMO), non-GMO, organic, or conventional. In some examples, compositions may be sprayed on the plant aerial parts, or applied to the roots by inserting into furrows in which the plant seeds are planted, watering to the soil, or dipping the roots in a suspension of the composition. In some examples, compositions may be dehydrated in a suitable manner that maintains cell viability and the ability to artificially inoculate and colonize host plants. The bacterial species may be present in compositions at a concentration of between $10^8$ to $10^{10}$ CFU/ml. In some examples, compositions may be supplemented with trace metal ions, such as molybdenum ions, iron ions, manganese ions, or combinations of these ions. The concentration of ions in examples of compositions as described herein may between about 0.1 mM and about 50 mM. Some examples of compositions may also be formulated with a carrier, such as beta-glucan, carboxylmethyl cellulose (CMC), bacterial extracellular polymeric substance (EPS), sugar, animal milk, or other suitable carriers. In some examples, peat or planting materials can be used as a carrier, or biopolymers in which a composition is entrapped in the biopolymer can be used as a carrier. The compositions comprising the bacterial populations described herein can improve plant traits, such as promoting plant growth, maintaining high chlorophyll content in leaves, increasing fruit or seed numbers, and increasing fruit or seed unit weight.

The compositions comprising the bacterial populations described herein may be coated onto the surface of a seed. As such, compositions comprising a seed coated with one or more bacteria described herein are also contemplated. The seed coating can be formed by mixing the bacterial population with a porous, chemically inert granular carrier. Alternatively, the compositions may be inserted directly into the furrows into which the seed is planted or sprayed onto the plant leaves or applied by dipping the roots into a suspension of the composition. An effective amount of the composition can be used to populate the sub-soil region adjacent to the roots of the plant with viable bacterial growth, or populate the leaves of the plant with viable bacterial growth. In general, an effective amount is an amount sufficient to result in plants with improved traits (e.g. a desired level of nitrogen fixation).

Bacterial compositions described herein can be formulated using an agriculturally acceptable carrier. The formulation useful for these embodiments may include at least one member selected from the group consisting of a tackifier, a microbial stabilizer, a fungicide, an antibacterial agent, a preservative, a stabilizer, a surfactant, an anti-complex agent, an herbicide, a nematicide, an insecticide, a plant growth regulator, a fertilizer, a rodenticide, a desiccant, a bactericide, a nutrient, or any combination thereof. In some examples, compositions may be shelf-stable. For example, any of the compositions described herein can include an agriculturally acceptable carrier (e.g., one or more of a fertilizer such as a non-naturally occurring fertilizer, an adhesion agent such as a non-naturally occurring adhesion agent, and a pesticide such as a non-naturally occurring pesticide). A non-naturally occurring adhesion agent can be, for example, a polymer, copolymer, or synthetic wax. For example, any of the coated seeds, seedlings, or plants described herein can contain such an agriculturally acceptable carrier in the seed coating. In any of the compositions or methods described herein, an agriculturally acceptable carrier can be or can include a non-naturally occurring compound (e.g., a non-naturally occurring fertilizer, a non-naturally occurring adhesion agent such as a polymer, copolymer, or synthetic wax, or a non-naturally occurring pesticide). Non-limiting examples of agriculturally acceptable carriers are described below. Additional examples of agriculturally acceptable carriers are known in the art.

In some cases, bacteria are mixed with an agriculturally acceptable carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in the composition. Water-in-oil emulsions can also be used to formulate a composition that includes the isolated bacteria (see, for example, U.S. Pat. No. 7,485,451). Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the bacteria, such as barley, rice, or other biological materials such as seed, plant parts, sugar cane bagasse, hulls or stalks from grain processing, ground plant material or wood from building site refuse, sawdust or small fibers from recycling of paper, fabric, or wood.

For example, a fertilizer can be used to help promote the growth or provide nutrients to a seed, seedling, or plant. Non-limiting examples of fertilizers include nitrogen, phosphorous, potassium, calcium, sulfur, magnesium, boron, chloride, manganese, iron, zinc, copper, molybdenum, and selenium (or a salt thereof). Additional examples of fertilizers include one or more amino acids, salts, carbohydrates, vitamins, glucose, NaCl, yeast extract, $NH_4H_2PO_4$, $(NH_4)_2SO_4$, glycerol, valine, L-leucine, lactic acid, propionic acid, succinic acid, malic acid, citric acid, KH tartrate, xylose, lyxose, and lecithin. In one embodiment, the formulation can include a tackifier or adherent (referred to as an adhesive agent) to help bind other active agents to a substance (e.g., a surface of a seed). Such agents are useful for combining bacteria with carriers that can contain other compounds (e.g., control agents that are not biologic), to yield a coating composition. Such compositions help create coatings around the plant or seed to maintain contact between the microbe and other agents with the plant or plant part. In one embodiment, adhesives are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers.

In some embodiments, the adhesives can be, e.g. a wax such as carnauba wax, beeswax, Chinese wax, shellac wax, spermaceti wax, candelilla wax, castor wax, ouricury wax, and rice bran wax, a polysaccharide (e.g., starch, dextrins, maltodextrins, alginate, and chitosans), a fat, oil, a protein (e.g., gelatin and zeins), gum arables, and shellacs. Adhesive agents can be non-naturally occurring compounds, e.g., polymers, copolymers, and waxes. For example, non-limiting examples of polymers that can be used as an adhesive agent include: polyvinyl acetates, polyvinyl acetate copolymers, ethylene vinyl acetate (EVA) copolymers, polyvinyl alcohols, polyvinyl alcohol copolymers, celluloses (e.g., ethylcelluloses, methylcelluloses, hydroxymethylcelluloses, hydroxypropylcelluloses, and carboxymethylcelluloses), polyvinylpyrolidones, vinyl chloride, vinylidene chloride copolymers, calcium lignosulfonates, acrylic copolymers, polyvinyl acrylates, polyethylene oxide, acylamide polymers and copolymers, polyhydroxyethyl acrylate, methylacrylamide monomers, and polychloroprene.

In some examples, one or more of the adhesion agents, anti-fungal agents, growth regulation agents, and pesticides (e.g., insecticide) are non-naturally occurring compounds (e.g., in any combination). Additional examples of agriculturally acceptable carriers include dispersants (e.g., polyvinylpyrrolidone/vinyl acetate PVPIVA S-630), surfactants, binders, and filler agents.

The formulation can also contain a surfactant. Non-limiting examples of surfactants include nitrogen-surfactant blends such as Prefer 28 (Cenex), Surf-N (US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision). In one embodiment, the surfactant is present at a concentration of between 0.01% v/v to 10% v/v. In another embodiment, the surfactant is present at a concentration of between 0.1% v/v to 1% v/v.

In certain cases, the formulation includes a microbial stabilizer. Such an agent can include a desiccant, which can include any compound or mixture of compounds that can be classified as a desiccant regardless of whether the compound or compounds are used in such concentrations that they in fact have a desiccating effect on a liquid inoculant. Such desiccants are ideally compatible with the bacterial population used, and should promote the ability of the microbial population to survive application on the seeds and to survive desiccation. Examples of suitable desiccants include one or more of trehalose, sucrose, glycerol, and Methylene glycol. Other suitable desiccants include, but are not limited to, non reducing sugars and sugar alcohols (e.g., mannitol or sorbitol). The amount of desiccant introduced into the formulation can range from about 5% to about 50% by weight/volume, for example, between about 10% to about 40%, between about 15% to about 35%, or between about 20% to about 30%. In some cases, it is advantageous for the formulation to contain agents such as a fungicide, an antibacterial agent, an herbicide, a nematicide, an insecticide, a plant growth regulator, a rodenticide, bactericide, or a nutrient. In some examples, agents may include protectants that provide protection against seed surface-borne pathogens. In some examples, protectants may provide some level of control of soil-borne pathogens. In some examples, protectants may be effective predominantly on a seed surface.

In some examples, a fungicide may include a compound or agent, whether chemical or biological, that can inhibit the growth of a fungus or kill a fungus. In some examples, a fungicide may include compounds that may be fungistatic or fungicidal. In some examples, fungicide can be a protectant, or agents that are effective predominantly on the seed surface, providing protection against seed surface-borne pathogens and providing some level of control of soil-borne pathogens. Non-limiting examples of protectant fungicides include captan, maneb, thiram, or fludioxonil.

In some examples, fungicide can be a systemic fungicide, which can be absorbed into the emerging seedling and inhibit or kill the fungus inside host plant tissues. Systemic fungicides used for seed treatment include, but are not limited to the following: azoxystrobin, carboxin, mefenoxam, metalaxyl, thiabendazole, trifloxystrobin, and various triazole fungicides, including difenoconazole, ipconazole, tebuconazole, and triticonazole. Mefenoxam and metalaxyl are primarily used to target the water mold fungi *Pythium* and *Phytophthora*. Some fungicides are preferred over others, depending on the plant species, either because of subtle differences in sensitivity of the pathogenic fungal species, or because of the differences in the fungicide distribution or sensitivity of the plants. In some examples, fungicide can be a biological control agent, such as a bacterium or fungus. Such organisms may be parasitic to the pathogenic fungi, or secrete toxins or other substances which can kill or otherwise prevent the growth of fungi. Any type of fungicide, particularly ones that are commonly used on plants, can be used as a control agent in a seed composition.

In some examples, the seed coating composition comprises a control agent which has antibacterial properties. In one embodiment, the control agent with antibacterial properties is selected from the compounds described herein elsewhere. In another embodiment, the compound is Streptomycin, oxytetracycline, oxolinic acid, or gentamicin.

Other examples of antibacterial compounds which can be used as part of a seed coating composition include those based on dichlorophene and benzylalcohol hemi formal (Proxel® from ICI or Acticide® RS from Thor Chemie and Kathon® MK 25 from Rohm & Haas) and isothiazolinone derivatives such as alkylisothiazolinones and benzisothiazolinones (Acticide® MBS from Thor Chemie).

In some examples, growth regulator is selected from the group consisting of: Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyl adenine, paclobutrazol, prohexadione phosphorotrithioate, 2,3,5-tri-iodobenzoic acid, trinexapac-ethyl and uniconazole. Additional non-limiting examples of growth regulators include brassinosteroids, cytokinines (e.g., kinetin and zeatin), auxins (e.g., indolylacetic acid and indolylacetyl aspartate), flavonoids and isoflavanoids (e.g., formononetin and diosmetin), phytoaixins (e.g., glyceolline), and phytoalexin-inducing oligosaccharides (e.g., pectin, chitin, chitosan, polygalacuronic acid, and oligogalacturonic acid), and gibellerins. Such agents are ideally compatible with the agricultural seed or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

Some examples of nematode-antagonistic biocontrol agents include ARF18; 30 *Arthrobotrys* spp.; *Chaetomium* spp.; *Cylindrocarpon* spp.; *Exophilia* spp.; *Fusarium* spp.; *Gliocladium* spp.; *Hirsutella* spp.; *Lecanicillium* spp.; *Monacrosporium* spp.; *Myrothecium* spp.; *Neocosmospora* spp.; *Paecilomyces* spp.; *Pochonia* spp.; *Stagonospora* spp.; vesicular-arbuscular mycorrhizal fungi, *Burkholderia* spp.; *Pasteuria* spp., *Brevibacillus* spp.; *Pseudomonas* spp.; and Rhizobacteria. Particularly preferred nematode-antagonistic biocontrol agents include ARF18, *Arthrobotrys oligospora, Arthrobotrys dactyloides, Chaetomium globosum, Cylindrocarpon heteronema, Exophilia jeanselmei, Exophilia pisciphila, Fusarium aspergilus, Fusarium solani, Gliocladium catenulatum, Gliocladium roseum, Gliocladium vixens, Hirsutella rhossiliensis, Hirsutella minnesotensis, Lecanicillium lecanii, Monacrosporium drechsleri, Monacrosporium gephyropagum, Myrotehcium verrucaria, Neocosmospora vasinfecta, Paecilomyces lilacinus, Pochonia chlamydosporia, Stagonospora heteroderae, Stagonospora phaseoli,* vesicular-arbuscular mycorrhizal fungi, *Burkholderia cepacia, Pasteuria penetrans, Pasteuria thornei, Pasteuria nishizawae, Pasteuria ramosa, Pastrueia usage, Brevibacillus laterosporus* strain G4, *Pseudomonas fluorescens* and Rhizobacteria.

Some examples of nutrients can be selected from the group consisting of a nitrogen fertilizer including, but not limited to Urea, Ammonium nitrate, Ammonium sulfate, Non-pressure nitrogen solutions, Aqua ammonia, Anhydrous ammonia, Ammonium thiosulfate, Sulfur-coated urea, Urea-formaldehydes, IBDU, Polymer-coated urea, Calcium nitrate, Ureaform, and Methylene urea, phosphorous fertilizers such as Diammonium phosphate, Monoammonium phosphate, Ammonium polyphosphate, Concentrated superphosphate and Triple superphosphate, and potassium fertilizers such as Potassium chloride, Potassium sulfate, Potassium-magnesium sulfate, Potassium nitrate. Such compositions can exist as free salts or ions within the seed coat composition. Alternatively, nutrients/fertilizers can be complexed or chelated to provide sustained release over time.

Some examples of rodenticides may include selected from the group of substances consisting of 2-isovalerylindan-1, 3-dione, 4-(quinoxalin-2-ylamino) benzenesulfonamide, alpha-chlorohydrin, aluminum phosphide, antu, arsenous oxide, barium carbonate, bisthiosemi, brodifacoum, bromadiolone, bromethalin, calcium cyanide, chloralose, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, hydrogen cyanide, iodomethane, lindane, magnesium phosphide, methyl bromide, norbormide, phosacetim, phosphine, phosphorus, pindone, potassium arsenite, pyrinuron, scilliroside, sodium arsenite, sodium cyanide, sodium fluoroacetate, strychnine, thallium sulfate, warfarin and zinc phosphide.

In the liquid form, for example, solutions or suspensions, bacterial populations can be mixed or suspended in water or in aqueous solutions. Suitable liquid diluents or carriers include water, aqueous solutions, petroleum distillates, or other liquid carriers.

Solid compositions can be prepared by dispersing the bacterial populations in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

Application of Bacterial Populations on Crops

The composition of the bacteria or bacterial population described herein can be applied in furrow, in talc, or as seed treatment. The composition can be applied to a seed package in bulk, mini bulk, in a bag, or in talc.

The planter can plant the treated seed and grows the crop according to conventional ways, twin row, or ways that do not require tilling. The seeds can be distributed using a control hopper or an individual hopper. Seeds can also be distributed using pressurized air or manually. Seed placement can be performed using variable rate technologies. Additionally, application of the bacteria or bacterial population described herein may be applied using variable rate technologies. In some examples, the bacteria can be applied to seeds of corn, soybean, canola, sorghum, potato, rice, vegetables, cereals, pseudocereals, and oilseeds. Examples of cereals may include barley, fonio, oats, palmer's grass, rye, pearl millet, sorghum, spelt, teff, triticale, and wheat. Examples of pseudocereals may include breadnut, buckwheat, cattail, chia, flax, grain amaranth, hanza, quinoa, and sesame. In some examples, seeds can be genetically modified organisms (GMO), non-GMO, organic or conventional.

Additives such as micro-fertilizer, PGR, herbicide, insecticide, and fungicide can be used additionally to treat the crops. Examples of additives include crop protectants such as insecticides, nematicides, fungicide, enhancement agents such as colorants, polymers, pelleting, priming, and disinfectants, and other agents such as inoculant, PGR, softener, and micronutrients. PGRs can be natural or synthetic plant hormones that affect root growth, flowering, or stem elongation. PGRs can include auxins, gibberellins, cytokinins, ethylene, and abscisic acid (ABA).

The composition can be applied in furrow in combination with liquid fertilizer. In some examples, the liquid fertilizer may be held in tanks. NPK fertilizers contain macronutrients of sodium, phosphorous, and potassium.

The composition may improve plant traits, such as promoting plant growth, maintaining high chlorophyll content in leaves, increasing fruit or seed numbers, and increasing fruit or seed unit weight. Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, tolerance to low nitrogen stress, nitrogen use efficiency, resistance to nematode stress, resistance to a fungal pathogen, resistance to a bacterial pathogen, resistance to a viral pathogen, level of a metabolite, modulation in level of a metabolite, proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the introduced and/or improved traits) grown under identical conditions. In some examples, the desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the introduced and/or improved traits) grown under similar conditions.

An agronomic trait to a host plant may include, but is not limited to, the following: altered oil content, altered protein content, altered seed carbohydrate composition, altered seed oil composition, and altered seed protein composition, chemical tolerance, cold tolerance, delayed senescence, disease resistance, drought tolerance, ear weight, growth improvement, health enhancement, heat tolerance, herbicide tolerance, herbivore resistance improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome, compared to an isoline plant grown from a seed without said seed treatment formulation.

In some cases, plants are inoculated with bacteria or bacterial populations that are isolated from the same species of plant as the plant element of the inoculated plant. For example, an bacteria or bacterial population that is normally found in one variety of *Zea mays* (corn) is associated with a plant element of a plant of another variety of *Zea mays* that in its natural state lacks said bacteria and bacterial populations. In one embodiment, the bacteria and bacterial populations is derived from a plant of a related species of plant as the plant element of the inoculated plant. For example, an bacteria and bacterial populations that is normally found in *Zea diploperennis* Iltis et al., (diploperennial teosinte) is applied to a *Zea mays* (corn), or vice versa. In some cases, plants are inoculated with bacteria and bacterial populations that are heterologous to the plant element of the inoculated plant. In one embodiment, the bacteria and bacterial populations is derived from a plant of another species. For example, an bacteria and bacterial populations that is normally found in dicots is applied to a monocot plant (e.g., inoculating corn with a soybean-derived bacteria and bacterial populations), or vice versa. In other cases, the bacteria and bacterial populations to be inoculated onto a plant is derived from a related species of the plant that is being inoculated. In one embodiment, the bacteria and bacterial populations is derived from a related taxon, for example, from a related species. The plant of another species can be an agricultural plant. In another embodiment, the bacteria and bacterial populations is part of a designed composition inoculated into any host plant element.

In some examples, the bacteria or bacterial population is exogenous wherein the bacteria and bacterial population is isolated from a different plant than the inoculated plant. For example, in one embodiment, the bacteria or bacterial population can be isolated from a different plant of the same species as the inoculated plant. In some cases, the bacteria or bacterial population can be isolated from a species related to the inoculated plant.

In some examples, the bacteria and bacterial populations described herein are capable of moving from one tissue type to another. For example, the present invention's detection and isolation of bacteria and bacterial populations within the mature tissues of plants after coating on the exterior of a seed demonstrates their ability to move from seed exterior into the vegetative tissues of a maturing plant. Therefore, in one embodiment, the population of bacteria and bacterial populations is capable of moving from the seed exterior into the vegetative tissues of a plant. In one embodiment, the bacteria and bacterial populations that is coated onto the seed of a plant is capable, upon germination of the seed into a vegetative state, of localizing to a different tissue of the plant. For example, bacteria and bacterial populations can be capable of localizing to any one of the tissues in the plant, including: the root, adventitious root, seminal 5 root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In one embodiment, the bacteria and bacterial populations is capable of localizing to the root and/or the root hair of the plant. In another embodiment, the bacteria and bacterial populations is capable of localizing to the photosynthetic tissues, for example, leaves and shoots of the plant. In other cases, the bacteria and bacterial populations is localized to the vascular tissues of the plant, for example, in the xylem and phloem. In still another embodiment, the bacteria and bacterial populations is capable of localizing to the reproductive tissues (flower, pollen, pistil, ovaries, stamen, fruit) of the plant. In another embodiment, the bacteria and bacterial populations is capable of localizing to the root, shoots, leaves and reproductive tissues of the plant. In still another embodiment, the bacteria and bacterial populations colonizes a fruit or seed tissue of the plant. In still another embodiment, the bacteria and bacterial populations is able to colonize the plant such that it is present in the surface of the plant (i.e., its presence is detectably present on the plant exterior, or the episphere of the plant). In still other embodiments, the bacteria and bacterial populations is capable of localizing to substantially all, or all, tissues of the plant. In certain embodiments, the bacteria and bacterial populations is not localized to the root of a plant. In other cases, the bacteria and bacterial populations is not localized to the photosynthetic tissues of the plant.

The effectiveness of the compositions can also be assessed by measuring the relative maturity of the crop or the crop heating unit (CHU). For example, the bacterial population can be applied to corn, and corn growth can be assessed according to the relative maturity of the corn kernel or the time at which the corn kernel is at maximum weight. The crop heating unit (CHU) can also be used to predict the maturation of the corn crop. The CHU determines the amount of heat accumulation by measuring the daily maximum temperatures on crop growth.

In examples, bacterial may localize to any one of the tissues in the plant, including: the root, adventitious root, seminal root, root hair, shoot, leaf, flower, bud tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In another embodiment, the bacteria or bacterial population is capable of localizing to the photosynthetic tissues, for example, leaves and shoots of the plant. In other cases, the bacteria and bacterial populations is localized to the vascular tissues of the plant, for example, in the xylem and phloem. In another embodiment, the bacteria or bacterial population is capable of localizing to reproductive tissues (flower, pollen, pistil, ovaries, stamen, or fruit) of the plant. In another embodiment, the bacteria and bacterial populations is capable of localizing to the root, shoots, leaves and reproductive tissues of the plant. In another embodiment, the bacteria or bacterial population colonizes a fruit or seed tissue of the plant. In still another embodiment, the bacteria or bacterial population is able to colonize the plant such that it is present in the surface of the plant. In another embodiment, the bacteria or bacterial population is capable of localizing to substantially all, or all, tissues of the plant. In certain embodiments, the bacteria or bacterial population is not localized to the root of a plant. In other cases, the bacteria and bacterial populations is not localized to the photosynthetic tissues of the plant.

The effectiveness of the bacterial compositions applied to crops can be assessed by measuring various features of crop growth including, but not limited to, planting rate, seeding vigor, root strength, drought tolerance, plant height, dry down, and test weight.

Plant Species

The methods and bacteria described herein are suitable for any of a variety of plants, such as plants in the genera

*Hordeum, Oryza, Zea,* and *Triticeae.* Other non-limiting examples of suitable plants include mosses, lichens, and algae. In some cases, the plants have economic, social and/or environmental value, such as food crops, fiber crops, oil crops, plants in the forestry or pulp and paper industries, feedstock for biofuel production and/or ornamental plants. In some examples, plants may be used to produce economically valuable products such as a grain, a flour, a starch, a syrup, a meal, an oil, a film, a packaging, a nutraceutical product, a pulp, an animal feed, a fish fodder, a bulk material for industrial chemicals, a cereal product, a processed human-food product, a sugar, an alcohol, and/or a protein. Non-limiting examples of crop plants include maize, rice, wheat, barley, sorghum, millet, oats, rye triticale, buckwheat, sweet corn, sugar cane, onions, tomatoes, strawberries, and asparagus.

In some examples, plants that may be obtained or improved using the methods and composition disclosed herein may include plants that are important or interesting for agriculture, horticulture, biomass for the production of biofuel molecules and other chemicals, and/or forestry. Some examples of these plants may include pineapple, banana, coconut, lily, grasspeas and grass; and dicotyledonous plants, such as, for example, peas, alfalfa, tomatillo, melon, chickpea, chicory, clover, kale, lentil, soybean, tobacco, potato, sweet potato, radish, cabbage, rape, apple trees, grape, cotton, sunflower, thale cress, canola, citrus (including orange, mandarin, kumquat, lemon, lime, grapefruit, tangerine, tangelo, citron, and pomelo), pepper, bean, lettuce, *Panicum virgatum* (switch), *Sorghum bicolor* (sorghum, sudan), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp. *Sorghum* spp., *Miscanthus* spp., *Saccharum* spp., *Erianthus* spp., *Populus* spp., *Secale cereale* (rye), *Salix* spp. (willow), *Eucalyptus* spp. (*eucalyptus*), *Triticosecale* spp. (triticum-25 wheat X rye), Bamboo, *Carthamus tinctorius* (safflower), *Jatropha curcas* (Jatropha), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea, Manihot esculenta* (cassaya), *Lycopersicon esculentum* (tomato), *Lactuca saliva* (lettuce), *Musa paradisiaca* (banana), *Solanum tuberosum* (potato), *Brassica oleracea* (broccoli, cauliflower, brussel sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis saliva, Camptotheca acuminate, Catharanthus roseus, Vinca rosea, Cinchona officinalis, Coichicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum (Huperzia serrata), Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (*petunia*), *Poinsettia pulcherrima* (poinsettia), *Nicotiana tabacum* (tobacco), *Lupinus albus* (lupin), *Uniola paniculata* (oats), *Hordeum vulgare* (barley), and *Lolium* spp. (rye).

In some examples, a monocotyledonous plant may be used. Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales. Plants belonging to the class of the Gymnospermae are Cycadales, Ginkgoales, Gnetales, and Pinales. In some examples, the monocotyledonous plant can be selected from the group consisting of a maize, rice, wheat, barley, and sugarcane.

In some examples, a dicotyledonous plant may be used, including those belonging to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Middles, Juglandales, Lamiales, Laurales, Lecythidales, Leitneriales, Magniolales, Malvales, Myricales, Myrtales, Nymphaeales, Papeverales, Piperales, Plantaginales, Plumb aginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violates. In some examples, the dicotyledonous plant can be selected from the group consisting of cotton, soybean, pepper, and tomato.

In some cases, the plant to be improved is not readily amenable to experimental conditions. For example, a crop plant may take too long to grow enough to practically assess an improved trait serially over multiple iterations. Accordingly, a first plant from which bacteria are initially isolated, and/or the plurality of plants to which genetically manipulated bacteria are applied may be a model plant, such as a plant more amenable to evaluation under desired conditions. Non-limiting examples of model plants include *Setaria, Brachypodium*, and *Arabidopsis*. Ability of bacteria isolated according to a method of the disclosure using a model plant may then be applied to a plant of another type (e.g. a crop plant) to confirm conferral of the improved trait.

Traits that may be improved by the methods disclosed herein include any observable characteristic of the plant, including, for example, growth rate, height, weight, color, taste, smell, changes in the production of one or more compounds by the plant (including for example, metabolites, proteins, drugs, carbohydrates, oils, and any other compounds). Selecting plants based on genotypic information is also envisaged (for example, including the pattern of plant gene expression in response to the bacteria, or identifying the presence of genetic markers, such as those associated with increased nitrogen fixation). Plants may also be selected based on the absence, suppression or inhibition of a certain feature or trait (such as an undesirable feature or trait) as opposed to the presence of a certain feature or trait (such as a desirable feature or trait).

Concentrations and Rates of Application of Agricultural Compositions

As aforementioned, the agricultural compositions of the present disclosure, which comprise a taught microbe, can be applied to plants in a multitude of ways. In two particular aspects, the disclosure contemplates an in-furrow treatment or a seed treatment For seed treatment embodiments, the microbes of the disclosure can be present on the seed in a variety of concentrations. For example, the microbes can be found in a seed treatment at a cfu concentration, per seed of: $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, or more. In particular aspects, the seed treatment compositions comprise about $1 \times 10^4$ to about $1 \times 10^8$ cfu per seed. In other particular aspects, the seed treatment compositions comprise about $1 \times 10^5$ to about $1 \times 10^7$ cfu per seed. In other aspects, the seed treatment compositions comprise about $1 \times 10^6$ cfu per seed.

In the United States, about 10% of corn acreage is planted at a seed density of above about 36,000 seeds per acre; ⅓ of the corn acreage is planted at a seed density of between about 33,000 to 36,000 seeds per acre; ⅓ of the corn acreage is planted at a seed density of between about 30,000 to 33,000 seeds per acre, and the remainder of the acreage is variable. See, "Corn Seeding Rate Considerations," written by Steve Butzen, available at: https://www.pioneer.com/home/site/us/agronomy/library/corn-seeding-rate-considerations/

Table B below utilizes various cfu concentrations per seed in a contemplated seed treatment embodiment (rows across) and various seed acreage planting densities ($1^{st}$ column: 15K-41K) to calculate the total amount of cfu per acre, which would be utilized in various agricultural scenarios (i.e. seed treatment concentration per seed×seed density planted per acre). Thus, if one were to utilize a seed treatment with $1 \times 10^6$ cfu per seed and plant 30,000 seeds per acre, then the total cfu content per acre would be $3 \times 10^{10}$ (i.e. 30K*$1 \times 10^6$).

TABLE B

| Total CFU Per Acre Calculation for Seed Treatment Embodiments | | | | | | | | |
|---|---|---|---|---|---|---|---|---|
| Corn Population (i.e. seeds per acre) | 1.00E+02 | 1.00E+03 | 1.00E+04 | 1.00E+05 | 1.00E+06 | 1.00E+07 | 1.00E+08 | 1.00E+09 |
| 15,000 | 1.50E+06 | 1.50E+07 | 1.50E+08 | 1.50E+09 | 1.50E+10 | 1.50E+11 | 1.50E+12 | 1.50E+13 |
| 16,000 | 1.60E+06 | 1.60E+07 | 1.60E+08 | 1.60E+09 | 1.60E+10 | 1.60E+11 | 1.60E+12 | 1.60E+13 |
| 17,000 | 1.70E+06 | 1.70E+07 | 1.70E+08 | 1.70E+09 | 1.70E+10 | 1.70E+11 | 1.70E+12 | 1.70E+13 |
| 18,000 | 1.80E+06 | 1.80E+07 | 1.80E+08 | 1.80E+09 | 1.80E+10 | 1.80E+11 | 1.80E+12 | 1.80E+13 |
| 19,000 | 1.90E+06 | 1.90E+07 | 1.90E+08 | 1.90E+09 | 1.90E+10 | 1.90E+11 | 1.90E+12 | 1.90E+13 |
| 20,000 | 2.00E+06 | 2.00E+07 | 2.00E+08 | 2.00E+09 | 2.00E+10 | 2.00E+11 | 2.00E+12 | 2.00E+13 |
| 21,000 | 2.10E+06 | 2.10E+07 | 2.10E+08 | 2.10E+09 | 2.10E+10 | 2.10E+11 | 2.10E+12 | 2.10E+13 |

TABLE B-continued

Total CFU Per Acre Calculation for Seed Treatment Embodiments

| Corn Population (i.e. seeds per acre) | 1.00E+02 | 1.00E+03 | 1.00E+04 | 1.00E+05 | 1.00E+06 | 1.00E+07 | 1.00E+08 | 1.00E+09 |
|---|---|---|---|---|---|---|---|---|
| 22,000 | 2.20E+06 | 2.20E+07 | 2.20E+08 | 2.20E+09 | 2.20E+10 | 2.20E+11 | 2.20E+12 | 2.20E+13 |
| 23,000 | 2.30E+06 | 2.30E+07 | 2.30E+08 | 2.30E+09 | 2.30E+10 | 2.30E+11 | 2.30E+12 | 2.30E+13 |
| 24,000 | 2.40E+06 | 2.40E+07 | 2.40E+08 | 2.40E+09 | 2.40E+10 | 2.40E+11 | 2.40E+12 | 2.40E+13 |
| 25,000 | 2.50E+06 | 2.50E+07 | 2.50E+08 | 2.50E+09 | 2.50E+10 | 2.50E+11 | 2.50E+12 | 2.50E+13 |
| 26,000 | 2.60E+06 | 2.60E+07 | 2.60E+08 | 2.60E+09 | 2.60E+10 | 2.60E+11 | 2.60E+12 | 2.60E+13 |
| 27,000 | 2.70E+06 | 2.70E+07 | 2.70E+08 | 2.70E+09 | 2.70E+10 | 2.70E+11 | 2.70E+12 | 2.70E+13 |
| 28,000 | 2.80E+06 | 2.80E+07 | 2.80E+08 | 2.80E+09 | 2.80E+10 | 2.80E+11 | 2.80E+12 | 2.80E+13 |
| 29,000 | 2.90E+06 | 2.90E+07 | 2.90E+08 | 2.90E+09 | 2.90E+10 | 2.90E+11 | 2.90E+12 | 2.90E+13 |
| 30,000 | 3.00E+06 | 3.00E+07 | 3.00E+08 | 3.00E+09 | 3.00E+10 | 3.00E+11 | 3.00E+12 | 3.00E+13 |
| 31,000 | 3.10E+06 | 3.10E+07 | 3.10E+08 | 3.10E+09 | 3.10E+10 | 3.10E+11 | 3.10E+12 | 3.10E+13 |
| 32,000 | 3.20E+06 | 3.20E+07 | 3.20E+08 | 3.20E+09 | 3.20E+10 | 3.20E+11 | 3.20E+12 | 3.20E+13 |
| 33,000 | 3.30E+06 | 3.30E+07 | 3.30E+08 | 3.30E+09 | 3.30E+10 | 3.30E+11 | 3.30E+12 | 3.30E+13 |
| 34,000 | 3.40E+06 | 3.40E+07 | 3.40E+08 | 3.40E+09 | 3.40E+10 | 3.40E+11 | 3.40E+12 | 3.40E+13 |
| 35,000 | 3.50E+06 | 3.50E+07 | 3.50E+08 | 3.50E+09 | 3.50E+10 | 3.50E+11 | 3.50E+12 | 3.50E+13 |
| 36,000 | 3.60E+06 | 3.60E+07 | 3.60E+08 | 3.60E+09 | 3.60E+10 | 3.60E+11 | 3.60E+12 | 3.60E+13 |
| 37,000 | 3.70E+06 | 3.70E+07 | 3.70E+08 | 3.70E+09 | 3.70E+10 | 3.70E+11 | 3.70E+12 | 3.70E+13 |
| 38,000 | 3.80E+06 | 3.80E+07 | 3.80E+08 | 3.80E+09 | 3.80E+10 | 3.80E+11 | 3.80E+12 | 3.80E+13 |
| 39,000 | 3.90E+06 | 3.90E+07 | 3.90E+08 | 3.90E+09 | 3.90E+10 | 3.90E+11 | 3.90E+12 | 3.90E+13 |
| 40,000 | 4.00E+06 | 4.00E+07 | 4.00E+08 | 4.00E+09 | 4.00E+10 | 4.00E+11 | 4.00E+12 | 4.00E+13 |
| 41,000 | 4.10E+06 | 4.10E+07 | 4.10E+08 | 4.10E+09 | 4.10E+10 | 4.10E+11 | 4.10E+12 | 4.10E+13 |

For in-furrow embodiments, the microbes of the disclosure can be applied at a cfu concentration per acre of: $1 \times 10^6$, $3.20 \times 10^{10}$, $1.60 \times 10^{11}$, $3.20 \times 10^{11}$, $8.0 \times 10^{11}$, $1.6 \times 10^{12}$, $3.20 \times 10^{12}$, or more. Therefore, in aspects, the liquid in-furrow compositions can be applied at a concentration of between about $1 \times 10^6$ to about $3 \times 10^{12}$ cfu per acre.

In some aspects, the in-furrow compositions are contained in a liquid formulation. In the liquid in-furrow embodiments, the microbes can be present at a cfu concentration per milliliter of: $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, or more. In certain aspects, the liquid in-furrow compositions comprise microbes at a concentration of about $1 \times 10^6$ to about $1 \times 10^{11}$ cfu per milliliter. In other aspects, the liquid in-furrow compositions comprise microbes at a concentration of about $1 \times 10^7$ to about $1 \times 10^{10}$ cfu per milliliter. In other aspects, the liquid in-furrow compositions comprise microbes at a concentration of about $1 \times 10^8$ to about $1 \times 10^9$ cfu per milliliter. In other aspects, the liquid in-furrow compositions comprise microbes at a concentration of up to about $1 \times 10^{13}$ cfu per milliliter.

EXAMPLES

The examples provided herein describe methods of bacterial isolation, bacterial and plant analysis, and plant trait improvement. The examples are for illustrative purposes only and are not to be construed as limiting in any way.

Example 1: Isolation of Microbes from Plant Tissue

Topsoil was obtained from various agricultural areas in central California. Twenty soils with diverse texture characteristics were collected, including heavy clay, peaty clay loam, silty clay, and sandy loam. Seeds of various field corn, sweet corn, heritage corn and tomato were planted into each soil, as shown in Table 1.

TABLE 1

| Crop Type and Varieties planted into soil with diverse characteristics | | | | |
|---|---|---|---|---|
| Crop Type | Field Corn | Sweet Corn | Heritage Corn | Tomato |
| Varieties | Mo17 | Ferry-Morse 'Golden Cross Bantam T-51' | Victory Seeds 'Moseby Prolific' | Ferry-Morse Roma VF |
| | B73 | Ferry-Morse 'Silver Queen Hybrid' | Victory Seeds 'Reid's Yellow Dent' | Stover Roma |
| | DKC 66-40 | Ferry-Morse 'Sugar Dots' | Victory Seeds 'Hickory King' | Totally Tomatoes 'Micro Tom Hybrid' |
| | DKC 67-07 | | | Heinz 1015 |
| | DKC 70-01 | | | Heinz 2401 |
| | | | | Heinz 3402 |
| | | | | Heinz 5508 |
| | | | | Heinz 5608 |
| | | | | Heinz 8504 |

Plants were uprooted after 2-4 weeks of growth and excess soil on root surfaces was removed with deionized water. Following soil removal, plants were surface sterilized with bleach and rinsed vigorously in sterile water. A cleaned, 1 cm section of root was excised from the plant and placed in a phosphate buffered saline solution containing 3 mm steel beads. A slurry was generated by vigorous shaking of the solution with a Qiagen TissueLyser II.

Figure 1B:
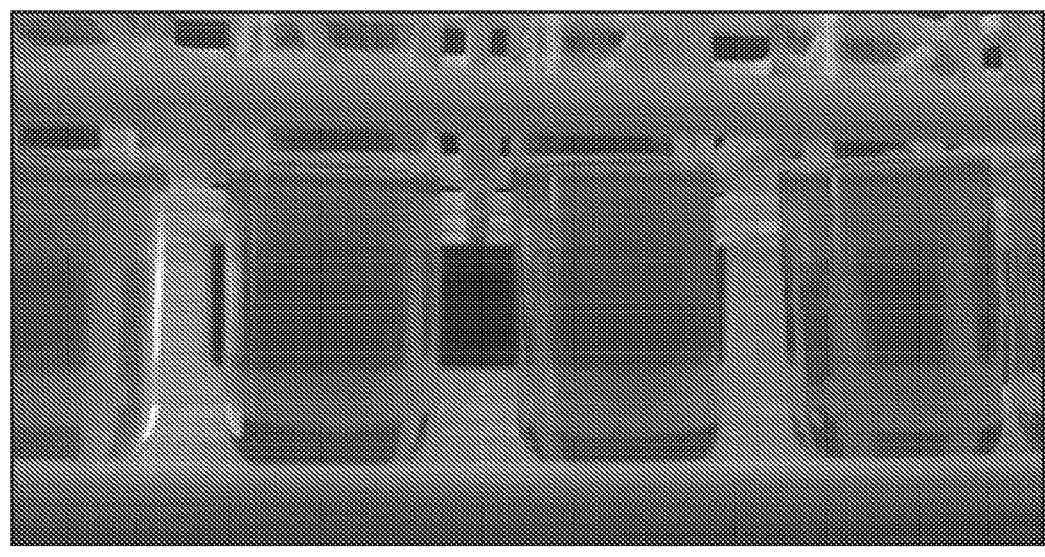

The root and saline slurry was diluted and inoculated onto various types of growth media to isolate rhizospheric, endophytic, epiphytic, and other plant-associated microbes. R2A and Nfb agar media were used to obtain single colonies, and semisolid Nfb media slants were used to obtain populations of nitrogen fixing bacteria. After 2-4 weeks incubation in semi-solid Nfb media slants, microbial populations were collected and streaked to obtain single colonies on R2A agar, as shown in FIG. 1A-B. Single colonies were resuspended in a mixture of R2A and glycerol, subjected to PCR analysis, and frozen at −80° C. for later analysis. Approximately 1,000 single colonies were obtained and designated "isolated microbes."

Figure 2:
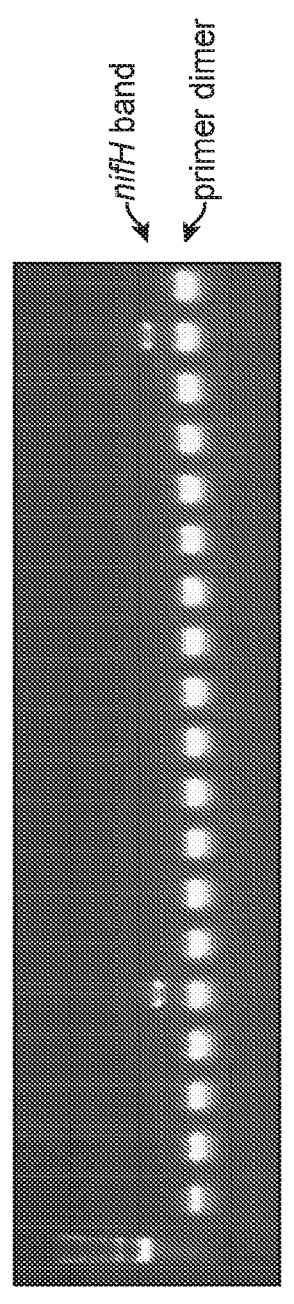
FIG. 2 depicts a representative nifH PCR screen. Positive bands were observed at ~350 bp for two colonies in this screen. Lower bands represent primer-dimers.

Isolates were then subjected to a colony PCR screen to detect the presence of the nifH gene in order to identify diazotrophs. The previously-described primer set Ueda 19F/388R, which has been shown to detect over 90% of diazotrophs in screens, was used to probe the presence of the nif cluster in each isolate (Ueda et al. 1995; J. Bacteriol. 177: 1414-1417). Single colonies of purified isolates were picked, resuspended in PBS, and used as a template for colony PCR, as shown in FIG. 2. Colonies of isolates that gave positive PCR bands were re-streaked, and the colony PCR and re-streaking process was repeated twice to prevent false positive identification of diazotrophs. Purified isolates were then designated "candidate microbes."

Example 2: Characterization of Isolated Microbes

Sequencing, Analysis and Phylogenetic Characterization

Sequencing of 16S rDNA with the 515f-806r primer set was used to generate preliminary phylogenetic identities for isolated and candidate microbes (see e.g. Vernon et al.; BMC Microbiol. 2002 Dec. 23; 2:39). The microbes comprise diverse genera including: *Enterobacter, Burkholderia, Klebsiella, Bradyrhizobium, Rahnella, Xanthomonas, Raoultella, Pantoea, Pseudomonas, Brevundimonas, Agrobacterium,* and *Paenibacillus,* as shown in Table 2.

TABLE 2

Diversity of microbes isolated from tomato plants
as determined by deep 16S rDNA sequencing.

| Genus | Isolates |
|---|---|
| *Achromobacter* | 7 |
| *Agrobacterium* | 117 |
| *Agromyces* | 1 |
| *Alicyclobacillus* | 1 |
| *Asticcacaulis* | 6 |
| *Bacillus* | 131 |
| *Bradyrhizobium* | 2 |
| *Brevibacillus* | 2 |
| *Burkholderia* | 2 |
| *Caulobacter* | 17 |
| *Chryseobacterium* | 42 |
| *Comamonas* | 1 |
| *Dyadobacter* | 2 |
| *Flavobacterium* | 46 |
| *Halomonas* | 3 |
| *Leptothrix* | 3 |
| *Lysobacter* | 2 |
| *Neisseria* | 13 |
| *Paenibacillus* | 1 |
| *Paenisporosarcina* | 3 |
| *Pantoea* | 14 |
| *Pedobacter* | 16 |
| *Pimelobacter* | 2 |
| *Pseudomonas* | 212 |
| *Rhizobium* | 4 |

TABLE 2-continued

Diversity of microbes isolated from tomato plants
as determined by deep 16S rDNA sequencing.

| Genus | Isolates |
|---|---|
| *Rhodoferax* | 1 |
| *Sphingobacterium* | 13 |
| *Sphingobium* | 23 |
| *Sphingomonas* | 3 |
| *Sphingopyxis* | 1 |
| *Stenotrophomonas* | 59 |
| *Streptococcus* | 3 |
| *Variovorax* | 37 |
| *Xylanimicrobium* | 1 |
| unidentified | 75 |

Subsequently, the genomes of 39 candidate microbes were sequenced using Illumina Miseq platform. Genomic DNA from pure cultures was extracted using the QIAmp DNA mini kit (QIAGEN), and total DNA libraries for sequencing were prepared through a third party vendor (SeqMatic, Hayward). Genome assembly was then carried out via the A5 pipeline (Tritt et al. 2012; PLoS One 7(9):e42304). Genes were identified and annotated, and those related to regulation and expression of nitrogen fixation were noted as targets for mutagenesis.

Transcriptomic Profiling of Candidate Microbes

Transcriptomic profiling of strain CI010 was performed to identify promoters that are active in the presence of environmental nitrogen. Strain CI010 was cultured in a defined, nitrogen-free media supplemented with 10 mM glutamine. Total RNA was extracted from these cultures (QIAGEN RNeasy kit) and subjected to RNAseq sequencing via Illumina HiSeq (SeqMatic, Fremont CA). Sequencing reads were mapped to CI010 genome data using Geneious, and highly expressed genes under control of proximal transcriptional promoters were identified.

Tables 3A-C lists genes and their relative expression level as measured through RNASeq sequencing of total RNA. Sequences of the proximal promoters were recorded for use in mutagenesis of nif pathways, nitrogen utilization related pathways, or other genes with a desired expression level.

TABLE 3A

| Name | Minimum | Maximum | Length | Direction |
|---|---|---|---|---|
| murein lipoprotein CDS | 2,929,898 | 2,930,134 | 237 | forward |
| membrane protein CDS | 5,217,517 | 5,217,843 | 327 | forward |
| zinc/cadmium-binding protein CDS | 3,479,979 | 3,480,626 | 648 | forward |
| acyl carrier protein CDS | 4,563,344 | 4,563,580 | 237 | reverse |
| ompX CDS | 4,251,002 | 4,251,514 | 513 | forward |
| DNA-binding protein HU-beta CDS | 375,156 | 375,428 | 273 | forward |
| sspA CDS | 629,998 | 630,636 | 639 | reverse |
| tatE CDS | 3,199,435 | 3,199,638 | 204 | reverse |
| LexA repressor CDS | 1,850,457 | 1,851,065 | 609 | forward |
| hisS CDS | <3999979 | 4,001,223 | >1245 | forward |

TABLE 3B

| Name | Differential Expression Absolute Confidence | Differential Expression Ratio | RNASeq_ nifL- Raw Read Count | RNASeq_ nifL- Raw Transcript Count | RNASeq_ WT- Raw Read Count | RNASeq_ WT- Raw Transcript Count |
|---|---|---|---|---|---|---|
| murein lipoprotein CDS | 1000 | −1.8 | 12950.5 | 10078.9 | 5151.5 | 4106.8 |

TABLE 3B-continued

| Name | Differential Expression Absolute Confidence | Differential Expression Ratio | RNASeq_ nifL- Raw Read Count | RNASeq_ nifL- Raw Transcript Count | RNASeq_ WT- Raw Read Count | RNASeq_ WT- Raw Transcript Count |
|---|---|---|---|---|---|---|
| membrane protein CDS | 1000 | −1.3 | 9522.5 | 5371.3 | 5400 | 3120 |
| zinc/ cadmium- binding protein CDS | 3.3 | 1.1 | 6461 | 1839.1 | 5318 | 1550.6 |
| acyl carrier protein CDS | 25.6 | 1.6 | 1230.5 | 957.6 | 1473.5 | 1174.7 |
| ompX CDS | 1.7 | 1.1 | 2042 | 734.2 | 1687.5 | 621.5 |
| DNA-binding protein HU- beta CDS | 6.9 | −1.3 | 1305 | 881.7 | 725 | 501.8 |
| sspA CDS | 0.2 | 1 | 654 | 188.8 | 504.5 | 149.2 |
| tatE CDS | 1.4 | 1.3 | 131 | 118.4 | 125 | 115.8 |
| LexA repressor CDS | 0.1 | −1.1 | 248 | 75.1 | 164 | 50.9 |
| hisS CDS | 0 | −1.1 | 467 | 69.2 | 325 | 49.3 |

TABLE 3C

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| murein lipoprotein CDS | GCCTCTCGGGGC GCTTTTTTTTATT CCGGCACTAGCC GCTATTAATAAA AATGCAAATCGG AATTTACTATTTA ACGCGAGATTAT CTAAGATGAATC CGATGGAAGCGC GCTGTTTTCACTC GCCTTTTTAAAGT TACGTGATGATT TCGATGCTTCTTT GAGCGAACGATC AAAAATAAGCGT ATTCAGGTAAAA AAATATTCTCAT CACAAAAAAGTT TGTGTAATACTT GTAACGCT--- ACATGGAGATTA ACTC | 3 | ATGAATCGTACT AAACTGGTACTG GGCGCGGTAATC CTGGGTTCTACTC TGCTGGCTGGTT GCTCCAGCAATG CTAAAATCGATC AGCTGTCTTCTG ACGTTCAGACTC TGAACGCTAAAG TTGACCAGCTGA GCAACGACGTGA ACGCAATGCGTT CCGACGTTCAGG CTGCTAAAGATG ACGCAGCTCGCG CTAACCAGCGTC TGGACAACGCAG CTACTAAATACC GTAAGTAA | 13 | ATGAAAAAGACC AAAATTGTTTGC ACCATCGGTCCG AAAACCGAATCC GAAGAGATGTTG ACCAAAATGCTG GACGCGGGCATG AACGTTATGCGT CTGAACTTCTCTC ACGGTGACTATG CGGAACACGGTC AGCGCATCCAGA ATCTGCGCAATG TGATGAGTAAAA CCGGTAAGAAAG CGGCAATCCTGC TGGACACCAAAG GTCCGGAAATCC GTACCATTAAGC TGGAAGGCGGCA ACGACGTCTCCC TGAAAGCGGGCC AGACCTTCACCT TCACCACCGATA AATCCGTTGTCG GTAATAACGAAA TCGTTGCGGTGA CCTATGAAGGCT TCACCAGCGACC TGAGCGTTGGCA ACACGGTACTGG TTGACGATGGTC TGATCGGTATGG AAGTGACCGCTA TCGAAGGCAACA AAGTTGTTTGTA AAGTGCTGAACA ACGGCGACCTCG GCGAGAACAAAG GCGTTAACCTGC CGGGCGTATCTA TCGCGCTGCCGG CGCTGGCTGAAA AAGACAAACAGG ATCTGATCTTCG GTTGCGAACAGG | 23 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|------|------|------|------|------|------|------|
| | | | | | GCGTTGACTTTGT | |
| | | | | | TGCGGCATCCTTT | |
| | | | | | ATCCGTAAGCGT | |
| | | | | | TCTGACGTTGTTG | |
| | | | | | AAATCCGTGAGC | |
| | | | | | ACCTGAAAGCCC | |
| | | | | | ACGGCGGCGAGA | |
| | | | | | AGATCCAGATCA | |
| | | | | | TCTCCAAAATCG | |
| | | | | | AAAACCAGGAAG | |
| | | | | | GCCTGAACAACT | |
| | | | | | TCGACGAAATCC | |
| | | | | | TCGAAGCCTCTG | |
| | | | | | ACGGCATCATGG | |
| | | | | | TAGCCCGTGGCG | |
| | | | | | ACCTGGGCGTTG | |
| | | | | | AAATCCCGGTTG | |
| | | | | | AAGAAGTTATCT | |
| | | | | | TCGCGCAGAAGA | |
| | | | | | TGATGATCGAGA | |
| | | | | | AATGTATCCGCG | |
| | | | | | CGCGTAAAGTCG | |
| | | | | | TTATCACCGCGA | |
| | | | | | CCCAGATGCTGG | |
| | | | | | ATTCCATGATCA | |
| | | | | | AAAACCCGCGTC | |
| | | | | | CGACCCGTGCGG | |
| | | | | | AAGCAGGCGACG | |
| | | | | | TGGCCAACGCCA | |
| | | | | | TCCTCGACGGCA | |
| | | | | | CCGACGCAGTTA | |
| | | | | | TGCTGTCCGGCG | |
| | | | | | AATCCGCGAAAG | |
| | | | | | GTAAATACCCGC | |
| | | | | | TGGAAGCGGTCA | |
| | | | | | CCATCATGGCGA | |
| | | | | | CCATCTGCGAAC | |
| | | | | | GTACCGACCGCG | |
| | | | | | TCATGACCAGCC | |
| | | | | | GTCTTGAGTACA | |
| | | | | | ACAACGACAACC | |
| | | | | | GTAAGCTGCGCA | |
| | | | | | TCACCGAAGCGG | |
| | | | | | TGTGCCGCGGTG | |
| | | | | | CGGTAGAAACGG | |
| | | | | | CTGAAAAACTGG | |
| | | | | | AAGCGCCGCTGA | |
| | | | | | TCGTTGTGGCAA | |
| | | | | | CCCAGGGCGGTA | |
| | | | | | AATCCGCGCGCG | |
| | | | | | CCGTACGTAAAT | |
| | | | | | ACTTCCCGGATG | |
| | | | | | CCACTATCCTGG | |
| | | | | | CGCTGACCACCA | |
| | | | | | ACGAAACCACCG | |
| | | | | | CGCGTCAGCTGG | |
| | | | | | TGCTGAGCAAAG | |
| | | | | | GCGTTGTGGCAC | |
| | | | | | AGCTGGTTGAAG | |
| | | | | | ATATCTCCTCTAC | |
| | | | | | CGATGCGTTCTA | |
| | | | | | CATCCAGGGTAA | |
| | | | | | AGAACTGGCGCT | |
| | | | | | GCAGAGCGGTCT | |
| | | | | | GGCGCGTAAAGG | |
| | | | | | CGACGTGGTTGT | |
| | | | | | TATGGTTTCCGG | |
| | | | | | CGCGTTAGTCCC | |
| | | | | | GAGCGGAACCAC | |
| | | | | | CAATACCGCTTC | |
| | | | | | CGTGCACGTGCT | |
| | | | | | GTAA | |
| membrane protein CDS | GGTTCACATAAA CATAATTATCGC CACGGCGATAGC | 4 | ATGGCCAACCGA GCAAACCGCAAC AACGTAGAAGAG | 14 | ATGTATTTAAGA CCCGATGAGGTG GCGCGTGTTCTT | 24 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | CGTACGCTTTTTG | | AGCGCTGAAGAT | | GAAAAAGCCGGC | |
| | CGTCACAACATC | | ATCCATAACGAT | | TTCACCATGGAT | |
| | CATGGTGAAGCC | | GTCAGCCAATTA | | GTTGTGACGCAA | |
| | GGCTTTTTCAAG | | GCGGATACGCTG | | AAAGCGTACGGC | |
| | AACACGCGCCAC | | GAAGAGGTGCTG | | TATCGCCGTGGC | |
| | CTCATCGGGTCTT | | AAATCGTGGGGC | | GATAATTATGTTT | |
| | AAATACATACTC | | AGCGACGCCAAA | | ATGTGAACCGTG | |
| | ATTCCTCATTATC | | GACGAAGCGGAG | | AAGCTCGTATGG | |
| | TTTTACCGCACGT | | GCCGCGCGCAAA | | GGCGTACCGCGT | |
| | TAACCTTACCTTA | | AAAGCGCAGGCG | | TAATTATTCATCC | |
| | TTCATTAAAGGC | | CTGCTGAAAGAG | | GGCTTTAAAGA | |
| | AACGCTTTCGGA | | ACCCGCGCCCGG | | GCGCAGCACAAC | |
| | ATATTCCATAAA | | CTTAACGGCAAC | | GCTTGCGGAGCC | |
| | GGGCTATTTACA | | AACCGCGTCCAG | | CGCGTCGGATAT | |
| | GCATAATTCAAA | | CAGGCGGCGTGC | | CAAAACCTGCGA | |
| | ATCTTGTCCTACA | | GACGCCATGGGC | | TCATTATGAGCA | |
| | CTTATAGACTCA | | TGCGCTGACAGC | | GTTCCCGCTCTAT | |
| | ATGGAATTAAGG | | TACGTGCGCGAC | | TTAGCGGGGGAT | |
| | GA | | AAACCGTGGCAA | | GCTCAACAGCAT | |
| | | | AGCGTCGGCGCC | | TATGGTATTCCA | |
| | | | GCAGCAGCCGTT | | CACGGGTTCAGT | |
| | | | GGGGTATTTATT | | TCGCGAATGGCG | |
| | | | GGCGTATTACTG | | CTTGAGCGTTTTC | |
| | | | AATTTACGTCGA | | TGAGTGGCCTGT | |
| | | | TAA | | TTGGCGAAACGC | |
| | | | | | AGTATAGCTGA | |
| zinc/ cadmium-binding protein CDS | GCGCGGAAAATC | 5 | ATGACCAAAAAG | 15 | ATGGATAGCGAC | 25 |
| | GACGCATAGCGC | | ATTTCCGCCCTA | | ATTAATCAGGTC | |
| | ATTCTCAGAAGC | | GCGTTTGGCATT | | ATTGATTCTTTTG | |
| | CGGCCTGGTCTC | | GGCATGGTAATG | | TTAAAGGCCCGG | |
| | GGTGGAAAAGCG | | GCGAGCAGCCAG | | CGGTCGTGGGAA | |
| | AATCTTTCCCAC | | GCTTTTGCCCAC | | AGATTCGCTTTTC | |
| | GACCGCCGGGCC | | GGTCACCATAGT | | CACCGAGACCAG | |
| | TTTAACAAAAGA | | CATGGCCCGGCG | | GCCGGCTTCTGA | |
| | ATCAATGACCTG | | CTGACCGAAGCG | | GAATGCGCTATG | |
| | ATTAATGTCGCT | | GAACAAAAGGCG | | CGTCGATTTTCCG | |
| | ATCCATTCTCTCT | | AGTGAAGGCATT | | CGCCTCGAAATC | |
| | CCGCGTAATGCG | | TTTGCTGACCAG | | ATGCTTGCGGGT | |
| | ATCTTTTTTCATC | | GACGTAAAGGAC | | CAGCTTCACGAT | |
| | ATACCTAACAAA | | AGGGCGCTGAGC | | CCGGCGATTAAA | |
| | CTGGCAGAGGGA | | GACTGGGAGGGG | | GCCGATCGCGCC | |
| | AAAGCCGCGCGG | | ATCTGGCAGTCG | | CAGCTCATGCCG | |
| | TTTTTCTGCGAAG | | GTTAACCCCTAT | | CACGATGTGCTG | |
| | TGTATTGTAAGA | | CTGCTGAACGGG | | TATATTCCCGCTG | |
| | TTTGTTTGATATG | | GATTTAGATCCG | | GCGGATGGAATG | |
| | TTATATCGTAAC | | GTTCTGGAGCAG | | ACCCGCAATGGC | |
| | ATATTATTGCAA | | AAGGCCAAAAAG | | TGGCGCCCTCCA | |
| | ACAT | | GCCGGTAAAAGC | | CTCTGCTCACTAT | |
| | | | GTGGCGGAATAT | | CTTATTTGGTAA | |
| | | | CGGGAATATTAT | | ACAGCAGCTGGA | |
| | | | AAGAAGGGCTAC | | ATTCGTCCTGCG | |
| | | | GCTACCGATGTC | | CCACTGGGACGG | |
| | | | GACCAGATTGGT | | CAGCGCGCTTAA | |
| | | | ATCGAGGATAAC | | CGTGCTGGATAA | |
| | | | GTCATGGAGTTT | | ACAGCAGGTTCC | |
| | | | CACGTCGGGAAA | | GCGCCGCGGTCC | |
| | | | ACCGTCAACGCC | | CCGGGTCGGCTC | |
| | | | TGTAAGTACAGC | | TTTTCTGCTGCAG | |
| | | | TATTCCGGTTAC | | GCGCTGAATGAA | |
| | | | AAAATTCTGACC | | ATGCAGATGCAG | |
| | | | TACGCATCCGGT | | CCGCGGGAGCAG | |
| | | | AAAAAAGGCGTG | | CACACGGCCCGC | |
| | | | CGCTACCTGTTC | | TTTATTGTCACCA | |
| | | | GAATGCCAGCAG | | GCCTGCTCAGCC | |
| | | | GCGGATTCAAAA | | ACTGTGCCGATC | |
| | | | GCGCCGAAGTTT | | TGCTGGGCAGCC | |
| | | | GTTCAGTTTAGC | | AGGTACAAACCT | |
| | | | GATCACACCATC | | CATCGCGCAGCC | |
| | | | GCGCCACGCAAG | | AGGCGCTTTTTG | |
| | | | TCCCAGCATTCC | | AAGCGATTCGTA | |
| | | | ACATCTTTATGG | | AGCATATTGACG | |
| | | | GCAATGAGTCCC | | CCCACTTTGCCG | |
| | | | AGGAAGCGCTGC | | ACCCGTTAACCC | |
| | | | TGAAAGAGATGG | | GGGAGTCGGTGG | |
| | | | ATAACTGGCCAA | | CGCAGGCGTTTT | |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | | | CCTACTATCCTTA TGCGCTGCATAA AGAGCAGATTGT CGACGAAATGCT GCACCACTAA | | ACCTCTCGCCAA ACTATCTATCCC ACCTGTTCCAGA AATGCGGGCCAA TGGGCTTTAACG AGTATCTGAATC ACATCCGCCTGG AGCAGGCCAGAA TGCTGTTAAAAG GCCACGATATGA AAGTGAAAGATA TCGCCCACGCCT GCGGTTTCGCCG ACAGCAACTACT TCTGCCGCCTGTT TCGCAAAAACAC CGAACGCTCGCC GTCGGAGTATCG CCGTCAATATCA CAGCCAGCTGAC GGAAAAAACAGC CCCGGCAAAAAA CTAG | |
| acyl carrier protein CDS | CTGACGAAGCGA GTTACATCACCG GTGAAACTCTGC ACGTCAACGGCG GAATGTATATGG TCTGACCGAGAT TTGCGCAAAACG CTCAGGAACCGC GCAGTCTGTGCG GTTCACTGTAAT GTTTTGTACAAA ATGATTTGCGTT ATGAGGGCAAAC AGCCGCAAAATA GCGTAAAATCGT GGTAAGACCTGC CGGGATTTAGTT GCAAATTTTTCA ACATTTTATACA CTACGAAAACCA TCGCGAAAGCGA GTTTTGA | 6 | ATGAGCACTATC GAAGAACGCGTT AAGAAAATTATC GGCGAACAGCTG GGCGTTAAGCAG GAAGAAGTTACC AACAATGCTTCC TTCGTTGAAGAC CTGGGCGCTGAT TCTCTTGACACC GTTGAGCTGGTA ATGGCTCTGGAA GAAGAGTTTGAT ACTGAAGATTCCG GACGAAGAAGCT GAGAAAATCACT ACTGTTCAGGCT GCCATTGATTAC ATCAACGGCCAC CAGGCGTAA | 16 | ATGAGTTTTGAA GGAAAAATCGCG CTGGTTACCGGT GCAAGTCGCGGG ATTGGCCGCGCA ATCGCTGAAACG CTCGTTGCCCGT GGCGCGAAAGTT ATCGGGACTGCG ACCAGCGAAAGC GGCGCGCAGGCG ATCAGCGATTAT TTAGGTGCTAAC GGTAAAGGTCTG CTGCTGAATGTG ACCGATCCTGCA TCTATTGAATCTG TTCTGGGAAATA TTCGCGCAGAAT TTGGTGAAGTTG ATATCCTGGTGA ACAATGCCGGGA TCACTCGTGATA ACCTGTTAATGC GCATGAAAGATG ATGAGTGGAACG ATATTATCGAAA CCAACCTGTCAT CTGTTTTCCGTCT GTCAAAAGCGGT AATGCGCGCTAT GATGAAAAAGCG TCATGGACGTAT TATCACTATCGG TTCTGTGGTTGGT ACCATGGGAAAT GCGGGTCAGGCC AACTACGCTGCG GCGAAAGCGGGT CTGATTGGCTTC AGTAAATCACTG GCTCGCGAAGTT GCGTCCCGCGGT ATTACTGTAAAC GTTGTTGCTCCG GGCTTTATTGAA ACGGACATGACG CGTGCGCTGACC GATGAGCAGCGT GCGGGTACGCTG GCGGCAGTTCCT GCGGGGCGCCTC | 26 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | | | | | GGCTCTCCAAAT GAAATCGCCAGT GCGGTGGCATTT TTAGCCTCTGAC GAAGCGAGTTAC ATCACCGGTGAA ACTCTGCACGTC AACGGCGGAATG TATATGGTCTGA | |
| ompX CDS | ACGCCTGGGGCG CCGACCAGCGGG AAGAGTGATTTG GCCAACGAGGCG CCGCTCTGAATG GAAATCATGGCG ATTAAAATAACC AGTATCGGCAAC CATGCCGGTACC TTACGAGACGAG CCGGGCATCCTT TCTCCTGTCAATT TTGTCAAATGCG GTAAAGGTTCCA GTGTAATTGAAT TACCCCGCGCCG GTTGAGCTAATG TTGAAAAAAAGG GTCTTAAAAGCA GTACAATAGGGC GGGTCTGAAGAT AATTTCA | 7 | ATGAATAAAATT GCACGTTTTTCA GCACTGGCCGTT GTTCTGGCTGCA TCCGTAGGTACC ACTGCTTTCGCTG CGACTTCTACCG TTACCGGTGGCT ACGCGCAGAGCG ACATGCAGGGTG AAGCGAACAAAG CTGGCGGTTTCA ACCTGAAGTACC GCTACGAGCAAG ACAACAACCCGC TGGGTGTTATCG GTTCTTTCACCTA CACCGAAAAAGA TCGTTCTGAATCT GGCGTTTACAAA AAAGGCCAGTAC TACGGCATCACC GCAGGTCCGGCT TACCGTCTGAAC GACTGGGCTAGC ATCTACGGCGTA GTGGGTGTTGGT TACGGTAAATTC CAGGACAACAGC TACCCGAACAAA TCTGATATGAGC GACTACGGTTTC TCTTACGGCGCT GGTCTGCAGTTC AACCCGATCGAA AACGTTGCCCTG GACTTCTCCTAC GAGCAGTCTCGC ATTCGTAACGTT GACGTTGGCACC TGGATTGCTGGC GTAGGTTACCGC TTCTAA | 17 | ATGCCCGGCTCG TCTCGTAAGGTA CCGGCATGGTTG CCGATACTGGTT ATTTTAATCGCC ATGATTTCCAT | 27 |
| DNA- binding protein HU-beta CDS | TCTGATTCCTGAT GAAAATAAACGC GACCTTGAAGAA ATTCCGGATAAC GTTATCGCCGAT TTAGATATCCAT CCGGTGAAACGA ATCGAGGAAGTT CTGGCACTTGCG CTACAGAACGAA CCGTTTGGAATG GAAGTCGTCACG GCAAAATAGTGA TTTCGCGCAAAT AGCGCTAAGAAA AATAGGGCTGGT AAGTAAATTCGT ACTTGCCAGCCT TTTTTTGTGTAGC | 8 | GTGAATAAATCT CAACTGATTGAC AAAATTGCTGCC GGTGCGGACATT TCTAAAGCCGCA GCTGGACGTGCG TTAGATGCTTTA ATCGCTTCTGTTA CTGAATCTCTGC AGGCTGGAGATG ACGTTGCGCTGG TAGGGTTTGGTA CTTTTGCTGTTAA AGAGCGCGCTGC CCGTACTGGTCG CAATCCGCAAAC AGGCAAAGAAAT CACCATTGCTGC TGCTAAAGTTCC | 18 | ATGAATCCTGAG CGTTCTGAACGC ATTGAAATCCCC GTATTGCCGTTG CGCGATGTGGTG GTTTATCCGCAC ATGGTCATACCC CTGTTTGTAGGG CGGGAAAAATCT ATCCGTTGTCTCG AAGCAGCCATGG ACCATGATAAAA AAATCATGCTGG TTGCGCAGAAAG AAGCCTCGACGG ATGAGCCGGGTG TAAACGATCTTTT CACCGTCGGGAC CGTGGCGTCTAT | 28 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | TAACTTAGATCG CTGGCAGGGGGG TCAATT | | GGGTTTCCGCGC AGGTAAAGCGCT GAAAGACGCGGT AAACTGA | | TTTGCAAATGCT GAAGCTACCGGA CGGTACTGTTAA AGTGCTGGTCGA AGGTTTGCAGCG CGCGCGCATCTC TGCGCTGTCTGA TAATGGCGAACA TTTTTCGGCGAA GGCGGAATACCT TGAATCGCCGGC GATTGACGAACG CGAGCAGGAAGT GCTGGTTCGTAC CGCTATCAGCCA GTTTGAAGGCTA CATCAAGCTGAA CAAAAAAATCCC TCCGGAAGTGCT GACGTCGCTGAA TAGCATCGACGA TCCGGCGCGTCT GGCGGATACCAT CGCTGCGCATAT GCCGCTGAAGCT GGCGGACAAACA GTCCGTGCTGGA GATGTCCGACGT TAACGAGCGTCT GGAATATCTGAT GGCGATGATGGA GTCGGAAATCGA TCTGCTGCAGGT GGAGAAGCGTAT TCGCAACCGCGT GAAAAAGCAGAT GGAGAAATCTCA GCGCGAGTACTA TCTGAATGAGCA AATGAAAGCCAT TCAAAAAGAGCT CGGCGAGATGGA CGACGCCCCGGA CGAGAACGAAGC GCTGAAGCGTAA GATCGACGCGGC GAAAATGCCGAA AGAGGCAAAAGA GAAAACCGAAGC GGAACTGCAAAA ACTGAAAATGAT GTCCCCGATGTC GGCGGAAGCGAC CGTCGTTCGCGG CTACATCGACTG GATGGTGCAGGT ACCGTGGAACGC TCGCAGCAAGGT TAAAAAAGACCT GCGTCAGGCTCA GGAGATCCTCGA TACCGATCACTA CGGCCTTGAGCG CGTGAAGGATCG CATTCTTGAGTA CCTCGCGGTGCA GAGCCGTGTTAA CAAGCTCAAAGG GCCGATCCTGTG CCTGGTTGGGCC TCCGGGGGTAGG TAAAACCTCTCT CGGCCAATCCAT CGCCAAAGCAAC TGGACGCAAATA TGTGCGTATGGC | |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | | | | | GCTGGGCGGCGT | |
| | | | | | GCGTGATGAAGC | |
| | | | | | GGAAATCCGCGG | |
| | | | | | TCACCGCCGTAC | |
| | | | | | CTATATTGGCTC | |
| | | | | | AATGCCGGGCAA | |
| | | | | | ACTGATCCAGAA | |
| | | | | | AATGGCTAAAGT | |
| | | | | | GGGCGTTAAAAA | |
| | | | | | CCCGCTGTTCTTG | |
| | | | | | CTGGATGAGATC | |
| | | | | | GACAAGATGTCT | |
| | | | | | TCTGACATGCGC | |
| | | | | | GGCGATCCGGCC | |
| | | | | | TCGGCGCTGCTG | |
| | | | | | GAGGTGTTGGAT | |
| | | | | | CCGGAACAGAAC | |
| | | | | | GTGGCCTTTAAC | |
| | | | | | GACCACTATCTG | |
| | | | | | GAAGTGGATTAC | |
| | | | | | GATCTCAGCGAC | |
| | | | | | GTGATGTTCGTT | |
| | | | | | GCGACCTCTAAC | |
| | | | | | TCCATGAACATC | |
| | | | | | CCGGCGCCGCTG | |
| | | | | | CTGGATCGTATG | |
| | | | | | GAAGTGATCCGC | |
| | | | | | CTCTCCGGCTAT | |
| | | | | | ACCGAAGATGAG | |
| | | | | | AAGCTAAACATC | |
| | | | | | GCCAAACGCCAT | |
| | | | | | CTGCTGTCAAAA | |
| | | | | | CAGATTGAGCGT | |
| | | | | | AACGCGCTCAAG | |
| | | | | | AAAGGCGAGCTG | |
| | | | | | ACGGTGGATGAC | |
| | | | | | AGCGCGATTATC | |
| | | | | | GGCATCATTCGC | |
| | | | | | TACTACACCCGT | |
| | | | | | GAAGCAGGCGTG | |
| | | | | | CGTGGTCTGGAG | |
| | | | | | CGTGAAATCTCG | |
| | | | | | AAACTGTGCCGC | |
| | | | | | AAAGCGGTGAAA | |
| | | | | | CAGCTGCTGCTG | |
| | | | | | GATAAGTCGCTG | |
| | | | | | AAACACATCGAG | |
| | | | | | ATTAACGGCGAC | |
| | | | | | AACCTGCACGAT | |
| | | | | | TTCCTTGGCGTGC | |
| | | | | | AGCGCTACGACT | |
| | | | | | ATGGTCGTGCGG | |
| | | | | | ATAGCGAAAACC | |
| | | | | | GCGTAGGTCAGG | |
| | | | | | TGACCGGACTGG | |
| | | | | | CGTGGACGGAAG | |
| | | | | | TGGGCGGCGATC | |
| | | | | | TGCTGACCATTG | |
| | | | | | AAACCGCCTGCG | |
| | | | | | TTCCGGGTAAAG | |
| | | | | | GCAAACTGACCT | |
| | | | | | ACACCGGTTCAC | |
| | | | | | TGGGTGAAGTCA | |
| | | | | | TGCAGGAATCCA | |
| | | | | | TCCAGGCGGCGC | |
| | | | | | TGACGGTGGTTC | |
| | | | | | GTTCACGTGCGG | |
| | | | | | ATAAGCTGGGTA | |
| | | | | | TTAACTCAGACT | |
| | | | | | TTTACGAAAAAC | |
| | | | | | GTGATATTCACG | |
| | | | | | TTCACGTGCCGG | |
| | | | | | AAGGCGCGACGC | |
| | | | | | CGAAGGATGGTC | |
| | | | | | CAAGCGCCGGTA | |
| | | | | | TCGCGATGTGCA | |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | | | | | CCGCGCTGGTTT CCTGTCTGACGG GTAATCCGGTAC GCGCCGACGTGG CGATGACCGGTG AGATTACCCTCC GTGGCCAGGTAT TGCCGATTGGTG GTCTGAAGGAAA AACTGTTGGCCG CGCATCGCGGCG GCATTAAGACTG TTCTGATTCCTGA TGAAAATAAACG CGACCTTGAAGA AATTCCGGATAA CGTTATCGCCGA TTTAGATATCCAT CCGGTGAAACGA ATCGAGGAAGTT CTGGCACTTGCG CTACAGAACGAA CCGTTTGGAATG GAAGTCGTCACG GCAAAATAG | |
| sspA CDS | GTAAGAAAGTCG GCCTGCGTAAAG CACGTCGTCGTC CTCAGTTCTCCA AACGTTAATTGT TTTCTGCTCACGC AGAACAATTTGC GAAAAAACCCGC TTCGGCGGGTTTT TTTATGGATAAA TTTGCCATTTTCC CTCTACAAACGC CCCATTGTTACC ACTTTTTCAGCAT TTCCAGAATCCC CTCACCACAACG TCTTCAAAATCT GGTAAACTATCA TCCAATTTTCTGC CCAAATGCAGGT GATTGTTCATTTT T | 9 | ATGGCTGTCGCT GCCAACAAACGT TCGGTAATGACG CTGTTTTCTGGTC CTACTGACATCT ATAGCCATCAGG TCCGCATCGTGC TGGCCGAAAAAG GTGTTAGTTTTGA GATAGAGCACGT GGAGAAGGACAA CCCGCCTCAGGA TCTGATTGACCTC AACCCGAATCAA AGCGTACCGACG CTTGTGGATCGT GAGCTCACTCTG TGGGAATCTCGC ATCATTATGGAA TATCTGGATGAG CGTTTCCCGCATC CGCCGCTCATGC CGGTTTACCCGG TGGCGCGTGGGG AAAGCCGTCTGT ATATGCAGCGTA TCGAAAAGGACT GGTATTCGTTGA TGAATACCATTC AGACCGGTACCG CTGCGCAGGCTG ATACTGCGCGTA AGCAGCTGCGTG AAGAACTACAGG CGATTGCGCCAG TTTTCACCCAGA AGCCCTACTTCCT GAGCGATGAGTT CAGCCTGGTGGA CTGCTACCTGGC ACCACTGCTGTG GCGTCTGCCGGT TCTCGGCGTAGA GCTGGTCGGCGC TGGCGCGAAAGA GCTTAAAGGCTA TATGACTCGCGT ATTTGAGCGCGA CTCTTTCCTCGCT TCTTTAACTGAA | 19 | ATGGCTGAAAAT CAATACTACGGC ACCGGTCGCCGC AAAAGTTCCGCA GCTCGCGTTTTCA TCAAACCGGGCA ACGGTAAAATCG TTATCAACCAGC GTTCTCTGGAAC AGTACTTCGGTC GTGAAACTGCCC GCATGGTAGTTC GTCAGCCGCTGG AACTGGTCGACA TGGTTGAGAAAT TAGATCTGTACA TCACCGTTAAAG GTGGTGGTATCT CTGGTCAGGCTG GTGCGATCCGTC ACGGTATCACCC GCGCTCTGATGG AGTACGACGAGT CCCTGCGTGGCG AACTGCGTAAAG CTGGTTTCGTTAC TCGTGATGCTCG TCAGGTTGAACG TAAGAAAGTCGG CCTGCGTAAAGC ACGTCGTCGTCC TCAGTTCTCCAA ACGTTAA | 29 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | | | GCCGAACGTGAA ATGCGTCTCGGT CGGGGCTAA | | | |
| tatE CDS | GTCAAAGCCGTA TTATCGACCCCTT AGGGACAACGCT TGCCGGGGCGGG AGAGCGGCCGCA GTTGATTTTTGCC GAACTTTCAGCT GATTATATTCAG CAGGTACGCGAG CGCCTGCCGGTG TTGCGCAATCGC CGCTTTGCGCCA CCGCAATTATTA TGACGTTTTTTTA AACAAGGCTTGA TTCACCTTGTTAC AGATTGCTATTG TGTCCGCGCGTC AAATAGCCGTTA ATTGTATGCGTG TATGATGGCGTA TTCG | 10 | ATGGGTGAGATT AGTATTACCAAA CTGCTGGTAGTC GCAGCGCTGATT ATCCTGGTGTTTG GTACCAAAAAGT TACGCACGCTGG GTGGAGACCTGG GCTCGGCTATCA AAGGCTTTAAAA AAGCCATGAGCG ATGACGATGACA GTGCGAAGAAGA CCAGTGCTGAAG AAGCGCCGGCAC AGAAGCTCTCTC ATAAAGAGTAA | 20 | ATGTTTGTTGCTG CCGGACAATTTG CCGTAACGCCGG ACTGGACGGGAA ACGCGCAGACCT GCGTCAGCATGA TGCGCCAGGCCG CGGAGCGGGGGG CGTCGCTTCTGGT TCTGCCTGAGGC GTTGCTGGCGCG AGACGATAACGA TGCGGATTTATC GGTTAAATCCGC CCAGCAGCTGGA TGGCGGCTTCTT ACAGCTCTTGCT GGCGGAGAGCGA AAACAGCGCTTT GACGACGGTGCT GACCCTGCATAT CCCTTCCGGCGA GAATACGCTGGT GGCCCTGCGTCA GGGGAAGATTGT GGCGCAATATCA GAAACTGCATCT CTATGATGCGTT CAATATCCAGGA ATCCAGGCTGGT CGATGCCGGGCG GCAAATTCCGCC GCTGATCGAAGT CGACGGGATGCG CGTCGGGCTGAT GACCTGCTACGA TTTACGTTTCCCT GAGCTGGCGCTG TCGTTAGCGCTC AGCGGCGCGCAG CTCATAGTGTTG CCTGCCGCGTGG GTAAAAGGGCCG CTGAAGGAACAT CACTGGGCGACG CTGCTGGCGGCG CGGGCGCTGGAT ACAACCTGCTAT ATTGTCGCCGCA GGAGAGTGCGGG ACGCGTAATATC GGTCAAAGCCGT ATTATCGACCCC TTAGGGACAACG CTTGCCGGGGCG GGAGAGCGGCCG CAGTTGATTTTTG CCGAACTTTCAG CTGATTATATTCA GCAGGTACGCGA GCGCCTGCCGGT GTTGCGCAATCG CCGCTTTGCGCC ACCGCAATTATT ATGA | 30 |
| LexA repressor CDS | GAGGCGGTGGTT GACCGTATCGGT CCCGAGCATCAT GAGCTTTCGGGG CGAGCGAAAGAT ATGGGATCGGCG | 11 | ATGAAAGCGTTA ACGACCAGGCAG CAAGAGGTGTTT GATCTCATTCGG GATCATATCAGC CAGACGGGCATG | 21 | ATGGCCAATAAT ACCACTGGGTTA ACCCGAATTATT AAAGCGGCCGGG TATTCCTGGAAA GGATTCCGTGCG | 31 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|------|------|------|------|------|------|------|
| | GCGGTACTGCTG | | CCGCCGACGCGT | | GCGTGGGTCAAT | |
| | GCGATTATCATC | | GCGGAGATTGCT | | GAGGCCGCATTT | |
| | GCGCTGATCGCG | | CAGCGCTTGGGG | | CGTCAGGAAGGC | |
| | TGGGGAACGCTG | | TTTCGCTCCCCAA | | ATCGCGGCCGTT | |
| | CTGTGGGCGAAC | | ACGCGGCGGAAG | | ATTGCCGTGGCG | |
| | TACCGCTAAGTC | | AGCATCTGAAAG | | ATCGCCTGCTGG | |
| | TTGTCGTAGCTG | | CGCTGGCGCGTA | | TTGGACGTCGAT | |
| | CTCGCAAAACGG | | AAGGCGCAATCG | | GCCATCACGCGG | |
| | AAAGAAACTCCT | | AGATCGTTTCCG | | GTGCTGCTCATT | |
| | GATTTTTGTGTGA | | GCGCCTCCCGCG | | AGCTCGGTCCTG | |
| | AATGTGGTTCCA | | GTATTCGTCTGCT | | TTAGTGATGATA | |
| | AAATCACCGTTA | | GACGGAAGAAGA | | GTTGAAATTATC | |
| | GCTGTATATACT | | AACCGGTCTGCC | | AATAGCGCGATT | |
| | CACAGCATAACT | | GCTTATTGGCCG | | GAGGCGGTGGTT | |
| | GTATATACACCC | | CGTCGCGGCAGG | | GACCGTATCGGT | |
| | AGGGGGC | | TGAGCCGCTGCT | | CCCGAGCATCAT | |
| | | | AGCGCAGCAGCA | | GAGCTTTCGGGG | |
| | | | CATTGAAGGCCA | | CGAGCGAAAGAT | |
| | | | CTACCAGGTGGA | | ATGGGATCGGCG | |
| | | | CCCGGCCATGTT | | GCGGTACTGCTG | |
| | | | TAAGCCGAACGC | | GCGATTATCATC | |
| | | | CGATTTTCTGCTG | | GCGCTGATCGCG | |
| | | | CGTGTTAGCGGT | | TGGGGAACGCTG | |
| | | | ATGTCGATGAAG | | CTGTGGGCGAAC | |
| | | | GATATCGGTATT | | TACCGCTAA | |
| | | | CTCGATGGCGAC | | | |
| | | | CTGCTGGCTGTC | | | |
| | | | CATAAAACGCAG | | | |
| | | | GATGTGCGCAAT | | | |
| | | | GGTCAGGTGGTT | | | |
| | | | GTGGCGCGTATC | | | |
| | | | GACGAAGAAGTG | | | |
| | | | ACCGTGAAGCGT | | | |
| | | | CTGAAAAAACAG | | | |
| | | | GGTAACGTCGTG | | | |
| | | | GAATTGCTGCCG | | | |
| | | | GAAAACAGCGAA | | | |
| | | | TTCTCGCCGATC | | | |
| | | | GTGGTCGACCTT | | | |
| | | | CGCGAACAAAGC | | | |
| | | | TTTACTATTGAA | | | |
| | | | GGCCTGGCCGTC | | | |
| | | | GGCGTTATCCGC | | | |
| | | | AACGGCAACTGG | | | |
| | | | CAATAA | | | |
| hisS CDS | TAAGAAAAGCGG | 12 | ...ATGAACGATTA | 22 | ATGCATAACCAG | 32 |
| | CCTGTACGAAGA | | TCTGCCGGGCGA | | GCTCCGATTCAA | |
| | CGGCGTACGTAA | | AACCGCTCTCTG | | CGTAGAAAATCA | |
| | AGACAGGCTGGA | | GCAGCGCATTGA | | AAACGAATTTAC | |
| | TAACGACGATAT | | AGGCTCACTGAA | | GTTGGGAATGTG | |
| | GATCGATCAGCT | | GCAGGTGCTTGG | | CCGATTGGCGAT | |
| | GGAAGCGCGTAT | | TAGCTACGGTTA | | GGCGCCCCCATC | |
| | TCGCGCTAAAGC | | CAGCGAAATCCG | | GCCGTACAGTCG | |
| | ATCGATGCTGGA | | TTTGCCGATTGTA | | ATGACAAACACG | |
| | TGAGGCGCGTCG | | GAGCAGACCCCG | | CGCACCACCGAT | |
| | TATCGATATCCA | | TTATTCAAACGC | | GTGGCGGCGACG | |
| | GCAGGTTGAAGC | | GCTATCGGCGAA | | GTAAATCAAATT | |
| | GAAATAACGTGT | | GTGACCGACGTG | | AAAGCCCTCGAG | |
| | TGGGAAGCGATA | | GTTGAAAAAGAG | | CGCGTTGGCGCG | |
| | CGCTTCCCGTGT | | ATGTACACCTTT | | GATATCGTGCGC | |
| | ATGATTGAACCT | | GAGGACCGTAAC | | GTTTCGGTGCCG | |
| | GCGGGCGCGAGG | | GGCGATAGCCTG | | ACGATGGATGCG | |
| | CGCCGGGGTTCA | | ACTCTACGTCCG | | GCGGAAGCGTTC | |
| | TTTTTGTATATAT | | GAAGGCACGGCT | | AAACTTATCAAA | |
| | AAAGAGAATAAA | | GGCTGCGTACGC | | CAGCAGGTTAAC | |
| | CGTGGCAAAGAA | | GCCGGTATCGAA | | GTCCCGCTGGTT | |
| | CATTCAA | | CATGGTCTCCTGT | | GCCGATATCCAC | |
| | | | ACAATCAAGAAC | | TTCGATTACCGC | |
| | | | AGCGCCTGTGGT | | ATTGCGCTGAAG | |
| | | | ACATTGGGCCGA | | GTAGCGGAATAC | |
| | | | TGTTCCGCCACG | | GGCGTTGATTGC | |
| | | | AACGTCCGCAAA | | CTGCGTATTAAC | |
| | | | AAGGCCGCTACC | | CCGGGCAATATC | |
| | | | GTCAGTTCCACC | | GGCAACGAAGAG | |
| | | | AGATTGGCGCCG | | CGTATCCGCATG | |

TABLE 3C-continued

| Name | Prm (In Forward direction, -250 to +10 region) | SEQ ID NO: | Expressed Sequence | SEQ ID NO: | Neighbor Sequence | SEQ ID NO: |
|------|------|------|------|------|------|------|
| | | | AAGCGTTTGGCC | | GTGGTGGACTGC | |
| | | | TGCAGGGGCCGG | | GCTCGCGATAAA | |
| | | | ATATCGATGCCG | | AATATTCCTATCC | |
| | | | AGCTGATTATGC | | GTATCGGGGTAA | |
| | | | TGACCGCCCGCT | | ACGCCGGTTCTC | |
| | | | GGTGGCGCGAGC | | TGGAAAAAGATC | |
| | | | TGGGCATCTCCG | | TCCAGGAAAAAT | |
| | | | GCCACGTTGCGC | | ACGGCGAACCGA | |
| | | | TGGAGCTGAACT | | CTCCGCAGGCGC | |
| | | | CTATCGGTTCGCT | | TGCTGGAATCGG | |
| | | | GGAGGCTCGCGC | | CAATGCGCCATG | |
| | | | TAACTATCGCGA | | TTGATCATCTCG | |
| | | | CGCGCTGGTGGC | | ATCGTCTCAACTT | |
| | | | CTATCTTGAGCA | | CGATCAGTTTAA | |
| | | | GTTTAAAGATAA | | AGTCAGCGTAAA | |
| | | | GCTGGACGAAGA | | AGCCTCCGATGT | |
| | | | CTGCAAACGCCG | | GTTCCTCGCGGTT | |
| | | | CATGTACACCAA | | GAATCCTATCGC | |
| | | | CCCGCTGCGCGT | | CTGTTGGCGAAA | |
| | | | GCTGGATTCTAA | | CAGATCGATCAG | |
| | | | AAACCCGGACGT | | CCTCTGCACCTC | |
| | | | CCAGGCGCTGCT | | GGGATCACCGAA | |
| | | | GAACGACGCCCC | | GCGGGCGGCGCG | |
| | | | GACGCTGGGCGA | | CGCAGCGGCGCG | |
| | | | CTATCTTGATGA | | GTGAAGTCCGCG | |
| | | | AGAGTCCAAAAC | | ATCGGCCTCGGC | |
| | | | GCATTTTGCCGG | | CTGCTGCTGTCTG | |
| | | | GCTGTGCGCGCT | | AAGGGATTGGCG | |
| | | | GCTGGATGATGC | | ATACGCTGCGCG | |
| | | | CGGTATTCGCTA | | TCTCTCTGGCGG | |
| | | | TACCGTGAATCA | | CGGATCCCGTTG | |
| | | | GCGTCTGGTACG | | AAGAGATCAAAG | |
| | | | CGGTCTCGACTA | | TGGGCTTCGATA | |
| | | | CTACAACCGCAC | | TTCTCAAGTCGCT | |
| | | | CGTGTTTGAGTG | | GCGTATTCGCTCT | |
| | | | GGTCACCACCAG | | CGCGGGATCAAC | |
| | | | CCTCGGTTCCCA | | TTTATTGCCTGCC | |
| | | | GGGCACCGTCTG | | CGACCTGTTCAC | |
| | | | CGCCGGAGGCCG | | GTCAGGAGTTTG | |
| | | | TTACGATGGTCT | | ACGTTATCGGTA | |
| | | | GGTTGAGCAGCT | | CCGTTAACGCGC | |
| | | | TGGCGGTCGCGC | | TGGAGCAGCGCC | |
| | | | TACCCCTGGCGT | | TGGAAGATATCA | |
| | | | CGGCTTTGCGAT | | TTACGCCGATGG | |
| | | | GGGGCTGGAACG | | ATATTTCGATCAT | |
| | | | TCTTGTTTTACTG | | TGGCTGCGTGGT | |
| | | | GTTCAGGCAGTG | | AAACGGTCCCGG | |
| | | | AATCCGGAATTT | | CGAGGCGCTGGT | |
| | | | AAAGCCGATCCT | | TTCCACCCTCGG | |
| | | | GTTGTCGATATA | | CGTAACCGGCGG | |
| | | | TACCTGGTAGCC | | CAATAAGAAAAG | |
| | | | TCCGGAACTGAC | | CGGCCTGTACGA | |
| | | | ACCCAGTCCGCA | | AGACGGCGTACG | |
| | | | GCAATGCGTCTG | | TAAAGACAGGCT | |
| | | | GCTGAACAGGTA | | GGATAACGACGA | |
| | | | CGCGATGCGTTA | | TATGATCGATCA | |
| | | | CCCGGCGTTAAG | | GCTGGAAGCGCG | |
| | | | CTGATGACCAAC | | TATTCGCGCTAA | |
| | | | CATGGCGGCGGC | | AGCATCGATGCT | |
| | | | AACTTTAAGAAG | | GGATGAGGCGCG | |
| | | | CAGTTTGCGCGC | | TCGTATCGATAT | |
| | | | GCTGATAAATGG | | CCAGCAGGTTGA | |
| | | | GGCGCTCGCGTT | | AGCGAAATAA | |
| | | | GCGCTGGTGCTG | | | |
| | | | GGCGAATCAGAA | | | |
| | | | ATCGCCGACGGA | | | |
| | | | AACGTGGTAGTG | | | |
| | | | AAAGATTTACGC | | | |
| | | | TCAGGTGAGCAA | | | |
| | | | ACTACCGTAACG | | | |
| | | | CAGGATAGCGTT | | | |
| | | | GCTGCGCATTTG | | | |
| | | | CGCACACTTCTG | | | |
| | | | GGTTAA | | | |

| | | | | | Mutagenic DNA | | Gene 1 | Gene 2 |
| Sort | First Reference | Current Name | Universal Name | Lineage | Description | Genotype | mutation | mutation |
|---|---|---|---|---|---|---|---|---|
| 1 | Application text | CI006 | CI006 | Isolated strain from *Enterobacter genera* | None | WT | | |
| 2 | Application text | CI008 | CI008 | Isolated strain from *Burkholderia genera* | None | WT | | |
| 3 | Application text | CI010 | CI010 | Isolated strain from *Klebsiella genera* | None | WT | | |
| 4 | Application text | CI019 | CI019 | Isolated strain from *Rahnella genera* | None | WT | | |
| 5 | Application text | CI028 | CI028 | Isolated strain from *Enterobacter genera* | None | WT | | |
| 6 | Application text | CI050 | CI050 | Isolated strain from *Klebsiella genera* | None | WT | | |
| 7 | Application text | CM002 | CM002 | Mutant of CI050 | Disruption of nifL gene with a kanamycin resistance expression cassette (KanR) encoding the aminoglycoside O-phosphotransferase gene aph1 inserted. | ΔnifL:: KanR | SEQ ID NO: 33 | |
| 8 | Application text | CM011 | CM011 | Mutant of CI019 | Disruption of nifL gene with a spectinomycin resistance expression cassette (SpecR) encoding the streptomycin 3"-O-adenylyltransferase gene aadA inserted. | ΔnifL:: SpecR | SEQ ID NO: 34 | |
| 9 | Application text | CM013 | CM013 | Mutant of CI006 | Disruption of nifL gene with a kanamycin resistance expression cassette (KanR) encoding the aminoglycoside O-phosphotransferase gene aph1 inserted. | ΔnifL:: KanR | SEQ ID NO: 35 | |
| 10 | FIG. 4A | CM004 | CM004 | Mutant of CI010 | Disruption of amtB gene with a kanamycin resistance expression cassette (KanR) encoding the aminoglycoside O-phosphotransferase gene aph1 inserted. | ΔamtB:: KanR | SEQ ID NO: 36 | |
| 11 | FIG. 4A | CM005 | CM005 | Mutant of CI010 | Disruption of nifL gene with a kanamycin resistance expression cassette (KanR) encoding the aminoglycoside O-phosphotransferase gene aph1 inserted. | ΔnifL:: KanR | SEQ ID NO: 37 | |
| 12 | FIG. 4B | CM015 | CM015 | Mutant of CI006 | Disruption of nifL gene with a fragment of the region upstream of the ompX gene inserted (Prm5). | ΔnifL:: Prm5 | SEQ ID NO: 38 | |
| 13 | FIG. 4B | CM021 | CM021 | Mutant of CI006 | Disruption of nifL gene with a fragment of the region upstream of an | ΔnifL:: Prm2 | SEQ ID NO: 39 | |

Table of Strains

-continued

Figures 4A, 4B:
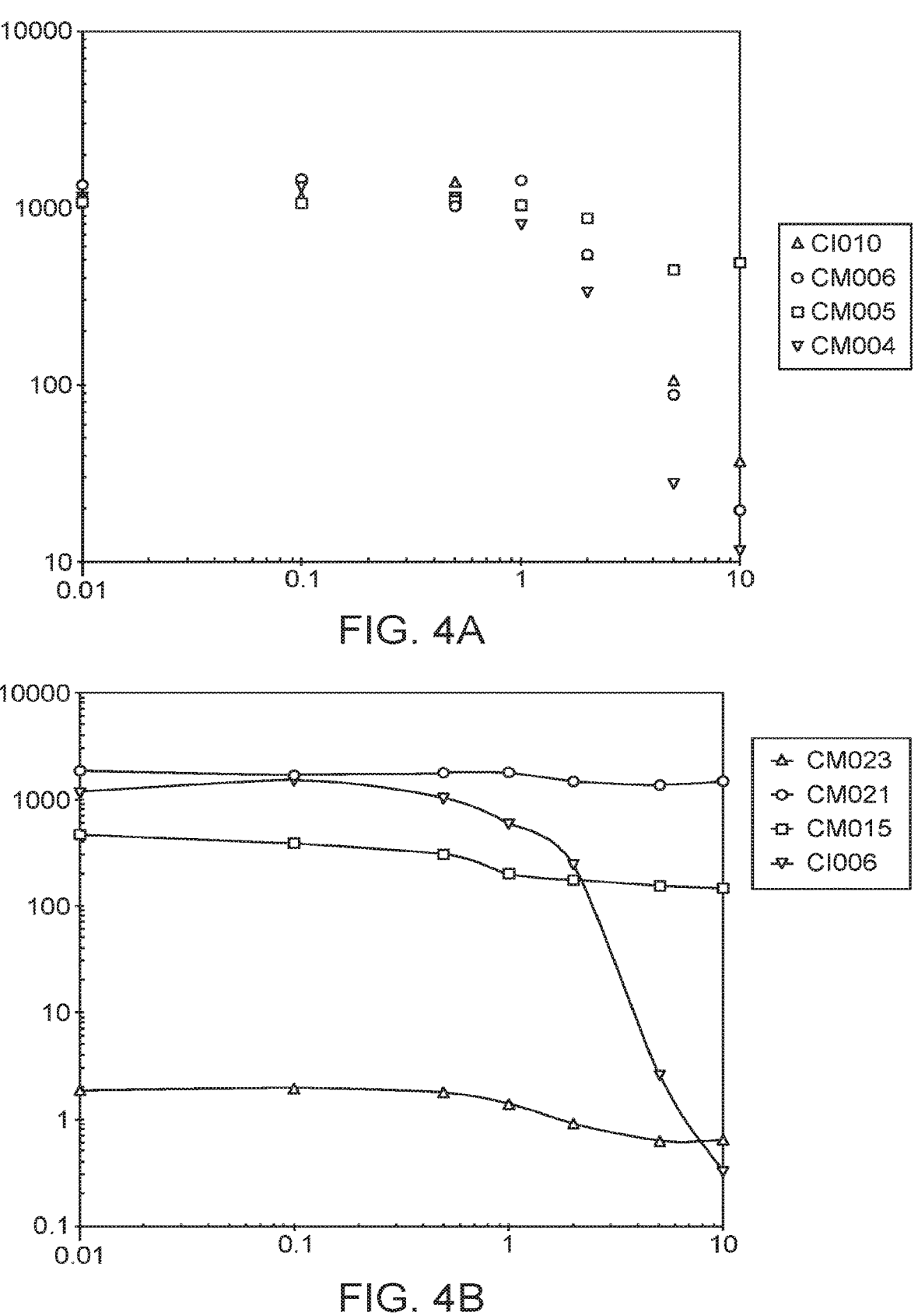
FIGS. 4A-D depict in vitro phenotypes of various strains. The Acetylene Reduction Assay (ARA) activities of mutants of strain CI010 (FIG. 4A) and mutants of strain CI006 (FIG. 4B) grown in nitrogen fixation media supplemented with 0 to 10 mM glutamine. ARA activities of additional strains are shown in FIG. 4C, and the ammonium excretion profile across time of two strains is shown in FIG. 4D.
Figure 10A:
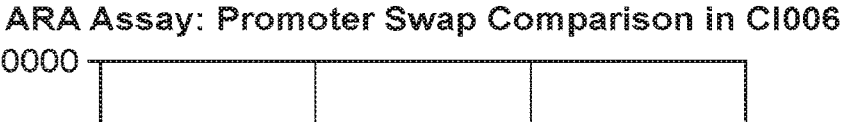
FIGS. 10A-C depict additional results for ARA activities of candidate microbes and counterpart candidate mutants grown in nitrogen fixation media supplemented with 0 to 10 mM glutamine.
Figure 10A:
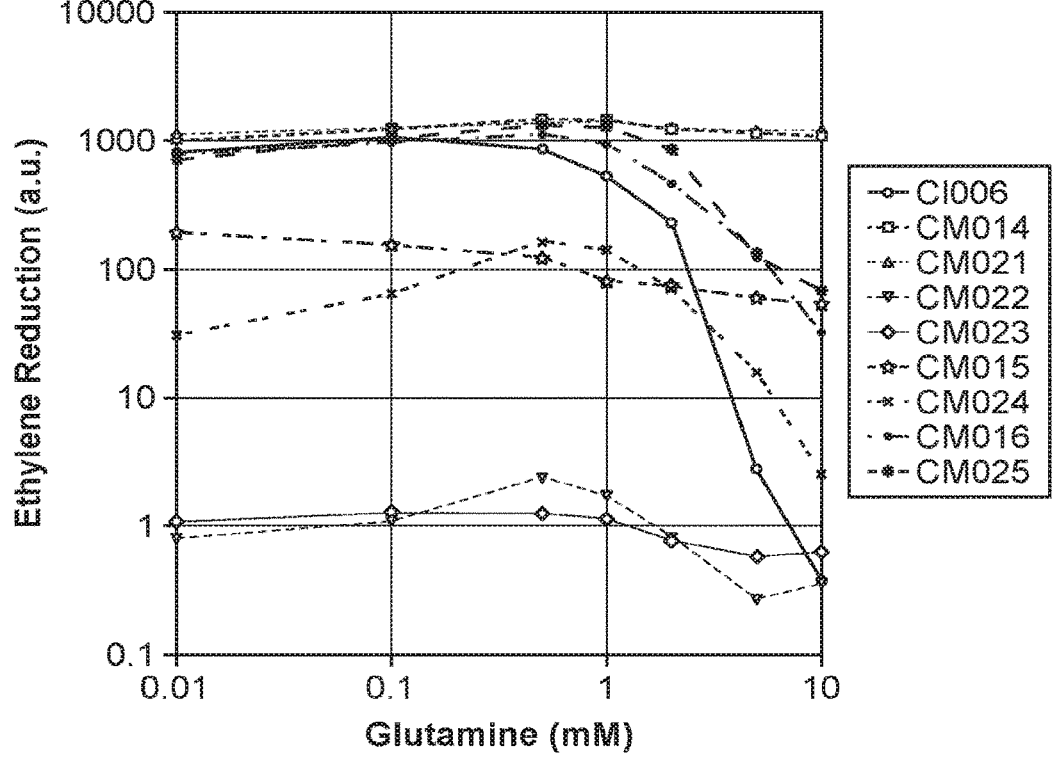
Figure 10B:
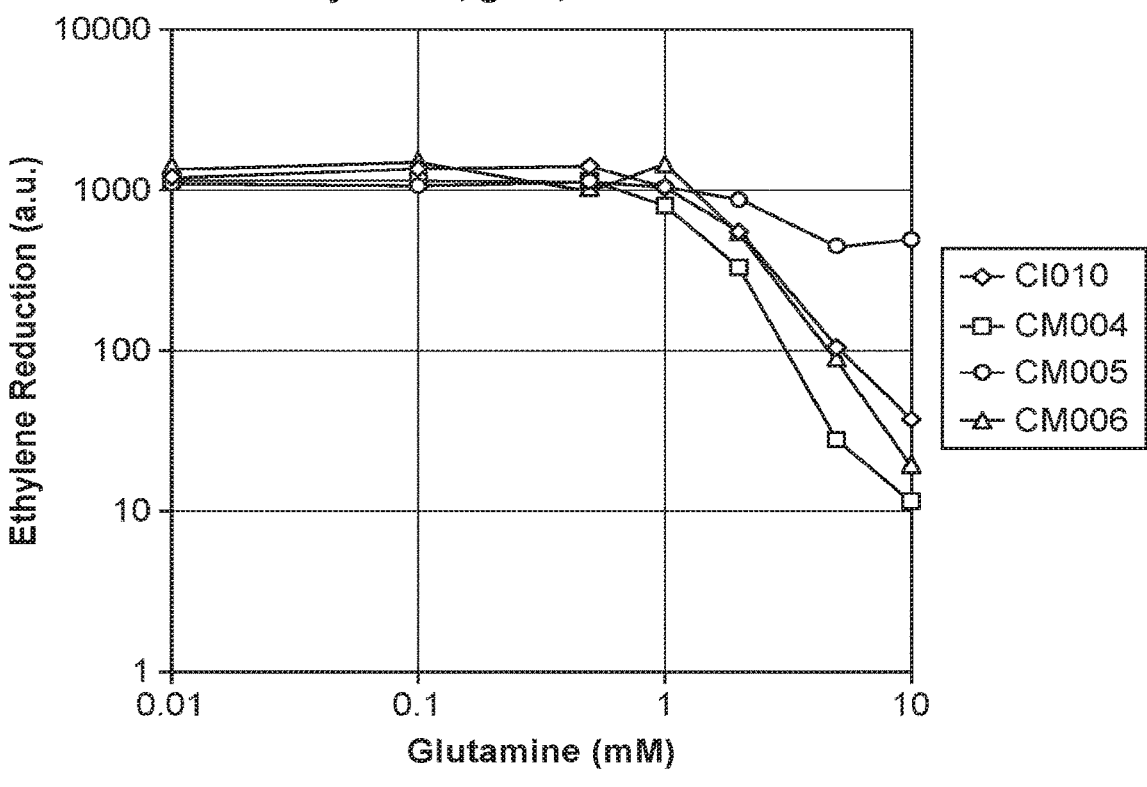

| | | | | | Mutagenic | | | |
| | First | Current | Universal | | DNA | | Gene 1 | Gene 2 |
| Sort | Reference | Name | Name | Lineage | Description | Genotype | mutation | mutation |
|---|---|---|---|---|---|---|---|---|
| 14 | FIG. 4B | CM023 | CM023 | Mutant of CI006 | unanotated gene and the first 73 bp of that gene inserted (Prm2). Disruption of nifL gene with a fragment of the region upstream of the acpP gene and the first 121 bp of the acpP gene inserted (Prm4). | ΔnifL:: Prm4 | SEQ ID NO: 40 | |
| 15 | FIG. 10A | CM014 | CM014 | Mutant of CI006 | Disruption of nifL gene with a fragment of the region upstream of the lpp gene and the first 29 bp of the lpp gene inserted (Prm1). | ΔnifL:: Prm1 | SEQ ID NO: 41 | |
| 16 | FIG. 10A | CM016 | CM016 | Mutant of CI006 | Disruption of nifL gene with a fragment of the region upstream of the lexA 3 gene and the first 21 bp of the lexA 3 gene inserted (Prm9). | ΔnifL:: Prm9 | SEQ ID NO: 42 | |
| 17 | FIG. 10A | CM022 | CM022 | Mutant of CI006 | Disruption of nifL gene with a fragment of the region upstream of the mntP 1 gene and the first 53 bp of the mntP 1 gene inserted (Prm3). | ΔnifL:: Prm3 | SEQ ID NO: 43 | |
| 18 | FIG. 10A | CM024 | CM024 | Mutant of CI006 | Disruption of nifL gene with a fragment of the region upstream of the sspA gene inserted (Prm7). | ΔnifL:: Prm7 | SEQ ID NO: 44 | |
| 19 | FIG. 10A | CM025 | CM025 | Mutant of CI006 | Disruption of nifL gene with a fragment of the region upstream of the hisS gene and the first 52 bp of the hisS gene inserted (Prm10). | ΔnifL:: Prm10 | SEQ ID NO: 45 | |
| 20 | FIG. 10B | CM006 | CM006 | Mutant of CI010 | Disruption of glnB gene with a kanamycin resistance expression cassette (KanR) encoding the aminoglycoside O-phosphotransferase gene aph1 inserted. | ΔglnB:: KanR | SEQ ID NO: 46 | |
| 21 | FIG. 10C | CI028 nifL: KanR | CM017 | Mutant of CI028 | Disruption of nifL gene with a kanamycin resistance expression cassette (KanR) encoding the aminoglycoside O-phosphotransferase gene aph1 inserted. | ΔnifL:: KanR | SEQ ID NO: 47 | |
| 22 | FIG. 10C | CI019 nifL: SpecR | CM011 | Mutant of CI019 | Disruption of nifL gene with a spectinomycin resistance expression cassette (SpecR) encoding the streptomycin 3"-O-adenylyltransferase gene aadA inserted. | ΔnifL:: SpecR | SEQ ID NO: 48 | |
| 23 | FIG. 10C | CI006 nifL: KanR | CM013 | Mutant of CI006 | Disruption of nifL gene with a kanamycin resistance expression cassette (KanR) encoding the | ΔnifL:: KanR | SEQ ID NO: 49 | |

-continued

Figure 10C:
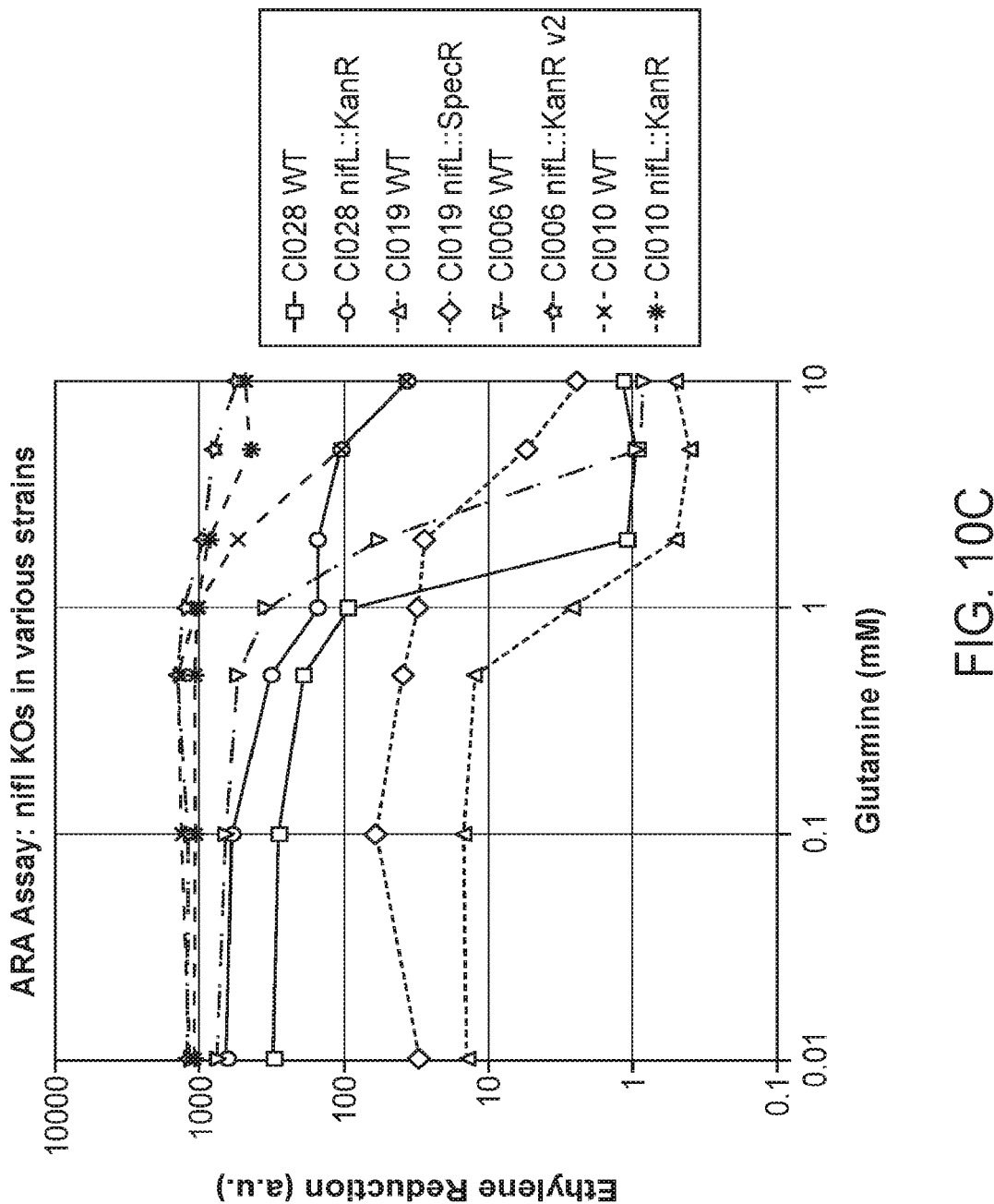

| | | | | | Mutagenic | | | |
| Sort | First Reference | Current Name | Universal Name | Lineage | DNA Description | Genotype | Gene 1 mutation | Gene 2 mutation |
|---|---|---|---|---|---|---|---|---|
| 24 | FIG. 10C | CI010 nifL: KanR | CM005 | Mutant of CI010 | aminoglycoside O-phosphotransferase gene aph1 inserted. Disruption of nifL gene with a kanamycin resistance expression cassette (KanR) encoding the aminoglycoside O-phosphotransferase gene aph1 inserted. | ΔnifL:: KanR | SEQ ID NO: 50 | |
| 25 | FIG. 4C | Strain 2 | CI006 | Isolated strain from *Enterobacter genera* | None | WT | | |
| 26 | FIG. 4C | Strain 4 | CI010 | Isolated strain from *Klebsiella genera* | None | WT | | |
| 27 | FIG. 4C | Strain 1 | CI019 | Isolated strain from *Rahnella genera* | None | WT | | |
| 28 | FIG. 4C | Strain 3 | CI028 | Isolated strain from *Enterobacter genera* | None | WT | | |
| 29 | FIG. 4B | Strain 2 | CI006 | Isolated strain from *Enterobacter genera* | None | WT | | |
| 30 | FIG. 4B | High | CM014 | Mutant of CI006 | Disruption of nifL gene with a fragment of the region upstream of the lpp gene and the first 29 bp of the lpp gene inserted (Prm1). | ΔnifL:: Prm1 | SEQ ID NO: 51 | |
| 31 | FIG. 4B | Med | CM015 | Mutant of CI006 | Disruption of nifL gene with a fragment of the region upstream of the ompX gene inserted (Prm5). | ΔnifL:: Prm5 | SEQ ID NO: 52 | |
| 32 | FIG. 4B | Low | CM023 | Mutant of CI006 | Disruption of nifL gene with a fragment of the region upstream of the acpP gene and the first 121 bp of the acpP gene inserted (Prm4). | ΔnifL:: Prm4 | SEQ ID NO: 53 | |
| 33 | FIG. 4D | Strain 2 | CI006 | Isolated strain from *Enterobacter genera* | None | WT | | |
| 34 | FIG. 4D | Evolved | CM029 | Mutant of CI006 | Disruption of nifL gene with a fragment of the region upstream of the ompX gene inserted (Prm5) and deletion of the 1287 bp after the start codon of the | ΔnifL:: Prm5 ΔglnE-AR_KO1 | SEQ ID NO: 54 | SEQ ID NO: 61 |

-continued

Figure 14A:
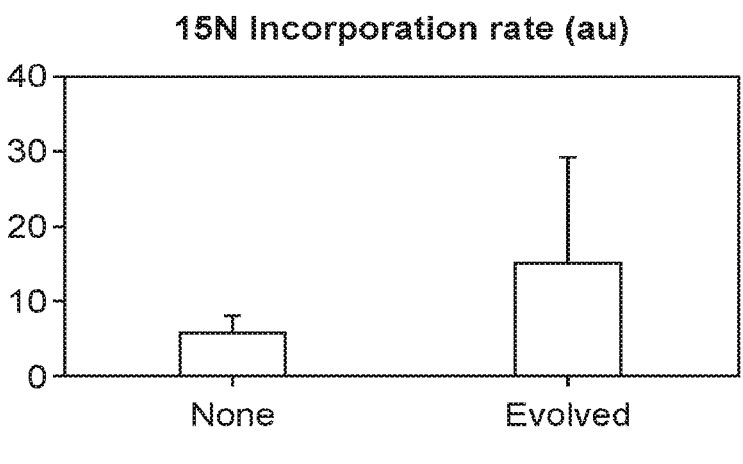
FIG. 14A depicts rate of incorporation of 15N gas. Plants inoculated with evolved strain showed increase in 15N gas incorporation compared to uninoculated plants.
Figure 14B:
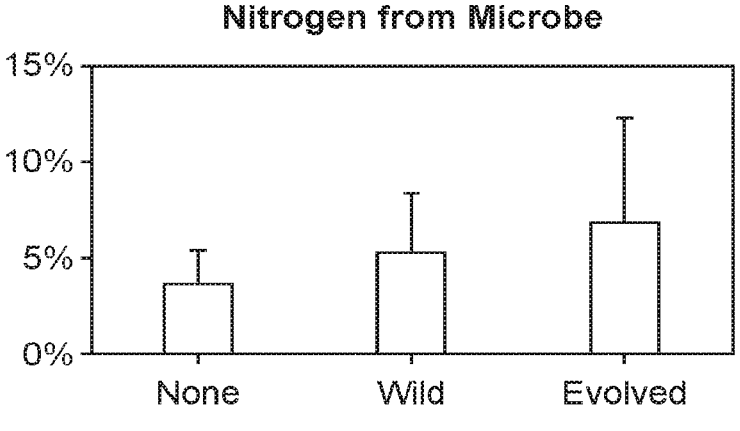
FIG. 14B depicts 4 weeks after planting, up to 7% of the nitrogen in plants inoculated with an evolved strain is derived from microbially fixed nitrogen.
Figure 14C:
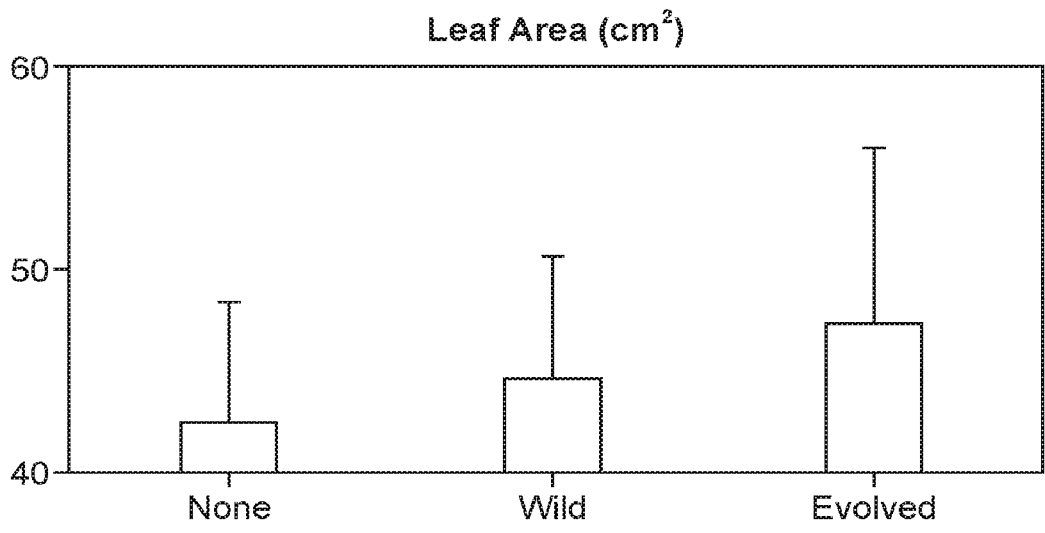
FIG. 14C depicts leaf area (and other biomass measurement, data not shown) is increased in plants inoculated with an evolved strain when compared to uninoculated or wild type inoculated plants.
Figure 15A:
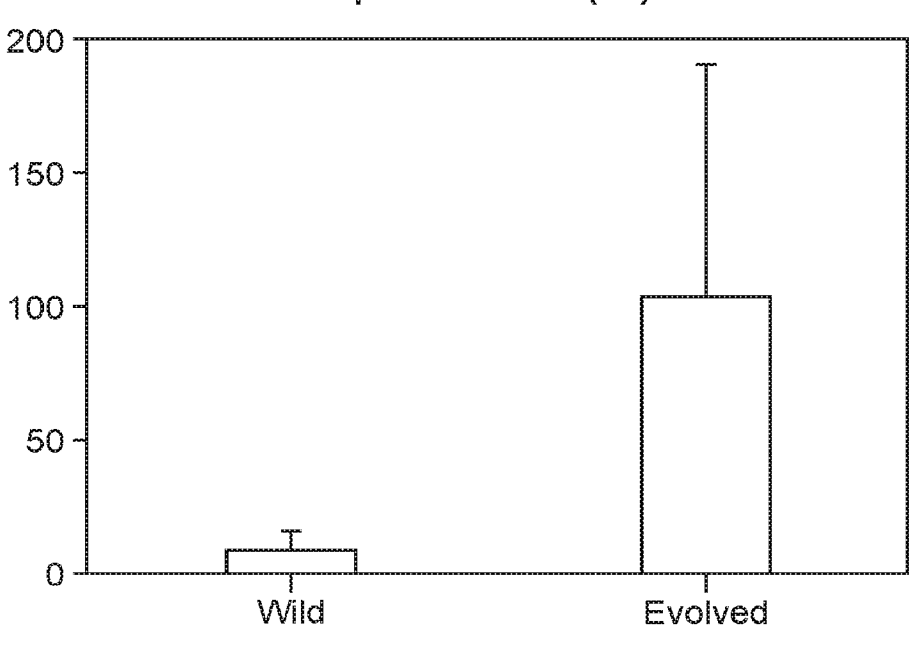
FIG. 15A depicts evolved strains that show significantly higher nifH production in the root tissue, as measured by in planta transcriptomic study.
Figure 15B:
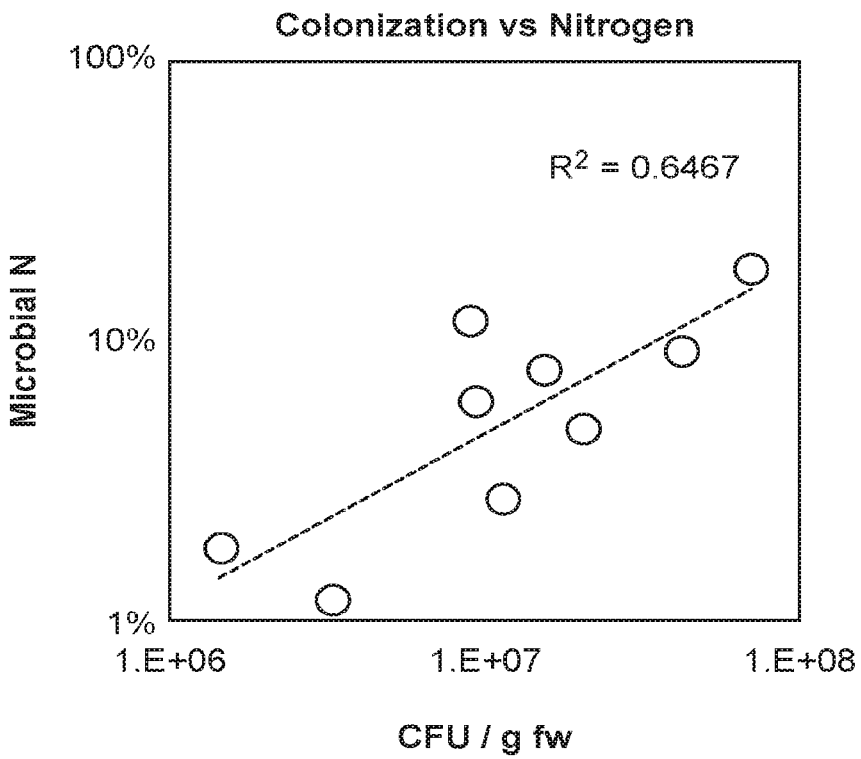
FIG. 15B depicts that rate of fixed nitrogen found in plant tissue is correlated with the rate in which that particular plant is colonized by HoME optimized strain.

| | | | | | Mutagenic | | | |
| | First | Current | Universal | | DNA | | Gene 1 | Gene 2 |
| Sort | Reference | Name | Name | Lineage | Description | Genotype | mutation | mutation |
|---|---|---|---|---|---|---|---|---|
| | | | | | glnE gene containing the adenylyl-removing domain of glutamate-ammonia-ligase adenylyltransferase (ΔglnE-AR_KO1). | | | |
| 35 | FIG. 14C | Wild | CI006 | Isolated strain from *Enterobacter genera* | None | WT | | |
| 36 | FIG. 14C | Evolved | CM014 | Mutant of CI006 | Disruption of nifL gene with a fragment of the region upstream of the lpp gene and the first 29 bp of the lpp gene inserted (Prm1). | ΔnifL:: Prm1 | SEQ ID NO: 55 | |
| 37 | FIG. 14B | Wild | CI019 | Isolated strain from *Rahnella genera* | None | WT | | |
| 38 | FIG. 14B | Evolved | CM011 | Mutant of CI019 | Disruption of nifL gene with a spectinomycin resistance expression cassette (SpecR) encoding the streptomycin 3"-O-adenylyltransferase gene aadA inserted. | ΔnifL:: SpecR | SEQ ID NO: 56 | |
| 39 | FIG. 14A | Evolved | CM011 | Mutant of CI019 | Disruption of nifL gene with a spectinomycin resistance expression cassette (SpecR) encoding the streptomycin 3"-O-adenylyltransferase gene aadA inserted. | ΔnifL:: SpecR | SEQ ID NO: 57 | |
| 40 | FIG. 15A | Wild | CI006 | Isolated strain from *Enterobacter genera* | None | WT | | |
| 41 | FIG. 15A | Evolved | CM013 | Mutant of CI006 | Disruption of nifL gene with a kanamycin resistance expression cassette (KanR) encoding the aminoglycoside O-phosphotransferase gene aph1 inserted. | ΔnifL:: KanR | SEQ ID NO: 58 | |
| 42 | FIG. 15B | No name | CM011 | Mutant of CI019 | Disruption of nifL gene with a spectinomycin resistance expression cassette (SpecR) encoding the streptomycin 3"-O-adenylyltransferase gene aadA inserted. | ΔnifL:: SpecR | SEQ ID NO: 59 | |
| 43 | FIG. 16B | Strain 5 | CI008 | Isolated strain from *Burkholderia genera* | None | WT | | |
| 44 | FIG. 16B | Strain 1 | CM011 | Mutant of CI019 | Disruption of nifL gene with a spectinomycin resistance expression cassette (SpecR) | ΔnifL:: SpecR | SEQ ID NO: 60 | |

-continued

| | | | | | Mutagenic | | | |
| | First | Current | Universal | | DNA | | Gene 1 | Gene 2 |
| Sort | Reference | Name | Name | Lineage | Description | Genotype | mutation | mutation |
|---|---|---|---|---|---|---|---|---|
| | | | | | encoding the streptomycin 3"-O-adenylyltransferase gene aadA inserted. | | | |

Table of Strains

Table of Strains sequences

| SEQ ID NO: | Sequence |
|---|---|
| 33 | ATGAGCCATATTCAACGGGAAACGTCTTGCTCCAGGCCGCGATTAAATT CCAACATGGATGCTGATTTATATGGGTATAAATGGGCTCGCGATAATGT CGGGCAATCAGGTGCGACAATCTATCGATTGTATGGGAAGCCCGATGC GCCAGAGTTGTTTCTGAAACATGGCAAAGGTAGCGTTGCCAATGATGTT ACAGATGAGATGGTCAGACTAAACTGGCTGACGGAATTTATGCCTCTTC CGACCATCAAGCATTTTATCCGTACTCCTGATGATGCATGGTTACTCAC CACTGCGATCCCCGGGAAAACAGCATTCCAGGTATTAGAAGAATATCC TGATTCAGGTGAAAATATTGTTGATGCGCTGGCAGTGTTCCTGCGCCGG TTGCATTCGATTCCTGTTTGTAATTGTCCTTTTAACAGCGATCGCGTATT TCGTCTCGCTCAGGCGCAATCACGAATGAATAACGGTTTGGTTGATGCG AGTGATTTTGATGACGAGCGTAATGGCTGGCCTGTTGAACAAGTCTGGA AAGAAATGCATAAGCTTTTGCCATTCTCACCGGATTCAGTCGTCACTCA TGGTGATTTCTCACTTGATAACCTTATTTTTGACGAGGGGAAATTAATA GGTTGTATTGATGTTGGACGAGTCGGAATCGCAGACCGATACCAGGAT CTTGCCATCCTATGGAACTGCCTCGGTGAGTTTTCTCCTTCATTACAGA AACGGCTTTTTCAAAAATATGGTATTGATAATCCTGATATGAATAAATT GCAGTTTCATTTGATGCTCGATGAGTTTTTCTAATAAGCCTGCCTGGTTC TGCGTTTCCCGCTCTTTAATACCCTGACCGGAGGTGAGCAATGA |
| 34 | ATGAGCATCACGGCGTTATCAGCATCATTTCCTGAGGGGAATATCGCCA GCCGCTTGTCGCTGCAACATCCTTCACTGTTTTATACCGTGGTTGAACA ATCTTCGGTGGCGAGCGTGTTGAGTCATCCTGACTAGCTGAGATGAGG GCTCGCCCCTCGTCCCGACACTTCCAGATCGCCATAGCGCACAGCGCC TCGAGCGGTGGTAACGGCGCAGTGGCGGTTTTCATGGCTTGTTATGACT GTTTTTTTGGGGTACAGTCTATGCCTCGGGCATCCAAGCAGCAAGCGCG TTACGCCGTGGGTCGATGTTTGATGTTATGGAGCAGCAACGATGTTACG CAGCAGGGCAGTCGCCCTAAAACAAAGTTAAACATCATGAGGGAAGCG GTGATCGCCGAAGTATCGACTCAACTATCAGAGGTAGTTGGCGTCATC GAGCGCCATCTCGAACCGACGTTGCTGGCCGTACATTTGTACGGCTCCG CAGTGGATGGCGGCCTGAAGCCACACAGTGATATTGATTTGCTGGTTAC GGTGACCGTAAGGCTTGATGAAACAACGCGGCGAGCTTTGATCAACGA CCTTTTGGAAACTTCGGCTTCCCCTGGAGAGAGCGAGATTCTCCGCGCT GTAGAAGTCACCATTGTTGTGCACGACGACATCATTCCGTGGCGTTATC CAGCTAAGCGCGAACTGCAATTTGGAGAATGGCAGCGCAATGACATTC TTGCAGGTATCTTCGAGCCAGCCACGATCGACATTGATCTGGCTATCTT GCTGACAAAAGCAAGAGAACATAGCGTTGCCTTGGTAGGTCCAGCGGC GGAGGAACTCTTTGATCCGGTTCCTGAACAGGATCTATTTGAGGCGCTA AATGAAACCTTAACGCTATGGAACTCGCCGCCCGACTGGGCTGGCGAT GAGCGAAATGTAGTGCTTACGTTGTCCCGCATTTGGTACAGCGCAGTAA CCGGCAAAATCGCGCCGAAGGATGTCGCTGCCGACTGGGCAATGGAGC GCCTGCCGGCCCAGTATCAGCCCGTCATACTTGAAGCTAGACAGGCTTA TCTTGGACAAGAAGAAGATCGCTTGGCCTCGCGCGCAGATCAGTTGGA AGAATTTGTCCACTACGTGAAAGGCGAGATCACCAAGGTAGTCGGCAA ATAATGTCTAACAATTCGTTCAAGCCGACGCCGCTTCGCGGCGCGGCTT AACTCAAGCGTTAGATGCACTAAGCACATAATTGCTCACAGCCAAACT ATCAGGTCAAGTCTGCTTTTATTATTTTTAAGCGTGCATAATAAGCCCT ACACAAATGGTACCCGACCGGTGGTGAATTTAATCTCGCTGACGTGTA GACATTCCCTTATCCAGACGCTGATCGCCCATCATCGCGGTTCTTTAGA TCTCTCGGTCCGCCCTGATGGCGGCACCTTGCTGACGTTACGCCTGCCG GTACAGCAGGTTATCACCGGAGGCTTAAAATGA |
| 35 | CTGATCCTTCAACTCAGCAAAAGTTCGATTTATTCAACAAAGCCACGTT GTGTCTCAAAATCTCTGATGTTACATTGCACAAGATAAAAATATATCAT CATGAACAATAAAACTGTCTGCTTACATAAACAGTAATACAAGGGGTG TTATGAGCCATATTCAACGGGAAACGTCTTGCTCCAGGCCGCGATTAAA TTCCAACATGGATGCTGATTTATATGGGTATAAATGGGCTCGCGATAAT GTCGGGCAATCAGGTGCGACAATCTATCGATTGTATGGGAAGCCCGAT GCGCCAGAGTTGTTTCTGAAACATGGCAAAGGTAGCGTTGCCAATGAT GTTACAGATGAGATGGTCAGACTAAACTGGCTGACGGAATTTATGCCT |

| Table of Strains sequences | |
| --- | --- |

| SEQ ID NO: | Sequence |
| --- | --- |
| | CTTCCGACCATCAAGCATTTTATCCGTACTCCTGATGATGCATGGTTAC |
| | TCACCACTGCGATCCCCGGGAAAACAGCATTCCAGGTATTAGAAGAAT |
| | ATCCTGATTCAGGTGAAAATATTGTTGATGCGCTGGCAGTGTTCCTGCG |
| | CCGGTTGCATTCGATTCCTGTTTGTAATTGTCCTTTTAACAGCGATCGCG |
| | TATTTCGTCTCGCTCAGGCGCAATCACGAATGAATAACGGTTTGGTTGA |
| | TGCGAGTGATTTTGATGACGAGCGTAATGGCTGGCCTGTTGAACAAGTC |
| | TGGAAAGAAATGCATAAGCTTTTGCCATTCTCACCGGATTCAGTCGTCA |
| | CTCATGGTGATTTCTCACTTGATAACCTTATTTTTGACGAGGGGAAATT |
| | AATAGGTTGTATTGATGTTGGACGAGTCGGAATCGCAGACCGATACCA |
| | GGATCTTGCCATCCTATGGAACTGCCTCGGTGAGTTTTCTCCTTCATTAC |
| | AGAAACGGCTTTTTCAAAAATATGGTATTGATAATCCTGATATGAATAA |
| | ATTGCAGTTTCATTTGATGCTCGATGAGTTTTTCTAATAAGCCTTGACCC |
| | TACGATTCCCGCTATTTCATTCACTGACCGGAGGTTCAAAATGA |
| | |
| 36 | ATGAAGATAGCAACAATGAAAACAGGTCTGGGAGCGTTGGCTCTTCTT |
| | CCCTGATCCTTCAACTCAGCAAAAGTTCGATTTATTCAACAAAGCCACG |
| | TTGTGTCTCAAAATCTCTGATGTTACATTGCACAAGATAAAAATATATC |
| | ATCATGAACAATAAAACTGTCTGCTTACATAAACAGTAATACAAGGGG |
| | TGTTATGAGCCATATTCAACGGGAAACGTCTTGCTCCCGTCCGCGCTTA |
| | AACTCCAACATGGACGCTGATTTATATGGGTATAAATGGGCTCGCGAT |
| | AATGTCGGGCAATCAGGTGCGACAATCTATCGCTTGTATGGGAAGCCC |
| | GATGCGCCAGAGTTGTTTCTGAAACATGGCAAAGGTAGCGTTGCCAAT |
| | GATGTTACAGATGAGATGGTCCGTCTCAACTGGCTGACGGAGTTTATGC |
| | CTCTCCCGACCATCAAGCATTTTATCCGTACTCCTGATGATGCGTGGTT |
| | ACTCACCACCGCGATTCCTGGGAAAACAGCCTTCCAGGTATTAGAAGA |
| | ATATCCTGATTCAGGTGAAAATATTGTTGATGCGCTGGCCGTGTTCCTG |
| | CGCCGGTTACATTCGATTCCTGTTTGTAATTGTCCTTTTAACAGCGATCG |
| | TGTATTTCGTCTTGCTCAGGCGCAATCACGCATGAATAACGGTTTGGTT |
| | GATGCGAGTGATTTTGATGACGAGCGTAATGGCTGGCCTGTTGAACAA |
| | GTCTGGAAAGAAATGCACAAGCTCTTGCCATTCTCACCGGATTCAGTCG |
| | TCACTCATGGTGATTTCTCACTTGATAACCTTATTTTTGACGAGGGGAA |
| | ATTAATAGGTTGTATTGATGTTGGACGGGTCGGAATCGCAGACCGTTAC |
| | CAGGACCTTGCCATTCTTTGGAACTGCCTCGGTGAGTTTTCTCCTTCATT |
| | ACAGAAACGGCTTTTTCAAAAATATGGTATTGATAATCCTGATATGAAT |
| | AAATTGCAGTTTCATTTGATGCTCGATGAGTTTTTCTAATAAGCCTGTG |
| | AAGGGCTGGACGTAAACAGCCACGGCGAAACGCCTACAACGCCTGA |
| | |
| 37 | ATGACCCTGAATATGATGCTCGATAACGCCGTACCCGAGGCGATTGCC |
| | GGCTGATCCTTCAACTCAGCAAAAGTTCGATTTATTCAACAAAGCCACG |
| | TTGTGTCTCAAAATCTCTGATGTTACATTGCACAAGATAAAAATATATC |
| | ATCATGAACAATAAAACTGTCTGCTTACATAAACAGTAATACAAGGGG |
| | TGTTATGAGCCATATTCAACGGGAAACGTCTTGCTCCCGTCCGCGCTTA |
| | AACTCCAACATGGACGCTGATTTATATGGGTATAAATGGGCTCGCGAT |
| | AATGTCGGGCAATCAGGTGCGACAATCTATCGCTTGTATGGGAAGCCC |
| | GATGCGCCAGAGTTGTTTCTGAAACATGGCAAAGGTAGCGTTGCCAAT |
| | GATGTTACAGATGAGATGGTCCGTCTCAACTGGCTGACGGAGTTTATGC |
| | CTCTCCCGACCATCAAGCATTTTATCCGTACTCCTGATGATGCGTGGTT |
| | ACTCACCACCGCGATTCCTGGGAAAACAGCCTTCCAGGTATTAGAAGA |
| | ATATCCTGATTCAGGTGAAAATATTGTTGATGCGCTGGCCGTGTTCCTG |
| | CGCCGGTTACATTCGATTCCTGTTTGTAATTGTCCTTTTAACAGCGATCG |
| | TGTATTTCGTCTTGCTCAGGCGCAATCACGCATGAATAACGGTTTGGTT |
| | GATGCGAGTGATTTTGATGACGAGCGTAATGGCTGGCCTGTTGAACAA |
| | GTCTGGAAAGAAATGCACAAGCTCTTGCCATTCTCACCGGATTCAGTCG |
| | TCACTCATGGTGATTTCTCACTTGATAACCTTATTTTTGACGAGGGGAA |
| | ATTAATAGGTTGTATTGATGTTGGACGGGTCGGAATCGCAGACCGTTAC |
| | CAGGACCTTGCCATTCTTTGGAACTGCCTCGGTGAGTTTTCTCCTTCATT |
| | ACAGAAACGGCTTTTTCAAAAATATGGTATTGATAATCCTGATATGAAT |
| | AAATTGCAGTTTCATTTGATGCTCGATGAGTTTTTCTAATAAGCCTTGGT |
| | TCTGCGTTTCCCGCTCTTTAATACCCTGACCGGAGGTGAGCAATGA |
| | |
| 38 | ATGACCCTGAATATGATGATGGATGCCGGCGGACATCATCGCGACAAA |
| | CAATATTAATACCGGCAACCACACCGGCAATTTACGAGACTGCGCAGG |
| | CATCCTTTCTCCCGTCAATTTCTGTCAAATAAAGTAAAAGAGGCAGTCT |
| | ACTTGAATTACCCCCGGCTGGTTGAGCGTTTGTTGAAAAAAAGTAACTG |
| | AAAAATCCGTAGAATAGCGCCACTCTGATGGTTAATTAACCTATTCAAT |
| | TAAGAATTATCTGGATGAATGTGCCATTAAATGCGCAGCATAATGGTGC |
| | GTTGTGCGGGAAAACTGCTTTTTTTTGAAAGGGTTGGTCAGTAGCGGAA |
| | ACAACTCACTTCACACCCCGAAGGGGGAAGTTGCCTGACCCTACGATT |
| | CCCGCTATTTCATTCACTGACCGGAGGTTCAAAATGA |
| | |
| 39 | ATGACCCTGAATATGATGATGGATGCCGGCTCACCACGGCGATAACCA |
| | TAGGTTTTCGGCGTGGCCACATCCATGGTGAATCCCACTTTTTCCAGCA |
| | CGCGCGCCACTTCATCGGGTCTTAAATACATAGATTTTCCTCGTCATCTT |

-continued

| Table of Strains sequences | |
| --- | --- |
| SEQ ID NO: | Sequence |
| | TCCAAAGCCTCGCCACCTTACATGACTGAGCATGGACCGTGACTCAGA |
| | AAATTCCACAAACGAACCTGAAAGGCGTGATTGCCGTCTGGCCTTAAA |
| | AATTATGGTCTAAACTAAAATTTACATCGAAAACGAGGGAGGATCCTA |
| | TGTTTAACAAACCGAATCGCCGTGACGTAGATGAAGGTGTTGAGGATA |
| | TTAACCACGATGTTAACCAGCTCGAACTCACTTCACACCCCGAAGGGG |
| | GAAGTTGCCTGACCCTACGATTCCCGCTATTTCATTCACTGACCGGAGG |
| | TTCAAAATGA |
| 40 | ATGACCCTGAATATGATGATGGATGCCGGCTGACGAGGCAGGTTACAT |
| | CACTGGTGAAACCCTGCACGTCAATGGCGGAATGTATATGGTTTAACC |
| | ACGATGAAAATTATTTGCGTTATTAGGGCGAAAGGCCTCAAAATAGCG |
| | TAAAATCGTGGTAAGAACTGCCGGGATTTAGTTGCAAATTTTTCAACAT |
| | TTTATACACTACGAAAACCATCGCGAAAGCGAGTTTTGATAGGAAATTT |
| | AAGAGTATGAGCACTATCGAAGAACGCGTTAAGAAAATTATCGGCGAA |
| | CAGCTGGGCGTTAAGCAGGAAGAAGTTACCAACAATGCTTCCTTCGTT |
| | GAAGACCTGGGCGCTGATTCTCTTGACACCGAACTCACTTCACACCCCG |
| | AAGGGGGAAGTTGCCTGACCCTACGATTCCCGCTATTTCATTCACTGAC |
| | CGGAGGTTCAAAATGA |
| 41 | ATGACCCTGAATATGATGATGGATGCCGGCCGTCCTGTAATAATAACC |
| | GGACAATTCGGACTGATTAAAAAAGCGCCCTTGTGGCGCTTTTTTTATA |
| | TTCCCGCCTCCATTTAAAATAAAAAATCCAATCGGATTTCACTATTTAA |
| | ACTGGCCATTATCTAAGATGAATCCGATGGAAGCTCGCTGTTTTAACAC |
| | GCGTTTTTTAACCTTTTATTGAAAGTCGGTGCTTCTTTGAGCGAACGATC |
| | AAATTTAAGTGGATTCCCATCAAAAAAATATTCTCAACCTAAAAAAGTT |
| | TGTGTAATACTTGTAACGCTACATGGAGATTAACTCAATCTAGAGGGTA |
| | TTAATAATGAATCGTACTAAACTGGTACTGGGCGCAACTCACTTCACAC |
| | CCCGAAGGGGGAAGTTGCCTGACCCTACGATTCCCGCTATTTCATTCAC |
| | TGACCGGAGGTTCAAAATGA |
| 42 | ATGACCCTGAATATGATGATGGATGCCGGCATATTGACACCATGACGC |
| | GCGTAATGCTGATTGGTTCTGTGACGCTGGTAATGATTGTCGAAATTCT |
| | GAACAGTGCCATCGAAGCCGTAGTAGACCGTATTGGTGCAGAATTCCA |
| | TGAACTTTCCGGGCGGGCGAAGGATATGGGGTCGGCGGCGGTGCTGAT |
| | GTCCATCCTGCTGGCGATGTTTACCTGGATCGCATTACTCTGGTCACAT |
| | TTTCGATAACGCTTCCAGAATTCGATAACGCCCTGGTTTTTTGCTTAAAT |
| | TTGGTTCCAAAATCGCCTTTAGCTGTATATACTCACAGCATAACTGTAT |
| | ATACACCCAGGGGGCGGGATGAAAGCATTAACGGCCAGGAACTCACTT |
| | CACACCCCGAAGGGGGAAGTTGCCTGACCCTACGATTCCCGCTATTTCA |
| | TTCACTGACCGGAGGTTCAAAATGA |
| 43 | ATGACCCTGAATATGATGATGGATGCCGGCATCATATTGCGCTCCCTGG |
| | TTATCATTTGTTACTAAATGAAATGTTATAATATAACAATTATAAATAC |
| | CACATCGCTTTCAATTCACCAGCCAAATGAGAGGAGCGCCGTCTGACA |
| | TAGCCAGCGCTATAAAACATAGCATTATCTATATGTTTATGATTAATAA |
| | CTGATTTTTGCGTTTTGGATTTGGCTGTGGCATCCTTGCCGCTCTTTTCG |
| | CAGCGTCTGCGTTTTTGCCCTCCGGTCAGGGCATTTAAGGGTCAGCAAT |
| | GAGTTTTTACGCAATTACGATTCTTGCCTTCGGCATGTCGATGGATGCTT |
| | TAACTCACTTCACACCCCGAAGGGGGAAGTTGCCTGACCCTACGATTCC |
| | CGCTATTTCATTCACTGACCGGAGGTTCAAAATGA |
| 44 | ATGACCCTGAATATGATGATGGATGCCGGCCGCGTCAGGTTGAACGTA |
| | AAAAAGTCGGTCTGCGCAAAGCACGTCGTCGTCCGCAGTTCTCCAAAC |
| | GTTAATTGGTTTCTGCTTCGGCAGAACGATTGGCGAAAAAACCCGGTGC |
| | GAACCGGGTTTTTTTATGGATAAAGATCGTGTTATCCACAGCAATCCAT |
| | TGATTATCTCTTCTTTTTCAGCATTTCCAGAATCCCCTCACCACAAAGCC |
| | CGCAAAATCTGGTAAACTATCATCCAATTTTCTGCCCAAATGGCTGGGA |
| | TTGTTCATTTTTTGTTTGCCTTACAACGAGAGTGACAGTACGCGCGGGT |
| | AGTTAACTCAACATCTGACCGGTCGATAACTCACTTCACACCCCGAAGG |
| | GGGAAGTTGCCTGACCCTACGATTCCCGCTATTTCATTCACTGACCGGA |
| | GGTTCAAAATGA |
| 45 | ATGACCCTGAATATGATGATGGATGCCGGCCCTGTATGAAGATGGCGT |
| | GCGCAAAGATCGCCTGGATAACAGCGATATGATTAGCCAGCTTGAAGC |
| | CCGCATTCGCGCGAAAGCGTCAATGCTGGACGAAGCGCGTCGTATCGA |
| | TGTGCAACAGGTAGAAAAATAAGGTTGCTGGGAAGCGGCAGGCTTCCC |
| | GTGTATGATGAACCCGCCCGGCGCGACCCGTTGTTCGTCGCGGCCCCGA |
| | GGGTTCATTTTTTGTATTAATAAAGAGAATAAACGTGGCAAAAAATATT |
| | CAAGCCATTCGCGGCATGAACGATTATCTGCCTGGCGAACTCACTTCAC |
| | ACCCCGAAGGGGGAAGTTGCCTGACCCTACGATTCCCGCTATTTCATTC |
| | ACTGACCGGAGGTTCAAAATGA |

| Table of Strains sequences | |
| --- | --- |
| SEQ ID NO: | Sequence |
| 46 | ATGAAAAAGATTGATGCGATTATTAAACCTTTCAAACTGGATGACGTGC GCTGATCCTTCAACTCAGCAAAAGTTCGATTTATTCAACAAAGCCACGT TGTGTCTCAAAATCTCTGATGTTACATTGCACAAGATAAAAATATATCA TCATGAACAATAAAACTGTCTGCTTACATAAACAGTAATACAAGGGGT GTTATGAGCCATATTCAACGGGAAACGTCTTGCTCCCGTCCGCGCTTAA ACTCCAACATGGACGCTGATTTATATGGGTATAAATGGGCTCGCGATA ATGTCGGGCAATCAGGTGCGACAATCTATCGCTTGTATGGGAAGCCCG ATGCGCCAGAGTTGTTTCTGAAACATGGCAAAGGTAGCGTTGCCAATG ATGTTACAGATGAGATGGTCCGTCTCAACTGGCTGACGGAGTTTATGCC TCTCCCGACCATCAAGCATTTTATCCGTACTCCTGATGATGCGTGGTTA CTCACCACCGCGATTCCTGGGAAAACAGCCTTCCAGGTATTAGAAGAA TATCCTGATTCAGGTGAAAATATTGTTGATGCGCTGGCCGTGTTCCTGC GCCGGTTACATTCGATTCCTGTTTGTAATTGTCCTTTTAACAGCGATCGT GTATTTCGTCTTGCTCAGGCGCAATCACGCATGAATAACGGTTTGGTTG ATGCGAGTGATTTTGATGACGAGCGTAATGGCTGGCCTGTTGAACAAGT CTGGAAAGAAATGCACAAGCTCTTGCCATTCTCACCGGATTCAGTCGTC ACTCATGGTGATTTCTCACTTGATAACCTTATTTTTTGACGAGGGGAAAT TAATAGGTTGTATTGATGTTGGACGGGTCGGAATCGCAGACCGTTACCA GGACCTTGCCATTCTTTGGAACTGCCTCGGTGAGTTTTCTCCTTCATTAC AGAAACGGCTTTTTCAAAAATATGGTATTGATAATCCTGATATGAATAA ATTGCAGTTTCATTTGATGCTCGATGAGTTTTTTCTAATAAGCCTCGCGCG TGATTCGTATCCGCACCGGCGAAGAAGACGACGCGGCGATTTAA |
| 47 | ATGACCATGAACCTGATGACGGATGTCGTCTCAGCCACCGGGATCGCC GGGTTGCTTTCACGACAACACCCGACGCTGTTTTTTACACTAATTGAAC AGGCCCCCGTGGCGATCACGCTGACGGATACCGCTGCCCGCATTGTCTA TGCCAACCCGGGCGTGTTGAGTCATCCTGACTAGCTGAGATGAGGGCT CGCCTGATCCTTCAACTCAGCAAAAGTTCGATTTATTCAACAAAGCCAC GTTGTGTCTCAAAATCTCTGATGTTACATTGCACAAGATAAAAATATAT CATCATGAACAATAAAACTGTCTGCTTACATAAACAGTAATACAAGGG GTGTTATGAGCCATATTCAACGGGAAACGTCTTGCTCCAGGCCGCGATT AAATTCCAACATGGATGCTGATTTATATGGGTATAAATGGGCTCGCGAT AATGTCGGGCAATCAGGTGCGACAATCTATCGATTGTATGGGAAGCCC GATGCGCCAGAGTTGTTTCTGAAACATGGCAAAGGTAGCGTTGCCAAT GATGTTACAGATGAGATGGTCAGACTAAACTGGCTGACGGAATTTATG CCTCTTCCGACCATCAAGCATTTTATCCGTACTCCTGATGATGCATGGTT ACTCACCACTGCGATCCCCGGGAAAACAGCATTCCAGGTATTAGAAGA ATATCCTGATTCAGGTGAAAATATTGTTGATGCGCTGGCAGTGTTCCTG CGCCGGTTGCATTCGATTCCTGTTTGTAATTGTCCTTTTAACAGCGATCG CGTATTTCGTCTCGCTCAGGCGCAATCACGAATGAATAACGGTTTGGTT GATGCGAGTGATTTTGATGACGAGCGTAATGGCTGGCCTGTTGAACAA GTCTGGAAAGAAATGCATAAGCTTTTGCCATTCTCACCGGATTCAGTCG TCACTCATGGTGATTTCTCACTTGATAACCTTATTTTTTGACGAGGGGAA ATTAATAGGTTGTATTGATGTTGGACGAGTCGGAATCGCAGACCGATAC CAGGATCTTGCCATCCTATGGAACTGCCTCGGTGAGTTTTCTCCTTCATT ACAGAAACGGCTTTTTCAAAAATATGGTATTGATAATCCTGATATGAAT AAATTGCAGTTTCATTTGATGCTCGATGAGTTTTTTCTAATAAGCCTGAC CGGTGGTGAATTTAATCTCGCTGACGTGTAGACATTCATCGATCTGCAT CCACGGTCCGGCGGCGGTACCTGCCTGACGCTACGTTTACCGCTCTTTT ATGAACTGACCGGAGGCCCAAGATGA |
| 48 | ATGAGCATCACGGCGTTATCAGCATCATTTCCTGAGGGGAATATCGCCA GCCGCTTGTCGCTGCAACATCCTTCACTGTTTTATACCGTGGTTGAACA ATCTTCGGTGGCGAGCGTGTTGAGTCATCCTGACTAGCTGAGATGAGG GCTCGCCCCCTCGTCCCGACACTTCCAGATCGCCATAGCGCACAGCGCC TCGAGCGGTGGTAACGGCGCAGTGGCGGTTTTCATGGCTTGTTATGACT GTTTTTTTGGGGTACAGTCTATGCCTCGGGCATCCAAGCAGCAAGCGCG TTACGCCGTGGGTCGATGTTTGATGTTATGGAGCAGCAACGATGTTACG CAGCAGGGCAGTCGCCCTAAAACAAAGTTAAACATCATGAGGGAAGCG GTGATCGCCGAAGTATCGACTCAACTATCAGAGGTAGTTGGCGTCATC GAGCGCCATCTCGAACCGACGTTGCTGGCCGTACATTTGTACGGCTCCG CAGTGGATGGCGGCCTGAAGCCACACAGTGATATTGATTTGCTGGTTAC GGTGACCGTAAGGCTTGATGAAACAACGCGGCGAGCTTTGATCAACGA CCTTTTGGAAACTTCGGCTTCCCCTGGAGAGAGCGAGATTCTCCGCGCT GTAGAAGTCACCATTGTTGTGCACGACGACATCATTCCGTGGCGTTATC CAGCTAAGCGCGAACTGCAATTTGGAGAATGGCAGCGCAATGACATTC TTGCAGGTATCTTCGAGCCAGCCACGATCGACATTGATCTGGCTATCTT GCTGACAAAAGCAAGAGAACATAGCGTTGCCTTGGTAGGTCCAGCGGC GGAGGAACTCTTTGATCCGGTTCCTGAACAGGATCTATTTGAGGCGCTA AATGAAACCTTAACGCTATGGAACTCGCCGCCCGACTGGGCTGGCGAT GAGCGAAATGTAGTGCTTACGTTGTCCCGCATTTGGTACAGCGCAGTAA CCGGCAAAATCGCGCCGAAGGATGTCGCTGCCGACTGGGCAATGGAGC GCCTGCCGGCCCAGTATCAGCCCGTCATACTTGAAGCTAGACAGGCTTA |

-continued

| Table of Strains sequences | |
|---|---|
| SEQ ID NO: | Sequence |

TCTTGGACAAGAAGAAGATCGCTTGGCCTCGCGCGCAGATCAGTTGGA
AGAATTTGTCCACTACGTGAAAGGCGAGATCACCAAGGTAGTCGGCAA
ATAATGTCTAACAATTCGTTCAAGCCGACGCCGCTTCGCGGCGCGGCTT
AACTCAAGCGTTAGATGCACTAAGCACATAATTGCTCACAGCCAAACT
ATCAGGTCAAGTCTGCTTTTATTATTTTTAAGCGTGCATAATAAGCCCT
ACACAAATGGTACCCGACCGGTGGTGAATTTAATCTCGCTGACGTGTA
GACATTCCCTTATCCAGACGCTGATCGCCCATCATCGCGGTTCTTTAGA
TCTCTCGGTCCGCCCTGATGGCGGCACCTTGCTGACGTTACGCCTGCCG
GTACAGCAGGTTATCACCGGAGGCTTAAAATGA

49   CTGATCCTTCAACTCAGCAAAAGTTCGATTTATTCAACAAAGCCACGTT
GTGTCTCAAAATCTCTGATGTTACATTGCACAAGATAAAAATATATCAT
CATGAACAATAAAACTGTCTGCTTACATAAACAGTAATACAAGGGGTG
TTATGAGCCATATTCAACGGGAAACGTCTTGCTCCAGGCCGCGATTAAA
TTCCAACATGGATGCTGATTTATATGGGTATAAATGGGCTCGCGATAAT
GTCGGGCAATCAGGTGCGACAATCTATCGATTGTATGGGAAGCCCGAT
GCGCCAGAGTTGTTTCTGAAACATGGCAAAGGTAGCGTTGCCAATGAT
GTTACAGATGAGATGGTCAGACTAAACTGGCTGACGGAATTTATGCCT
CTTCCGACCATCAAGCATTTTATCCGTACTCCTGATGATGCATGGTTAC
TCACCACTGCGATCCCCGGGAAAACAGCATTCCAGGTATTAGAAGAAT
ATCCTGATTCAGGTGAAAATATTGTTGATGCGCTGGCAGTGTTCCTGCG
CCGGTTGCATTCGATTCCTGTTTGTAATTGTCCTTTTAACAGCGATCGCG
TATTTCGTCTCGCTCAGGCGCAATCACGAATGAATAACGGTTTGGTTGA
TGCGAGTGATTTTGATGACGAGCGTAATGGCTGGCCTGTTGAACAAGTC
TGGAAAGAAATGCATAAGCTTTTGCCATTCTCACCGGATTCAGTCGTCA
CTCATGGTGATTTCTCACTTGATAACCTTATTTTTGACGAGGGGAAATT
AATAGGTTGTATTGATGTTGGACGAGTCGGAATCGCAGACCGATACCA
GGATCTTGCCATCCTATGGAACTGCCTCGGTGAGTTTTCTCCTTCATTAC
AGAAACGGCTTTTTCAAAAATATGGTATTGATAATCCTGATATGAATAA
ATTGCAGTTTCATTTGATGCTCGATGAGTTTTTCTAATAAGCCTTGACCC
TACGATTCCCGCTATTTCATTCACTGACCGGAGGTTCAAAATGA

50   ATGACCCTGAATATGATGCTCGATAACGCCGTACCCGAGGCGATTGCC
GGCTGATCCTTCAACTCAGCAAAAGTTCGATTTATTCAACAAAGCCACG
TTGTGTCTCAAAATCTCTGATGTTACATTGCACAAGATAAAAATATATC
ATCATGAACAATAAAACTGTCTGCTTACATAAACAGTAATACAAGGGG
TGTTATGAGCCATATTCAACGGGAAACGTCTTGCTCCCGTCCGCGCTTA
AACTCCAACATGGACGCTGATTTATATGGGTATAAATGGGCTCGCGAT
AATGTCGGGCAATCAGGTGCGACAATCTATCGCTTGTATGGGAAGCCC
GATGCGCCAGAGTTGTTTCTGAAACATGGCAAAGGTAGCGTTGCCAAT
GATGTTACAGATGAGATGGTCCGTCTCAACTGGCTGACGGAGTTTATGC
CTCTCTCCCGACCATCAAGCATTTTATCCGTACTCCTGATGATGCGTGGTT
ACTCACCACCGCGATTCCTGGGAAAACAGCCTTCCAGGTATTAGAAGA
ATATCCTGATTCAGGTGAAAATATTGTTGATGCGCTGGCCGTGTTCCTG
CGCCGGTTACATTCGATTCCTGTTTGTAATTGTCCTTTTAACAGCGATCG
TGTATTTCGTCTTGCTCAGGCGCAATCACGCATGAATAACGGTTTGGTT
GATGCGAGTGATTTTGATGACGAGCGTAATGGCTGGCCTGTTGAACAA
GTCTGGAAAGAAATGCACAAGCTCTTGCCATTCTCACCGGATTCAGTCG
TCACTCATGGTGATTTCTCACTTGATAACCTTATTTTTGACGAGGGGAA
ATTAATAGGTTGTATTGATGTTGGACGGGTCGGAATCGCAGACCGTTAC
CAGGACCTTGCCATTCTTTGGAACTGCCTCGGTGAGTTTTCTCCTTCATT
ACAGAAACGGCTTTTTCAAAAATATGGTATTGATAATCCTGATATGAAT
AAATTGCAGTTTCATTTGATGCTCGATGAGTTTTTCTAATAAGCCTTGGT
TCTGCGTTTCCCGCTCTTTAATACCCTGACCGGAGGTGAGCAATGA

51   ATGACCCTGAATATGATGATGGATGCCGGCCGTCCTGTAATAATAACC
GGACAATTCGGACTGATTAAAAAAGCGCCCTTGTGGCGCTTTTTTTATA
TTCCCGCCTCCATTTAAAATAAAAAATCCAATCGGATTTCACTATTTAA
ACTGGCCATTATCTAAGATGAATCCGATGGAAGCTCGCTGTTTTAACAC
GCGTTTTTTAACCTTTTATTGAAAGTCGGTGCTTCTTTGAGCGAACGATC
AAATTTAAGTGGATTCCCATCAAAAAAATATTCTCAACCTAAAAAAGTT
TGTGTAATACTTGTAACGCTACATGGAGATTAACTCAATCTAGAGGGTA
TTAATAATGAATCGTACTAAACTGGTACTGGGCGCAACTCACTTCACAC
CCCGAAGGGGGAAGTTGCCTGACCCTACGATTCCCGCTATTTCATTCAC
TGACCGGAGGTTCAAAATGA

52   ATGACCCTGAATATGATGATGGATGCCGGCGGACATCATCGCGACAAA
CAATATTAATACCGGCAACCACACCGGCAATTTACGAGACTGCGCAGG
CATCCTTTCTCCCGTCAATTTCTGTCAAATAAAGTAAAAGAGGCAGTCT
ACTTGAATTACCCCCGGCTGGTTGAGCGTTTGTTGAAAAAAAGTAACTG
AAAAATCCGTAGAATAGCGCCACTCTGATGGTTAATTAACCTATTCAAT
TAAGAATTATCTGGATGAATGTGCCATTAAATGCGCAGCATAATGGTGC
GTTGTGCGGGAAAACTGCTTTTTTTTTGAAAGGGGTTGGTCAGTAGCGGAA

| Table of Strains sequences | |
| --- | --- |

| SEQ ID NO: | Sequence |
| --- | --- |
| | ACAACTCACTTCACACCCCGAAGGGGGAAGTTGCCTGACCCTACGATT CCCGCTATTTCATTCACTGACCGGAGGTTCAAAATGA |
| 53 | ATGACCCTGAATATGATGATGGATGCCGGCTGACGAGGCAGGTTACAT CACTGGTGAAACCCTGCACGTCAATGGCGGAATGTATATGGTTTAACC ACGATGAAAATTATTTGCGTTATTAGGGCGAAAGGCCTCAAAATAGCG TAAAATCGTGGTAAGAACTGCCGGGATTTAGTTGCAAATTTTTCAACAT TTTATACACTACGAAAACCATCGCGAAAGCGAGTTTTTGATAGGAAATTT AAGAGTATGAGCACTATCGAAGAACGCGTTAAGAAAATTATCGGCGAA CAGCTGGGCGTTAAGCAGGAAGAAGTTACCAACAATGCTTCCTTCGTT GAAGACCTGGGCGCTGATTCTCTTGACACCGAACTCACTTCACACCCCG AAGGGGGAAGTTGCCTGACCCTACGATTCCCGCTATTTCATTCACTGAC CGGAGGTTCAAAATGA |
| 54 | ATGACCCTGAATATGATGATGGATGCCGGCGGACATCATCGCGACAAA CAATATTAATACCGGCAACCACACCGGCAATTTACGAGACTGCGCAGG CATCCTTTCTCCCGTCAATTTCTGTCAAATAAAGTAAAAGAGGCAGTCT ACTTGAATTACCCCCGGCTGGTTGAGCGTTTGTTGAAAAAAAGTAACTG AAAAATCCGTAGAATAGCGCCACTCTGATGGTTAATTAACCTATTCAAT TAAGAATTATCTGGATGAATGTGCCATTAAATGCGCAGCATAATGGTGC GTTGTGCGGGAAAACTGCTTTTTTTTGAAAGGGTTGGTCAGTAGCGGAA ACAACTCACTTCACACCCCGAAGGGGGAAGTTGCCTGACCCTACGATT CCCGCTATTTCATTCACTGACCGGAGGTTCAAAATGA |
| 55 | ATGACCCTGAATATGATGATGGATGCCGGCCGTCCTGTAATAATAACC GGACAATTCGGACTGATTAAAAAAGCGCCCTTGTGGCGCTTTTTTTATA TTCCCGCCTCCATTTAAAATAAAAAATCCAATCGGATTTCACTATTTAA ACTGGCCATTATCTAAGATGAATCCGATGGAAGCTCGCTGTTTTAACAC GCGTTTTTTAACCTTTTATTGAAAGTCGGTGCTTCTTTGAGCGAACGATC AAATTTAAGTGGATTCCCATCAAAAAAATATTCTCAACCTAAAAAAGTT TGTGTAATACTTGTAACGCTACATGGAGATTAACTCAATCTAGAGGGTA TTAATAATGAATCGTACTAAACTGGTACTGGGCGCAACTCACTTCACAC CCCGAAGGGGGAAGTTGCCTGACCCTACGATTCCCGCTATTTCATTCAC TGACCGGAGGTTCAAAATGA |
| 56 | ATGAGCATCACGGCGTTATCAGCATCATTTCCTGAGGGGAATATCGCCA GCCGCTTGTCGCTGCAACATCCTTCACTGTTTTATACCGTGGTTGAACA ATCTTCGGTGGCGAGCGTGTTGAGTCATCCTGACTAGCTGAGATGAGG GCTCGCCCCCTCGTCCCGACACTTCCAGATCGCCATAGCGCACAGCGCC TCGAGCGGTGGTAACGGCGCAGTGGCGGTTTTCATGGCTTGTTATGACT GTTTTTTTGGGGTACAGTCTATGCCTCGGGCATCCAAGCAGCAAGCGCG TTACGCCGTGGGTCGATGTTTGATGTTATGGAGCAGCAACGATGTTACG CAGCAGGGCAGTCGCCCTAAAACAAAGTTAAACATCATGAGGGAAGCG GTGATCGCCGAAGTATCGACTCAACTATCAGAGGTAGTTGGCGTCATC GAGCGCCATCTCGAACCGACGTTGCTGGCCGTACATTTGTACGGCTCCG CAGTGGATGGCGGCCTGAAGCCACACAGTGATATTGATTTGCTGGTTAC GGTGACCGTAAGGCTTGATGAAACAACGCGGCGAGCTTTGATCAACGA CCTTTTGGAAACTTCGGCTTCCCCTGGAGAGAGCGAGATTCTCCGCGCT GTAGAAGTCACCATTGTTGTGCACGACGACATCATTCCGTGGCGTTATC CAGCTAAGCGCGAACTGCAATTTGGAGAATGGCAGCGCAATGACATTC TTGCAGGTATCTTCGAGCCAGCCACGATCGACATTGATCTGGCTATCTT GCTGACAAAAGCAAGAGAACATAGCGTTGCCTTGGTAGGTCCAGCGGC GGAGGAACTCTTTGATCCGGTTCCTGAACAGGATCTATTTGAGGCGCTA AATGAAACCTTAACGCTATGGAACTCGCCGCCCGACTGGGCTGGCGAT GAGCGAAATGTAGTGCTTACGTTGTCCCGCATTGGTACAGCGCAGTAA CCGGCAAAATCGCGCCGAAGGATGTCGCTGCCGACTGGGCAATGGAGC GCCTGCCGGCCCAGTATCAGCCCGTCATACTTGAAGCTAGACAGGCTTA TCTTGGACAAGAAGAAGATCGCTTGGCCTCGCGCGCAGATCAGTTGGA AGAATTTGTCCACTACGTGAAAGGCGAGATCACCAAGGTAGTCGGCAA ATAATGTCTAACAATTCGTTCAAGCCGACGCCGCTTCGCGGCGCGGCTT AACTCAAGCGTTAGATGCACTAAGCACATAATTGCTCACAGCCAAACT ATCAGGTCAAGTCTGCTTTTATTATTTTTAAGCGTGCATAATAAGCCCT CACACAAATGGTACCCGACCGGTGGTGAATTTAATCTCGCTGACGTGTA GACATTCCCTTATCCAGACGCTGATCGCCCATCATCGCGGTTCTTTAGA TCTCTCGGTCCGCCCTGATGGCGGCACCTTGCTGACGTTACGCCTGCCG GTACAGCAGGTTATCACCGGAGGCTTAAAATGA |
| 57 | ATGAGCATCACGGCGTTATCAGCATCATTTCCTGAGGGGAATATCGCCA GCCGCTTGTCGCTGCAACATCCTTCACTGTTTTATACCGTGGTTGAACA ATCTTCGGTGGCGAGCGTGTTGAGTCATCCTGACTAGCTGAGATGAGG GCTCGCCCCCTCGTCCCGACACTTCCAGATCGCCATAGCGCACAGCGCC TCGAGCGGTGGTAACGGCGCAGTGGCGGTTTTCATGGCTTGTTATGACT GTTTTTTTGGGGTACAGTCTATGCCTCGGGCATCCAAGCAGCAAGCGCG |

-continued

| Table of Strains sequences |
| --- |

SEQ
ID
NO:     Sequence

```
        TTACGCCGTGGGTCGATGTTTGATGTTATGGAGCAGCAACGATGTTACG
        CAGCAGGGCAGTCGCCCTAAAACAAAGTTAAACATCATGAGGGAAGCG
        GTGATCGCCGAAGTATCGACTCAACTATCAGAGGTAGTTGGCGTCATC
        GAGCGCCATCTCGAACCGACGTTGCTGGCCGTACATTTGTACGGCTCCG
        CAGTGGATGGCGGCCTGAAGCCACACAGTGATATTGATTTGCTGGTTAC
        GGTGACCGTAAGGCTTGATGAAACAACGCGGCGAGCTTTGATCAACGA
        CCTTTTGGAAACTTCGGCTTCCCCTGGAGAGAGCGAGATTCTCCGCGCT
        GTAGAAGTCACCATTGTTGTGCACGACGACATCATTCCGTGGCGTTATC
        CAGCTAAGCGCGAACTGCAATTTGGAGAATGGCAGCGCAATGACATTC
        TTGCAGGTATCTTCGAGCCAGCCACGATCGACATTGATCTGGCTATCTT
        GCTGACAAAAGCAAGAGAACATAGCGTTGCCTTGGTAGGTCCAGCGGC
        GGAGGAACTCTTTGATCCGGTTCCTGAACAGGATCTATTTGAGGCGCTA
        AATGAAACCTTAACGCTATGGAACTCGCCGCCCGACTGGGCTGGCGAT
        GAGCGAAATGTAGTGCTTACGTTGTCCCGCATTTGGTACAGCGCAGTAA
        CCGGCAAAATCGCGCCGAAGGATGTCGCTGCCGACTGGGCAATGGAGC
        GCCTGCCGGCCCAGTATCAGCCCGTCATACTTGAAGCTAGACAGGCTTA
        TCTTGGACAAGAAGAAGATCGCTTGGCCTCGCGCGCAGATCAGTTGGA
        AGAATTTGTCCACTACGTGAAAGGCGAGATCACCAAGGTAGTCGGCAA
        ATAATGTCTAACAATTCGTTCAAGCCGACGCCGCTTCGCGGCGCGGCTT
        AACTCAAGCGTTAGATGCACTAAGCACATAATTGCTCACAGCCAAACT
        ATCAGGTCAAGTCTGCTTTTATTATTTTTAAGCGTGCATAATAAGCCCT
        ACACAAATGGTACCCGACCGGTGGTGAATTTAATCTCGCTGACGTGTA
        GACATTCCCTTATCCAGACGCTGATCGCCCATCATCGCGGTTCTTTAGA
        TCTCTCGGTCCGCCCTGATGGCGGCACCTTGCTGACGTTACGCCTGCCG
        GTACAGCAGGTTATCACCGGAGGCTTAAAATGA

58      CTGATCCTTCAACTCAGCAAAAGTTCGATTTATTCAACAAAGCCACGTT
        GTGTCTCAAAATCTCTGATGTTACATTGCACAAGATAAAAATATATCAT
        CATGAACAATAAAACTGTCTGCTTACATAAACAGTAATACAAGGGGTG
        TTATGAGCCATATTCAACGGGAAACGTCTTGCTCCAGGCCGCGATTAAA
        TTCCAACATGGATGCTGATTTATATGGGTATAAATGGGCTCGCGATAAT
        GTCGGGCAATCAGGTGCGACAATCTATCGATTGTATGGGAAGCCCGAT
        GCGCCAGAGTTGTTTCTGAAACATGGCAAAGGTAGCGTTGCCAATGAT
        GTTACAGATGAGATGGTCAGACTAAACTGGCTGACGGAATTTATGCCT
        CTTCCGACCATCAAGCATTTTATCCGTACTCCTGATGATGCATGGTTAC
        TCACCACTGCGATCCCCGGGAAAACAGCATTCCAGGTATTAGAAGAAT
        ATCCTGATTCAGGTGAAAATATTGTTGATGCGCTGGCAGTGTTCCTGCG
        CCGGTTGCATTCGATTCCTGTTTGTAATTGTCCTTTTAACAGCGATCGCG
        TATTTCGTCTCGCTCAGGCGCAATCACGAATGAATAACGGTTTGGTTGA
        TGCGAGTGATTTTGATGACGAGCGTAATGGCTGGCCTGTTGAACAAGTC
        TGGAAAGAAATGCATAAGCTTTTGCCATTCTCACCGGATTCAGTCGTCA
        CTCATGGTGATTTCTCACTTGATAACCTTATTTTTGACGAGGGGAAATT
        AATAGGTTGTATTGATGTTGGACGAGTCGGAATCGCAGACCGATACCA
        GGATCTTGCCATCCTATGGAACTGCCTCGGTGAGTTTTCTCCTTCATTAC
        AGAAACGGCTTTTTCAAAAATATGGTATTGATAATCCTGATATGAATAA
        ATTGCAGTTTCATTTGATGCTCGATGAGTTTTTTCTAATAAGCCTTGACCC
        TACGATTCCCGCTATTTCATTCACTGACCGGAGGTTCAAAATGA

59      ATGAGCATCACGGCGTTATCAGCATCATTTCCTGAGGGGAATATCGCCA
        GCCGCTTGTCGCTGCAACATCCTTCACTGTTTTATACCGTGGTTGAACA
        ATCTTCGGTGGCGAGCGTGTTGAGTCATCCTGACTAGCTGAGATGAGG
        GCTCGCCCCCTCGTCCCGACACTTCCAGATCGCCATAGCGCACAGCGCC
        TCGAGCGGTGGTAACGGCGCAGTGGCGGTTTTCATGGCTTGTTATGACT
        GTTTTTTTTGGGGTACAGTCTATGCCTCGGGCATCCAAGCAGCAAGCGCG
        TTACGCCGTGGGTCGATGTTTGATGTTATGGAGCAGCAACGATGTTACG
        CAGCAGGGCAGTCGCCCTAAAACAAAGTTAAACATCATGAGGGAAGCG
        GTGATCGCCGAAGTATCGACTCAACTATCAGAGGTAGTTGGCGTCATC
        GAGCGCCATCTCGAACCGACGTTGCTGGCCGTACATTTGTACGGCTCCG
        CAGTGGATGGCGGCCTGAAGCCACACAGTGATATTGATTTGCTGGTTAC
        GGTGACCGTAAGGCTTGATGAAACAACGCGGCGAGCTTTGATCAACGA
        CCTTTTGGAAACTTCGGCTTCCCCTGGAGAGAGCGAGATTCTCCGCGCT
        GTAGAAGTCACCATTGTTGTGCACGACGACATCATTCCGTGGCGTTATC
        CAGCTAAGCGCGAACTGCAATTTGGAGAATGGCAGCGCAATGACATTC
        TTGCAGGTATCTTCGAGCCAGCCACGATCGACATTGATCTGGCTATCTT
        GCTGACAAAAGCAAGAGAACATAGCGTTGCCTTGGTAGGTCCAGCGGC
        GGAGGAACTCTTTGATCCGGTTCCTGAACAGGATCTATTTGAGGCGCTA
        AATGAAACCTTAACGCTATGGAACTCGCCGCCCGACTGGGCTGGCGAT
        GAGCGAAATGTAGTGCTTACGTTGTCCCGCATTTGGTACAGCGCAGTAA
        CCGGCAAAATCGCGCCGAAGGATGTCGCTGCCGACTGGGCAATGGAGC
        GCCTGCCGGCCCAGTATCAGCCCGTCATACTTGAAGCTAGACAGGCTTA
        TCTTGGACAAGAAGAAGATCGCTTGGCCTCGCGCGCAGATCAGTTGGA
        AGAATTTGTCCACTACGTGAAAGGCGAGATCACCAAGGTAGTCGGCAA
        ATAATGTCTAACAATTCGTTCAAGCCGACGCCGCTTCGCGGCGCGGCTT
```

-continued

| Table of Strains sequences | |
| --- | --- |

SEQ
ID
NO:     Sequence

```
        AACTCAAGCGTTAGATGCACTAAGCACATAATTGCTCACAGCCAAACT
        ATCAGGTCAAGTCTGCTTTTATTATTTTTAAGCGTGCATAATAAGCCCT
        ACACAAATGGTACCCGACCGGTGGTGAATTTAATCTCGCTGACGTGTA
        GACATTCCCTTATCCAGACGCTGATCGCCCATCATCGCGGTTCTTTAGA
        TCTCTCGGTCCGCCCTGATGGCGGCACCTTGCTGACGTTACGCCTGCCG
        GTACAGCAGGTTATCACCGGAGGCTTAAAATGA
```

60      ```
        ATGAGCATCACGGCGTTATCAGCATCATTTCCTGAGGGGAATATCGCCA
        GCCGCTTGTCGCTGCAACATCCTTCACTGTTTTATACCGTGGTTGAACA
        ATCTTCGGTGGCGAGCGTGTTGAGTCATCCTGACTAGCTGAGATGAGG
        GCTCGCCCCCTCGTCCCGACACTTCCAGATCGCCATAGCGCACAGCGCC
        TCGAGCGGTGGTAACGGCGCAGTGGCGGTTTTCATGGCTTGTTATGACT
        GTTTTTTTGGGGTACAGTCTATGCCTCGGGCATCCAAGCAGCAAGCGCG
        TTACGCCGTGGGTCGATGTTTGATGTTATGGAGCAGCAACGATGTTACG
        CAGCAGGGCAGTCGCCCTAAAACAAAGTTAAACATCATGAGGGAAGCG
        GTGATCGCCGAAGTATCGACTCAACTATCAGAGGTAGTTGGCGTCATC
        GAGCGCCATCTCGAACCGACGTTGCTGGCCGTACATTTGTACGGCTCCG
        CAGTGGATGGCGGCCTGAAGCCACACAGTGATATTGATTTGCTGGTTAC
        GGTGACCGTAAGGCTTGATGAAACAACGCGGCGAGCTTTGATCAACGA
        CCTTTTGGAAACTTCGGCTTCCCCTGGAGAGAGCGAGATTCTCCGCGCT
        GTAGAAGTCACCATTGTTGTGCACGACGACATCATTCCGTGGCGTTATC
        CAGCTAAGCGCGAACTGCAATTTGGAGAATGGCAGCGCAATGACATTC
        TTGCAGGTATCTTCGAGCCAGCCACGATCGACATTGATCTGGCTATCTT
        GCTGACAAAAGCAAGAGAACATAGCGTTGCCTTGGTAGGTCCAGCGGC
        GGAGGAACTCTTTGATCCGGTTCCTGAACAGGATCTATTTGAGGCGCTA
        AATGAAACCTTAACGCTATGGAACTCGCCGCCCGACTGGGCTGGCGAT
        GAGCGAAATGTAGTGCTTACGTTGTCCCGCATTTGGTACAGCGCAGTAA
        CCGGCAAAATCGCGCCGAAGGATGTCGCTGCCGACTGGGCAATGGAGC
        GCCTGCCGGCCCAGTATCAGCCCGTCATACTTGAAGCTAGACAGGCTTA
        TCTTGGACAAGAAGAAGATCGCTTGGCCTCGCGCGCAGATCAGTTGGA
        AGAATTTGTCCACTACGTGAAAGGCGAGATCACCAAGGTAGTCGGCAA
        ATAATGTCTAACAATTCGTTCAAGCGCGACGCCGCTTCGCGGCGCGGCTT
        AACTCAAGCGTTAGATGCACTAAGCACATAATTGCTCACAGCCAAACT
        ATCAGGTCAAGTCTGCTTTTATTATTTTTAAGCGTGCATAATAAGCCCT
        ACACAAATGGTACCCGACCGGTGGTGAATTTAATCTCGCTGACGTGTA
        GACATTCCCTTATCCAGACGCTGATCGCCCATCATCGCGGTTCTTTAGA
        TCTCTCGGTCCGCCCTGATGGCGGCACCTTGCTGACGTTACGCCTGCCG
        GTACAGCAGGTTATCACCGGAGGCTTAAAATGA
```

61      ```
        ATGTTTAACGATCTGATTGGCGATGATGAAACGGATTCGCCGGAAGAT
        GCGCTTTCTGAGAGCTGGCGCGAATTGTGGCAGGATGCGTTGCAGGAG
        GAGGATTCCACGCCCGTGCTGGCGCATCTCTCAGAGGACGATCGCCGC
        CGCGTGGTGGCGCTGATTGCCGATTTTCGCAAAGAGTTGGATAAACGC
        ACCATTGGCCCGCGAGGGCGGCAGGTACTCGATCACTTAATGCCGCAT
        CTGCTCAGCGATGTATGCTCGCGCGACGATGCGCCAGTACCGCTGTCAC
        GCCTGACGCCGCTGCTCACCGGAATTATTACCCGCACCACTTACCTTGA
        GCTGCTAAGTGAATTTCCCGGCGCACTGAAACACCTCATTTCCCTGTGT
        GCCGCGTCGCCGATGGTTGCCAGTCAGCTGGCGCGCTACCCGATCCTGC
        TTGATGAATTGCTCGACCCGAATACGCTCTATCAACCGACGGCGATGA
        ATGCCTATCGCGATGAGCTGCGCCAATACCTGCTGCGCGTGCCGGAAG
        ATGATGAAGAGCAACAGCTTGAGGCGCTGCGGCAGTTTAAGCAGGCGC
        AGTTGCTGCGCGTGGCGGCGGCGGATATTGCCGGTACGTTGCCAGTAA
        TGAAAGTGAGCGATCACTTAACCTGGCTGGCGGAAGCGATTATTGATG
        CGGTGGTGCAGCAAGCCTGGGGGCAGATGGTGGCGCGTTATGGCCAGC
        CAACGCATCTGCACGATCGCGAAGGGCGCGGTTTTGCGGTGGTCGGTT
        ATGGCAAGCTGGGCGGCTGGGAGCTGGGTTACAGCTCCGATCTGGATC
        TGGTATTCCTGCACGACTGCCCGATGGATGTGATGACCGATGGCGAGC
        GTGAAATCGATGGTCGCCAGTTCTATTTGCGTCTCGCGCAGCGCGTGAT
        GCACCTGTTTAGCACGCGCACGTCGTCCGGCATCCTTTATGAAGTTGAT
        GCGCGTCTGCGTCCATCTGGCGCTGCGGGGATGCTGGTCACTACTACGG
        AATCGTTCGCCGATTACCAGCAAAACGAAGCCTGGACGTGGGAACATC
        AGGCGCTGGCCCGTGCGCGCGTGGTGTACGGCGATCCGCAACTGACCG
        CCGAATTTGACGCCATTCGCCGCGATATTCTGATGACGCCTCGCGACGG
        CGCAACGCTGCAAACCGACGTGCGAGAAATGCGCGAGAAAATGCGTGC
        CCATCTTGGCAACAAGCATAAAGACCGCTTCGATCTGAAAGCCGATGA
        AGGCGGTATCACCGACATCGAGTTTATCGCCCAATATCTGGTGCTGCGC
        TTTGCCCATGACAAGCCGAAACTGACGCGCTGGTCGGATAATGTGCGC
        ATTCTCGAAGGGCTGGCGCAAAACGGCATCATGGAGGAGCAGGAAGC
        GCAGGCATTGACGCTGGCGTACACCACATTGCGTGATGAGCTGCACCA
        CCTGGCGCTGCAAGAGTTGCCGGGACATGTGGCGCTCTCCTGTTTTGTC
        GCCGAGCGTGCGCTTATTAAAACCAGCTGGGACAAGTGGCTGGTGGAA
        CCGTGCGCCCCGGCGTAA
```

Assessment of Genetic Tractability

Candidate microbes were characterized based on transformability and genetic tractability. First, optimal carbon source utilization was determined by growth on a small panel of relevant media as well as a growth curve in both nitrogen-free and rich media. Second, the natural antibiotic resistance of each strain was determined through spot-plating and growth in liquid culture containing a panel of antibiotics used as selective markers for mutagenesis. Third, each strain was tested for its transformability through electroporation of a collection of plasmids. The plasmid collection comprises the combinatorial expansion of seven origins of replication, i.e., p15a, pSC101, CloDF, colA, RK2, pBBR1, and pRO1600 and four antibiotic resistance markers, i.e., CmR, KmR, SpecR, and TetR. This systematic evaluation of origin and resistance marker compatibility was used to identify vectors for plasmid-based mutagenesis in candidate microbes.

Example 3: Mutagenesis of Candidate Microbes

Lambda-Red Mediated Knockouts

Several mutants of candidate microbes were generated using the plasmid pKD46 or a derivative containing a kanamycin resistance marker (Datsenko et al. 2000; PNAS 97(12): 6640-6645). Knockout cassettes were designed with 250 bp homology flanking the target gene and generated via overlap extension PCR. Candidate microbes were transformed with pKD46, cultured in the presence of arabinose to induce Lambda-Red machinery expression, prepped for electroporation, and transformed with the knockout cassettes to produce candidate mutant strains. Four candidate microbes and one laboratory strain, *Klebsiella oxytoca* M5A1, were used to generate thirteen candidate mutants of the nitrogen fixation regulatory genes nifL, glnB, and amtB, as shown in Table 4.

TABLE 4

List of single knockout mutants created through Lambda-red mutagenesis

| Strain | nifL | glnB | amtB |
|--------|------|------|------|
| M5A1 | X | X | X |
| CI006 | X | X | X |
| CI010 | X | X | X |
| CI019 | X | X | |
| CI028 | X | X | |

Oligo-Directed Mutagenesis with Cas9 Selection

Oligo-directed mutagenesis was used to target genomic changes to the rpoB gene in *E. coli* DH10B, and mutants were selected with a CRISPR-Cas system. A mutagenic oligo (ss1283: "G*T*T*G*ATCAGACCGATGTTCGGACCTT CcaagGTTTCGATCGGACATACGCGAC CGTAGTGGGTCGGGTGTACGTCTCGAACTT-CAAAGCC" (SEQ ID NO: 2), where * denotes phosphorothioate bond) was designed to confer rifampicin resistance through a 4-bp mutation to the rpoB gene. Cells containing a plasmid encoding Cas9 were induced for Cas9 expression, prepped for electroporation, and then electroporated with both the mutagenic oligo and a plasmid encoding constitutive expression of a guide RNA (gRNA) that targets Cas9 cleavage of the WT rpoB sequence. Electroporated cells were recovered in nonselective media overnight to allow sufficient segregation of the resulting mutant chromosomes.

After plating on selection for the gRNA-encoding plasmid, two out of ten colonies screened were shown to contain the desired mutation, while the rest were shown to be escape mutants generated through protospacer mutation in the gRNA plasmid or Cas9 plasmid loss.

Lambda-Red Mutagenesis with Cas9 Selection

Figure 3:
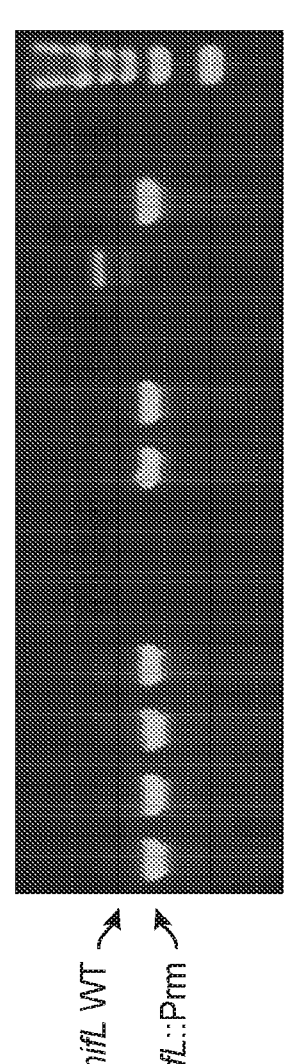
FIG. 3 depicts an example of a PCR screen of colonies from CRISPR-Cas-selected mutagenesis. CI006 colonies were screened with primers specific for the nifL locus. The wild type PCR product is expected at ~2.2 kb, whereas the mutant is expected at ~1.1 kb. Seven of ten colonies screened unambiguously show the desired deletion.

Mutants of candidate microbes CI006 and CI010 were generated via lambda-red mutagenesis with selection by CRISPR-Cas. Knockout cassettes contained an endogenous promoter identified through transcriptional profiling (as described in Example 2 and depicted in Tables 3A-C) and ~250 bp homology regions flanking the deletion target. CI006 and CI010 were transformed with plasmids encoding the Lambda-red recombination system (exo, beta, gam genes) under control of an arabinose inducible promoter and Cas9 under control of an IPTG inducible promoter. The Red recombination and Cas9 systems were induced in resulting transformants, and strains were prepared for electroporation. Knockout cassettes and a plasmid-encoded selection gRNA were subsequently transformed into the competent cells. After plating on antibiotics selective for both the Cas9 plasmid and the gRNA plasmid, 7 of the 10 colonies screened showed the intended knockout mutation, as shown in FIG. 3.

Example 4: In Vitro Phenotyping of Candidate Molecules

The impact of exogenous nitrogen on nitrogenase biosynthesis and activity in various mutants was assessed. The Acetylene Reduction Assay (ARA) (Temme et. al. 2012; 109(18): 7085-7090) was used to measure nitrogenase activity in pure culture conditions. Strains were grown in air-tight test tubes, and reduction of acetylene to ethylene was quantified with an Agilent 6890 gas chromatograph. ARA activities of candidate microbes and counterpart candidate mutants grown in nitrogen fixation media supplemented with 0 to 10 mM glutamine are shown in FIGS. 4A-B and FIGS. 10A-C.

Figure 4C:
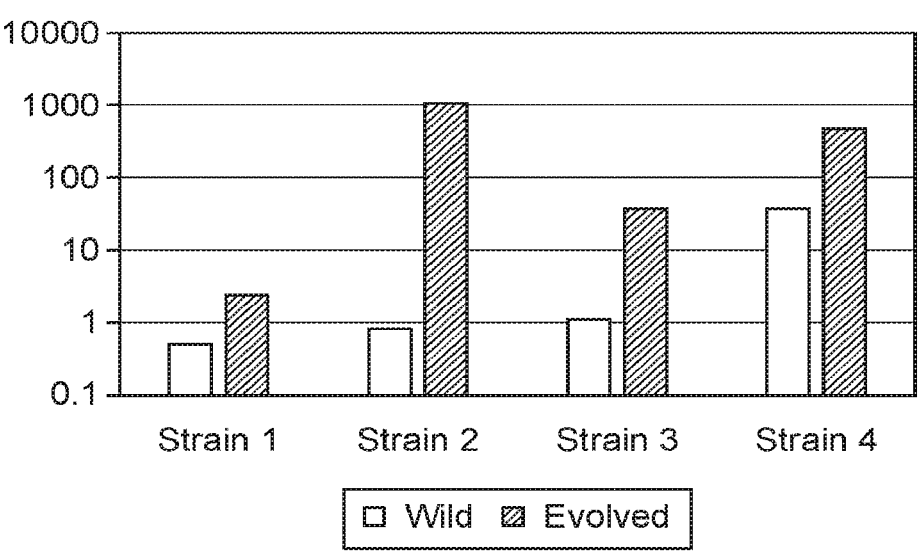
Figure 4D:
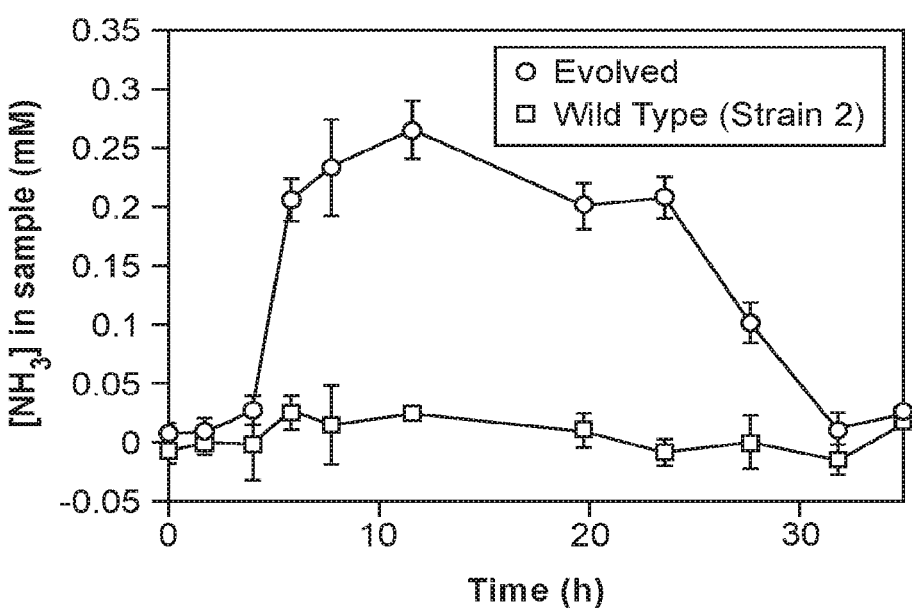
Figure 11:
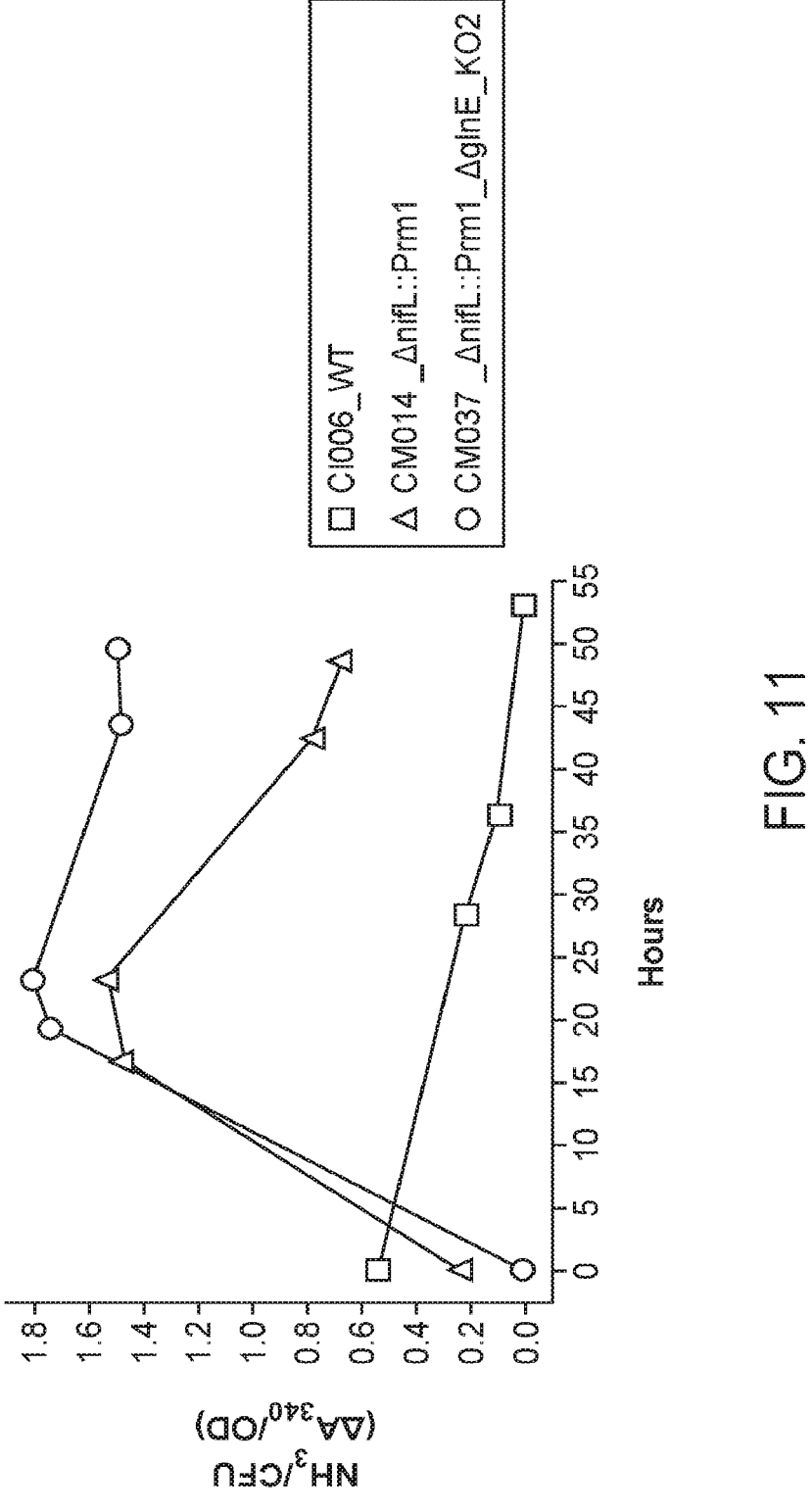
FIG. 11 depicts a double mutant that exhibits higher ammonia excretion than the single mutant from which it was derived.

Under anaerobic culture conditions, a range of glutamine and ammonia concentrations was tested to quantify impact on nitrogen fixation activity. In wild-type cells, activity quickly diminished as glutamine concentrations increased. However, in a series of initial knock-out mutations, a class of mutation was validated enabling expression of nitrogen fixation genes under concentrations of glutamine that would otherwise shut off activity in wild type. This profile was generated in four different species of diazotrophs, as seen in FIG. 4C. In addition, by rewiring the regulatory network using genetic parts that have been identified, the nitrogen fixation activity level was tuned predictably. This is seen in FIG. 4B, which illustrates strains CM023, CM021, CM015, and CI006. Strain CM023 is an evolved strain low; strain CM021 is an evolved strain high; strain CM015 is an evolved strain mid; strain CI006 is a wild-type (strain 2). Ammonia excreted into culture supernatants was tested using a enzymatic-based assay (MEGAZYME). The assay measures the amount of NADPH consumed in the absorbance of 340 nm. The assay was conducted on bacterial cultures grown in nitrogen-free, anaerobic environment with a starting density of 1E9 CFU/ml. Across a panel of six evolved strains, one strain excreted up to 100 μM of ammonia over a course of a 48 hour period, as seen in FIG. 4D. Further, a double mutant exhibited higher ammonia excretion than the single mutant from which it was derived, as seen in FIG. 11. This demonstrates a microbial capacity to produce ammonia in excess of its physiological needs.

Transcription Profiling of Pure Cultures

Transcriptional activity of CI006 was measured using the Nanostring Elements platform. Cells were grown in nitrogen-free media and 10E8 cells were collected after 4 hours incubation. Total RNA was extracted using the Qiagen RNEasy kit. Purified RNA was submitted to Core Diagnostics in Palo Alto, CA, for probe hybridization and Digital Analyzer analysis, as shown in FIG. 5.

Example 5: In Planta Phenotyping of Candidate Microbes

Colonization of Plants by Candidate Microbes

Figure 6:
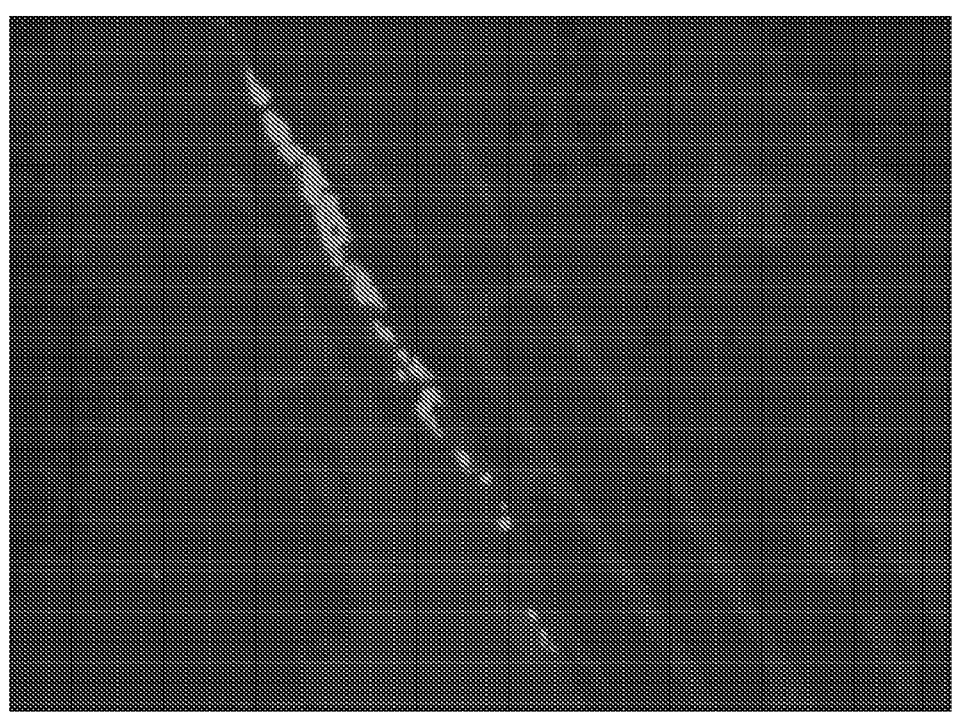
FIG. 6 depicts CI006 colonization of corn roots. Corn seedlings were inoculated with CI006 harboring an RFP expression plasmid. After two weeks of growth and plasmid maintenance through watering with the appropriate antibiotic, roots were harvested and imaged through fluorescence microscopy. Colonization of the root intercellular space is observed.

Colonization of desired host plants by a candidate microbe was quantified through short-term plant growth experiments. Corn plants were inoculated with strains expressing RFP either from a plasmid or from a Tn5-integrated RFP expression cassette. Plants were grown in both sterilized sand and nonsterile peat medium, and inoculation was performed by pipetting 1 mL of cell culture directly over the emerging plant coleoptile three days post-germination. Plasmids were maintained by watering plants with a solution containing the appropriate antibiotic. After three weeks, plant roots were collected, rinsed three times in sterile water to remove visible soil, and split into two samples. One root sample was analyzed via fluorescence microscopy to identify localization patterns of candidate microbes. Microscopy was performed on 10 mm lengths of the finest intact plant roots, as shown in FIG. 6.

A second quantitative method for assessing colonization was developed. A quantitative PCR assay was performed on whole DNA preparations from the roots of plants inoculated with the endophytes. Seeds of corn (Dekalb DKC-66-40) were germinated in previously autoclaved sand in a 2.5 inch by 2.5 inch by 10 inch pot. One day after planting, 1 ml of endophyte overnight culture (SOB media) was drenched right at the spot of where the seed was located. 1 mL of this overnight culture is roughly equivalent to about $10^9$ cfu, varying within 3-fold of each other, depending on which strain is being used. Each seedling was fertilized 3× weekly with 50 mL modified Hoagland's solution supplemented with either 2.5 mM or 0.25 mM ammonium nitrate. At four weeks after planting, root samples were collected for DNA extraction. Soil debris were washed away using pressurized water spray. These tissue samples were then homogenized using QIAGEN Tissuelyzer and the DNA was then extracted using QIAmp DNA Mini Kit (QIAGEN) according to the recommended protocol. qPCR assay was performed using Stratagene Mx3005P RT-PCR on these DNA extracts using primers that were designed (using NCBI's Primer BLAST) to be specific to a loci in each of the endophyte's genome. The presence of the genome copies of the endophytes was quantified. To further confirm the identity of the endophytes, the PCR amplification products were sequenced and are confirmed to have the correct sequence. The summary of the colonization profile of strain CI006 and CI008 from candidate microbes are presented in Table 5. Colonization rate as high as $10^7×$ cfu/g fw of root was demonstrated in strain CI008.

TABLE 5

Colonization of corn as measured by qPCR

| Strain | Colonization Rate (CFU/g fw) |
|---|---|
| CI006 | $1.45 \times 10^5$ |
| CI008 | $1.24 \times 10^7$ |

In Planta RNA Profiling

Biosynthesis of nif pathway components in planta was estimated by measuring the transcription of nif genes. Total RNA was obtained from root plant tissue of CI006 inoculated plants (planting methods as described previously). RNA extraction was performed using RNEasy Mini Kit according to the recommended protocol (QIAGEN). Total RNA from these plant tissues was then assayed using Nanostring Elements kits (NanoString Technologies, Inc.) using probes that were specific to the nif genes in the genome of strain CI006. The data of nif gene expression in planta is summarized in Table 6. Expression of nifH genes was detected in plants inoculated by CM013 strains whereas nifH expression was not detectable in CI006 inoculated plants. Strain CM013 is a derivative of strain CI006 in which the nifL gene has been knocked out.

Highly expressed genes of CM011, ranked by transcripts per kilobase million (TPM), were measured in planta under fertilized condition. The promoters controlling expression of some of these highly expressed genes were used as templates for homologous recombination into targeted nitrogen fixation and assimilation loci. RNA samples from greenhouse grown CM011 inoculated plant were extracted, rRNA removed using Ribo-Zero kit, sequenced using Illumina's Truseq platform and mapped back to the genome of CM011. Highly expressed genes from CM011 are listed in Table 7.

TABLE 6

Expression of nifH in planta

| Strains | Relative Transcript Expression |
|---|---|
| CI006 | 9.4 |
| CM013 | 103.25 |

TABLE 7

| Gene Name | Gene Location | Direction | Raw Read Count | TPM (Transcripts Per Kilobase Million) |
|---|---|---|---|---|
| rpsH CDS | 18196-18588 | reverse | 4841.5 | 27206.4 |
| rplQ CDS | 11650-12039 | reverse | 4333 | 24536.2 |
| rpsJ CDS | 25013-25324 | reverse | 3423 | 24229 |
| rplV CDS | 21946-22278 | reverse | 3367.5 | 22333 |
| rpsN CDS | 18622-18927 | reverse | 2792 | 20150.1 |
| rplN CDS | 19820-20191 | reverse | 3317 | 19691.8 |
| rplF CDS | 17649-18182 | reverse | 4504.5 | 18628.9 |
| rpsD CDS | 13095-13715 | reverse | 5091.5 | 18106.6 |
| rpmF CDS | 8326-8493 | forward | 1363.5 | 17923.8 |
| rplW CDS | 23429-23731 | reverse | 2252 | 16413.8 |
| rpsM CDS | 14153-14509 | reverse | 2269 | 14036.2 |
| rplR CDS | 17286-17639 | reverse | 2243.5 | 13996.1 |
| rplC CDS | 24350-24979 | reverse | 3985 | 13969.2 |
| rplK CDS | 25526-25954 | reverse | 2648.5 | 13634.1 |
| rplP CDS | 20807-21217 | reverse | 2423 | 13019.5 |
| rplX CDS | 19495-19809 | reverse | 1824 | 12787.8 |
| rpsQ CDS | 20362-20616 | reverse | 1460.5 | 12648.7 |
| bhsA 3 CDS | 79720-79977 | reverse | 1464 | 12531.5 |
| rpmC CDS | 20616-20807 | reverse | 998.5 | 11485 |
| rpoA CDS | 12080-13069 | reverse | 4855 | 10830.2 |

TABLE 7-continued

| Gene Name | Gene Location | Direction | Raw Read Count | TPM (Transcripts Per Kilobase Million) |
|---|---|---|---|---|
| rplD CDS | 23728-24333 | reverse | 2916.5 | 10628.5 |
| bhsA 1 CDS | 78883-79140 | reverse | 1068 | 9141.9 |
| rpsS CDS | 22293-22571 | reverse | 1138.5 | 9011.8 |
| rpmA CDS | 2210-2467 | forward | 1028.5 | 8803.7 |
| rpmD CDS | 16585-16764 | reverse | 694.5 | 8520.8 |
| rplB CDS | 22586-23410 | reverse | 3132 | 8384 |
| rpsC CDS | 21230-21928 | reverse | 2574.5 | 8133.9 |
| rplE CDS | 18941-19480 | reverse | 1972.5 | 8066.9 |
| rplO CDS | 16147-16581 | reverse | 1551 | 7874.2 |
| preprotein translocase subunit SecY CDS | 14808-16139 | reverse | 4657 | 7721.2 |
| rpsE CDS | 16771-17271 | reverse | 1671.5 | 7368 |
| rpsK CDS | 13746-14135 | reverse | 1223.5 | 6928.2 |
| tufA CDS | 27318-28229 | reverse | 2850 | 6901.3 |
| rpmI CDS | 38574-38771 | forward | 615 | 6859.5 |
| rplU CDS | 1880-2191 | forward | 935.5 | 6621.7 |
| rplT CDS | 38814-39170 | forward | 1045 | 6464.4 |
| bhsA 2 CDS | 79293-79550 | reverse | 754 | 6454.1 |
| rpmB CDS | 8391-8627 | reverse | 682 | 6355.1 |
| rplJ CDS | 23983-24480 | reverse | 1408 | 6243.9 |
| fusA 2 CDS | 481-2595 | reverse | 5832 | 6089.6 |
| rpsA CDS | 25062-26771 | reverse | 4613 | 5957.6 |
| rpmJ CDS | 14658-14774 | reverse | 314 | 5926.9 |
| rpsR CDS | 52990-53217 | forward | 603 | 5840.7 |
| rpsG CDS | 2692-3162 | reverse | 1243 | 5828.2 |
| rpsI CDS | 11354-11746 | reverse | 980.5 | 5509.8 |
| cspC 1 CDS | 8091-8300 | reverse | 509 | 5352.8 |
| rpsF CDS | 52270-52662 | forward | 916 | 5147.4 |
| rpsT CDS | 55208-55471 | reverse | 602 | 5035.9 |
| infC CDS | 38128-38478 | forward | 755 | 4750.3 |
| cspG CDS | 30148-30360 | forward | 446 | 4624.2 |

$^{15}$N Assay

The primary method for demonstrating fixation uses the nitrogen isotope 15N, which is found in the atmosphere at a set rate relative to 14N. By supplementing either fertilizer or atmosphere with enriched levels of 15N, one can observe fixation either directly, in heightened amounts of 15N fixed from an atmosphere supplemented with $15N_2$ gas (Yoshida 1980), or inversely, through dilution of enriched fertilizer by atmospheric $N_2$ gas in plant tissues (Iniguez 2004). The dilution method allows for the observation of cumulative fixed nitrogen over the course of plant growth, while the $15N_2$ gas method is restricted to measuring the fixation that occurs over the short interval that a plant can be grown in a contained atmosphere (rate measurement). Therefore, the gas method is superior in specificity (as any elevated $15N_2$ levels in the plant above the atmospheric rate can be attributed unambiguously to fixation) but cannot show cumulative activity.

Figure 7:
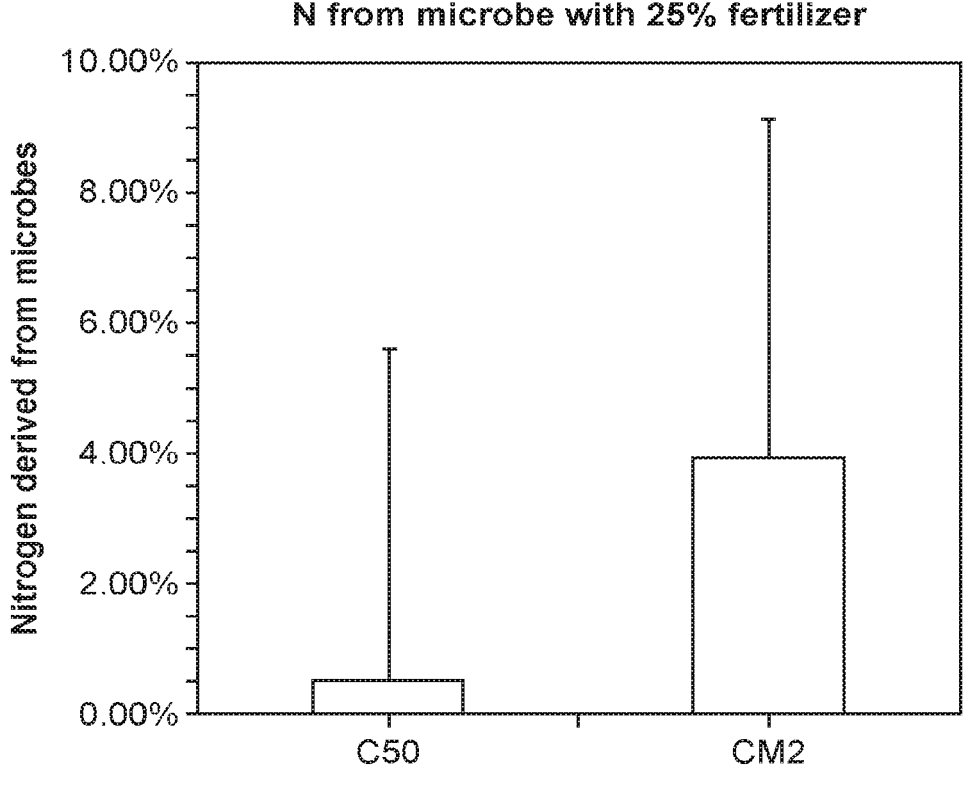
FIG. 7 depicts nitrogen derived from microbe level in WT (CI050) and optimized (CM002) strain.
Figure 12:
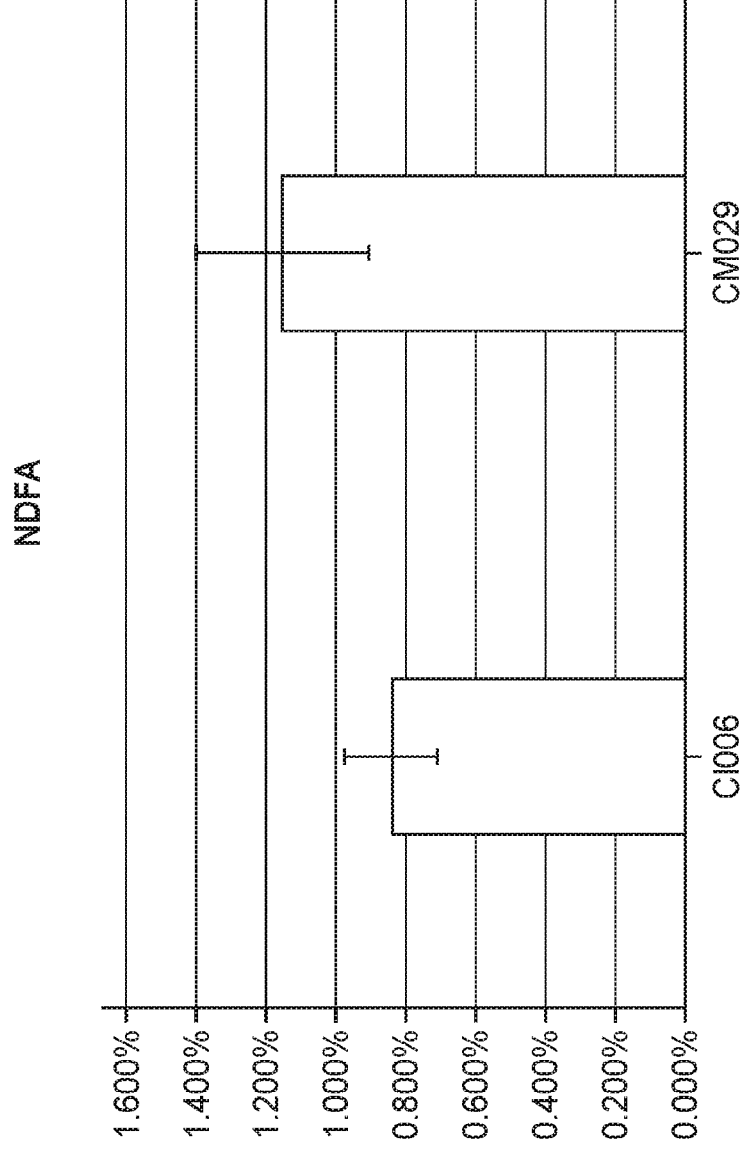
FIG. 12 depicts NDFA obtained from 15N Gas Uptake experiment (extrapolated back using days exposed) to measure NDFA in Corn plants in fertilized condition.
Figure 13:
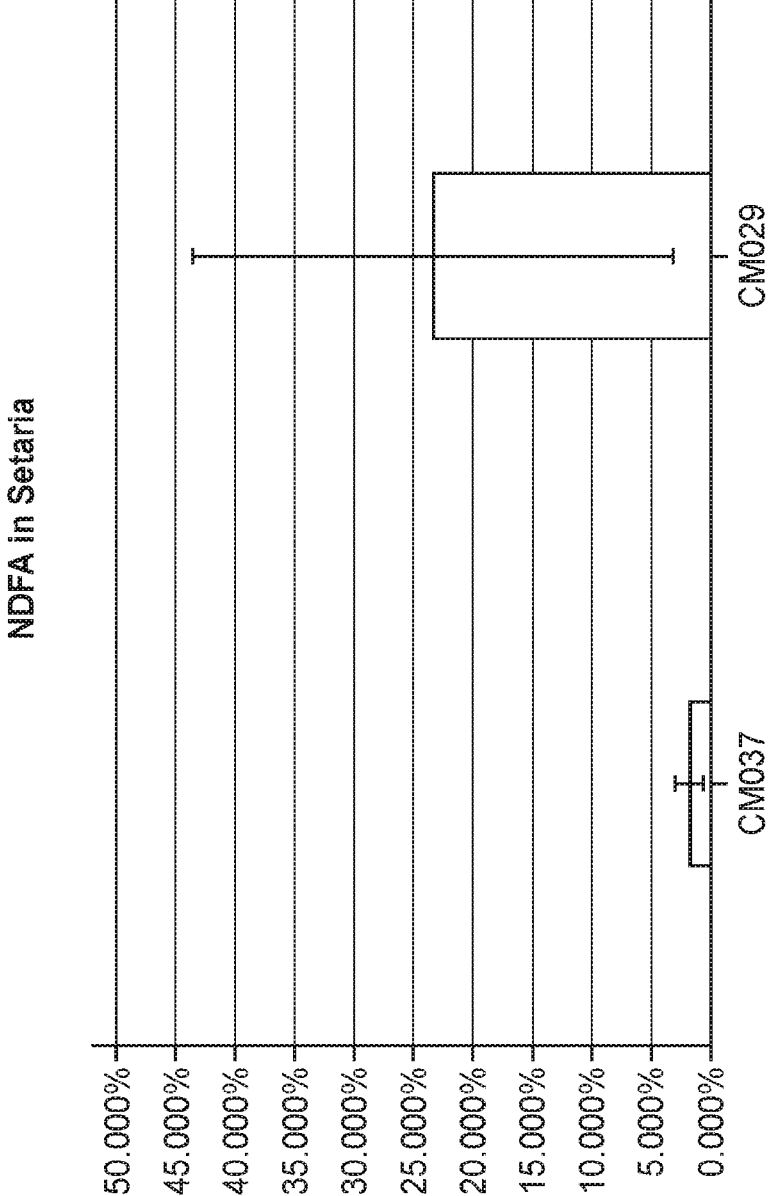
FIG. 13 depicts NDFA value obtained from 15N Gas Uptake experiment (extrapolated back using days exposed) to measure NDFA in Setaria plants in fertilized condition.

Both types of assay has been performed to measure fixation activity of improved strains relative to wild-type and uninoculated corn plants, and elevated fixation rates were observed in planta for several of the improved strains (FIG. 12, FIG. 14A, and FIG. 14B). These assays are instrumental in demonstrating that the activity of the strains observed in vitro translates to in vivo results. Furthermore, these assays allow measurement of the impact of fertilizer on strain activity, suggesting suitable functionality in an agricultural setting. Similar results were observed when *setaria* plants were inoculated with wild-type and improved strains (FIG. 13). In planta fixation activity shown in FIGS. 14A-14C is further backed up by transcriptomic data. Evolved strains exhibit increased nifH transcript level relative to wild-type counterparts. Furthermore, the microbe derived nitrogen level in planta is also correlated with the colonization level on a plant by plant basis. These results (FIG. 12, FIG. 13, FIGS. 14A-14C, FIG. 15A, and FIG. 15B) support the hypothesis that the microbe, through the improved regulation of the nif gene cluster, is the likely reason for the increase in atmospheric derived nitrogen seen in the plant tissue. In addition to measuring fixation directly, the impact of inoculating plants with the improved strains in a nitrogen-stressed plant biomass assay was measured. While plant biomass may be related to many possible microbe interactions with the plant, one would expect that the addition of fixed nitrogen would impact the plant phenotype when nitrogen is limited. Inoculated plants were grown in the complete absence of nitrogen, and significant increases in leaf area, shoot fresh and dry weight, and root fresh and dry weight in inoculated plants relative to untreated controls was observed (FIG. 14C). Although these differences cannot be attributed to nitrogen fixation exclusively, they support the conclusion that the improved strains are actively providing nitrogen to the plant. Corn and *setaria* plants were grown and inoculated as described above. Fertilizer comprising 1.2% $^{15}$N was regularly supplied to plants via watering. Nitrogen fixation by microbes was quantified by measuring the $^{15}$N level in the plant tissue. Fourth leaf tissue was collected and dried at 4 weeks after planting. Dried leaf samples were homogenized using beads (QIAGEN Tissue-lyzer) and aliquoted out into tin capsules for IRMS (MBL Stable Isotope Laboratory at The Ecosystems Center, Woods Hole, MA). Nitrogen derived from the atmosphere (NDFA) was calculated, and nitrogen production by CI050 and CM002 are shown in FIG. 7.

Phytohormone Production Assay

Figure 8:
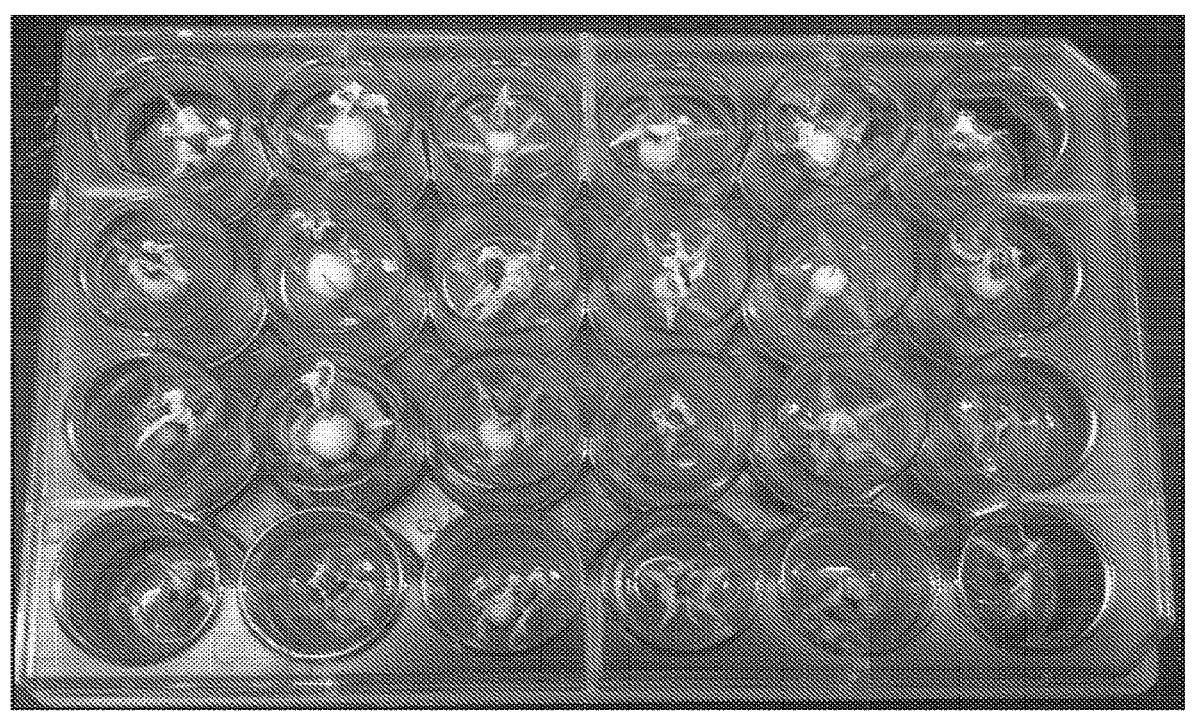
FIG. 8 shows an experimental setup for a Micro-Tom fruiting mass assay.
Figure 9:
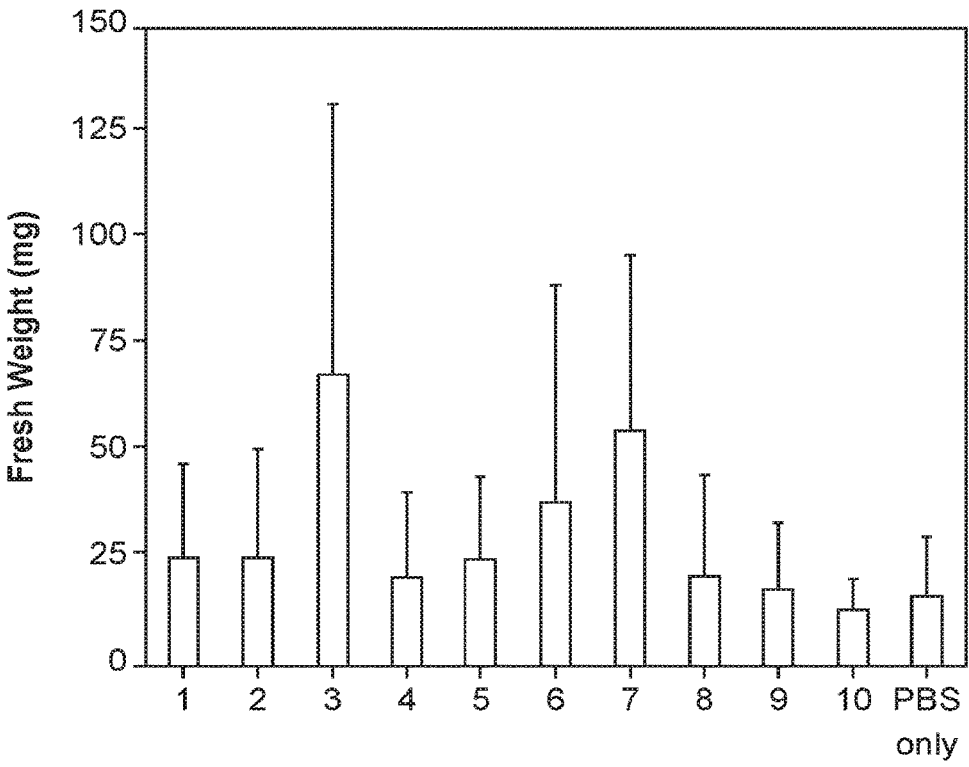
FIG. 9 shows a screen of 10 strains for increase in Micro-Tom plant fruit mass. Results for six replicates are presented. For column 3, p=0.07. For column 7, p=0.05.

The dwarf tomato (*Solanum lycopersicum*) cultivar 'Micro-Tom' has previously been used to study the influence of indole-3-acetic acid on fruit ripening through an in vitro assay (Cohen 1996; J Am Soc Hortic Sci 121: 520-524). To evaluate phytohormone production and secretion by candidate microbes, a plate-based screening assay using immature Micro-Tom fruit was developed. Twelve-well tissue culture test plates were prepared by filling wells with agar medium, allowing it to solidify, and spotting 10 uL of overnight microbial cultures onto the agar surface, as shown in FIG. 8. Wells with agar containing increasing amounts of gibberellic acid (GA) but no bacterial culture were used as a positive control and standards. Flowers one day post-anthesis abscised from growing Micro-Tom plants were inserted, stem-first, into the agar at the point of the bacterial spot culture. These flowers were monitored for 2-3 weeks, after which the fruits were harvested and weighed. An increase in plant fruit mass across several replicates indicates production of plant hormone by the inoculant microbe, as shown in FIG. 9.

Example 6: Cyclical Host-Microbe Evolution

Corn plants were inoculated with CM013 and grown 4 weeks to approximately the V5 growth stage. Those demonstrating improved nitrogen accumulation from microbial sources via $^{15}$N analysis were uprooted, and roots were washed using pressurized water to remove bulk soil. A 0.25 g section of root was cut and rinsed in PBS solution to remove fine soil particles and non-adherent microbes. Tissue samples were homogenized using 3 mm steel beads in QIAGEN TissueLyser II. The homogenate was diluted and plated on SOB agar media. Single colonies were resuspended in liquid media and subjected to PCR analysis of 16s rDNA and mutations unique to the inoculating strain. The process of microbe isolation, mutagenesis, inoculation, and re-isolation can be repeated iteratively to improve microbial traits, plant traits, and the colonization capability of the microbe.

Example 7: Compatibility Across Geography

The ability of the improved microbes to colonize an inoculated plant is critical to the success of the plant under field conditions. While the described isolation methods are designed to select from soil microbes that may have a close relationship with crop plants such as corn, many strains may not colonize effectively across a range of plant genotypes, environments, soil types, or inoculation conditions. Since colonization is a complex process requiring a range of interactions between a microbial strain and host plant, screening for colonization competence has become a central method for selecting priority strains for further development. Early efforts to assess colonization used fluorescent tagging of strains, which was effective but time-consuming and not scalable on a per-strain basis. As colonization activity is not amenable to straightforward improvement, it is imperative that potential product candidates are selected from strains that are natural colonizers.

An assay was designed to test for robust colonization of the wild-type strains in any given host plant using qPCR and primers designed to be strain-specific in a community sample. This assay is intended to rapidly measure the colonization rate of the microbes from corn tissue samples. Initial tests using strains assessed as probable colonizers using fluorescence microscopy and plate-based techniques indicated that a qPCR approach would be both quantitative and scalable.

A typical assay is performed as follows: Plants, mostly varieties of maize and wheat, are grown in a peat potting mix in the greenhouse in replicates of six per strain. At four or five days after planting, a 1 mL drench of early stationary phase cultures of bacteria diluted to an OD590 of 0.6-1.0 (approximately 5E+08 CFU/mL) is pipetted over the emerging coleoptile. The plants are watered with tap water only and allowed to grow for four weeks before sampling, at which time, the plants are uprooted and the roots washed thoroughly to remove most peat residues. Samples of clean root are excised and homogenized to create a slurry of plant cell debris and associated bacterial cells. We developed a high-throughput DNA extraction protocol that effectively produced a mixture of plant and bacterial DNA to use as template for qPCR. Based on bacterial cell spike-in experiments, this DNA extraction process provides a quantitative bacterial DNA sample relative to the fresh weight of the roots. Each strain is assessed using strain-specific primers designed using Primer BLAST (Ye 2012) and compared to background amplification from uninoculated plants. Since some primers exhibit off-target amplification in uninoculated plants, colonization is determined either by presence of amplification or elevated amplification of the correct product compared to the background level.

Figures 16A, 16B:
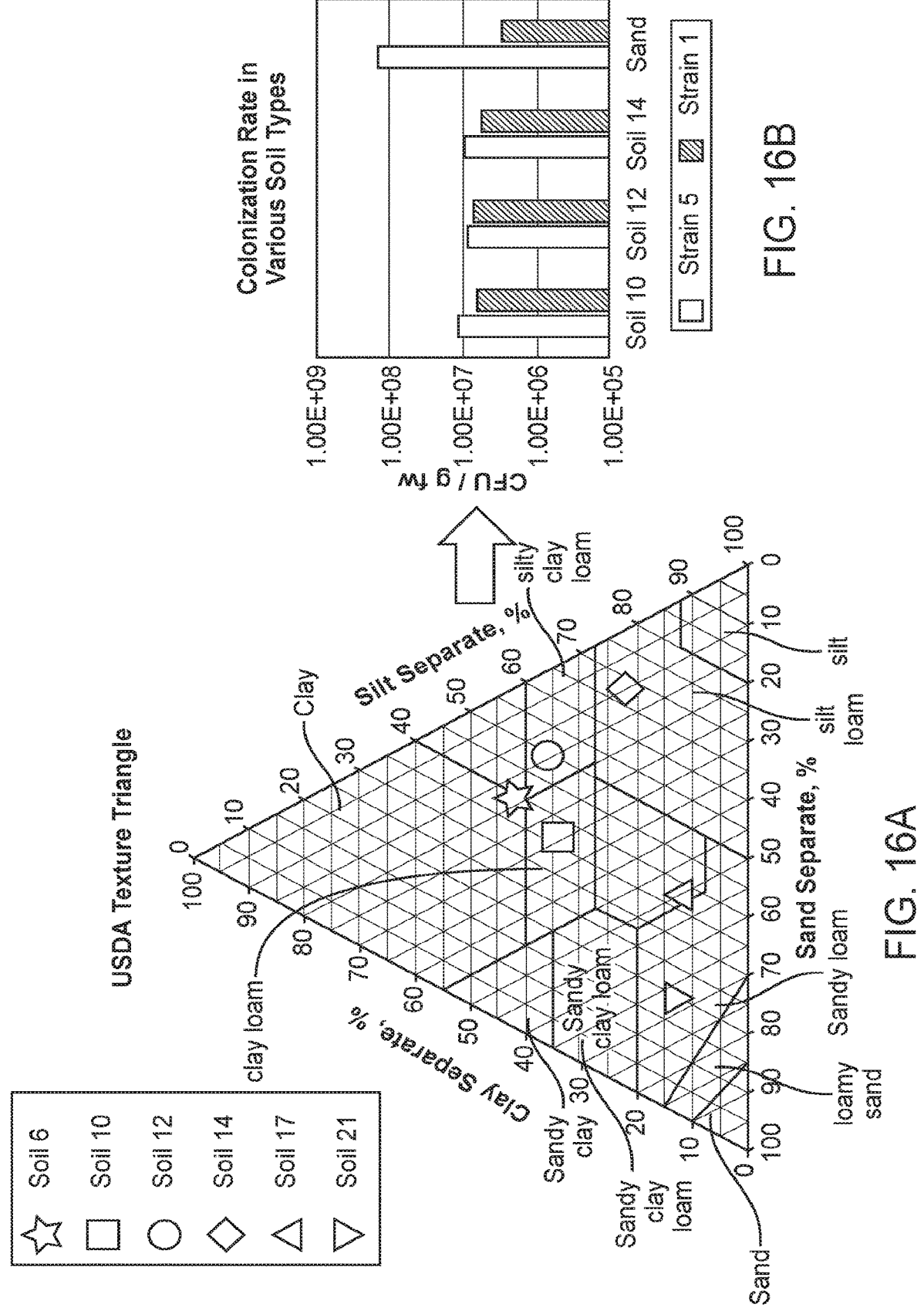
FIG. 16A depicts a soil texture map of various field soils tested for colonization. Soils in which a few microbes were originally source from are indicated as stars.
FIG. 16B depicts the colonization rate of Strain 1 and Strain 5 that are tested across four different soil types (circles). Both strains showed relatively robust colonization profile across diverse soil types.

This assay was used to measure the compatibility of the microbial product across different soil geography. Field soil qualities and field conditions can have a huge influence on the effect of a microbial product. Soil pH, water retention capacity, and competitive microbes are only a few examples of factors in soil that can affect inoculum survival and colonization ability. A colonization assay was performed using three diverse soil types sampled from agricultural fields in California as the plant growth medium (FIG. 16A). An intermediate inoculation density was used to approximate realistic agricultural conditions. Within 3 weeks, Strain 5 colonized all plants at 1E+06 to 1E+07 CFU/g FW. After 7 weeks of plant growth, an evolved version of Strain 1 exhibited high colonization rates (1E+06 CFU/g FW) in all soil types. (FIG. 16B).

Figure 16C:
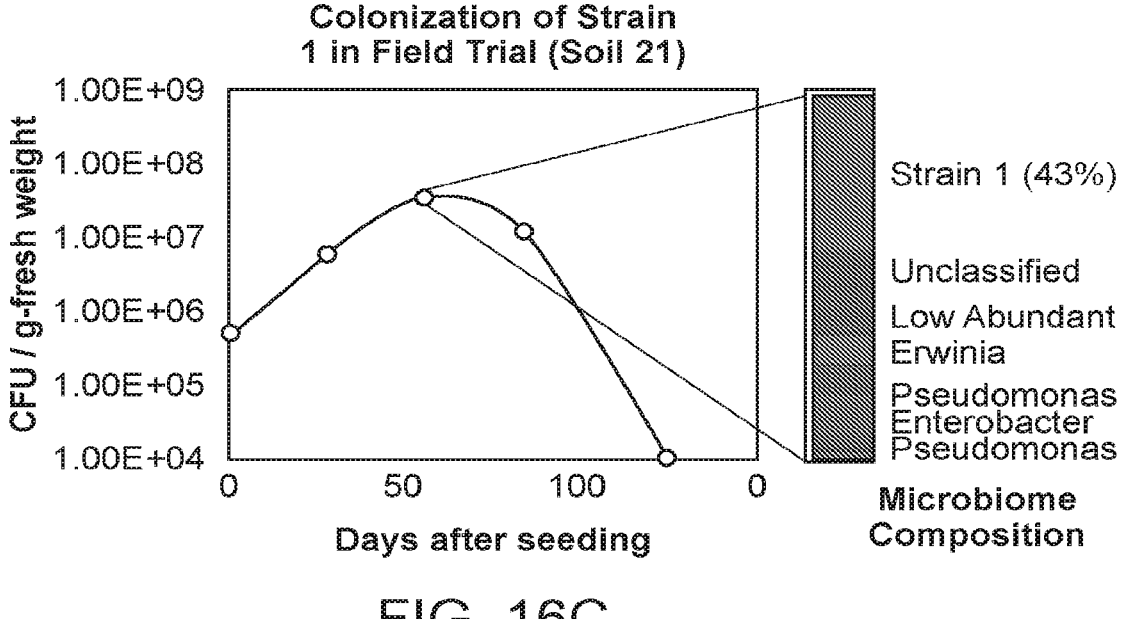
FIG. 16C depicts colonization of Strain 1 as tested in a field trial over the span of a growing season. Strain 1 persists in the corn tissue up to week 12 after planting and starts to show decline in colonization after that time.

Additionally, to assess colonization in the complexity of field conditions, a 1-acre field trial in San Luis Obispo in June of 2015 was initiated to assess the impacts and colonization of seven of the wild-type strains in two varieties of field corn. Agronomic design and execution of the trial was performed by a contract field research organization, Pacific Ag Research. For inoculation, the same peat culture seed coating technique tested in the inoculation methods experiment was employed. During the course of the growing season, plant samples were collected to assess for colonization in the root and stem interior. Samples were collected from three replicate plots of each treatment at four and eight weeks after planting, and from all six reps of each treatment shortly before harvest at 16 weeks. Additional samples were collected from all six replicate plots of treatments inoculated with Strain 1 and Strain 2, as well as untreated controls, at 12 weeks. Numbers of cells per gram fresh weight of washed roots were assessed as with other colonization assays with qPCR and strain-specific primers. Two strains, Strain 1 and Strain 2, showed consistent and widespread root colonization that peaked at 12 weeks and then declined precipitously (FIG. 16C). While Strain 2 appeared to be present in numbers an order of magnitude lower than Strain 1, it was found in more consistent numbers from plant to plant. No strains appeared to effectively colonize the stem interior. In support of the qPCR colonization data, both strains were successfully re-isolated from the root samples using plating and 16S sequencing to identify isolates of matching sequence.

Example 8: Microbe Breeding

Examples of microbe breeding can be summarized in the schematic of FIG. 17A. FIG. 17A depicts microbe breeding wherein the composition of the microbiome can be first measured and a species of interest is identified. The metabolism of the microbiome can be mapped and linked to genetics. Afterwards, a targeted genetic variation can be introduced using methods including, but not limited to, conjugation and recombination, chemical mutagenesis, adaptive evolution, and gene editing. Derivative microbes are used to inoculate crops. In some examples, the crops with the best phenotypes are selected.

Figure 17B:
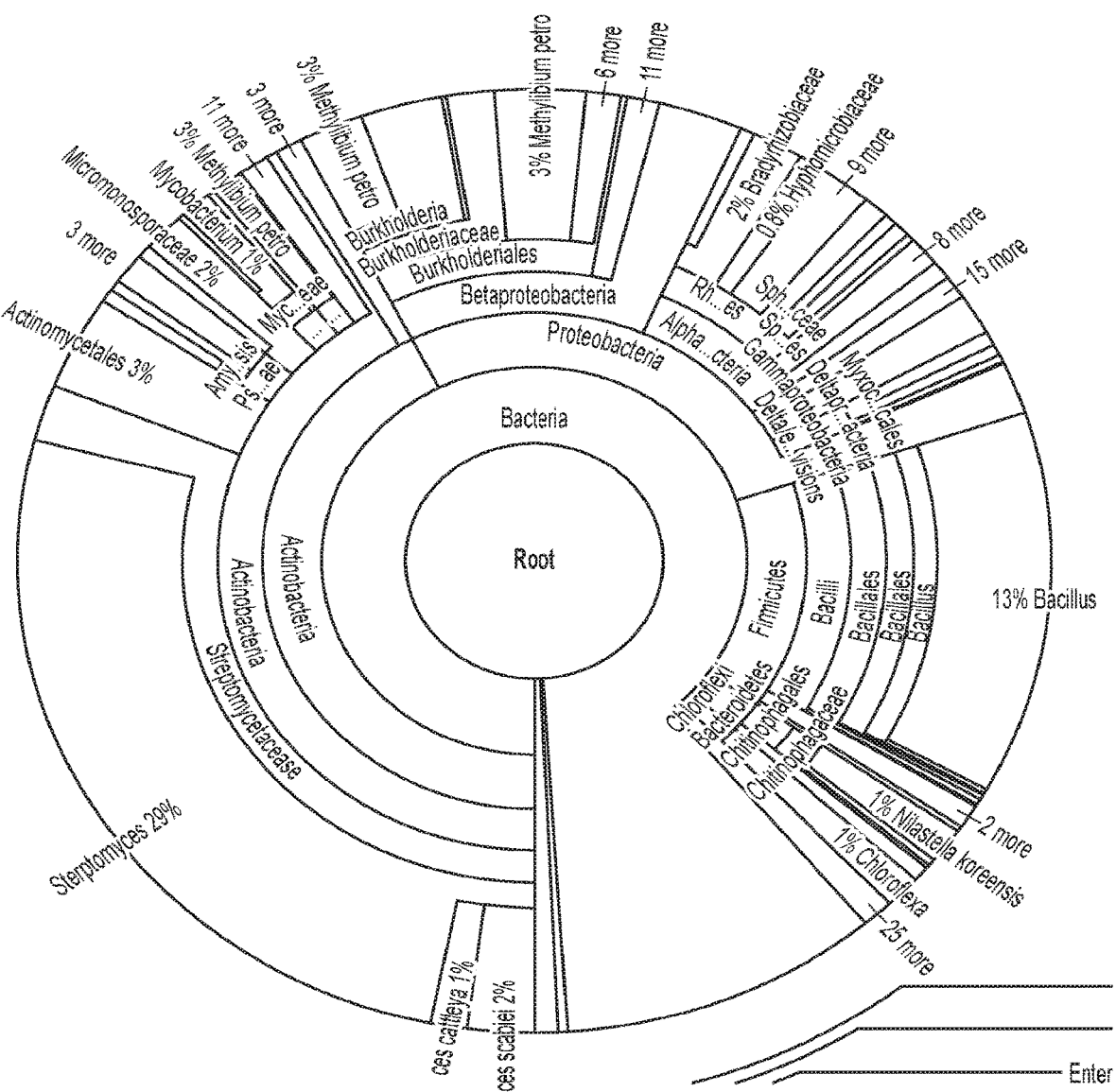
FIG. 17B depicts an expanded view of the measurement of microbiome composition as shown in FIG. 17A.

As provided in FIG. 17A, the composition of the microbiome can be first measured and a species of interest is identified. FIG. 17B depicts an expanded view of the measurement of the microbiome step. The metabolism of the microbiome can be mapped and linked to genetics. The metabolism of nitrogen can involve the entrance of ammonia ($NH_4^+$) from the rhizosphere into the cytosol of the bacteria via the AmtB transporter. Ammonia and L-glutamate (L-Glu) are catalyzed by glutamine synthetase and ATP into glutamine. Glutamine can lead to the formation of biomass (plant growth), and it can also inhibit expression of the nif operon. Afterwards, a targeted genetic variation can be introduced using methods including, but not limited to, conjugation and recombination, chemical mutagenesis, adaptive evolution, and gene editing. Derivative microbes are used to inoculate crops. The crops with the best phenotypes are selected.

Example 9: Field Trials with Microbes of the
Disclosure—Summer 2016

In order to evaluate the efficacy of strains of the present disclosure on corn growth and productivity under varying nitrogen regimes, field trials were conducted.

Trials were conducted with (1) seven subplot treatments of six strains plus the control—four main plots comprised 0, 15, 85, and 100% of maximum return to nitrogen (MRTN) with local verification. The control (UTC only) was conducted with 10 100% MRTN plus, 5, 10, or 15 pounds. Treatments had four replications.

Plots of corn (minimum) were 4 rows of 30 feet in length, with 124 plots per location. All observations were taken from the center two rows of the plots, and all destructive sampling was taken from the outside rows. Seed samples were refrigerated until 1.5 to 2 hours prior to use.

Local Agricultural Practice: The seed was a commercial corn without conventional fungicide and insecticide treatment. All seed treatments were applied by a single seed treatment specialist to assure uniformity. Planting date, seeding rate, weed/insect management, etc. were left to local agricultural practices. With the exception of fungicide applications, standard management practices were followed.

Soil Characterization: Soil texture and soil fertility were evaluated. Soil samples were pre-planted for each replicate to insure residual nitrate levels lower than 50 lbs/Ac. Soil cores were taken from 0 cm to 30 cm. The soil was further characterized for pH, CEC, total K and P.

Assessments: The initial plant population was assessed 14 days after planting (DAP)/acre, and were further assessed for: (1) vigor (1 to 10 scale, w/10=excellent) 14 DAP & V10; (2) recordation of disease ratings any time symptoms are evident in the plots; (3) record any differences in lodging if lodging occurs in the plots; (4) yield (Bu/acre), adjusted to standard moisture pct; (5) test weight; and (6) grain moisture percentage.

Sampling Requirements: The soil was sampled at three timepoints (prior to trial initiation, V10-VT, 1 week post-harvest). All six locations and all plots were sampled at 10 grams per sample (124 plots×3 timepoints×6 locations).

Colonization Sampling: Colonization samples were collected at two timepoints (V10 and VT) for five locations and six timepoints (V4, V8, V10, VT, R5, and Post-Harvest).

Figure 17C:
FIG. 17C depicts sampling of roots utilized in Example 7.

Samples were collected as follows: (1) from 0% and 100% MRTN, 60 plots per location; (2) 4 plants per plot randomly selected from the outside rows; (3) 5 grams of root, 8 inches of stalk, and top three leaves—bagged and IDed each separately—12/bags per plot; (4) five locations (60 plots×2 timepoints×12 bags/plot); and one location (60 plots×6 timepoints×12 bags/plot). See, FIG. 17C illustrating colonization sampling.

Normalized difference vegetation index (NDVI) determination was made using a Greenseeker instrument at two timepoints (V4-V6 and VT). Assessed each plot at all six locations (124 plots×2 timepoints×6 locations).

Root analysis was performed with Win Rhizo from one location that best illustrated treatment differentiation. Ten plants per plot were randomly sampled (5 adjacent from each outside row; V3-V4 stage plants were preferred) and gently washed to remove as much dirt as reasonable. Ten roots were placed in a plastic bag and labelled. Analyzed with WinRhizo Root Analysis.

Stalk Characteristics were measured at all six locations between R2 and R5. The stalk diameter of ten plants per plot at the 6" height were recorded, as was the length of the first internode above the 6" mark. Ten plants were monitored; five consecutive plants from the center of the two inside rows. Six locations were evaluated (124 plots×2 measures×6 locations).

The tissue nitrates were analyzed from all plots and all locations. An 8" segment of stalk beginning 6" above the soil when the corn is between one and three weeks after black layer formation; leaf sheaths were removed. All locations and plots were evaluated (6 locations×124 plots).

The following weather data was recorded for all locations from planting to harvest: daily maximum and minimum temperatures, soil temperature at seeding, daily rainfall plus irrigation (if applied), and any unusual weather events such as excessive rain, wind, cold, or heat.

Yield data across all six locations is presented in Table 8. Nitrogen rate had a significant impact on yield, but strains across nitrogen rates did not. However, at the lowest nitrogen rate, strains CI006, CM029, and CI019 numerically out-yielded the UTC by 4 to 6 bu/acre. Yield was also numerically increased 2 to 4 bu/acre by strains CM029, CI019, and CM081 at 15% MRTN.

TABLE 8

| | | | | | | | |
|---|---|---|---|---|---|---|---|
| | | | Yield data across all six locations | | | | |
| MRTN % | YLD (bu) | Vigor_E | Vigor_L | Stalk Diameter (mm) | Internode Length (in) | NDVI_Veg | NDVI_Rep |
| 0 | 143.9 | 7.0 | 5.7 | 18.87 | 7.18 | 64.0 | 70.6 |
| 15 | 165.9 | 7.2 | 6.3 | 19.27 | 7.28 | 65.8 | 72.5 |
| 85 | 196.6 | 7.1 | 7.1 | 20.00 | 7.31 | 67.1 | 74.3 |
| 100 | 197.3 | 7.2 | 7.2 | 20.23 | 7.37 | 66.3 | 72.4 |
| Strain | YLD (bu) | Vigor_E | Vigor_L | Stalk Diameter (mm) | Internode Length (in) | NDVI_Veg | NDVI_Rep |
| CI006 (1) | 176.6 | 7.2 | 6.6 | 19.56 | 18.78 | 66.1 | 72.3 |
| CM029 (2) | 176.5 | 7.1 | 6.5 | 19.54 | 18.61 | 65.4 | 71.9 |
| CM038 (3) | 175.5 | 7.2 | 6.5 | 19.58 | 18.69 | 65.7 | 72.8 |
| CI019 (4) | 176.0 | 7.1 | 6.6 | 19.51 | 18.69 | 65.5 | 72.9 |
| CM081 (5) | 176.2 | 7.1 | 6.6 | 19.57 | 18.69 | 65.8 | 73.1 |
| CM029/ CM081 (6) | 174.3 | 7.1 | 6.6 | 19.83 | 18.79 | 66.2 | 72.5 |
| UTC (7) | 176.4 | 7.1 | 6.6 | 19.54 | 18.71 | 65.9 | 71.7 |

TABLE 8-continued

| MRTN/ Strain | | YLD (bu) | Vigor_E | Vigor_L | Stalk Diameter (mm) | Internode Length (in) | NDVI_Veg | NDVI_Rep |
|---|---|---|---|---|---|---|---|---|
| 0 | 1 | 145.6 | 7.0 | 5.6 | 19.07 | 7.12 | 63.5 | 70.3 |
| 0 | 2 | 147.0 | 7.0 | 5.5 | 18.74 | 7.16 | 64.4 | 70.4 |
| 0 | 3 | 143.9 | 7.0 | 5.5 | 18.83 | 7.37 | 64.6 | 70.5 |
| 0 | 4 | 146.0 | 6.9 | 5.7 | 18.86 | 7.15 | 63.4 | 70.7 |
| 0 | 5 | 141.7 | 7.0 | 5.8 | 18.82 | 7.05 | 63.6 | 70.9 |
| 0 | 6 | 142.2 | 7.2 | 5.8 | 19.12 | 7.09 | 64.7 | 69.9 |
| 0 | 7 | 141.2 | 7.0 | 5.8 | 18.64 | 7.32 | 64.0 | 71.4 |
| 15 | 1 | 164.2 | 7.3 | 6.1 | 19.09 | 7.21 | 66.1 | 71.5 |
| 15 | 2 | 167.3 | 7.2 | 6.3 | 19.32 | 7.29 | 65.5 | 72.7 |
| 15 | 3 | 165.6 | 7.3 | 6.3 | 19.36 | 7.23 | 64.8 | 72.5 |
| 15 | 4 | 167.9 | 7.3 | 6.4 | 19.31 | 7.51 | 66.1 | 72.3 |
| 15 | 5 | 169.3 | 7.2 | 6.2 | 19.05 | 7.32 | 66.0 | 72.8 |
| 15 | 6 | 161.9 | 7.1 | 6.3 | 19.45 | 7.20 | 66.2 | 72.2 |
| 15 | 7 | 165.1 | 7.3 | 6.4 | 19.30 | 7.18 | 66.0 | 73.3 |
| 85 | 1 | 199.4 | 7.3 | 7.2 | 19.70 | 7.32 | 67.2 | 74.0 |
| 85 | 2 | 195.1 | 7.1 | 7.2 | 19.99 | 7.09 | 66.5 | 74.4 |
| 85 | 3 | 195.0 | 7.0 | 7.0 | 20.05 | 7.26 | 67.3 | 74.6 |
| 85 | 4 | 195.6 | 7.2 | 7.1 | 20.04 | 7.29 | 66.4 | 74.4 |
| 85 | 5 | 196.4 | 7.2 | 7.0 | 19.87 | 7.39 | 67.3 | 74.5 |
| 85 | 6 | 195.1 | 7.0 | 6.9 | 20.35 | 7.34 | 67.4 | 74.4 |
| 85 | 7 | 199.5 | 6.9 | 7.2 | 19.97 | 7.48 | 67.4 | 74.1 |
| 100 | 1 | 197.1 | 7.2 | 7.3 | 20.38 | 7.68 | 67.5 | 73.4 |
| 100 | 2 | 196.5 | 7.0 | 7.1 | 20.11 | 7.21 | 65.3 | 70.2 |
| 100 | 3 | 197.6 | 7.5 | 7.3 | 20.08 | 7.42 | 66.3 | 73.4 |
| 100 | 4 | 194.6 | 7.1 | 7.1 | 19.83 | 7.40 | 66.1 | 74.1 |
| 100 | 5 | 197.4 | 7.2 | 7.3 | 20.53 | 7.36 | 66.2 | 74.3 |
| 100 | 6 | 198.1 | 7.2 | 7.4 | 20.40 | 7.16 | 66.6 | 73.6 |
| 100 | 7 | 199.9 | 7.2 | 7.2 | 20.26 | 7.32 | 66.2 | 68.1 |

Another analysis approach is presented in Table 9. The table comprises the four locations where the response to nitrogen was the greatest which suggests that available residual nitrogen was lowest. This approach does not alter the assessment that the nitrogen rate significantly impacted yield, which strains did not when averaged across all nitrogen rates. However, the numerical yield advantage at the lowest N rate is more pronounced for all strains, particularly CI006, CM029, and CM029/CM081 where yields were increased from 8 to 10 bu/acre. At 15% MRTN, strain CM081 outyielded UTC by 5 bu.

TABLE 9

Yield data across four locations 4 Location Average - SGS, AgIdea, Bennett, RFR

| Table 16 MRTN % | YLD (bu) | Vigor_E | Vigor_L | Stalk Diameter (mm) | Internode Length (in) |
|---|---|---|---|---|---|
| 0 | 137.8 | 7.3 | 5.84 | 18.10 | 5.36 |
| 15 | 162.1 | 7.5 | 6.63 | 18.75 | 5.40 |
| 85 | 199.2 | 7.4 | 7.93 | 19.58 | 5.62 |
| 100 | 203.5 | 7.5 | 8.14 | 19.83 | 5.65 |

| Strain | YLD (bu) | Vigor_E | Vigor_L | Stalk Diameter (mm) | Internode Length (in) |
|---|---|---|---|---|---|
| CI006 (1) | 175.4 | 7.5 | 7.08 | 19.03 | 5.59 |
| CM029 (2) | 176.1 | 7.4 | 7.08 | 19.09 | 5.39 |
| CM038 (3) | 175.3 | 7.5 | 7.05 | 19.01 | 5.59 |
| CI019 (4) | 174.8 | 7.5 | 7.16 | 19.02 | 5.45 |
| CM081 (5) | 176.7 | 7.4 | 7.16 | 19.00 | 5.53 |
| CM029/ CM081 (6) | 175.1 | 7.4 | 7.17 | 19.33 | 5.46 |
| UTC (7) | 176.0 | 7.3 | 7.27 | 18.98 | 5.55 |

TABLE 9-continued

Yield data across four locations 4 Location Average - SGS, AgIdea, Bennett, RFR

| MRTN/ Strain | | YLD (bu) | Vigor_E | Vigor_L | Stalk Diameter (mm) | Internode Length (in) |
|---|---|---|---|---|---|---|
| 0 | 1 | 140.0 | 7.3 | 5.69 | 18.32 | 5.28 |
| 0 | 2 | 140.7 | 7.4 | 5.69 | 18.19 | 5.23 |
| 0 | 3 | 135.5 | 7.3 | 5.63 | 17.95 | 5.50 |
| 0 | 4 | 138.8 | 7.3 | 5.81 | 17.99 | 5.36 |
| 0 | 5 | 136.3 | 7.3 | 6.06 | 18.05 | 5.34 |
| 0 | 6 | 141.4 | 7 5 | 6.00 | 18.43 | 5.30 |
| 0 | 7 | 131.9 | 7.3 | 6.00 | 17.75 | 5.48 |
| 15 | 1 | 158.0 | 7.6 | 6.44 | 18.53 | 5.34 |
| 15 | 2 | 164.1 | 7.5 | 6.56 | 19.13 | 5.42 |
| 15 | 3 | 164.3 | 7.6 | 6.63 | 18.68 | 5.51 |
| 15 | 4 | 163.5 | 7.6 | 6.81 | 18.84 | 5.34 |
| 15 | 5 | 166.8 | 7.5 | 6.63 | 18.60 | 5.39 |
| 15 | 6 | 156.6 | 7.4 | 6.56 | 18.86 | 5.41 |
| 15 | 7 | 161.3 | 7.5 | 6.81 | 18.62 | 5.42 |
| 85 | 1 | 199.4 | 7.6 | 8.00 | 19.15 | 5.63 |
| 85 | 9 | 199.0 | 7.4 | 8.09 | 19.49 | 5.46 |
| 85 | 3 | 198.2 | 7.4 | 7.75 | 19.88 | 5.69 |
| 85 | 4 | 196.8 | 7.4 | 8.00 | 19.65 | 5.60 |
| 85 | 5 | 199.5 | 7.4 | 7.75 | 19.26 | 5.70 |
| 85 | 6 | 198.7 | 7.3 | 7.81 | 19.99 | 5.61 |
| 85 | 7 | 202.8 | 7.2 | 8.13 | 19.66 | 5.65 |
| 100 | 1 | 204.3 | 7.4 | 8.19 | 20.11 | 6.10 |
| 100 | 2 | 200.6 | 7.3 | 8.00 | 19.53 | 5.46 |
| 100 | 3 | 203.3 | 7.7 | 8.19 | 19.55 | 5.67 |
| 100 | 4 | 200.2 | 7.6 | 8.00 | 19.59 | 5.49 |
| 100 | 5 | 203.9 | 7.4 | 8.19 | 20.08 | 5.68 |
| 100 | 6 | 203.8 | 7.5 | 8.31 | 20.05 | 5.52 |
| 100 | 7 | 208.1 | 7.4 | 8.13 | 19.90 | 5.63 |

The results from the field trial are also illustrated in FIGS. 21-27. The results indicate that the microbes of the disclosure are able to increase plant yield, which points to the ability of the taught microbes to increase nitrogen fixation in an important agricultural crop, i.e. corn.

The field based results further validate the disclosed methods of non-intergenerially modifying the genome of selected microbial strains, in order to bring about agriculturally relevant results in a field setting when applying said engineered strains to a crop.

FIG. 18 depicts the lineage of modified strains that were derived from strain CI006 (WT *Kosakonia sacchari*). The field data demonstrates that an engineered derivative of the CI006 WT strain, i.e. CM029, is able to bring about numerically relevant results in a field setting. For example, Table 8 illustrates that at 0% MRTN CM029 yielded 147.0 bu/acre compared to untreated control at 141.2 bu/acre (an increase of 5.8 bu/acre). Table 8 also illustrates that at 15% MRTN CM029 yielded 167.3 bu/acre compared to untreated control at 165.1 bu/acre (an increase of 2.2 bu/acre). Table 9 is supportive of these conclusions and illustrates that at 0% MRTN CM029 yielded 140.7 bu/acre compared to untreated control at 131.9 bu/acre (an increase of 8.8 bu/acre). Table 9 also illustrates that at 15% MRTN CM029 yielded 164.1 bu/acre compared to untreated control at 161.3 bu/acre (an increase of 2.8 bu/acre).

FIG. 19 depicts the lineage of modified strains that were derived from strain CI019 (WT *Rahnella aquatilis*). The field data demonstrates that an engineered derivative of the CI019 WT strain, i.e. CM081, is able to bring about numerically relevant results in a field setting. For example, Table 8 illustrates that at 15% MRTN CM081 yielded 169.3 bu/acre compared to untreated control at 165.1 bu/acre (an increase of 4.2 bu/acre). Table 9 is supportive of these conclusions and illustrates that at 0% MRTN CM081 yielded 136.3 bu/acre compared to untreated control at 131.9 bu/acre (an increase of 4.4 bu/acre). Table 9 also illustrates that at 15% MRTN CM081 yielded 166.8 bu/acre compared to untreated control at 161.3 bu/acre (an increase of 5.5 bu/acre).

Further, one can see in Table 9 that the combination of CM029/CM081 at 0% MRTN yielded 141.4 bu/acre compared to untreated control at 131.9 bu/acre (an increase of 9.5 bu/acre).

Example 10: Field Trials with Microbes of the Disclosure

A diversity of nitrogen fixing bacteria can be found in nature, including in agricultural soils. However, the potential of a microbe to provide sufficient nitrogen to crops to allow decreased fertilizer use may be limited by repression of nitrogenase genes in fertilized soils as well as low abundance in close association with crop roots. Identification, isolation and breeding of microbes that closely associate with key commercial crops might disrupt and improve the regulatory networks linking nitrogen sensing and nitrogen fixation and unlock significant nitrogen contributions by crop-associated microbes. To this end, nitrogen fixing microbes that associate with and colonize the root system of corn were identified.

Figure 30:
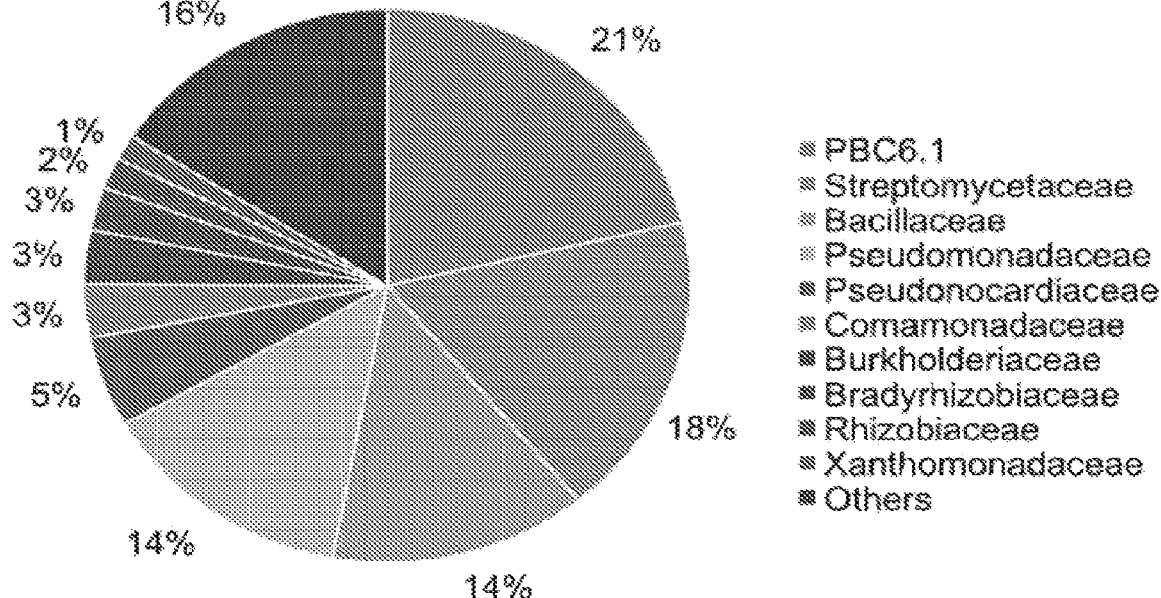
FIG. 30 illustrates PBC6.1 colonization to nearly 21% abundance of the root-associated microbiota in corn roots. Abundance data is based on 16S amplicon sequencing of the rhizosphere and endosphere of corn plants inoculated with PBC6.1 and grown in greenhouse conditions.

Root samples from corn plants grown in agronomically relevant soils were collected, and microbial populations extracted from the rhizosphere and endosphere. Genomic DNA from these samples was extracted, followed by 16S amplicon sequencing to profile the community composition. A *Kosakonia sacchari* microbe (strain PBC6.1) was isolated and classified through 16S rRNA and whole genome sequencing. This is a particularly interesting nitrogen fixer capable of colonizing to nearly 21% abundance of the root-associated microbiota (FIG. 30). To assess strain sensitivity to exogenous nitrogen, nitrogen fixation rates in pure culture were measured with the classical acetylene reduction assay (ARA) and varying levels of glutamine supplementation. The species exhibited a high level of nitrogen fixing activity in nitrogen-free media, yet exogenous fixed nitrogen repressed nif gene expression and nitrogenase activity (Strain PBC6.1, FIGS. 28C and 28D). Additionally, when released ammonia was measured in the supernatant of PBC6.1 grown in nitrogen-fixing conditions, very little release of fixed nitrogen could be detected (FIG. 28E).

We hypothesized that PBC6.1 could be a significant contributor of fixed nitrogen in fertilized fields if regulatory networks controlling nitrogen metabolism were rewired to allow optimal nitrogenase expression and ammonia release in the presence of fixed nitrogen. Sufficient genetic diversity should exist within the PBC6.1 genome to enable broad phenotypic remodeling without the insertion of transgenes or synthetic regulatory elements. The isolated strain has a genome of at least 5.4 Mbp and a canonical nitrogen fixation gene cluster. Related nitrogen metabolism pathways in PBC6.1 are similar to those of the model organism for nitrogen fixation, *Klebsiella oxytoca* m5al.

Figures 28A, 28B, 28C, 28D, 28E:
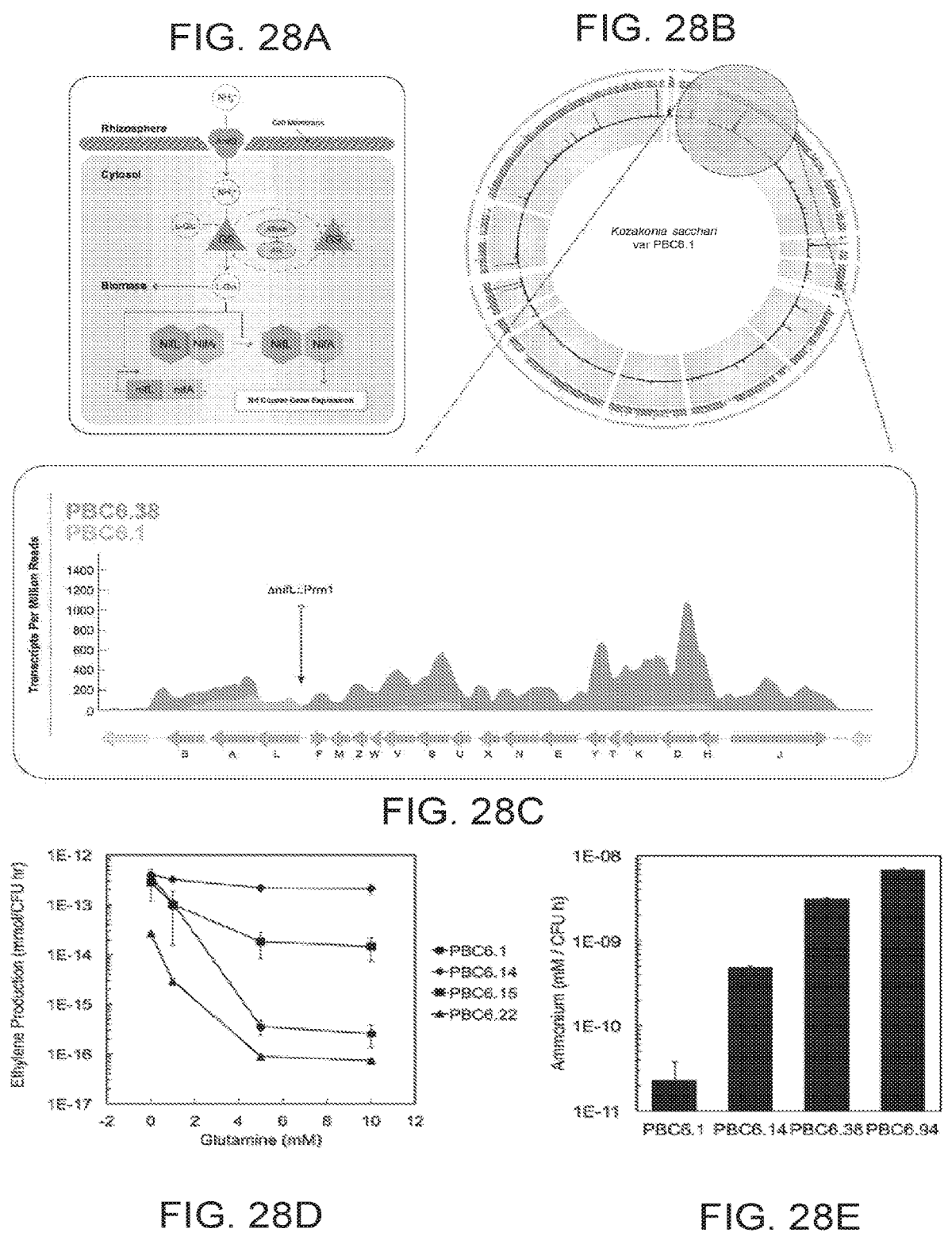

Several gene regulatory network nodes were identified which may augment nitrogen fixation and subsequent transfer to a host plant, particularly in high exogenous concentrations of fixed nitrogen (FIG. 28A). The nifLA operon directly regulates the rest of the nif cluster through transcriptional activation by NifA and nitrogen- and oxygen-dependent repression of NifA by NifL. Disruption of nifL can abolish inhibition of NifA and improve nif expression in the presence of both oxygen and exogenous fixed nitrogen. Furthermore, expressing nifA under the control of a nitrogen-independent promoter may decouple nitrogenase biosynthesis from regulation by the NtrB/NtrC nitrogen sensing complex. The assimilation of fixed nitrogen by the microbe to glutamine by glutamine synthetase (GS) is reversibly regulated by the two-domain adenylyltransferase (ATase) enzyme GlnE through the adenylylation and deadenylation of GS to attenuate and restore activity, respectively. Truncation of the GlnE protein to delete its adenylyl-removing (AR) domain may lead to constitutively adenylated glutamine synthetase, limiting ammonia assimilation by the microbe and increasing intra- and extracellular ammonia. Finally, reducing expression of AmtB, the transporter responsible for uptake of ammonia, could lead to greater extracellular ammonia. To generate rationally designed microbial phenotypes without the use of transgenes, two approaches were employed: creating markerless deletions of genomic sequences encoding protein domains or whole genes, and rewiring regulatory networks by intragenomic promoter rearrangement. Through an iterative mutagenesis process, several non-transgenic derivative strains of PBC6.1 were generated (Table 10).

TABLE 10

List of isolated and derivative *K. sacchari* strains used in this work. Prm, promoter sequence derived from the PBC6.1 genome; $\Delta glnE_{AR}1$ and $\Delta glnE_{AR}2$, different truncated versions of glnE gene removing the adenylyl-removing domain sequence.

| Strain ID | Genotype |
| --- | --- |
| PBC6.1 | WT |
| PBC6.14 | ΔnifL::Prm1 |
| PBC6.15 | ΔnifL::Prm5 |
| PBC6.22 | ΔnifL::Prm3 |
| PBC6.37 | ΔnifL::Prm1 $\Delta glnE_{AR}2$ |

127

TABLE 10-continued

List of isolated and derivative *K. sacchari* strains used in
this work. Prm, promoter sequence derived from the PBC6.1
genome; AglnE$_{AR}$1 and AglnE$_{AR}$2, different truncated
versions of glnE gene removing the adenylyl-removing domain sequence.

| Strain ID | Genotype |
|-----------|----------|
| PBC6.38 | ΔnifL::Prm1 AglnE$_{AR}$1 |
| PBC6.93 | ΔnifL::Prm1 AglnE$_{AR}$2 ΔamtB |
| PBC6.94 | ΔnifL::Prm1 AglnE$_{AR}$1 ΔamtB |

Figure 31:
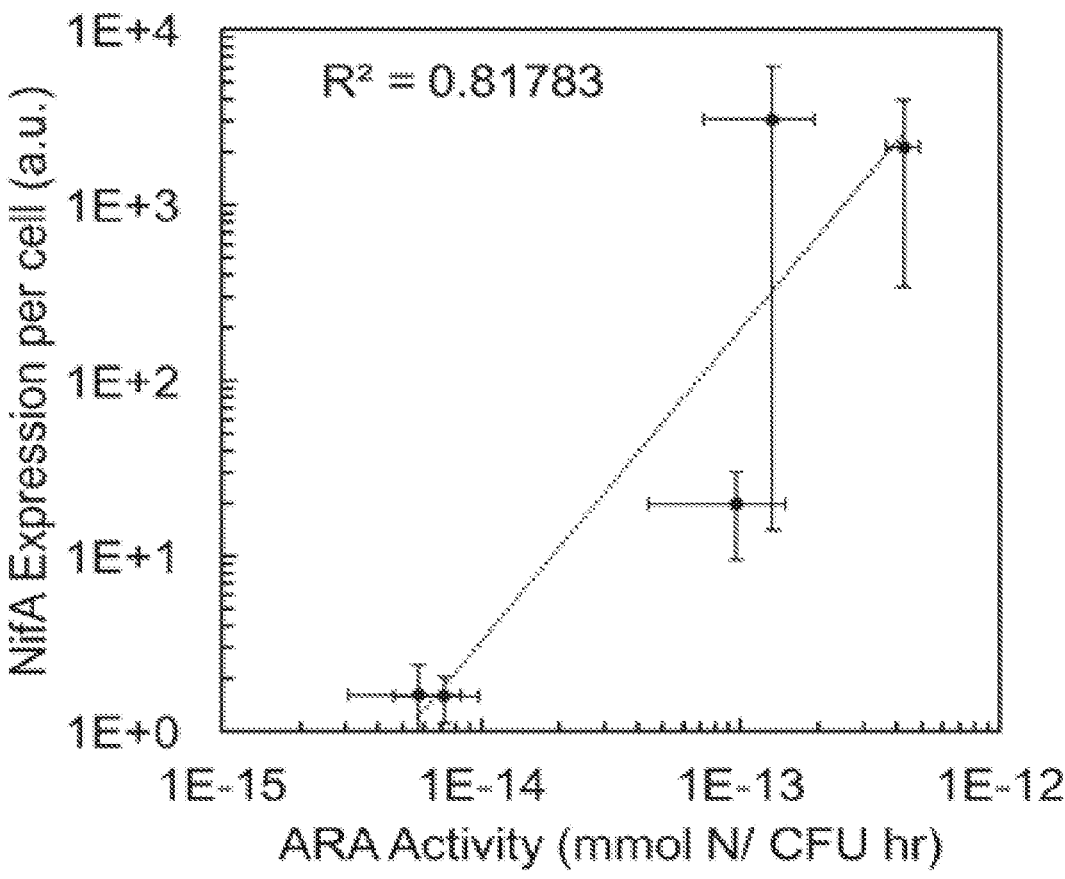
FIG. 31 illustrates transcriptional rates of nifA in derivative strains of PBC6.1 correlated with acetylene reduction rates. An ARA assay was performed as described in the Methods, after which cultures were sampled and subjected to qPCR analysis to determine nifA transcript levels. Error bars show standard error of the mean of at least three biological replicates in each measure.

Several in vitro assays were performed to characterize specific phenotypes of the derivative strains. The ARA was used to assess strain sensitivity to exogenous nitrogen, in which PBC6.1 exhibited repression of nitrogenase activity at high glutamine concentrations (FIG. 28D). In contrast, most derivative strains showed a derepressed phenotype with varying levels of acetylene reduction observed at high glutamine concentrations. Transcriptional rates of nifA in samples analyzed by qPCR correlated well with acetylene reduction rates (FIG. 31), supporting the hypothesis that nifL disruption and insertion of a nitrogen-independent promoter to drive nifA can lead to nif cluster derepression. Strains with altered GlnE or AmtB activity showed markedly increased ammonium excretion rates compared to wild type or derivative strains without these mutations (FIG. 28E), illustrating the effect of these genotypes on ammonia assimilation and reuptake.

Two experiments were performed to study the interaction of PBC6.1 derivatives with corn plants and quantify incorporation of fixed nitrogen into plant tissues. First, rates of microbial nitrogen fixation were quantified in a greenhouse study using isotopic tracers. Briefly, plants are grown with 15N labeled fertilizer, and diluted concentrations of 15N in plant tissues indicate contributions of fixed nitrogen from microbes. Corn seedlings were inoculated with selected microbial strains, and plants were grown to the V6 growth stage. Plants were subsequently deconstructed to enable measurement of microbial colonization and gene expression as well as measurement of 15N/14N ratios in plant tissues by isotope ratio mass spectrometry (IRMS). Analysis of the aerial tissue showed a small, nonsignificant contribution by PBC6.38 to plant nitrogen levels, and a significant contribution by PBC6.94 (p=0.011). Approximately 20% of the nitrogen found in above-ground corn leaves was produced by PBC6.94, with the remainder coming from the seed, potting mix, or "background" fixation by other soilborne microbes (FIG. 29C). This illustrates that our microbial breeding pipeline can generate strains capable of making significant nitrogen contributions to plants in the presence of nitrogen fertilizer. Microbial transcription within plant tissues was measured, and expression of the nif gene cluster was observed in derivative strains but not the wild type strain (FIG. 29B), showing the importance of nif derepression for contribution of BNF to crops in fertilized conditions. Root colonization measured by qPCR demonstrated that colonization density is different for each of the strains tested (FIG. 29A). A 50 fold difference in colonization was observed between PBC6.38 and PBC6.94. This difference could be an indication that PBC6.94 has reduced fitness in the rhizosphere relative to PBC6.38 as a result of high levels of fixation and excretion.

Methods

Media

Minimal medium contains (per liter) 25 g Na$_2$HPO$_4$, 0.1 g CaCL$_2$-2H$_2$O, 3 g KH$_2$PO$_4$, 0.25 g MgSO$_4$·7H$_2$O, 1 g NaCl, 2.9 mg FeCl$_3$, 0.25 mg Na$_2$MoO$_4$·2H$_2$O, and 20 g sucrose. Growth medium is defined as minimal medium supplemented with 50 ml of 200 mM glutamine per liter.

Isolation of Diazotrophs

Corn seedlings were grown from seed (DKC 66-40, DeKalb, IL) for two weeks in a greenhouse environment controlled from 22° C. (night) to 26° C. (day) and exposed to 16 hour light cycles in soil collected from San Joaquin County, CA Roots were harvested and washed with sterile deionized water to remove bulk soil. Root tissues were homogenized with 2 mm stainless steel beads in a tissue lyser (TissueLyser II, Qiagen P/N 85300) for three minutes at setting 30, and the samples were centrifuged for 1 minute at 13,000 rpm to separate tissue from root-associated bacteria. Supernatants were split into two fractions, and one was used to characterize the microbiome through 16S rRNA amplicon sequencing and the remaining fraction was diluted and plated on Nitrogen-free Broth (NfB) media supplemented with 1.5% agar. Plates were incubated at 30° C. for 5-7 days. Colonies that emerged were tested for the presence of the nifH gene by colony PCR with primers Ueda19f and Ueda406r. Genomic DNA from strains with a positive nifH colony PCR was isolated (QIAamp DNA Mini Kit, Cat No. 51306, QIAGEN, Germany) and sequenced (Illumina MiSeq v3, SeqMatic, Fremont, CA). Following sequence assembly and annotation, the isolates containing nitrogen fixation gene clusters were utilized in downstream research.

Microbiome Profiling of Isolation Seedlings

Genomic DNA was isolated from root-associated bacteria using the ZR-96 Genomic DNA I Kit (Zymo Research P/N D3011), and 16S rRNA amplicons were generated using nextera-barcoded primers targeting 799f and 1114r. The amplicon libraries were purified and sequenced with the Illumina MiSeq v3 platform (SeqMatic, Fremont, CA). Reads were taxonomically classified using Kraken using the minikraken database (FIG. 30).

Acetylene Reduction Assay (ARA)

A modified version of the Acetylene Reduction Assay was used to measure nitrogenase activity in pure culture conditions. Strains were propagated from single colony in SOB (RPI, P/N S25040-1000) at 30° C. with shaking at 200 RPM for 24 hours and then subcultured 1:25 into growth medium and grown aerobically for 24 hours (30° C., 200 RPM). 1 ml of the minimal media culture was then added to 4 ml of minimal media supplemented with 0 to 10 mM glutamine in air-tight Hungate tubes and grown anaerobically for 4 hours (30° C., 200 RPM). 10% headspace was removed then replaced by an equal volume of acetylene by injection, and incubation continued for 1 hr. Subsequently, 2 ml of headspace was removed via gas tight syringe for quantification of ethylene production using an Agilent 6850 gas chromatograph equipped with a flame ionization detector (FID).

Ammonium Excretion Assay

Excretion of fixed nitrogen in the form of ammonia was measured using batch fermentation in anaerobic bioreactors. Strains were propagated from single colony in 1 ml/well of SOB in a 96 well DeepWell plate. The plate was incubated at 30° C. with shaking at 200 RPM for 24 hours and then diluted 1:25 into a fresh plate containing 1 ml/well of growth medium. Cells were incubated for 24 hours (30° C., 200 RPM) and then diluted 1:10 into a fresh plate containing minimal medium. The plate was transferred to an anaerobic chamber with a gas mixture of >98.5% nitrogen, 1.2-1.5% hydrogen and <30 ppM oxygen and incubated at 1350 RPM, room temperature for 66-70 hrs. Initial culture biomass was compared to ending biomass by measuring optical density at 590 nm. Cells were then separated by centrifugation, and supernatant from the reactor broth was assayed for free ammonia using the Megazyme Ammonia Assay kit (P/N K-AMIAR) normalized to biomass at each timepoint.

Extraction of Root-Associated Microbiome

Roots were shaken gently to remove loose particles, and root systems were separated and soaked in a RNA stabilization solution (Thermo Fisher P/N AM7021) for 30 minutes. The roots were then briefly rinsed with sterile deionized water. Samples were homogenized using bead beating with ½-inch stainless steel ball bearings in a tissue lyser (TissueLyser II, Qiagen P/N 85300) in 2 ml of lysis buffer (Qiagen P/N 79216). Genomic DNA extraction was performed with ZR-96 Quick-gDNA kit (Zymo Research P/N D3010), and RNA extraction using the RNeasy kit (Qiagen P/N 74104).

Root Colonization Assay

Four days after planting, 1 ml of a bacterial overnight culture (approximately $10^9$ cfu) was applied to the soil above the planted seed. Seedlings were fertilized three times weekly with 25 ml modified Hoagland's solution supplemented with 0.5 mM ammonium nitrate. Four weeks after planting, root samples were collected and the total genomic DNA (gDNA) was extracted. Root colonization was quantified using qPCR with primers designed to amplify unique regions of either the wild type or derivative strain genome. QPCR reaction efficiency was measured using a standard curve generated from a known quantity of gDNA from the target genome. Data was normalized to genome copies per g fresh weight using the tissue weight and extraction volume. For each experiment, the colonization numbers were compared to untreated control seedlings.

In Planta Transcriptomics

Transcriptional profiling of root-associated microbes was measured in seedlings grown and processed as described in the Root Colonization Assay. Purified RNA was sequenced using the Illumina NextSeq platform (SeqMatic, Fremont, CA). Reads were mapped to the genome of the inoculated strain using bowtie2 using '—very-sensitive-local' parameters and a minimum alignment score of 30. Coverage across the genome was calculated using samtools. Differential coverage was normalized to housekeeping gene expression and visualized across the genome using Circos and across the nif gene cluster using DNAplotlib. Additionally, the in planta transcriptional profile was quantified via targeted Nanostring analysis. Purified RNA was processed on an nCounter Sprint (Core Diagnostics, Hayward, CA).

15N Dilution Greenhouse Study

A 15N fertilizer dilution experiment was performed to assess optimized strain activity in planta. A planting medium containing minimal background N was prepared using a mixture of vermiculite and washed sand (5 rinses in DI H₂O). The sand mixture was autoclaved for 1 hour at 122° C. and approximately 600 g measured out into 40 cubic inch (656 mL) pots, which were saturated with sterile DI H₂O and allowed to drain 24 hours before planting. Corn seeds (DKC 66-40) were surface sterilized in 0.625% sodium hypochlorite for 10 minutes, then rinsed five times in sterile distilled water and planted 1 cm deep. The plants were maintained under fluorescent lamps for four weeks with 16-hour day length at room temperatures averaging 22° C. (night) to 26° C. (day).

Five days after planting, seedlings were inoculated with a 1 ml suspension of cells drenched directly over the emerging coleoptile. Inoculum was prepared from 5 ml overnight cultures in SOB, which were spun down and resuspended twice in 5 ml PBS to remove residual SOB before final dilution to OD of 1.0 (approximately $10^{-17}$ CFU/ml). Control plants were treated with sterile PBS, and each treatment was applied to ten replicate plants.

Plants were fertilized with 25 ml fertilizer solution containing 2% 15N-enriched 2 mM KNO₃ on 5, 9, 14, and 19 days after planting, and the same solution without KNO₃ on 7, 12, 16, and 18 days after planting. The fertilizer solution contained (per liter) 3 mmol CaCl₂, 0.5 mmol KH₂PO₄, 2 mmol MgSO₄, 17.9 μmol FeSO₄, 2.86 mg H₃BO₃, 1.81 mg MnCl₂·4H₂O, 0.22 mg ZnSO₄·7H₂O, 51 μg CuSO₄·5H₂O, 0.12 mg Na₂MoO₄·2H₂O, and 0.14 nmol NiCl₂. All pots were watered with sterile DI H₂O as needed to maintain consistent soil moisture without runoff.

At four weeks, plants were harvested and separated at the lowest node into samples for root gDNA and RNA extraction and aerial tissue for IRMS. Aerial tissues were wiped as needed to remove sand, placed whole into paper bags and dried for at least 72 hours at 60° C. Once completely dry, total aerial tissue was homogenized by bead beating and 5-7 mg samples were analyzed by isotope ratio mass spectrometry (IRMS) for δ15N by the MBL Stable Isotope Laboratory (The Ecosystems Center, Woods Hole, MA). Percent NDFA was calculated using the following formula: % NDFA=(δ15N of UTC average−δ15N of sample)/(δ15N of UTC average)×100.

Example 11: Field Trials with Microbes of the Disclosure—Summer 2017

In order to evaluate the efficacy of strains of the present disclosure on corn growth and productivity under varying nitrogen regimes, field trials were conducted. The below field data demonstrates that the non-intergeneric microbes of the disclosure are able to fix atmospheric nitrogen and deliver said nitrogen to a plant—resulting in increased yields—in both a nitrogen limiting environment, as well as a non-nitrogen limiting environment.

Trials were conducted at seven locations across the United states with six geographically diverse Midwestern locations. Five nitrogen regimes were used for fertilizer treatments: 100% of standard agricultural practice of the site/region, 100% minus 25 pounds, 100% minus 50 pounds, 100% minus 75 pounds, and 0%; all per acre. The pounds of nitrogen per acre for the 100% regime depended upon the standard agricultural practices of the site/region. The aforementioned nitrogen regimes ranged from about 153 pounds per acre to about 180 pounds per acre, with an average of about 164 pounds of nitrogen per acre.

Within each fertilizer regime there were 14 treatments. Each regime had six replications, and a split plot design was utilized. The 14 treatments included: 12 different microbes, 1 UTC with the same fertilizer rate as the main plot, and 1 UTC with 100% nitrogen. In the 100% nitrogen regime the $2^{nd}$ UTC is 100 plus 25 pounds.

Plots of corn, at a minimum, were 4 rows of 30 feet in length (30 inches between rows) with 420 plots per location. All observations, unless otherwise noted, were taken from the center two rows of the plants, and all destructive sampling was taken from the outside rows. Seed samples were refrigerated until 1.5 to 2 hours prior to use.

Local Agricultural Practice: The seed was a commercial corn applied with a commercial seed treatment with no biological co-application. The seeding rate, planting date, weed/insect management, harvest times, and other standard management practices were left to the norms of local agricultural practices for the regions, with the exception of fungicide application (if required).

Microbe Application: The microbes were applied to the seed in a seed treatment over seeds that had already received a normal chemical treatment. The seed were coated with fermentation broth comprising the microbes.

Soil Characterization: Soil texture and soil fertility were evaluated. Standard soil sampling procedures were utilized, which included soil cores of depths from 0-30 cm and 30-60 cm. The standard soil sampling included a determination of nitrate nitrogen, ammonium nitrogen, total nitrogen, organic matter, and CEC. Standard soil sampling further included a determination of pH, total potassium, and total phosphorous. To determine the nitrogen fertilizer levels, preplant soil samples from each location were taken to ensure that the 0-12" and potentially the 12" to 24" soil regions for nitrate nitrogen.

Prior to planting and fertilization, 2 ml soil samples were collected from 0 to 6-12" from the UTC. One sample per replicate per nitrogen region was collected using the middle of the row. (5 fertilizer regimes×6 replicates=thirty soil samples).

Post-planting (V4-V6), 2 ml soil samples were collected from 0 to 6-12" from the UTC. One sample per replicate per nitrogen region was collected using the middle of the row. (5 fertilizer regimes×6 replicates=thirty soil samples).

Post-harvest (V4-V6), 2 ml soil samples were collected from 0 to 6-12" from the UTC. One sample per replicate per nitrogen region was collected using the middle of the row. Additional post-harvest soil sample collected at 0-12" from the UTC and potentially 12-24" from the UTC (5 fertilizer regimes×6 replicates=thirty soil samples).

A V6-V10 soil sample from each fertilizer regime (excluding the treatment of 100% and 100%+25 lbs [in the 100% block] for all fertilizer regimes at 0-12" and 12-24". (5 fertilizer regimes×2 depths=10 samples per location).

Post-harvest soil sample from each fertilizer regime (excluding the treatment of 100% and 100%+25 lbs [in the 100% block] for all fertilizer regimes at 0-12" and 12-24". (5 fertilizer regimes×2 depths=10 samples per location).

Assessments: The initial plant population was assessed at ~50% UTC and the final plant population was assessed prior to harvest. Assessment included (1) potentially temperature (temperature probe); (2) vigor (1-10 scale with 10=excellent) at V4 and V8-V10; (3) plant height at V8-V10 and V14; (4) yield (bushels/acre) adjusted to standard moisture percentage; (5) test weight; (6) grain moisture percentage; (7) stalk nitrate tests at black layer (420 plots×7 locations); (8) colonization with 1 plant per plot in zip lock bag at 0% and 100% fertilizer at V4-V6 (1 plant×14 treatments×6 replicates×2 fertilizer regimes=168 plants); (9) transcriptomics with 1 plant per plot in zip lock bag at 0% and 100% fertilizer at V4-V6 (1 plant×14 treatments×6 replicates×2 fertilizer regimes=168 plants); (10) Normalized difference vegetative index (NDVI) or normalized difference red edge (NDRE) determination using a Greenseeker instrument at two time points (V4-V6 and VT) to assess each plot at all 7 locations (420 plots×2 time points×7 locations=5,880 data points); (11) stalk characteristics measured at all 7 locations between R2 and R5 by recording the stalk diameter of 10 plants/plot at 6" height, record length of first internode above the 6" mark, 10 plants monitored (5 consecutive plants from center of two inside rows) (420 plots×10 plants×7 locations=29,400 data points).

Monitoring Schedule: Practitioners visited all trials at V3-V4 stage to assess early-season response to treatments and during reproductive growth stage to monitor maturity. Local cooperator visited research trial on an on-going basis.

Weather Information: Weather data spanning from planting to harvest was collected and consisted of daily minimum and maximum temperatures, soil temperature at seeding, daily rainfall plus irrigation (if applied), and unusual weather events such as excessive wind, rain, cold, heat.

Data Reporting: Including the data indicated above, the field trials generated data points including soil textures; row spacing; plot sizes; irrigation; tillage; previous crop; seeding rate; plant population; seasonal fertilizer inputs including source, rate, timing, and placement; harvest area dimensions, method of harvest, such as by hand or machine and measurement tools used (scales, yield monitor, etc.)

Results: Select results from the aforementioned field trial are reported in FIG. 32 and FIG. 33.

Figure 32:
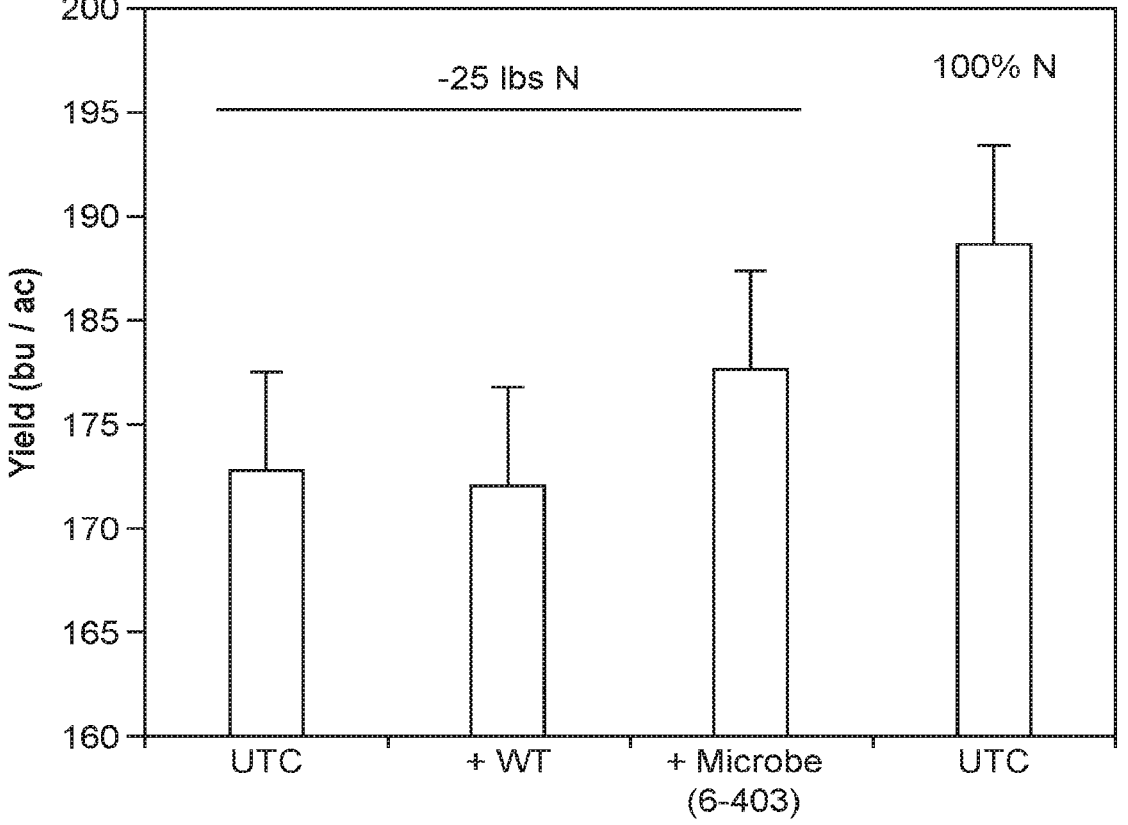
FIG. 32 illustrates results from a summer 2017 field testing experiment. The yield results obtained demonstrate that the microbes of the disclosure can serve as a potential fertilizer replacement. For instance, the utilization of a microbe of the disclosure (i.e. 6-403) resulted in a higher yield than the wild type strain (WT) and a higher yield than the untreated control (UTC). The "−25 lbs N" treatment utilizes 25 lbs less N per acre than standard agricultural practices of the region. The "100% N" UTC treatment is meant to depict standard agricultural practices of the region, in which 100% of the standard utilization of N is deployed by the farmer. The microbe "6-403" was deposited as NCMA 201708004 and can be found in Table A. This is a mutant *Kosakonia sacchari* (also called CM037) and is a progeny mutant strain from CI006 WT.

In FIG. 32, it can be seen that a microbe of the disclosure (i.e. 6-403) resulted in a higher yield than the wild type strain (WT) and a higher yield than the untreated control (UTC). The "−25 lbs N" treatment utilizes 25 lbs less N per acre than standard agricultural practices of the region. The "100% N" UTC treatment is meant to depict standard agricultural practices of the region, in which 100% of the standard utilization of N is deployed by the farmer. The microbe "6-403" was deposited as NCMA 201708004 and can be found in Table A. This is a mutant *Kosakonia sacchari* (also called CM037) and is a progeny mutant strain from CI006 WT.

Figure 33:
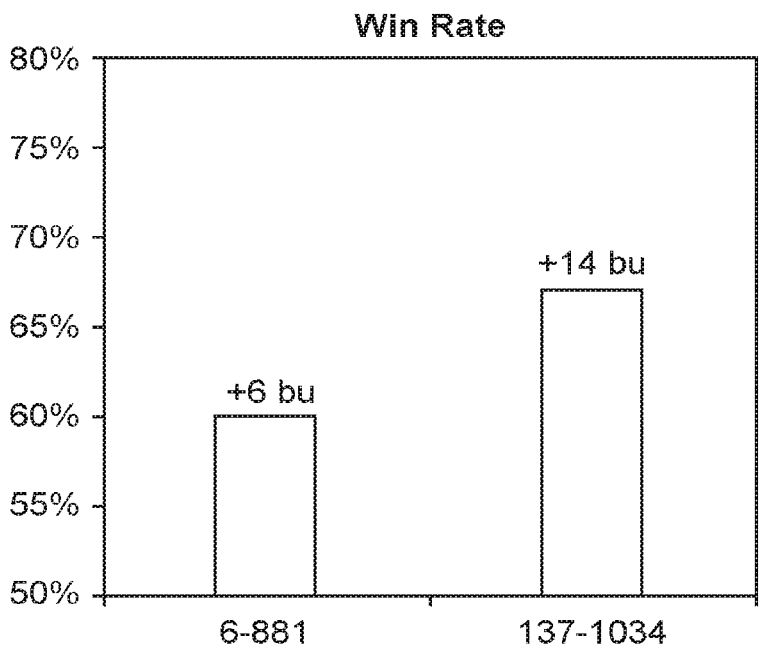
FIG. 33 illustrates results from a summer 2017 field testing experiment. The yield results obtained demonstrate that the microbes of the disclosure perform consistently across locations. Furthermore, the yield results demonstrate that the microbes of the disclosure perform well in both a nitrogen stressed environment, as well as an environment that has sufficient supplies of nitrogen. The microbe "6-881" (also known as CM094, PBC6.94), and which is a progeny mutant *Kosakonia sacchari* strain from CI006 WT, was deposited as NCMA 201708002 and can be found in Table A. The microbe "137-1034," which is a progeny mutant *Klebsiella variicola* strain from CI137 WT, was deposited as NCMA 201712001 and can be found in Table A. The microbe "137-1036," which is a progeny mutant *Klebsiella variicola* strain from CI137 WT, was deposited as NCMA 201712002 and can be found in Table A. The microbe "6-404" (also known as CM38, PBC6.38), and which is a progeny mutant *Kosakonia sacchari* strain from CI006 WT, was deposited as NCMA 201708003 and can be found in Table A. The "Nutrient Stress" condition corresponds to the 0% nitrogen regime. The "Sufficient Fertilizer" condition corresponds to the 100% nitrogen regime.
Figure 33:
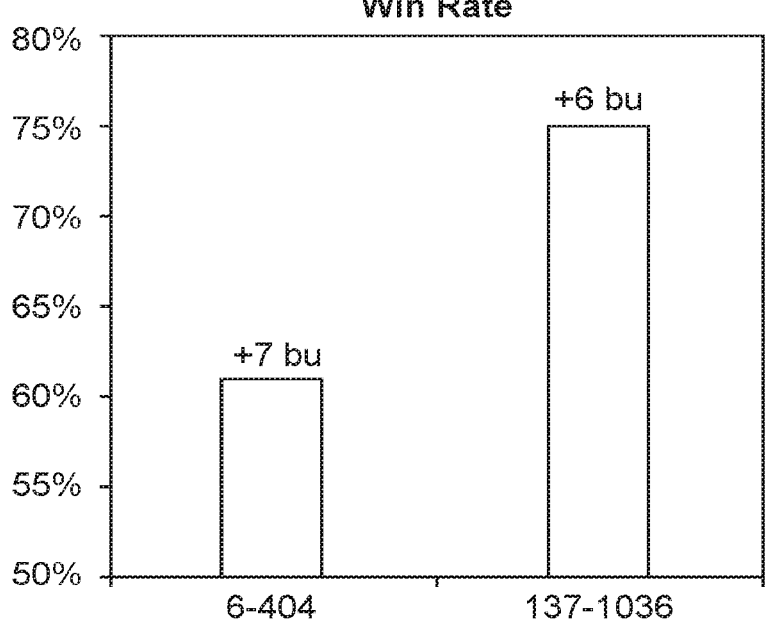
Figure 34:
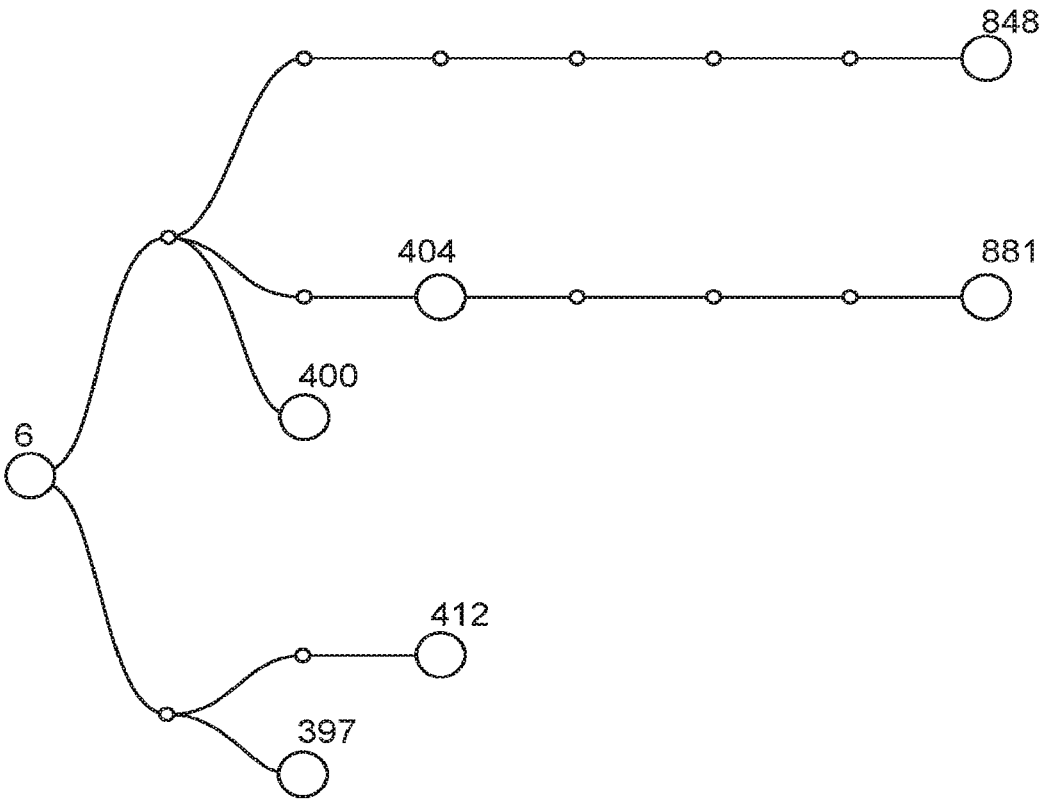
FIG. 34 depicts the lineage of modified strains that were derived from strain CI006 (also termed "6", *Kosakonia sacchari* WT).
Figure 35:
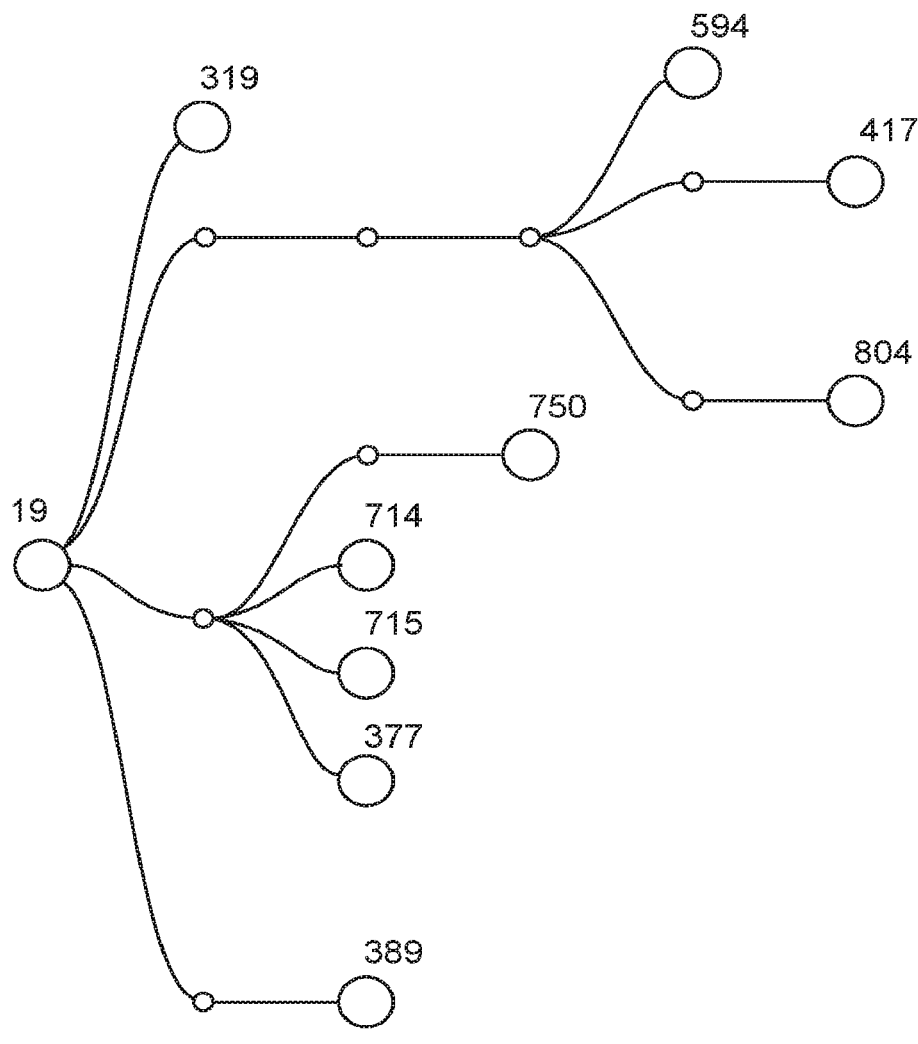
FIG. 35 depicts the lineage of modified strains that were derived from strain CI019 (also termed "19", *Rahnella aquatilis* WT).
Figure 36:
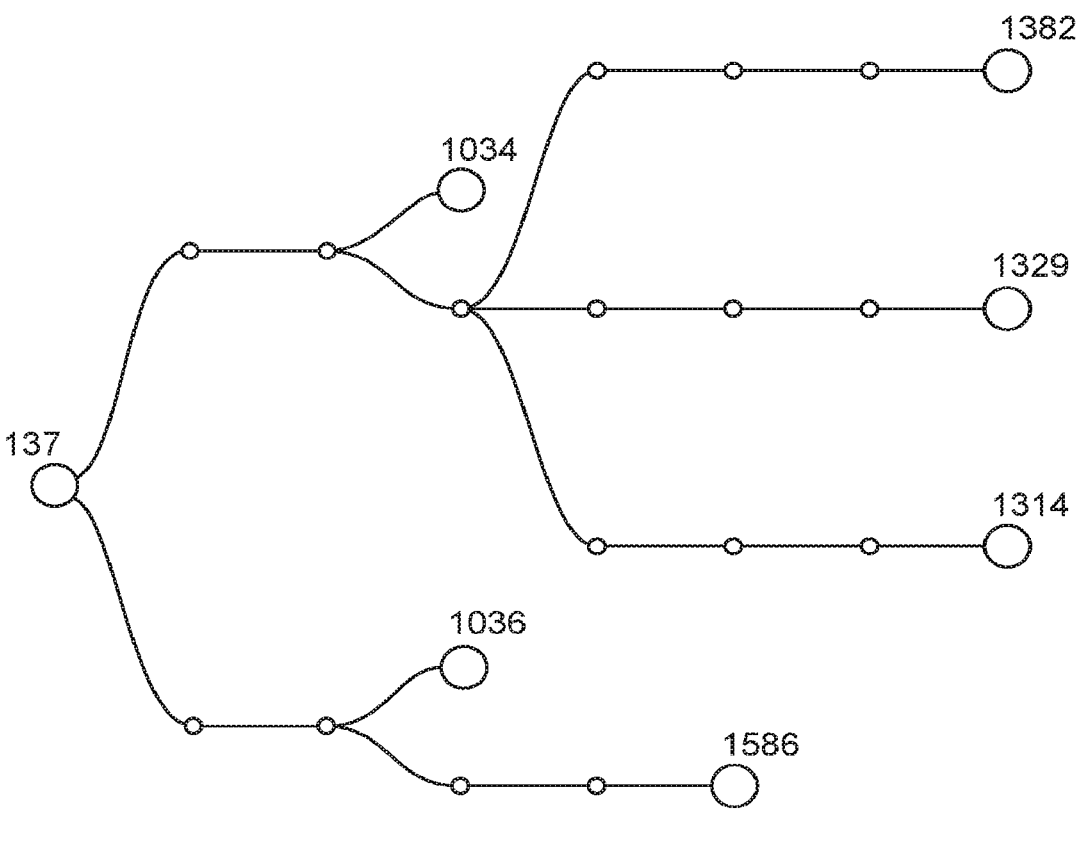
FIG. 36 depicts the lineage of modified strains that were derived from strain CI137 (also termed ("137", *Klebsiella variicola* WT).
Figure 37:
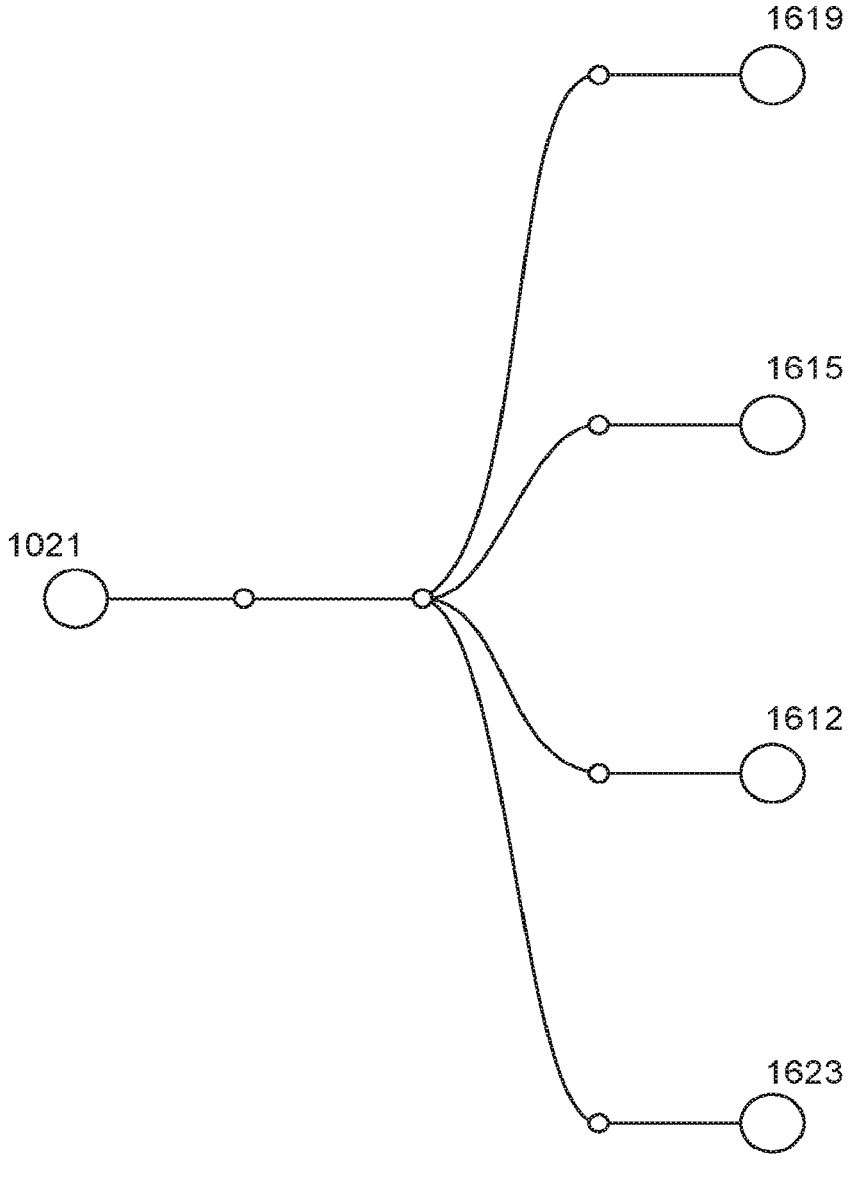
FIG. 37 depicts the lineage of modified strains that were derived from strain 1021 (*Kosakonia pseudosacchari* WT).
Figure 38:
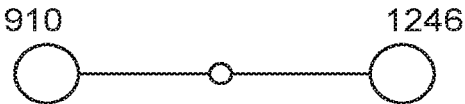
FIG. 38 depicts the lineage of modified strains that were derived from strain 910 (*Kluyvera intermedia* WT).
Figure 39:
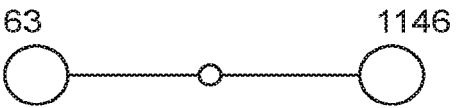
FIG. 39 depicts the lineage of modified strains that were derived from strain 63 (*Rahnella aquatilis* WT).

In FIG. 33, the yield results obtained demonstrate that the microbes of the disclosure perform consistently across locations. Furthermore, the yield results demonstrate that the microbes of the disclosure perform well in both a nitrogen stressed environment (i.e. a nitrogen limiting environment), as well as an environment that has sufficient supplies of nitrogen (i.e. a non-nitrogen-limiting condition). The microbe "6-881" (also known as CM094, PBC6.94), and which is a progeny mutant *Kosakonia sacchari* strain from CI006 WT, was deposited as NCMA 201708002 and can be found in Table A. The microbe "137-1034," which is a progeny mutant *Klebsiella variicola* strain from CI137 WT, was deposited as NCMA 201712001 and can be found in Table A. The microbe "137-1036," which is a progeny mutant *Klebsiella variicola* strain from CI137 WT, was deposited as NCMA 201712002 and can be found in Table A. The microbe "6-404" (also known as CM38, PBC6.38), and which is a progeny mutant *Kosakonia sacchari* strain from CI006 WT, was deposited as NCMA 201708003 and can be found in Table A.

Example 12: Genus of Non-Intergeneric Microbes Beneficial for Agricultural Systems The microbes of the present disclosure were evaluated and compared against one another for the production of nitrogen produced in an acre across a season. See FIG. 20, FIG. 40, and FIG. 41

It is hypothesized by the inventors that in order for a population of engineered non-intergeneric microbes to be beneficial in a modern row crop agricultural system, then the population of microbes needs to produce at least one pound or more of nitrogen per acre per season.

Figure 20:
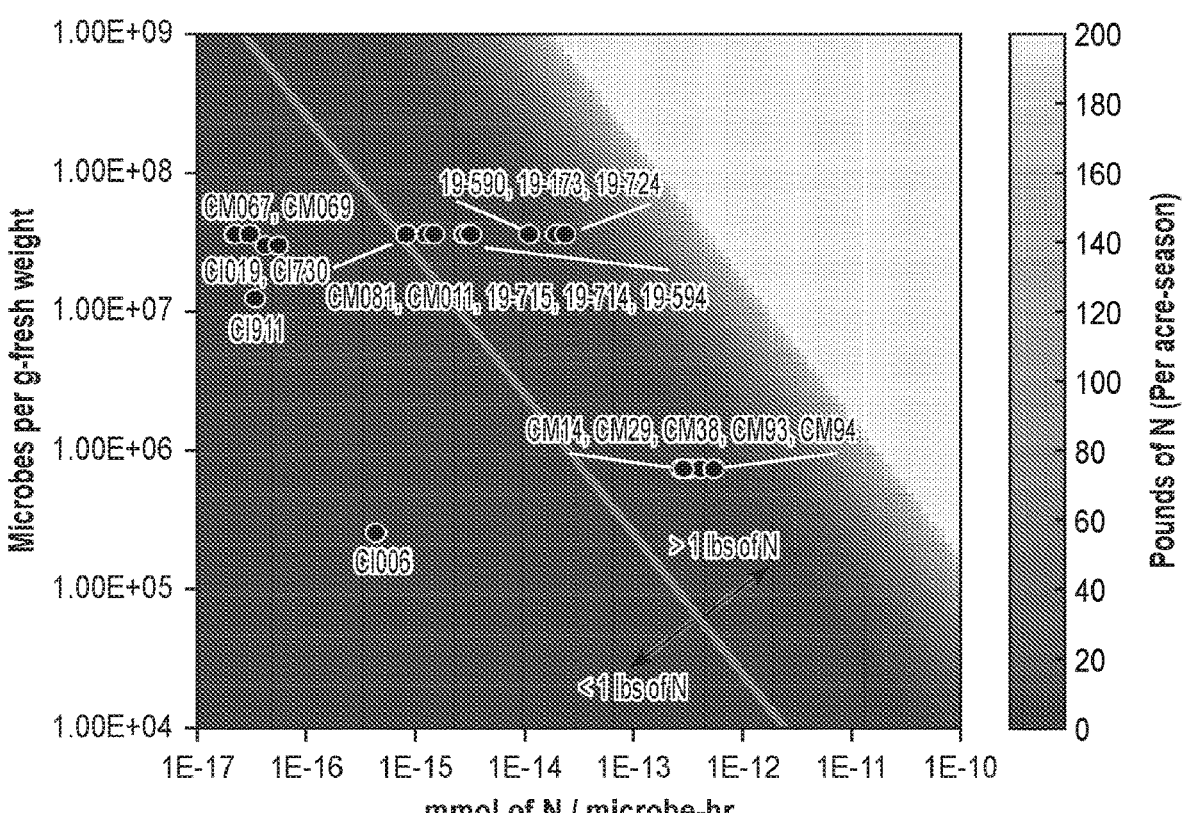
FIG. 20 depicts a heatmap of the pounds of nitrogen delivered per acre-season by microbes of the present disclosure recorded as a function of microbes per g-fresh weight by mmol of nitrogen/microbe-hr. Below the thin line that transects the larger image are the microbes that deliver less than one pound of nitrogen per acre-season, and above the line are the microbes that deliver greater than one pound of nitrogen per acre-season. The table below the heatmap gives the precise value of mmol N produced per microbe per hour (mmol N/Microbe hr) along with the precise CFU per gram of fresh weight (CFU/g fw) for each microbe shown in the heatmap. The microbes utilized in the heatmap were assayed for N production in corn. For the WT strains CI006 and CI019, corn root colonization data was taken from a single field site. For the remaining strains, colonization was assumed to be the same as the WT field level. N-fixation activity was determined using an in vitro ARA assay at 5 mM glutamine.
Figure 21:
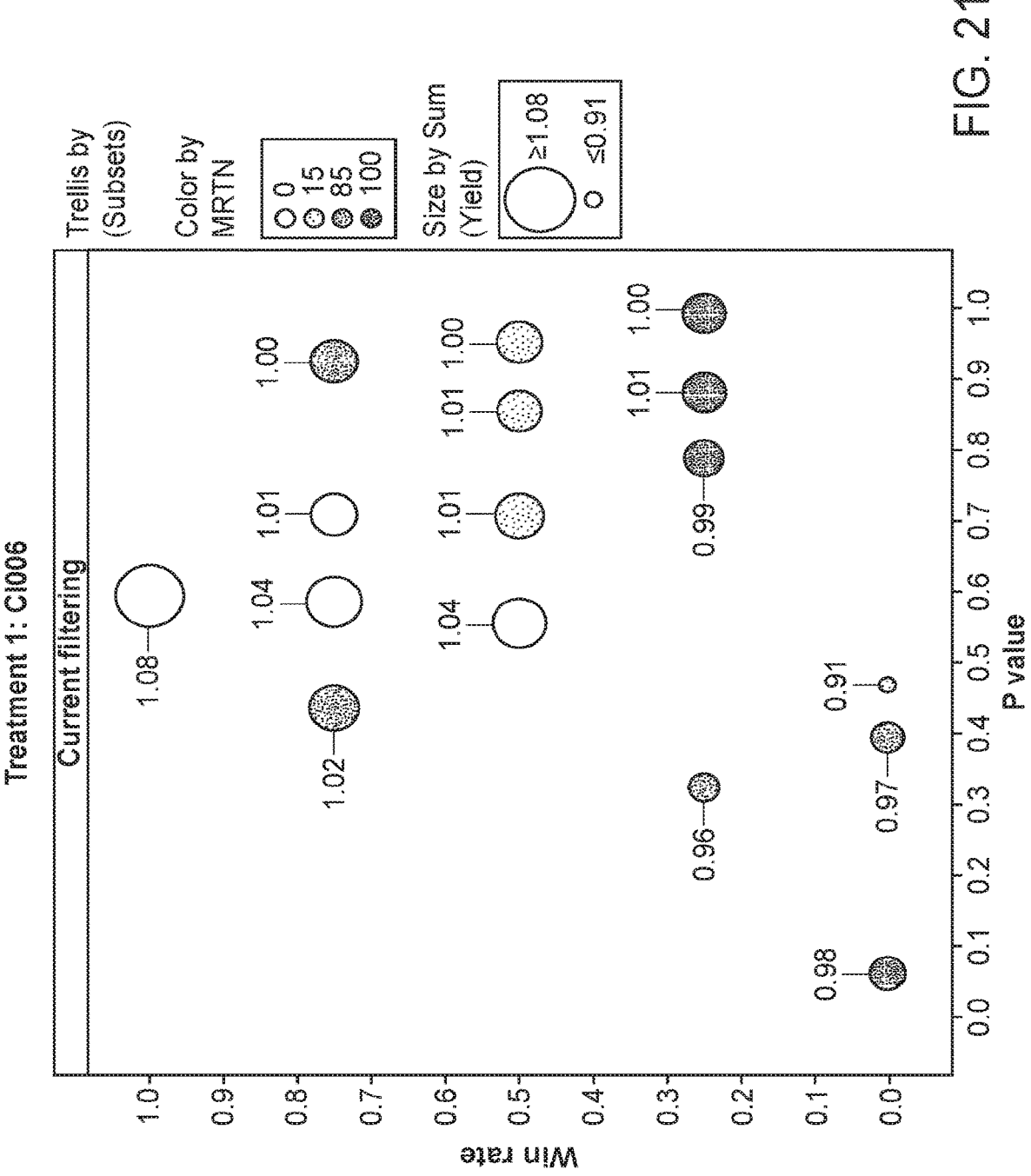
FIG. 21 depicts the plant yield of plants having been exposed to strain CI006. The area of the circles corresponds to the relative yield, while the shading corresponds to the particular MRTN treatment. The x-axis is the p value and the y-axis is the win rate.
Figure 22:
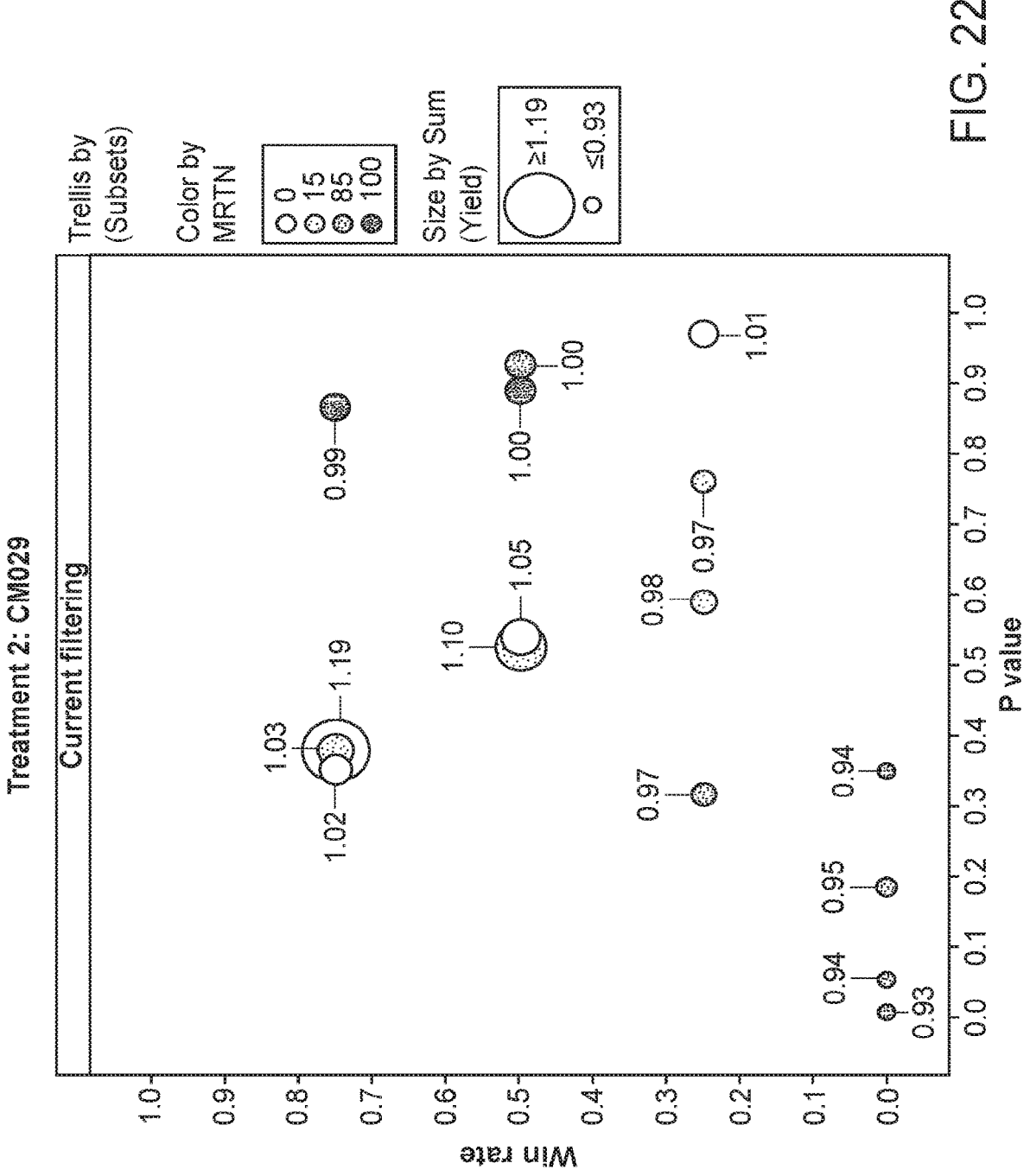
FIG. 22 depicts the plant yield of plants having been exposed to strain CM029. The area of the circles corresponds to the relative yield, while the shading corresponds to the particular MRTN treatment. The x-axis is the p value and the y-axis is the win rate.
Figure 23:
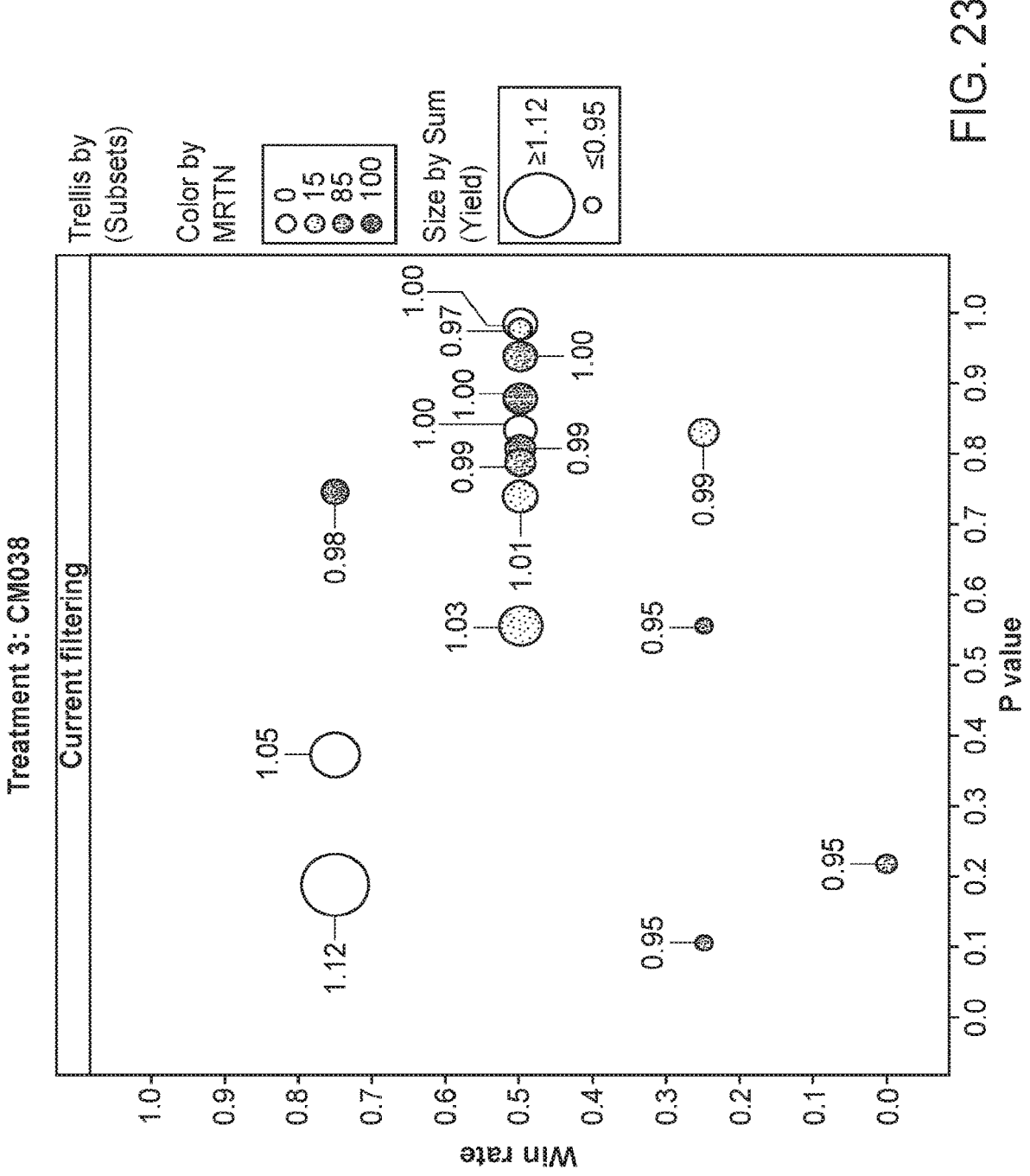
FIG. 23 depicts the plant yield of plants having been exposed to strain CM038. The area of the circles corresponds to the relative yield, while the shading corresponds to the particular MRTN treatment. The x-axis is the p value and the y-axis is the win rate.
Figure 24:
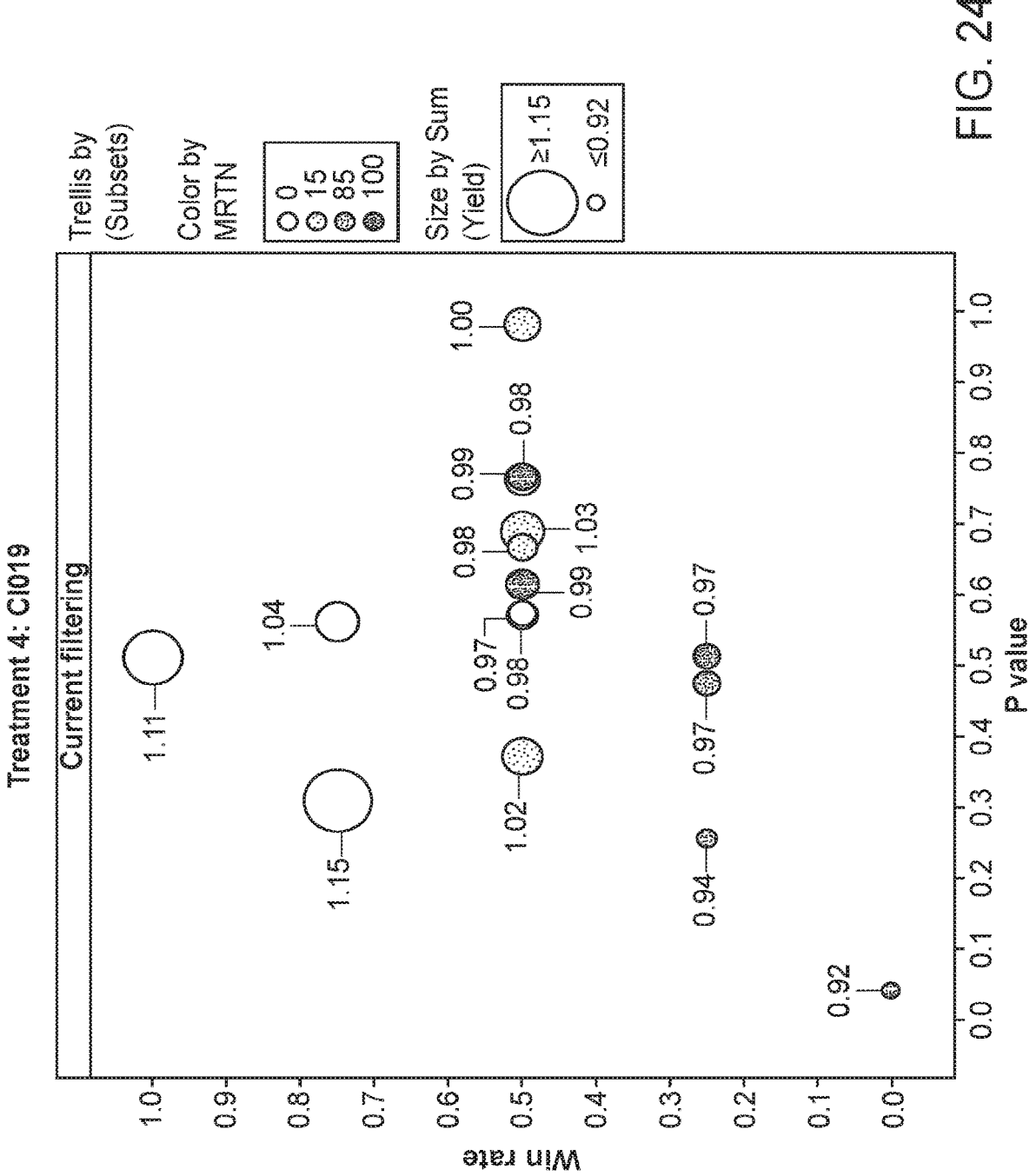
FIG. 24 depicts the plant yield of plants having been exposed to strain CI019. The area of the circles corresponds to the relative yield, while the shading corresponds to the particular MRTN treatment. The x-axis is the p value and the y-axis is the win rate.
Figure 25:
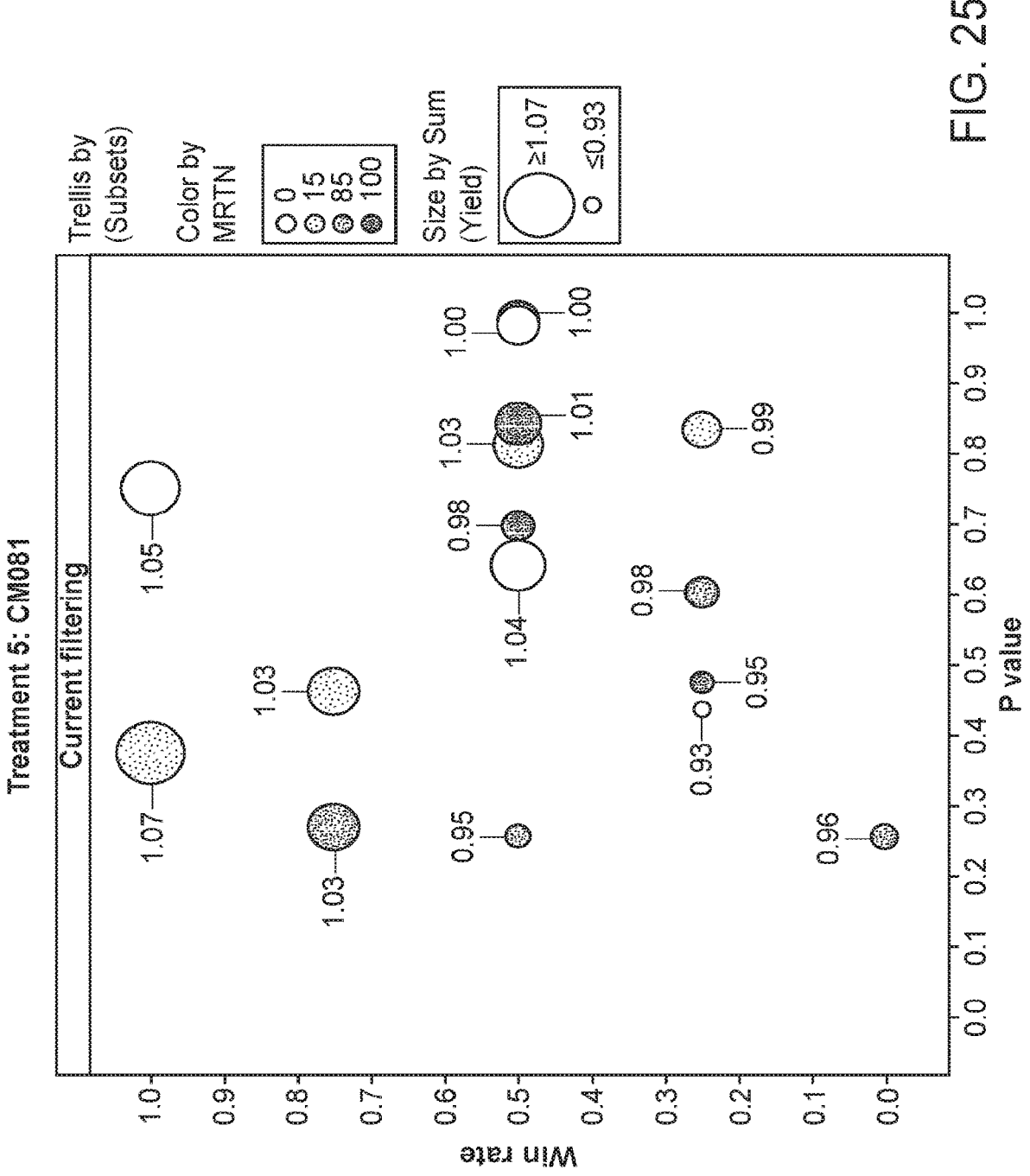
FIG. 25 depicts the plant yield of plants having been exposed to strain CM081. The area of the circles corresponds to the relative yield, while the shading corresponds to the particular MRTN treatment. The x-axis is the p value and the y-axis is the win rate.
Figure 26:
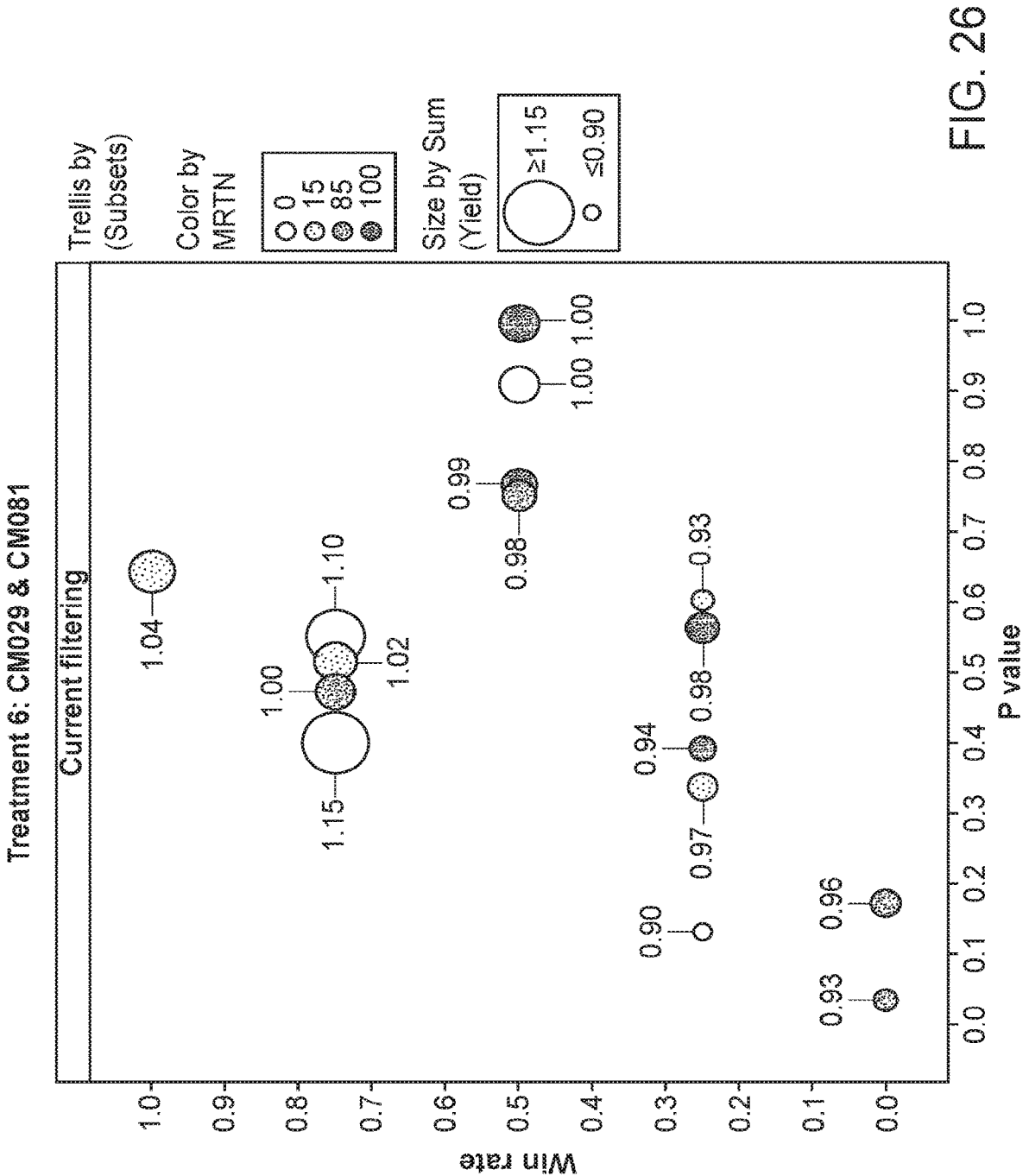
FIG. 26 depicts the plant yield of plants having been exposed to strains CM029 and CM081. The area of the circles corresponds to the relative yield, while the shading corresponds to the particular MRTN treatment. The x-axis is the p value and the y-axis is the win rate.
Figure 27:
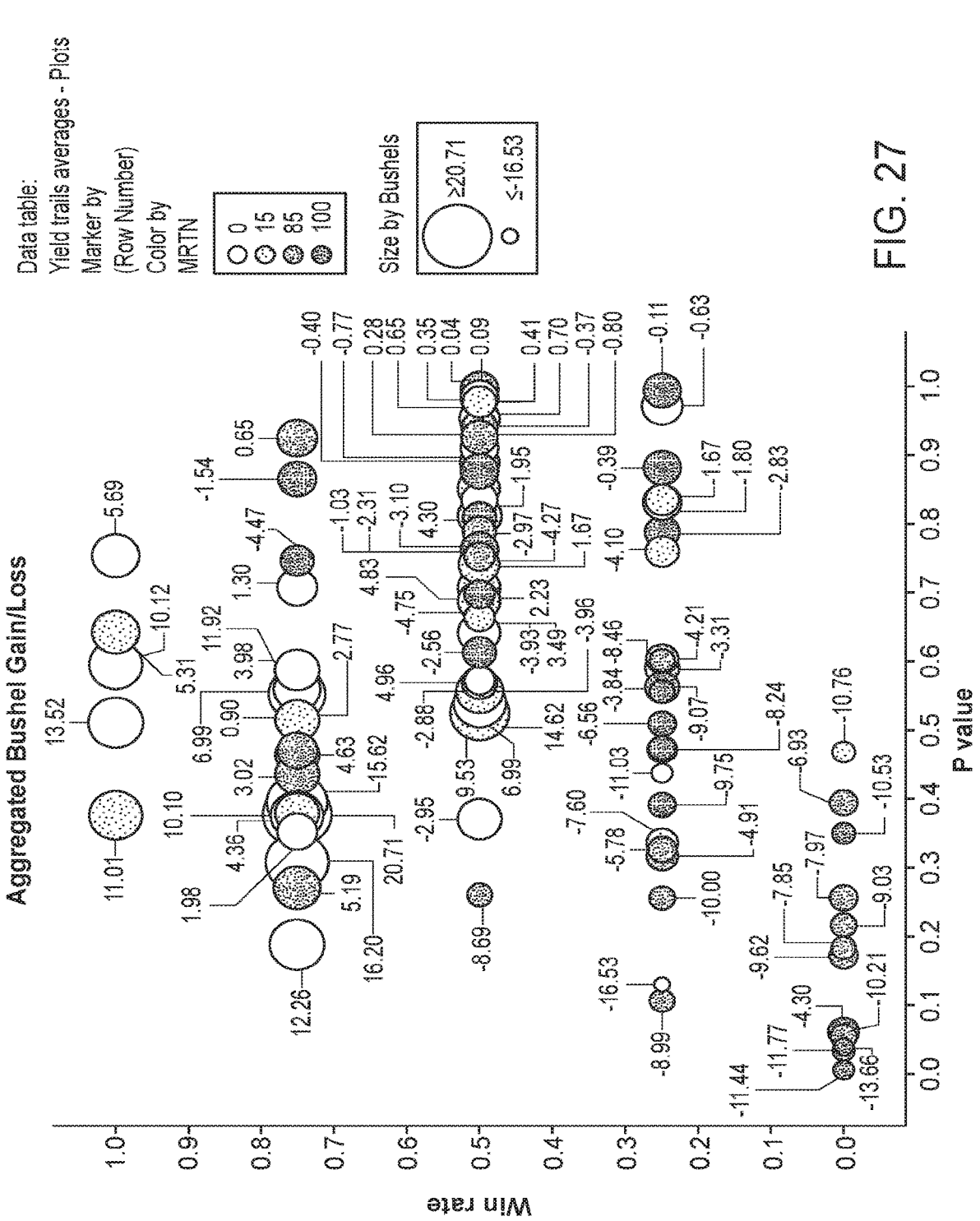
FIG. 27 depicts the plant yield of plants as the aggregated bushel gain/loss. The area of the circles corresponds to the relative yield, while the shading corresponds to the particular MRTN treatment. The x-axis is the p value and the y-axis is the win rate.
Figure 40:
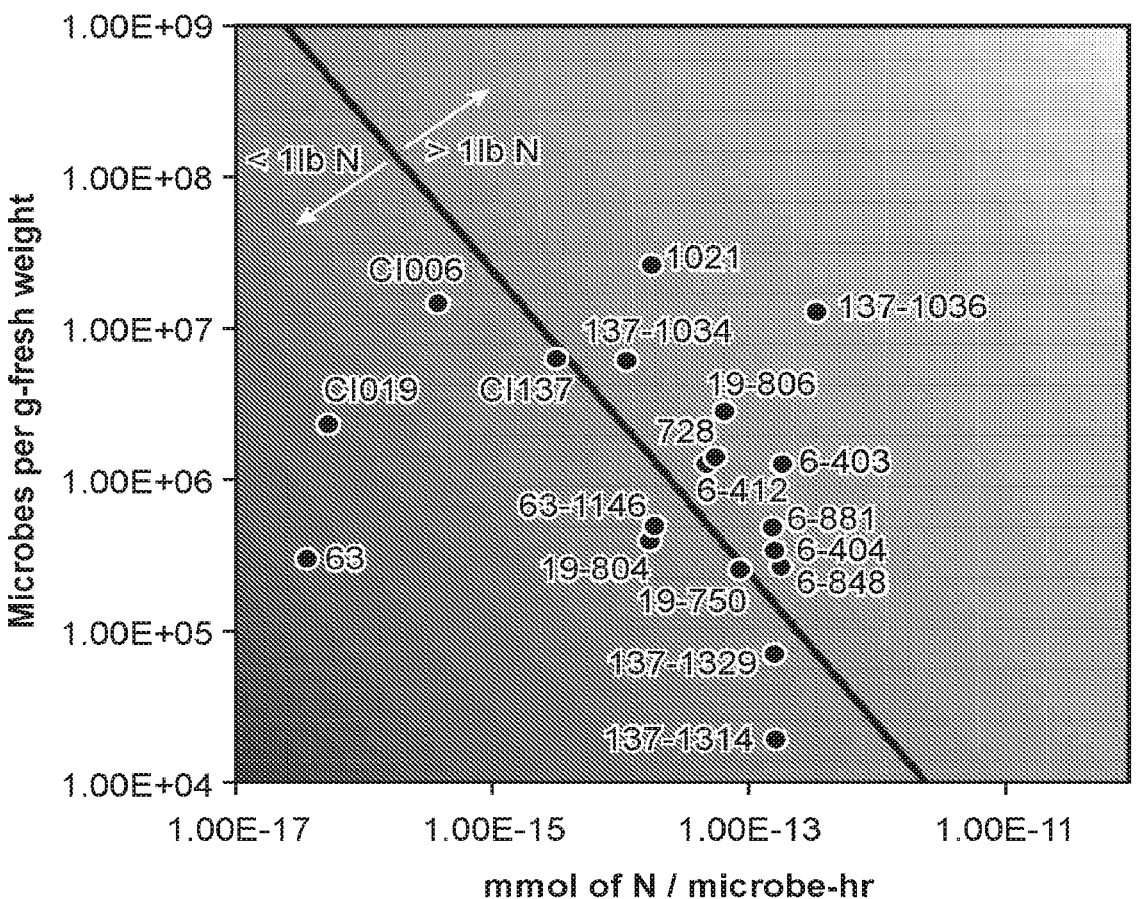
FIG. 40 depicts a heatmap of the pounds of nitrogen delivered per acre-season by microbes of the present disclosure recorded as a function of microbes per g-fresh weight by mmol of nitrogen/microbe-hr. Below the thin line that transects the larger image are the microbes that deliver less than one pound of nitrogen per acre-season, and above the line are the microbes that deliver greater than one pound of nitrogen per acre-season. The Table C in Example 12 gives the precise value of mmol N produced per microbe per hour (mmol N/Microbe hr) along with the precise CFU per gram of fresh weight (CFU/g fw) for each microbe shown in the heatmap. The data in FIG. 40 is derived from microbial strains assayed for N production in corn in field conditions. Each point represents lb N/acre produced by a microbe using corn root colonization data from a single field site. N-fixation activity was determined using in vitro ARA assay at 5 mM N in the form of glutamine or ammonium phosphate.
Figure 41:
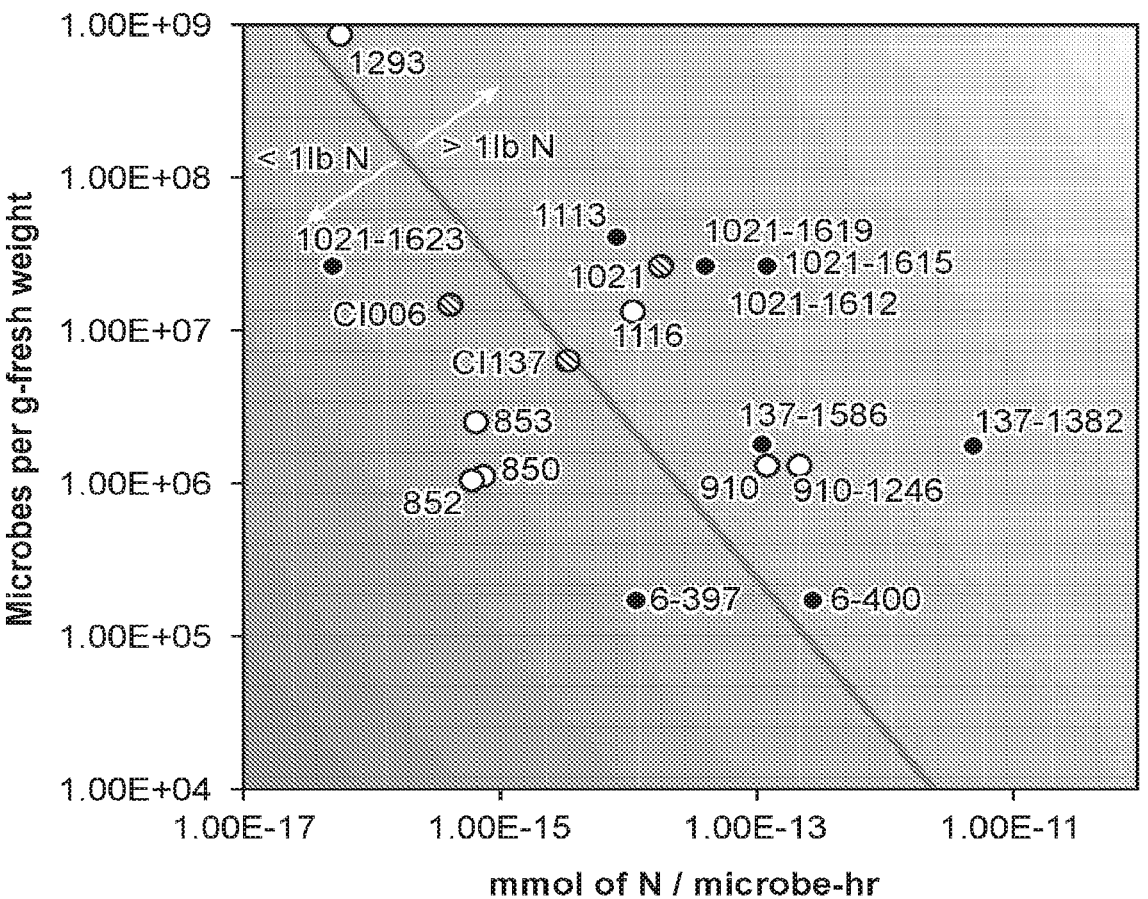
FIG. 41 depicts a heatmap of the pounds of nitrogen delivered per acre-season by microbes of the present disclosure recorded as a function of microbes per g-fresh weight by mmol of nitrogen/microbe-hr. Below the thin line that transects the larger image are the microbes that deliver less than one pound of nitrogen per acre-season, and above the line are the microbes that deliver greater than one pound of nitrogen per acre-season. The Table D in Example 12 gives the precise value of mmol N produced per microbe per hour (mmol N/Microbe hr) along with the precise CFU per gram of fresh weight (CFU/g fw) for each microbe shown in the heatmap. The data in FIG. 41 is derived from microbial strains assayed for N production in corn in laboratory and greenhouse conditions. Each point represents lb N/acre produced by a single strain. White points represent strains in which corn root colonization data was gathered in greenhouse conditions. Black points represent mutant strains for which corn root colonization levels are derived from average field corn root colonization levels of the wild-type parent strain. Hatched points represent the wild type parent strains at their average field corn root colonization levels. In all cases, N-fixation activity was determined by in vitro ARA assay at 5 mM N in the form of glutamine or ammonium phosphate.

To that end, the inventors have surprisingly discovered a functional genus of microbes that are able to contribute, inter alia, to: increasing yields in non-leguminous crops; and/or lessening a farmer's dependence upon exogenous nitrogen application; and/or the ability to produce at least one pound of nitrogen per acre per season, even in non-nitrogen-limiting environments, said genus being defined by the product of colonization ability×mmol of N produced per microbe per hour (i.e. the line partitioning FIGS. 20, 40, and 41).

With respect to FIGS. 20, 40, and 41, certain data utilizing microbes of the disclosure was aggregated, in order to depict a heatmap of the pounds of nitrogen delivered per acre-season by microbes of the disclosure, which are recorded as a function of microbes per g-fresh weight by mmol of nitrogen/microbe-hr. Below the thin line that transects the larger images are the microbes that deliver less than one pound of nitrogen per acre-season, and above the line are the microbes that deliver greater than one pound of nitrogen per acre-season.

Field Data & Wild Type Colonization Heatmap: The microbes utilized in the FIG. 20 heatmap were assayed for N production in corn. For the WT strains CI006 and CI019, corn root colonization data was taken from a single field site. For the remaining strains, colonization was assumed to be the same as the WT field level. N-fixation activity was determined using an in vitro ARA assay at 5 mM glutamine. The table below the heatmap in FIG. 20 gives the precise value of mmol N produced per microbe per hour (mmol N/Microbe hr) along with the precise CFU per gram of fresh weight (CFU/g fw) for each microbe shown in the heatmap.

Field Data Heatmap: The data utilized in the FIG. 40 heatmap is derived from microbial strains assayed for N production in corn in field conditions. Each point represents lb N/acre produced by a microbe using corn root colonization data from a single field site. N-fixation activity was determined using in vitro ARA assay at 5 mM N in the form of glutamine or ammonium phosphate. The below Table C gives the precise value of mmol N produced per microbe per hour (mmol N/Microbe hr) along with the precise CFU per gram of fresh weight (CFU/g fw) for each microbe shown in the heatmap of FIG. 40.

Greenhouse & Laboratory Data Heatmap: The data utilized in the FIG. 41 heatmap is derived from microbial strains assayed for N production in corn in laboratory and greenhouse conditions. Each point represents lb N/acre produced by a single strain. White points represent strains in which corn root colonization data was gathered in greenhouse conditions. Black points represent mutant strains for which corn root colonization levels are derived from average field corn root colonization levels of the wild-type parent strain. Hatched points represent the wild type parent strains at their average field corn root colonization levels. In all cases, N-fixation activity was determined by in vitro ARA assay at 5 mM N in the form of glutamine or ammonium phosphate. The below Table D gives the precise value of mmol N produced per microbe per hour (mmol N/Microbe hr) along with the precise CFU per gram of fresh weight (CFU/g fw) for each microbe shown in the heatmap of FIG. 41.

TABLE C

| | | | | |
|---|---|---|---|---|
| | | FIG. 40 - Field Data Heatmap | | |
| Strain Name | Activity (mmol N/ Microbe hr) | Peak Colonization (CFU/g fw) | N Produced/ acre season | Taxonomic Designation |
| CI006 | 3.88E−16 | 1.50E+07 | 0.24 | *Kosakonia sacchari* |
| 6-404 | 1.61E−13 | 3.50E+05 | 2.28 | *Kosakonia sacchari* |
| 6-848 | 1.80E−13 | 2.70E+05 | 1.97 | *Kosakonia sacchari* |

TABLE C-continued

| | | | | |
|---|---|---|---|---|
| | | FIG. 40 - Field Data Heatmap | | |
| Strain Name | Activity (mmol N/ Microbe hr) | Peak Colonization (CFU/g fw) | N Produced/ acre season | Taxonomic Designation |
| 6-881 | 1.58E−13 | 5.00E+05 | 3.20 | *Kosakonia sacchari* |
| 6-412 | 4.80E−14 | 1.30E+06 | 2.53 | *Kosakonia sacchari* |
| 6-403 | 1.90E−13 | 1.30E+06 | 10.00 | *Kosakonia sacchari* |
| CI019 | 5.33E−17 | 2.40E+06 | 0.01 | *Rahnella aquatilis* |
| 19-806 | 6.65E−14 | 2.90E+06 | 7.80 | *Rahnella aquatilis* |
| 19-750 | 8.90E−14 | 2.60E+05 | 0.94 | *Rahnella aquatilis* |
| 19-804 | 1.72E−14 | 4.10E+05 | 0.29 | *Rahnella aquatilis* |
| CI137 | 3.24E−15 | 6.50E+06 | 0.85 | *Klebsiella variicola* |
| 137-1034 | 1.16E−14 | 6.30E+06 | 2.96 | *Klebsiella variicola* |
| 137-1036 | 3.47E−13 | 1.30E+07 | 182.56 | *Klebsiella variicola* |
| 137-1314 | 1.70E−13 | 1.99E+04 | 0.14 | *Klebsiella variicola* |
| 137-1329 | 1.65E−13 | 7.25E+04 | 0.48 | *Klebsiella variicola* |
| 63 | 3.60E−17 | 3.11E+05 | 0.00 | *Rahnella aquatilis* |
| 63-1146 | 1.90E−14 | 5.10E+05 | 0.39 | *Rahnella aquaiilis* |
| 1021 | 1.77E−14 | 2.69E+07 | 19.25 | *Kosakonia pseudosacchari* |
| 728 | 5.56E−14 | 1445240.09 | 3.25 | *Klebsiella variicola* |

TABLE D

| | | | | |
|---|---|---|---|---|
| | | FIG. 41 - Greenhouse & Laboratory Data Heatmap | | |
| Strain Name | Activity (mmol N/ Microbe hr) | Peak Colonization (CFU/g fw) | N Produced/ acre season | Taxonomic Designation |
| CI006 | 3.88E−16 | 1.50E+07 | 0.24 | *Kosakonia sacchari* |
| 6-400 | 2.72E−13 | 1.79E+05 | 1.97 | *Kosakonia sacchari* |
| 6-397 | 1.14E−14 | 1.79E+05 | 0.08 | *Kosakonia sacchari* |
| CI137 | 3.24E−15 | 6.50E+06 | 0.85 | *Klebsiella variicola* |
| 137-1586 | 1.10E−13 | 1.82E+06 | 8.10 | *Klebsiella variicola* |
| 137-1382 | 4.81E−12 | 1.82E+06 | 354.60 | *Klebsiella variicola* |
| 1021 | 1.77E−14 | 2.69E+07 | 19.25 | *Kosakonia pseudosacchari* |
| 1021-1615 | 1.20E−13 | 2.69E+07 | 130.75 | *Kosakonia pseudosacchari* |
| 1021-1619 | 3.93E−14 | 2.69E+07 | 42.86 | *Kosakonia pseudosacchari* |
| 1021-1612 | 1.20E−13 | 2.69E+07 | 130.75 | *Kosakonia pseudosacchari* |
| 1021-1623 | 4.73E−17 | 2.69E+07 | 0.05 | *Kosakonia pseudosacchari* |
| 1293 | 5.44E−17 | 8.70E+08 | 1.92 | *Azospirillum lipoferum* |
| 1116 | 1.05E−14 | 1.371+07 | 5.79 | *Enterobacter sp.* |
| 1113 | 8.05E−15 | 4.13E+07 | 13.45 | *Enterobacter sp.* |
| 910 | 1.19E−13 | 1.34E+06 | 6.46 | *Kluyvera intermedia* |

TABLE D-continued

| | FIG. 41 - Greenhouse & Laboratory Data Heatmap | | | |
|---|---|---|---|---|
| Strain Name | Activity (mmol N/ Microbe hr) | Peak Colonization (CFU/g fw) | N Produced/ acre season | Taxonomic Designation |
| 910-1246 | 2.16E−13 | 1.34E+06 | 11.69 | *Kluyvera intermedia* |
| 850 | 7.2301E−16 | 1.17E+06 | 0.03 | *Achromobacter spiritinus* |
| 852 | 5.96E−16 | 1.07E+06 | 0.03 | *Achromobacter marplatensis* |
| 853 | 6.42E−16 | 2.55E+06 | 0.07 | *Microbacterium murale* |

Conclusions: The data in FIGS. 20, 40, 41, and Tables C and D, illustrates more than a dozen representative members of the described genus (i.e. microbes to the right of the line in the figures). Further, these numerous representative members come from a diverse array of taxonomic genera, which can be found in the above Tables C and D. Further still, the inventors have discovered numerous genetic attributes that depict a structure/function relationship that is found in many of the microbes. These genetic relationships can be found in the numerous tables of the disclosure setting forth the genetic modifications introduced by the inventors, which include introducing at least one genetic variation into at least one gene, or non-coding polynucleotide, of the nitrogen fixation or assimilation genetic regulatory network.

Consequently, the newly discovered genus is supported by: (1) a robust dataset, (2) over a dozen representative members, (3) members from diverse taxonomic genera, and (4) classes of genetic modifications that define a structure/function relationship, in the underlying genetic architecture of the genus members.

Example 13: Methods and Assays for Detection of Non-Intergeneric Engineered Microbes The present disclosure teaches primers, probes, and assays that are useful for detecting the microbes utilized in the various aforementioned Examples. The assays are able to detect the non-natural nucleotide "junction" sequences in the derived/mutant non-intergeneric microbes. These non-naturally occurring nucleotide junctions can be used as a type of diagnostic that is indicative of the presence of a particular genetic alteration in a microbe.

The present techniques are able to detect these non-naturally occurring nucleotide junctions via the utilization of specialized quantitative PCR methods, including uniquely designed primers and probes. The probes can bind to the non-naturally occurring nucleotide junction sequences. That is, sequence-specific DNA probes consisting of oligonucleotides that are labelled with a fluorescent reporter, which permits detection only after hybridization of the probe with its complementary sequence can be used. The quantitative methods can ensure that only the non-naturally occurring nucleotide junction will be amplified via the taught primers, and consequently can be detected via either a non-specific dye, or via the utilization of a specific hybridization probe. Another aspect of the method is to choose primers such that the primers flank either side of a junction sequence, such that if an amplification reaction occurs, then said junction sequence is present.

Consequently, genomic DNA can be extracted from samples and used to quantify the presence of microbes of the disclosure by using qPCR. The primers utilized in the qPCR reaction can be primers designed by Primer Blast (https://www.ncbi.nlm.nih.gov/tools/primer-blast/) to amplify unique regions of the wild-type genome or unique regions of the engineered non-intergeneric mutant strains. The qPCR reaction can be carried out using the SYBR GreenER qPCR SuperMix Universal (Thermo Fisher P/N 11762100) kit, using only forward and reverse amplification primers; alternatively, the Kapa Probe Force kit (Kapa Biosystems P/N KK4301) can be used with amplification primers and a TaqMan probe containing a FAM dye label at the 5' end, an internal ZEN quencher, and a minor groove binder and fluorescent quencher at the 3' end (Integrated DNA Technologies).

Certain primer, probe, and non-native junction sequences—which can be used in the qPCR methods—are listed in the below Table E. Specifically, the non-native junction sequences can be found in SEQ ID NOs: 372-405.

TABLE E

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| 1021 | ds1131 | up | 304 | TGGTGTCCGGGC GAACGTCGCCAG GTGGCACAAATT GTCAGAACTACG ACACGACTAACC GACCGCAGGAGT GTGCGATGACCC TGAATATGATGA TGGA | 338 | TTCTTGGTTCTCT GGAGCGCTTTAT CGGCATCCTGAC TGAAGAATTTGC AGGCTTCTTCCCA ACCTGGCTTGCA CCCGTGCAGGTA GTTGTGATGAAC AT | 372 | 5'- TGGTGTCCGGGC GAACGTCGCCAG GTGGCACAAATT GTCAGAACTACG ACACGACTAACC GACCGCAGGAGT GTGCGATGACCC TGAATATGATGA TGGA/ TTCTTGGTTCTCT GGAGCGCTTTAT CGGCATCCTGAC TGAAGAATTTGC AGGCTTCTTCCCA ACCTGGCTTGCA CCCGTGCAGGTA GTTGTGATGAAC AT-3' | disrupted nifL gene/ PinfC | N/A | N/A | N/A |
| 1021 | ds1131 | down | 305 | CGGAAAACGAGT TCAAACGGCGCG TCCCAATCGTATT AATGGCGAGATT CGCGCCACGGAA GTTCGCTTAACAG GTCTGGAAGGCG AGCAGCTTGGTA TT | 339 | GCGATAGAACTC ACTTCACGCCCC GAAGGGGGAAGC TGCCTGACCCTAC GATTCCCGCTATT TCATTCACTGACC GGAGGTTCAAAA TGACCCAGCGAA C | 373 | 5'- CGGAAAACGAGT TCAAACGGCGCG TCCCAATCGTATT AATGGCGAGATT CGCGCCACGGAA GTTCGCTTAACA GGTCTGGAAGGC GAGCAGCTTGGT ATT/ GCGATAGAACTC ACTTCACGCCCC GAAGGGGGAAGC TGCCTGACCCTA CGATTCCCGCTAT TTCATTCACTGAC CGGAGGTTCAAA ATGACCCAGCGA AC-3' | Pinfc/ disrupted nifL gene | N/A | N/A | N/A |
| 1021 | ds1133 | N/A | 306 | CGCCAGAGAGTT GAAATCGAACAT TTCCGTAATACCG CCATTACCCAGG AGCCGTTCTGGTT | 340 | TCCCTGTGCGCCG CGTCGCCGATGG TGGCCAGCCAAC TGGCGCGCTACC CGATCCTGCTCG | 374 | 5'- CGCCAGAGAGTT GAAATCGAACAT TTCCGTAATACC GCCATTACCCAG | 5' UTR and ATG/ truncated glnE gene | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | GCACAGCGGAAA ACGTTAACGAAA GGATATTTCGCAT G | | ATGAACTGCTCG ACCCGAACACGC TCTATCAACCGA CGG | | GAGCCGTTCTGG TTGCACAGCGGA AAACGTTAACGA AAGGATATTTCG CATG/ TCCCTGTGCGCC GCGTCGCCGATG GTGGCCAGCCAA CTGGCGCGCTAC CCGATCCTGCTC GATGAACTGCTC GACCCGAACACG CTCTATCAACCG ACGG-3' | | | | |
| 1021 | ds1145 | up | 307 | CGGGCGAACGTC GCCAGGTGGCAC AAATTGTCAGAA CTACGACACGAC TAACCGACCGCA GGAGTGTGCGAT GACCCTGAATAT GATGATGGATGC CAGC | 341 | CGTTCTGTAATAA TAACCGGACAAT TCGGACTGATTA AAAAAGCGCCCT CGCGGCGCTTTT TTATATTCTCGAC TCCATTAAAATA AAAAATCCAATC | 375 | 5'- CGGGCGAACGTC GCCAGGTGGCAC AAATTGTCAGAA CTACGACACGAC TAACCGACCGCA GGAGTGTGCGAT GACCCTGAATAT GATGATGGATGC CAGC/ CGTTCTGTAATA ATAACCGGACAA TTCGGACTGATT AAAAAAGCGCCC TCGCGGCGCTTTT TTTATATTCTCGA CTCCATTAAAAT AAAAAATCCAAT C-3' | disrupted nifL gene/ Prml | N/A | N/A | N/A |
| 1021 | ds1145 | down | 308 | TCAACCTAAAAA AGTTTGTGTAATA CTTGTAACGCTAC ATGGAGATTAAC TCAATCTAGAGG GTATTAATAATG AATCGTACTAAA CTGGTACTGGGC GC | 342 | AACTCACTTCAC GCCCCGAAGGGG GAAGCTGCCTGA CCCTACGATTCCC GCTATTTCATTCA CTGACCGGAGGT TCAAAATGACCC AGCGAACCGAGT CG | 376 | 5'- TCAACCTAAAAA AGTTTGTGTAAT ACTTGTAACGCT ACATGGAGATTA ACTCAATCTAGA GGGTATTAATAA TGAATCGTACTA AACTGGTACTGG GCGC/ AACTCACTTCAC GCCCCGAAGGGG GAAGCTGCCTGA CCCTACGATTCCC GCTATTTCATTCA CTGACCGGAGGT TCAAAATGACCC AGCGAACCGAGT CG | Prml/ disrupted nifL gene | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
|  |  |  |  |  |  |  |  | GAAGCTGCCTGA CCCTACGATTCCC GCTATTTCATTCA CTGACCGGAGGT TCAAAATGACCC AGCGAACCGAGT CG-3' |  |  |  |  |
| 1021 | ds1148 | up | 309 | CGGGCGAACGTC GCCAGGTGGCAC AAATTGTCAGAA CTACGACCGCA TAACCGACCGCA GGAGTGTGCGAT GACCCTGAATAT GATGATGGATGC CAGC | 343 | CGCGTCAGGTTG AACGTAAAAAAG TCGGTCTGCGCA AAGCACGTCGTC GTCCGCAGTTCTC CAAACGTTAATT GGTTTCTGCTTCG GCAGAACGATTG GC | 377 | 5'- CGGGCGAACGTC GCCAGGTGGCAC AAATTGTCAGAA CTACGACCGAC TAACCGACCGCA GGAGTGTGCGAT GACCCTGAATAT GATGATGGATGC CAGC/ CGCGTCAGGTTG AACGTAAAAAAG TCGGTCTGCGCA AAGCACGTCGTC GTCCGCAGTTCTC CAAACGTTAATT GGTTTCTGCTTCG GCAGAACGATTG GC-3' | disrupted nifL gene/ Prm7 | N/A | N/A | N/A |
| 1021 | ds1148 | down | 310 | AATTTTCTGCCCA AATGGCTGGGAT TGTTCATTTTTTG TTTGCCTTACAAC GAGAGTGACAGT ACGCGCGGGTAG TTAACTCAACATC TGACCGGTCGAT | 344 | AACTCACTTCAC GCCCCGAAGGGG GAAGCTGCCTGA CCCTACGATTCCC GCTATTTCATTCA CTGACCGGAGGT TCAAAATGACCC AGCGAACCGAGT CG | 378 | 5'- AATTTTCTGCCCA AATGGCTGGGAT TGTTCATTTTTTG TTTGCCTTACAAC GAGAGTGACAGT ACGCGCGGGTAG TTAACTCAACAT CTGACCGGTCGA T/ AACTCACTTCAC GCCCCGAAGGGG GAAGCTGCCTGA CCCTACGATTCCC GCTATTTCATTCA CTGACCGGAGGT TCAAAATGACCC AGCGAACCGAGT CG-3' | Prm4/ disrupted nifL gene | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| CI006 | ds126 | N/A | 311 | GTAACCAATAAA GGCCACCACGCC AGACCACACGAT AGTGATGGCAAC ACTTTCCAGCTGC ACCAGCACCTGA TGGCCCATGGTC ACACCTTCAGCCG AAA | 345 | CCGATCCCCATC ACTGTGTGTCTTG TATTACAGTGCC GCTTCGTCGGCTT CGCCGGTACGAA TACGAATGACGC GTTGCAGCTCAG CAACGAAAATTT TG | 379 | 5'- GTAACCAATAAA GGCCACCACGCC AGACCACACGAT AGTGATGGCAAC ACTTTCCAGCTGC ACCAGCACCTGA TGGCCCATGGTC ACACCTTCAGCG AAA/ CCGATCCCCATC ACTGTGTGTCTTG TATTACAGTGCC GCTTCGTCGGCTT CGCCGGTACGAA TACGAATGACGC GTTGCAGCTCAG CAACGAAAATTT TG-3' | 5' UTR up to ATG- 4 bp of amt13 gene/ disrupted amt13 gene | N/A | N/A | N/A |
| CI019 | ds172 | down | 312 | TGGTATTGTCAGT CTGAATGAAGCT CTTGAAAAAGCT GAGGAAGCGGGC GTCGATTTAGTAG AAATCAGTCCGA ATGCCGAGCCGC CAGTTTGTCGAAT C | 346 | CCGTCTCTGAAG CTCTCGGTGAAC ATTGTTGCGAGG CAGGATGCGAGC TGGTTGTGTTTTG ACATTACCGATA ATGTGCCGCGTG AACGGGTGCGTT ATG | 380 | 5'- TGGTATTGTCAGT CTGAATGAAGCT CTTGAAAAAGCT GAGGAAGCGGGC GTCGATTTAGTA GAAATCAGTCCG AATGCCGAGCCG CCAGTTTGTCGA ATC/ CCGTCTCTGAAG CTCTCGGTGAAC ATTGTTGCGAGG CAGGATGCGAGC TGGTTGTGTTTTG ACATTACCGATA ATGTGCCGCGTG AACGGGTGCGTT ATG-3' | Prml.2/ disrupted nifL gene | SEQ ID NO: 406 CAAG AAGT TCGC CTCA CAGG | SEQ ID NO: 407 TGCC TCGC AACA ATGT TCAC | N/A |
| CI019 | ds172 | up | 313 | ACCGATCCGCAG GCGCGCATTTGTT ATGCCAATCCGG CATTCTGCCGCCA GACGGGTTTTGC ACTTGAGACACTT | 347 | TGAACATCACTG ATGCACAAGCTA CCTATGTCGAAG AATTAACTAAAA AACTGCAAGATG CAGGCATTCCG | 381 | 5'- ACCGATCCGCAG GCGCGCATTTGTT ATGCCAATCCGG CATTCTGCCGCC AGACGGGTTTTG AGACGGGTTTTG | disrupted nifL gene/ Prml.2 | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | | | TTAAAGCCGACT TGAGAAATGAGA AGAT | | CACTTGAGACAC TTTTGGGCGAGA ACCACCGTCTGC TGG/ TGAACATCACTG ATGCACAAGCTA CCTATGTCGAAG AATTAACTAAAA AACTGCAAGATG CAGGCATTCGCG TTAAAGCCGACT TGAGAAATGAGA AGAT-3' | | | | |
| CI019 | ds175 | down | 314 | CGGGAACCGGTG TTATAATGCCCGCG CCCTCATATTGTG GGGATTTCTTAAT GACCTATCCTGG GTCCTAAAGTTGT AGTTGACATTAG CGGAGCACTAAC | 348 | CCGTCTCTGAAG CTCTCGGTGAAC ATTGTTGCGAGG CAGGATGCCGAGC TGGTTGTGTTTTG ACATTACCGATA ATGTGCCCGCTG AACGGGTGCGTT ATG | 382 | 5'- CGGGAACCGGTG TTATAATGCCCG GCCCTCATATTGT GGGGATTTCTTA ATGACCTATCCT GGGTCCTAAAGT TGTAGTTGACATT AGCGGAGCACTA AC/ CCGTCTCTGAAG CTCTCGGTGAAC ATTGTTGCGAGG CAGGATGCCGAGC TGGTTGTGTTTTG ACATTACCGATA ATGTGCCCGCTG AACGGGTGCGTT ATG-3' | Prm3.1/ disrupted nifL gene | SEQ ID NO: 408 CGCC CTCA TATT GTGG GGAT | SEQ ID NO: 409 GGCA TAAC GCAC CCGT TCA | SEQ ID NO: 410 /56- FAM/ TAACCCG TC/ ZE NIT CTG AAG CTC TCG GT/ 3IABkFQ/ |
| CI019 | ds175 | up | 315 | ACCGATCCGCAG GCGCGCATTTGTT ATGCCAATCCGG CATTCTGCCGCCA GACGGGTTTTGC ACTTGAGACACTT TTGGGCGAGAAC CACCGTCTGCTGG | 349 | TACAGTAGCCGCC TCTCAAAATAG ATAAACGGCTCA TGTACGTGGGCC GTTTATTTTTTCT ACCCATAATCGG GAACGGGTGTTA TAATGCCCGCGCC CTC | 383 | 5'- ACCGATCCGCAG GCGCGCATTTGTT ATGCCAATCCGG CATTCTGCCGCC AGACGGGTTTTG CACTTGAGACAC TTTTGGGCGAGA ACCACCGTCTGC TGG/ TACAGTAGCCGCC TCTCAAAATAG ATAAACGGCTCA | disrupted nifL gene/ Prm3.1 | N/A | N/A | N/A |

TABLE E-continued

Microbial Detection

| base CI | Junction Name | up/down stream junction | 100 bp upstream of junction | SEQ ID NO | 100 bp downstream of junction | SEQ ID NO | Junction SEQ "/" indicating junction | SEQ ID NO | Junction des. | F primer SEQ | R primer SEQ | Probe SEQ |
|---------|---------------|-------------------------|------------------------------|-----------|-------------------------------|-----------|---------------------------------------|-----------|---------------|--------------|--------------|-----------|
| | | | | | | | TGTACGTGGGCC GTTTATTTTTCT ACCCATAATCGG GAACCGGTGTTA TAATGCCGCGCC CTC-3' | | | | | |
| CI006 | ds20 | down | TCAACCTAAAAA AGTTTGTGTAATA CTTGTAACGCTAC ATGGAGATTAAC TCAATCTAGAGG GTATTAATAATG AATCGTACTAAA CTGGTACTGGGC GC | 316 | AACTCACTTCAC ACCCCGAAGGGG GAAGTTGCCTGA CCCTACGATTCCC GCTATTTCATTCA CTGACCGGAGGT TCAAAATGACCC AGCGAACCGAGT CG | 350 | 5'- TCAACCTAAAAA AGTTTGTGTAAT ACTTGTAACGCT ACATGGAGATTA ACTCAATCTAGA ACTCAATCTAGA GGGTATTAATAA TGAATCGTACTA AACTGGTACTGG GCGC/ AACTCACTTCAC ACCCCGAAGGGG GAAGTTGCCTGA CCCTACGATTCCC GCTATTTCATTCA CTGACCGGAGGT TCAAAATGACCC AGCGAACCGAGT CG-3' | 384 | Prm1/ disrupted nifL gene | SEQ ID NO: 411 TAAA CTGG TACT GGGC GCAA CT | SEQ ID NO: 412 CAAA TCGA AGCG CCAG ACGG TAT | SEQ ID NO: 413 /56- FAM/ AAG TTGC CT/Z EN/G ACC CTAC GATT CCC/ 3IABkFQ/ |
| CI006 | ds20 | up | GGGCGACAAACG GCCTGGTGGCAC AAATTGTCAGAA CTACGACACGAC TAACTGACCGCA GGAGTGTGCGAT GACCCTGAAATAT GATGATGGATGC CGGC | 317 | CGTCCTGTAATA ATAACCGGACAA TTCGGACTGATTA AAAAGCGCCCT TGTGGCGCTTTTT TTATATTCCCGCC TCCATTTAAAATA AAAAATCCAATC | 351 | 5'- GGGCGACAAACG GCCTGGTGGCAC AAATTGTCAGAA CTACGACACGAC TAACTGACCGCA GGAGTGTGCGAT GACCCTGAAATAT GATGATGGATGC CGGC/ CGTCCTGTAATA ATAACCGGACAA TTCGGACTGATT AAAAAGCGCCCC TTGTGGCGCTTTT TTTATATTCCCGC CTCCATTTAAAAT AAAAAATCCAAT C-3' | 385 | disrupted nifL gene/ Prm1 | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| CI006 | ds24 | up | 318 | GGGCGACAAACG GCCTGGTGGCAC AAATTGTCAGAA CTACGACGAC TAACTGACCGCA GGAGTGTGCGAT GACCCTGAATAT GATGATGGATGC CGGC | 352 | GGACATCATCGC GACAAACAATAT TAATACCGGCAA CCACACCGGCAA TTTACGAGACTG CGCAGGCATCCT TTCTCCCGTCAAT TTCTGTCAAATAA AG | 386 | 5'- GGGCGACAAACG GCCTGGTGGCAC AAATTGTCAGAA CTACGACGAC TAACTGACCGCA GGAGTGTGCGAT GACCCTGAATAT GATGATGGATGC CGGC/ GGACATCATCGC GACAAACAATAT TAATACCGGCAA CCACACCGGCAA TTTACGAGACTG CGCAGGCATCCT TTCTCCCGTCAAT TTCTGTCAAATA AAG-3' | disrupted nifL gene/ Prm5 | SEQ ID NO: 414 GGTG CACT CTTT GCAT GGTT | SEQ ID NO: 415 GCGC AGTC TCGT AAAT TGCC | SEQ ID NO: 416 /56-FAM/ CA GGA GTG T/ZE N/G CGA TGA CCC TGA AT/3I ABkFQ |
| CI006 | ds24 | down | 319 | TAAGAATTATCTG GATGAATGTGCC ATTAAATGCGCA GCATAATGGTGC GTTGTGCGGGAA AACTGCTTTTTT TGAAAGGGTTGG TCAGTAGCGGAA AC | 353 | AACTCACTTCAC ACCCGAAGGGG GAAGTTGCCTGA CCCTACGATTCCC GCTATTTCATTCA CTGACCGGAGGT TCAAAATGACCC AGCGAACCGAGT CG | 387 | 5'- TAAGAATTATCT GGATGAATGTGC CATTAAATGCGC AGCATAATGGTG CGTTGTGCGGGA AAACTGCTTTTTT TTGAAAGGGTTG GTCAGTAGCGGA AAC/ AACTCACTTCAC ACCCGAAGGGG GAAGTTGCCTGA CCCTACGATTCCC GCTATTTCATTCA CTGACCGGAGGT TCAAAATGACCC AGCGAACCGAGT CG-3' | Prm5/ disrupted nifL gene | N/A | N/A | N/A |
| CI006 | ds30 | N/A | 320 | CGCCAGAGAGTC GAAATCGAACAT TTCCGTAATACCG CGATTACCCAGG AGCCGTTCTGGTT GCGCAGCGGAAA ACGTTAACGAAA | 354 | TTTAACGATCTGA TTGGCGATGATG AAACGGATTCGC CGGAAGATGCGC TTTCTGAGAGCTG GCGGGAATTGTG GCAGATGCGCTT | 388 | 5'- CGCCAGAGAGTC GAAATCGAACAT TTCCGTAATACC CGATTACCCAG GAGCCGTTCTGG GCGGGAATTGTG TTGCACAGCGGA | 5' UTR and ATG/ truncated glnE gene | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | GGATATTTCGCATG | | GCAGGAGGAGGATT | | AAACGTTAACGAAAGGATATTTCGCATG/TTTAACGATCTGATTGGCGATGATGAAACGGATTCGCCGGAAGATGCGCTTTCTGAGAGCTGGCGCGAATTGTGGCAGGATGCGTTGCAGGAGGAGGATT-3' | | | | |
| CI006 | ds31 | N/A | 321 | CGCCAGAGAGTCGAAATCGAACATTTCCGTAATACCGCGATTACCCAGGAGCCGTTCTGGTTGCACAGCGGAAAACGTTAACGAAAGGATATTTCGCATG | 355 | GCACTGAAACACCTCATTCCCTGTGTGCCGCGTCGCCGATGGTTGCCAGTCAGCTGGCGCGCTACCCGATCCTGCTTGATGAATTGCTCGACCCGAATA | 389 | 5'-CGCCAGAGAGTCGAAATCGAACATTTCCGTAATACCGCGATTACCCAGGAGCCGTTCTGGTTGCACAGCGGAAAACGTTAACGAAAGGATATTTCGCATG/GCACTGAAACACCTCATTCCCTGTGTGCCGCGTCGCCGATGGTTGCCAGTCAGCTGGCGCGCTACCCGATCCTGCTTGATGAATTGCTCGACCCGAATA-3' | 5' UTR and ATG/ truncated glnE gene | N/A | N/A | N/A |
| CI019 | ds34 | N/A | 322 | GATGATGGATGCTTTCTGGTTAAACGGGCAACCTCGTTAACTGACTGACTAGCCTGGGCAAACTGCCCCGGGCTTTTTTTTGCAAGGAATCTGATTTCATG | 356 | GCGCTCAAACAGTTAATCCGTCTGTGTGCCGCCTCGCCGATGGTCGCGACACAACTTGCACGTCATCCTTTATTGCTCGATGAACTGCTCGACCCGCGCA | 390 | 5'-GATGATGGATGCTTTCTGGTTAAACGGGCAACCTCGTTAACTGACTGACTAGCCTGGGCAAACTGCCCGGGCTTTTTTTGCAAGGAATCTGATTTCATG/GCGCTCAAACAGTTAATCCGTCTGTGTGCCGCCTCGCCGATGGTCGCGA | 5' UTR and ATG/ truncated glnE gene | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | | | | | CACAACTTGCAC GTCATCCTTATT GCTCGATGAACT GCTCGACCCGCG CA-3' | | | | |
| CI019 | ds70 | up | 323 | ACCGATCCGCAG GCGCGCCATTTGTT ATGCCAATCCGG CATTCTGCCGCCA GACGGGTTTTGC ACTTGAGACACTT TTGGGCGAGAAC CACCGTCTGCTGG | 357 | AGTCTGAACTCA TCCTGCGGCAGT CGGTGAGACGTA TTTTTGACCAAAG AGTGATCTACAT CACGGAATTTTGT GGTTGTTGCTGCT TAAAAGGGCAAA T | 391 | 5'- ACCGATCCGCAG GCGCGCATTTGTT ATGCCAATCCGG CATTCTGCCGCC AGACGGGTTTTG CACTTGAGACAC TTTTGGGCGAGA ACCACCGTCTGC TGG/ AGTCTGAACTCA TCCTGCGGCAGT CGGTGAGACGTA TTTTTGACCAAA GAGTGATCTACA TCACGGAATTTT GTGGTTGTTGCTG CTTAAAAGGGCA AAT-3' | disrupted nifL gene/ Prm4 | N/A | N/A | N/A |
| CI019 | ds70 | down | 324 | CATCGGACACCA CCAGCTTACAAA TTGCCTGATTGCG GCCCCGATGGCC GGTATCACTGAC CGACCATTTCGTG CCTTATGTCATGC GATGGGGGCTGG G | 358 | CCGTCTCTGAAG CTCTCGGTGAAC ATTGTTGCGAGG CAGGATGCGAGC TGGTTGTGTTTTG ACATTACCGATA ATGTGCCGCCTG AACGGGTGCGTT ATG | 392 | 5'- CATCGGACACCA CCAGCTTACAAA TTGCCTGATTGCG GCCCCGATGGCC GGTATCACTGAC CGACCATTTCGT GCCTTATGTCATG CGATGGGGGCTG GG/ CCGTCTCTGAAG CTCTCGGTGAAC ATTGTTGCGAGG CAGGATGCGAGC TGGTTGTGTTTTG ACATTACCGATA ATGTGCCGCCTG AACGGGTGCGTT ATG-3' | Prm4/ disrupted nifL gene | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| 137 | ds799 | down | 325 | TCTTCAACAACTG GAGGAATAAGGT ATTAAAGGCGGA AAACGAGTTCAA ACGGCACGTCCG AATCGTATCAAT GGCGAGATTCGC GCCCTGGAAGTT CGC | 359 | GCCATTGAGCTG GCTTCCCGACCG CAGGGCGGCACC TGCCTGACCCTG GTTTCCCGCTGTT TAACACCCTGAC CGGAGGTGAAGC ATGATCCCTGAA TC | 393 | 5'- TCTTCAACAACT GGAGGAATAAGG TATTAAAGGCGG AAAACGAGTTCA AACGGCACGTCC GAATCGTATCAA TGGCGAGATTCG CGCCCTGGAAGT TCGC/ GCCATTGAGCTG GCTTCCCGACCG CAGGGCGGCACC TGCCTGACCCTG CGTTTCCCGCTGT TTAACACCCTGA CCGGAGGTGAAG CATGATCCCTGA ATC-3' | PinfC/ disrupted nifL gene | SEQ ID NO: 417 CTCG GCAG CATG AAAC GACG TAA | SEQ ID NO: 418 AGGG TGTT AAAC AGCG GGAA A | SEQ ID NO: 419 /56-FAM/ AA CGG CAC G/ZE NIT CCG AAT CGT ATC AA/3I ABkFQ/ |
| 137 | ds799 | up | 326 | TCCGGGTTCGGCT TACCCCGCCGCGT TTTGCCACGGTG TCGGACAATTTGT CATAACTGGC ACAGGAGTTTGC GATGACCCTGAA TATGATGCTCGA | 360 | AGCCGTCAGGTAC CGGTCATGATTC ACCGTGCGATTCT CGGTTCCCTGGA GCGCTTCATTGGC ATCCTGACCGAA GAGTTCGCTGGC TTCTTCCCAACCT G | 394 | 5'- TCCGGGTTCGGC TTACCCCGCCGC GTTTTGCCACG GTGTCGGACAAT TTGTCATAACTGC GACACAGGAGTT TGCGATGACCCT GAATATGATGCT CGA/ AGCGTCAGGTAC CGGTCATGATTC ACCGTGCGATTC ACCGTGCGATTC TCCGGTTCCCTGG AGCGCTTCATTG AGCGCTTCATTG ATCCTGACCGG AAGAGTTCGACCG GCTTCTTCCCAAC CTG-3' | disrupted nifL gene/ Pinfc | N/A | N/A | N/A |
| 137 | ds809 | N/A | 327 | ATCGCAGCGTCTT TGAATATTTCCGT CGCCAGGCGCTG GCTGCCGAGCCG TTCTGGCTGCATA GTGGAAAACGAT | 361 | GCGCTGAAGCAC CTGATCACGGTCT GCGCGGGCGTCGC CGATGGTCGGCCA GCCAGCGGCGGC GCCACCGCGTGC | 395 | 5'- ATCGCAGCGTCT TTGAATATTTCCG TCGCCAGGCGCT GGCGGGGCGTGC GTTCTGGCTGCAT GTTCTGGCTGCAT-3' | 5' UTR and ATG/ truncated glnE gene | SEQ ID NO: 420 GAGC CGTT | SEQ ID NO: 421 GCCG TCGG | SEQ ID NO: 422 /56-FAM/ |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | AATTTCAGGCCA GGGAGCCCTTAT G | | TGCTGGATGAGC TGCTGGATCCCA ACA | | AGTGGAAAACGA TAATTTCAGGCC AGGGAGCCCTTA TG/ GCCGCTGAAGCAC CTGATCACGCTCT GCGCGGCGTCGC CGATGGGTCGCGC GCCAGCTGGCGC GCCACCCGCTGC TGCTGGATGAGC TGCTGGATCCCA ACA-3' | | CTGG CTGC ATAG | CTGA TAGA GG | TTAT GGC GC/Z EN/T GAA GCA CCTG ATC A/3IA BkFQ/ |
| 137 | ds843 | up | 328 | TCCGGGTTCGGCT TACCCCGCCGCGT TTTGCGCACGGTG TCGGACAATTTGT CATAACTGCGAC ACAGGAGTTGC GATGACCCTGAA TATGATGTCTGA | 362 | GCCCGCTGACCG ACCAGAACTTCC ACCTTGGACTCG GCTATACCCTTGG CGTGACGGCGCG CGATAACTGGGA CTACATCCCCATT CCGGTGATCTTAC C | 396 | 5'- TCCGGGTTCGGC TTACCCCGCCGC GTTTTGCGCACG GTGTCGGACAAT TTGTCATAACTGC GACACAGGAGTT TGCGATGACCCT GAATATGATGCT CGA/ GCCCGCTGACCG ACCAGAACTTCC ACCTTGGACTCG GCTATACCCTTG GCGTGACGGCGC GCGATAACTGGG ACTACATCCCCA TTCCGGTGATCTT ACC-3' | disrupted nifL gene/ Prml.2 | N/A | N/A | N/A |
| 137 | ds843 | down | 329 | TCACTTTTTAGCA AAGTTGCACTGG ACAAAAGGTACC ACAATTGGTGTA CTGATACTCGAC ACAGCATTAGTG TCGATTTTTCATA TAAAGGTAATTTT G | 363 | GCCATTGAGCTG GCTTCCCGACCG CAGGGCCGGCACC TGCCTGACCCTGC GTTTCCCGCTGTT TAACACCCTGAC CGGAGGTGAAGC ATGATCCCTGAA TC | 397 | 5'- TCACTTTTTAGCA AAGTTGCACTGG ACAAAAGGTACC ACAATTGGTGTA CTGATACTCGAC ACAGCATTAGTG TCGATTTTTCATA TAAAGGTAATTT TG/ GCCATTGAGCTG GCTTCCCGACCG CAGGGCCGCACC | Prml.2/ disrupted nifL gene | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | | | | | TGCCTGACCCTG CGTTTCCCGCTGT TTAACACCCTGA CCGGAGTGAAG CATGATCCCTGA ATC-3' | | | | |
| 137 | ds853 | up | 330 | TCCGGGTTCGGCT TACCCCGCCGCGT TTTGCGCACGGTG TCGGACAATTTGT CATAACTGCGAC ACAGGAGTTTGC GATGACCCTGAA TATGATGCTCGA | 364 | GCTAAAGTTCTC GGCTAATCGCTG ATAACATTTGAC GCAATGCGCAAT AAAAGGGCATCA TTTGATGCCCTTT TTGCACGCTTTCA TACCAGAACCTG GC | 398 | 5'- TCCGGGTTCGGC TTACCCCGCCGC GTTTTGCGCACG GTGTCGGACAAT TTGTCATAACTGC GACACAGGAGTT TGCGATGACCCT GAATATGATGCT CGA/ GCTAAAGTTCTC GGCTAATCGCTG ATAACATTTGAC GCAATGCGCAAT AAAAGGGCATCA TTTGATGCCCTTT TTGCACGCTTTCA TACCAGAACCTG GC-3' | disrupted nifL gene/ Prm6.2 | N/A | N/A | N/A |
| 137 | ds853 | down | 331 | GTTCTCCTTTGCA ATAGCAGGGAAG AGGCGCCAGAAC CGCCAGCGTTGA AGCAGTTTGAAC GCGTTCAGTGTAT AATCCGAAACTT AATTTCCGTTTGG A | 365 | GCCATTGAGCTG GCTTCCCGACCG CAGGGCGGCACC TGCCTGACCCTGC GTTTCCCGCTGTT TAACACCCTGAC CGGAGGTGAAGC ATGATCCCTGAA TC | 399 | 5'- GTTCTCCTTTGCA ATAGCAGGGAAG AGGCGCCAGAAC CGCCAGCGTTGA AGCAGTTTGAAC GCGTTCAGTGTA TAATCCGAAACT TAATTTCCGTTTG GA/ GCCATTGAGCTG GCTTCCCGACCG CAGGGCGGCACC TGCCTGACCCTG CGTTTCCCGCTGT TTAACACCCTGA CCGGAGGTGAAG CATGATCCCTGA ATC-3' | Prm6.2/ disrupted nifL gene | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| 137 | ds857 | up | 332 | TCCGGGTTCGGCT TACCCCGCCGCGT TTTGCCACGGTG TCGGACAATTTGT CATAACTGCGAC ACAGGAGTTTGC GATGACCCTGAA TATGATGCTCGA | 366 | CGCCGTCCTCGC AGTACCATTGCA ACCGACTTTACA GCAAGAAGTGAT TCTGGCACGCAT GGAACAAATTCT TGCCAGTCGGGC TTTATCCGATGAC GAA | 400 | 5'-TCCGGGTTCGGC TTACCCCGCCGC GTTTTGCCACG GTGTCGGACAAT TTGTCATAACTGC GACACAGGAGTT TGCCGATGACCCT GAATATGATGCT CGA/CGCCGTCCTCGC AGTACCATTGCA ACCGACTTTACA GCAAGAAGTGAT TCTGGCACGCAT GGAACAAATTCT TGCCAGTCGGGC TTTATCCGATGAC GAA-3' | disrupted nifL gene/ Prm8.2 | N/A | N/A | N/A |
| 137 | ds857 | down | 333 | GATATGCCTGAA GTATTCAATTACT TAGGCATTTACTT AACGCAGGCAGG CAATTTTGATGCT GCCTATGAAGCG TTTGATTCTGTAC TTGAGCTTGATC | 367 | GCCATTGAGCTG GCTTCCCGACCG CAGGGCGCCACC TGCCTGACCCTGC GTTTCCCGCTGTT TAACACCCTGA CCGGAGGTGAAGC ATGATCCCTGAA TC | 401 | 5'-GATATGCCTGAA GTATTCAATTACT TAGGCATTTACTT AACGCAGGCAGG CAATTTTGATGCT GCCTATGAAGCG TTTGATTCTGTAC/ GCCATTGAGCTG GCTTCCCGACCG CAGGGCGCCACC TGCCTGACCCTG CGTTTCCCGCTGT TTAACACCCTGA CCGGAGGTGAAG CATGATCCCTGA ATC-3' | Prm8.2/ disrupted nifL gene | N/A | N/A | N/A |
| 63 | ds908 | down | 334 | TGGTATTGTCAGT CTGAATGAAAGCT CTTGAAAAAGCT GAGGAAGCGGGC GTCGATTTAGTAG AAATCAGTCCGA | 368 | TCTTTTAGATCTCT CGGTCCGCCCTG ATGGCGGCACCT TGCTGACGTTAC GCCTGCCGGTAC AGCAGGTTATCA | 402 | 5'-TGGTATTGTCAGT CTGAATGAAAGCT CTTGAAAAAGCT GAGGAAGCGGGC GTCGATTTAGTA | PinfC/ disrupted nifL gene | SEQ ID NO: 423 GGAA AACG | SEQ ID NO: 424 GGGC GGAC | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | ATGCCGAGCCGC CAGTTTGTCGAAT C | | CCGGAGGCTTAA AATGACCCAGTT ACC | | GAAATCAGTCCG AATGCCGAGCCG CCAGTTTGTCGA ATC/ TCTTTAGATCTCT CGGTCCGCCCTG ATGGCGGCACCT TGCTGACGTTAC GCCTGCCGGTAC AGCAGGTTATCA CCGGAGGCTTAA AATGACCCAGTT ACC-3' | | AGTT CAAC CGGC | CGAG AGAT CTAA | |
| 63 | ds908 | up | 335 | TGCAAATTGCAC GGTTATTCCGGGT GAGTATATGTGT GATTTGGGTTCCG GCATTGCGCAAT AAAGGGGAGAAA GACATGAGCATC ACGGCGTTATCA GC | 369 | TGAATATCACTG ACTCACAAGCTA CCTATGTCGAAG AATTAACTAAAA AACTGCAAGATG CAGGCATTCGCG TTAAAGCCGACT TGAGAAATGAGA AGAT | 403 | 5'- TGCAAATTGCAC GGTTATTCCGGG TGAGTATATGTG TGATTTGGGTTCC GGCATTGCGCAA TAAAGGGGAGAA AGACATGAGCAT CACGGCGTTATC AGC/ TGAATATCACTG ACTCACAAGCTA CCTATGTCGAAG AATTAACTAAAA AACTGCAAGATG CAGGCATTCGCG TTAAAGCCGACT TGAGAAATGAGA AGAT-3' | disrupted nifL gene/ PinfC | N/A | N/A | N/A |
| 910 | ds960 | up | 336 | TCAGGGCTGCGG ATGTCGGGCGTT CACAACACAAA TGTTGTAAATGCG ACACAGCCGGGC CTGAAACCAGGA GCGTGTGATGAC CTTTAATATGATG C | 370 | CTGGGGTCACTG GAGCGCTTTATC GGCATCCTGACC GAAGAATTTGCC GGTTTCTTCCCGA CCTGGCTGGCCC CTGTTCAGGTTGT GGTGATGAATAT CA | 404 | 5'- TCAGGGCTGCGG ATGTCGGGCGTT TCACAACACAAA ATGTTGTAAATG CGACACAGCCGG GCCTGAAACCAG GAGCGTGTGATG ACCTTTAATATG ATGC/ CTGGGGTCACTG GAGCGCTTTATC GGCATCCTGACC | disrupted nifL gene/ PinfC | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---------|---------------|------------------------|-----------|------------------------------|-----------|-------------------------------|-----------|--------------------------------------|---------------|--------------|--------------|-----------|
| | | | | | | | | GAAGAATTTGCC GGTTTCTTCCCGA CCTGGCTGGCCC CTGTTCAGGTTGT GGTGATGAATAT CA-3' | | | | |
| 910 | ds960 | down | 337 | CGGAAAACGAGT TCAAACGGCACG TCCGAATCGTATC AATGGCGAGATT CGCGCCCAGGAA GTTCGCTTAACTG GTCTGGAAGGTG AGCAGCTGGGTA TT | 371 | GCAATAGAACTA ACTACCCGCCCT GAAGGCGGTACC TGCCTGACCCTGC GATTCCCGTTATT TCATTCACTGACC GGAGGCCCACGA TGACCCAGCGAC C | 405 | 5'- CGGAAAACGAGT TCAAACGGCACG TCCGAATCGTAT CAATGGCGAGAT TCGCGCCCAGGA AGTTCGCTTAACT GGTCTGGAAGGT GAGCAGCTGGGT ATT/ GCAATAGAACTA ACTACCCGCCCT GAAGGCGGTACC TGCCTGACCCTG CGATTCCCGTTAT TTCATTCACTGAC CGGAGGCCCACG ATGACCCAGCGA CC-3' | PinfC/ disrupted nifL gene | N/A | N/A | N/A |

TABLE F

| Engineered Non-intergeneric Microbes | | |
| --- | --- | --- |
| Strain Name | Genotype | SEQ ID NO |
| CI006 | 16S rDNA - contig 5 | 62 |
| CI006 | 16S rDNA - contig 8 | 63 |
| CI019 | 16S rDNA | 64 |
| CI006 | nifH | 65 |
| CI006 | nifD | 66 |
| CI006 | nifK | 67 |
| CI006 | nifL | 68 |
| CI006 | nifA | 69 |
| CI019 | nifH | 70 |
| CI019 | nifD | 71 |
| CI019 | nifK | 72 |
| CI019 | nifL | 73 |
| CI019 | nifA | 74 |
| CI006 | Prm5 with 500 bp flanking regions | 75 |
| CI006 | nifLA operon - upstream intergenic region plus nifL and nifA CDSs | 76 |
| CI006 | nifL (Amino Acid) | 77 |
| CI006 | nifA (Amino Acid) | 78 |
| CI006 | glnE | 79 |
| CI006 | glnE_KO1 | 80 |
| CI006 | glnE (Amino Acid) | 81 |
| CI006 | glnE_KO1 (Amino Acid) | 82 |
| CI006 | GlnE ATase domain (Amino Acid) | 83 |
| CM029 | Prm5 inserted into nifL region | 84 |

TABLE G

Engineered Non-intergeneric Microbes

| Strain | Strain ID | SEQ ID NO | Genotype | Description | Associated Novel Junction If Applicable |
|--------|-----------|-----------|----------|-------------|------------------------------------------|
| CI63; CI063 | 63 | SEQ ID NO 85 | 16S | N/A | N/A |
| CI63; CI063 | 63 | SEQ ID NO 86 | nifH | N/A | N/A |
| CI63; CI063 | 63 | SEQ ID NO 87 | nifD1 | 1 of 2 unique genes annotated as nifD in 63 genome | N/A |
| CI63; CI063 | 63 | SEQ ID NO 88 | nifD2 | 2 of 2 unique genes annotated as nifD in 63 genome | N/A |
| CI63; CI063 | 63 | SEQ ID NO 89 | nifK1 | 1 of 2 unique genes annotated as nifK in 63 genome | N/A |
| CI63; CI063 | 63 | SEQ ID NO 90 | nifK2 | 2 of 2 unique genes annotated as nifK in 63 genome | N/A |
| CI63; CI063 | 63 | SEQ ID NO 91 | nifL | N/A | N/A |
| CI63; CI063 | 63 | SEQ ID NO 92 | nifA | N/A | N/A |
| CI63; CI063 | 63 | SEQ ID NO 93 | glnE | N/A | N/A |
| CI63; CI063 | 63 | SEQ ID NO 94 | amtB | N/A | N/A |
| CI63; CI063 | 63 | SEQ ID NO 95 | PinfC | 500 bp immediately upstrea of the ATG start codon of the infC gene | N/A |
| CI137 | 137 | SEQ ID NO 96 | N/A | N/A | |
| CI137 | 137 | SEQ ID NO 97 | nifH1 | 1 of 2 unique genes annotated as nifH in 137 genome | N/A |
| CI137 | 137 | SEQ ID NO 98 | nifH2 | 2 of 2 unique genes annotated as nifH in 137 genome | N/A |
| CI137 | 137 | SEQ ID NO 99 | nifD1 | 1 of 2 unique genes annotated as nifD in 137 genome | N/A |

TABLE G-continued

Engineered Non-intergeneric Microbes

| Strain | Strain ID | SEQ ID NO | Genotype | Description | Associated Novel Junction If Applicable |
|--------|-----------|-----------|----------|-------------|------------------------------------------|
| CI137 | 137 | SEQ ID NO 100 | nifD2 | 2 of 2 unique genes annotated as nifD in 137 genome | N/A |
| CI137 | 137 | SEQ ID NO 101 | nifK1 | 1 of 2 unique genes annotated as nifK in 137 genome | N/A |
| CI137 | 137 | SEQ ID NO 102 | nifK2 | 2 of 2 unique genes annotated as nifK in 137 genome | N/A |
| CI137 | 137 | SEQ ID NO 103 | nifL | N/A | N/A |
| CI137 | 137 | SEQ ID NO 104 | nifA | N/A | N/A |
| CI137 | 137 | SEQ ID NO 105 | glnE | N/A | N/A |
| CI137 | 137 | SEQ ID NO 106 | PinfC | 500 bp immediately upstream of the TTG start codon of infC | N/A |
| CI137 | 137 | SEQ ID NO 107 | amtB | N/A | N/A |
| CI137 | 137 | SEQ ID NO 108 | Prm8.2 | internal promoter located in nlpI gene; 299 bp starting at 81 bp after the A of the ATG of the nlpI gene | N/A |
| CI137 | 137 | SEQ ID NO 109 | Prm6.2 | 300 bp upstream of the secE gene starting at 57 bp upstream of the A of the ATG of secE | N/A |
| CI137 | 137 | SEQ ID NO 110 | Prm1.2 | 400 bp immediately upstream of the ATG of cspE gene | N/A |
| none | 728 | SEQ ID NO 111 | 16S | N/A | N/A |
| none | 728 | SEQ ID NO 112 | nifH | N/A | N/A |
| none | 728 | SEQ ID NO 113 | nifD1 | 1 of 2 unique genes annotated as nifD in 728 genome | N/A |

TABLE G-continued

Engineered Non-intergeneric Microbes

| Strain | Strain ID | SEQ ID NO | Genotype | Description | Associated Novel Junction If Applicable |
|--------|-----------|-----------|----------|-------------|----------------------------------------|
| none | 728 | SEQ ID NO 114 | nifD2 | 2 of 2 unique genes annotated as nifD in 728 genome | N/A |
| none | 728 | SEQ ID NO 115 | nifK1 | 1 of 2 unique genes annotated as nifK in 728 genome | N/A |
| none | 728 | SEQ ID NO 116 | nifK2 | 2 of 2 unique genes annotated as nifK in 728 genome | N/A |
| none | 728 | SEQ ID NO 117 | nifL | N/A | N/A |
| none | 728 | SEQ ID NO 118 | nifA | N/A | N/A |
| none | 728 | SEQ ID NO 119 | glnE | N/A | N/A |
| none | 728 | SEQ ID NO 120 | amtB | N/A | N/A |
| none | 850 | SEQ ID NO 121 | 16S | N/A | N/A |
| none | 852 | SEQ ID NO 122 | 16S | N/A | N/A |
| none | 853 | SEQ ID NO 123 | 16S | N/A | N/A |
| none | 910 | SEQ ID NO 124 | 16S | N/A | N/A |
| none | 910 | SEQ ID NO 125 | nifH | N/A | N/A |
| none | 910 | SEQ ID NO 126 | Dinitrogenase iron-molybdenum cofactor CDS | N/A | N/A |
| none | 910 | SEQ ID NO 127 | nifD1 | N/A | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 910 | SEQ ID NO 128 | nifD2 | N/A | N/A |
| none | 910 | SEQ ID NO 129 | nifK1 | N/A | N/A |
| none | 910 | SEQ ID NO 130 | nifK2 | N/A | N/A |
| none | 910 | SEQ ID NO 131 | nifL | N/A | N/A |
| none | 910 | SEQ ID NO 132 | nifA | N/A | N/A |
| none | 910 | SEQ ID NO 133 | glnE | N/A | N/A |
| none | 910 | SEQ ID NO 134 | amtB | N/A | N/A |
| none | 910 | SEQ ID NO 135 | PinfC | 498 bp immediately upstream of the ATG of the infC gene | N/A |
| none | 1021 | SEQ ID NO 136 | 16S | N/A | N/A |
| none | 1021 | SEQ ID NO 137 | nifH | N/A | N/A |
| none | 1021 | SEQ ID NO 138 | nifD1 | 1 of 2 unique genes annotated as nifD in 910 genome | N/A |
| none | 1021 | SEQ ID NO 139 | nifD2 | 2 of 2 unique genes annotated as nifD in 910 genome | N/A |
| none | 1021 | SEQ ID NO 140 | nifK1 | 1 of 2 unique genes annotated as nifK in 910 genome | N/A |
| none | 1021 | SEQ ID NO 141 | nifK2 | 2 of 2 unique genes annotated as nifK in 910 genome | N/A |
| none | 1021 | SEQ ID NO 142 | nifL | N/A | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 1021 | SEQ ID NO 143 | nifA | N/A | N/A |
| none | 1021 | SEQ ID NO 144 | glnE | N/A | N/A |
| none | 1021 | SEQ ID NO 145 | amtB | N/A | N/A |
| none | 1021 | SEQ ID NO 146 | PinfC | 500 bp immediately upstream of the ATG start codon of the infC gene | N/A |
| none | 1021 | SEQ ID NO 147 | Prm1 | 348 bp includes the 319 bp immediately upstream of the ATG start codon of the 1 pp gene and the first 29 bp of the 1 pp gene | N/A |
| none | 1021 | SEQ ID NO 148 | Prm7 | 339 bp upstream of the sspA gene, ending at 46 bp upstream of the ATG of the sspA gene | N/A |
| none | 1113 | SEQ ID NO 149 | 16S | N/A | N/A |
| none | 1113 | SEQ ID NO 150 | nifH | N/A | N/A |
| none | 1113 | SEQ ID NO 151 | nifD1 | 1 of 2 unique genes annotated as nifD in 1113 genome | N/A |
| none | 1113 | SEQ ID NO 152 | nifD2 | 2 of 2 unique genes annotated as nifD in 1113 genome | N/A |
| none | 1113 | SEQ ID NO 153 | nifK | N/A | N/A |
| none | 1113 | SEQ ID NO 154 | nifL | N/A | N/A |
| none | 1113 | SEQ ID NO 155 | nifA partial gene | due to a gap in the sequence assembly, we can only identify a partial gene from the 1113 genome | N/A |
| none | 1113 | SEQ ID NO 156 | glnE | N/A | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 1116 | SEQ ID NO 157 | 16S | | N/A |
| none | 1116 | SEQ ID NO 158 | nifH | | N/A |
| none | 1116 | SEQ ID NO 159 | nifD1 | 1 of 2 unique genes annotated as nifD in 1116 genome | N/A |
| none | 1116 | SEQ ID NO 160 | nifD2 | 2 of 2 unique genes annotated as nifD in 1116 genome | N/A |
| none | 1116 | SEQ ID NO 161 | nifK1 | 1 of 2 unique genes annotated as nifK in 1116 genome | N/A |
| none | 1116 | SEQ ID NO 162 | nifK2 | 2 of 2 unique genes annotated as nifK in 1116 genome | N/A |
| none | 1116 | SEQ ID NO 163 | nifL | N/A | N/A |
| none | 1116 | SEQ ID NO 164 | nifA | N/A | N/A |
| none | 1116 | SEQ ID NO 165 | glnE | N/A | N/A |
| none | 1116 | SEQ ID NO 166 | amtB | N/A | N/A |
| none | 1293 | SEQ ID NO 167 | 16S | N/A | N/A |
| none | 1293 | SEQ ID NO 168 | nifH | N/A | N/A |
| none | 1293 | SEQ ID NO 169 | nifD1 | 1 of 2 unique genes annotated as nifD in 1293 genome | N/A |
| none | 1293 | SEQ ID NO 170 | nifD2 | 2 of 2 unique genes annotated as nifD in 1293 genome | N/A |
| none | 1293 | SEQ ID NO 171 | nifK | 1 of 2 unique genes annotated as nifK in 1293 genome | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 1293 | SEQ ID NO 172 | nifK1 | 2 of 2 unique genes annotated as nifK in 1293 genome | N/A |
| none | 1293 | SEQ ID NO 173 | nifA | N/A | N/A |
| none | 1293 | SEQ ID NO 174 | glnE | N/A | N/A |
| none | 1293 | SEQ ID NO 175 | amtB1 | 1 of 2 unique genes annotated as amtB in 1293 genome | N/A |
| none | 1293 | SEQ ID NO 176 | amtB2 | 2 of 2 unique genes annotated as amtB in 1293 genome | N/A |
| none | 1021-1612 | SEQ ID NO 177 | ΔnifL::PinfC | starting at 24 bp after the A of the ATG start codon, 1375 bp of nifL have been deleted and replaced with the 1021 PinfC promoter sequence | ds1131 |
| none | 1021-1612 | SEQ ID NO 178 | ΔnifL::PinfC with 500 bp flank | starting at 24 bp after the A of the ATG start codon, 1375 bp of nifL have been deleted and replaced with the 1021 PinfC promoter sequence; 500 bp flanking the nifL gene upstream and downstream are included | ds1131 |
| none | 1021-1612 | SEQ ID NO 179 | glnEAAR-2 | glnE gene with 1673 bp immediately downstream of the ATG start codon deleted, resulting in a truncated glnE protein lacking the adenylyl-removing (AR) domain | ds1133 |
| none | 1021-1612 | SEQ ID NO 180 | glnEAAR-2 with 500 bp flank | glnE gene with 1673 bp immediately downstream of the ATG start codon deleted, resulting in a truncated glnE protein lacking the adenylyl-removing (AR) domain; 500 bp flanking the glnE gene upstream and downstream are included | ds1133 |
| none | 1021-1615 | SEQ ID NO 181 | ΔnifL::Prm1 | starting at 24 bp after the A of the ATG start codon, 1375 bp of nifL have been deleted and replaced with the 1021 Prm1 promoter sequence | ds1145 |

TABLE G-continued

Engineered Non-intergeneric Microbes

| Strain | Strain ID | SEQ ID NO | Genotype | Description | Associated Novel Junction If Applicable |
|--------|-----------|-----------|----------|-------------|------------------------------------------|
| none | 1021-1615 | SEQ ID NO 182 | ΔnifL-Prml with 500 bp flank | starting at 24 bp after the A of the ATG start codon, 1375 bp of nifL have been deleted and replaced with the 1021 rml promoter sequence; 500 bp flanking the nifL gene upstream and downstream are included | ds1145 |
| none | 1021-1615 | SEQ ID NO 183 | glnEΔAAR-2 | glnE gene with 1673 bp immediately downstream of the ATG start codon deleted, resulting in a truncated glnE protein lacking the adenylyl-removing (AR) domain | ds1133 |
| none | 1021-1615 | SEQ ID NO 184 | glnEΔAAR-2 with 500 bp flank | glnE gene with 1673 bp immediately downstream of the ATG start codon deleted, resulting in a truncated glnE protein lacking the adenylyl-removing (AR) domain; 500 bp flanking the glnE gene upstream and downstream are included | ds1133 |
| none | 1021-1619 | SEQ ID NO 185 | ΔnifL::Prml | starting at 24 bp after the A of the ATG start codon, 1375 bp of nifL have been deleted and replaced with the 1021 Prml promoter sequence | ds1145 |
| none | 1021-1619 | SEQ ID NO 186 | ΔnifL-Prml with 500 bp flank | starting at 24 bp after the A of the ATG start codon, 1375 bp of nifL have been deleted and replaced with the 1021 rml promoter sequence; 500 bp flanking the nifL gene upstream and downstream are included | ds1145 |
| none | 1021-1623 | SEQ ID NO 187 | glnEΔAAR-2 | glnE gene with 1673 bp immediately downstream of the ATG start codon deleted, resulting in a truncated glnE protein lacking the adenylyl-removing (AR) domain | ds1133 |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 1021-1623 | SEQ ID NO 188 | glnEAAR-2 with 500 bp flank | glnE gene with 1673 bp immediately downstream of the ATG start codon deleted, resulting in a truncated glnE protein lacking the adenylyl-removing (AR) domain; 500 bp flanking the glnE gene upstream and downstream are included | ds1133 |
| none | 1021-1623 | SEQ ID NO 189 | ΔnifL::Prm7 | starting at 24 bp after the A of the ATG start codon, 1375 bp of nifL have been deleted and replaced with the 1021 Prm7 promoter sequence | ds1148 |
| none | 1021-1623 | SEQ ID NO 190 | ΔnifL-Prm7 with 500 bp flank | starting at 24 bp after the A of the ATG start codon, 1375 bp of nifL have been deleted and replaced with the 1021 rm7 promoter sequence; 500 bp flanking the nifL gene upstream and downstream are included | ds1148 |
| none | 137-1034 | SEQ ID NO 191 | glnEAAR-2 | glnE gene with 1290 bp immediately downstream of the ATG start codon deleted, resulting tn a truncated glnE protein lacking the adenylyl-removing (AR) domain | ds809 |
| none | 137-1034 | SEQ ID NO 192 | glnEAAR-2 with 500 bp flank | glnE gene with 1290 bp immediately downstream of the ATG start codon deleted, resulting tn a truncated glnE protein lacking the adenylyl-removing (AR) domain; 500 bp flanking the glnE gene upstream and downstream are included | ds809 |
| none | 137-1036 | SEQ ID NO 193 | ΔnifL::PinfC | starting at 24 bp after the A of the ATG start codon, 1372 bp of nifL have been deleted and replaced with the 137 PinfC promoter sequence | ds799 |
| none | 137-1036 | SEQ ID NO 194 | ΔnifL::PinfC with 500 bp flank | starting at 24 bp after the A of the ATG start codon, 1372 bp of nifL have been deleted and replaced with the 137 PinfC promoter sequence; 500 bp flanking the nifL gene upstream and downstream are included | ds799 |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 137-1314 | SEQ ID NO 195 | glnEAAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain | none |
| none | 137-1314 | SEQ ID NO 196 | glnEAAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain; 500 bp flanking the nifL gene upstream and downstream are included | none |
| none | 137-1314 | SEQ ID NO 197 | ΔnifL::Prm8.2 | starting at 24 bp after the A of the ATG start codon, 1372 bp of nifL have been deleted and replaced with the 137 Prm8.2 promoter sequence | ds857 |
| none | 137-1314 | SEQ ID NO 198 | ΔnifL::Prm8.2 with 500 bp flank | starting at 24 bp after the A of the ATG start codon, 1372 bp of nifL have been deleted and replaced with the 137 Prm8.2 promoter sequence; 500 bp flanking the nifL gene upstream and downstream are included | ds857 |
| none | 137-1329 | SEQ ID NO 199 | glnEAAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain | none |
| none | 137-1329 | SEQ ID NO 200 | glnEAAR-2 36 bp deletion | glnE gene with 1290 bp immediately downstream of the ATG start codon deleted AND 36 bp deleted beginning at 1472 bp downstream of the start codon, resulting in a truncated tn a truncated glnE protein lacking the adenylyl-removing (AR) domain; 500 bp flanking the nifL gene upstream and downstream are included | none |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 137-1329 | SEQ ID NO 201 | ΔnifL::Prm6.2 | starting at 24 bp after the A of the ATG start codon, 1372 bp of nifL have been deleted and replaced with the 137 Prm6.2 promoter sequence | ds853 |
| none | 137-1329 | SEQ ID NO 202 | ΔnifL::Prm6.2 with 500 bp flank | starting at 24 bp after the A of the ATG start codon, 1372 bp of nifL have been deleted and replaced with the 137 Prm6.2 promoter sequence; 500 bp flanking the nifL gene upstream and downstream are included | ds853 |
| none | 137-1382 | SEQ ID NO 203 | ΔnifL::Prml.2 | starting at 24 bp after the A of the ATG start codon, 1372 bp of nifL have been deleted and replaced with the 137 Prml.2 promoter sequence | ds843 |
| none | 137-1382 | SEQ ID NO 204 | ΔnifL::Prml.2 with 500 bp flank | starting at 24 bp after the A of the ATG start codon, 1372 bp of nifL have been deleted and replaced with the 137 Prml.2 promoter sequence; 500 bp flanking the nifL gene upstream and downstream are included | ds843 |
| none | 137-1382 | SEQ ID NO 205 | glnEAAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain | none |
| none | 137-1382 | SEQ ID NO 206 | glnEAAR-236 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain; 500 bp flanking the nifL gene upstream and downstream are included | none |
| none | 137-1586 | SEQ ID NO 207 | ΔnifL::PinfC | starting at 24 bp after the A of the ATG start codon, 1372 bp of nifL have been deleted and replaced with the 137 PinfC promoter sequence | ds799 |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 137-1586 | SEQ ID NO 208 | ΔnifL::PinfC with 500 bp flank | starting at 24 bp after the A of the ATG start codon, 1372 bp of nifL have been deleted and replaced with the 137 PinfC promoter sequence; 500 bp flanking the nifL gene upstream and downstream are included | ds799 |
| none | 137-1586 | SEQ ID NO 209 | glnEΔAAR-2 | glnE gene with 1290 bp immediately downstream of the ATG start codon deleted, resulting in a truncated glnE protein lacking the adenylyl-removing (AR) domain | ds809 |
| none | 137-1586 | SEQ ID NO 210 | glnEΔAAR-2 with 500 bp flank | glnE gene with 1290 bp immediately downstream of the ATG start codon deleted, resulting tn a truncated glnE protein lacking the adenylyl-removing (AR) domain; 500 bp flanking the glnE gene upstream and downstream are included | ds809 |
| none | 19-594 | SEQ ID NO 211 | glnEΔAAR-2 | glnE gene with 1650 bp immediately downstream of the ATG start codon deleted, resulting in a truncated glnE protein lacking the adenylyl-removing (AR) domain | ds34 |
| none | 19-594 | SEQ ID NO 212 | glnEΔAAR-2 with 500 bp flank | glnE gene with 1650 bp immediately downstream of the ATG start codon deleted, resulting in a truncated glnE protein lacking the adenylyl-removing (AR) domain; 500 bp flanking the glnE gene upstream and downstream are included | ds34 |
| none | 19-594 | SEQ ID NO 213 | ΔnifL::Prm6.1 | starting at 221 bp after the A of the ATG start codon, 845 bp of nifL have been deleted and replaced with the CI019 Prm6.1 promoter sequence | ds180 |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 19-594 | SEQ ID NO 214 | ΔnifL-Prm6.1 with 500 bp flank | starting at 221 bp after the A of the ATG start codon, 845 bp of nifL have been deleted and replaced with the CI019 Prm6.1promoter sequence; 500 bp flanking the nifL gene upstream and downstream are included | ds180 |
| none | 19-714 | SEQ ID NO 215 | ΔnifL::Prm6.1 | starting at 221 bp after the A of the ATG start codon, 845 bp of nifL have been deleted and replaced with the CI019 Prm6.1 promoter sequence | ds180 |
| none | 19-714 | SEQ ID NO 216 | ΔnifL-Prm6.1 with 500 bp flank | starting at 221 bp after the A of the ATG start codon, 845 bp of nifL have been deleted and replaced with the CI019 Prm6.1promoter sequence; 500 bp flanking the nifL gene upstream and downstream are included | ds180 |
| none | 19-715 | SEQ ID NO 217 | ΔnifL::Prm7.1 | starting at 221 bp after the A of the ATG start codon, 845 bp of nifL have been deleted and replaced with the CI019 Prm7.1 promoter sequence | ds181 |
| none | 19-715 | SEQ ID NO 218 | ΔnifL-Prm7.1 with 500 bp flank | starting at 221 bp after the A of the ATG start codon, 845 bp of nifL have been deleted and replaced with the CI019 Prm76.1promoter sequence; 500 bp flanking the nifL gene upstream and downstream are included | ds181 |
| 19-713 | 19-750 | SEQ ID NO 219 | ΔnifL::Prm1.2 | starting at 221 bp after the A of the ATG start codon, 845 bp of nifL have been deleted and replaced with the CI019 Prm1.2 promoter sequence | ds172 |
| 19-713 | 19-750 | SEQ ID NO 220 | ΔnifL-Prm1.2 with 500 bp flank | starting at 221 bp after the A of the ATG start codon, 845 bp of nifL have been deleted and replaced with the CI019 Prm1.2 promoter sequence; 500 bp flanking the nifL gene upstream and downstream are included | ds172 |
| 17-724 | 19-804 | SEQ ID NO 221 | ΔnifL::Prm1.2 | starting at 221 bp after the A of the ATG start codon, 845 bp of nifL have | ds172 |

TABLE G-continued

Engineered Non-intergeneric Microbes

| Strain | Strain ID | SEQ ID NO | Genotype | Description | Associated Novel Junction If Applicable |
|---|---|---|---|---|---|
| 17-724 | 19-804 | SEQ ID NO 222 | ΔnifL-Prm1.2 with 500 bp flank | been deleted and replaced with the CI019 Prm1.2 promoter sequence<br>starting at 221 bp after the A of the ATG start codon, 845 bp of nifL have been deleted and replaced with the CI019 Prm1.2 promoter sequence; 500 bp flanking the nifL gene upstream and downstream are included | ds172 |
| 17-724 | 19-804 | SEQ ID NO 223 | glnEAAR-2 | glnE gene with 1650 bp immediately downstream of the ATG start codon deleted, resulting in a truncated glnE protein lacking the adenylyl-removing (AR) domain | ds34 |
| 17-724 | 19-804 | SEQ ID NO 224 | glnEAAR-2 with 500 bp flank | glnE gene with 1650 bp immediately downstream of the ATG start codon deleted, resulting in a truncated glnE protein lacking the adenylyl-removing (AR) domain; 500 bp flanking the glnE gene upstream and downstream are included | ds34 |
| 19-590 | 19-806 | SEQ ID NO 225 | ΔnifL::Prm3.1 | starting at 221 bp after the A of the ATG start codon, 845 bp of nifL have been deleted and replaced with the CI019 Prm3.1 promoter sequence | ds175 |
| 19-590 | 19-806 | SEQ ID NO 226 | ΔnifL-Prm3.1 with 500 bp flank | starting at 221 bp after the A of the ATG start codon, 845 bp of nifL have been deleted and replaced with the CI019 Prm3.1 promoter sequence; 500 bp flanking the nifL gene upstream and downstream are included | ds175 |
| 19-590 | 19-806 | SEQ ID NO 227 | glnEAAR-2 | glnE gene with 1650 bp immediately downstream of the ATG start codon deleted, resulting in a truncated glnE protein lacking the adenylyl-removing (AR) domain | ds34 |
| 19-590 | 19-806 | SEQ ID NO 228 | glnEAAR-2 with 500 bp flank | glnE gene with 1650 bp immediately downstream of the ATG start codon deleted, resulting in a truncated glnE protein lacking the adenylyl-removing | ds34 |

TABLE G-continued

Engineered Non-intergeneric Microbes

| Strain | Strain ID | SEQ ID NO | Genotype | Description | Associated Novel Junction If Applicable |
|---|---|---|---|---|---|
| | | | | (AR) domain; 500 bp flanking the glnE gene upstream and downstream are included | |
| none | 63-1146 | SEQ ID NO 229 | ΔnifL::PinfC | starting at 24 bp after the A of the ATG start codon, 1375 bp of nifL have been deleted and replaced with the 63 PinfC promoter sequence | ds908 |
| none | 63-1146 | SEQ ID NO 230 | ΔnifL-PinfC with 500 bp flank | starting at 24 bp after the A of the ATG start codon, 1375 bp of nifL have been deleted and replaced with the 63 PinfC promoter sequence; 500 bp flanking the nifL gene upstream and downstream are included | ds908 |
| CM015; PBC6.15 | 6-397 | SEQ ID NO 231 | ΔnifL::Prm5 | starting at 31 bp after the A of the ATG start codon, 1375 bp of nifL have been deleted and replaced with the CI006 Prm5 promoter sequence | ds24 |
| CM015; PBC6.15 | 6-397 | SEQ ID NO 232 | ΔnifL-Prm5 with 500 bp flank | starting at 31 bp after the A of the ATG start codon, 1375 bp of nifL have been deleted and replaced with the CI006 Prm5 promoter sequence; 500 bp flanking the nifL gene upstream and downstream are included | ds24 |
| CM014 | 6-400 | SEQ ID NO 233 | ΔnifL::Prm1 | starting at 31 bp after the A of the ATG start codon, 1375 bp of nifL have been deleted and replaced with the CI006 Prm1 promoter sequence | ds20 |
| CM014 | 6-400 | SEQ ID NO 234 | ΔnifL-Prm1 with 500 bp flank | starting at 31 bp after the A of the ATG start codon, 1375 bp of nifL have been deleted and replaced with the CI006 Prm1 promoter sequence; 500 bp flanking the nifL gene upstream and downstream are included | ds20 |
| CM037; PBC6.37 | 6-403 | SEQ ID NO 235 | ΔnifL::Prm1 | starting at 31 bp after the A of the ATG start codon, 1375 bp of nifL have been deleted and replaced with the CI006 Prm1 promoter sequence | ds20 |

TABLE G-continued

Engineered Non-intergeneric Microbes

| Strain | Strain ID | SEQ ID NO | Genotype | Description | Associated Novel Junction If Applicable |
|---|---|---|---|---|---|
| CM037; PBC6.38 | 6-403 | SEQ ID NO 236 | ΔnifL-Prm1 with 500 bp flank | starting at 31 bp after the A of the ATG start codon, 1375 bp of nifL have been deleted and replaced with the CI006 Prm1 promoter sequence; 500 bp flanking the nifL gene upstream and downstream are included | ds20 |
| CM037; PBC6.39 | 6-403 | SEQ ID NO 237 | glnEΔAAR-2 | glnE gene with 1644 bp immediately downstream of the ATG start codon deleted, resulting in a truncated glnE protein lacking the adenylyl-removing (AR) domain | ds31 |
| CM037; PBC6.40 | 6-403 | SEQ ID NO 238 | glnEΔAAR-2 with 500 bp flank | glnE gene with 1644 bp immediately downstream of the ATG start codon deleted, resulting in a truncated glnE protein lacking the adenylyl-removing (AR) domain; 500 bp flanking the glnE gene upstream and downstream are included | ds31 |
| CM038; PBC6.38 | 6-404 | SEQ ID NO 239 | glnEΔAAR-1 | glnE gene with 1287 bp immediately downstream of the ATG start codon deleted, resulting in a truncated glnE protein lacking the adenylyl-removing (AR) domain | ds30 |
| CM038; PBC6.38 | 6-404 | SEQ ID NO 240 | ΔnifL::Prm1 | starting at 31 bp after the A of the ATG start codon, 1375 bp of nifL have been deleted and replaced with the CI006 Prm1 promoter sequence | ds20 |
| CM038; PBC6.38 | 6-404 | SEQ ID NO 241 | ΔnifL-Prm1 with 500 bp flank | starting at 31 bp after the A of the ATG start codon, 1375 bp of nifL have been deleted and replaced with the CI006 Prm1 promoter sequence; 500 bp flanking the nifL gene upstream and downstream are included | ds20 |

TABLE G-continued

Engineered Non-intergeneric Microbes

| Strain | Strain ID | SEQ ID NO | Genotype | Description | Associated Novel Junction If Applicable |
|---|---|---|---|---|---|
| CM038; PBC6.38 | 6-404 | SEQ ID NO 242 | glnEAAR-1 with 500 bp flank | glnE gene with 1287 bp immediately downstream of the ATG start codon deleted, resulting in a truncated glnE protein lacking the adenylyl-removing (AR) domain; 500 bp flanking the glnE gene upstream and downstream are included | ds30 |
| CM029; PBC6.29 | 6-412 | SEQ ID NO 243 | glnEAAR-1 | glnE gene with 1287 bp immediately downstream of the ATG start codon deleted, resulting in a truncated glnE protein lacking the adenylyl-removing (AR) domain | ds30 |
| CM029; PBC6.29 | 6-412 | SEQ ID NO 244 | glnEAAR-1 with 500 bp flank | glnE gene with 1287 bp immediately downstream of the ATG start codon deleted, resulting in a truncated glnE protein lacking the adenylyl-removing (AR) domain; 500 bp flanking the glnE gene upstream and downstream are included | ds30 |
| CM029; PBC6.29 | 6-412 | SEQ ID NO 245 | ΔnifL::Prm5 | starting at 31 bp after the A of the ATG start codon, 1375 bp of nifL have been deleted and replaced with the CI006 Prm5 promoter sequence | ds24 |
| CM029; PBC6.29 | 6-412 | SEQ ID NO 246 | ΔnifL-Prm5 with 500 bp flank | starting at 31 bp after the A of the ATG start codon, 1375 bp of nifL have been deleted and replaced with the CI006 Prm5 promoter sequence; 500 bp flanking the nifL gene upstream and downstream are included | ds24 |
| CM093; PBC6.93 | 6-848 | SEQ ID NO 247 | ΔnifL::Prm1 | starting at 31 bp after the A of the ATG start codon, 1375 bp of nifL have been deleted and replaced with the CI006 Prm1 promoter sequence | ds20 |
| CM093; PBC6.93 | 6-848 | SEQ ID NO 248 | ΔnifL-Prm1 with 500 bp flank | starting at 31 bp after the A of the ATG start codon, 1375 bp of nifL have been deleted and replaced with the CI006 Prm1 promoter sequence; 500 bp flanking the nifL gene upstream and downstream are included | ds20 |

TABLE G-continued

Engineered Non-intergeneric Microbes

| Strain | Strain ID | SEQ ID NO | Genotype | Description | Associated Novel Junction If Applicable |
|---|---|---|---|---|---|
| CM093; PBC6.93 | 6-848 | SEQ ID NO 249 | glnEAAR-2 | glnE gene with 1644 bp immediately downstream of the ATG start codon deleted, resulting in a truncated glnE protein lacking the adenylyl-removing (AR) domain | ds31 |
| CM093; PBC6.93 | 6-848 | SEQ ID NO 250 | glnEAAR-2 with 500 bp flank | glnE gene with 1644 bp immediately downstream of the ATG start codon deleted, resulting in a truncated glnE protein lacking the adenylyl-removing (AR) domain; 500 bp flanking the glnE gene upstream and downstream are included | ds31 |
| CM093; PBC6.93 | 6-848 | SEQ ID NO 251 | ΔamtB | First 1088 bp of amtB gene and 4 bp upstream of start codon deleted; 199 bp of gene remaining lacks a start codon; no amtB protein is translated | ds126 |
| CM093; PBC6.93 | 6-848 | SEQ ID NO 252 | ΔamtB with 500 bp flank | First 1088 bp of amtB gene and 4 bp upstream of start codon deleted; 199 bp of gene remaining lacks a start codon; no amtB protein is translated | ds126 |
| CM094; PBC6.94 | 6-881 | SEQ ID NO 253 | glnEAAR-1 | glnE gene with 1287 bp immediately downstream of the ATG start codon deleted, resulting in a truncated glnE protein lacking the adenylyl-removing (AR) domain | ds30 |
| CM094; PBC6.94 | 6-881 | SEQ ID NO 254 | glnEAAR-1 with 500 bp flank | glnE gene with 1287 bp immediately downstream of the ATG start codon deleted, resulting in a truncated glnE protein lacking the adenylyl-removing (AR) domain; 500 bp flanking the glnE gene upstream and downstream are included | ds30 |
| CM094; PBC6.94 | 6-881 | SEQ ID NO 255 | ΔnifL::PrmI | starting at 31 bp after the A of the ATG start codon, 1375 bp of nifL have been deleted and replaced with the CI006 PrmI promoter sequence | ds20 |
| CM094; PBC6.94 | 6-881 | SEQ ID NO 256 | ΔnifL-PrmI with 500 bp flank | starting at 31 bp after the A of the ATG start codon, 1375 bp of nifL have been | ds20 |

TABLE G-continued

Engineered Non-intergeneric Microbes

| Strain | Strain ID | SEQ ID NO | Genotype | Description | Associated Novel Junction If Applicable |
|---|---|---|---|---|---|
| | | | | deleted and replaced with the CI006 Prml promoter sequence; 500 bp flanking the nifL gene upstream and downstream are included | |
| CM094; PBC6.94 | 6-881 | SEQ ID NO 257 | ΔamtB | First 1088 bp of amtB gene and 4 bp upstream of start codon deleted; 199 bp of gene remaining lacks a start codon; no amtB protein is translated | ds126 |
| CM094; PBC6.94 | 6-881 | SEQ ID NO 258 | ΔamtB with 500 bp flank | First 1088 bp of amtB gene and 4 bp upstream of start codon deleted; 199 bp of gene remaining lacks a start codon; no amtB protein is translated | ds126 |
| none | 910-1246 | SEQ ID NO 259 | ΔnifL::PinfC | starting at 20 bp after the A of the ATG start codon, 1379 bp of nifL have been deleted and replaced with the 910 PinfC promoter sequence | ds960 |
| none | 910-1246 | SEQ ID NO 260 | ΔnifL::PinfC with 500 bp flank | starting at 20 bp after the A of the ATG start codon, 1379 bp of nifL have been deleted and replaced with the 910 PinfC promoter sequence; 500 bp flanking the nifL gene upstream and downstream are included | ds960 |
| PBC6.1, 6, CI6 | CI006 | SEQ ID NO 261 | 16S-1 | 1 of 3 unique 16S rDNA genes in the CI006 genome | N/A |
| PBC6.1, 6, CI6 | CI006 | SEQ ID NO 262 | 16S-2 | 2 of 3 unique 16S rDNA genes in the CI006 genome | N/A |
| PBC6.1, 6, CI6 | CI006 | SEQ ID NO 263 | nifH | N/A | N/A |
| PBC6.1, 6, CI6 | CI006 | SEQ ID NO 264 | nifD2 | 2 of 2 unique genes annotated as nifD in CI006 genome | N/A |
| PBC6.1, 6, CI6 | CI006 | SEQ ID NO 265 | nifK2 | 2 of 2 unique genes annotated as nifK in CI006 genome | N/A |
| PBC6.1, 6, CI6 | CI006 | SEQ ID NO 266 | nifL | N/A | N/A |

TABLE G-continued

Engineered Non-intergeneric Microbes

| Strain | Strain ID | SEQ ID NO | Genotype | Description | Associated Novel Junction If Applicable |
|--------|-----------|-----------|----------|-------------|------------------------------------------|
| PBC6.1, 6, CI6 | CI006 | SEQ ID NO 267 | nifA | N/A | N/A |
| PBC6.1, 6, CI6 | CI006 | SEQ ID NO 268 | glnE | N/A | N/A |
| PBC6.1, 6, CI6 | CI006 | SEQ ID NO 269 | 16S-3 | 3 of 3 unique 16S rDNA genes in the CI006 genome | N/A |
| PBC6.1, 6, CI6 | CI006 | SEQ ID NO 270 | nifD1 | 1 of 2 unique genes annotated as nifD in CI006 genome | N/A |
| PBC6.1, 6, CI6 | CI006 | SEQ ID NO 271 | nifK1 | 1 of 2 unique genes annotated as nifK in CI006 genome | N/A |
| PBC6.1, 6, CI6 | CI006 | SEQ ID NO 272 | amtB | N/A | N/A |
| PBC6.1, 6, CI6 | CI006 | SEQ ID NO 273 | Prm1 | 348 bp includes the 319 bp immediately upstream of the ATG start codon of the 1 pp gene and the first 29 bp of the 1 pp gene | N/A |
| PBC6.1, 6, CI6 | CI006 | SEQ ID NO 274 | Prm5 | 313 bp starting at 432 bp upstream of the ATG start codon of the ompX gene and ending 119 bp upstream of the ATG start codon of the ompX gene | N/A |
| 19, CI19 | CI019 | SEQ ID NO 275 | nifL | N/A | N/A |
| 19, CI19 | CI019 | SEQ ID NO 276 | nifA | N/A | N/A |
| 19, CI19 | CI019 | SEQ ID NO 277 | 16S-1 | 1 of 7 unique 16S rDNA genes in the CI019 genome | N/A |
| 19, CI19 | CI019 | SEQ ID NO 278 | 16S-2 | 2 of 7 unique 16S rDNA genes in the CI019 genome | N/A |
| 19, CI19 | CI019 | SEQ ID NO 279 | 16S-3 | 3 of 7 unique 16S rDNA genes in the CI019 genome | N/A |
| 19, CI19 | CI019 | SEQ ID NO 280 | 16S-4 | 4 of 7 unique 16S rDNA genes in the CI019 genome | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| 19, CI19 | CI019 | SEQ ID NO 281 | 16S-5 | 5 of 7 unique 16S rDNA genes in the CI019 genome | N/A |
| 19, CI19 | CI019 | SEQ ID NO 282 | 16S-6 | 6 of 7 unique 16S rDNA genes in the CI019 genome | N/A |
| 19, CI19 | CI019 | SEQ ID NO 283 | 16S-7 | 7 of 7 unique 16S rDNA genes in the CI019 genome | N/A |
| 19, CI19 | CI019 | SEQ ID NO 284 | nifH1 | 1 of 2 unique genes annotated as nifH in CI019 genome | N/A |
| 19, CI19 | CI019 | SEQ ID NO 285 | nifH2 | 2 of 2 unique genes annotated as nifH in CI019 genome | N/A |
| 19, CI19 | CI019 | SEQ ID NO 286 | nifD1 | 1 of 2 unique genes annotated as nifD in CI019 genome | N/A |
| 19, CI19 | CI019 | SEQ ID NO 287 | nifD2 | 2 of 2 unique genes annotated as nifD in CI019 genome | N/A |
| 19, CI19 | CI019 | SEQ ID NO 288 | nifK1 | 1 of 2 unique genes annotated as nifK in CI019 genome | N/A |
| 19, CI19 | CI019 | SEQ ID NO 289 | nifK2 | 2 of 2 unique genes annotated as nifK in CI019 genome | N/A |
| 19, CI19 | CI019 | SEQ ID NO 290 | glnE | N/A | N/A |
| 19, CI19 | CI019 | SEQ ID NO 291 | Prm4 | 449 bp immediately upstream of the ATG of the dscC 2 gene | N/A |
| 19, CI19 | CI019 | SEQ ID NO 292 | Prm1.2 | 500 bp immediately upstream of the TTG start codon of the infC gene | N/A |
| 19, CI19 | CI019 | SEQ ID NO 293 | Prm3.1 | 170 bp immediately upstream of the ATG start codon of the rplN gene | N/A |
| 19, CI20 | CI020 | SEQ ID NO 294 | Prm6.1 | 142 bp immediately upstream of the ATG of a htghly-expressed hypothetical protein (annotated as PROKKA_00662 in CI019 assembly 82) | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| 19, CI21 | CI021 | SEQ ID NO 295 | Prm7.1 | 293 bp immediately upstream of the ATG of the 1 pp gene | N/A |
| 19-375, 19-417, CM067 | CM67 | SEQ ID NO 296 | glnEAAR-2 | glnE gene with 1650 bp immediately downstream of the ATG start codon deleted, resulting in a truncated glnE protein lacking the adenylyl-removing (AR) domain | ds34 |
| 19-375, 19-417, CM067 | CM67 | SEQ ID NO 297 | glnEAAR-2 with 500 bp flank | glnE gene with 1650 bp immediately downstream of the ATG start codon deleted, resulting in a truncated glnE protein lacking the adenylyl-removing (AR) domain; 500 bp flanking the glnE gene upstream and downstream are included | ds34 |
| 19-375, 19-417, CM067 | CM67 | SEQ ID NO 298 | ΔnifL::null-v1 | starting at 221 bp after the A of the ATG start codon, 845 bp of nifL have been deleted and replaced with the 31 bp sequence "GGAGTCTGAACTCATCCTGCGA TGGGGGCTG" | none |
| 19-375, 19-417, CM067 | CM67 | SEQ ID NO 299 | ΔnifL::null-v1 with 500 bp flank | starting at 221 bp after the A of the ATG start codon, 845 bp of nifL have been deleted and replaced with the 31 bp sequence "GGAGTCTGAACTCATCCTGCGA TGGGGGCTG"; 500 bp flanking the nifL gene upstream and downstream are included | none |
| 19-377, CM069 | CM69 | SEQ ID NO 300 | ΔnifL::null-v2 | starting at 221 bp after the A of the ATG start codon, 845 bp of nifL have been deleted and replaced with the 5 bp sequence "TTAAA" | none |
| 19-377, CM069 | CM69 | SEQ ID NO 301 | ΔnifL::null-v2 with 500 bp flank | starting at 221 bp after the A of the ATG start codon, 845 bp of nifL have been deleted and replaced with the 5 bp sequence "TTAAA"; 500 bp flanking the nifL gene upstream and downstream are included | none |

TABLE G-continued

Engineered Non-intergeneric Microbes

| Strain | Strain ID | SEQ ID NO | Genotype | Description | Associated Novel Junction If Applicable |
|--------|-----------|-----------|----------|-------------|------------------------------------------|
| 19-389, 19-418, CM081 | CM81 | SEQ ID NO 302 | ΔnifL::Prm4 | starting at 221 bp after the A of the ATG start codon, 845 bp of nifL have been deleted and replaced with the CI19 Prm4 sequence | ds70 |
| 19-389, 19-418, CM081 | CM81 | SEQ ID NO 303 | ΔnifL-Prm4 with 500 bp flank | starting at 221 bp after the A of the ATG start codon, 845 bp of nifL have been deleted and replaced with the CI19 Prm4 sequence; 500 bp flanking the nifL gene upstream and downstream are included | ds70 |

TABLE H

| SEQ ID NO: | Sequence |
| --- | --- |
| 61 | atgtttaacgatctgattggcgatgatgaaacggatcgccggaagatgcgcttctgagactggcgctggcgcagatgcgcggcgaagatgcgttcgaggagga<br>ggattccacgcccgtgctgctggcgcgatcctcagaggacgatcgccgccgcgtggtggcgtgattgcgcgatttcgcaaagagttggataaacgcacc<br>attggccgcgacgggcgcaggtactcgatcactactacccgcaccacttacccttgagtgtgcaccgctatggcgccgacgggcgcaccgctgctcggcgatactatcacccgatcctgcttatgataagaacagcatcctgaagctggcgcacgcctattctccgcctgtgccgc<br>gtcgccgatgctagctcagctcacctgcgcctgcgctgcgctgatgaagatgataaaaccaacagctctatcaaccgacggcagtgaatgcctactcgcgatgcgctgcctctcagggtgaagagtgaacacgctgggctgcggcagttgct<br>gccgtgtcgggggcaagatgtggcggtcgttatggccagccaacgcatctgcacgatcgcagggccggttttcggtggtcggtttatgcaag<br>cagcaagcgtgggggcagtgggtacagtccgatctgatctgtattcctcgacgacgcccgatgatgataccgatgcggcgctgaaatcg<br>cctggcggctggagcgtggagccgcgattctcatttcgctccggcgcgtgatgcaccgtcctgttagcacgcgacgccgatcctttatgaagtgatgcgccgtctgcgt<br>ccatctggacgctgtggaggatgctgctcactacgcaccgctccgattacccagcaaacgaacagcctggaacatcaggcgctggcc<br>cgtcgccgccgtggtgtacggcgatccgacctgtccgaagaaatgcgcgaacttgacgccattcgccgaatttgacgcgctcgcccgatgctaaacgcgccgatctgcgatgacgctcggcatgatagacgcccgcaactgacccagccggtatca<br>ccgcacactgcagttatcgcccaatattcggtgctgcgctcttgcccatgacacagctgtacctggacgatgctgcaacagccatcagccgcaacctccgaaggc<br>tggccgacaaacggcatcatggagacagtcacggaaggccgacgcagcagcagcaggagctgtacctatcgccttgtacatgcgccagctcgcgaagggc<br>gagttgcccgacaatgtgggtactccctggttcggcgacggctgcgcttatataaacccagctggacaagctggtggacctggtggaaaccccggc<br>gtaa |
| 62 | ttgaagagtttgatcatggctcagattgaacgctggcggcaggcctaacacatgcaagtcgaacggtagcacagagagctgcttctcgggtgacgagt<br>gggaggacggtgagtaatgtctgggaaactgcctgatggagggggataacttactactggaaacggtagctaataccgcatcaagtcgcaagaccaaaga<br>gggggacttcgggcctcttgccatcggatggccgatggttagctagttagtgggtaacggctcacctaggcgacgatccctagctggtctg<br>agaggatgaccagccacactggaactgagacacggtccagactcctacggaggcagcagtggggaataattggacaatgggcgcaagcctgatgc<br>agccatggcgtgtgtgaagaaggcctttcgggttgtaaagcactttaagcatttaataacctattcattcattgacgttacccg<br>cagagaagaagcaccggctaactccgtgccagcagccgcggtaatacggaggggtcaagcgttaatcggaattactgggcgtaaagcgcagcgc<br>ggtctgtcaagtcggatgtgaaatcccgggcttcaacctgggaactgcatccgaaactgggaagctagagtccggtagagggggtagaattccagg<br>tgtagcggtgaaatgcgtagagatctggaggaatacccgtaaaccgatgtcgatttggaggttgtgccctgaggcgtggcttccggagctaacgcgttaaacgatgtcaacgc<br>gaagaagctaccggccttgacatccacagaacttccagagatggattggtgccttcgggaactgtgagacaggtgctgcatggctgtcgtcagctc<br>gtgttgtgaaatgttgggttaagtcccgcaacgagcgcaacccttatcctttgttgccagcggtcaccatacgggcgggcactctaaggagactgccagtgata<br>actggaggaaggtggggatgacgtcaagtcatcatggcccttacgaccagggctacacacgtgctacaatggtggacttaataagcagttaagccgactcg<br>cgagagcaagcggacctcataaagtgctgcatcagttcggatcgcagtctgcaactcgactgcgtgaagtcggaatcgctagtaatcgtggatcagaat<br>gccacggtgaatacgttcccgggccttgtacacaccgcccgtcacaccatgggagtggttggttgcaaaagaagtagctagttaaccttcgggaggc<br>gcttaccacttgtgattcatgactgggtgaagtcgtaacaaggtagccgtaacaggtgaagtgggaacctgcggttggatcactccctt |
| 63 | ttgaagagtttgatcatggctcagattgaacgctggcggcaggcctaacacatgcaagtcgaacggtagcacagagagcttgctctcgggtgacgagt<br>ggcggacgggtgagtaatgtctgggaaactgcctgatggagggggataacttactactggaaacggtagctaataccgcatcaagtcgcaagaccaaaga<br>gggggaccttcgggcctcttgccatcggatggccgatggttagctagttagtgggtaacggctcacctaggcgacgatccctagctggtctg<br>agaggatgaccagccacactggaactgagacacggtccagactcctacggaggcagcagtggggaatattgggacaatgggcgcaagcctgatgc<br>agccatggcgtgtgtgaagaaggcctttgggttgtaaagcacttaagcacttgttaccagcacattaaggtaaccgtttaatctgtgtgtgaaaactgggaggaagnantangg<br>cgagaagaagcaccggctaactccgtgccagcagccgcggtaatacggaggggtgcaagcgttaatcggaattactgggcgtaaagcgcacgcag<br>gcggtctgtcaagtcggatgtgaaatcccggggctcaacctgggaactgcatccgaaactggcaggctagagtctcgtagagggaggtagaattcca<br>ggtgtagcggtgaaatgcgtagagatctggaggaatacccggtggcgaaggcggccccttctggtctgtactgacgctgaggtgcgaaagcgtggg<br>gagcaaacaggattagataccctggtagtccacgccgtaaacgatgtcgacttggaggttgtgcccttgaggcgtggcttccggagctaacgcgttaa<br>gtcgaccgcctggggagtacggccgcaaggttaaaactcaaatgaattgacgggggcccgcacaagcggtggagcatgtggtttaattcgatgcaac<br>gcgaagaaccttaccctggtcttgacatccacagaacttggcagagatgccttgtgccttcgggaactctgagacaggtgctgcatggctgtcgtcagc<br>tcgtgttgtgaaatgttgggttaagtcccgcaacgagcgcaacccttatcctttgttgccagcggtcgggaactctgatgcacaggctacaaggagactgccagtgat<br>aaactggaggaaggtggggatgacgtcaagtcatcatggcccttacgaccagggctacacacgtgctacaatggcgcatacaaagagaagcgacct |

TABLE H-continued

| SEQ ID NO: | Sequence |
|---|---|
| 64 | cgcgagagtaagcggacctcataaagtcgtcgtagtccgattgagtctgcaactcgactccatgaagtcggaatcgctagtaatcgtggatcaga<br>atgccacggtgaatacgttcccgggccttgtacacaccgcccgtcacacatgggatggggttgcaaaagaagtaggtagcttaaccttcgggaggg<br>cgcttaccacttttgtgattcatgactgggtgaagtcgtaacaaggtaaccgtaggggaacctgcggttggatcacctcctt |
| 64 | attgaagagtttgatcatggctcagattgaacgctggcggcaggcctaacacatgcaagtcgagcggcancggaagtagcttgctacttgccggc<br>gagcggcggacgggtgagtaatctggaaactgcctgatggaggggggataactactggaaacggtagctaataccgtcataccccaagaagagc<br>aaagtggggggatcttcgacctcacgccatcgatgtcccgatgggattagctaggtagctggtgggtaatggctnacctaggcgacgatccctagct<br>gttctgagaggatgatcaccaccgctccgggatcgagtacctgagactcctacgagaggcagcagtgggaatattgcacaatgggcgcaagc<br>ctgatgcagccatgccgcgtgtgtgaagaaggccttaggggttgtaaagcacttcagcggaggaaggcancanacttaatacgtgntgattgac<br>gtactcgcagaagaagcaccggctaactccgtgccagcagccgcggtaatacgagggggtgcaagcgttaatcggaattactgggcgtaaagcgca<br>ccaggcggtttgttaagtcagatgtgaaatccccgggctcaacctgggaactgcattcgaaactggcaagctggagtgtgtcagagggggtagaatt<br>ccaggtgtagcggtgaaatgcgtagagatctggaggaataccggtggcgaaggcgccccctggacaaagactgacgctcaggtgcgaaagcgt<br>gggagcaaacaggattagataccctggtagtccacgccgtaaacgatgtcgacttggaggttgtgcccttgaggcgtggcttccggagctaacgcgt<br>taagtcgaccgcctggggagtacggccgcaaggttaaaactcaaatgaattgacgggggcccgcacaagcggtggagcatgtggtttaattcgatgc<br>aacgcgaagaaccttacctactcttgacatccagagaacttagcagagatgctttggtgccttcgggaactctgagacaggtgctgcatggctgtcgt<br>cagctcgtgttgtgaaatgttgggttaagtcccgcaacgagcgcaacccttatccttgttgtgccagcggtcaacgtggtgggaactcaaaggagactgccg<br>gtgataaaccggaggaaggtggggatgacgtcaagtcatcatggcccttacgaccagggctacacacgtgctacaatggcatacaagagaag<br>gaactcgcgagagcgaacaagcggacctcataaagtgtcgtagtccggattggagtctgcaactcgactccatgaagtcggaatcgctagtaatcgtgg<br>tcagaatgcagcggtgaatacgttcccgggccttgtacacaccgcccgtcacaccatgggagtgggttgcaaaagaagtaggtagcttaaccttcggg<br>agggcgcttaccacttttgtgattcatgactggggtgaagtcgtaacaaggtaaccgtaggggaacctgcggttggatcacctccctt |
| 65 | atgaccatgcgtcaatcgcccattacggcaaagtgggatcggcaaatcgaccacaccacagaacctggtcgccgcgtcggcggagatgggtaaa<br>aagtccatgattgtcggctgtgaccgccgaaagccgatcccacgcgttgatcctcgcatgcgaaagcgcagaacacccattatggagatggctgctgaagt<br>cggtcctggaagacctggagtcaccggatcaacttcctggggtacgggcggtctgctgggcgatgccgattcgattctgtttctacgacgtgctgggc<br>gagctggtgatgcggtggttctgccatcgccgattcgtgaaaacaaagcgcaggagatctacatcgtggctggtgccccagattgtactcgcgggatgcgt<br>caacaacatctccaaaggcatcggtgaaataccgccaaatccggtaaagtgatccccacttgttcccgcgacaacatgttgcagtcggcagcaccgtgaagat<br>ggtttatcgaactgccagaccgaaccccgaatgcagcaataatcgtcaacaccacaaatgtggtgtccaccccc<br>tgcaccatgggatgaactgcgaagaactgctgatggagtccgatggagttcggcattatggatgtggaagacaccagcattggtaaaacccgccgcgaagaaacg<br>ccgtctga |
| 66 | atgagcaatgcaacaggcgaacgcaacctggagataatcgagcaggtgctcgaggtttccgaggagacagacgcgcaagaaacgcagaaacacat<br>gatggtgacggaccgggagcaggagaaagcgtcgagcagcgaaggcgtcgtaagtgcatcatcctaaccgcaaatcgcagcccaatcgagccatctccgcggccgggcg<br>tgccggttcgaagggtggtattggccaatcaaggatatggcgcatatctcggcacgctcaacttcacctcagcttcaggagcgcgacatcgtgttggcggcgataa<br>cggaactactacaccggcgtcagcggcgtgaaagcgctgaagacgtgttcccgcacgccaaaggcattcgatcagtcggacgtcagcgcctgattggcgatg<br>aagcgcccaactgcaacaatgtgatcccgactggtctgctccgaaggcaaaccgttattccggtgcgctcggcgtctgccatcctcggg<br>acattgagccgccgcgaacgccgcagccgcagccatcaaacaccggtatttcgtgaaggcaaaccgttggcggcacagtgctgctcgtacgctggt<br>attacacacggcggcgggctcgctccatggtctccacaactgtctgccatcatctgaccgaactgcagttgacgacaccattcgccaacccga<br>agcggtgatcgcagagtaccaactcttggtccgacgaaaacgacccattatcgcccgactggaatggcgcaaagtgctgcntatatgggcgg<br>cctgcgggatcttgaaagggccgcgacgtcgtgtgatgatgcagcgttgatgatgccagacgggcgttcgtcaacgcgctgaaccgatctcatcggtt<br>ccgcatcaaagagaagtacactctttcagaaaatggggctgcgttcgcagtgacactccgggattactcgccgtaccagcctatgacggc<br>ttcgccatccttcgcccgatatggatgacgctcaacaacccgcgtgggcgcagttgacgcgggcgttgacggtgtgctgaaatccgcctga |
| 67 | atgagccagagactgctgagaaaatacagaattgccatccccctgttgaacaggatgctgtttgccggtaaacgggcactcgaagaggc<br>gcactcgccggagcgggcgaggaagaagttgtgatgacgaccacccccgaataggaccagaacttaaccgaagcgctgactaccatcgaccc |

TABLE H-continued

| SEQ ID NO: | Sequence |
|---|---|
| | ggcaaaagcctgccagccgctggcgcggcggtgctcttgttcgctgggtttgccaataccctaccgtatgtgcacggttcacaggtgttcgttggcctattt |
| | cgcacgtactttaaccgccacttaaagaaccgagcggctgctcgctggtgtcggattcaatgacgagaacgcggcggtgtcggcgggaataacaacctc |
| | aacaccggcttacaaaacgccagcgcggctgtaaaaccggagattatcgcctctaccacctgtaccacctgtatgcggaagtgatcggtgatgattgcaggc |
| | ctttatcgccaacgccaaaaaagatggttcttccgatcgccatcccccgagtaccccccagtttatcggcgacaccccagttcatcaccccggctg |
| | ggataacatgttgaaggtttgccggaccttacggcagaccatgaactcagcgccggcggaacaaatggacgtgcctgggagtggtgctctcaacctgtaagctcacctgccg |
| | ctatctcggcaattccgtgctgaaacgcatgatggaacacgacgccagtgaagatggaggcgccgagcgcgagcgccgatgctctccgatccgtcggaagtgctggatactcccg |
| | ccaacggcattaccagatgtacggcgggacgacgcagcaagagatgcgcgagcgccgatgctatcgacaccctgttgctcagccctg |
| | gcaacctgtgaaaagcaaaagatgtgcaggagtggaatcagcccgcccgaggtttctgttccggtgacgacgaggaagacgacgaact |
| | gttgatggcggattagccagttaaccggtaaccggcaagccattcccgatccactgcgctggaggcgcggcgtggtgcatatgatgtcggattccacacct |
| | ggtgcacggtaaaaaatcggccctgttggcgatccggattttgtcatggattgaccggttcctgctgagctgggctgcgaaccgacctgtacctc |
| | tgtgggcattccgtcgctgattaccggcgacgattttatgattgatgcgccaactgttatcaagctttatcaactgcgatt |
| | gcagtttgaagttccgtcgatccggcctcggttttcccctgttcgacccgccaccatctgaccgccagacaccttagccagggcgccatagca |
| | ttctcactaccctgtgaatgggtactggagcagaaagtggacaaagagaccaccaagctcggcaaaaccgataccaagctcgatcttatccgttaa |
| 68 | atgacccctgaatatgatgatgcggcggccgcccgaggcaatcgccggtgcgcttcgcgacaccatcctcggcgtgtttttttaccatcgttgaagaa |
| | gcgcccgtcgccattcgctgactgatccgcgacgcgatccgcggcacgccattgtctctatgccaaccccacggaaatcttatcaggatatgtgccaaccaggcgctt |
| | cagcaaaaatcccgcgcttcaagtcgccaaaccacggccggcagcctgctttttgacccagatcagcgggaatcttatcaggatatgtgcactactactggca |
| | aattgataaccgcaccgacgcgacgcggcagctgcctatgcgttatgcgagcagcggttcggcgacaatcacaaaaacgtctgcgcgactgcggcggaaaagagctctgacgaactc |
| | gtggttgtagtgacttgatgaacgccatcggttatggattggataacctgctgcggccgttagcgttctgccgctggtgtcgcggtggtgtcggtgacctgtgggcgc |
| | tgccgggcgtcagcgagaagccagtcgctacttttattgataacaggctgacggccacacctactggcgtgcgcggcgcacccaaacgccagc |
| | agcaggacaaggcgctgacttgaccgccatcaatatgctggcggcgacggtaaccgcgatccgcagccttgaccgcgcggctgatc |
| | cagcttaactgccccatcaatactggcgtgcaggcgggttaaacgcagcatggcggccgaagtcgacgccgcggtcggcgcggcgaaggt |
| | gaagaggcgatggcggcggctgaaacgttgccgccgtcgctgcgaactggaaaagtgcggcgctgatgggaagcgtggccaactgtacgcaactgttagcct |
| | ggcttatcacaccccgctacgagcaggggaaaaattgcagtgcccggcggattgtgccaacctcggggctgggcaaagcagattacgcccgcaaaggcttagcggctg |
| | gctcctttgtatcactgacgatgtgcgccatctggatgaacctgctgccgctcaccacccggatcgtcgttaacgtccgggaaaaaggcatggagcgtgc |
| | gcctgatccagacgctggtggcaccaccacccggcgcaataagaactcacttcacacccccgaagggggaagttgcctgaccctacgatcccgctattt |
| | tcattcactgacggaggttcaaatga |
| 69 | atgaccagcgaccgagtcggtaatacgtctggcgctgcttcgattgtcccagcagttcactgcgatgcgcataagcgtgtactcagccggg |
| | cgaccgagtcgatcagacgctccagcaagtgctgtcgtattgcacaatgacgcccttttcgagcacgcacgtgatcgtctcgtacgacagccagcag |
| | gcgatttgaatattgaagcgttgcaggaagccgatcagcagttaatcccgcagctcgagctcgccagtctcgtcgggcgaaggctggctcggga |
| | cggtgcttcgcaggcaatcattagtgctggcgatcagcgcgctggcctgcttcctttgaccggctgcagcgcttttgacggttgatgattacaacctgccgtttatc |
| | gccgcgctgatggtccgcagatgcgcagcaccctggtagcgcttcgcgagaagcgcacacccggctctgtcgagaggcgcgcgctgcgctgccaccgcgc |
| | ttctcggaaacggtcgctcaacctggtccgcgcaaccggtcgtttgatggcgcgccaacgcgccctgttcctgatggtggccccataacacacaggccg |
| | ccagcccgaaaatcctgacggcctcagcggcgcattgttttgaaaatatggtctggaaagcgaatcgttcgtcacggaaaggcaattaccgccgtcc |
| | gttcgcctggggacaccaccggtctcggtacggcggcgagcggtccagaggcgcggcaggagcgatgttcctggaaaagcgaattgtccggcgctgcggtcggggcggcg |
| | tacgccagcgtaaggccgtttgagccggcttcggcggccatggcgcacgtctgttcctgacgagatcggcgagtagcgccctggttcaggctaagctgct |
| | cgcatttgcaggaagccgaaatgaacgcggcgaaatggaactgaaagtggacacggcgatcagtgagaatgcggcctcattaccgccgcagaaccgccaatcttgaa |
| | gatgaagccggctgggcacttcctgtgctgcgaagatctcattacgccgaagatcccgccgccactacgccgaaacggcaggagacat |
| | tgccgagtcggcggacttaatgtcggccgaaactgcctgagcctcagcgtgatgtggagaaacggctgatcgagatggcctgatctgattttgttatc |
| | atcggcgaccagcgagcaaaccgccagtacaccgccagctctcgcatgatgataactggcttccgataacaacctgacgagcgccagcggccgacggtgcggc |
| | gctggaaaagcgggacgtgggtacaagccaaacccgccgcggccttgctgtgtgggatgacgacggccaggtgcgccgctcatcattcagcagcagtgcgccatataac |
| | cctgccaaggctataa |

TABLE H-continued

| SEQ ID NO: | Sequence |
|---|---|
| 70 | atggcaatgcgtcaattgtcaatctacgggaaggggtattggtaaatccaccactaccaaaaccttgtagcggctcttggccgaaatgaataagaa<br>ggtcatgatcgtcggctgtgacccctaggctgattcaaccgccctcattctgcatggcaaagcacagaacacatcatggaatggccgctgaagtgg<br>gtccggtggaagatctggagctggaagatgtgatgcaaatcgctatggcgcgtgcgtgctgtcgtgtgggaatcaggcggcctgagcctgtgtggtt<br>gtgccgacgcgggtgatcaccgccatcaacttcctcgaagaagaggcgtatgcggccggatcttcgtgtttacgacgtattggcgat<br>gtggtctgtggcggttcgcgatgcgccaattcgcgaaacaaagcgcaggaaatctacatcgtatgtctgaaatgatgcgatgatgccgccaa<br>caacattccaaggcgctgcgcgtgaaatacgcgaatacgggcaaagttcgctgccggctgaactccgcccagacggatcgcgaagatgaa<br>ctgatcatccgcgctggctggtgaaaaacttggcacgcaaatgatcactcgtgtgcgcgtgacaacattgcaacgcgtgaaatccgccatgacggt<br>catcgaatcgaccgacggttgcgcaggcagatcagtcagtgccaggcaaatggtgtgcaaccaaagtgtgtcgccgcaccggtc<br>accatgatgagctggagccgttaatgaattggcattatggaagagaagaaactgaccatcgtcggtcgtaccgccgcgaagaggcgtga |
| 71 | atgaccagtgaacaccgcaacgctaacgaggcattgatccaggaagtgctggagatcttcccgagaggcgcttaaagatcgtaagaaacacatg<br>atgaccaccgacccgagcggatgcagtgatctcgcgcagtgaccggtgaaatcgtcaacaaccgcaaaccgcccggtcgaggctggcgcttacg<br>ccggttccaaaggcgtgcttggcgtctggcgccgatcaaagacaatggcgcatatctcccacgcccgttggttcggcgcgagatctcgtcggcgaccgt<br>aactattacaccggctggagcggcggcgtgaacacttgcacctcaacttcccagtgattcaggaacggggcaatcgtattggcgggcgataaaaag<br>ctcggtcgctgcgcagtcgagacagtgtgttccgctgaccaaagcattcggtacgatcggtcccggtcggtccgatcggcgatgacatt<br>tctgcgcgtgccagcagcgcgcaagtcgagtccggtacgctcgacgggggttcgcggtgttcgcaatcgctcggccat<br>cacattgctaacgatgtcatccgcgactgggtgctggataacgcgaggcaatgaattgaaccacgcctacgacgtgcggattatcgggcgacta<br>caacatcggccggtgaccctggcctcacgtattcctctgaagaaatgggctgcttgcgtggtgctgcacagtgtccggcgacggcacgctgtgga<br>gatggaaacaccccgaaagtcgcaccaattggcgccactccaattctgccggaatctgcggcaaatgcctgaatgacataccaacccggaaaaacacgcattccgt<br>ggttggaatacaacttcttggccggacaaaatatgccggatcgacaaatggcagatcagcaaataccgccgcgatgatccgaatatcggcggttac<br>gtccgcgccacatcatcgggggctgtatgaagactctggaatggatggaaatcatcgtaccgtacctggaagcgttcggttcgcttaaggcttggaacatcggttacctacgacccaccttac<br>cgatgctcaaagaaggcacgttgctgttcgataacgaaaatgggcgtgcgttccgcgttctcgccgatgacctcgggggtcagcaggc<br>atcaaagaaaatacatttccagaaaatacgtcgaacatacgccatgctggctggaactggccggtgaattggctgggtggggtgggtttcggtgatcttaagggtcgttgatctcgggctctgggctcagac<br>ttttgccggtgacatggacatagcgtgaacatcgccgttccgatggcggagtggaagtttttcaggcttcga |
| 72 | atgagtcaagatcttggcgcacccgcaaatcctgttccgctgttcgagcagatgaatcagcagagtatgttaccccacaaacgcgcgctggaagaagca<br>cacggcgaggcgaaagtgcggaagtgtttgaatggaccaccacgcaggaaatatcagatctgaacttctcgcgtgaagcgtgaccgtcgacccg<br>gcgaagctgcccgtgcgccacgtcaggcggtattgcccagtgcctgttccgactcaatgaccgaagatcgcgcttttggcggaaataacaacaatgaatgtc<br>cgtacctcatttaatcgtcattcaaagagccgtgacaagccggaattattgctgctcccaccactgtattggcggaagtgatccggtcgagtgacctgcacggtttttatc<br>ggtctgaaaaagcccagccgcgcgtgtacaagccggaaattattggtcgtggtcgtccatcaaccgtgtggcgaaagtaaccccagttctctggcagtcggggacatggcatgtcaacggctgggacaa<br>catgttgaagtcgctgctacttaccacgcgacccacgcggaactataaccgcagaaactgaccgtgaacctggtgaccggtttgaaa<br>cttatctcggcaactaccggatctgccgccggccaactaccgcatatgagcagatagggggtcgaatctgatcgcacccgaagctgatcgccaccgagttgatgcctgccttctgcggctgcaaacctgtgc<br>ctgacggccaataccggatcatgccgggcgaccaccgaagatgcggcaccgaagtcagtgtacccgagtcaggtactgagcggcgacggtctttg<br>aattgcagaaaacaaaaagtggtcagggcgaagtgttgaatggcaccgtggctgactgaagccggtgtgagctgcgcagttcccacacct<br>ctatgacggttggcaactgcggccaaaggagatgaactcatcggttcggtctctacggtgaccggtctctacggttctgatgggcatgacaagccgaaagtatgtgaactgcga<br>cagccataacggcaaaaacggccaacgccgatgaaagccatgaaagggcctgaacgccatcacggtaagccggaaatcattcagcgtgaacgacctgagcagcagcgaaagtgtatgtgaactgcga<br>tctgtggcattccgcgctgatgttcccgggcatcggtttccgattttgtgatggcgaacagggtgaacgagctggcatatgatgggcaaccaggacaggaggggcggcggatgagcg<br>aacagttcaagtcgctggccggccgcatgatctccgattttccgattttcgattttatgatcggcaactactggatgttgatggcgaacacttgcacctgagacacggggatcagaagggggcgagatgagcg<br>atactgacggacaactggtactgacggtggtgataaccgatcggcgaacaactggatcgcgaacaactgacactgacactgacctgacgga |
| 73 | atgagcatcacgcgctatcagcatcattcctgagggagatatcgcagcgctgcgctgctgctttgaactgtgaccaatct<br>tcggtggcgatttcgctgacgatcgcgatccgaggcgcattgtatgtatgccaatccgaatgaactctgccgcagacggtttgcacttgagcactttgggcg<br>agaaccaccgtctgctgccagcacgaccgagaacatactatagcgaataatggtggcgcactttgtgtcggggcaaatcctggaacggccaact<br>gatcaaccggctaataaccgtctgccttatctggcggatgtcactatcacgcctttaggcggaggggcaagtggggcagcattacctcggcatgca<br>caaagatatcagcgagaaatacggcgtggaacagcggttgcgcaaccatcacctgttccacggtggagcctgaacaatactcccgcgccgtggtg<br>gtggtggatgaccgccaatggtgatgacaactggatcggcggtgcaagatgagcggaggctgcaaagcgtgcgtggtctgaaatgggc<br>tatccggccaactcaagagtggcaacggtgccgggttccatgccggcaacgtacgtcggttctccatggcggcaactgttattgcagg |

TABLE H-continued

| SEQ ID NO: | Sequence |
|---|---| gcgttaatgaagaggcagccgccttttaccggcattaccgcgccggaaaactgattgttctgaccgactgcacatgcagcatcaccggcagcag
caggtatcttgaccggcttaagcaaaaactcaccaacggcaaatattgcggccatccgagtcgctcgatccggagtcgctcgtttatccagctcaacgg
gccaatcaatatgctgcggctgcgctgcgtcttaacggcgaagaagcaacaacatggcgtggaattcgctcggcggcgaaggcgagcagccgg
tgagtcgctacaggccgcgcgctgcgtcgctggatttgagcgcgcagaatgccgcagtgaattcttgacatcttgacgctcgagcgcgtgacgaca
gccattttctcagtgacggtgaattgcgttacggtcatgccatcgtcgagtctcggtgacacgctgcggcaacgaacaatcctt accgcgctgagcttatg
gatgatcacacgctgcacagcgccaggccatgccatgccctctgaagtctcggtgacacttgtgcgaggcaggatggcatggacgtgtgttttgacatt
accgataatgtgccgcgtgaacggtgcgctgttatgcccgccgaaggcgcgtttccgtccgggaatggcatggacgtcgccttatccagacgc
tgatcgcccatcatcgcggttctttagatctctcggtccgtccgctgatgggcgacctgatgggggtacagcaggtatcaccggag
gcttaaaatga 74
atgaccagttacctaccgcgggcccggttatccggccgtttgatatgtctgcccagttacggcgcttatccgcatcagcgtggcgctgagtcaggaa
agcaacaccggcggcgcactggcgacctcgaagctgaagtcctcgaatcgcagtggtgcctgttcgatcgtaaagaacgcaat
gcactctttgtgaatcctgcatggcatcgcagccggcgaaagaaaagagacccgcatgtccgtcaccgcatgggaaggcgtgatcggcgcg
gtgatgagccaacgtcaggccgtggttatccaggacgtcagcgtttctcgaccgcgctgaatattacgattacagcctgccgttgattgg
gctgcgatccccgggtcggacaataatcagccatcagggcgtggtggccatggcgctgcacgaagaccggtgactgccagtacggcggtt
tttagaatggtgccaatctcatcagccagccatctcgttctgccacgcccgcgagatcattgctctcaaacgccggtcagtgttccgcg
ccagttggttttcgagcagatggtcggaaagcaggaaagtcaggcgatgcgccagacgatgaacattacggcaggttccaaatggataccacggtctggt
gcgtggtgaaagcggcaccggcaaggaactt atcgcaacgacctgtgtcggtcaatgcataaaagggccttcaccgggtctaccgtcaaagccgcttgactggc
ggacggggcacgttattcctcgatgaaatcgacggccgtgttcaggccaaattgcgccattttgcaggaggtgaaatggaacgg
gtcggcggcgatatccgctgaaagttgatgtcggcgcattatcgtcgccgccaaccagtaatcttgaagaggaagtgcgccgggaatttcgcgaaga
cctgtattatcgcctgaacgtgatgccgcggttcgcttcgctgcaccgacggtgcggtgatctgagacctacagcagcagcaacgtcggtggcaacgtgtcgtgaaaa
gctgctcgaacgggcgtcggtaatgaccgtcggtaaggctgaagcgcgctgcaccagcagatcccgctctgtcaataccaccatgaatcccggtgtcgctcaaac
ccggcctcgcgcgcgacagatgaaagtcggcagaactgcgcagcgacgcacgacagcacgccgcagcggtgattggcgacacaggacaaaacggtgggt
gcaggccaaagcggcccgactgctgggcatgacaccgccgaccgccgagattgctacccgtatccagattatgacatcaaacatgcaccgtatcctga 75
aaaactaccgcgcaattaatgaacccaacgctactgttgccggccatgctcttcccgcgcggcgctgccggaaaagatagattgcccagcacg
cgccagcaccaagcgcgcgcagtgagatcgacgcggccagtgagatcgacgcagcagatcaagaggccaagtaccgccag
gatcacccagatgaaatccacccggcgctgaggcaaaaagcgccacgcccgagcgacaggccataaaacagcagtggcaggcgttgtttcacgggtaaatgtaaac
tatcgtctggatcgataaatagaacatatagttcacgcgccgagcgacaggccataaaacagcagtggcaggcggtgtttcacggaaacgtgatttc
gccagggcttgaacactacgacaacaataagggtgcaagtgacacgcggcgcggtgacgcgtgcggtgcgccaacaatcggaaacagtgatttc
ctcccgtcaattctcgtcactgtcaaataaagtaaagaggcagtcagtctacttcaattactgatgaattactgtatttactaccccgctggttgttgaaaaaagtaactgaaaaaatccgta
gaatagcgccactcgatggttggtcagtagcggaaacttcaattactcgatgaatgtgccattaaatgcgcagcataatggtcgttgtgcggggaaaa
ctgcttattttgaaaggtggctcagtacggcagaaacttctgtctacatcaaatggcgaaaaaatgaactcccgcaaagagttcttaactaatttgatat
attttaacgctacggctaggattcactggaactcaacgtaactcttatcggcgccatcaaacgtacggtgctctaactcgggttggtgcgccaacctgaa
gcaggttcgcagtacggcaggacaacaacccggccggctaacgtatcggttccttacttacacgtgaaaaagatcgcaccgaaaagcagcagtttaacaaagcga
atatcgtacgagcaggcaggacaaaccggccggctaacgtatgcatcaacgctggcgagcatctcggtgtgggtcgatgtacggtaaatccagcagactg
gtactacggcacaccgcgggattaaccgttggcgaactggaagacacctacctgggcgagcactacctggcgtgtacggtaaatccagcagactg
tagacaccgctaaagtgctgaccaccagcgactacg 76
aacacacgctcctgttgaaaaagagatcccgcggaaatggtgaacgtgtctgatattcgaagagtgtgccagtttgtgtcggcaaacct
gaccaggttggttattaatgaccagctgcgcttttctcggccagttctccctcgctaatgccccgctaatggcgcggcttggcgctgatagcgcgctg
aatacgatctggatcaaggtttgcggttatcagccaaaggtgcactctttgcgactcttgcatggtttacgtgcctgacatgttgtccgggcgacaaacggcct
ggtggcacaaattgtcagaactacgacagacaccatcctggctgttttaccatcgttgaagaagcgcccgtcgccattcgtgctgactgatgccgacgcacgcattg
tctatgcaaccggatctcgcgcgcagaccggtatgaactagaaacgctggtcgagaactggatccttcgaagcaaaatcccgctgcttcgaagtcgcagaaacccccacgg
gaaatctatcaggatatggcacacctgttacaacgcacctggcgcgggcaatggatcccgggttaccgcctccacctgatccgcagcatcagcgctgatatc
gatcgatatcacccggattaaccgttggcgaactggaacactaccggatcagccggatatcagcgcagttatcgcgtggagcgcggt TABLE H-continued

| SEQ ID NO: | Sequence |
|---|---|
|  | tgcgcaatcacatgacctgaccgaagcggtgctgataacatccggcggcggtggttgtagtgatgaacgcgatcatgtggtattgatgataaccttg |
|  | cctacaaaacgttctgtccgactggcggtggcggaaaagagctcctgagcgaactcaatttttcagccgcgaaaacgcggactggcaaacggccaggtctt |
|  | accggtggctgccggtgaggtgctggttgtctggtgacctgctggccgtgccgggcgtcagcgaagaagccgacttgaccgccttaacacagcagatga |
|  | aggctgaccgcaccgctgtggtgatcaccgacgacaaccagcagccaggaccacaatgggccacttgacgcgctaaacagcagatga |
|  | ccaacgcaaactactggcagcgatccgcgaacggcttgacgcgcgtggccgtgccgaaggtgaagaggccgatggccgcggtgaaaattgcaggt |
|  | aacggcagtgataacaacaatggcggcctcgacgccgtcgacaccccttttgacgatctgcgcggcgttcatcacaccacccgctacgacggggaaaatttgcaggt |
|  | gaactggaaagtggccgtccgcctggccgtcgccaacatttgacgatctgcggcgcgttatcacaccacccgctacgacggggaaaatttgcaggt |
|  | cacgctggaggggattcccatcacctgcgtccatctggaatgggcacaacctgatcgagctgctgcgatattgccgccgg |
|  | gctggtgattcaccgcggcaacgcagatttacgcccggaaaagcatgagccgcgctctccttgtatatcactgacaatgtgcgctgatcccgctgcg |
|  | caacaccactcgccggatcgcgcttaacgctccggaaaagccctagatcccgctacctgacctgaaccgaggttcaaaatgaccagcgaaccgagt |
|  | cgggtaataccgctgcctcgatttgtcccagcgatgctcactgagctcaagcgtgactcagccggccgaccgaggtcgatcagac |
|  | gccccagcaagtgctgtcgtattgcacaatgacgcatttgcagcacggcaagcatcgtctgacagcagcagcatggaatattgaagcg |
|  | ttgcaggaagcgatcagcagttaatcccgcagcctcgcaaatccgcttcttgacccggggcgtgatgattacaacctccgggcggcgtatatctccgtggacaccac |
|  | agatgccgagacttcgtgctgacgcgacacaaccatgctcgatgctccgttacgaggaggccgttcagtcgccgccgatagggcc |
|  | ctggtctgcgcaaacgtcgtttgatggcaccaacccggcagtcgcgccctcccgccgccgcctaaacacagacggccgaaatcctgac |
|  | ggcctcacgcgcatttgttttgaaaatatgtcggtaacagtccggcgatcaacgccatcaccacccatccgggtgccgttcgccgcattgtgaaattc |
|  | cgttctggcaccgggcgagagtggcaacctctgcaagagcgcaattgctcaacgccatgctccgcctcggttcggccagcgtaaagccg |
|  | aactggccgtccggacctcgggcgcaccgctgttttctgacagatcggcacgtcgcgatcagctcgcagttcaggcgattttgcaggaaggcga |
|  | aatggaaacgcgtcggcggcggcgacagatctcattatcgccgaatgctgatgcccatcgcggccgccgtaagaacgctgaaggtgaagatgaagtccgctggggca |
|  | cttccggaagactctattatcgcccagagcgctacgctgcaggggtctatcgaccgatgagctacaaccggccatggcttctgcc |
|  | ggtcgtaaaatcgccatagcgtgaatgtgctacgctggcagcaacgggtctatcggatgagctacaaccggccatggcttctgcc |
|  | gaactggaaaactgcctgagccgctcggtatgtgggaacgcgccgagcagtgatttgttaatcatcgcgaccagcgcagccaa |
|  | ccgcagttatcagcgcgccagccgccttcgcatgatgataactggtgacgagccgcaggtcgcatcgtattcagacgatggatataacccctgccaaggctataa |
|  | gtacaagccaagccgccgccttctgctgggatgacgccgccaggtcgcatcgtattcagacgatggatataacccctgccaaggctataa |
| 77 | MTLNMNIMDAGAPEAIAGALSRHHPGLFFTIVEEAPVAISLTDADARIVYANPAFCRQTGYELE |
|  | ALLQQNPRLLASRQTPREIYQDMWHTLLQRRPWRGQLINRHRDGSLYLVEIDITPVINPFGELE |
|  | HYLAMQRDISASYALEQRLRNHMTLTEAVLNNIPAAVVVDERDHVVMDNLAYKTFCADCG |
|  | GKELLSELNFSARKAELANGQVLPVVLRGEVRWLSVTCWALPGVSEEASRYFIDNRLTRTLVV |
|  | ITDDTQQRQQEQGRLDRLKQQMTNGKLLAAIREALDALIQLNCPINMLAAARRLNGSDNN |
|  | NVALDAAWREGEEAMARLKRCRPSLELESAAVWPLQPFFDDLRALYHTRYEQGKNLQVTLD |
|  | SHHLVGFGQRTQLLACLSLWLDRTLDIAAGLGDFTAQTQIYAREEEGWLSLYITDNVPLIPLRH |
|  | THSPDALNAPGKGMELRLIQTLVAHHHGAIELTSHPEGGSCLTLRFPLFHSLTGGSK |
| 78 | MIQRTESGNTVWRPDLSQQFTAMQRISVVLSRATEVDQTLQQVLCVLHNDAFLQHGMICLYD |
|  | SQQAILNIEALQEADQLIPGSSQIRYRPGEGLVGTVLSQGQSLVLARVADDQRFLDRLGLYDY |
|  | NLPIAVPLIGPDAQTFGVLTAQPMARYEERLPACTRFLETVANLVAQTVRLMAPPAVRPSPRA |
|  | AITQAASPKSCTASRAFGFENMVGNSPAMRQTMEIIRQVSRWDTTVLVRGESCTGKELIANAIH |
|  | HHSPRAGAPFVKFNCAALPDTLLESELFGHEKGAFTGAVRQRKGRFELADGGTLFLDEIGESSA |
|  | SFQAKLLRILQEGEMERVGGDETLQVNVRIIAATNRNLEDEVRLGHFPREDLYRLNVMPIALPP |
|  | LRERQEDIAELAHFLVRKIAHNQSRTLRISEGAIRLLMSYNWPGNVRELENCLERSAVMSENGL |
|  | IDRDVILFNHRDQPAKPPVISVSHDDWLDNNLDERQRLIAALEKAGWVQAKAARLLGMTPR |
|  | QVAYRIQTMDITLPRL |
| 79 | atgccgcaccacagcaggattgtcgcagcactggcgacactggcaaacggtattttctcgtctgccgaatcgctcaccgcgccagccattgagcgcgcaggcgcagt |
|  | cagtgctcactttagtgatttgttcaggacagcatcatccgcatccggcatcctgagtgctcagacgcgccggcctgcgaacagcgtcggcgatggc |
|  | aacactatgccaatggccgcaagcggcgatggctcaccgatgggctcacggtgctgcgctcgccgctgttccgcgtccgcatcatggt |

TABLE H-continued

| SEQ ID NO: | Sequence |
|---|---| gcgcatcgcctggagcaggcggttacagttggtggcggaggaagaagatatcctgcaacagcttagcgtgctggcggaaacccctgatcgtcgcgcgcg
cgactggctttatgagcctcgtgctgcgtgagtgggaacgccgagcaatccacaagcgtgcgcaccgatgctggtactcggcatggcgcaaact
gggtggcggcgaactcaatttctcatccgatatcgattttgattttcgctggcctggcacgcgtgaaaatggcgcaacgcggatgttgaccgcgtgataacg
cgcaattttcaccgcctggtcaacgccgtgattaagtcccgaccagccaacgcaggatggcttgtctaccgccgatatgccgcttgcgcccgttt
ggcgacaaggccgctggtgctgagcttgcgcgctggaagattactaccaggagcagggcgcgattggaacgctacgcgatggtgaaagc
gcgcatatggcgataacgacgcggaccatcgcgcggagtgcgcgccgttggcgccaatgctgccgccgttgtttccgccgtatatgcgacttcagcgtgattca
gtccctggctaacatgaaaggcatgattgcccgcgaaggcgcgccgtggcctgaggacaacattaagctcggcgggggatccgcgaaat
agaatttatcgtccaggttcccagtttccgccgtccgcgagcgtccgcgcaggacgctgcgctgtcactgttgccgacagtcgctgccatagatcaactg
catctgtcgcc gatggcgacgcaaccgtcgccgagccgtattgtggctcgacgcttggagaaccgtgtgcaaagcatcaatgacgaacag
acacagacgctccgggcgatgaactgaaactggatcagtattcaacgatctgattggcgatgatgaaacgtatcgcgcggaagatcggcttctgagagctggcgaattgt
ggcaggacgcgacgtgtcgaggagga gatcccaagccgtctcgagcgatggcgtgaagcgttggtttccgccgatttcg
caaagagttggataaacgcaccattggcccgcgagggcggcagttactactcgcgcggtgcttggtcacacactctaatgccattaaccggctggtcgg
gcgccagtaccgctcgacgccgctgacccgtgcggccgatggttcaccgcagcctgctgcgatggtgcagttgccgttcaccgtcagttcccggcgcgcaactgaaa
aaccgacgcgatgaatcccatcgcgatgagcgcgccaatacctgcgctcggcgcggtgagctcagcgatggcctgcgctgatgcggt
cagttaagcaggcggcagttcgcgccgcgccggccggcgacaagcgatattgcgcgcgtgcgttatgcgcggcagcagatgctggcgtcacggcgaaggcgcggtt
ttcgggtggtcggttatggcaagcgggcgggttggggtacagctccgatctggatcagctcggatctggcgttattctctcgcacgcaccgccccgatgacctgatga
ccgatggcgaggcgtgaaatcgatggtgccagtcgatctgccgcctcgctgcgctctgagcgggatcgtctgtcaactactacggaatcgttcgccgatcacc tgttcgcggcatcttt
atgaagttgatggtcgggtcgcttcgccatcggcgcgcggcgacttacggcccgtgaattgcgaagacgttcgcgatctccagctaccagcaaacggacgc
tggaaacatcaggcgggcgcaaccgccgacagcgcaagaaatgcgcagaaaatgcgcccatcttggttgctgccctcagccaacaagcatataaagaccgcattcttgatcgcga
ctcgcgacgcgccaacgctgcaaacgacgtgcgagaaaacgacgtgcagaaagcgcgcaggcattaaagacatatcggggaat
aatgtgcgcattctcggggcgctgcaaggggcgcgaaaacgacatcatggaggagcaggaagcgcaggcattgacgccaggcattgagcatgacttgagcgcagtgatga
gctgcacccacctggcgctgcaagagttgcgcggacacgtgctggcgcaacatgctggcctgccgcacgcggctgcttattaaaacagctgggacaagtggc
tggtggaaccgttgcgcggcccccggcgtaa 80 | atgtttaacgatctgattggcgatgataacggattcgcgcggaagatgcgcttctgagagctggcgaatgtgcgaggatgcgttgcaggagga
ggattccaagccccgttggctggcgcatctccagaagaacgatcgcgcggccgtgtggctgatgcggccgatttctgcaaagagttggataaacgcacc
attggcccgcgctgtcaccggaatcggagcgaatttcccgggcgcactgaaacacctcattcccctgtgtcgcgc
gtcgcgacatgaaaggcggtgaaatcgatggtgccagtcgatctgttgatgaatgcgctcttgataggatcgatgctctatcaacgacgacgatgaatgcgcta
tcgcgatgagctgatgctcgccaatacccctgctgcgctgcgctgtggataatgataaaacgatgaaatgaaacgtatcgcggaagcgctggcggaggtt
gcgcgtggctgggcgggccatattgccgctacgttgccgacgatgtcgctggcgacgcgcgaaggcgcgcagctgccggcgattattgatgcggtggtg
ctgggcggtaggtctaagcggcgactggtttacgagcccgaatctggactctgatctggctatccgcagagatcggatgatatcctgagacgccgtgaaatcg
gcatcctgcgcggcggatgtgtacgcggatctgcagaagaaatcgcggcgctcgcgctgttgccaatggataccgccattcgccgacatctggggaacatcaggcgcgtgg
cgtggcgcctgcgtccggtgtacgacgcgatctggctaatttcgccgacatattcgcgcgccatatggatactgttgatgagctcgcacacgcggttatca
ccgacatcagttatcgcccaatatcggtgtcgctgcctcgtgcgtggctgatcggaagcgcaagcggttggatgctgcgcattctcaagggc
tggcgcaaacgcatcatggaggagcaggaagcgcaggcattgacgcctgtacaccacattgcctgatgagctcgcaccacttgcgctgcaa
gagtcgcgcgctgcaatggcggggcgcttattaaaacagctggacaagtggcggtggaaccgttgcgcggccccccggc 81 | MPHHAGLSQHWQTVFSRLPESLTAQPLSAQAQSVLTFSDFVQDSIIAHPEWLAELESAPPANE
WQHYAQWLQAALDGVTDEASLMRALRLFRRIMVRIAWSQALQIVAEEDILQQLSVLAETLI
VAARDWLYEACCREWGTPSNPQGVAQPMLVLGMGKLGGELNFSSDIDLIFAWPENGATRG
GRRELDNAQFFTRLGQRLIKVLDQPTQDGFVYRVDMRLRPFGDSGPLVLSFAALEDYYQEQGR
gtaa TABLE H-continued

| SEQ ID NO: | Sequence |
|---|---|
| | DWERYAMVKARIMGDNDCGDHARELRAMLRPFVFRRYIDFSVIQSLRNMKGMIAREVRRGL<br>KDNIKLGAGGIREIEFIVQVFQLIRGGREPALQSRSLLPTLAAIDQLHLLPGDATRLREAYLWL<br>RRLENLLQSINDEQTQTLPGDELNRARLAWGMGKDSWEALCETLEAHMSAVRQIFNDLIGDD<br>ETDSPEDALSESWRELWQDALQEEDSTPVLAHLSEDDRRRVVALIADPRKELDKRTIGPRGRQ<br>VLDHLMPHLLSDVCSRDDAPVPLSRLITPLLTGIITRTTYLELLSEFPGALKHLISLCAASPMVAS<br>QLARYPIILDELLDPNTLYQPTAMNAYRDELRQYLLRVPEDDEEQQLEALRQFKQAQLLRVA<br>AADIAGTLPVMKVSDHLTWLAEAIIDAVVQQAWGQMVARYGQPTHLHDREGRGFAVVGYG<br>KLGGWELGYSSDLDLVFLHDCPMDVMTDGEREIDGRQFYLRLAQRVMHLFSTRTSSGILYEV<br>DARLRPSGAAGMLVTTTESFADYQQNEAWTWEHQALARARVVYGDPQLTAEFDAIRRDILM<br>TPRDGATLQTDVREMREKMRAHLGNKHKDRFDLKADEGGITDIEFIAQYLVLRFAHDKPKLT<br>RWSDNVRILEGLAQNGIMEEQEAQALTLAYTTLRDELHHLALQELPGHVALSCFVAERALIKT<br>SWDKWLVEPCAPA |
| 82 | MFNDLIGDDETDSPEDALSESWRELWQDALQEEDSTPVLAHLSEDDRRRVVALIADPRKELDK<br>RTIGPRGRQVLDHLMPHLLSDVCSRDDAPVPLSRLITPLLTGIITRTTYLELLSEFPGALKHLISLC<br>AASPMVASQLARYPILLDELLDPNTLYQPTAMNAYRDELRQYLLRVPEDDEEQQLEALRQFKQ<br>AQLLRVAAADIAGTLPVMKVSDHLTWLAEAIIDAVVQQAWGQMVARYGQPTHLHDREGRGF<br>AVVGYGKLGGWELGYSSDLDLVFLHDCPMDVMTDGEREIDGRQFYLRLAQRVMHLFSTRTSS<br>GILYEVDARLRPSGAAGMLVTTTESFADYQQNEAWTWEHQALARARVVYGDPQLTAEFDAIR<br>RDILMTPRDGATLQTDVREMREKMRAHLGNKHKDRFDLKADEGGITDIEFIAQYLVLRFAHD<br>KPKLTRWSDNVRILEGLAQNGIMEEQEAQALTLAYTTLRDELHHLALQELPGHVALSCFVAER<br>ALIKTSWDKWLVEPCAPA |
| 83 | EEQQLEALRQFKQAQLLRVAAADIAGTLPVMKVSDHLTWLAEAIIDAVVQQAWGQMVARYG<br>QPTHLHDREGRGFAVVGYGKLGGWELGYSSDLDLVFLHDCPMDVMTDGEREIDGRQFYLRL<br>AQRVMHLFSTRTSSGILYEVDARLRPSGAAGMLVTTTESFADYQQNEAWTWEHQALARARV<br>VYGDPQLTAEFDAIRRDILMTPRDGATLQTDVREMREKMRAHLGNKHKDRFDLKADEGGITD<br>IEFIAQYLVLRFAHDKPKLTRWSDNVRILEGLAQNGIMEEQEAQALTLAYTTLRDELHHLALQE<br>LPGHVALSCFVAERALIKTSWDKWLVEPCAPA |
| 84 | ccgagcgcgggtgcctaatatcagcaccggatacgagagaaagtgtctacatcggttcggttgatattgaccggcgcatccgcagcccgccca<br>gttctcggtggactcgtttggcgattttgcggttcggttcttgccggtgtccggtgtccggtgccgaaaaaaataccaatatttgccataacacacgctcctgttgaaaaagag<br>atcccgccggaaatcggtgaacggtctgatatcgcaagatgtcgcggcggcttggcgctggacacaaacctgccaccagttggttcgttattaatgcacca<br>gtctggcgcttttttccgccgagttctccctcgctaatgcccgccagcgcgcttggcgctgatagccgcgctgataccgatctgatcaaggtttttgtc<br>gggttatcagccaaaagtgcactctttgcatggttacgcctgataatgatgatggcgccgggcggacacatccgcgacaacaatattaataccggcaacc<br>acacggcaattacgagacgtgcgcaggcatcctctcccccgcaccctcgatggttaattaacctattcaattaagaattatctgatgaatgtgccatta<br>aggtttgttgaaaaaagtaactgagaaaatccgtagaatagccgccactctagatgcagcaatagtgcggtgtgtggtccagatggttcagtagcggaaacaaactccttcggtgcgcttcgatttgt<br>gttgcctgacccctacgatcccgctattcattcactgaccggaggtcaaaatgaccagcgaggtcagaccgctccagcaagtcgtgtcgtattgacca<br>cccagcagctcactggcgatgcacgcagccatagccctggtactcacgacaccgaggcgatttgaatattgaagcgttgcaggaacggtcagcagatcccatgatccc<br>atgaccgcctttttgcgagcagcggatgatcgtccgggcgaaaggctggtcggagacggctccggagacgcactcggaaaatttcgcaggaggggggaagtcagcagtaatccc<br>cggcagtcgcaaatccgctatcgtccgggcgaaaggctggtcggagacggctgcttcgcaggaagtttcgcaggaggggaagtgtcttgtgctagtcaagtcattaatcg<br>cagcgcgttcctgaccggctcgggtttgatgattacaaacctgccgtttatc |
| 85 | attgaaaagagtttgatcatggtccagattgaaacgctgggcgaggcagacctaacacatgcaagtcgagcggcagcggagtagcttgctactttgccggc<br>gagcggcggacgggtgagtaatgtctgggaaactgcctgatggagggggatactactggagacagcttgattaatgctagagccctggtaatcggtatattaagcatggggatcttcggacctcatcgacaagagtctctggtatattaatgctagagccctggtaatcggtatatt<br>aagtggggggatcttcggacctcacgccatcggatgtgcccagatggattagctagttagtggtggggtaatggctcacctaggcgacgatccctagct<br>ggtctgagaggatgatgaccagccacactggaactgagacacggtccagactcctacgggaggcagcagtgggaatattggacaatgggcgcaagc<br>ctgatcagcatgccgcgtgtgtgaagaaggccttagggttgtaaagcactttcagcggaggaggaaggcatcanacttaatacgtgtggtgaggattgac |

TABLE H-continued

| SEQ ID NO: | Sequence |
|---|---|
|  | gttactcgcagaagaagcaccgcgctaactccgtgccagcagccggctaatacggaggggtgcaagcgttaatcggaattactgggcgtaaagcgca ccaggcggtttgttaagtcagatgtgaaatccccgcgcttaacctgggaactgcatttgaaactggcaagctagagtacttgagaggggggtagaatt ccaggtgtagcggtgaaatgcgtagagatctggaggaataccggtggcgaaggcggccccctggacaaagactgacgctcaggtgcgaaagcgt gggagcaaacaggattagataccctggtagtccacgctgtaaacgatgtcgacttggaggttgtcccttgaggcgtgcttccggagctaacgcgt taagtcgaccgcctggggagtacggccgcaaggttaaaactcaaatgaattgacgggggcccgcacaagcggtggagcatgtggtttaattcgatgc aacgcgaagaaccttacctactcttgacatccacggaattcggccagagatggccggtgtgaaagcaagttaactcttgaccggagatcatggccca cagctcgtgtcgtgagatgttgggttaagtcccgcaacgagcgcaacccttatccttttgttgccagcgattcggtcgggaactcaaaggagactgc cggtgataaaccggaggaaggtggggatgacgtcaagtcatcatggcccttacgaccagggctacacacgtgctacaatggcatatacaaagagaag cgaactcgcgagg |
| 86 | atggcaatgcgtcaatcacgtacggagaaaggggggtattggaaatccaccactacccaaccctgtagcggtctctggccgaaatgaataaga agtcatgatcgctcgctaaggctgaccctaaggcctcatcctcaccccctgtgaaagcacagacaccatcatgaaatgccgcgcctgaagtg ggctccgtcgagaatctggagctggaaaatgtgatcgcaaatcggctatggcggcgtctgcagggccgtatgtgccggatctggatttttacgaccgtattgggggat tgtgccgacgcggggtggttcgcgactgcgcattcaaactccgtgagaagaaaggccgcggaaatctacactcgtgctccgcggtgaaatgatatgcgatgatgcgccaa caacattccaaaggcatcgtgaaatacggacaaagtccgcggatcctgaactccgccgcacacaaattcgcaacgtctcgcggtaactcgcgcatcctgacacattggtcaacgcgctgaaatccgcgcatgacccat atgataacgcgggggaactgcaggtagtcaataattggcacgcaacatgatccactcgtgccgcggcgcaaataggtatctgcgcggtcaagccgtatggatatgcgcgcaa ctgatcactcgcgctggctgaaaaacttggcaggcagcagtcagttagtctgcactgcagatctgtgaagaaggagactgatccgctcgggttaactcgcgagatgaa catcgaataacgacccgactggtgcggaggcagatcagttctgcactggaatcccactctgcgcgtgaacacaaatcgtcaacaacacaaatggtggtgccgacaccggtc accatggtgagctggagcccgtgttaatggaattggcattatggtcattggcattggtgt cgatccgggagctggagcccgttaatggaattggcattatggtcattggcattggtga |
| 87 | atgaaggcaaaagagattctggcgctgattgatgagcctgtgagcctgtcgagcataaccacaagcagcagagtcggttgcagcctgcgaaccgggcgc gacggcaggcggttgtcgtgcggcgcagattgcggccagattgtcgctcggcgttctgatgtcgctctggtcgcacggcccgattggctgtaccgg cagtcatgggacaacggcggcagcccagtccgggccttcatcaccgatggtgtcttcattacacctcgctacccgcgatggaagggggtagaagcagcgattacctataccattccgtcgcctcggcgtcgctaccgaagcgcggttctgatgtcccggccgtcacaccatc cgtaaccgcattgccggggacgtgatggtcaaaaagtgatcggcggcgctatctcgtgcgatctggcgcggcgtctcgctgaactccggagatcatggccgtcctgtcgc caccgcccacagcatcacccgtgattggcgacatccaataattgccggcggcatcaataattgccggcggcgcaacatggcgcaagttctgtcggcggcatagcaccgttctggggtgtcaacatggcgcaagttctgtcg aaaatggaagagcgtaccgagatccggttgaggcagttatgtgctggcacggtatcctcgccgtatcatcaacattctctcggcg gacccgattcaggcgcacagagacgtctgattgagcggagagcggcgacacatcttgcgctgcctacggtggtgcgaccggcaccga aatcaaccgaagaagacaagcagcgtattccgaactgatgggtgaagacggctgatgctcgacgaaggcaatggcaaaagcaacctgtgctgacacc tctatccgttcggcgacacatcatgatcggcgggccggcaacatctataccgccggatatcaatcaggagcg cgagcatgcgtttgccggatatcacggtcggtaaatctggcggtaaattggccgaacagttgtatcaccccggaagccccgaaagcccgtctggcggcaggtcaaccgtctg gcgccggtggcgctaa |
| 88 | atgaccagtgaaacacccgaactgaaacaacgctaacgaggcattgatccaggaagtcttccccgaggaagcgcttaaagatcgtaagacacatg atgaccaccgaccccggccgatggaatctgtcggcaagtgtattgtctcaaacccgaaaatcacacgccgggcgtgatgaccggtcgcgcttacg ccggttcaaagcgtggtattggcccgatcaaagacatggcgcacctcaacttcacagtgattcaggaacggaccgtatttggcggcgataaaaag aactattacaccgcggtgactggcggctgaacagtggatgttcccgtgacaaaggcattgcgtgcgtcgagtggctcgcgtgtcgcgaatcgcaagagacatt ctgacgaaattgatcgatcgatgaactgaacgccaaaatcgtaacgcgtgcgtcggtgtggtgtttcgcgcatcggcatcgcaatcgcgaggcatc acattgctaacgatgtcatccgactgggtcggtgatgaacagcgcgaagcaatgaatttgaaaccaccgcttacgacggcgatattcggcgactac aacatcggcaggacccggctgggcctcaatctgctcttcgtactgctcactgctacactccgtcatatggaagaaaacacggcattccgt ggatgaatacaacttcttggcccgaccaaattgccgaaatcgcggcggcggtttgaccacctccggataccatccgaaaaacgccgaagc ggtgattgaaaaatatcaggcggcaaacgcaggcggtgatcgacaaataccgtccgtctgaaggcaaaaggtgcgttgattctcggcggtttac |

TABLE H-continued

| SEQ ID NO: | Sequence |
|---|---|
| | gtccggccacatcatcgggcgtatgaagatcctgggaatgaaatcatcggtaccggctatgaattcggtcataacgatgattacgaccgcaccttac |
| | cgatgctcaaagaaggcacgttgctgttcgataacctgagccagttatgagcgtggaacgcttcgttaagcggtgaaaccggatcttcgggtcaggta |
| | tcaaagaaaaatacattttccagaaaatgggcgtccgttccgcagatgcatcctggattattccggcctatcacggctacgacggttcggcat |
| | tttgcccgtgactggacatgagctgagctgaacaatccgggctgaagtcagctcagtcagctgagtacgaacgcctga |
| 89 | atggctcaaattctgcgctaatgccaagccgctgccaccacgcctgctcaaaagcgggcaaccgctcggggcgatcctggccagtcaggggctgaa |
| | aattgcatccccggctggttcacgcgcgcaaggtgtgagcggtagcggcctcacaagtttctcatccagcatttcccagcatttcacgatccgttgcagtccgttgcagtccggc |
| | gatgatgaccgaccacatcatggctcggatctgcagcgcagtactggtgtcagccgcagtaatccaaagccattgtgatttg |
| | agcaccggactgtcagaagcgcaggggcagtgattgttcgatggcgtcgtgagttcgcgacaaagaaccggcttaatgccatcgcattcctgac |
| | cgttaacacgcggatttcacggctgccagccgcgcgacgcgcgtgacgcgggggaatctcgctggccatatctcgagtctgtcagccgccgac |
| | cgcatggtcgtaacaagcggtgaacctgctcggtgagccatctactcaccagtgcctgcggggatctgaatactgcgcagtctggaagccttggcctg |
| | caaccggtgatcctgcggattcaccacggctgcgacgtctggaccgcagggcgatccaacgcgcaacgcc |
| | agattgaacaaatgggcgagagcgctgaccacctgacaccattaccatggacagtctgactcgctctgcgctgcgccagtctgatggcgcgacggtggc |
| | gctgaactgcgcgcactgatgacgctggacgacgcatgactggacgcgccataacctgagtcagccggacgatagctcgcggcagaagcggggattgag |
| | cgccagccgggcaactgctcggacgcatcggatcgcggtcctgcggcgcgcgttaatcagcgatcactggccggtctcgccggtcagccggatttggctggtg |
| | gctggtgcgatttgttcctcaggccggagcagcggaatcgcggccgttcatggcggtcggggctgaacatcagctgtggcgggaactcaccgtggccgaaa |
| | gtgtgatcggcgatctggaagattacaaaaccggccctcgaaccgccgcagcgctacccgggctttcaatgtcacctgcgttctgcggcggctgcctctcgggattcaggctaccggcgtatccggacacc |
| | aaaacggtatccggtacgtgctgccggttcccgcgcttacgaccggtccgggaattcgcgcgtcggcaggctatgcgggctatctgcgctagcgcggtgttcggctcgacgatccgacggtaccgg |
| | ttgttcgaactgcgaacctgatcgcgggttatcaccgcagacggcgtcatctacatctgacggcgtatcacatcgacggcgctatcaccgccgtctcggccggctatccgccagccggggctccgtatccgacggtatccgggtattccgcaccacgctgacgccggtaccgg |
| | aggccagtcatgaaggcgcgctaa |
| 90 | atgagtcaagatcttggcacccaaatcctgttcccgctgttcgagcaggtgaataatgttacccacaaacgcggctgaagaagca |
| | cacgggcaggcgaaagtgcgggagctgttgaatggaccaccacggccagtacgttacccacaacgttgcgtatccatggttctcgctgtgtgggctattcc |
| | gcgaaagctcgccagccgttaggcgcggttactttgcgcggtcggtttctgccactccctcggtgtcctggcaggtaagtgctgtgtggcgtattcc |
| | gtacctttaatcgtcatcaaagagccggtggcggtgctgtgttcccactcaatgacgaagatgcgcgcgtttggcggaaataacaacatgaatgtc |
| | ggctcgaaaacgccagccgccgtacaagccggaaattattgcggtctccccaccgtatggcggaagtgatcggtgatgactggaggctcaggctttatc |
| | gccaaccgcaaaaagacggattgtgatgccggatatgccaatcccgtatgcccatacaccgagttctcggcagtcatgtcaccggctgggacaa |
| | catgttgaaggtcgcgcgtacatctaccaccgacgccacgcgggaataccacgcgaaaccgaaatgcgcggcaaactgaacctgacggtttgaaa |
| | cttatcctcgcaactaccgggttattcaccgatgtagcggtgacgcagatgagccgtgccccgaagtgctgaagtccgacaccccgg |
| | ctgacggccaataccgcatgtatgccgcggcaccacggccaaaaccgaaatgcgtgatgcaccgaagtcagctgccaaaacgtgcccctgccactcgctgctctgctcgccgacgatgcctg |
| | aataacagaaaaccaaaaaggtggtgcaggggactgaaaaccgatagctgacggctgcggactgaaaggtggctggctggactatgatgtctcaacct |
| | ctgatgacggctaagcgaactgaacgccagcagcagcgagcgcgcgattttgtgatggccgaaccggcttgatgaacggaccgaaccgaccaccattc |
| | tcagccaatcaacgggcaacaaaacgctgcagaaagccatgaagaatactgctgcaagatagctcgatataggaacacgtatgtgaactgcg |
| | atctgtgcacattccgctccgctgatgtttaccgtaaccgactttatgatcggcaactgacttatgatcggcaacctctacggaaatctcatcagcgtgacacgtggccaaggc |
| | gaacagtcgaagtcgccgctgctcgctatcggattcccggattttgaccgggcaccatttgcaccgtcagaccaccgtgggatacgagggcgcgatgag |
| | catcctgaacgactggctggtgctcgaacagcctggactgctgcgaaaccatgaagctcggacaacaacttcgatctgatccgctaa |
| 91 | atgagcatcacggcgtatcagcatccttcctgagggggaatatcgccagccgcttcgcgtcgcaacatccttcactgtttatccgtgttgaacaatca |
| | tcggtggcgattcgctgaccgatccggagcggcagtcgcaaatccggcattctcgcgcgcagacgggtttgcacttgagacactttgggcg |
| | agaaccgccgttcggagctgtaataaccgtctgcctttatcggatgaccaaatatccactacacgcctgttgccagggcaaatcctgaagcagcgcaact |
| | gatcaaccgccgtaataaccgtcgcttatctcggcggatgtcactacacgcctgtgttcagcggcaggtcagggaggtgttggacattacctcggcatgca |
| | caagatatcagcgagaaatacgcctgagcacgcggttcgccaaccacaccttgttcacggaggtgctgaacaatatccccgcgccgtggtg |
| | gcggtggatgagcaggacatggatgggcaatctggctcacttggcaccttaattctggctgctaaccgttccccctgatggcgcgaaatgggc |
| | tatcggatgcaaaggatgctcaaagcggtcacctttttaccggcattaccgggcaacaaactgatgttctcacgcagccaccggcagca |
| | gcgggttatctgaccggtctctggtcggctcaagcaaaaacttaccaacggcaaattgctggcagccatccgagtcgttgatgccgtggtcattgcag |
| | ggccaatcaatatgctggcgtgcctgggctgcgcgtggcgtcttaacggcaggaggcaacaatggcctgaattcgcctgcgcgaagcggaggcaggcg |
| | gtgagtcgcttcagcagggctgacggtgatttgagccggcagcagaatggccggtcagtgaattctcgacgatcggtgagcgctcgtacga |
| | cagccattttctcagtgacggtgaattgcttcacggcgtcctcgttctgacctgggctcggcgcaacgaacaaatcctgcggctaccgcgagcttat |

TABLE H-continued

| SEQ ID NO: | Sequence |
|---|---|
| | ggattgatcacacgctgtcacaggcgcaggccatgcctcgtctcctgaagctctcggtgaacattgttcgcgaagcaggatgcgagctggtgtgtttgaca<br>taccgataatgtgcccgtgaacgggtgcgttatgcccgccgaagcgggcgttccgctccgggaaggcatggaactggcatggagctgcccttatccagac<br>gctgatcgcccatcatcgcggttcttagatcctcggtccgccctgatggcggcaccttgcgacgttacgcctcggtacagcaggttatcaccgga<br>ggcttaaaatga |
| 92 | atgaccagttacctaccgcgggcccggttatccggcgcttttgatatgtctgcccagtttacggcgcttatcgcatcagcgtggcgctgagtcaggaa<br>agcaataccggcgcgcactggcggcgatcctcgaagtgcttcaatacgcatggtgtgtgtctgtcgataaagaacgcaat<br>gcactgtttgctggcgaatccctgacatgacgtggcacggggaaaagaagagacccatgtcgcatcaccgggaaggcgtgatcggcgc<br>ggtgatgagccagccagcgccgtggttgttaccggcattcagacgatcagcgtttctcgaccgcctgaatatttacgattacagcctgccgctgatt<br>ggtgtgcgatcccggtgcggcgataatcagcgcgggtgtgctggtcagccgcatggcgttgcacgacagacaggtcgggctgcagtactgcgcg<br>gttttagaaatggtcggccaattcatcagcagccactgcgttctgccacgccgggaatcatcgcctgtcaaacgccggtccggtcagtgttccg<br>cgccagttggtttgacgcagcatggtcggagaaagcggatgatggccgtcggcaggtttccaaatggatcaccaccggttctg<br>gtcggtggtgaaagcggcaccggccaagaactgatcgccaatgccaatgttcggtcatgaaacgaatgtcggtcccgcgcatttgtgaaattcaaatgcgc<br>cgcgctccggataacctgctgaaaacgaatgtcggttcggtcatgcaatcgagcggccgtttctgctgaagcggcctttgaact<br>cgggtcggcgggcaatacccgctgcaaagttgatgtgccgccattattgctgccaccaactaactttgaggagggaagttgccgggaattttcgcga<br>agacctgtattacgccgacgatgccggttcgcgccgcagttcggttgctggtgcggtgtatcgccgatcgcactacagctggccagcaagtgcgtaactggaa<br>attggctgcgtcaggggcgggaactgcgcatcagtgatgtgcggtgtgctgatgacctacagcgtcaatcaccatgtcccggcctgtcgtca<br>aaccggtctgccgtggccagatgaaagctgcagcgtggaatcgaaccgcagccggtgattgctggaactggctgaaaaaccggctgg<br>gtgcaggccaaagccgcgactgctggcacaccgccgctcgacaccagtcgctgcaccgggttctgcctgattatgaacctcaacatgcaccgtatctga |
| 93 | atgttgcacttctcttcgttttgcaaagccacgcgcagagttgctggcatgaacatcctgaaaacctgccctcccgatgatgaacagct<br>ggctgtgtgagcagcagtgaattcatgacgacgacgttgctggctgtttccgagtggtgcatgaaaatgtccaaaatctcgaggcgcaggagtg<br>gcaacttaccgctcgcagtggctggatgaatcagctgacgcaggtgactgacgaagccgggttaatgaaagcttcgtctgtcgcgcgcattctgac<br>ccgaattggtggtgtcacagtccgcgcaaccagcgaagcaaagatacgcttcaccagctgagtgaactggcggaattattgattgtcagcgccgt<br>gactggctgtatgccgttgtcgcggggttcgcggcacatcgatgtttgctcatcatcggagatgaaatgctgaatgagcccgatggcaactc<br>ggcggtggcgagctgaattctcatcatcgactcgacctgatttttgctcatccggaaaaatggccgccagcagttttgtctacactggataacgc<br>acaattttccaccgggccgccagcgtcgaacagcgctgatcagcccatcatcgacgtggtcatcatcgggcatgctggctgtcggctcgtcg<br>gcgacagtggcccgctggatgagctccccggcactggagattattatcaggaacacaggggcgactggaacgcaatggtgaaagcg<br>cgtctgatgggtgggcggcgggagacatcagcagttaggaacttcgctaaaatgtcgtcgcgctattatcgattcagtgtgatccagtc<br>cctgcgtaacagtgaaagcggtgctgctgtggaaagacaaacatcaaactcggccgcaggcggtatcgtgaaattgaa<br>tttatcggtcagtattcagccgcgatgaatcgacgcaggtgactgacgaagcccgttaatgaaagcttcgtctgtcgcgcggtgaaatctgggg<br>ctgctgccgcagcagtgtcgagttcgcgccgctgccgctgaacacctatctgtctcctgcgacgtctggaacacgctgtgacgagcaaacgcaa<br>acttaccgtccgatgctgactgatttaacgatctgattggcgatgacacgcagatgccgaagatgacgtgcaactctccggttcgatgacagtttatggattgatac<br>gctgagcctgacgatcgtatcggctgcgttgctgcgcaactgacgaaaatgctcacatcagttttacatcagatgctgatttcgccgtgacgtggat<br>aaacgcacgacgacggccagtgcagtcggcgtcaatatgtcacgcgcacgacgtatcgagctgcgtggaatatcccgtggcgctcaaaaatgcgttaatacgtacgtta<br>cagcggctgatcgcagttgcagtgcagttgtggggcacgcaactctgcgcgccatccttattgccgccaacaagaactctgaaccggca<br>ggcggctaccgttgatgaactgaccgtcgcccggaggcccgtgctgccgcgccatgaagtgcagaagactgagtgagcaacaacctgtttcacctccgacgtt<br>acagcattacgctattggcgcccgcgggatattctcggttgcgttgccggtgcagcagcaacccatcttcagcacgctagaagggcggattgccgttggttacg<br>gtggtgcaaccggtgcgtgggagcaacaaatgtcgtaaaatacggtcagccaaaatacggcgcggaagtcatgaccgacgaacgcag<br>gaaaacccggtgcgtgctgctgggtgcggctgggcagcgatcggatctggactcgcctcgctggcgcctggcattcgcgttgacccggtc<br>cattgacgggcgctcagttctatctgcgctggcaggctcggtgctggtcatcctgatctatcagcgaccgaccaacgacggctcattcttatgaggtttgaccggctg<br>tcgggcctggccgtccggtgctccgatgctgtgtagccaccatgaagctttttgctcagcatagcatcggcacgaagcctggagctcagcggcgctg<br>gtccgccgctgtggtttggtttatgtgatccgcaactgacgcagcaaattaatgccacgctcgcaacgttcttttgccgcgacgttatcgctggcgtacggcttg |

TABLE H-continued

| SEQ ID NO: | Sequence |
|---|---|
| 94 | cgtaaggaagtccgtgaaatgcgcgagaaatgtatgcccatctgggcagcaaaagagccgacgagtttgatctgaaagccgatccggtgcata acggatattgaattcatcgcacaatactggttctcggcttcggcgcatgatgagccgaagctgaaccgctgctgataacgtgcggatttcgaactgat ggcgcgacatgacatcatgccgaagaggaagcacgccatctgacgcaggcttacgtgacattgcgcgatgaaattcatcatctggcgttcgcaggaa cacgcgcggaaagtggccgcgacagcgcttgccactgagcgcgccaaatccgcgccagctgggcgaactggcttggctga |
| 95 | atgaaaaactttatccatcgatgtgggcttggtgcagtgggcttgctacctt cgcttgcatggcagcgagcaggcggcaaacggtgctgataac gcctttatgatgattggtaccggcgctggtattgttcatgaccgtaccccggtggtgtctacggcggtcttctacggcggtctctaaaaacgttttgccatgct gacccggttattgttactcttcctcgtgtgctcctgatcctccgatcctcagctcagctcagctcagcgaagtaaccgtctccgtgtggtttcagca acgaatgatgaaaggcattggctgaacgtgcgtgatatctctctcagcagttctgatttcactgatccggctgacttctctctatattccgatggctcacatggtatggg tgatcgtagtggtattctgaacgtcagcaggttctcgccgtggtatccggtgtcatgctgctcgcatctctgatccggtaggggggctatctgctg ggtaaacgccggttcttggcaaagaagcttccaacaacacaccggccctcaatcctgtatggcgcctttggggctggctccgcttca atcgggttcagcaagtgccgcaagtcctgttgcccgctggcttcctgaacactgtcattgctactcgtgccgcaatcctcgtctggacgctggttga gtggatggtgcgcggtgagctgccactggtcggtcggcaggtcggtatcactggtctgtggggggttgttctgccgtgtgatgacccctgatgtgtt cgtgttcatggcgtcgtggttgtcgtgttgtcgtgacggtgttcacgtcagctcactggcggtacggctacgcagaaggcgctgaccat ggccatcaggtttgggcgcagttcttcagcgtgcgtgaacattggtctcggtcaggcgttgttgcctcatcgtgtacaaagtggctgacatgatcgtag gtctgcgtgttcctgaagaacagaacgcgaaggtctggacgttaacagcacctagtataaaaaacgttacacacaataa |
| 95 | tgaatatcactgactccaagctacctatgtcgaagatta actaaaaact tcaagatgcaggcattcgcgttaaagccgacttgagaaatgagagaga ttgcttaaaatcgcgaacacacgcctacgccgtgttccttatatgtagttgtgcgataaagaggtcgaagcaggcaaagttgtcgttcgtactcgtc gcggcaaagactaggaagcatggatgttagcgaagtcgttgacaaactgctggacaaatccgcagcaggagtcatcatcaactgaggaataaa gtattaaaggcggaaaacgagctcaaccggcgcgtccaatcgcattaacaaagagattcgcgcgcaagaagttcgcctcaccggccgcgatggcga gcagattggtattgtcagtctgaatgaagctgaataaaaagtgaggaacgggcgtcgattagtagaaatcagtccgaatcccagccgccgcagtttg tcgaatc |
| 96 | attgaagagttgatcatggctcagattgaacgctggcggcaggcctaacacatgcaagtcgagcggtagcacagagagcttgctctcgggtgacga gcgggcggacgggtgagtaatgtctggaaaactgcctgatgggagggggataactactgaacggtagctaataccgcataacgtcgcaagaccaaa gtgggggacctccgccatcgcatcagactggtaccaaatcaacacggtcagagcgcggtaacggctcgtggtggaacagtcacatggcggatcctgggt tggcggatgatgaccagccgtcgtgtgaagaagcctccggttgtgaagctaactcgcagcgccggctaacacggtagctataccacgatgacgtta cccggagaagaacggcacctacctcgggttaggctcacagtccacgggaatagccgcggtaatcggctcagaagcttttaccgttacggctcaagc aggcgtcgtcaagtgccgccgctgagaagcccccggctcaaactcgaagtctaggtgcttgagggggtagaattc caggtgtagcggtgaaatgcgtagagatctgaggaataccggtggcgaaggcggcccctggctcacagactgacgaagcgtg gggagcaaacagatgattagataccctggtagtccacgccgtaaacgatgaattgagctgttgggcgctttcgggagctaacgcggtta aatcgaccgcctggggagtacggtcgcgcaagattaaaactcaaatgaattgacgggggcccgcacaagcggggagcatgtggtttaattcgatgca aacgcgaagaaccttacctggtccttgacatccacagaactttccagagatgatggcgtgcctccgggaactgtgagacaggtgctgcatggctgtcgt cagctcgtgtcgtgaaatgttgggttaagtcccgcaacgagcgcaacc |
| 97 | atgaccatggcgtcaatcgcgctatctcacggtaaagcggtatcggttcgtatcggttaaagcgatgggccctcgcgcctcgagatgggtaaga aagtagatcgtgagtcacggatcagactcaggacgtctctgcaaatcgcagtggcatggcgatgtccgtcgtcgcaccggcgatgtgatggcggaagt ggctcggccggaggatcggagctcgaagacgtctcaaatcagctatggccatggcgatctggcgtcagatttcgtcttctatgacgtcctcggc gacgtggtctcgggtcgcaccgttggatcggtcggaggatctacatcatcatcgtcatctcgcggagctgtctcatcaacagagtcaacaacatcatatcatgatcatctcccaaagggatggtcggaggtacggcaacaccggcaagatgcttcacgcgacaatcttgcccgcgacaacattgcagcggcacgcggagatccgcgga acgaatcatcatcagccggcgagaagctggcacctgagctgatatcgtcaactgacgcagaagatcgtcaataacaccaaaaagtggtgccga tgacggtgatcggttacgacccgacctgctgtcagcaggcgaatgaatatcggcaacttccacagcggagttcggcatccgatggactggatctgtctgtctgtca cgccgtgaccatgggcgacgagctggacctgctgatggagttggaatcatcccacaccacaccccgaattctcgtcgccctccgccgagatgggtaaga aaaacgcggcctga |

TABLE H-continued

| SEQ ID NO: | Sequence |
|---|---|

98 atggttaggaaagtagaagtaaaatacaaatatagaactaactgacatgaccattattaataagtcaataaaaaagcttaaaacacaaaccacttg
cttttaataataaaggaggggtggaagactacattagtagcagaagtatcaataaacttagtgcaaaagttcttattggtggatgcc
gaccctcaatgtaatctcacgcagtatgtattaagtgatgaagaaactcaggacttatatggcaagaaaatccagatagtatttatacagtaataagacc
actatccttggctaaaggatatgaaagtgaccccctataaggcatgaggagaattcggtttgacctaattgtcggtgacctagcttgctttacaggaa
gacctttagctggagactggcgagatgcgagatgcgaggaattaggacaactttgtattgcagagttaattaagaaagctcgtgag
ctaaatatgatttgtttcttgacatgggaccatcattaggcgcaatcaacaggcagtattactgacatggaattattgtctcccaatgtcaatcga
tgtatttcactatggctattaaaaatattggctccacggttcaatatggaaaaaagaattagacacaggattcggctttcagaggaacctagcgaatt
atcacaattatcaccccaagaaaaacaaagttctcgtgctaccaccaacaacaaagaacgcctggatacgtacgatcacattcagcttgagaatctg
aggaagaataaaaatcgaaacgtcgggtaaaagcgtatgagacacatggagaggtgttcctctcaaattactgagcatcttcataaactttatgcatca
aagatatgaacccaccacctggagatatacgtcattcaggtagttagctccgaaatcacaatcacaacagtccgatgatcagtgtctggtacagg
aaattacaccagactttgaaaaaagcgcgtgaacttatcgagatattgcaagaagatattcagactgctgctaatgtggcgagaaatag

99 atgaaggggaaggaaattctggcgctgctggacgaaccgcctgctgcacaaccagaagcaaaatcggctgcagccgctcaagccggcg
ctaccgccgggcggttggccttcgacggcgcagcggccgccagcgcgccccatcgccccatcgccgcacggccccatcggctgcgcg
ggcagccgtcgggataaccgccggccgcctgccacctgctgcacactcgcgccggcgcttatctacaacaacctgctaccggcga
tggaggggcgatgaaatcaggccgtctgccagccgcacagcacgcgcaccggcgtccgcgtctctgagcagtgttctacggcgta
aaatctggcaaccgaatggggcgacgtgatgctcaggcagtgattggccagccagtctggccaggtctcggacgagcggggatccgc
cggcccgcacgcacgcgtatgcgcctgattggcgaatcaatatcgccggaatcggcaggttctggcaggtctcgcgtgtgctcggcggcgctgatc
aacgtgaccgcgggggctgagctgcacggcgacgcgtggttgaaggcagctctcacggatccgcacctccgacgcttgctcgcagct
ggcgacctgctgtgggatgacaactccgcgacgcgcgccaggcgggcgtgatccgccgaagagcagggcggagcaggtcttgccgt
ggcgtgagcagtccgggcgacggcaaatgctgctctataccggcggaggcgtgaatcctggtcgtggtatcggccgcaggatgcggac
tggtggccacccgctgtcagcgtggtaccgctcaggcgacggcgacgcgtgatgtggcgcgcgtggaaagccggcccggctgc
atcccgaccgcctgctgcagtgtgccgtcatcaggccgcgcgctgatgatcgccgccgacctcaccctcgaaagcccggctgc
cgttctcgatatcaatcaggaggcgctgcgcctagccgggctatcaggcgtcatcaccctcgccgcctcgtctgacctgccagcccc
gctggccgcaaccgcataccgcgccggtggctag

100 atgaccaacgcaacaggcgcacctgcgctaacctgcgctcatccagggaagtcctggaggtgttccgaaccgcgccgcaaagagcgcagaaagcacat
gatgatcagcgatccgcgatggagagcgtcgaagtcgcattatcctgaacgtaaatcgcagcccgagctgatgcgatgaccgtgcgcgctta
tcgggctcgaaaggggtggtgtttggccaatcaaagacatggcccatatctcggcacctcgaactcacctctgattttcaggagccgatattgtttcgggcgcgataaa
gcgcaactactaccggctcagcggtgtcgacagctcggcacctcgaactcacctctgattttcaggagacctggccgataatcggcaatcgct
aagctgaccgcctgatcgaagagagcggcaccgtccgcctgaccacaggctgtatcgtcccgtggcctgcccgctgatcggcgcgat
gacatcagcgcgtagccagcaagcgcgctggatcaatccggtcgctgaacaatccggaaggagaatgaggggctgctgtcgcggatcgcaatcgct
ggccaccacatcggcgcaacgacgcggtggtcgcggcaatcgcgcgctcgcatgatggggctgtcgcgcgtttgcagcaccgtacaccggtggtgccgacggca
ccctgctgaccgccgggggcgcgacgcgggcgatcctcggccgctctaagcttaacctgctcgatcccccatatcggagagctgaaacctaacgggcca
agatcccatggatgaataaacttcttcggcccgaccagatggggcagcgccaaaatatcgcgccaatatcgccgatcaattgatgaccaccattcgccccaatg
cggaagggtgatcgcgcgcgcgcacgtcatcggagatcatcgcgtggagatcatcgcgccgctacgagttgcccataacgatgactac
ggggggtcgcgctgcagatcaggggcaccagcctcgtttacgatgccgcagctatggggtcgcgtccggagctcggaggcctgaaacctgac
ctcatcggctccgggatcaaagagagaaaatatatcttccagaaaatgggggtgcgttcgcgtcccgacgtattccggcgcgtatccggccctatcacgg
ctatgacgggcttcgccatctcttgcccggatatggattgatgaacggtcgtggaacgactgactgccccgtgctggctggaagtctgcgtga

101 atggcagatattatccgcagtgaaaaaccgctgccggtgagccgattaaaaccgggcaaccgctcgggcgcaatcctccgcaccctcggggctggc
ccaggccatcccgcctggtccacggccccaggcgcgggcgcctttttattcagcattcagcaggagatcgccggtgccgcgtagtcgac
ggccatggaagtcaccaggttggggggccgaagatgggccggcgaatcatcttcaccctctgacaccctctgccgagcatcaagacggcatcg
tgctgctccagcaggctggagaagcgcaggcagcagcagtcgagatggctgcgccagttcgcgaggcatcggcagcctataacgaatgac
gtgatgcctccacgcaatacccggattttttggctctatgaaaaacgtcagcggtgatcgagaaaaacgtacagcgggtgcggccgac
gccgtcgcggggcagccgcccgggatcaaccgggtcaacctgctggtcagcaccctctcgttcgcagggatatcgaatggctcagccgtcggtgag TABLE H-continued

| SEQ ID NO: | Sequence |
|---|---|
| | gcctttggcctgcagccggtgatcctgccggacctctcgcagtcaatggatggccacctcggtgaaggggatttacgccctgacccagggcggcg<br>cctcgctgcgccagatgcccagagtctgggcaggcagcttcgccatggcgtgtcgccagcggcgcgatcgtcctgacccacgca<br>gccgcggcgacgtgatcgcctcgccgatcctcgaccatcgatgacctcgaccttatccatcagctggccgaagatgtccggacgccggtacc<br>ggccggatcgagtgagccggaccagctgatgaccctcaggggatcgactgactgcatatggcttcaggcgatggcgatggtgggcggggagg<br>gcgacctgctggcgggcggtggtgattcgccgcagcaggggatcgagcagctgctgagccaccaacccgcgctgatcctgtgtggctaactctcacgc<br>gtgccggatctggcggagcagtctgccctgcgctgcccgtcgtttcccctcttcgacggctcggtgagttcgtcgtcgtcagggtacgc<br>cggatgatcgagatacgcgtttgaactctgctgcgcaaccgccatcacacccgctcacccgctcgccgtcgccaggggcgcgac<br>cccagccggcttcaggagacgcttatgcgccattaa |
| 102 | atgagcaaacgatcgatgatcagcgtgtatccgttgaacaggatgaatccagaccgtgttccagaataaaagaccctgaaggaggcg<br>cacgacgcgcgcgaggaggttttgcctgaccaccaccgcggaggctcgagctccagcggcgctgaccgtcgaccc<br>ggccaaagcctgcagccgcctcggcgcgctggtcctgactctgcgctgggtcgcgcgggtcgcggcaacaacaac<br>atttcccacccacttcaacccccatttaaagagcggtgcctgccctcgcgactccatgaccggagacggcggtgtcggcgggcaacacgatctgca<br>ggaattcggccgcgaatgcagcggcctgtataaacccgagatatatccgcgttccaccaccgtatgccggaggtacggccgacgatctgca<br>gggttatcgccaaccgccaaaaagaggggattgcttggctgaccgacgcatcgcgccatcctccaccccagcttatcgcgaccaccatgtccaccgg<br>ctggacaatatgtccgaagggtcgcgaagaccttaccgctgactacgccggcgagcgagcggcaaaagcaaagccaatctggtcgaccgattt<br>gagacctatctcggcgcaacttccgcgtgctgaagcgcggtggatggcgcagatgatgtccggatgatcccaaagcagaggtgctcgaca<br>ccccggccgacggcactaccggatgacgcggccgacccaccagggtcgcccatgaccctgctgccggcatt<br>gccgtggcgtggtgaaaagcaaaagtggttcaggagatgtggaaccagccgcgtctgaccgcggcggcgttcgctgtgacatgtggat<br>gacgttgctgctgatgaccgtcagctgaccggccgaaacgatcgccgacgtcctctacggcgatcctgtcgtgagcgtgggctggctgagcc<br>tcccacaccctgctgctcatcaaagcgcaaaaatcggcctctacggcgatgaaaaatgctgatgtctcagccggacgtatcgatgaagacggaagtgttc<br>tggcaaaggcaaagcctcgaagtgcgctcggatcgcttcgttcgctgatcgccgccgccatcactcgacccgccaacgctgggcctgaa<br>ggcgcaatgaacatcgtcacgacgctggtgaacgccgctggtgaacgcccgagttggcaaaaccgattacacagcttcgac<br>ctcgttcgttaa |
| 103 | atgacccctgaatatgctctgataacgcgcgccggaggccatcgccggcggcgactcaacaacatccggggcgtgttttaccatggtggaaca<br>ggctcggtggccatcctcctcaccgatgccgatgcccagggatcattacgccaccggctttgcgccagaccggctattcgctggccaattgtt<br>aaaccagaacccgcctgtgccagacgccagagcccgccgagatctatcaggagatgacatcacccggtgctagccgcaagggactggagcattatct<br>gtcagctgattaatcagcgtcgggacggcgcggcctgtacctggtggagattgacaacctcacccgatgacctgctgaatatatccccgc<br>ggccggacgcgggatatcagctcagtcaccaatcagccgacactcaacggtggcttgatgatggacaacctcctgccctgactgcgcggagactgctcac<br>cgccggtggagtgtgagacgacagaggaagtcgggtggtgatgacagcgccggatgacgcgcggcggcgctgcgtcggtaacc<br>cagctgccagtgctcccctggccggcgtcagtgagacgacagcgagccgctacttatcgacgacgcgccggcggaccctgtggtggatcgccgactgacccag<br>cagcgtgacaggcagcaggcaaggcccctgaacggtgccaaatgaccgccgccgaagcctgatccgcagtcctggac<br>gccgcgctgaactcagctgcccgattaatatgtcggcggcctgtcggcgctcgtgctcgcatcgtgccatcctggcgctcagcccttt<br>cctggcgtgaaggggaagaggcgatgccggacgcgccggcggcctgtgcctcgatcgcttcgatcggctccgacggcccgatcaggccccgcagg<br>ccactgacgctgctaagcctggctcgctcgatctgacacaactacgctgtctgccgctgacaaaacctcctgacggctgcgatccactcgccgatcggcggca<br>agaacgacgactgcgctgctgtctgatccagacctggtggcaccatcggggcaccatcgcgggcgcaccatcgcacaggccgaactcgccgggca<br>aggcatggagtcgcgctgatccagacctggtggcaccatcgcggggcaccatcgcggcaccatcgcaggggcgcaggcgatcagcgtgg<br>ctgcgttcccctgcttaacaccctgaccggaggtgaagcatga |
| 104 | atgatccctgaatccggaccccgacaccacccgtcagacctctcagcagttcaccgcgatcaccggatgagcgggcggt<br>ccaccgagccgcaggccagcaaaacgctgcaggaggtgctcagcgctattacacaagatgctttatgcagcacacggactgatctgctcgtacgacagccgagc<br>aggagatcctcagtatcgaagcgctgcagcaaccggcagcgccctccgcagcacccgcagatccgctatcgccccgcgagggactggt<br>gggaccgtgctggccaggggcagtcgctggctgccccgggatcagcgcaatagggtgcgggagcggacggatcagcgtttctgaccgcgattcctacgatctg<br>ccgtttatcgccgtaccgttgatgggccgcaacgccggccaataggggtgctggcgcggcgccggatctggcgcgccaggagcggctgacc |

TABLE H-continued

| SEQ ID NO: | Sequence |
|---|---|

105

```
cctgcacccgttttctcgaaaccgtcgccaacctcgtcgcccagaccatccggctgatgatccttccggcctcaccccgcctgtcgagccgccagccg
ccgaaggtggaacggccgccctgctcgtcgtcgcgctgggcctgggcctggacaaatggtcggcaagagcccggcgatgcgcagatcgtgg
agtgatccgtcaggttcggcgctggcgacaccccgtctggtacggcgcaccgggaaagagtgatcgccaacgccatccatcac
catccgcacggcggctggcgcgcctctgtcaaattaactgcgcgacaccctgttcctcgatgagattggtgaaagcagcgcctcgtt
gccttaccgggcggtcgtcagcgtaaagacgtttgacgtggcgatggcgaggcggcggcgatgagaccctcggcctgaatgtccgatcatcgcgcc
ccaggccaagctgctgctgtatcctccaggagggggagatggagcgggtcggcggcgatgagaccgcggcgggtgaatgtcggatcatccggcgc
accaacgtcacctggagaggcagggagtccggctggcccattccgcgaggatcttctactatcgctgaacgtgatgccctgccccgctgc
gcgaggtgcaggaggaacatcgccagaggtgccacctcctggtacggcaaaatcgaccagggccgtcctcggtcagggcgaggggcg
cgatccggctgcgtgatgagtacagcggctggccgggtaacgttcggaacttcgcgaactgagaactgctcgccggcccaaagcccgtgcaggccga
tcgatccgacgctgatcctcttcactcaccaggatcgcccgcgtggaaaaagccgtgggtcgaggggcacgcggccagtgacgccgccgcagccg
tggacgaacgtcagcgactgatcgacgtcacccgcgtctgg
tcgcttatcgcttatccgatcatggatcatcaccctgccgcgccgtctgag
```

106

```
atgatgcgcttctctcgcaatacacagcagcactggcagacagtccgtgacgtcgtgcgccagcgagcctccagcggatttccatttgccgaactgagccacaggccag
gtcggtcatggcgtccgagattttgtcgaacagagttgatcgccccagccgggcctgaatgagcttggcgactcctccggcgaggcggaagag
tggcgagcattacgaggccgttggccgcctgcacggcctgcatgaggcgggggttgatgcgaagcgggggtctcttccgccggcgccagatg
atggtccgcatccctggcgcagccgctgtcctggtgagcgaagaagactgccaatgccaagccgagccgcagccgccgtcttcggatgg
gcccgactggctgctacgcccgcctgtataggagttgggaaacgccatgcaatctgataatctgtcctggccagcatggcgcaccgcgccgagct
gaaagctggcggcggcggccgtgaactctctcccgatcagcacatctttgaagggcctcgggcgaaagtcggcgacccgagct
gatataacgccccagttattaccgtctggggcgcctgataccagttcggcgctgaagattattaccaggagcaggtgggactggaacgctatcgat
tcgggccgttggcgacagtgggcgcctggtactcagttcgcgccagcagctgcgtggaccagcgtgcgcgatgtgctcattcgtcttccgcgcttatcgacttca
ggtgaaagcgggatcatgggaatacgacggcgtgtacgcagtcgcggcgagcggccgagtgagtcgcggcggccagcagctggatgcatcaagctcggccgcggcgg
gcgtgatccagcgctcgcgtcaacatgaaagcgcatgaactcaatgatcgccgatgttaatgaactgggcgatgaggatgcctaaacgcaaccatcaagctggccga
gtactggcgcgagctggcgctggcggaagaagatgagcgaccccggcgccgctggccgcatttaaacgataccgacccgctagcgtgtgg
cgctgattcgtaagagctggatcggaagctgccgccaccatgccgccgcgcccgcccagtgctgatcgccagtcgctgagcga
aactctgctcgcgcgccgatgcgccgctctcgccggatcacggcgttgaccgggatcgtaccccggaccaactatcttgagctgctgagc
gaattcccccgggccgcggagcgacctgatcacgctccgcgacggctcacgcgacgagctcgccgccgagctgcgtcgcgtgcgccagtcgct ggatga
agagcgacgaggccgatttctaagagctggcgcagttcacgaagtgacagcccgcggcgatatcagcgggcggggatcctcgctcgtccgccggatgaagg
tcagcgatcacttaacctggctgccgaagcgatcctgcgacgggtggtgacaggcgcgtacggctgggctggaagctggcctacagctcgatcgtgttc
acctgcgcatgcccgggtccgggaggtgatgaccgacggcggagattgacggcgcctcttctacctgcggcggcagtctacctcggctgcccagccgatcatgcacct
ctccatgactgcgccgcgcggaggtgatgaccgaacaccctctcacgaagtgacgcctcctcggcgccggcggctggtcaccaccgccgccgag
gttgctgactatcagcagaacgaagccgcggtatctccgatcgcggcggaacatcaggcgcggacccgggatcaccgatattattattcagtatctggtccctacgctatgcc
cacctggcaacaaacatcccgatcgtttgatcatcaaagcctgcggttcttgagctgctggacaacgtcatgacgaggaggcgcgggcc
agtgacggtgaccctgacgctggcgcaactacctcgtcttgagctgctgacaaccacgtcgtggaagagatcgaa
gccggcaaagtgccgttgacccgctggcacccgcgcgggagaaagaccctcggcgcacgaccctgcaaagaatcgcaaggctagaattcgca
cttaacgcatgcgacacaccctgcgtgatggctccatcacctggcctgcagaggcagccggaacgtggcgacgttcagccggga
gcgtcagccaggtcagccggtcagccaggtcatgagcgaggctggctgatggcttaa
```

106

```
agcgtcaggtaccggtcatgattcaccgtgcgattctcggttccctgagcgtcatggcatcctgagccgcgccgctcattggcatcctgacgaagagttcggtgcttcttcccaacctg
gattgcaccagtcaggtcaggtagtgtcatgaataattaccgattccaggctgaatcagcgctaacgaatcgacgcgaaactacaaaatgcgggcattcgtgta
aaagcagcagacttgagaaatgagaagattggctttaaatcccgagcacacnacgtcgtgtcccgtatattggtcgtggcgacaaagaagagtcgaa
gccggcaaagtgccgttggcgcacccgctgcgacctcggcacgaccggcaaaagcggggaaaagaccctggcaacaaagaagattcgca
gccgcagcttcaacaactgggaggaataaggtattaaagcggcgaaaacgagtcaaacggcacgtccgaatcgtatcaatggcgagattcgccccct
ggaagttcgc
```

TABLE H-continued

| SEQ ID NO: | Sequence |
|---|---|
| 107 | atgaaaatggcaacaatgaaatcgggtctgggggcattagcccttcttccgggactggcaatggccgcccgcagtggcggacaaagccgataac<br>gcgtttatgatgatttgcaccggcgtggttctgttcgtttatgaccatccgggggatccgcggtgtttacgggcgctgatccggcaaaaagtccttccat<br>gctgactcaggtgattggtgacccttggcctggcctggcctctgctgttatggctataccggcctatacctccacggccttccaggcgcttcgcctgtcggtagttt<br>tgactgggtgatgctgaaaaatattgactgaaagcgtgatgccacctctcatcagtacatccacgtgccttcaggcgtcgttcgcctgtatcacc<br>gtcgggctgatcgtggggcggcgctgctgtcggcgaccaccgcgctgacttcgccgcgtcgcgggcaaccatcaacgccgtgcctgtgcggtggt<br>aggtctggcacatgatggcaaacgtggggctcggcaaagaagtcaaaccgcacgaggtcaccgacctggttcaccgaaccgccatcctctac<br>gtgggctgtgtcggctcaacgccggctcgccagcgagcgacgaaattgccgcattggcttcgtcaaacacgtcgtccggggcttggcgtcacacca<br>tcctggcgtggcgacctttggcgatggcgaatggccctcgcggcgtaatctcactgcctggggcgatctgggcgtctggggtctggttggcgtcacacca<br>gctgatgcaccctcgcgacgtccgacgtcccaggcgcgtcccgagtctcctgacgctatcctcggcgcaccctctcctggcggcgt<br>gggtatgcagaaggcgtcaccatggcgacgtgggcgtcggcgtcggcgtggctccatctcgtcggtcgggcgttcgtcgcttcattgg<br>ctacaaagtgggggacgatgacggtggggctgggcgtgcgcctaccagaagagcaggagcgcgaaggactggacgtcaacagccatgccggcaaacgccta<br>caacgcctga |
| 108 | cgccgtcctcgcagtaccattgcaaccgacttcaacgccgacttcacagcaagaagtgatcctgcacgcatggaacaaattcttgcagtcgggcttatccgatgacga<br>aacgcacagcttttatgagcgcggagtgttgtatgtatagtctcggctctgaggcattagccgcattgggcgattttcacaagcgctggcaatccgaccc<br>gatatgcctgaagtatcaattcaattacttactaaccaggcaggcaattttgatgtgccatgatctgatctgcctatgcctctgactctgatc |
| 109 | gctaaagttctcggctaatcgctgataacattgacgcaatggcatcattgatgccctttgcacgcttcatccagaacctggctc<br>atcagtgattttttttgtcataatcattgctgagacaggctctgagaaacgcggcgttatacaccaaaccatcgagcgagcgtagcgcacggcaagtcagcgtt<br>ctccttgcaatagcaggggagaggcccagaaccgcagcgttgaacggcttcagtgtataatccgaaacttaatttcggttgga |
| 110 | gcccgctgaccgaccagaacttccacctggactggctatacccttggcgtgacggcggcgatactggactacatccccattccggtgatctta<br>ccattggcgtcaataggttacggtccggcgacttccagatgacctattccgggcacctacataatcgggctgagatgatttaattcgctggcggtcgtataca<br>gtttaattcgtcaagtcgttagcaataaatgagataagcggtgtcttgtggaaaaacaaggactaaagcgtaccccactaaaaagatagcgactttat<br>cacttttagcaaagtgcactggacaaaaggtaccacaattggtgtactgactactactgactcgattttcatataaaggtaattttg |
| 111 | ttgaagagtttgatcatggctcagattgaacgctggcggcaggcctcacacatgcaagtcgagcggtagcacagacttgtctctcgggtgacgag<br>cggcggacgggtgagtaatgtctgggaaactgcctgatggagggggataacactactggaacctgcacaagctagcaataccgcaagacccaaag<br>tgggggaccttcgggcctcatcgccatcagatggtgcccagatgggattagctagttaggtgaggtaacggctcaccaaggcgacgatccctagctggtct<br>gagagatgaccagccacctggaactgagacactggtccagactcctacgggaggcagcagtggggaatattgcacaatgggcgcaagcctgat<br>gcagccatgccgcgtgtgtgaagaaggccttcggggttgtaaagcactttcagcggggaggaaggcgntnaggttaataccctgattgacgttac<br>ccgcagaagaagcaccggctaactccgtgccagcagccgcggtaatacggagggtgcaagcgttaatcggaattactgggcgtaaagcgcacgca<br>ggcggtctgtcaagtcggatgtgaaatccccgggctcaacctgggaactgcatccgaaactggcaggctagagtctgtagagggggtagaattcc<br>agggtgtagcggtgaaatgcgtagagatctggaggaataccggtggcgaaggcggccccctggacgaagactgacgctcaggtgcgaaagcgtgg<br>ggagcaaacaggattagataccctggtagtccacgccgtaaacgatgtcgacttggaggttgtgcccttgaggcgtggcttccggagctaacgcgttaa<br>atcgaccgcctggggagtacggccgcaaggttaaaactcaaatgaattgacgggggcccgcacaagcggtggagcatgtggtttaattcgatgcaa<br>cgcgaagaaccttaccggtcttgacatccacagaacttcagagatgagatgtggccttcggggaactgtgagacaggtgctgcatggctgtcgtcagctcgtg<br>ttgtgaaatgttgggttaagtcccgcaacgagcgcaacccttatcctttgttgccagcggtcggatgggaactcaaaggagactgccagtg<br>ataaactcgaggaaggtggggatgacgtcaagtcatcatggcccttacgaccagggctacacacgtgctacaatggcgcatacaaagagaagcgac<br>ctcgcgagagcaagcggacctcataaagtgtcgtcgtagtccggattggagtctgcaactcgactccatgaagtcggaatcgctagtaatcgtggatca<br>gaatgctacggtgaatacgttcccgggccttgtacacaccgcccgtcacaccatgggagtgggttgcaaaagaagtaggtagcttaaccttcgggag<br>ggcgcttaccacttgtgattcatgactggggtgaagtcgtaacaaggtaaccgtaggggaacctgcggttggatcacctcctt |
| 112 | atgaccaatgcggtcaatgcgctatctacggtaaaggcgtatcggtaaatccaccaccaccaccagaatctcgtcgcggccgcctcgcgagatgggtaaga<br>aagtgatgatcgtcggtcgcggctgcgatccggaaagcggactccgacacgtctgatccttcacgctaaagccagaacaccatcatggagatgtcgggcggaagt<br>gggctcggtcggaggaccgggattcggcaggatcgagaagacgttcgcccatgcagtgatgtccgttgccgcaatccggccgggaccgcaggccgtcg<br>gctcgcccagaaccgcggggtgatcaccgccatcactctcgaggaagaaggccatgaggagatttggatttcgttcttatgacggctcctcggc |

TABLE H-continued

| SEQ ID NO: | Sequence |
| --- | --- |
| 113 | gacgtagtctcggcggcttcgccatgccgatccgcgcgaaaacaaagccaggagatctacatcgtctgctccggcgagatgatggcgatgtatgccg<br>ccaacaatatctccaagggaccgggccatctgaagtgcgaagctggcaaggtgcgcctcggcggcctgatctgtaactccgcaaaacgaccggaag<br>acgaactgatcatcgccgtggagagaagcttggcacgcagatgatccactcgttccccgcgacaacattgtcagcgcggagatccgccgga<br>tgacggtgatcgagatacgacccgtcagcaggcgaatgaatatcgtcaactggcgcagagatcgtcaataacaacaaaaggtgtgccaa<br>cgccgtgcaccatggacgagagctggaatcgctgctgatggagttcggcatcatggaagaagacacaccagcatcattggtaaaaccgcgctgaag<br>aaaacgcggcctga |
| 114 | atgaccaacgcaacaggcgaacgtaaccttgcgctcatccaggaagtcctggaggtgttcccgaaaccgcgcgaaagagcgcagaaagcacat<br>gatgatcagcgatccgcagatgagagcgtcggcaagtgcattatctcgaaccgtaaatcgcagcccgggtgatgaccggcgtggtgcgcctat<br>gcgggctcgaaggtgggtggtgttggccaatcaaagacatggcccatcacatcgcacggcccatccgctgcggccagtactcgcgccgacg<br>gcgcaactactataccggcgtcagcggtgtcagacttcggcacctcgaacttcacctctgatttcaggagcgcgatattgtttcggcggcgataaa<br>aagctgaccaaacgtcgaagaagtgagcgatccatccagtgagagtccggtgagccgtggccgtgccctgatcggcgat<br>gacatcagcgcgtggccaacgcagcagcaagcgcgtggataaaccggtaaaccggtcccgtgcgctgcgaaggcttcgcggcgatcgaatcgct<br>gggccaccatatcgccaacgacgtggtgcgcgcgacctggtgtgcgcggcgcagccgttgccagcaccccgtatgtggttgctgccatcatt<br>cctgtggatgggatgaacaccccattcgttaagcttaacccttcgcatgactatcgcccgccatatggaggagaaacatc<br>agatcccgggatggaatataacttcttcggccccgaccaaaatcgcccgaccgaatcgctgcccaagatccgcgatcaattgatgaccattcgccccaatg<br>cggaagggtgatcgccaaatatgagggcagatggcgccatcatcgccccggttggagggcaaagtgctcgtacatg<br>gggggctcgcgccgccactcagtcggcggctcatcgccgccggatggagatcatcgccgcgcctacgagttgcccataacgatgattac<br>gaccgccctgcgaaagaggcaccctgaaggaagaggcacccgtgttgacgatgccagcagctagctgaggccttgtcaaagcgtgaaacctgac<br>ctatcggctccggatcaaagagaaatatattcttcagaaaatggggtgccgttccgccagtgactatctcgggactatcggcccctatcacgg<br>ctatgacgcttcgccatcttgcccgatatggatatgaccgcgtggaacaatccggcgtgaacgaactgactgcccgtggctgaagtctgcgtga |
| 115 | atgaaggaaagaaattctggcgctgctgacgaaccgctgcgagcacaaccagcagaagcaaaaatccggctgcagcgctcctaagccgcggcg<br>caaccgcggcggcctgccttcgacgcgcgacgcgagataacgcctccgccatcgccacctggtcacggcacccgccatcggctgcgcc<br>ggcagtcgtgggataaccgcggcctgttccacgcgccgcgctcccgcgcgcgtcagcggtcttatctacaacaccgtccgtaccggcg<br>atggaggggatgacctggaggcgtcggaggcgtgcgtcggcaggcgagctatcaggcgtggtcatcgccatcgaccgccggttctacggcag<br>taaaattctggcaccgaatggcccgccggggccgatggcctcagcgaggcggcgcctgtcagcgcagacacacccctttg<br>cccggccagcgccacgatatcggcctgatggctgatggcgaaaattcaatatcgccggagatcatcggtgtgctgcagagctgggatcc<br>gcgtcccggcaccgcctccgggccgacgcgcgtcggcgtacggcacgccggttgaaggcagctctacaggatctcccgcgcggctgacgccggcggctga<br>tggcgggccgtcgtgggggatgaaccgccgccaccggagatgatcgaccagggcgctgatcggcgcgtgacaggacaggcggctggcgccgg<br>tggcgcgagcagctccggtggcgcaaagtgttgctctacaccgaggagacaaacagcgatccgtgacctgatgggcgacggacgcaatatcggcgatcaccctcggcatgacc<br>aatgcccgcctatcaatccaggagcgccggaaatcaacgctatcaggcggaacctgacgctcgccggcggacgatatggtacacccgctgtggaaagcccggctg<br>ccgtttctcgatatcaatcaaccgaatcaaccaggcccatcaggcgcgcgacccactccccgccgtcctgtctgacccctgccagtcc<br>cgctcggccgcaaacgcataccccgcccgccctggccgctag |

TABLE H-continued

| SEQ ID NO: | Sequence |
|---|---|

116 agctgccgtcgatcagtcgtcgtcgcggggatcttgaggatctgcagcagtcgctgagccaccaacccgcgatctcttgttggctaactcttcacgc
ccgatctggcggagcagttgccctgccgctgcgtcggtcggttttccctcttcgaccggctcggttcgtcgtcgtcccagggtacgc
cgtatgcgagatacgctgtttgagctggccaatctgctgccgaccgccatcaccaccacccgcctcaccgctcgccgttcgccagggcgccgac
ccctgccggcttcaggagacgcttatgccgcccattaa

117 atgacccgaatatgatgctcgataacgccgcaccggaggccatcgccggcgcgctgactcaacaacatccgggcgtgtttttttaccatggtggaaca
ggcctcgtggccatatccctcaccgatgccagccaggatcattacgcaccccagcggtttgcgccagacggctattcgttggccaattgt
aaaccagaaccgccgctcgtggccagacgaccgggccggccttatcaggagatgtggcataccccctgctccagcgtcagccctggccg
gtcgattaatcacgctgggacggcgggctgtgccctgcgccggagagcttcaccggggcactggaactgaagcattatct
ggcgatgcagcgggatatcagcgtcagcaggatcggtggtgatggacaacctctgccgtcgccgcgctgctgcctggcctggcagtcccgc
cccgtggtggtgacgagcgacgacgaggtcggacgccccggcgtgagcgatcctgccggtagcctgccgggccgcgccggctgtcgtgtca
ctgctggccgttgcccccggcgtcagtgaagaggccagcgccgctacttatcgacgcagggccttggcgggatgggatcccgacctgtaccca
gcagcgtcagcacgaggcaaggagcgcttgaccggcgatttaatatctgggcggcagcagaaatgaccgccgcgtgtggcgtgctgga
cgccgcgctgacctcagttgaatacgctggctggcgttcagcgttgctcagctgtgccccacctcgcctcggtcctgcgctgaactcgtctgagccctt
tttcgaacatctgtgcccctctaccccgttcgacgccacctgcctgcggtctgacatggccatcgatccccttggccagcgcaccgcac
cccgtctgtcggccgtctgcttaagcctgtgactccatctgacctgatgatctgacccatcgggggtctgccaccaccccccgacggccgggctatgccggta
gagaacgacggcttggctggcgtgctgtacctgactgataacctaccggctgggcaccatcgggggctgtccggtctggggccacctgcgctgaccc
aggcatggagctgcgcgccgatccagaccctggtggcgacctgtggggctccgtctggccgcatctggtggcggccaccatctgaactcgctggcctaac
ctgcgttcccgctgttaacacacctgaccggaggtgaagcatga

118 atgatccctgatccggacaccaccgtcagacctctccagcagttcaccgcagtcaccgcttaccgcttcaccgcctggatgtcggtgtgtgctgagccggg
ccacccgaggccgcaaaacgctgcaggaggtactcaactgccttatgcacaacgatgccttatgcagcacgggatgatctgcctgtacgacagcgagca
ggagatcctcagtatcgaagcgctgcaacagcgccctccccggcgccagcgagatccgcatctgccccgcgaggacctgtgtg
gggacgtctgccagggcagtcgctggtgccccggtgctgccgacgatcacggtttctcgacgctacgcctacgattacctgc
cgtttatcgcgtgatgggcccaacgcgccggctggcctgatgccctaccggctgatcctctcggcgccgcgcggaagaagagcggctgccgc
ctgcaccccgttctctgcaaaccgtcgcccaacctcgtcgcgcgggcgtggggccttgacaatatggtcggcaagagccccggcagtcgccgcagatcgtgga
cgaaggtggaaacggccggccgggcctcgtcgtgcgcgggcgtgggccttgacaatatggtcggcaagagcccggcagatcgtgga
ggtgatccgtcaggttcgcgctgcgacccacccgtgaccctggggaaaagtgatcgccaaccgcaccatccatcacc
atccgccacgggcggtccgtcgctcgcagcgtaagcacagggccgcctcgcagctgaccttacctcgcctggcgcctcgcaaatttaactcgcggttgagctggcggatgcggccacccgtttcccagcgatgctctattatctgaacgtgacctgcgatattggtgaaagcagcggcctcgttc
cctttaccgggcggcggtcggccttgcactcctccacggagaactgccctgcgacctcggggtgaatgcgcatcaticgcccgcca
ccaaccgcaagcgctgctgctgatccgccgggagagagtcggtggtgaacgcggccatcatcctgcccccgccctgcgc
gagcgtcaggaggacatcgaccgctgctgatggagtacagctgccgggtacaggctgccggggtaacgcttcggccatgagaaaagcg
atccgctgctatggagctgatccctcactcaccaggacttcggcaacttcgcggagaactgcctcagcggggtcgaacgtctgagagttgtgttc
gatcgcgacgtgatcctctcattccaccagccggctcccgcgggtgcagtgggaggacgccgcgcaggctggctggaacagcctt
gggcattacgggcgtgcggcagcctgcgctgtcctctccgaggcagctgccgccacgcagaaaagccgcggtgttggctggacaacagcct
gaacgtcaggagcttccgagctgacgctgacctgccctacgggcctgacctgccacctgcctgtcggtgcaagagcacccgcacggccgccgcgacggtcggggatgacgccggccagt
gagcgtcaggaggacatcgaccgctgctgatggagtacagctgccgggtacaggctgccgggtaacgcttcggccatgagaaaagcg
cgctaccgatccagatcatggatcacccgcccgtctgtag

119 atgatgccgcttctctcgcaattacacgcagactggcagacgtcgctgaccgtcgtcgccagcgttccccattgcagaactgagcccacaggccag
gtcggtcatggcggtcagatttgtcgaacagagtgatcgtgatcgcccagccgggcttgagcttgcggacttcctcgccgaggcggaagag
tggcggcattacagaggcctggcgcggatgccgctgcgcactgacgaaggcgggttatgtcgacagacccctgagagccgccgagatg
atggtccgcagcatcgctgggcggcggcaggcgctgtcgctggtgagcgaagaagagaaccctgagcagcgccgggacccctgattgtcgc
cgccgcgactggctcctcacgcgctgctgcacggagagaacgcatgcagcgagggcgccagccgcaccgtcgtgatcctcggggatgg
gaaaagctgggcgggtggcgggagctgacctgaactctctcggagctgctgaggatcgattctgatattgtctgatatcgataattgctctcgacgacgagccagcgt
ggataacagccgaccagttcttaccctgtgggcagcgatcaaggcccttgaccagcgacgacggacggggtttgctatcgggtgacatgcgcc

TABLE H-continued

| SEQ ID NO: | Sequence |
|---|---|
| | tgcggccgtttggcgacagtgggccgctggtactcagattgcggcactggaagattattaccaggacgcaggtcggactggaacgctatcgat |
| | ggtgaaagcgcggatcatgggcgatacgacgggcgagtcgctggtgatgctccgcatcgcgtcgcctcttccgcgttatatcgacttca |
| | gcgtgatccagttccagtcgctgctcgtaacatgaaaggcatgatcgcccggccgagtgcgctgccgaacctgaagacaacatcaagctcggccgcggcg |
| | gatccgtgaaatgagttatccgtcaggtattcagcgtcgccggtgatccgcggctgcgcgaggcctatccgtccgctgcgggctgcg |
| | cgattgatgagtcacatctgctccggaaggcgacgcgcgtgtcgcgaggccatctgtccgctgaaaacctgctgaaagcat |
| | caacgatgaacagaccagaccctgccgcaggatgaacttaaccgccagctgggctggcggaagatgcataccgaagactggagacgctgagc |
| | gcgagtcggcagtcgcatgccaacgtgcgcgggagtgcggcgagcgtgttaatgaactgatcggccatgctccggatgagcaactggccga |
| | gtactggcgaggctggccgaggaagaacgccccgcgccgctgccgctgctttaaacgatacgacgctagcgtgctgg |
| | cgctgattgcccgatttcgtaaagagctggatcggcgacaccatcggccctggccgccgggccgcgtcgatcagcagctgctgatgctgtgagcga |
| | aatctgtcgcgtgccgcgtgaagcacctgatcacgctctgcggccggctgcaccgcgtggcgcagcgtggcgccacccgctgctgctggatgag |
| | ctgctgatcccaacaccctctatcagccgacccgatctcgctcgcgagctgtcgtgccagatcatgcaacctgt |
| | gagcagcagctgagggcgttgcggcccagttaacgaggcgcagcggcagctgcatatcgcggcggatatcgcggcggatatcgcgaggata |
| | cagcgatcaactaaccggcttgccgagcgatctcgcgcagcggccgcggagctcggatgagctacggtcgctcagccgaccca |
| | cctgcacgatcgcccaggtcgcgcgctcgctgtcggcctgtcggatcgcgcgcgcgcgccagtttcacctgccagcgatcatcatgcacctgt |
| | tccatgactgccgggcggagtgatgaccgacggcgaggtttacggccgcccgcagttcacctcggtacgatcctggatcatcatgcaccctgt |
| | tcagcaccccgcacctcgtccggtcattcctacacaagtgaagtgacagtggggaacatcaggcgtggtgcgcgccgggtagtctgcgcgaggttc |
| | tgctgactatcagcagaacgaagcctgacggaacgtgggaacatcaggcgtggtgcgcccgcgtggtctatggcgacggccgctggaccggcgct |
| | ttgacgcggtccattcgcgcgatatcctcgcgatccccgggagggagccgaccctgcagaccgagttccggctcgccaccac |
| | cttggccaacaaacatcccgatcgtttgatatcaaagccgatcaccggggatcaccgctatctgaacgttacttattatactcagtatccgtacgctatgccagt |
| | gacaagccgaagtgacccgccgctgtcgtcgacaacgtgcgtccatcacctgagctcggccgagaacgacacatgccggacacctggccgcggccgcctta |
| | agcatgtcatacaccacttcgtgaccgtcggctccatcacctgagctcggccgggacacctggcgccaggaggagcagcccggcgggagacg |
| | tcagcagtcagcgcagctgcagctggcgcagaagtggctgtgatggcttaa |
| 120 | atgaaaatggcaacaatgaaatcgggtctggggcattagccatcttccgggactggcaatgcgcgccccgagtggcggcaaagccgataac |
| | gcgttatgatgatttgcaccgcgtcggttcgttttatgacaccatccgggatcgcgctgttttaccggcgctgatccgcgcgcaaaaagtccttccat |
| | gctgactcaggtgattgacctttgcctgctgactgtgggtacttggcgcacctttatcagtacacatccaccagcttccgcctgtatcacc |
| | tgaccggttgatgtgaaaaatattgaactgaagagctgactgagcgtatcgtcgattttcgtggtgtggtgacggtctctttattgtccgattcggca |
| | gtcggcgatcggggcgcggctgctgcggcgaccacggccgtgacttcgcggggcgctcgcggggcgccacggccgcgttgcggggctgg |
| | catgtgctggccgtatgatggcgctgctgcggaccacggccgcgtccagcggtcggcaaagaagcttcaacatcaacacgccggtgccggctgg |
| | tgggtgcgtatatgatgggcaacgtgctgggcttcaacgcgcggctccgccagcgcgaggcgaactgcccagcgaaattgcccgtcaaactgccccggccgaacctg |
| | atcctgcctggcgaccttgcgcgaatggccgccaaacttcactggccgccggctctccggggtaacgcgctgaaacgctggctgc |
| | agccctgtgatgacctgccacgctttcggccgctccaccgccgtctccggctgtatcgatcgcggccatctcgtcggcctctcggggcggc |
| | ggttgatgacccttatcggcgagaaggccgtcaccatgggccatgggccggtcgtgggctgccaccatcagctctcggtctgctctctcattg |
| | gctacaagatggcggactgaccgtggggcgtcgcgtgaccggtaccagagagcgaggagcgcatggcaacagcgtcaacgacccggcaaaacgcct |
| | acaacgcctga |
| 121 | ctgaaagttgatcctggctcagattgaacgctggcggcatgtcgtctacacactgcaagtcgagcgcagcacggacctcggtctggtggcggtgggc |
| | gaacggctgagtaagtatccgatgtcagctacacaccgggtaataacgggggaaaagcag |
| | gggatcgcaagacctcgactattagacgcagccgatacggaatagcgagttcagctcgaagggtgcgtggtgcacaggtggtttgag |
| | aggacgaccagccagcacactgagtacaacgccagatcctacgggaggcagcagtgggaatttggacataatggcgcaaatggggaaacctgatcca |
| | gcaatcccgtcgtgcatgaaggtcggcgtataaaagcacctttggcaggaaagaaacactcatgggnataacccgtgaaactgacggtacctg |
| | cagaataagcaccggctaactacgtgccagcagccgcggtaatacgtagggtgctgtaggttaatcggctgg |
| | gttcggaagaaagatgtgaaatccccgggctcacttctcaactgcatttgaactaccggactgagactggtgtcagggaggagtgaattccgcggtgta |
| | gcagtgaaatggtagatatgtggaggaacaccgatggcgaaggcagtccctggcttctagctgacactgagctagcgaaagcgtggggagcaa |
| | gccgtgggagtacggtacggtgccaagatcaaacgcctgaaactacaggaaattgacgggggcccgcacaagcggtggattaattcgatgatgcaacgcgaaa |
| | aaccttaccctacccttgacatgtctggaattcgaagagatatccttctcgaagctctgacgaagtgacaacacaggtgctgcatggctgtcgtcgctcgt |

TABLE H-continued

| SEQ ID NO: | Sequence |
|---|---|
| 122 | gtcgtgagtgttgggttaagtcccgcaacgagcgcaaccctgtcattagttgctacgaaagggcactcaatgagactgccggtgacaaaccggag<br>gaaggtgggatgacgtcaagtcctcatggcccttatgggctaggggaacttcacacgtcacacatggtcggaacagaggtcgccaaccgcgaggg<br>gagcgaatcccagaaaccgatcgtagtccgatccggatccggatcctgcaactcgactcgtgaagtcggaatcgcgtagtcgtagctggttgag<br>gtgaatacgttcccgggtcttgtacacaccgcccgtcacaccatgggagtgggtttaccagaagtagttagcctaacc |
| 122 | ctgaagagtttgatcctggctcagattgaacgctgagtgggatgccttacacatgcaagtcgaacggcagcacggactcggtctggcgagtggc<br>gaacgggtgagtaatgtatcggaacgtgcctagtagcgggggataactacgcgaaagcgtagctaataccgcatacgccctacgggggaaagcag<br>gggatccgcaagaccttgcactattcagagcggccgatacgtagattagctagttgggtgggtaaggcctaccaaggcgacgatccgtagctggttgag<br>aggacgaccagcagccacactgggactggacacgcccagactcctacgggaggcagcagtgggaattttggacaatgggggaaaccctgatcca<br>gccatcccgcgtgtgcgatgaaggccttcgggttgtaaagcacttttggcaggaagaaaacctcatgggttaatacccgtgaaatgacgttaacctg<br>cagaataagcaccggctaactacgtgccagcagccgcggtaatacgtagggtgcaagcgttaatcggaattactgggcgtaaagcgtgcgcaggcg<br>gttcggaaagaaagatgtgaaatcccagggcttaacctgggaactgcatttttaactccgaggaggtcagcggtggaattccgcgtgta<br>gcagtgaaatgcgtagatatggcaggaacaccgatggcgaaggcagccctctggcctgaactgacactgaggcgcgaaagcgtgggggagcaa<br>acaggattagataccctggtagtccacgccgtaaacgatgtcaactagcgttgggctcct agcgtgggtgggtaacactgtcaaggtgactgccgaagttgacc<br>gcctggggagtacggccgcaagattaaaactcaaatgaattgacgggggcccgcacaagcggtggagcatgtggtttaattcgatgcaacgcgaaa<br>aaccttacctaccctttgacatcctgcgaatcngaagagattgagaagtgccttcgggaaccgcaggaccccggtccatcccgtggttagctacgctc<br>tgtcgtgagatgttgggttaagtcccgcaacgagcgcaacccttatcgttagttgctacgcaaagggcactctacccagactgccgccacacc<br>ggaaggtggggatgacgtcaagtcatcatggcccttatgggtttaggctacacacgtgctacaatggcgatacaaagagaagcgacctcgcgagagc<br>ggagccaatcccaaaaaccgatcgtagtccggatcgcagtctgcaactcgactgcgtgaagtcggaatcgctagtaatcgcggatcagcatgccgcggtgaatacgttcccgggtcttgtacacaccgcccgtcacaccatgggagtggggttaccgagaagtagttagctaaccggcgagacggtgatacc |
| 123 | tacggagagtttgatcctggctcagattgaacgctgaggggcgtctcagaacatgcaagtcgaacggtagcacagaggagcttgctcctctgggatcagtg<br>gcgaacgggtgagtaacacgtgagtaatctgacccccctgactctgggataagcctggagaacggggtctaatactgggtcgtggtgtcgccatggt<br>ctcggtctggaaagaattcggtcggggatggctcctcggcctatcacttagttgatggtggtgatatctgggattcacctcctgggaagcagtcggcct<br>agagggtgaccggccacactgggactgagacacggcccagactcctacggggaggcagcagtggggaatattgcacaatggcggaaagcccgg<br>ctaactacgtgccagcagccgcggtaataacggtaggggctcagcgttgttcggaattattgggcgtaaagagctcgtaggcggtttgtcgcgtctgctgt<br>gaaatccgaggctcaacctcggatcggcagtcagcggcggtgaagatgtcggctagggctcctgtgacggtagcggtgaatcgc<br>agatatcaggaggaacaccgatggcgaaggcagatctctgggccgagactgacgctgaggagcgaaagcgtggggagcaaacaggcttagatac<br>cctggtagtccacgccgtaaacgttggggaactaggtgtgggttccattgtcggatctccgacgctaacgcgctaagttccccgcctggggagta<br>cggccgcaaggctaaaactcaaaggaattgacgggggcccgcacaagcggcggagcatgtggattaattcgatgcaacgcgaagaaccttaccaa<br>ggcttgacatacggacgcaaaatctgcagagatgcagagttcccttcgggggacagtcctggcaggtggtgcatggttgtcgtcagctcgtgtcgtgagatgttg<br>ggttagtcccgcaacgagcgcaacccctgtctctatgttgccagcatcagttggggcactctatagggactgccggcgacaaaccggaggaaggt<br>gggatgacgtcaaatcatcatgccccttatgagtctgggctacacacgtgctacaatggctggggggtagagggggaat<br>ccaaaaagccgtaaaccggagcgggagttgctcctaaaagccgatcgtagtccggattggagtctgcaactcgactccatgaagtcggaatcgctagtaata<br>cgtccagcatctgaacactcgcgggtgcctgtaacacggcccgtcacaccatggagtctgtacaccctcgctcggccttaaaccttcccttgacggaattgcaggtgaata<br>ggatcggcaattaggactaagtcgtaacaaggtagccgtaccggaaggtgcggctggatcacctccttt |
| 124 | attgaagagtttgatcctggctcagattgaacgctgaggggcgtctacaacatgcaagtcgagcgagtagagagcttgctctctcggtgacga<br>gtggcgaacgggtgagtaatgtctgggaaactgcccgatggagggggataactaactgagaaactctggctaataccgcataatgtcgcaagaccaaa<br>gagggggaccttcgggcctcttgccatcggatgtgcccagatgggattagctagttggtgaggtaatggctcaccaaggcgacgatccctagctggtc<br>tgagaggatgaccagccacactggaactgagacacggtcccagactcctacgggaggcagcagtggggaatattgcacaatggggggaaaccctgatggtgacacacggcgtatcgggatgacgaatacctcgggaacacctccgggacgttactgctgtgtaaaccgcacctgttaaaccgttagggtta<br>cctatgtggtt<br>cgccatgatggcggtggcgactacctcggggcaggactacctcggtgatggcgtaaagcctcggctaacctctccagctctccggggacgccgggggggaattattcagcatgcccgcaaggcgaggtggcaaggggcttaattcgatgcaacgcgaagaaccttacc<br>gtcgacccgctcgggggacgacggccaaggttaaaactcaaatgaattgacgggggcccgcacaagcggtggagcatgtggtttaattcgatgcaa<br>cgcgaagaaccttacctggtcttgacatccacacgaagtagcattgtcagctcggtcggccttcgggaacgtgagacaggtgctgcatggctgtca |

TABLE H-continued

| SEQ ID NO: | Sequence |
|---|---|
| 125 | (DNA sequence) |
| 126 | (DNA sequence) |
| 127 | (DNA sequence) |
| 128 | (DNA sequence) |

TABLE H-continued

| SEQ ID NO: | Sequence |
|---|---|

129

```
ggatggagtacaacttcacggccgccgaccaacaaatcgctgctgtaagatcgccgatcaattgacgacaccaccccgccaatgcggaagc
ggtgatcgccaaatatcaggccaaaacgatcgattatcggccaaataccgccgcgcctcgaaggccgcaaggtgtgtcttatatgggtggcctg
cgtcctcgccacgtgattggccggtatgaggatggcatggagtactgtcgcgcgccggtatgtgccgcataacgacgattacgacccaccct
gccggacctcaagagggcagcgtcgtgtcgacgatccgcagctgtgaacggagggacccttgaaggcctgaaggtgacctcattggctca
ggcatcaaggaaaatacattttccagaaaatgggggtaccgttcgccagatgccattactccggccgtatcacgctatgacggcttt
gccatcctttgcccgcctgaccatggacatggcacaatcccgtcgggccgagtgaccgaccctggcgaatcagcctga
```

130

```
atgagcaaactgctgaagaacctgtgaaaaatgtcacctgttgaacaggacgagataccagacgctgtttcgcaatagcggtctggaagaggc
gcacgaccgcagccgcgcgtcgaagaggtttgaatggaccaccggcaggttttgccaccggcgaacttaagctgaagctgtaaccgtcgatccg
gcaaagcctgcagctgcagccttaggatcgtactcgtggggttcgccaatacgctgcctatgcgacggttccgcaggcgtgtggcctattccg
cacctattttaaccgtcattcaaaagagccgcgtcgcttggttccgactctatgacagaggatcggcggcgcttcggcggcaacacaaccttaacacc
gggttgcaaaatgccagcgccctgaaaatgtcgctgctcccataactgtgctctataacggcaagttatcggtagccacacaccggctggacaa
gccaacgcccaaaagacagggtttattgatgccgccataccggtgccctacgccaagtttatcggtagctcggtagcacacacaccgctggacaa
catgttgaaggttcgccgggcattaccggcatcacgtggagtgcccagcggcaaactgctagtcctgagtgtagatacgccagccgacg
tgcaactaccgctgtcaaacgcatgtacgggcggcacaacgcaacaagagatgcgcgacgcccgacgctgctctcgatctcgcaacctggcatctgg
tgaagacaaaaagtcgggccgtggttccggacgtcctcgacccaagagttccatcccaatggcgagccggccgacgaactgctatg
gcagtcagtcagtaagaaattcggtctccacggcgatccggatttgtgatggggctgaactgacgcggcggccgttcctgctggaactggccgacgcgttatcctcctgtca
aacggtagcaagcggctggcaagaaagcgatgaagaaaatgtgctgagcgcatcggccaatcaggacgagtgttcatcaactgatctgtg
gcattgccgctgctgaggtttaccgcagacgacttatcatgcgccaatccgacaccgtgctgaaaagcggaaccgggaaca
gttgaagttccgctgatccgtcgctcttgcctcccgttcgacccgcagcatcgcaccaccacatgggtatgaagggcgatgaatatcgtc
accaccccggtcaacgccgtgctggaaaagtcgaccgcgatcaccattcaaacggactacagcttcgacttcgcctcaa
```

131

```
atgaccttaattatgtctggagacaccggaccagcgcgaccgacattgcggcaacctcacttcaactcccggactgtttccacgatggttgaacag
gctccggatcgcgatttcgtgacgaccgacccggacggcgaggattctgtacgctacgctaatccgccagccggttatagcctgaagaagctgctc
aaccagaaccaccctgcatcgcccgcggatggcagcctttattcgctggctacggcgattatcaggaactgtggcaaacgctgctgcaaacatgtgcgcggt
cagctcatcaaccgctcgggatggcagctcttattcggctgaggcgatatcacccgcgtcaatacaaggcgcaactacctcctgccgcc
catgcaaggtgatatcgccgtccagctatgcgtgcctgcaatcacacaaaacctctcgccgactgagcgagggtgctgaaaaggcgaaca
gtgtggtggtcaacgacgaggacaggtagtcattgcgccatacagctcggatatgacagaccagaggagctgtcaccgaa
ctggattttctcccggcgcaaagcgatcttctatgcgggcaaatactgctggctgcgccacccggtggtcacccgctcctgtcacctgctggac
cctgccggggttgagcgaacagggcgtctgcgatctcgatccgctccaaacaggagctgacccaccggtggtgatcaacgactgccgacccagcaacaca
acaggcaagcaggcgtctgacgccgaacagccgccgatctcaacaggaagcctggaggtgaagctgctcgcccgatccgtgaacggctggttcccgtggt
tcagctaaactgccccatcaatatgctggcggggcgacgacgctcaacggtgaagactaaccataacggtggccctggcgcggcgaggg
```

TABLE H-continued

| SEQ ID NO: | Sequence |
|---|---|
| 132 | ggaagaggcggctggccgcccgcctgcaacgctgcgcccttctctcgatctggaagagagcgcggctggcctctgcaaccgctgtttgacgacctgcg<br>cgccttaccataccgctataacaatggcgaaaatctgcacgttgaaatggccttccgcatctggcggggtttggtcagcgcacgcagatccttgc<br>ctgtctcagtttgtggctcgacgatcatgtgcgctggccctggccctcatccatgtgcgatacgccactccccgatgcctgaccgccccgcaaaggggatggagct<br>ggctgtccattggctgacagataatgtgccctcgcctcatccccatggcgataccgcccttcccccgatgcctgaccgccccgcaaaggggatggagct<br>gcgattgattcaaaccggtgccatcatcggggcgcaatagaactaactaccccgcccctgaaggcggtactgctgacctgcgattcccgttattt<br>cattcactgacggagcccacgatga |
| 133 | atgatgcgcactctccacagctacagcagcactggcaaactgtactggccccgctgcctgagtcattcagtgaacaccgcttagtgaacaagcgca<br>gttagtgcttacttcagtgattctgattctgcaggatagcctgcgcgcatcctgactggctgcctgagctgcatcattaagcgtcgtccgtcgccatcatgatgg<br>gaagcagtgtcagccagatgatgcaaaccctcgcgaatcgctggaagtggagatgagcatcattaagcgtcgctgcctgttccgtcgccatcatgatgg<br>tgcgcaatccctggcgcggcagtcctggtggagaagatgagacgttcacgagcgtacgcagagtgactggcagcacccctgactcgccgctcac<br>gcgactggctttacgatgcctgcgtcgtcgtcgagtggggaacgccgtgcaatcagcaggggaacgccagccgttgctgatcctggcatggcaag<br>ctggtggcggggagcgttaactttcgtccgatctgattttgcctggccgaaaacggttcaaccgcggtgggcgacgcgaacttgataac<br>tttggcagcaggtccctggtgctgagttctgcccgcgacgctgaagatattatcaggccatgacgggaacgttatgctggtgatggtgaaagc<br>ccgaattatgggcgataaggacgatgttaccccgcgaagtgcgcggaagtgcgcgcggttcgtctccgcgctatatcgattcagcgttattcagt<br>cctgcgcaacatgaaaggagcggatgattgcccgtgggcgccgtggtcgagactggaaacccctgaccgctggcaatgggacgttgaaagcaga<br>gttatcgtcagttcagttgcatacgggtgggcccgtcagtccgctcactgttaccgacgtggacgtatcgatagcagctgggt<br>ttgctgcgcctggcgtggacgccgctacgggcatactgctacgcagactctggcctgtcgcagcgagttcctgtgcgctaagcatctga<br>gtaccggttgtctcgcgtacgccgctgatggtggccagtaagctgcgcctatcacggggaatgtgcacgacgtatcctgatgagcgtaagcatcatctga<br>tttcactcctgtcgtcgccgatggtggccagtaagctgcgcctcgtgtctgatgagttgctcgatcccggatacccttatcagcccacg<br>gcggcaatggatgagctacgtcgtgcgtcgtgtgccggatgacgaagagcagcaactacgggcgttgagaaagtgagcgatcacttaacatggccttgcgcgaagccatcatt<br>aagctcaattgttgttggcctgtacaacaggcgtggtacgacctatcgcaggtatggcgagcgcaaacactacgacgacggcgggttgcagttgtc<br>gaagccggtggtacaacaggcggtacgacctatcgcaggtatggcgagcgcaaacactacgacgacggcgggttgcagttgtc<br>ggttacggcaaactgggcgggttgggagctggactggggctctatagttccgatctggattttgatttccttcatgactgtccggtggacgtgagcgatacctgatgaggtagacg<br>gggaaatcgatggcgccgccaatttatctggcctgccagcggtgatccagttcctgtggcgctaagcatctga<br>cgcgcttgccgccgccgtttcgcgccggtgtctatggccgatcccaataaaaccgcaattcaaccgcactgcatccgcgctaccaccatgaccgcgctaatggtg<br>aggcgcggttcgccgccgccgtttcgcgccggtgtctatggccgatcccaataaaaccgcaattcaaccgcactgcatccgcgctaccaccatgaccgcgctaatggtg |

TABLE H-continued

| SEQ ID NO: | Sequence |
|---|---|
| | caacgttacaaaccgagtgcgcgagatgcgcgaaaaaatgcgcgccacttgagcaataagcacaaggatcgcttgatattaaagccgatgagg |
| | gtggaattaccgatatcgaattatcacccagtcttggtcgtgcgttatgccatgccaaccgaaactgacgcggtcggacaatgtccgcattct |
| | ggaaggctggcgcaaacggcattatgaagagcaggacggcaacttaccaccgcctatacaacgttgcgtgatgagctgcatcacctgg |
| | cgctacagagcgccaggacactgttccaggacatgttttgcccgtgaacgcgacgagccgtgaacaagtggttgggagccgtg |
| | cgaggacgcgtaa |
| 134 | atgaagaaagcactattaaagcggggtctggcctcgctcgctgtctggcctatgcagccgatccggttcgtgtctgcgataaagccgacaat |
| | gcctttatgatgcaccgcacgggcgtgctgttttatgtcaattccgggacgccctgttcatcgtggtttaatccggtaaaaagtctcttctatgct |
| | gacacagtgcggtacgttcgcactggttcgtcgtgtgtggtttacggcttacggctactctcggccttgcactggcggcagcttcttcgtagcttcg |
| | acgggtgatgctgaaaatatgacttgagctgaagacggctgatggcacatcacattcacgtgcttcagggctgttcctgctgattaccgtc |
| | ggcctgattgtcggtcgctggctggcaacccatgccgatccggatttctcgccgagtactgatttcgtcggtggtaggctgacgtcctacgtgccgatcgcacacat |
| | gcttacccgatgtggcaaacgtcgcggttcggtcaaaggccctgaaagaagcgttaaacccgcacaacgctgtagcgcctggctgggt |
| | gctttacctgattgcaacgagccggttcgcaaccggcgcgaaatgcgggctcggcnifgttaaccaccgtcgtggcaacagcgggtgcaatcctcctctg |
| | gtcggattcaacgcgggtcgcggccgctgcgcggcaaccggtcctgttgggtccgctggtctctgggtgggcgcctgttggtgtcggggtgggtta |
| | cgtggttgggtggggcggcgcgtgatcgtgacgggcgcggtcaggccctgggcgttaccggctgaaacgctggcgctgttgacgac |
| | ccgttgcgatgctcggtgttcacggcggtggtacaactgaaattatccgccattactatcgtatggtctggatcgtcgtcctatcggtacaaactggctg |
| | atatgacaagtgggctccgtgtccggaagacaggaacgccgaaggctggacgtcaacagccacgcgagaacgctacacgcctga |
| 135 | ctgggtcactggagcgcttatcggccatcctgaccgaagaattgccggttcttccgacctggctggccctgttcaggttgtggtgatgaatatcac |
| | tgattctcaagtgaatatgtcaacgaattgaccggtaaatgcaaatgggcattcgtaaaagcggcattcgtaaaacgcagaagagattggcttaaa |
| | atccgcagcacacttacgtcgtgtccctttatgttggtcgttgtttgagtcgtgagagaccggcaaagtggccgttcgcaccgcgccggtaa |
| | agacctggcagcctggacctgaagtgaagtaaggctccagaagacgattcaaacaagagattcgagcccgcagtctcaacaactaaggtattaaa |
| | ggcggaaaacgagttcaaacggacgtcaaacggcacgtccgaatcaatggcgagatcgcggagccaccgagtcgcttaactggctggaggttgagcagctg |
| | ggtatt |
| 136 | attgaagagttgatcatggtcagattgaacgctggcggcaggcctaacacatgcaagtcgaacgtgagcacagagagagcttgctctcggggtgacga |
| | gtggcgacgggacggtgaagtaatgtcctgatggggggaaactgcctgatgggggcaactgcctggatacaactcaaggtggatttgatgggaccaaa |
| | gaggggggacctcggcgctccctgccatcgaactggacacggtccagaactcctcacggagccaagtgggaaatattgcaacatggcgcaagcctga |
| | tgcagcatgccgcgtgatgaagacggtcccggttggaagtacttttcagcggggaaggacggagacccggttaataacgtgtgattgacgtta |
| | ccccggaagaagacggctcactcctgcagcccgaggaggggcgagagagagcgttaatcggaattacgggcctaaagcccacgc |
| | aggcggttcgtcgtcagtccggatgtgaaatgcccccggctcaacctgggaactgcatccgaaactgggcggcttgagtctgagaggaggtagaattc |
| | caggtgtagcggtgaaatgcgtagagatctggaggaatatccggtggcgaaggccgctatttggagctctatttggaggcttccggacgcgta |
| | actgcggactgagaggcgaaagcgtggggagcaaacaggattagataccctggtagtccacgccgtaaacgatgtcgactcagtgttggggctaagcgta |
| | aacgagcgcaaccttaccggtcttgacatccccagacttaatcatcttgttgcagcgcccaaacagggaactgacctcgcagttggatcggatc |
| | gtctgtgttgagatggttggtaatctgccgcaagcgcaacctatccttttgttgcagcaggtcacgtcacaatggctggaattctggatcggac |
| | cctcgcgagactgccagcaaagctgaaaggtggggatgacgtcaaggtgaggtgtcacctagtcccatgagactggattcgcactgctagtggaatcggctggatc |
| | agaatgccccggtgacaatacgttccgggccttgcacaccgccccgtcacaccacgggtggttgcaaaaagaagtaggtagcttaacctttcggga |
| | gggcgcttaccactttgtgattcatgactgggtgaagtcgtaacaaggtagtcgtaacaaggtagccgtagggaacctgcggttggatcaccctt |
| 137 | atgaccacctgctcaatgccgccatttacggcaaggtggatcggtcaaaggtgaatcgacataatccgacaccacacgaaacctggtcgccgctcggcggatgggtaag |
| | aaagtcatgatcgtcggctcgcgatccgaaagcgaactcgccaggttgatcctgatcctcgacggttgatcctgcgatggcagagaacccagcgacccagcccaccattatggagatggccgccgaag |
| | tcggctccgtcgaagacgtggaattagaaagacgtgctgcaaatcggttacgggcgctgctgccgatccggtggcggaatttccctacgacctggctgggcg |
| | ggttggtgcccggtcgtggcgctgatcaccgcgatcactaacctcgccgattttctgctctggccgaaatgatggcgatgctacgccgcc |
| | aataacactctccaaaggcatcggtgaaatatgccaaatccggtaaagtccggtaaagtcggtaaatcgccgatttgtaactccgccgcaccgacccgacccgaagatg |

TABLE H-continued

| SEQ ID NO: | Sequence |
|---|---|

138 atgagcaatgcaacagcgaactaacctggaaatcatcgacgcaggtgctgaggtttcccggaaagacgcgcagaaaacacat
gatggtgacggacccgagcaggagacgtcggcaagtgcatcatcctcaaccgacaaatcgagccgggcgtgatgaccgtcgttcgt
atgccggatcaaagggtggtatttgggccaatcaaagatacgatgatccccgatcgcgatattccagttcactcaacctcgccgccggc
gggctaactactataccggcgcaaactgattcagcgcgtggacagttccggcgacgtcaacttcaactcaccctcgatcagcgagcagacat...

139 atgaaggggaacgacatcctgctctctgctcgatgaaccagcctgcgagcataaccataacagaaaaccggctgtagcgcgcaaaaccggcgc
caccgcggaggctgcccttcgacgcgcacagatcacccgtcgctgcacttccgatgtgcgcactcggtacatggccgattggctcgcggc
agctcatggataaccgctggcagcctggtttcacgcggcagcctgagttcgagcggccatatccctgattaaccgactcggatta...

140 atgagccagactgctgaaaatacagaattgccatcccctgtttgaacaggacgcgctaccagacacatcattgccggtaaacggcactcgaagagg
ctcactcgccgagcgggtgcaggaagtgttcaatggacccaccccggaatacggagcctgaacttcaaacggaagcgcgcaactgactatcgacc
cggcaaagtgccagcgcggggcgcgctcgtccgttcgtcggttgccaacacccgcggttcgatgacggaagacggcggtgt...

TABLE H-continued

| SEQ ID NO: | Sequence |
|---|---|
| 141 | ttgtggcattccgctcgctgatgttcacccgccagccggatttatgattggcaactcgtacgcaagtttattcagcgcgacaccttagcaaggcga<br>acagttgaagtccccgtgatccgccggtttccgctgttcgaccgtcgacctcgaccgacaaccactgggcgtacgagggcgcgatgagca<br>tcttcacgacgctggtgaatgcggtactggagaaagtggacaagagaccatcaagctcggcaaaaccgactacagcttcgatcttatccgttaa |
| 142 | atggctgatattgttcgtagtaaaaaccgctggcgtgagccgtgagccagccgtcggggggatcctgcagccttcgggtttcgaac<br>agtgcataccggtgacacggcgctcaggggtgcacgcgtcgcgctgcgaaagtgtcttatcaacattcacgacccgatcccgtgcaatcgacgg<br>cgatggacccgacttccaccattatgggcggccgatgaaaacatttaccgcgtcaatgttcctctgcagccgcaaccgccaaagccatcgtgctgc<br>tcagcaccggaccagaaggccaggacagtgcaccggcaggtcggcgcagtttcatcgcgtgactttccgcggcacaaacagtggcgctgctc<br>accgtcaacaacccggattttcacggcttccgctgcgttggaaacgcctacagcgccgtcgctggaaaagcagatggtgaaacagtggtccgcgcacgccgccg<br>gccagcctcgcaaccctgcgcctcaactgctcggtccgcatctatcgcagtcggcagatcggctggcaacggtgatttttcgccctgcacccgctgctgcca<br>caaccgggtgattgtcgcccggatctatcgcgatgacggagctgctgcaaccgttgtttgtgcgatggcgccgctggcgctttcacccagggcggcgca<br>tgatcgcccctgcgctgatcgacgcgcgttgatcgtggcgacacctttatccatcgcgcgaaaacctttatcccaccggatgcgccggtgttcacctggc<br>cgccagcgggcaagtgcagatgcagctgcaatgatcgatcccggccggttgtcgccgcgggttgcgcagccaggcgcgatcaactggc<br>ggtggtcatcggcgatcggaagatatcgaggatatgcgggcctgtcgccgacgcccgatcgcttcatcgccgccaattctcatcgcgccacgc<br>agttgatgtcgcttatccgcgcgggtttccggtcgtatgcacccggtatatcagccgcttccgcccgctggcggcgtcggggaataacgcatcggcgcgcgcgg<br>tgtttgagctggcgaatgtgatgcgcgcgaaacgccatttcgcgctggtcaacgcttcgccgctcgtcagcgcttcgcgcagccttcggccgacaagttacgccagg<br>agatcggtatcgcatgttaa |
| 143 | atgacccagcgaaccgagtcgggtaataccgtctggcgcttcgattatcccagcagttcaccgcgatgcgatgcagccggatcagcctggttctcagcgcggg<br>cgaccggaggttgaacagaacacctccagcaggtgctgtcgtattgcacaatgacgcatttgagcacggccatgatctgtctgtacgacagcagcag<br>gcgatttgacttggcattggagcgtgcaggagccgatcagcgatcagcagtgacccggcagtcgccaattcgcagtcgcggtcgccggaggtggctcggga<br>cggtgttcgccaggttctggccaatgtcgatggcgagacttgcagcgtatgacgggcgcaccaggcgtccagcagcggttaccgccctcgcacccg<br>ctttctggaaacggtccgaatctggtggccagaccgtgcgtttgtcgaaaatatgtgcaacacccggcaaatgcgtacgaggcgttacccggtccatcacgcctcaaccc<br>gcagccaaggttctggatcgcaagttcccaccggtcggaggtcgaacccggcgcaacggcaggacttcgccgatacccacagcgtc<br>agtttcgccattgtgaaatcaacgtccggcgccccggtgacggagaattattggtcatgaaaagcgcttaccggcggcgg<br>ccagtgcgccattgcgaaggcgtttgagtcggcgccatggcagcagctgttcttgacgaaagcagcgcctgtttcaagctggctgctg<br>tacgcggctacgtcatcggcgtaaatgaacggcggtcggtgacgacaggttctgagacattgcagaaatgggaaagcagcagcgatgattacaacctgccgtttatc<br>cgtattcgcagaggggcgaaactgggacttcgccgaagatctctattacgcctgaatgtgatgcccatcgcccgtgcgccgctgcgcctaagctgctg<br>atgaagtacgccggcacatttctggtcgtaaatcgcccaacagaccgcacgcgcattaggagggcgtatccgctgccctgatgagtgagtaca |

TABLE H-continued

| SEQ ID NO: | Sequence |
|---|---|

144

```
gctggccggccgcaatgtgcgcgaactggagaaaactgcctgagcgctctgcgtgatgtcggaaaacggtctgatcgatcggacgtgattttatttatttaatc
atcgcgaccagccagccaaaccgccggttatcagcgtcacgccgacgcgatcacctgacgacccccttgacgagcgcagcggctgattgccg
cgctggaaaaagcgggatgggtacaagccaaagccgcccgcttgctgggatgacgcgccagtcgcttatcgtattcagaccatggatatca
ccctgccaaggctataa
```

145

```
atgaccgcaccacgcaggattgtcgcagcactggcaaacggtttttctcgtctgccggaagcgctccaccgcaaccattgagcgcgcaggcgcagt
cagtgctcacttttagtgattttgttcaggacagcatcatcgtgcatcctgagtggtcggcatccggtgtcgaaagcgccagcgaacgagtggc
aacactacgcgcaatgcgtcgaggcggcgcaccggataaacctcgatgaaacctcagcgtgctgccgtttcgcgtcgccattatggt
gcgatcgcctgagtcagtgcttaacgtcatggcggaagaggatatcctgcaacagcgtcccgcgatccgcggaaaactctgatcgtcgcgcgg
cgactggctctatgacccctgctgcgcgagtgctgttcgcgcgtgagtttgattttgcctgcgccggcgagctgccgatgctcggatgctggcaaact
tggcggcggacctcaattcccatccatccgatcgatttgatttttgcctgccggcgaaaatggcaccacgcggcgtggcgagcgcgtgaactgga
cgcagttttaccggcctggctcaacgtgctcattaaagtgctccacccgccgtcgatatgcgccttcagcttgcgtcccttt
ggcgacagcgggccgctgtgctgagttttgccgcgctggaagatta tactaccaggaggcaggcgcgactggaacgataccgcgatgtgaaagc
agctctctgcgcacagccacatgaaaggctgattcccaggtttccagtcgatgatcgtggcggcggcggatcgctagcgagctgatcaacag
atagagtttatctgcacgagtttccagttccctgagttcgacggtggcgaattcgcgcaacgcttgctcgtgtcgcattgatcaact
acatctgcgccgatgggatcacccgacctcgcgcaagcgctatttgtggcgcgacggcggaaaacttctgcaagcattaatgacgaacag
acacagacgctccggccgatgatttgaatcgcgacgcggcctcgctggggaatgggcaaagagagtcggaagcgttctgcgaaaagctgaag
cgcatatgccggcgtcggcgcagattttcaacgatctgattggcgatgatgaaacgagatcgcgcttctcgagggcggcgcgaattgt
ggcaggatcggttgcaggaagaggactctacgccgtcgtggcgcattctccaggacgcagttttcgaggcgattgtggtggcggctgattttcg
caagagagtcggataaacgcaccattggcccgcgcgggcgacaggtactcgatccatccatcatatgcgcatctgcctcagcgatgtcgtcgtgacgat
ggccagtgccgctgtcgtcgcccgcgccgatggtgacggcgagcagccagcaactggcggcggcagcagcagcacttagcggcgctgcgggcgc
cacctcattttcctgtcgccgtcccgccgatggtgactgatgaactcggcagcaactggcgctgatgaactgctcgatgaactgctgaaggatgaaagagcaactggaggcgtac
tcaaccgacggcatgaacagcctatcggatgaactctgcggaacataccgttcgcgtaacccctcatgaaagtgacgttaccccggcgacttaacctggctggc
ggcagttaagcaggcggcagttgtcgcgtagcggcgggatatcgcggatatcccggatgcagtacccgggtacccgttgccatgaagagcgcatcattaaccctggctggc
ggaagcgattatcgatcggtcggtggtgcagcaagcctgaacaagactggcgcaaactggccgttacagctccgatcctggatttatcgctcagtatctgagttta
gcttcgccgtgtggcagcgtgaaatcgatggccgccagttctattgcctccgcagccgtgatgcccacgtgacacgcccacgtcggcatt
cttatgaagctgacgcggttggcgccgcggaatcgctggtacctgcagttgctgaatgctggtgaacactgcaggacagcggttcgccgatatcaaaaaatgaagcctg
gacatgggagcatcaggcgtcggccgcggtgcgcgggtgtacggcgatccgcaactgaccgcgcccatcttgagcgcaatcgcccgatacctgat
gacctcccgatgcgcatgccgctaccctgcaaacgcaagtgcgggaaatgcgcgaaagtgctgagcaaatgcgcgcccatcttggtaacaagcacaaagaccgtttcga
tctgaaagcgatgaaggcggtatcaccgatattgagtttatacgctcagtatctggctgcgctggtgcctcatgagaagccgaaactgacgcgctggtc
ggataatgcgaatcatccgaggtcgcggcggcctcatcatgacgaggaagccgacggatcaccggcgtacccaccgttgctg
atagctcgaccaacctggccgctgcaagagctgccaggacaatggcgggcgctctcctggtttgtcgccgacgtgcgcttatcaaaaaccagctggacaa
gtggctggtggaaccggtgcgcgccccggcgtaa
```

146

```
atgaaaaacacaacattaaaaacggctcctcggctctgctcgctggcgctgccgctcagccggctgcctggccgggctgtccgtgtgcggataaagccgacaacg
gctttatgatgatttgcaccgcgtggtgtctgttatgaccaccctcggccattccccggcatccgctcgtggtgatccggtcacggggttgatccgcggtaaaaacgtgtcgtcgatgc
tgaccgcaggttgcccgtccattcgctcggtggtgcatccctgggtggttaccggcactcctgccatcgaggggcaaacagttcttcggcagtttc
aactgggcgatgtgaaaaacatcgaattgaagcccgtgggagcgattcgctgccgcgtgattttttggtgatgtgggcgcgcgttcttttgttgtgatattgcgcacat
ggcctgggtgggtggtcgctgcggcaaccacgcgcgctgcaatggctgcggccaccacgccgatcaacgccgatccgcgatcgcaggtctggggg
ggcttacctgattggcaaacgtgggctttggcaaagaacgtcaaacctggctggccatcgcagccgatttcgctgcagggcctcgctgatcttcaccatcaacgccgccgatcctctatgttgg
ctggttttggctgctttggcgagttggcaatgccgatccagagctaagccgttcctctcgctccgggcggtcgctggtaggggcgctatcaccccggcgtgcg
gttatgtgggtcgcggcgcgccggctgattgcgcggtcgcggtgctgcaggcggtcggggcgttactgcacgtggtactgacctgaaacgatggttcgttgatga
cccatgcgatgtcttccgtgtgcacggcggtggtgctccatcctggggcatcggaagcgtatcctgaccgttggtcggcttcgctgggcgtggttcgctggtcggttcgct
gaaggggtgaccatgggaccatcaggtactggtacagctgaaagcgttgcatcacctacacatcgtggtcggtggcctttatcggtctatcggttacaaactg
gcggatatgacgggtaggccgtacgcgggaagagcaagaagagcgtgaaggggctggataagtgaacagcaggatgtgaacgctgtaacgcctga
```

TABLE H-continued

| SEQ ID NO: | Sequence |
|---|---|
| 146 | tcttggttcttctggacgcgcttatcgcgatcctgactgagagaattgcaggcttcttcccaacctgcttgcacccgtgcaggtagttgtgatgaacatca<br>ctgattcgcaggctgatcacgttaacgaattgaccacgtaaatgcaaaatgcggagccattcgtgtaaagcagactcgtgaaagcgagaaacgagaagattggcttta<br>aaatccgcgagcacacttacgtcgtgccccttatatgctcggttttgtggtgacaaagaggtcgaaagcggcaacaaaggaacaagtgctgtgcgtaccgtcgccggta<br>aagcccggtgacggctgagctaaatgatgttatcgagaagagagatctcgagcgcagcttcaacaactggaggatttaaa<br>ggccggaaaacgagtcaaacggcgcgtcccaatcgtattaatggcgagattcgcgccacggaagttcgcttaacaggtctggaaggcgagcagctt<br>ggtatt |
| 147 | cgtctgtaataataaccggacaattcggactgattaaaaaagcgcctcgcgggcgctttttatatctcgactccattaaaaatacaatcgga<br>tttcactatttaaacctggccattatctaagatgaatccgatggaagctcgctgtttaacacgcgttttttaacctttatgaaagtcggtgcttcttgagcga<br>acgatcaaatttaagtggattcccatcaaaaaaatattctcaacctaaaaaagttcgtgaatacttgtaacgctactggagattaactcaatctagagggt<br>attaataatgaatcgtactaaactggtactgggcgc |
| 148 | cgcggtcaggttgaacgtaaaaagtcgtctcgcaagcacgtcgtcgtccgagttctccaaacgtaattggttctcgcttcggcagaacgattggc<br>gaaaaaaccggtcggaacggggtttttatggatcaaagatcgtgttatccacagcaatccattgatatctcttcttttcagcattccagaatcccctca<br>ccacaaagccgccgcaaatctggtaaactcatcccaattttctgcccaaatgctcggaattgttcatttttgttcgtcacaacgagagtgacagtacgc<br>gcgggtagttaactcaacatctgaccggtcgat |
| 149 | ttgaagagtttgatcatggctcagattgaacgctgggcggcaggcctcaacacatgcaagtcgngcggaagcacaggagcagttgctctctggtgacg<br>agcggcggacggacggtgagtaatrtctcggggaaatgccctgatggagggggataactactggaaacggtagctaactacgtgccaagaccaa<br>agaggggggacccttcgggcctcttgccatcagatgtgcccagatggtagcctagggttactaagtagtggggaataacgtggggaatattgcacaatgggcgcaagcct<br>gatgcagccatcgcgcgtgtatgaagaaggccttcggttgtaaagtactttcagcgggggaggaagtgtgnggttaataaccncagcaattgacgt<br>taccgcagaagaagcaccggctaactccgtgccagcagccgcggtaatacggcccgtaataccggaagtgcaagcgttancggaatnantgggcgtaaagcgtn<br>cgcaggcggtntgtnaagtcggatgtgaaatcccggggctcaacctcggaactgcattcgaaactgggcaactggagtgaagcggtaggnggtag<br>aattccnggtgtagcggtgaaatgcgtagagatcnggangaanaccngtggcgaaggcgccnctggacaagggccnctgacgctnagggncgaa<br>agcgtgggagcaaacaggattagataccctggtagtccacgccgtaaacgatgtcgacttggaggttgttgcccttgaggcgtggcttccggagcta<br>acgcgttaagtcgaccgcctggggagtacggtacggccgcaaggttaaaactcaaatgaattgacgggggcccgcacaagcggtggagcatgtggtttaatt<br>cgatgcaacgcgaagaaccttacctactccttgacatccagagaacttngcagagatgntttggtgccttcgggaactctgagacaggtgctgcatggc<br>tgtcgtcagctcgtgttgtgaaatgttgggttaagtcccgcaacgagcgcaacccttgtctttgttgccagcggtcacacacgtgctacatggccgtacaaaggagac<br>tgccagtgataaactggaggaaggtgggggatgacgtcaaagtcatcatggcccttacggagctgctcaagctcggagtacacacgtgctacataggcgcatacaaagag<br>gtagatcagaatgctccggtgaatacggtcctcattcccggcctgtacacaccgcccgtcacaccatggagagtttgttgcaaaagaagtaggtagcttaacct<br>tcgggagggcgcttaccactttgtgattcatgactggggtgaagtcgtaacaaggtagccgtatcggaaggtgcggctggatcacctcctt |
| 150 | atgaccatgcaatgcaacaggtgaacgtaatctggcaaggtgtatcgtgttaataaccggcaaggaatgtcgtccgcgctggccgagatggcaaga<br>aagtaatgatctggtgcggtcgaccggaaagcagactccactgtcggtaaagctatctctgatcctgtccatgcggaacaccattatggagatggcggctgaagt<br>cggcttcctggaagacctgaaagctgcggtaattaccgccgatcaacttcctggaagacaaagcgcaggagcctgattcctttacgacgtgttgggcga<br>cctggttgcggggcgatcgcatgccatgccgattcgcgatgcctgaatacaagccaaaccccggggtaatcacatccgcggcagatatggcggatgtaccgccggc<br>caacaacatcttcaaaggtgaacatgccggcagaatacccggcaaataccggcagattatcgcttcggtcaacatgccgggctgaaatccgcggatg<br>gagctgattcatcagctgcggacaacatcggtcggcggccgacaacaaagactcgagatgctgcctggcgcaaagatgtcgcacgt<br>acgtgattgagtcacgacgaaccggacggcaatgcaaccagccatgccacgccgacgagcatgttgaagacaacaccagcattatcggtaaaaccgccgcagaagaaa<br>acgcgttgtta |
| 151 | atgagcaatgcaacaggcgaacgtaatctggaactgtggtcatccaggagaagtcatgctggagatttctcggaaaaaaccgcaagaaacgcagaaagcacatg<br>atggtgagcgaccgggatgaaaagcgtcggaaatgatctcttctccgatctgatctcgcgacctgatgctggcgataaatcggttcggtcggtttgcttcttac<br>gccggttctaagggtggtatctggccgcgatcaaagatatggtgctcgggtaatcaagatatggccctcgcgctatcgctatccctcccggctcggctgcggggccggcc<br>gtaactactacaccggctcggtgtgataagctcggatctgtcggtaaacttcacctccgattcattcagtccgataaaagccgaaggctgatctcgttggcggcgataaaa<br>gctgacgaccaaactgttgaagagatgatggagacgcgtcgtcccgctgaccaaaggatcctccattcagtccgataaacccggcggatctggcgacgac |

TABLE H-continued

| SEQ ID NO: | Sequence |
|---|---|
| 152 | attgaagccgttgccaacgacgtgcagccgcagccatcaataaaaccggtcattccggtgctgctcgcgaaggtttcgcggcgcgttcccagtcactcggtca<br>cacattgccaacgacgtgatccggcgactgggtactggcactgattgctcgaagaggatggccgtcctttgaggccggtcctttatgacggcgatcatcggcgat<br>tacaacatcggcggcgaacttgctgacccggtttgctcgaaactcaacctctggtgctgactacactctccgacaacggatatccg<br>gagatggagaacacgccgttcgtcaaactcaacctctgctgcaatgaactatatctccgacacatggaggagaaacacggcattccg<br>tggatggagtacaaacttcttcgtccgaccaaagtcgcgaccgccatcatcgccaaaatcgccgatacggtctgccaaatccgcgcaaccattcgccaacgccgaagc<br>ggtgatcgccaatatcaggcgccagaacgacgcatcatccggatggaaattatcgtgcgggttatgaattcgccaacaagcgatgactacgaccgcaccctg<br>cgcctcgccatgtgatcggcggcttatgaagatcggcgacgtcgacgtcgtcgacgagtacgaagaccttgtcaaagtcgatgctgacaccgacccgtccgg<br>cattaaagagaagtacatcttccagaaataagggcgtgccgtttcgccagatgcactccggattactccggtactacacggttatgacggcttgcc<br>atcttcgcccgcgatatggatacgactatgagcgatcaacaccccgtgggcgactgaccgccagtgacccggtgcaggccgctga |
| 153 | atggacgcggcaggcggcgcgctgttcatgcgtcgcgccactgtcaaccgctcaccccggccgcgcgtcttatctataacaacctgcggttcccgc<br>gatggaggcgacgatatcgaagccgtctgccaggcgcagaaaccgccatcggcgtaccggtgatccgtcgttgatgtcgccggtttacgcag<br>caaaaatctcggcaccgcacggtatgggcgatgtggaaatgatgtgtgaaaaagtgattggcggggcgttctggcatattcagccgctgtcgatattcgcgt<br>gctcggcgaccctccggcgcgatgggcgctcagtgaacgacgaggtcagggtcaatatgctgtctctccagggcgctgatcaa<br>cgtcgccctcgctggacgcagcgctacggcagccgcggtttgaaggcagtttaggtggtcgcccaccctgacgccctgcgcaactggcg<br>gggtgaccggagaaccgcgattgatcgagcagccgcaccgaacagctcattgccgcgaagagcagcagcagagcaggcgctggccccgctgcgc<br>gagcgcctgccgcgggcgcaaagcgctctctattnccggcgggtgaatcctggtcggtggttcgcgcttcaggatctggcggcatggagagtggtg<br>gcgaccgcacgcgcaaatccaccgaagcggatgatgaaagcgccatccgcgaacctgaaaccgcgggggacgcaatcatgtaccgcctacaaagcgcgctgccgtcct<br>gctcgctgctgacctggttaccgctacagcggcgaacatgatgatccggcgggtacccgttgtcaccggccattgtcaacagctctgctgaccagatgcctggtctg<br>cgatatcaatcaggagcgcgagaccagcccttgccgggctccgaaccagttagttcgccaccatgatcgctgccaatgctgaaagccggtctg<br>gccgcaaaccattcccggcaccgtggcaataa |
| 154 | atgatggagcaaatggcttgcgtgcagcctgctttcctccgatcctccgaagtgctgacgagctcataccacatgtatgcgggcg<br>gtacgaccaggaggatgccgaagcgctacctgcaggtgcaaatcccaatgcgtggctggcggatatgatgatgtctgccgactcccacactggtgcacggcaagaaattcggctgttc<br>gaaagctgggaaccgaccgagctggcacaaggcgcaccagcatggcaggtcaacctgaagcgactggaaggtaaccagcagt<br>agccaattccggatagtcctagcgtgaaacgggtccgtctggagcgtgatatgatctcgactccacactggtcacgcaagcaggaaaattcggctgttc<br>ggtgaccggatttgtcatggggctgaccgcctcctgctgaactcgtgaccgacctgctgctgctgctgaccagcagccggtggc<br>agaaagcgatgaagaaaatgcttgaagcctccgacactggctgaagcgggaaagagagcgaagtcttatcaactcgattgtggcattcgctcgctgatgtttac<br>ccgtcagccggactttatgatcggcaactcctacgccaagttatccagcgcgatacgctgcgaagggtgagcagttgaagtgcgctgatccgcc<br>tggggtcccgtcgtttgtcgatcgacgaagacgccagaccggcgggtacgaagggccatgagtaccctaccaccgctggtaatgcggtg<br>ctggagaagtcgcacaggagaccatcaagctcggcaaaaccgacacacagctcgatcttatccgttaa |
| 155 | atgactcagcgacgaaccgagtcgggtacaaccgtcggcgctttgacctctcccaacagttacagccatgcagcgtatcagtgtggtttaagccgcgc<br>gacggagatcgggcagacgctacagaggaagtgctgctgcgtgcacaggaagtgcttatgcacgcgaggatgatctgtccgtacgcgggtgcg<br>cgtcttccgagcgtatggcttga |

TABLE H-continued

| SEQ ID NO: | Sequence |
| --- | --- |
| 156 | atgcgctggaagactggtcaacgctgaccgacgtgctcgatgccgatgccgaatcttaacgaactgatcgtgatgacgaaa<br>gtgagtcgcaggacgatgcgcttccgagcactggccgaggctgcggaagatgacaccaccgcggtgctgacgcactta<br>accgacgacgcgcgccatcgacgctgctgctcgctgatcgctgcgtatccgcganifccgcttgagctgacaaacgcatcgcccgngtctgcgcaggtgctg<br>gatcacctgatcgccgcacctgctgagcgaagtctgctcgcgtgccgatgcgccgtgtcccgagatgccctctgagcggattatca<br>ccgtactacctacctgaacctctgagcgagtcccctgagcgcgcttaagcacctgacctgatcctctcgccgacgcggtgccaacaagtgg<br>cgcgttacccgtgctgctggatgagtgctcgatcgcgaataccctttatcaacgacgacgactgctcccggacgaactgctcagatctg<br>ctccgcgaccggcgaagaagacgcaacgctcggaggacgctcagttaagcagccagatatcacgccgtggtgcatcaggctggtgcagatggt<br>ccggaacgctgccgtggtgataaagtgagctgagcgatcacttaacctgcttcgcggagcgattatcgacccggtgggttacggctaagcctgcggttggagctggcta<br>ggcgcgtcatgccagccgaacatcggctgaccgtgatcgcccggtgatggtgaccgacgcgggaggatgacacgcggtctcagttctacctgcgcct<br>tagctccgatctggattaatcttcctccacgactgccggtgatggatgaccgagcggagcgcgagattgacgggcgtcagttctacctgcgcct<br>ggcgacgcgccatcatgccaccgtcagcaccgcctgcacctgtcagtggatcggcgtccggacatggcgcaaaacgacattatggac<br>ctggtcacctcgacggagtccttcgctgattaccagagagaatgaagctcagacatgaaggggcatcagggcgggcaccagacgctatggcgcgccttgtgtatgcg<br>atccgctgctgaaaaacacagttgacctgacctgataaacatccgatcgcttgatattaaagccgtattaccgatcttatattacccagta<br>tctggtgctgcaacgcatgacaagcgagcctggtgagtgaagtgtcgggagttctgtgaactcgacctcggcgcaaaacgacattatggac<br>gagcaggaggcaggcctaacctggacacgctgaaccggatcgcagctgcagttccagatgcgctcgcagacgcagcgggacacctggcgct<br>ggactgtttcaccgctgaacgcgctcaggtaacgcgcgcagtctgcgcagagtggctggtggtgaaccgtgtaacaaatcaagtgtga |
| 157 | agatgtgcccagatgggattagctagtagtggagtaacggcgncacctaggcgacgatccctagctggtctgagaggatgacgacactggaa<br>ctgacacggtccagactcctacgggaggcagcagtgggaatattgcacaatgggcgcaagcctgatgcagccatcgccgtgtatgaagaag<br>gccttcggggttgtaaagtactttcagcgggaggaagaagtgttgtggttaataaccncagcaattgacgttacccgcagaagaagcaccggctaactcc<br>gtgccacgcagccgcggtaatacggaggtgcaagcgttaatcggaattactggcgtaaagggtgcgtaggcggtctgtcaagtcgatgtgaaat<br>ccccgggctcaacctgggaactgcattcgaaactgctgagagtcttgtgagagggggtagaattccaggtgtagcggtgaaatgcgtagagat<br>ctggaggaataccggtggcgaaggcggcccccctggacaagaagactgacgctgaggtgcgaaagcgtggggagcaaacaggattagataccctggt<br>agtccacgccgtaaacgatgtcgacttggaggttgtgcccttgaggcgtggcttccgagcagctaagtgcaaccgttaagtcgaccgcctgggagtacggccg<br>caaggttaaaactcaaatgaattgacgggggcccgcacaagcggtggagcatgtggtttaattcgatgcaacgcgaagaaccttacctactcttgacat<br>ccagagaacttnncagagatgnniifggtgccttcgggaactctgagacaggtgctgcatggctgtcgtcagctcgtgtcgtgagatgttgggttaagtc<br>ccgcaacgagcgcaacccttatccttttgtgccgagcggtccgccggacaaagccgcaatggggactgataaactggaggaaggtggggatgac<br>gtcaagtcatcatgccccttacgagtaggggctacacacgtgctacaatggcgcatacaatggggaaagaagcaagggaccgagcaagcgagacctcataa<br>agtgcgtcgtagtccggattggagtcgcaactcgactacatgaagtcggaatcgctagtaatcgcggatcagcatgccgcggtgaatacgttcccggg<br>ccttgtacacaccgcccgtcacaccatgggagtttgttgcaccagaagtaggtagcttaaccttcgggagggcgcttaccacttgtgattcatgactg<br>gggtgaagtcgtaacaaggtagccgtaggggaacctgcggttggatcacctcctt |
| 158 | atgaccatggcaatgcccattacggcaaggtgtatcgtaatccactaccacgcaaaactggtcgccgctggcggatggcaaga<br>aagtaatgatccggctcgcgaccggaagcagactccacctgctgatccctgcatgcgaagccgaaaccattatggagatggcggctgaagt<br>cgcttcctggaagacctgacgtcggacactggcttgccaattcggtacgctcgccaatccgatttcctcttttacgacgtgtgggcga<br>gctgtgctcggtgtcgcggggggtttcgcatgccgattcgccggtaattaccgccatcaacttctcctggaagaacaaagccaggagatctcacatgatcatctgtttcgcggcgatgagat<br>ccccatcagccttaaaggcgacatcgtgctgaaatacggctgcggcgaaatgatggcgatggcaagcgc<br>caacaacatcttaaaggcatcgtgatgatacgcggcaaatacggctgcgcgttgcccggcgcgaaatcccgtgaaatccgtgatg<br>gagctgatcatagccgctgcgggaaaactcggcaccccagcagatgatcaccgacccgcgacaagatcgtcaacacacaaaatggtctgccaacg<br>acggtgattgagctacgaccggaaccagccaggcatcatgatgttgatgagccatggaattcggcattatgattgtggaagacaccaccgcattatcggtaaaaccgccgcagaagaaa<br>acggtttga |
| 159 | atgagcaatgcaacaggcgaacgtaatctggagatcatccaggaagtgctggagatcttccggaaaaaacgcagaagcacatg<br>atggtgagcgaccccgggatggaaagcgtcgggaaatgcatcatctccaacgtaagtcgcagccggccgtaatgaccgtgcgcgttgcttcttac<br>gccggttctaaaggggtggtattcggccgcgatcaaagatatcatggccccatattccccacggccggtcggcttgagtactccagcggggtgcggggcggc<br>gtaactactacacggcgttcaggtgagctcggtacgctcaactatccgttcactcgattttcaggagcgcgatatcgttttggcggcgataaaaa<br>gctgaccaaactgattgaagagatgagagcgcgtcccgcgtaccccgaccaaaggatcccattcagtccgacggctcgcggcggcgattgggcgacgac |

TABLE H-continued

| SEQ ID NO: | Sequence |
|---|---|
| 160 | attgaagccgttgccaacgcagccgagcgcgcaaagccatcaataaaccggtcattccggtcgctgcgtcgcgctcgaaggtttcgcggcgttcccagtcactcggtca cacattgccaacgacgctgatccggcgactgggtactggcactggatcatggaccgcggttgagcgcggtccttatgacggtcaatcggcgat tacaacatcggcggcggcgatgcctggcgtcgccgatttgctcgaagagatggcctggcctggtggtcgcgtcggtccggccgacggcacgctggtt gagatggagaacagccgcctgctgtcaacctcaacctctgcaatgactatctccgcatatcatccggcatatggagaagaaacacggattccg tggatggagtacaactcttcgtccgaccaagtcgccgacgacgccatcatcgccaaatcgccgatactgttgatgacaccatcgcgcaacgccgaagc ggtgatcgccaatatcaggccgcagacgaccgccatcatcgccaaataccgtccgcgctcggaagccgcaagtgctgcgtatatggcgggttta cgcctcgccatgtgatcggcggcgcttatgaagatcggggatggaaattatcctgcggggttatgaattcgccaacgacgatactgacccgacccctg ccgatcagcggcatggcaccggcggcttcaacggagctggtgttgtcaaagccgtgcgcctatgaagctgaagcctgaacccgccctcgatcggctcggcctccgg cattaaagagaagtacatctccagaaatgggcggtgccgttcgccagatgcactcctggattactccggctctacacggttatgacggcttgcc atcttcgcccgatatggataatgacgatcaacaccccgtgggcgggccccgtggctcaaccccgtgcagttgacccgcagtccgctga |
| 161 | atgaagggaaccagagatcctggctttgctcgatgaactgctccgatgaacctaaacagaaatccggccgccggccgaaaccggcagcggcgcgc gacagcggcggcggctgcgcctttgacggtgcgcagatcaccctgctccgcctcctgctaacctcccgatgtgccaacctggtacacggcccccattggttgtaccggta gtcatggattaaccggcgcacttcagttccggccgacgatcaaccgggtcgggtttaccaccgatctgagcgaacaggatgtgatcatgggacg cggcgagcgccgtcgttccagcgccgtcgctgccaacgacatcctaccaccccggccgccgcttatctctataacacctgggtttccgccgatggag gcaacggagctggatatcgcgcccagcagaacggcccatcggtccggcagaaggggtcttatggacggcgtgaaccgccgtgaacctgtttacggcagcaaaatct cggcaaccggtcggccgcggggaagtgatggtgaaaaggtgatggcggcgtcaatattcaatctcgtcgcactcgcccggctatggtcatcgcagtcgctcggca gctcttctccggcgacggcgctcagtgaacctcagaccagcgatctggttgaagaacggggcctccaggcggagcagactggtgtaccgtgacttt gttgaggcagttttatgtgcatattatccgcgccaaaatgatccggccaccctcgcccgcctgatcagcggaaagcgctgaagtgggacgatgattatgatgaaggcgtcaatattatagcacttgacatgatgggacggcaataacgtctcggggtttactgatatcaat cggacccggatgctgatcgagcgagcaacgacccgagggggacgacgagcagcaggctgaccccccgtgcgacagagctga cacggcgcaaagccgtgctatcaccgaagaggataaacagcgacacggtgatacttacacccgtcaccggccgattatgggccgaccaagtgatgattgctgatgaaggtaacgccccgctcgtgc tggacgtggtttaccggtacaggcggcagacgatgatggcggggaagcaatatgacgcctgccgatctgatatcat ttattggcattctcgctgcgtgatgtttaccgtcaagcaggccgcaatcattgtcgtctccaccacctgtgctggcgaggcatcgggaggtcatcgcagcgccatatcaccggctgg gacaataacgtctaattccggtcgccgctgaaacgcatggaccccatgaagcgcaagaatgacggccgcggccagctgaccccggcaa acatccgtcaattccggtgctgccgaaacgcatggaccgcgcaataatccgatcctccgaagtgctcagcgataccccggctg ctggtgaaaatccaaaagtggtcaggcagaaagcgcgtaaccggccgaaatccccaatgggctggtggtggatatgatgtgtcgactcccaccccacctg tgatgacggtaagccagtaaccggcaagatcggctgtgtccggtacggctaggcgttcatcggcgtcggctggtggtcgatgatgctggctggtcgaaccgacggtgattct gtgcaacggcgacagccggccgcagcctgatgtggtgatgacgtgttattgagcgtggcagctgagctgtccgataacgtggtttatcaactgcga tttgtggcattccgctcgcctgatgttatacccgtgatctgctgagtctgtgttaccgtgagcgactttatgatcggccgactttatccaagctggctggccgaagggtg agcagttgaagcgcgatacgccgcgatcgcgcgatcgcgcgtgggatcgggcgtgttccctgttcgatcgcacccgcagccaccggggttacaggggccatgag tatcctcaccgtcggttaatgcgttgctggagaaagtcgacagaaaatcgcagagagaccacatcaagccgacaaaaccgactacagcttatcgttaa |
| 162 | atggcagaaaattatcctcgagtaaaaaagccgctcggccgtcagcctgatcggccgcctggcgcgcgccgccgattctggccgagcgtaggcttgaa cagagatccggcggttcatcggccgtcaggccgctgcagcccttcgcagacgtcggccgccctcgcaaggcttttttatccagccatcttcacgatccgatccgcaatcgacgg caatgaccccgacatcaccattatggtgccgatgagaacatcttaaccgcgctgaatgtgctgttcacgcaacaacccgaaaccgattgttctgct gagcactggccttccaggccaggcagcgaatattcgccgtgctgcgccagtcgcgcgatatgaataatccggccataaagggggtgggcgtctgct gaccgtcaacacggccgggatttttaccggccgctacagacggctacagcggtgagagcatggttgaacagtggcctggtccggaaaaaacgc agccggggcgtcaatcgccgtgctcagccattgcttgctaccgcggcacattgctgagctgcgacattagtgtcgaggcgcaattggc |

TABLE H-continued

| SEQ ID NO: | Sequence |
|---|---|

163

164

165

TABLE H-continued

| SEQ ID NO: | Sequence |
|---|---| tggcgcgctgcgagctgaacttctccctgatatcgacctgattttgctcgtcggcggagaacggctccacgcgcggaggcgcgcgagctggacaa
cgcgcagttcttaccgctgcgccagcgctgagctgagcttgcggctggaagattattaccaggagcaagtcgcgactgggagcgttacggcctggtcaa
gtttggcgacacgggccgctggtgctagcttgcggctggaagattattaccaggagcaagtcgcgactgggagcgttacggcctggtcaa
agcgcgatcatggccagcagcgacgacgctatgccacgaacgactgcgccgccatgcgcgtcgtcgtatatcgacttcagcgtca
tccagtccctgcgaaatatgaaaggatgattgcccgcgagtgcgctgcggacgtgagccgtcgctgggctgaaagacaatatcaagctcggtcgggcggcatccgc
gaaatcgaattatcgtcgccagtctaccagcttcagcttcgcgggcggacgcgccgagccgtcctctccgctcgaaaacctgctgacaaacctgctgaaagcattaatgacgaa
agctgcatcctcctgccgacggcgacggcgcaaacctgcctctattctttccgtcgtcgtggaaaacctgctgcaaacctgctgacaaacctgctg
cagaccacaacctgcctgacggcgacacctaaccggccgcgcctaaccggccgcgcctggctggctgagacgcgtggaagactggcgcaagactctggcaacggcgctg
atgcccatatggcagacggctgcgcggccgaatctttaacgaactgatcggtgatgacgaaagtgagtcgcagggacgatgcgctccgacacctggcgcg
agctggtggcagacgctcaggaagatgacaacaacccgccatcgacctggctcggcggcctgagctgagcgaaacctgctgagcgaagtctgctcgc
gattccgtcctgagctgaacaaacgccatcgacctggctcggcggtcgcaggtgctgagcggctgagcgactactaccctgcctatcaccggagtctcctgc
gtccgacctgacaggatgccgctgcgctgcgacgatgccccgtcgagcggattatcaccgctacttaccgtgctcgcgacgtgctcgcgacgtgctcgcgaa
gcgcttaagcacctgattcacctgccgcgcgccgagccgatggtcaaacaggagttacggtgacgatctcgccgctggcgtctcgacggagagacagctgg
taccctatcaacgcgacggacgacggcgcacacggcggaccctagagatgtcgccgctgcgccgctgcgacctgtctgaaagtgaggctggagtctgctctgtccgagacttaa
aggcggctgcgcagtttaagcaggcaggacatgatgcggcgctgcgtctctgcgccgcgtcaggacgagcaggcagcgtctgattcgtaagga
cctggttcgcgaaggattatcgacgggtggcgctcaggcctggtgatggcgaatccgctcgtgtatggcgtatagcaccggcagttgacgttgaatccgtaagga
atgtcgcggcttcgcgggtggttacgtaagctcggcggtcagttctacctggccgcgttaccgcaggagcaggcagttgacgttgattcgtaagga
ttgatgtgatgaccggacggagcgcgagattgacaggcggttcagttctaccctggccgcgttaccgcatcatgctcatcatgcaactctgctactaccagaga
gcggcattttgtatgaagtggatgccgcgtctgcgccccgtcgctgcgccgtcgtggtgcgccgcaggagttgacgttgacgttgactaccctacaac
atgaagcggtgggagcattcagacggtggacatggcgccgccatcacctgctcagcgcgaaatcgcctggcgcaggacacacactgctgtcgcgtaccacctggcgaactgctacgccgctt
agtcatgaccaccgtcgcgatcgcaggctgcgccaaggagtgcgcgaaacctgctttcaccgctgcctttaggcaataaacatcgc
gatcgctttgattatcaagccgatgaggcgggtattaccgatatgagttattaccagatctggttgctgcacgcgccatgacaagccgaagctgac
gcgctggcggctaacgtgcgctatcttcggaactgctggcgcaaaacgacatatggacgagcaggagccaggccttaacccgtgcctaaccgtgcctatacaac
gctcggcgatgagtcgatcatctggcgttgcaggacggcacgtggactgttcaccgtgcctgctggtaagcgctcaggttcaacgccag
ctgcagaagtgctggctgacgctcgctaacaaatcaagtgtga atgaagatagcaacacttaaaacgggtctgggctcgtggcactgctgcgcggccctggcgctggcgacctgcgctgctgcaccgctgcggtggcagacaaagccgat
aacgcctttatgatgatcagcaccgcgctggtgctgttcatgtccattccggacttcatggccattggcgccatcgcgcggcaaaaaacgttctctc
catgctgagcaggtgccgtaagctcggtgggtggttctacggtactgctcagcggtggtctcaggctccaggcaacgcgtctcttggta
acttcgactggggtgatgctgaaaaatattgaactgacgctctggttctaccagtatattcacgtgcttctgcggctcgtcgttcgcctgcgatta
ccgtcggcctgtgatcgtgtaggcgcgtctgctgccgacgcgtatcgttctctcgctggtcgtctggtctgcacattaacgccgggttagcgggtctg
cacatggctgcggggtgctgcgtctgctgccgacgacgcatgatgctcaagccgggtcaccgtgtcacattaacgccgggttagcgggtctg
gttggccgcataccgtgatggggacgcaagaagtcgccgctgcaacctgcgccggctgctacggtggctctgtctaacgccgttagcgggtctg
cttggctcgttggttcaacgcggtcgcaggcctggctggtgctgcgccaggtcctggccggggcctggctggtgaaaacgatcttcgcg
tctctcctgggtcttggccggtgctggctggccgcggtaaaacctcctggtcaggcaagtcgcgctgcgcaggtggcaggtgcaa
atgtggtatgtcgggtggcagtggtctggccgcgctccaggccgggtcaggccggggcctggtgaaacgatcttcgcgg
ttgatgaccccttcgcatggtgccgatctgtgccaccgggtctgcgggctgctcattcgccagacgaatctgcagaatgtcggtgccgggtgg
gctcacgcagaaggcgcatcaccatggtgccgatctggcgccaggtgctcaggtggtgcgccgaagtatgtgtcgctgcccgttgtcgttgtcgtctttcattggcta
caaactggcggacatgaccgggtcgggtctcgcggctgccggaagacgcaggaagctcgaagtccaacagccacgggagaatgcgtatac
gcatga gccgagagagggcgccgtcgattagtagtggtgaggtaatggccaccaagccttcgatccgctagcggtggatgaccagcacca
ctggactgagactgacacgccggaacgtcctacggacgaggcagcagctggggaatattgaccaatggccgccagccagctgatccagcccggtgagtg
atgaaggccttaggctgaaggttccggacgacgagctggctagcgactggccgcgttnagtcagaaggaaatctccccggctcagctcaactctgg
atacgnaggggngcagcgttnntcggaattactggcgtaaagngcgcgtgttnagtcagaagtgaatncgtagatattggangaacaccngtgg
gaatagctttgatactgcaggctgagttccggaggaggtggaatccgtagaatncgtagatattggangaacaccngtgg
cgaaggcggcnatctgacggaacttgacgctcacgtgtgggcgaaagcgtgggagcaaacaggattagataccctngtagtccacgccgtaaacga
tgaatgctagacgtcgggtgcatgaccatcgtcgggtgccgcgaacgcattccgcctggggagtacggccaaggttaaaactcaaagg
aattgacgggggcccgcacaagcggtggagcatgtggtttaattcgaagcaacgcgaagaaccttaccaaggtccacttgggctcgag
agatnggctccttcagttcggctcgggcggtggaacaggtcgtcgtcagtcgtgtcgtgagatttgggttaagtccgcaacgagcgc TABLE H-continued

| SEQ ID NO: | Sequence |
|---|---|
| 168 | aacccctaccgtcagttgccatcattcagttgggcactctggtggaaccgccggtgacaagccggtgacaagccggaaggcggggatgacgtcaagtcctcatg gccttatgggtgggctacaacgtgctacaatggcggtgggaacgaagtcgcgagatgggaacgaagtcgcgagatcccaaaagccgtctcagttc ggatcgcactctgcaactcgagtcgtgaagttggaatcgctagtaatcgcggatcagcacgcgcggtgaatacgttccgggccttgtacacacc gcccgtcacaccatggagttggtttaccgcaaggtggtgcctcaaccgcaaggaggcagccaaccacgtgaggtcagcggactggggtgaagt cgtaacaaggtagccgtaggggaacctggggctggatcacctcctt |
| 169 | atggccaaagccgcctctgcgtcagatgcgcattacggcaaggcgggtatcggcaagtcaagtcccaccacctctcagacacacgctggccgcggtggtcgag cttgatcaggatgatccctcatcgtcgtcgaccgaccgcaaggcgccctgatcgtcgaagccccctcacgcaaggcccaggacacgtctgatcctg gccgcgaggccgcggctcgtcgaggatctggagctcgaggacgttctccaagatcggctacaagaacatcaggtcgttcggcggtcgga gccggggtcggctgccgcgcgcggcggttctcgggcgggtctccgggatcaacttcctggaagagaacggcgcctacgacgcgacgacta tgtcctacga ctgtcgggcgacgtggtctcgggcgggttctcggctcgagatccagtccatcctggtggaaatcctacacatcgtcactcagacgtctga cctggccagt gctgtaccgcgacaaccatcgccaaggcatcctgaagtacgcgacctgggcgcctcgagctccgatcctgcaacgagcgccag accgacaaggaattggatctggcgcgacgcgtcggcgaccgctgggcctggtgccggctcgaagctgagcacgcc cgagctcgcgccatgagcgtgcatcccgaccccgacctaccaccctggaagagcgagaggatgtgaagcaggtcgaaggtgacct ggccaggttgcatcccgacctcggcctcggcgcgccgcggctgggctgccaacagcaggcggcaagcatcggagcagcgagctcgc cgagctcgccgcaaggaaggcggccggaaggcggcgcctga |
| 170 | atgctctcaggacaagatccagatgtcttcaacgaacggtggcgaccaccaagccaaatcggccaagagggacaaggaagaagggctgcacca agtccggctgaaaccgggggcggcagccggggtcggcctagacggggcggcctatgacggggatgatcctcagccgatgacgccgcccatctggtccat ggccccgactcatcggccgcggcggagagaagtctccaccggccccaaccgcttcaccaaccgatcctgtcgg aactggactgcccctatcggccgcggcggacgacatcgcggggtctcgcagttcgcagcaatacgaccgccgccgccgtcttcgctatcaga cctgcggcgcccatgaccggcgaccagcatcgccggggtctgcaagacagctggcaacggctggcaagccggtgatccggtgactcgcc gggcttcgcgggtcgagaatcttcgcggccaagagcctggcggcgaaggctcatcgctggcacagagacggcgcagcagtcacccacccacc cgaccgagcgctgcatcatcggccgatccaccgctatcggctatgcggcgtcaatctctgcgaggagatcgacaaaacgctgcaatccg catttccggcgacgcgcctaccggagatacgacctaccgctatttcgaggggtccttctcaccggacggggtgatcgcggccaagctc cgcaagatggaggacggcgcagctacggctacggccgacgacgagaggcgcatcatgatggtcgcagagtgaaagcggtcagggtcggggctgacc tacaagccggcttcgacgggtcgtgccttcctcttcaccgggcggcaagagaagatgaaggcgcatcatgatggtcgcagagtgaaggcgggggctgacc atcctgggcaccccaccaagaaatcgaccaggaggacaggagcgcaacatcatgatgtcggctatcggcatcgtcaatctctgcaggagatcgacaaaacgctgcaatccg ctggctgacacaacaggagcgcgccaccaccgctatcggctatcggctatgcggcgatcgtcaatctctgcgaggagatcgacaaaacgctgcaatccg gatctggctggtcaggtcgctgcagccgacgccggggagtccggcgcgcgcgtcctccaccctctcgatgcggcgggagtga |

TABLE H-continued

| SEQ ID NO: | Sequence |
|---|---|
| 171 | atgtcccacatccagcgcttccctccgcgccaaggccgcctccaccaaccgctgaagatgagccagccgcctggtgcggctctggcctatctcg gcgtcgaaccgctgcctccgcgcttcatggctgcgcaggcctcgggctgcaccgcctcggcgtggtcctggtgctgccattccgagggcgatcccgct ccagaccacgggcgatgatcagtcgccaccacctggaggctacgacaatctggacgaacatcctggagcgcacccatctcgagcgcaaccagcc gccatgatcggcgccgccaccacggccgccaccacccgaccaaggcggacggagaatacagcacgctgtccgccgacaacccccgactt ggccgacaaggccctggtcttcgccaacaccccgaccaggcaacgtgcgcctcgcggccgcttcgcccgccggtcaccgcgatggtcgagcggt tggtcgaaccggtcgcgcggtgcgcatcccgacccaggtcaactgctgcgcctgcatctgtcccccggcagccggccgacttcaccgcctcggtcggcg atcgaaggcttcggcctgccgtcgccgatcttccctgcccgaccctgcggccgtcgatgtgggccgccagccggaccggccgacttcaccgctcggcggcg gcgtgacctcgatcagatccgcgatccatcgggggctcgtgtcgccccaccatcggcgtggtcggcgaggcagcatatcggcgtcgcggccggagtctgga agaccgactgcgccagccattcttcaacgcgcctgaccggctggaggcgacaagctggtccgggctgatgagtgtgcgggcaagccg gcgccccgccgctgcgcggcgacccggcgaaagcctggctccagtccgatcgagtcacgggcgttcctcctcgcgcgggtgaacatcctcgtcccagctccagggc ggagccgcgacctgctctatgcgctcaccggtttcctcccgcagacgctgtcccaccgagagtgatcgccgcggtcatgggggcgcggggctggg acgcggttgaaggcgccaccatcatggtgacgccctggcctacgctgacccgatcctcccaactcgacggg cggcaggggagccgcggccgatcggcgtgctctcacccgatggcctccgccgcgcgacgtggtccgggccgtccagtcggct accgcggggccacggacccacggctgtgctgcgacaatgcatcgcggatgcaaccgcggcacggcacgagcacgagagcacgaccacg gggaatcccacggctgcggagggatcatgcggatgcaacgccgtctga |
| 172 | atgaccgacaagcttcgcagagcgccgacaagtctcgaccactacacccttccggcagccgaatacgcggcgatgttcgagaagaag acgagttcgatacggccattcggacgggagaggaagtcgcccgccgtgtccgaatggaccaagatcggaggactacaagcgcgaaagaacttcgcccgtga agcggtcgtcaccaaccgacaaggcctgccagccgatcgggcacgtctcgcctcgccaggcttcgaagcaccgcacctgccttcgctccacggctc ccaggtcgcgctattaccgacaccacctgaccctgacctgtcaaggaggcgaacaagccgaagatatcgccggtgatgaccctgcatggccga gttcggcggcctgaacaacatgatcgacgggccctcatcgccaatgcagaccaaggacaagcagtccggccgggacttccgtcccggtccctacgccacccggc cttcgtcggcagccacctgatccggttcttactacgacaacatgatcaaggggacttctgggctacgtcggcgcatcgcgcgacgatcaagctcgca gagcagatcaacctgatcccgagtgtcggcacaattcgacacgccgatggatggcgagtaccgcacctgtatgacgcgcaccaccacacccaagacc cctgcacgcaaggccaccatctccatgcaggagtacaacacgaccccagacctgcccgaactgtcggcgcaaggctgtcggcgacttctgcctcatggccga ctacccgatgggcggcgatgtcgacgccgatcgaagcgagtgctgctgaagccgccaccacaccatgcaggccaaggacctgccggccaagctgggaggcgc gagtccgtcggttcggacggagcggcccgtcacatccgcgacctggcacctgcgctgcgctgacctcactcaaggaagtggtgcttggacgg ctcgccttcggcgccgcctcgggcaaggccatggcgccgacgacaccaaggttcgcctgatccgctgacgctgcgtgatcttcacgacaaggtgactacatcatcggc aacagcacggcaagtatctgagcgcggcgacaccaaggttccgctgacctcgccgctcgacgcctgaccactaccacctacccg acctgggctaccaaggcgcgcgtgaacctgctggtacggatcctggaccggatcttcgagacactcgacgcgcaacaccaacatcgtcggccagac cgactactcgttcgacctgatccgctga |
| 173 | atgttgacctctgatattgttgcaaattgcctgctgctcgcagcacgacccgaggcatcgcaaggggcctcgacccgggacgacgaagatc ggtccgtttgggaggtgacgtgggcgacaccgtgattcgaagcgctgaagccgtcggccagggcagtccagctccctgtctgaaacatctgaatccatgt gctccgggcggccggccgcggcgaccgcgcatcgccgccggccagcgccagcgcggctctgctggcgttcccgacgacaccggccgccgccggggcc ccggcaggggaggacgcatccccaacagcgcagctgcgcggtgatcgacacggttcggcaccgacggttcggctcatcggtcgtggaccgcgcgaatatctccg cgtcctggtcggtgcgacaaggaagaacacggagagcgggcaccgcccggagaggcagcatgacggcgccgccccagatgattcgacgctcgctgctgggcgaaac cagttcctgggccgccaacggaatcgatccggcagccgcgaatcaggctcaagcggcggaagctgggcgcgcccgccggatgattcgacgctcgctgctgggcgaaac cgggaccggcaaggagccgctgccacgaatcaatccgcgccagccagatcggcgcgttccgggcgaccgacaaggctctgcgcggcaaccgcgccaac aaacccgtgaggcgaggtcttccgacgagatcggcgcacgatcggccgcgcttcacccggtgctccggagacgacaagggagatcgagccgct ggcgggcacccgttcccgacaagtggtgcgggtcgatgtcgggtcatcgcggcaccgccgggcgccaagctctgcgcggtgcaccggagatatcctccg cgtccaacaaggtggtcgcggtcgatgtcgggtcatcgcggcaccgccgggcgccaagctctggttcggtgcagaagcagttccgcgcctg |

TABLE H-continued

| SEQ ID NO: | Sequence |
| --- | --- |

```
acctcttattaccggctgaatgtggtgccgatcaccctgccgccgctgcgaccggccggaggacatcgagaagcatcgccgaccgatcctggaac
agctggcgatccagcagggcacgccgccgcgccgagctgctggaatcggcctgtgcaggtgctcgcgactagtgaccgtgcccggccagcatccgg
gctttacaacacgctggaacggtggtggctgccgatcgccgcgatcctgaccgagcgtgccggccgccatccgcagcaggaggtgctcaccgagctg
ccggccgcctggccgctgcggcggcggcggccgcgtgaggaggtgcacgccgacgccatccgcgcggcggcttg
aggaggcgaacggcgtcaaggcgcgggcggcgaagctgctgggcattcgccgcgtcgctgtacgaacgcatggtgacggctggggtgggg
cgacgcagtag
```

```
174
atgccggtccatcgcttccaagcccctgccgagccttcgacagccgcagcggcctggggatgagcggctggcgccaggccgc
cgggcggagccggagcacccgacctgggcggaagcctttcgccgatttcggccacgatctgagcgcgatcctggaacagcc
cgtatccggccagcaggctggcgagacaggaaatcgatggaccggctcggtggccgaagccggcggcggccgtgatcggcctgc
ccatgccgcagcaggcgaggagaaatcgatggaccggctcggtggccgaagccggccggcctgatcggcgctgc
cgacatcgcaccgcgccgtccggtgccgatccgagactggtggcggagaccggcgcgcagttcctgctgc
gccgcgccaggagcgggagcgggacgctgacgtcccggacccgagagctggtcggtcctgtttgggcatggtaagcttggc
gggcgcaacaacatccaaactattccagcgacatcgacctgacctgatggatgaacggaccaagggacgacgctttccgaccgctcggcttaggcccgatcccggc
tcatcaggctcgcacgcgatctgtccgcacatatggatgaacggaccaagggacgtcggcctgtcccgaccgagaaattattacggccgagctggaacggcgtatgatcaaggcccgatggc
gcaacgggtcggccggttccgtccggaccggcgaaattattacggccgagctggaacggcgtcagaactggaacggccgatgataacaaggccccgtccc
atcgcgggatcggagcgggcgccaattgccgggttccaccttccgcttccggagccttcgtctggccgccgcaacctggattccccgcgccatccaggacatcca
ttcgatcaaacgccagatcaaacgccagaccagcagctgatcttcggcgggcgggaccgacccccgcgatcgtcccgacccctgatgcgccgaacatcaaggtcggccggcgggcatccgcgca
gatcgagttctccgccagaccagcagctgatcttcggcgggcgggaccgacctgatcgccgagccctgatggcgaacgaggcgtgc
gcgacgtcggccggccgcgacggtgaagagcttgccgggcctatcattcctggccgtgcaacatccagatgatcgacg
accagcagaccatcgtattcccgcgacgatcgcgggtggcattggcgaccttggcacctcctcggcgtatgacgaccccgcgccttccggcggaact
gctggcgacgctgggcaggtgaggaccggctatgccgagctgttcgaggagcggccgtcgctcttccggcgccggcaatcgtgtcttcaccggca
cgacccgatccgggacgatggagacggctgaaaggcgcatggcttcgccggcgcttcgcggagcttcgcggccggcgtgttctcgccggctcctggctcctggagctg
cgatccggccgtgatgaacttcgacgattccggccaagctgccggccggcttcgcggagcttcgcggctcctggctcctggagctg
gtggcggagatcatggccagctgcgccgccgcaagctgtcgcgcaaccgtgtcctgcgcgcgtgtcctgtcgcgccggacttcttcgac
cgctgccggcaaggagggaccgggctggccgaccagcgcgccgacgccaccgatgcgccgacccgatttcgaggatgcggctgaccctgcgcgg
cgactcgctgccccgaacttgcccgccgacatccggccggccggcctgcctgccacgccacagccaatattccggccggtggtggtggtggga
tggcaagtcgcagcggagccggctgaccatcacgtccgacatcgacctgtcgcccaacgagtattacatcaagtgactcagcgttcgacaacgccatcaccgccgatgggc
tccccgttgtcggatgtgccaagcgcctcacgaggtcgacatgcggcctgcgccgtcgcgccgtgggcaacgccacctcgcctgaaatatcaggc
gacggcgcgctcacggctggagaccatggcgccctgaccgccgtcgcgccgtgatcggccggtgtcggccggtgtcggccagcgatc
cgctcggtcggctgacgggcgcggccggatccgccgggcggccggctgctcgacaatcggccgggactgcggcgggcgatcagaagagttcgggacgacc
aatgtctggaactgcaaataccccgcaaggcgtgggctggccggcgcgcctgatcgacatcggccggccggctgctcgacaatcggccgggcggacggcggac
atcctgcacatcggcaccggcaaggctgggctgggctgccgcccgatggtgccgccgggccgatcctcggcgtggctgggctgggctgcctgctgcgatctggc
gggctgctcgacgggtgcaggcttctcggcgtggcttcaggcgatgccaccgccggcgtgtgacttcccgatgtgcactgttgacttcccgaactgacaccaaaatccgtccgccggctgccggctggt
ccggccgccttcctgcgacttcaggcgacgtgagccggccgcactgttgacttcccgaactgacaccaaaatccgtccgccggctgccggctggt
gcccatggtcattcaagacccggtcgaggaaccgggccgtctggcccacccggccgcaccggccgaatgcgctggccgatcctcggccgatc
```

```
175
atgaaccgtctgttcctatggccgcgaccgatgatgcggttcgctctggccgcggtcggcatgccggtcggcatgcctggccagccccttgcccaggatccggccggctg
ccgcgccgccggccggctggtcgggctgccgccgctggcgccgcacgggctgggcggctcgggcgtgaatgcgctggcctcccggctgaatggcgacaccgcctggatgctcat
ctccaccggcggctggtgctggtgatgacatcccgcggcctgctgcatcccggccgccggctgtggacggcctgctcacggacggccgcatgtgcctcacggcgcctatggcggcctatcgcgacggtgatgcag
gctgttcctcaacggctgcgacttcggctcatcaccgcggcctggacggcctcacggacggccgcatgcgcctacacggcctatcggcggtctcgaccg
gatgttccagtagacgcttggcgatcatcaccccgcgatgacaccggcgctctgcggcttcctccctctgcgctggttcaccgcgctg
tggtcgatcggtggtctatcggccgatcgccccggcaggccttctcggcgctgcggccgccgcttcctcgtgccgcttcggcgctggcttcaccgcggcggt
cggcacatcaacgcgccggctgcggcgcctgctcggctgggctcgggctggtgatcggccgggctcggcaagcgccgctaccgaggcagcgcctggccgccgatcggcggcgcacaac
cggtgtgctgctggctgctcctcggctgggctgcggcgctgggcctggacggccgtcggcggccgggtcggcctcaagcgccggtcggccgcggatgg
cgctggccgccgcacgcacccggccggctgcggccgggtcggcagctgggcggcatgctgctcggatgtcggcgcgctccggccggatcatcctcggccgatc
```

TABLE H-continued

| SEQ ID NO: | Sequence |
|---|---|

176
atctccggccgtcgccggcctggtcgcggtcgcggtcgacccggccgccggcttcgtcgacccgacgggcgccatcgtcatcggcatcgtcgccggcgt
ggctgttctgtcctcggctctcaagcacatgctggctacagccggacaggccctcggcgtgcacgcgccttcggcctcgtcctctgtgtcctcgccgatcgg
cgccatcctgaccggcgtcttcgccaagatgtcggtgtcaacagcaggcggcttcgcctccgtcctgctgagcgaaggcttcgaccgtccgcacgtgg
gcctgtggaagcaacgcgccgccggctggatccagtccagtccaatggtcctacacacgtctggtgcgccatcgtcctgtcctgtgaa
gatcgtcgatggtgcatggcgtgtcgcgtcgaagaggatgtggagcgcgacggtctcgacctcgcggctccgcctcgcgctggcgagagcatccactaa 177
atggatgtcggcaaagacgggtggcgacgtcctttcgtcgctgatgggcgcggtgatgtgctggcgatgcattgccgcctgctggaggtcg
ggacgtccggccagagaatcagtcaacgcgctggtgaagatcccggtgaagacctcgcgactcgcgacatcgcctattttctcggttatgccgtgg
cctacggcatcgacctctctcgccgacgcccacacgtctcggcgggcatcgtctcggcggcatcgccagcgtgctcaggtctctgcccaggcccgcacctggcgct
ctggcgacctcgccgccggtgccgacccgccatcgtccgggcacccgtctcggcctgcaaagctgatggccgccgacctcggccagccttccacg
aactcgcggctgtctatccattgctggaggcacgtctcggcgctggcggtcgactgcaaccgccgtctgaacggcctaccgtccga
acggctcgctgatccgccattccgccgtcgaacatccccttcctcggcgctgggcccctggtcgcggtgggtgtcggcttcaacgtgatgagc
gcccagtgctgcgatggccgtgaccggcgccggccggtcggtcggccgcgagtcagtgtcggccgagtgtcaccctcgctgtgatcagccgcacc
gatcccggcttcgtcccacaacggcgctgctctggcccttcaacaatgccagatcgcgaggcactggacgtctggcgcgtgcacggtctg
tgcggcccgacccggcgctgctcggcctcggttcgccggtgcggttcggcctgtcggcctgcgctgctcgtcgctgcggtcatccgcctcagccagatcgtcggcac
ggcaaggcggccagcttcggattcgtcgttgtccaccatcaccgtaccggaagaggacgcgcgaccccctgtaa 178
atgacccctgaatatgatgatgatgaacatcggcatcctgactgaagaattgcaggcttcttcccaactggctgcacccgt
gcaggtagttgtgatgaacatcactgattcgcaggctgaatacgttacgaatgacccgtaaactgcaaaatcgtcaaaatcgttaaaagcagactt
gagaaacagagagattggcttaaaatccggagcacacttcacgtcgtgtccttatatgtggttgtgacaaagaggtcgaagccggcaaagt
tgctgtcggtacccgtcgcgtaaagacctggtagcctggagctaaatgatgttatcgagaagctgcaacaagaattcgcagccgcagtcttcaac
aactggaggaataaggtattaaggcggaaacagctcaaacgcgctcacttcacgcccgaaggggggaagctgctgacctcacgattccgctatttcattcact
agtctgaaggcgagcagcttggtattgcgatagaactcacttcacgcccccgaaggggggaagctgctgacctcacgattccgctatttcattcact
gaccgggagttcaaaatga 179
accggataagagagaaaagtgcgacgtcggtcggtcggtgatattgacggcgcatccgcacctcgccagctcgccagttttgtggtgatctgttggcgatttgc
gggtcttgccggtcggtgcggcgaaaaaaatccatacacggctcctgttgaaaaagagatccgggggaaaatgcggtgaacat
gtcagccattgcgaagagtgtgccagtttgctcacggcaaagctgattaatgcaccagatgggtattaatgcaccagatgggtatctggcgcgacgtc
ccctggctaatgccgtcctgacggcgctgacctgaccggcagattcgtcaataccgatccggattacgcaaggctctggatgccaccctggcgtt
tttgcatgttataagtgccgacatgatgacgctccggccacgccagaacaattgcacaaattgcacaatggtctgaacctgatctggttcttgccaagctgcactc
gtgcgatgaccctgaatatgatgatgagaacatctcggtctctgcggtcggtctggttcttggtctgcgatccctacgcccacctggccagtgtcaatgaggctcacgatggctcggtggcatcgctcggttactggctctggttcttggtctgcgatccctacgcccaccctggccagtgtcaacggctgtaaaagca
ccgtcaggtagtgcgcaagacgagaattggcttaaaatccggccagcacacttacgtcggttctggttcttcccaactcgtgaaaagca
aagttgctgtcggtacccgtcgcgtaagacctggtcgacctggagctaatgatgttatcgagaagctgcaacaagaatcgcagccgcagctct
tcaacaactggaggaataaggtattaagcggaaacagagtcaactcaaacgcgcggcgtctcaccgtgagcgccctgagtcgc
ttactggacctggaaggcgagacgctctgtgacggcgagttgacaacgcactccatcacccgtctggcgttcatcccggacacgccagtgtcatgctgcatcat
agcgtggttctcagcagcaggcgatttcaacattgacctgttgctgcatggaaagctgcattcacaatgacattgcgacatggatctgcagattgcagcagtct ...

TABLE H-continued

| SEQ ID NO: | Sequence |
|---|---|
| 180 | tggtcggttacggcaaacttgggcggctgggaattagttacgtccgatctggattcggtgttcctgcacgactgcccatggatgtgatgaccgatg gcgagcgtgaaacgatggcccccagtctcattggcctcgcagcgcgtgatgacctgtcagcacgcacgcgacgcgtccggcattctttatgaag tcgatggcggtttgcgcgctggcgtccggcaaatgctcggtgaccactgcggaagcgttcgccgattatcaaaaaatgaagcctggacatggg agcatcaggcgcggcggcgcgcgggtgacggtgaacgagcccgatcctgacgccgaatttgacgccatctcctgatgacccccg cgatgccgctaccctgcaaaccgacgatattgagtttatcgcctacgatctggtggctcgcgttgcccatgaggaagcgcgaaatgacgcgctggtggctcggtgatgatgtg cgatgaggacgcggcatcaccgatattgagtttatcgctctggtgcctcgcgctgagaggaagcgcgaaatgacgcgctggtggctcggtgatgatgtg ccactcggctgccaggacgtgccaggaacactgaacgcaagctggacaagtggctggtg gaaccgtgcgccccggcgtaa |
| 181 | atgacccctgaatatgatgatgatgatgccagccgttctgtaataataaccggacaattcggactgattaaaaaagcgccctcgcgcgcctttttatattctc gactccattaaaatctaaactccatccgatttcactcattcaaactggccattatcaaactgacccgcgatggaagctcgctgtttaacacgcgttttttaa catttattgaaagtcggtgcttcttgagcgaacgacaatttaagtggatctcccatcaaaaaaatattcccaacctaaaaaagtttgtgtaatacttgtaac gctactggttaagtccgctaacctaacctgagggtataactggatgatcgtgctactaactggcgctactggaacgacatttcgggttatcgtccaaaaggtgcactc ctgacccacgattcccgctattccattcattcactgaccggagttcaaaatga |
| 182 | accggataagaagagaaaagtgtcgacctcggtcggtcggtgatattgacaccggccgatcccgcctcgccagtcgccagtttttggtgatctgtgttggcgattttgc gggtcttgccggttgcggtcggtgccaaaaaaataccaatattgccataacacacaccgtcctgttgaaaaaagacaccccgcgggggaaaatgcggtggtgaacat gtcagctattgcgaagcgtgcagttgccagtttgctcacggcaaaagctgcaccagaatggtataatcgccaccagaatggtataatcgccagctccgcgactc cctcgctaatgcccgtctggcgggctttgacgctgataaggcgctgataaagcgctgtttgatgaactggccggtcaagactacgacagacaccgacgacatcaacgtgacgagacactcggcggaagctgc tttgcatggttataagtgcttacgctgtcctctggacccgagttggctcggtgacaccgaccaatgtcaggaactactacgacagccgccggcgctttttat atctcgactccattaaaataaaaatccaatcggattcactatttcactattcactattcatctaaacctacagaacctgacctgcccagatccccatcaaaaaaatattctcaacctaaaaaagtttgtaatactt tttaaccttttatgaaagtcggtgcttcttgagcgaacgacgatcaaattcactatcatttggcttctcttgagcgaacgacatcaaattgaactatcatttggcttcttgagcgaacgacatcaaattgaactatcataaatggcttctgactacgaccagccagccgacactccagcgtgctattcaca |

TABLE H-continued

| SEQ ID NO: | Sequence |
|---|---|
| | atgacgccttttgcagcacggcatgatctgtctgtacgacagcagcagtgcgatttgactattgaagcgttgcaggaagccgatcagcagttgatccc |
| | cgcagctcgcaaattcgctaccgtccggtgaaggctggtggcacggctcggggacggtgcttcgcagggggcaatcgtagtgtggccgtggctggctgacgat |
| | cagcgctttcttgaccgcctggactgatgattacaacctgccgttatccgcggtgacgggaaacagatggtggcgtgcttacagctcggcgtccgatgccgatctggatcggcgtccggatctgcgcgtcctgatagtcggatcctgatccagcgggg |
| | gcgcaaccgatggccgatggccgcgtacgaagacggtacccgcctgacccgcctttctcggaaacggtc |
| 183 | tccctgtgcgccgtcgccgatggtggccaactggccgctcgccacccgtctcgatgaactgctcgaccgcaatacgcctctatcaaccga |
| | cggcgatgaacgcctatccgctgatggacgcacaataacctgttcgcgtgcgtggaggacggtaagagctcagagagagcaacaacgccagtta |
| | agcagccgcagttgtccgccgtcgcgggcggacccggtaccggtaacggcgatcgagaaagtgacgatcacttaacctggctggcgggaagcga |
| | ttatcgatgcggtggtgcagcaagcctggaacggtggaaggcaggtagttacagctcccgtccgcctctggatgtggtgttcgacgtcgatgttcgccg |
| | tggtcggttacggcaaactgcgcgccggccagtcattttgcgcctccgcagcgcgtgatgatgcaggacaagcgcgccgctgcctggatgtgatgatgaccgatg |
| | gcgagcgctgaaactggaccgcgggcgtgcaccggtcggtaccctgcacactgcgcgcgccgccgactgcgatgatcaaaaaatgaagctgacatggg |
| | tcgatgcgtctgccgcgacccggtaccggcgcgtccccgaacactcgacctgagcgtcccgatatcaaaaaatgaagcctgacatggg |
| | agcatcagccgcgctcggcgcgtgcgggtggggtgtacgggagatccgaattcgacgcgcccgaattgcacgccattcgccgcgatatcctgatgtccccg |
| | cgatgcgctaccctgcaaaacgaagtggcggggaaatcgtgagaaatgcggcgcccatcgtccggtaacaagccgcaaacggccttcgatctcgaaagc |
| | cgcatcctcgcaggacgtggcgcaaaacgcatcatggacgacgacgaggaaggccgtgataccaacgtgctgctggctgatgagctgca |
| | ccaacctggcgctgcaagagctgccaggacaatggcgttgcttgtgcccgagcgtggcttatcaaaccagctgggacaagtggcggtg |
| | gaaccgtgcgccccggcgtaa |
| 184 | taaagcgagcgctcacttacgtgatctgttgacgctcgaagcgagcgaccattacttcagcgtcagcgatacgggcggtgtgagtgcgcaatcag |
| | cctggcgaacctggtcgtcaccgagtggttagcgacgcaggtctggcgaacctcctgatgaaaaagcgcaggctaagttgccgactccttaa |
| | cgctttgctgacgtcatcgtctgccaccgcgggcgcgagctgaaaaaagccttgccagccgctggcgcgacagccttaccgcggc |
| | tggcgctgcatcgacagcgcgtttatcgtccggacattccgtataaccgccattaccccaggagcgcaccggaaaacgctaacgaaag |
| | ctattgaaacgcgcccgtccccgcgctccgtcgccgtccggcgtcaaccctgatcctgatacccgataacgggccgctcgaccgatacccgccggcccg |
| | gatattcgattcccgtccctgcggcgtcctgctgcgcggaccgcgtcatcgcggcgaacatcgatgaactcgctcagtatcgtggagttatccccgacggacagcgatacgcggacgaggaggaggatgagagcagcaactgaggc |
| | ctctatcaaccgacgcgatgaacgcctatcgatgaactcgacaataccgtgcgccggacgttacccgtcatgaaagtgaggccatctcacgcatcgcgaagg |
| | ctggcgaacgattatcgatcggtggtgcgcaagcctggaaccagagcctggagaaccggaattaggttacagctcgatctggtgtcctgcgacctgcgcccatga |
| | gcgcggttcgccgatggcgaacgtgaaatcgatggcgcgtccgattctcattgcgcctcgcggaaatgctggtcagacgcgccgatccaggcgcaccgtcgtccg |
| | gcatccttatgaagtcgatggcgaatcgcagcacccacctaaccgaccggtcgggaacggcacccaggaagaccgtcgccgattatcaaaaaatgaa |
| | gcctggacatggagcatcaggcgcatcccctgcgaaggctggcgcaaaccgcatcaagggctgtgcaggcagaagcagcctggcgcttgtcgcctgga |
| | ctagtgagctccgcgacctaccctgcaaaaccgaagtgcggaaagccttgtgtctctccaggagcaggaaatggaaagttcgctgccagtctgcca |
| | ttcgatctgaaagcgcatgaagccgatcagcgcgtatcaccgatattggttatcgctcagttagttctcgcttcgcagccatggcatcgccgcgatccgct |
| | ggtcggataatgcgcatcgccaccacctggccgcaaagctgtgaccccacgcattagaaaatgacgtgcggcattgacgcatcgccgcaccgttg |
| | gtcgatgagctgcaccaccctggccgtgccaggacatggcgctcctctcgttgtccgcgagcgtgcttatcaaaaaacagctggga |
| | caagtgagctggtggaacgcgtaccggaagtgctcatcgccgcacaattttgtctctcaggagacaggaatgaaagttacgctgcca |
| | gagttcaatcaacgcggtgtcatcggtgggtgatgtctggaatcgtgtgatgatgatgtggcggcggcgcaaacgtgggcggcgattctctctccggaagcgccagttcc |
| | ggttgtcaatcaggtcatgtgtggcgcgccgctgcccggcgcgcgcgaacgcggcgaaggccgtcgtgcggttggc |
| | ctaagctgcgctgcgtgctgccgtgccgcggcacctgcaacctgcaaccagcaactgatccgc |
| 185 | atgaccctgaatatgatgaatgatgctcagccacgcgttctgtaataataaccggacaattcggactgattaaaaaagcgccctccggcgcgcttttttatattctc |
| | gactccattaaaatcaaaaatccaatccggatttcactcattcaaacggccattatctaagatgaatccggatcggagctccgttttaa |
| | cctttattgaagtcggtgcttcttgagccgaacgatcaaattaaagtggattcccatcaaaaaatattctcaacctaaaaaagtttgtaatacttgtaac |
| | gctacatggagattaactcaatcagagggtattaataataaaatgatcgtactaaactggctactgcttaactcaggtaaggatcggcca |
| | ctgaccctacgatcccgctattcattcactcactgacggcgagggttcaaaatga |
| 186 | accggataagagagagaaaaagtcgacgtcgaaaaaaaataccaatattgccataacacagctccctgtgaaaagagataccgcgggggaatcggtgaacat |
| | gggtcttgccggtcggtgccgaaaataccatattggccataacacagctccctgtgaaaagagataccgcggggaatcggtgaacat |

TABLE H-continued

| SEQ ID NO: | Sequence |
|---|---|

187

```
gtcagctattgcgaagagtgtgccagtttgctcacggcaaaagctcgaccagaatgggtattaatgcaccagcctggcgcttttttcggcacgtc
ccctcgctaatgcccgctggccggcttgacgctgagcaatgcccgatctggtcaaggctcggccggtttcggggttatcgtcaaaaggtgcactc
tttgcatggttataagtgcctgacatggtgtccggcgacgccagtggcacaaattgtcagaactacgaactaccgaccgcaggagt
gtgcggatgaccgaatatgatgatggcagcgccgtctgtaataataacggacaattcggactgtaaaaaagcgcctcgccggcgcttattat
attctgactccattaaaataaaaatccattggattcttcactattcactatttaaactggccattatctaagatgaatcgatgaagctcgtgttttaacacgcgtt
tttaacctttattgaaggtcggtgcttcttgagcgaacgatcaaattttaagtgactacactggtcccatcaaaaatattctcaacctaaaaaagttttgtaatactt
gtaacgtcacatggagattaactcaactctagagggtattaatatgatcgtactaaactggtactggcgcaactcactcacgccccgaagggggaa
gctgcgaccctacgcacctacccgttcatcattcattcactaccgacggggtcaaaatgaccagcgaaccaggttgacaacctcagcggctcgatta
tcccagcagtccaccgttcaccgcgatgcagcggataaagcgtggttctcagccgggcagacccggcaggccagggcatgggccagaagcacctccagaacagttgatcccc
atgagccgtttctgcacacgcacggccatgctcctaccgtccggtgaaggtgcgtgcttcgcagggcaatgctagtgtgtcggcggtcgtggctgacgat
cagcgctttctgacccggtgatcaacctggacctgcccgctggtatacgccgatagggccgatgccgagacttttggcggctgacg
gcgcaaccgatggcgcgtacgagagcgggtaccccgctgcgacccgcttctcggaaacggtc
```

```
tccctgtgccgtgccgcgatgccgtgtggccagccaaatggcccgcctaccgctctgtcgataacgtctgcgaccgaactgcgtctatcaaccga
cggcgatgaacgcctatcgccgatgaactccgacgatcacctgttgccgctggcgtgccggaagaggcagcagctgaagagcgtcacggcagttta
agcaggcgagttgttgcgcgtagcggccgggatatcgccggtacgctaccgtcagccgacggcattcgcacgatcggcaagggcggcgttcgccg
ttatcgatgcggttggtcagcaagcctggaacagagtggcgcggtacgctccgatcctgtattaggttacagctccgatccggattccggtctggattcgtgatgacccgatg
tggcggttacggcaaactgcgcgctgggaattagttacctgcgctccggcctcgtcgatctattgccggcgtgacactcgcgtgttcctgcggcattcttatgaag
tcgatgcgcggttgcgcccgtccggcggcggccgaatcgtcggtgaccactcggagcggttcgccgatatcaaaaaatgaagcctggacatggg
agcatcaggccggctggccggcgtgcgcgtggtgtggcggatccgatccgacctgaccgcgaattgaccgcgcattgacctgacgcgacgatatcctgatgacctcccg
cgatgcgctacctgcaaaacgaagtcgggaaatgccgggaaatgcgggaaacggttcgatctgaaagc
cgatgaaggcggtatcaccggatatggagttatcgctcagtatcggcttgcccatgaagcaactgacgcgctggtcggataatgtg
cgcatcccgaaggctgtgcgcaaaaacggcgcatatcatgatgacgaggagggccgcggatgatgagctggtacccaccctggctgatgagctga
caactcggcgctgcaagagctgccaggacatgtggcctcttctgttgtgcggagcgtcgcttatcaaaacaacaagctggacaagtggctggtg
gaaccgtgcgcgccccggcgtaa
```

188

```
taaagcgagcgctcacttacgtacgtcttgtgacgcagtccgaagcgaccattcactcagccgttcagcagatacggcggtgggagtgcgcaatcag
ccctggcgaaactggtctcacgagtggttagtgacgcagggctggcgaacctccctgatgaaaaagcgcaggctaagttgcgactccttaaa
cgcttgctgacgttcatctgcacgcagcgcgtggccggatattgacgcgtcggaaaaagccttgccccagccgccgtggcgacagttacgccggc
tggcgcggtgatatcgacagccgcgttattgctgctcggcgaacttcccggacgcggagtgctggaaaaactgccaggggcttcagcacg
ctattgaacgcaccggccagagagtgaaatcgaacattccgttaccccgaggacgcgccgaccattcccggaaaaacttaacgaaag
gatatttcgcatgccctccgtgcgccgacgatgtgcgcgtatcttccgagctgcggcaacctcggcgcgcaattccgatgaactctcgatgaactgcgacccgtcgacgacacg
cctatcaaccacggcgatgaacgcctatcgccgatcaacttcccgacgtcgacagctccccggctgctccgatatatgcgtcgccggagagatgaagacaactggaggc
gtggcggacgagttaagcaggccgagttgttgcgcgggcggcggatatcgccggtacgctaccgtcacttaacctgg
ctggcggaaccgattatcgatgcggttggtcagcaagcctggaacagagtggcgcggtacgctccgatcctgtattaggttacagctccgatccccatgga
tgtgataccggatggcgaggtgaaatcgatggcccgccgcaaactggcgcccagctctattgtgtcctgcgacgacgcgcacgtcgtccg
gcatcctttatgaagtcgacagcgcgttgaccgcggtgaaaatcccggaacgttcgcgctggaacactttgacgcacttgacgaacaagagcacctgcaaggcttcagcacg
ctattgaacgcgccagagcgtcaggtccgctaccctcggcgtctttcagatatgggccgcgccatcttggtaacaagcacaaagaccgt
ttcgattctgaaagtcgatttatcgcgtgtcttcaccgatattggttctcagtatctggttcgctgatgaaactcggcctcgcgccgccgcgatatc
ggcggataatggtcgaccaccgcgcgccccatcatggatggaggaaggcgcatcaggaaatgctggaggaaggcgaaactgacgcgct
cgtgatgagctgcgaccacctggcgtcgaaagctgcgaaagctggcccccgctttgtgcgacggtcgttatcaaaaccagctggga
caagtggcggtggaaccgtgcgcgcccggcgtaaggctggtgatcatcgcgcaaattttgtatctccaggagacaggaatgaaagtacgctgcca
gagttcaatcaagccggtgtcatgtggtggttgatgctgatcgtcgacgcgctactgacgtcaacgaacattctgcgatcccgaagcgccagttcc
ggttgtaaagtcgatactattgaagagcgaccgggcggtggtgccgcaaacctggcggatgcaacctggcagaacattgcctcgctgggcgcgccgctggttggc
ctgactggcgcattgatgatgcgggcggcgccgaaagcgctggcgaaagcgctgagcaagtttaatgtgacctcgtctcgacctccgacctccaccaccatca
ctaagctcgcggctgccgctgccggctaacagcagcaactgatccgc
```

TABLE H-continued

| SEQ ID NO: | Sequence |
|---|---|
| 189 | atgaccctgaaatgatgatgatgccgagcccgtcaggttgaacgtaaaaagtcggtctgcgcaagcacgtcgtcgtcgcagttctccaaacgtt aatggttctgcttcagcattccagaatccctcaccacaagccgcaaaatcggtaactccaattctgccaaatggcgggatcggttcattttt cttctcttttcagcattccagaatccctcaccacaagccgcaaaatcggtaactccaattctgccaaatggcgggatcggttcattttt gttgccttacaacgagagtgacagtacgcgcggtagtaactcaacatctgaccggtcgataactcacttcacgcccgaaggggaagctgcctg acctacgattcccgctattcactcactgacggaggtcaaaatga |
| 190 | accggataagagagaaaagtgcgacgtcggtcggtgatattgaccggcgcatccgccagctcgccagtttttgtggatctgttggcgatttgc gggtcttgccggtcggtggtgcgaaaaaaataccaatattcgcataacaacagctcctgttgaaaaagagatcccgggggaaaatcggtgaacat gtcagccattgcgaagtgtgccagtttgctcacggcaaaagcgctgaataccgatctggataaggtttgtcggttatcgtccaaaaggtgcactc cctctgcaatgccgtctggccggctgagcgtgataaggcgctgataaggccgcaacaattgcagaactacgaccagtacccgaccggcaggagt tttgcatggttataagtcgtgacatggtgccggcacgacgggctggcagcgtcgtcgtccagaagcacgtcgtccgcagttccca gtcgatgacccgaatatgatgatgcgcaacgttgacgtaaaaaagcggttttttatggatggaacacggtaagctgctctttcaca aacgttaattgttctcgcttggcagaacgatggcgaaaaaccggtgcgaaccggtttttatggataaaatcgtgttaccacagcaatccatt atttttgtttgcctcacaacgagagtgacagtacgcgcggtagttaactcaactgacggtaactcatccatccaaatgctgggattgttc gccgaccctacgattcccgctattcattcactcacgtgcctgcaaatgaccacggggtattaactaccgtcggccgttcgattatcc cagcagttcacgcgacacggcatgatcgtcgtacgacacagcaggcgatttgactattgaacgtcaggagccgatcacgatcgagttgatcccc ggcagcgtttgacgcaattgctaccgtccggtgaaggggtgttcgcaggtggtcaattgttctagtgctggcgctggctgacgatc agcgcttcttgacgcgctgggactgatgatataacaactgcgttatcgccgtgccgatagggccgatgcagcgtttgcgtgtgacgg cgcaaccgatggcggcgttacgaagagcggttacccgcctgccaccgtctggaaacggt |
| 191 | atggcgctgaagcacctgaccgatcacgctccgcgcggcgtctgcgcggcgtcgccgatggtcgccgcgccagccgtctgctgctgatgagctgctggat cccaacaccctatcagccgacggcgaccgatcctcacggcggcacaccctctgcgccgtgccgccggaagaggatgaagacagca gctggaggcggtggcgccagttaagcaggcggagcagctgcatatcgcggcgccggatatcggctggcggtaccctgccggtgatgaagtcagcgatca cttaactggctgccgaagcgatcctcgaccggtcgctggctcacgggcagctaggggcaggagctgctgggttgggggtccagttggggagctcgtctccatgac tgccggcggtgatgaccgacgggcgagagattgacggccgctgcatagttcaactgaccctgccgagatcatgccacctgtcagcac ccgcacccgtccggtatctctcacgaagtggacgcccggctcgtctttcggcgccgcggtctctatggcggccccgctgcctgatgctgctctgctgctgact atcagcagaacgaaggctgacgtgggaacatcaggcgtgatggggaccctgcgagaccgaggtcgcgagtgcgagatgcgcgagaagatgcggcgcccaccttggca acaaacatccccgatcgtttgatatcaaagccgtatgcggcgggacgatcgaattttattactccagtcgtatctccagtgacaag ccgaagctgaccccgctggtctgacaacgcgctattcttgagctgctggcgcagaacacatcatgacgaggaggagcggcgccttaaccat ggtaccaccacctgcctgatcgcgtccatcacctgcccctgcaggagcagcggacgagcagcggcgcagaggagccttcagccgggagcgtcagca ggtcagccgcagtggcagaagtggcttgatggcttaa |
| 192 | cgtaaggcgcaccaccagctccgcgcgttgctgaacgacgctgaagccgttctgctgccgcggacacaccgccacgaggcgttattccgcaccga ggtcgtcgggcgcaaatggcctgatgaatggctggtccagccgcgctgcccgttcctcaacgaggcaggaagaaaatagccggat cgttcaaacggttgccgatattaacctctcggggtcggcggcgaccgccgatcggcccggttgaagatgccgccgaccagtt gccgaagtcggtcccgcgacatgacacgagatcgcagcgtcttgaatattccgcgccaggcggcgccgagccgtctcgtcagtgaacgata attcaggcggagacggaccctatggcctgaagcacctgatcagccgacgagcggcagcagtcgcctatcgctgctcgctctgcggcctcg ctgctgatgagctgactgggatccaacacccctatcagccggtttaagcaggcggcagcagtatcggcggcgatatcgctggtaccctgcc gaagaggatgaagacagcaccggtcagcgatcacttaactggctcgccgaagcgatcctcgaccggtcgctgggggcagatgtcgcctacgg ccagccgaccaccacttgcctgatcgcgtccatcacctcgccctgcaggcgttgaagctggcgtcggagctggagctgctacagctccgatct cgatctggttgtcctccatgacatgccggagggatggatgaccgacgggcgaggagattgacggccgctgcatagttcaactgaccctgccgagatcatgccacctgtcagcgc gatcatgccaccgttgctgactatcagcagaacgaaggctgacgtgggaacatcaggcgtgggatgcctgtgtatgggggatgctggttggttctcacca ccgccgaccgcttgctgctcatcagccgaaggcctggcagcctggttcgtcggggcgccgtgtcgcgcccgtgctatggcggacaccgccgacggcg |

TABLE H-continued

| SEQ ID NO: | Sequence |
|---|---|

193

```
ctgcaggcgcgcttgacgcttgacgccattcgtcgcgatatcctgaccaccccgcgggaggggatgacctgcagaccgagttcgcgagatgcgcgagaa
gatgcggcgcccacctgcaacaaacatcccgatcgtttgatatcaaagccgatgcgcgcgcgggatcaccgatattgaattattactcagtatctggtcc
tacgctatgccagtgacaagccgaagtgaccgcgctggtctgacaacctgtctgacagctatgacgagacacatcatggacgaggagga
ggcggcgcctaacgcatgcgtgacacacccgtcggtctgcaacacctggcctgcaggagcagcccggacccgcagaggcct
tcagccgggaggagcgtcagcagtcagcgcagttgaacgtgaaagtggctgatggctaactataaatcggtgtgctattatccgcgcaaagttgcgt
ctcgcaggagagagtcatgaagtaacgctgccggacttgaacgtgaacgtgctgtggtgtgatggtgggtgatgtggtggcaaacgctagcgatgaa
cccaccagtcgtattccccggaagcccccggtgccggtgcggtgagtggtggaaaatatcgaagaaccgtcctggcggcaaacgctagcgatgaa
catcgccctcggaggtcacgctcgcgcgggatcgacgggatcgacgggatcgaccggatgaccggagctgaagtgccaggcgctgaccgcaaatgtgaatgt
gaagtgcgactcgtctcgtccgcgaccaccgaccatcaccaagctgcgggtgctgctgcgcaatcagcagctgatccgcctcgacctttgaagag
ggcttctccggcgtggatccgcagccgatgcatgagccgcattcagcggccgggcgctgggagcgccattggcgcactgg
```

194

```
atgaccctgaatatgatgctagaagcgtcaggtaccgtcatgattcaccgtcgcgattctcggttccctggagcgcttcattggcatcctgaccgaagag
ttcgctggctcttcttcccaacctggattgcaccagtgcagtagtgcatgaaatcgatattaccgattctcaggctgaatactgaataacgaatggacgtaaacta
caaaatccgggcattcgtgtaaaagtcgaatcgggattaggaaagatttgataaaatccggagcacttacgcgtgtccgtaatatgttggtct
ggtgcgcaaagaagtcgaagcgggcaagtgccgtgcgccacgcgtgcgcaccgtcggcagcaccgagcgaagtgactgagacctcggcagaa
gctgcaacaagaattcgcagccgcagtcttcaacaactggaggattaaggtattaaagccggaaagcgagtcaacacgagtcgatcaatcgtatc
aatggcgagattcgcgcctggaagttcgcgcctgagctccgacggccgcagggcggacccgctgctccgaccctcgccgtttcccgtgttaacac
cctgaccggaggtgaagcatga
```

195

```
ggccgtcgcccagcgtcgcgcgtcccacagcaggggcggtaggccagcagtccgcgcagcgtgccggcggttaatattgaccggggcggcgg
cggcctccccagcgtcgctgtggatcattccgatctcggatttacggtaccggtacaaagaaaatgccagtccgccatgtcgcgttctgt
cggaatggtgttgaaaaaggaatgacagaggtatgcgaaggcgtgccgaggctacaccgcgaatttccccctcggatcaatgttcgcgtg
tcgttcgataaggggcgcacactgcgatggttatccgggctatccggtaccccggcggtacacccgtgaatctccgtctaccgatttgcataacttgtcataactggaca
caggagttgcgatgacctgaatatgatcagaagctagagcgtcagggtaccggtcgcaccgtcatgattcaccgttccggttcctggcatctggcatc
ctgaccgaagagttcgctggctcttcttcccaacctggattgcaaagcggcggcaagtgaataagagaggatttaaaatccggagcacacttacgtcgtgtccc
gtatatgttggtctgtgtgacaaagaagctcgaagcgggcaagtgccgtgcgccgacgcgtctcaacattggaaacggaagaattcaaacgcac
gtccgaatcgtatcaatacccgacggcaggtgaagcatggaagccagcaaaacgtgcaggggtgctgctgcgctgcctctcagcagttcaccgcc
cgctgttaaccgaggtgagccgggatgaggtgagccgggacaccgagaggtgagttgaaacgtgcaggcaggtgctcagcgtattacacaacgatgcctttatgcag
cacggagttgcgatgaccctgaatatgatcagaagctagagcgtcagggtaccgtgcgtcacgcctcccccggcggcgaccg
agatccgctatccgcgaggggacccctacgattacgatctcgccggttatcgcgccgtaccggtctggcccagggcagctgctgggccagcgtttt
ctcgaccgcctagccctacgattacgatctcgccggttatcgcgccgtaccggtctggcccagggccaataggggtgtcggcggcccagc
cgatggcggcgcaggaagagcggctgcgccgctgcgccctcgcaccggttctgcgaaaccgtc
```

195

```
atggcgctgaagcacctgatcacgctctgcgccgcgtcgccgatggtcgccagccagtcgcgcgcaccccgtgctgctgatgagctgctggat
cccaacaccctatcagccgacggcgaccgatgccatcggcgacgagctgcggccagtacctgcgccggaggagatgaagacgcagca
gtgcatatcgcggcgcggcgatatcgtcggtacccgtcggtgatgaaggtcagcgatcactaacctggcttgcgcttcgcgctcggctacg
gtaagctggccgtggcggctggctacctgcgcggctacagcgccgatctcggatctggttcctcgatgacgccgcgggaggtgatgacgacgcgcgggg
agattgacggccgtcagttctaccctgcgggctgcaccgggcgctgagcatcgccgtgatcgcgcgggatcatcctgcacatgcctcggggaacatcag
cgctggtcggccctctcgcgcgggcggcgcggcgggctgttatcagacgacctggcggtgcaccaccgtctgacctaccgggagg
gatgacctgcgacagccgaggttgcgagcggcaggcgcgaccagccaccttggcaaacaacatcccgatcgtttgatatcaaagccgatgcc
gcgggatcaccgcgatattgaattattactcagtatctggtctctaccgatctatgccagtgacaagccgaagtgaccgcgctggtctgacaacctgtgcttcaacctggc
tgacgctggcagaacgacatcaccggacggtaagctgctccaacctggcctgcaggagcagcccggacccgcagaggcct
cctgcaggcgcaggccgcagaggccttcagccgggaggagcgtcagcagtcagcgcagttgaagctggcttaa
```

TABLE H-continued

| SEQ ID NO: | Sequence |
|---|---|
| 196 | cgtaaggcgaccaccagctccgcggttgctgaacgacgctgaagccgttctgctgctgccgccggaaccgccgacgaggcgttattccgcaccga ggtcgtcggccgcaaatggcctgaagggcctgcttggtggctccagcgagtcgctcgttcctcaacgaggcaggagaagaaaatagccggat cgttcaaacggttgccgatattaacctccgggttggccgtcagcgtgcgccgagcgcctcatcggcgttgaagatgcgccgaccagtt gccgaagcgtccgcgacacgacgtccagcgtcttgaatattccgtcgccaggcgctggctcgcgagcgtggctcgcgagcgcgaggagctt caccgtcaatagcacatgacgatcgcagcgtcttgaatattccgtcgccaggcgctggctcgcgagcgtgctgctatagtgaaaacgata attcagccaggagccctctatggcctgaagcacctgatcaccgtcgacggcgtcgccagccagctcgccagcgacctcgcgcgtgccg ctgctgatgagctgctggatcccaacacccctatcagccaggcgaccgatgctctatcgcgacgagtcgcgcacctaacctggcttgcc gaagaggatgaagacgcagcagcctgtatcgccggtgatgaccggtaccgcggcgtgatgaagctgacgcaactcaacctggcttgcc gaagcgatcctcgacgcgtggtcggtcacgcaacggtcagcaggcagatggtcgctcgctacggccagccaccacctgcacgatcgcggtcg gctcgcgtctcggctcggcaactgctaaggtggccgccgcagtctctcacctgcggtcggccagcgatctcacgaccgtcctgccacctcgtccggt attctctacgaagcgaggccgctccgccgccgccgggatcgtctcggctgactatcagcagaacgaag cctggacgtgggaacatcaggcgctggtgtcgcccggcgtggcgtgctcatggcgacacgtgcgccagggccgcttgaccgccattcgtcgcgatatcc tgaccacccgcgggagggaggacctgcagaccgaggttcgcgagagatgccgagaagatgccgcccaactgggcaacaatccccgatcg tttgatatcaagcgatgccggcgggatcaccgatattgaatttattaactcagtatctcggcctcacgctatgccagtgacaagcgagctgaccgct ggtctgacaacgtcgtattcttgagctgacgcacgcacatctgacgaggaggaggaggccttcagcaggaggaacatcggtgtaccacccttgc gtgatgcgctccatcaccggccctgcaggagcagcggacacgtggcgccagaggcttcagccgggagcgtcagcaggtcagcgcagctg gcgaagatggctggcaggagtgttggtggtgatgatcgctgggcgcgggcgaaatcaggatcttcccgcaagttggtctcgcagagagagtcatgaaagtaaacgctgccg gagtttgaacgtgcaggagtgggatgaccgccggtgtcgagcaggcgccccacagctcgtattcccgggagcccgttcagcgggagcttcagccggggtcgg gcagaagtggctgtcgcaggagtgttggtggtgatgatcgctgggcgcgcaaccatgaacattgcttgaagtgaacatgtgaagtgacttgaagtgagcatgtgaagtgacttgaagtgagccgac gatggtgaaggtggaaaatatcggaaagaacgctcctggccgcgtgagcaggtgaacatggtcgccaatgtgaatcagtgaagtgaagatttgaagaggcttcgctgatcgtcctcgtccgacatcaccgac catcaccaagctgggtgctgttcgcgcaatcagcagctgatccgctgatctcggcgtggatccgcagccgatcgcatgag cgcattcagcaggcgctgggagccattggcgcactgg |
| 197 | atgacccctgaatatgatgctcgacgccgtcctcgagtaccgtcctcgcagtaccattgcaaccgacttcacgaaccgacgcatgcaacaaattcttgcca gtcgggcttatccgatgacgaacgcgcacagctttatatgagcgcggagtggttgtatagttcggtctgagcgcattcactaaccagcaggcaattt gatgctgctgatgaagcggcattttcagcaggaggaatttgatgctgctcgtgaggcggtttgat caagcgtggcaatccgccgcatatgcctgagctggtggctttgagcttacctcaacccgcaggcggggcgggtcgcctgagctggtggctttgagcttacccgccaggcggggcgggt tctgtacttgagcttgatcgccattgagctggctcccgaccgcaggcgggacctggcttcccgcttctccccggctttaacacccctgaccggaggt gaagcatga |
| 198 | cccaacagcaggccggtaggccagcaggtccgccagcgtgccgcgttaatattgaccggggcggcggccgcctcccccagctgttgtgga tcatttcgcgatcttgcgggtttaccggtatcggtaccaaagaaaatgccaaagtgctggagtggttgaaaaaggaat gacgacgaggtattgcgaaggcgttaccggtgcctcgaccgcccatcacgcagcgccgc gccaaggcgcaccccggggagagtaaaaatccgtgaattttccccccgtcgatcaatgttcgtcggtcgttccgataaggcgcacac tttgcatgtttatccggttccgcttaccctccgcgactttacgacgcaagaagtgaattctttggcacgcagcgagaatatttggcagctgccagaat ccgatgacgaaccgcgtccgctcagctacttacagacgaagaagtgattctggcacgcatgaacaaatttcttcacaagcgctggc aaccgaccgcattgagctgcctcccgaccgcaggcggcaccatgctctacaccctgaccgagagggaagcggcaccatgat cttgatcgccattgagctggctcccgaccgcaggcggcaccatgctctacaccctgaccgtcgctgacacaagcggtcctacggggcgggtc ttgatcgccattgagctggtctcccgaccgcaggcggcacaccatgagtcagctctagactgtataccaacagccccgaccgatcacccgcgagggactggtggg cctggaccgcagcaaaacgccggacaccaccggacgagggttcagctttatccagcacccgatcagggtccgcagcctcacctcgcccggggactggtggg gatcctcagtatcgaagcgctgagcaaacggcagcaacccgaccgagatcagcgttttctcgaccgctgagccttacgattacgattctgccgtt acgtgctggccaggggcagtcgctggtgctgcccaaccgcccggtgctccggcgatcagcgttttctcgaccgctgagccttacgattacgattctgccgtt tatcgccgtaccgtgatgggcccaacgccagcgacccctcgctcgcagcgaccctggccaggggcagtcgctggtgctcgccggctgc acccgtttctcgaaaccgtc |
| 199 | atggcggctgaagcacctgatcacgctctgcggcgtcgtcgtgccgatggtcgccagcagcgtggcgcgccaccgtgctggtcgtgatgagctgctggat ccaacaccctatcagcgacgacgatcggacgaccgcatcggcgtgctgcgagctgccagcgagcgctggtgctgaagaggatgaagagcagca gtgcatatcggcggcggatatcggcggtatcgccctgccggtacccggccgcagcgacacccgaccgacgatcctcgacgcgggtg gtgcaggcaggcatgggcgagatggtcgctcgcatgccagcgcagccgaccacctgcagctgcgcagcgatctccgaccgcggtctacg |

TABLE H-continued

| SEQ ID NO: | Sequence |
|---|---|

200

```
gtaagcttggcggctgggagctggctacagctccgatctcgatctgtgttcctccatgactgccggcggaggcgatgaccgacggcgagcggg
agattgacggcgtcagttctctctcggctggccggggatgctggtcaccaccgcacgggttgctgactatcagcagaacgaagcctggacgtgggaacatcag
cggctggctccttctggcgccgcggggggatggcggctcatggcggacccgcgagcgcgcttgaccgccattcgtccgatctcgtcgacgccgggaggg
gcgcctggctggcgccgccgctggctatggcgacatccgcgagagatgcgcgcgagaagatgcgcgcccacctgcaacaaacatcccgatcgtttgatcatcaaagccgatgcc
gccgggatcaacgcgatattgaattattactcagtatctggtcctcacgctatccagtgacagccggccgcctcaccacccttgcctgatgcgctccatcacctggc
cctcgcaggagcagccgggacacgtggccagcggcctcagccggagcgtcagcaggtcgcagggtcgcagcaggtggctgatggcttaa
```

```
cgtaaggcgaccaccagctccgccgctgctgaacgacacgctgaagccgtctcgtcgccggacaccggcgacgaggcgttattccgcaccga
ggctcgtcggcgccaaatggccctggtctggtcagcgtgtcggtccgtccgtcggtccttccaacgaggcaggagaagaaaatagccggat
cgtcaaacggttgccgcatattaacctccgcggtggatgctggcggcgcctgcgacctgcgtgaagatgcgccgaccagtt
gccgaagctgcccgcacatcgacgatcgagcgcttcagctggtcggcggcctatggcgaccgcgctggtggtcgccgggtcgctgagaactggcaggagctt
caccgtgcaatagcacgatcgacatgaccctatggcgctgaagtccgagcgctggctgcgccagcgcgttcggctctgctgcatagtggaaacgata
ctcgtgatgacggcctgctatcccaacccctatcgcaggcgaccgatgcctcatccgacgatgcctcatccgacgcctgctccctgtcgcggtcgcg
gaagaggtagaagcagcagcgtgcatatcgcggcggcggatatccggcggcgatatcgcggtaccgtcgcggtgatgaaggtcagcgacttaaccctggcttgcc
gaagcgtcctgacgcggttcggcggtggtcgcatccgttcccgagacctctcgacttcgtctgacagtgacgctgcctccggcggttcggtgtct
cgtcgccgctcggttacggtcggtacggtaagcttgcggcatgggcggcagtggtcagtccttcaccaacaccccggatcatgacctcgaggtt
atgaccgaccgggagaattgacccgggccgtcgttccctcgcggcggggatgcgtacccaccgcgacgcgttgctgactatcagcagaacgaag
cctggacgtgggaacatcaggagggggatgacccgttcggacagtaagcctggagagatgcggaggaacagatgcgcgcccacctggcaacaaacatcccgatccg
tacccaccccgggagggggatgaccggcggggatcaccgatttgaattttattacttcagtatctcgtcgctcatgccaagtcgaccgaccgct
ggctgaacggcgcgtattcttgagctgctgggcaacaacatgagcggagaggcgcgcctcaacgatgcctaccaccctgc
gtgatgcgctccatcacctggcctcgaggagcaggcacggcaggacaccggcaggccttcagccggagcgtcagcagcgtcagcgc
gagaagtggctgatgcctgatggcttaactataaaatcggctcgcgcggtgcttatcgcgccgcaaagttgcgtctcgcaggagagagtcatgaaagtaacgctgccg
gagttgaaggtgaagatgcgctatctcttcgagctcggctgctgtgatggtgatgtcgcgcgggtactggtgacgccccaacgcgtattcccggagcccgggtgcc
ggggtgaaggtggaaaaaatcagaagaacgccctggcggcaacgtagcactgaatgtgaagtgcaatgtgaatgtgaagagggcttcggctggggtggg
gattgacccggattgatgacgcggctgctccgcgcaatcagcagctgatcccgccctgacttgaatgtgaagagggcttccggcgtggatccgcgcagccgtatgag
cgcattcagcagcgcgctgggagcgccattggcgcactgg
```

201

```
atgacccctgaatatgatgtctcgagctaaagtctcggctaatcgctgataacattgacgcaatgcgcaatataaaggcatcatttgatgccctttttgcac
gcttcatcaccgaacctggctcatcagtgattttttgtcataatcattgctgagacagcctgaagagggcggttatcacacaaaccattcgagcggt
agcgcgacggcagtcagcgttctccttgcaatagcaggaagaggcgccagaaccgccagcgttgaagcgttcagtgtataatc
cgaaacttaattcggttgagccattgagctggctgcctcccgaccggggcacctgcctgttaacaccctgaccgg
aggtgaagcatga
```

202

```
ggcgtcgcccagcgtcggcgtcgccacaacagcaggcggaggctaggccagcggagtcccgcagcgtgggcgtggcgcgtggcgcggctaatattgaccgggcggcgg
cgcctccccagcgtgctgcgcctgccagtgttcggcgtgatcattctgccggtttgggttttgccggttaccggtattggttaccggtaacgttcggccccatagcttctggttaccgtcagcgttacagctacgctcctgt
cggaatggtgtgaaaaaaggaatgacgacagaggtattgcgaaggcgttgcgaaggcgtgccaggtgcgcggcgccaggcgcgcggcgccatcctgcccatcagga
tcgcttcgcatcacgatcgcgcgcacactttcggtgtcatccggtcggctaaagttcggcttatccgcggtgtccggacctgacaattgtcataactgcgaca
caggagttgcgatgacctgatgatgatgtcggctaaagtctcggctcaatgtgtcataatcattgctcataatcattgtggcagcggcggcccgtttatacaccaaac
gccttttcgcacgttcatcaccagaccaccggctttatcttcggttcataacagcggcagacggaaggaagcgccagggcggcaccgttgaagcagttgaacgcgt
cattcgacgggtagcgacggcaagccaagtcaggttgtccttgcaatagcaggaagaggcgcagcggcggcacccgcgcttgaacgggttcgccgctgtttaac
tcagtgtataatccgggaggtgaagcatgatgatcccggataatgactctcgaggcacccgagaccttctcagcagttcaccgccatgcagcggat
aacgctggtgctagccgggacagctgcaaaacgtcaggaggtgctcagcgtattacaacaagatgcctttatgcagcggagcacgggggatgat
```

TABLE H-continued

| SEQ ID NO: | Sequence |
|---|---|

203

```
atgacccgaatatgatgctgagcccgctgaccgaccagaacttccacccttggacttggctatacccttggcgtgacggcgcgataactggact
acatcccattccggtgatcttaccattggcgtcaataggttacggtccggcgacttttccagataacatccggcaacttacaataacggtaacgttt
actcgcctggctcgctatacacttttaattcgctaagtcttaaatcaaatgacgtagaagcggtgtgctcttgtggaaaaacaaggactaaaagcggttaccca
ctaaaaagatagcgacttttatcacttttagcaaagtgccaacaaaagtaccacaattggtactgtactactcgacacagcattagtgtcgattt
tcatataaaggtaattttggccattgagctggctcccgaccgcaggcggcgccacctgcccgcgttcccgcgttcccgcgttaacaccctgaccggaggt
gaagcatga
```

204

```
ggccgtcgcccagcgtcggcgtcccaacagcaggcggtaggccagcaggtccgcagcgtggccggttaatattgacgggcggcgg
cgcctcccccagctgttgtgatcatttcgcgatctggcgggtttacccgtatcggttccggcaggtaccaaagaaatgccaatgttcgccatagtacgctcctgt
cggaatggtgtgaaaaaggaatgacacagaggtattgccaaggctgccgaggtgtccaaggctgccggttgccgacgggtcgaaagtttcgggtg
tcgtcctgcatcacgacgcccacacttgcatggttatccgggttcggctaccccgcccgttttgcgacggtcgacaattgtcataactgcgaca
caggagttgcgatgacctgaatatgatgctcgagcccgctgaccgaccagaacttccacctggactcggctccagtaccttggcgtcactggcgtgatgtcgacca
ataactgggacacatccccatccggtgatcttaccattggcgtggcaattcgctacatattccggcaacctacaat
aacggtaacgttttactctcggctcggctgtgtatacagtgttaattcgctaagtcttcagcaaatgagataagcggtgtgcttgtggaaaaacaaggacta
aagcgttaccacctaaaaagatagcgacttttatcactttagcaaagtgccacaaagtaccacaattggtactgtactactcgacacagca
ttagtgtcgattttcatataaaggtaattttggccattgagctgggtcccgaccgcaggcggcgccacctctcagcagttcaccgcaccgatg
ctgacggaggtgaagcagtaccggggacgcaggagcatcgctgtactacaaacggtgccaggggcagtcgctgtgctgtccgccgctatcgcc
cggcgaggactggttgggacacgttgtcgcgttatcgccgtaccgggtgatggggcccaacccgcaaggggtcgcagccgcagaccgggcggccgccag
cctacgattacgatctgccggttatcgcgttatcgccgtaccgttttctcgaaaccgtc
gaagagcggctgccggcctgcacccgtttctcgaaaccgtc
```

205

```
atggcgctgaagccgtgatcacgctcgcgcgcgtcgcgatggtcgccagccagctggcgcgccaccgtggcgcgccaccgtgctgctgatgagctgctggat
cccaacaccctcatcagccgacggcgaccgatgcctatcgccggtgatgaaggccagtacctcgcgcgtgcgccgaagaggatgaagcagca
gtcgcatatcggcggcgggatatcgccggcatcgcggggctggtacagctccgatctcgctcgggtcggacagcgatcctcgacgcggtg
gtcgcgacacggcagtggcggctggagctggagctctacctgcggcgcggctacagctccgatctcgtgtgctgtgttctctccatgactgctcggtcacg
gtaagcttggcggcggccgtcagttctacctcgggctgcggcgcgggtgctggcgggaggtgatgacggacgcgaggggg
agattgacgggccgcagtctctacctgcggcggctggacaccaccgcagcgccgttgctgactatcagcagaacgaagctgggaacatcag
gcgctgcgcctctcgccgggtctatggcggcgggatgctgcgagatgcgcgagagatgcgcgccaccttggcaacaaacatccgatcgttttgatctcaaagccgatgcc
gatgaccccgcagaccgaggttgcgagaccggttcgcggatgcgcgagaagtcgcggccaccttctatccggtctcaccctgctctccatcacctggc
tgagctgctgggcggcagaacgacacattatactccagtatctggtctccagtgacgaggaggacggcgcgccgcctccaccttgctgatgctccatcacctggc
cctggcgcagccggcaccgacggggccttcagccgggagcgtcagccgaggcgttcagccagtcgcagaagtggctgatggcttaa
```

206

```
cgtaaggcgaccacccagctccgcgttgctgaacgacgctgaagccgtttctgctggccggaccaccgcgaccgaggcgttattccgcaccga
ggtcgtcggcgcccaaatcgcgcaaacttaacctctccggggttgcggcgagctgcgtccgtcctcaacgaggcagggagaaaaaatagccggat
cgttcaaacggttgcgccatattaacctccgggttggcggcgagctgccctatggcgacggcggcgcggtgccgtcggacgggactggcctggagggactggcaggagctt
gccgagtcgccggacatcgacagtgcagccccttgaatattccgcgcaggcggtggcggcgcggctgctcggtgctgcgcagtggaaaacgata
caccgtgcaatagcacgtgacgatcgcagccctttatgcgctgaagcacctgacacgctgcgcggcgatgctcatccggacgagctgctcgcggtgccg
atttcaggccaggagccctttatggccgcgagatccggcagcacctgatccaccagccagctgtaccctgctggtgatgaatgctcgccgtggtcg
ctgctgatgagctgctggatcgaccggcggatatcagccggggatatcgcaggtcggatggtaccctgcggtgatgaagtggctgatggcttaa
gaagaggatgaagagcagcagcagcgtgtcgccggtgatcggggtaccctgcggtgatgaagtggctgatggcttgc
```

TABLE H-continued

| SEQ ID NO: | Sequence |
|---|---|
| | gaagcgatcctcgaccggtggtgcagcaggcatggggcagatggtcgctcgctacggccagcgaccaccctgacgatcgccaggtcgcg gctcgccgtcgcggctcggtacggatggcggagctggcgagctgggctgacagctccgatctcgatctggtgttcctccatgactgccgccggaggtg atgaccgacggggagcggcccgccgacgccgagcccggcgtcagttctacctgcgcggcgcgggatggcgaccacccggcttgctgactatcagcgaacgaag cctgacgtgggaacatcaggcgctggtcgcgcccgcgtcgtcatggcgacccgcgagaagatcgcgcccaccttggcaacaaatccggatcg tttgatatcaaagccgatcgcggcggatcaaccgatattgaattattaactaccagtactcggtcctacgctatggtgacaagcgaagtgacccgct ggtctgacaacggtcgtattcttgagctgtcgcacgaacgaacgatgcgggagaggaggcgcctaacgactgctgctacaccacctgc gtgatgcgtccatcaccggccgtgatgcggccggcgagcgcggaacgacggggacacagggttcagccggagcgtcagcggccagctg gcagaagtgggctgtgatgcgttaactaaaaatcggggtggttggtggtgatgctgatgctggagacgtgctattcggccctactggtacggacccgccaaagttgccccgagcgtattccccggaagtaacccgtgcc ggtggtgaaggtgaaaatatcagaagaacgtcctgcggccgaacatcgcgagctagctaacgccgccctggtgg gattgacccggattgatagcgcctgcccggcgtgctcgcgtgagccaggcgtgcaatcagctgccgcctcgtccgctcccgactcaccccgac catcaccaagcgcgggtgtcgtctgccgccaatcagcagctgatccgcctcgactttgaagagggcttctccgccgtgatccgcagccgatgccatgag cgcattcagcaggcgcgctgggagccatggcgactgg |
| 207 | atgaccctgaatatgatgtctagaagcgtcaggtaccggtcatgattcaccggtacggcgctgattcctggagcgcttcattggcatcctgacgaagag ttcgctggcttcttcccaacctggattgcaccagtgcaggtcaggtagtgctcatgataatcaccgattctcaggtgaatacgttaacgattgacgcgtaaacta caaatcgcggcattcgtcgtaaaagcgactcgaagatgagaagatggcttaaatcccgagcacacttcacgtcgtcccgtatatgttggtct gtggcgcacaaagaagtcgaagccggcaaagtggccttgtacccgtcgcggaaagacctcggcagcatggcagatggaagtgaagtgattgagaa gctgcaacagagattcgcagccgcagtctcaacaactggagcttcaaaccggaataaggtattaaggcggaaaacgagtcaaacgagtcagttcaaacgtctatc aatggcgagattcgcgccctggaagttcgcgccattgagctgctttcccgaccccggcttcaaccctgcggcttcccgttcccgttccgttaaacac cctgaccggaggtgaagccatga |
| 208 | ggccgtcgccagcgtcgccgtcccacagcaggccggtaggccagcaggccggcaggtccgcagcgtggccggtcggtaatattgaccggggcggcggcg cggctccccccagctgttgtggatcattcgcgatcttcggggttaccggtatcggtaccggtatcggtatccgtatgtatctgttcggcatgt cggaatggtgaaaaaggaatgacgacagaggtattgcgaaggtgtcgcaaggtaaaaatcgtgaattccccgtcggatcaatgttcgcgtg gtcgttccgataaggcgcacacttgcatggttatccggtcggcttcgccccgcgtttcggccaatttgtcataactggcgaca caggagttgcgatgagagtcgatgaccggatgtcaggtaccggtcaggtgcaccagtgcaggtcaggtgaggaaatgagagtctcaggtgctcattcctgacgtccaggagcttcaggatgcggcacacttcctcggttcccgttccctgagcgcttcattggcatc ctgaccgaagagagtccgcaggtcgcggcattcgtggctgtcggcaaaatgcggcattccaccgcaacctaccgttctaaaatccgcgagcacacttacgtgtcgtgtcccc gtatgtgttgcggtacaggtgctattgcgctacggtgggaatcactggaattataaaggcgaaaacgagtcaaacggcac gtccgatcgtgatcagcctgcttaacacccgaccggaggtgaagcatgatcgacccctcaggctcgaccggccagagcatggagcttcctgcgtgcgcc atccgacgataaggctctggatcggctttcgcggttatccccgggggtggccgcagcagcaaccgcccagccccgccagcgaccc agatcccctatcgccccggcgaggatgtggggggacccggtgtgggggccgagcagtcggctgcgtctgcgccccggcgcgcgcgacgatcaggtttt cctgaccgcctgagcctacgattacgatccgccgttatcgccgtaaccgccgcccgtagctgcggcggtgctcggcgggggcacgcccagc cgatggcggccaggaagaggcggctgccccgttctcgaaaccgtc |
| 209 | atggcggctgaagcctgatcacgctctgcggcggtcttctgcggccggtcagcgctgggcggccgccaccgctggcggcgtgctgctgatgagctgctggat cccaacaccctcatcgccgacgagccgatgcctatcggcgacgagctcggcgcagctacagctgctggagcgcgagaggatgaagagcagca gctggagcgttgccgaacagttaagcagccgaagctgttaacagctggcggcagctgggcgcagtggcgctcagcagcgtcggcgcagccacctgacg cttaacctggcttgccgaagcctcgacggtggtcagcggtggtcggcagctggtgacagctcctacgcgagctgcagtcggc atcgccaggtcgcggtcttcgcctcgcggtcggcttacggtaagctcggcctggagctggaggcgaggaattgacggccgcagtctacctggttcctccatgac tgcccgcggcgaggtgatgccgaccgacggggagattcttcgggcggctcgaccgcagcgtgatgccgatcatgacctgttcagcac cgcacccgtccgtccggctattctcacgaagtgacgccggccgcctggtgctcatggcgccaggagccacctgctt cggcatcgacaggaacatcgggaacatgggaacatcaggcgtgctatggcgaccccggcgcgaggcgcgcttgacgc |

TABLE H-continued

| SEQ ID NO: | Sequence |
|---|---|

210

```
cattcgtcgcgatatcctgaccaccccgcgggagggggatgaccctgcagaccgagttcgcgagacgatgcgcgccacctggca
acaaacatcccgatccgtttgatatcaaagccgatgccggcgggatcaccgattattactcagtatctggtcctacgctatgccagtgacaag
ccgaagctgacccgctggtctgacaacgtcgctattcttgagctgctggcgagaacgacatcatggacgagagcggcgcgcccttaacgcat
 gcgcacaccacctgcgtgatgcgtcatcacctgccctgcaggagcagccggacacagtggcgcgggaccgtcagca
ggtcagccgcagctggcgtcgatggctgatgcttaa
```

```
cgtaaggcgaccaccaccgctccggcgttctggtctgaacgacgcgtgaagccgctgaagcacaccgcgcagcaggcgttattccgcaccga
ggtcggcgcgccaaacctgacccttgacctagagccgccgcgtgaatgcgtcaagcggcgcctcctccaacaggcaggagagaaaaaatagccggat
cgtcaaacggttgcggcgatattaacctctcggggttggcggccgagcgccgtgcagacgtctggcggttgaagatgcgccgaccagtt
gccgaagctgtcccgcgacatcgacacgtccagccgtcttgaatattttccgtcgccaggccggtgcttctggctgcgcatagtggaaacgata
attccggtcaataagcacatgacgatcgcagccgtctatgcgctcgccgccagctccaagctgtgccagcgcgcgcagcagcacccgctg
ctgctgatgagctgctggatccaaacccttatcacgccgagcgccatcagccgccagcggcgcgatgcgctgttctgtcgccacctgggcgtccg
gaagaggatgaagcagcagctgacgatcattaacctgcttgcctgccaagcgatcctcgacggcggtgcagccgccatgggcagatgcgtcgctcacgg
ccagccgacccacctgcaggcttgacctgctcaggtcgcggctcgcgtggcgtgaagctggccggtcagcagctgctacagctccgatct
cgatcgtggtttctccatgactcgcccggcagggtgatgaccgacgggagttgaactgacgacgtgcgaccgtcagttctacctcgccggcccagcg
gatcatcaccgttcagcaccgcaccgtctctcgcttctagcagaacgaagcctggacgtggaacatcagccgccgtggtgcgcccgcgtctatgcgaccccgcg
ccgtcaggccgtttgacctactcagccatcctgacgcgatatcctgaacacaaacatcccgatcgttgatcaaaagccgggattgcggggatgaacctcagcggaacgtcgcgagaa
gatgcgcgccaccttgcaacaaacatcccgatcgtttgatcaaagccgggattgcggggatccgagcgatattaccagtatctggtcc
tacgctatgccagtgacaagccgaagctgacccgctggtctgacaacgtgctattcttgagctgctggcgcagaacgacatcatggacgagagga
ggcgcgccctaacgcatgcgcggaccgtacacacccttgcgatggggtcagtcgcagaagtggctgaactggtgctcattatcgcgccaaagtttgcgt
ctgcaggagagtcatgaaagtaacgctgcgcggagttgacctgctgaggatgtgttggtgggatgtggagcgtactggtgtacggc
cccaccagtcgtattcccggggcgaacctcgcgccctgcgtcccgactcaccgaccatcaccaagtcgcggtgctgtcgcgcgcaatcagcagctgatcgcctcgactttgaagtg
catcgctccctggggcaactgcgcgctgctgccagccgggtacgccagcacctgcaggaccagccggctgctgacctgggtccgactttgaagag
gaagtgacttcgtctccgtcccgactcaccgacatcaacaagtcgcggtgctgtcgcgcgcgtgatccgcctcgactttgaagag
ggcttctccgggcggatcccgagccgatgcgatgccagtcagcaggccggagccattggcgcactg
```

211

```
atggcgctcaaacagtaatccgtctgtgtcgcgcctcgcctgatggtcgcgcacacttgcacgtcatcctttatgtcgatgaactgctcgacccgc
gcacgctttaccagccgattgagccggccttaccgcgacgaacctcgtcagtatccgatgcgggtccaacagagacgagaaacagcagcttg
aagccgtgccagtcaaacagtatcctcaaacaccgccggccattgacccggcagtcagcggccgatgaaagtcagtgacaccatttaacc
tacctgccgaggccattctccgatgtcggttgcagcatcgtgggaacaaatggtctaaaataccggccgccgcatcttcagcaccgtgagg
ggcggggttttgccgtgttcgtgtttacgggaaactcgactgcggacgaccgcagtttatcttcgctgtcggctggtcttcctgctcgattgcggcgccgg
ggcattcttacgaggtcggacaacgcgctccgcgtccgcagcgacctttacttccggctgctggcagcgcaccggacatcgtca
cctgacgtgggacacatcagccgtcggttctgccgtcggttccgcgcgcgtggttacgggatccgcaacagcacaagccgtccgcacattct
ttgccgcacgtggagccgatggcgacagccgatggggccggtgatattgaatccatcgcacataacccggttccgttcgcgatgagccgaagctgacgcgcgctg
gtctgataagcgcggattttgaactgacgcgatatgaatccattgacacaccggttctgcgttcgacatgctgaccaggaagggaagaggaagctgacctatgggatgggacgcgcg
atgaaatctcatcatccggcttgcaggaacacagcgggaacagccgggaaagtgccgccgagctttgctactgacgcgcgcagatccgcagccgggcaa
agtggctcggctga
```

212

```
cgtactggaacagaaatcggccgatccggatggcgcaggaaatttgttatgacaccggcctgtctgaagtgcagttagtgcttacttcctgcgtggcaacctcag
gctggacccggttatttgatgataaaatcgcgaagaacactggacgcttcctcaaacgtttctgcgacatcatcggtcgtcgaccggatctgaaa
gaagccttgccgcaccttgcgccgcaaagttatcgcggctcagctcgcgcagccctgaaacgccagatcattacctccattgctcggcgttac
cctgaaaaagacgcgatcatgctgtatattcggctgggtggacctgcaacagccatcgtcagcagcaacacgcggggaggattcggcccgttctc
acgcgggtgatgatgcttctctggttaaacgggcaacctcgttaactgacctgtaactgacctagcctggcaacaacttgacgctcagctcttttgcaaggaatctgat
ttcatggccgtcaaacagtaatccgtctcgtcggcgcgcctcgcctgatggtcgcgacacaacttgacgtcatcctttattgctgcgccgatgaactgctcgaccc
```

TABLE H-continued

| SEQ ID NO: | Sequence |
|---|---|

213 gcgcacgccttaccagccgatgagccgggccgcttaccgcgacgaactgctgcagtatctgatgcgggtgcaacagaagacgaagaacagcagct
tgaagccgtgccgccagttcaaacaggcccagcattcgcgtatcgcacgcgtgggaacattgcgggtgatgaaagtcagtgaccatttaa
cctacccttgccgaggccattctcgatgtcgttggtgcatgcgtgggaacaaatgtcgtaaaatacggcagccgcgcatcttcagcaccgtga
ggggcgcgtttgccggtcggtttacgggaaacctggtcggctgggtggttatagctcagatctgatctcctgtctctgcgattgcgcgcc
ggaggtgatgacggacggcgaacgcagcatcgacggagtcagtttatcttcggctggcgagcgcattatgcacttattcagcaccggacatcgt
caggcaattcttacggggtgggagcatcaggcggctggttcgcgcgcgtggttcgcggacgtccggatccgcaactgacacagcaattaacgccacgctcgcgacat
tctttgacgtgggagcatcaggccgtcaaggatgcccatcaggaaatgtatcccatctgggagtaaaaagcccacga
gtttgatctgaaagccgatccggattttgaactgggtcatcacgatggcacatgacatctccgttctgcgttctcggcacgtgatgagccgaagctgacgctgcg
tgtctgataacgtgcgatttcggcgttgctgtgagaacacagcggaaagtgctactgagccgcgcagatccgtcagctcgtagcgctggc
aaagtgcctcgagcactggaattttatccggccaacagcggcattgatctacccggcatgattatccgttttgggagtcttgggat
gaagtgacttgcctgatttccaccggcaggtgcgtcggttggtgtcgcttgtcggtgacgtaatgcagcggctggtgcgctgccaatcgtattcctccgga
agctccgtgcgggtggtgaagtcagtaccatgaagagcggcctgcggtgcagctaactggcggatgaacattcatcctggcgccttcctcct
tctggccttatccagacgcgagacgacgctgcgctccctcagctgcgcctccagtgagccctgcgcagaagtgaaagttaactgcgattcgtcgcactatccaca
catcctaccatcaccaactgcgaattttgtcccgtaaccagcaactgatccgcctgacttgaggaaggtttgaggcgttgatctcgagccgatgct
gaccaaaataga

214 atgagcatcacgcgtatcagcatcattcctgagggggaatatcgccagccgcttcgctgcaacatcctcactgtttatacgtggttgaacaatct
tcggtggcgatttcgctgacgatccggagccgcattgttatgccaatccggcatttgtctgcgccgcaggtttcgacctgagcgcactttgggcg
agaaccaccgtctgctggaattttttcacaaggcgagcgttattgaatcgcacatttaaactgtgccgctggaacattgtgaaggtg
cggtttaaggccttttctttgacttctcgtcgttacaaagttaatatgcgccctccgtctctgaagctctcggtgaacattgttgcgaggcaggatgcg
actggttgtgtttgacattaccggataatgtgccggtgacgggtgcgttatgccgcgcggaagcggcgtttccgtccgggaatgcatggag
ctggccttatccagacgcgagacgacgctgcgcgtctctcggtcccgtcttagatctccggtacggtctccggtacgcctgccggtac
agcggttatcaccggaggcttaaatga

215 atgagcatcacgcgtatcagcatcattcctgagggggaatatcgccagccgcttcgctgcaacatcctcactgtttatacgtggttgaacaatct
tcggtggcgatttcgctgacgatccggagccgcattgttatgccaatccggcatttgtctgcgccgcaggtttcgacctgagcgcactttgggcg
agaaccaccgtctgctggaattttttcacaaggcgagcgttattgaatcgcacatttaaactgtgccgctggaacattgtgaaggtg
cggtttaaggccttttctttgacttctcgtcgttacaaagttaatatgcgccctccgtctctgaagctctcggtgaacattgttgcgaggcaggatgcg TABLE H-continued

| SEQ ID NO: | Sequence |
|---|---|

216  tgtttcgtctcgaggccggcaactgagcggcccgtgaaaccgacctggctggcatctgttgtgtgcgaacaaattcgctcgcgcaaccctgc
cgaaagccgaagccttaacgcgggtgcgtcagcaactgatgcccggcaacagaaacattatcagcgcagtggctgcaacaactgatcaacgcct
gagcctgttctccttcttgtgatgcagacgggttaatgcccgtttgcacgaaaaatgcacataaatgcctggtgcttataacagcgcagggaaat
cctgcccccgcccttgtccaccgcgcttcctgttggtaaaaacgaccacccgttcagatcaacct
ttgggcagataagcccgaaaggcccgcaaattgcacgacggtcaaatttcgacccggttgagtatatgtcggcattggttccggactgcaataaagggaga
aagacatgagcatcaacggcgtatcagcatctcctgagggaatatcgccagccgcttcgcgtcgcaacatcctcactgtttatacctggttgaa
caatcttcggtgtcggcgattcgctgaccgatcgtgtgggtgaacattggtgggcccaattgttatcccagcggttcctgtgacgttccgggaatggc
gggcgagacaccccgtcgtcggcgaattttttcacaagcgcgttaataatcgacaagttaaactgtctggtggaagcgaatattggtga
aagtgcggttttaaggcattttcttgactctctgtcgttacaaagttaatatgccgcgttacaaagttaatatgtgaacattgttgcgagcag
gatgcgagctggtgtgttttgacattaccgatcgcgccatcatccggtcgccccatcatccggtccgcctgatcggcggcacctgacgttacgcctgc
cgtacgcacagcagtatcaccggaggcttaaaatgaccggaggcttaaaatgaccgggcccgttgatatgtcgccagttacggcgctt
tatcgcacaccaggcggcctgagcaggaacaacacgggcgcactggtcgtttcacgatcatgcatcatgcgtcacagcatcatgcaatacg
gcatggtgttcgtttgataagaacgcaatgcacctttgtggatccctgcatggcatcgacggcgaaggaaaaagaaggaccccgcatgtcgtt
accgcatgggggaaggcgatcggccgtgatgagccggtgatgagccgggcggcatatgcctgtgttaccggcgcttcagacgcagcgtttctgaccgcct
gaatatttacgattacagcgtgccggttgattggctgccgatcccggtgccgataaccagcagcgcagccgatggcgttgc
acgagacccggctgccagtagcaccgacgacgggtttagaaatggtc 217  atgagcatcacggcgttatcagcatcattcctgagggaatatcgccagccgcttcgcgtcgcaacatcctcactgtttatacctggttgaacaatct
tcggtggcgattcgctgaccgaccggcgagcggcgccattgttatgccaatccggcagacggtttgcactgagacactttgggcg
agaaccaccgctgcgtgctggtaaaacgtgaccagcaggcattaataaacgccacgaaatggcggtttattttcaactatcgtaaaaagtg
ctaaatgcagtacgagcagcaaaaattattctcattagaaatatgtaactgtgaataactgtaacactcgtaaaaaagatgttcttgagcgaac
taccgtcctcgaagctcggttgaacattgttgcgagcaggatgcgagctggtttgacattaccgataaatgtgccgcggtgaacggtgcgtat
gcccgcccggaagcggcgtttccccgtggtaaaacgtgaaacgcgtaatccagacgcagcctgagctcttagatctctcg
gtccgccctgatggcggcgaacctgctgacgttacgcctgcggcacgaggcttaaaatga 218  gttcgtctcgaggccggcaactgagcggcccgtgaaaccgacctggctggcatctgttgtgtgcgaacaaattcgctcgcgcaaccctgc
cgaaagccgaagccttaacgcgggtgcgtcagcaacttatcagcgcagtggctgcaacaactgatcaacgcct
gagcctgttctccttcttgtgcacccgcttgcctgttggtaaaaatgcacataaatgcgccgcttaaaacaccccgttcagatcaacct
ttgggcagataagcccgaaaggcccgcaaattgcacgacggtcaaatttcgcagcctgctaatgtcggcgcattggttcggactgcaaataagggaga
aagacatgagcatcaacggcgtatcgacagccgatcccggcgcttatcgccagccgcttcgcgtcgcaacatcctcactgtttatacctggttgaa
caatcttcggtggcggcgattcgctgaccgatcgtgtgggtgaacattggtggcgcccattattatccagcggttcctgtgacgttccggg
ggcgagaaaccacccgtcgtcagtagcagacggataagtaagcctgagctccattggtgcaattttcgatcattgcgaagatttggaagattttcttgag
cgaacgactcaaaaatagtgccggcaaaatggtcaactgaacctgtcggtcattaacgctttggtttgatcatactggatttaacttaatctagagg
gtttataccgtcctcgaagctcggttgaacattgtgctgctttgataacagcgtgttctgcggggaaggcgtgatcggcggtgaacgggtg
cgttatgccggccgcccctgacctttgatatgtcggcacttgcctgctttatcgacgggcatggttttcggcatgggggaaaaaataagaccaggggcgcact
gggcggatcctgaagtgtcacgatcatgcatcatgcaaacccgcgttctgcagcgtgttctgcaagctgggaaggcgtgatcggcgtgatcggcgcagc
atggcatcgacggcgaaaggaaaaagaagagaccgcatctcagacgatcagcgtttctgcagcgtgtcggatgaataccgcgccggttggccctgcgtgatccccggtgcgcgg
ataatcagcagcctgggcgtgctggtgcacagaccggcgttgcacgacccgctgccagtaccgactgccagtacaccggcgtttagaaatggtcg TABLE H-continued

| SEQ ID NO: | Sequence |
|---|---|
| 219 | atgagcatcacggcggtcatcagcatcattcctgagggaatatcgccagcgccgcttgcgctgcaacatcctcactgtttataccgtggttgaacaatct<br>tcggtggcgattcgctcgctgtgacatcccgaggcgcgcattgttatgccaatccggcattctgccgcacccggaataacggcattcgcgttaaagcc<br>agaaccaccgtctgctggtgaacatcactgatgcacaagctacctattgaaacaaaaacctgaagatgcaggcattcgcgttaaagcc<br>gactgagaaatggaagaattggcttaaaatcggcaacacacgctacgcccgttcctatatgtagttgtggcgataaagaggtcgagcaggca<br>aagttgcttgttcgtaccgcgcggcaaagtattaaggcggaaaacgagtctcaacggcgccgtcctaataccggtattcgctaaagca... |
| 220 | tgtttcgctcgaggccggcaactgagcggcccgtgaaaccgacctggttgtgtgcgaacaatcgcgctcgcgcaaccctgc<br>cgaaagccgaagccttaacgcgggtggcgtcagcaactgattgcccggcaacagaaaacattatcagccgcagtggctcaacaactgatcaacgcct<br>gagcctgttctcctctgtgatgcgacgggttaatgcccgtttgccacggacaataaatgcacataaatgcctgtcgcttccggtg... |
| 221 | atgagcatcacggcggtcatcagcatcattcctgagggaatatcgccagcgccgcttgcgctgcaacatcctcactgtttataccgtggttgaacaatct<br>tcggtggcgattcgctcgctgtgacatcccgaggcgcgcattgttatgccaatccggcattctgccgcacccggaataacggcattcgcgttaaagcc<br>agaaccaccgtctgctggtgaacatcactgatgcacaagctacctattgaaacaaaaacctgaagatgcaggcattcgcgttaaagcc... |
| 222 | tgtttcgctcgaggccggcaactgagcggcccgtgaaaccgacctggttgtgtgcgaacaatcgcgctcgcgcaaccctgc<br>cgaaagccgaagccttaacgcgggtggcgtcagcaactgattgcccggcaacagaaaacattatcagccgcagtggctcaacaactgatcaacgcct<br>gagcctgttctcctctgtgatgcgacgggttaatgcccgtttgccacggacaataaatgcctatcagccgcagggaaat... |

TABLE H-continued

| SEQ ID NO: | Sequence |
|---|---|
| 223 | ttgggcagataagcccgcgaaaggcctgcaaattgcacacggttattccggtagtatgtgtgattggttccggcattcgcaataaaggggaga<br>aagacactagcactcacggcgttatcagcatccgacctcctgagggaaatatcgccagccgccgctgcgctgcaacatcctcactgtttatacgtggttgaa<br>caatcttcggtcgcgattcgtcgacgaaccaccgtcgctgctgaacatcatgcacggccattgttatgccatccggattcgcccagacgggtttgcacttgagacacttt<br>gggcgagaaccaccgtcgctgctgaacatcactgatgcacaagctaccatatcgagaattaactaaaactgcagatgcaggcagatcgcgtta<br>aagccgacttgagaaatgagaagattggcttaaaattcgcgaacacacgctacgcgtgttcctatatgtttagttgtgcgataaagaggtcgaagc<br>agccaaagtgtgtgtgttcgtaccgcgccgccggcaaagacttaggaacgacatggaaaacgagttcaaccggcgcgtccaatcgctgcgggaaatccggcagcaga<br>agcttcatcaactggaggaataaagtattaaaggcggaaaacgagtcaacccggccgtccgtccaatcgcattaacaaagagatcgcgtcagaagt<br>tcgcctcacaggcgtcgatcgatcctgcgtcgaagaagttcctgcagaatgcctgaggaagcgcgaagagatcgcgtcgctaagtagtagaaatca<br>gtccgaatcgccgagccgcagttgtcgaatcccgtcctcggtgaacattgtcggggaacaatgtgcgaggcaggatggcagtgcgtgttgacattac<br>cgataatgtgccgccagtgctgaacggtgcgctgatgccccgcccggaggcggcgtttcccctcggtgacgttaccgccctgctgacagcagtacatatcaccggaggct<br>atcgcccatcatccggcgcggttcttagatctccggttcggtccgccctgatggcgaactgccagtgaccctgatatcggccgctgctacgggcagat<br>taaaatgaccagttacctaccgcggcccggctatccgaacctgctacagcgtccatcgacggctgccgcgtctgcgag<br>gaaagcaacaccggccgcgaccgcggcgatcctgccgaagtgctccacgatcatgcattatcgaatacggcatggtgtcgttgataaagaacg<br>caatgcactcttgtgaactcctgcatggcaccgacggcgaagcagactccgatggctccgtctcgggttgtgcgtctgggaaggcgtgatcgg<br>ccgggtgatgacgcagccgcaggtgttaccgcgcattcagacgacgacacggactcttttctccggacccgcctgaatattacgatacagcctcgcgttg<br>attgggcctccgatcccggtcggatgcaggcttatcagccatcggggatcgctggtcgtcctggcgacagccgatggcgttgcacagagaccggctgcggactgccagtacg<br>cggttttagaaatggtc |
| 224 | atggcgctcaaacagtcaatcctcgtctgtgtgcgcctcgcctcgccgatggtcgcgcacaacaacttgcacgtcatctccttattgctcgatgaactgctcgaaccgc<br>gcaagcttaccagcgacttgagccggcgaactcgatatccgcgaacctgcagtattcggatgctatgcggtgccaacagagacgaagaacagcttg<br>aagccgtgcggccagttcaaacagcccagcattgcgttcgggatgttccgggtcaggcatcgtatcagaagtcatgaaagtcagtgaccattaacc<br>taccttgccgagccattctcgatgtcgtggtcagcatgctgggaaactcggtcgctggaactcggtgatctagctcagctttatctcggtatagctggcaccatcggtcgccgg<br>ggcgcgggtttcgcgtggtcggtcacgggaaactcgacggcgacgaacaccgcgagacgacggactcagtttatcttcggtggcagggtttatcttcggtcgccgacactgtca<br>agttgatgacggacagccgcaccgcagccaggtcctggatcctgcggttatctgctggttacctatcagcagtcagtcatgcattgcagttacagcgatgttatcaggccaatgaag<br>ggcacgcttcttatctcggacttcggccgctctacagccgcgacggaaactgcaggtctcgcattggcctgcttctggacggctaattaaccgcacgtcgcgcgacattct<br>ctggaccggggagccgatggcgacgccgctgcgtaaggagtccgatattgaatcattgcacaatacggggaaagtatgtgcccatctgggagtaaaaaagcccacagtt<br>tgatctgaaagccgatcccggtcgtcgacgttggaagcttgaatttcattgccacaccacgtgtcgccatgatgtctgatatgagccgaggccgaggctgacgcgcgcg<br>gtctgataacgctgcggatttttgaactgacgacgtcggaacacatcgaagagagaggaagcggccatctacgcaggcttatgtgacgcgcgcg<br>atgaaattcatcatctggtcggttgcaggaacacagcgggaaagtggccggcgatccgctcgcgcgcgcagctcgcgcgcagctggcaa<br>agtgcccggctga |
|  | cgtactggaacagaaatcggccgatcggcagaaatttgttatgacaccggcctgtcgaagtgcagttagtcgtctactcttcctggctgcaacctcag<br>gctggacgccgttattgatgataaatctgcgaagaaactgcgatgcttcctcaaacgtttctgacatcatgtccgtcgtcgcgagcgatctgaaa<br>gaagcctttgccagcaactgacggaagaagttatcgcgatcagcagggctatcagccgccagaatcaattacctcttgcctgttgcgtcgttgcgttac<br>cctgaaaaagacgtcgatcgcatcggcgcgtatattgccggtggttgaactcggcaacacacgccatctcttgggaggattcgggccgttctc<br>acgggtgatgatgatcgacacagtctttctgtccgctaacggctcaactgactgcagcttgcctggcaacaacttcgcccgggcttttttcgcaaggaatcctgat<br>ttcatggcgctcaaacagtaatccgtcgtgtgcgcctcgccgatggtcgcgcacaagttcgagctgcatccttattgctcgatcgaactctcgaccc<br>gggcacgcttaccagccgggacctgagccgaccaggtctcgcgcggggccgttcaacttcccgggggtcggtgccaacagttccgcatcttcagccagcagct<br>tgaagccgtcggccagttcaaacagcccagcattcggtatccggcgcatgcatcggtgtcgaggaaaatgtatggtcaccgggccgcatccttcagcacggtga<br>cctaccggtgccgcgcaccattcatgcgatggttacggaaaacctcggttgtggctgttatagctggcagcggcttggttcctgctgcgtcgatctgcgc<br> gggcgcgccggttttgcccggtgcgtcggttacgggaaacctcggtggtggctgttatagctggcagcgcgcttatcagcaccggacatcgt<br>ggaggtgatgacgacggcggacgcgcagcagcatcctcggcgacgttcatcttcggtcggctggcagccgccgcattatcatgtttgcagattatcaggccaatga<br>agcctggaagccgcaccatcggttgccagccttttgaacttgacgaggtcgtaagcagctgcatatcggatggcacgaatgagaccagcaataacctggttccgcgatatcaggccacga<br>tctttgccgccgccgctgcggatcggctcggacacggtcgtctatcttggaaacctcggtccctatcgtgctggggctgttatagttggcacacgtgttcggggaccta<br>ggtctgataacgctcggatttttgaactgacgatggcacgatatgagccgggaaagtgctactggacgtttgctactgacgtgctcactggggtattatacccgacatttgctattatccgatttgattatctgtttggagttctgggat<br>aaagtggctcggctcgagggttttatctggcctaacagggcgttgtgatattaccggacatttgctattatctgtttggagttctgggat |

TABLE H-continued

| SEQ ID NO: | Sequence |
|---|---|
| | gaaagtgacttgcctgatttcaccgcgcaggtgtgtcggtgtcggtgacgtaatgttagaccgttactgtgatgccgaccaatcgtatttctcgga |
| | agctccggtcggcccggtggtgaagtcagtaccattgagagcggcctggcgggtgcagctaacggcgatgaacattcatcctggcgcctcttcct |
| | gtctgatcggctcgacggccgtcgacgacgctgcgctgcctcagtgagcgctcggcagaagtgaaagttaactgcgattcgtcgcactatccaca |
| | catctaccattcaccaaactgcgaatttgtcccgtaccagcaactatcgcctccgacctgatcccggaaacttgaggaaggttgaccgtgagccgatgct |
| | gaccaaataga |
| 225 | atgagcatcacggcgtatcagcatcattcctgaggggaaatcgccagccgccttgcgctcgcctgcacatccttcactgtttatacggtggtgaacaatct |
| | tcggtggcgatttcgctgaccgatccgagcgagcggcatcgtatgcaatccggcgcatcttgctcgcgccgcagctggtttgccactgagcacatttggcg |
| | agaaccacccgtcgctgtgacaagtagcggcctcaaaataagataaaacggctcatgtacgtggccgttcattctttctaccatatcgggacacccgggtgt |
| | tataatgccggccgcctcatattgggggatttcttaatgacctaccggttgttctgttttgacattaccgataatgtgccgcggtggcgggtcgcgtatgcccgcccggaagcg |
| | cggtgaacattgttgcgaggcaggatgcgagctgcgccctatccagacgcctgatcgccatccggttcttagatctctcggtcgccctgatggcg |
| | gcacctgtgctgacgtacgcctccggtacagcaggttatcaccggaggcttaaaatgca |
| 226 | tgtttcgtctcgaggcggcggcaactgccggtccgccgtgaaacctgaaacgcgccggtggcatcgtgtcgtgtgcgaacaaattcgcctcgcgcaacccttgc |
| | cgaaagccgaagccttaacgcgggtgcctcagcaactattacgccagacagaaactattcagccgaggtgctgcaacactgatcaacgcct |
| | gagccgtgtctctccttgtgatgcagacgggttaagcgccgtttgcacgaaaaatgccgcgtttgccttaaaacaccgttcagatcaacct |
| | cctgcccctgcttgtgccaaccggcgcttgcctggttgtggtaaaatgccggagtagtatagttctgatttgggtcgcatagcgcataaaggggaa |
| | ttgggcagataagccgcgaaaggcctgcaaatgacggtgttatctgcacggtgagtgagatatggatgtgttataccgttttatacctggttgaa |
| | caatcttcggtggcgattcgctgaccatccgcggcggcatttgtatgcaatccggcatctctcgccgcagacgggtttgcactggagacacttt |
| | gggcgagaaccaccgtctgctgtacagtacgcgccccatattgtggaggcaggatgcgagctgcgccctcaaaataaatagataaaacggctcatgtacggcgttatttttctaccataatcgggaac |
| | aagctctcggtgaacattgttgcgaggcaggatggcatggaggcgtggtttgacattaccgataatgtcgccgcggtggcgggtcgtgccgcccg |
| | gaagcggcgtttccgtcggggaatggcatcgagctgcgcctatccagacgcctatccagacgcgatcgccatccgttcttagatctctcggtcgccctg |
| | gatggcgcacctgtgctgacgttacgccagttactcagtatcacgcgtggcgttaaatgccggttatcaccggcgcacagcaggttatcagcaggttatccg |
| | gcgcttgatatgtctcacgatcatgcattatgcatacggcatggtgtctgttgtaaagaccgcaggaaagcaacaccgggcgactggcggcactcg |
| | aagaagaaaaagaaccatgccatgtccatgctggaaggcgcgcgtgatgacgcaggcgcagcgcaggcgtcaggcgcaggtgacccc |
| | gcattcagacgatcagcgtttctctgacggcgctgaatatttacgattacagcctgcgcgttgattggcgtgcgatcccggtgcgaataatcagccatcg |
| | ggcgtgctggtggcacgccgatggcgttgcacgaacggctgcacgagccggttttagaaatggtc |
| 227 | atggcgctcaaacagtcaatcctgtgctgctgccctcgcgatgtgcgaccaacttgcacgctcatctttattgctcgatgaactgctgcgacccgc |
| | gcacgcttaccagcgattgagccgggcgcttaaccggacgaactcgatcgggtccaacagaagacgagaacagcagcttg |
| | aagccggtcgcagttcaaaacaggcccagcattcgccggggtaaaacgtgatgaaagtcagtgaccatttaacc |
| | tacctgccggagccgcattctcgattcgtggtcgagcatgcgggaaacaaatgcgcgccgccgccattcagcaccgtgagg |
| | ggcgcggttgcgcgtggcgtacgggaaactggtatagctcgatcgctgctggccgcgtgcgcgg |
| | aggatgacggacggcgcaacgcagcatccggaacgacgccaaggcttatctctcggctggtggcatcgcagcaccgtattcagaccccgacaccgtca |
| | ggcattcttacgaggttgatccgcggctgcgcgacccttccggcagccatccggagcgtggtcagctatcacctattcagccgccaatgaag |
| | cctggacggggagcacaggcgcagcctcgtcggcggcgggttacgggttacgggtgtggtggaaaaaatgctaccgcacgcgtcgcgacattct |
| | ttgccgccagcgacgtggcagaggtcatcgtcggggtgccatcacgacgattgaattcattggcaccggtattgataattgacaacacccggtcgtcgccatgtcggtgggatccgttccatgtgagccgaggtacgggcttg |
| | gtctgataacgtgcgggattttgaactgatggcacgatatgcacacatggccgcgcgcaaccctggtcgcgcagtgagccagtgacgcgctg |
| | atgaaatcatcatctcggcgttgcaggaacacagcgggagaaagtggccgccatcctgcactttgctcagcttcgggctcccatttgctccattgtgccggttctac |
| | agtggctcgggctga |
| 228 | cggtactggaacagagaaatcggcggatgcgcaggaaatttgttatgacggcggcctgtctgaagtgcaagttagtgcttacttcctggctggcaacctcag |
| | gctggacgcggtttatgtgatgaatctgcgaagaaactgaagctgacgcttctgctgacatgctcggtcgcagcggatcgaaa |
| | gaagcgcctttgccgcacctgacgaagaagtttgcgcccctggcgcctgaaaccgccagatcattacctccaattgcttgccggtgcttac |
| | cctgaaaaagacgctgcgcgatgctaattgccgggctgggcgacctcgtcaacaggccatccgttcagcaggttccagcccctgcggcctgggcaa |

TABLE H-continued

| SEQ ID NO: | Sequence |
|---|---|
| | acgcggtgatgatggatgctttctggttaaacgggcaacctcgttaactgactgactagcctggcaaactgcccggcgttttttttgcaaggaatctgat tcatggcgctcaaacagttaatccgtcgtgtgcgcccctcgccgatggtccgacacaacctgcagtcatccttattggtcgatgaactgctcgaccc gcgcacgcttaccagccgattgagccggccgcttaccgacgaactcgtcagtatctgatgcggtgtgcccaacagaagaaagaacagcagct tgaagcacggcgccagtcaaacaggccagcagtcgtatcgaacgcgggatattccgggatcagtgaaagtcatcggaccacattaa cctacttgccgaggccattctcgatcgtcgtggtgcagcatggcgttcgtgtggaacaaatgtcgtaaaaatacggcagcccgcacttcagcaccgtga ggcgcggttttgcccgtcggttcgggttacgggaaactcggtcggtggagctcggccagcgcattatgcacttattcagcaccggacatcgt cagccattcttacgaggttgatccgtcctccgccaccgttcggcaccattgaagcgttcgcgcaccattcagccgatgccaatga agcctgacgtgggagcatcaggcggcgggcgcgaccagcgcgtggttccgcgcggtggttacgggatccgcaacctacgacagcattaacgcacgctcgcgacat tctttgccgccagccgatccgggctggcagagcgcgctaaggaggtccgtaaatccgaagaaatacgtggtctcgcgtctcggcgcatgatgagccgaagtgacgcgc tggtcgataacgtcagtcgtttgaactgatgaccgacgcatgaagaggagaggcggcccagtctatcgtacgcgctcgcg cgatgaaatcatcatcctggcgttgcaggaacacagcgggaaaagtggccgcgcgcgacagctttgctacttgcctactgagcgcgcagctggc aaagtggctcgctgcgaggtttatcaccgcgcaaggcgtggtggttgtcgctgacgttgtccggtgtgcgcgattacttgttggagtcttgggat gaaagtgacttgcctgatttcaccgcgcgaggtgtcggttggtcgcgtaagcgtgtcgtgggtcgatgtgctcgagctgatgaacattcatcctcggcggcctcttcct agctccgtgccggtggtgaagtcagtaccattgaagagcgcgcgctgaggaagcgggcgttgtcagtcgaactgctatggaagtaactgcgattcgtcgctactatccaca gtctgatcggccgacggcgtgacgacgctcggcgcgtgaccatcgggtgcccctgagcgctgaggcggctgacggacgcttagttgacgctgcg catcctaccatcaccaaactgcgaatttgtcccgtaaccagcaactgatccgctccgattgattatcgttttggagtcttgatctcgagccgatgct gaccaaataga |
| 229 | atgagcatcacggcgtatcagctgactcacaagctacctatgtcgaagaattaactaaaaaactgcaagatgcaggcattcgcgttaaa gccgacttgagaaatgagaagattggcttaaaattcgcgaacacacgctacgcgtgttccttatatgtagttgtggcgataaaagagtcgagcag gcaaagtgctgttcgtactcgcgcgcaagactaggaagactaggaagactaggaagcatggatgttagcgaaactcgttcacaaactcgcagcagt catcatcaactgaggaataagtattaaaggcggaaaacagagttcaaccggcgtcctaatcgcaataacaaagagattcgcggcaagaagtc gcctcaccgcgcggcgatgcgacgagcgctgtattgcgactgctgaattcttcttagatctgaaagcttgaataatcgttctttagtagaaatcagt ccgaatgccgagccgcagttgtcgaatctccttagatctcttagcggtcgccgctgacgttacgcctgcgcgggtacagcaggtta tcaccggaggcttaaaatga |
| 230 | tgttcgtctcgaagccggcaactgaggcaactgaggcagcccggtgaaaccgactggctggcatcgtcgttgtgtgcgaacaaattcgcctcgcgcaacccttgc cgaaagccgaggccttaacgcgggtcgtcgcagcaactgattgcccggcaacagaatcattatcagcgcaagtggctgcaacaactgatcaacgcct gagcctgtctcctcttcgtctggtgcagcacggttatgcgcggtttgcacgaaaactggcccgcttaaaacaacccgtcagatcaacctt ctgcctcctgcctgtgccacgcccgccggttgccctggttggtaaaaaactggcgatgtttaaacacccgcaatacacatggggggaagaa ggcgcagaacgccgaaaggtcccgcgaagggctccacgctcattgttgggctccgcatgcaacaataaagggggagaa gacatgagcatcacggcgtcgtatcagctgaatatcactgactcaccaagctaaaaaattcggaacaacagcacactatgtcgaagaattaactaaaaaactgcaagatgcaggcatcgcgtt aagccgacctagaagttgctttggcctacgatcgtcggcaagaatgagaagattgcggcaaagcaagtcggcatcaactgtaccatatgaggctatttccaagctggtgttcaaacgtttgggatgcagaatgcaagaagggggagaa caggcaaagttgctttgctcgtcacatccggcggcaaagaagtatcttaaaaggcggaataagttcaaccggcttaacctgcaataatgc gttcgcctcaccggcgtcgatgcgccacttgtcgaatcttcttagatctgtcagttgttgtcagtctcctcggtccgcgccctgacctgtacagcag agtccgatgccgcgagggccattgtcgaatctgtggataccccggccggcttgataaatgctggcaacacctcgctgcgccgtttatcggcgccgtacagcagc gttatcaccggaggcttaaaatgccagttcacctagctacctgccgggcccgtggttgggtaccgccgttacgtctccaagtcattaatacggcattacggatcagc gtcgataaagaacgcaatgcacctcggttgggatcccatgcatcgacggcaagaggaaaagaaaccgcatgtcgtccgtaccgcatggg gaaggcgtgatcggccggtgatgagccgagcagtcaatcagcccggtgttaccgccgcattcagacgatcagcgtttctcgaccgccgatatttacgat tcagcctgcctgattgttgtcgccaaagcctcgcggtgtgctggtgcaatacgcgtcgcgggtgtcgctggtgcacacgcgcggttgcacgaagaccgg ctggctgccagtacgcggtttttagaaatggtc |

TABLE H-continued

| SEQ ID NO: | Sequence |
|---|---|
| 231 | atgaccctgaatatgatgatgatgatgatgccggcggacatcatcggcgacaaacaatattaataccggcaaccaccaccggcaatttacgagactgcgcaggc<br>atcctttctccgtgacttctgtgacgcgccaccgcatcattaacctaagaatatcctgaattaccccgctggttgagcgttgtgaaaaaagtaactgaaaaa<br>tccgtagaatagcgccaccgcattaacttaacctatcaattatctggtgatatgtcgcattaaatgctgcatggtgcgttgtgtgcgg<br>gaaaactgctttttttgaaaggttggtcagtagcgaacaactcacttcacaccccgaaggggaagtgcctacgatccgctattcat<br>tcactgacccgaggttcaaaatga |
| 232 | accggatacgagagaaagtgctacatcggttcggtgatattgacggcgcatccgcagccgccagttctcgttcgtggatctgttggcgatttgc<br>gggtcttgccggtcgtgggcgcgaaaaataccaatattgccataacacacgctcctgtgaaaaagagatcccgcggaaatgcggtgaacgtg<br>tctgatatcggcaagagtgtgcagttgcgccggctttggctgcgggtgcaaaactgccaccagttcgctgttctcgccgagttctcct<br>cgtaatgcccgccagcgcggcgttgcggcttgtcctggcgacaaacgtcagaactacgacacgcaagtgcactcttt<br>gcatgttgatacgtgccgacacgtgtccggcgcacaaatgtcagaactacgacacgcaagaagtgt<br>gcgatgacccgaatatgatggatggtccggggacatcatcggcgaaacaatattaataccggcaaccacaccggcaattacgagactgcgca<br>gcatcctttccccgcaaattctgtcagaaagaggcagtcctacttgaatcaccccggctggttgacgttcttgttgaaaaaagtaactgaa<br>aaatccgtagaatagcgccactcactcactcacctcaagaagattactggatgaattctggcgttgccattaatgcgcagcaatggtgcgttgtg<br>cgggaaaactgctttttttgaaaggttggtcagtagcgaacaactcacttcacaccccgaaggggaagtgcctacgatccgctatt<br>tcattcactgacccgaggttcaaaatgacccagcgcggtcaaaatgacccgaggtgtaataccgctccggcaagctccagcatctcgatcagcgc<br>ataagcgtggtactcagccagcagcgcgattttgaatattgaagcgtgcgaggaagccgatcagcagttaatcccggcacatgatcgtcc<br>gggcgaaggggtcggacgtgtcggggagcggtttcgcaggcgcaatcattagtgctggcgacgttgctggcgaccgttcttgacgctgcggttgt<br>atgattacacccgcgcgtttatcgccgtgccggtgatgggccagatgccagatcggttgcgtgcgagacttcggttgcgacaaccatggccgttacgaacggtc<br>cgattaccgcgcctgcacccgcttctgaaacggtc |
| 233 | atgacccgaatatgatgatgatggatggtgccggcggcgcctgtaataataaccggacaattcggactgattaaaaagcgccttggcgcttttttacattccc<br>gctccattaaaataaaaatccaatcggattttcactcacttaaactggccattatctaagatgaatccgtttaacacgcgttttaa<br>ccttttattgaaagtcggtgctttcttgagcgaacgatcaaattaagtggattcccatcaaaaatattctcaacctaaaaagttgtaatacttgtaac<br>gctacatggagattaactcaactcagagggtattaataatgatcgtactaaactggtactgactcactccacacccgaggggaagttgc<br>ctgacccctacgatcccgctattcattcactgacccgaggttcaaaatga |
| 234 | accggatacgagagaaagtgctacatcggttcggtgatattgacggcgcatccgcagccgccagttctcgttcgtggatctgttggcgatttgc<br>gggtcttgccggtcgtgggcgcgaaaaataccaatattgccataacacacgctcctgtgaaaaagagatcccgcggaaatgcggtgaacgtg<br>tctgatattggcaagagtgtgcagttgcgccggctttggctgcgggtgcaaaactgccaccagttcgctgttctcgccgagttctcct<br>cgtaatgcccgccagcgcggcgttgcgggctgacatgtccggcgcacaaatgtcagaactacgacacgcaaggtgcactctt<br>gcatggttatacgtgccgacacgtgtccggcgcacaaatgtcagaactacgacaactgacacgcaaggtgt<br>gcgatgacccgaatatgatggatggtccggggacgccggcatcaacggcgattataaaacgcccctgtgcgcgttttaacacgcgtttt<br>ccgcctccatttaaaatccaatcggattttcactattaaactggccattatctaagatgaatccgtttaacacgcgttt<br>taacctttatttgaaagtcggtgctttcttgagcgaacgatcaaattaagtggattcccatcaaaaaatattctcaacctaaaaagttgtaatacttgt<br>aacgctacatggagattaactcaatccgctattcattcactcagaggtgattaataatgatcgtactaaactggtactgactcactccacacccgaaggggaagt<br>tgcctgacccctacgatcagcgcatgatccggggcagcctgtctttacgacgccagcagccgatgggacggtgcttcgcaggcgcaatcattagtgctggcgacatc<br>ccagcagttcactcggcgtcaagctggtaacccgctccagcaacgcagcacggtacggcgctccaaggctgcgcattgcacat<br>ggcggctcgcaaatccgcatcgccggggcgaggcgtgcggcgaggcggacggtgcttcgccgtgtctgacgatc<br>ggcagcttcttgaccggctcggttgatgattacaacctgccgtttatcgccgtgccggtgataggcgccagatgcgcagatcggttcggttgctgacggc<br>acaacccatggcggttacgaagcgattaccgcgcctgcacccgcttctgaaacggtc |
| 235 | atgacccgaatatgatgatgatggatggtgccggcggcgcctgtaataataaccggacaattcggactgattaaaaagcgccttggcgcttttttatattccc<br>gctccattaaaataaaaatccaatcggattttcactcacttaaactggccattatctaagatgaatccgatttaacacgcgttttttaa<br>ccttttattgaaagtcggtgctttcttgagcgaacgatcaaattaagtggattcccatcaaaaaatattctcaacctaaaaagttgtaatacttgtaac<br>gctacatggagattaactcaactcagagggtattaataatgatcgtactaaactggtactgactcactccacacccgaggggaagttgc<br>ctgacccctacgatcccgctattcattcactgacccgaggttcaaaatga |

TABLE H-continued

| SEQ ID NO: | Sequence |
|---|---|
| 236 | accggatacgagagaaaagtgtctacatcggttcggttgatattgaccggcgcatccgccgcaccgccccagttctcggtggatctgtttggcgatttgc<br>gggtcttgccggtcggtcggtgcggaaaaaaataccaatatttgccataacacccgctcctgtgaaaaagagatccccgcggaaatgcggtgaacgtg<br>tctgatattggcgaagagtgccagtttggtcggtccggcgcatggccaaaacctggcttattaatcgaccagtctgcgctttttcgccgagtttctcct<br>cgctaatgcccgccagcgcggcttggcgctgatagcgccgtgaataccgatctgatcaaggtttgtcggttatcagccaaaagtgcactctt<br>gcatggttatacgcgtgacatgttgccgggcgacaaacgcctggtggcacaaatgtcagaactacgacgactaactgaccgcaggagtgt<br>ccgcctccattaaaataaaaatccaatgactgattcactattcactattgcccattatctggcttaacggcggttttaacacgcgtttt<br>taaccttttattgaaagtcggtgctcttttgagcgaacgatcaaatttaagtggattcccatcaaaaaatattctcaacctaaaaaaagttgtgtaatacttgt<br>aacgctacatggagattaactcaatcagagggtattaatatgaatcgtacaaatggaccggcaactcacttcaccacccgaaggggggaagt<br>tgcctgacccctacgattcccgctattcattcactactgacactggaggtcaaaatgaccagcgaccggatcggtaataccgtctggccgcttcgattgtc<br>ccagcagttcactcggctgacagccgatcagccggtgtactcagccggcgatcagccaagtcgctgcgcgattgcacaat<br>gacgcctttgcgcacgacgtatgctctgctctacgacagcgcagcaggtcggagcggtgttgaataattgaagcgtgaggagcgatcagagtcagtaatcccc<br>gcagctcgcgcgaatcccgctatcgtccgggcgaaggggtcggtcggagaagccgtgcgccgccgtaccccgctgtctgacgatc<br>agggcttcttgaccggcccggttgtgatgatccagcaggattaccccgctgcaccgggttctcggtgtgctgacggc<br>acaacccatggccgttacgaaggcgattaccccgctcctgcacccgcttctggaaacggtc |
| 237 | atggcactgaaacacctcattcccctgtgctgccgcgtcgccgatggtgccgagtcagtcagctgcggcgagctctgctgcttgatgattgctcgacccg<br>aatacgctctacaacgacgctgaatgctatcgcgatgagctgcgcgcataactgctgcgctgcgccggaagatgatgaagagcaacagcttg<br>aggctgcggaggctgttaagcaggcagttgctgctgcggcggccggcgatattggcagcggcgcttgccggtcagtaaagtgagcgatcacttaac<br>ctgctggcggaagcgatattatgatcggtggtgcaagctggcgtggggctgggagctggctggcggctggagcgccgagctgggtacagctgattgctggtcagtccggcctgacgctcgga<br>agggcgcggttttgcgtgatgagcgtggtcggtatggcaagctcgatcgccgccagttctattgcgtctcgccagcgcgtgatgcaccgccgcacgcgt<br>tggatgatgaccgatggcgagcgtgaaatcgatcgggagcgtctgctcccatctgcgtcggtcgccaggtcggggatgcgttgtcggctcggtcgtctgatgtgtctcacgggatggatgtcgtctgtcggggatgcgttacatccgacatggacacgcgaaaacg<br>aagcctggcagagtcatcaggcgcgctcggcggcgtcaaacgacgtgcgaaaatgctccgagatttgacgcctctgctcgccgcgata<br>tctgatgacgctcgcgacgcgcaacgctcgatcacccgacctcagttatcgcccaatatctggtgctgcgctttgcccatgacaagctgagagaactgacgc<br>gctctcgatctggataatgtccgcattctcgaaggctggcgcaaaacgcatcatggaggagcaggcaggcattgagcgtggctgctgcacccaca<br>ttgctgatgagccgcaccggctgcaagctgcgctggcaggagtccccggacacgtggcggaacatggcggatgcgatggcgcctcctattaaaaccagctgg<br>gacaagtggctggtggaa |
| 238 | gcgcaaagcgagtgcgctcacttacgtcacttactgatgctcgttgacacaatctgaagcgcgaccataacttctgccgttcagcgaatacaggcggcgtggtgtgtggagcgcacaatc<br>agcctggcggcacctgaagcctgcgcgagtgggccgagtgcagcggccgagtgccaggcgccagaacctgatgaaaaagcgccaaatcgccgacctcctt<br>aaacgctttgctgacatccatctgtcacgcagccgcgcggagctgaaaaaagcttgcccaaccgtgggccgacagctatccgaccagtctgccgc<br>gctggcggcgtatatcgacctcggccgagagtcgaacatttccgtaataccggatctaccgagagcggttcaccagcagcgcgtcttggttgcacaagcgaaaacgttaacg<br>aaaggatattccacggggaactagacacctcttcttccctgccctgctgtccctggtcagtgccagcagtctgccgccgatcctgcttgatga<br>attgctcgaccccgaatacgctctcatccaacgacgacgcgatgaagtcctatcccgacgctgccatcggctgcgctggctggcgcgttggctgcgcgttggctggcggcggcgagatgatgaa<br>gagcaaacagcttgaggcctggcgggagctgaagcaagcagttgctgtgccgggcgacggcgcacttgcgcagctgcccagtaatgaaagtg<br>ctgacacttaacctggcgcagctggcgggagctgattattgatggcggcgcagctggcgcggctgcagctggtacgcctgatctggattattcct<br>gcacgactgcccgatgaggtgatgacgagcgtgaaatcgatgctgagcgtcctgcagtctcattgtctcgcgcacgcgggcgctgatcgccgtgcctcgttag<br>cacgcgcacgtgtccgcacatccttatgaagttgatgccgtctgtcgtctgctgcgcggatggtgctgcgctggccgctggcctactaacacggcgttcgcgga<br>taccagcaaaacgaagcgaaggacgtgggaacatcaacgcgccggtcgtctggtgctggccaagttgatcgcagccaaacgtgccatcttggca<br>ccattcgcgcgatattctgatgacgccgctcgacctcgaaagccgatgaggcgtatcaccgacatcagttatctcgccgcttatctcgtcgttgcccatgaca<br>acaagcataaaagaccgacagctatgccgcggccgtgtcggtatcaccggggcgaagttgtcggtgtcgcttgcctggcggcgagctgcggctt<br>agccgaaactgacgcggctcgtcgttcggataatgtcggataatgtcgcgatccattccgaaaggctgggctgcaggagtgcccggacacgtggcgcaagagtgcgctggccgctggcggacaaccagctg<br>attaaaaaccagctgacgcgcactagttaagcaagccggttaagcaagcggttaagcaagcggtgatggtgggtgatctgatcatcgcgcgcaaatttgtatctctcaggagacaggaa<br>tgaaagtgacgctccagagtttaagcaagccggtaatggtggtgatgctggcgatcgttactggtatgggccaccagccgtatctctc |

TABLE H-continued

| SEQ ID NO: | Sequence |
|---|---|

239
```
cggaagcgcagtcccggttgttaaagtcgataccattgaagagcgtcctggcggcggcaaacgtggcgatgaatatcgcctcactgggcgcca
cggcggctcgctggcctgactggcatggcagtcgatgggcgcggcgatgctgaccagcgctgctgactactcgtttctgttc
cgcagcgatcccaccatcactaagctgcgtgctgtcgtcgtaccagcagcctgatctgctgactggacgaggagtcgatccgcaa
ccgatcgatgaacgatcagccaggcgctggaatattggccgcctggtgctcgatt
```

239
```
atgtttaacgatctgattggcgatgatgaaacggatcgccggaagatgcgtttctgagactggcgcttctgagagctggcggcgttgtgtagga
ggattccacgccgtgtgttggcgatcctcagaggacgatccgccggcgtgtggtgcgttggcgccgatttccgcaaagagagttggatataagcacc
attggcccgggaggcgaggcagtgactgctcgtcactaatgccgcctatgtgctatgtcgccgcacgcctgtcacgcc
tgacgccgtgctcaccgaattattaccgcaccactacctacctgctgatgaattcccgggcgcactgaaacacctcattcccgtgtgccgc
gtcgccgatgggtgccagtcagctgacgagctttagacgccttgaagtcgtgctcggcccttcctgctggagcgggagcctgaatgcggta
tcgcgatgagctgcgccaatacctgctgcgccgggaagatgaggagcagcaacagcttgaggcctggcgcagtttaagcaggcagcagttgct
gcgcgagctcgcggacgtgtgcaggacggggatataccgcaccctgccggcacactctgcggggtg
cagcaagcgcgggggcagatggcggcgtatggccagccgatccctctgcaccgcactcggcggccccgaccgatggcggcggttatggcaag
ctgggcggctggagcgtggagcgtacagctccgatctgcttcctgcgacgatcgtgtattcctgacgagcgccgatgggatggcgacgtgaaatcg
atggtcgcagtctattttgcgctccggcagcgccgtgatggcccgtcgcccgcacgtgcaccgcctttcatgaagtgatgccgcgtctgcgt
ccatctgggcagtctgattgcgctcactatgcggatcactacaccgttcgcggatcaccaagcgtgggaactcaggcgtggcc
cgtcgcggcgtggtacggcgatccgcaactgaccgcgcgaatttgacgccatctcgcggatctcgatgagcgccgcgcaaccgc
aaaccgacgtgcggaaatgccgagaaatgcgtgcccaatattggtgcgcctttgcccatgacaagcataaaagaccgcttcgatcgtgaaaggc
tggcaaaaacggcatcagtgcgcggactccgggagagcggaaagtcggaaccggcgtggaacatcaggcgttggcaa
gagtgccgggacatgtgcgctccctgttttgtccgacgcgcttagcgagcgtgtgtcgaaccgtacctgctggtgggaaccggcgcccggc
gtaa
```

240
```
atgacctgaatatgatgatgatgcgcggcgcctgtaataataaccggacaattcggactgattaaaaagcgcccttggcgtttttatattccc
gctccatttaaataaaaatccaatcggattcacttatcactattaaactggccattaaactagatgaatccgatggaagtcgctttaacacgcgttttaa
cctttattgaagtcggtgcttcttgagcgaacgatcaaattaagtggattcccatcaaaaataatattcccaactcaaaaagttgtaatacttgtaac
gctacatggagattaactcaatccagagggtattaataatgatcgtactaactggactgactaaaaagcgcctgtaccgacccaggtcaaaatga
ctgacccacgatccgctatttcattcactgacccgaggtc
```

241
```
accggatacgagagaaagtgtctacatcggttcggttgatattgacggcgcatccgcggccgcgcccagttctcgtggtgatctgttggcgatttgc
gggtcttgccggtgcggtgcgccgaaaaataccaatattgccatacacacgctcctgtgaaaagagatcccgccgggaaatgcggtgaacgtg
tctgatattgcgaagagtgtcgaagatggtgccagtttggctcgcgggcaaaacctgcaccagttggcttattatgcaccgatctggcctgttctcct
cgctaataccccgccgccgcggttgccttgaacctactgatagcgcggtatcagtttgtcggttatcagccaaaagtgcactctt
gcatggttatacgtgacccgacatgtgcccggcgacaaagtgtccggcggcaccaaattgtcagaactacgacgacgactaaccgcaggagtgt
gcgatgaccctgaaatatgatgatgacggccgccgccgtcctgaataataacggacaattcggacctgattaataacagccctgtggcgcttattatt
taacctttaaaataaaaatccaatcggattcacttatcactattaaagcctggcatccaaaaaaaaatattctcacacaaaaagttgtgtaataacttgt
aacgctacatggagattaactcaatcctagaggggtattaataatgaatcggtactgggcgcaactcactcacaccccgaaggggaagt
tgcctgacccacgatccgctattcattcactgaccgaggttcaaaatgaccggggtactgagtttgaaattgaaggttggcaactcccgcgattgtc
ccagcagttcactggcgctcgatgcagcgtgtgtacggacggcagcagccgtgattcgcagggccaatcattagtgcgcgcgtgtcgacatc
ggcggctcgcaaatccgtatcgcccggggcgggctatcccggcgcgggtgattcgcgtgccgatagggccagatgcgcagacttcggttgctgacggc
acaacccatggcgcgtacgaggcgattacccgctgcaccggctttctgaaacggtc
```

242
```
gcgcaagcgagtgctcacttacgtgctcgttgacacaatctgaagcgaccataacttctgccgttcagcgaatacggcgtgtgtgagcgcacaatc
agccctggcgaagctggtgctcaccgagtggctcagccgaggctggcggaacctcctgatgaaaaagccaggccaaattcgccgactcctt
aacgattgctgacatccatctgcacgacgcgccgagtgaaaagcattgcccaaccgctgggcagacgcatcgcgaccagttgcgc
gctggcgctgagactgcggcgttactgctggccgggggcagttgcctgaaacctggccatggctgtgcgccgtgtgacatc
aagccatggcgcgtacgaggcgattaccccgctcggcgcaccgatcgcctaccaggagccgttctggttgcacacgggaaaacgttaacg
```

TABLE H-continued

| SEQ ID NO: | Sequence |
|---|---|

243

244

TABLE H-continued

| SEQ ID NO: | Sequence |
|---|---|

245

```
atgaccctgaatatgatgatgatgcgcggcggacatcatcgcggacaaacaatattaataccggcaaccacaccggcaatttacgagactgcgcag atccttctcccgtcaattctgtcaaataaagtaaactaaccttcacttcaattaccccccgctggttgagcgtttgtgaaaaaagtaactgaaaa tccgtagaatagcgccactctgatggttaattaacctattcaattaagaattatctgataagtgcattaaatgcgcagcataatggtcgttgtgcgg gaaaactgcttttttgaaagggttggtcagtagcggaaacaactcacttcacacccgagggggaagtttgcctgacctacgattccgctatttcat tcactgaccgaggttcaaaatga
```

246

```
accggatacgagagaaaagtgtctacatcggttcggttgatattgaccggcgcatccgcgcccagtttctgtggatctgtttggcgatttgc gggtcttgccgtgcggtgccgaagagtgccagtttggtcgcggcaaaaaaataccaattttgccataacacacgctcctgttgaaaaagagatcccccgggaaatgcggtgaacgtg tctgatattgcgaaggtgccagtttggtcgcggcaaaaccgtgacccagttgcttaatgcaccgctctggcgcttttttttcgccagttctcct cgctaagatagcgccgcggccgctttggcgttgatacgcgtgatcaaggtttgtcggttacagcacgactaactgaccggcactctttt gcatggtataccgtctgacatgttcccgggcgacaaacgcgtggtggcacaaattaatatccggcacaaattaataccggcaactacgaccggagtgt gcgatgaccctgaatatgatgatgatgcggcggacatcatcgcggacaaacaatattaatataccccgcgctggttgagcgttgttgttgaaaaaagtaactgaa aaatctgaatatgcgccgcggtcattaactattcaatcaagaacaactcatatctgcagcataatggtcgcgcgcagcataatggtcgcgtgtg cgggaaaactgcttttttgaaagggttggtcagtagcggaaacaactcacttcacacccgagggggaagtttgcctgacctacgattccgctatt tcattcactgaccgaggttcaaaatgaccggcctccagttctgtggcgtcgattgcacggcagtgatgcgcgggttacaagaactgaa ataagcggtggtactcagccggcgaccgaggtcgatcagacgctccagcaagtgctggcgtattgcacaatgacgccttttgcagcacgacgat ctgtcgtacgacggaagcggctgccgccctggcgctttcgcaggcgcaatcattagtgcgtcgcgccgttgcgacgatcagcgattcatgccccgtatcgtcc ggcgaaggcgtgtcgggacggcgcttcgcaggcgccctgataggggcaatcattagtgcgtcgcgccgagacttcggtgtgctgacgacacaacccagtgccgttacgaagag cgattaccccgctgcaccccgcttctggaaacggtc
```

247

```
atgaccccgaatatgatgatgatgcgcggccgccgatttcacttcactattccatgcggccattatctaagatgaatccgatggagctcgctgtttaacacgcgttttttaa gctccattaaaataaaaaatccaatcggattcacttatccatgcggcacttatccatgcggccattatctaagatgaatccgatggagctcgctgtttaacacgcgttttttaa cctttattgaagtcggtgcttcttgacgaacgacaaattaagtggattcccatcaaaaaaatattccaactggatgatccataacattctttgtaatacttgtaac gctacatggagattaactaactctagagggtattaataatgaatcgtctaaactggtactgagcgcaacttcactaactcacacctgcggaggtcaaaatga ctgacccacgatcccgctattcattcactgaccgaggttcaaaatga
```

248

```
accggatacgagagaaaagtgtctacatcggttcggttgatattgaccggcgcatccgcgcccagtttctgtggatctgtttggcgatttgc gggtcttgccgtgcggtcggtgccgaagagtgccagtttggtcgcggcaaaaaataccaattttgccataacacacgctcctgttgaaaaagagagatcccccgggaaatgcggtgaacgtg tctgatattgcgaaggtgccagtttggtcgcgggcaaaacctgaccccagttggttattaatgcaccggtctattaatgcgcagcataatggtcgcgcagttctcct
```

TABLE H-continued

| SEQ ID NO: | Sequence |
|---|---|

249

```
cgctaatgccgccccagccgcgcggcttggcgctgatagcgcgctgaataccgatctgatcaaggtttgtcggttatcagccaaaggtgcactcttt
gatggttatacgcgtctgacatgttgccggcgacaaacggcctggtggcacaaattgtcagaactacgacgactaactgaccggcaggagtgt
gcatgaccctgaatatgatgatggatgccggccgctccgtcctgtaataataaccggactgattaaaaaagcgccctgtggcgcttttttatatt
cccgcctccattaaaaatccaatcgatttcactattaaactggccattatctagatgaatcctagcggaagctgcgtttaacacgcgtttt
taacctttattgaaagtcggtgctcttggcgaacgatcaaatttaagtggattcccatcaaaaaatattctcaacctaaaaaagttgtgtaatacttgt
aacgctacactggagataactcaatcagaggtgtataataatgaatcgattcaaaatgaccagcgaaccttcggcgcttcgattggtc
tgcctgacctacgatcccgctcattcattcactcactgacgggtcaaatgaccagcgatcgacaagtgcggtattgcacaat
ccagcagttcactcggtacgatcagcggtactcagcggcagcagcagcgatttgaatattgaacgttcgcaggatctttatcggcgtgctgacgatc
gacgcctttttcgcagcacgcatgatctgtctcgggcgaaggggtggtcggacggtgcttccaggcccaatcatagtgtggccgcggtttgctgacgatc
ggcagccgcaatcccgctatcgtcggttgatgattacaacctgccgttatcgcgcgtgataggggccagatggccagacttcggtgtgctgacggc
acaacccatggccgcgttacgaaggcgagattaccccgcgtcacccgctttctgaaacggtc
```

250

```
gcgcaaaagcggagtgctcacttcagtgctgctgttgacacaatctgaagcgctgaacataacttctcgcgtttcagcgaatacggcggtgtgagcgcacaatc
agccctggcgaacgtggctcaccgagtggctgctgagtgacgcaggcggccgacctttcctgatgaaaaagcaaggccagcaaatcgccgactcctt
aaacgcttgctgacatcatcatgctactgctcacgcacgcggcggccgagtggaaaagccttgccaacgcgctggatggctggaaaactgcagggcttcagc
gctggcgcgtatatcgctactctgctggccggcattccgtaatcaccggtgaatggctgaaaactgcagcggggaaaacgttaacg
aaaggatattccgcatgctcattcctgttcctggtgcgccagccgcgtcgccagcccgatcctgcttgatgga
attgctctgaccccgaataccgctctatcaacgacgctgaagtgcctatcgcgatggaatgcctatcgcgctgcgctgcgcggaagatgatgaa
gagcaaacagcttgaggcgtgcggcgcagttaagcaggcgattattgatggctggtcagcaagctggggcagatcggcggcgtatgcagccaacgcat
ctgcacgactcgcccatgtcagatcgcgatgaactggtctgcggtcaatcgtatggtgccagtctcattcggctctcgccagcgctgatcaccgcgttag
gcacgactgcccgatctcgtcggccatctttatgaagttgatcgcgagcgtgaaatcgataatggtcgctcgcggggcgtgctcactaacgcgttcgcga
ttaccagcaaacgaagctgacgatctgatgcggaacatcaccagcggccgcgcaaaccgacctgcgagaaaatgcgcgagaaaatgcgcgctgcgcctcggca
ccattcgccgcgatattctgatgaccgctgatcagcggccgcgagaaaacctcgcaaatttgtatctctcaggagacaggaa
attaaaaccagtgacgctgccaaggttaagcaagccgttgggttaatgggtgatcgtgatcgtactgatttggcccaaccacgtatctctc
tgaaagtgacgctgccaagtttaagcgtgaacgcgccgatgtatcgcgggcggcaaaccgcgctgagttactggtatatggtggccctgccgtatcctc
cggaagcgcagttcccggttgttaaagtcgataccattgaagacgttgaagcgctgggcggatatcgacaatggcagctttactggcgca
cgcgctcggcgtcgtgctgccgactggcatcgatatcgagcgtgatcgcgcgggacttcgcgctgcctaacgacagctgcgtttctgttc
ccgatcgcatgaacgactcagccagccggcctggaatattggccgctgctgtcgtcgatt
```

TABLE H-continued

| SEQ ID NO: | Sequence |
|---|---|

251 tttcgctgaagtgtgaccatggccatcaggtgctgtgtgcagctggaagtgttgccatcactatcgtgtggtctggcgtggtggccttattggttaca
aactggcggacatgacgtagcctgcgctaccggaagaacaagaacgtgaaggtcgatgaacagccacggcgaaaacgcctataacgc
ctga

252 tttcctttctgactctgcccgtccggccgcactaacgggctcgaaatactccctcttcattcctggcacacgcctataactccggctcgttgcgtgct tagctgcg
gccattatcgaattcgactggaggggatctatgaagctggttaccgtggtgattaagccattcaaactgaagacgtgcgtgaagcgcttcttcttattg
gtattcaaggttgaccgtaactgaagtgaaggttggcgtcagaggtcacgctagcgtgtggaatatagcgtaattcctgc
cgaaagtgaaaatcgttcgtgctgagctgcaaccgtcattcgtattcgatccgaagtaatcgatgtgatcagcaacgccgactgatgatcagcagcacagtgatgggatc
caaatttcgttcgtgctgaggtgtgaccatcaggtgtcgtgtcagctggaaagtgttgccatcactacgtcgtggtcggcgtggtggcctttattggtta
caaacggcggacatgacgtagcctgcgctaccggaagaacaagaacgtgaaggtcgatgaacagccacggcgtataac
gcctgattcgtcgttgagttatctcctgacatcaaaaaaagcctccattcggaggctttctttttttaagttaagcgcggttagtcgatcgcatgacgcc
ttcctgacgcggaccggacaccaccccctgcgtatagaactcgcccgcacaaaaccggaacctgcataccggcgtcaggaagcccacgccgt
gggcgaagtgaactcgtccatatcaaacgggcgatgagaccacatggagtggccaatgtggcaacctgcaaacatatgtccgaaacgtcccgttcgcg
gaccatacctggcggggtggacaccggacacggtgccttcaggcggttatgaaactcaaccgggcggatcctccagtgtctctatcacttcaagaacttctc
tttggcctgcgg

253 atgtttaacgactgattggcgatgatgaaacgattcgccggaagatgcgcttctgagactcggcggcgaattgttgcaggatgcgttgcaggagga
ggattccacgccgtgctgcggcgcatctcagaggacgatcgcgccgcggtggtcggctgattcgcaaggaaccacc
attggcccgcgagggcggcagttactgctacttaatgcgcatcacttactgacctgctcagctgcatggaatttcccggcgcactgaaacacctcattccctgtgtgccgc
tgacgcgctgtccacggaattattaccgaccaccttacctgcgctaagtgaattgctcgaccgaatacgggtcactcaaccggcgatgaatgccta
tcgcgatgagctcgccaataacctgctcgcgtggccccagatgataacaacagcttgaggcgtgcagctggcagtgcagttgct
gcgttggcggcgggcgatatggcgtacgttgccagtgccagcagcacgatcctgaccacgcgcgaagggcggttgcggtgcggttattgatgcggggtg
cagcaaagcctggggcagatggcgtactggttacagtccgatctgaatctcctgccacgacggcccgatgatgtgcgacgcggcgtgaaatcg
atgtggcgccaagttctattcggctccgcagggccaatatcgtgggtcgctttgcccatccggtggttacagtggttagcacgctcgttatgagcgcttatgaagttgatgcgcgtcttcgtcgcgt
ccatctggcgctcggggatgtgtacggcgatcccgcaactgacgccccatcttgacgcaagcagcatataaagacgcgcttggcagctcgcgatcgcgacggtatca
aaaccgacgtgcgagaaatgcgcgagaaatgcggtgcccatcagctgtagagttgaagctgaagaactgcggcggcaacaactgcgcagcgctggc
ccgattgcggtacgggcgatcccgagacaagatgcgagaagcgcaggcgcattgacgtgcgtacacacacattgcgtgcgatgagctgcaccactgccgctctcgaagggc
tggccaaaacggcatcatggagacgcaggaagcgcaggcatgcgagctgttcgcccgagccgtgttgtcgccagcgtgggcgctgcgccccggc
gagttgcggacgcatgggcgtctcctgtttgtccgagcgtgcgcttattaaaaccagctgggacaagtggtggtggaacgtgcggcgcccggc
gtaa

254 gcgcaaagcgagtgctcacttacgtgatctgtgttgacacaatctgaagcgaccataacttctgcgtttcagcgaatacggcgtgtggagcgcacaatc
agccctggcgaagtcgaagctgctaccagtggtgctacccagagtgacgcaggcggtggcaaccttctcctgatgaaaaagcaggccaattcgccgatcctt
aaacggcttgcacaccatctgcacacgagcaccttgcccaaccgtgggcgaccatcgcgaccagtgcgcgcg
gctggcttgctgatatcacgcgcaagacttctgcgtcggggccattacctcagatccgcctaccagagccgcttctggttgacagcggaaacgttaacg
acgccattgaaacgcgcagagagtcgaaatcgaactaccggattacaccgatggtggcagatcgcgggccaggattcgccggaagatgcggccgaattggtggcaggatg
cgttgcaggaggaggattccacgccgcgggcgagggcgggtactgtttctgcgctactcgtggtgtcggctgcgatttcagatttcgcaaggagtt
ggataaacgacaccattggcccggagctggcgggaacgtcgcagtcactcacactaatgcgcactcactaacagctttgcctttagctgctaagtgaattctccggcgcactgaaacacctcattt
cctgtgtgccgctgacgcgtcgccgatggttccagtcagctggccaataccgtcgcggtacgtcagggtactgcggaaagatgatgaggagcaacagcctgatggttaag
gcgatgaatgcctatcgcgatgagctcgccgtaacctggggcggcagggccgataattcatttgagctgcccgagtgaatctcgaccgaatacgcttcatcaaccgacg
caggcgcagttgctgcgttggcggcgcaagcctggggcacgatggtgcggcgtatggttccagccagctacctgtgcgtaatgagtactgcagtc
ttgatgcggtggtgggcagccagcaagcctggcggcgtttatggccagcgacatgtcgacggcggcattgtgcggtgg TABLE H-continued

| SEQ ID NO: | Sequence |
|---|---|
| | tcggttatggcaagctgggcgctgggagctggttacagctccgatctggatctcggtattcctgacgactgccgatgatgtgaccgatggc gagcgtgaaatcgatggcgccagttctattgcgttctcgcgacgccgtgatgcacctgttagcacgcgcgacgtcgtccgcatccttatgaagttg atgccggctctgccatctggcctgcggcggatcgtggtcactacggacgatcgttcgcgattaccagcaaaacgaagcctggacgtgggaaca tcaggcgctggcccgacgtgcgccggctggtgatgaccgcagtaccgccgatatctgatgaccgcctccgac ggcgcaaccgactgcgaaaccgactgcgcgagaaatgcgcgagaaatcggtgctgcgctttatccgcggcttcgatctgctgaaagccgat gaaggcggtatcaccgacatcagttatctcggcccaatatctggtgctgctgttcgccatctggccatgcaagcataaagaccgcttcgatctggaaagcgat cattctcgaaggctgcgaaaacggcatcatgatgagcggaggcggaagcgcagcgtgacgattgacctgcgtacggcgacccacacattcgctgatgagctgacc aactggcgtgaaagatgtgccggagacatggcgctctcctttcttcgccgagacgatgtgactgctatttaaaaccagcggacaagtggctggtggaa cgtggcgcccggcgtgagtgtgggatgtgatgtgggcgcggcaaacggctaactggtatcatcgcgcaaattgtatctctcaggagacaggaatgaagctgccgtatctctcggaagttgtcgtagtcagatcgatac gatgaaggtgtggtgggcgcggcaaacggctaactggtatcatcgcgcaaattgtatctctcaggagacaggaatgaagctgccgtatctctcggaagttgtcgtagtcagatcgatac cattgaaaagcgcctggcgcgcggcaaacggctaactggtatcatcgcgcaaattgtatctctcaggagacaggaatgaagctgccgtatctctcggaagttgtcgtagtcagatcgatac tgcggcggcgcccggcgcggctggtgatccgaacgatgtcaaatgacgcgccgatgttccacctactactaagctcgccgtgct gtccggtaaccagcagctgattgcgttcgccggcctgatcgcccatcccgatcagccgcatcagccaggccgctggta atattggcgcgctggtgctgtcggatt |
| | atgacccctgaatatgatgatgtggcgcggccgtcctgtaatataaccggacaattcggactgttaaaaagcgccctgttggcggcttttttatattccc gccccattaaaatattaaaaatccaatcggattctcactattcaaactggccattatctcaagatgaatccgatggaagtcgcgtttaacacgcgttttaa ccttattattgaaagtccgtgctcttttgagcgaacagatcaaattaagtggattcccatcaaaaaaatattctcaactcaaaaagttgtaatacttgtaaac ctacactggagattaactcaatctagagggttaataatgatcgtactaaactgtactaacgtgggcgcaactcacttcacacccgagggggaagttgc ctgaccctcacgattcccgctattcattcactgaccggaggttcaaaatga |
| | accggatacgagagaaaagtgtctacatcggttcggttgatattgaccggcgcatccgccgcccgccagtttctggtgatctgttttggcgatttgc gggtcttgccggttgccggtgtgtggtggcgaaaaaataccaatattgccataacacacgctcctgtgaaaagagatcccgcgggaaatgcggtgaacgtg tctgatattgccaaagatgtgcaagtttggtctggcaaaactgaccgtggttattaatgaccagttgcgctattcgcccagttctcct cgctaatgccggccgccgggcttggcgtgatcagccgatagcgcgtgatcagcaaggttgtcggttatcagccaaaggtgcactcttt gcatggtatacggccctgacatgtgcggcgccgtgtccggcgcacaaacggctggtggcaaatgtcagaactacgacactaactgacccggagtgt gcgataggtcaaatatcaatcgatgatatcagcccgtcctgtaataaactcactatctacttaaactggactgatgaatcatcctatatatt ccgccctccattaaaatcaatccaatcggattcactttaaaataaccggcaataaggccattgcgtttttaacacggcgtttt taacctttattgaaagtcggttcttgagcaactataatcggttctatactggatcggttatcaatacagccgcaaaatgacgagatgaatataactgt aacgctacatggagattaactccaatcttagaggtattaatatgagatcgtaaaacctgatttcaaaatgaccgaggttcaaaatgaccgaggttggtcaggggaagt tgcctgaccctcacgtgcagcgataagcgtactcagccgggcgacgaggtcgatcagacgctccagcaagtgctcgattgtgcacaat gagcgttttgcacgacgacaccggcgatggtttgaatattgaaagctgcaggaagcgcgatcagcagcagttaatcccc ggcagctgcaaatccgtatcgtccgggcgaaggcgtggtcggacggtgcttcgccgtcgctcgcgcgtctgcgagatc agcgcttcttgaccggctcggttgtgatgattacaacccgctggtgtcgccgcgcctcggtgtgctgcggc acaacccatggcgtacgaagagcgattaccccgcttctgccacccgcttctgaaacggtc |
| | tttcgctgaaggtgtgaccatggccgtccaggtgctgttgcgcactgagaagtgttgccatcactctcgtgtcgctggcttgttggcttcgttttattggttaca aactgggggcacatgacgacggtagccttggcgtcgacggagaacaagaacggctgagggctggaagttaaacagccacggcgaaaacgcctataacgc ctga |
| | tttcctttctgactctgccgtccgggcgcactaaacggcctgaaatactccctcttttcattccctggcacacgattgcaatgtctgtgcgtgtagctgcg gcattatcgcttcgactcgaggggatctttatgaagctggttaccgtggtgattaccgccattcaaacttgaagacgtcgtgaagcgcttctttttcttcttattg gtattcaaggggttgaccgtaactgagtgaaggcttggccctggatatcagcggaccagtaatcgatcagcagcaacggcactaatacaacagcgatgggatc cgaaagtgaaaattgcgttgcgagcggtctgcaacggctcattcgtatcttcgaccgacggcaaggtaatccggaaaaattggcacgg caaatttcgttgctgagctgacaaggcgccatcaggtcgccggaaagtgttgccatcactcgtggtgcgcggtggttgccttattggtta ggttcgctgaaggtgtgaccatggcctaccggcgaccggaagaacaagaaacctgatgatcagccagaaggtggaaagtggaaagcgctataac gcctgatggcgttgagttatctcctgacgcataaaaagcctccattcggaggcttcttctctttttaagtttaaagtcgcggttagttgcgtgatctgcgcatgacgcc ttcctgcacgctggacgcgacaccgacacccctttgctataagactcgccgcacaaaaccgagcgtgaggtgacgtgactggtgcttccacactg |

TABLE H-continued

| SEQ ID NO: | Sequence |
|---|---|

259 tagagcagccattcgttcatattaaacgggcgatggaaccacatggagtggtcaatgtggcaacctgcataccggctcaaggaagcccacgccgt
gcggctgaagtgcaaccggcaggaagtaaagtctgaggcatctccagcagcatattgatgtacggcaaaatcgtccggcaccgtgccgtttgcgcg
gatccataccggcgggtggggatcggcaacgtggccttcagcgggttatgaaactcaaccgggcgatctccagtgtttatcactaagaaacttctc
tttggcctgcgg

260 atgacctttaatatgatgctgggtcactggagccgrnatcggcatcctgaccgaagaatttgccggttcttcccgacctggctggccctgttcagg
ttgtggtgatgaatatcactgattctcaagctgaatatgtcaacgaattgacccgtaaatgcaaaatgcgggcattcgtgtaaaagcggactgagaaac
gagaagatggcttaaaatccggagcacacttacctgtcccctatacgtgctggttggtgaaggtgaagaggtgagagtggcaagtggccgttc
gcaccgcgcggtaaagacctggcagcctggcgaaaacagagtcaaacggcacgtccgaatcgatcaatggccagagaattcgcagcgcagtcttcaacaactgg
aggaataaggtattaaaggcggaaaacgagtttcaaacggaccgacctaaacgccctgaggccgatgcggtaggctcggcttaactggttctg
gaaggtgagcagctgggtattgcaataccctgagagctaataacttcctcttgacactctcacagcaatttagcatgagctgcaagtggcct
ggcccacgtgaccccgagtcgggcacccaccgtggtcgtgtttgatctctcacagcaattaccggcatcagcagcgcatcagcgtggtgttg
agtcgcgcaacgagataagcacgagacgctgcaggaggtgctgtgttctgcataatgacacggcatttatgcaacacggcatgctgtctgtatgacaaac
cagcaggaaaaatctgagtattgaagcctgcaggagcagacaacaatctgatccccggcagctcgcaaattcgacagttctcgacagctggcatctatgattacaacctgcc
taggagccgtactgtccaggagacaatctcttgtgctcgcggtgtcgcgcgacattggctgcgcgcagccgatggccgcagctgaggggctgg
gttatcgcgtccccctaatggggcggcgcaggcggcgcgacgattggcgtcgtaacaagtaaccgtagaggagcgcttcctttctgt
acggcttctggaaaccgtc

261 ttgaaagagtttgatcatcggctcagattgaacgctggcggcaggcctaacacatgcaagtcgaacggtagcagcaggacttgctctcgggtgacgagt
ggcggacgggtgagtggtctggaagacgacctggatactaccgataccgctgaagctacagaccaaaga
ggggggacctcggcctttgccactgaactcggctttcatcagatggatctcggatcctacgggaggcacgtgagtctcactaggcgatcctagctgtctg
agaggatgaccagccagcagactgagacacggcccaactacgaccttttcagcaggagcacgtaataacctttcatcatgggacgtaaccgg
cagagaagcagccaccaacaatctcggcgcggtataacggcgcgcgtaaactctggaagaagttaatcgccggggacggacctaaagcgacgacggc
ggctgtcagtcgagtggatggtgaaatcccgggctcaactccgggaactgcatccgaaactggcaggctcaagactggcaaaagcgacgcagggc
tgtagcggtgaaatgcgtagagatctgggaggaacatccagtggcgaaggcggcctctggtcctggttgacgctgaggagcgaaagcgtgggga
gcaaacaggattagataccctggtagtccaacgccgtaaacgatgtcactaggtgttgggggtctggtttattccgtgtgtccagc
gaagaaaccttaccggcttgacatccacagaacttcccagagatggattggtgccttcgggaactgtgagacaggtgctgcatggctgtcgtcagctc
gtgttgtgaaatgttgggttaagtcccgcaacgagcgcaacccttatccttgttgccagcacgtaaggtgggcactctaaggagactgccggtgataa
actggaggaaggtggggatgacgtcaagtcatcatggcccttacgaccagggctacacacgtgctacaatggtcggtacagagggcagctacctcg
cgagagcaaggcgacctcataaagttgctcgtagtccggattggagtctgcaactcgactccatgaagtcggaatcgctagtaatcgtggatcagaat
gccacggtgaatacgttcccgggccttgtacacaccgcccgtcacaccatgggagtttgttgcaccagaagtaggtagcttaacctttcgggaggc
gcttaccacttgtgattcatgactggggtgaagtcgtaacaaggtaaccgtaggggaacctgcggttggatcacctcctt

262 ttgaaagagtttgatcatggctcagattgaacgctggcggcaggcctaacacatgcaagtcgaacggtagcagcaggacttgctctcgggtgacgagt
ggcggacgggtgagtaatgtctgggaaactgcctgatggagggggataactactggaaacggtagctaataccgcaagtcgcaagaccaaaga TABLE H-continued

| SEQ ID NO: | Sequence |
|---|---|

263

264

265

TABLE H-continued

| SEQ ID NO: | Sequence |
|---|---|

266

```
ccaacgggcattaccagatgtacgcggcgggacgacgcagcagcaagaagatgcgcgaggcgccgatgctatcgacaccctgttgctcagccctg
gcaactggtgaaaagcaaaaagtggtgcaggagatggcaggagatcagccgcaccgaggttctgttccgttgggctggcaggaacagacgaact
gttgatgcggattagcagtaaccggcaaggccattcccgattcactggcgctggacgctggtcgatatgatgctcgattcccacacct
ggttgcacgtaaaaaatcggccgtgtttggcgatccggattttgtcatgggattgaccgtttcctgtgagctggctgcgaacgaccgttatcctc
tgccacaacggtaacaaacgctggcagaaagcaatgagaaaaaatgcttgacgtctcgcctacggcaggagagcgaagtgttatcaactgcgatt
tgtggcattccgctccgctgatgttcgtgatccgcctcggttttccctgttcgacaactgcaactcattcagcgcgacacctagccaaaggcga
gcagttgaagttccgttccgtcgatccgtcactttcccctgtttcgacccgcaagagcagagaccatcaagcecggcaaaaccgactcggtatccgttaa
ttctccactcacccgttgaatgcggtactggacgagaaagtggacaagaagaccatcaagccggcaaaaccgactcagctctatccgttaa atgaccctgaatatgatgatgatgacggcgtcggcggcgcgggacgacgcagcaatcgccggtcgcttccgcgacaccatcctgggctgttttttaccatcgttgagaa
gcgcccgcgcgcattcgctgactgatcgccgacgcacgcattgtctatgccaccggaattctgccgccagaccggctatgaactagaagcgttgttg
cagcaaaaatccccgcctgtgctgcaagtgccaagtgccaagtgcatcatcaggatatgtgacacctgtatacaccggggtcaacccgcgccggggc
aatgattaaccgccacccgacgcagcagcgcgagatcgatcgtcgtgatcgatatataccgtcgattaaccgttggcgaactcgaactgaacctggca
atgcagcggcgatatcaagcgccagctacgcgccagtgagctggagcaggtgtcgcccaataccacgtacgagtcgcaggtgcggaatcctcggggcgg
aatttttcagccgcagcgccgaaaacgggagcgtcaaaacgttctgtcggcggggcggaggtgagttctcggttgcgcgtgcctgctgggcgc
tgccgggggtcagcgaagcaggagaagccagtcgctacttctattgataacagcggcaaactactggccgtcaaactactggcgcaacacgcgcagc
agcaggaacaggggcgacttgaccgcttgaccgctttaaacagcagagtgaccgttaaacgccagtgtataacaaatggcctcgacgccgtcgccgcgtgatc
cagcttaactgccaccatcaaatgctggccgggcggcgacgttcacacacgctcacccacgtgctgcaacccttttgacgattcgcgc
gcgcttatcacaccgctacgagcagggaaaaatttgcagtcacgctgggcgcggattcttggtcagctcgcaactgttagcct
gctgagtcgtggctcgatccgcacgatgccgtgatccgctgcgcgatgccctgcgccacaccactgccgccctcgcgaagaagaggggctg
gctctctttgtatcactgacaatgcgctgccaccacacacacggcgcccgtggcgtgatccgctgcaacacggcaccactcacacccctacgattcccgctatt
tcattcactgacccggaggttcaaaatga
```

267

```
atgaccagcgaaccgagtcgggtaataccgtctggcggcttcgattttgtcccagcagttcactgcgatgcagcgcataagcgtggtactcagccggg
cgaccgaggtcgatcagacgcttccagcaagctgctgtggtattgcacaatgacgcatttgcacaagcgccgcaaatcggctattgtctgacgacagcagcag
gcgcattttgaatattgaagcgtcaggaagaagcgcagtaatccccggcaccgtgaatcccgtcatccgtggcgaggtggtcgggga
cggtgcttcgcaggccaatcattagtgctggcgcgcgttggtcggcgatcagcgcttcttcgaccgatcagccggttgatgattacaacctgccgtttatc
gccgtgcgctgataggcagcagatgccgtaaccgcgtcggtgtctgacggcacaaccatggcgcagtcgccctcccgccggcgccgccataacacagcgccg
tttctggaaacggtcgtcaaccggtcgtaaccgctgtgatggcaacaccggcagtgccgtgtccgccgccagaccatggagatatccgtcag
ccagccgaaatcgccaccgcaccgctggttgtgaaaatatggcgcattggcaaggagctgattgccaacgccatcccaacattccggcgtgcc
gttccgcgctgggacaccaccgttctggtacgcggcggcggcgagagtgcaccgcaggagtctcatcgcgaaagcgaatgtgttcgtacgcagccgcgg
tacgcagcgctgaaattcaactgtgaaatttgagagccgtgttctctggacgatcggcaaagcgatggcgaaagcatcaggctgctgtacgacgctgctg
cgcattgcaggagcggcgaaatgaacgcgtcaggggggcgagacgacgtcagctgatctattatcgcctgaactgtgatgcccatcgcgcgacggagacat
tgccgactgggcgcacttctgtgctgcgactggaaagaccgtcaaaaatgcctgagccgtacgaccgggtgatgatgcggagaacgctgctcttatc
atcggaccaagccagcaaccggtatctatcagcgtcgcatgatgataactggtgatgataactggctataccggtgatactggtgattgatttgttaatc
gctggaaaagcgggatgggatggtaacaggacgcaaagcgcgcgcgctttcgcgctataagcgctggagaccgtttcgatttgttggc
cctgccaaggctataa
```

268

```
atgcgcaccacgcaggattgtcgcagcactgcagcactgcacaaacggtatatttttcgtctgccgaatcgctcaccgcgcagccattgagcgcgcaggcgcagt
cagtgctcacttttagtatttgttcaggacagcatcatccgcatctgagtgcggcagcttgaaagcggcgcgccctcgaacgaatggc
aacactatgcgaatggctcgcaagcggcgctgatggcgctcgacctcgatgcggccgctttcgcggctcgccatcatggt
gcgcatcgctgagcggcaggcgttacagtggtgttggcggaagagatatcctgcaacagcttagcgtggcgcagcgtactcggctcgcccgcg
cgactggcttatgagccgcaggctcgccgcgagtggtggggaacgccgcaatccacaaggcgtggccagcgccgatcggtactcggcaaact
gggtggcggcgaactcaattcctcatccgatatccgattttgatttcgcctggcgacgcacacgtctgccggctcaccgcgcagccgctgagctgataaac
```

TABLE H-continued

| SEQ ID NO: | Sequence |
|---|---|
| | cgcaattttcactcgccttggtcaacggctgattaaagtcctcgaccagcagcaacgcaggatggcttgttccaccgtcgatatcgcttcgcccgttt<br>ggcgacagcggccgctggtcgagcttgcgcgtcggcggaagattactaccaggaccagggcgcgattgggaacgctacgcagtggtgaaagc<br>gcgcattatgggcgatcacgacgacgaccatgccccgagtgtgccgcgtgctgccgaatgctgccgcgttgttccgccgttatatcgacttcagcgtgattca<br>gtccctgctacactgaaaggcatgattgcccgcgaagtgccgcgcggctgaagacaacattaagctagctgagcggcgggcggatccgcgaat<br>agaatttatcgtccaggtttcagtctgattcgtggtcgtcgagcctcgagcgctgcaatcgtcactgttgccgcacgcttgctgccatagatcaactg<br>catctgctgccgatggccgaccaacccggctgcgcgaggcgtattgtggctgcgaggcgcaaagtagctggaagcgctcgcaaagcgtggaag<br>cgcatatcgcgggtcgtgcagtcaagctatattaacgatctgatgcccgatgaaacggatcgccggaagatcgtcctgagagtcggcggcaattgt<br>ggcaggatcgcgttgcagaggaggatccacgccgcgtgctcggcgccgcgcgccgtggcttcctctcagaggacgatcgccgcgcgcttgccgattttcg<br>caaagagtcggatcaaacgcaccattgccccgacgcgacggcctccacgcagctccggtactcaataccccaccttacctggctcaagtgaatcccggcgactgaaa<br>cacctcattccctgtcgcgcgcgcccgatgttgccagtcgccgatgatctcgacccgcgatactgctcatc<br>aacgacggcgatgaatcgcctatccgcgatgagctgcgcgctgagctcgcccaataaccgtgttgcgccggcagatgaagagcaacagcttgaggcgctgcgg<br>cagtttaagcaggcgcagtgtggcgctgctgcgtggcgtgcggcggcgaatgggctttatgccagctcgtatggcgttgccagtctgattgtgtggcgcggtt<br>ttcggtggcgtattgcgaaggtcggacctggttacagctcggattctcgctgcggacactggttccgcgacgcgcccgatgggatgtgatga<br>ccgatggcgagcgaaatcgatcggtcgccagttctattgctctcgcgcagcgtgatgcaccttagcacgcgcacctcgtccggcatcctt<br>atgaagttgatgcgcgtctcgtcctctggctcgcggggatgtgctcactacggatcgttcgccgattacccagcaaaacgaagcgctggacg<br>tgggaacatcaggcgctggccggctgaaggcgtggttgacgcgcgatccgcggcgaattgacacccattccgccgaaaagcataaagaccgtttcgatcacgc<br>cttgcgcgccaaccggctgcaaacgcagcgtgagaataccggtgcgagaaatcggcattatcgccccaatatcggtgttgccaatcggagagctcgatgacagccggaggcatatctggtgcgcgtcttgcccatcgacactggcaacaagcataaagaccgcttcgatctga<br>aagccgatgaaggcgtgcggtatcaccgacatcgagttatcgcgccaaacgcgcatacggatgggacacgttggcggacaagtggc<br>gttgcaccaccggcgtgcaggagttgcggatcgcaaaacgcatcaccgagacatgtggggacactgtccggaaaactggcagtgtcggaagtc<br>tggtggaaccgtgcgcccggctaa |
| 269 | attgaagagttgatcatggctcagattgaacgctggcggcaggcctaacacatgcaagtcgaacggtagcacagagagcttgctctcggtgacga<br>gtggcggacgggtgagtaatgtctggggatctgcctgatggagggggataactactaccggaaacggtagctaatactgggaataaccggtagt<br>gaggggcacttcggggtcctcctcgctgccatcagatgtgcccagatggcattagctagttagtggtgggtaacggctcaccaaggcgacgatccctagctggt<br>ctgagaggatgaccagccacacgagactgagacacggtcccagactcctacggaggcagcagtggggaatattgcacaatgggcgcaaggcctga<br>tgcagccatgccgcgtgtgtgaagaaggccttcgggttgtaaagcacttcagcgggaggaaggaagtgtaataacctgcggatcggtcattgcgatcattagctggatgttcagcggcggtgtaatcggcgcgccagaagaagcacct<br>ccgcagaagaagcaccggctaactccgtgccagcagccgcggtaatacggagggtgcaagcgttaatcggaattactgggcgtaaagcgcacgca<br>ggcggtctgtcaagtcggatgtgaaatccccgggctcaacctgggaactgcatccgtgactgggcaggctagagtctcgtagaggggagtagaattcc<br>agtgtagcggtgaaatgcgtagagatctggaggaataccagtggcgaaggcggctctctggacagtcagctgacgctgaggtgcgaaagcgtggg<br>mnmnnaacaggattagataccctggtagtccatacccgtaaacgatgtctactagccgttggggccttgagccttagtggcgcagctaaccgata<br>agtagaccgcctggggagtacggccgcaagactaaaactcaaatgaattgacgggggcccgcacaagcggtggagcatgtggtttaattcgatgca<br>ctcgtcgtcgatgtgggttacttttctacgattaactatccagaagaaagtccttcgggcctcttacacaggtgctgcatggctgtcgtcagctcgtgttgtgaaatgttgggttaagtcccgtacgagcgcaacccttatccttagttgccagcattcaagttgggcactctaaggtgactgccggtgacaaa<br>ccggaggaaggtggggatgacgtcaagtcatcatggcccttacggggccagggctacacacgtgctacaatggcggtacaaagggttgccaaccccc<br>gcaaggtgagctaatctcataaagccgtctcagttcggattgcactctgcaactcgtgtgcatgaagttgcaatcgctagtaatcgcggatcagcatcagcggtgaatgcctttcccaggtctgtacacaccgcccgtcacaccatgggagtggttactgcactagcaccaaaagcaaggagttacccctt<br>attaccacgggggtttcgtgactggggtggtgaagtcgtaacaaggtagccgtatcggaaggtgcggctggatcacctcctt |
| 270 | atgaccatcgtcaatcggtcaattacggcacaaggtgggatcggcaaatcgacatccacaccgttcggtcgccactggtcgcgcgctggtgaggatgggtaaa<br>aagtcatgatctgcgtctgtgaccggaaagcatcgaccacccgttgatcctcgcatgcaacggtgaaagcgcaggaacaccattatggagatggctgctgaagt<br>cgctcctggaagactcggagtagaagacgttgcaaatcggttacggcggtcgctacgtgccggatctcgatttttgttttctacgacgtgctgggc<br>gacgtggtatggggtcgcggggtgttcgccatgcgattcctcgtgaaaacaaaggcaggagatccacatcgtttgctctggcgaaatgatggcgatgtacgccgc<br>caacaacatctccaaaggcatcgtgaaataccgcaaatccggtaagaaatccggtgaaatccgacatcaatcggggctgatcacatgctcgaactgtcagacatgtgcagcctgtaatcgctgataacaatcgccgagatgtgttcccgatgaacattgttctcagcgaatgatcgccatggtatgac<br>ggttatcgaataatgaccggaacctgaccaggcgaacgaatatccgcagcttgcagaacgaataacgcaccaccaaaatgtggtgcccacccc |

TABLE H-continued

| SEQ ID NO: | Sequence |
|---|---|
| | tgcaccatggatgaactggaagaactgctgatggagttcggcattatggatgtggaagacaccagcattcattggtaaaacgcgccgaagaaaacg |
| | ccgtctga |
| 271 | atggccgaaattctgcgcagtaaaaaccgctggcggtcagcccgataaaaagcggccagccgcctgggggcgatcctcgcaagcctggtgtcga |
| | acagtgcataccgctggtacacggcgcacaggatgtagccgtccgcaaggtgtcttattcaacattaacgcgtttcacgatccgatccgctgcaatcgac |
| | ggcgatggatccgactccacattatgggcgccgatgaaaacattttaccggcgtctcgctgcggatcgttccccggcataaaggcgttggcgtgc |
| | gtccagcaccgggcttcaggagccaggcagcggacattcgtggtcgccagttcgtgatgattctcccggcataaaggcgttggcgctgc |
| | tcaccgtcaacaccgcctttctacggctctgtgaaaacgctcacgcgcggtgaaagcgatgatgcaacaggggtactcgcacagcccg |
| | ccgcagcctgcgcaaccgcgcgtcaacctgctggtcagccaccattactgacaccaccagcgatcatcgaactgttgcgcagttatgttgaagccttcggcc |
| | tgcaaccggtgattgtgccggatcctgcgctgctcgctggctcgctggacgggcatctggcagacgtgattttccgcctgttaccccaaggggaacatcgctggcgc |
| | atgattgaacagatgggcaaaacctggccacctttgatggtcgccaccttgatgtggcgcctcgtggaccgcgcgcgtactggcgcagccggcagccgtggcgag |
| | gtgatccgcctgcgccgcactctgatgagacgctgcgacctgcgaacactgcgaaaacctcccgcgcgtgattgag |
| | cgcagccggcgccaagttcaggatgcgatgatcgattcccatgtgaccctggcgctatcgcccagccgggttgcaaaatgcgccggttgaaaacc |
| | gatggtgcgatttcggccgcatcagcagcaggcatgatccgtgccgccgacctgcgctgctccgacgctctgccgcgacctcgccacgca |
| | gttgattgtcacttatccgccgcgggttccggtgctgatgaccaagggtgaattcgcagttcagcggcggcattcgtgacaccgct |
| | gtttgagctggcgaatgtgatgcgcgagccgatccatccgccgcgtctcccccatccacctgcaacctcacgcgcgacgcacgttacgcctgg |
| | agatctgtatgccgcatgttaa |
| 272 | atgaaaaacacaacacattaaaaacagcgctttgctctcgctcgcgttactgcctgccgttgcggctccggttgcccgtgctggcggcggataaagcgacaacg |
| | gcttatgatgattgcaccgcctggtctgtttatgaccatccgggcatgcgcgtgtccacggcggttgatccgcgggtaaaaacgtgtcgtgtcgatgc |
| | tgacgcaggtcgccgtcaccttcgcactggttgcgcattctgggtggtgatttcagtgatacccacgcggccgcattggcgaggcaacagttctccgggagtttt |
| | aactggccgatgtgaaaaacatcgaactggggcggaaccgtattcatcagttatcagcactgctcctctcgctgatccaccg |
| | ttggcctgattgtcggttgcactggctgagcgtattcgtctcggatgctgattttgtggtgatggtgacgctttcttcagtcggcgcggattgcacacat |
| | ggtggcggcggctgcggtctggcaaccacggtgcgtcttgcaggcgcggattcggcagctgctgcggcgg |
| | gcttacctgatggcaaacgcgtgggcttggcaaagaagcattcaaaccgcataaacctgcgatggtcttcactgcaccgtatcctgtatgttggct |
| | ggtttggttcaacgccggctccgcaagtcgcggcgaagtgctctctgctcgtctggtccgtgttctgcggctgtattcaccccgcctggttat |
| | gttggtgtcgcggtcgggctgatttgtggctcgatggtcggcattggggtctgctgtctgaacgtgttactgcgtgaaacggatgtgtcgatgaccg |
| | tgtgacgcattcggttgcgacgcggtgctggtgcaggttgcactggtattatccgggtgaaagtgagggcggcaacgcctataacgcctga |
| | gtgtgaccatggcctgcgcaggtgctgggtgctgacggaagaacaagaacgtgaggggctgatgtaaacagcacggcgaaaacgcctataacgcctga |
| | catgacggtaggccctgcgggtaccgaagaacaagaacgtgaggggctgatgtaaacagcacggcgaaaacgcctataacgcctga |
| 273 | cgtcctgtaataacaccgacaattcggactgattaaaaaagcgccttgtggcgcttttttatatccccgcctcattaaaatatcccatcga |
| | tttcaactcatttaaactgccattatccaagatgaatccgatggaagtcgctgttaacacgcgtttttaaccttttatggaaatcggtgctcctttgagcga |
| | acgatcaaatttaagtggattcccatcaaaaaaataattctcaacctaaaaagttgtaatacttgtaacgctacatggagattaactcaatctagagggt |
| | attaataatgaatcgtactaaactggtactgggcgc |
| 274 | ggacatcatcggcgacaaacaatattaataccggcaacacaccggcaattacgagactgcgcaggcatccttctccgcaatttctgtcaaataaag |
| | taaaagaggcagctcatcatcactgaattcacccccggctggtgagcgttgttgaaaaaaagctacacctacaagatcatctgatggttaatt |
| | aacctattcaattcaagaattattcggatgaattgccattaaatgcgcagcaatggtgcgttgcggggaaaacgtcttttttgaaagggttgtcagt |
| | agcggaaac |
| 275 | atgaccctgaatatgtctgcgataacgcgcgccggaggccatcgccggcgcggaggccaggatcattcagccgttttgcccgcaacccgcgtttgccctggcgctatttggctggaaca |
| | ggcctcgggtgcccatcctcctacccgatgccggcgcaggattcattacgccacccggatctctaggattcgctggcgcaattgtt |
| | aaacagaaccgcggcgcctgctgctggcagcggcgcagacgccgcgagatctattcaggagatggttgcatcacccgcgtcagcctgttagccgcaggggaactgagcattatct |
| | gtcagctgattaatcagcgtcggacgggccggctgtacctggtggagattgacatcaccccggttgagatggcggtgctgaatatccccgc |
| | ggcgatcaggcgggatatcagcgtcagctcacctacaccctcgaacagcggtcgcgcaacccatatgaccctatgacgtgctgggcggcgggagctgctcac |
| | cgccgtggtagtggtgacgagcgaggatgaggatgctgggtgatgaacctcctgcctgactgcgcgcgcgtgactgcgcggcggtgtcctac |
| | cgagctgcaggtcccctggccagggatgacgcccggccgagcgagcgcgcgcgcggcgggcctggctgctggtcggtaacc |

TABLE H-continued

| SEQ ID NO: | Sequence |
|---|---|
| 276 | tgctggccgttgcccggcgtcagtgaagaggcagcgcgctactttatcgacagcgcgctggcggcgacccctgtggtgatcgccgactgtacccag
cagcgtcagcacgcaggacaggcaaggcgcttgaccggctgaacgcagcagcagccgcgccggcaagctgtggcggcgatcctgcggcgagtcgtggac
gccgcgctgatccagctcagctgaactgcccgattaatatgctggccgcagccgtcggctggcggcaagaccgggaatgtgcgctgagccg
cctggcgtgaaggggaagaggcctggcgggctccagctccagcgtccaccgtccgtcgaactcgaaaacctcggaactcgagctcgcagccctct
tcgacgattcgttgcgccctaccgtacacgttcgatcgccacgtccgacggctgcagtcgacatggcgtcaccgcatcgattcggttgccagcgcacc
ccactgctggccgtgctgctaagcctgtcgatcgcacgccctgatcgccctcgctccgtggcctgctgccgatcgagcttacgccgagg
agaacgacggcggctggctgctggctgctgactgacaacgtggccaccatcgagccgtggtgccacctgcctgttgagctgcttcctccgagcca
aagcgactggagctgcggacccgtgtggcgccaccatgcgcagggccattgagctgcttgctagcgtgccattaacaccctgacggaggtgaagcatga
ctgcggttcccgctgttaacacccttgacggaggtgaagcatga |
| 276 | atgatccctgaatccgacccggacaccaccgtcagacgcttcgacctctctcagcagttcaccgccatgcagcggataagcctgctgagccggg
cccaccgaggccggacaaaacgctcagcgtattacacaccagcggctcttatcgcagcgacacggatgatctcgctcgtacacgcagcagcggagc
agagaatcctcgtatcaagcgtcagcaaaccggctgcagaaaccggccctccccggccagcagatcgctatcgcccgagctctacgattacgatctg
gggaccgtgctggccagggggcagtgctgtgtcgcacgcccggctcgccagacgcagcagcgtttctcgacgctcagcggcgagaggcggctgcgg
ccgttacgcgctaccgtgatggggccaacgcgccggcaatagggtgcggtggcctgacaatggtcggcaagagccgcatgcccaggatcgtgg
cctgacaacctttctgcaaacctcgccaaacctcgccgtcaccggtgatgatcctcgagcccggtcaccgcctccgtgagccgcc
ccgaaggtggaacgcgccggctgctgcgtcgtccgcggctgggccttgacaatggtcggcaagagccgcatgcccaggatcgtgg
agtgatccgtcaggttcgcgctggcgcgcccttcgtcaaattcactggcgtggtacgcggcagcgggaaagcgcatccatcac
catccgcaccggctgcgcgccgccttcgtcaaattcactggcgtggtacgcgggatcgtcctgatgagattggtgaaagcagcggcctcgtt
ccaggccaagctgctcggctatcctccaggagagggatggaccggcgcgatggacccgtgatgagacctcgggtgaatgtccgatcatcgcgcgc
accaaccgtcacctggaggaggagatcgccgagtggcgcacttcctcgtgctcgcacaaatcggccagcacggggtcgacgctgcagcactgtccccgctgc
gcgagcctcaggaggaacatcgccgagtcgagtcgctggcgggtaacgtcctcgaacgatcggcgatgtcggagagtggcctga
cgatccgctgatgatgaagtacgatcggcgggtaacgtcgcccgcaaaagcccgctgggctgcaggacgcggaagacgctggcgacaacagcc
tggacgaacgtcagcgactgatccgccgatcggcgcgctgggtgcgaaaaagccgctgggtgcaggacgcggaagacgctggcgacaacagcc
tcgcttatccggatccagatcatggatcacccctgcccgtctgtag |
| 277 | attgaagagtttgatcatggctcagattgaacgctggcgcaggcctaacacatgcaagtcgagcggcagcgggaagctagcttgctactttgccggc
gagcgcggacgggtgagtaatgtctgggaaactgcctgatggagggggataactactggaaacggtagctaataccgcatgacgctgagagagc
aaagtggggggatcttcggacctcacgccaccatcgaactgcgagaactgcgagatggatggatattgcaacatggcgcaag
ctgatcgcgagaggatgaaggagcctaggcctggcgtctgagcagtctcacaatgctttaacaagccatgcagctgtaacatgcggaatattgcacaatggcgcaag
ttactcgagaagaagcaccggctaaactccgtgccagcagccgcggtaatacggagggtcaataggcgttatcggaattactgggcgtaaagcgcac
gcaggcggtttgtaagtcagatggtgaaatcccccgggctcaacctgggaactgcatctgaaactggcaagctagagtgtcagaggggggtagaattc
caggtgtagcggtgaaatgcgtagagatctggaggaataccggtggcgaaggcggccccctggacgaagactgacgctcaggtgcgaaagcgtg
gggagcaaacaggattagataccctggtagtccacgccgtaaacgatgtcgacttggaggttgtgcccttgaggcgtggcttccggagctaacgcgtt
aagtcgaccgcctggggagtacggccgcaaggttaaaactcaaatgaattgacgggggcccgcacaagcggtggagcatgtggtttaattcgatgc
aacgcgaagaaccttacctactcctttgacatccagagaattttccagagatggattggtgccttcgggaactctgagacaggtgctgcatggctgt
cgtcagctcgtgttgtgaaatgttgggttaagtcccgcaacgagcgcaacccttatcctttgttgccagcggtccggccgggaactcaaaggagactgccg
gtgataaactcgaagaaggtggggatgacgtcaagtcatcatggcccttacgaccagggctacacacgtgctacaatggcgcatacaaagagaagc
gaactcgcgagagcaagcggacctcataaagtgtcgtcggatcgagtcggattggcctgctacaccgcccgtcacaccatgggagtgggttgcaaaagaagt
tcagaatgcacggtgaatacgttcccgggccttgtacacaccgcccgtcacaccatgggagttggttgcaaaagaagtagttaagcttcggg
aggcgcttaccacttgtgattcatgactggggtgaagtcgtaacaaggtaaccgtaggggaacctgcggttggatcaccccctt |
| 278 | attgaagagtttgatcatggctcagattgaacgctggcggcaggcctaacacatgcaagtcgagcggcatcggcgaagctgctactttgccggcg
agcggcggacggggtgagtaatgtctgggaaactgcctgatggagggggataactactggaaacggtagctaataccgcatgacgacctgagagagca
agtggggggatcttcggacctcacgccatggatgagcccgatgtcgattatcgtcgtacaccgataaaagtgcttatagttcccgggccttgtacacaccgtctagctg
gtctgagaggatgaccagccacactggaactgagacacggtccagactcctacgggaggcagcagtggggaatattgcacaatgggcgcaagcct
gatgcagccatgccgcgtgtatgaagaaggccttcgggttgtaaagtactttcagcggggaggaaggcatcaaggtgactaatacctgtaatgactgacgtt TABLE H-continued

| SEQ ID NO: | Sequence |
|---|---|
| 279 | actcgcgaagaagcaccggctaactccgtgccagcagccgcggtaatacggaggtgcaagcgttaatcggaattactgggcgtaaagcgcacg caggcggtttgttaagtcagatgtgaaatccccgagctcaacttgggaactgcatctgatactgggcaagctagagtattgcagaggggagatcca ggtgtagcggtgaaatgcgtagagatctggaggaatacggtggcgaaggcggccccctggacaaagactgacgctcagtgcgaaagcgtggg gagcaaacaggattagataccctggtagtccacgccgtaaacgatgtcaactagccgttgggttcttcgagactgcaacgccgtta gtcgaccgcctggggagtacggccgcaaggttaaaactcaaatgaattgacgggggcccgcacaagcggtggagcatgtggtttaattcgatgc cgcgaagaaccttacctactcttgacatccagagaattcctgagagatcaggtgtagaccctgatactgggggaatacggtggtgtgca gtctcgtgtgtctgaaagtcttgggttaagtcccgcaacgagcgcaaccct agggcttacctactcttgacatggaagtacggccagaggggaactgcatctgatactgggggaataacggtggtgttgcca |
| 280 | attgaagagtttgatcatggctcagattgaacgctggcggcaggcctaacacatgcaagtcgagcggcagcacgggagtagcttgctactttgccggc gagcgggcgacgggtgagtaatgtctgggaaactgcctgatggagggggataaactacgggaaactgttgctaatacccatcatg aaagtgggggatcttcggacctcacgctaacagatgcccagatgtgcccagcggcctccagagctcctagggttgtaaag gtctagcagccatgccgcgtgtgtgaagaaggctaggttggttaaagcacctgctgttgtgaagaaggcagcctaggggaggc ggtctagcagcagcaccggctaactccgtgtgaagaaggatcaactggat |
| 281 | attgaagagtttgatcatggctcagattgaacgctggcggcaggcctaacacatgcaagtcgagcggcagcacgggagtagcttgctactttgccggc gagcgggcgacgggtgagtaatgtctgggaaactgcctgatggagggggataaactacgggaaactgttgctaatacccatcatg aaagtgggggatcttcggacctcacgctaacagatgcccagatgtgcccagcggcctccagagctcctagggttgtaaag ggtctagcagccatgccgcgtgtgtgaagaaggctaggttggttaaagcacctgctgttgtgaagaaggcagcctaggggaggc ggtctgagaggatgaccagccacactggaactgagacacggtccagactcctacgggaggcagcagtgggaatattgcacaatgggcgcaagc |

TABLE H-continued

| SEQ ID NO: | Sequence |
|---|---|
|  | ctgatgcagccatgccgtgtgtgaagaaggcctttagggttgtaaagcactttcagcgaggaggaagcatcacacttaatacgtgtgttgattgacg tactccgaagaagacaccggctaatccgtccgcagccgagctaacttgggaactgcattgaaactgcaagcgtaatcggaatactggcgtaaagcgcac gcaggcggttgtaagtcagatgtgaaatcccgagctcaacttgggaactgcatctgatactgcaagcgctagaggtcttgtagagggggtagaattc cagtgtagcggtgaaatgcgtagagatctggaggaatacctggaggaataccggtggcgaaggcgccccctgactggcaaagacgctgaaggctggacgt gggagcaacacaggattagataccctggtagtccacgctgtaaacgatgattgacggggcccacaagcggtggacatggtcgttaattcgatgc aagtcgaccgcctggggagtacggtcgcaagattaaaactcaaatgaattgacggggggcccgcacaagcggtggagcatgtggtttaattcgatgc cactcgtgtctgtgaaatcgttagtcccagagcgcactgctatcccttgtcgcagccggtgatgtggtgggaactctggttgtgcagtggtgtcgt cactcgtgtctgtgaaatcgttggtcgagctcccagagcgcactgctatcccttgtcgcagcgctgatgtggggaactctggttgtgcatggtcg gtgataaaccggaggaaggtggggatgacgtcaagtcatcatggcccttacggaggtcgcaagtctgcaactacaccaaggagaagc gaactccgagacgcagcaaccggacctcataaagtatcgtcgtagtccggctggtcgtcaactcgacctcatgaagtcggaatccgcagtaatcgtaga tcagaatgctaccacttgtgatcatgacttgggcttaggttcatagcggtgaatcgtcggtgaatcttcggg aggccgctcaccacttcgtgatcatgacttgggcttaggttcatagcggtgaatcttgggg aggccgctcaccacttcgtgatcatgactgggcttaggtcatagcggtgaatcgctgatcacctcctt |
| 282 | gtagctaatacggcatcgaacctcgaaaagagcaaagtggggatcttccgacctcacgcactccggatgtgccagatgggattagctagtagtgaggt aatggctcaccaaggccgacgatcccctagctggtctgagaggatgaccagccaccagggactccagcaccgtccagactccacgggaggcagca gtgggaatattgcacaatggcgaagtctgatgacgagaggcctaggtctgtgaagaaggccttaggttgtaaagcacttcagcggaggag ggctacatggcaggaattcaatacggtgntgatcgcagaagcaccggctactccgtgcagaagcaccggctactccgtgcacggctaatacggagggtgcaagc gttaatcgaattactgggcgtaaagcgcacgcaggcggtttgttagtcagttggtctgtgaaatctccggagctcaactcggaactgcatttgaaactgcattgaaactggca agctagagctctgagggggggctagaattccaggtgtagcggtgaaatgcgtagagatatggaggaataccggtggcgaaggcggccccctggac aaagactgacgctcaggtgcgaaagcgtggggagcaaacaggattagataccctggtagtccacgccgtaaacgatgtcgacttgggaggttgtgccc ttgaggcgtggcttccggagctaacgcgttaagtcgaccgcctggggagtacggccgcaaggttaaaactcaaatgaattgacgggggcccgcaca agcggtggagcatgtggtttaattcgatgcaacgcgaagaacttacctactcttgacatccagagaacttagcagagatgcgaaggtgcttcgggaa cctgagacaggtgctgcatggctgtcgtcagctcgtgttgtgaaatgttgggttaagtcccgcaacgagcgcaaccctatccttgttgccagcacgt natggtgggaactcaaaggagactgccggtgataaac |
| 283 | attgaagagttgatcatggctcagattgaacgctggcggcaggcctaacacatgcaagtcgagcggcagcgggaagtagcttgctacttgccggc gagcggcggacggtgagtaatgtctgggaaactgcctgatggaggggataaactactgggcctacgtcctacctggcggtacgtcctacctggc agccacacggaactctacgggaggcagcagtggggaatattggacaatgggcgcaaagcctgatccagccatgccgcgtgtatgaagaaggccttcgggttgtaaagcactttcagcggggaggaagggcagtaaagttaataccttgctgttttgacgttaccaacagaataagcacc agcccggtaccaccgcgggttggatggggggaagcctaactactgctgttttgacgttaccaacagaataagcacc ggctaactccgtgccagcagccgcggtaatacggagggtgcaagcgttaatcggaattactgggcgtaaagcgcacgcaggcggtttgttaagtca gatgtgaaatccccgggctcaacctgggaactgcatctgatactggcaagcttgagtctcgtagagggggatgtagaattccaggtgtagcggtgaaatgc gtagagatctggaggaataccggtggcgaaggcggccctctggacgaagactgacgctcaggtgcgaaagcgtggggagcaaacaggattaata cctggtagtcacgccgtaaacgatgtcgacttggaggttgtgcccttgaggcgtggcttccggagctaacgcgttaagtcgaccgcctgggggtacg gccgcaaggttaaaactcaaatgaattgacggggggcccgcacaagcggtggagcatgtggtttaattcgatgcaacgcgaagaaccttacctggt cttgacatccagagaatcctgtagagatacggagtgccttcgggaatctgcgacacaggtgctgcatggctgtcgtcagctcgtgttgtgaaatgttg ggttaagtccgcaacgagcgcaacccttatccttgtttgccagcgcatctaaactgggaactctaaggagactgccggtgacaaaccggaggaaggtg gggatgacgtcaagtcatcatggcccttacgaccagggctacacacgtgctacaatggcgcatacaaagagaagcgacctcgcgagagcaagcgga cctcataaagtgcgtcgtagtccggattggagtctgcaactcgactccatgaagtcggaatcgctagtaatcgtggatcagaatgccacggtgaatacgttcc cggccttgtacacaccgcccgtcacaccatgggagtgggttgcaaaagaagtaggtagcttaaccttcggggggggcgcttaccacttttgtgattcatg actggggtgaagtcgtaacaaggtagccgtatcggaaggtgcggctggatcacctcctt |
| 284 | atgaccatgcgtcaatcggctatctcacggtaaaggcgtatcggtaaatccaccaccaccagaattcgtcgcgcgccctcgccgagatgggtaaga aagtgatgatcgtcggtcggtgcgatccgaagcgagaatctcaactgccgatccctccacgctaagcccagacaccatcggagatggcgcggaagt gggctcgtcgaggattctgaaagtcgagacgttctgcaaataggcttatgcgaagacgttcggttgcgccgaatccgaagcccaggcgtcg gctgcgccgacgcggggatcaccgacatcgccatcaactcctcgcgcgaaaacaaccagagatccaggagatccaacatcgtctgctctgctatctgtcggc gacgtgtctcgggcggcttcgtcgtatcgccgacactcatcgtctgctcggcgagatgatggcgatgtatgccg caacatatctcccaaagggatcgtgaagtcggcatcgtcaagtcgaggcgacgatatctgctgctgctctgctctgtaactctgcaatggcaatctgtgatgatgactg acgaactgatcatcgcgcctcgcggcctggcacgcagcacgatgatctgctctgcctcgtctcccggacaacattgcctgcgtcggcggatcgccgga tgacggtcgagtgatcgacgccgctgcagcgggactggacaattgcctcactgggacaacattgcctcactgggacaacattgcctgcgtcactggcaggtgcaataaccacaaaaggtgcga |

TABLE H-continued

| SEQ ID NO: | Sequence |
|---|---|
| 285 | cgccgtgcaccatggacgagctggaatcgctgctgatggagtcggcatcatggaagaagagacaccagcatcattggtaaaacgccgctgaag
aaaacgcggcctga |
| 286 | atggttaggaaaagtagaagctaaaaatacaaatatgaactactgacactgaccattattaataagtcaaataaaaagctaaaacacaaaccacttg
cttttaatataaaggagggttgggaagactacattagtagcaaattaggagcagagctatcaataaacttagtgcaaaagttcttattgtggatgcc
gaccccaatgtaatcccaatcagagtattaatgatgaagcaaataccatagatagagaatttcggtttgacataattgtcggtgacctagacttgcttacaggaa
actatcctttggtaaagtagaaagtgacctcccctataaggcatgtaagcatgagagaatttcggtttgacataattgtcggtgacctagacttgcttacaggaa
gacctttagctggacgtgagagcatagccaaggcggtggatgcgaggaaatcaggactattaggacaacttgatttgcagattaattaagaaagccgtgag
ctaaattatgattttgttttcttgacatggaccatcattggctccacggttcctggttacgtcaccaccacaacaatatggcgaatcaacagtcagcagtcaatcga
tgtatttcactatggctattaaaaatatattgctccacggttcctggttacgtcaccaccacaacaatatgcagcaggatccggctcgtcgtcccatgtcaatcga
atcacaattatcaccctcaaggaaaactaaagttctctggttacgtcacccaccacaacaatatgagctcacggcaacaacttcctcaaacttatgcatca
aggaagaaaatcgaaacgtcgaaagcgtgaagagtgttcctctaaaattacgagcatcttctaaaacttatgcatca
aagatatgaaccacacttggagataacgatatacggtgttagtgtctccgaaatcacaatcacaacacgttccatgatatcagtgtctggtacagg
aattaccaccgacttagaaaaagcggcgtgaacttatcgagatattgcaagaagatactcagactgcattcagactgcttaatggcagaaatag |
| 287 | atgaagggaaggaaattctggcgctgctgacgaaccgctcggagcaaccagaagcaaaaatccggctgcgcagccgcctaagcccgcg
ctaccgccggcggttgccttcgacgcgccgcgagataacgctcctgccgacgtcgcgcacctggtgcacgcccatcggctgcgcg
ggcagctcgtggatgaaccgccctgttccagccgtcgtccagcggcggtcttatcatccgggcggtcttatctcacaacctcgtaccggcga
tggaggcggatgacatcgaggcgtgctggcgacgtcagggcagccgcgccgggtccggtcatcgtattggacgcgacccgtttcaccggcagta
aaaatcttggcaaccgaatggcgggcgacgtgatgtcaggcaggtgattggcagcgccgaacgcctgttcagcgtctcggcagttccagcgcaggcgcctttgcc
cggcccagccagcgccacgatatcggcctgattggcgaattcaaatcgcccggcgagtctggaggccagagctcacggcagtgattctgccgagctgccgagtggcgcggcgctgatc
gtcctcggcagcctctccggcgacgacggccgcttgcccgagatccagaccagaccgtcgacaacctcacgagatcgcgaaccctgtgtgtccgagagcttcagccgagct
aacgtcgcccggggctggagctggagctccgggcccgcgggcgtccaccgggtctcgagctacgagactcgacatcggacgcaggcggcgttgcgccgt
ggcgtgagcagtccgcgggcgcaaagtgctgctctataccgggcggtgaaatcctggtggtatcgtgcggacgcaatatccggcgatgctctggaggggca
tgtggccaccgaccctgcgacggtgtggtaccggctatcaggccgccgctatcgatgatcgcccaatatgcgaagcgctgatggccgaaagccggctgc
cgttctcgatatcaatcaggacgcgagccgcgcacgccctaccggctatcaggacgccgctatcgatccgccagagctcgtctgacccctcgccagcccc
gtctggccgcaaacgcatcaccgccgcccgtggctag |
| 287 | atgaccaacgcaacagcgaacgctaacctgccctcatccaggaagtcctccaggaagtccaggagggtttcccgaagaccgcgcgagaaagcacat
gatgatcagcgatcccgcagatgagagcgtcgcaagtgcattatctcgaaccgtaaatcgcagccgggggtgatgaccgtcgcggctgcgcctta
tgcggcgtcaaaggcgttggcgcaacaccagccatctgctggtcgcgaccacatcgcccatctgcgcccgccgggtctgattccccgccgcgacg
gcgcaactactaccggcgtcgaaagatgagcgtcagcggcgtcgtccctgaccaaaggatcaccatccagtcggagcgcgatgtcggccgataccggcgcagcatcacctctgatcatcg
aagctgaccaaactgatcgaagagatgagcgcagcagcaggcgcaagcggcctgaccacatcggatgcctccaattcggacctcgctatatgtcggcggcgataaa
gacatcggctccgggatcaacgacagcgatggtggctgaacaatcgcgacaaccggttgccgacaccccgtacgatgttgccatcatt
gggcagccacatatcggcgacgactcggtgaacaatcgcgacaaccggttgccgacaccccgtacgatgttgccatcatt
ggcgattacaacatcggcgcgccgctgcgcccgccatcgttaacgtccgttcaactcgtccactcgtcgatgaactatcgccccgatcaatcggagagagaaacatc
cctggtgagctggagaacaccccattcggtcccgaccaaaatccccgaagatcgcgatcaatcggcctcggagggccaaagtgctgtgtactg
agatcccatggtgatgatgaatataacctcctcggcccgaccgcctaagctcggcggccctaatatccgcgcccatctgcgcgcccgggctcgaaactac
cggaagcggtgatcgcgccgcacgtcatcggggccggccaaatatggagacaccccgtacgatgttgagcccatctgcgatgtactg
gggggcgcgcgccctgccggcacgtcatcgcggatccgcgatcttcggcagagatctaacctctgcaaagcgctgaaactgac
gaccggcacccctgccggacctgaaagaggacgatctctgagacgatgccatatctcaagaaatgggggtcgcgttcggacgcgctattcggccgccctatcacctacggt
ctatgacggcttcgcatcttgcccggatatggatattgacctgaacaatcagggcctgaacgaactgacgaacctgaagtctgcgtga |
| 288 | atggcagatattatccgcagtgaaaaaccgctcggcggtgagccgtgagccccgattaaaaaccggcaaccgctcggggcgatcctcggcagcctcgggctggc
ccaggccatcccgctggtccacggccgaacgccaggggggccacgcccgcggagcgcttcgccaagttccttcaatcggctgccgcagtcgacgt
ggccatgatccgatcccgcgacgcacgtcatgggggccgacggcaatatcttcaccgggctcgacaccctgtgccagcccgccaggccatcg
tgctgctcagcgacgtcggggccgaagcgcaggcacgcggcacgatatcgcccccgtggtccagtccgccatcggctgccgcaacgacggctg |

TABLE H-continued

| SEQ ID NO: | Sequence |
|---|---|

289

290

```
gcgatcctcaccgtcaataccccggatttattggctctatggaaaacggctcagcgccggtgatcgagacgtgatcgagcagtgggtcgcgccgac
gccgcgtccgggcagcggccccggcggccgggtcaacctgctggtcagctgccacctcggtaaggggat atcgaatggctgggccgctgcgtggag
gctttggcctgagccggcggtgatcctgcgcgacctctcgcagtcgatggccactcggtgaaggggat atacgccctgaccagggcggcg
cctcgctggccagatgccccggacctcgccagagtctggcaagctggcccatggcgaatcgccagcgggacgcctctgaccaacgca
gccgcggcgacgtgatcgccgcgatccctgatgaccctcgacccattcgataccttatccatcagcgtcggaagatgtccggacgccgcgtacc
ggcctgattgagcgcgcagcggtggccagcgtgcaggatgcgatgcatatggccgcgcatcggtgttcaggcgcagcgcatggcggcggagg
ggacctgctgcggcgcgtggtgattcgcgagcagcaggggatgagcgccgcgtggtcgcccaacccagcgatctgcggcca
gctgggtgcgacgaagtcgtgccggggatcctgaggatctgagctgctgcgagccaccaacccgacctgctgctaactctcacgc
ccggatctggcggagcagtttgccctgcgccgtcgatccgcgtcggttttccccctcttcgaccggtcggtgagtacgtcgcgccaggggtacgc
cgtatcgcagatacgcgtgtttgaactggccaatctgctgcgcgaccgccatcaccacccgcgccctctacgctcgccgctcgccaggggccgac
cccagccggcttcaggagacggttatgcgccgccattaa
```

289
```
atgagcaaacgatcgataaaattcacagctgttatccgtgtttgaacaggatgaataccgacccgtgttcagaataaaagaccctgaagaggcg
cacgaccgcacgcgtgtgcaggaggtatgctgcagcacccacgcgcgagtgaagcgtgaacttccagcgcgaggcggtgacgtcgaccc
gacaaggcctgagcctggccggctgctcggtctgggtctcggccggctcccgatctccatcgcacccgctggacagggctcgtcgcct
attacgcacctcactttaaccgacgcatttaaagccgcgctgcgtccaggttcgttggctgcggcgtgttcggcgcaacaacaac
atgaatctggccgtgcagaatgcagcgcgctgataaacccagattatcgcgtctccacccctacgccaatccttacgccagcttatcggcagccatgtcaccgg
ggcgtttatcgccaacgcaaaaagagggattgagacgaccgcatgcgggcaaacagcaaagtcaatctggtgaccgatt
ctgggacaatatgtcgaaggtcggcgaagacctttaccgtgactacgcgcggcagcggtgaggtctcgtcagccatcagaggtgctcgaca
gagacctatctcggcaacttccgtgctgaagcgagtgatgacggtcgcagatggatgtccgtgacgtcttccgacccatcagaggtgctcgaca
cccccgacggccattaccggatgtacgccgggcgaccagcaggacgatcaaaaccgccgagggtgccgttccgctggcctgccgccacc
gccgtggcagctgctgatgacctgactcagctcagctgaccggcaaaccgatctgccgacctgctgaggcggcgtggttgacatgatgctggat
tcccaccctggctgcatgcagcaaaaattcggcttcgtgattcgtgatgggcgtgaagcagatctcgatggcctgcccgtcgtggcgttgcggagcc
gacggtgatcctcagtcataacgccaatcaaacctggcaaaaagcgatgaagaaatctcgatgcctgcgcctggcaaagcgaagtgac
atcaactggcacctgcgcgcactccggtcgctgctgatgacccgcagccggacttatgatcggtaactcctacgcaagttatccagcgcgataccc
tggcaaaggcgaaagccttcgaagtgcgcgctgaagtgccctcggcttccggctgctccggctgccgcatcatctgacccgaccaacctgggggctatgaa
ggcgcaatgaacatcgtcacgacgctgctgaacgcgctggtgaacgcgcctgctgaaaactggaccacgaccagaggcaaaaccgattacagcttcgac
ctcgttcgttaa
```

290
```
atgatgccgcttctctccgcaattacagcagcgactggcagacgtcgctgaccgtcgtccagcggatttcccattgccgaactgagcccacaggccag
gtcggtcatggcgtcagcgatttgtcgaacacagagtcgatcgcccagccgggctggtgaatgagcttggcgactcctccgcggaggcggaaagag
tggcgcattacgaggccggctgatcgcgcaggccctgccactgacggaaggggttgatgcagacgctgcgctcttccgccgccagatg
atggtccgcatccgcatcgcctggcgcaggctgtcctggtgagcgaagagagactctgagcgactgagggccagccgccagccgctgatctgcggatgg
gaaagctgggcgtggcgggagcgcagcgtgaacttctctccgaatctgatctcggcgcctggcctgagcaggccgcaccgcgggccgccgagct
ggataacgcccagttcttaccgctggatcaaggccgggcgatcaaggcgacgcaggacgacgtgactgtgtgactgcagatggctgacatgcgcc
tgcggcgcgttggcgacagtgggcgcggctggtgtaccagtttggcgggcggctaccagtttggcggctggaactgctatcgat
ggtgaaagcggcgatcagtgggcggtgatcaactgaaaggcatgaccgcccggccccgaggtgcgtcagtgcgtgcgggactgagcgatgcgcctgcggtccggcctggccgctcctcgcctgcgcctcgcctgcggtccggcctggccgctcctcgcctgcgcgcctgcgactctgagtgac
cgattgatgagctacatctgctccgaggcgacgcgccgctatccctcggccgctgaaaactgctgcaagcat
caacgatgagcagccagacctgccgcaggatgaacttaaccgcgaccgcccagctggctggcgtggggatgcatacgcaggctggagacgctgagc
gtactggcggcagctggcagatcgcctggaaagagatagcgctggaagaagatgagcacaaccgtcccggatgagcaactggccga
cgctgattgccgatatcgtaaagagctgccgctgatgcgcgcggtgaccgccgccaggagtcatcgtcgatcagctggatctgctgacga
aatctgctcgccgcgatgcgccgctgctgcgcggatcacgcgcgttgaccggatcgtcacccgtaccacctcttgagctgctgagc
gaattccccgcggcgaagcaatcgatcacgctctgcgcggcgtcctggcaggatgcggagctgctgcgccagcctcttgagctgctgagc
gctgctgatccccaacaccctcatcagccagcgaccgatgcctatcgcgacgggctgcgtgcggcagctgtccggtcgccggaagaggatga
agagcagcagcaggtggagcgtgcccagttaaagcaggcgagcgatgcgatgcgcgagctgcagcgcggatatcggcgccgaccctgcgacctgcggtgatgaagg
```

TABLE H-continued

| SEQ ID NO: | Sequence |
|---|---|

291

292

293

294

295

296

297

TABLE H-continued

| SEQ ID NO: | Sequence |
|---|---|
| 298 | gaagcctttgccgcagccactgacggagagaaggttatcgcgatcagctggcgcgcggcctgaaacgccagatcattacctccattgcttgccggtgcttac<br>cctgaaaagagtcgatgcgtgtatattgccgctgggtggacctgcaacagccatcgtcagcagcaacgcctgggaggattcggccgttctc<br>acgcggtgatggatgctttctggttaaacgggcaacctcgttaactgactgactagcctggcaaactgcccgggcttttttgcaaggaatctgat<br>ttcatggcgcctcaaacagttaatccgtctgtgccgatgtcgcgacacaactgcactgcatcctcttattgctgccgatgaactgctcgaccc<br>gcgcacgcttaccagccgatgagccgggcgcttaccgcacgaactcgtcagtatctgatgcggtgccaacagaagaagacagcagct<br>tgaagccgtgccgccagtcaaacaggcccagcattgcgtatcgcaccgcgggaattccgggagctgtgagtcagtgaccatttaa<br>cctacctgccgaggccattccgatgtcgtggtgcatgcgtgggaacaaaatgctcgtaaaaatacgggcagcccgcatctcagcaccgtga<br>gggcgcggtttgtcggtcggtacggaaaccgtggtcgttacgggagctggtctgatctcagatctgagtctgcggatctgcgccgcc<br>ggaggtgatgacggacggcgaaacggcagcatcgacggagtcagttatcttcggctggcgcagcgcattatcttcggcgccggaatcgt<br>caggcattcttacgaggttgatccgacttctcgacttctccggcgggcgggtggttacgggaatcgggagtgctgcaatatcaggccaatga<br>agcctggacgtgggagcatcaggcggcttggttcgcgcgcggtggttacgggggtgtaaggggtgataatcgggagtaaaaaagcccacga<br>gtttgatctgaagccgatccgggttggcatcacgggatatgaattcattgcacaatacctggttctgcgttctcggtcatgatgagccgaacgcgc<br>tggtctgataacgtgcggatttttgaactgatggcacgatatgacatcatccgggaaagcagctgcatttacccgatttatctgtttgagtcttggat<br>cgatgaaaatctcattggcgttggcttacatcttattcgctaacaggcggtgatatttaccgcgtgacgttactgaccgttacctactgtactactgtattctccgga<br>agctccgtgccggtggttgaagtgcgttgaagagcggcctcgcagtgagcgctcggcagctggttatacgggcctctcttcct<br>gttgcagccgtggcgcggagcgacgacgctgcgtgcctaaccagcaactgatccgcctgacttcggaaggcgttgatcctgagccgatgct<br>catcctaccatcaccaaactgcgaattttgtccgtaaccagcaactgatccgcctgacttcggaaggcgttgatcctgagccgatgct<br>gaccaaataga |
| 299 | atgagcatcaccgcgtatcagcatcacttcctgagggaaatatcgcacgccgcgttgcgtcgcaacatcttcactgtttatacgcgtggttgaacaatct<br>tcggtggcgattcgctgaccgatccgcgaggcgccatttgtatgccacgggtttgcacttgagcactttgggcg<br>agaaccaccgtctgctgagctgaactcatcctgcgtggacgggttggctcggtgaacattgtcggtgaacattgtcggtgagcggatgcgagct<br>ggttgtgtttgacattaccgataatatgccggtgaacggtgcgtttatcgcccgccgggaatgccgtttcccgtccgggaatggcatggacctgc<br>gccttatccagacgctgatccgccatcatcggggttcttagatctctcggtccggctcgacgttacgcctcgcggtacagca<br>ggttatcaccggaggcttaaaatga |
| 300 | tgttcgctctcgaggccggcaactgagcggcccgtgaaaccgactctggctggctgcatctgttgttgtgcgaacaaattcgctcgcgcaacccttgc<br>cgaaagccgaagccttaacggcgggtgcgtcagcaactgagttgcccggccaacgaacagaaacattatcagccgcagtggctgcaacaactgatcaacgcct<br>ggccctgttctccttctgttgatgcgacgggttaatgcccgtttgcacgaaacataaattgcctgttgcctataacagcgcgagggaaat<br>cctgcccgagcctgccaccccgccttcactgctgccttcggtaaaaacggccaccccgtcaaacaccccgttcagatcaacct<br>ttgggcagataagccggaaagcctgcaaattgcacaggttattccggtgagtatgagttcggatgtgatttggggtccggcaatgcgcaataaaaggggaga<br>aagacatgagcatcaccgcgtatcagcatcactctcgagggaatatcgccagccgcgttgtattcgctgcacatcctcactgtttataccgtggttgaa<br>caatctccggtggcgattcgcctgaccgttatatgcggtcgcggtttatgtatccggcatccgaccatcaccggattcctgagaacatggtgcgcag<br>ggcagtgagaaccaccgtctgagctgagctgaaccatctgcgtggaacatttgcccgggaaagctgacttgcggggaatgcgcatgggg<br>cagcctggtgtttgacattaccagacgctgaccccatcatcggggttatttacccggggaaatgcgcggtggcaatgggaatgcatcgg<br>agctggcctatccagacgctgatcccccatccggttcttagatcctcgtgagtgtcgcacccgcggccctgtgactgccgcttacgggcctttatc<br>acagcaggttatcaccggaggctaaaatgaccgacacctcttttggaatcccgcatgcgacgcatgcatccggtaccgcgaagtggtttctgaccgcctacc<br>ggtgtgctgttgataaagaacggcaatgcaacctcttttggaatcccgcatgcgacgccatccggtaccgcgaagtggtttctgaccgcctacc<br>tatttacgattcagctcgcgccggtgattggcgtgagcctgagcatcagcctgaaggagttctgaagctgcatggcttcacgcgctcggcttgcacg<br>aagaccggctgactgccagtacgcgcgcggtacagcaggttcaccgaggcttaaaatga<br>atgagcatcaccgcgtatcagcatcacttcctgagggaaatatcgccagccgcgttgcgtcgcaacatccttcactgtttataccgtggttgaacaatct<br>tcggtggcgattcgcctgaccgatccgcgaggcgccatttgtatgccaaccatcggtttgtatgccaccggtttgcacttgagcacttttgggcg<br>agaaccaccgtctgctggtaagccatcggcctaaagcctgaaggcagcaggttcaccgaggcttaaaatga |

TABLE H-continued

| SEQ ID NO: | Sequence |
|---|---|
| 301 | tgtttcgtcctcgaggccggcaactgagcggcgcccgttgaaaccgactcggctggcatcttgttgttgtcgcaacaaattcgctcgccgcaaccctgc<br>cgaaagccgaagccttaacgcgggtgcgtcagcaacggttcagccagagaaacattatcagccagtggctgcaacaactgatcaacgcct<br>gagccgtgtctccttcttgttgatgcgacaggtctgaactccgctttgcacgaacataaatgcccgttgcatcctggttgcacatcaacagcgcaggaaat<br>cctgcctccggcctgctgccacacgcgcctttgcctggttggtaaaacctggcccgcgcttaaacccccgttcagatcaacct<br>ttgggcagtaagcccgcgaaaggcccgcaaattgcacggttattccggtgagtatatgtgattggttccggcattggcaataaagggaga<br>aagacatgagcatcaagccggttatcagcatcattcctgagggaaatatcgccagccgccttgccgctgcaacatcctcactgttttataccggttgaa<br>caatcttcggtggcgatttcgtgacgacttcgctgacgcaggttatgccaatccggcattcctgagcccaacgggtttgcacttgagacactttt<br>gggcgagaaccaccgttgctggttaaagcctcggcaggttatcagcagttcatccagcgcagggggcctggccaacatcctagcgcccgttat<br>ccggcgcttgatatgtcgccagttacgggcgcttatcgcataccgcatgtgtcgtgataaagcaccagaagcaaacacgggcgcactggcggcgatc<br>ctcgaagtgcttcacgatcatgcatccgatcatatgcacagccatggcctgaccggggaaggcgtgatcggccggtgatgagccaggcggtgttac<br>cgcgcattcagacggcagcgttctcgaccgctgccgcaatattacgattacgactacggcttctgacgttcgatccctggcctgcggataatcagcc<br>atcgggcgtgctggtggcacagccgatggcgttgcacgaagaccggctgactcgccagaagaccgacgcggttttagaaatggtc |
| 302 | atgagcatcaacgcgttatcagcatgcatgtttcctgagggaaatatcgccagccgccttgctcgctgcaacatccttcactgttttataccggttgaacaatct<br>tcggtggcgattctgtgacgacgccgacgggcccgcattgcgctgtggccaatccgccgcagcgggtttgcacttgacacttttgggcg<br>agaaccaccgctgctgggagtctgaacctcatccgcgcagtcggcagttgagacgcatttgaccaagagtgatctacatcacggaatttgtggttgtgtgc<br>tgcttaaagggcaaatctaccctagaatcaactgttatatcaggggatcagagagattgcacaagcaagcattctctatccaacatgctcaaatgctcaagtttggccttcatatc<br>ataacgccatgaaaaatgctaatactacggcgtaaaaaacaaatcagtacgcagtagtatggtcattccttagttcatcggatatggtcatcctagtacagccaactggcatcctgagggaaa<br>gcaacgaaaatgctaatactaagcgccctgcgacagttcgtcgctcatggcgcaatccgcagcattcatcgcatccatccggacacaagctacaccaccagtttcctgaacattgctgcg<br>ggcccgatggccgtatcactgaccgacagcattcgtcgtcctatgtcatcgcgatgggcgtggccgtcctgaagctctcgtgaacattgtgcgag<br>gcaggatcgagctggttgtgtttgacattaccgatgctgcggcgtgaacaggtgcgtgctatgcccggcccgaaggcggcgtttccggtccggga<br>atggcatggagctggctgcgccttatccagacgctgatcgcccatcatcggcggttcttagatcttcggtccgctgcggcggccaccttgctgacgttacg<br>cctgccggtacagcagtatcaccggaggcttaaaaatga |
| 303 | tgtttcgtcctcgaggccggcaactgagcggcgcccgttgaaaccgactcggctggcatcttgttgttgtcgcaacaaattcgctcgccgcaaccctgc<br>cgaaagccgaagccttaacgcgggtgcgtcagcaacggttcagccagagaaacattatcagccagtggctgcaacaactgatcaacgcct<br>gagccgtgtctccttcttgttgatgcgacaggtctgaactccgctttgcacgaacataaatgcccgttgcatcctggttgcacatcaacagcgcaggaaat<br>cctgcctccggcctgctgccacacgcgcctttgcctggttggtaaaacctggcccgcgcttaaacccccgttcagatcaacct<br>ttgggcagtaagcccgcgaaaggcccgcaaattgcacggttattccggtgagtatatgtgattggttccggcattggcaataaagggaga<br>aagacatgagcatcaagccggttatcagcatcattcctgagggaaatatcgccagccgccttgccgctgcaacatcctcactgttttataccggttgaa<br>caatcttcggtggcgattctgtgacgacctcggagctggcaggttatgccaatccggcattctgagcccaacaggtttgcacactcacggattttgtggt<br>tgttgcgtgcttaaagggcaaatctaccctagaaataacaaaacaaatcagtacgctctactacccttagaatcaactggccatcatcggattagcacaac<br>atcatgataaccgcatgaaaatgctaatactacggcgcctatcggctgctaaatgcaccatcagtatgtgccgtgaacatcagtacagccaacatcatgcct<br>catatgcacagccataaagtgccggttatactggcggttgacatcctccagtcatggccgaccaccagcttacaaattgcct<br>gatgcgggcaggatcgagctggctgcgccttatccagacgctgatcgcccatcatcggcgttcttagatcttcgggtccgctgcgggacttgtt<br>gcgaggcaggatcgcgagctggtggtgtttgacattaccgatgctgcggcgtgaacaggtgcgtgctatgcccggcccgaaggcggcgtttccgtcc<br>gggaatggcatggagctgcgagccttataccagacgctgagcgccatcatcagtatgtgccgtgaacatcagtacacctgggaagcggcgtttccgtcc<br>gttacgcctgccggtacagcaggttatcaccggcggcgtgtcgttgataaagaacgcaatcagacaccagctcttcatggaatcccccggcgctacaccgcttcacgatcatt<br>tatgcaatacggccgttatcgtgtgtttgataagaacgcaatccggcgtcggggcgctggcagcctcgacggcatcgacggccgccgatcagcgttt<br>gccatgtcgaccgttacccgatgggggaaggcgtgatcggccggtgatggcgccgcaaggaaaaagagacc<br>tctcgaccgcctgaatattacgattacagctctgccgttgatggcgtcgagcagctcatcaccgatctcagagcgttt<br>gatggcgttgcacgacgcggctgactgccagtgccagtcgccagtacgcggttttagaaatggtc |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

CLAUSES

1. A method of increasing nitrogen fixation in a non-leguminous plant, comprising:
  a. applying to the plant a plurality of non-intergeneric bacteria, said plurality comprising non-intergeneric bacteria that:
    i. have an average colonization ability per unit of plant root tissue of at least about $1.0 \times 10^4$ bacterial cells per gram of fresh weight of plant root tissue; and/or
    ii. produce fixed N of at least about $1 \times 10^{-17}$ mmol N per bacterial cell per hour, and
    wherein the plurality of non-intergeneric bacteria, in planta, produce 1% or more of the fixed nitrogen in the plant, and
    wherein each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

2. The method according to clause 1, wherein the plurality of non-intergeneric bacteria comprise bacteria that: have an average colonization ability per unit of plant root tissue of at least about $1.0 \times 10^4$ bacterial cells per gram of fresh weight of plant root tissue.

3. The method according to clause 1, wherein the plurality of non-intergeneric bacteria comprise bacteria that: produce fixed N of at least about $1 \times 10^{-17}$ mmol N per bacterial cell per hour.

4. The method according to clause 1, wherein the plurality of non-intergeneric bacteria comprise bacteria that: have an average colonization ability per unit of plant root tissue of at least about $1.0 \times 10^4$ bacterial cells per gram of fresh weight of plant root tissue and produce fixed N of at least about $1 \times 10^{-17}$ mmol N per bacterial cell per hour.

5. The method according to clause 1, wherein the at least one genetic variation comprises an introduced control sequence operably linked to the at least one gene of the nitrogen fixation or assimilation genetic regulatory network.

6. The method according to clause 1, wherein the at least one genetic variation comprises a promoter operably linked to the at least one gene of the nitrogen fixation or assimilation genetic regulatory network.

7. The method according to clause 1, wherein the at least one genetic variation comprises an inducible promoter operably linked to the at least one gene of the nitrogen fixation or assimilation genetic regulatory network.

8. The method according to clause 1, wherein the plurality of non-intergeneric bacteria do not comprise a constitutive promoter operably linked to a gene of the nitrogen fixation or assimilation genetic regulatory network.

9. The method according to clause 1, wherein the plurality of non-intergeneric bacteria do not comprise a constitutive promoter operably linked to a gene in the nif gene cluster.

10. The method according to clause 1, wherein the plurality of non-intergeneric bacteria, in planta, excrete nitrogen-containing products of nitrogen fixation.

11. The method according to clause 1, wherein the plurality of non-intergeneric bacteria applied to the plant do not stimulate an increase in the uptake of exogenous non-atmospheric nitrogen.

12. The method according to clause 1, wherein the plant is grown in soil from a field which has been administered at least about 50 lbs of nitrogen-containing fertilizer per acre, and wherein the nitrogen-containing fertilizer comprises at least about 5% nitrogen by weight.

13. The method according to clause 1, wherein the plant is grown in soil from a field which has been administered at least about 50 lbs of nitrogen-containing fertilizer per acre, and wherein the nitrogen-containing fertilizer comprises at least about 5% nitrogen by weight, and wherein the nitrogen-containing fertilizer comprises ammonium or an ammonium containing molecule.

14. The method according to clause 1, wherein the exogenous nitrogen is selected from fertilizer comprising one or more of: glutamine, ammonia, ammonium, urea, nitrate, nitrite, ammonium-containing molecules, nitrate-containing molecules, and nitrite-containing molecules.

15. The method according to clause 1, wherein the plurality of non-intergeneric bacteria, in planta, produce 5% or more of the fixed nitrogen in the plant.

16. The method according to clause 1, wherein the plurality of non-intergeneric bacteria, in planta, produce 10% or more of the fixed nitrogen in the plant.

17. The method according to clause 1, wherein the plurality of non-intergeneric bacteria, in planta, fix atmospheric nitrogen in non-nitrogen-limiting conditions.

18. The method according to clause 1, wherein the plurality of non-intergeneric bacteria, in planta, excrete nitrogen-containing products of nitrogen fixation.

19. The method according to clause 1, wherein the fixed nitrogen produced by the plurality of non-intergeneric bacteria is measured through dilution of enriched fertilizer by atmospheric $N_2$ gas in plant tissue.

20. The method according to clause 1, wherein the at least one gene, or non-coding polynucleotide, of the nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

21. The method according to clause 1, wherein the at least one genetic variation is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD.

22. The method according to clause 1, wherein the at least one genetic variation is selected from: (A) a knock-out mutation; (B) alters or abolishes a regulatory sequence of a target gene; (C) comprises the insertion of a heterologous regulatory sequence; or (D) a domain deletion.

23. The method according to clause 1, wherein the at least one genetic variation is a mutated nifL gene that has been altered to comprise a heterologous promoter inserted into said nifL gene.

24. The method according to clause 1, wherein the at least one genetic variation is a mutated glnE gene that results in a truncated GlnE protein lacking an adenylyl-removing (AR) domain.

25. The method according to clause 1, wherein the at least one genetic variation is a mutated amtB gene that results in the lack of expression of said amtB gene.

26. The method according to clause 1, wherein the at least one genetic variation is selected from: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof.

27. The method according to clause 1, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain.

28. The method according to clause 1, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.

29. The method according to clause 1, wherein the plant comprises the seed, stalk, flower, fruit, leaves, or rhizome.

30. The method according to clause 1, wherein the plurality of non-intergeneric bacteria are formulated into a composition.

31. The method according to clause 1, wherein the plurality of non-intergeneric bacteria are formulated into a composition comprising an agriculturally acceptable carrier.

32. The method according to clause 1, wherein the plurality of non-intergeneric bacteria are applied into furrows in which seeds of said plant are planted.

33. The method according to clause 1, wherein the plurality of non-intergeneric bacteria are formulated into a liquid in-furrow composition comprising bacteria at a concentration of about $1\times10^7$ to about $1\times10^{10}$ cfu per milliliter.

34. The method according to clause 1, wherein the plurality of non-intergeneric bacteria are applied onto a seed of said plant.

35. The method according to clause 1, wherein the plurality of non-intergeneric bacteria are formulated into a seed coating and are applied onto a seed of said plant.

36. The method according to clause 1, wherein the plurality of non-intergeneric bacteria are formulated into a seed coating and are applied onto a seed of said plant, at a concentration of about $1\times10^5$ to about $1\times10^7$ cfu per seed.

37. The method according to clause 1, wherein the plant is a cereal crop.

38. The method according to clause 1, wherein the plant is selected from the group consisting of: corn, rice, wheat, barley, sorghum, millet, oat, rye, and triticale.

39. The method according to clause 1, wherein the plant is corn.

40. The method according to clause 1, wherein the plant is an agricultural crop plant.

41. The method according to clause 1, wherein the plant is a genetically modified organism.

42. The method according to clause 1, wherein the plant is not a genetically modified organism.

43. The method according to clause 1, wherein the plant has been genetically engineered or bred for efficient nitrogen use.

44. The method according to clause 1, wherein the plurality of non-intergeneric bacteria comprise at least two different species of bacteria.

45. The method according to clause 1, wherein the plurality of non-intergeneric bacteria comprise at least two different strains of the same species of bacteria.

46. The method according to clause 1, wherein the plurality of non-intergeneric bacteria comprise bacteria selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof.

47. The method according to clause 1, wherein the plurality of non-intergeneric bacteria are endophytic, epiphytic, or rhizospheric.

48. The method according to clause 1, wherein the plurality of non-intergeneric bacteria comprise bacteria selected from: a bacteria deposited as PTA-122293, a bacteria deposited as PTA-122294, a bacteria deposited as NCMA 201701002, a bacteria deposited as NCMA 201708004, a bacteria deposited as NCMA 201708003, a bacteria deposited as NCMA 201708002, a bacteria deposited as NCMA 201712001, a bacteria deposited as NCMA 201712002, and combinations thereof.

49. A bacterial composition, comprising:
   at least one genetically engineered bacterial strain that fixes atmospheric nitrogen in an agricultural system that has been fertilized with more than 20 lbs of Nitrogen per acre.

50. A bacterial composition, comprising:
   at least one bacterial strain that has been bred to fix atmospheric nitrogen in an agricultural system that has been fertilized with more than 20 lbs of Nitrogen per acre.

51. The bacterial composition of clause 49 or clause 50, wherein said fertilizer is a chemical fertilizer selected from the group consisting of anhydrous ammonia, ammonia sulfate, urea, diammonium phosphate, urea-form, UAN (urea ammonium nitrate) monoammonium phosphate, ammonium nitrate, nitrogen solutions, calcium nitrate, potassium nitrate, and sodium nitrate.

52. A bacterial composition, comprising:

at least one genetically engineered bacterial strain that fixes atmospheric nitrogen, the at least one genetically engineered bacterial strain comprising exogenously added DNA wherein said exogenously added DNA shares at least 80% identity to a corresponding native bacterial strain.

53. The bacterial composition of clause 52, wherein said exogenously added DNA shares at least 85% identity to a corresponding native bacterial strain.

54. The bacterial composition of clause 52, wherein said exogenously added DNA shares at least 90% identity to a corresponding native bacterial strain.

55. The bacterial composition of clause 52, wherein said exogenously added DNA shares at least 95% identity to a corresponding native bacterial strain.

56. The bacterial composition of clause 52, wherein said exogenously added DNA shares at least 99% identity to a corresponding native bacterial strain.

57. The bacterial composition of clause 52, wherein said exogenously added DNA is derived from a same bacterial strain as said corresponding native bacterial strain.

58. The bacterial composition of any of the preceding clauses, wherein said bacterial composition is a fertilizing composition.

59. The bacterial composition of any of the preceding clauses, wherein said at least one genetically engineered bacterial strain comprises at least one variation in a gene or intergenic region within 10,000 bp of a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

60. The bacterial composition of any of the preceding clauses, further comprising at least one additional component selected from the group consisting of a tackifier, a microbial stabilizer, a fungicide, an antibacterial agent, a preservative, a stabilizer, a surfactant, an anti-complex agent, an herbicide, a nematicide, an insecticide, a plant growth regulator, a fertilizer, a rodenticide, a desiccant, a bactericide, and a nutrient.

61. The bacterial composition of any of the preceding clauses, further comprising at least one additional component selected from the group consisting of a colorant, primer, pellet, disinfectant, plant growth regulator, safener, and a nematicide.

62. The bacterial composition of any of the preceding clauses, wherein said bacterial composition is formulated to be applied to a field.

63. The bacterial composition of clause 62, wherein said bacterial composition is formulated to be applied in-furrow.

64. The bacterial composition of clause 62, wherein said bacterial composition is formulated to be applied as a seed coating, seed dressing, or seed treatment.

65. The bacterial composition of clause 61 or clause 62, wherein said bacterial composition is formulated to be applied at, prior to, or post planting of the seed.

66. A seed composition comprising a seed of a plant that is inoculated with a bacterial composition of any of the preceding clauses.

67. A method of growing a crop using a plurality of seeds having a seed composition of clause 66.

68. The method of clause 67, further comprising harvesting said crop.

69. A method of applying a bacterial composition of any of the preceding clauses to a field.

70. The method of clause 69, wherein said bacterial composition is applied to said field in a form selected from the group consisting of a liquid form, a dry form, a granule, a powder, and a pellet.

71. The method of clause 69, wherein said bacterial composition is applied to said field as a seed coating, seed dressing, or seed treatment.

72. The method of clause 69, wherein said bacterial composition is applied to said field as an in-furrow treatment.

73. The method of clause 69, wherein said bacterial composition is applied to said field at, prior to, or post planting of the seed.

74. A fertilizer composition comprising a bacterial composition of any of the preceding clauses.

75. The fertilizer composition of clause 74, wherein said fertilizer composition is a seed coating, seed dressing, or seed treatment composition.

76. The fertilizer composition of clause 74, wherein said fertilizer composition is an in-furrow composition.

77. The fertilizer composition of clause 74, wherein said fertilizer composition is provided to a crop at, prior to, or post planting.

78. The fertilizer composition of clause 74, further comprising a porous carrier.

79. The fertilizer composition of clause 74, further comprising an additional synergistic component that, when combined with said bacterial composition, increases a fertilizing benefit of said fertilizer composition to a crop that is beyond a cumulative benefit of its individual components.

80. A method of maintaining soil nitrogen levels, comprising:

planting, in soil of a field, a crop inoculated by a genetically engineered bacterium that fixes atmospheric nitrogen; and harvesting said crop, wherein no more than 90% of a nitrogen dose required for producing said crop is administered to said soil of said field between planting and harvesting.

81. The method of clause 80, wherein no more than 80% of a nitrogen dose required for producing said crop is administered to said soil of said field between planting and harvesting.

82. The method of clause 80, wherein no more than 70% of a nitrogen dose required for producing said crop is administered to said soil of said field between planting and harvesting.

83. The method of clause 80, wherein no more than 60% of a nitrogen dose required for producing said crop is administered to said soil of said field between planting and harvesting.

84. The method of clause 80, wherein no more than 50% of a nitrogen dose required for producing said crop is administered to said soil of said field between planting and harvesting.

85. The method of clause 80, wherein no more than 40% of a nitrogen dose required for producing said crop is administered to said soil of said field between planting and harvesting.

86. The method of clause 80, wherein said genetically engineered bacterium comprises a bacterial composition of any of the preceding clauses.

87. The method of clause 80, wherein said genetically engineered bacterium consists of a bacterial composition of any of the preceding clauses.

88. A method of delivering a probiotic supplement to a crop plant, comprising:
  coating a crop seed with a seed coating, seed treatment, or seed dressing, wherein said seed coating, seed dressing, or seed treatment comprises living representatives of said probiotic; and
  applying, in soil of a field, said crop seeds.

89. The method of clause 88, wherein said seed coating, seed dressing, or seed treatment is applied in a single layer to said crop seed.

90. The method of clause 88, wherein said seed coating is applied in multiple layers to said crop seed.

91. The method of clause 88, wherein said seed coating is applied in a blend to said crop seed.

92. The method of clause 88, wherein said crop seed is non-nodulating.

93. The method of clause 88, wherein said seed coating comprises a bacterial composition of any of the preceding clauses.

94. The method of any of the proceeding clauses, wherein the genetically engineered bacterial strain is a genetically engineered Gram-positive bacterial strain.

95. The method of clause 94, wherein the genetically engineered Gram-positive bacterial strain has an altered expression level of a regulator of a Nif cluster.

96. The method of clause 94, wherein the genetically engineered Gram-positive bacterial strain expresses a decreased amount of a negative regulator of a Nif cluster.

97. The method of clause 94, wherein the genetically engineered bacterial strain expresses a decreased amount of GlnR.

98. The method of any one of the proceeding clauses, wherein the genome of the genetically engineered bacterial strain encodes a polypeptide with at least 75% identity to a sequence from the Zehr lab NifH database.

99. The method of any one of the proceeding clauses, wherein the genome of the genetically engineered bacterial strain encodes a polypeptide with at least 85% identity to a sequence from the Zehr lab NifH database.

100. The method of any one of the proceeding clauses, wherein the genome of the genetically engineered bacterial strain encodes a polypeptide with at least 75% identity to a sequence from the Buckley lab NifH database.

101. The method of any one of the proceeding clauses, wherein the genome of the genetically engineered bacterial strain encodes a polypeptide with at least 85% identity to a sequence from the Buckley lab NifH database.

102. A method of breeding microbial strains to improve specific traits of agronomic relevance, comprising:
  providing a plurality of microbial strains that have the ability to colonize a desired crop;
  improving regulatory networks influencing the trait through intragenomic rearrangement;
  assessing microbial strains within the plurality of microbial strains to determine a measure of the trait; and
  selecting one or more microbial strains of the plurality of microbial strains that generate an improvement in the trait in the presence of the desired crop.

103. The method of clause 102, wherein the specific trait which is improved is the ability of the microbial strain to fix nitrogen.

104. The method of clause 103, wherein the specific trait which is improved is the ability of the microbial strain to fix atmospheric nitrogen in the presence of N-fertilized growing conditions.

105. A method of breeding microbial strains to improve specific traits of agronomic relevance, comprising:
  providing a plurality of microbial strains that have the ability to colonize a desired crop;
  introducing genetic diversity into the plurality of microbial strains;
  assessing microbial strains within the plurality of microbial strains to determine a measure of the trait; and
  selecting one or more microbial strains of the plurality of microbial strains that generate an improvement in the trait in the presence of the desired crop.

106. The method of clause 105, wherein the specific trait which is improved is the ability of the microbial strain to fix nitrogen.

107. The method of clause 106, wherein the specific trait which is improved is the ability of the microbial strain to fix atmospheric nitrogen in the presence of N-fertilized growing conditions.

108. A method of increasing the amount of atmospheric derived nitrogen in a non-leguminous plant, comprising:
  exposing said non-leguminous plant to engineered non-intergeneric microbes, said engineered non-intergeneric microbes comprising at least one genetic variation introduced into a nitrogen fixation genetic regulatory network or at least one genetic variation introduced into a nitrogen assimilation genetic regulatory network.

109. The method of clause 108, wherein said engineered non-intergeneric microbes comprise at least one genetic variation introduced into said nitrogen fixation genetic regulatory network.

110. The method of clause 108, wherein said engineered non-intergeneric microbes comprise at least one genetic variation introduced into said nitrogen assimilation genetic regulatory network.

111. The method of clause 108, wherein said engineered non-intergeneric microbes comprise at least one genetic variation introduced into said nitrogen fixation genetic regulatory network and at least one genetic variation introduced into said nitrogen assimilation genetic regulatory network.

112. The method of clause 108, wherein said engineered non-intergeneric microbes are applied into furrows in which seeds of said non-leguminous plant are planted.

113. The method of clause 108, wherein said engineered non-intergeneric microbes are coated onto a seed of said non-leguminous plant.

114. The method of clause 108, wherein said non-leguminous plant is a non-leguminous agricultural crop plant selected from the group consisting of sorghum, canola, tomato, strawberry, barley, rice, corn, wheat, potato, millet, cereals, grains, and maize.

115. The method of clause 108, wherein said engineered non-intergeneric microbes colonize at least a root of said non-leguminous plant such that said engineered non-intergeneric microbes are present in said non-leguminous plant in an amount of at least $10^5$ colony forming units per gram fresh weight of tissue.

116. The method of clause 108, wherein said engineered non-intergeneric microbes are capable of fixing atmospheric nitrogen in non-nitrogen-limiting conditions.

117. The method of clause 108, wherein said engineered non-intergeneric microbes, in planta, excrete nitrogen-containing products of nitrogen fixation.

118. The method of clause 108, wherein said at least one genetic variation is introduced into a gene selected from the group consisting of nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

119. The method of clause 108, wherein said engineered non-intergeneric microbes, in planta, produce at least 1% of fixed nitrogen in said non-leguminous plant.

120. The method of clause 119, wherein said fixed nitrogen in said non-leguminous plant produced by said engineered non-intergeneric microbes is measured by dilution of 15N in crops grown in fields treated with fertilizer containing 1.2% 15N.

121. The method of clause 119, wherein said engineered non-intergeneric microbes, in planta, produce 5% or more of the fixed nitrogen in said non-leguminous plant.

122. The method of clause 108, wherein said non-intergeneric microbes are engineered using at least one type of engineering selected from the group consisting of directed mutagenesis, random mutagenesis, and directed evolution.

123. A method of increasing an amount of atmospheric derived nitrogen in a corn plant, comprising exposing said corn plant to engineered non-intergeneric microbes comprising engineered genetic variations within at least two genes selected from the group consisting of nifL, glnB, glnE, and amtB.

124. The method of clause 123, wherein said engineered non-intergeneric microbes, in planta, excrete nitrogen-containing products of nitrogen fixation.

125. The method of clause 123, wherein said engineered non-intergeneric microbes are applied into furrows in which seeds of said corn plant are planted.

126. The method of clause 123, wherein said engineered non-intergeneric microbes are coated onto a seed of said corn plant.

127. A method of increasing an amount of atmospheric derived nitrogen in a corn plant, comprising: exposing said corn plant to engineered non-intergeneric microbes comprising at least one genetic variation introduced into a nitrogen fixation genetic regulatory network and at least one genetic variation introduced into a nitrogen assimilation genetic regulatory network, wherein said engineered non-intergeneric microbes, in planta, produce at least 5% of fixed nitrogen in said corn plant as measured by dilution of 15N in crops grown in fields treated with fertilizer containing 1.2% 15N.

128. A method of increasing nitrogen fixation in a non-leguminous plant, comprising:
a. applying to the plant a plurality of non-intergeneric bacteria, said plurality comprising non-intergeneric bacteria that:
i. have an average colonization ability per unit of plant root tissue of at least about $1.0 \times 10^4$ bacterial cells per gram of fresh weight of plant root tissue; and
ii. produce fixed N of at least about $1 \times 10^{-17}$ mmol N per bacterial cell per hour, and
wherein the product of (i) the average colonization ability per unit of plant root tissue and (ii) produced fixed N per bacterial cell per hour, is at least about $2.5 \times 10^{-8}$ mmol N per gram of fresh weight of plant root tissue per hour, and
wherein the plurality of non-intergeneric bacteria, in planta, produce 1% or more of the fixed nitrogen in the plant, and
wherein each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

129. The method according to clause 128, wherein the at least one genetic variation comprises an introduced control sequence operably linked to the at least one gene of the nitrogen fixation or assimilation genetic regulatory network.

130. The method according to clause 128, wherein the at least one genetic variation comprises a promoter operably linked to the at least one gene of the nitrogen fixation or assimilation genetic regulatory network.

131. The method according to clause 128, wherein the at least one genetic variation comprises an inducible promoter operably linked to the at least one gene of the nitrogen fixation or assimilation genetic regulatory network.

132. The method according to clause 128, wherein the plurality of non-intergeneric bacteria do not comprise a constitutive promoter operably linked to a gene of the nitrogen fixation or assimilation genetic regulatory network.

133. The method according to clause 128, wherein the plurality of non-intergeneric bacteria do not comprise a constitutive promoter operably linked to a gene in the nif gene cluster.

134. The method according to clause 128, wherein the plurality of non-intergeneric bacteria, in planta, excrete the nitrogen-containing products of nitrogen fixation.

135. The method according to clause 128, wherein the plurality of non-intergeneric bacteria applied to the plant do not stimulate an increase in the uptake of exogenous non-atmospheric nitrogen.

136. The method according to clause 128, wherein the plant is grown in soil from a field which has been administered at least about 50 lbs of nitrogen-containing fertilizer per acre, and wherein the nitrogen-containing fertilizer comprises at least about 5% nitrogen by weight.

137. The method according to clause 128, wherein the plant is grown in soil from a field which has been administered at least about 50 lbs of nitrogen-containing fertilizer per acre, and wherein the nitrogen-containing fertilizer comprises at least about 5% nitrogen by weight, and wherein the nitrogen-containing fertilizer comprises ammonium or an ammonium containing molecule.

138. The method according to clause 128, wherein the exogenous nitrogen is selected from fertilizer comprising one or more of: glutamine, ammonia, ammonium, urea, nitrate, nitrite, ammonium-containing molecules, nitrate-containing molecules, and nitrite-containing molecules.

139. The method according to clause 128, wherein the plurality of non-intergeneric bacteria, in planta, produce 5% or more of the fixed nitrogen in the plant.

140. The method according to clause 128, wherein the plurality of non-intergeneric bacteria, in planta, produce 10% or more of the fixed nitrogen in the plant.

141. The method according to clause 128, wherein the plurality of non-intergeneric bacteria, in planta, fix atmospheric nitrogen in non-nitrogen-limiting conditions.

142. The method according to clause 128, wherein the plurality of non-intergeneric bacteria, in planta, excrete nitrogen-containing products of nitrogen fixation.

143. The method according to clause 128, wherein the fixed nitrogen produced by the plurality of non-intergeneric bacteria is measured through dilution of enriched fertilizer by atmospheric $N_2$ gas in plant tissue.

144. The method according to clause 128, wherein the at least one gene, or non-coding polynucleotide, of the nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

145. The method according to clause 128, wherein the at least one genetic variation is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD.

146. The method according to clause 128, wherein the at least one genetic variation is selected from: (A) a knock-out mutation; (B) alters or abolishes a regulatory sequence of a target gene; (C) comprises the insertion of a heterologous regulatory sequence; or (D) a domain deletion.

147. The method according to clause 128, wherein the at least one genetic variation is a mutated nifL gene that has been altered to comprise a heterologous promoter inserted into said nifL gene.

148. The method according to clause 128, wherein the at least one genetic variation is a mutated glnE gene that results in a truncated GlnE protein lacking an adenylyl-removing (AR) domain.

149. The method according to clause 128, wherein the at least one genetic variation is a mutated amtB gene that results in the lack of expression of said amtB gene.

150. The method according to clause 128, wherein the at least one genetic variation is selected from: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof.

151. The method according to clause 128, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain.

152. The method according to clause 128, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.

153. The method according to clause 128, wherein the plant comprises the seed, stalk, flower, fruit, leaves, or rhizome.

154. The method according to clause 128, wherein the plurality of non-intergeneric bacteria are formulated into a composition.

155. The method according to clause 128, wherein the plurality of non-intergeneric bacteria are formulated into a composition comprising an agriculturally acceptable carrier.

156. The method according to clause 128, wherein the plurality of non-intergeneric bacteria are applied into furrows in which seeds of said plant are planted.

157. The method according to clause 128, wherein the plurality of non-intergeneric bacteria are formulated into a liquid in-furrow composition comprising bacteria at a concentration of about $1 \times 10^7$ to about $1 \times 10^{10}$ cfu per milliliter.

158. The method according to clause 128, wherein the plurality of non-intergeneric bacteria are applied onto a seed of said plant.

159. The method according to clause 128, wherein the plurality of non-intergeneric bacteria are formulated into a seed coating and are applied onto a seed of said plant.

160. The method according to clause 128, wherein the plurality of non-intergeneric bacteria are formulated into a seed coating and are applied onto a seed of said plant, at a concentration of about $1 \times 10^5$ to about $1 \times 10^7$ cfu per seed.

161. The method according to clause 128, wherein the plant is a cereal crop.

162. The method according to clause 128, wherein the plant is selected from the group consisting of: corn, rice, wheat, barley, sorghum, millet, oat, rye, and triticale.

163. The method according to clause 128, wherein the plant is corn.

164. The method according to clause 128, wherein the plant is an agricultural crop plant.

165. The method according to clause 128, wherein the plant is a genetically modified organism.

166. The method according to clause 128, wherein the plant is not a genetically modified organism.

167. The method according to clause 128, wherein the plant has been genetically engineered or bred for efficient nitrogen use.

168. The method according to clause 128, wherein the plurality of non-intergeneric bacteria comprise at least two different species of bacteria.

169. The method according to clause 128, wherein the plurality of non-intergeneric bacteria comprise at least two different strains of the same species of bacteria.

170. The method according to clause 128, wherein the plurality of non-intergeneric bacteria comprise bacteria selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof 171. The method according to clause 128, wherein the plurality of non-intergeneric bacteria are endophytic, epiphytic, or rhizospheric.

172. The method according to clause 128, wherein the plurality of non-intergeneric bacteria comprise bacteria selected from: a bacteria deposited as PTA-122293, a bacteria deposited as PTA-122294, a bacteria deposited as NCMA 201701002, a bacteria deposited as NCMA 201708004, a bacteria deposited as NCMA 201708003, a bacteria deposited as NCMA 201708002, a bacteria deposited as NCMA 201712001, a bacteria deposited as NCMA 201712002, and combinations thereof 173. A method of increasing nitrogen fixation in a non-leguminous plant, comprising:

a. applying to the plant a plurality of bacteria, said plurality comprising bacteria that:

i. have an average colonization ability per unit of plant root tissue of at least about $1.0 \times 10^4$ bacterial cells per gram of fresh weight of plant root tissue; and/or ii. produce fixed N of at least about $1 \times 10^{-17}$ mmol N per bacterial cell per hour, and wherein the plurality of bacteria, in planta, produce 1% or more of the fixed nitrogen in the plant.

174. The method according to clause 173, wherein the plurality of bacteria comprise bacteria that: have an average colonization ability per unit of plant root tissue of at least about $1.0 \times 10^4$ bacterial cells per gram of fresh weight of plant root tissue.

175. The method according to clause 173, wherein the plurality of bacteria comprise bacteria that: produce fixed N of at least about $173 \times 10^{-17}$ mmol N per bacterial cell per hour.

176. The method according to clause 173, wherein the plurality of bacteria comprise bacteria that: have an average colonization ability per unit of plant root tissue of at least about $1.0 \times 10^4$ bacterial cells per gram of fresh weight of plant root tissue and produce fixed N of at least about $1 \times 10^{-17}$ mmol N per bacterial cell per hour.

177. The method according to clause 173, wherein the plurality of bacteria comprise bacteria that: have an average colonization ability per unit of plant root tissue of at least about $1.0 \times 10^4$ bacterial cells per gram of fresh weight of plant root tissue and produce fixed N of at least about $1 \times 10^{-17}$ mmol N per bacterial cell per hour, and wherein the product of (i) the average colonization ability per unit of plant root tissue and (ii) produced fixed N per bacterial cell per hour, is at least about $2.5 \times 10^{-8}$ mmol N per gram of fresh weight of plant root tissue per hour.

178. The method according to clause 173, wherein the plurality of bacteria, in planta, excrete the nitrogen-containing products of nitrogen fixation.

179. The method according to clause 173, wherein the plurality of bacteria applied to the plant do not stimulate an increase in the uptake of exogenous non-atmospheric nitrogen.

180. The method according to clause 173, wherein the plant comprises the seed, stalk, flower, fruit, leaves, or rhizome.

181. The method according to clause 173, wherein the plurality of bacteria are formulated into a composition.

182. The method according to clause 173, wherein the plurality of bacteria are formulated into a composition comprising an agriculturally acceptable carrier.

183. The method according to clause 173, wherein the plurality of bacteria are applied into furrows in which seeds of said plant are planted.

184. The method according to clause 173, wherein the plurality of bacteria are formulated into a liquid in-furrow composition comprising bacteria at a concentration of about $1 \times 10^7$ to about $1 \times 10^{10}$ cfu per milliliter.

185. The method according to clause 173, wherein the plurality of bacteria are applied onto a seed of said plant.

186. The method according to clause 173, wherein the plurality of bacteria are formulated into a seed coating and are applied onto a seed of said plant.

187. The method according to clause 173, wherein the plurality of bacteria are formulated into a seed coating and are applied onto a seed of said plant, at a concentration of about $1 \times 10^5$ to about $1 \times 10^7$ cfu per seed.

188. The method according to clause 173, wherein the plant is a cereal crop.

189. The method according to clause 173, wherein the plant is selected from the group consisting of: corn, rice, wheat, barley, sorghum, millet, oat, rye, and triticale.

190. The method according to clause 173, wherein the plant is corn.

191. The method according to clause 173, wherein the plant is an agricultural crop plant.

192. The method according to clause 173, wherein the plant is a genetically modified organism.

193. The method according to clause 173, wherein the plant is not a genetically modified organism.

194. The method according to clause 173, wherein the plant has been genetically engineered or bred for efficient nitrogen use.

195. The method according to clause 173, wherein the plurality of bacteria comprise at least two different species of bacteria.

196. The method according to clause 173, wherein the plurality of bacteria comprise at least two different strains of the same species of bacteria.

197. The method according to clause 173, wherein the plurality of bacteria comprise bacteria selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof.

198. The method according to clause 173, wherein the plurality of bacteria are endophytic, epiphytic, or rhizospheric.

199. The method according to clause 173, wherein the plurality of bacteria are selected from: a bacteria deposited as NCMA 201701003, a bacteria deposited as NCMA 201701001, and a bacteria deposited as NCMA 201708001.

200. A non-intergeneric bacterial population capable of increasing nitrogen fixation in a non-leguminous plant, comprising:

a. a plurality of non-intergeneric bacteria, that:

i. have an average colonization ability per unit of plant root tissue of at least about $1.0 \times 10^4$ bacterial cells per gram of fresh weight of plant root tissue; and/or ii. produce fixed N of at least about $1 \times 10^{-17}$ mmol N per bacterial cell per hour, and wherein the plurality of non-intergeneric bacteria, in planta, produce 1% or more of the fixed nitrogen in a plant grown in the presence of the plurality of non-intergeneric bacteria, and wherein each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

201. The non-intergeneric bacterial population according to clause 200, wherein the plurality of non-intergeneric bacteria comprise bacteria that: have an average colonization ability per unit of plant root tissue of at least about $1.0 \times 10^4$ bacterial cells per gram of fresh weight of plant root tissue.

202. The non-intergeneric bacterial population according to clause 200, wherein the plurality of non-intergeneric bacteria comprise bacteria that: produce fixed N of at least about $1 \times 10^{-17}$ mmol N per bacterial cell per hour.

203. The non-intergeneric bacterial population according to clause 200, wherein the plurality of non-intergeneric bacteria comprise bacteria that: have an average colonization ability per unit of plant root tissue of at least about $1.0 \times 10^4$ bacterial cells per gram of fresh weight of plant root tissue and produce fixed N of at least about $1 \times 10^{-17}$ mmol N per bacterial cell per hour.

204. The non-intergeneric bacterial population according to clause 200, wherein the at least one genetic variation comprises an introduced control sequence operably linked to the at least one gene of the nitrogen fixation or assimilation genetic regulatory network.

205. The non-intergeneric bacterial population according to clause 200, wherein the at least one genetic variation comprises a promoter operably linked to the at least one gene of the nitrogen fixation or assimilation genetic regulatory network.

206. The non-intergeneric bacterial population according to clause 200, wherein the at least one genetic variation comprises an inducible promoter operably linked to the at least one gene of the nitrogen fixation or assimilation genetic regulatory network.

207. The non-intergeneric bacterial population according to clause 200, wherein the plurality of non-intergeneric bacteria do not comprise a constitutive promoter operably linked to a gene of the nitrogen fixation or assimilation genetic regulatory network.

208. The non-intergeneric bacterial population according to clause 200, wherein the plurality of non-intergeneric bacteria do not comprise a constitutive promoter operably linked to a gene in the nif gene cluster.

209. The non-intergeneric bacterial population according to clause 200, wherein the plurality of non-intergeneric bacteria, in planta, excrete nitrogen-containing products of nitrogen fixation.

210. The non-intergeneric bacterial population according to clause 200, wherein the plurality of non-intergeneric bacteria applied to the plant do not stimulate an increase in the uptake of exogenous non-atmospheric nitrogen.

211. The non-intergeneric bacterial population according to clause 200, wherein the plant is grown in soil from a field which has been administered at least about 50 lbs of nitrogen-containing fertilizer per acre, and wherein the nitrogen-containing fertilizer comprises at least about 5% nitrogen by weight.

212. The non-intergeneric bacterial population according to clause 200, wherein the plant is grown in soil from a field which has been administered at least about 50 lbs of nitrogen-containing fertilizer per acre, and wherein the nitrogen-containing fertilizer comprises at least about 5% nitrogen by weight, and wherein the nitrogen-containing fertilizer comprises ammonium or an ammonium containing molecule.

213. The non-intergeneric bacterial population according to clause 200, wherein the exogenous nitrogen is selected from fertilizer comprising one or more of: glutamine, ammonia, ammonium, urea, nitrate, nitrite, ammonium-containing molecules, nitrate-containing molecules, and nitrite-containing molecules.

214. The non-intergeneric bacterial population according to clause 200, wherein the plurality of non-intergeneric bacteria, in planta, produce 5% or more of the fixed nitrogen in the plant.

215. The non-intergeneric bacterial population according to clause 200, wherein the plurality of non-intergeneric bacteria, in planta, produce 10% or more of the fixed nitrogen in the plant.

216. The non-intergeneric bacterial population according to clause 200, wherein the plurality of non-intergeneric bacteria, in planta, fix atmospheric nitrogen in non-nitrogen-limiting conditions.

217. The non-intergeneric bacterial population according to clause 200, wherein the plurality of non-intergeneric bacteria, in planta, excrete nitrogen-containing products of nitrogen fixation.

218. The non-intergeneric bacterial population according to clause 200, wherein the fixed nitrogen produced by the plurality of non-intergeneric bacteria is measured through dilution of enriched fertilizer by atmospheric $N_2$ gas in plant tissue.

219. The non-intergeneric bacterial population according to clause 200, wherein the at least one gene, or non-coding polynucleotide, of the nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

220. The non-intergeneric bacterial population according to clause 200, wherein the at least one genetic variation is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD.

221. The non-intergeneric bacterial population according to clause 200, wherein the at least one genetic variation is selected from: (A) a knock-out mutation; (B) alters or abolishes a regulatory sequence of a target gene; (C) comprises the insertion of a heterologous regulatory sequence; or (D) a domain deletion.

222. The non-intergeneric bacterial population according to clause 200, wherein the at least one genetic variation is a mutated nifL gene that has been altered to comprise a heterologous promoter inserted into said nifL gene.

223. The non-intergeneric bacterial population according to clause 200, wherein the at least one genetic variation is a mutated glnE gene that results in a truncated GlnE protein lacking an adenylyl-removing (AR) domain.

224. The non-intergeneric bacterial population according to clause 200, wherein the at least one genetic variation is a mutated amtB gene that results in the lack of expression of said amtB gene.

225. The non-intergeneric bacterial population according to clause 200, wherein the at least one genetic variation is selected from: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof.

226. The non-intergeneric bacterial population according to clause 200, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain.

227. The non-intergeneric bacterial population according to clause 200, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.

228. The non-intergeneric bacterial population according to clause 200, wherein the plant comprises the seed, stalk, flower, fruit, leaves, or rhizome.

229. The non-intergeneric bacterial population according to clause 200, wherein the plurality of non-intergeneric bacteria are formulated into a composition.

230. The non-intergeneric bacterial population according to clause 200, wherein the plurality of non-intergeneric bacteria are formulated into a composition comprising an agriculturally acceptable carrier.

231. The non-intergeneric bacterial population according to clause 200, wherein the plurality of non-intergeneric bacteria are formulated into a liquid in-furrow composition comprising bacteria at a concentration of about $1\times10^{-17}$ to about $1\times10^{10}$ cfu per milliliter.

232. The non-intergeneric bacterial population according to clause 200, wherein the plurality of non-intergeneric bacteria are formulated into a seed coating.

233. The non-intergeneric bacterial population according to clause 200, wherein the plant is a cereal crop.

234. The non-intergeneric bacterial population according to clause 200, wherein the plant is selected from the group consisting of: corn, rice, wheat, barley, sorghum, millet, oat, rye, and triticale.

235. The non-intergeneric bacterial population according to clause 200, wherein the plant is corn.

236. The non-intergeneric bacterial population according to clause 200, wherein the plant is an agricultural crop plant.

237. The non-intergeneric bacterial population according to clause 200, wherein the plant is a genetically modified organism.

238. The non-intergeneric bacterial population according to clause 200, wherein the plant is not a genetically modified organism.

239. The non-intergeneric bacterial population according to clause 200, wherein the plant has been genetically engineered or bred for efficient nitrogen use.

240. The non-intergeneric bacterial population according to clause 200, wherein the plurality of non-intergeneric bacteria comprise at least two different species of bacteria.

241. The non-intergeneric bacterial population according to clause 200, wherein the plurality of non-intergeneric bacteria comprise at least two different strains of the same species of bacteria.

242. The non-intergeneric bacterial population according to clause 200, wherein the plurality of non-intergeneric bacteria comprise bacteria selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof.

243. The non-intergeneric bacterial population according to clause 200, wherein the plurality of non-intergeneric bacteria are endophytic, epiphytic, or rhizospheric.

244. The non-intergeneric bacterial population according to clause 200, wherein the plurality of non-intergeneric bacteria comprise bacteria selected from: a bacteria deposited as PTA-122293, a bacteria deposited as PTA-122294, a bacteria deposited as NCMA 201701002, a bacteria deposited as NCMA 201708004, a bacteria deposited as NCMA 201708003, a bacteria deposited as NCMA 201708002, a bacteria deposited as NCMA 201712001, a bacteria deposited as NCMA 201712002, and combinations thereof.

245. A bacterial population capable of increasing nitrogen fixation in a non-leguminous plant, comprising:
   a. a plurality of bacteria, that:
      i. have an average colonization ability per unit of plant root tissue of at least about $1.0\times10^4$ bacterial cells per gram of fresh weight of plant root tissue; and/or
      ii. produce fixed N of at least about $1\times10^{-17}$ mmol N per bacterial cell per hour, and
      wherein the plurality of bacteria, in planta, produce 1% or more of the fixed nitrogen in the plant.

246. The bacterial population according to clause 245, wherein the plurality of bacteria comprise bacteria that: have an average colonization ability per unit of plant root tissue of at least about $1.0\times10^4$ bacterial cells per gram of fresh weight of plant root tissue.

247. The bacterial population according to clause 245, wherein the plurality of bacteria comprise bacteria that: produce fixed N of at least about $245\times10^{-17}$ mmol N per bacterial cell per hour.

248. The bacterial population according to clause 245, wherein the plurality of bacteria comprise bacteria that:

have an average colonization ability per unit of plant root tissue of at least about $1.0\times10^4$ bacterial cells per gram of fresh weight of plant root tissue and produce fixed N of at least about $1\times10^{-17}$ mmol N per bacterial cell per hour.

249. The bacterial population according to clause 245, wherein the plurality of bacteria comprise bacteria that: have an average colonization ability per unit of plant root tissue of at least about $1.0\times10^4$ bacterial cells per gram of fresh weight of plant root tissue and produce fixed N of at least about $1\times10^{-17}$ mmol N per bacterial cell per hour, and wherein the product of (i) the average colonization ability per unit of plant root tissue and (ii) produced fixed N per bacterial cell per hour, is at least about $2.5\times10^{-8}$ mmol N per gram of fresh weight of plant root tissue per hour.

250. The bacterial population according to clause 245, wherein the plurality of bacteria, in planta, excrete the nitrogen-containing products of nitrogen fixation.

251. The bacterial population according to clause 245, wherein the plurality of bacteria applied to the plant do not stimulate an increase in the uptake of exogenous non-atmospheric nitrogen.

252. The bacterial population according to clause 245, wherein the plant comprises the seed, stalk, flower, fruit, leaves, or rhizome.

253. The bacterial population according to clause 245, wherein the plurality of bacteria are formulated into a composition.

254. The bacterial population according to clause 245, wherein the plurality of bacteria are formulated into a composition comprising an agriculturally acceptable carrier.

255. The bacterial population according to clause 245, wherein the plurality of bacteria are applied into furrows in which seeds of said plant are planted.

256. The bacterial population according to clause 245, wherein the plurality of bacteria are formulated into a liquid in-furrow composition comprising bacteria at a concentration of about $1\times10^7$ to about $1\times10^{10}$ cfu per milliliter.

257. The bacterial population according to clause 245, wherein the plurality of bacteria are applied onto a seed of said plant.

258. The bacterial population according to clause 245, wherein the plurality of bacteria are formulated into a seed coating and are applied onto a seed of said plant.

259. The bacterial population according to clause 245, wherein the plurality of bacteria are formulated into a seed coating and are applied onto a seed of said plant, at a concentration of about $1\times10^5$ to about $1\times10^7$ cfu per seed.

260. The bacterial population according to clause 245, wherein the plant is a cereal crop.

261. The bacterial population according to clause 245, wherein the plant is selected from the group consisting of: corn, rice, wheat, barley, sorghum, millet, oat, rye, and triticale.

262. The bacterial population according to clause 245, wherein the plant is corn.

263. The bacterial population according to clause 245, wherein the plant is an agricultural crop plant.

264. The bacterial population according to clause 245, wherein the plant is a genetically modified organism.

265. The bacterial population according to clause 245, wherein the plant is not a genetically modified organism.

266. The bacterial population according to clause 245, wherein the plant has been genetically engineered or bred for efficient nitrogen use.

267. The bacterial population according to clause 245, wherein the plurality of bacteria comprise at least two different species of bacteria.

268. The bacterial population according to clause 245, wherein the plurality of bacteria comprise at least two different strains of the same species of bacteria.

269. The bacterial population according to clause 245, wherein the plurality of bacteria comprise bacteria selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof 270. The bacterial population according to clause 245, wherein the plurality of bacteria are endophytic, epiphytic, or rhizospheric.

271. The bacterial population according to clause 245, wherein the plurality of bacteria are selected from: a bacteria deposited as NCMA 201701003, a bacteria deposited as NCMA 201701001, and a bacteria deposited as NCMA 201708001.

272. A bacterium that:
  i. has an average colonization ability per unit of plant root tissue of at least about $1.0\times10^4$ bacterial cells per gram of fresh weight of plant root tissue; and/or
  ii. produces fixed N of at least about $1\times10^{-17}$ mmol N per bacterial cell per hour.

273. A non-intergeneric bacterium, comprising: at least one genetic variation introduced into at least one gene, or non-coding polynucleotide, of the nitrogen fixation or assimilation genetic regulatory network, such that the non-intergeneric bacterium is capable of fixing atmospheric nitrogen in the presence of exogenous nitrogen, and wherein said bacterium:
  i. has an average colonization ability per unit of plant root tissue of at least about $1.0\times10^4$ bacterial cells per gram of fresh weight of plant root tissue; and/or
  ii. produces fixed N of at least about $1\times10^{-17}$ mmol N per bacterial cell per hour.

274. The non-intergeneric bacterium according to clause 273, wherein the bacterium has an average colonization ability per unit of plant root tissue of at least about $1.0\times10^4$ bacterial cells per gram of fresh weight of plant root tissue.

275. The non-intergeneric bacterium according to clause 273, wherein the bacterium produces fixed N of at least about $1\times10^{-17}$ mmol N per bacterial cell per hour.

276. The non-intergeneric bacterium according to clause 273, wherein the bacterium has an average colonization ability per unit of plant root tissue of at least about $1.0\times10^4$ bacterial cells per gram of fresh weight of plant root tissue and produces fixed N of at least about $1\times10^{-17}$ mmol N per bacterial cell per hour.

277. The non-intergeneric bacterium according to clause 273, wherein the bacterium has an average colonization ability per unit of plant root tissue of at least about $1.0\times10^4$ bacterial cells per gram of fresh weight of plant root tissue and produces fixed N of at least about $1\times10^{-17}$ mmol N per bacterial cell per hour, and wherein the product of (i) the average colonization ability per unit of plant root tissue and (ii) produced fixed N per bacterial cell per hour, is at least about $2.5 \times 10^{-8}$ mmol N per gram of fresh weight of plant root tissue per hour.

278. The non-intergeneric bacterium according to clause 273, wherein the at least one genetic variation comprises an introduced control sequence operably linked to the at least one gene of the nitrogen fixation or assimilation genetic regulatory network.

279. The non-intergeneric bacterium according to clause 273, wherein the at least one genetic variation comprises a promoter operably linked to the at least one gene of the nitrogen fixation or assimilation genetic regulatory network.

280. The non-intergeneric bacterium according to clause 273, wherein the at least one genetic variation comprises an inducible promoter operably linked to the at least one gene of the nitrogen fixation or assimilation genetic regulatory network.

281. The non-intergeneric bacterium according to clause 273, wherein the bacterium does not comprise a constitutive promoter operably linked to a gene of the nitrogen fixation or assimilation genetic regulatory network.

282. The non-intergeneric bacterium according to clause 273, wherein the bacterium does not comprise a constitutive promoter operably linked to a gene in the nif gene cluster.

283. The non-intergeneric bacterium according to clause 273, wherein the bacterium, in planta, excretes the nitrogen-containing products of nitrogen fixation.

284. The non-intergeneric bacterium according to clause 273, wherein the at least one gene, or non-coding polynucleotide, of the nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

285. The non-intergeneric bacterium according to clause 273, wherein the at least one genetic variation is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD.

286. The non-intergeneric bacterium according to clause 273, wherein the at least one genetic variation is selected from: (A) a knock-out mutation; (B) alters or abolishes a regulatory sequence of a target gene; (C) comprises the insertion of a heterologous regulatory sequence; or (D) a domain deletion.

287. The non-intergeneric bacterium according to clause 273, wherein the at least one genetic variation is a mutated nifL gene that has been altered to comprise a heterologous promoter inserted into said nifL gene.

288. The non-intergeneric bacterium according to clause 273, wherein the at least one genetic variation is a mutated glnE gene that results in a truncated GlnE protein lacking an adenylyl-removing (AR) domain.

289. The non-intergeneric bacterium according to clause 273, wherein the at least one genetic variation is a mutated amtB gene that results in the lack of expression of said amtB gene.

290. The non-intergeneric bacterium according to clause 273, wherein the at least one genetic variation is selected from: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof.

291. The non-intergeneric bacterium according to clause 273, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain.

292. The non-intergeneric bacterium according to clause 273, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.

293. The non-intergeneric bacterium according to clause 273, formulated into a composition.

294. The non-intergeneric bacterium according to clause 273, formulated into a composition comprising an agriculturally acceptable carrier.

295. The non-intergeneric bacterium according to clause 273, formulated into a liquid in-furrow composition.

296. The non-intergeneric bacterium according to clause 273, formulated into a seed coating.

297. The non-intergeneric bacterium according to clause 273, wherein said bacterium is selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof.

298. The non-intergeneric bacterium according to clause 273, wherein said bacterium is endophytic, epiphytic, or rhizospheric.

299. The non-intergeneric bacterium according to clause 273, wherein said bacterium is selected from: a bacteria deposited as PTA-122293, a bacteria deposited as PTA-122294, a bacteria deposited as NCMA 201701002, a bacteria deposited as NCMA 201708004, a bacteria deposited as NCMA 201708003, a bacteria deposited as NCMA 201708002, a bacteria deposited as NCMA 201712001, a bacteria deposited as NCMA 201712002, and combinations thereof.

300. A method of increasing nitrogen fixation in a plant, comprising administering to the plant an effective amount of a composition comprising:
  i. a purified population of bacteria that comprises bacteria with a 16S nucleic acid sequence that is at least about 97% identical to a nucleic acid sequence selected from SEQ ID NOs: 85, 96, 111, 121, 122, 123, 124, 136, 149, 157, 167, 261, 262, 269, 277-283;
  ii. a purified population of bacteria that comprises bacteria with a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, 284-295; and/or iii. a purified population of bacteria that comprises bacteria with a nucleic acid sequence that is at least about 90% identical to a nucleic acid sequence selected from SEQ ID NOs: 177-260, 296-303; and wherein the plant administered the effective amount of the composition exhibits an increase in nitrogen fixation, as compared to a plant not having been administered the composition.

301. The method of clause 300, wherein the composition comprises: a purified population of bacteria that comprises bacteria with a 16S nucleic acid sequence that is at least about 97% identical to a nucleic acid sequence selected from SEQ ID NOs: 85, 96, 111, 121, 122, 123, 124, 136, 149, 157, 167, 261, 262, 269, and 277-283.

302. The method of clause 300, wherein the composition comprises: a purified population of bacteria that comprises bacteria with a 16S nucleic acid sequence that is at least about 99% identical to a nucleic acid sequence selected from SEQ ID NOs: 85, 96, 111, 121, 122, 123, 124, 136, 149, 157, 167, 261, 262, 269, and 277-283.

303. The method of clause 300, wherein the composition comprises: a purified population of bacteria that comprises bacteria with a 16S nucleic acid sequence selected from SEQ ID NOs: 85, 96, 111, 121, 122, 123, 124, 136, 149, 157, 167, 261, 262, 269, and 277-283.

304. The method of clause 300, wherein the composition comprises: a purified population of bacteria that comprises bacteria with a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, and 284-295.

305. The method of clause 300, wherein the composition comprises: a purified population of bacteria that comprises bacteria with a nucleic acid sequence that is at least about 95% identical to a nucleic acid sequence selected from SEQ ID NOs: 86-95, 97-110, 112-120, 125-135, 137-148, 150-156, 158-166, 168-176, 263-268, 270-274, 275, 276, and 284-295.

306. The method of clause 300, wherein the composition comprises: a purified population of bacteria that comprises bacteria with a nucleic acid sequence that is at least about 99% identical to a nucleic acid sequence selected from SEQ ID NOs: 86-95, 97-110, 112-120, 125-135, 137-148, 150-156, 158-166, 168-176, 263-268, 270-274, 275, 276, and 284-295.

307. The method of clause 300, wherein the composition comprises: a purified population of bacteria that comprises bacteria with a nucleic acid sequence selected from SEQ ID NOs: 86-95, 97-110, 112-120, 125-135, 137-148, 150-156, 158-166, 168-176, 263-268, 270-274, 275, 276, and 284-295.

308. The method of clause 300, wherein the composition comprises: a purified population of bacteria that comprises bacteria with a nucleic acid sequence that is at least about 90% identical to a nucleic acid sequence selected from SEQ ID NOs: 177-260 and 296-303.

309. The method of clause 300, wherein the composition comprises: a purified population of bacteria that comprises bacteria with a nucleic acid sequence that is at least about 95% identical to a nucleic acid sequence selected from SEQ ID NOs: 177-260 and 296-303.

310. The method of clause 300, wherein the composition comprises: a purified population of bacteria that comprises bacteria with a nucleic acid sequence that is at least about 99% identical to a nucleic acid sequence selected from SEQ ID NOs: 177-260 and 296-303.

311. The method of clause 300, wherein the composition comprises: a purified population of bacteria that comprises bacteria with a nucleic acid sequence selected from SEQ ID NOs: 177-260 and 296-303.

312. The method of clause 300, wherein the composition comprises: a purified population of bacteria that comprise bacteria with at least one genetic variation introduced into a gene selected from the group consisting of nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

313. The method of clause 300, wherein the composition comprises: a purified population of bacteria that comprise bacteria with at least one genetic variation introduced into a gene selected from the group consisting of nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme, wherein the genetic variation (A) is a knock-out mutation; (B) alters or abolishes a regulatory sequence of a target gene; (C) comprises the insertion of a heterologous regulatory sequence; or (D) a domain deletion.

314. The method of clause 300, wherein the composition comprises: a purified population of bacteria that comprise bacteria with at least one mutation that results in one or more of: increased expression or activity of NifA or glutaminase; decreased expression or activity of NifL, NtrB, glutamine synthetase, GlnB, GlnK, DraT, or AmtB; decreased adenylyl-removing activity of GlnE; or decreased uridylyl-removing activity of GlnD.

315. The method of clause 300, wherein the composition comprises: a purified population of bacteria that comprise bacteria with a mutated nifL gene that has been altered to comprise a heterologous promoter inserted into said nifL gene.

316. The method of clause 300, wherein the composition comprises: a purified population of bacteria that comprise bacteria with a mutated glnE gene that results in a truncated GlnE protein lacking an adenylyl-removing (AR) domain.

317. The method of clause 300, wherein the composition comprises: a purified population of bacteria that comprise bacteria with a mutated amtB gene that results in the lack of expression of said amtB gene.

318. The method of clause 300, wherein the composition comprises: a purified population of bacteria that comprise bacteria with at least one of the following genetic alterations: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof 319. The method of clause 300, wherein the composition comprises: a purified population of bacteria that comprise bacteria with a mutated nifL gene that has been altered to comprise a heterologous promoter inserted into said nifL gene and a mutated glnE gene that results in a truncated GlnE protein lacking an adenylyl-removing (AR) domain.

320. The method of clause 300, wherein the composition comprises: a purified population of bacteria that comprise bacteria with a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.

321. The method of clause 300, wherein the composition comprises: a purified population of bacteria that comprise bacteria with a nifL modification that expresses a NifL protein at less than about 50% of a bacteria lacking the nifL modification.

322. The method of clause 300, wherein the composition comprises: a purified population of bacteria that comprise bacteria with a nifL modification that expresses a NifL protein at less than about 50% of a bacteria lacking the nifL modification, wherein the modification is a disruption, knockout, or truncation.

323. The method of clause 300, wherein the composition comprises: a purified population of bacteria that comprise bacteria with a nifL modification that expresses a NifL protein at less than about 50% of a bacteria lacking the nifL modification, and wherein the bacteria further comprise a promoter operably linked to a nifA sequence.

324. The method of clause 300, wherein the composition comprises: a purified population of bacteria that comprise bacteria with a nifL modification that expresses a NifL protein at less than about 50% of a bacteria lacking the nifL modification, and wherein the bacteria lack a nifL homolog.

325. The method of clause 300, wherein the composition comprises: a purified population of bacteria that comprise bacteria with a glnE modification that expresses a GlnE protein at less than about 50% of a bacteria lacking the glnE modification.

326. The method of clause 300, wherein the composition comprises: a purified population of bacteria that comprise bacteria with a glnE modification that expresses a GlnE protein at less than about 50% of a bacteria lacking the glnE modification, wherein the modification is a disruption, knockout, or a truncation.

327. The method of clause 300, wherein the composition comprises: a purified population of bacteria that comprise bacteria with a glnE modification that expresses a GlnE protein at less than about 50% of a bacteria lacking the glnE modification, and wherein the GlnE protein sequence lacks an adenylyl removing (AR) domain.

328. The method of clause 300, wherein the composition comprises: a purified population of bacteria that comprise bacteria with a glnE modification that expresses a GlnE protein at less than about 50% of a bacteria lacking the glnE modification, and wherein the GlnE protein sequence lacks adenylyl removing (AR) activity.

329. The method of clause 300, wherein the purified population of bacteria, in planta, provide at least 1% of fixed nitrogen to the plant.

330. The method of clause 300, wherein the purified population of bacteria, in planta, provide at least 5% of fixed nitrogen to the plant.

331. The method of clause 300, wherein the purified population of bacteria, in planta, provide at least 10% of fixed nitrogen to the plant.

332. The method of clause 300, wherein the purified population of bacteria are capable of fixing atmospheric nitrogen in non-nitrogen-limiting conditions.

333. The method of clause 300, wherein the purified population of bacteria, in planta, excrete nitrogen-containing products of nitrogen fixation.

334. The method of clause 300, wherein the purified population of bacteria, in planta, provide at least 1% of fixed nitrogen to the plant, and wherein said fixed nitrogen is measured through dilution of enriched fertilizer by atmospheric $N_2$ gas in plant tissue.

335. The method of clause 300, wherein the purified population of bacteria colonize a root of said plant and are present in an amount of at least about $1.0 \times 10^4$ bacterial cells per gram of fresh weight of plant root tissue.

336. The method of clause 300, wherein the plant comprises the seed, stalk, flower, fruit, leaves, or rhizome.

337. The method of clause 300, wherein the composition comprises: an agriculturally acceptable carrier.

338. The method of clause 300, wherein the composition comprising the purified population of bacteria is administered into furrows in which seeds of said plant are planted.

339. The method of clause 300, wherein the composition comprising the purified population of bacteria is formulated as a liquid in-furrow composition comprising bacteria at a concentration of about $1 \times 10^7$ to about $1 \times 10^{10}$ cfu per milliliter.

340. The method of clause 300, wherein the composition comprising the purified population of bacteria is administered onto a seed of said plant.

341. The method of clause 300, wherein the composition comprising the purified population of bacteria is formulated as a seed coating and is administered onto a seed of said plant.

342. The method of clause 300, wherein the composition comprising the purified population of bacteria is formulated as a seed coating and is administered onto a seed of said plant, at a concentration of about $1 \times 10^5$ to about $1 \times 10^7$ cfu per seed.

343. The method of clause 300, wherein the plant is non-leguminous.

344. The method of clause 300, wherein the plant is a cereal crop.

345. The method of clause 300, wherein the plant is selected from the group consisting of:
corn, rice, wheat, barley, sorghum, millet, oat, rye, and triticale.

346. The method of clause 300, wherein the plant is corn.

347. The method of clause 300, wherein the plant is a legume.

348. The method of clause 300, wherein the plant is a grain crop.

349. The method of clause 300, wherein the purified population of bacteria comprise bacteria selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof.

350. The method of clause 300, wherein the purified population of bacteria comprise a bacteria of genus *Rahnella*.

351. The method of clause 300, wherein the purified population of bacteria comprise a bacteria of species *Rahnella aquatilis*.

352. The method of clause 300, wherein the purified population of bacteria comprise a bacteria deposited as PTA-122293.

353. The method of clause 300, wherein the purified population of bacteria comprise a bacteria deposited as NCMA 201701003.

354. The method of clause 300, wherein the purified population of bacteria comprise a bacteria of genus *Kosakonia*.

355. The method of clause 300, wherein the purified population of bacteria comprise a bacteria of species *Kosakonia sacchari*.

356. The method of clause 300, wherein the purified population of bacteria comprise a bacteria deposited as PTA-122294.

357. The method of clause 300, wherein the purified population of bacteria comprise a bacteria deposited as NCMA 201701001.

358. The method of clause 300, wherein the purified population of bacteria comprise a bacteria deposited as NCMA 201701002.

359. The method of clause 300, wherein the purified population of bacteria comprise a bacteria deposited as NCMA 201708004.

360. The method of clause 300, wherein the purified population of bacteria comprise a bacteria deposited as NCMA 201708003.

361. The method of clause 300, wherein the purified population of bacteria comprise a bacteria deposited as NCMA 201708002.

362. The method of clause 300, wherein the purified population of bacteria comprise a bacteria of genus *Klebsiella*.

363. The method of clause 300, wherein the purified population of bacteria comprise a bacteria of species *Klebsiella variicola*.

364. The method of clause 300, wherein the purified population of bacteria comprise a bacteria deposited as NCMA 201708001.

365. The method of clause 300, wherein the purified population of bacteria comprise a bacteria deposited as NCMA 201712001.

366. The method of clause 300, wherein the purified population of bacteria comprise a bacteria deposited as NCMA 201712002.

367. An isolated bacteria, comprising:
   i. a 16S nucleic acid sequence that is at least about 97% identical to a nucleic acid sequence selected from SEQ ID NOs: 85, 96, 111, 121, 122, 123, 124, 136, 149, 157, 167, 261, 262, 269, 277-283;
   ii. a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, 284-295; and/or
   iii. a nucleic acid sequence that is at least about 90% identical to a nucleic acid sequence selected from SEQ ID NOs: 177-260, 296-303.

368. The isolated bacteria of clause 367, comprising: a 16S nucleic acid sequence that is at least about 97% identical to a nucleic acid sequence selected from SEQ ID NOs: 85, 96, 111, 121, 122, 123, 124, 136, 149, 157, 167, 261, 262, 269, and 277-283.

369. The isolated bacteria of clause 367, comprising: a 16S nucleic acid sequence that is at least about 99% identical to a nucleic acid sequence selected from SEQ ID NOs: 85, 96, 111, 121, 122, 123, 124, 136, 149, 157, 167, 261, 262, 269, and 277-283.

370. The isolated bacteria of clause 367, comprising: a 16S nucleic acid sequence selected from SEQ ID NOs: 85, 96, 111, 121, 122, 123, 124, 136, 149, 157, 167, 261, 262, 269, and 277-283.

371. The isolated bacteria of clause 367, comprising: a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, and 284-295.

372. The isolated bacteria of clause 367, comprising: a nucleic acid sequence that is at least about 95% identical to a nucleic acid sequence selected from SEQ ID NOs: 86-95, 97-110, 112-120, 125-135, 137-148, 150-156, 158-166, 168-176, 263-268, 270-274, 275, 276, and 284-295.

373. The isolated bacteria of clause 367, comprising: a nucleic acid sequence that is at least about 99% identical to a nucleic acid sequence selected from SEQ ID NOs: 86-95, 97-110, 112-120, 125-135, 137-148, 150-156, 158-166, 168-176, 263-268, 270-274, 275, 276, and 284-295.

374. The isolated bacteria of clause 367, comprising: a nucleic acid sequence selected from SEQ ID NOs: 86-95, 97-110, 112-120, 125-135, 137-148, 150-156, 158-166, 168-176, 263-268, 270-274, 275, 276, and 284-295.

375. The isolated bacteria of clause 367, comprising: a nucleic acid sequence that is at least about 90% identical to a nucleic acid sequence selected from SEQ ID NOs: 177-260 and 296-303.

376. The isolated bacteria of clause 367, comprising: a nucleic acid sequence that is at least about 95% identical to a nucleic acid sequence selected from SEQ ID NOs: 177-260 and 296-303.

377. The isolated bacteria of clause 367, comprising: a nucleic acid sequence that is at least about 99% identical to a nucleic acid sequence selected from SEQ ID NOs: 177-260 and 296-303.

378. The isolated bacteria of clause 367, comprising: a nucleic acid sequence selected from SEQ ID NOs: 177-260 and 296-303.

379. The isolated bacteria of clause 367, comprising: at least one genetic variation introduced into a gene selected from the group consisting of nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

380. The isolated bacteria of clause 367, comprising: at least one genetic variation introduced into a gene selected from the group consisting of nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme, wherein the genetic variation (A) is a knock-out mutation; (B) alters or abolishes a regulatory sequence of a target gene; (C) comprises the insertion of a heterologous regulatory sequence; or (D) a domain deletion.

381. The isolated bacteria of clause 367, comprising: at least one mutation that results in one or more of: increased expression or activity of NifA or glutaminase; decreased expression or activity of NifL, NtrB, glutamine synthetase, GlnB, GlnK, DraT, or AmtB; decreased adenylyl-removing activity of GlnE; or decreased uridylyl-removing activity of GlnD.

382. The isolated bacteria of clause 367, comprising: a mutated nifL gene that has been altered to comprise a heterologous promoter inserted into said nifL gene.

383. The isolated bacteria of clause 367, comprising: a mutated glnE gene that results in a truncated GlnE protein lacking an adenylyl-removing (AR) domain.

384. The isolated bacteria of clause 367, comprising: a mutated amtB gene that results in the lack of expression of said amtB gene.

385. The isolated bacteria of clause 367, comprising: at least one of the following genetic alterations: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof.

386. The isolated bacteria of clause 367, comprising: a mutated nifL gene that has been altered to comprise a heterologous promoter inserted into said nifL gene and a mutated glnE gene that results in a truncated GlnE protein lacking an adenylyl-removing (AR) domain.

387. The isolated bacteria of clause 367, comprising: a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.

388. The isolated bacteria of clause 367, comprising: a nifL modification that expresses a NifL protein at less than about 50% of a bacteria lacking the nifL modification.

389. The isolated bacteria of clause 367, comprising: a nifL modification that expresses a NifL protein at less than about 50% of a bacteria lacking the nifL modification, wherein the modification is a disruption, knock-out, or truncation.

390. The isolated bacteria of clause 367, comprising: a nifL modification that expresses a NifL protein at less than about 50% of a bacteria lacking the nifL modification, and wherein the bacteria further comprise a promoter operably linked to a nifA sequence.

391. The isolated bacteria of clause 367, comprising: a nifL modification that expresses a NifL protein at less than about 50% of a bacteria lacking the nifL modification, and wherein the bacteria lack a nifL homolog.

392. The isolated bacteria of clause 367, comprising: a glnE modification that expresses a GlnE protein at less than about 50% of a bacteria lacking the glnE modification.

393. The isolated bacteria of clause 367, comprising: a glnE modification that expresses a GlnE protein at less than about 50% of a bacteria lacking the glnE modification, wherein the modification is a disruption, knock-out, or a truncation.

394. The isolated bacteria of clause 367, comprising: a glnE modification that expresses a GlnE protein at less than about 50% of a bacteria lacking the glnE modification, and wherein the GlnE protein sequence lacks an adenylyl removing (AR) domain.

395. The isolated bacteria of clause 367, comprising: a glnE modification that expresses a GlnE protein at less than about 50% of a bacteria lacking the glnE modification, and wherein the GlnE protein sequence lacks adenylyl removing (AR) activity.

396. The isolated bacteria of clause 367, wherein the bacteria, in planta, provide at least 1% of fixed nitrogen to a plant exposed to said bacteria.

397. The isolated bacteria of clause 367, wherein the bacteria, in planta, provide at least 5% of fixed nitrogen to a plant exposed to said bacteria.

398. The isolated bacteria of clause 367, wherein the bacteria, in planta, provide at least 10% of fixed nitrogen to a plant exposed to said bacteria.

399. The isolated bacteria of clause 367, wherein the bacteria is capable of fixing atmospheric nitrogen in non-nitrogen-limiting conditions.

400. The isolated bacteria of clause 367, wherein the bacteria, in planta, excretes nitrogen-containing products of nitrogen fixation.

401. The isolated bacteria of clause 367, wherein the bacteria, in planta, provide at least 1% of fixed nitrogen to a plant exposed to said bacteria, and wherein said fixed nitrogen is measured through dilution of enriched fertilizer by atmospheric $N_2$ gas in plant tissue.

402. The isolated bacteria of clause 367, wherein the bacteria colonize a root of a plant exposed to said bacteria to a concentration of at least about $1.0 \times 10^4$ bacterial cells per gram of fresh weight of plant root tissue.

403. The isolated bacteria of clause 367, formulated into an agricultural composition.

404. The isolated bacteria of clause 367, formulated into an in-furrow composition.

405. The isolated bacteria of clause 367, formulated as a liquid in-furrow composition that comprises bacteria at a concentration of about $1 \times 10^7$ to about $1 \times 10^{10}$ cfu per milliliter.

406. The isolated bacteria of clause 367, formulated as a seed treatment or seed coating.

407. The isolated bacteria of clause 367, formulated as a seed treatment or seed coating that comprises bacteria at a concentration of about $1 \times 10^5$ to about $1 \times 10^7$ cfu per seed.

408. The isolated bacteria of clause 367, wherein the bacteria is in contact with a plant and increases nitrogen fixation in the plant.

409. The isolated bacteria of clause 367, disposed on a non-leguminous plant.

410. The isolated bacteria of clause 367, disposed on a cereal crop.

411. The isolated bacteria of clause 367, disposed on a plant selected from the group consisting of: corn, rice, wheat, barley, sorghum, millet, oat, rye, and triticale.

412. The isolated bacteria of clause 367, disposed on corn.

413. The isolated bacteria of clause 367, disposed on a legume.

414. The isolated bacteria of clause 367, disposed on a grain crop.

415. The isolated bacteria of clause 367, selected from: *Rahnella aquatilis, Klebsiella variicola, Achromobacter spiritinus, Achromobacter marplatensis, Micro-*

*bacterium murale, Kluyvera intermedia, Kosakonia pseudosacchari, Enterobacter* sp., *Azospirillum lipoferum, Kosakonia sacchari,* and combinations thereof.

416. The isolated bacteria of clause 367, wherein the bacteria is of the genus *Rahnella.*

417. The isolated bacteria of clause 367, wherein the bacteria is of the species Rahnella *aquatilis.*

418. The isolated bacteria of clause 367, deposited as PTA-122293.

419. The isolated bacteria of clause 367, deposited as NCMA 201701003.

420. The isolated bacteria of clause 367, wherein the bacteria is of the genus *Kosakonia.*

421. The isolated bacteria of clause 367, wherein the bacteria is of the species Kosakonia *sacchari.*

422. The isolated bacteria of clause 367, deposited as PTA-122294.

423. The isolated bacteria of clause 367, deposited as NCMA 201701001.

424. The isolated bacteria of clause 367, deposited as NCMA 201701002.

425. The isolated bacteria of clause 367, deposited as NCMA 201708004.

426. The isolated bacteria of clause 367, deposited as NCMA 201708003.

427. The isolated bacteria of clause 367, deposited as NCMA 201708002.

428. The isolated bacteria of clause 367, wherein the bacteria is of the genus *Klebsiella.*

429. The isolated bacteria of clause 367, wherein the bacteria is of the species *Klebsiella variicola.*

430. The isolated bacteria of clause 367, deposited as NCMA 201708001.

431. The isolated bacteria of clause 367, deposited as NCMA 201712001.

432. The isolated bacteria of clause 367, deposited as NCMA 201712002.

433. A composition comprising any one or more bacteria of clauses 415 to 432.

434. A method of detecting a non-native junction sequence, comprising: amplifying a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 372-405.

435. The method according to clause 434, wherein said amplifying is by conducting a polymerase chain reaction.

436. The method according to clause 434, wherein said amplifying is by conducting a quantitative polymerase chain reaction.

437. A method of detecting a non-native junction sequence, comprising: amplifying a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least a contiguous base pair fragment contained in SEQ ID NOs: 372-405, said contiguous base pair fragment being comprised of nucleotides at the intersection of: an upstream sequence comprising SEQ ID NOs: 304-337 and downstream sequence comprising SEQ ID NOs: 338-371.

438. The method according to clause 437, wherein said amplifying is by conducting a polymerase chain reaction.

439. The method according to clause 437, wherein said amplifying is by conducting a quantitative polymerase chain reaction.

440. A non-native junction sequence, comprising: a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 372-405.

441. A non-native junction sequence, comprising: a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least a 10 contiguous base pair fragment contained in SEQ ID NOs: 372-405, said contiguous base pair fragment being comprised of nucleotides at the intersection of: an upstream sequence comprising SEQ ID NOs: 304-337 and downstream sequence comprising SEQ ID NOs: 338-371.

442. A bacterial composition, comprising:
at least one remodeled bacterial strain that fixes atmospheric nitrogen, the at least one remodeled bacterial strain comprising exogenously added DNA wherein said exogenously added DNA shares at least 80% identity to a corresponding native bacterial strain.

443. A method of maintaining soil nitrogen levels, comprising:
planting, in soil of a field, a crop inoculated by a remodeled bacterium that fixes atmospheric nitrogen; and
harvesting said crop, wherein no more than 90% of a nitrogen dose required for producing said crop is administered to said soil of said field between planting and harvesting.

444. A method of delivering a probiotic supplement to a crop plant, comprising:
coating a crop seed with a seed coating, seed treatment, or seed dressing, wherein said seed coating, seed dressing, or seed treatment comprising living representatives of said probiotic; and
applying in soil of a field, said crop seeds.

445. A method of increasing the amount of atmospheric derived nitrogen in a non-leguminous plant, comprising:
exposing said non-leguminous plant to remodeled non-intergeneric microbes, said remodeled non-intergeneric microbes comprising at least one genetic variation introduced into a nitrogen fixation genetic regulatory network or at least one genetic variation introduced into a nitrogen assimilation genetic regulatory network.

446. A method of increasing an amount of atmospheric derived nitrogen in a corn plant, comprising:
exposing said corn plant to remodeled non-intergeneric microbes comprising remodeled genetic variations within at least two genes selected from the group consisting of nifL, glnB, glnE, and amtB.

447. A method of increasing an amount of atmospheric derived nitrogen in a corn plant, comprising:
exposing said corn plant to remodeled non-intergeneric microbes comprising at least one genetic variation introduced into a nitrogen fixation genetic regulatory network and at least one genetic variation introduced into a nitrogen assimilation genetic regulatory network, wherein said remodeled non-intergeneric microbes, in planta, produce at least 5% of fixed nitrogen in said corn plant as measured by dilution of 15N in crops grown in fields treated with fertilizer containing 1.2% 15N.

448. The method of any of the previous clauses, wherein the bacterium produces fixed N of at least about $1 \times 10^{-17}$ mmol N per bacterial cell per hour when in the presence of exogenous nitrogen.

449. The bacterium of any of the previous clauses, wherein the bacterium produces fixed N of at least about $1 \times 10^{-17}$ mmol N per bacterial cell per hour when in the presence of exogenous nitrogen.

450. The bacterial population of any of the previous clauses, wherein the bacterium produces fixed N of at least about $1 \times 10^{-17}$ mmol N per bacterial cell per hour when in the presence of exogenous nitrogen.

451. The isolated bacteria of any of the previous clauses, wherein the bacterium produces fixed N of at least about $1 \times 10^{-17}$ mmol N per bacterial cell per hour when in the presence of exogenous nitrogen.

452. The non-intergeneric bacterial population of any of the previous clauses, wherein the bacterium produces fixed N of at least about $1 \times 10^{-17}$ mmol N per bacterial cell per hour when in the presence of exogenous nitrogen.

453. The non-intergeneric bacterium of any of the previous clauses, wherein the bacterium produces fixed N of at least about $1 \times 10^{-17}$ mmol N per bacterial cell per hour when in the presence of exogenous nitrogen.

454. The method of any of the previous clauses, wherein the plurality of bacteria, in planta, produce 5% or more of the fixed nitrogen in the plant.

455. The method of any of the previous clauses, wherein the plurality of non-intergeneric bacteria, in planta, produce 5% or more of the fixed nitrogen in the plant.

456. The bacterium of any of the previous clauses, wherein the plurality of bacteria, in planta, produce 5% or more of the fixed nitrogen in the plant.

457. The bacterial population of any of the previous clauses, wherein the plurality of bacteria, in planta, produce 5% or more of the fixed nitrogen in the plant.

458. The isolated bacteria of any of the previous clauses, wherein the plurality of bacteria, in planta, produce 5% or more of the fixed nitrogen in the plant.

459. The non-intergeneric bacterial population of any of the previous clauses, wherein the plurality of non-intergeneric bacteria, in planta, produce 5% or more of the fixed nitrogen in the plant.

460. The non-intergeneric bacterium of any of the previous clauses, wherein the plurality of non-intergeneric bacteria, in planta, produce 5% or more of the fixed nitrogen in the plant.

461. The method of any of the previous clauses, wherein the plurality of bacteria, in planta, produce 10% or more of the fixed nitrogen in the plant.

462. The method of any of the previous clauses, wherein the plurality of non-intergeneric bacteria, in planta, produce 10% or more of the fixed nitrogen in the plant.

463. The bacterium of any of the previous clauses, wherein the plurality of bacteria, in planta, produce 10% or more of the fixed nitrogen in the plant.

464. The bacterial population of any of the previous clauses, wherein the plurality of bacteria, in planta, produce 10% or more of the fixed nitrogen in the plant.

465. The isolated bacteria of any of the previous clauses, wherein the plurality of bacteria, in planta, produce 10% or more of the fixed nitrogen in the plant.

466. The non-intergeneric bacterial population of any of the previous clauses, wherein the plurality of non-intergeneric bacteria, in planta, produce 10% or more of the fixed nitrogen in the plant.

467. The non-intergeneric bacterium of any of the previous clauses, wherein the plurality of non-intergeneric bacteria, in planta, produce 10% or more of the fixed nitrogen in the plant.

468. The method of any of the previous clauses, wherein the plurality of bacteria, in planta, produce 15% or more of the fixed nitrogen in the plant.

469. The method of any of the previous clauses, wherein the plurality of non-intergeneric bacteria, in planta, produce 15% or more of the fixed nitrogen in the plant.

470. The bacterium of any of the previous clauses, wherein the plurality of bacteria, in planta, produce 15% or more of the fixed nitrogen in the plant.

471. The bacterial population of any of the previous clauses, wherein the plurality of bacteria, in planta, produce 15% or more of the fixed nitrogen in the plant.

472. The isolated bacteria of any of the previous clauses, wherein the plurality of bacteria, in planta, produce 15% or more of the fixed nitrogen in the plant.

473. The non-intergeneric bacterial population of any of the previous clauses, wherein the plurality of non-intergeneric bacteria, in planta, produce 15% or more of the fixed nitrogen in the plant.

474. The non-intergeneric bacterium of any of the previous clauses, wherein the plurality of non-intergeneric bacteria, in planta, produce 15% or more of the fixed nitrogen in the plant.

475. The method of any of the previous clauses, wherein the plurality of bacteria, in planta, produce 20% or more of the fixed nitrogen in the plant.

476. The method of any of the previous clauses, wherein the plurality of non-intergeneric bacteria, in planta, produce 20% or more of the fixed nitrogen in the plant.

477. The bacterium of any of the previous clauses, wherein the plurality of bacteria, in planta, produce 20% or more of the fixed nitrogen in the plant.

478. The bacterial population of any of the previous clauses, wherein the plurality of bacteria, in planta, produce 20% or more of the fixed nitrogen in the plant.

479. The isolated bacteria of any of the previous clauses, wherein the plurality of bacteria, in planta, produce 20% or more of the fixed nitrogen in the plant.

480. The non-intergeneric bacterial population of any of the previous clauses, wherein the plurality of non-intergeneric bacteria, in planta, produce 20% or more of the fixed nitrogen in the plant.

481. The non-intergeneric bacterium of any of the previous clauses, wherein the plurality of non-intergeneric bacteria, in planta, produce 20% or more of the fixed nitrogen in the plant.

482. The method of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

483. The bacterium of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

484. The bacterial population of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

485. The isolated bacteria of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

486. The non-intergeneric bacterial population of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

487. The non-intergeneric bacterium of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

488. The method of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

489. The bacterium of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

490. The bacterial population of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

491. The isolated bacteria of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

492. The non-intergeneric bacterial population of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

493. The non-intergeneric bacterium of any of the previous clauses, wherein the product of (i) the average colonization ability per unit of plant root tissue and (ii) produced fixed N per bacterial cell per hour, is at least about $2.0 \times 10^{-17}$ mmol N per gram of fresh weight of plant root tissue per hour.

494. The method of any of the previous clauses, wherein the plant has been remodeled or bred for efficient nitrogen use.

495. The bacterial composition of any of the previous clauses, wherein said at least one remodeled bacterial strain comprises at least one variation in a gene or intergenic region within 10,000 bp of a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

496. The method of any of the previous clauses, wherein said remodeled bacterium comprises a bacterial composition of any of the preceding clauses.

497. The method of any of the previous clauses, wherein said remodeled bacterium consists of a bacterial composition of any of the preceding clauses.

498. The method of any of the previous clauses, wherein the remodeled bacterial strain is a remodeled Gram-positive bacterial strain.

499. The method of any of the previous clauses, wherein the remodeled Gram-positive bacterial strain has an altered expression level of a regulator of a Nif cluster.

500. The method of any of the previous clauses, wherein the remodeled Gram-positive bacterial strain expresses a decreased amount of a negative regulator of a Nif cluster.

501. The method of any of the previous clauses, wherein the remodeled bacterial strain expresses a decreased amount of GlnR.

502. The method of any of the previous clauses, wherein the genome of the remodeled bacterial strain encodes a polypeptide with at least 75% identity to a sequence from the Zehr lab NifH database.

503. The method of any of the previous clauses, wherein the genome of the remodeled bacterial strain encodes a polypeptide with at least 85% identity to a sequence from the Zehr lab NifH database.

504. The method of any of the previous clauses, wherein the genome of the remodeled bacterial strain encodes a polypeptide with at least 75% identity to a sequence from the Buckley lab NifH database.

505. The method of any of the previous clauses, wherein the genome of the remodeled bacterial strain encodes a polypeptide with at least 85% identity to a sequence from the Buckley lab NifH database.

506. The method of any of the previous clauses, wherein said remodeled non-intergeneric microbes comprise at least one genetic variation introduced into said nitrogen fixation genetic regulatory network.

507. The method of any of the previous clauses, wherein said remodeled non-intergeneric microbes comprise at least one genetic variation introduced into said nitrogen assimilation genetic regulatory network.

508. The method of any of the previous clauses, wherein said remodeled non-intergeneric microbes comprise at least one genetic variation introduced into said nitrogen fixation genetic regulatory network and at least one genetic variation introduced into said nitrogen assimilation genetic regulatory network.

509. The method of any of the previous clauses, wherein said remodeled non-intergeneric microbes are applied into furrows in which seeds of said non-leguminous plant are planted.

510. The method of any of the previous clauses, wherein said remodeled non-intergeneric microbes are coated onto a seed of said non-leguminous plant.

511. The method of any of the previous clauses, wherein said remodeled non-intergeneric microbes colonize at least a root of said non-leguminous plant such that said remodeled non-intergeneric microbes are present in said non-leguminous plant in an amount of at least $10^5$ colony forming units per gram fresh weight of tissue.

512. The method of any of the previous clauses, wherein said remodeled non-intergeneric microbes are capable of fixing atmospheric nitrogen in non-nitrogen-limiting conditions.

513. The method of any of the previous clauses, wherein said remodeled non-intergeneric microbes, in planta, excrete nitrogen-containing products of nitrogen fixation.

514. The method of any of the previous clauses, wherein said remodeled non-intergeneric microbes, in planta, produce at least 1% of fixed nitrogen in said non-leguminous plant.

515. The method of any of the previous clauses, wherein said fixed nitrogen in said non-leguminous plant produced by said remodeled non-intergeneric microbes is measured by dilution of 15N in crops grown in fields treated with fertilizer containing 1.2% 15N.

516. The method of any of the previous clauses, wherein said remodeled non-intergeneric microbes, in planta, produce 5% or more of the fixed nitrogen in said non-leguminous plant.

517. The method of any of the previous clauses, wherein said non-intergeneric microbes are remodeled using at least one type of engineering selected from the group consisting of directed mutagenesis, random mutagenesis, and directed evolution.

518. The method of any of the previous clauses, wherein said remodeled non-intergeneric microbes, in planta, excrete nitrogen-containing products of nitrogen fixation.

519. The method of any of the previous clauses, wherein said remodeled non-intergeneric microbes are applied into furrows in which seeds of said corn plant are planted.

520. The method of any of the previous clauses, wherein said remodeled non-intergeneric microbes are coated onto a seed of said corn plant.

521. The method of any of the previous clauses, wherein said remodeled non-intergeneric microbes comprise at least one genetic variation introduced into a nitrogen fixation genetic regulatory network and at least one genetic variation introduced into a nitrogen assimilation genetic regulatory network.

522. The method of any of the previous clauses, wherein said non-intergeneric microbes comprise at least one genetic variation introduced into a nitrogen fixation genetic regulatory network and at least one genetic variation introduced into a nitrogen assimilation genetic regulatory network.

523. The method of any of the previous clauses, wherein said genetically engineered non-intergeneric microbes comprise at least one genetic variation introduced into a nitrogen fixation genetic regulatory network and at least one genetic variation introduced into a nitrogen assimilation genetic regulatory network.

524. The method of any of the previous clauses, wherein said remodeled non-intergeneric bacteria comprise at least one genetic variation introduced into a nitrogen fixation genetic regulatory network and at least one genetic variation introduced into a nitrogen assimilation genetic regulatory network.

525. The method of any of the previous clauses, wherein said non-intergeneric bacteria comprise at least one genetic variation introduced into a nitrogen fixation genetic regulatory network and at least one genetic variation introduced into a nitrogen assimilation genetic regulatory network.

526. The method of any of the previous clauses, wherein said genetically engineered non-intergeneric bacteria comprise at least one genetic variation introduced into a nitrogen fixation genetic regulatory network and at least one genetic variation introduced into a nitrogen assimilation genetic regulatory network.

527. The bacterium of any of the previous clauses, wherein said bacterium comprise at least one genetic variation introduced into a nitrogen fixation genetic regulatory network and at least one genetic variation introduced into a nitrogen assimilation genetic regulatory network.

528. The bacterial population of any of the previous clauses, wherein bacteria within said bacterial population comprise at least one genetic variation introduced into a nitrogen fixation genetic regulatory network and at least one genetic variation introduced into a nitrogen assimilation genetic regulatory network.

529. The isolated bacteria of any of the previous clauses, wherein said isolated bacteria comprise at least one genetic variation introduced into a nitrogen fixation genetic regulatory network and at least one genetic variation introduced into a nitrogen assimilation genetic regulatory network.

530. The non-intergeneric bacterial population of any of the previous clauses, wherein non-intergeneric bacteria within said non-intergeneric bacterial population comprise at least one genetic variation introduced into a nitrogen fixation genetic regulatory network and at least one genetic variation introduced into a nitrogen assimilation genetic regulatory network.

531. The non-intergeneric bacterium of any of the previous clauses, wherein said non-intergeneric bacterium comprises at least one genetic variation introduced into a nitrogen fixation genetic regulatory network and at least one genetic variation introduced into a nitrogen assimilation genetic regulatory network.

532. A composition comprising any one or more bacteria of any of the previous clauses.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for increasing the available nitrogen for a non-leguminous plant in a field, said method comprising applying to said non-leguminous plant in said field a plurality of engineered diazotrophic bacteria, wherein:

said engineered diazotrophic bacteria have a product of (i) colonization ability under field conditions and (ii) fixed N produced per bacterial cell per hour of at least about $2.5 \times 10^{-8}$ mmol N per gram of fresh weight of plant root tissue per hour; and said engineered diazotrophic bacteria comprises one or more genetic variations, wherein the one or more genetic variations comprise a complete or partial nifL deletion and insertion of a constitutive promoter operably linked to a nifA gene.

2. The method of claim 1, wherein said plurality of engineered diazotrophic bacteria, in planta, produce 5% or more of the available nitrogen in said non-leguminous plant.

3. The method of claim 1, wherein said engineered diazotrophic bacteria comprise a bacterium from a species selected from the group consisting of *Kosakonia sacchari, Rahnella aquatilis, Klebsiella variicola*, and *Kosakonia pseudosacchari*.

4. The method of claim 3, wherein said *Kosakonia sacchari* bacterium is a bacterium deposited under Patent Depository Designation No. 201701002, 201708004, 201708003, or 201708002.

5. The method of claim 3, wherein said *Rahnella aquatilis* bacterium is a bacterium deposited under Accession No. PTA-122293.

6. The method of claim 3, wherein said *Klebsiella variicola* bacterium is a bacterium deposited under Patent Depository Designation No. 201712002.

7. A non-leguminous plant colonized with a plurality of engineered diazotrophic bacteria, wherein:

said engineered diazotrophic bacteria have a product of (i) colonization ability under field conditions and (ii) N produced per bacterial cell per hour of at least about $2.5 \times 10^{-8}$ mmol N per gram of fresh weight of plant root tissue per hour; and said engineered diazotrophic bacteria comprise one or more genetic variations, wherein the one or more genetic variations comprise a complete or partial nifL deletion and insertion of a constitutive promoter operably linked to a nifA gene.

8. The non-leguminous plant of claim 7, wherein said non-leguminous plant is selected from the group consisting of corn, rice, wheat, barley, sorghum, millet, oat, rye, and triticale.

9. A composition comprising:

a) a plurality of engineered diazotrophic bacteria, wherein:

said engineered diazotrophic bacteria have a product of (i) colonization ability under field conditions and (ii) N produced per bacterial cell per hour of at least about $2.5 \times 10^{-8}$ mmol N per gram of fresh weight of non-leguminous plant root tissue per hour; and said engineered diazotrophic bacteria comprise one or more genetic variations, wherein the one or more genetic variations comprise a complete or partial nifL deletion and insertion of a constitutive promoter operably linked to a nifA gene; and b) a non-leguminous plant seed, wherein said plurality of engineered diazotrophic bacteria can provide at least one pound of nitrogen per acre per season to a non-leguminous plant produced from said plant seed in a field.

10. The composition of claim 9, wherein said plurality of engineered diazotrophic bacteria comprises two or more bacterial strains.

11. The composition of claim 9, wherein said plurality of engineered diazotrophic bacteria comprises a bacterium from a species selected from the group consisting of *Kosakonia sacchari, Rahnella aquatilis, Klebsiella variicola*, and *Kosakonia pseudosacchari*.

12. The composition of claim 11, wherein said *Kosakonia sacchari* bacterium is a bacterium deposited under Patent Depository Designation No. 201701002, 201708004, 201708003, or 201708002.

13. The composition of claim 11, wherein said *Rahnella aquatilis* bacterium is a bacterium deposited under Accession No. PTA-122293.

14. The composition of claim 11, wherein said *Klebsiella variicola* bacterium is a bacterium deposited under Patent Depository Designation No. 201712002.

15. The method of claim 1, wherein said plurality of engineered diazotrophic bacteria comprises a bacterium from a genus selected from the group consisting of *Kosakonia, Rahnella*, and *Klebsiella*.

16. The method of claim 1, wherein said plurality of engineered diazotrophic bacteria comprises two or more bacterial strains.

17. The method of claim 16, wherein said two or more bacterial strains are from a genus independently selected from the group consisting of *Kosakonia, Rahnella*, and *Klebsiella*.

18. The method of claim 16, wherein at least two bacterial strains of said two or more bacterial strains are from a genus independently selected from the group consisting of *Kosakonia* and *Rahnella*.

19. The method of claim 1, wherein said one or more genetic variations comprise a partial deletion of nifL and further comprise a partial deletion of glnE.

20. The method of claim 19, wherein said partial deletion of glnE results in deletion of the nucleotides encoding the adenylyl-removing domain of the GlnE protein.

21. The non-leguminous plant of claim 7, wherein said engineered diazotrophic bacteria comprise a bacterium from a species selected from the group consisting of *Kosakonia sacchari, Rahnella aquatilis, Klebsiella variicola*, and *Kosakonia pseudosacchari*.

22. The non-leguminous plant of claim 21, wherein said *Kosakonia sacchari* bacterium is a bacterium deposited under Patent Depository Designation No. 201701002, 201708004, 201708003, or 201708002.

23. The non-leguminous plant of claim 21, wherein said *Rahnella aquatilis* bacterium is a bacterium deposited under Accession No. PTA-122293.

24. The non-leguminous plant of claim 21, wherein said *Klebsiella variicola* bacterium is a bacterium deposited under Patent Depository Designation No. 201712002.

25. The non-leguminous plant of claim 7, wherein said plurality of engineered diazotrophic bacteria comprises two or more bacterial strains.

26. The non-leguminous plant of claim 7, wherein said plurality of engineered diazotrophic bacteria comprises a bacterium from a genus selected from the group consisting of *Kosakonia, Rahnella*, and *Klebsiella*.

27. The non-leguminous plant of claim 26, wherein said two or more bacterial strains are from a genus independently selected from the group consisting of *Kosakonia, Rahnella*, and *Klebsiella*.

28. The non-leguminous plant of claim 26, wherein at least two bacterial strains of said two or more bacterial strains are from a genus independently selected from the group consisting of *Kosakonia* and *Rahnella*.

29. The non-leguminous plant of claim 7, wherein said one or more genetic variations comprise a partial deletion of nifL and further comprise a partial deletion of glnE.

30. The non-leguminous plant of claim 29, wherein said partial deletion of glnE results in deletion of the nucleotides encoding the adenylyl-removing domain of the GlnE protein.

31. The composition of claim 9, wherein said plurality of engineered diazotrophic bacteria comprises a bacterium from a genus selected from the group consisting of *Kosakonia, Rahnella*, and *Klebsiella*.

32. The composition of claim 10, wherein said two or more bacterial strains are from a genus independently selected from the group consisting of *Kosakonia, Rahnella*, and *Klebsiella*.

33. The composition of claim 10, wherein at least two bacterial strains of said two or more bacterial strains are from a genus independently selected from the group consisting of *Kosakonia* and *Rahnella*.

34. The composition of claim 9, wherein said one or more genetic variations comprise a partial deletion of nifL and further comprise a partial deletion of glnE.

35. The composition of claim 34, wherein said partial deletion of glnE results in deletion of the nucleotides encoding the adenylyl-removing domain of the GlnE protein.

36. The method of claim 1, wherein said one or more genetic variations further comprise a complete or partial amtB deletion.

37. The non-leguminous plant of claim 7, wherein said one or more genetic variations further comprise a complete or partial amtB deletion.

38. The composition of claim 9, wherein said one or more genetic variations further comprise a complete or partial amtB deletion.

\* \* \* \* \*